United States Patent
Kawada et al.

(10) Patent No.: US 7,220,783 B2
(45) Date of Patent: *May 22, 2007

(54) PARA-TERPHENYL COMPOUNDS

(75) Inventors: Kenji Kawada, Osaka (JP); Mitsuaki Ohtani, Nara (JP); Ryuji Suzuki, Nara (JP); Akinori Arimura, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 193 days.

This patent is subject to a terminal disclaimer.

(21) Appl. No.: 10/704,876

(22) Filed: Nov. 12, 2003

(65) Prior Publication Data

US 2004/0127495 A1 Jul. 1, 2004

Related U.S. Application Data

(62) Division of application No. 09/214,277, filed as application No. PCT/JP97/02635 on Jul. 30, 1997.

(30) Foreign Application Priority Data

| Jul. 31, 1996 | (JP) | ................................... 8-201859 |
| Oct. 30, 1996 | (JP) | ................................... 8-287782 |
| Mar. 18, 1997 | (JP) | ................................... 9-86085 |

(51) Int. Cl.
| A61K 31/075 | (2006.01) |
| A61K 31/09  | (2006.01) |
| C07C 43/205 | (2006.01) |
| C07C 43/225 | (2006.01) |
| C07C 43/23  | (2006.01) |

(52) U.S. Cl. ...................... 514/650; 514/651; 514/721; 568/642; 568/643; 544/224; 544/242; 544/336; 544/182; 546/134; 546/285; 548/215; 548/304.4

(58) Field of Classification Search ................ 564/642; 514/520, 650, 651, 721; 568/642, 643
See application file for complete search history.

(56) References Cited

U.S. PATENT DOCUMENTS

| 3,624,142 A | 11/1971 | Shen et al. |
| 4,495,202 A | 1/1985 | Matsumoto et al. |
| 4,594,465 A | 6/1986 | Kam Ming Chan et al. |
| 4,728,670 A | 3/1988 | Haslanger et al. |
| 5,417,885 A | 5/1995 | Suzuki et al. |
| 5,487,845 A | 1/1996 | Reiffenrath et al. |
| 5,494,605 A | 2/1996 | Kurihara et al. |
| 5,560,864 A | 10/1996 | Goulding |
| 5,750,051 A | 5/1998 | Goulding et al. |
| 5,871,665 A | 2/1999 | Coates et al. |
| 5,968,980 A | 10/1999 | Kawashima et al. |

FOREIGN PATENT DOCUMENTS

| EP | WO 93/22397 A1 | 11/1993 |
| EP | 0 769 299 A1 | 4/1997 |
| GB | 2 198 743 A | 6/1988 |
| GB | 2 200 912 A | 8/1988 |
| GB | 2 240 778 A | 8/1991 |
| JP | 43-19935 B | 8/1943 |
| JP | 60-13730 A | 1/1985 |
| JP | 62-294650 A | 12/1987 |
| JP | 5-25145 A | 2/1993 |
| JP | 6-507987 A | 9/1994 |
| JP | 8-277247 A | 10/1996 |
| WO | WO 96/10012 A1 | 4/1996 |
| WO | WO 96-18606 A1 | 6/1996 |

OTHER PUBLICATIONS

West, Anthony R., Solid State Chemistry and its Applications, Wiley, New York, 1988, pp. 358 & 365.*
Akihide, K. :A Prototype Drug for IgE Antibody Synthesis Modulation, Agents and Actions Supplements, 1991, vol. 34, p. 369-378.
Kallitsis, J.K., Synthesis and Characterization of Soluble Aromatic Polyesters Containing Oligophenyl Moieties in the Main Chain., Macromolecules, 1994, vol. 27, p. 4509-4515.

(Continued)

*Primary Examiner*—Venkataraman Balasubramanian
(74) *Attorney, Agent, or Firm*—Birch, Stewart, Kolasch & Birch, LLP

(57) ABSTRACT

The present invention provides a selective suppressor of the IgE production comprising a compound which suppresses the IgE production in a process from a differentiation of a mature B cell into an antibody-producing cell to the production of an antibody and which does not suppress or weakly suppresses the production of IgG, IgM and/or IgA which are produced at the same time, a compound of the formula (I):

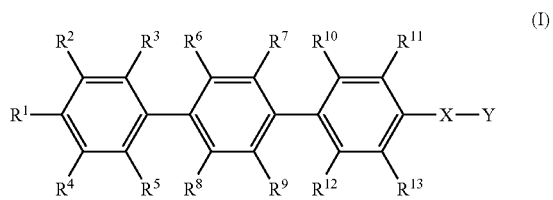

wherein $R^1$–$R^{13}$ are hydrogen, halogen, lower alkyl, lower alkoxy or the like, X is —O—, —$CH_2$—, —$NR^{14}$— or —S(O)p- and Y is lower alkyl, lower alkenyl or the like, a process for producing the same and a pharmaceutical composition comprising the same.

1 Claim, 2 Drawing Sheets

OTHER PUBLICATIONS

Kakali, F. et al. Synthesis and Characterization of Soluble Aromatic Polyesters Derived from Substituted Terphenyl and Quinquephenyl Diols, J. Polymer Science part A Polymer Chemistry, Jun. 1996, vol. 34, No. 2, p. 1581-1587.

Wagner, Gabriele et al. Ferrocene derivatives containing anthracene linked by spacers, J. Organomet. Chem., Jun. 1996, vol. 516, p. 225-232.

Akira Suzuki et al., New Synthetic Reactions of Organoboron Compounds By Transition Metal Catalysts (in Japanese) The Journal of Synthetic Organic Chemistry Japan, 1993, vol. 51, No. 11, pp. 91 to 100.

Tringali, C. et al. Previously unreported p-terphenyl derivatives with anti-biotic properties from the fruiting bodies of Sarcodon leucopus (Basidiomycetes)., Can. J. Chem., 1987, vol. 65, p. 2369-2372.

Yanagihara et al., "Suppression of IgE Production by IPD-1151T (Suplatast Tosilate), a New Dimethylsulfonium Agent: (2) Regulation of Human IgE Response," Japan J. Pharmacol. (1993), vol. 61, pp. 31-39.

Loh et al., "Disodium Cromoglycate Inhibits Sµ → Sε Deletional Switch Recombination of IgE Synthesis in Human B Cells," J. Exp. Med. (1994), vol. 180, pp. 663-671.

Loh et al. "Mechanisms of inhibition of IgE synthesis by nedocromil sodium: Nedocromil sodium inhibits deletional switch recombination in human B cells," J. Allergy Clin. Immunol. (1996), vol. 97, pp. 1141-1150.

Hasegawa et al. "Novel Naphthalene Derivatives as Inhibitors of Human Immunoglobulin E Antibody Production," J. Med. Chem. (1997), vol. 40, pp. 395-407.

Li et al., "Novel Terphenyl as Selective Cyclooxygenase-2 Inhibitors and Orally Active Anti-inflammatory Agents," J. Med. Chem. (1996), vol. 39, pp. 1846-1856.

Takahashi et al. "The Structures of Toxic Metabolites of *Aspergillus candidus*. I. The Compounds A and E, Cytotoxic p-Terphenyls," Chem. Pharm. Bulletin (1976), vol. 24, No. 4, pp. 613-620.

Vining et al. "3-Hydroxyterphenyllin, A New Metabolite of *Aspergillus candidus*," The Journal of Antibiotics (1979), vol. 32, No. 6, pp. 559-564.

Kobayashi et al. "p-Terphenyls with Cytotoxic Activity toward Sea Urchin Embryos," Agric. Biol. Chem. (1985), Vo. 49, No. 3, pp. 867-868.

STN search results (May 30, 1996 and Jun. 27, 1997).

\* cited by examiner

PARA-TERPHENYL COMPOUNDS

This application is a Divisional of co-pending application Ser. No. 09/214,277 filed on Mar. 1, 1999 and for which priority is claimed under 35 U.S.C. § 120. application Ser. No. 09/214,277 is the national phase of PCT International Application No. PCT/JP97/02635 filed on Jul. 30, 1997 under 35 U.S.C. § 371. The entire contents of each of the above-identified applications are hereby incorporated by reference. This application also claims priority of Application No. 8-201859, 8-287782 and 9-86085 filed in Japan on Jul. 31, 1996, Oct. 30, 1996 and Mar. 18, 1997, respectively under 35 U.S.C. § 119.

TECHNICAL FIELD

The present invention relates to a novel para-terphenyl compound, a process for producing the same, a selective suppressor of the IgE production, an immunosuppressor and an anti-allergic agent.

BACKGROUND ART

A serious problem of a transplantation of a tissue or an organ which is frequently performed in recent years is a rejection symptom for excluding a transplanted part after an operation. Prevention of the rejection symptom is very important for a success of the transplantation.

Various immunosuppressors such as azathioprine, corticoid, Cyclosporin A, Tacrolimus and the like are developed and come into practical use for prevention and a treatment of a rejection symptom against a transplantation of an organ or a tissue or a graft-versus-host reaction which is caused by a bone marrow transplantation. But they are not so satisfactory in view of their effects and side effects.

Allergic diseases such as atopic dermatitis, allergic rhinitis, bronchial asthma, allergic conjunctivitis and the like globally tend to increase in recent years and become serious problems. The conventional antiinflammatory agents are suppressors of releasing chemical mediators from mast cells, receptor inhibitors of the chemical mediators released, suppressors of allergic inflammation reaction or the like. All of these are agents for symptomatic therapy and are not fundamental therapeutic agents for allergic diseases.

As an fundamental therapeutic agent for allergic diseases, a suppressor of the IgE antibody production has been expected.

One of compounds which have a suppressive effect on the IgE production is Suplatast Tosilate (IPD-1151-T). This is reported to act on T cell of type 2 (Th2 cell) to suppress the IL-4 production and to suppress a differentiation of B cells to IgE antibody-producing cells (Jpn. Pharmacol. (1993) 61, 31–39).

As compounds which directly act on B cells to suppress the IgE antibody production, for example, DSCG (Intal) or Nedcromil sodium which are degranulation inhibitors of mast cells are exemplified. These are reported to inhibit a class-switch of B cells (J. Exp. Med. (1994) 180: 663–671, J. Allergy Clin. Immunol. (1996) 97: 1141–1150). In J. Med. Chem. (1997) 40: 395–407, a compound which directly acts on B cells to suppress the IgE production is described.

Because immune globulins are necessary for phylaxis and a suppression of immune globulins other than IgE antibody is not preferable, an inhibitor which has a high selectivity to IgE and a potent effect has been desired.

The compounds which have an antiinflammatory effect and ortho-terphenyl structure are described in JP-A 60-13730, J. Med. Chem. (1996) 39: 1846–1856 and WO96/10012, and the compounds which have the same effect and biphenyl structure are described in JP-B 43-19935, JP-A 62-294650 and WO96/18606.

The compounds which have para-terphenyl structure are described in Chemical & Pharmaceutical Bulletin, 24 (4), 613–620 (1976), The Journal of Antibiotics, 32 (6), 559–564 (1979) and Agricultural Biological Chemistry, 49 (3), 867–868 (1985) but an immunosuppressive or antiinflammatory effect of these compounds is not described at all.

DISCLOSURE INVENTION

An object of the present invention is to provide a selective suppressor of the IgE production, an immunosuppressor, and/or an anti-allergic agent which has a potent suppressive effect on the IgE production, an immunosuppressive effect and/or an anti-allergic effect. Other object of the present invention is to provide novel compounds which have the above effects and a process for producing the same.

The present invention provides a selective suppressor of the IgE production, an immunosuppressor and/or an anti-allergic agent comprising a compound which suppresses the IgE production in a process from a differentiation of a mature B cell into an antibody-producing cell to the production of an antibody and which does not suppress or weakly sup presses the production of IgG, IgM and/or IgA which are produced at the same time. The present invention provides a method for selectively suppressing the IgE production or for suppressing an immune reaction or a method for treating and/or preventing allergic diseases comprising administering the compound. In another embodiment, the present invention provides use of the compound for the manufacture of a medicament for selectively suppressing the IgE production, suppressing the immune reaction or treating and/or preventing allergic diseases.

The present invention provides a compound of the formula (I) as an example of the compounds which has the above effects:

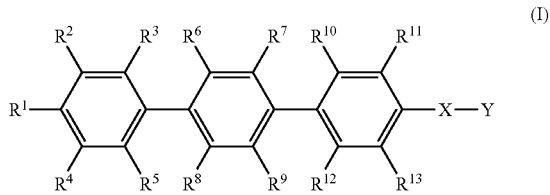

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —$CH_2$—, —$NR^{14}$— wherein $R^{14}$ is hydrogen, optionally substituted lower alkyl, optionally substituted lower alkenyl or acetyl, or —S(O)p- wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, R$^1$ and R$^4$, R$^1$ and R$^2$, R$^2$ and R$^3$, R$^4$ and R$^5$, R$^6$ and R$^7$, R$^8$ and R$^9$, R$^8$ and R$^9$, R$^{10}$ and R$^{11}$, R$^{12}$ and R$^{13}$, R$^{11}$ and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl and which may optionally be substituted, excluding compounds wherein one or more of R$^6$, R$^7$, R$^8$ and R$^9$ are halogen and the others are hydrogen, all of R$^6$, R$^7$, R$^8$ and R$^9$ are halogen and all of R$^2$–R$^{13}$ are hydrogen, halogen or cyano, provided that R$^1$ is not hydrogen, fluorine, optionally substituted lower alkyl or optionally substituted lower alkoxy, all of R$^2$, R$^3$, R$^4$, R$^5$ and R$^{12}$ are hydrogen, or R$^{13}$ is not hydrogen or halogen when R$^6$, R$^7$, R$^8$ and R$^9$ are all simultaneously hydrogen, and further provided that R$^1$ is not methyl or acetyloxy, R$^{13}$ is not hydrogen, optionally substituted lower alkoxycarbonyl or optionally substituted carbamoyl, or —X—Y is not methoxy when at least one of R$^6$, R$^7$, R$^8$ and R$^9$ is a substituent other than hydrogen, and excluding a compound of the formula (I'):

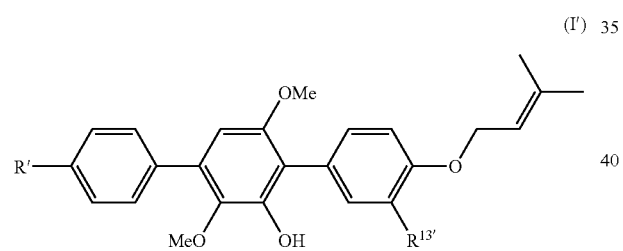

wherein R$^{1'}$ is hydrogen or hydroxy and R$^{13'}$ is hydroxy or methoxy, pharmaceutically acceptable salt, hydrate or prodrug thereof.

The present invention provides a pharmaceutical composition, more specifically a selective suppressor of the IgE production, an immunosuppressor or an anti-allergic agent, comprising the compound (I), pharmaceutically acceptable salt, hydrate or prodrug thereof.

The present invention provides a selective suppressor of the IgE production, an immunosuppressor and/or an anti-allergic agent comprising a compound of the formula (I"):

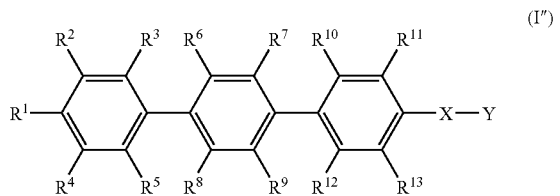

wherein R$^1$, R$^2$, R$^3$, R$^4$, R$^5$, R$^6$, R$^7$, R$^8$, R$^9$, R$^{10}$, R$^{11}$, R$^{12}$ and R$^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)p- wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{11}$, R$^{12}$ and R$^{13}$, R$^{11}$ and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl or optionally substituted arylsulfonyl and which may optionally be substituted, excluding a compound of the formula (I'):

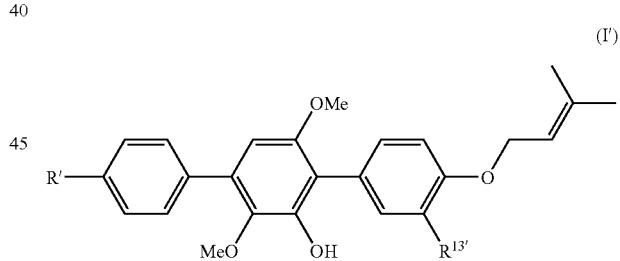

wherein R$^{1'}$ is hydrogen or hydroxy and R$^{13'}$ is hydroxy or methoxy, pharmaceutically acceptable salt, hydrate or prodrug thereof.

The present invention provides a method for selectively suppressing the IgE production, suppressing an immune reaction or treating or preventing allergic diseases comprising administering the compound (I) or (I"). In another embodiment, the present invention provides use of the compound (I) or (I") for manufacturing of a medicament for selectively suppressing the IgE production, suppressing the immune reaction or treating or preventing allergic diseases.

In one of the other embodiments, the present invention provides a process for producing a compound of the formula (I'''):

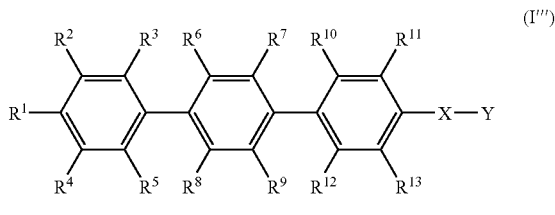

(I''')

the compound of the above formula (I) or (I'), pharmaceutically acceptable salt or hydrate thereof wherein $R^1, R^2, R^3, R^4, R^5, R^6, R^7, R^8, R^9, R^{10}, R^{11}, R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(o)p- wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl, and which may optionally be substituted, excluding a compound wherein one or more of $R^6$, $R^7$, $R^8$ and $R^9$ are halogen and the others are hydrogen, all of $R^6$, $R^7$, $R^8$ and $R^9$ are halogen and all of $R^2$–$R^{13}$ are hydrogen, halogen or cyano, provided that $R^1$ is not hydrogen, fluorine; optionally substituted lower alkyl or optionally substituted lower alkoxy, all of $R^2$, $R^3$, $R^4$, $R^5$ and $R^{12}$ are hydrogen or $R^{13}$ is not hydrogen or halogen when $R^6$, $R^7$, $R^8$ and $R^9$ are all simultaneously hydrogen, and further provided that $R^1$ is not methyl or acetyloxy, $R^{13}$ is not hydrogen, optionally substituted lower alkoxycarbonyl or optionally substituted carbamoyl or —X—Y is not methoxy when at least one of $R^6$, $R^7$, $R^8$ and $R^9$ is a substituent other than hydrogen, pharmaceutically acceptable salt or hydrate thereof, which comprises reacting a compound of the formula (II):

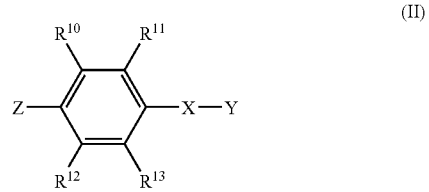

(II)

with a compound of the formula (III):

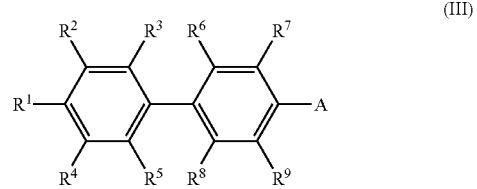

(III)

wherein, in the formulas (II) and (III), $R^1$–$R^{13}$, X and Y are the same as defined in the above formula (I), either of A and Z is dihydroxyborane, di(lower)alkoxyborane, di(lower)alkylborane,

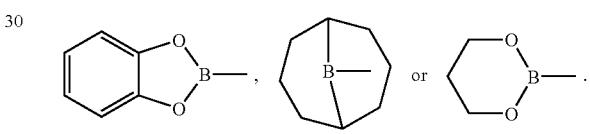

and the other is halogen or —OSO$_2$(C$_q$F$_{2q+1}$)— wherein q is an integer of 0 to 4, or reacting a compound of the formula (II'):

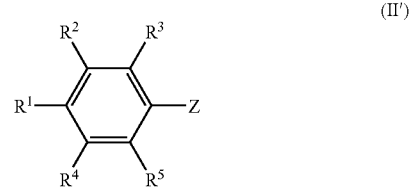

(II')

with a compound of the formula (III'):

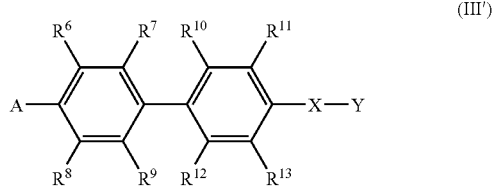

(III')

wherein, in the formulas (II') and (III'), $R^1$–$R^{13}$, X and Y are the same as defined in the above formula (I) and A and Z are the same as defined in the above formulas (II) and (III). As another process, the present invention provides a process for producing the compound of the above formula (I'''), (I) or (I'), pharmaceutically acceptable salt or hydrate thereof comprising the reaction of a compound of the formula (IV):

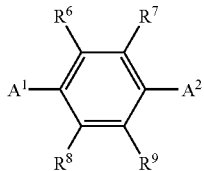
(IV)

with a compound of the formula (V):

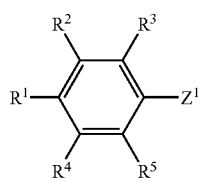
(V)

wherein, in the formulas (IV) and (V), $R^1$–$R^9$ are the same as defined in the above formula (I), $Z^1$ is the same as Z defined in the above formula (II), $A^1$ and $A^2$ are each independently the same as A defined in the above formula (III) and the reactivity of $A^1$ is higher than or equal to that of $A^2$, followed by the reaction with a compound of the formula (VI):

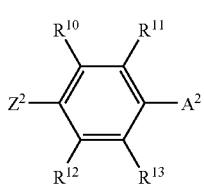
(VI)

wherein $R^{10}$–$R^{13}$, X and Y are the same as defined in the above formula (I) and $Z^2$ is the same as Z defined in the above formula (II) and a process for producing the compound of the above formula (I'''), (I) or (I'), pharmaceutically acceptable salt, hydrate thereof comprising the reaction of a compound of the formula (IV'):

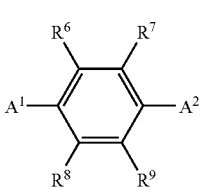
(IV')

wherein $R^6$–$R^9$ is the same as defined in the above formula (I), $A^1$ and $A^2$ are each independently the same as A defined in the above formula (III) and the reactivity of $A^2$ is higher than or equal to that of $A^1$, with a compound of the above formula (VI), followed by the reaction with a compound of the above formula (V).

BEST MODE FOR CARRYING OUT THE INVENTION

Figure 1:
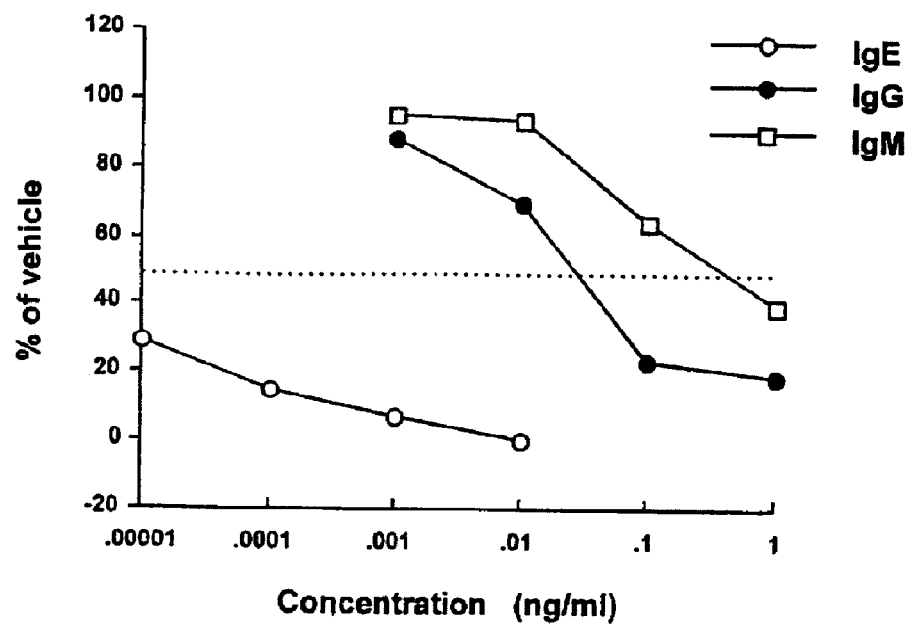
FIG. 1 shows an antibody production-suppressive effect on human peripheral lymphocytes of the compound (I-839) of the present invention. The ordinate represents a percentage of the amount of antibodies to that of antibodies which are produced in the absence of the compound. The abscissa represents a concentration of the compound.

In the present specification, the term "halogen" includes fluorine, chlorine, bromine and iodine. Fluorine or chlorine is preferable. The halogen in the term "halogeno(lower)alkyl", "halogeno(lower)alkenyl" and "halogenoaryl" is the same as above.

The term "lower alkyl" represents straight or branched chain alkyl having 1 to 10 carbon atoms, preferably 1 to 8 carbon atoms, more preferably 1 to 6 carbon atoms and most preferably 1 to 4 carbon atoms. For example, included are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

As substituents of the "optionally substituted lower alkyl" in $R^1$–$R^{13}$, $R^{14}$ and $R^{15}$ exemplified are halogen; hydroxy; lower alkoxy optionally substituted with lower alkoxy; carboxy; lower alkoxycarbonyl; acyloxy and the like and the lower alkyl may be substituted with one or more of these substituents at any possible positions.

As substituents for "optionally substituted lower alkyl" in Y exemplified are halogen; hydroxy; carboxy; lower alkoxycarbonyl; lower alkoxy optionally substituted with lower alkoxy; acyl; acyloxy; amino optionally substituted with hydroxy or lower alkyl; imino optionally substituted with hydroxy, lower alkoxy, carboxy(lower)alkoxy, aryl(lower)alkoxy or heterocyclyl; hydrazono optionally substituted with carbamoyl or lower alkoxycarbonyl; cycloalkyl optionally substituted with lower alkyl; cycloalkenyl optionally substituted with lower alkyl; cyano; carbamoyl optionally substituted with lower alkyl or amino; thiocarbamoyl optionally substituted with lower alkyl;

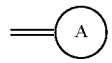

wherein ring A represents cycloalkyl or heterocyclyl;

aryl optionally substituted with lower alkyl, halogeno(lower)alkyl, carboxy(lower)alkyl, lower alkoxycarbonyl (lower)alkyl, halogen, hydroxy, lower alkoxy, carboxy, lower alkoxycarbonyl, lower alkenyloxycarbonyl, acyloxy, nitro, cyano, amino, lower alkoxycarbonylamino, acylamino, lower alkylsulfonylamino, lower alkylamino or guanidino; or heterocyclyl optionally substituted with lower alkyl (optionally substituted with heterocyclyl), halogen, hydroxy, carboxy, lower alkoxycarbonyl, lower alkylsulfonyl, lower alkylarylsulfonyl, mercapto, lower alkylthio or heterocyclyl optionally substituted with aryl.

The alkyl part of "halogeno(lower)alkyl", "hydroxy(lower)alkyl", "carboxy(lower)alkyl", "lower alkoxycarbonyl (lower)alkyl", "lower alkylthio", "lower alkylamino", "lower alkylsulfonyl", "lower alkylsulfonyloxy", "lower alkylsulfonylamino", "lower alkylsulfinyl", "lower alkylaryl", "lower alkylarylsulfonyl", "di(lower)alkylcarbamoyl", "di(lower)alkylborane", "lower alkoxy", "carboxy (lower)alkoxy", "aryl(lower)alkoxy", "lower alkoxy(lower)alkoxy", "lower alkoxyaryl" or "di(lower)alkoxyborane" is the same as defined in the above "lower alkyl". As substituents in the case of being "optionally substituted" exemplified are halogen; hydroxy; lower alkoxy; carboxy; lower alkoxycarbonyl; acyloxy; cycloalkyl; aryl optionally substituted with lower alkyl; heterocyclyl and the like. These substituents may substitute at one or more of any possible positions.

The part of lower alkyl in "lower alkoxycarbonyl" is the same as the above defined "lower alkyl" and substituents for "optionally substituted lower alkoxycarbonyl" are the same as those for the above "optionally substituted lower alkoxy".

The part of "lower alkoxycarbonyl" in "lower alkoxycarbonyl(lower)alkyl", "lower alkoxycarbonyl(lower)alkenyl" or "lower alkoxycarbonylamino" is the same as the above defined "lower alkoxycarbonyl".

The term "lower alkenyl" represents straight or branched chain alkenyl having 2 to 10 carbon atoms, preferably 2 to 8 carbon atoms and more preferably 3 to 6 carbon atoms. For example, included are vinyl, propenyl, isopropenyl, butenyl, isobutenyl, butadienyl, pentenyl, isopentenyl, pentadienyl, hexenyl, isohexenyl, hexadienyl, heptenyl, octenyl, nonenyl, decenyl and the like and these have one or more double bonds at any possible positions. Substituents for "optionally substituted lower alkenyl" are the same as that for the above "optionally substituted lower alkoxy".

The part of lower alkenyl in "lower alkoxycarbonyl (lower)alkenyl", "halogeno(lower)alkenyl", "lower alkenyloxy", "lower alkenyloxycarbonyl" or "lower alkenylamino" is the same as the above defined "lower alkenyl".

Substituents for "optionally substituted lower alkenyloxy" are the same as those for the above "optionally substituted lower alkoxy".

The term "lower alkynyl" represents straight or branched chain alkynyl having 2 to 10 carbon atoms, preferably 2 to 8 carbon atoms and more preferably 3 to 8 carbon atoms. Specifically, included are ethynyl, propynyl, butynyl, pentynyl, hexynyl, heptynyl, octynyl, nonyl, decynyl and the like. These have one or more triple bonds at any possible positions and may further have a double bond. Substituents for "optionally substituted lower alkynyl" are the same as those for the above "optionally substituted lower alkoxy".

The term "acyl" represents aliphatic acyl which includes chain acyl having 1 to 10 carbon atoms, preferably 1 to 8 carbon atoms, more preferably 1 to 6 carbon atoms, most preferably 1 to 4 carbon atoms and cyclic acyl having 3 to 8 carbon atoms, preferably 3 to 6 carbon atoms, and aroyl. Specifically, included are formyl, acetyl, propionyl, butyryl, isobutyryl, valeryl, pivaloyl, hexanoyl, acryloyl, propioloyl, methacryloyl, crotonoyl, cyclohexanecarbonyl, benzoyl and the like. Substituents for "optionally substituted acyl" are the same as those for "optionally substituted lower alkoxy" and aroyl may further be substituted with lower alkyl.

The part of acyl in "acyloxy" or "acylamino" is the same as the above identified "acyl" and substituents for "optionally substituted acyloxy" are the same as those for the above "optionally substituted acyl".

The term "cycloalkyl" represent cyclic hydrocarbon having 3 to 6 carbon atoms and includes, for example, cyclopropyl, cyclobutyl, cyclopentyl cyclohexyl and the like. As substituents for "optionally substituted cycloalkyl" exemplified are lower alkyl, halogen, hydroxy, carboxy, lower alkoxycarbonyl, lower alkoxy, aryl, heterocyclyl and the like and the cycloalkyl may be substituted at any possible positions.

The term "cycloalkenyl" represents the group having one or more double bonds at any possible positions in the above cycloalkyl and included are, for example, cyclopropenyl, cyclobutenyl, cyclopentenyl, cyclohexenyl, cyclohexadienyl and the like. Substituents for "optionally substituted cycloalkenyl" are the same as those for the above identified "cycloalkyl".

The term "optionally substituted amino" includes substituted amino and unsubstituted amino and substituents exemplified are lower alkyl optionally substituted with lower alkylaryl etc.; lower alkenyl optionally substituted with halogen; lower alkylsulfonyl; lower alkylarylsulfonyl; lower alkoxycarbonyl; sulfamoyl; acyl optionally substituted with halogen; carbamoyl and the like.

The term "optionally substituted carbamoyl" includes substituted carbamoyl and unsubstituted carbamoyl and substituents exemplified are lower alkyl; lower alkylsulfonyl; sulfamoyl; acyl optionally substituted with halogen; amino and the like.

The term "optionally substituted sulfamoyl" includes substituted sulfamoyl and unsubstituted sulfamoyl and substituents exemplified are lower alkyl optionally substituted with aryl; lower alkenyl and the like.

The term "aryl" includes phenyl, naphthyl, anthryl, indenyl, phenanthryl and the like. Substituents for "optionally substituted aryl" exemplified are lower alkyl optionally substituted with halogen or carboxy; hydroxy; halogen; lower alkoxy; lower acyloxy; carboxy; lower alkoxycarbonyl; lower alkenyloxycarbonyl; amino optionally substituted with lower alkyl, lower alkylsulfonyl, lower alkoxycarbonyl or acyl; guanidino; nitro; aryl; heterocyclyl and the like and "optionally substituted aryl" may be substituted with one or more of these substituents at any possible positions.

The part of aryl in "lower alkylaryl", "halogenoaryl", "lower alkoxyaryl", "arylsulfonyl", "aryl(lower)alkoxy", "lower alkylarylsulfonyl", "heterocyclyl substituted with aryl", "aroyl" or "aroyloxy" is the same as the above "aryl"

and the substituents for "optionally substituted" are also the same as those for in the above "optionally substituted aryl".

The term "heterocyclyl" represents a heterocyclic group which contains one or more of hetero atoms arbitrarily selected from a group of O, S and N and exemplified are 5- or 6-membered aromatic heterocyclyl such as pyrrolyl, imidazolyl, pyrazolyl, pyridyl, pyridazinyl, pyrimidinyl, pyrazinyl, triazolyl, triazinyl, isoxazolyl, oxazolyl, oxadiazolyl, isothiazolyl, thiazolyl, thiaziazolyl, furyl, thienyl etc., condensed aromatic heterocyclyl such as indolyl, carbazolyl, acridinyl, benzimidazolyl, indazolyl, indolizinyl, quinolyl, isoquinolyl, cinnolinyl, phthalazinyl, quinazolinyl, naphthyridinyl, quinoxalinyl, purinyl, pteridinyl, benzisoxazolyl, benzoxazolyl, benzoxadiazolyl, benzisothiazolyl, benzothiazolyl, benzothiaziazolyl, benzofuryl, benzothienyl, benzotriazolyl etc., and alicyclic heterocyclyl such as dioxanyl, thiiranyl, oxiranyl, oxathioranyl, azetidinyl, thianyl, pyrrolidinyl, pyrrolinyl, imidazolidinyl, imidazolinyl, pyrazolidinyl, pyrazolinyl, piperidyl, piperazinyl, morpholinyl etc. As substituents for "optionally substituted heterocyclyl" exemplified are lower alkyl, lower alkenyl, hydroxy, halogen, carboxy, lower alkoxycarbonyl, lower alkoxy, mercapto, lower alkylthio, lower alkylsulfonyl, aryl, heterocyclyl and the like and the heterocyclyl may be substituted with one or more of these substituents at any possible positions. The part of heterocycle in "heterocyclyl substituted with aryl" is the same as the above "heterocyclyl".

The term "5- or 6-membered ring which may contain one or more of O, S or $NR^{15}$ and may optionally be substituted" represents a 5- or 6-membered ring which is formed by $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y with the two carbon atoms constituting phenyl to which the above substituents are attached. For example, the above substituents taken together form —(CH$_2$)$_3$—, —(CH$_2$)$_4$—, —O(CH$_2$)$_m$O—, —O(CH$_2$)$_n$—, —(CH$_2$)$_n$O—, —S(CH$_2$)$_m$S—, —S(CH$_2$)$_n$—, —(CH$_2$)$_n$S—, —NR$^{15}$(CH$_2$)$_m$ NR$^{15}$, —NR$^{15}$(CH$_2$)$_n$—, —(CH$_2$)$_n$NR$^{15}$—, —O(CH$_2$)$_m$S—, —S(CH$_2$)$_m$O—, —S(CH$_2$)$_m$NR$^{15}$, —NR$^{15}$(CH$_2$)$_m$S—, —O(CH$_2$)$_m$NR$^{15}$—, —NR$^{15}$(CH$_2$)$_m$O—, —O—CH=CH—, —CH=CH—O—, —S—CH=CH—, —CH=CH—S—, —NR$^{15}$—CH=CH—, —CH=CH—NR$^{15}$—, —S—CH=N—, —N=CH—S—, —S—N=CH—, —CH=N—S—, —O—CH=N—, —N=CH—O—, —O—N=CH—, —CH=N—O—, —NR$^{15}$—CH=N—, —N=CH—NR$^{15}$—, —NR$^{15}$—N=CH—, —CH=N—NR$^{15}$—, —N=CH—CH=CH—, —CH=CH—CH=N—, —N=N—CH=CH—, —CH=CH—N=N—, —N=CH—N=CH—, —CH=N—CH=N—, —N=CH—CH=N— (m is 1 or 2 and n is 2 or 3) or the like and further these and the two carbon atoms constituting phenyl taken together form a 5- or 6-membered ring. These rings may be substituted with one or more of hydroxy; halogen; lower alkyl optionally substituted with lower alkoxycarbonyl or heterocyclyl; lower alkenyl optionally substituted with halogen; lower alkyliden optionally substituted with halogen; or the like. The substituents of "5- or 6-membered ring which may contain one or more of O or $NR^{15}$ and may optionally be substituted", "5- or 6-membered ring which contains one or more of O or $NR^{15}$ and may optionally be substituted" and "5- or 6-membered ring which contains one or more of O and may optionally be substituted" are the same as the above unless otherwise defined.

The term "lower alkylidene" represents straight or branched alkylidene having 1 to 6 carbon atoms, preferably 1 to 4 carbon atoms, more preferably 1 to 3 carbon atoms and includes, for example, methylene, ethylidene, isopropylidene, vinylidene, methylidyne and the like.

The term "all of $R^2$–$R^{13}$ are hydrogen, halogen or cyano" represents, for example, the case that $R^2$–$R^{13}$ are the same or different and hydrogen, halogen or cyano. For example, included are the case that all of $R^2$–$R^{13}$ are hydrogen, the case that all of them are halogen, the case that some are halogen and the others are hydrogen, the case that some are cyano and the others are hydrogen, the case that some are halogen, some are cyano and the others are hydrogen and the like.

The term "compound (I)", "compound (I")" or "compound (I'")" also includes formable and pharmaceutically acceptable salts of each compounds. As "the pharmaceutically acceptable salt", exemplified are salts with mineral acid such as hydrochloric acid, sulfuric acid, nitric acid, phosphoric acid, hydrofluoric acid, hydrobromic acid and the like; salts with organic acids such as formic acid, acetic acid, tartaric acid, lactic acid, citric acid, fumaric acid, maleic acid, succinic acid and the like; salts with organic bases such as ammonium, trimethylammonium, triethylammonium and the like; salts with alkaline metals such as sodium, potassium and the like and salts with alkaline earth metals such as calcium, magnesium and the like.

The compound of the present invention includes hydrates and all of stereoisomers, for example, atropisomers etc. thereof.

The compound of the present invention includes prodrugs thereof. The term "prodrug" means a group of compounds which are easily changeable to the compounds (I) or (I") which have activities in living bodies. The prodrug may be prepared by usual reactions. As usual methods for producing prodrugs exemplified is the substitution of hydroxy by acyloxy substituted with carboxy, sulfo, amino, lower alkylamino or the like, phosphonoxy or the like. The substitution of hydroxy attached to $R^1$ by —OCOCH$_2$CH$_2$COOH, —OCOCH=CHCOOH, —OCOCH$_2$SO$_3$H, —OPO$_3$H$_2$, —OCOCH$_2$NMe$_2$, —OCO-Pyr (Pyr is pyridine) or the like is preferable.

In the present specification, the term "compound (I)" represents a group comprising novel compounds excluding the compound (I'), the term "compound (I")" represents a group comprising the compound (I) and known compounds and the term "compound (I'")" represents a group comprising the compound (I) and the compound (I').

All of the compounds (I) and (I") have a suppressive effect on the IgE production, an immunosuppressive effect and/or an anti-allergic effect and the following compounds are specifically preferable.

In the formulas (I) and (I"), 1) a compound wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyloxy, formyl, optionally substituted amino, optionally substituted carbamoyl or optionally substituted sulfamoyl, X is —O—, —CH$_2$—, —NR$^{14}$— wherein $R^{14}$ is hydrogen or optionally substituted lower alkyl, or —S(O)p- wherein p is an integer of 0 to 2, Y is optionally substituted lower alkyl, optionally substituted lower alkenyl, optionally substituted lower alkynyl, optionally substituted acyl or optionally substituted cycloalkenyl, and $R^1$ and $R^4$, $R^1$ and $R^2$, $R^8$ and $R^9$, $R^{11}$ and —X—Y, or $R^{13}$ and —X—Y taken together may form a 5- or 6-membered ring which may contain one or more of O or $NR^{15}$, 2) a compound wherein $R^1$ is hydrogen, hydroxy, halogen, carboxy, optionally substituted lower alkyl, optionally substituted lower alkoxy, optionally substituted lower alkenyloxy, optionally substituted lower alkylthio, optionally substituted lower alkoxycarbonyl, optionally substituted lower alkylsulfonyloxy, lower alkylsulfonyl, formyl, optionally substituted amino, lower alkylsulfinyl, acyloxy, nitro, cyano, optionally substituted sulfamoyl or heterocyclyl, $R^2$ is hydrogen, hydroxy, halogen, optionally substituted lower alkyl or optionally substituted lower alkylsulfonyloxy, $R^3$ is hydrogen, hydroxy, halogen or optionally substituted lower alkoxy, $R^4$ is hydrogen, optionally substituted lower alkyl, halogen, optionally substituted lower alkoxy, nitro or optionally substituted amino, $R^5$ is hydrogen, optionally substituted lower alkoxy, lower alkoxycarbonyl or carboxy, $R^6$ is hydrogen, halogen, optionally substituted lower alkyl, carboxy, lower alkoxycarbonyl, nitro, formyl, amino or lower alkylsulfonyloxy, $R^7$ and $R^8$ are each independently hydrogen, halogen, optionally substituted lower alkyl, optionally substituted lower alkoxy, formyl or optionally substituted amino, $R^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino, $R^{10}$ is hydrogen or lower alkoxy, $R^{11}$ is hydrogen, halogen, optionally substituted lower alkyl, carboxy, lower alkoxycarbonyl, optionally substituted lower alkylsulfonyloxy, formyl, nitro or amino, $R^{12}$ is hydrogen, $R^{13}$ is hydroxy, halogen, carboxy, optionally substituted lower alkyl, optionally substituted lower alkoxy, optionally substituted lower alkenyloxy, optionally substituted acyloxy, optionally substituted lower alkylsulfonyloxy, formyl, nitro or optionally substituted amino, and further $R^{13}$ may be hydrogen in the formula (I''), Y is optionally substituted lower alkyl, optionally substituted lower alkenyl, optionally substituted lower alkynyl, optionally substituted acyl or optionally substituted cycloalkenyl and Y may be optionally substituted lower alkoxycarbonyl, optionally substituted lower alkylsulfonyl or optionally substituted arylsulfonyl when X is —O— or —$NR^{14}$—, and $R^1$ and $R^2$, $R^1$ and $R^4$, $R^8$ and $R^9$, $R^{11}$ and —X—Y, or $R^{13}$ and —X—Y taken together may form a 5- or 6-membered ring which contains one or more of O or $NR^{15}$ wherein $R^{15}$ is the same as defined above and which may optionally be substituted, 3) a compound wherein $R^1$ is hydrogen, hydroxy, halogen, carboxy, optionally substituted lower alkyl, optionally substituted lower alkoxy, optionally substituted lower alkenyloxy, optionally substituted lower alkylthio, optionally substituted lower alkoxycarbonyl, optionally substituted lower alkylsulfonyloxy, lower alkylsulfonyl, formyl, optionally substituted amino, lower alkylsulfinyl, acyloxy, nitro, cyano, optionally substituted sulfamoyl or heterocyclyl (hereinafter referred to as "$R^1$ is R1-1") or $R^1$ and $R^2$ or $R^4$ taken together form a 5- or 6-membered ring which contains one or more of O or $NR^{15}$ wherein $R^{15}$ is the same as defined above and which may optionally be substituted, preferably $R^1$ is hydrogen, hydroxy, halogen, optionally substituted lower alkoxy, optionally substituted lower alkenyloxy, optionally substituted lower alkylsulfonyloxy, optionally substituted amino, optionally substituted sulfamoyl (hereinafter referred to as "$R^1$ is R1-2"), or $R^1$ and $R^2$ or $R^4$ taken together form a 5- or 6-membered ring which contains one or more of O or $NR^{15}$ wherein $R^{15}$ is the same as defined above and which may optionally be substituted, more preferably, $R^1$ is hydrogen, hydroxy, halogen, lower alkoxy(lower)alkoxy, aryl(lower)alkoxy, lower alkenyloxy, lower alkylsulfonyloxy, amino, lower alkylamino or lower alkenylamino (hereinafter referred to as "$R^1$ is R1-3"), or $R^1$ and $R^2$ or $R^4$ taken together form a 5- or 6-membered ring which contains one or more of O or $NR^{15}$ wherein $R^{15}$ is the same as defined above and which may optionally be substituted, most preferably, $R^1$ is hydrogen, hydroxy, chlorine, fluorine, methoxymethyloxy, benzyloxy, 3-methyl-2-butenyloxy, methanesulfonyloxy, amino, dimethylamino or 3-methyl-2-butenylamino (hereinafter referred to as "$R^1$ is R1-4"), or $R^1$ and $R^2$ or $R^4$ taken together form —$OCH_2O$— or —CH=CH—NH—, 4) a compound wherein $R^2$ is hydrogen, hydroxy, halogen, lower alkyl or optionally substituted lower alkylsulfonyloxy (hereinafter referred to as "$R^2$ is R2-1") or $R^1$ and $R^2$ taken together form a 5- or 6-membered ring which contains one or more of O or $NR^{15}$ wherein $R^{15}$ is the same as defined above and which may optionally be substituted, preferably $R^2$ is hydrogen, halogen or alkyl having 1 to 3 carbon atoms (hereinafter referred to as "$R^2$ is R2-2"), 5) a compound wherein $R^3$ is hydrogen, hydroxy, halogen or optionally substituted lower alkoxy (hereinafter referred to as "$R^3$ is R3-1"), preferably $R^3$ is hydrogen or halogen (hereinafter referred to as "$R^3$ is R3-2"), more preferably $R^3$ is hydrogen or fluorine (hereinafter referred to as "$R^3$ is R3-3"), 6) a compound wherein $R^4$ is hydrogen, optionally substituted lower alkyl, halogen, optionally substituted lower alkoxy, nitro or optionally substituted amino (hereinafter referred to as "$R^4$ is R4-1") or $R^4$ and $R^1$ taken together may form a 5- or 6-membered ring which contains one or more of O or $NR^{15}$ wherein $R^{15}$ is the same as defined above and which may optionally be substituted, preferably $R^4$ is hydrogen, lower alkyl, lower alkoxy or halogen (hereinafter referred to as "$R^4$ is R4-2"), or $R^4$ and $R^1$ taken together may form —$OCH_2O$—, 7) a compound wherein $R^5$ is hydrogen, optionally substituted lower alkoxy, lower alkoxycarbonyl or carboxy (hereinafter referred to as "$R^5$ is R5-1"), preferably $R^5$ is hydrogen, lower alkoxycarbonyl or carboxy (hereinafter referred to as "$R^5$ is R5-2"), more preferably $R^5$ is hydrogen (hereinafter referred to as "$R^5$ is R5-3"), 8) a compound wherein $R^6$ is hydrogen, halogen, optionally substituted lower alkyl, carboxy, lower alkoxycarbonyl, nitro, formyl, amino or lower alkylsulfonyloxy (hereinafter referred to as "$R^6$ is R6-1"), preferably $R^6$ is hydrogen or lower alkyl or halogen (hereinafter referred to as "$R^6$ is R6-2"), more preferably $R^6$ is hydrogen, alkyl having 1 to 3 carbon atoms or halogen (hereinafter referred to as "$R^6$ is R6-3"), 9) a compound wherein $R^7$ is hydrogen, halogen, optionally substituted lower alkyl, optionally substituted lower alkoxy, formyl or optionally substituted amino (hereinafter referred to as "$R^7$ is R7-1"), preferably $R^7$ is hydrogen, lower alkyl or lower alkoxy (hereinafter referred to as "$R^7$ is R7-9"), 10) a compound wherein $R^8$ is hydrogen, halogen, optionally substituted lower alkyl, optionally substituted lower alkoxy, formyl or optionally substituted amino (hereinafter referred to as "$R^8$ is R8-1") or $R^8$ and $R^9$ taken together may form a 5- or 6-membered ring which contains one or more of O and which may optionally be substituted, preferably $R^8$ is hydrogen, lower alkyl or lower alkoxy (hereinafter referred to as "$R^8$ is R8-2"), 11) a compound wherein $R^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino (hereinafter referred to as "$R^9$ is R9-1") or $R^9$ and $R^8$ taken together may form a 5- or 6-membered ring which contains one or more of O and which may optionally be substituted, preferably $R^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino (hereinafter referred to as "$R^9$ is R9-2"), more preferably $R^9$ is hydrogen, hydroxy, lower alkyl, hydroxy(lower)alkyl, lower alkoxycarbonyl(lower)alkenyl, lower alkoxy(lower)alkoxy, lower alkylsulfonyloxy, di(lower)alkylcarbamoyl, carboxy, lower alkoxycarbonyl or amino (hereinafter referred to as "$R^9$ is R9-3"), most preferably $R^9$ is hydrogen, hydroxy, methyl, hydroxymethyl, ethoxycarbonylvinyl, methoxymethyloxy, methanesulfonyl, dimethylcarbamoyl, carboxy, methoxycarbonyl or amino (hereinafter referred to as "$R^9$ is R9-4"), 12) a compound wherein $R^{10}$ is hydrogen or lower alkoxy (hereinafter referred to as "$R^{10}$ is R10-1"), preferably $R^{10}$ is hydrogen (hereinafter referred to as "$R^{10}$ is R10-2"), 13) a compound wherein $R^{11}$ is hydrogen, halogen, optionally substituted lower alkyl, carboxy, lower alkoxycarbonyl, optionally substituted lower alkylsulfonyloxy, formyl, nitro or amino (hereinafter referred to as "$R^{11}$ is R11-1") or $R^{11}$ and —X—Y taken together form a 5- or 6-membered ring which contains one or more of O or $NR^{15}$ wherein $R^{15}$ is the same as defined above and which may optionally be substituted with lower alkenyl, halogeno(lower)alkenyl or the like, preferably $R^{11}$ is hydrogen or halogen (hereinafter referred to as "$R^{11}$ is R11-2"), 14) a compound wherein $R^{12}$ is hydrogen, 15) a compound wherein $R^{13}$ is hydrogen, hydroxy, halogen, carboxy, optionally substituted lower alkyl, optionally substituted lower alkoxy, optionally substituted lower alkenyloxy, optionally substituted acyloxy, optionally substituted lower alkylsulfonyloxy, formyl, nitro or optionally substituted amino (hereinafter referred to as "$R^{13}$ is R13-1") or $R^{13}$ and —X—Y taken together form a 5- or 6-membered ring which contains one or more of O or $NR^{15}$ wherein $R^{15}$ is the same as defined above and which may optionally be substituted with lower alkenyl, halogeno(lower)alkenyl or the like, preferably $R^{13}$ is hydrogen, hydroxy, halogen, carboxy, optionally substituted lower alkyl, optionally substituted lower alkoxy, optionally substituted acyloxy, optionally substituted lower alkylsulfonyloxy, formyl or optionally substituted amino (hereinafter referred to as "$R^{13}$ is R13-2"), more preferably $R^{13}$ is hydroxy; halogen; lower alkyl optionally substituted with hydroxy or halogen; lower alkoxy optionally substituted with lower alkoxycarbonyl or lower alkoxy; lower alkenyloxy optionally substituted with halogen; aroyloxyl; lower alkylsulfonyloxy; formyl or amino (hereinafter referred to as "$R^{13}$ is R13-3"), most preferably $R^{13}$ is hydroxy, fluorine, methyl, hydroxymethyl, iodomethyl, methoxy, ethoxy, isopropyloxy, ethoxycarbonylmethyloxy, methoxymethyloxy, chlorobutenyloxy, bromopropenyloxy, chloropropenyloxy, bromobutenyloxy, dichloropropenyloxy, ethoxycarbonyl, benzoyloxy, methanesulfonyloxy, formyl or amino (hereinafter referred to as "$R^{13}$ is R13-4"), 16) a compound wherein X is —O—, —$NR^{14}$— or —S(O)p- wherein p is an integer of 0 to 2 (hereinafter referred to as "X is X1"), or X, $R^{13}$ and Y taken together may form a 5- or 6-membered ring which contains one or more of O or $NR^{15}$ wherein $R^{15}$ is the same as defined above and may optionally be substituted, preferably X is —O—, —NH—, —NMe— or —$SO_2$— (hereinafter referred to as "X is X2"), more preferably X is —O—, —NH— or —NMe— (hereinafter referred to as "X is X3"), most preferably X is —O—, 17) a compound wherein Y is optionally substituted lower alkyl, optionally substituted lower alkenyl, optionally substituted lower alkynyl, optionally substituted cycloalkenyl, lower alkylsulfonyl, optionally substituted arylsulfonyl, lower alkoxycarbonyl or optionally substituted acyl (hereinafter referred to as "Y is Y1"), or Y, $R^{13}$ and X taken together may form a 5- or 6-membered ring which contains one or more of O or $NR^{15}$ wherein $R^{15}$ is the same as defined above and which may optionally be substituted, preferably Y is lower alkyl optionally substituted with halogen; hydroxy; amino optionally substituted with lower alkyl; lower alkoxy; carboxy; lower alkoxycarbonyl; acyl; cycloalkyl; cycloalkenyl; cyano; imino optionally substituted with hydroxy, lower alkoxy, carboxy(lower)alkoxy, aryl(lower)alkoxy or heterocyclyl; hydrazono optionally substituted with carbamoyl or lower alkoxycarbonyl; carbamoyl optionally substituted with lower alkyl or amino; thiocarbamoyl optionally substituted with lower alkyl; aryl optionally substituted with amino (optionally substituted with lower alkyl, acyl, lower alkoxycarbonyl or lower alkylsulfonyl), nitro, acyloxy, lower alkyl (optionally substituted with halogen or carboxy), halogen, lower alkoxy, carboxy, lower alkoxycarbonyl, lower alkenyloxycarbonyl or guanidino; or heterocyclyl optionally substituted with halogen or lower alkyl; lower alkenyl optionally substituted with halogen, hydroxy, cycloalkyl, lower alkoxycarbonyl or aryl-substituted heterocyclyl; lower alkynyl optionally substituted with halogen; or cycloalkenyl (hereinafter referred to as "Y is Y2"), more preferably Y is lower alkyl optionally substituted with lower alkoxycarbonyl, aryl, lower alkylaryl, halogenoaryl, lower alkoxyaryl, heterocyclyl or acyl; or lower alkenyl optionally substituted with hydroxy, halogen or aryl (hereinafter referred to as "Y is Y3"), most preferably Y is isopropyl, ethoxycarbonylmethyl, benzyl, methylphenylmethyl, fluorophenylmethyl, dichlorophenylmethyl, methoxyphenylmethyl, pyridylmethyl, benzoylmethyl, propenyl, methylpropenyl, methylbutenyl, hydroxymethylbutenyl, pentenyl, methylpentenyl, dimethyloctadienyl, chloropropenyl, dichloropropenyl, bromopropenyl, dibromopropenyl, fluoropropenyl, difluoropropenyl, butenyl, bromobutenyl, chlorobutenyl or phenylpropenyl (hereinafter referred to as "Y is Y4"), 18) a compound wherein $R^1$ is R1-2, $R^2$ is R2-1, $R^3$ is R3-1, $R^4$ is R4-1, $R^5$ is R5-1, $R^6$ is R6-1, $R^7$ is R7-1, $R^8$ is R8-1, $R^9$ is R9-2, $R^{10}$ is R10-1, $R^{11}$ is R11-1, $R^{12}$ is hydrogen, $R^{13}$ is R13-1, X is X1 and Y is Y1, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 19) a compound wherein $R^1$ is R1-2, $R^2$ is R2-1, $R^3$ is R3-1, $R^4$ is R4-1, $R^5$ is R5-1, $R^6$ is R6-1, $R^7$ is R7-1, $R^8$ is R8-1, $R^9$ is R9-1, $R^{10}$ is R10-1, $R^{11}$ is R11-1, $R^{12}$ is hydrogen $R^{13}$ is R13-2, X is X1 and Y is Y1, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 20) a compound wherein $R^1$ is R1-2, $R^2$ is R2-1, $R^3$ is R3-1, $R^4$ is R4-1, $R^5$ is R5-1, $R^6$ is R6-2, $R^7$ is R7-2, $R^8$ is R8-2, $R^9$ is R9-1, $R^{10}$ is R10-1, $R^{11}$ is R11-1, $R^{12}$ is hydrogen $R^{13}$ is R13-1, X is X1 and Y is Y2, and R1 and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 21) a compound wherein $R^1$ is R1-1, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R11-1, $R^{12}$ is hydrogen, $R^{13}$ is R13-2, X is X1 and Y is Y1, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 22) a compound wherein $R^1$ is R1-1, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R11-1, $R^{12}$ is hydrogen, $R^{13}$ is R13-1, X is X1 and Y is Y2, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 23) a compound wherein $R^1$ is R1-1, $R^2$ is R2-1, $R^3$ is R3-1, $R^4$ is R4-1, $R^5$ is R5-1, $R^6$ is R6-2, R7 is R7-1, $R^8$ is R8-2, $R^9$ is R9-1, $R^{10}$ is R10-1, $R^{11}$ is R11-1, $R^{12}$ and hydrogen, $R^{13}$ is R13-2, X is X1 and Y is Y2, and $R^1$ and $R^2$, $R^1$ and $R^4$, $R^8$ and $R^9$ or $R^{13}$ and —X—Y taken together may form a 5- or 6-membered ring which contains one or more of O or $NR^{15}$ wherein $R^{15}$ is the same as defined above and which may optionally be substituted, 24) a compound wherein $R^1$ is R1-2, $R^2$ is R2-1, $R^3$ is R3-1, $R^4$ is R4-1, $R^5$ is R5-1, $R^6$ is R6-2, $R^7$ is R7-2, $R^8$ is R8-2, $R^9$ is R9-2, $R^{10}$ is R10-1, $R^{11}$ is R11-1, $R^{12}$ is hydrogen, $R^{13}$ is R13-2, X is X1 and Y is Y1, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 25) a compound wherein $R^1$ is R1-2, $R^2$ is R2-1, $R^3$ is R3-1, $R^4$ is R4-1, $R^5$ is R5-1, $R^6$ is R6-2, $R^7$ is R7-2, $R^8$ is R8-2, $R^9$ is R9-2, $R^{10}$ is R10-1, $R^{11}$ is R11-1, $R^{12}$ is hydrogen, $R^{13}$ is R13-1, X is X1 and Y is Y2, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 26) a compound wherein $R^1$ is R1-2, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-1, $R^{10}$ is R10-1, $R^{11}$ is R11-1, $R^{12}$ is hydrogen, $R^{13}$ is R13-2, X is X1 and Y is Y2, and $R^1$ and $R^2$, $R^1$ and $R^4$, R8 and $R^9$, or $R^{13}$ and —X—Y taken together may form a 5- or 6-membered ring which contains one or more of O or $NR^{15}$ wherein $R^{15}$ is the same as defined above and which may optionally be substituted, 27) a compound wherein $R^1$ is R1-1, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R11-1, $R^{12}$ is hydrogen, $R^{13}$ is R13-2, X is X1 and Y is Y2, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 28) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{12}$ is hydrogen, $R^{13}$ is R13-2, X is X2 and Y is Y2, and $R^1$ and $R^4$, or $R^8$ and $R^9$ taken together may form a 5- or 6-membered ring which contains one or more of O, 29) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^1$ and $R^4$, or $R^8$ and $R^9$ taken together may form a 5- or 6-membered ring which contains one or more of O, 30) a compound wherein $R^1$ is R1-4, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-2, X is X2 and Y is Y2, and $R^1$ and $R^4$, or $R^8$ and $R^9$ taken together may form —OCH$_2$O—, 31) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{12}$ is hydrogen, $R^{13}$ is R13-2, X is X2 and Y is Y2, and $R^1$ and $R^4$, or $R^8$ and $R^9$ taken together may form a 5- or 6-membered ring which contains one or more of O, 32) a compound wherein R1 is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-4, $R^{10}$ is R10-2, $R^{11}$ is R11-2, $R^{12}$ is hydrogen, $R^{13}$ is R13-2, X is X2 and Y is Y2, and $R^1$ and $R^4$, or $R^8$ and $R^9$ taken together may form a 5- or 6-membered ring which contains one or more of O, 33) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R11-2, $R^{12}$ is hydrogen, $R^{13}$ is R13-3, X is X2 and Y is Y2, and $R^1$ and $R^4$, or $R^8$ and $R^9$ taken together may form a 5- or 6-membered ring which contains one or more of O, 34) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-4, X is X2 and Y is Y2, and $R^1$ and $R^4$, or $R^8$ and $R^9$ taken together may form a 5- or 6-membered ring which contains one or more of O, 35) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ us R11-2, $R^{12}$ is hydrogen, $R^{13}$ is R13-2, X is X2 and Y is Y3, and $R^1$ and $R^4$, or $R^8$ and $R^9$ taken together may form a 5- or 6-membered ring which contains one or more of O,
36) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-2, X is X2 and Y is Y2, and $R^1$ and $R^4$, or $R^8$ and $R^9$ taken together may form a 5- or 6-membered ring which contains one or more of O,
37) a compound wherein $R^1$ is R1-3, $R^2$ is R2-2, R3 is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-3, X is X2 and Y is Y2, and $R^1$ and $R^4$, or $R^8$ and $R^9$ taken together may form a 5- or 6-membered ring which contains one or more of O,
38) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-2, X is X2 and Y is Y3, and $R^1$ and $R^4$, or $R^8$ and $R^9$ taken together may form a 5- or 6-membered ring which contains one or more of O,
39) a compound wherein $R^1$ is R1-2, $R^2$ is R2-2, $R^3$ is R3-2, $R^4$ is R4-2, $R^5$ is R5-1, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-3, X is X2 and Y is Y2, and $R^1$ and $R^4$, or $R^8$ and $R^9$ taken together may form a 5- or 6-membered ring which contains one or more of O,
40) a compound wherein $R^1$ is R1-2, $R^2$ is R2-2, $R^3$ is R3-2, $R^4$ is R4-2, $R^5$ is R5-2, $R^6$ is R6-3, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-2, X is X2 and Y is Y3, and $R^1$ and $R^4$, or $R^8$ and $R^9$ taken together may form a 5- or 6-membered ring which contains one or more of O,
41) a compound wherein $R^1$ is R1-2, $R^2$ is R2-2, $R^3$ is R3-2, $R^4$ is R4-2, $R^5$ is R5-2, is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-3, X is X2 and Y is Y3, and $R^1$ and $R^4$, or $R^8$ and $R^9$ taken together may form a 5- or 6-membered ring which contains one or more of O,
42) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{11}$ is R10-2, $R^{12}$ is hydrogen, $R^{13}$ is R13-3, X is X2 and Y is Y2, and $R^1$ and $R^4$, or $R^8$ and $R^9$ taken together may form —OCH$_2$O—,
43) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-2, X is X2 and Y is Y3, and $R^1$ and $R^4$, or $R^8$ and $R^9$ taken together may form —OCH$_2$O—,
44) a compound wherein $R^1$ is R1-3, $R^2$ is R2-2, $R^3$ is R3-3, $R^4$ is R4-2, $R^5$ is R5-2, $R^6$ is R6-2, $R^7$ is R7-2, $R^8$ is R8-2, $R^9$ is R9-2, $R^{10}$ is R10-2, is $R^{11}$ is R11-2, $R^{12}$ is hydrogen, $R^{13}$ is R13-3, X is X2 and Y is Y3, and $R^1$ and $R^4$, or $R^8$ and $R^9$ taken together may form —OCH$_2$O—,
45) a compound wherein $R^1$ is R1-2, $R^2$ is R2-2, $R^3$ is R3-3, $R^4$ is R4-2, $R^5$ is R5-3, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-3, X is X2 and Y is Y3, and $R^1$ and $R^4$, or $R^8$ and $R^9$ taken together may form a 5- or 6-membered ring which contain one or more of O,
46) a compound wherein $R^1$ is R1-3, $R^2$ is R2-2, $R^3$ is R3-3, $R^4$ is R4-2, $R^5$ is R5-1, $R^6$ is R6-3, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-3, X is X3 and Y is Y4, and $R^1$ and $R^4$, or $R^8$ and $R^9$ taken together may form —OCH$_2$O—,
47) a compound wherein $R^1$ is R1-4, $R^2$ is R2-2, $R^3$ is R3-3, $R^4$ is R4-2, $R^5$ is R5-3, $R^6$ is R6-3, $R^7$ is R7-2, $R^8$ is R8-2, $R^9$ is R9-4, $R^{10}$ is R10-2, $R^{11}$ is R11-2, $R^{12}$ is hydrogen, $R^{13}$ is R13-4, X is X3 and Y is Y4, RI and $R^4$ taken together may form —OCH$_2$O— and $R^8$ and $R^9$ taken together may form —OCH$_2$CH$_2$O—,
48) a compound wherein the benzene ring which is substituted with $R^1$–$R^5$ is

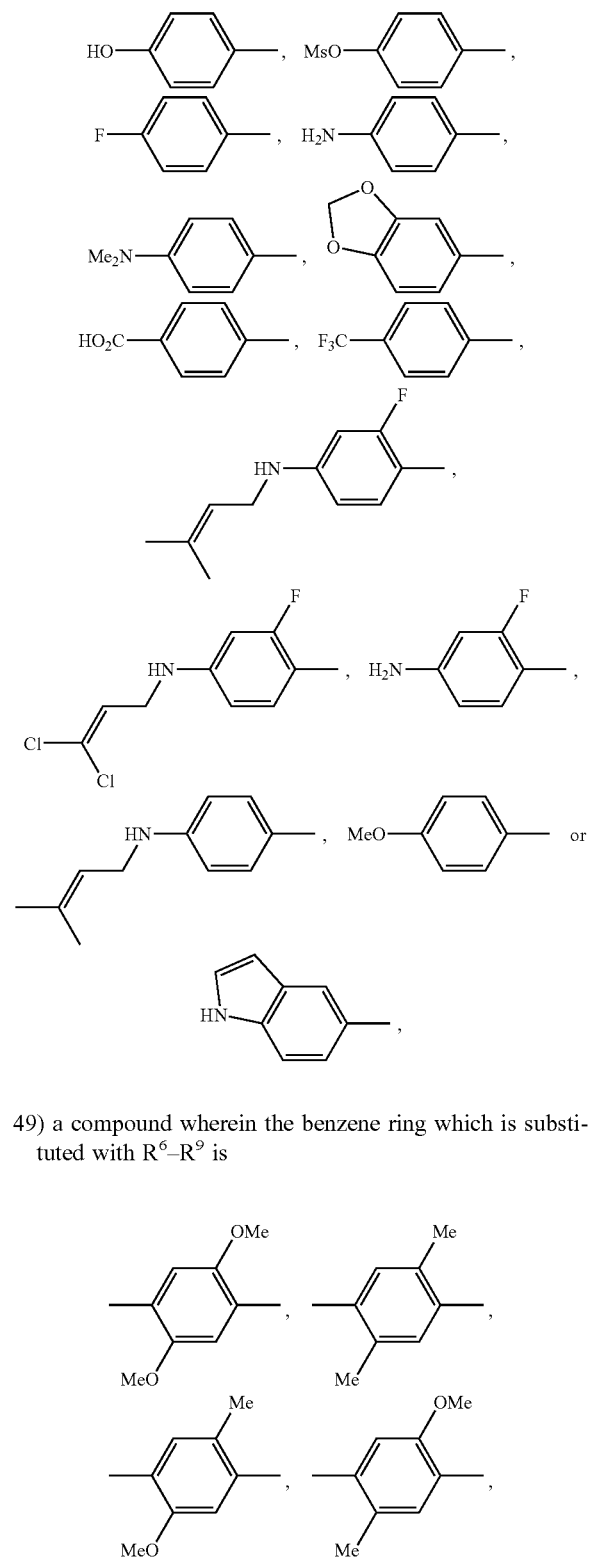

49) a compound wherein the benzene ring which is substituted with $R^6$–$R^9$ is -continued

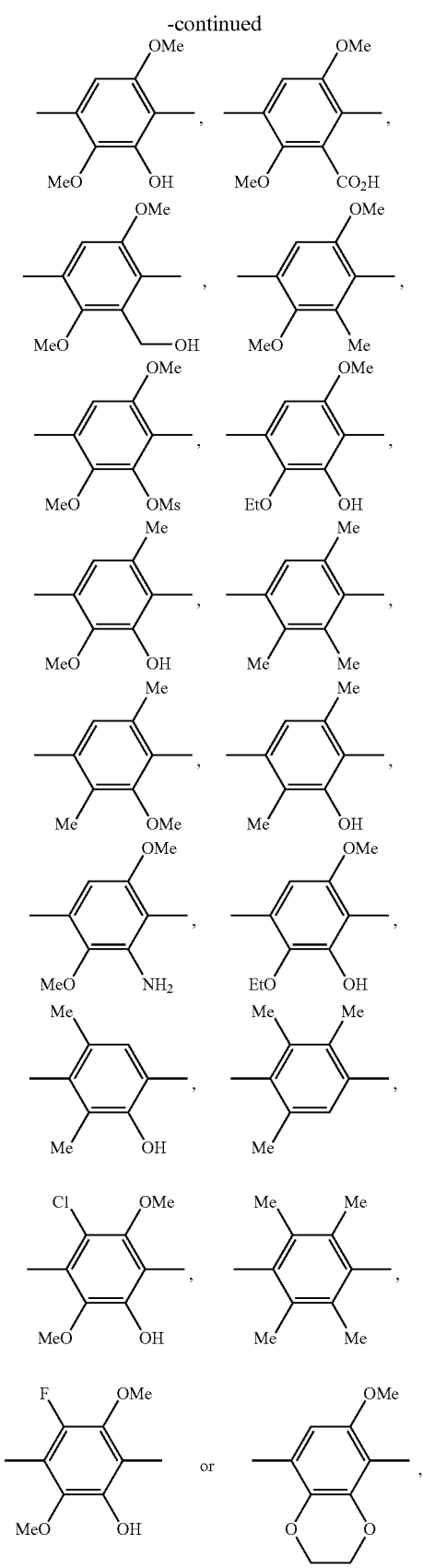

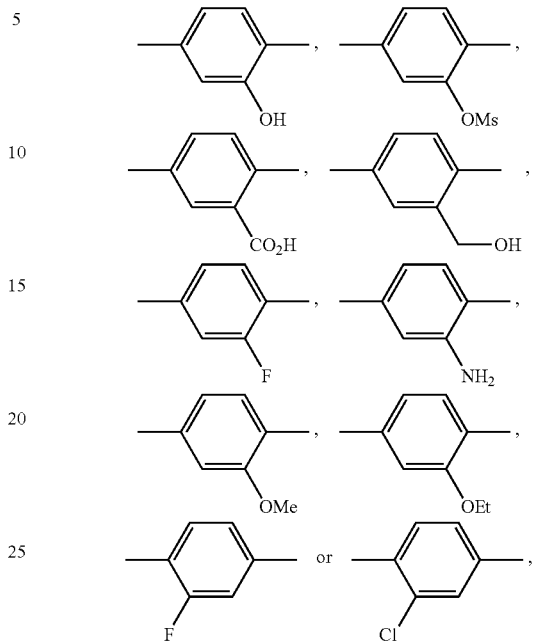

50) a compound wherein the benzene ring which is substituted with $R^{10}$–$R^{13}$ is 51) a compound wherein Y is —$CH_2CH=CMe_2$, —$(CH_2)_2$ $CH=CMe_2$, —$CH_2CH=CCl_2$, —$CH_2CH=CBr_2$, —$CH_2CH=CF_2$, —$CH_2CH=CHMe$, —$CH_2CH=C(Me)CH_2OH$, —$CH_2C\equiv CMe$, —$CH_2C_6H_4$-4-Me, —$CH_2C_6H_5$, —$CH_2CH_2CHMe_2$ or —Me, 52) a compound wherein —X—Y is —$OCH_2CH=CMe_2$, —$O(CH_2)_2CH=CMe_2$, —$OCH_2CH=CCl_2$, —$OCH_2CH=CBr_2$, —$OCH_2CH=CF_2$, —$OCH_2C\equiv CMe$, —$OCH_2C_6H_4$-4-Me, —$OCH_2C_6H_5$, —$NHCH_2CH=CMe_2$, —$N(Me)CH_2CH=CMe_2$, —$NHCH_2CH_2CHMe_2$, —$NHCH_2C\equiv CH$, or —$NMe_2$, or 53) a compound wherein at least seven of the substituents of $R^1$–$R^{13}$ are hydrogen, preferably at least eight are hydrogen, more preferably at least nine are hydrogen, and their pharmaceutically acceptable salts, their hydrates and their prodrugs.

A process for producing the compound (I''') is as follows.

Process for Producing the Compound (I''') [Process a]

The compound (I''') can be produced by the reaction of a borane compound of the formula (II) and (II') coupled with a biphenyl derivative of the formula (III) and (III') respectively, as shown below.

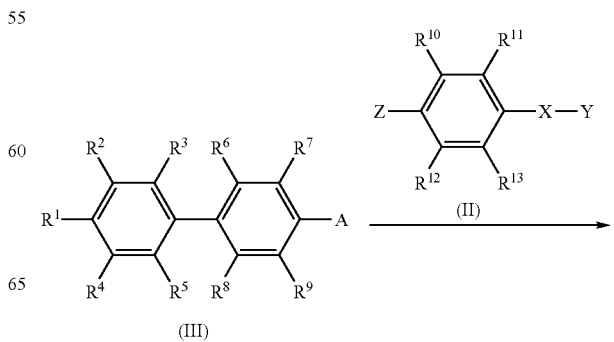

-continued

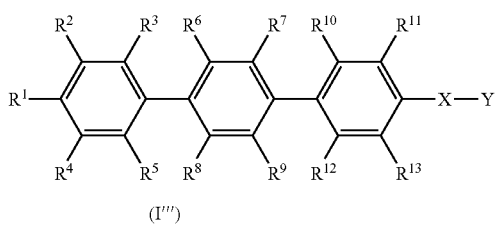

(I''')

wherein $R^1$–$R^{13}$, X and Y are the same as defined in the above formula (I'''), and A and Z are the same as defined in the above formulas (II) and (III), or

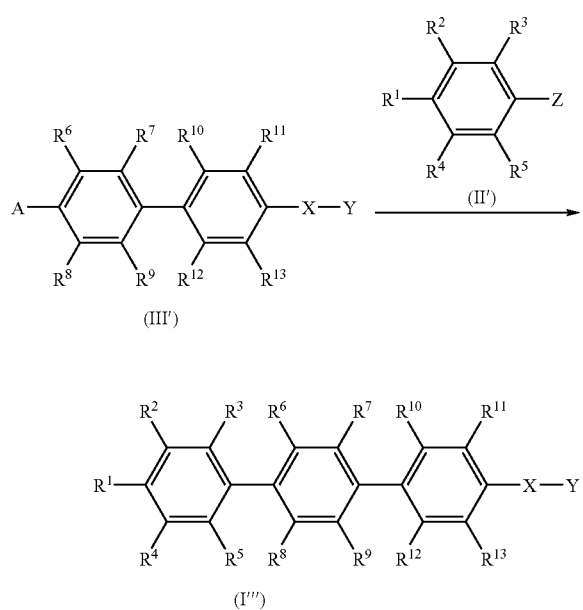

wherein $R^1$–$R^{13}$, X and Y are the same as defined in the above formula (I'''), and A and Z are the same as defined in the above formulas (II) and (III).

The compounds (II) and (II') are reacted with the compounds (III) and (III') respectively in a mixture system of an appropriate solvent such as benzene, toluene, dimethylformamide, dimethoxyethane, tetrahydrofuran, dioxane, ethanol, methanol or the like and water or in an anhydrous system in the presence of a palladium catalyst such as Pd(PPh$_3$)$_4$, PdCl$_2$(PPh$_3$)$_2$, PdCl$_2$(OAc)$_2$, PdCl$_2$(CH$_3$CN)$_2$ or the like, Pd(PPh$_3$)$_4$, under a basic condition (for example, by K$_3$PO$_4$, NaHCO$_3$, NaOEt, Na$_2$CO$_3$, Et$_4$NCl, Ba(OH)$_2$, Cs$_2$CO$_3$, CsF, NaOH, Ag$_2$CO$_3$ or the like) at room temperature or with heating for several tens minutes to several tens hours to obtain the compound (I''').

One of substituents A and Z of the compounds to be reacted may be any of the borane groups which are applicable in the Suzuki Reaction (Chemical Communication 1979, 866, Journal of Synthetic Organic Chemistry, Japan, 1993, Vol. 51, No. 11, 91–100) and dihydroxyborane is preferable. The other may be any of the leaving groups which are applicable in the Suzuki Reaction, for example, halogen, —OSO$_2$(C$_q$F$_{2q+1}$) wherein q is an integer of 0 to 4, or the like. Specifically, halogen, trifluoromethanesulfonyloxy (hereinafter referred to as OTf) or the like is preferable and bromine, iodine or OTf is more preferable.

The substituents $R^1$–$R^{13}$ and —X—Y of the compounds (II), (III), (II') and (III') may be any of the groups which do not affect the Suzuki Reaction, for example, any groups other than halogen and —OSO$_2$(C$_q$F$_{2q+1}$) wherein q is an integer of 0 to 4.

For example, Y may be optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, Y may be optionally substituted lower alkoxy when X is —CH$_2$— and Y may be optionally substituted lower alkoxycarbonyl, optionally substituted lower alkylsulfonyl or optionally substituted arylsulfonyl when X is —O— or —NR14—. Even if $R^1$–$R^{13}$ or Y is halogen, these reactions can be carried out without difficulty when the reactivity of the substituent A with the substituent Z is higher than that of halogen with either of substituents A and Z.

Even if one of $R^1$–$R^{13}$ and —X—Y is hydroxy, the above reactions can be carried out preferably after the protection of hydroxy group with a usual hydroxy-protecting group (for example, metoxymethyl, benzyl, tert-butyldimethylsilyl, methansulfonyl, p-toluenesulfonyl or the like), followed by the removal of them by usual methods.

As processes for producing the compound (I'''), the above mentioned Suzuki Reaction is most preferable in view of the efficiency and easiness but silicon, zinc, tin or the like can be used in place of the borane group in the above scheme.

For example, in the case that one of A and Z is —SiR$^{17}$$_{3-r}$(Hal)$_r$ wherein $R^{17}$ is independently lower alkyl, Hal is halogen and r is an integer of 1 to 3 and the other is halogen or —OSO$_2$(C$_q$F$_{2q+1}$) wherein q is an integer of 0 to 4, the coupling reaction may be carried out using a usual palladium catalyst (Synlett (1991) 845–853, J. Org. Chem. 1996, 61, 7232–7233). Examples of preferable palladium catalysts are (i-Pr$_3$P)$_2$PdCl$_2$, [(dcpe)PdCl$_2$](dcpe=Cy$_2$PCH$_2$CH$_2$PCy$_2$), (η$^3$—C$_3$H$_5$PdCl)$_2$ and the like.

Even in the case that one of A and Z is —SnR$^{18}$$_3$ wherein $R^{18}$ is each independently lower alkyl and the other is halogen, acetyloxy or —OSO$_2$(C$_q$F$_{2q+1}$) wherein q is an integer of 0 to 4, an objective compound can be obtained using a usual palladium catalyst (preferably Pd(PPh$_3$)$_4$ or the like) (Angew. Chem. Int. Ed. Engl. 25 (1986) 508–524).

In the case that one of A and Z is —Zn(Hal) wherein Hal is halogen and the other is halogen, an objective compound can be obtained (Acc. Chem. Res. 1982, 15, 340–348). Any usual palladium catalyst is applicable and Pd(PPh$_3$)$_4$, PdCl$_2$(dppf), PdCl$_2$(PPh$_3$)$_2$, PdCl$_2$(P(o-Tolyl)$_3$)$_2$, Pd(OAc)$_2$ and the like are exemplified as preferable examples.

All of these reactions may be carried out in a suitable solvent (for example, dimethylformamide, tetrahydrofuran or the like) at room temperature or with heating for several tens minutes to several tens hours.

Process for Producing the Compound (I''') [Process b]

As another easier processes for producing the compound (I'''), the following process wherein the compound of the formulas (IV), (V) and (VI) are coupled is also applicable.

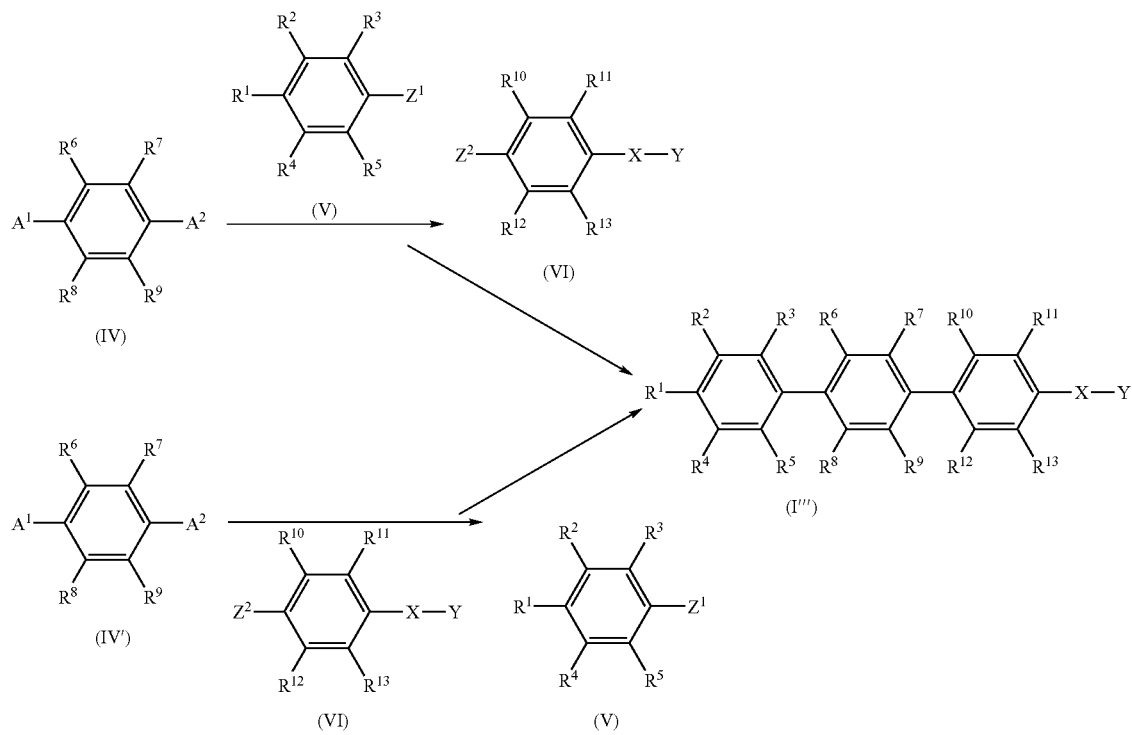

wherein $R^1$–$R^{13}$, X and Y are the same as defined in the above formulas (I), (II) and (III) and $A^1$, $A^2$, $Z^1$ and $Z^2$ are the same as defined in the above A and Z, respectively. The reactivity of $A^1$ is higher than or equal to that of $A^2$ in the compound (IV) and the reactivity of $A^2$ is higher than or equal to that of $A^1$ in the compound (IV').

For production of the compound (I''') by the above process the compound (IV) may be reacted with the compound (V), followed by the reaction with the compound (VI) without an isolation. The objective compound can be obtained also by a process wherein the compound (IV') is reacted with the compound (VI), followed by a reaction with the compound (V).

Because the reactions of the substituents $A^1$ and $Z^1$ and the substituents $A^2$ and $Z^2$ are necessary to obtain the objective compound, the reactivity of the substituent $A^1$ and that of $A^2$ should be different. A preferable example is the combination that $A^1$ is iodine and $A^2$ is bromine or OTf in the compound (IV). Conversely in the compound (IV') iodine for $A^2$ and bromine or OTf for $A^1$ are preferable. In the case that the compound (IV) or (IV') is a symmetry compound, the objective compound is obtained even if $A^1$ and $A^2$ are the same group.

The substituents $Z^1$ and $Z^2$ may be the same or different group.

Various other conditions in this process are the same as those in the "Process a".

In the above compounds, the substituents $R^1$–$R^{13}$ may be any of the groups which do not affect the reaction (for example, a group other than halogen and —$OSO_2(C_qF_{2q+1})$ wherein q is an integer of 0 to 4) or any of the groups which do not affect the reaction and are changeable to $R^1$–$R^{13}$ by a usual reaction. In the latter case the substituents may be changed to $R^1$–$R^{13}$ in suitable steps according to the reaction of each compound.

For example, in the case that a substituent is formyl and an objective substituent is hydroxy, after the substituent is changed to formyloxy by the Baeyer-Villiger reaction etc., a usual hydrolysis reaction may be carried out under an acidic or alkaline condition. Specifically, a compound which has formyl is reacted with a peroxy acid such as peracetic acid, perbenzoic acid, m-chloroperbenzoic acid, trifluoroperacetic acid, hydrogen peroxide or the like in a suitable solvent such as 1,2-dichloroethane, chloroform, dichloromethane, carbon tetrachloride, benzene or the like at –20° C. or with heating for several minutes to several tens hours, followed by the hydrolysis of the obtained compound which has formyloxy under an acidic condition (for example, with heating with hydrochloric acid) or under a basic condition (for example, with heating with sodium hydroxide).

In the case that a substituent is formyl and an objective substituent is hydroxymethyl, the compound which has formyl may be reacted with a reductant such as sodium borohydride, lithium borohydride, zinc borohydride, triethyllithium borohydride, alminium hydride, diisobutylalminium hydride or the like in a solvent (for example, methanol, ethanol, isopropanol, dimethylsulfoxide, diethylene glycol dimethoxyethane, tetrahydrofuran, benzene, toluene, cyclohexane or the like) which is suitable for the reductant at –20° C. to 80° C., preferably under ice-cooling or at room temperature, for several tens minutes to several hours.

In the case that a substituent is formyl and an objective substituent is alkenyl having additional carbon atoms, an objective compound can be obtained by the Wittig Reaction (Organic Reaction, 1965, vol. 14, p. 270).

In the case that a substituent is formyl and an objective substituent is carboxy, the compound which has formyl may be reacted with an oxidizing agent such as sodium chlorite, the Jones Reagent, chromic anhydride or the like in a solvent such as tert-butanol, acetone or the like which is suitable for the oxidizing agent at 0° C. or with heating for several hours. The reaction is preferably carried out by addition of 2-methyl-2-buten, sodium dihydrogenphosphate or the like if needed.

In the case that a substituent is hydroxy and an objective substituent is substituted lower alkoxy, the compound which has hydroxy may be reacted with a proper alkylating agent in the presence of a base such as sodium carbonate, sodium bicarbonate, potassium carbonate, calcium hydroxide, barium hydroxide, calcium carbonate or the like in a suitable solvent such as tetrahydrofuran, acetone, dimethylformamide, acetonitrile or the like. Specifically, the reaction of a compound which has hydroxy with a proper halogenated compound such as methyl iodoacetate, ethyl chloroacetate, propyl chloroacetate or the like can give a compound of which substituent is alkoxycarbonyl(lower)alkoxy.

In the case that a substituent is carboxy and an objective substituent is carbamoyl, the compound which has carboxy may be carbamoylated with an amine such as ammonia, dimethylamine or the like at 0° C. or with heating for several minutes to several hours in a suitable solvent such as tetrahydrofuran, dimethylformamide, diethyl ether, dichloromethane or the like, if necessary after activation by an activating agent such as thionyl chloride, an acid halide, an acid anhydride, an activated ester or the like.

In the case that a substituent is hydrogen and an objective substituent is halogen, the compound which has hydrogen may be halogenated by a halogenating agent which is generally used (for example, bromine, chlorine, iodine, sulfuryl chloride, N-bromosuccinimide, N-iodosuccinimide or the like) in a suitable solvent such as chloroform, dichloromethane, carbon tetrachloride, acetonitrile, nitromethane, acetic acid, acetic anhydride or the like, if necessary in the presence of a catalyst such as the Lewis acid, hydrochloric acid, phosphoric acid or the like at −20° C. or with heating for several minutes to several tens hours.

The compound (I) can be obtained by a reaction of the compound (II) which has a substituent —X—Y with the compound (III) or a reaction of the compound (III') which has a substituent —X—Y with the compound (II'). Further, the compound (I) can also be obtained by a reaction of the compound (II) or (III') which has a substituent —W which is convertible into a substituent —X—Y with the compound (III) or (II'), followed by a conversion of a substituent —W into a substituent —X—Y.

For example, in the case of a compound wherein —W is hydroxy or protected hydroxy, an objective substituent such as lower alkyl, lower alkenyl, lower alkynyl, acyl, cycloalkyl, cycloalkenyl, aryl, heterocyclyl, lower alkoxy or the like may be introduced by a usual reaction.

Concretely, to obtain a compound wherein X is —O—, a compound wherein —W is hydroxy is synthesized and dissolved in a suitable solvent (for example, dimethylformamide, tetrahydrofuran, acetone, benzene, dioxane, acetonitrile or the like), followed by addition of a base such as hydroxides or carbonates of alkaline metals or alkaline-earth metals (for example, sodium carbonate, sodium bicarbonate, potassium carbonate, calcium hydroxide, barium hydroxide, calcium carbonate and the like) or tertiary amines such as triethylamine and the like. To the reactant is added a compound Y—V wherein V is halogen or —OSO$_2$(C$_q$F$_{2q+1}$) wherein q is an integer of 0–4 (for example, prenyl bromide, cyclohexenyl bromide, cinnamyl bromide, 1-bromo-2-penten, geranyl bromide, 5-bromo-2-methyl-2-penten, 1,3-dichloro-2-buten, 3-chloropropyne, prenyl triflate, cyclohexenyl triflate, 1,3-trichloropropene or the like) at −20° C.

or with heating for several minutes to several tens hours to obtain an objective compound wherein —W has been converted into —O—Y.

To obtain a compound wherein X is —CH$_2$—, —NR$^{14}$— or —S—, a compound wherein —W is hydroxy is reacted with trifluoromethanesulfonic anhydride etc. in a solvent such as anhydrous dichloromethane, chloroform, carbon tetrachloride or the like in the presence of a base such as pyridine, triethylamine or the like to obtain a triflate. Then, the obtained compound is reacted with Y—V' wherein V' is —CH$_2$ZnI, —SH, —NHR$^{14}$ in the presence of a catalyst such as palladium, nickel or the like in a suitable solvent such as tetrahydrofuran, dimethylformamide, diethyl ether, dimethoxyethane or the like to give an objective compound.

In the case that X is NR$^{14}$, a compound wherein W is NH$_2$ may be reacted with a ketone or an aldehyde in a suitable solvent such as tetrahydrofuran, methanol or the like, followed by reduction with a suitable reductant such as sodium borohydride, sodium cyanoborohydride, zinc hydrochloride or the like or by catalytic reduction to obtain an objective compound.

A usual reaction of a compound wherein W is NH$_2$ with Y—V" wherein Y is acyl, lower alkylsulfonyl optionally substituted or arylsulfonyl optionally substituted and V" is a leaving group such as halogen gives a compound wherein —X—Y is —NH—Y.

To obtain a compound wherein X is —SO— or —SO$_2$—, a compound wherein X is —S— which is synthesized by the above mentioned process may be oxidized with a usual oxidizing agent such as m-chloroperbenzoic acid.

A compound of the present invention wherein —X—Y is lower alkenyloxy is dissolved in a solvent such as ethanol, ethyl acetate or the like and hydrogenated with a catalyst such as Pd-carbon powder, platinum, rhodium, ruthenium, nickel or the like to give a compound wherein —X—Y is lower alkoxy.

A reaction of a compound wherein —X—Y is lower alkenyloxy with m-chloroperbenzoic acid or the like in a solvent such as dichloromethane, chloroform, benzene, hexane, tert-butanol or the like gives a compound wherein —X—Y is epoxidated lower alkoxy.

In the case that a compound has a substituent interfering of a reaction, the substituent may be protected with a suitable protecting group in advance and the protecting group may be left in a suitable step by a usual method. For example, if hydroxy interferes the reaction, hydroxy may be protected with methoxymethyl, methanesulfonyl, benzyl, trifluoromethanesulfonyl, tert-butyldimethylsilyl or the like, followed by deprotection in a suitable step.

For example, for a protection of hydroxy with methanesulfonyl, a compound which has hydroxy may be reacted with methanesulfonyl chloride in a solvent such as dichloromethane, chloroform, carbon tetrachloride or the like in the presence of a base such as triethylamine, pyridine or the like under ice-cooling or at room temperature for several hours. The protected compound may be deprotected with 1–4 N sodium hydroxide, potassium hydroxide, aqueous solution thereof, sodium methoxide, ethyl magnesium bromide or the like in a solvent such as dimethylsulfoxide, dimethylformamide, tetrahydrofuran, dioxane, dimethoxyethane or the like at room temperature or with heating for several tens minutes to several hours.

When methoxymethyl is used as a protecting group of hydroxy, a compound which has hydroxy may be reacted with chloromethylmethylether in a solvent such as tetrahydrofuran, dioxane, dimethoxyethane or the like in the presence of sodium hydride, diisopropylethylamine or the like to obtain a compound which has a protected hydroxy group. The compound may be subjected to a usual deprotection reaction with hydrochloric acid, sulfuric acid or the like in a solvent such as methanol, tetrahydrofuran, acetic acid or the like for a deprotection.

When tert-butyldimethylsilyl is used as a protective group, a compound which has hydroxy may be reacted with tert-butyldimethylsilyl chloride, tert-butyldimethylsilyl triflate or the like in a solvent such as dimethylformamide, acetonitrile, tetrahydrofuran, dimethylformamide, dichloromethane or the like in the presence of imidazole, triethylamine, 2,6-lutidine or the like. For a deprotection reaction the protected compound may be reacted with tetrabutylammonium fluoride or the like in a solvent such as tetrahydrofuran or the like.

Both of known compounds and the compounds which are produced by the following process may be used as the compounds (III) and (III') in the above scheme.

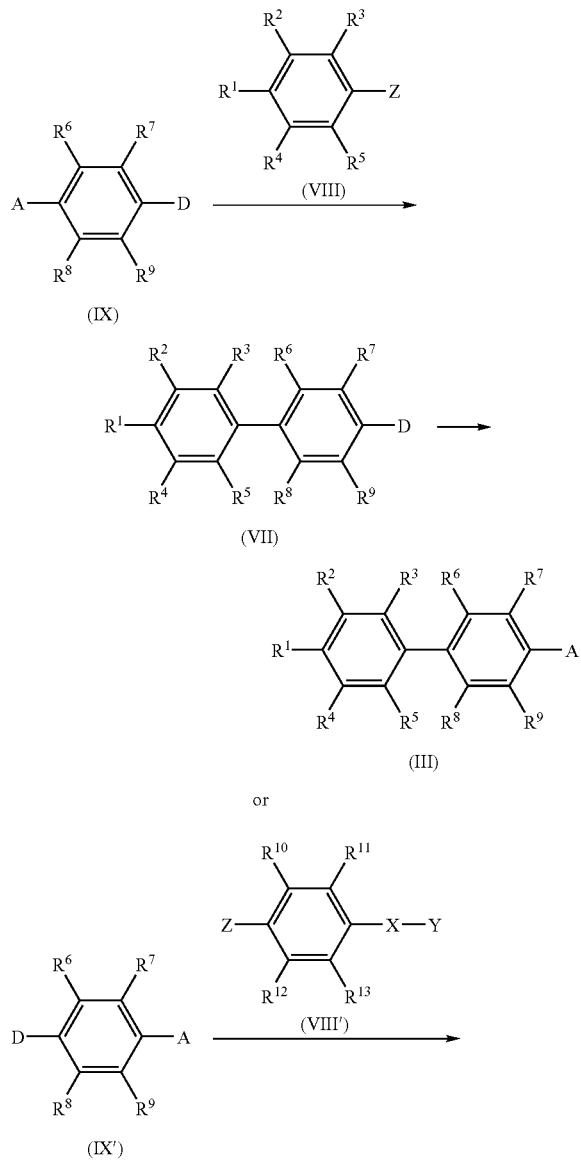

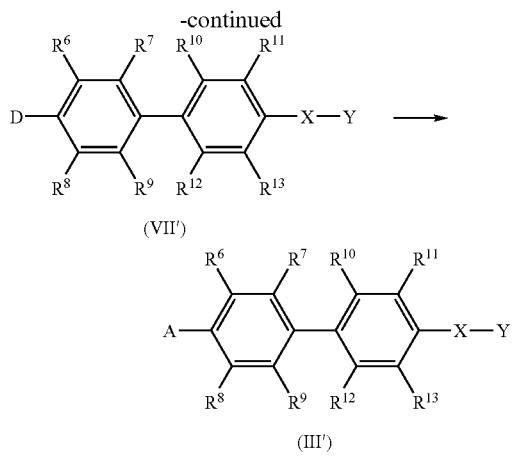

Known compounds (VIII) and (IX), or (VIII') and (IX') wherein A and Z are groups which can be subjected to a coupling reaction by the Suzuki Reaction with each other; for example, one is borane such as dihydroxyborane, di(lower)alkoxyborane or the like and the other is halogen or —$OSO_2(C_qF_{2q+1})$ wherein q is an integer of 0–4; D is a group other than halogen and —$OSO_2(C_qF_{2q+1})$ wherein q is the same as defined above are reacted by the same method as above to obtain a compound (VII) or (VII').

As described above, instead of a compound which has borane, a compound which has —$SiR^{17}_{3-r}(Hal)_r$ wherein $R^{17}$ is each independently lower alkyl, Hal is halogen and r is an integer of 1–3, —$SnR^{18}_3$ wherein $R^{18}$ is each independently lower alkyl or —Zn(Hal) wherein Hal is halogen may be used for a reaction to obtain an objective compound.

Then, a substituent D is converted into a substituent A which is applicable to the Suzuki Reaction.

For example, a compound wherein D is hydrogen may be reacted with a halogenating agent such as bromine, chlorine, iodine, sulfuryl chloride, N-bromosuccinimide or the like in a suitable solvent such as acetic acid, chloroform, dichloromethane, carbon tetrachloride, water, acetic acid-sodium acetate or the like at −20° C. or with heating for several minutes to several tens hours to give an objective compound wherein A is halogen.

A compound wherein D is protected hydroxy may be reacted with a trifluoromethanesulfonating agent such as trifluoromethanesulfonic anhydride, trifluoromethansulfonyl chloride or the like in a suitable solvent such as dichloromethane, chloroform, tetrahydrofuran or benzene in the presence of a base such as pyridine or triethylamine at −20° C. or with heating for several minutes to several tens hours to give an objective compound wherein A is OTf.

A compound of the present invention thus obtained can be converted into prodrug thereof. Any usual methods for conversion into a prodrug may be used. For example, hydroxy or amino which is attached a compound of the present invention at any position may be substituted with a usual group for a prodrug. An example of conversion into a prodrug is a substitution of hydroxy with acyloxy substituted with carboxy, sulfo, amino, lower alkylamino or the like, phosphonoxy etc. A substitution of hydroxy for $R^1$ with —$OCOCH_2CH_2COOH$, —OCOCH═CHCOOH, —$OCOCH_2SO_3H$, —$OPO_3H_2$, —$OCOCH_2NMe_2$, —OCO-Pyr wherein Pyr is pyridine or the like is preferable.

A selective suppressor of the IgE production of the present invention comprises a compound which suppresses the IgE production in a process from a differentiation of a mature B cell into an antibody-producing cell to the production of an antibody and which does not suppress or weakly suppresses the production of the immunoglobulins IgG, IgM and/or IgA which are produced at the same time.

The term "suppresses the IgE production in a process from a differentiation of a mature B cell into an antibody-producing cell to the production of an antibody" means to suppress the IgE production by inhibiting one of the following processes.

1) A process wherein mature B cells are activated by various factors such as cytokines, i.e., IL-4, IL-5, etc., anti-CD40 antibody or the like,
2) A process wherein the activated B cells differentiate into antibody-producing cells such as plasma cells etc. (concretely, a process of switching of the activated B cells to IgE class antibody-producing cells) and/or
3) A process wherein the antibody-producing cells produce immunoglobulins (specifically, a process of the IgE production)

An inhibition of "a process wherein a mature B cell is activated by various factors" in the process 1) does not include an inhibition of a process wherein the factors are produced from other cells and the like.

The term "suppresses the IgE production and does not suppress or weakly suppresses the production of the immunoglobulins IgG, IgM and/or IgA which are produced at the same time" means that the IgE production is suppressed enough to suppress allergy reactions and that the IgG, IgM and/or IgA production is not suppressed so potent as to badly affect an immune system concerning a living body protection under the condition that IgE and one or more of IgG, IgM and IgA can be produced at the same time. In other words, ① The suppression of the IgE production is 5,000 times, preferably 10,000 times, more preferably 15,000 times, most preferably 20,000 times or more as potent as those of the IgG, IgM and/or IgA production and/or
② The IgG, IgM and/or IgA production is not suppressed to less than 50% even at 5,000 times, preferably 10,000 times, more preferably 15,000 times, most preferably 20,000 times the concentration at which 50% of the IgE production is suppressed as compared with that in the absence of the suppressor.

The term "the concentration at which 50% of the IgE production is suppressed as compared with that in the absence of the suppressor" means a concentration at which the IgE production is limited to 50% of the production in the absence or without administration of the selective suppressor of the IgE production of the present invention under the condition that the IgE can be produced. The suppressor is useful as a medicament when it has a selectivity for the IgE as compared with at least one of IgG, IgM or IgA, preferably with all of them.

The selective suppressor of the IgE production of the present invention suppresses 90% or more of the IgE production as compared with that without administration of the suppressor at a dosage that the suppressor does not suppress or weakly suppresses the IgM, IgG and/or IgA production when the suppressor is administered to a mammal, which includes human, sensitized by an allergen. The term "allergen" means any substance that can induce the IgE production and an allergic reaction. Clinical examples are pollen, a acarid, house dust, albumin, milk, a soybean etc. and experimental examples are ovalbumin, bovine gamma globulin, bovine serum albumin, an antigen protein of cedar pollen (Cryj I and Cryj II), an antigen protein for acarid (Derf I and Derf II) etc. The term "a dosage that the suppressor does not suppress or weakly suppresses the IgM, IgG and/or IgA production" means the dosage at which the suppression rate of the IgG, IgM and/or IgA is 10% or less, preferably 5% or less, more preferably 3% or less as compared with those produced without administration of the selective suppressor of the IgE production of the present invention.

The selective suppressor of the IgE production of the present invention suppresses infiltration of an inflammatory cell to a tissue. The term "inflammatory cell" includes all of a lymphocyte, an eosinophil, a neutrophile and a macrophage, and an eosinophil and/or a neutrophile are preferable.

The effect of the selective suppressor on the IgE production of the present invention is potent for its direct action to B cells. Because the suppressor does not affect the humoral immunity concerning a biological protective reaction, it has many advantages, for example, little side effect such as infections etc., All of compounds that have the above effect are useful as an immunosuppressor regardless of the structure and one of the examples is the compound (I) or (I") of the present invention.

The compounds of the present invention also include ones which have the suppressive effect on a mitogen reaction and/or a cytokine reaction.

Specifically, the compounds have a potent antiproliferative effect on T and/or B cells and/or a suppressive effect on the IL-5 and/or IL-4 production. They selectively suppress the IL-4 and/or IL-5 production and do not suppress the IL-2 production.

The immunosuppressor or anti-allergic agent of the present invention is useful for prevention or a treatment of allergic diseases such as a rejection symptom against a transplantation of an organ or a tissue, a graft-versus-host reaction which is caused by a bone marrow transplantation, atopic allergic diseases (for example, a bronchial asthma, an allergic rhinitis, an allergic dermatitis and the like), a hypereosinophils syndrome, an allergic conjunctivitis, a systemic lupus erythematosus, a polymyositis, a dermatomyositis, a scleriasis, MCTD, a chronic rheumatoid arthritis, an inflammatory bowel disease, an injury caused by ischemia-reperfusion, a pollenosis, an allergic rhinitis, an urticaria, a psoriasis and the like.

When the compound of the present invention is administered as a immunosuppressor and/or anti-allergic agent, it can safely be administered both orally and parenterally. In the case of an oral administration, it may be in any usual forms such as tablets, granules, powders, capsules, pills, solutions, suspensions, syrups, buccal tablets, sublingual tablets and the like for the administration. When the compound is parenterally administered, any usual forms are preferable, for example, injections such as intravenous injections and intramuscular injections, suppositories, endermic agents, vapors and the like. An oral administration is particularly preferable.

A pharmaceutical composition may be manufactured by mixing an effective amount of the compound of the present invention with various pharmaceutical ingredients suitable for the administration form, such as excipients, binders, moistening agents, disintegrators, lubricants, diluents and the like. When the composition is of an injection, an active ingredient can be sterilized with a suitable carrier to give a pharmaceutical composition.

Specifically, examples of the excipients include lactose, saccharose, glucose, starch, calcium carbonate, crystalline cellulose and the like, examples of the binders include methylcellulose, carboxymethylcellulose, hydroxypropylcellulose, gelatin, polyvinylpyrrolidone and the like, examples of the disintegrators include carboxymethylcellulose, sodium carboxymethylcellulose, starch, sodium alginate, agar, sodium lauryl sulfate and the like, and examples of the lubricants include talc, magnesium stearate, macrogol and the like. Cacao oil, macrogol, methyl cellulose and the like may be used as base materials of suppositories. When the composition is manufactured as solutions, emulsified injections or suspended injections, dissolving accelerators, suspending agents, emulsifiers, stabilizers, preservatives, isotonic agents and the like may be added. For an oral administration, sweetening agents, flavors and the like may be added.

Although a dosage of the compound of the present invention as an immunosuppressor and/or anti-allergic agent should be determined in consideration of the patient's age and body weight, the type and degree of diseases, the administration route or the like, a usual oral dosage for human adults is 0.05–100 mg/kg/day and the preferable dosage is 0.1–10 mg/kg/day. In the case that it is parenterally administered, although the dosage highly varies with administration routes, a usual dosage is 0.005–10 mg/kg/day, preferably, 0.01–1 mg/kg/day. The dosage may be administered in one or some separate administrations.

The present invention is further explained by the following Examples and Experiments, which are not intended to limit the scope of the present invention.

EXAMPLE

The abbreviations which are used in EXAMPLE mean the following.

| | |
|---|---|
| Bn | benzyl |
| DME | 1,2-dimethoxyethane |
| DMF | N,N-dimethylformamide |
| DMSO | dimethylsulfoxide |
| MCPBA | m-chloroperbenzoic acid |
| MOM | methoxymethyl |
| Ms | methanesulfonyl |
| Py | pyridyl |
| TBS | tert-butyldimethylsilyl |
| Tf | trifluoromethanesulfonyl |
| Ts | p-toluenesulfonyl |

Example 1

Synthesis of the Compounds (I-1), (I-2) and (I-3)

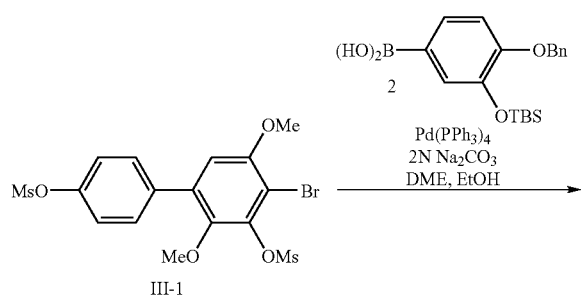

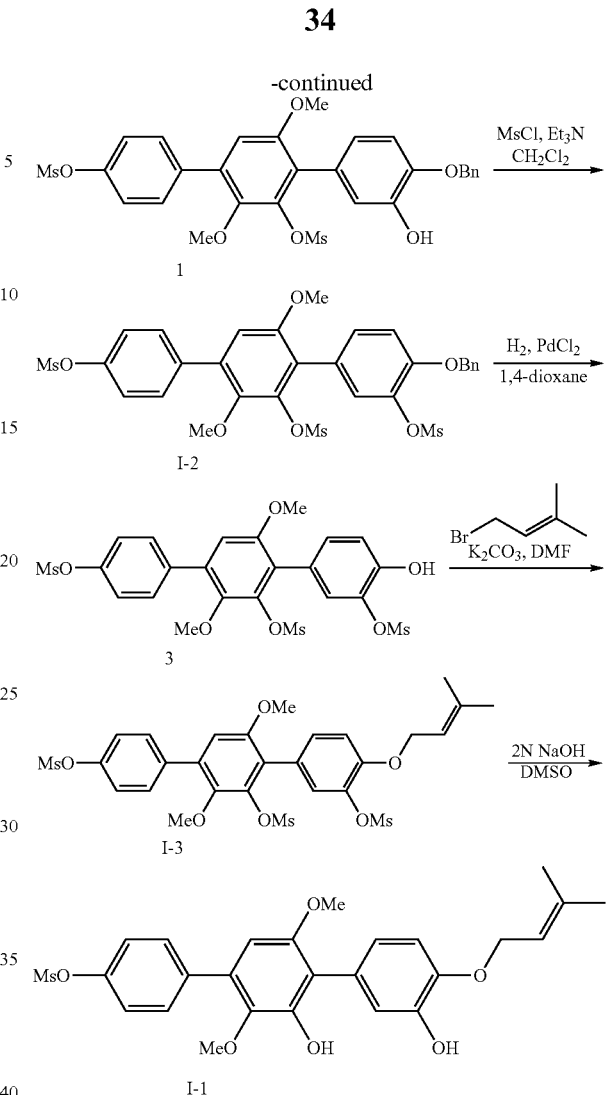

(Step 1) Synthesis of the Compound 1

To 300 ml of a solution of 10.63 g (22.08 mmol) of a compound (III-1) in 1,2-dimethoxyethane was added 3.60 g (3.12 mmol) of tetrakis(triphenylphosphine)palladium (0) at room temperature. To the mixture were added 80 ml of a solution of a compound 2 (9.50 g; 26.5 mmol) in 99% ethanol and 125 ml (250 mmol) of an aqueous solution of 2 M sodium carbonate and the reacted suspension was heated under refluxing in an argon atmosphere for 6 hours. After cooling, the reaction mixture was filtered off to remove an insoluble material and the filtrate was acidified with 2 N hydrochloric acid and extracted with ethyl acetate. The extract was washed with 5% aqueous solution of sodium bicarbonate and saturated brine successively, then dried and concentrated. After the residue was purified by silica gel chromatography (hexane-ethyl acetate 1:1), the obtained product was recrystallized from hexane-ethyl acetate to give the compound 1 (11.57 g; 87% yield) as colorless crystals.

(Step 2) Synthesis of the Compound (I-2)

To 60 ml of a suspension of the compound 1 (9.30 g; 15.48 mmol) in anhydrous dichloromethane was added 3.24 ml (23.22 mmol) of triethylamine, followed by addition of 1.80 ml (23.22 mmol) of methanesulfonyl chloride under ice-cooling and stirred for 2 hours at the same temperature.

After the solvent was removed, the residue was acidified with 80 ml of 1 N hydrochloric acid and extracted with chloroform. The extract was washed with 1 N hydrochloric acid, 5% aqueous solution of sodium bicarbonate and saturated brine successively, and the obtained product was dried and concentrated. The obtained residue was recrystallized from hexane-ethyl acetate to give 9.93 g of the compound (I-2) (95% yield) as colorless crystals.

(Step 3) Synthesis of the Compound 3

Stirred were 300 ml of a solution of 9.76 g (14.38 mmol) of the compound (I-2) and 765 mg (4.31 mmol) of palladium chloride (II) in 1,4-dioxane under a hydrogen atmosphere at room temperature for 15 hours. An insoluble material was removed off by filtration with celite and the obtained filtrate was concentrated. The residue was recrystallized from hexane-ethyl acetate to give the compound 3 (8.43 g; 100% yield) as colorless crystals.

(Step 4) Synthesis of the Compound (I-3)

To 40 ml of a solution of the compound 3 (4.01 g; 6.81 mmol) in anhydrous N,N-dimethylformamide were added successive, 1.45 g (10.5 mmol) of potassium carbonate and 1.21 ml (10.5 mmol) of prenyl bromide. After the mixture was stirred under a nitrogen atmosphere for 15 hours at room temperature, the reaction mixture was poured into 230 ml of 6% aqueous citric acid and extracted with ethyl acetate. The extract was washed with 5% citric acid, 5% aqueous solution of sodium bicarbonate and saturated brine successively, followed by being dried and concentrated. The residue was recrystallized from hexane-ethyl acetate to give 4.01 g of the compound (I-3) (90% yield) as colorless crystals.

(Step 5) Synthesis of the Compound (I-1)

To 38 ml of a solution of 3.80 g (5.79 mmol) of the compound (I-3) in dimethylsulfoxide was added 15 ml (60.0 mmol) of 4 N sodium hydroxide and the reaction mixture was warmed at 60° C. for 4 hours. After the mixture was cooled, 100 ml of 1 N hydrochloric acid was added to it and the obtained mixture was extracted with ethyl acetate. The extract was washed with 5% aqueous solution of sodium bicarbonate and saturated brine successively, then dried and concentrated. The residue was recrystallized from methanol to give 1.72 g of the compound (I-1) (70% yield) as colorless crystals.

Reference Example 1

Synthesis of the Compound 2

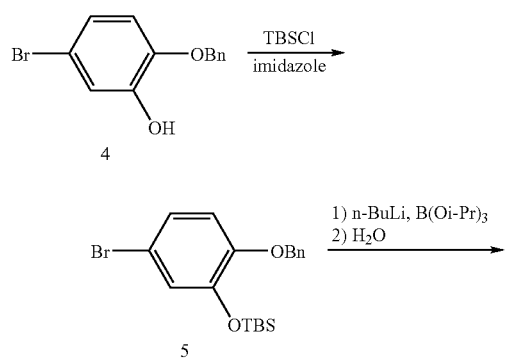

-continued

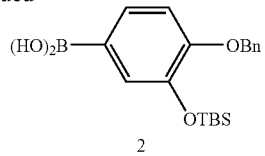

To a solution of the compound 4 (80.0 g; 0.287 mol) in 300 ml of N,N-dimethylformamide were added tert-butyldimethylsilyl chloride (45.87 g; 0.296 mol) and imidazole (21.46 g; 0.315 mol) and stirred at room temperature for 19 hours. The reaction mixture was poured into 1 L of water and extracted with ether. The extract was washed with water and saturated brine successively and then dried and concentrated. The residue was purified by silica gel chromatography (hexane-ethyl acetate 50:1) to give the compound 5 (97.20 g; 86% yield) as a colorless oil.

To 850 ml of a solution of the compound 5 (97.20 g; 0.247 mol) in annydrous tetrahydrofuran was added 152 ml (0.252 mol) of a solution of 1.66 N n-butyllithium in hexane under a nitrogen atmosphere at −70° C. and stirred at the same temperature for 1.5 hours. To the mixture was added 171 ml (0.741 mol) of triisopropyl borate at −70° C. and stirred for 3 hours with gradually warming to room temperature. Under cooling with ice, 500 ml of water and 320 ml of 5% citric acid were added to the mixture and stirred at the same temperature for 30 minutes. The solution was extracted with ethyl acetate and the extract was washed with water and saturated brine successively, then dried and concentrated. The residue was purified by silica gel chromatography (hexane-ethyl acetate 2:1) to give the compound 2 (51.10 g; 58% yield) as colorless crystals.

Reference Example 2

Synthesis of the Compound (III-1)

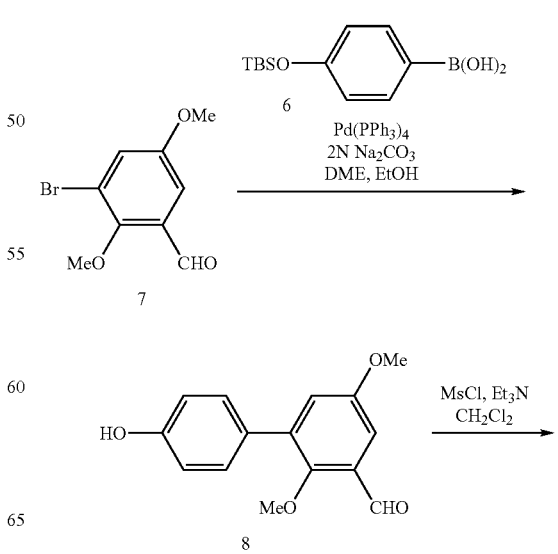

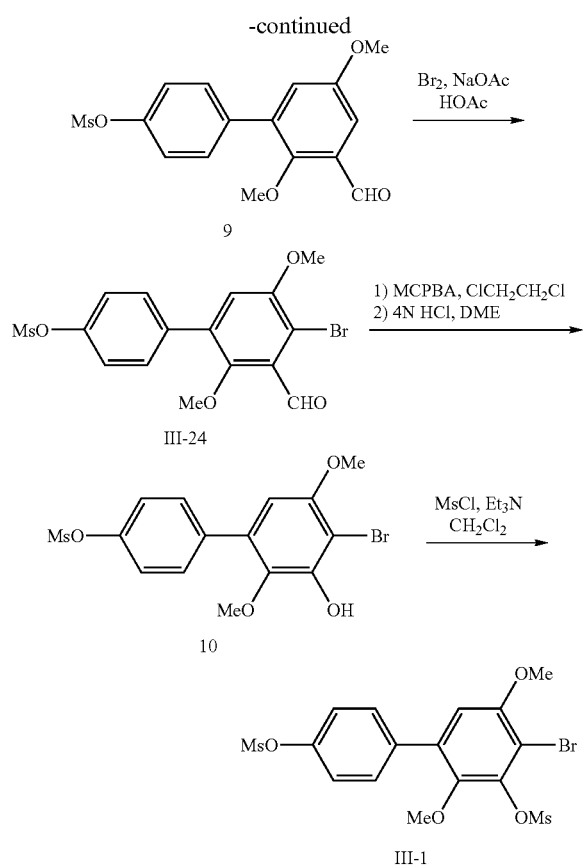

(Step 1) Synthesis of the Compound 8

To a solution of 15.30 g (62.4 mmol) of a compound 7 (Journal of Chemical Society, 1925, 1998) in 300 ml of 1,2-dimethoxyethane was added 3.60 g (3.12 mmol) of tetrakis(triphenylphosphine)palladium (0) at room temperature. To the mixture were added a solution of 18.89 g (74.9 mmol) of a compound 6 (GB-A No. 2276162) in 80 ml of 99% ethanol and 125 ml (250 mmol) of an aqueous solution of 2 M sodium carbonate and the reaction suspension was heated under refluxing in an argon atmosphere for 6 hours. After cooling, the reaction mixture was filtered off to remove an insoluble substance. The filtrate was acidified with 2 N hydrochloric acid and extracted with ethyl acetate. The extract was washed with 5% aqueous solution of sodium bicarbonate and saturated brine successively, then dried and concentrated. The residue was purified by silica gel chromatography (hexane-ethylacetate 1:1) and recrystallized from hexane-ethyl acetate to give the compound 8 (15.68 g; 97% yield) as colorless crystals.

(Step 2) Synthesis of the Compound 9

To a suspension of the compound 8 (15.34 g; 59.39 mmol) in 240 ml of anhydrous dichloromethane were added 16.6 ml (118.8 mmol) of triethylamine and 6.93 ml (89.09 mmol) of methanesulfonyl chloride under ice-cooling and stirred at the same temperature for 2 hours. After the solvent was removed, the residue was acidified with 1 N hydrochloric acid (100 ml) and extracted with ethyl acetate. The extract was washed with 1 N hydrochloric acid, 5% aqueous solution of sodium bicarbonate and, saturated brine successively, then dried and concentrated. The residue was recrystallized from hexane-ethyl acetate to give the compound 9 (17.24 g; 86% yield) as colorless crystals.

(Step 3) Synthesis of the Compound (III-24)

To 210 ml of a suspension of the compound 9 (17.03 g; 50.63 mmol) in acetic acid were added 6.23 g (75.95 mmol) of sodium acetate and 3.91 ml (75.95 mmol) of bromine at room temperature and stirred at the same temperature for 16 hours. After 3.91 ml (75.95 mmol) of bromine was added to the reacted suspension and stirred at 50° C. for 4 hours, 3.91 ml (75.95 mmol) of bromine was added and stirred at 50° C. for 3 hours. The reaction mixture was poured into 1 L of 1 M aqueous sodium thiosulfate and stirred for 30 minutes. The precipitate was collected by filtration and washed with water. The obtained crystals were dissolved in 800 ml of chloroform, washed with 5% aqueous solution of sodium bicarbonate and saturated brine successively, then dried and concentrated. The residue was recrystallized from hexane-ethyl acetate to give the compound (III-24) (18.12 g; 86% yield) as colorless crystals.

(Step 4) Synthesis of the Compound 10

To a suspension of the compound (III-24) (15.80 g; 38.05 mmol) in 400 ml of 1,2-dichloroethane was added 12.30 g (57.05 mmol) of 80% m-chloroperoxybenzoic acid at room temperature and stirred at the same temperature for 17 hours. The reaction mixture was poured into 360 ml of 0.2 M aqueous sodium thiosulfate and extracted with chloroform. The extract was washed with 300 ml of 0.2 M sodium thiosulfate and 200 ml of 5% of sodium bicarbonate (×2) successively, then dried and concentrated. The residue (15.80 g) was dissolved in 330 ml of 1,2-dimethoxyethane and 30 ml (120 mmol) of 4 N hydrochloric acid was added. After the reaction mixture was stirred at 50° C. for 12 hours and cooled, the solvent was removed and the residue was extracted with ethyl acetate. The extract was washed with 5% aqueous solution of sodium bicarbonate and saturated brine successively, then dried and concentrated to give the compound 10 (14.35 g; 97% yield) as pale brown crystals.

(Step 5) Synthesis of the Compound (III-1)

Using an analogous procedure for the compound (I-4), 12.63 g of the compound (III-1) as colorless crystals (88% yield) was obtained from the compound 10 (12.0 g; 29.76 mmol).

Example 2

Synthesis of the Compound (I-4)

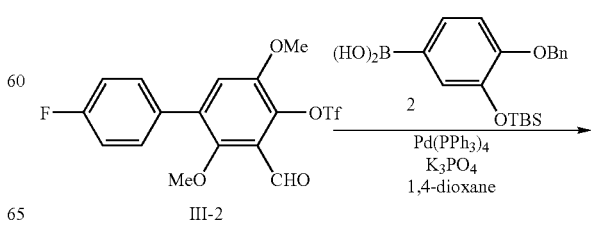

39

-continued

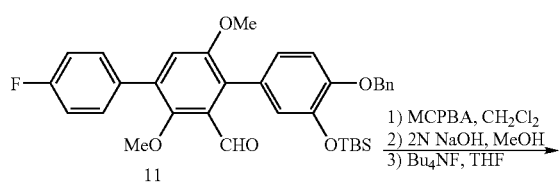

1) MCPBA, CH$_2$Cl$_2$
2) 2N NaOH, MeOH
3) Bu$_4$NF, THF

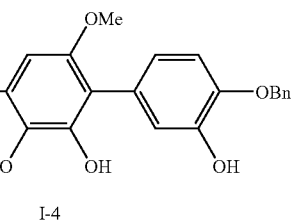

I-4

(Step 1) Synthesis of the Compound 11

To a solution of 816 mg (2 mmol) of a compound (III-2) in 40 ml of 1,4-dioxane were added 114 mg (0.1 mmol) of tetrakis(triphenylphosphine)palladium (0), 748 mg (2.09 mmol) of the compound 2 and 589 mg (2.77 mmol) of powders of anhydrous potassium phosphate at room temperature and heated in a nitrogen atmosphere at 85° C. for 23 hours. The reaction mixture was cooled and extracted with ethyl acetate. The extract was washed with 2 N hydrochloric acid, 5% aqueous sodium bicarbonate and saturated brine successively, then dried and concentrated. The residue was purified by silica gel chromatography (hexane-ethyl acetate 4:1) and crystallized from pentane to give the compound 11 (745 mg; 67% yield) as pale yellow crystals.

(Step 2) Synthesis of the Compound (I-4)

To a solution of the compound 11 (557 mg; 1 mmol) in 10 ml of dichloromethane was added 259 mg (1.2 mmol) of 80% m-chloroperbenzoic acid at room temperature and stirred for 15 hours. The reaction mixture was poured into 0.1 M aqueous sodium thiosulfate and extracted with ethyl acetate. The extract was washed with 0.1 M aqueous sodium thiosulfate, 5% aqueous sodium bicarbonate and saturated brine successively, then dried and concentrated. To a solution of 650 mg of the obtained residue in 5 ml of methanol was added a solution of 1 M sodium methoxide in 2 ml of methanol under ice-cooling and stirred for 30 minutes. After the reacted solution was acidified with 2 N hydrochloric acid and extracted with ethyl acetate, the extract was washed with saturated brine, then dried and concentrated. To a solution of 647 mg of the obtained residue in 10 ml of tetrahydrofuran was added 2 ml of 1 M tetrabutylammonium fluoride in tetrahydrofuran under ice-cooling and stirred for 30 minutes. The obtained reaction mixture was poured into 2 N aqueous hydrochloric acid under ice-cooling to acidify and extracted with ethyl acetate. The ethyl acetate layer was washed with water, 5% aqueous sodium bicarbonate and saturated brine successively, then dried and concentrated. The residue was purified by silica gel chromatography (hexane-ethyl acetate 2:1) to give 275 mg of the compound (I-4) (62% yield) as powders.

40

Reference Example 3

Synthesis of the Compound (III-2)

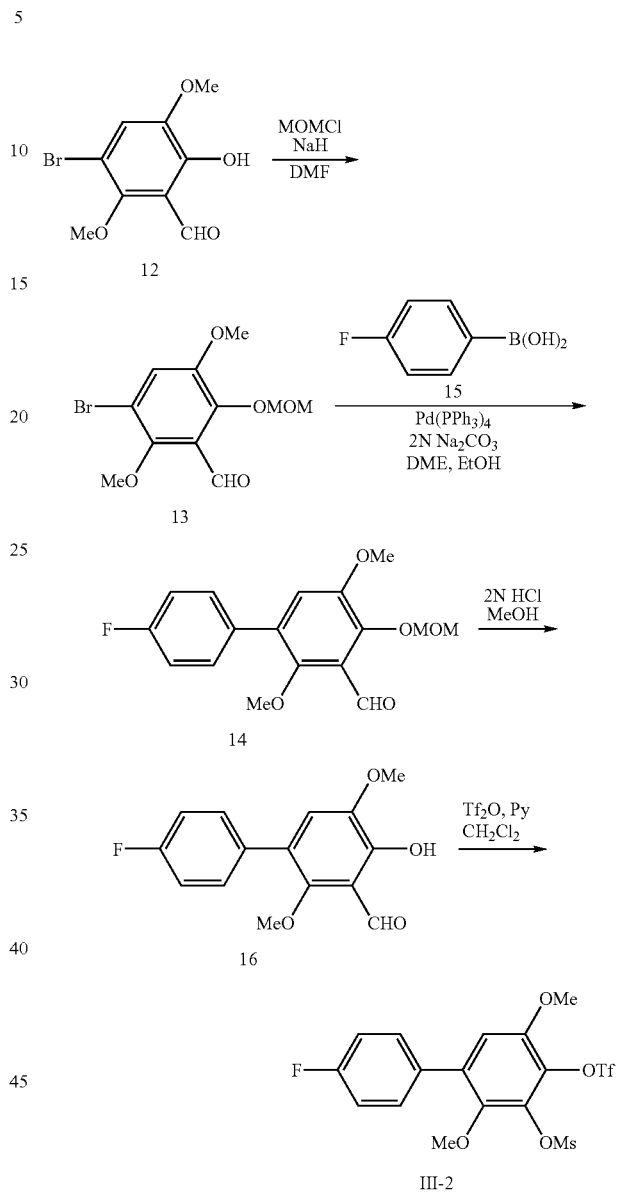

(Step 1) Synthesis of the Compound 13

To 26 ml of a solution of 2.61 g (10 mmol) of a compound 12 (Journal of Organic Chemistry, 1987, 52, 4485) in dimethylformamide were added 400 mg (10 mmol) of 60% sodium hydride dispersion in oil and 836 mg (11 mmol) of chloromethyl methyl ether under ice-cooling and stirred for 30 minutes. After warming to room temperature, it was further stirred for 1 hours. The reaction mixture was concentrated under reduced pressure and extracted with ethyl acetate. The extract was washed with 5% aqueous solution of sodium bicarbonate and saturated brine successively, then dried and concentrated. The residue was recrystallized from ethyl acetate-hexane-pentane to give the compound 13 (2.8 g; 92% yield).

(Step 2) Synthesis of the Compound 14

Using an analogous procedure for the compound 8, the compound 14 was obtained as a pale yellow oil (96% yield) from the compound 13 and the compound 15 (Tokyo Kasei Kogyo Co., Ltd.).

(Step 3) Synthesis of the Compound 16

To 16 ml of a suspension of 1.38 g (4.3 mmol) of the compound 14 in methanol was added 4 ml of 2 N aqueous hydrochloric acid and stirred for 1 hour under warming at 60° C. The reaction mixture was concentrated under reduced pressure and extracted with ethyl acetate. The extract was washed with 5% aqueous sodium bicarbonate and saturated brine successively, then dried and concentrated to give the compound 16 (1.12 g; 94% yield) as a yellow crystalline residue.

(Step 4) Synthesis of the Compound (III-2)

To 12 ml of a solution of the compound 16 (1.12 g; 4.05 mmol) in anhydrous dichloromethane was added 1.02 ml (6.08 mmol) of trifluoromethanesulfonic anhydride and then 980 ml (12.2 mmol) of pyridine under ice-cooling and stirred for 30 minutes. The reaction mixture was allowed to warm to room temperature and stirred for additional 2 hours and the solvent was removed. The residue was extracted with ethyl acetate, washed with 5% aqueous sodium bicarbonate and saturated brine successively, then dried and concentrated. The obtained crude product was purified by silica gel chromatography to give 1.23 g of the compound (III-2) (74% yield) as a white crystalline residue.

Example 3

Synthesis of the Compounds (I-5), (I-6) and (I-7)

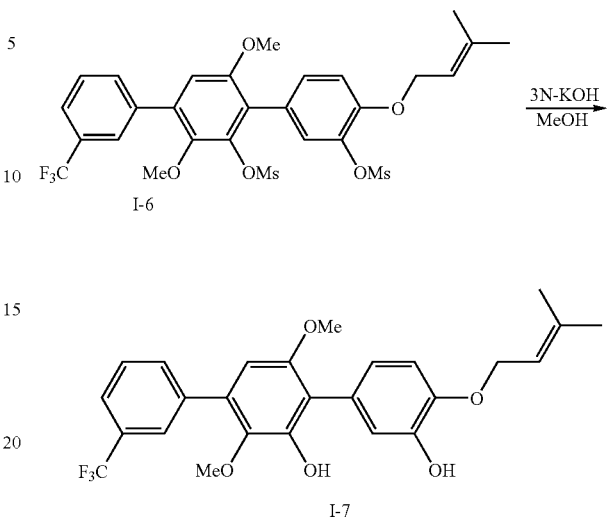

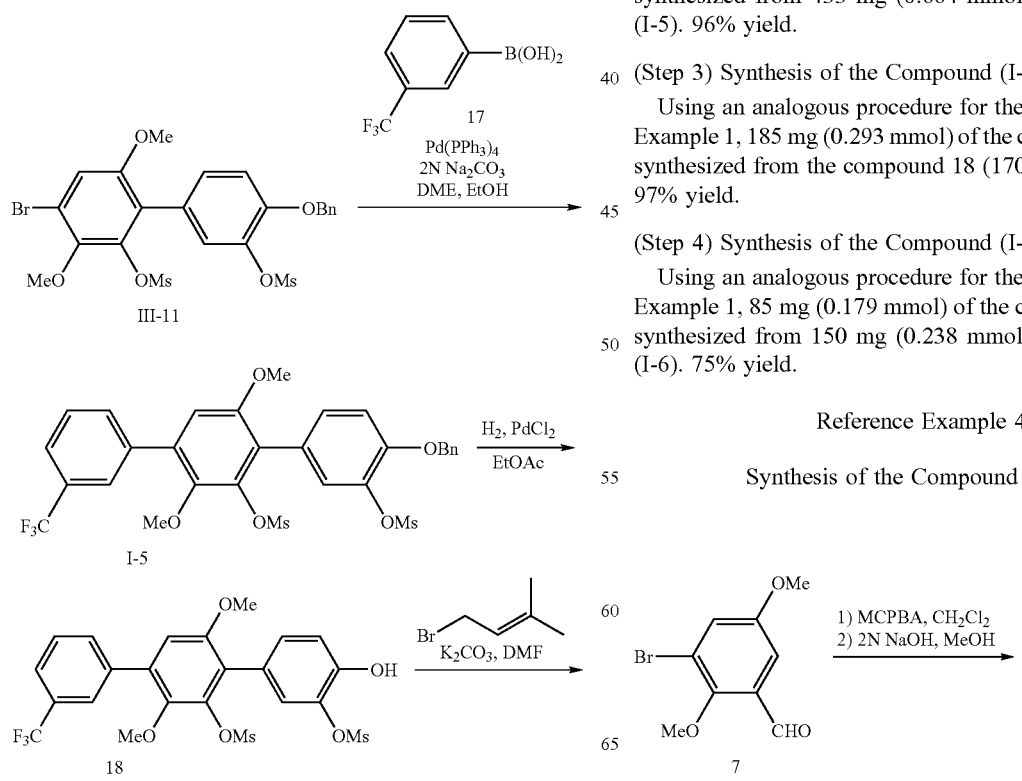

(Step 1) Synthesis of the Compound (I-5)

Using an analogous procedure for the compound 1 in Example 1, 634 mg (0.972 mmol) of the compound (I-5) was synthesized from 881 mg (1.50 mmol) of the compound (III-11) and 370 mg (1.95 mmol) of 3-trifluoromethyl boric acid. 65% yield.

(Step 2) Synthesis of the Compound 18

Using an analogous procedure for the compound 3 in Example 1, the compound 18 (360 mg; 0.640 mmol) was synthesized from 433 mg (0.664 mmol) of the compound (I-5). 96% yield.

(Step 3) Synthesis of the Compound (I-6)

Using an analogous procedure for the compound (I-3) in Example 1, 185 mg (0.293 mmol) of the compound (I-6) was synthesized from the compound 18 (170 mg; 0.302 mmol). 97% yield.

(Step 4) Synthesis of the Compound (I-7)

Using an analogous procedure for the compound (I-1) in Example 1, 85 mg (0.179 mmol) of the compound (I-7) was synthesized from 150 mg (0.238 mmol) of the compound (I-6). 75% yield.

Reference Example 4

Synthesis of the Compound (III-11)

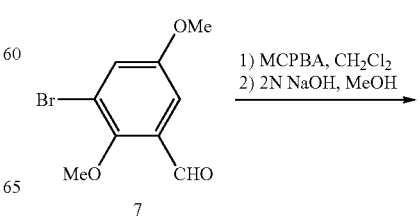

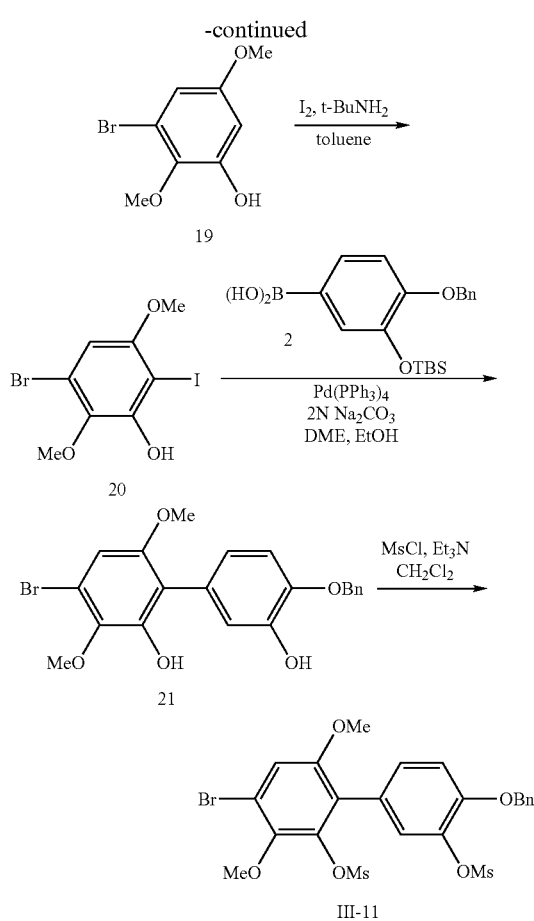

(Step 1) Synthesis of the Compound 19

Using an analogous procedure for the compound 10 in Reference Example 2, the compound 19 (24.04 g; 103 mmol) was synthesized from the compound 7 (40.03 g; 163 mmol). 63% yield.

(Step 2) Synthesis of the Compound 20

To a solution of tert-butylamine (5.0 ml; 47.8 mmol) in 10 ml of toluene was added iodine (5.94 g; 23.39 mmol) under a nitrogen atmosphere and stirred for 50 minutes at room temperature. The compound 19 (5.46 g; 23.43 mmol) was added to the solution under ice-cooling, then warmed to room temperature and stirred for 6 days. The reaction mixture was poured into 1 M of aqueous sodium thiosulfate and extracted with ethyl acetate. The extract was washed with 1 M aqueous sodium thiosulfate and saturated brine successively, then dried and concentrated to give the compound 20 (8.30 g; 23.16 mmol). 99% yield.

(Step 3) Synthesis of the Compound 21

Using an analogous procedure for the compound 1 in Example 1, the compound 21 (2.10 g; 4.87 mmol) was synthesized from the compound 20 (8.70 g; 24.20 mmol). 20% yield.

(Step 4) Synthesis of the Compound (III-11)

Using an analogous procedure for the compound (I-2) in Example 1, 2.61 g (4.44 mmol) of the compound (III-11) was synthesized from the compound 21 (3.20 g; 7.42 mmol). 60% yield.

Example 4

Synthesis of the Compound (I-9)

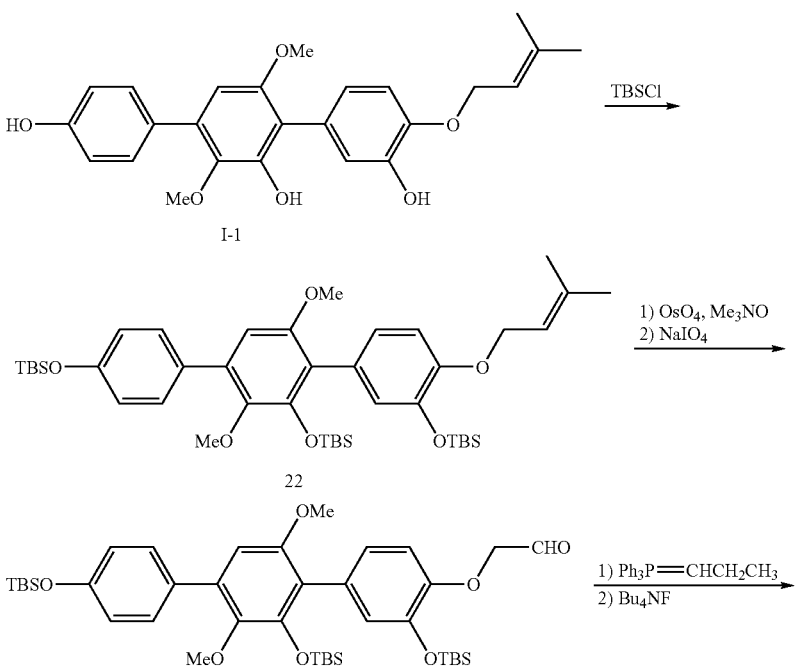

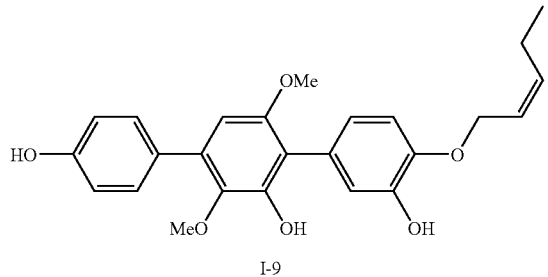

I-9

(Step 1) Synthesis of the Compound 22

Using an analogous procedure described in Reference Example 1, 1.53 g (3.63 mmol) of the compound (I-1) was silylated and the obtained crude product was crystallized from methanol to obtain the compound 22 (2.62 g; 95% yield) as colorless crystals.

(Step 2) Synthesis of the Compound 23

To a solution of the compound 22 (2.38 g; 3.1 mmol) in 90 ml of acetone were added 415 mg (3.74 mmol) of trimethylamine-N-oxide dihydrate and 1.60 ml of 5% aqueous solution of osmium tetroxide (0.3 mmol) and stirred for 1 hour at room temperature. After 20 ml of water was added to the reaction mixture, 4.0 g of sodium bicarbonate and 4.0 g of sodium bisulfite were added and stirred for 30 minutes. The reaction mixture was concentrated under reduced pressure and the residue was extracted with ethyl acetate. The extract was washed with saturated brine, then dried and concentrated.

A solution of 1.96 g (9.16 mmol) of sodium periodate in 33 ml of water was added dropwise to a solution of 2.46 g of the residue obtained by the above method in 90 ml of ethanol with stirring at room temperature. After stirring for 2 hours, 100 ml of water was added to the reaction mixture and the precipitate was collected by filtration and dried to give the compound 23 (1.98 g; 87% yield) as powder.

(Step 3) Synthesis of the Compound (I-9)

To a suspension of 146 mg (0.38 mmol) of n-propyltriphenylphosphonium bromide in 2.5 ml of anhydrous tetrahydrofuran was added 32 mg (0.29 mmol) of potassium tert-butoxide in a nitrogen atmosphere at 0° C. and stirred at the same temperature for 1 hour. The reaction mixture was cooled to −78° C., a solution of the compound 23 (70 mg; 0.095 mmol) in 1.5 ml of anhydrous tetrahydrofuran was added and stirred for 30 minutes at the same temperature and for additional 1 hour at room temperature. The reaction mixture was poured into an ice-cooling aqueous solution of saturated ammonium chloride and extracted with ethyl acetate. The extract was washed with saturated brine, then dried and concentrated.

Using an analogous procedure described in Example 2 Step 2, 70 mg of the residue obtained by the above method was desilylated and the obtained crude product was purified by silica gel chromatography (toluene-ethyl acetate 4:1) to give 37 mg of the compound (I-9) as pale yellow crystals.

Example 5

Synthesis of the Compound (I-565)

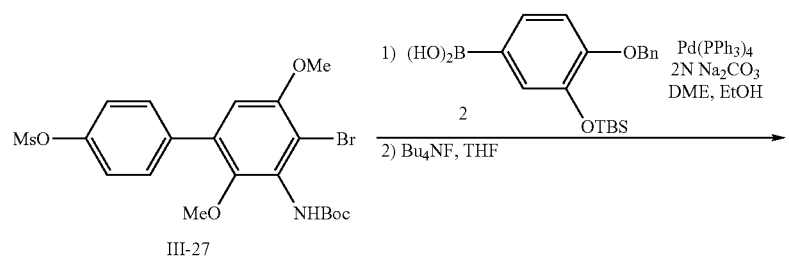

III-27

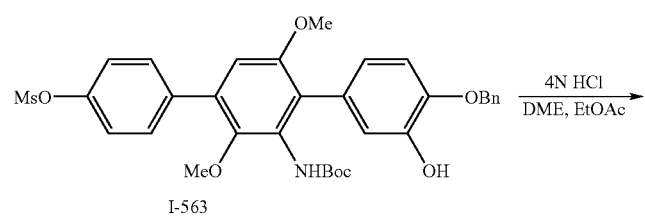

I-563

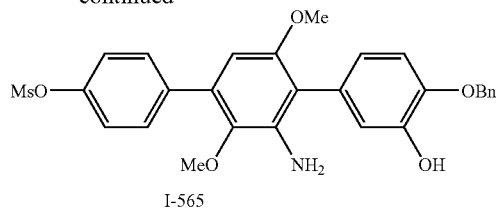
I-565

(Step 1) Synthesis of the Compound (I-563)

Using an analogous procedure for the compound 2 in Example 1, 850 mg of the compound (1–563) was obtained from a compound (III-27) (800 mg; 1.59 mmol) and the compound 2 (1.25 g; 3.50 mmol) as colorless crystals (86% yield).

(Step 2) Synthesis of the Compound (I-565)

To a solution of 120 mg (0.193 mmol) of the compound (I-563) in 3 ml dimethoxyethane and 1 ml of ethyl acetate was added 2.4 ml of 4 N hydrochloric acid at 40° C. and stirred at the same temperature for 2 hours 20 minutes. After cooling, the reaction mixture was neutralized with aqueous solution of saturated sodium bicarbonate and extracted with ethyl acetate. The extract was washed with saturated aqueous solution of sodium bicarbonate and saturate brine, then dried and concentrated. The obtained crude product was crystallized from hexane-ethyl acetate to give 93 mg of the compound (I-565) as pale yellow crystals (92% yield).

Reference Example 5

Synthesis of the Compound (III-27)

(Step 1) Synthesis of the Compound 24

In a mixture of 17.5 ml of tert-butanol and 5.3 ml of 2-methyl-2-butene was suspended 415 mg (1.00 mmol) of the compound (III-24), 6.7 ml of aqueous solution of 724 mg (8.00 mmol) of sodium chlorite and 968 mg (6.20 mmol) of sodium dihydrogen phosphate dihydrate was added and stirred at the same temperature for 4 hours 30 minutes. The solution of 1 M sodium thiosulfate was added to the reaction mixture and the mixture was extracted with ethyl acetate. Then, organic layer was extracted with aqueous solution of saturated sodium bicarbonate. Then the aqueous layer was acidified with conc. hydrochloric acid and extracted with ethyl acetate. The extract was washed with saturated brine, then dried and concentrated to give the compound 24 (384 mg; 89% yield) as colorless crystals.

(Step 2) Synthesis of the Compound (III-27)

To 10 ml of a suspension of the compound 24 (1.50 g; 3.48 mmol) in tert-butanol were added 0.533 ml (3.83 mmol) of triethylamine, followed by 0.825 ml (3.83 ml) of diphenyl phosphate azide, and the mixture was stirred at 100° C. for 23 hours. After the reaction mixture was cooled, water was added to it and the mixture was extracted with ethyl acetate. The extract was washed with saturated aqueous solution of sodium bicarbonate and saturated brine, then dried and concentrated. The residue was purified by silica gel chromatography (hexane-ethyl acetate 2.5:1) to give 1.43 g of the compound (III-27) as colorless form product (82% yield).

Example 6

Synthesis of the Compound (1–480)

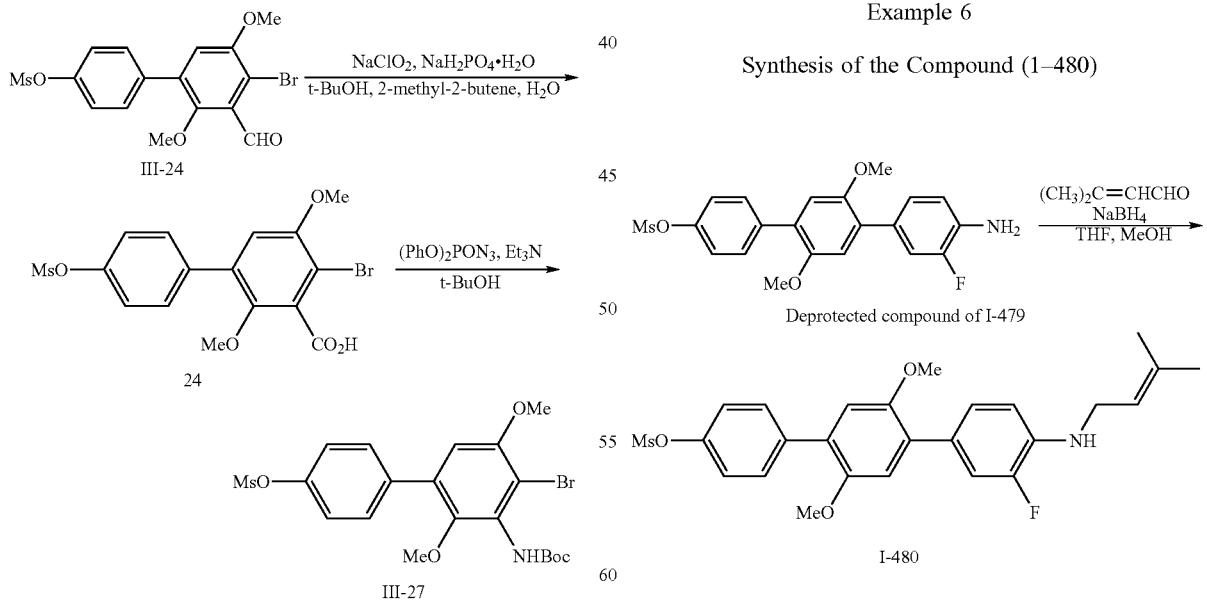

To a solution of 120 mg of a compound which was eliminated a Boc group of the compound (I-479) in 2 ml of tetrahydrofuran and 0.5 ml of methanol were added 33 ml (0.34 mmol) of 3-methyl-2-butenal and 90 ml (0.26 mmol) of 3 M aqueous solution of sulfuric acid at 0° C. and stirred for 10 minutes. Further, 19.6 mg of sodium borohydride was added in small portions to the mixture and stirred at room temperature for 1 hour. The saturated aqueous solution of sodium bicarbonate was added to the reaction mixture and extracted with ethyl acetate. The extract was washed with saturated brine, then dried and concentrated. The residue was purified by silica gel chromatography (hexane-ethyl acetate 3:1) to give 98 mg of the compound (I-480) as colorless crystals (78% yield).

Example 7

Synthesis of the Compound (I-628)

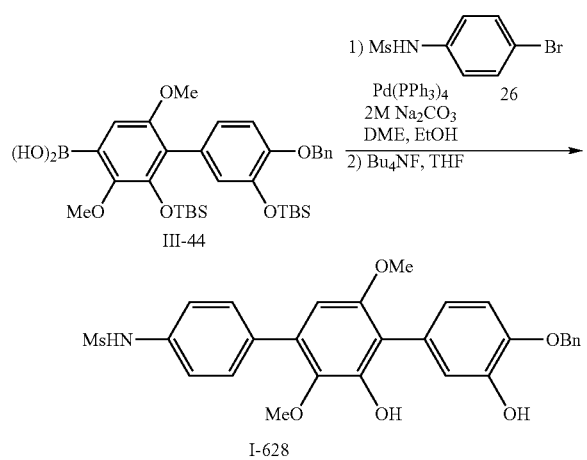

Using an analogous procedure for the compound 1 in Example 1, 1.2 g (2 mmol) of the compound (III-44) was reacted with 551 mg (2.2 mmol) of 4-bromomethanesulfonyl anilide were reacted, followed by desilylated by an analogous procedure described in Example 1 Step 2. The obtained crude product was crystallized from ethyl acetate-hexane to obtain 760 mg of the compound (I-628) as pale yellow crystals (73% yield).

Reference Example 6

Synthesis of the Compound (III-44)

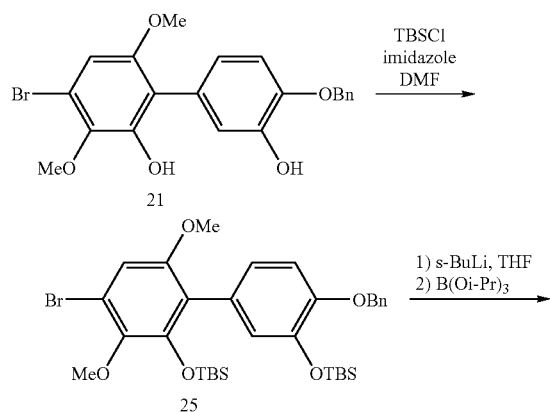

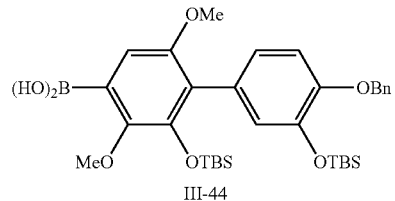

(Step 1) Synthesis of the Compound 25

Using an analogous procedure for the compound 5 in Reference Example 1, a crude product was synthesized by the reaction of 22.2 g (52.7 mmol) of the compound 21, 8.95 g (132 mmol) of imidazole and 17.5 g (1.16 mmol) of tert-butyldimethylsilyl chloride. The obtained product was purified by silica gel chromatography (ethyl acetate:hexane=1:20) and crystallized from ethyl acetate-hexane to give 29.7 g of the compound 25 as colorless crystals (85% yield).

(Step 2) Synthesis of the Compound (III-44)

Using an analogous procedure for the compound 2 in Reference Example 1,402.7 g (610 mmol) of the compound 25 was reacted with 678 ml (814 mmol) of 1.08 N s-butyl lithium in cyclohexane, followed by addition of 282 ml (1.22 mol) of triisopropyl borate to give 246 g of the compound (III-44) as colorless powders (65% yield).

Example 8

Synthesis of the Compound (I-233)

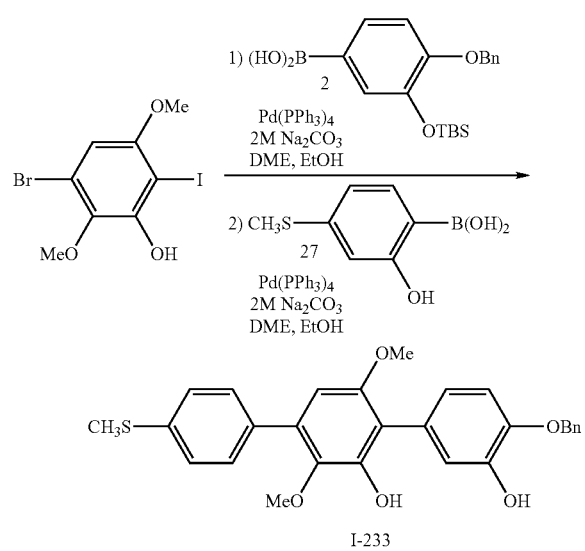

In an argon atmosphere, 2.87 g (8.0 mmol) of the compound 20 was dissolved in 32 ml of dimethoxyethane and 8 ml of ethanol, 3.01 g of the compound 2 and 16 ml of 2 M aqueous solution of sodium carbonate were added and the reaction mixture was degassed. To the mixture was added 462 mg (0.4 mmol) of palladium tetrakistriphenylphosphine and the mixture was heated under refluxing for 2 hours. After the reaction mixture was cooled to room temperature, 2.02 g (12.0 mmol) of 4-methylthiophenyl boronic acid, 462 mg (0.4 mmol) of palladium tetrakistriphenylphosphine, 16 ml of 2 M aqueous solution of sodium carbonate, 32 ml of dimethoxyethane and 8 ml of ethanol were added to it. Then, the reaction mixture was degassed again and heated under refluxing for 16 hours. After the reaction mixture was cooled to room temperature, 100 ml of 5% aqueous citric acid was added and stirred at the same temperature for 1 hour. Ethyl acetate was added to the reaction mixture and the organic layer was washed with 5% aqueous citric acid, water, saturated aqueous solution of sodium bicarbonate and saturated brine successively, then dried and concentrated. The residue was purified by silica gel chromatography (hexane-ethyl acetate 3:1) to obtain 2.13 g of crude crystals. The obtained crude crystals were recrystallized from hexane-ethyl acetate to give 1.66 g of the compound (1–233) as colorless crystals (44% yield)

Example 9

Synthesis of other Compounds

Following compounds (I) were synthesized by analogous procedures described above. The structures and physical constants of the compounds (III) and (I) are as follows.

III-1

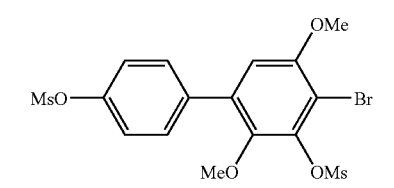

III-2

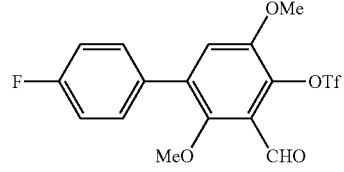

III-3

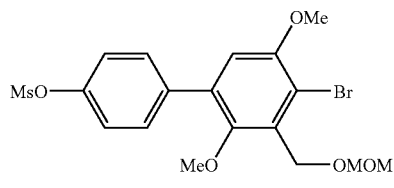

III-4

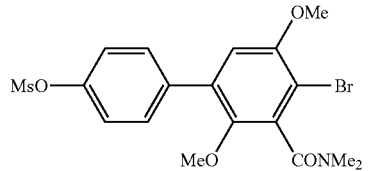

III-5

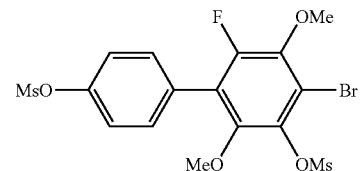

-continued

III-6

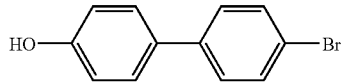

III-7

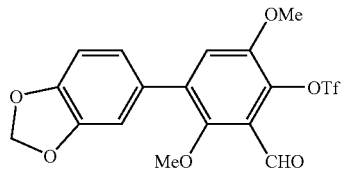

III-8

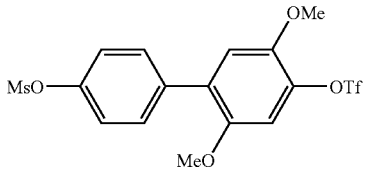

III-9

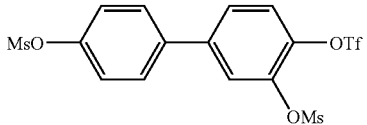

III-10

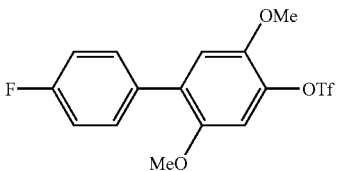

III-11

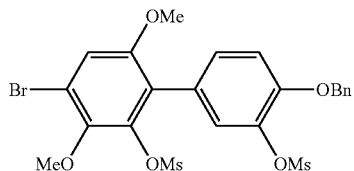

III-12

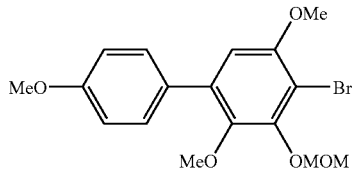

III-13

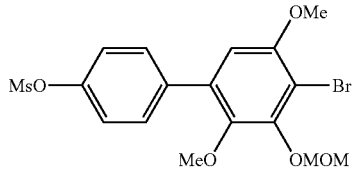

III-14

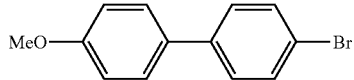

-continued
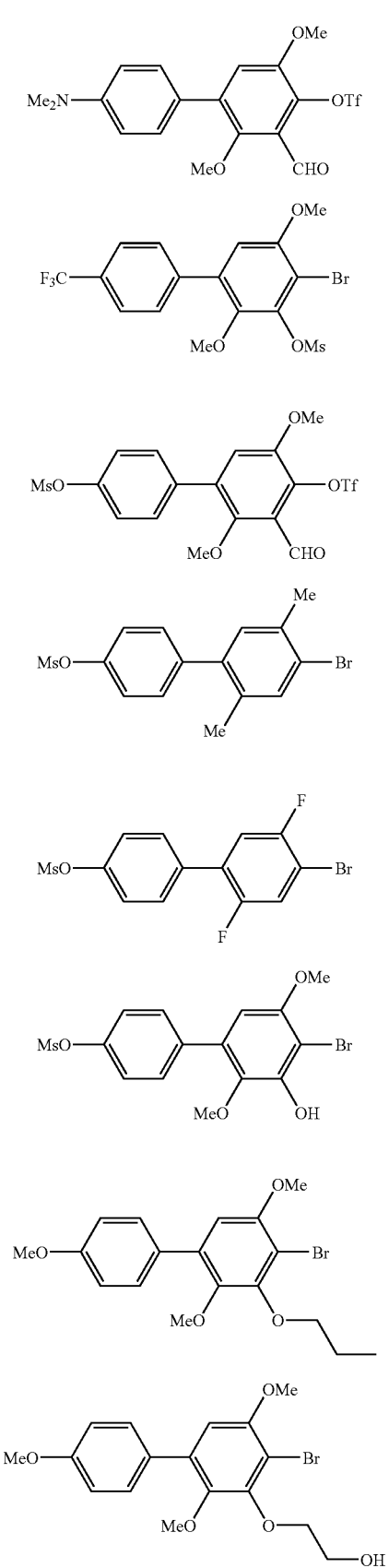
III-15
III-16
III-17
III-18
III-19
III-20
III-21
III-22
-continued
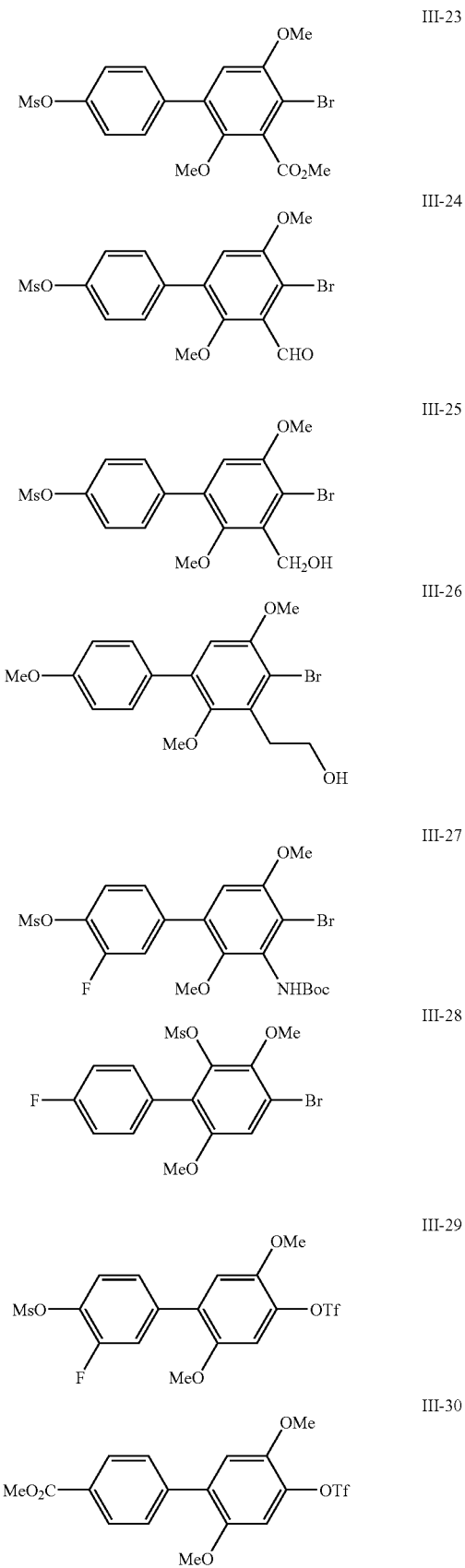
III-23
III-24
III-25
III-26
III-27
III-28
III-29
III-30

-continued
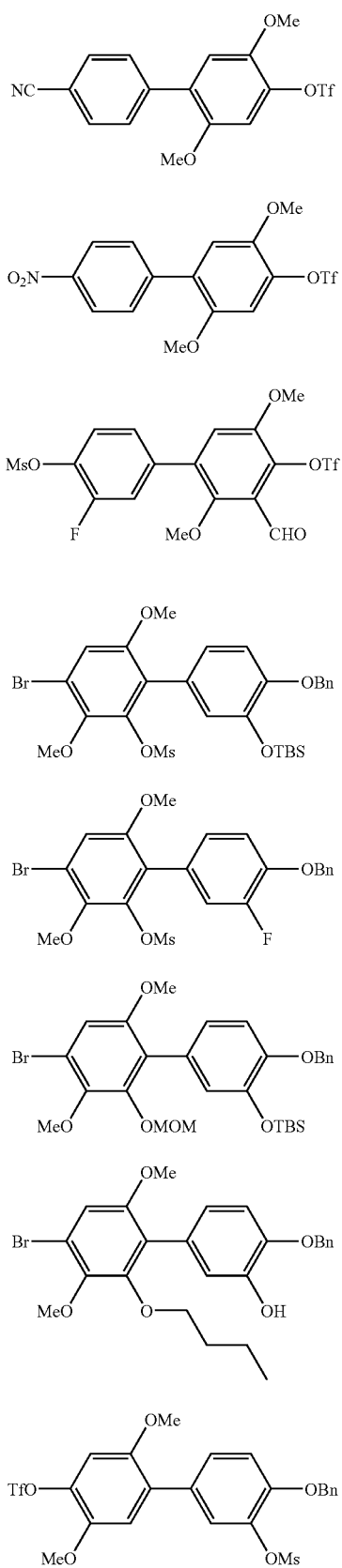
III-31
III-32
III-33
III-34
III-35
III-36
III-37
III-38
-continued
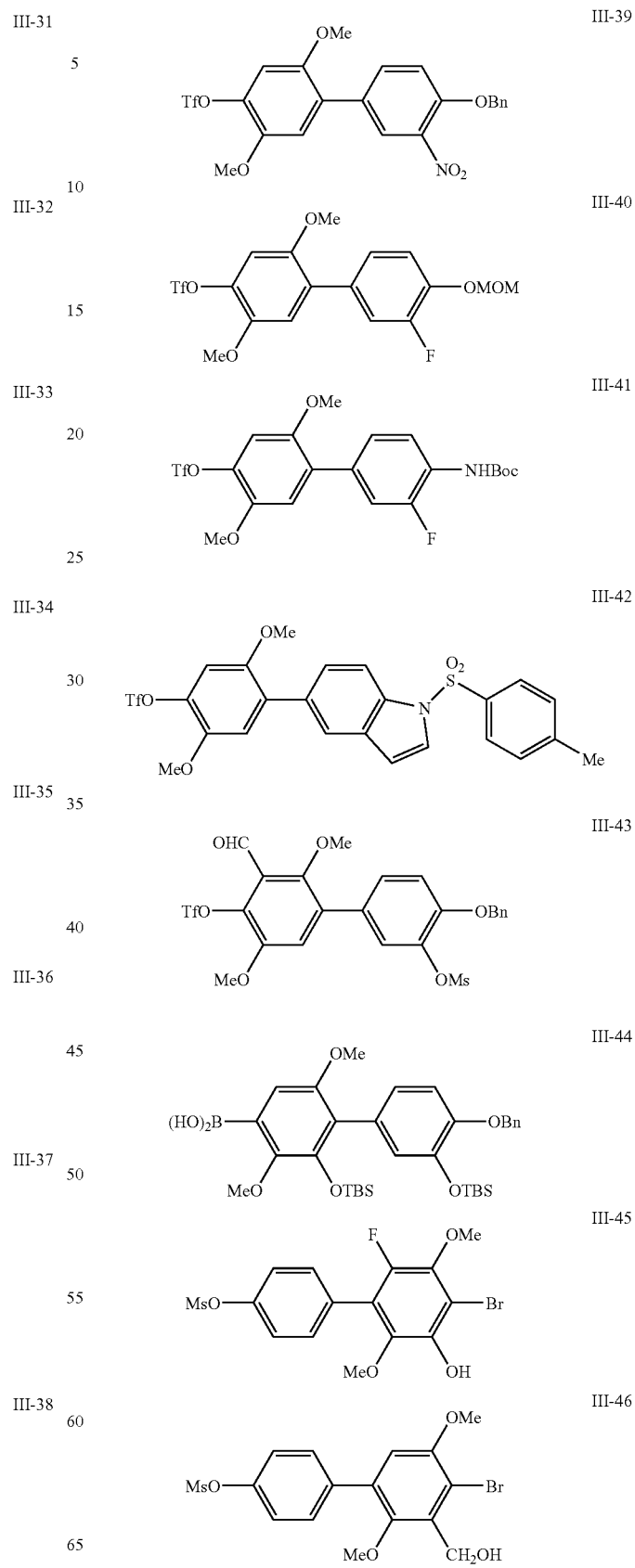
III-39
III-40
III-41
III-42
III-43
III-44
III-45
III-46

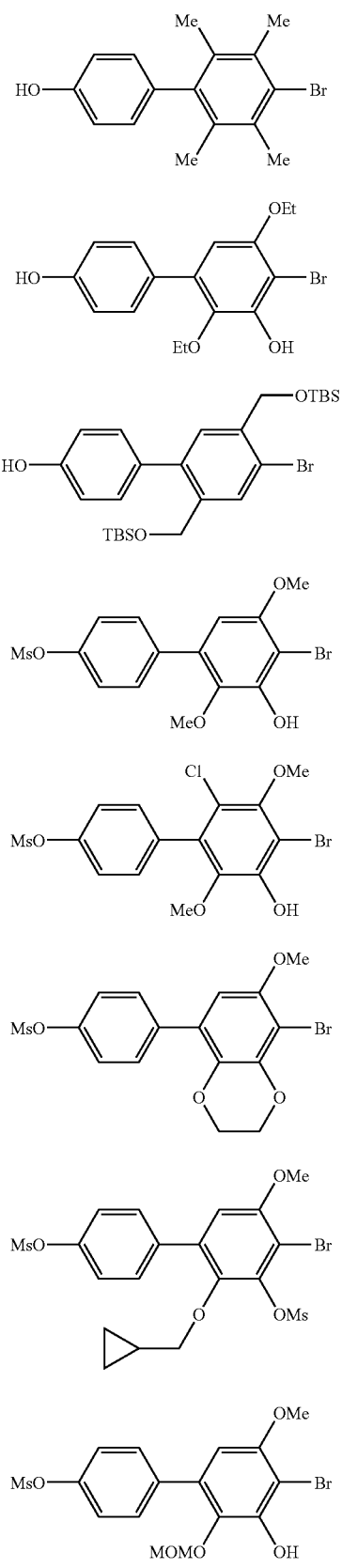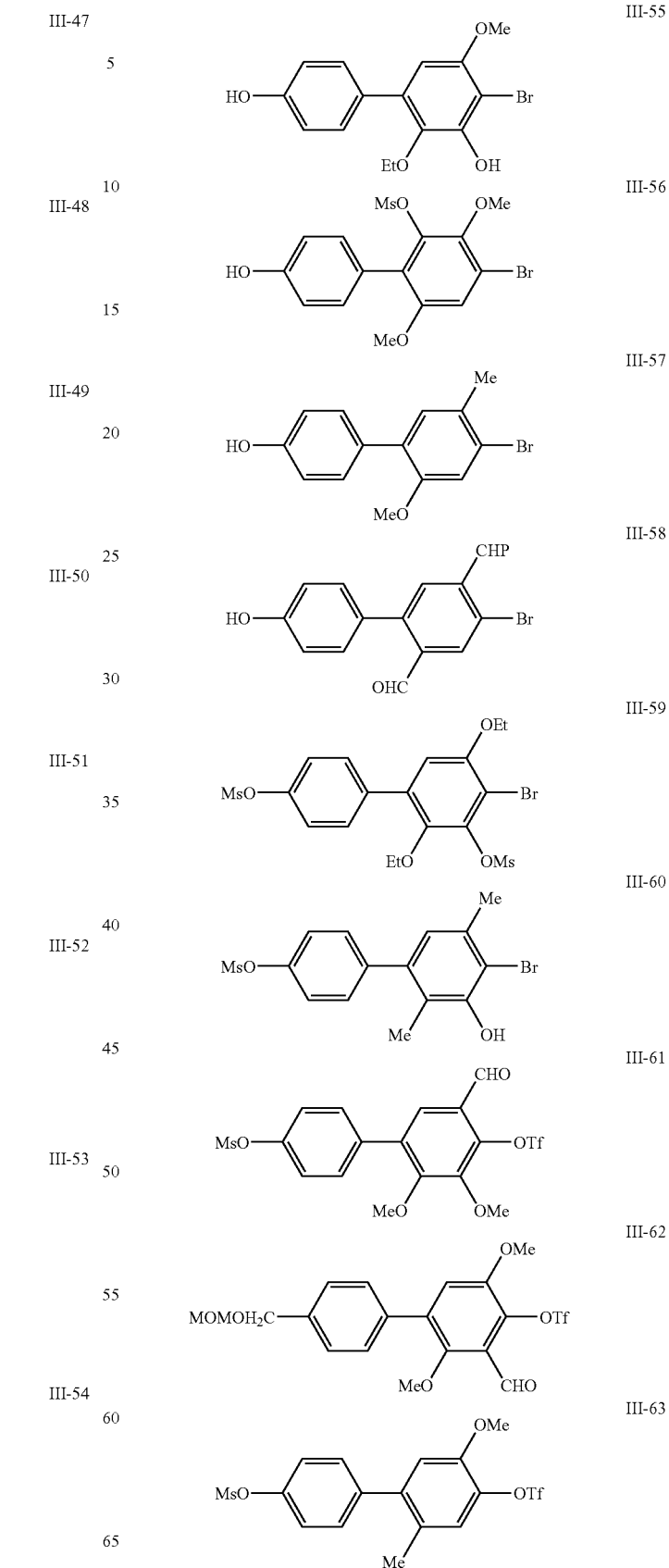

-continued
III-64
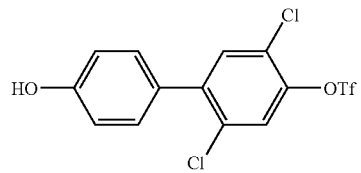
III-65
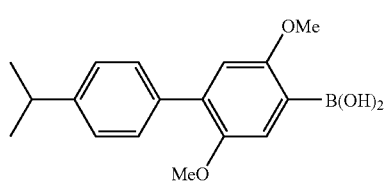
III-66
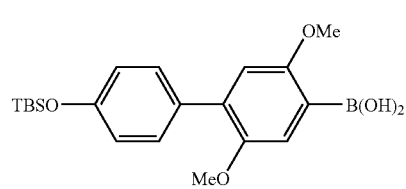
III-67
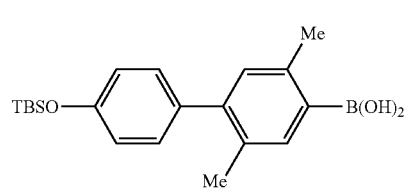
III-68
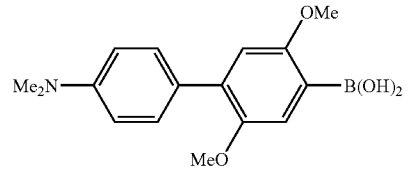
III-69
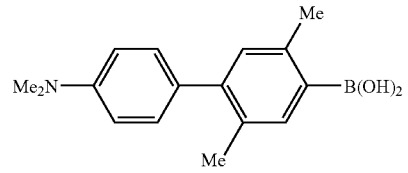
III-70
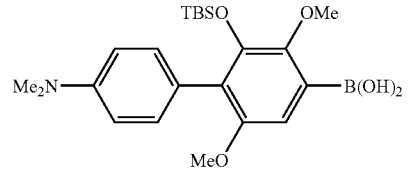
III-71
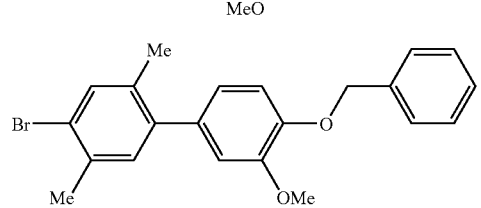
III-72
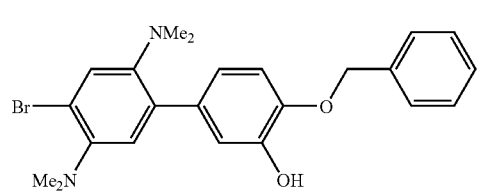
-continued
III-73
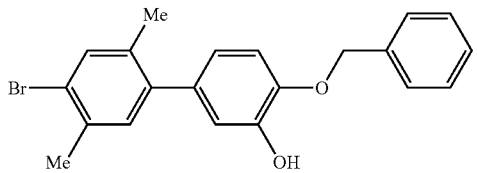
III-74
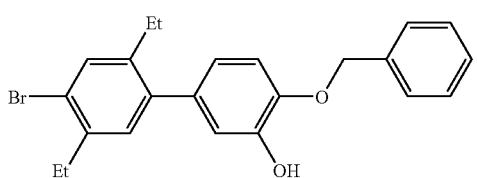
III-75
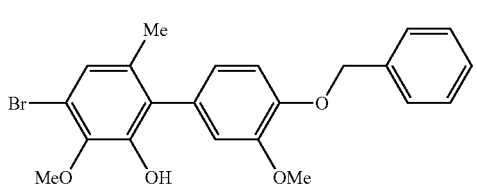
III-76
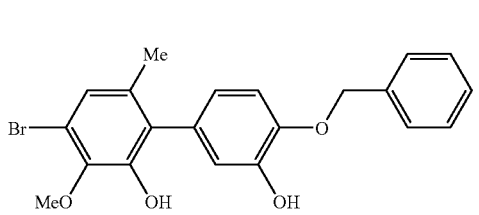
III-77
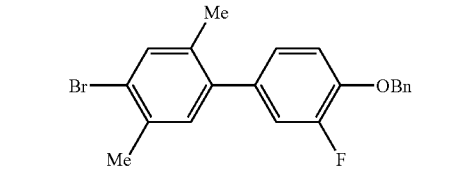
III-78
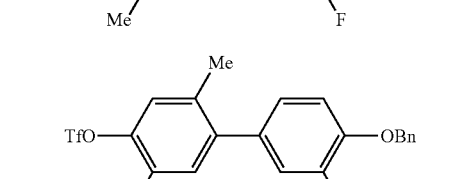
III-79
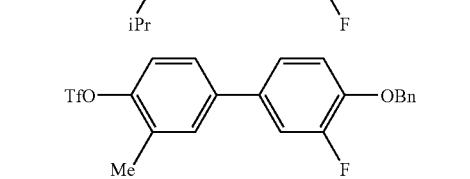
III-80
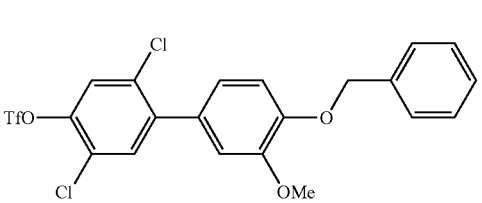
III-81
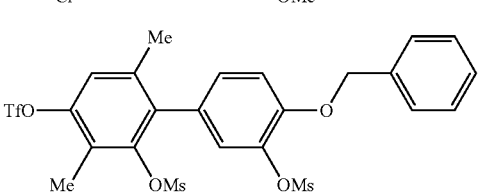

-continued

-continued
I-11
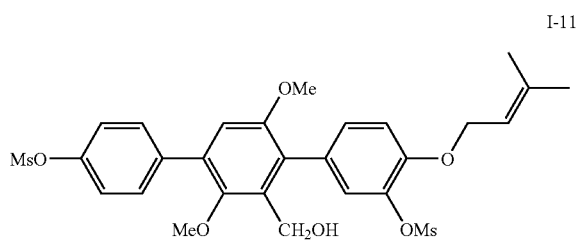
I-12
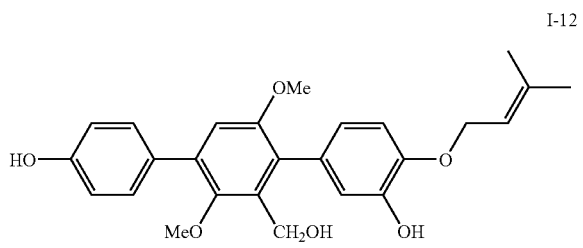
I-13
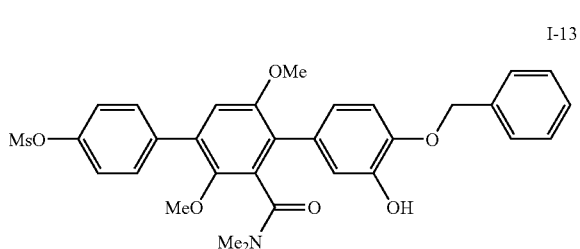
I-14
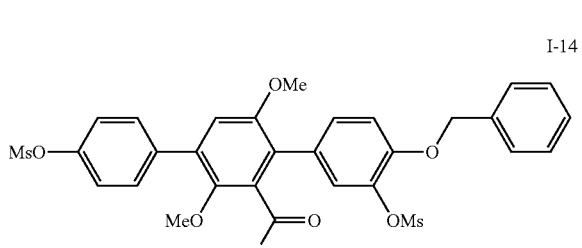
I-15
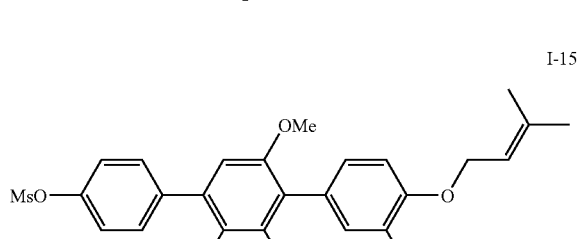
I-16
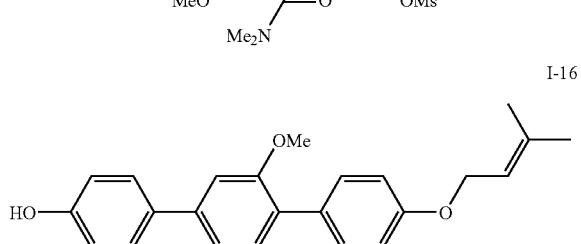
-continued
I-17
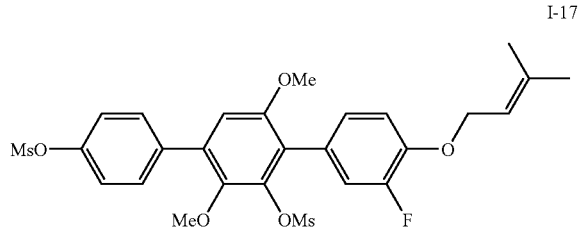
I-18
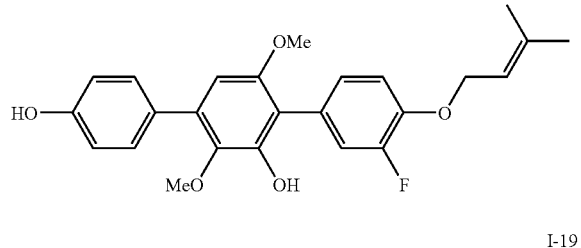
I-19
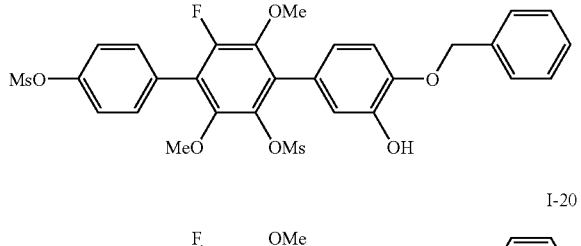
I-20
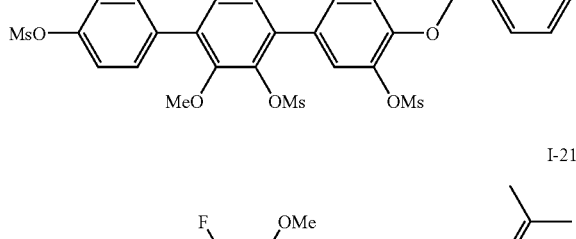
I-21
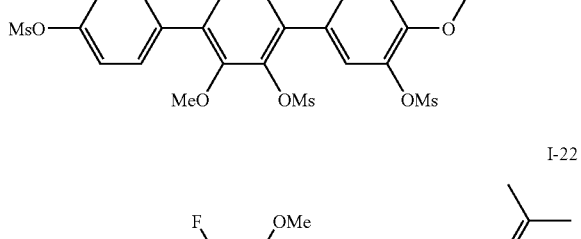
I-22
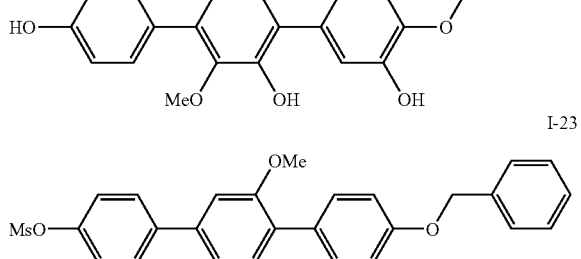
I-23

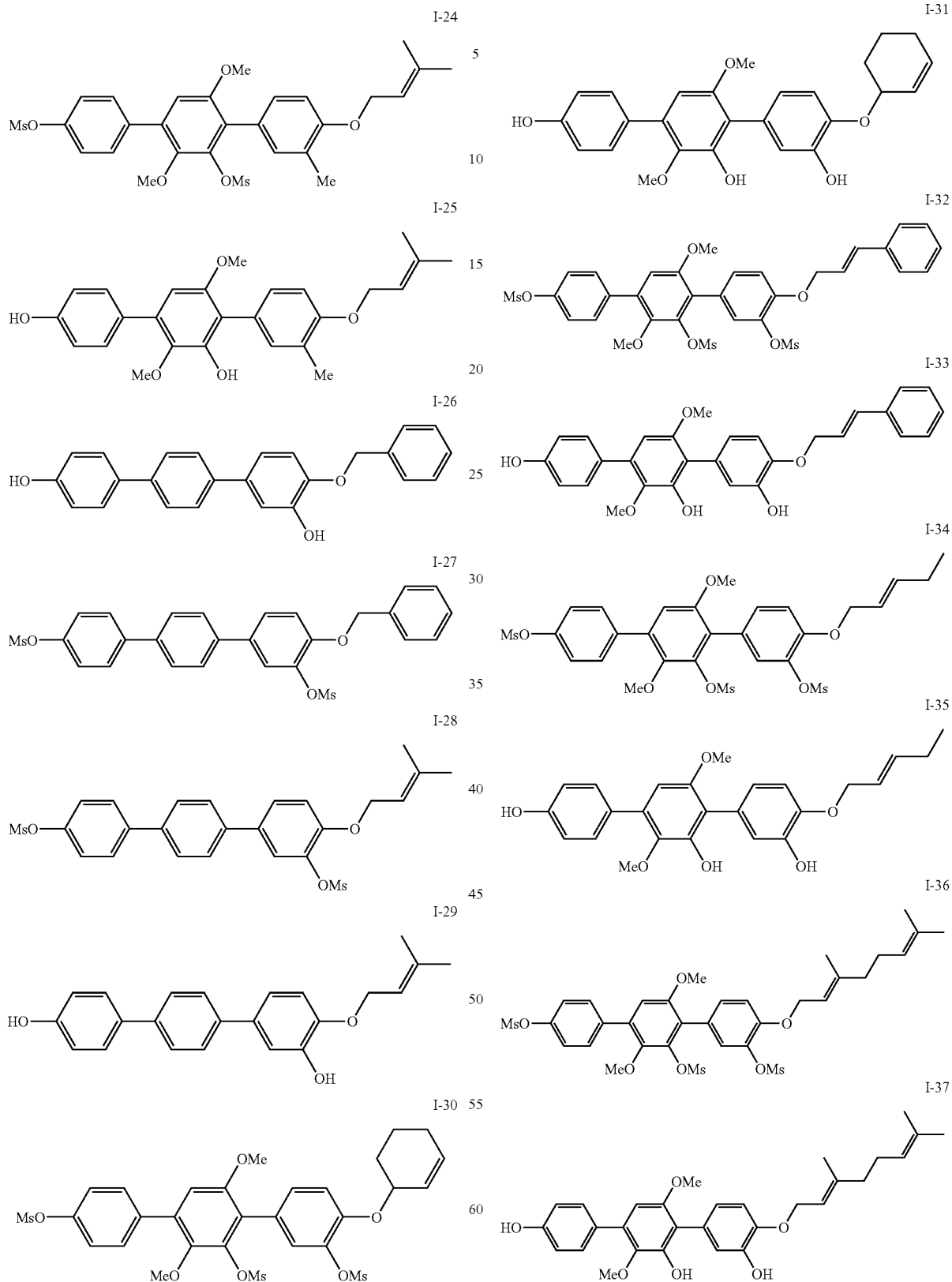



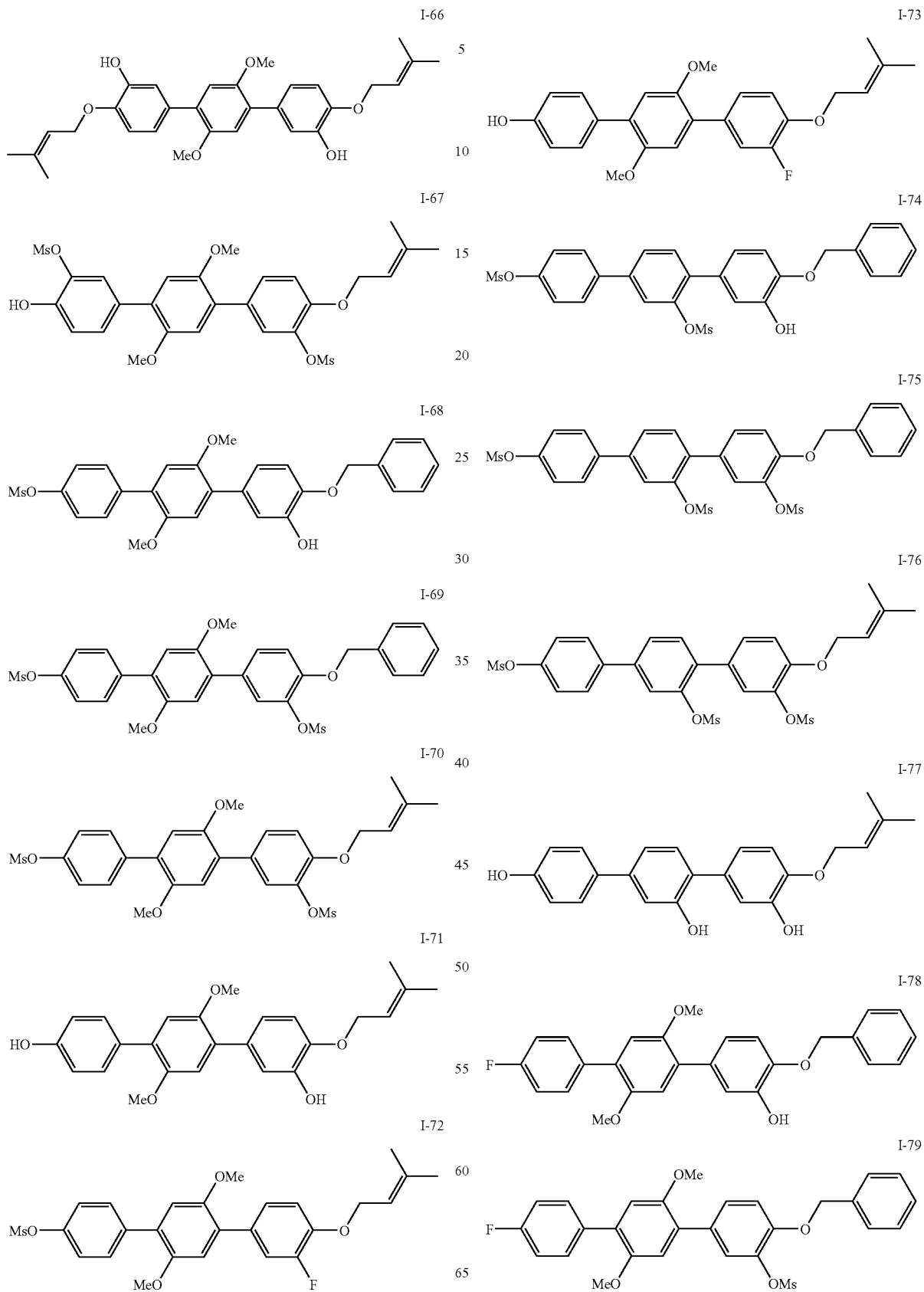

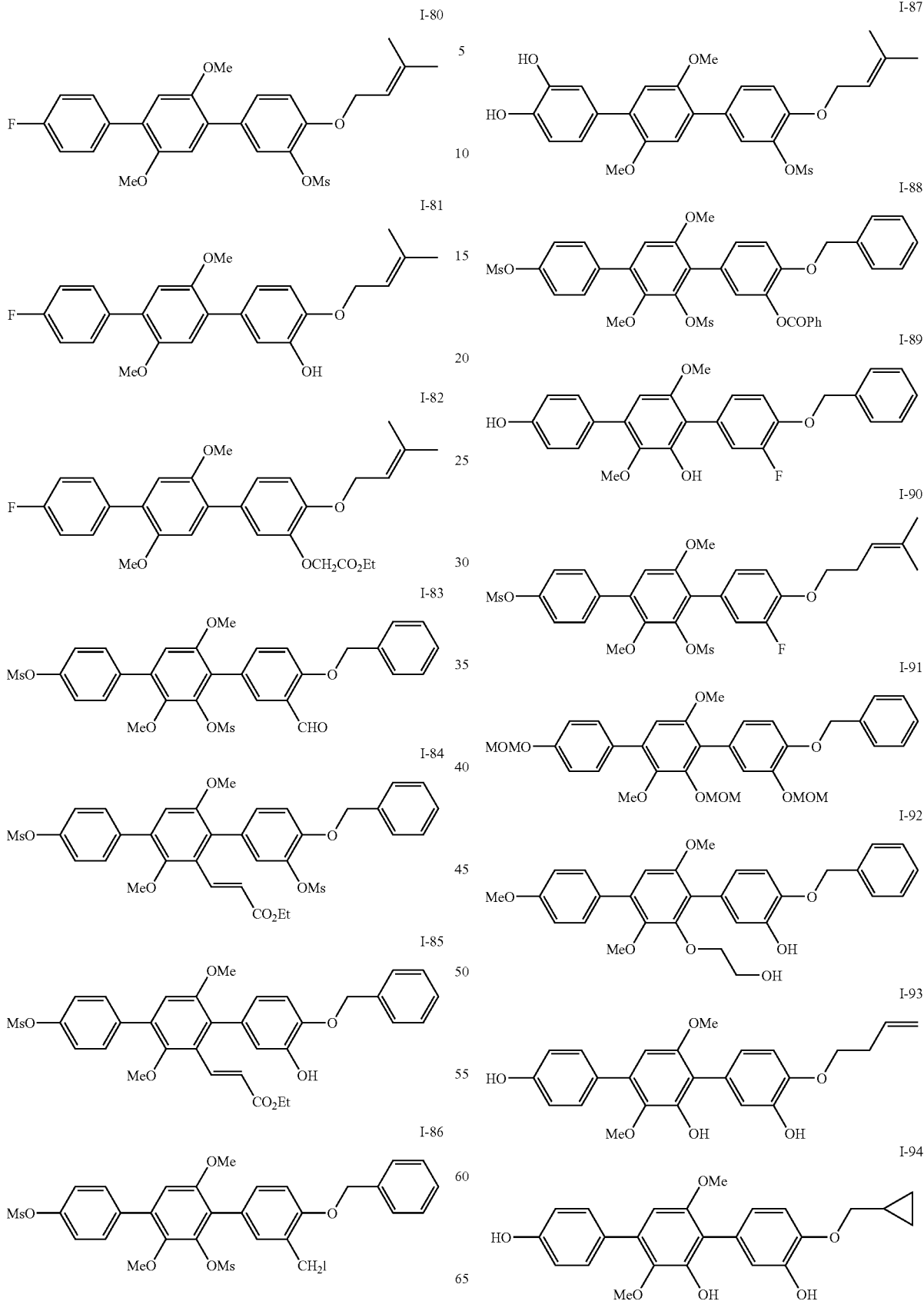

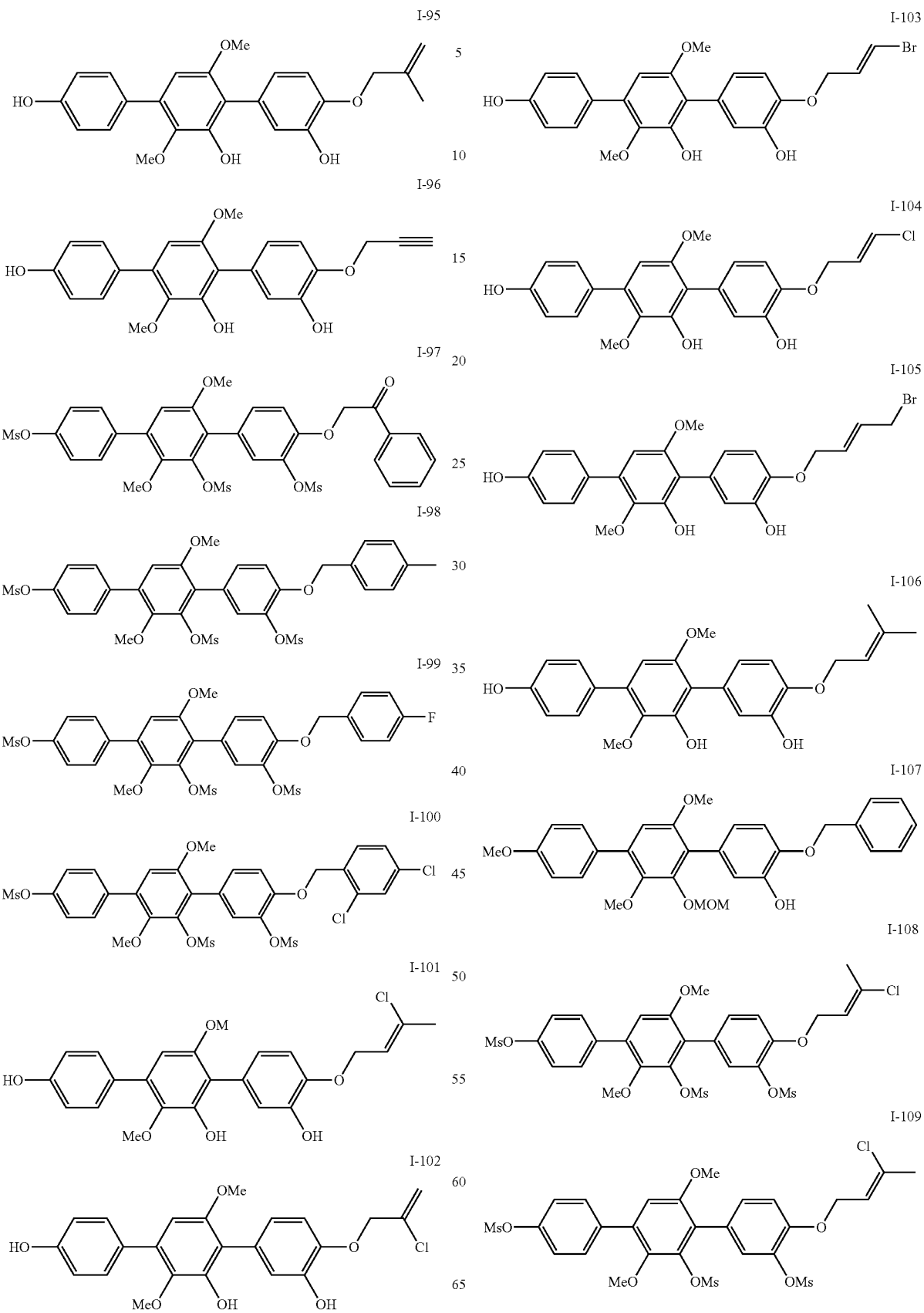

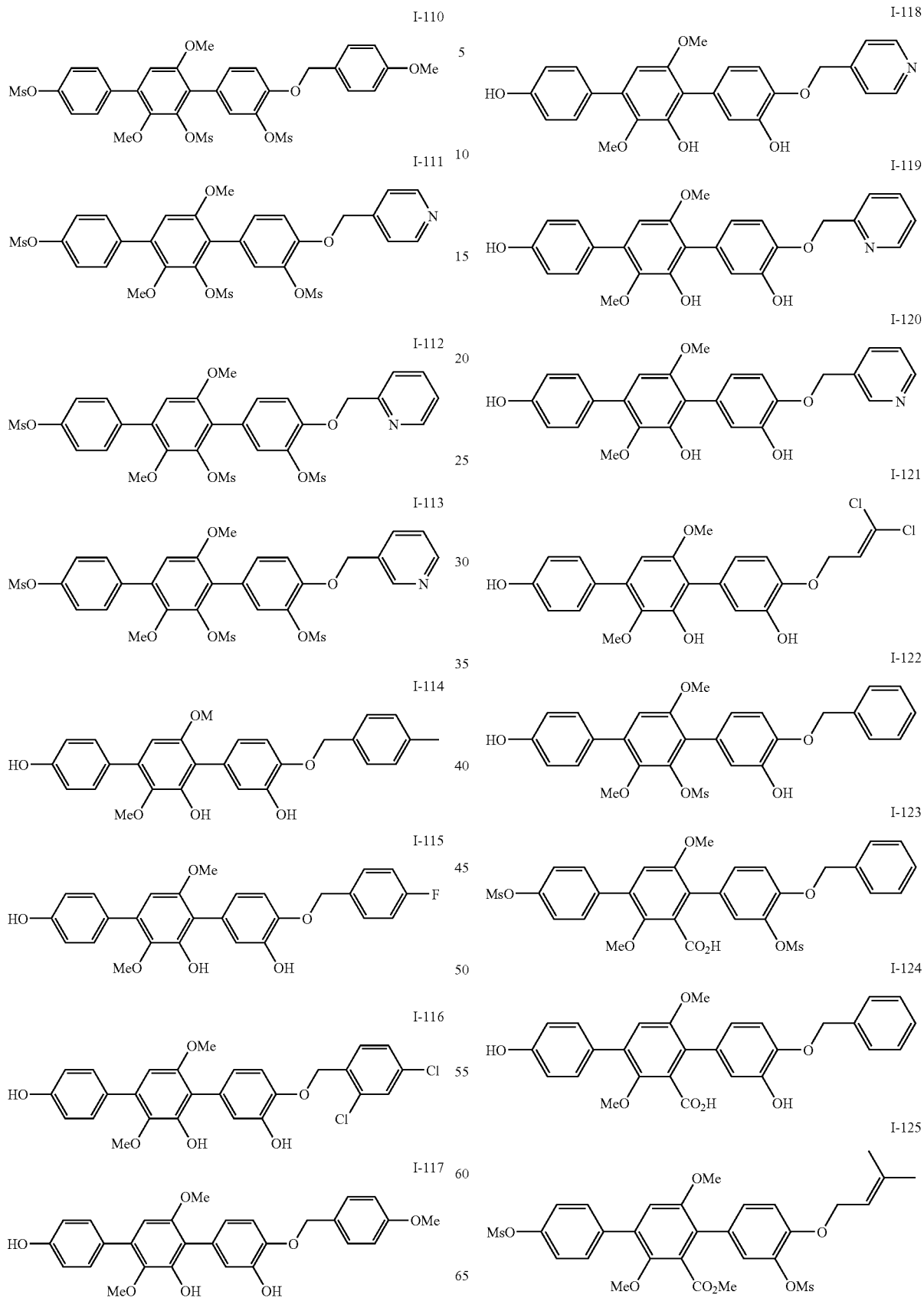

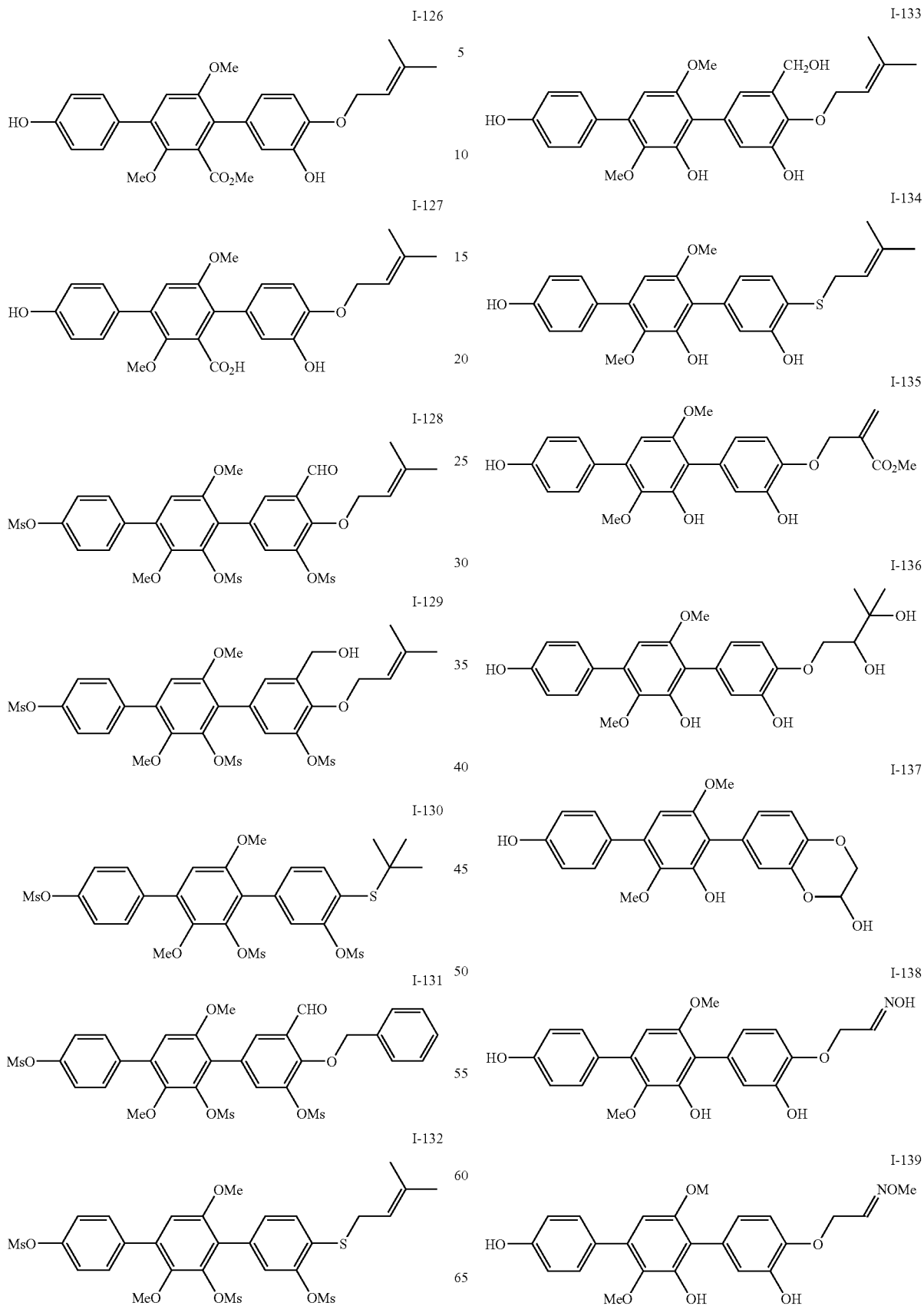

-continued
I-140
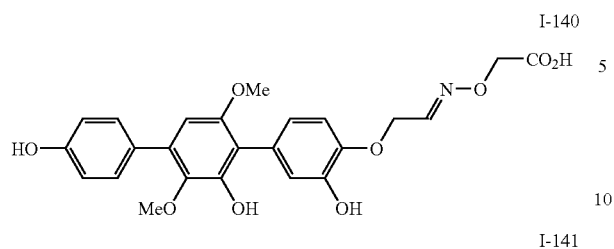
I-141
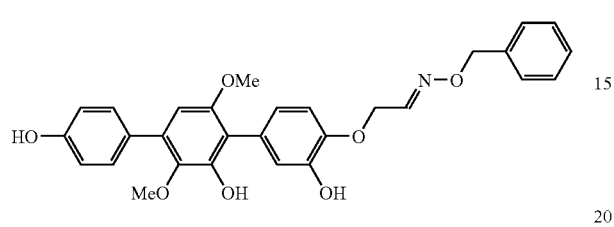
I-142
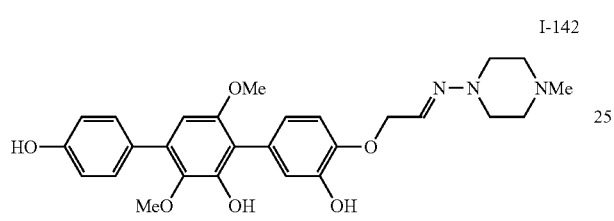
I-143
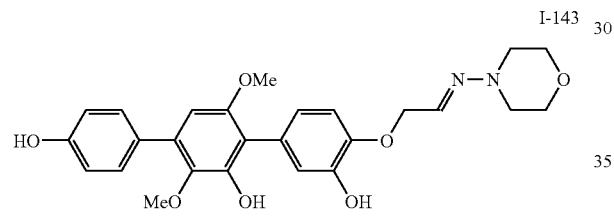
I-144
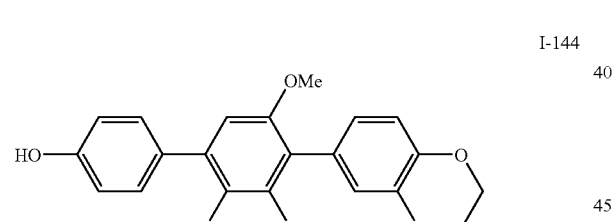
I-145
I-146
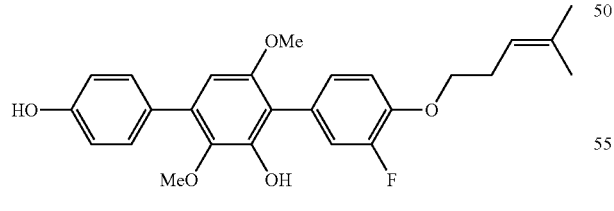
-continued
I-147
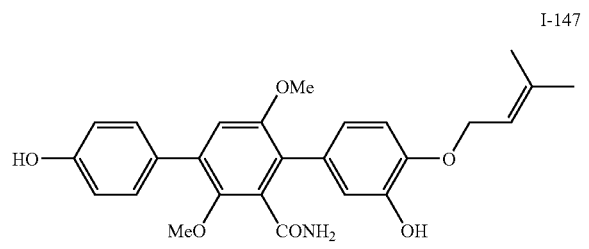
I-148
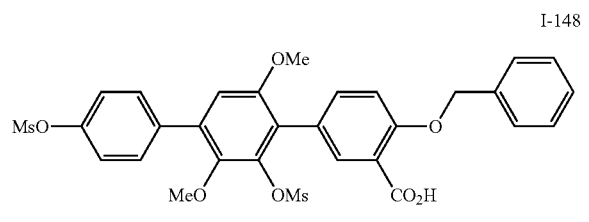
I-149
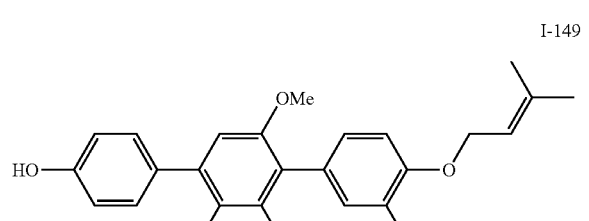
I-150
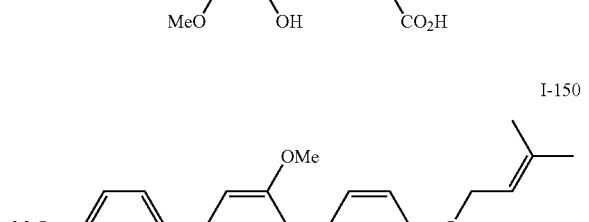
I-151
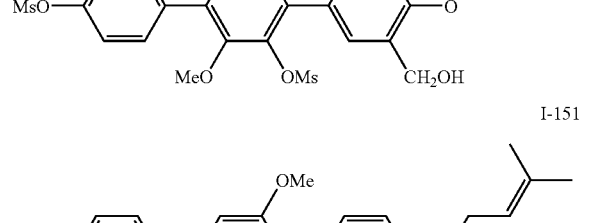
I-152
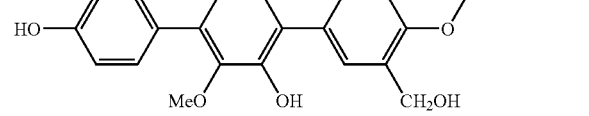
I-153
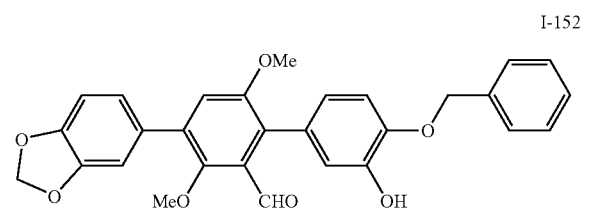

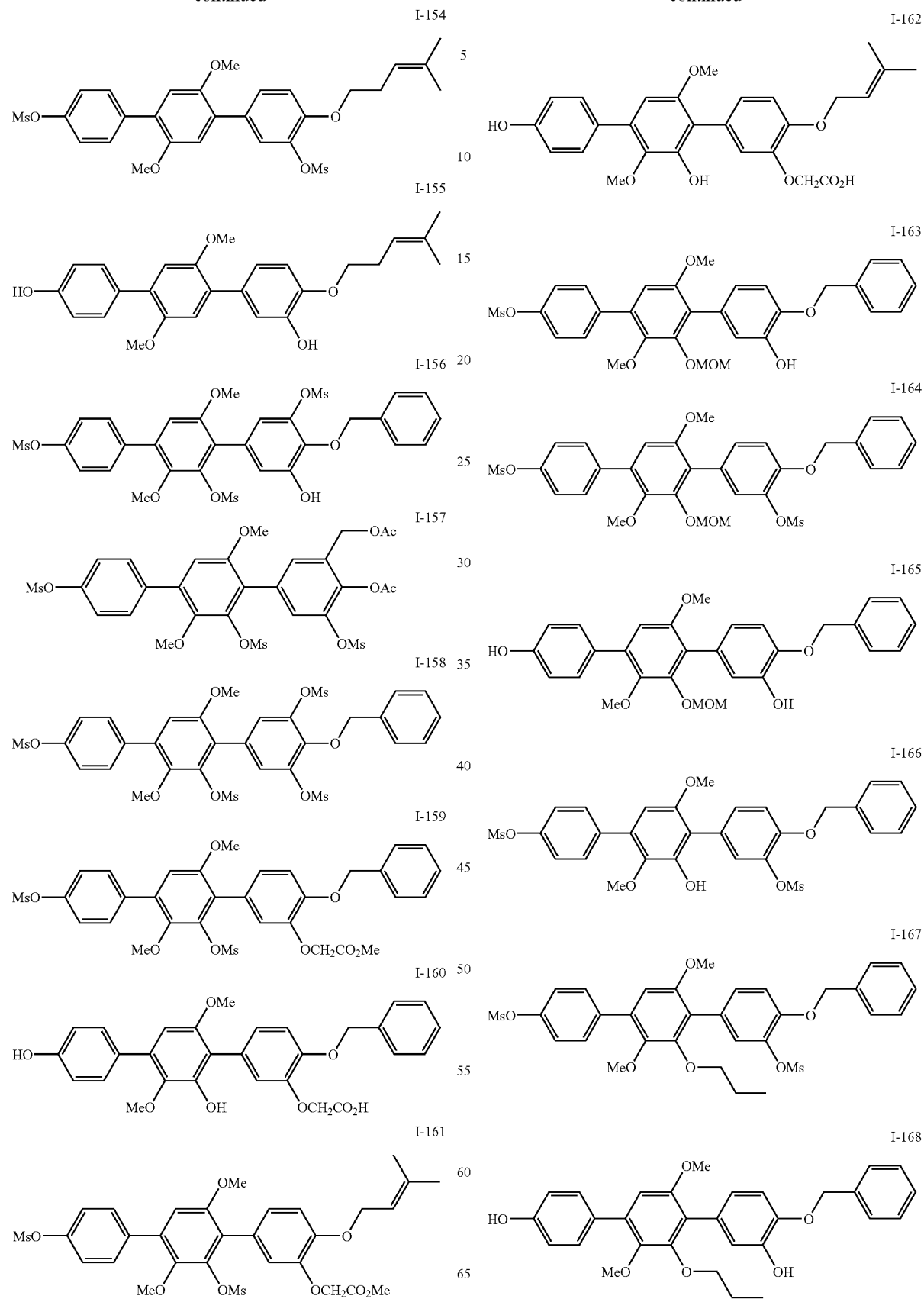

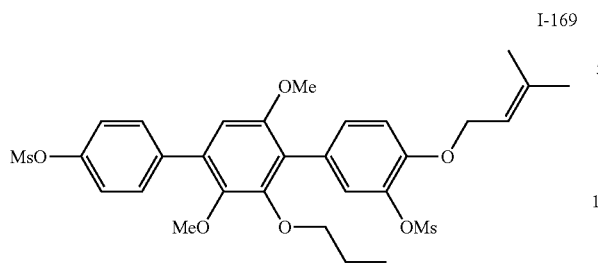
I-169
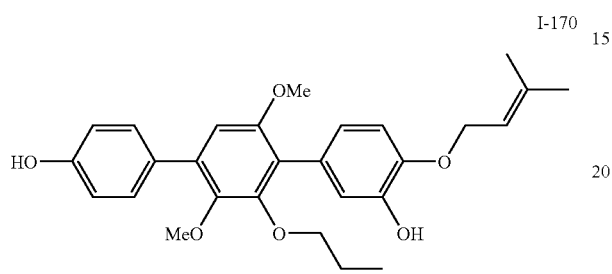
I-170
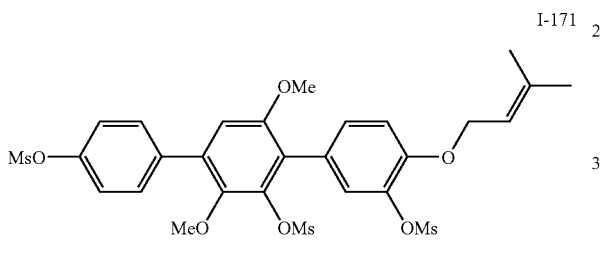
I-171
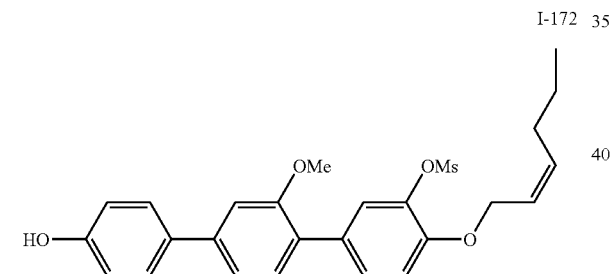
I-172
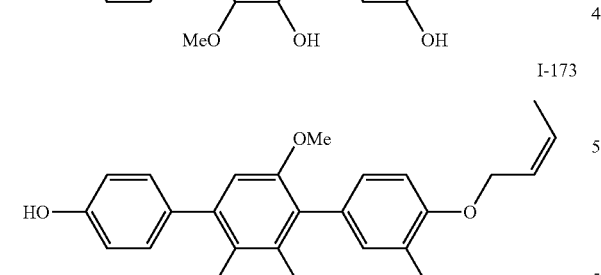
I-173
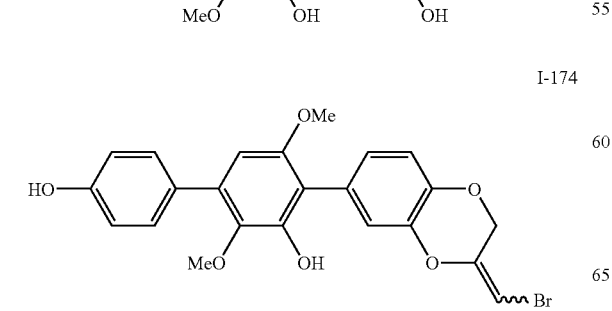
I-174
I-175
I-176

I-177
I-178

I-179
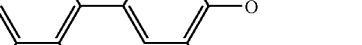
I-180

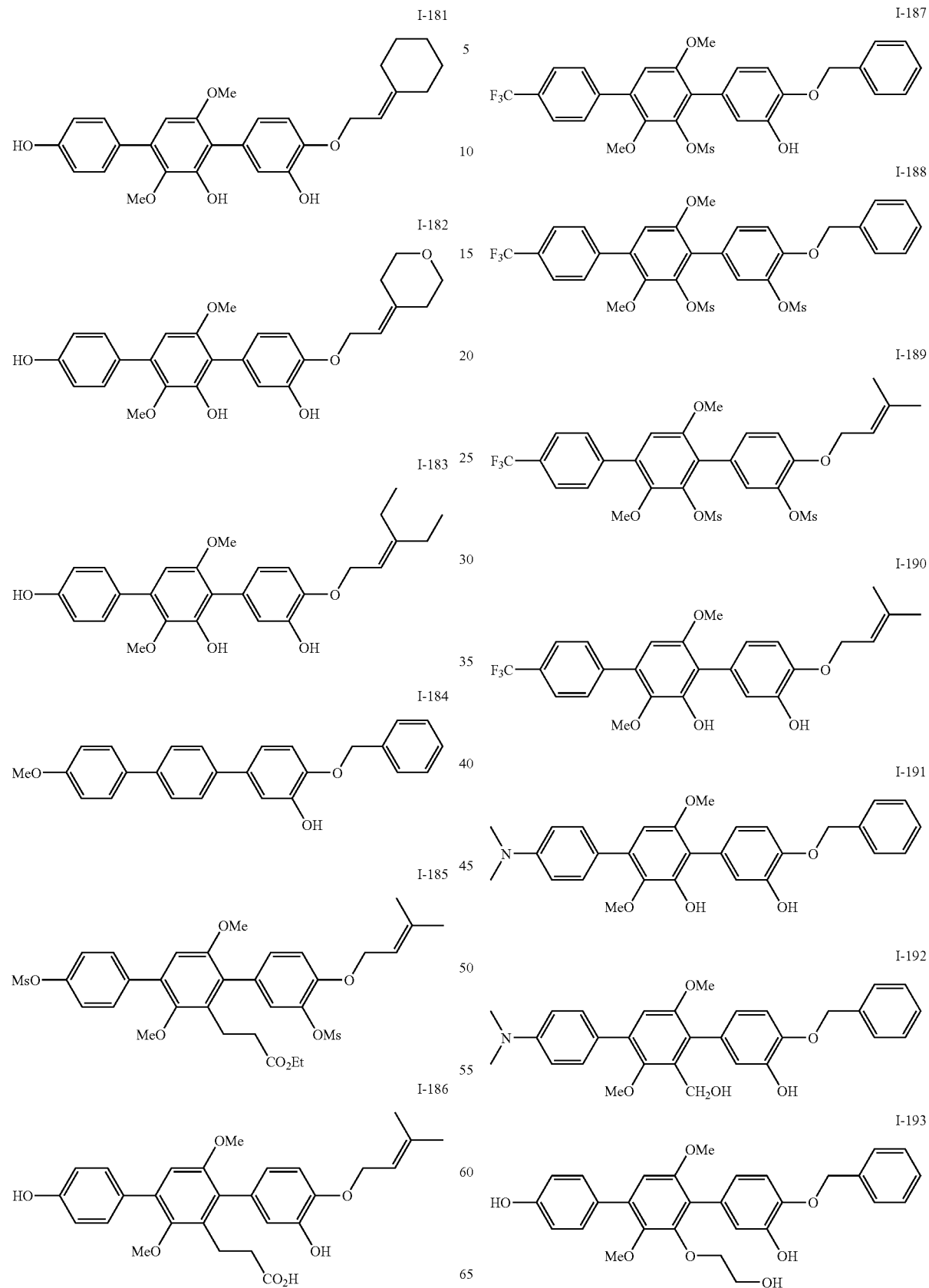

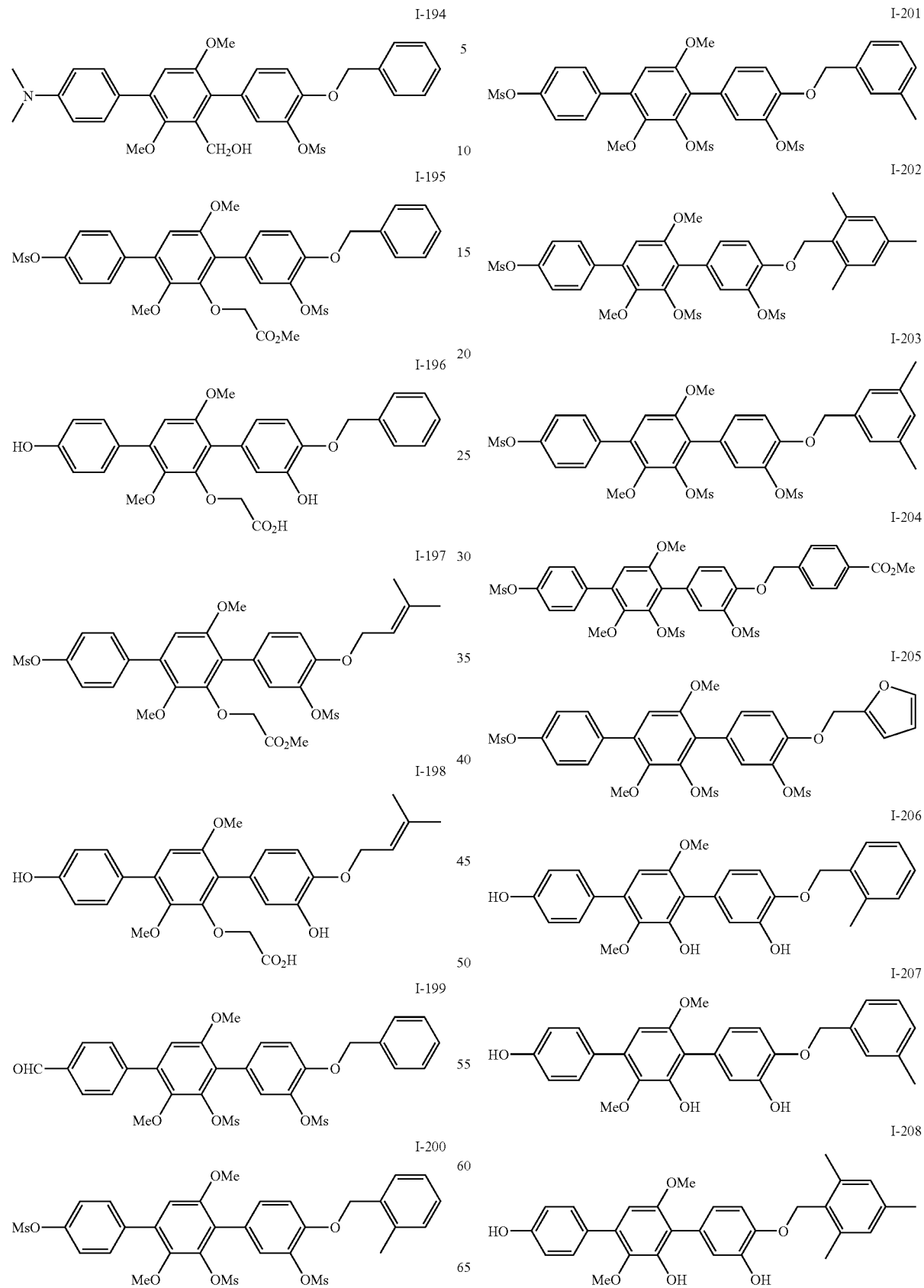

-continued
I-209
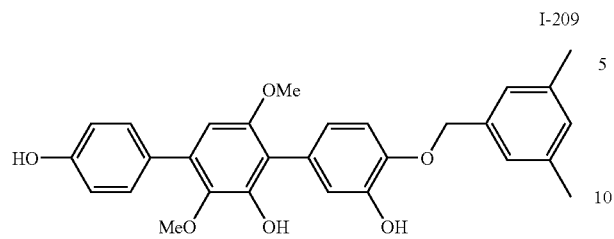
I-210
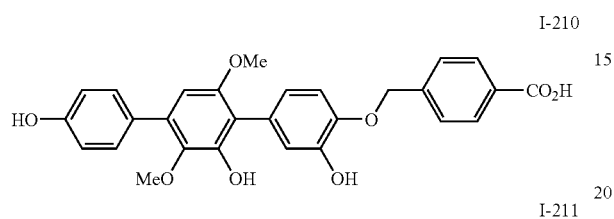
I-211
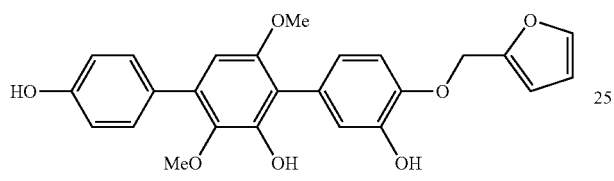
I-212

I-213

I-214

I-215

-continued
I-216
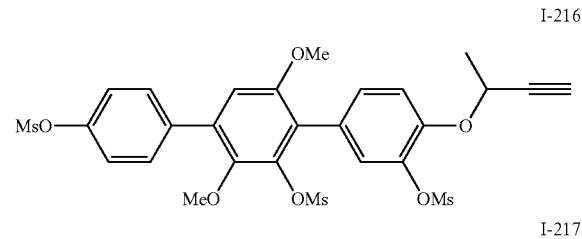
I-217
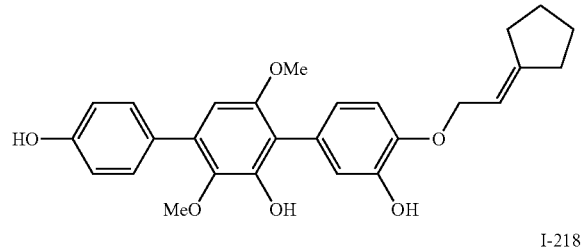
I-218
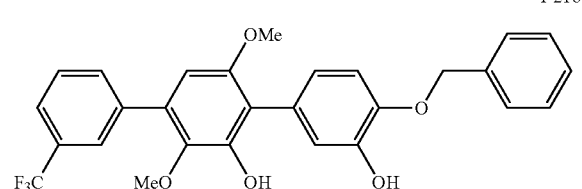
I-219
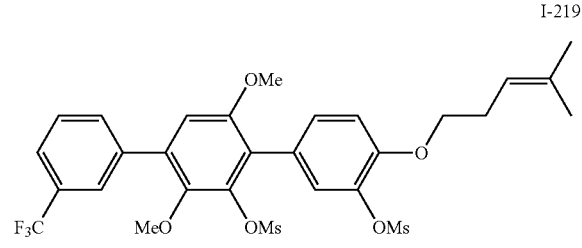
I-220
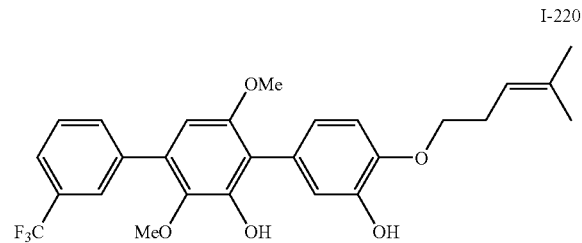
I-221
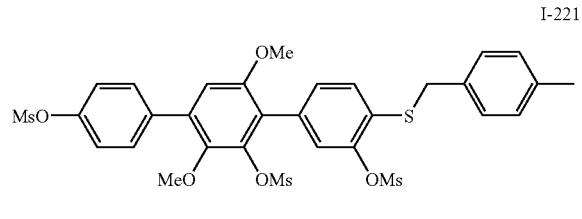
I-222
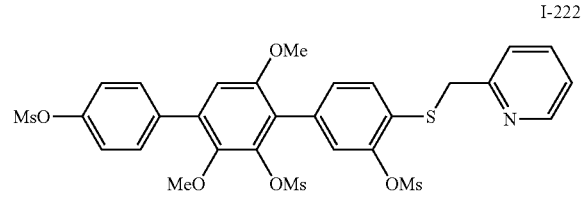

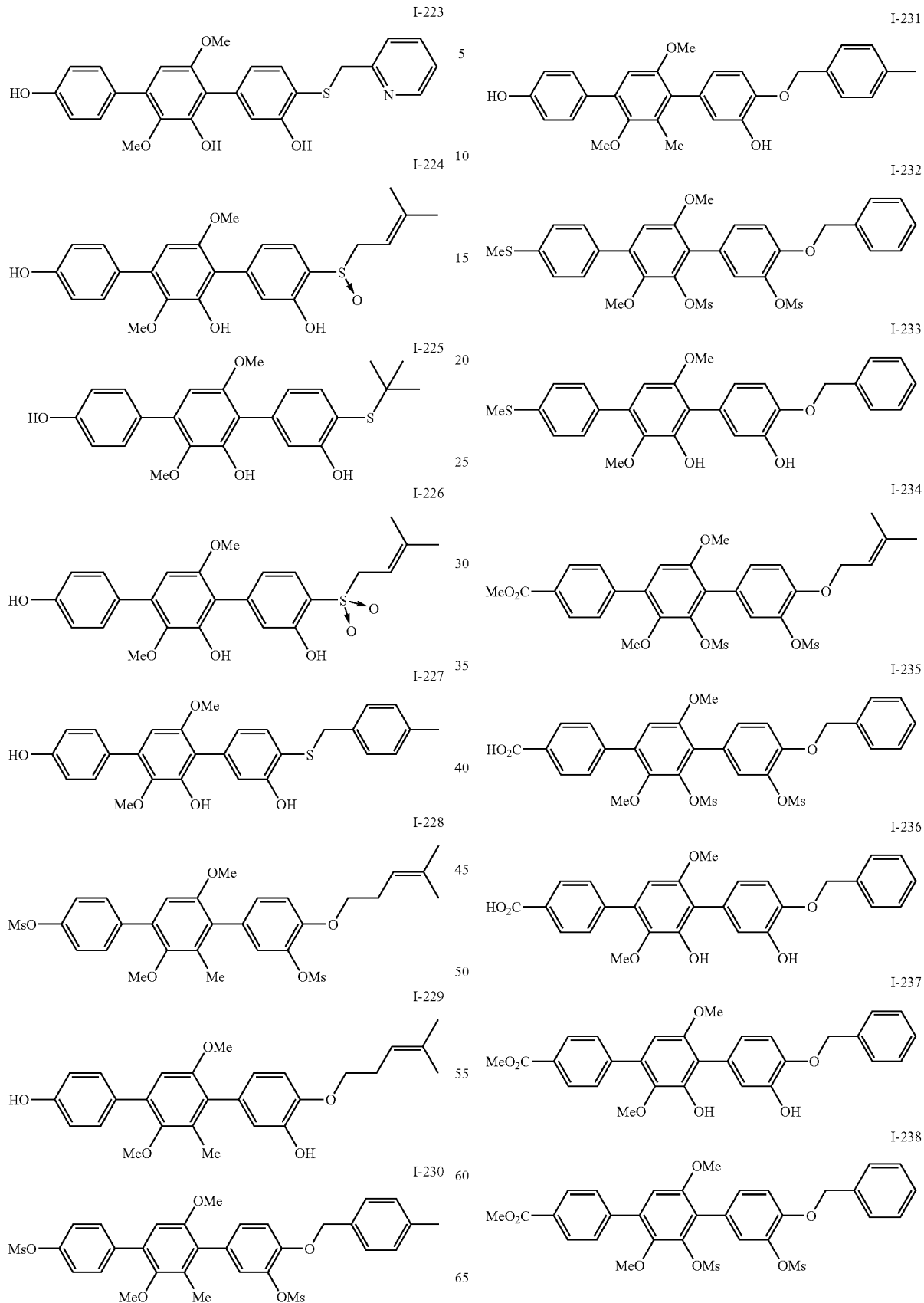

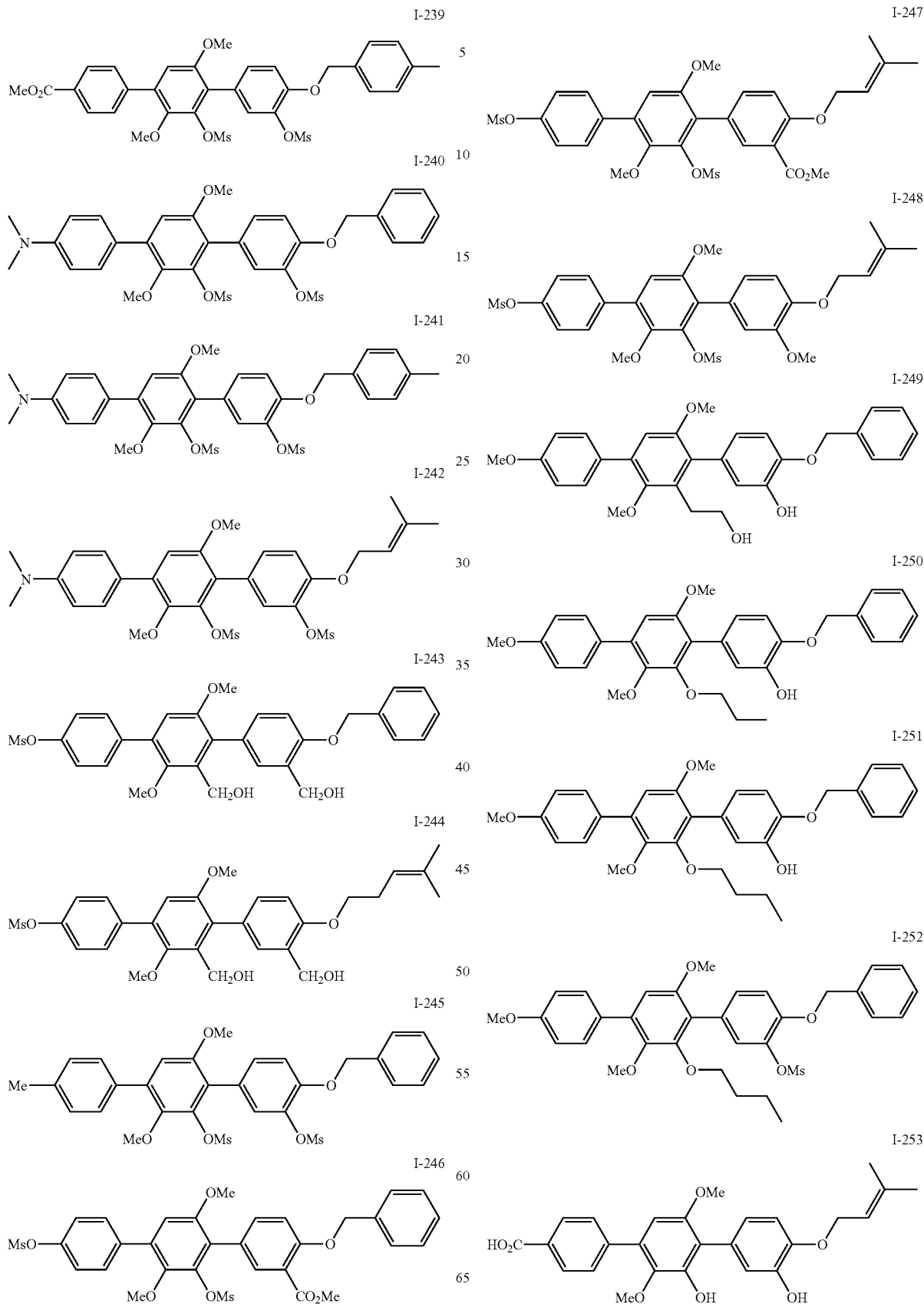

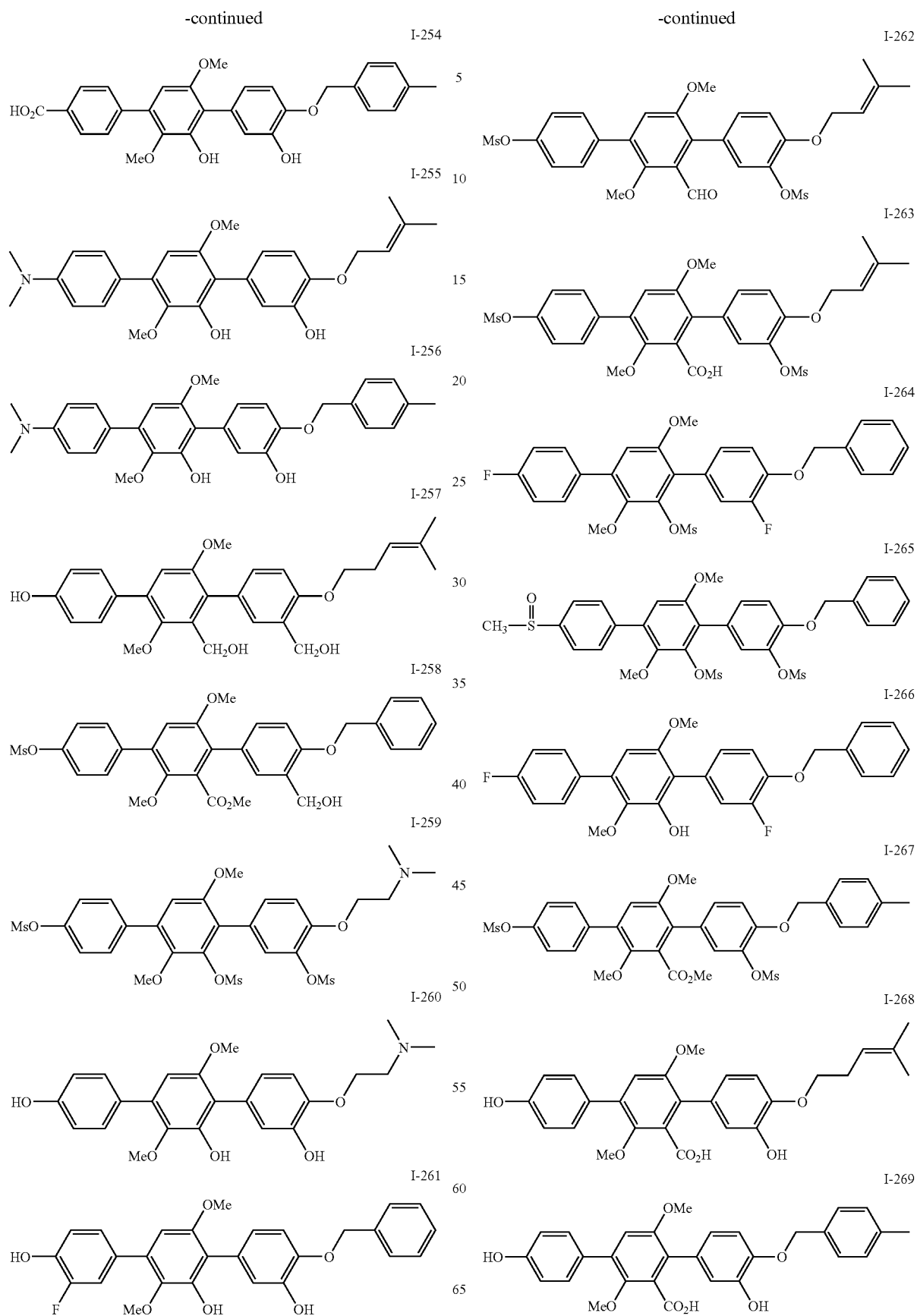

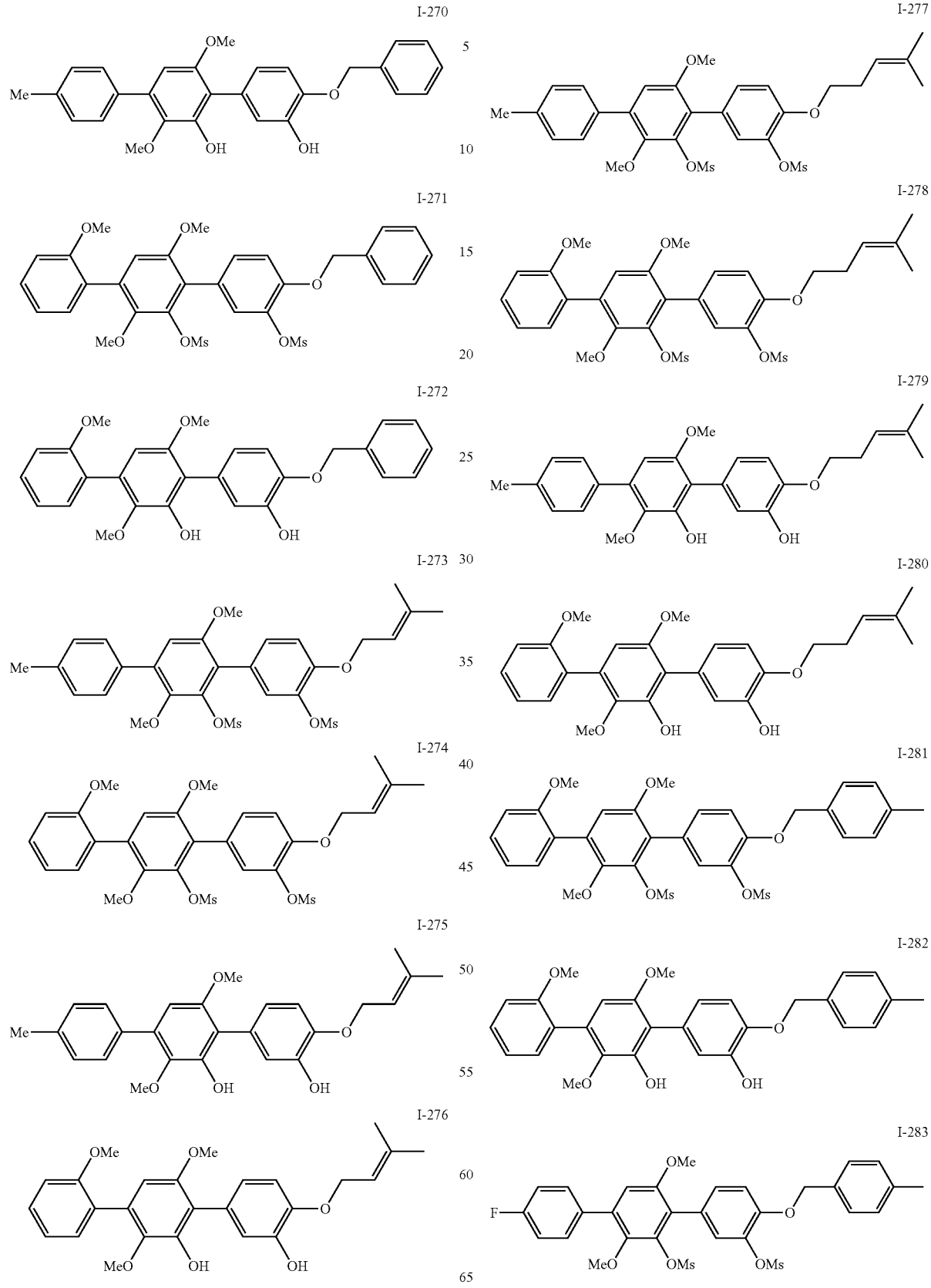

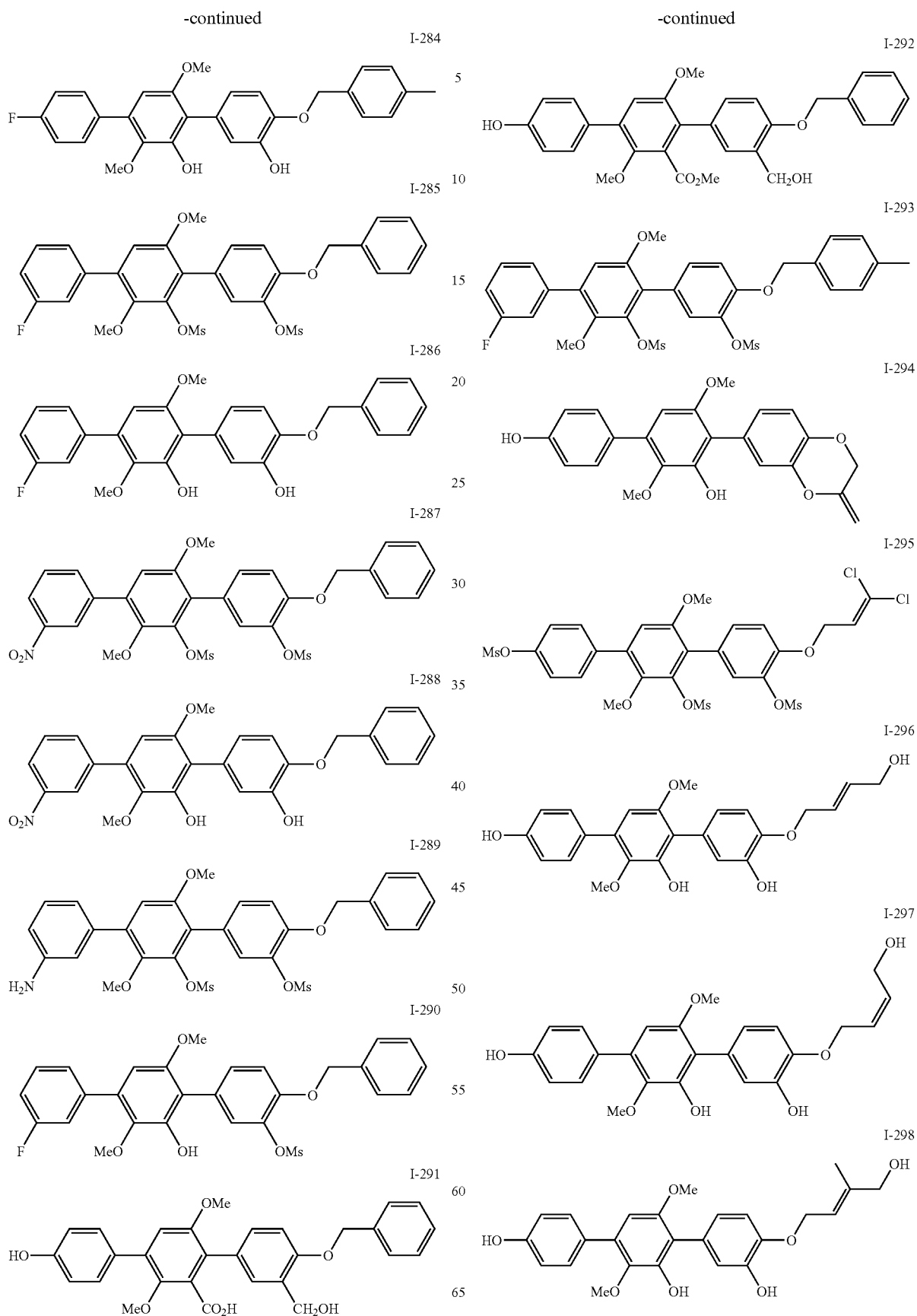

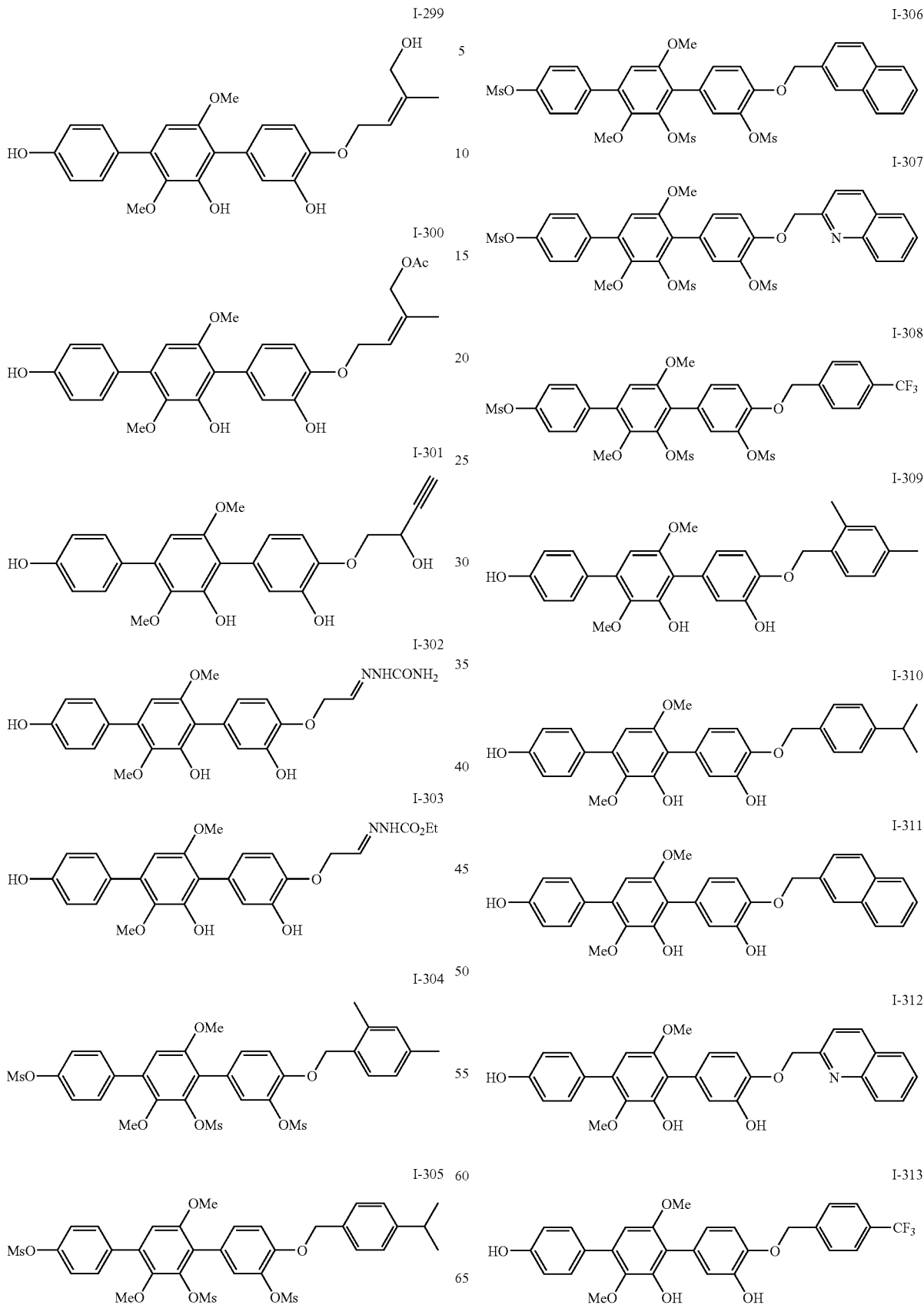

-continued
I-314
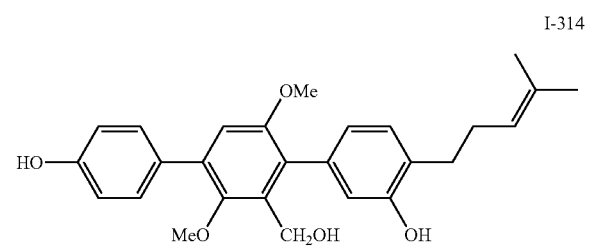
I-315
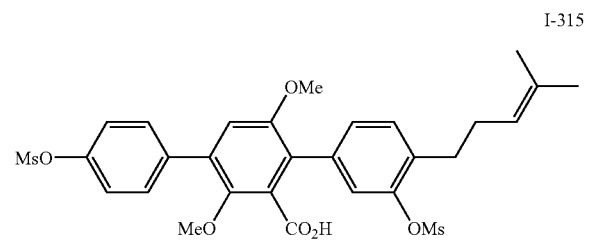
I-316
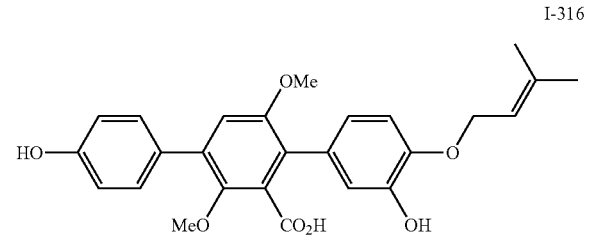
I-317
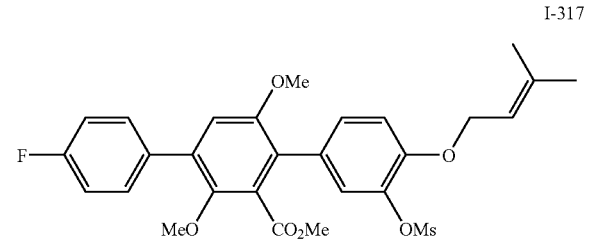
I-318
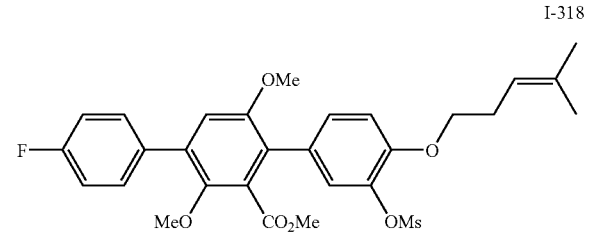
I-319
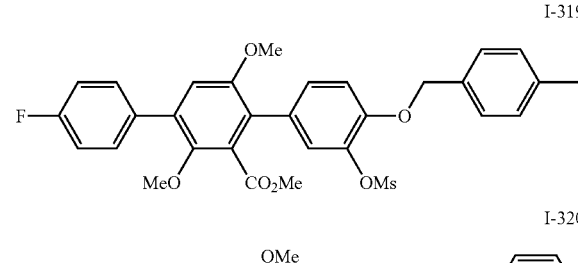
I-320
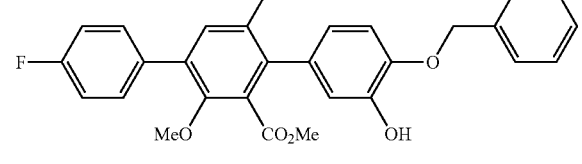
-continued
I-321

I-322

I-323
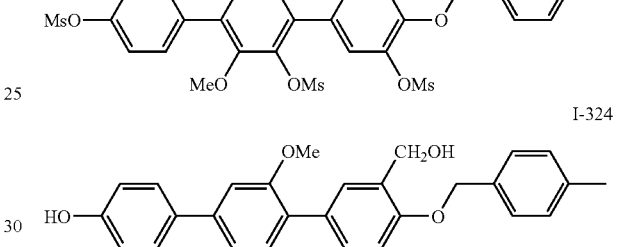
I-324
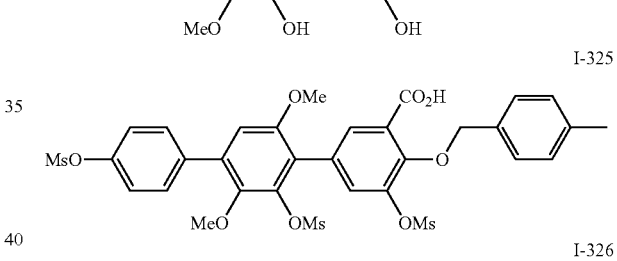
I-325
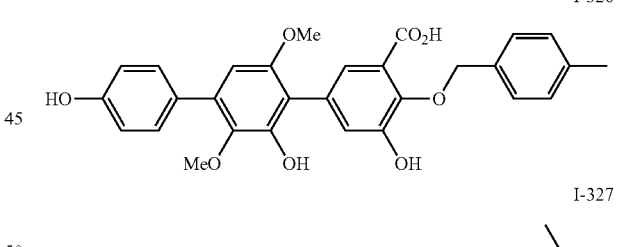
I-326
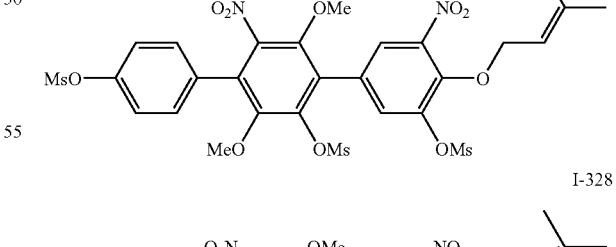
I-327
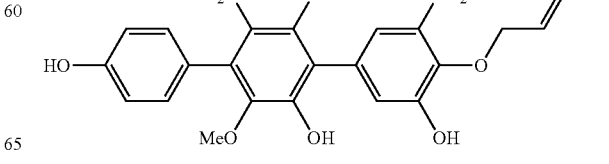
I-328

I-329
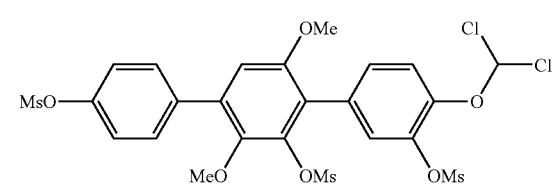
I-330
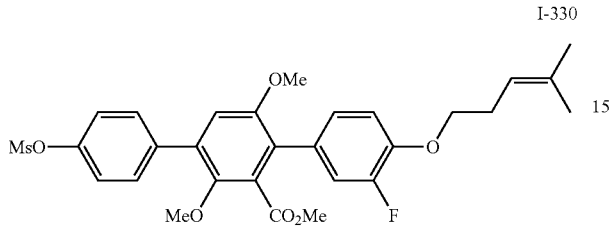
I-331
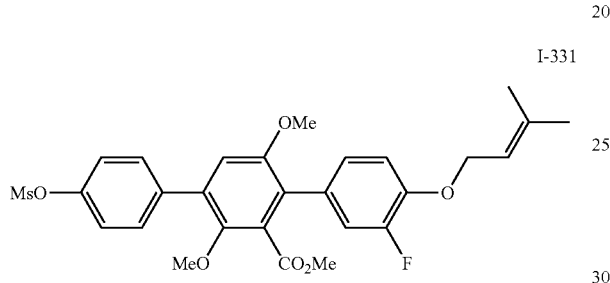
I-332
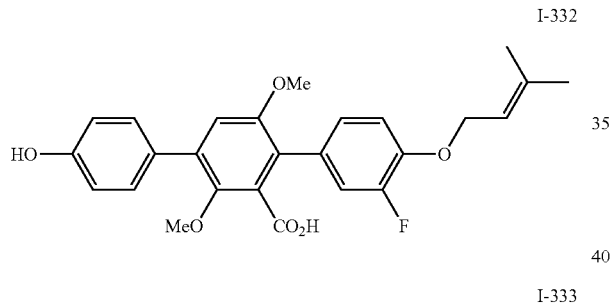
I-333
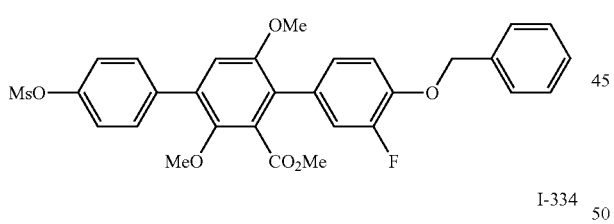
I-334
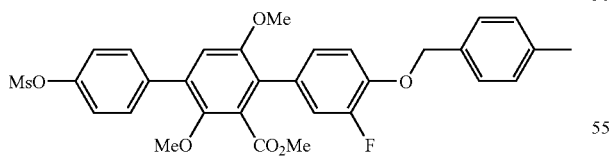
I-335
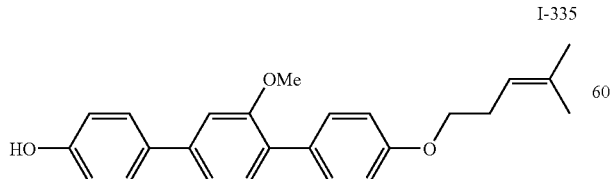
I-336
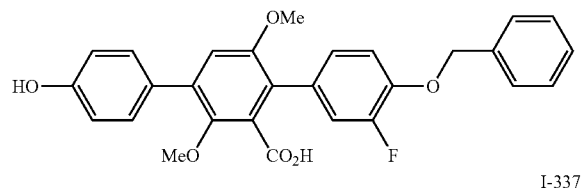
I-337
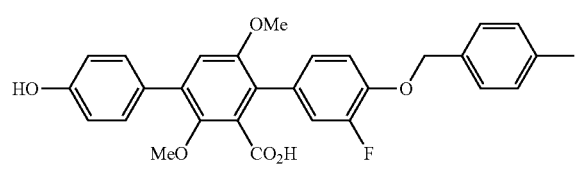
I-338
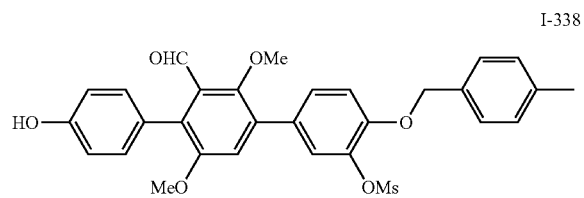
I-339
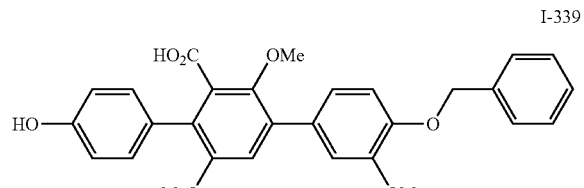
I-340
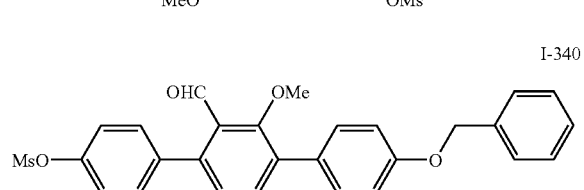
I-341
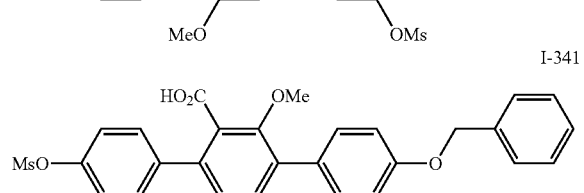
I-342
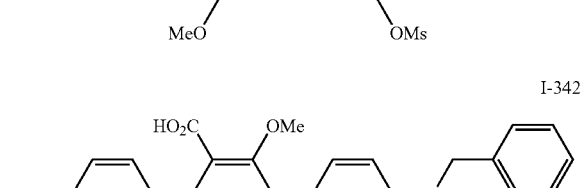
I-343
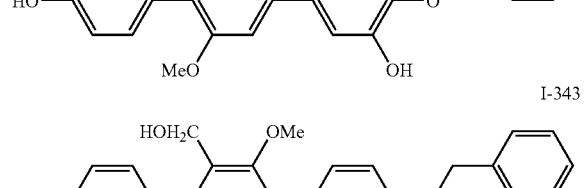

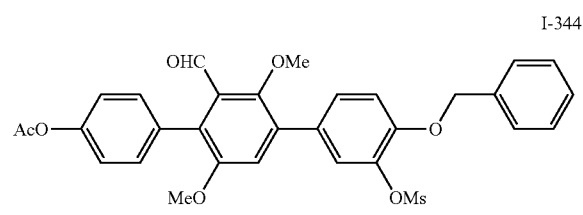
I-344
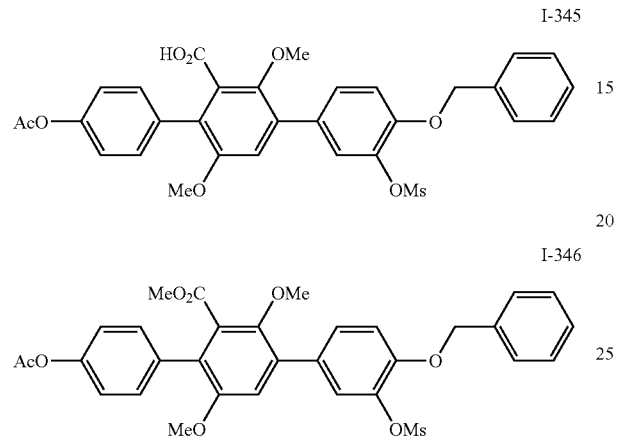
I-345
I-346
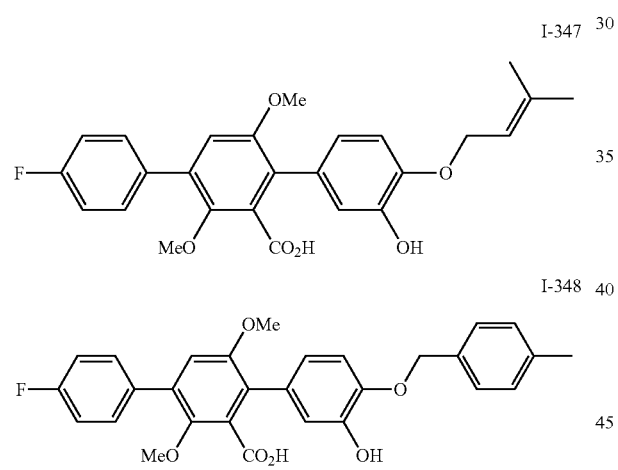
I-347
I-348
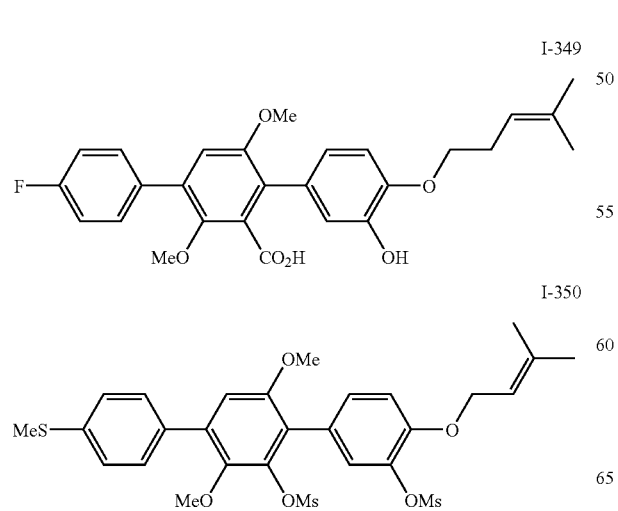
I-349
I-350
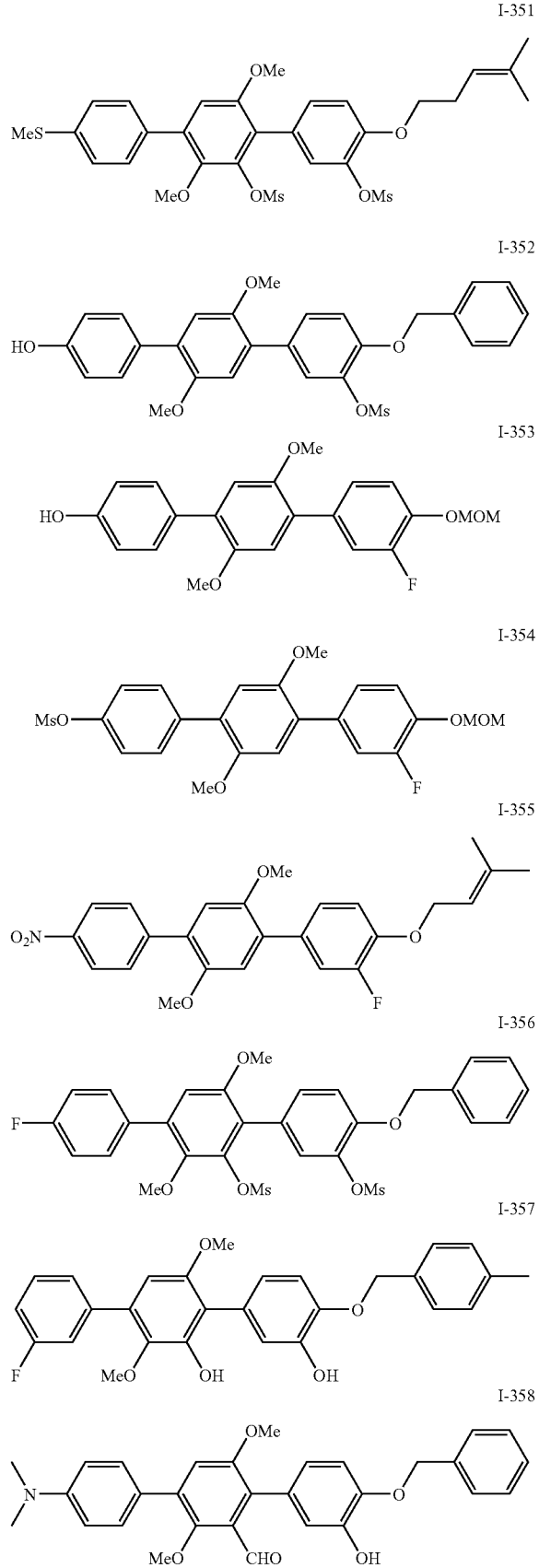
I-351
I-352
I-353
I-354
I-355
I-356
I-357
I-358

-continued
I-359
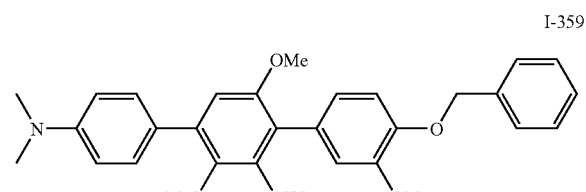
I-360
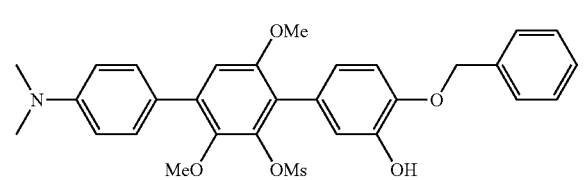
I-361
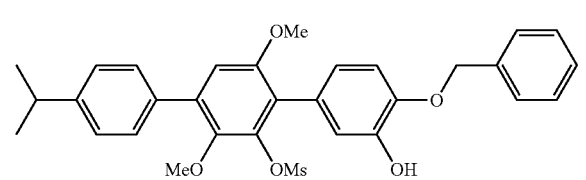
I-362
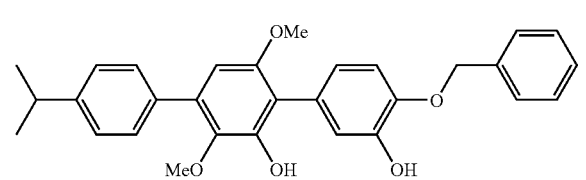
I-363
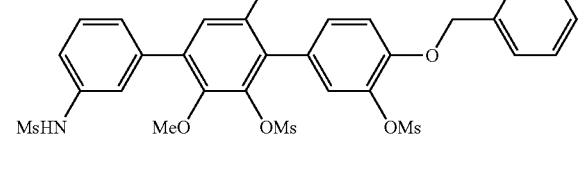
I-364
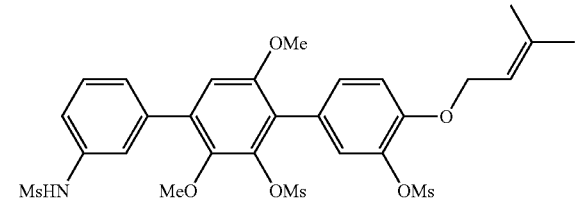
I-365
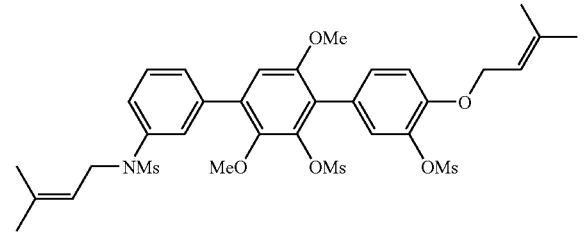
-continued
I-366
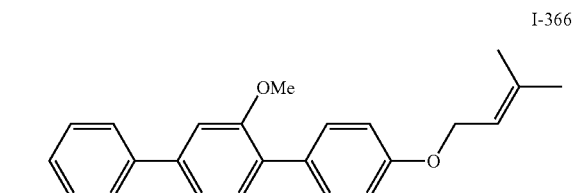
I-367
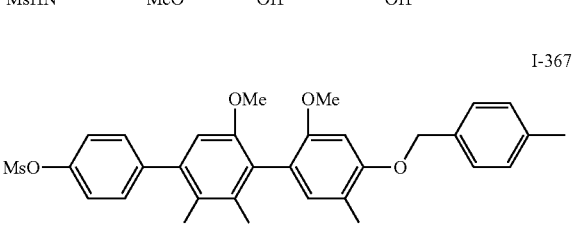
I-368
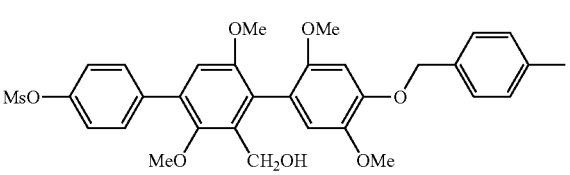
I-369
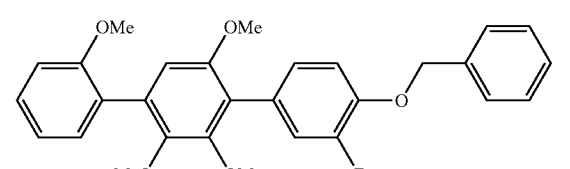
I-370
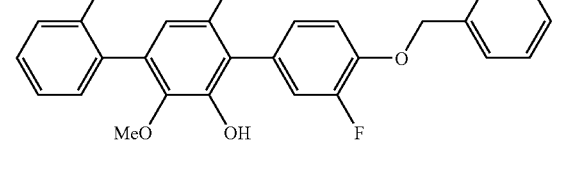
I-371
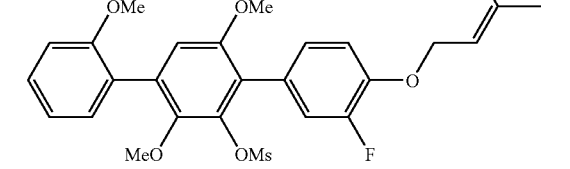
I-372
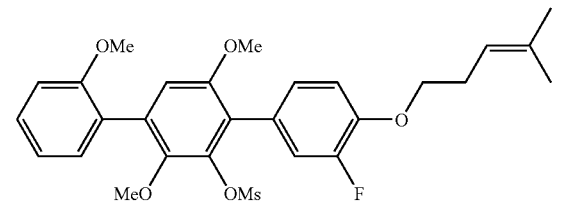

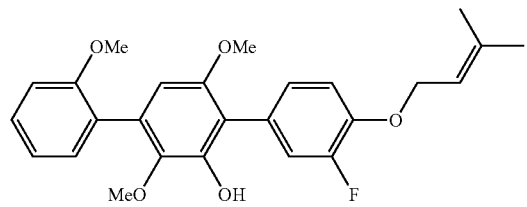
I-373
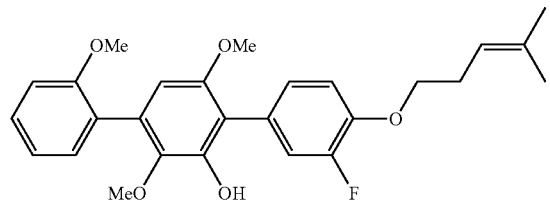
I-374
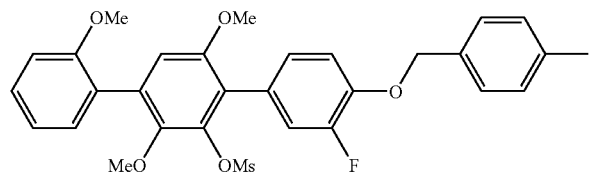
I-375
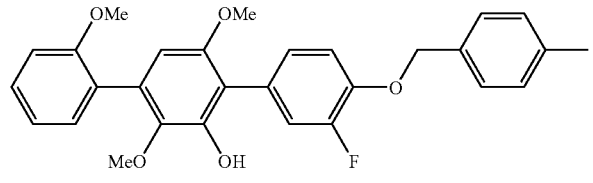
I-376
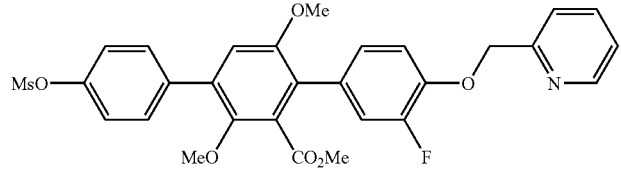
I-377
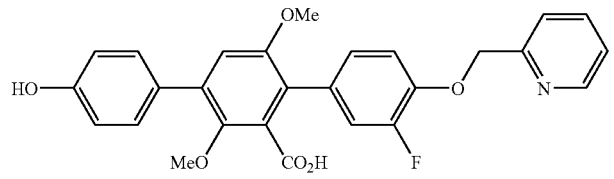
I-378
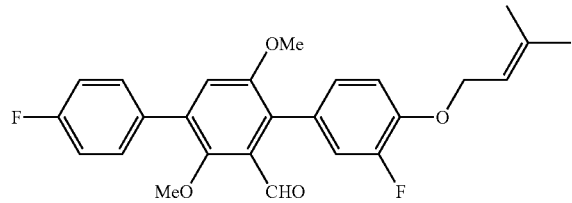
I-379
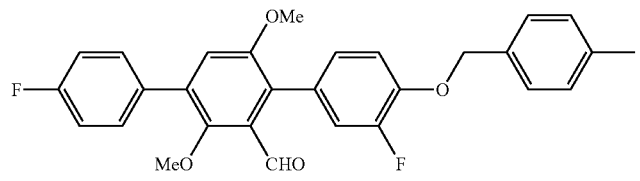
I-380

-continued
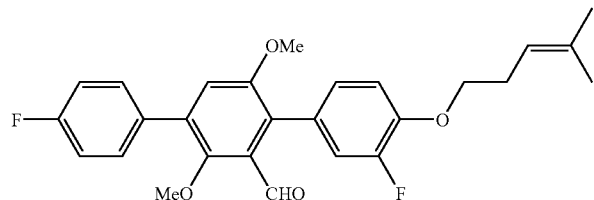
I-381
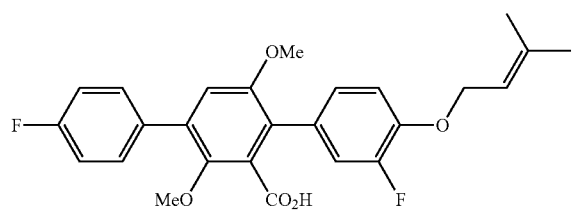
I-382
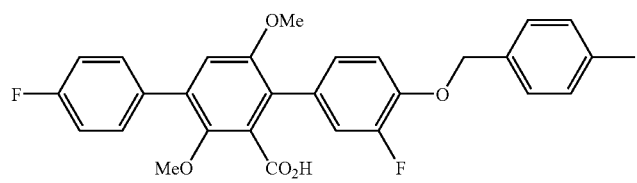
I-383
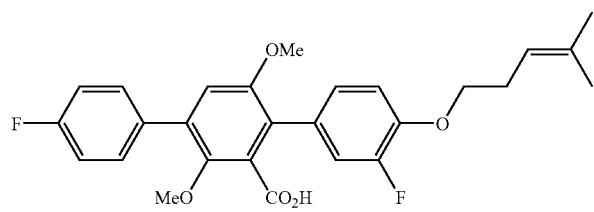
I-384
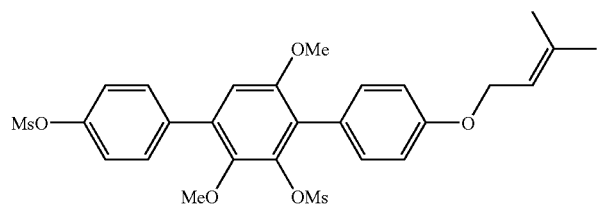
I-385
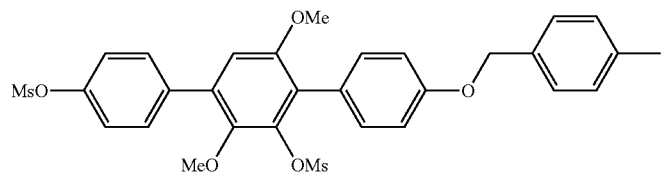
I-386
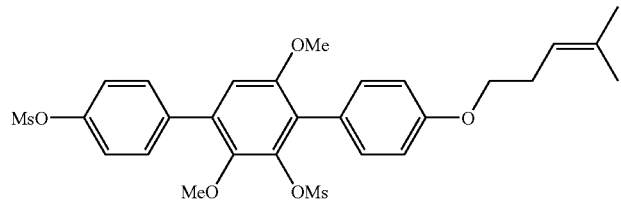
I-387
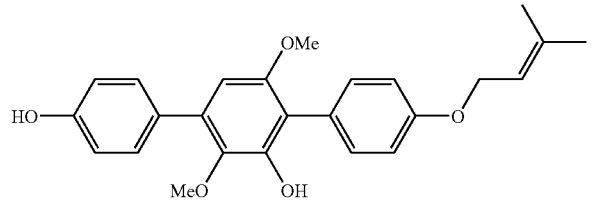
I-388

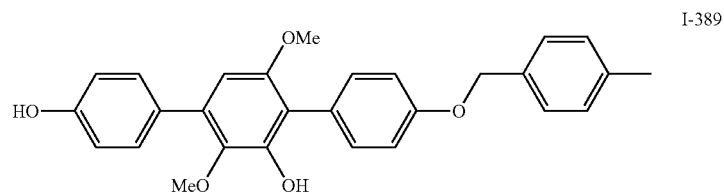
I-389
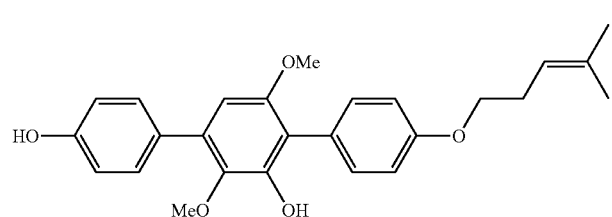
I-390
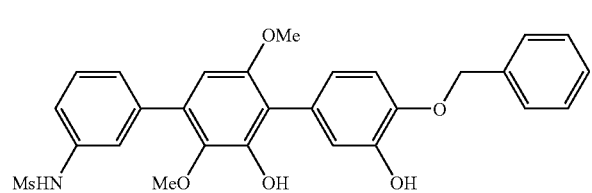
I-391
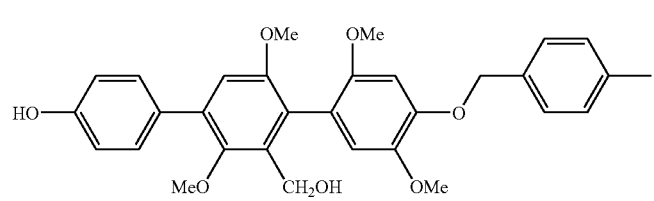
I-392
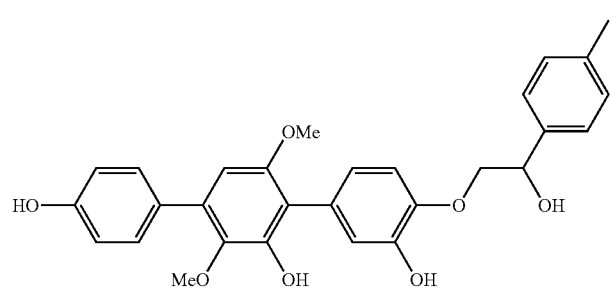
I-393
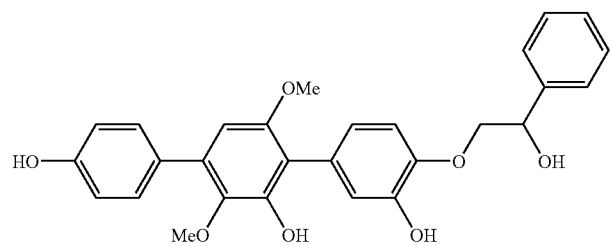
I-394
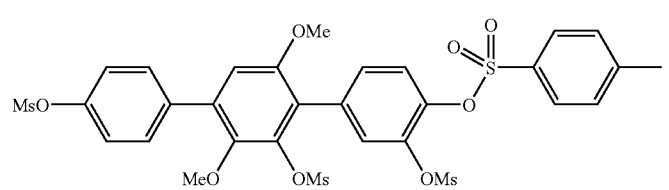
I-395

-continued
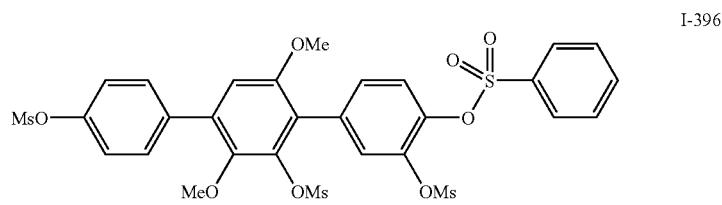
I-396
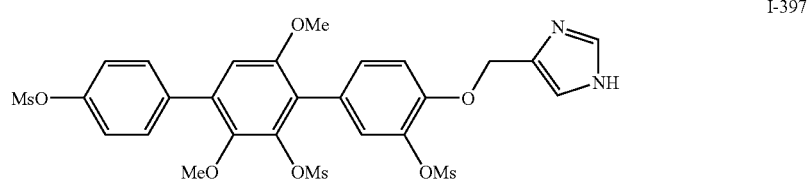
I-397
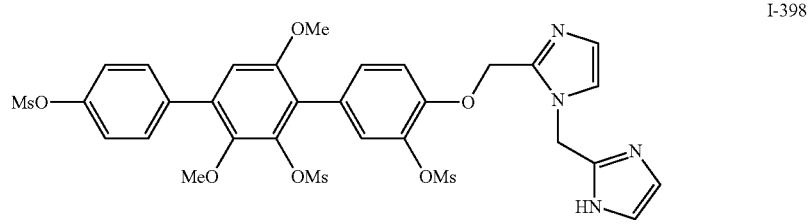
I-398
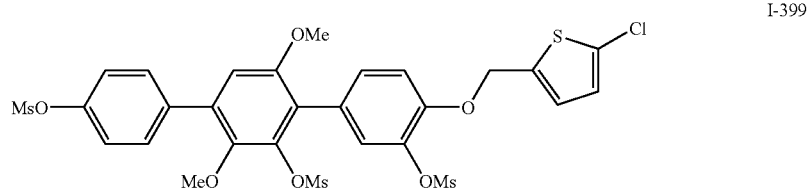
I-399
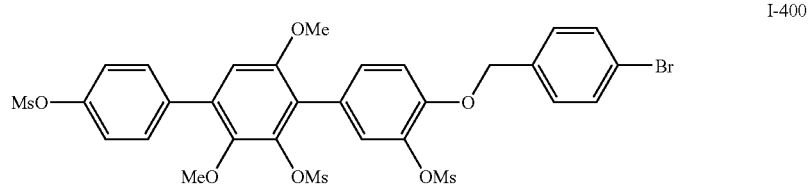
I-400
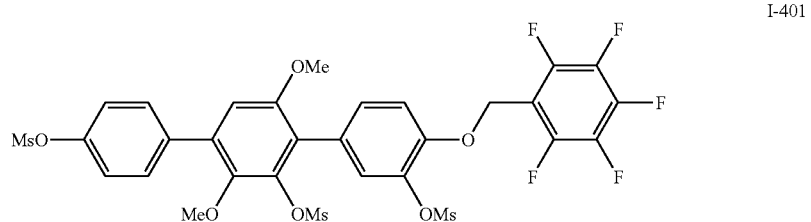
I-401
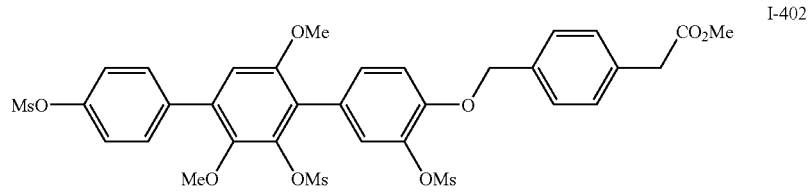
I-402
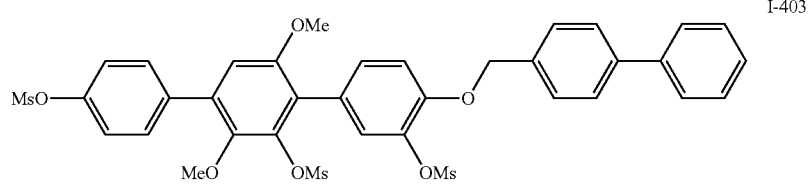
I-403

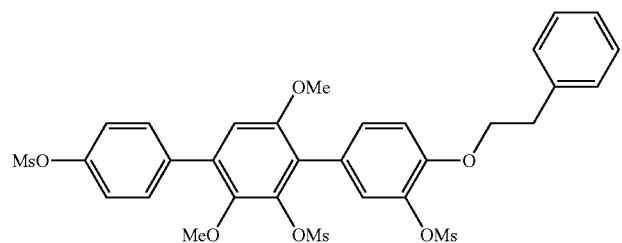
I-404
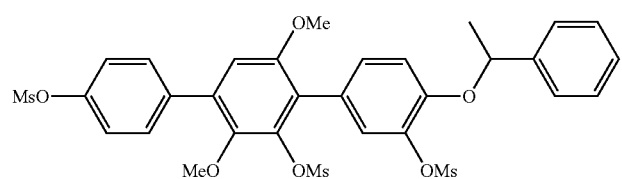
I-405
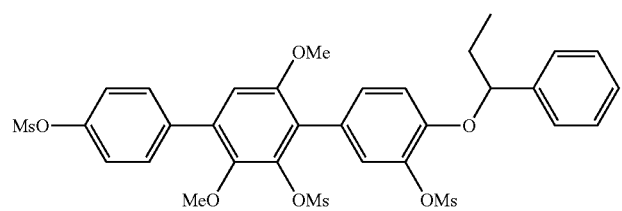
I-406
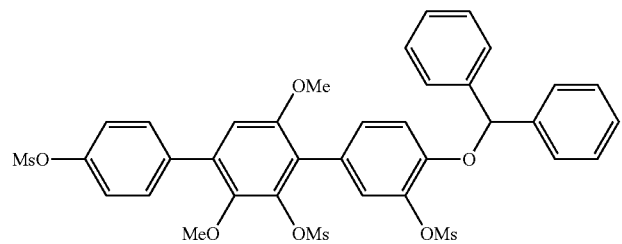
I-407
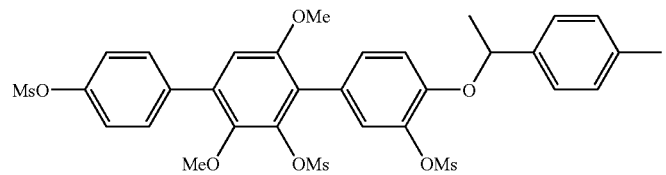
I-408
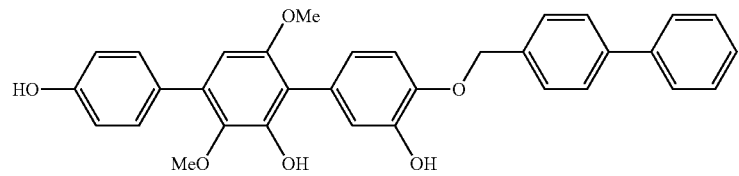
I-409
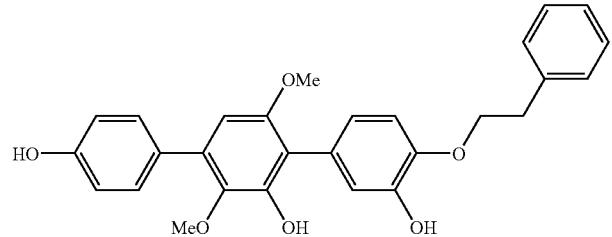
I-410

-continued
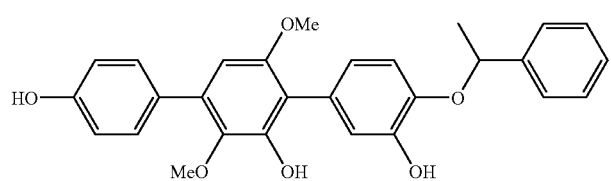
I-411
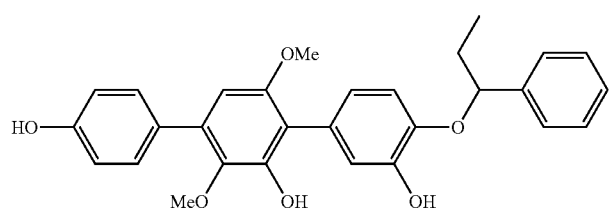
I-412
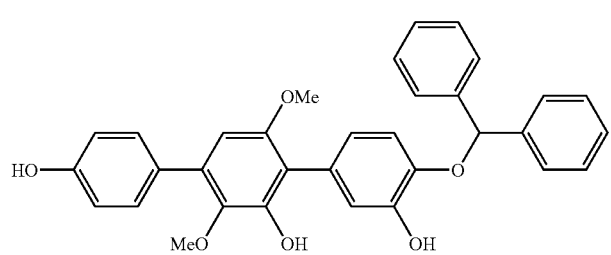
I-413
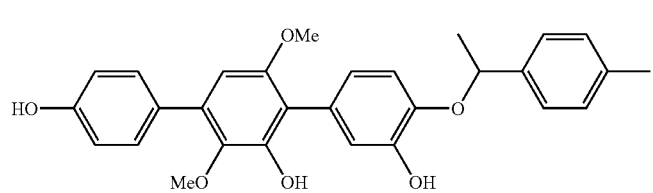
I-414
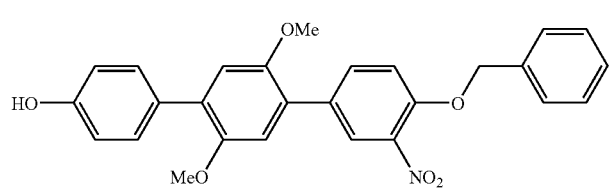
I-415
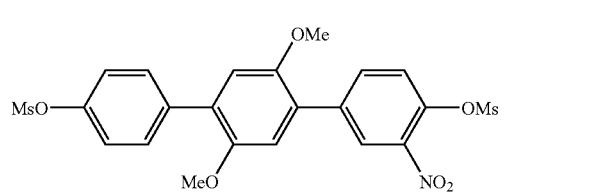
I-416
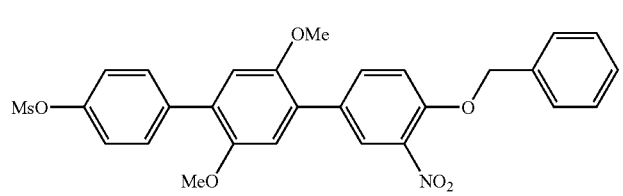
I-417
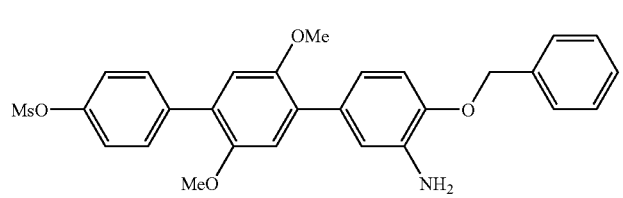
I-418

-continued
I-419
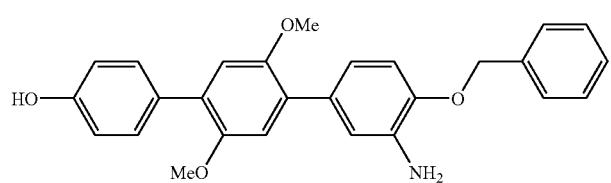
I-420
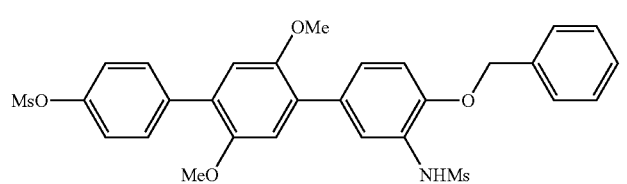
I-421
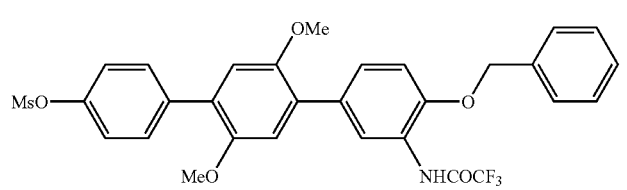
I-422
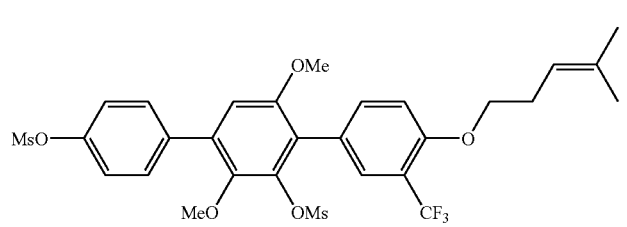
I-423
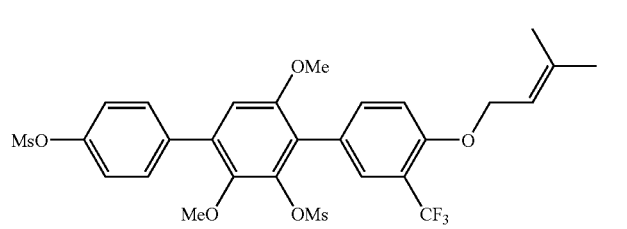
I-424
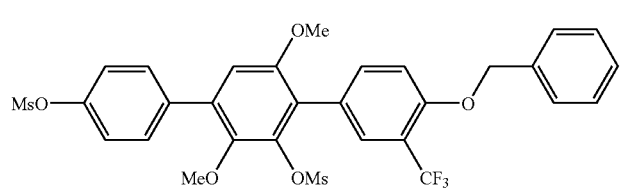
I-425
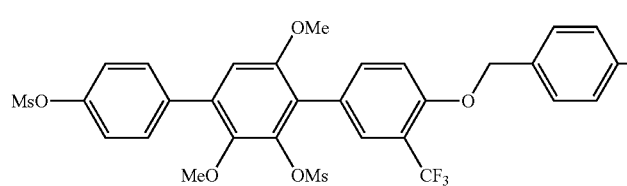
I-426
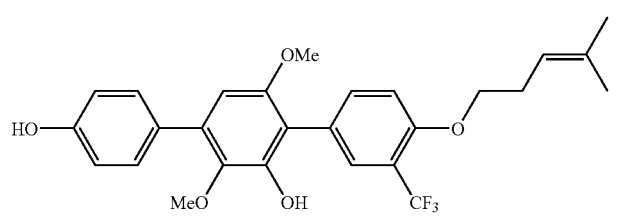

-continued
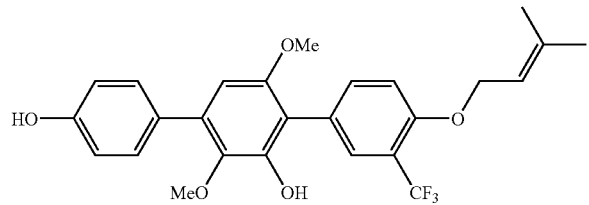
I-427
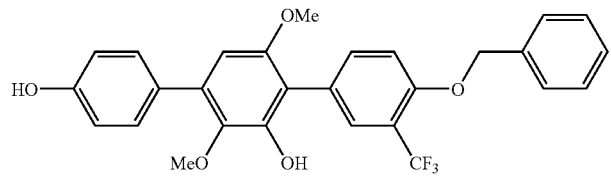
I-428
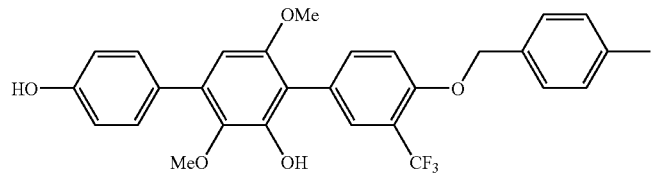
I-429
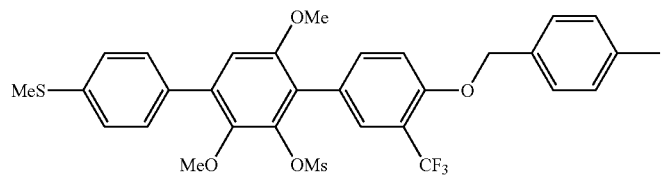
I-430
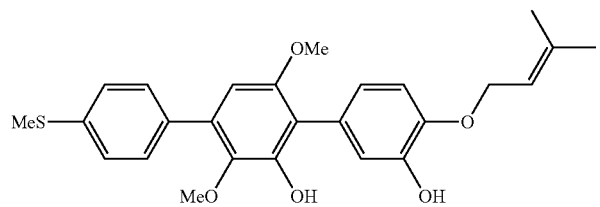
I-431
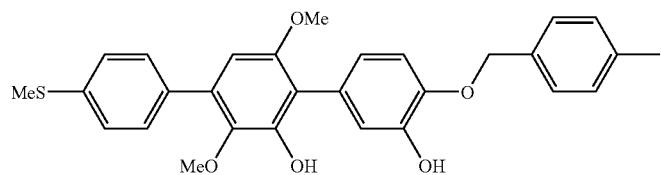
I-432
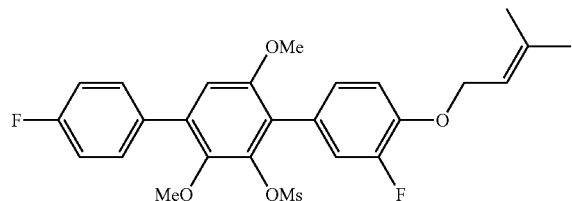
I-433
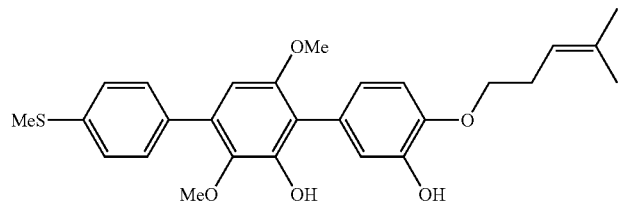
I-434

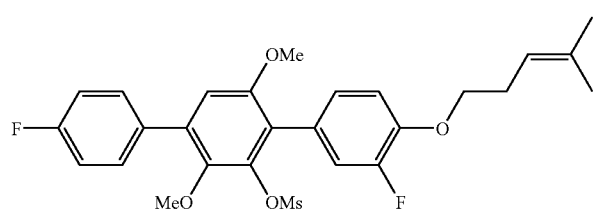
I-435
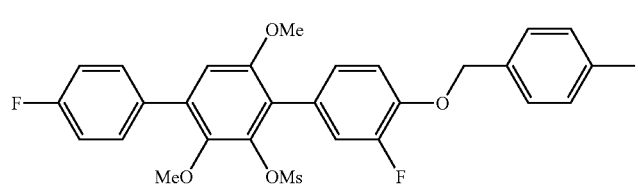
I-436
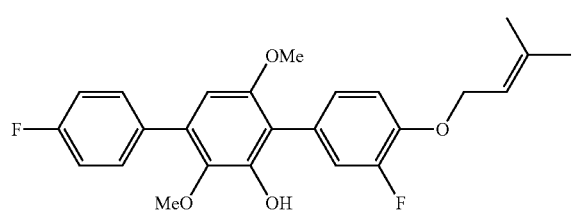
I-437
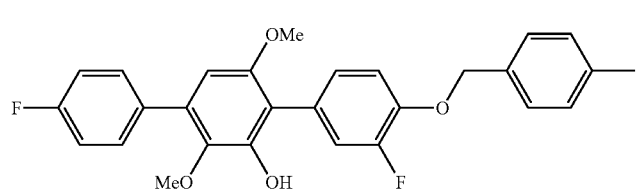
I-438
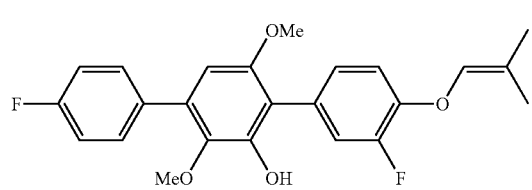
I-439
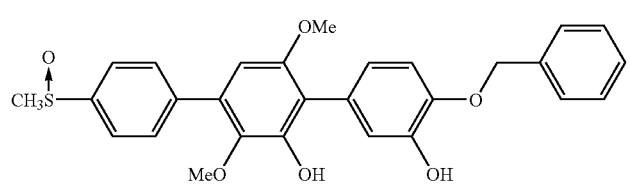
I-440
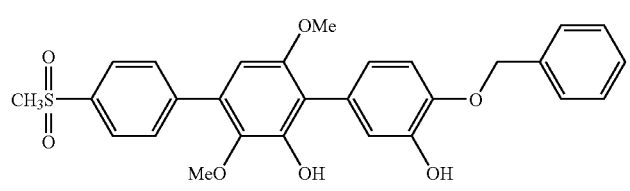
I-441
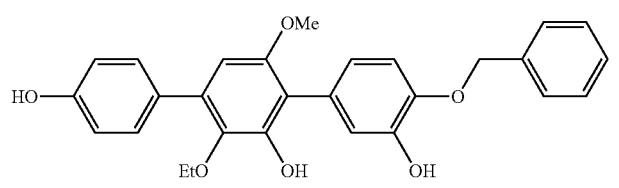
I-442

-continued
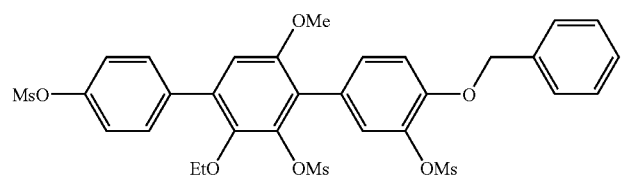
I-443
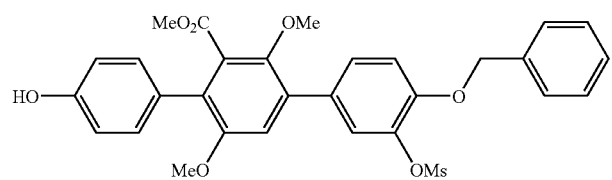
I-444
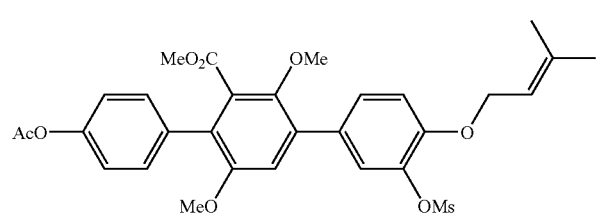
I-445
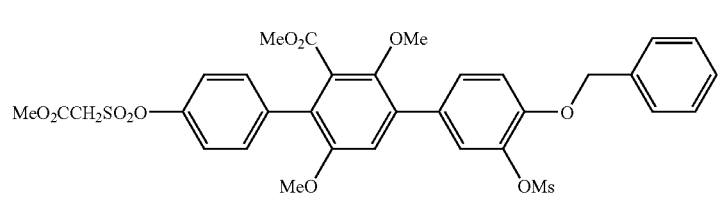
I-446
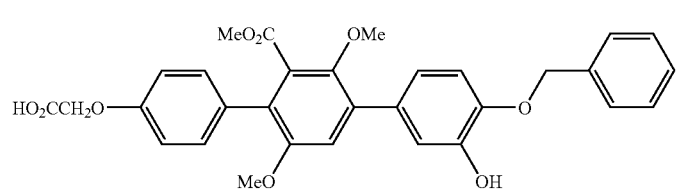
I-447
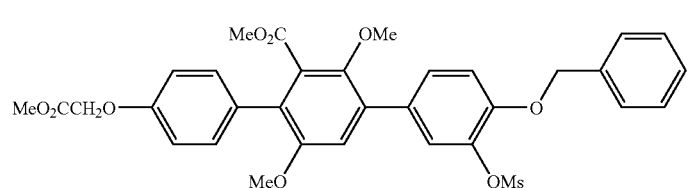
I-448
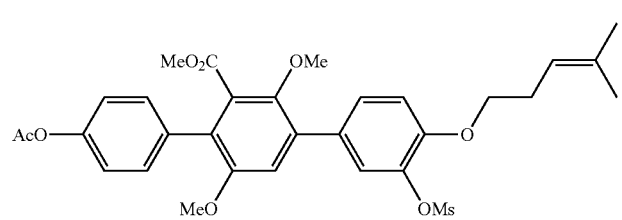
I-449
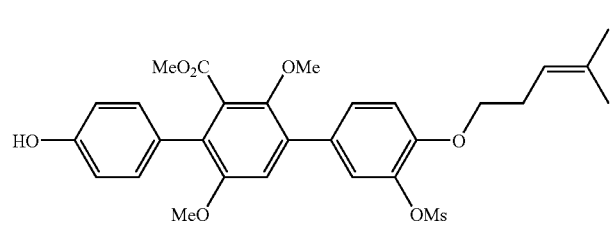
I-450

-continued
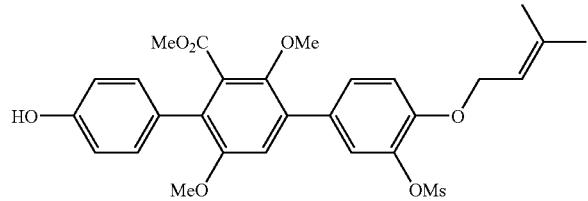
I-451
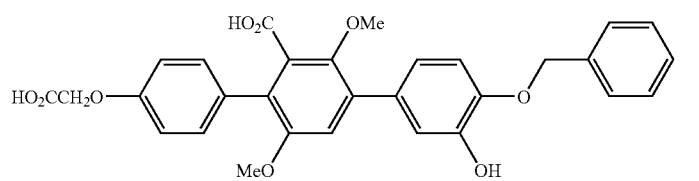
I-452
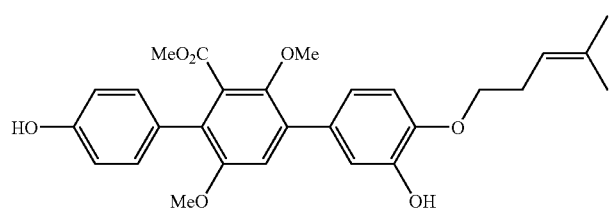
I-453
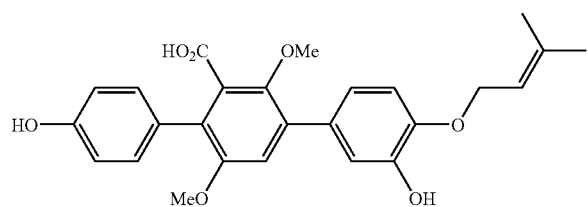
I-454
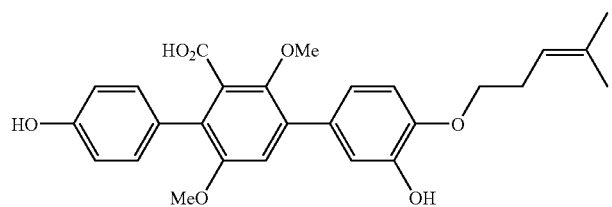
I-455
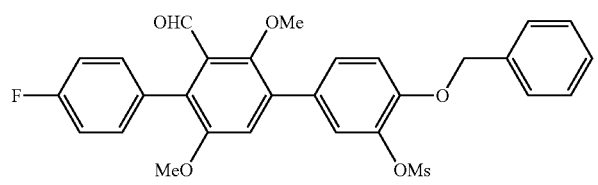
I-456
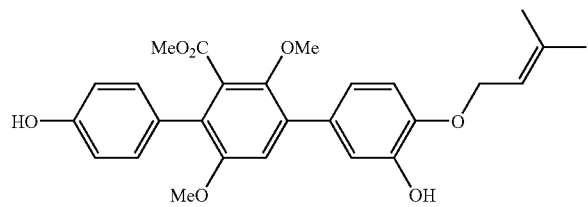
I-457
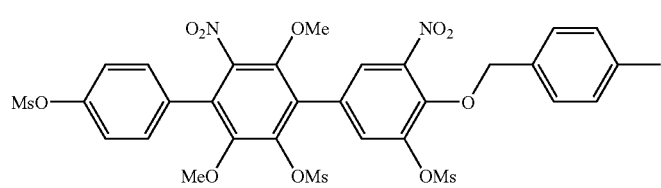
I-458

-continued
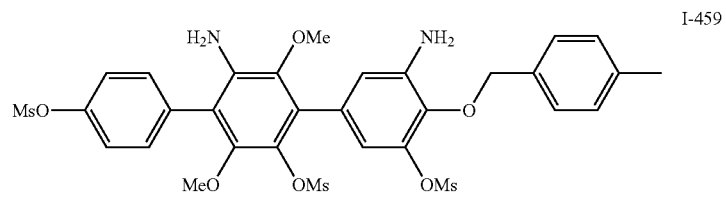
I-459
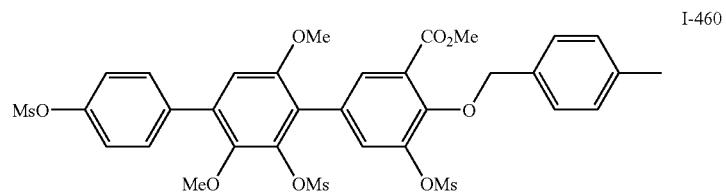
I-460
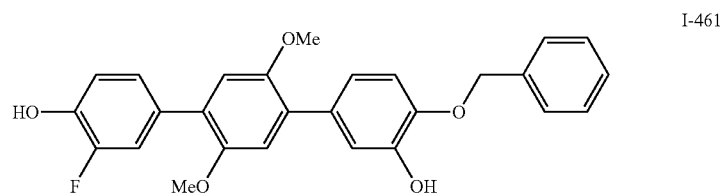
I-461
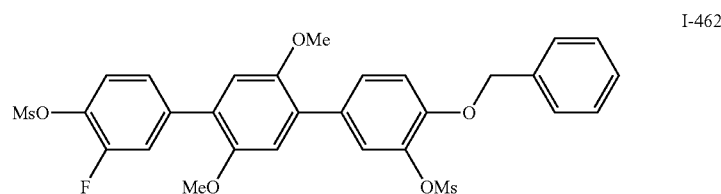
I-462
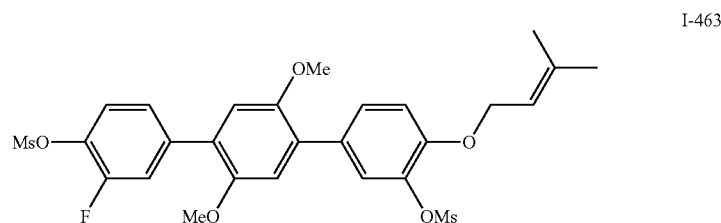
I-463
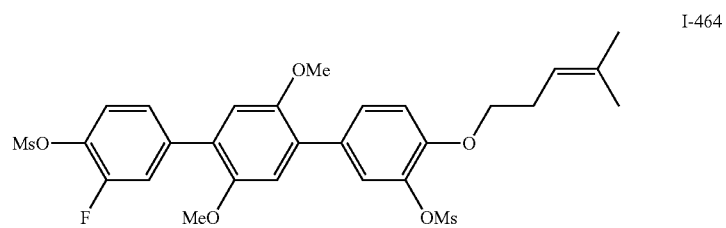
I-464
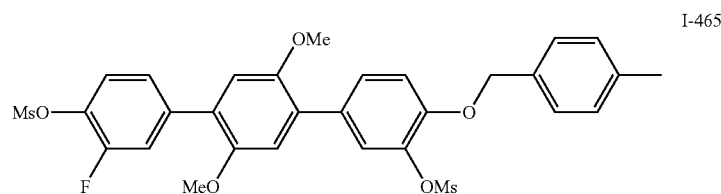
I-465
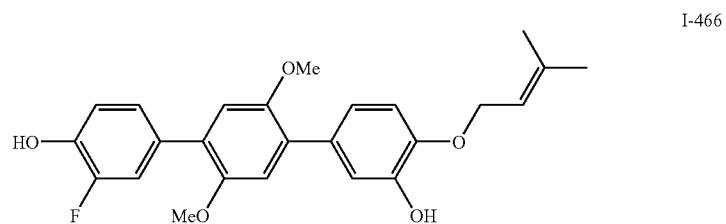
I-466

-continued
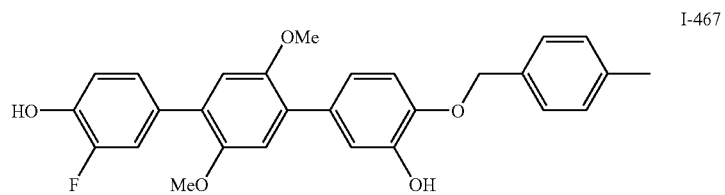
I-467
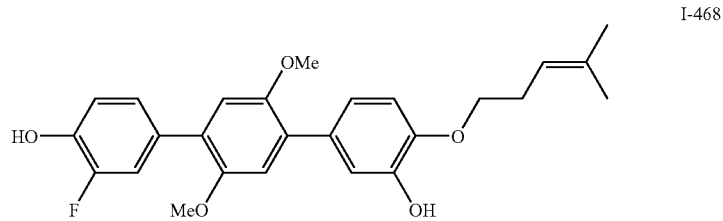
I-468
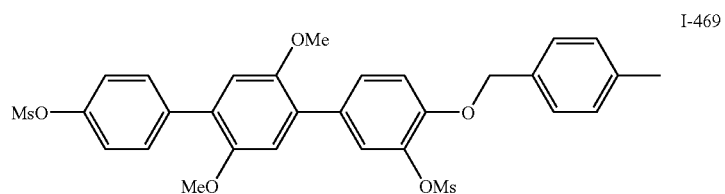
I-469
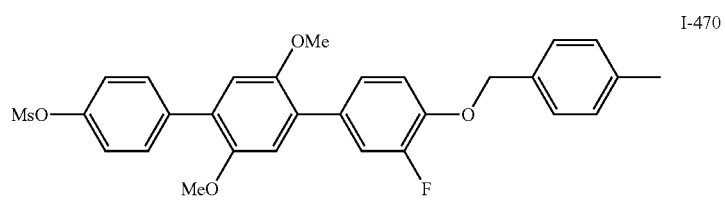
I-470
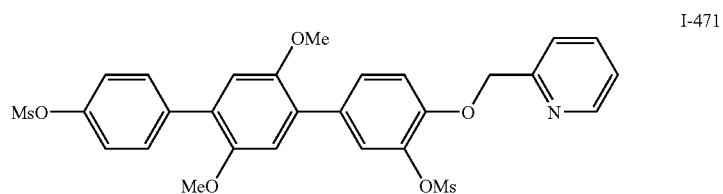
I-471
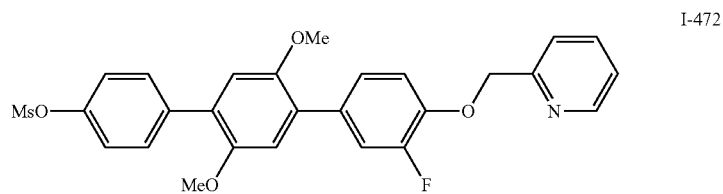
I-472
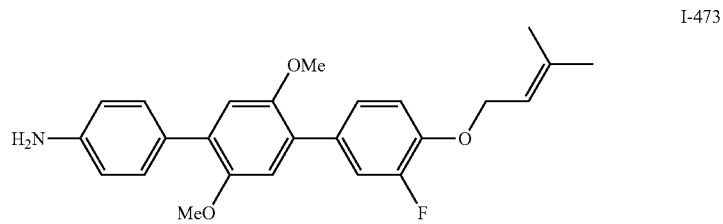
I-473
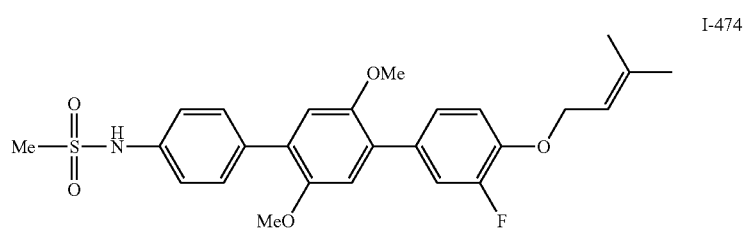
I-474

-continued
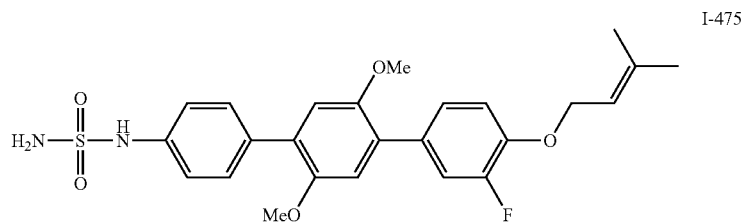
I-475
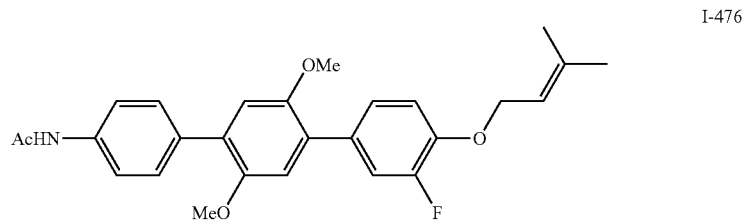
I-476
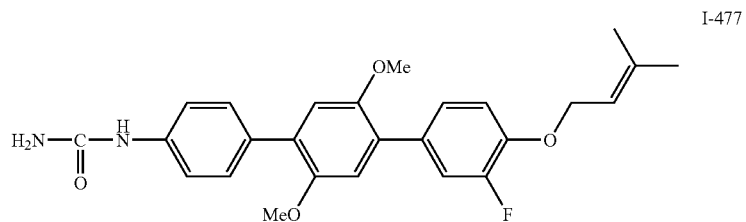
I-477
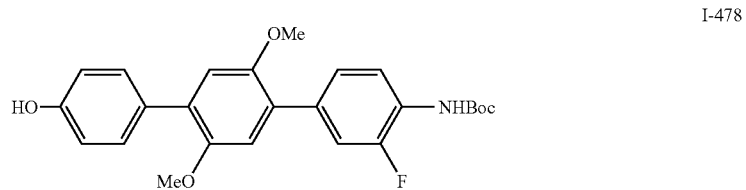
I-478
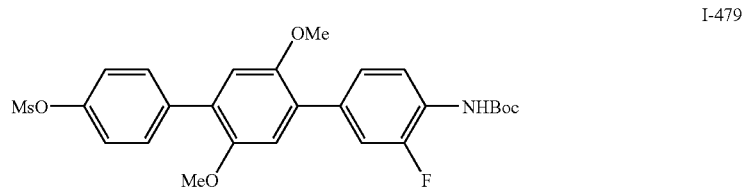
I-479
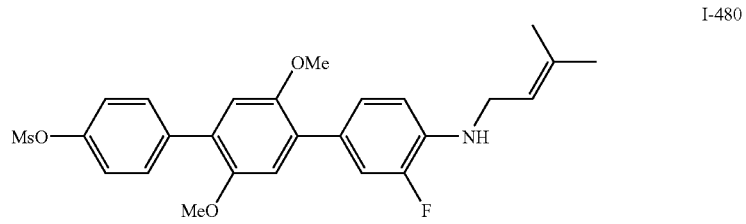
I-480
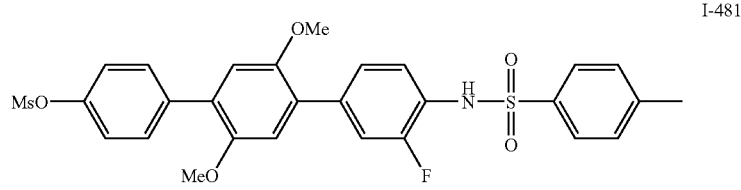
I-481
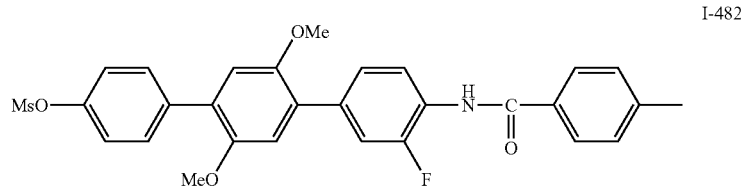
I-482

-continued
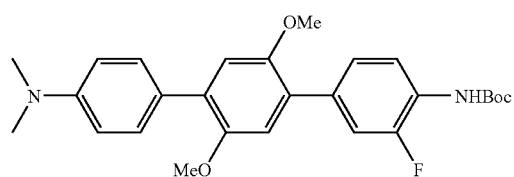
I-483
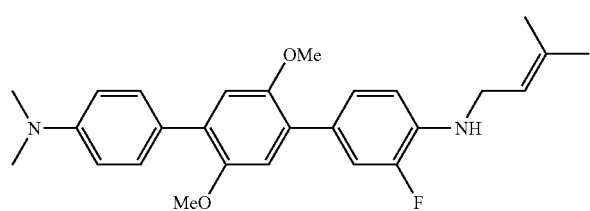
I-484
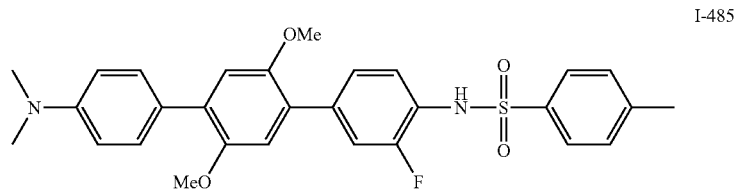
I-485
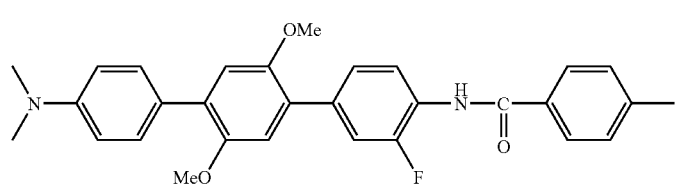
I-486
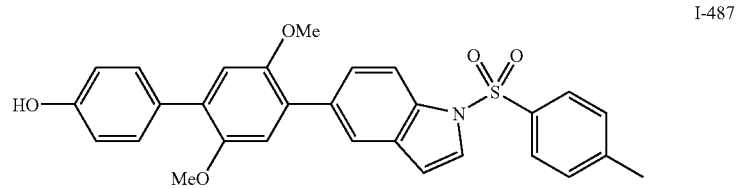
I-487
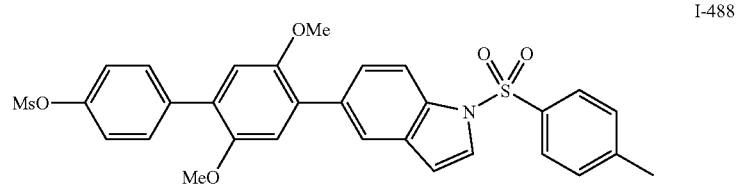
I-488
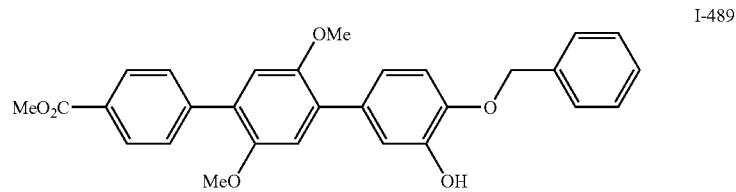
I-489
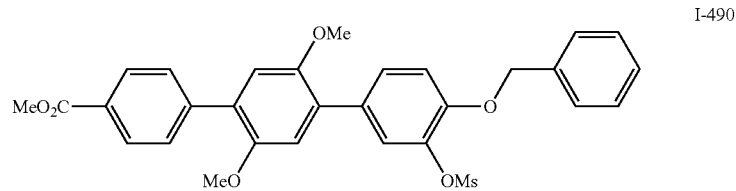
I-490

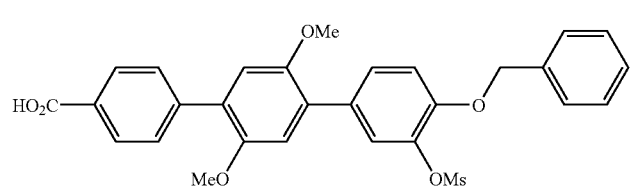
I-491
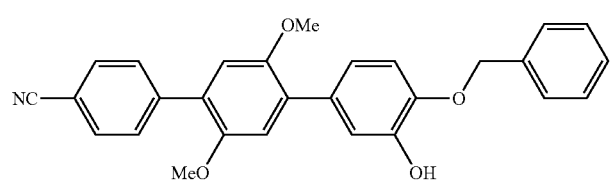
I-492
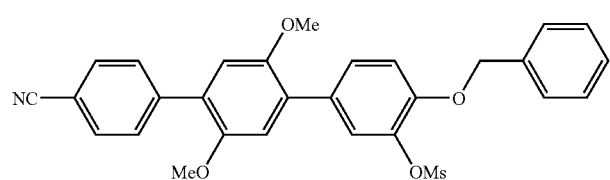
I-493
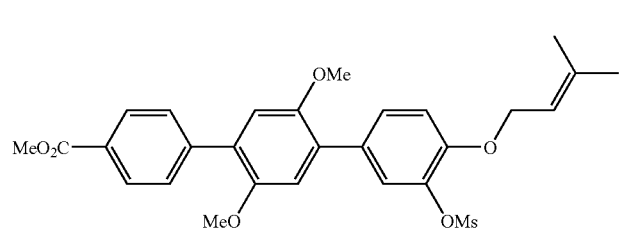
I-494
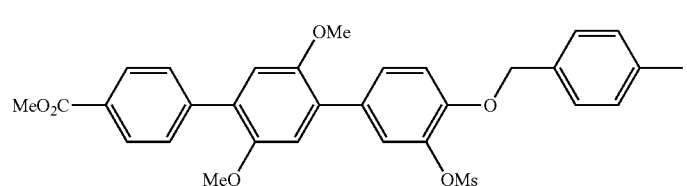
I-495
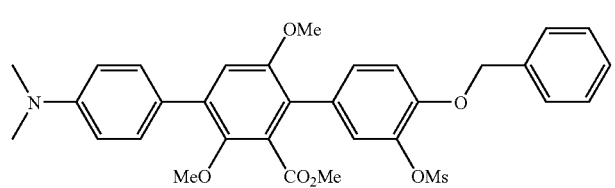
I-496
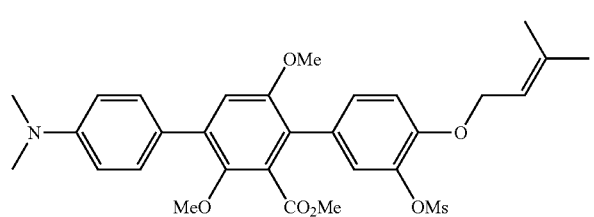
I-497
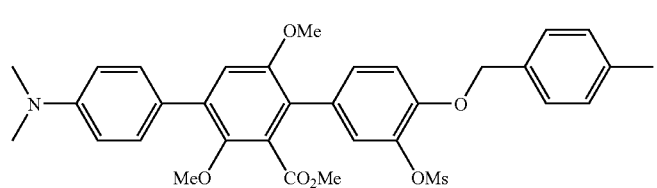
I-498

-continued
I-499
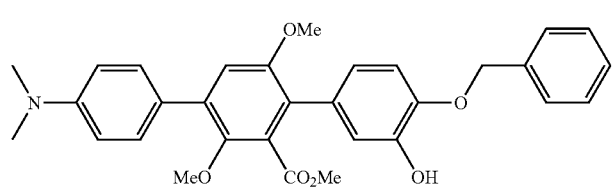
I-500
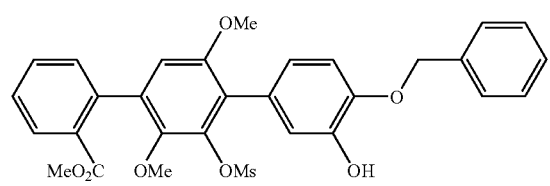
I-501
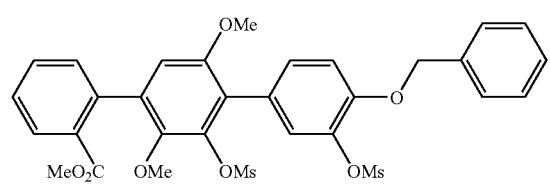
I-502
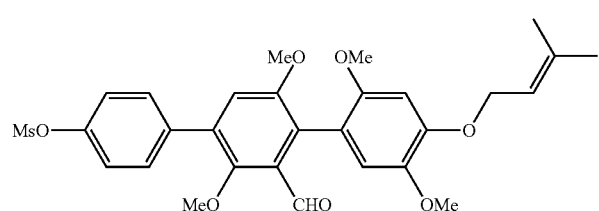
I-503
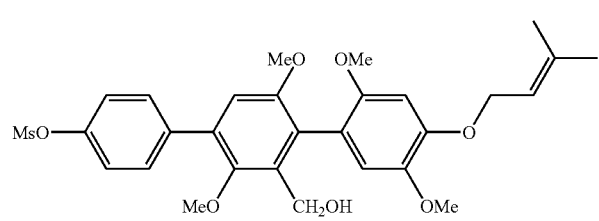
I-504
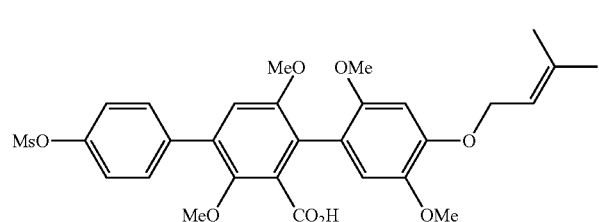
I-505
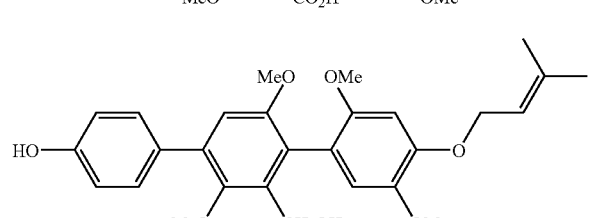
I-506
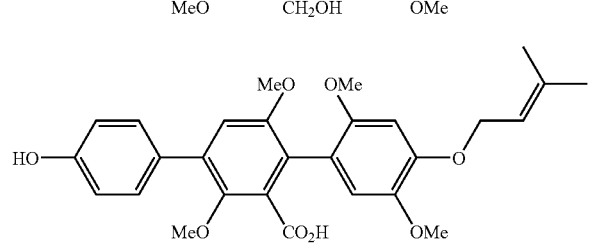

-continued
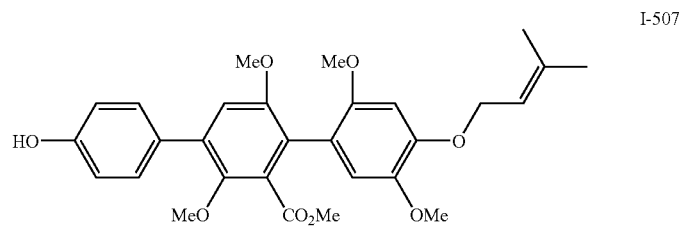
I-507
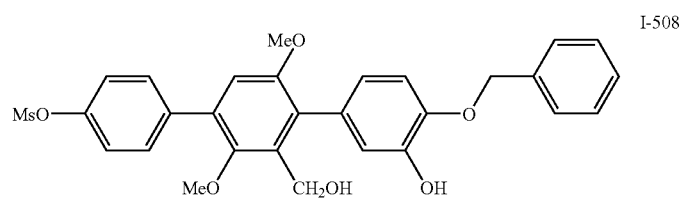
I-508
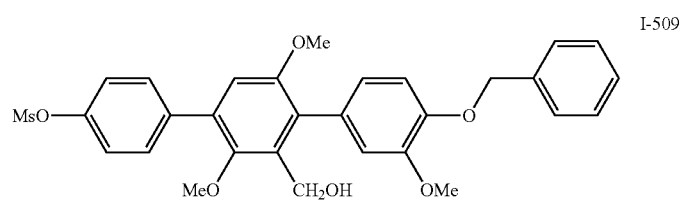
I-509
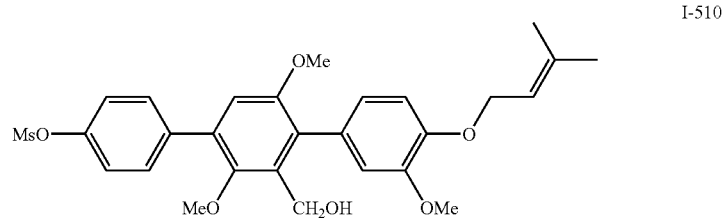
I-510
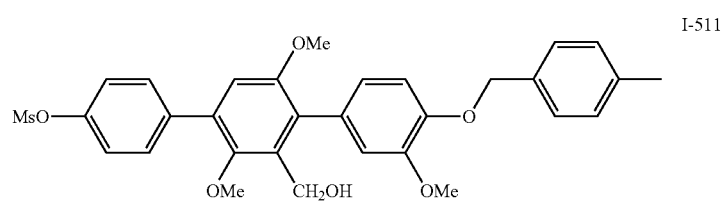
I-511
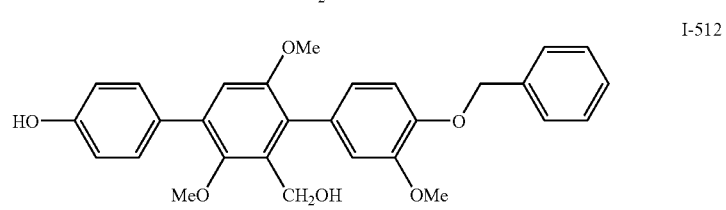
I-512
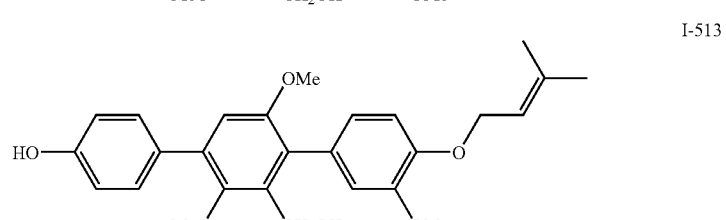
I-513
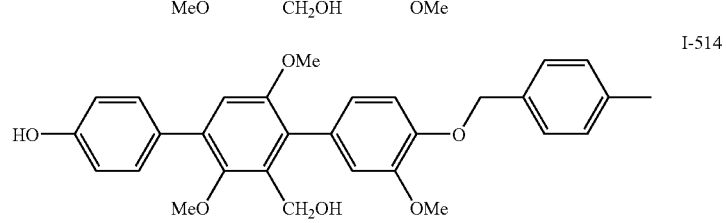
I-514

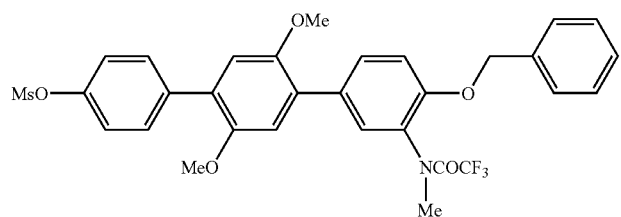
I-515
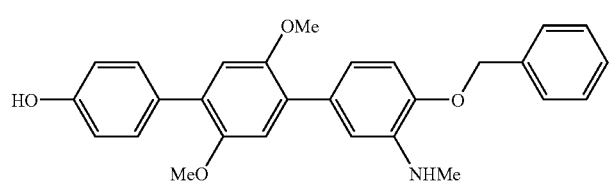
I-516
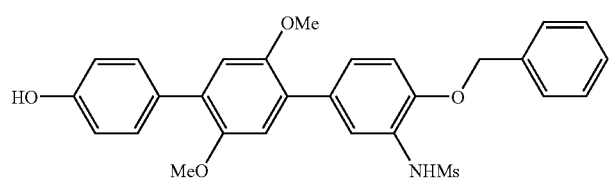
I-517
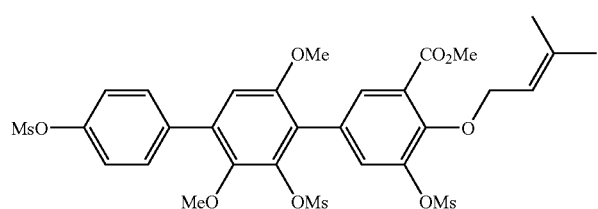
I-518
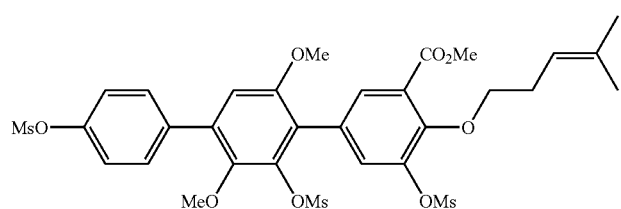
I-519
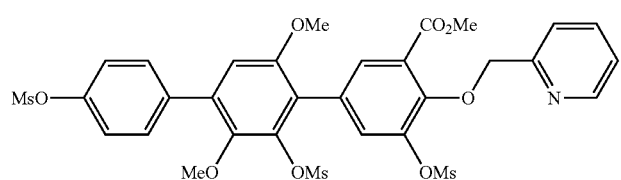
I-520
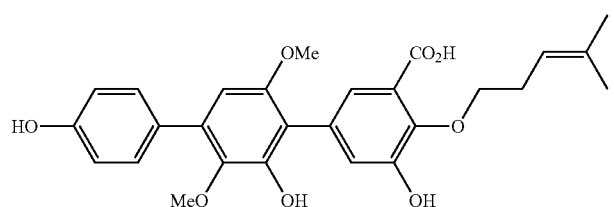
I-521
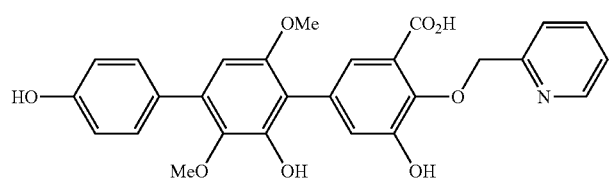
I-522

-continued
I-523
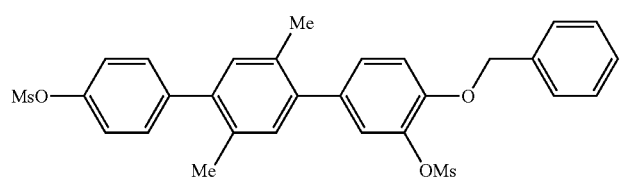
I-524
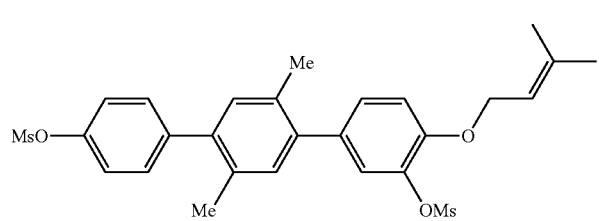
I-525
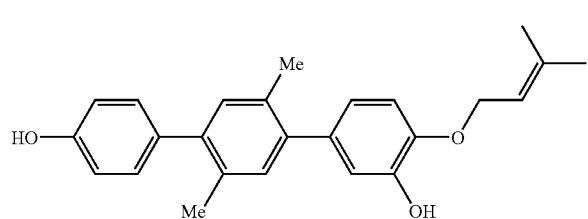
I-526
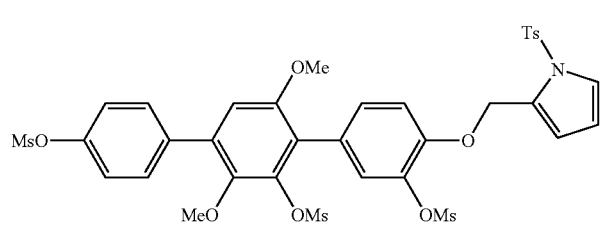
I-527
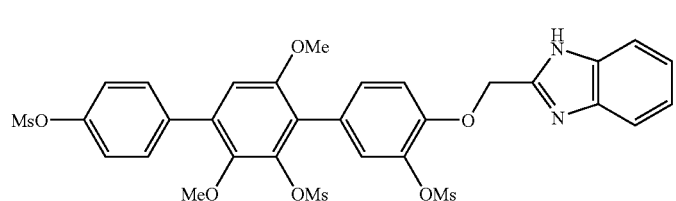
I-528
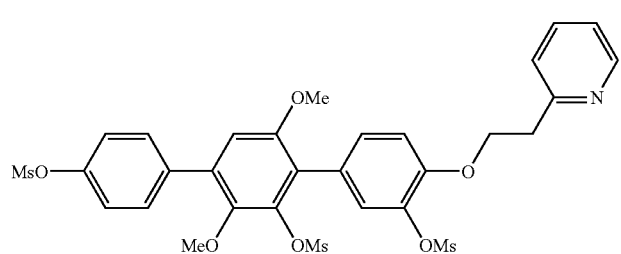
I-529
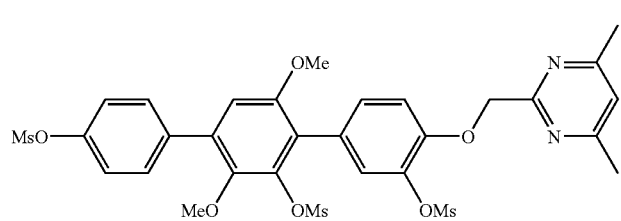

-continued
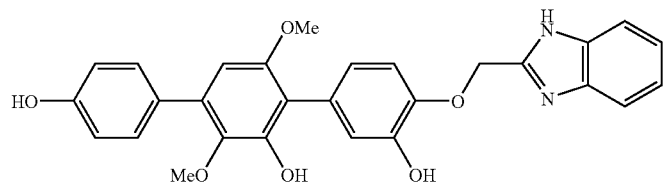
I-530
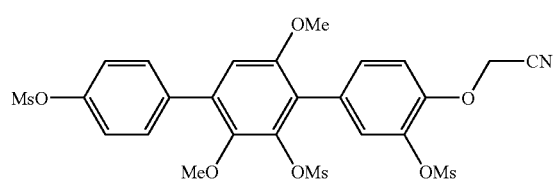
I-531
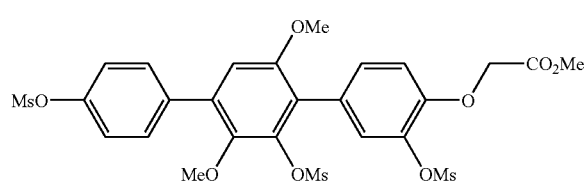
I-532
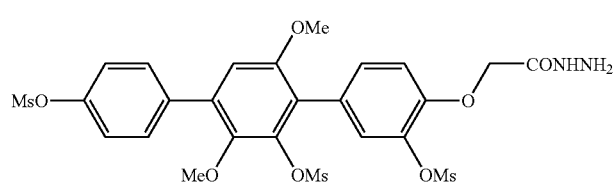
I-533
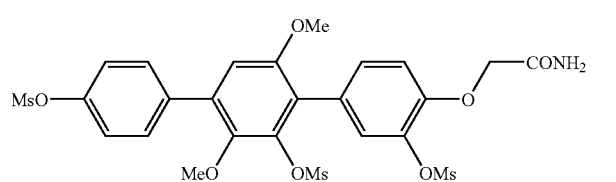
I-534
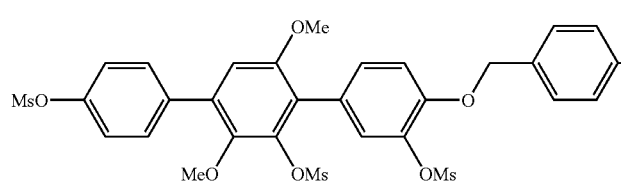
I-535
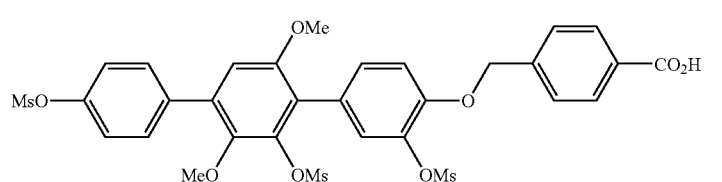
I-536
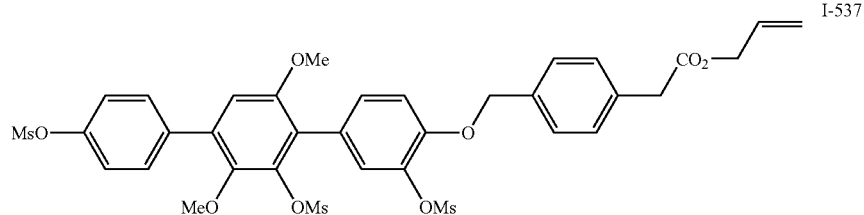
I-537

-continued
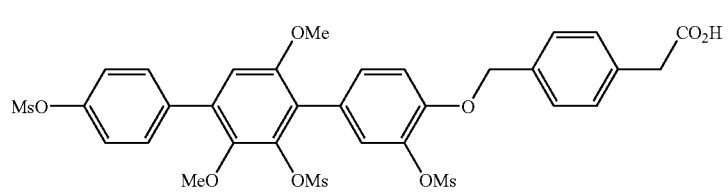
I-538
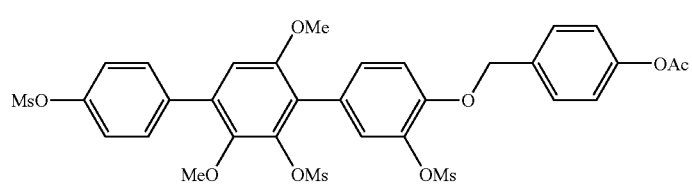
I-539
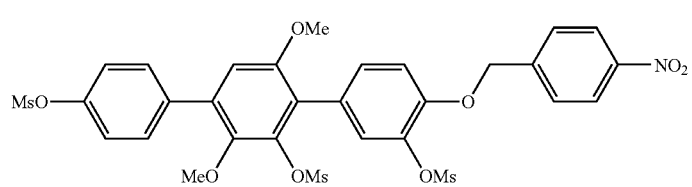
I-540
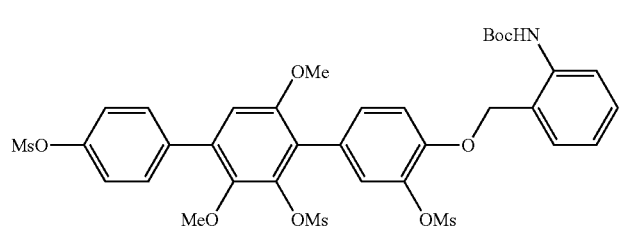
I-541
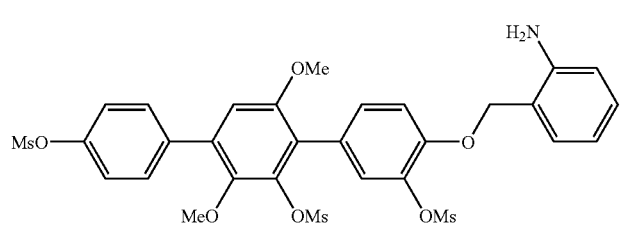
I-542
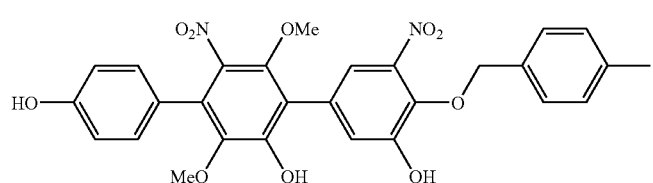
I-543
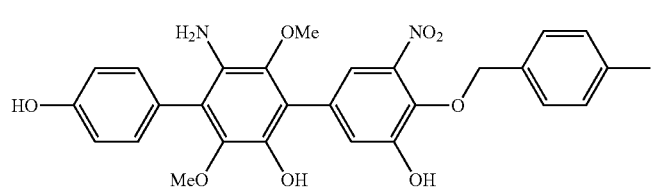
I-544
I-545
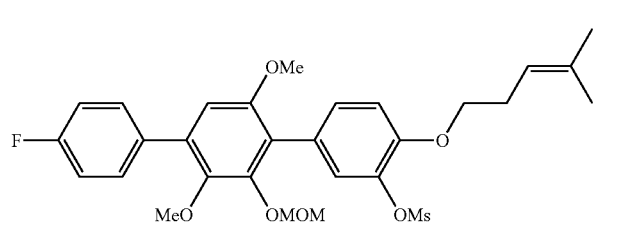

-continued
I-546
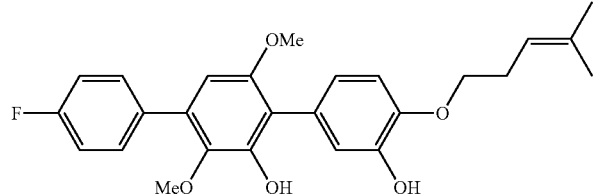
I-547
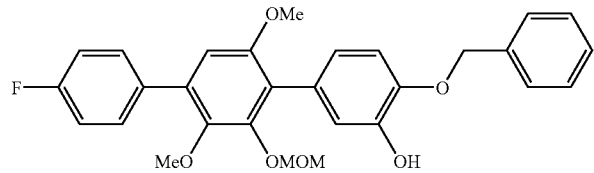
I-548
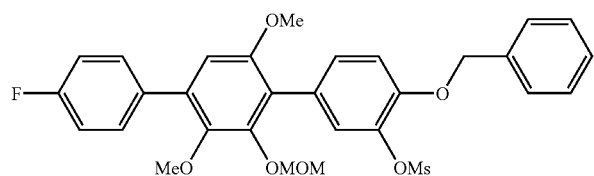
I-549
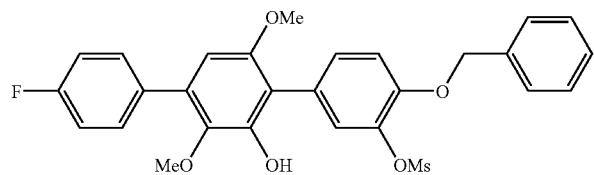
I-550
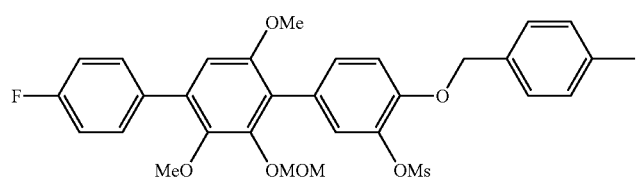
I-551
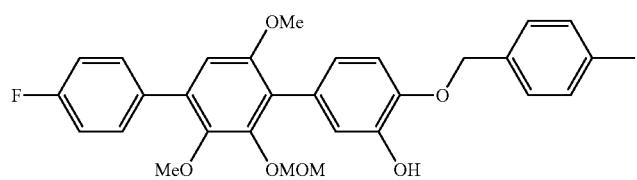
I-552
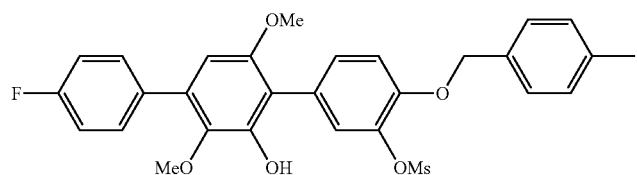
I-553
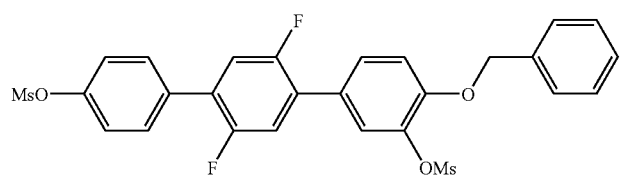

-continued
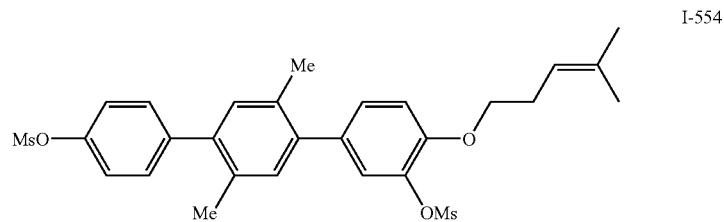
I-554
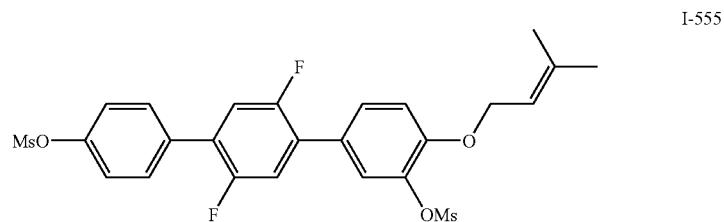
I-555
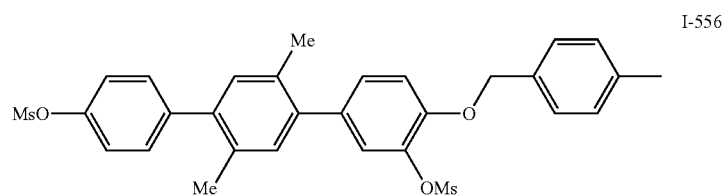
I-556
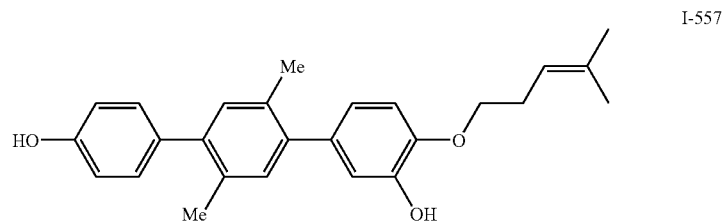
I-557
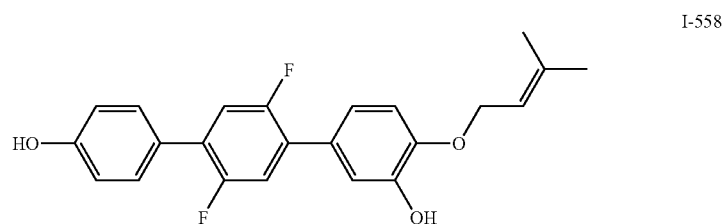
I-558
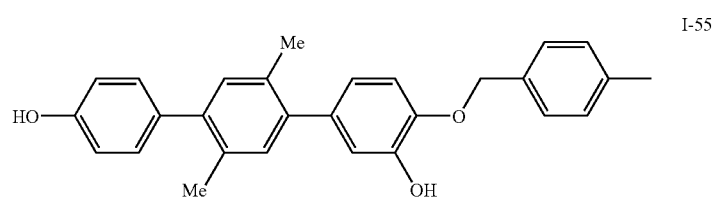
I-559
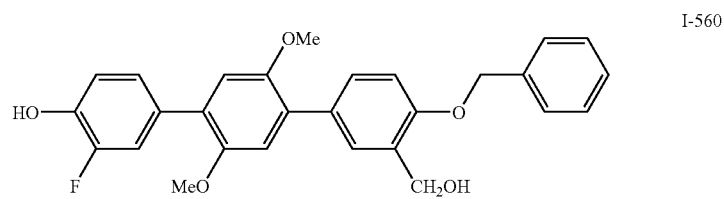
I-560
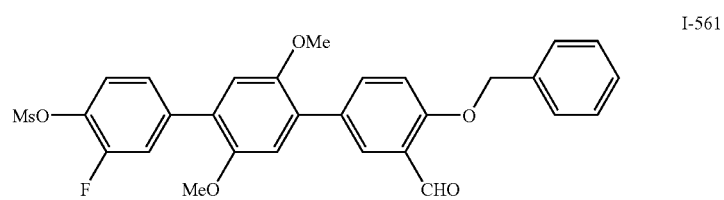
I-561

-continued
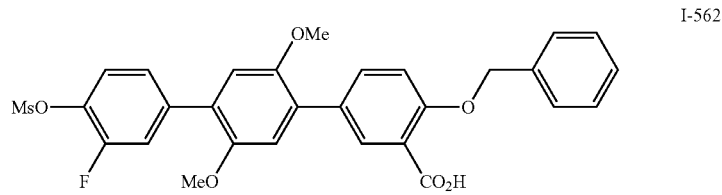
I-562
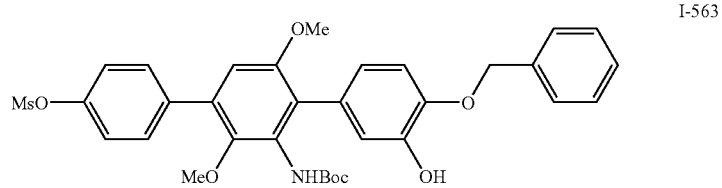
I-563
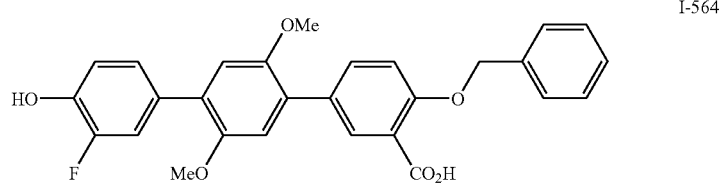
I-564
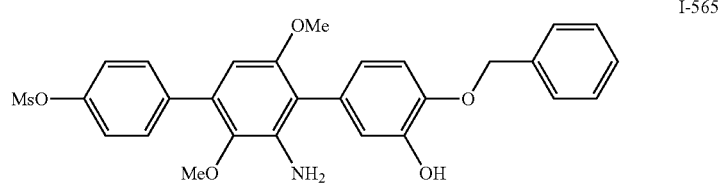
I-565
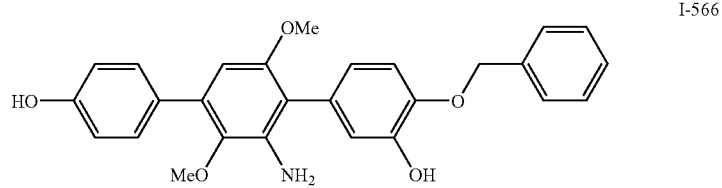
I-566
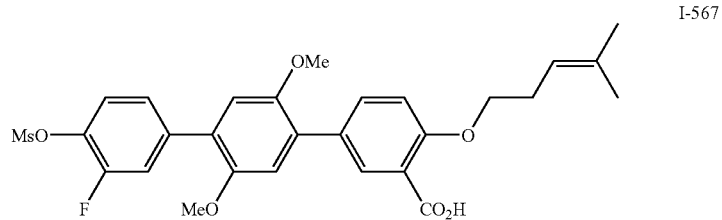
I-567
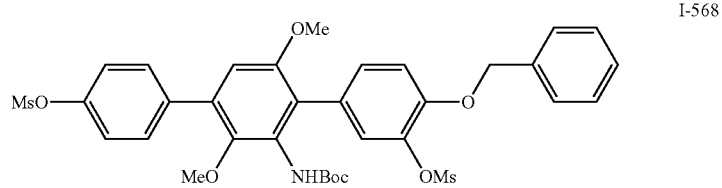
I-568
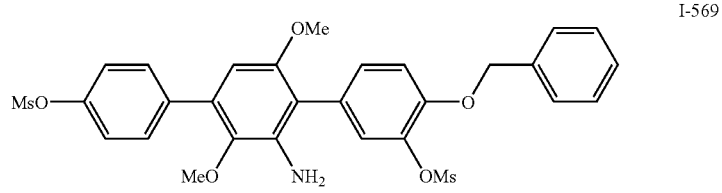
I-569

-continued
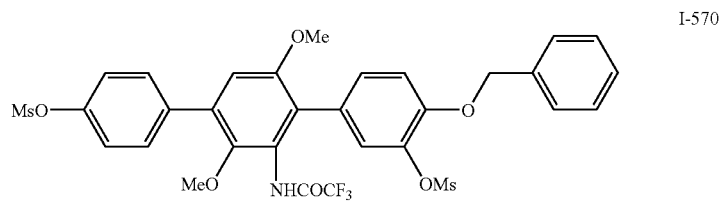
I-570
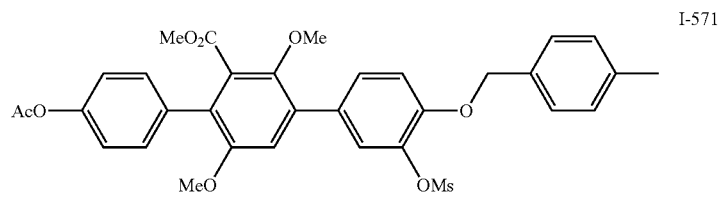
I-571
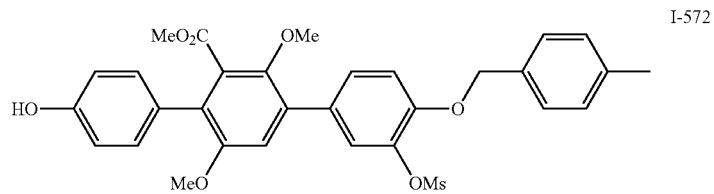
I-572
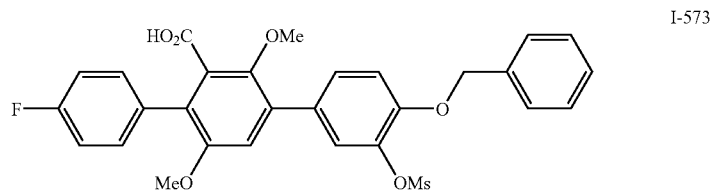
I-573
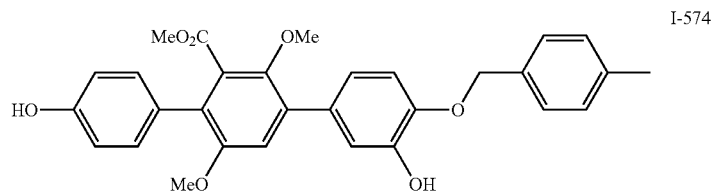
I-574
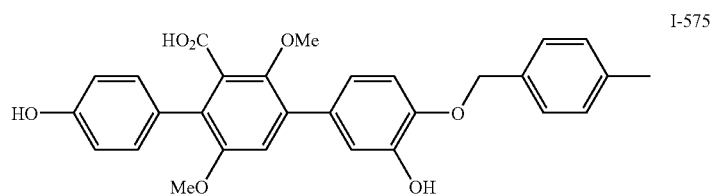
I-575
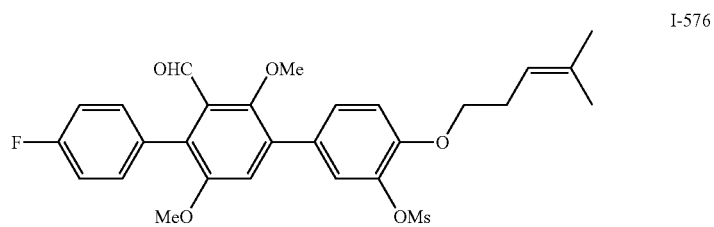
I-576
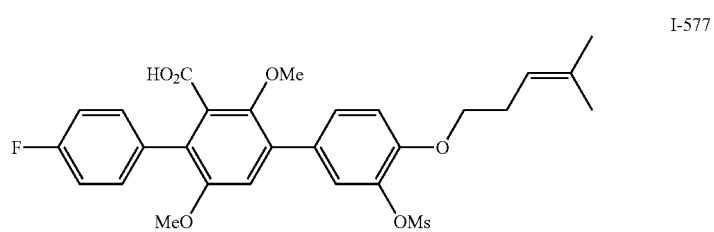
I-577

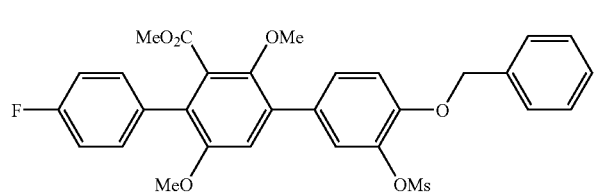
I-578
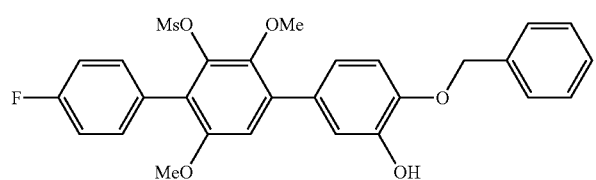
I-579
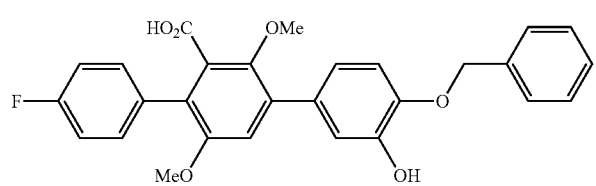
I-580
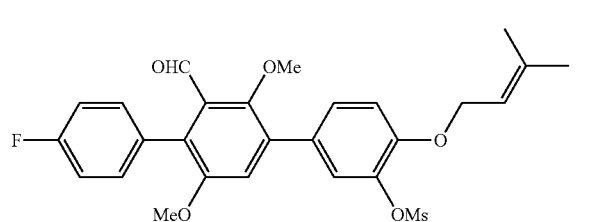
I-581
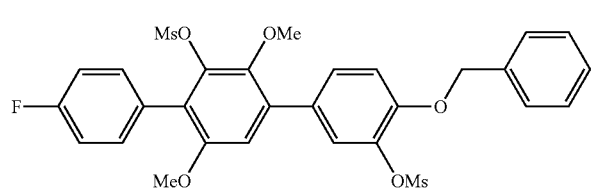
I-582
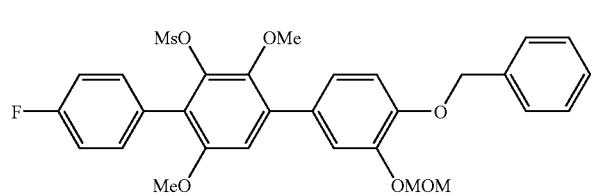
I-583
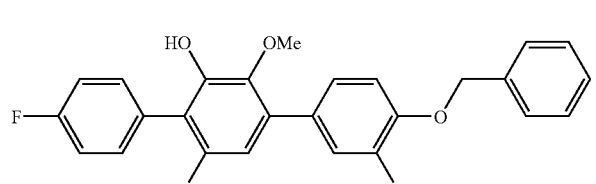
I-584
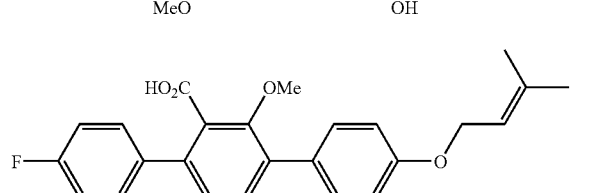
I-585

-continued
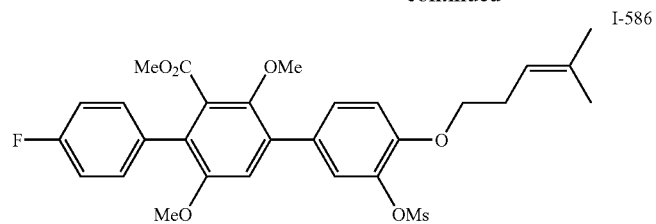
I-586
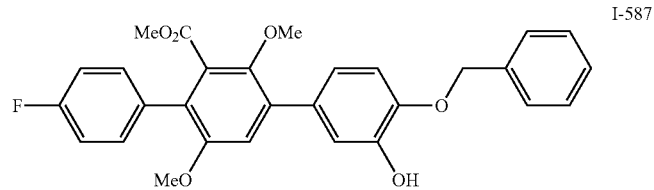
I-587
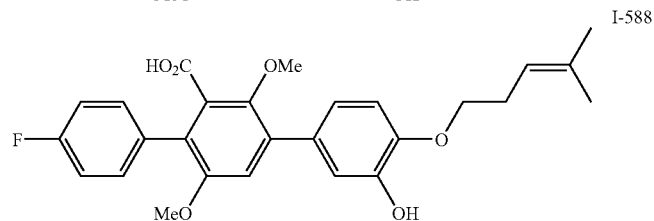
I-588
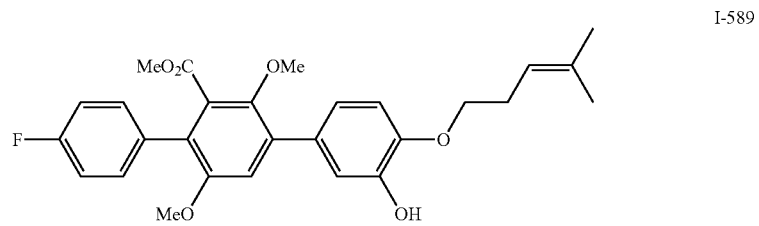
I-589
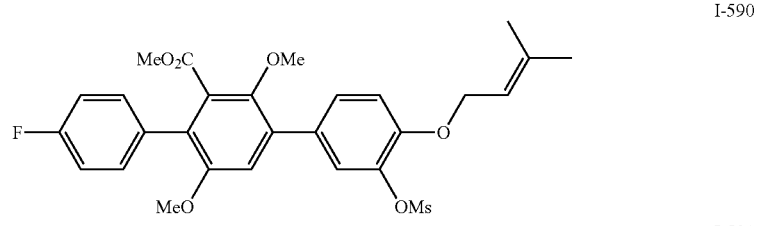
I-590
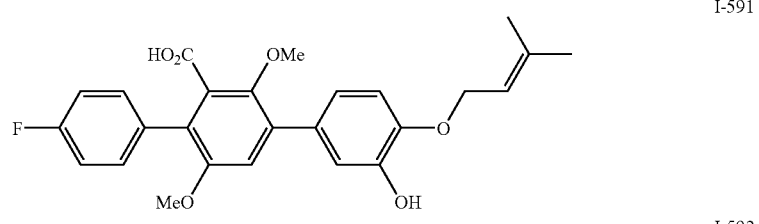
I-591
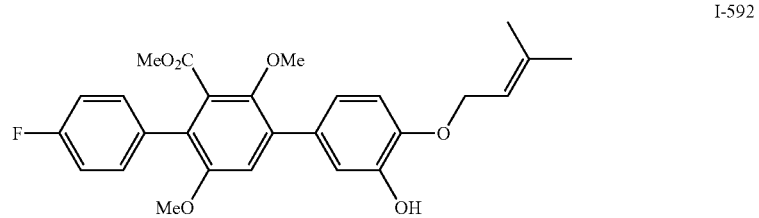
I-592
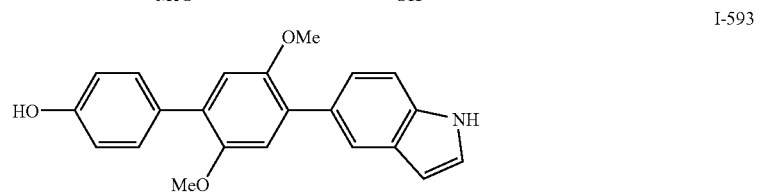
I-593

-continued
I-594
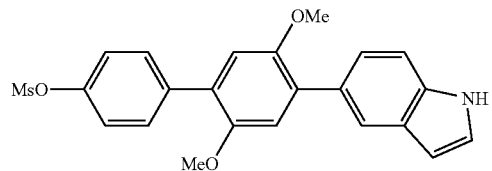
I-595
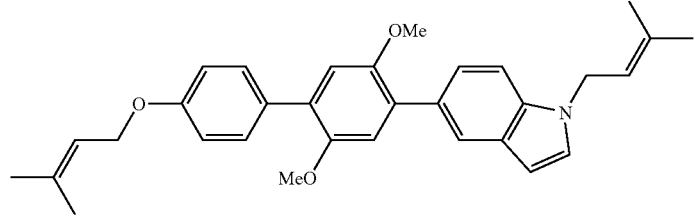
I-596
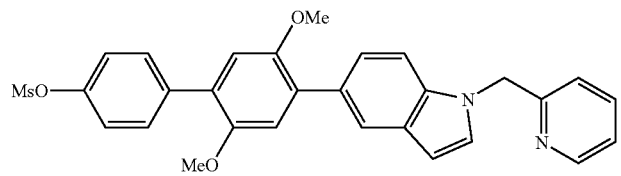
I-597
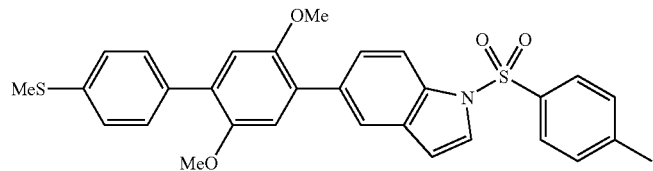
I-598
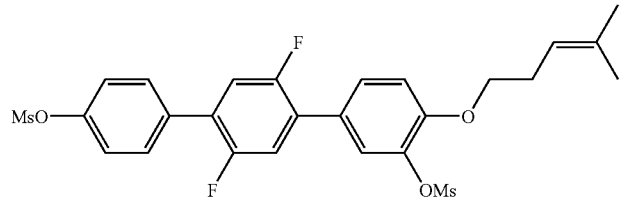
I-599
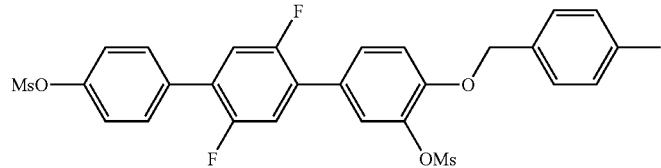
I-600
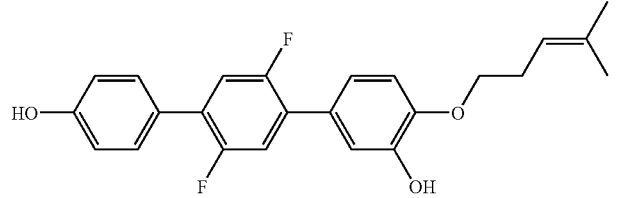
I-601
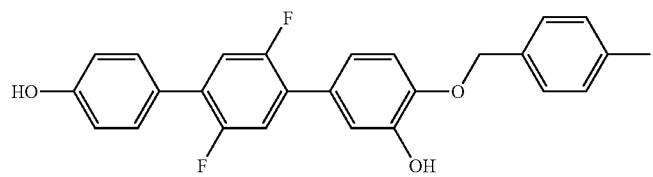

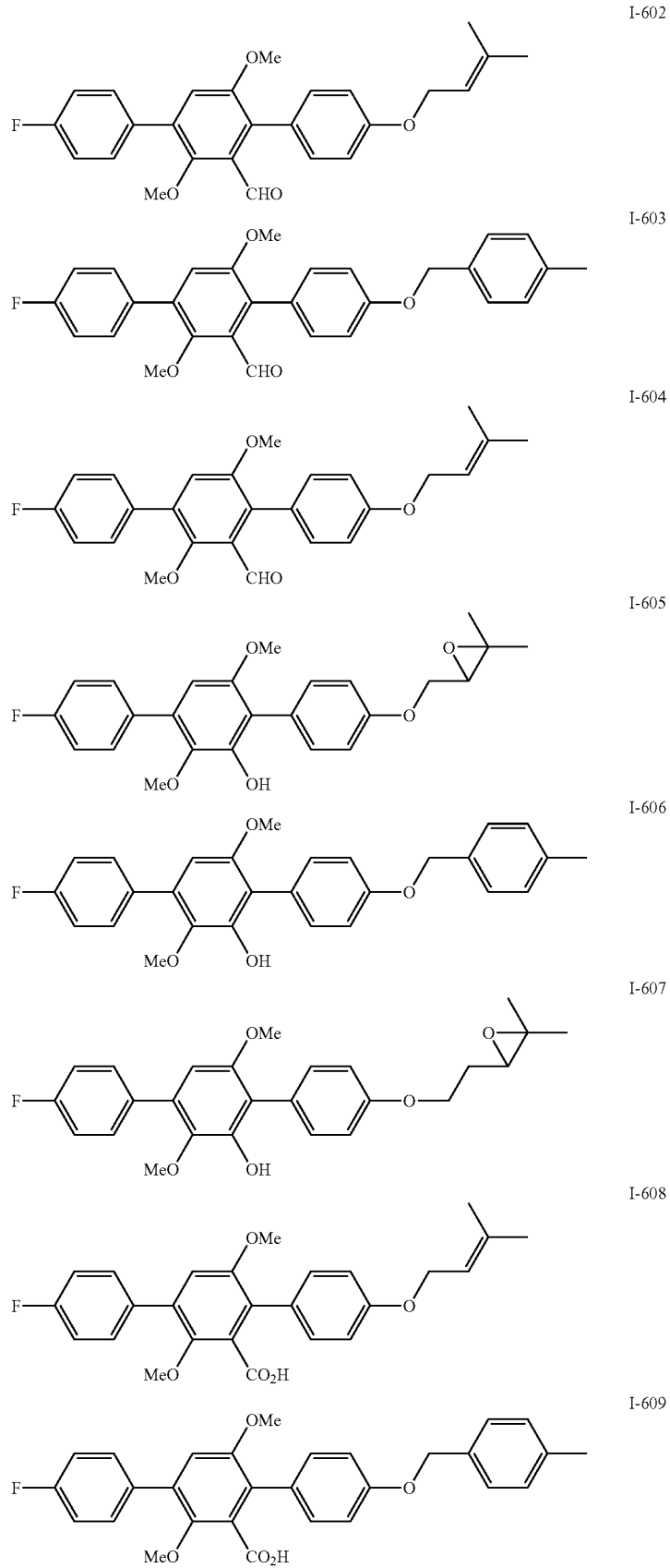

-continued
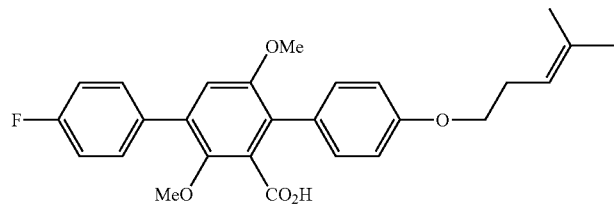
I-610
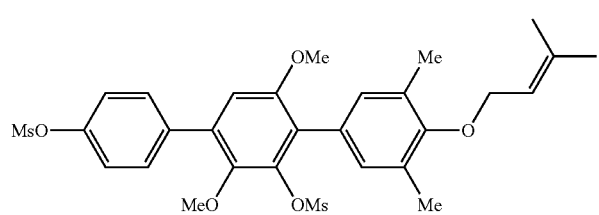
I-611
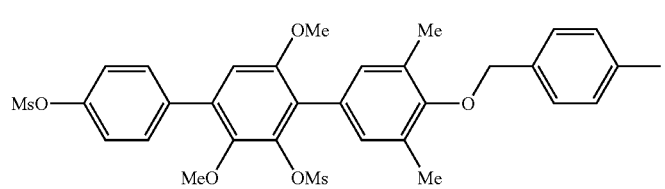
I-612
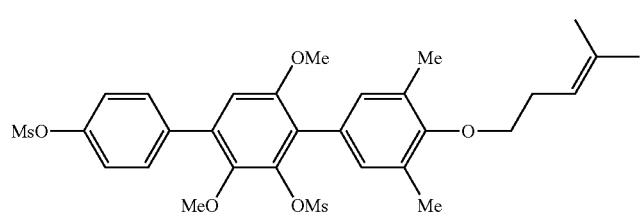
I-613
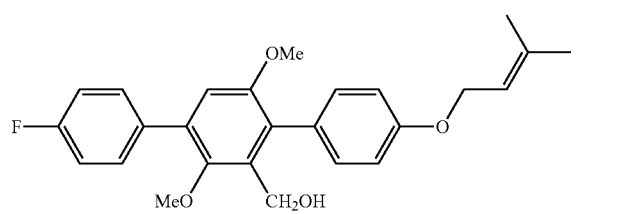
I-614
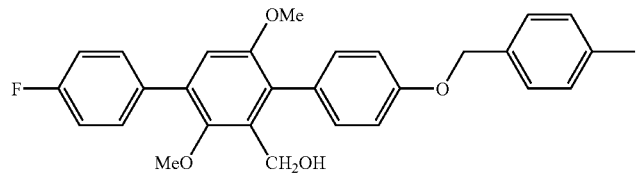
I-615
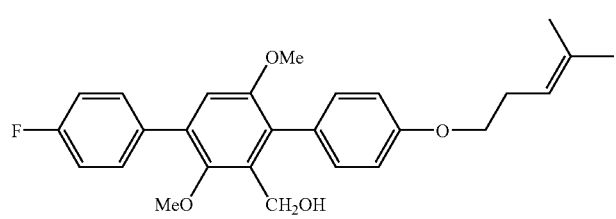
I-616
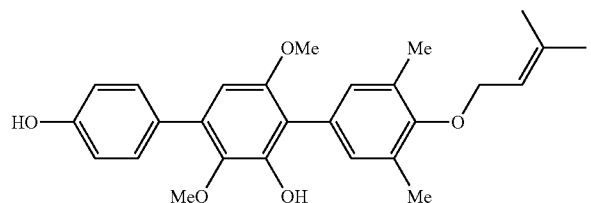
I-617

-continued
I-618
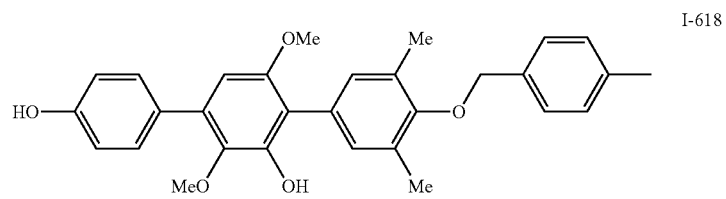
I-619
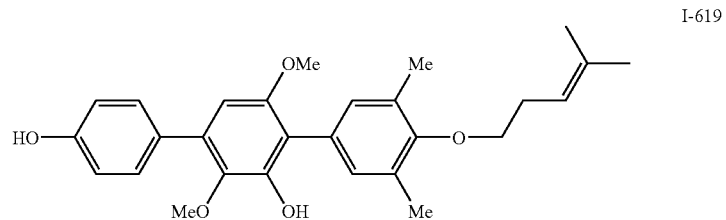
I-620
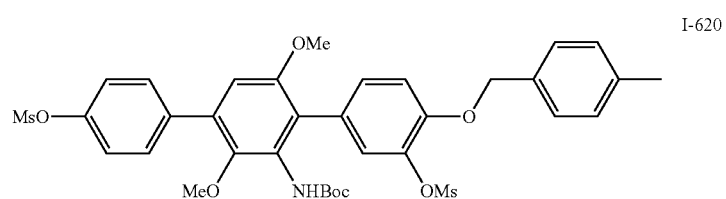
I-621
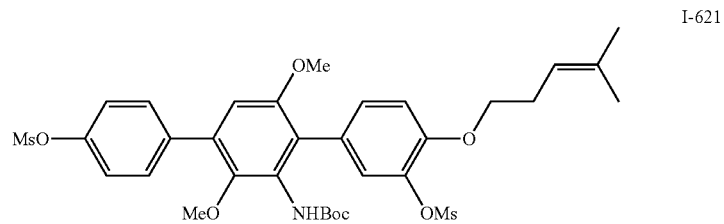
I-622
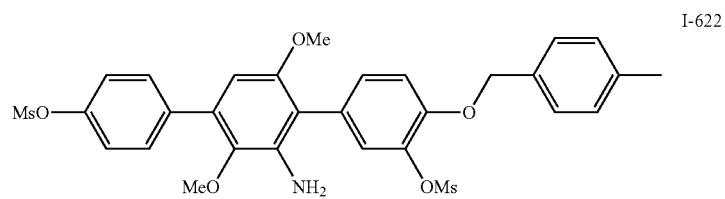
I-623
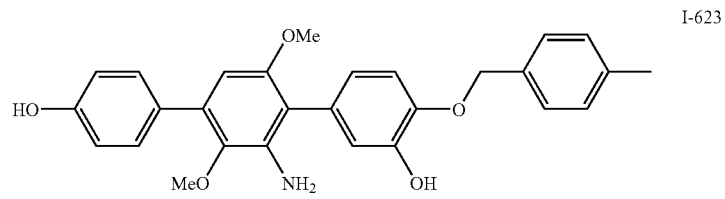
I-624
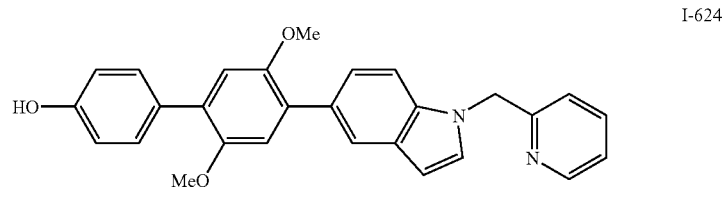
I-625
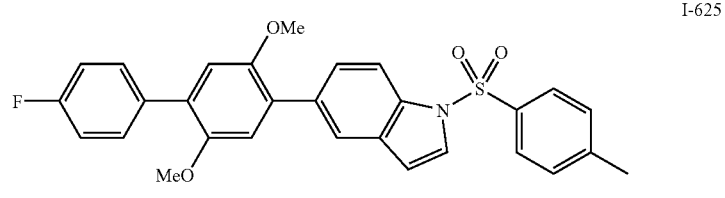

-continued
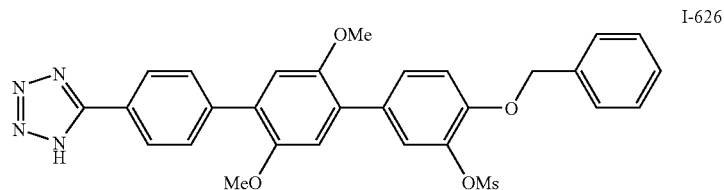
I-626
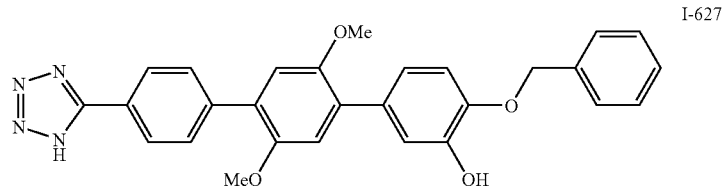
I-627
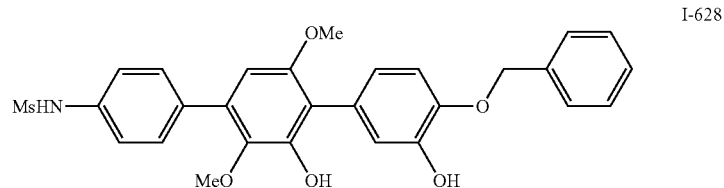
I-628
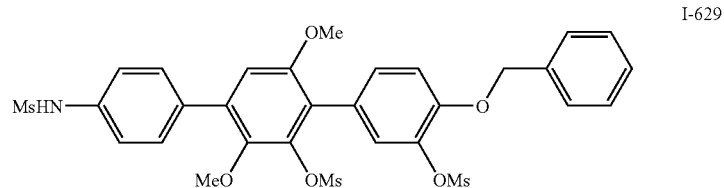
I-629
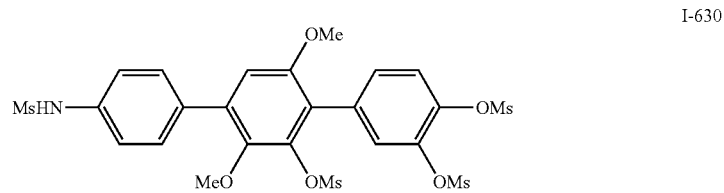
I-630
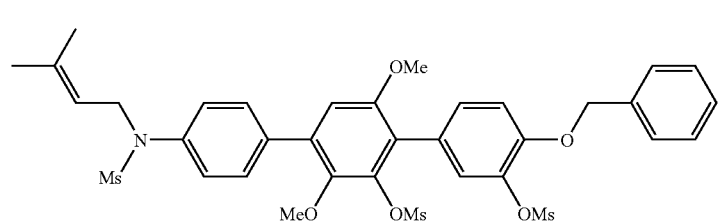
I-631
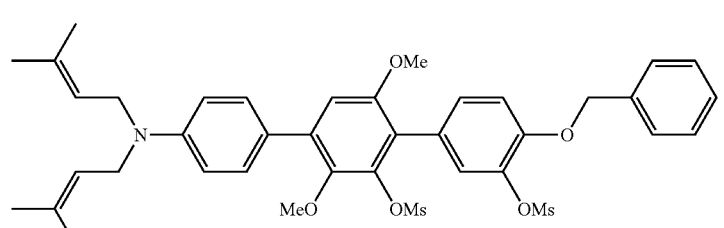
I-632
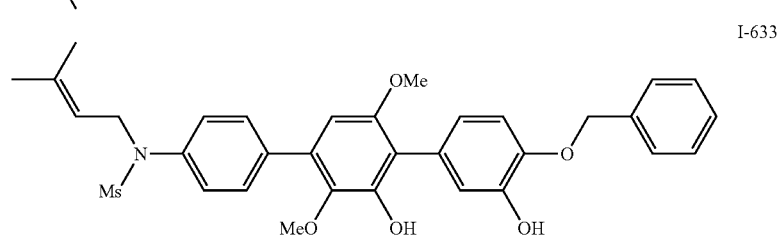
I-633

-continued
I-634
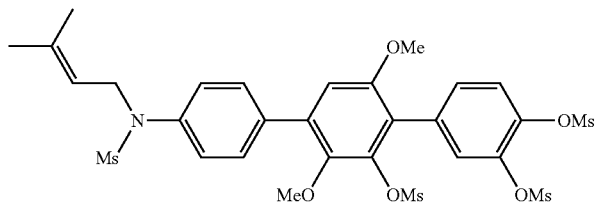
I-635
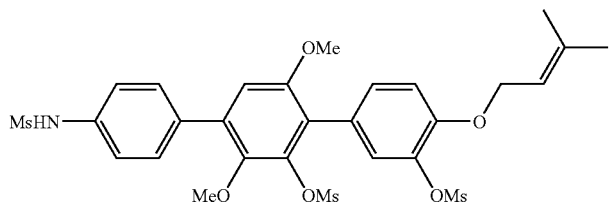
I-636
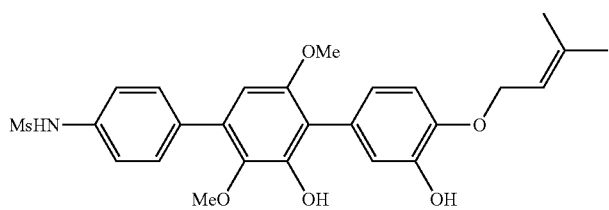
I-637
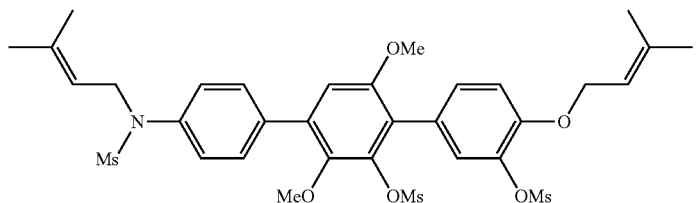
I-638
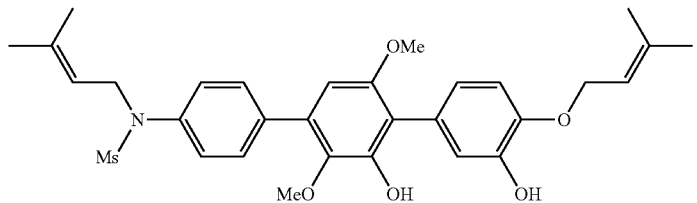
I-639
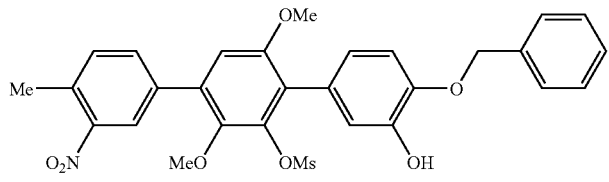
I-640
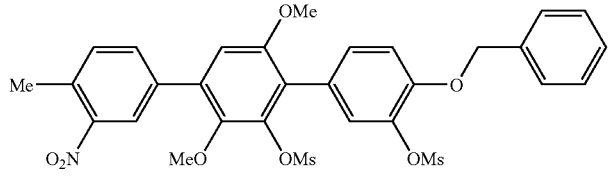
I-641
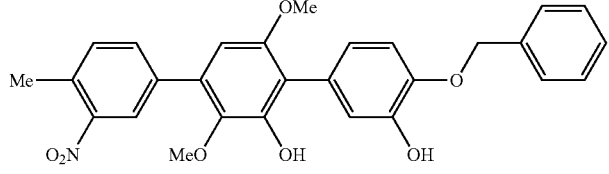

-continued
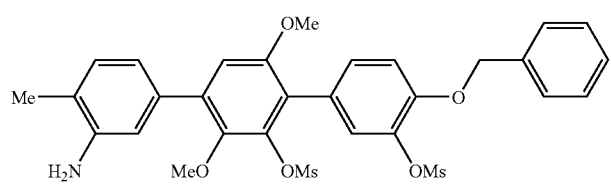
I-642
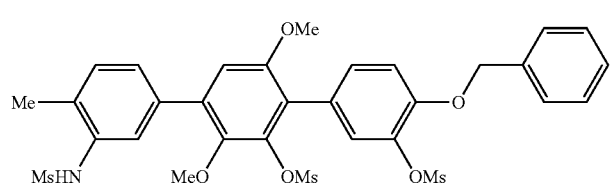
I-643
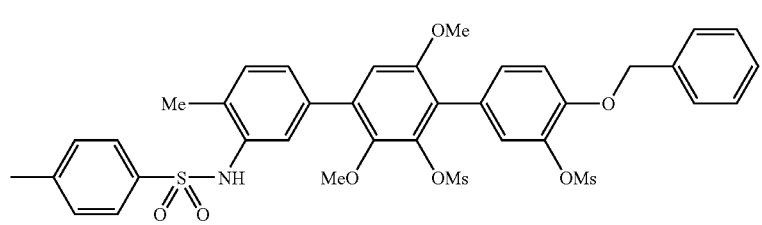
I-644
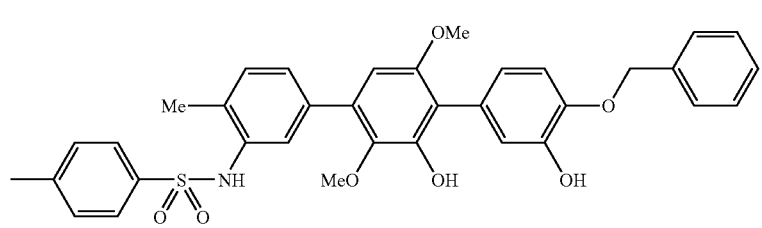
I-645
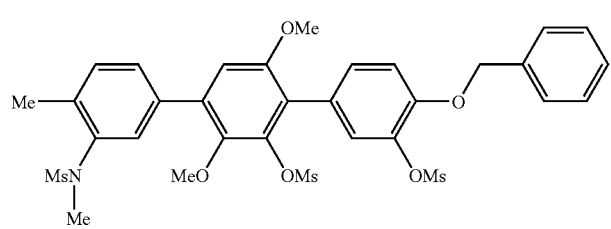
I-646
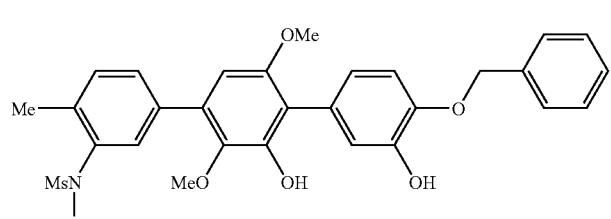
I-647
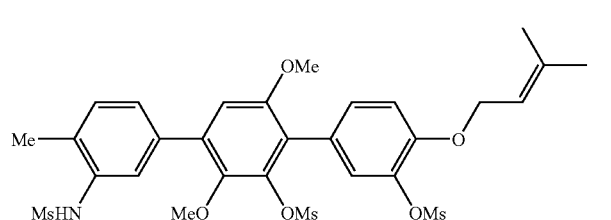
I-648

-continued
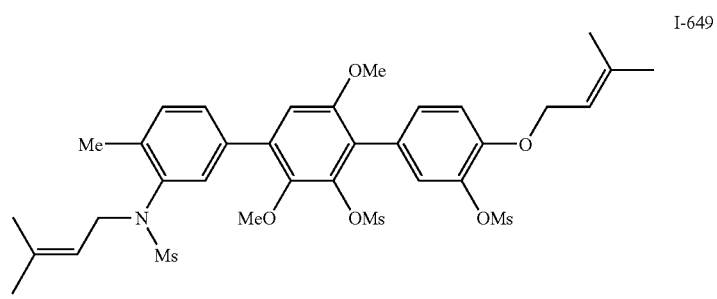
I-649
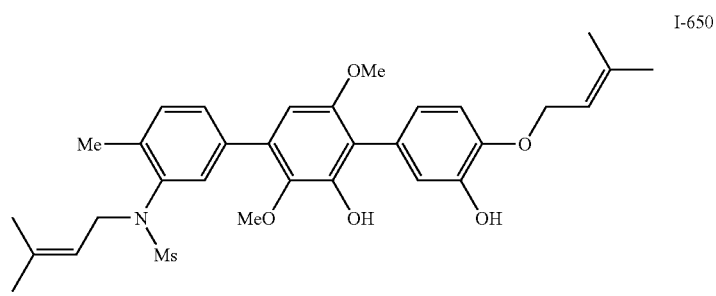
I-650
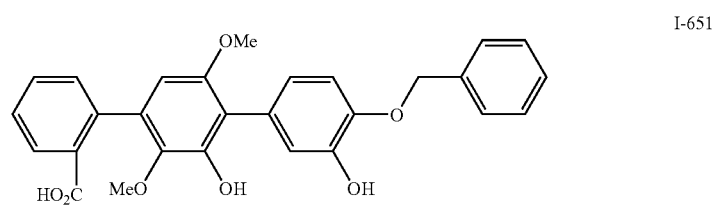
I-651
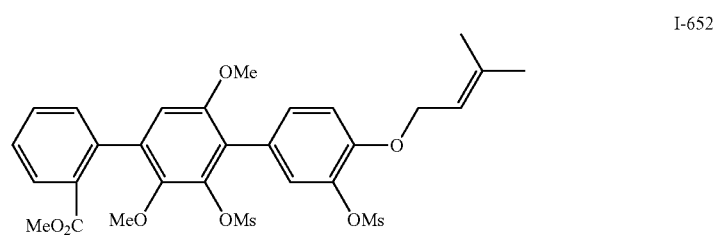
I-652
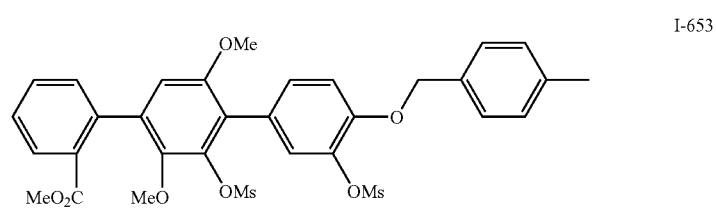
I-653
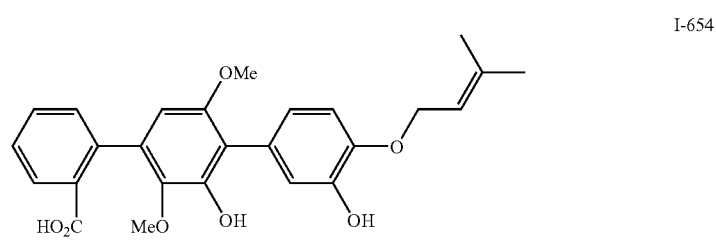
I-654
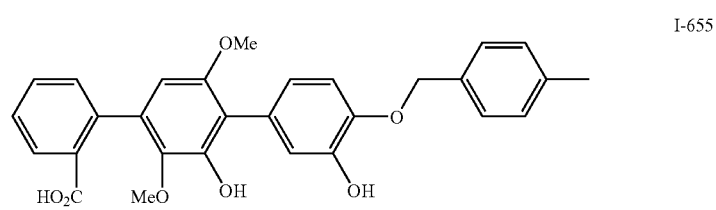
I-655

-continued
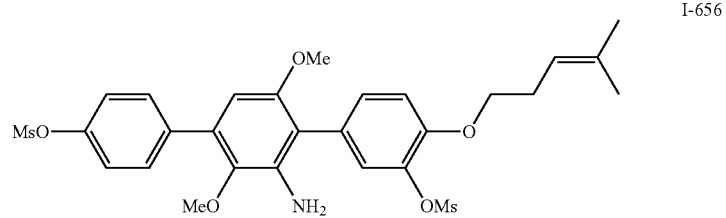
I-656
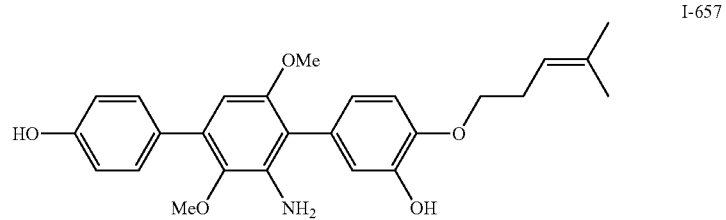
I-657
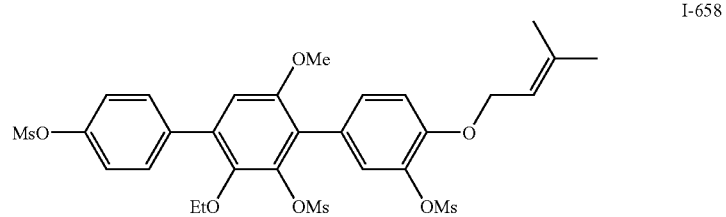
I-658
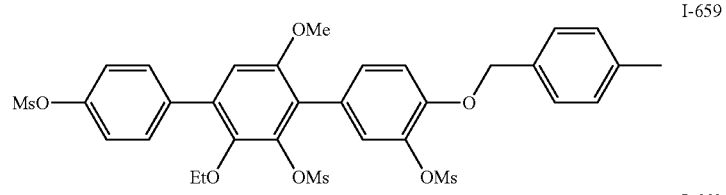
I-659
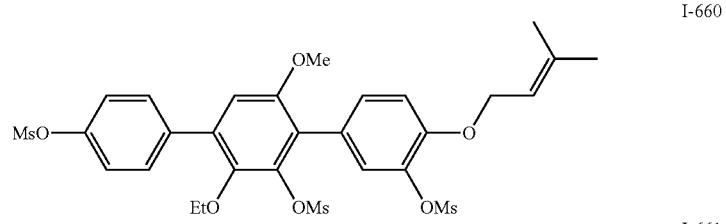
I-660
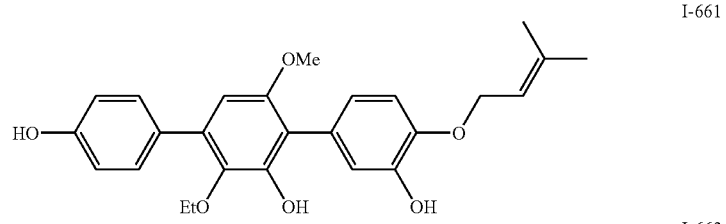
I-661
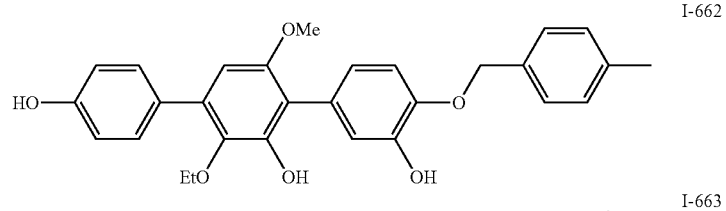
I-662
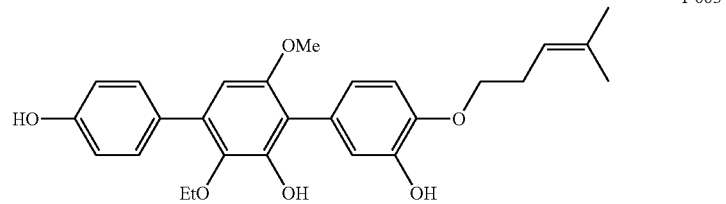
I-663

-continued
I-664
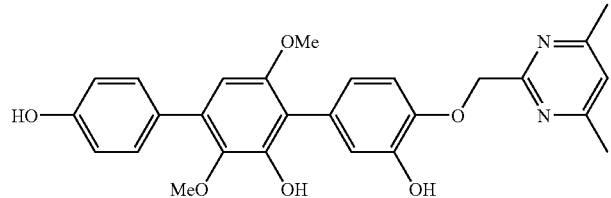
I-665
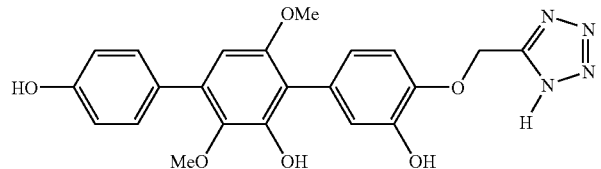
I-666
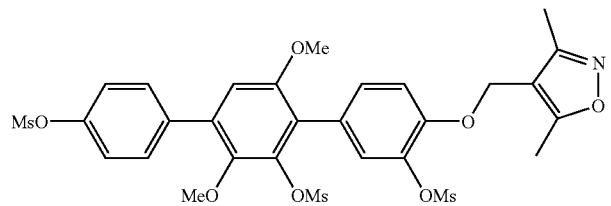
I-667
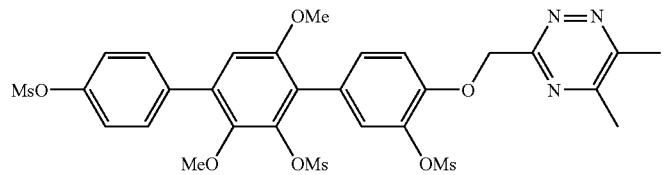
I-668
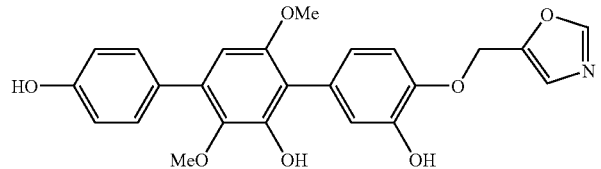
I-669
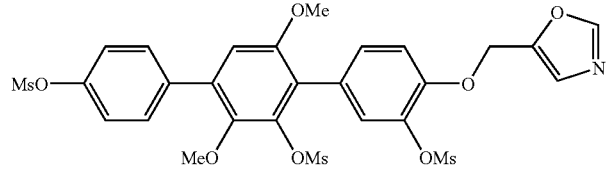
I-670
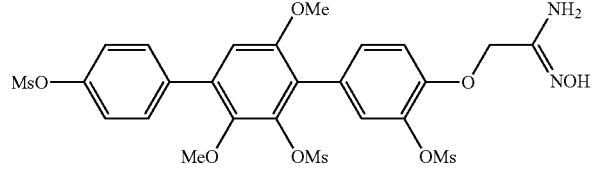
I-671
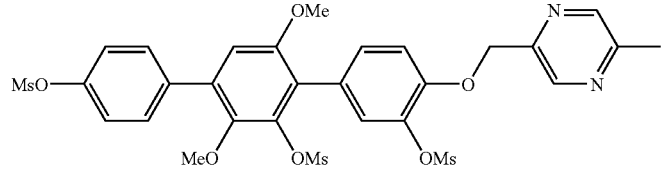

-continued
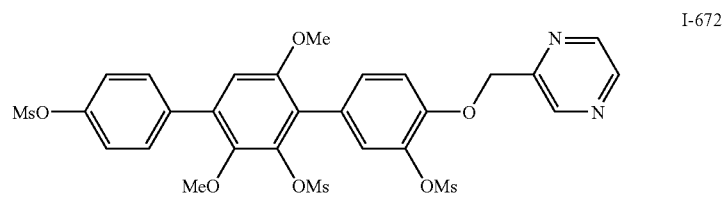 I-672
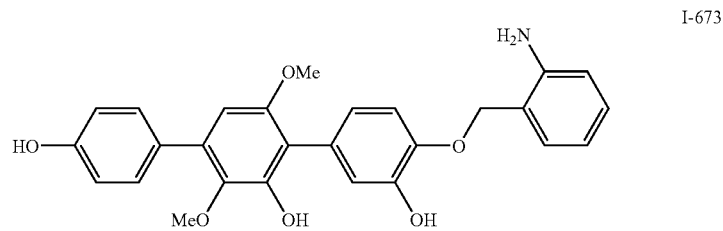 I-673
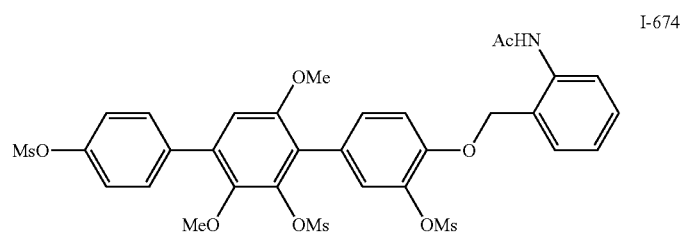 I-674
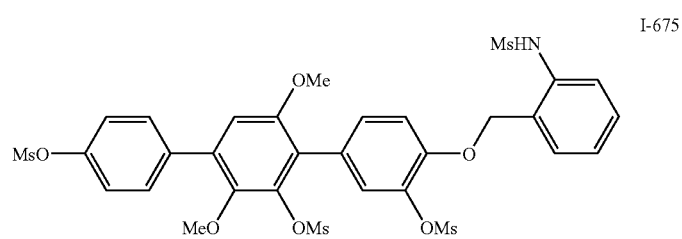 I-675
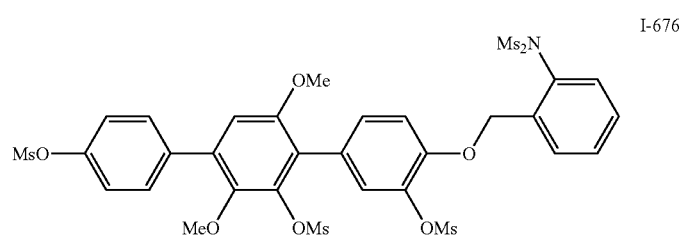 I-676
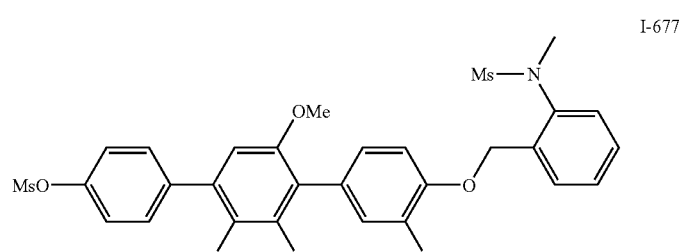 I-677
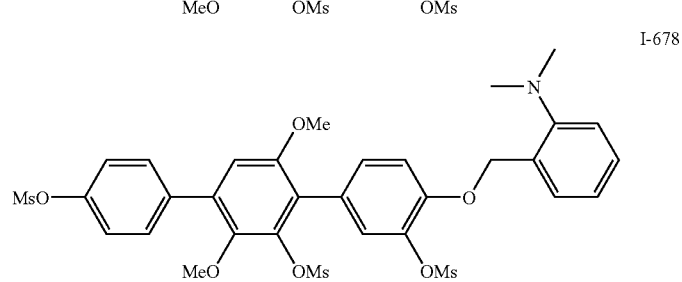 I-678

-continued
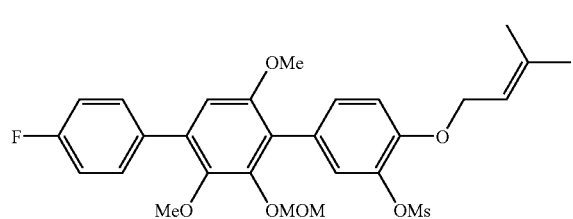
I-679
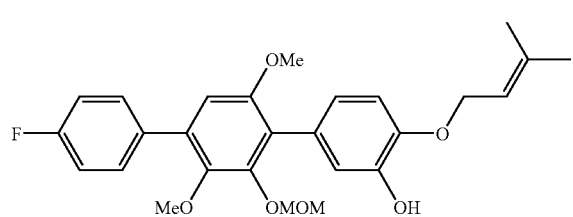
I-680
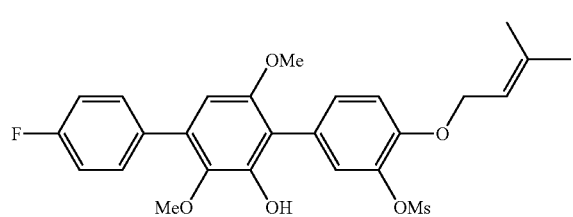
I-681
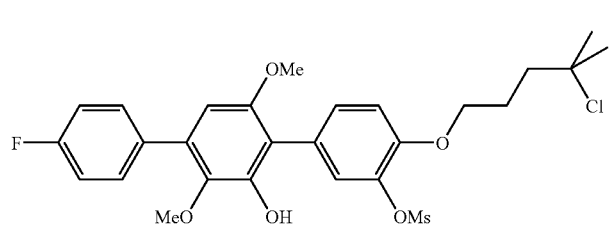
I-682
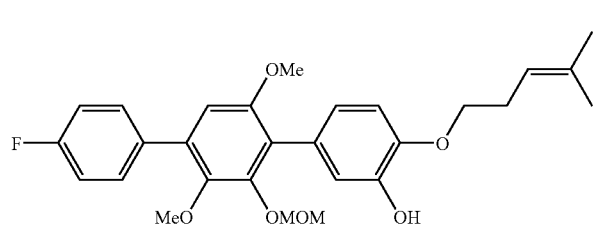
I-683
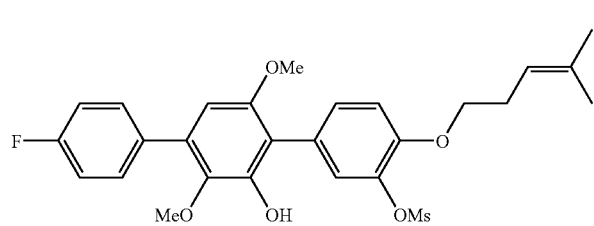
I-684
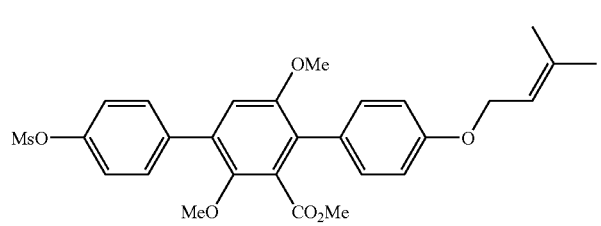
I-685

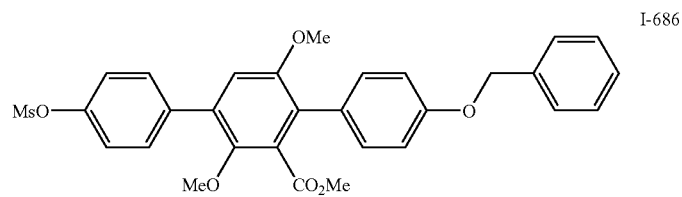
I-686
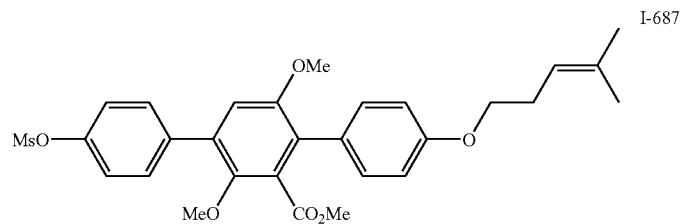
I-687
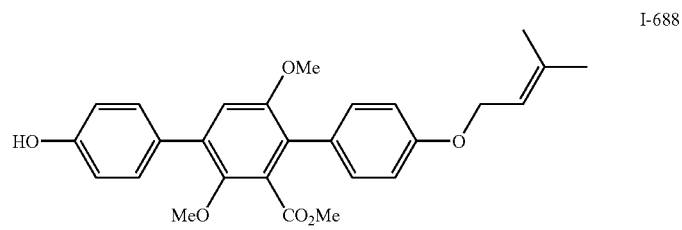
I-688
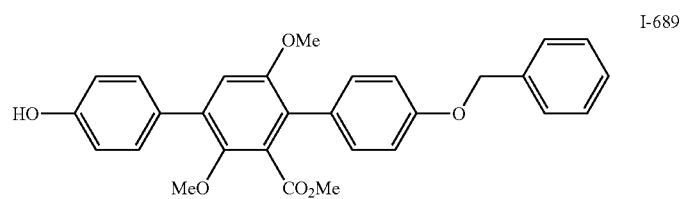
I-689
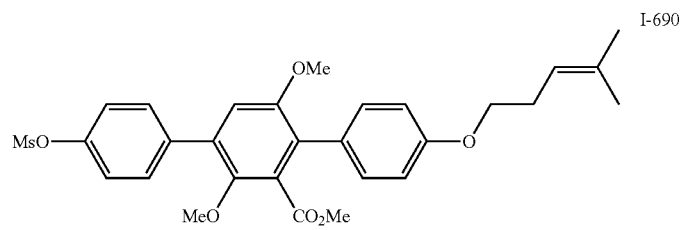
I-690
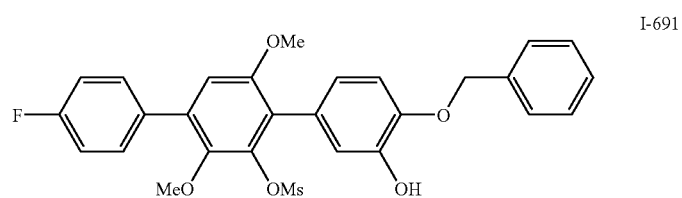
I-691
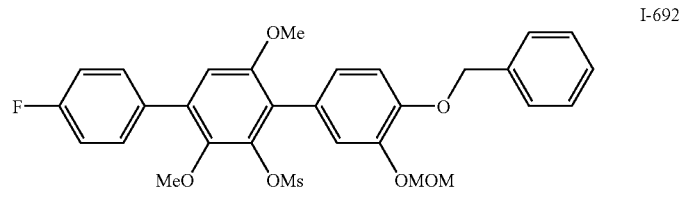
I-692
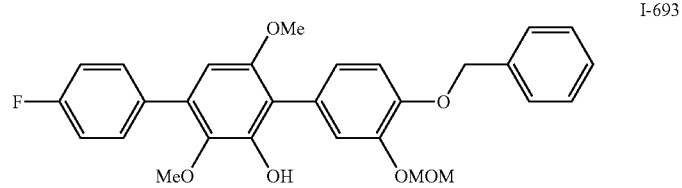
I-693

-continued
I-694
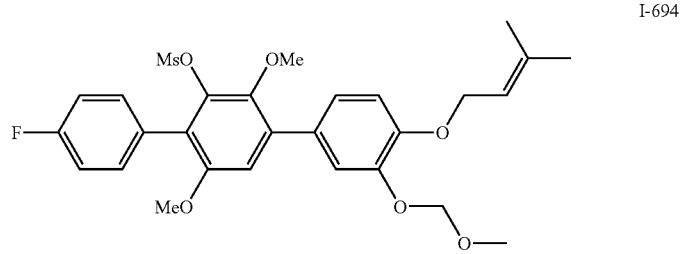
I-695
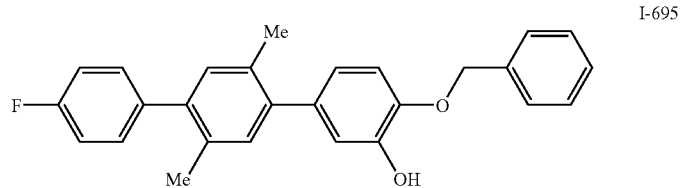
I-696
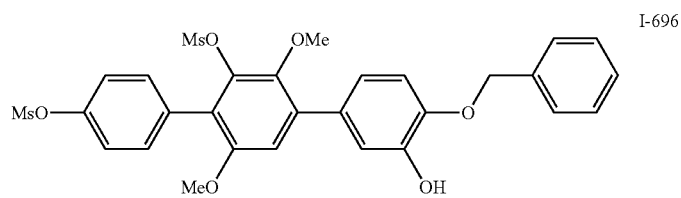
I-697
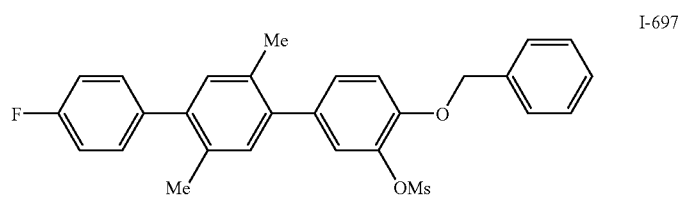
I-698
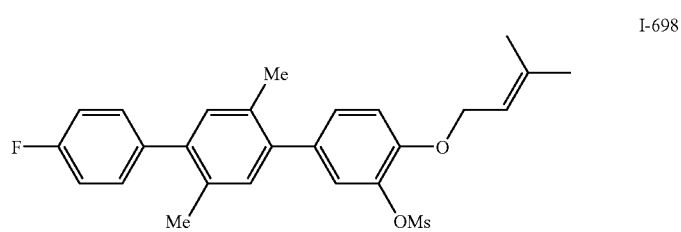
I-699
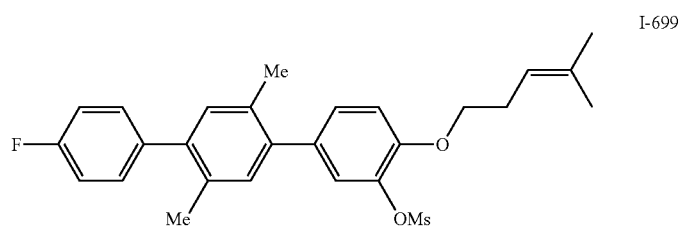
I-700
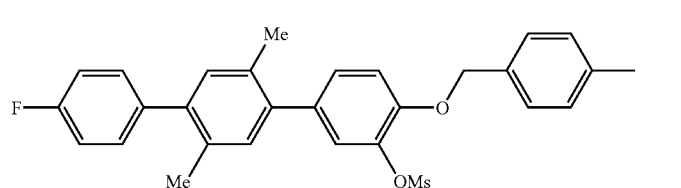
I-701
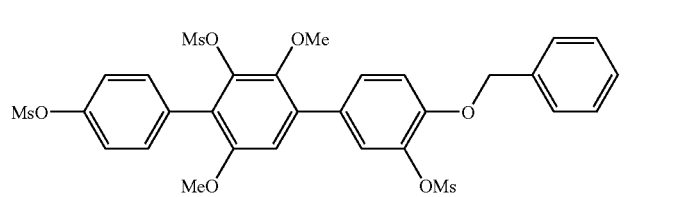

-continued
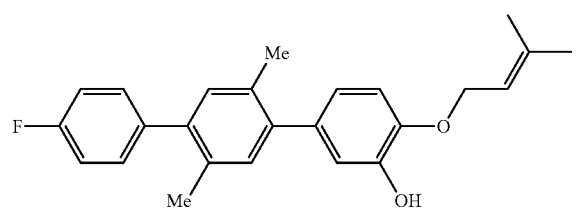
I-702
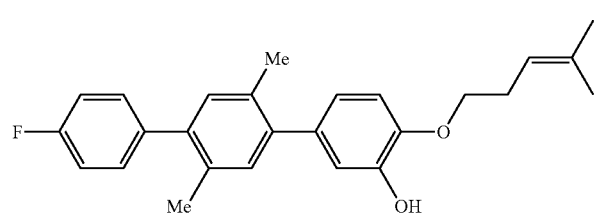
I-703
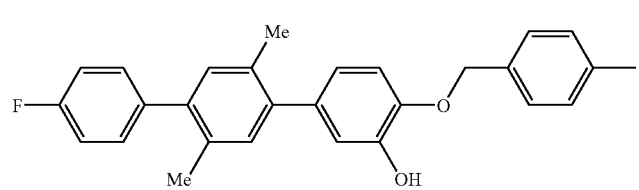
I-704
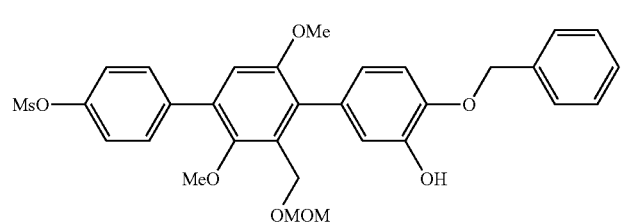
I-705
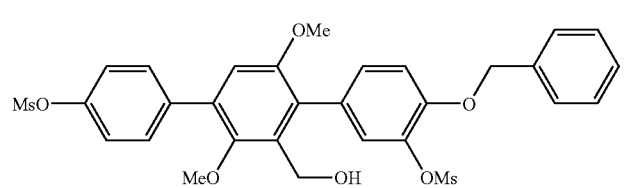
I-706
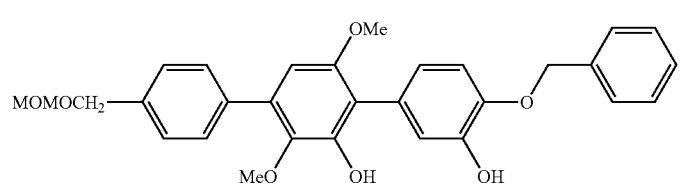
I-707
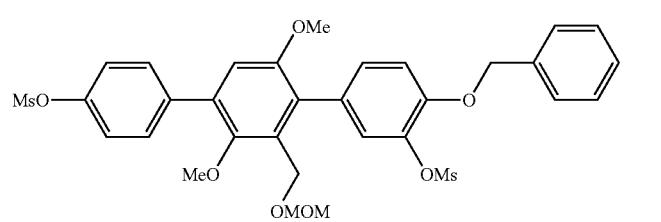
I-708
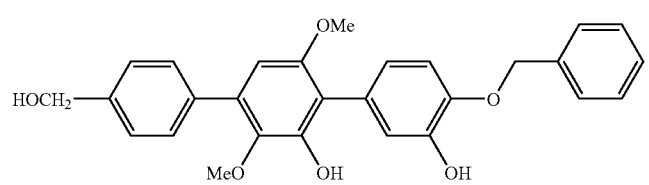
I-709

-continued
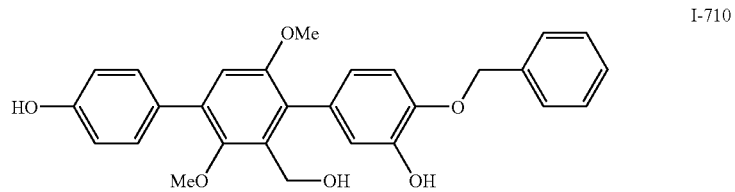
I-710
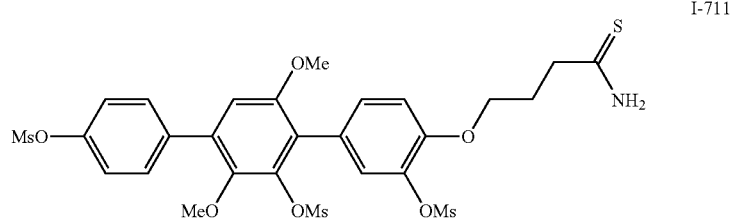
I-711
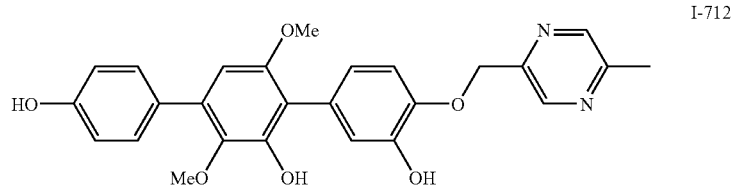
I-712
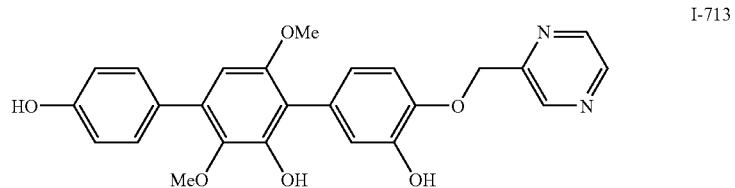
I-713
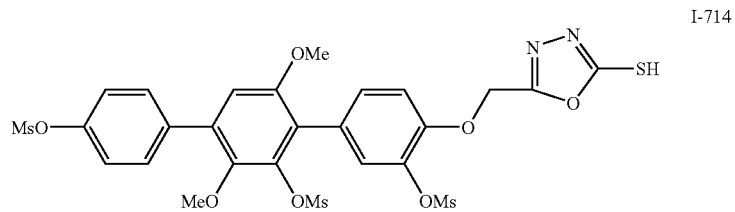
I-714
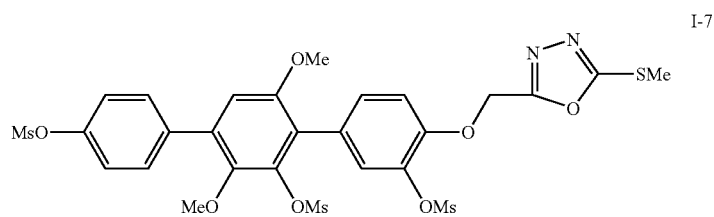
I-715
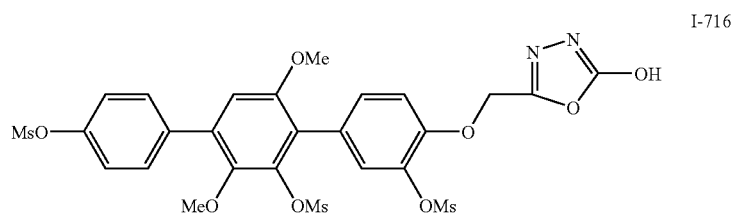
I-716
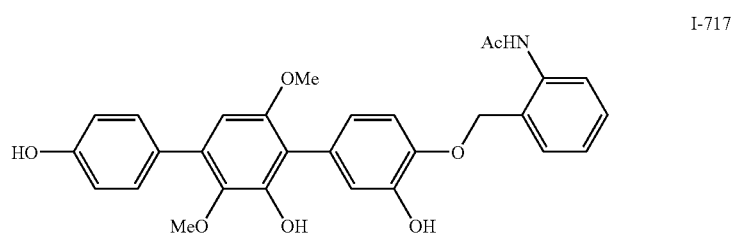
I-717

-continued
I-718
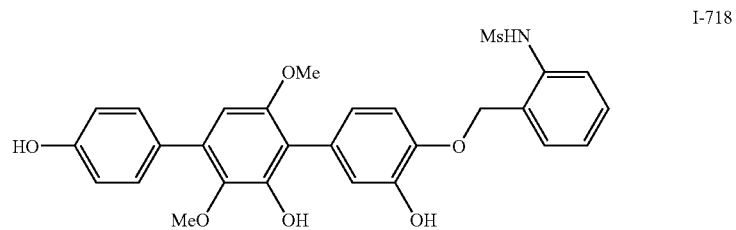
I-719
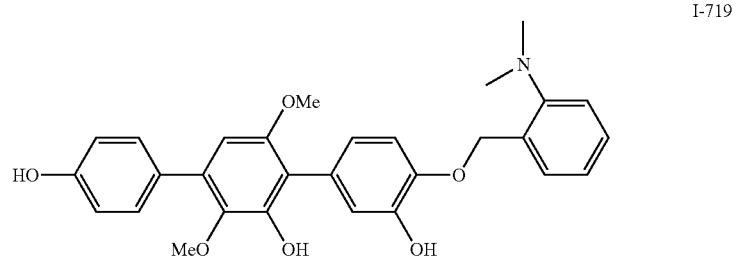
I-720
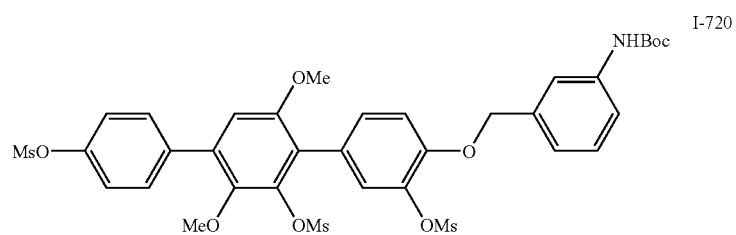
I-721
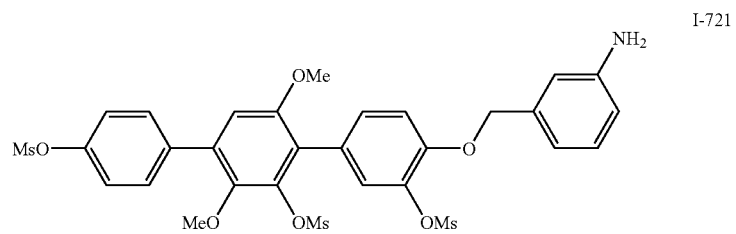
I-722
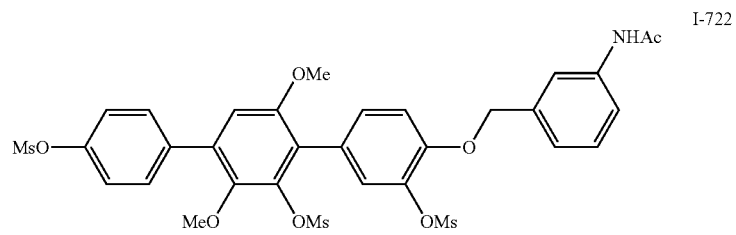
I-723
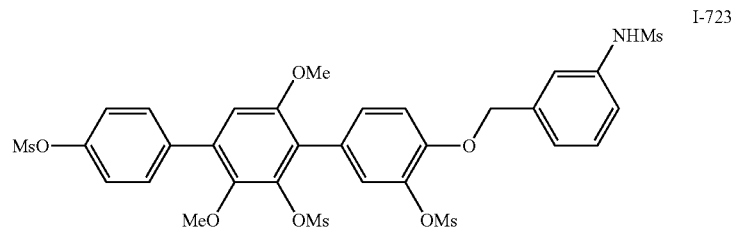
I-724
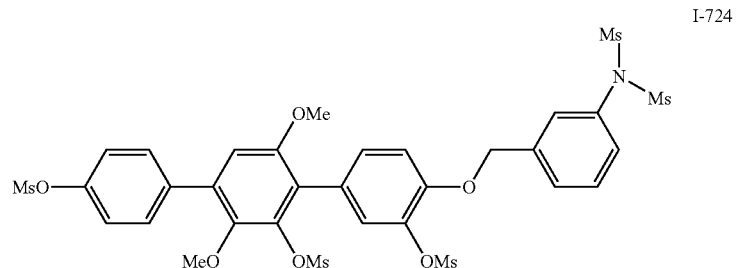

-continued
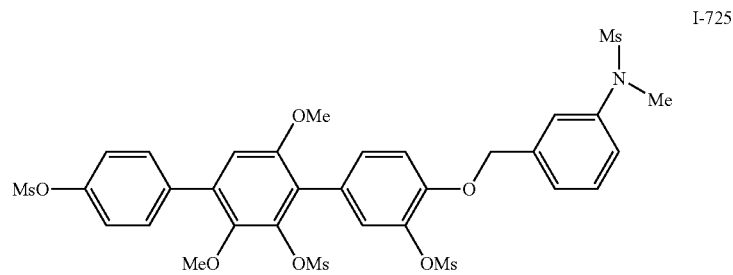
I-725
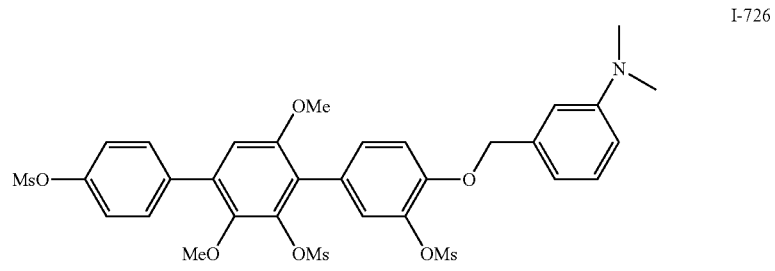
I-726
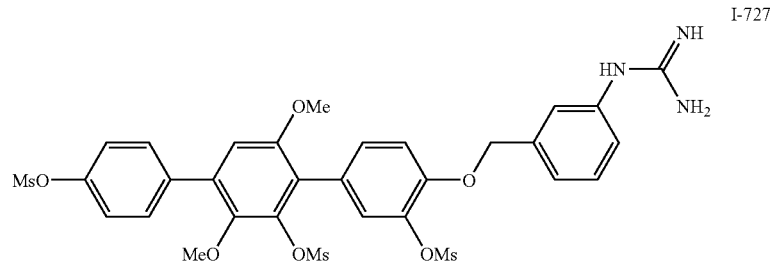
I-727
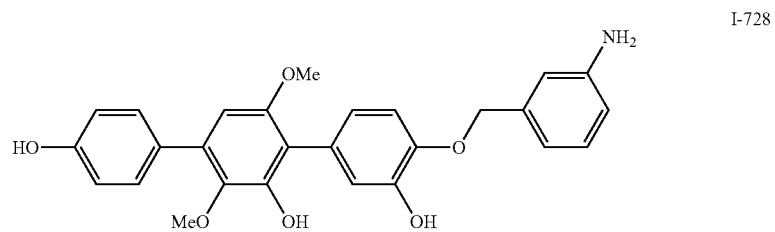
I-728
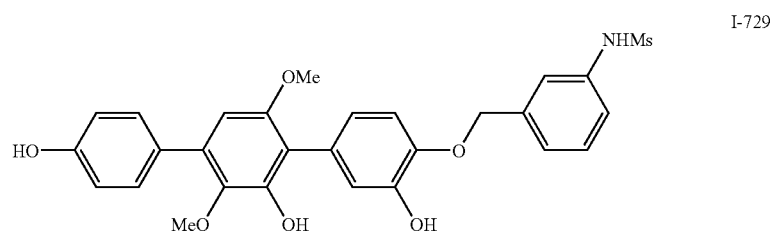
I-729
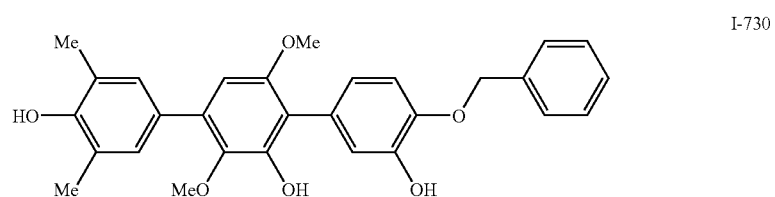
I-730
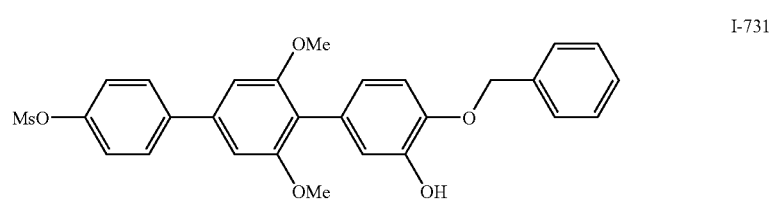
I-731

-continued
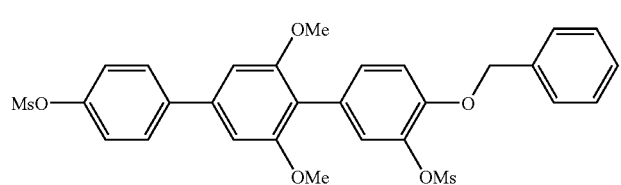
I-732
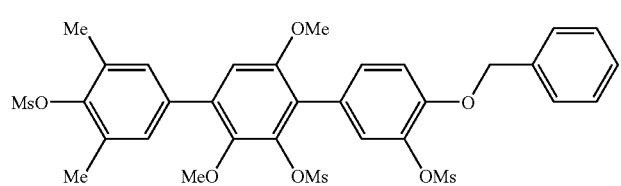
I-733
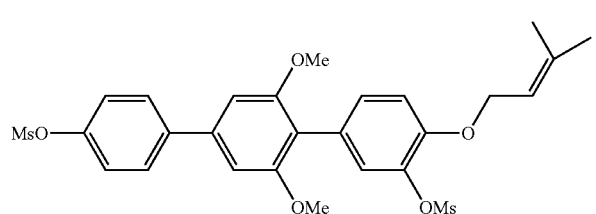
I-734
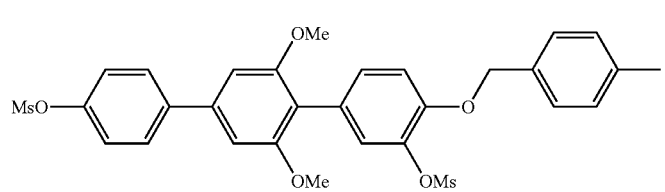
I-735
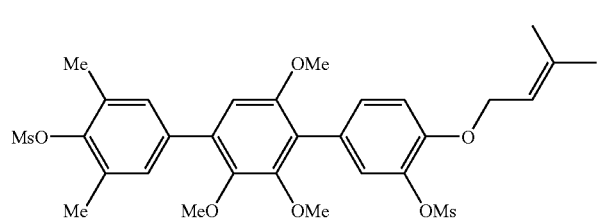
I-736
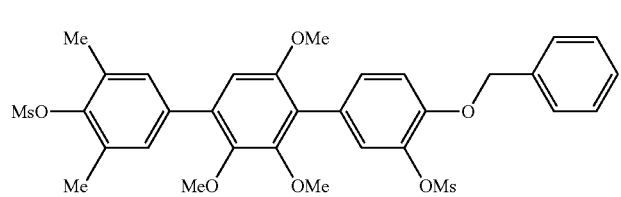
I-737
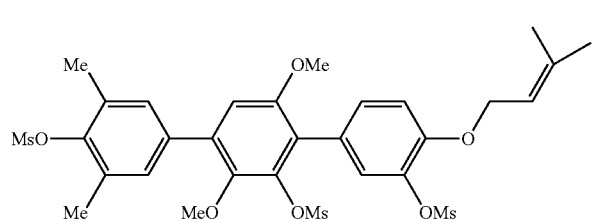
I-738
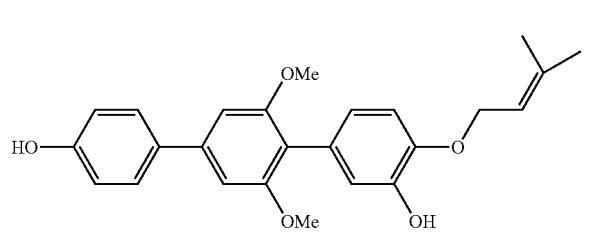
I-739

-continued
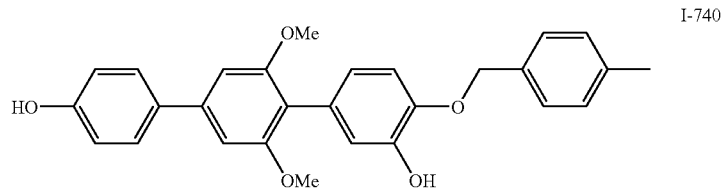
I-740
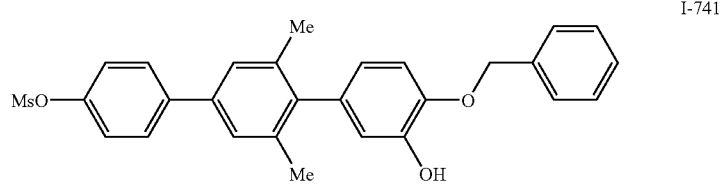
I-741
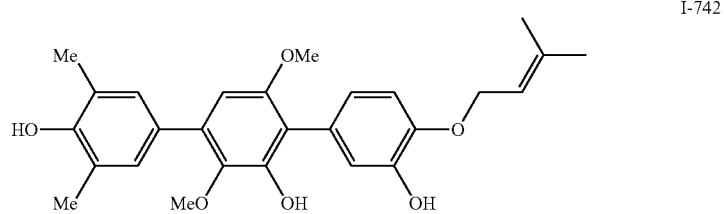
I-742
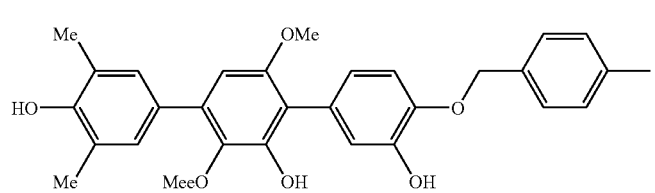
I-743
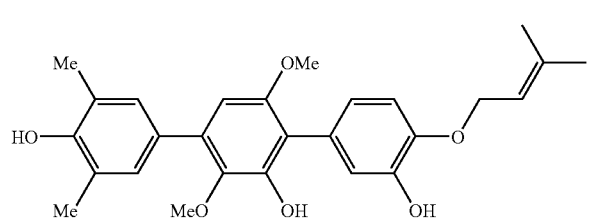
I-744
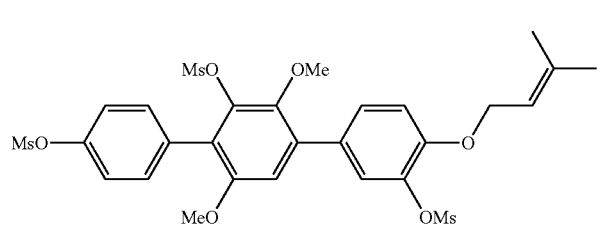
I-745
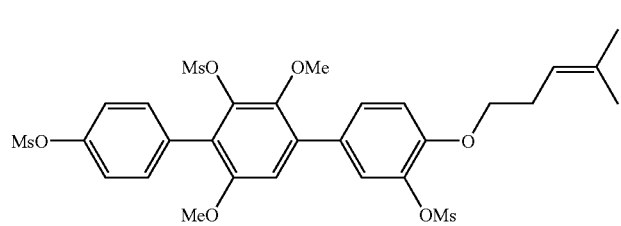
I-746
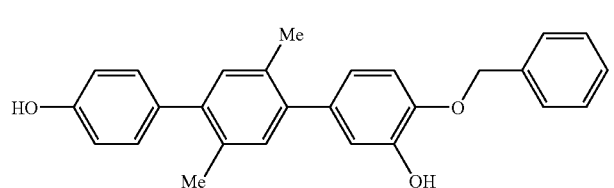
I-747

-continued
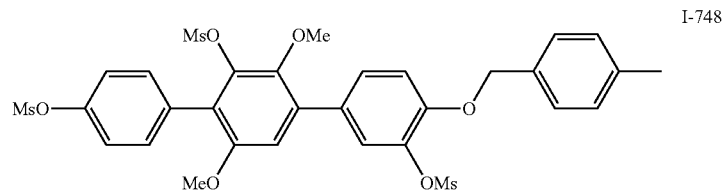 I-748
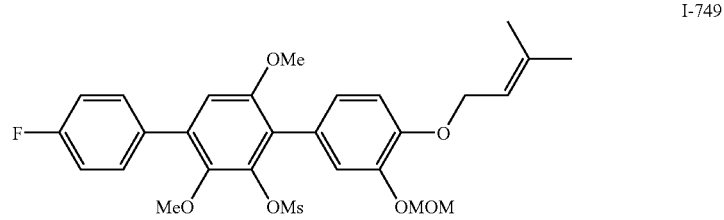 I-749
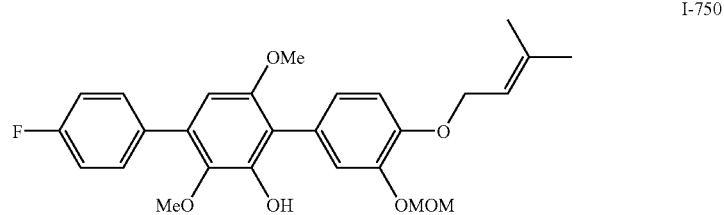 I-750
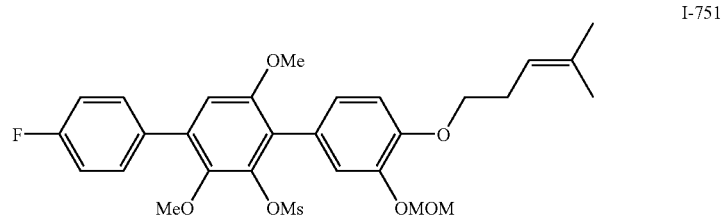 I-751
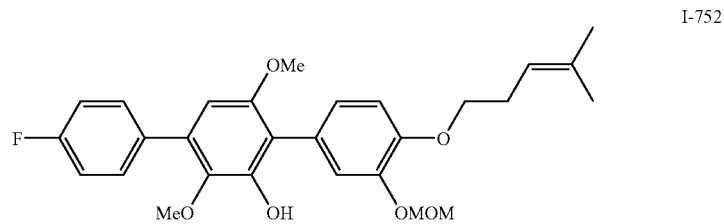 I-752
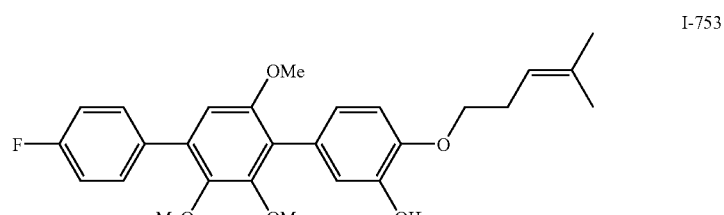 I-753
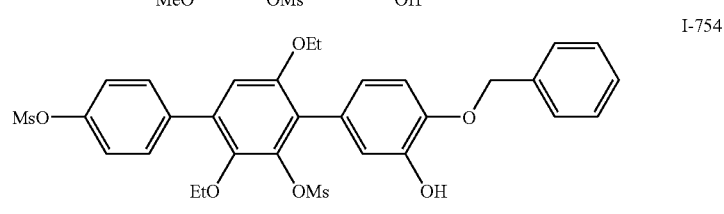 I-754
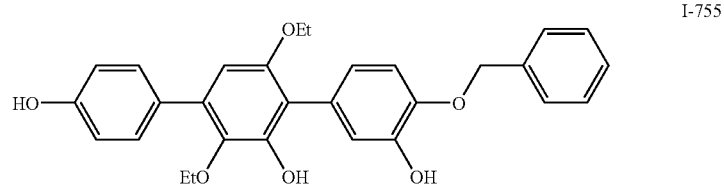 I-755

I-756
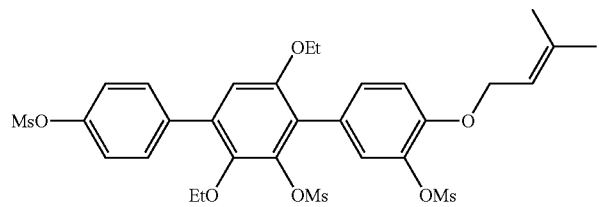
I-757
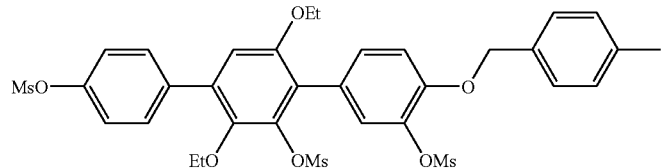
I-758
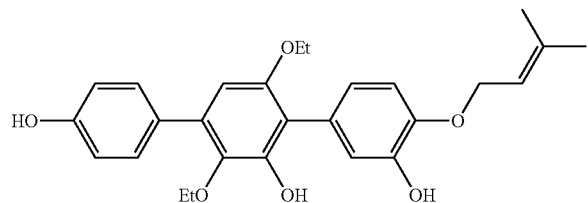
I-759
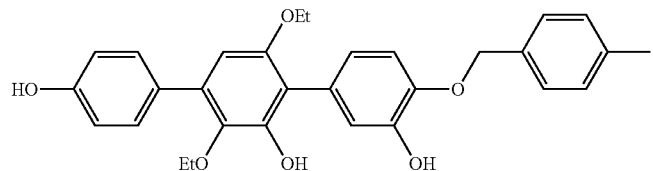
I-760
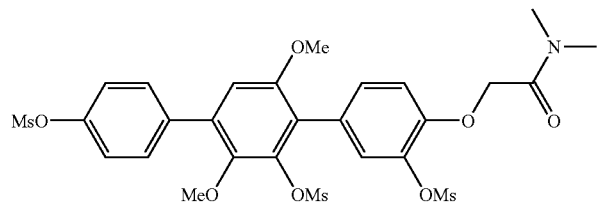
I-761
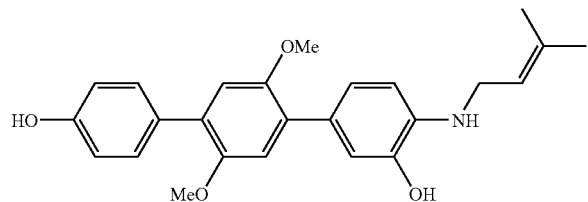
I-762
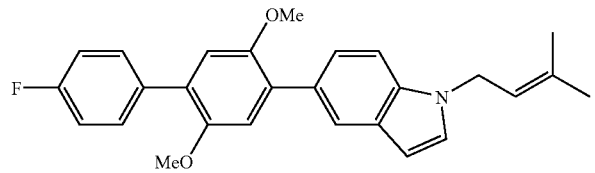
I-763
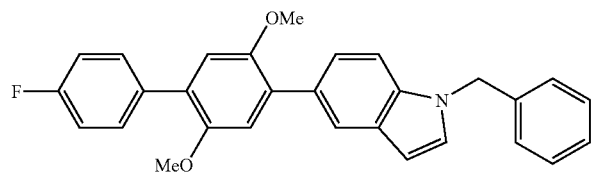

-continued
I-764
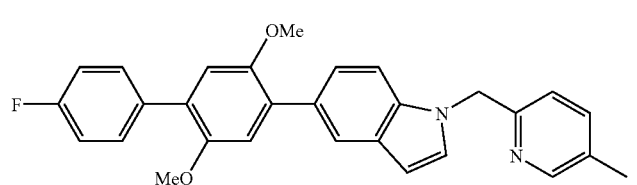
I-765
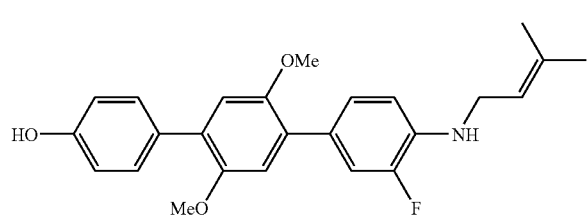
I-766
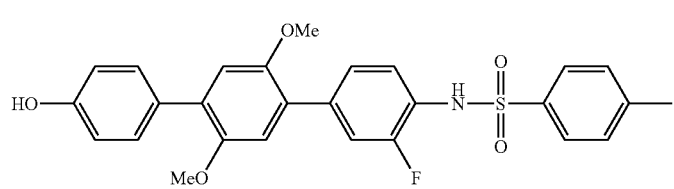
I-767
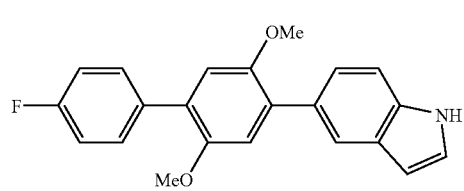
I-768
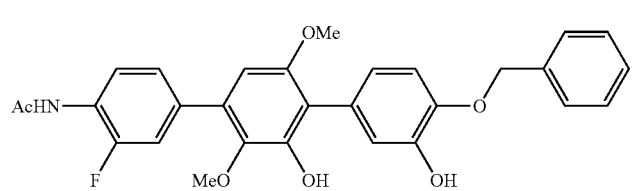
I-769
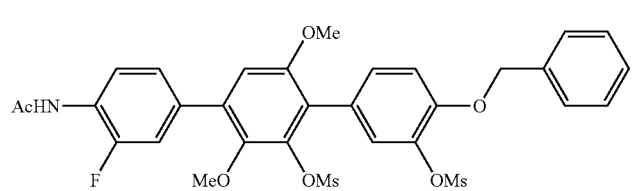
I-770
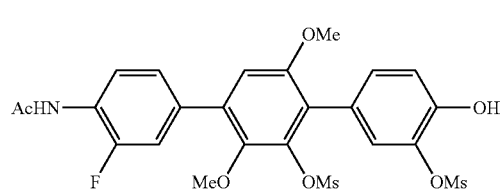
I-771
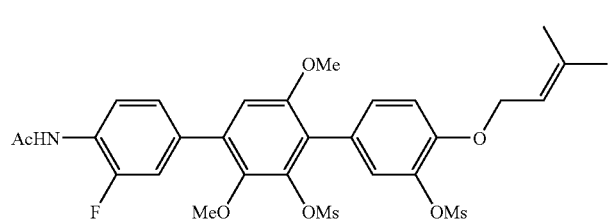

-continued
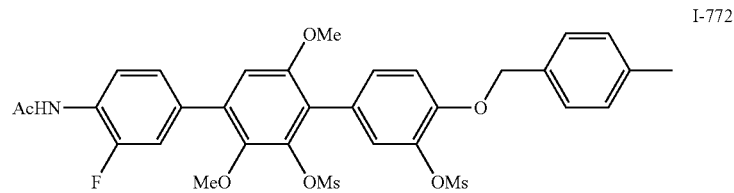
I-772
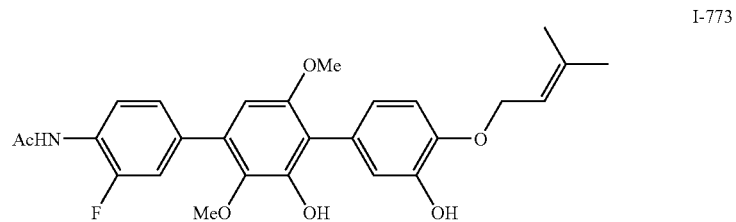
I-773
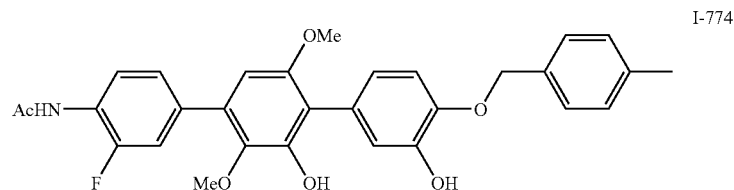
I-774
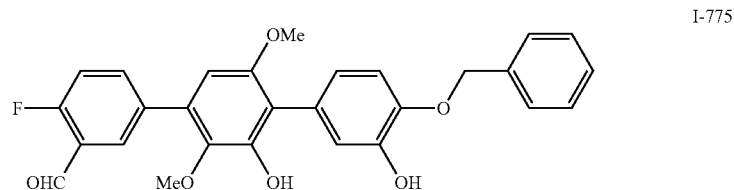
I-775
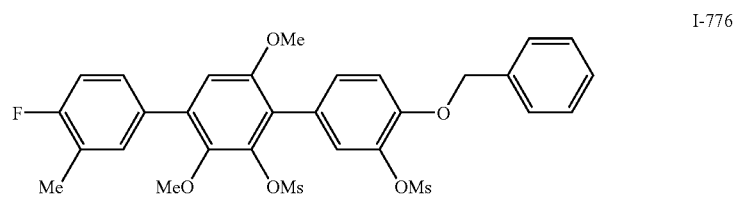
I-776
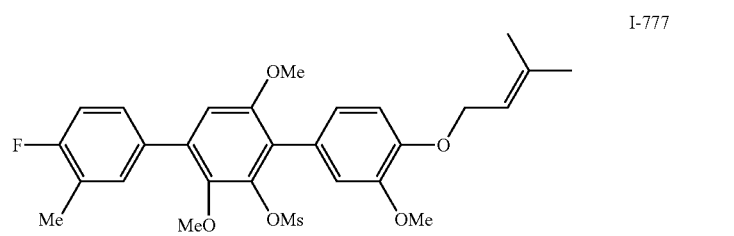
I-777
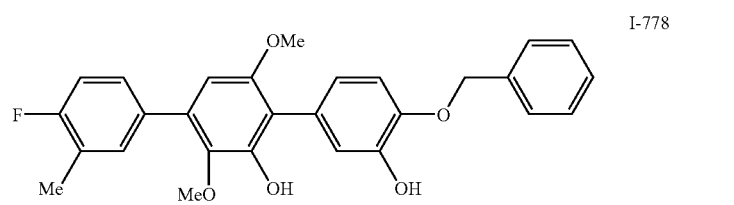
I-778
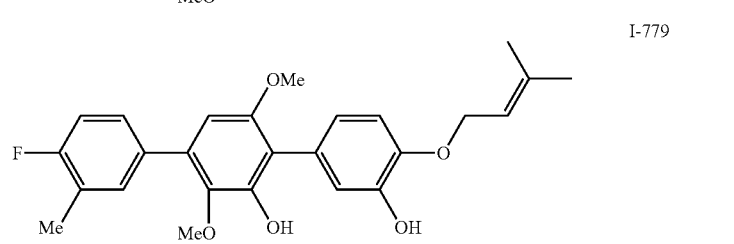
I-779

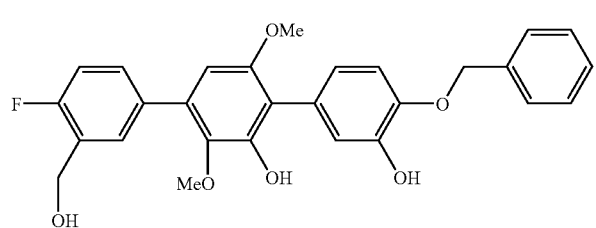
I-780
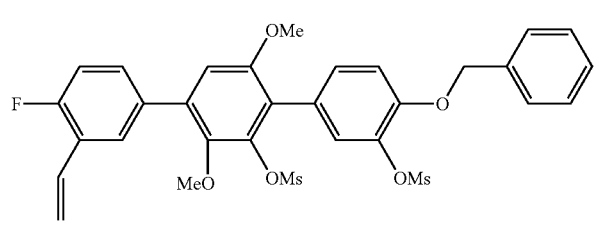
I-781
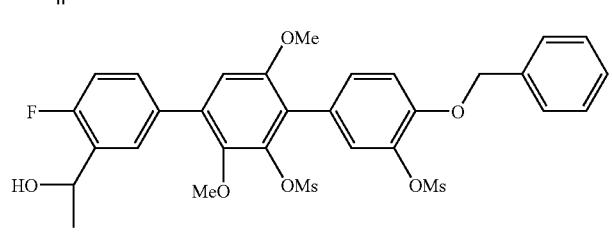
I-782
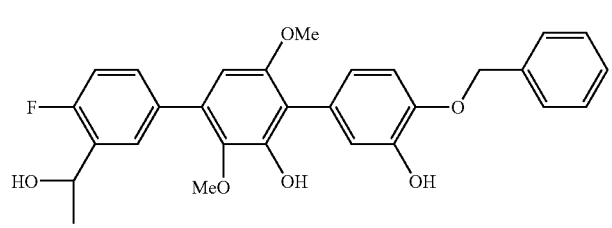
I-783
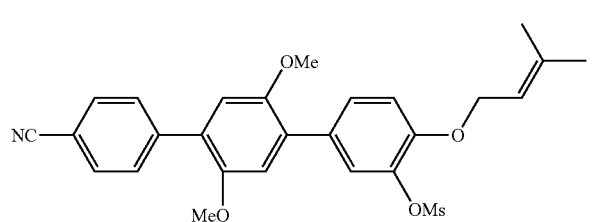
I-784
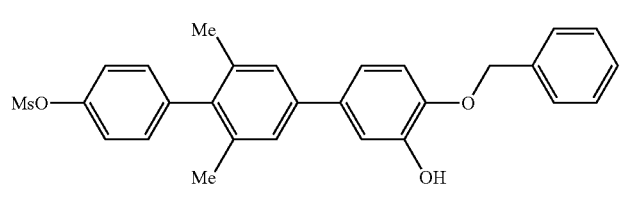
I-785
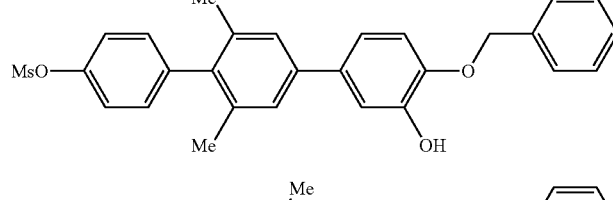
I-786
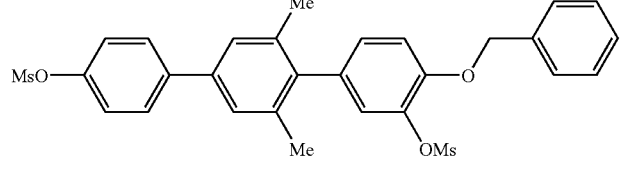
I-787
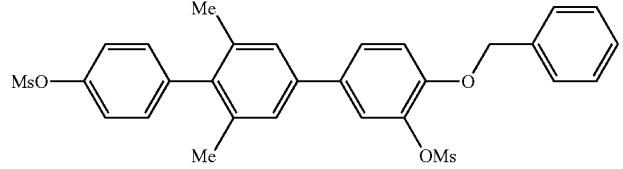

-continued
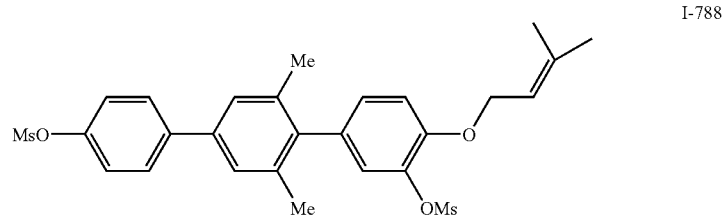
I-788
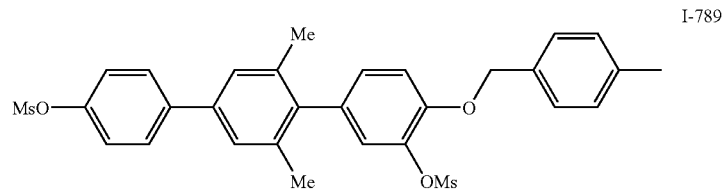
I-789
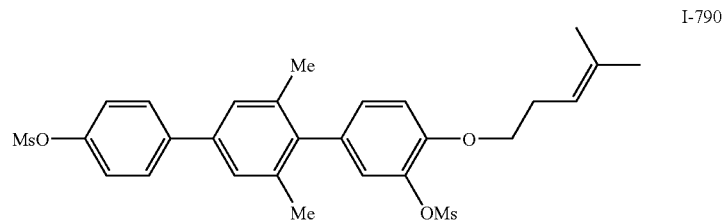
I-790
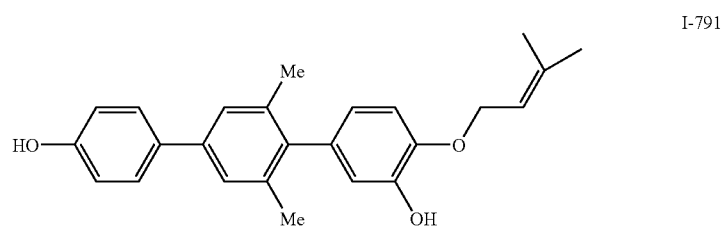
I-791
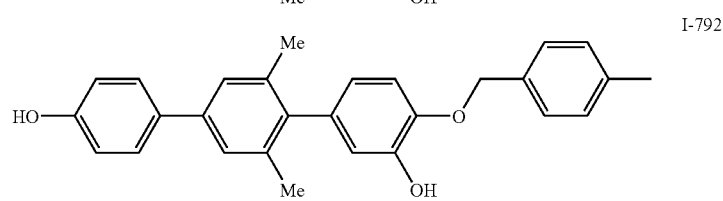
I-792
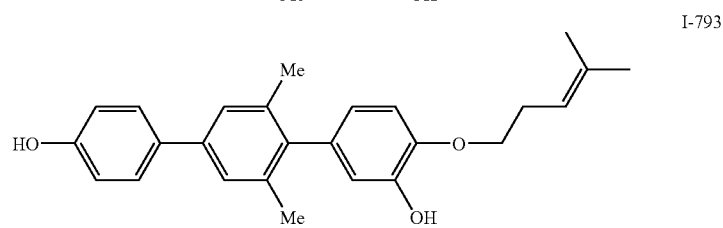
I-793
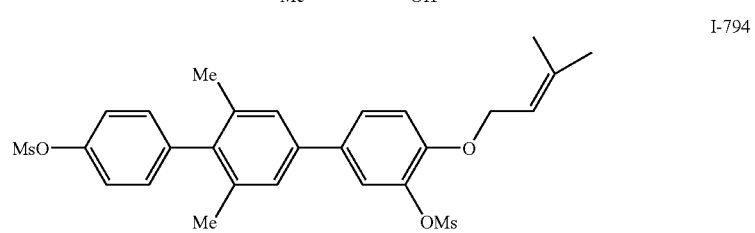
I-794
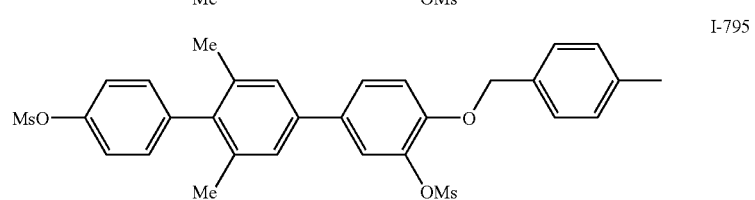
I-795

-continued
I-796
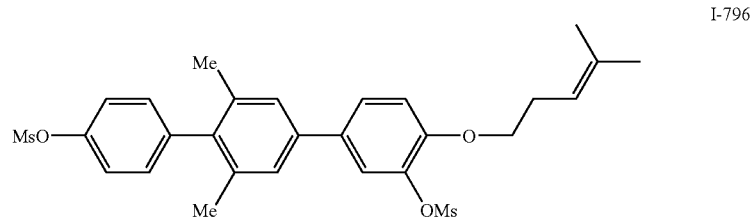
I-797
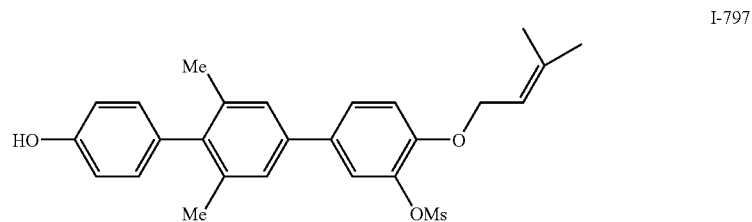
I-798
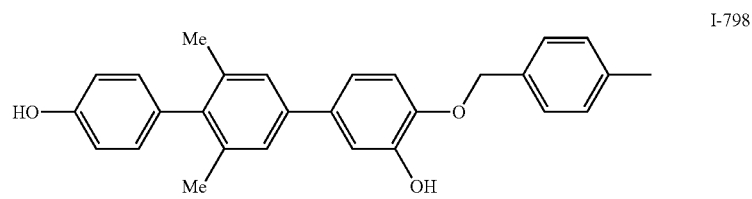
I-799
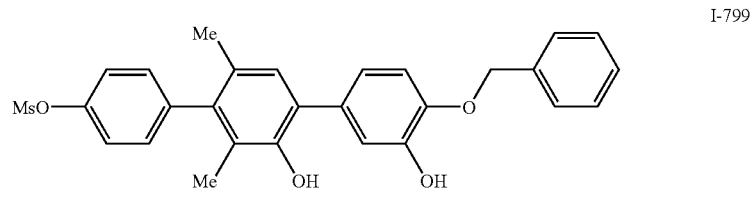
I-800
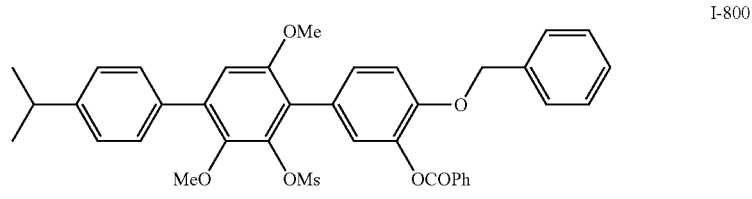
I-801
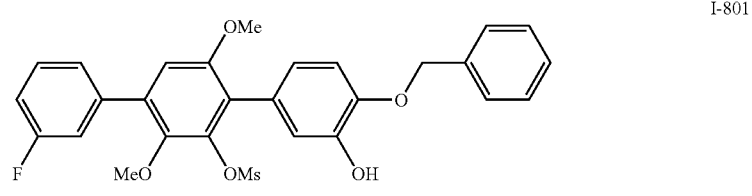
I-802
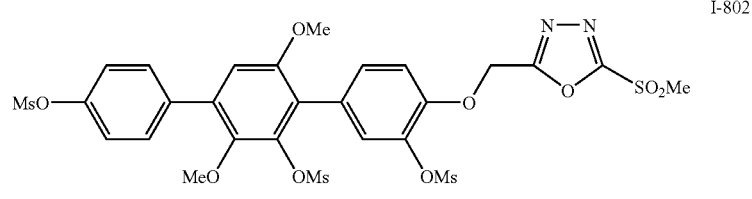
I-803
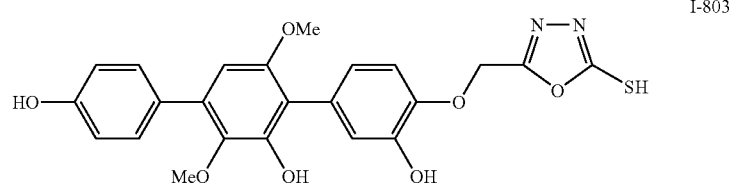

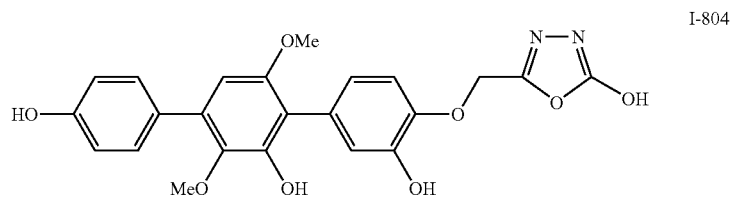
I-804
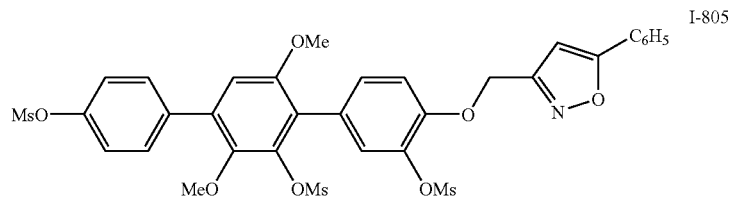
I-805
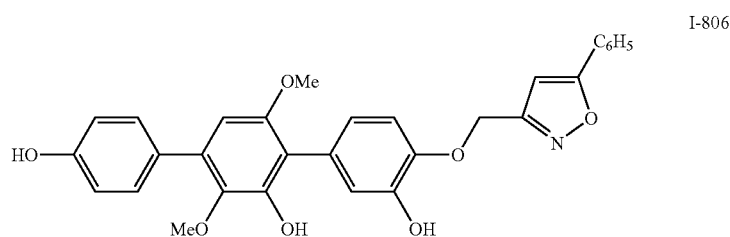
I-806
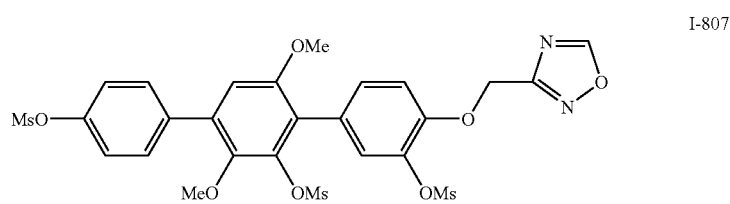
I-807
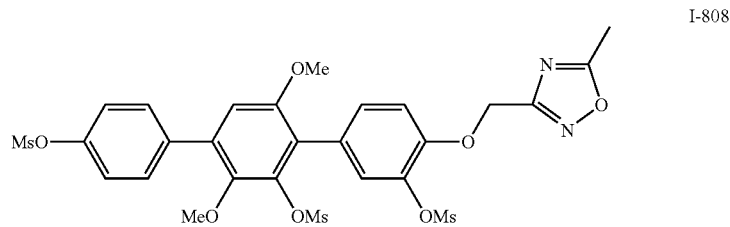
I-808
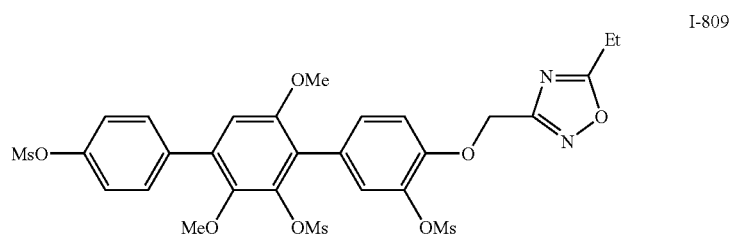
I-809
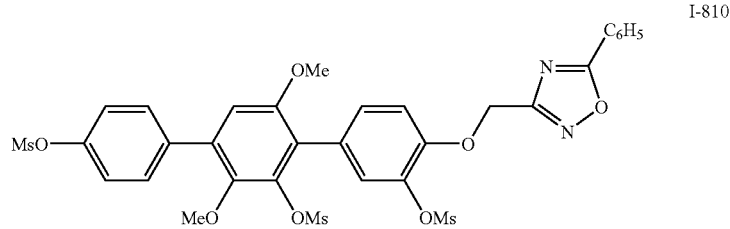
I-810

-continued
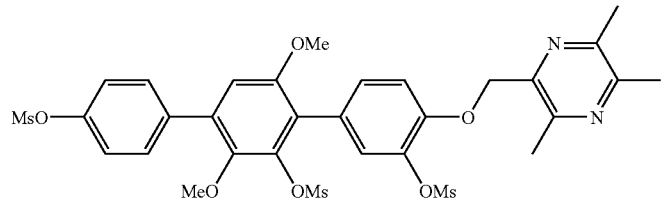
I-811
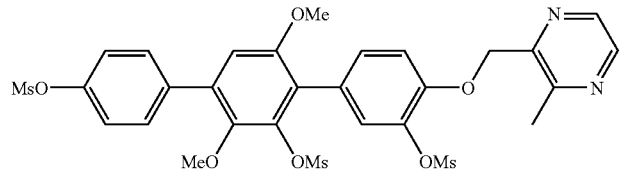
I-812
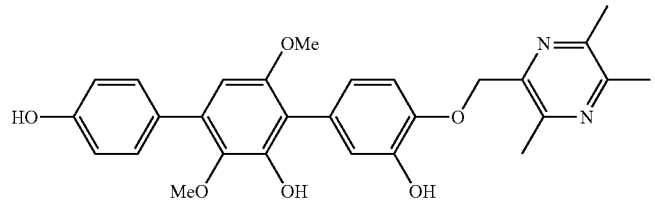
I-813
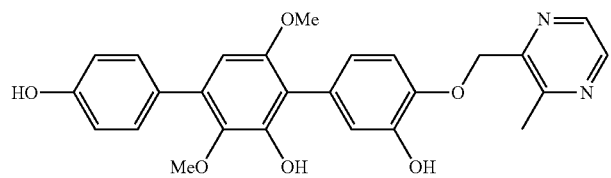
I-814
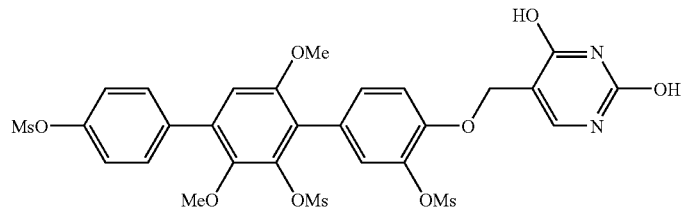
I-815
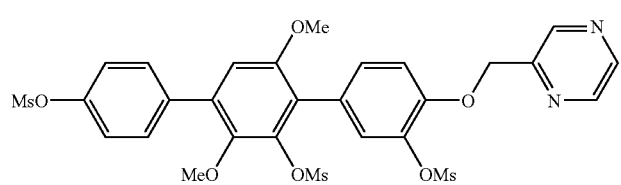
I-816
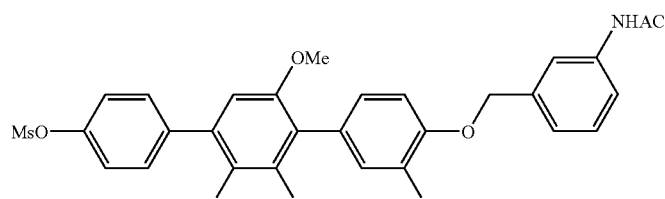
I-817
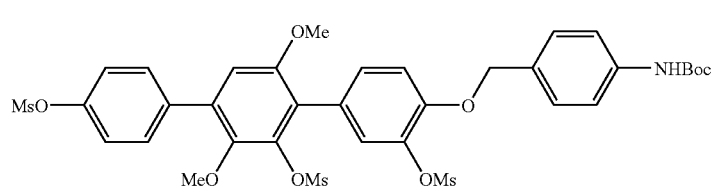
I-818

-continued
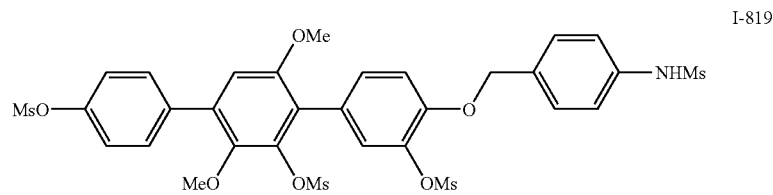
I-819
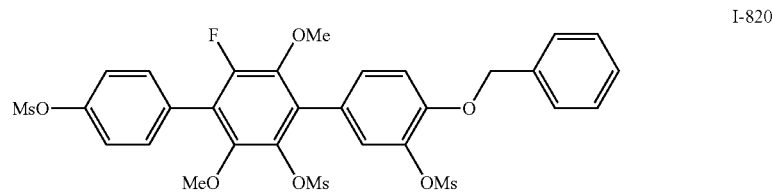
I-820
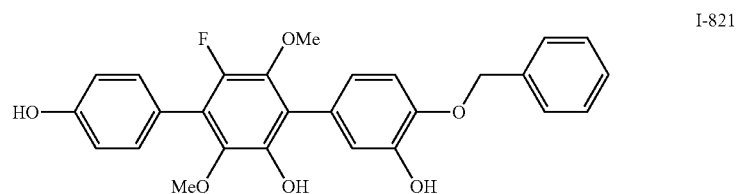
I-821
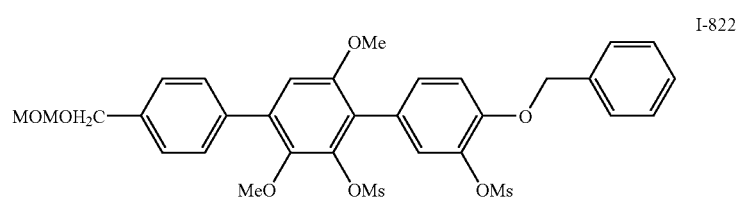
I-822
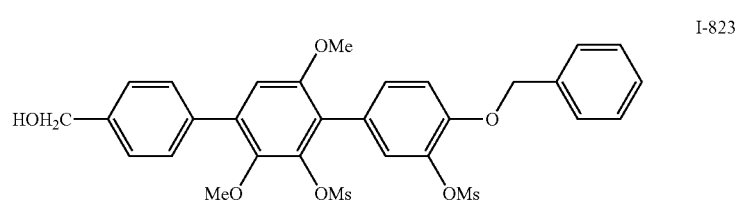
I-823
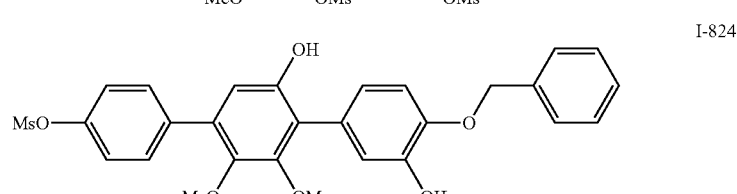
I-824
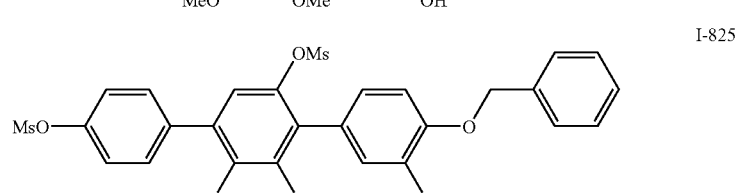
I-825
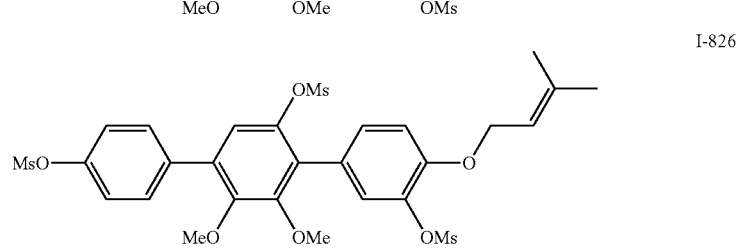
I-826

-continued
I-827
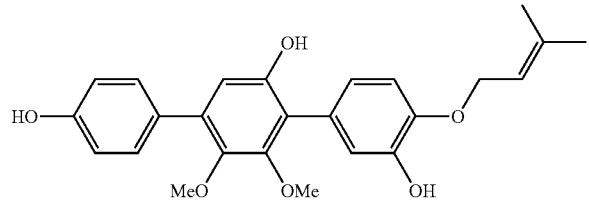
I-828
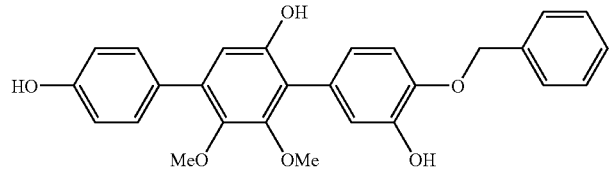
I-829
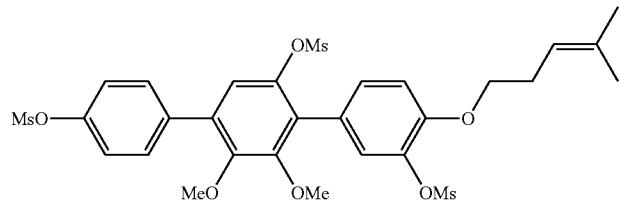
I-830
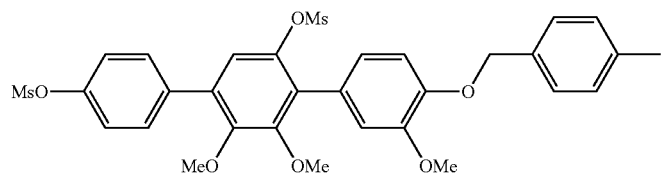
I-831
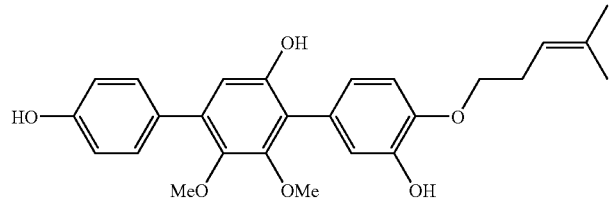
I-832
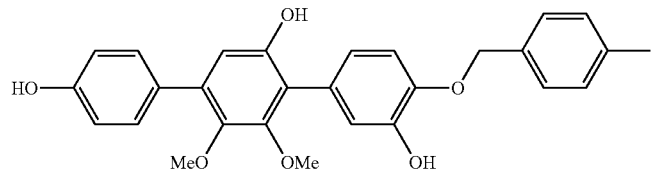
I-833
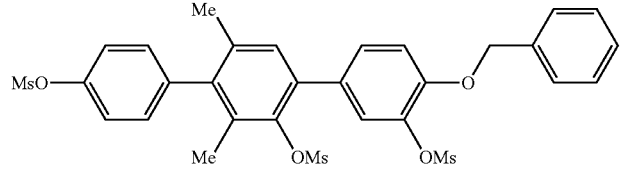
I-834
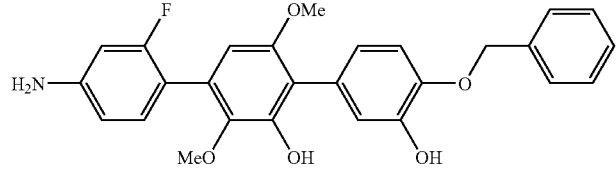

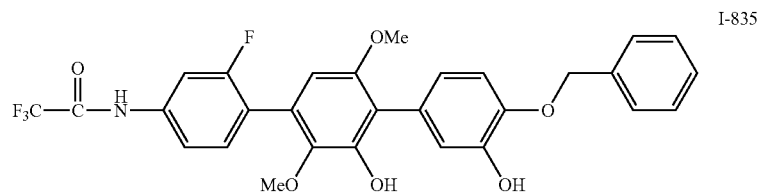
I-835
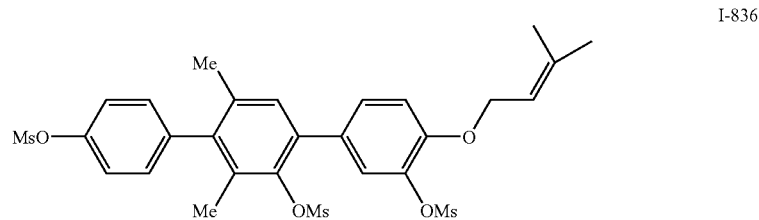
I-836
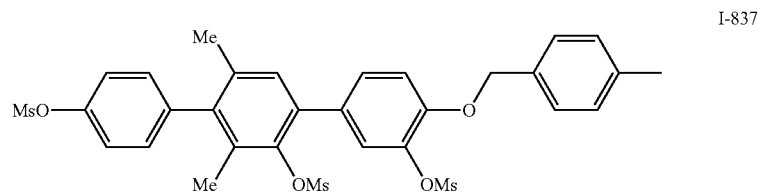
I-837
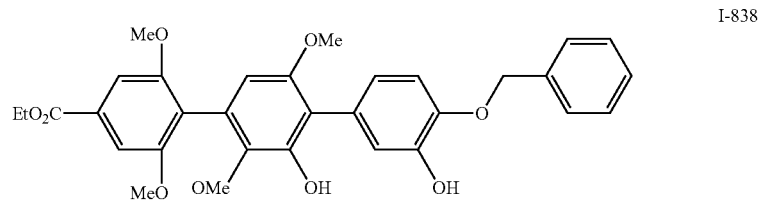
I-838
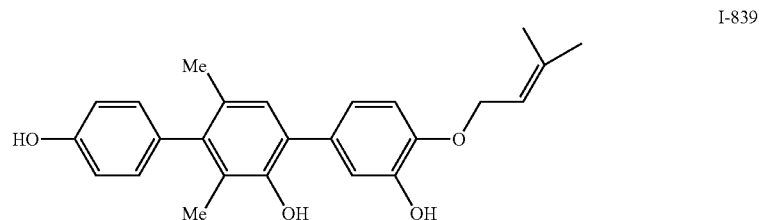
I-839
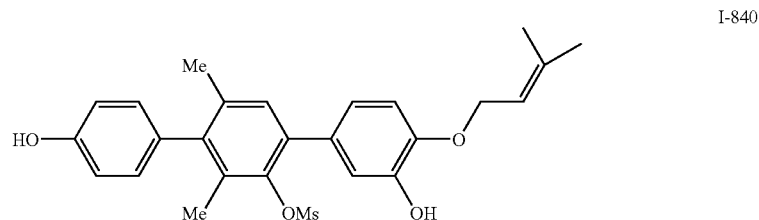
I-840
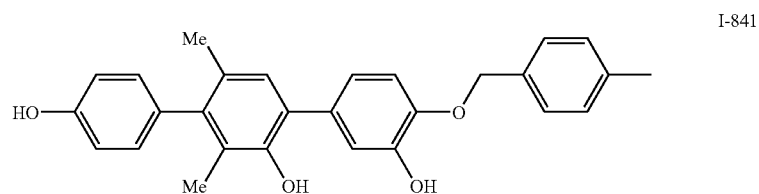
I-841
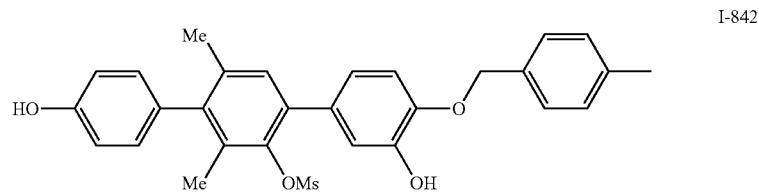
I-842

-continued
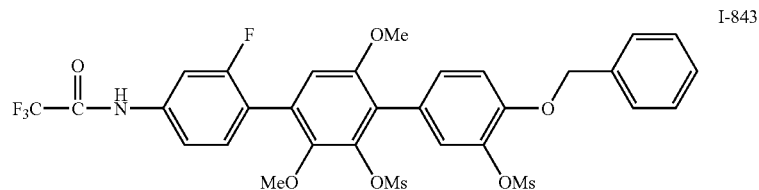
I-843
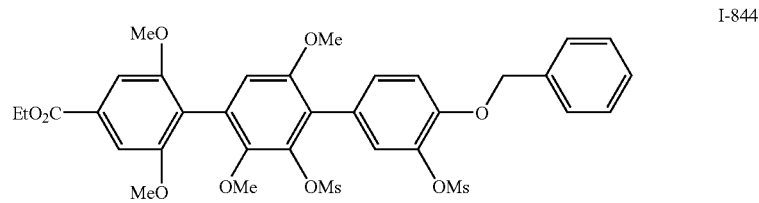
I-844
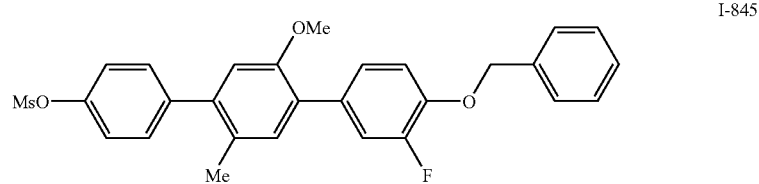
I-845
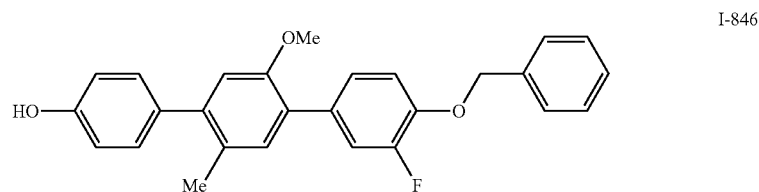
I-846
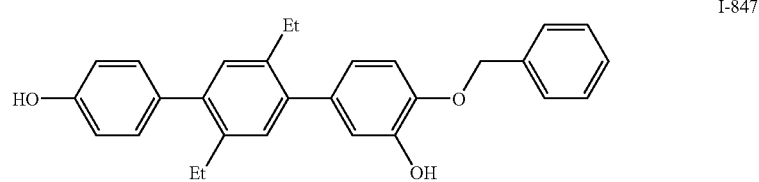
I-847
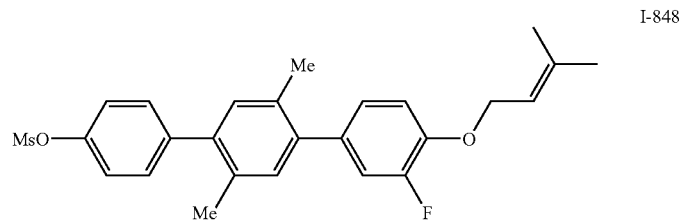
I-848
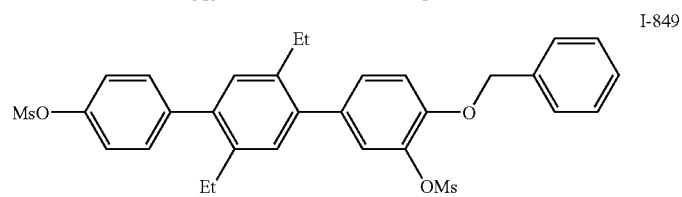
I-849
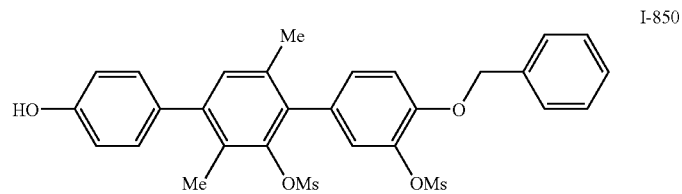
I-850

-continued
I-851
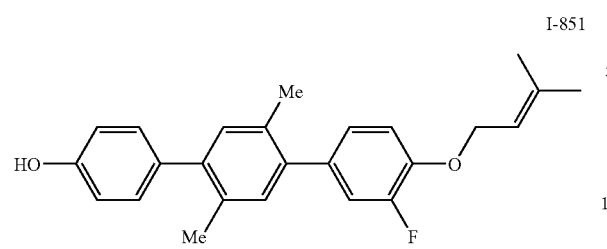
I-852
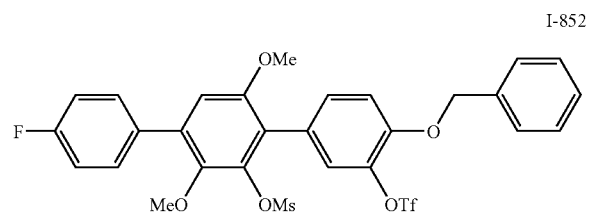
I-853
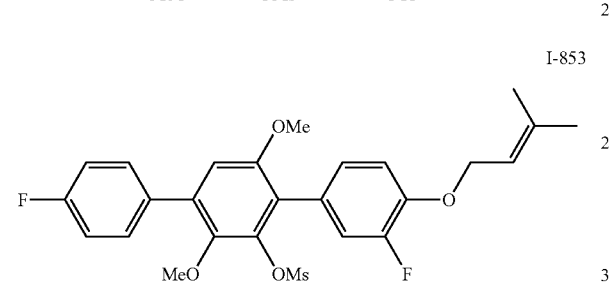
I-854
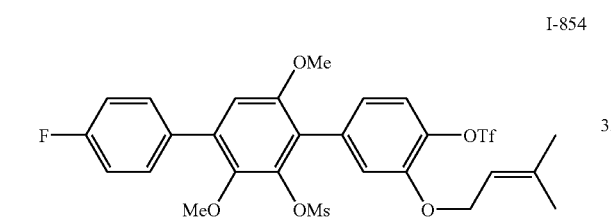
I-855
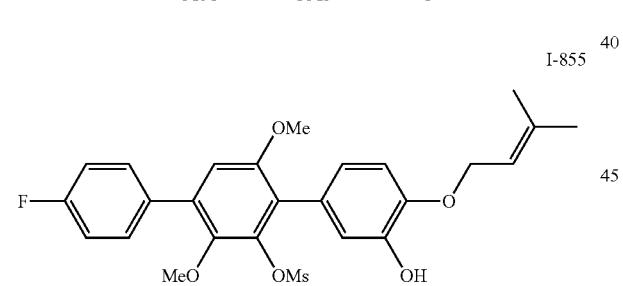
I-856
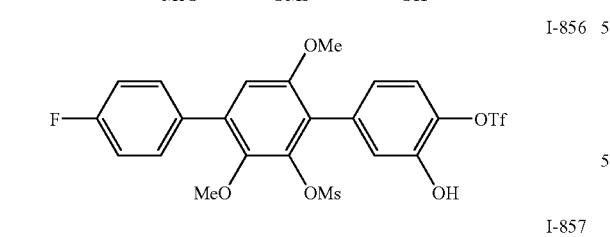
I-857
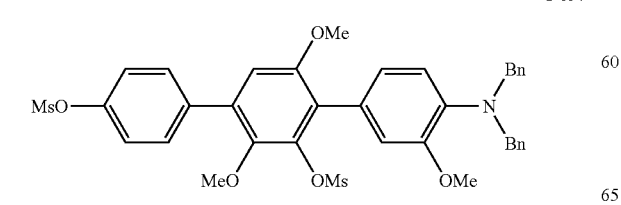
I-858
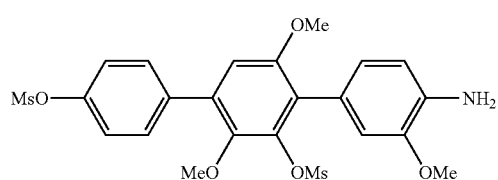
I-859
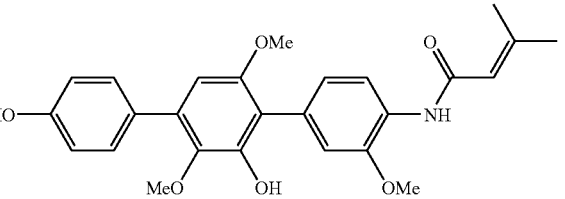
I-860
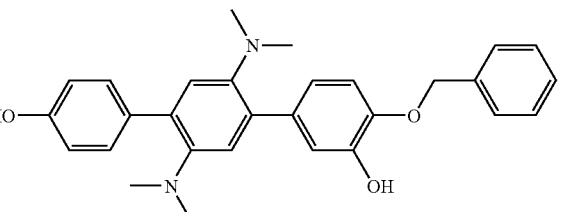
I-861
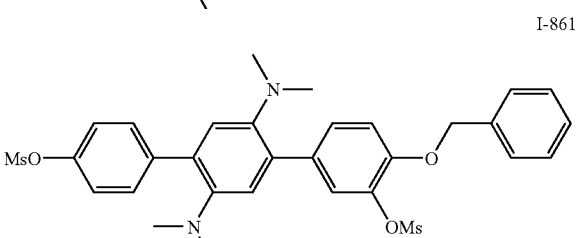
I-862
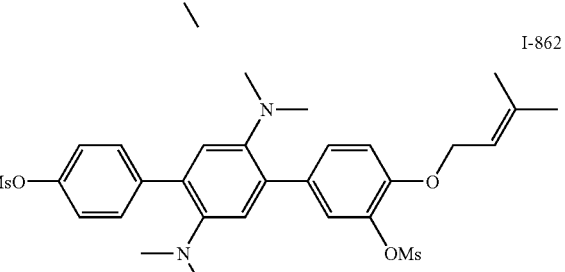
I-863
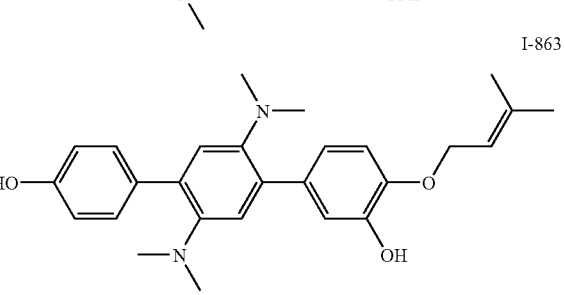
I-864

I-855
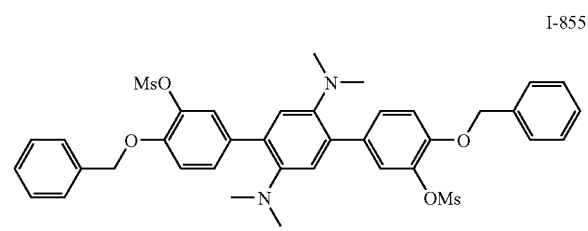
I-866
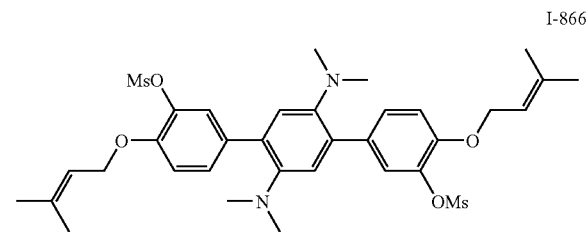
I-867
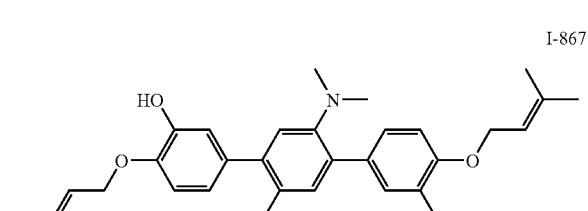
I-868
I-869
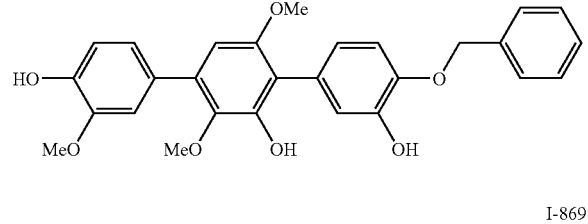
I-870
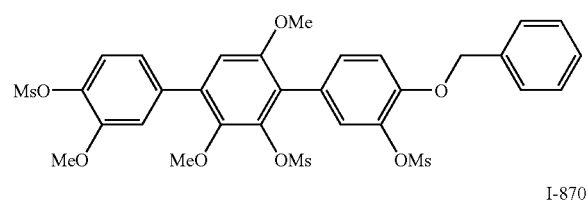
I-871
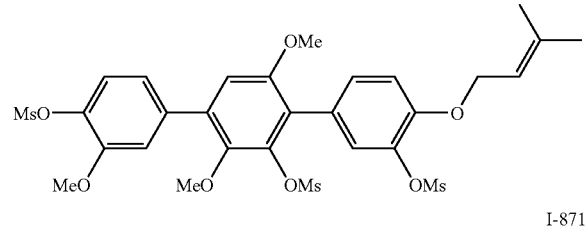
I-872
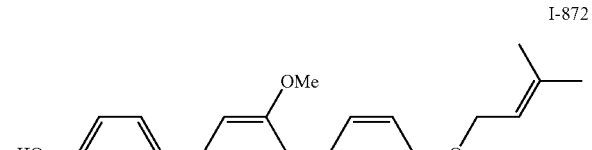
I-873
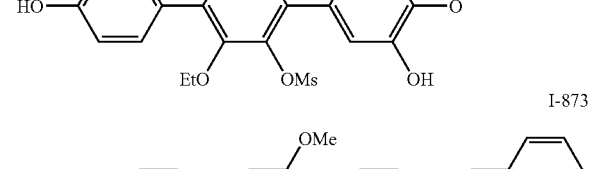
I-874
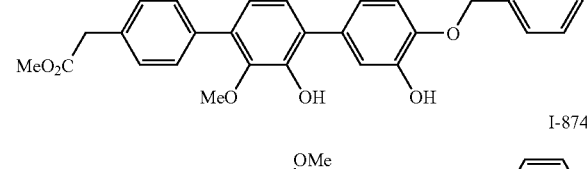
I-875
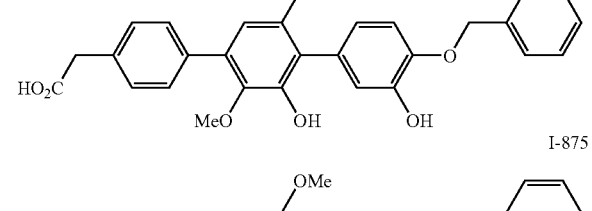
I-876
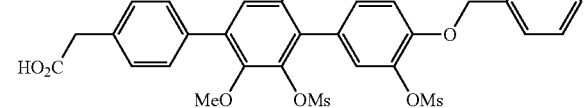
I-877
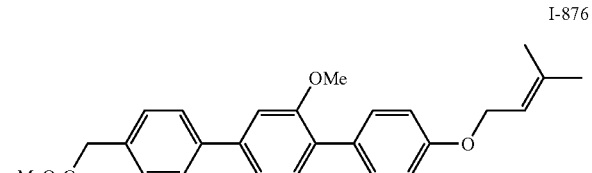
I-878
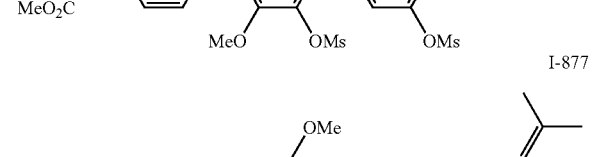
I-879
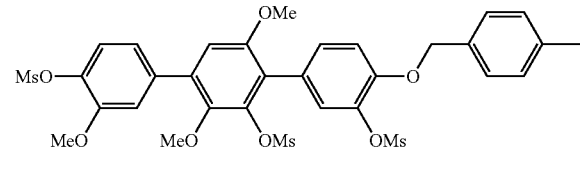

-continued
I-880
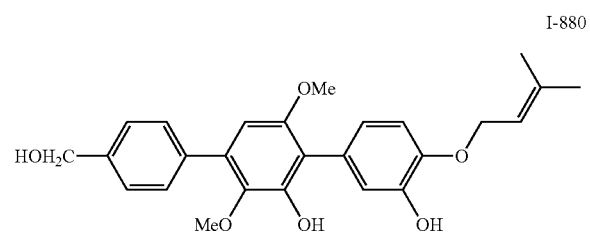
I-881
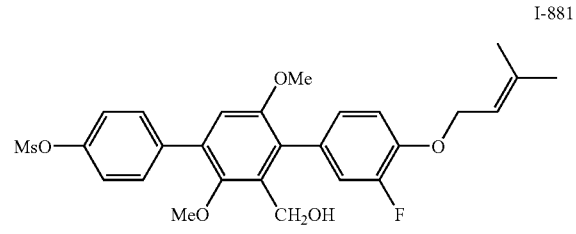
I-882
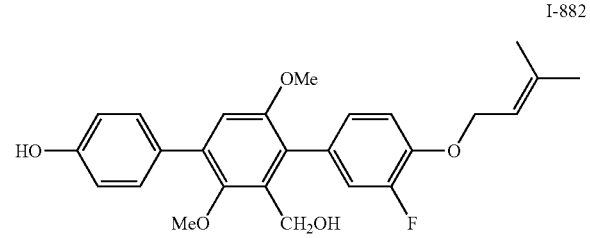
I-883
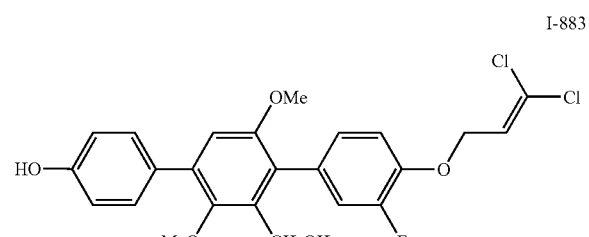
I-884
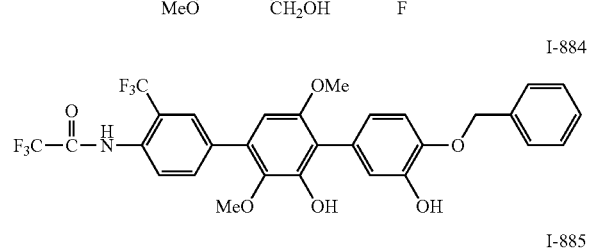
I-885
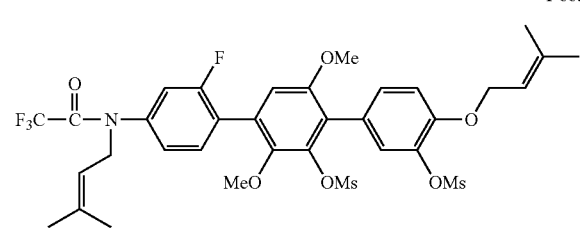
I-886
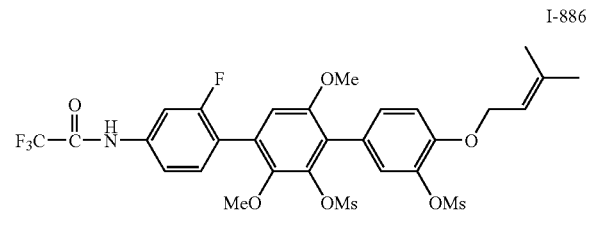
-continued
I-887
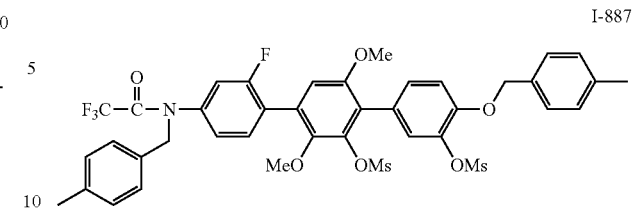
I-888
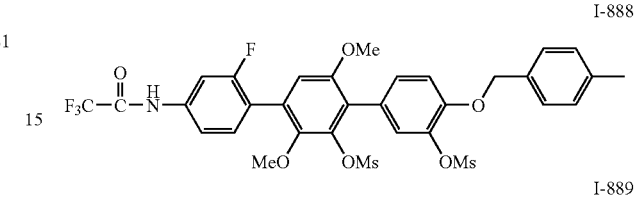
I-889
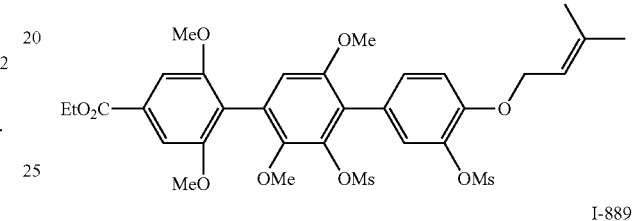
I-889
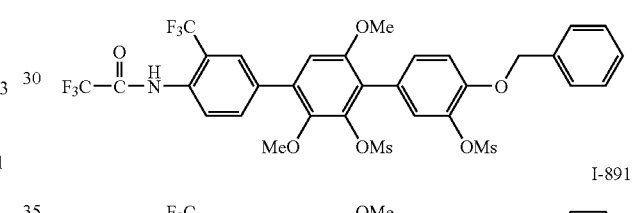
I-891
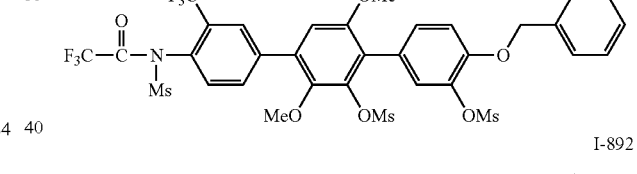
I-892
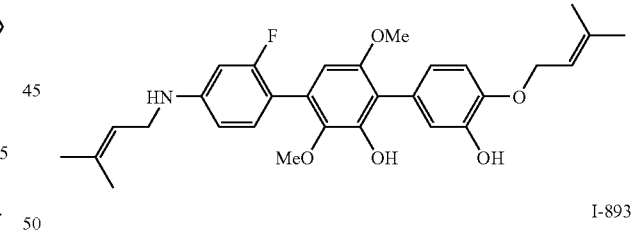
I-893
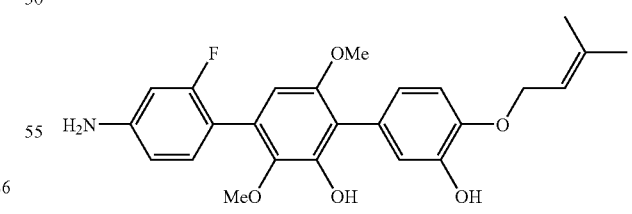
I-894
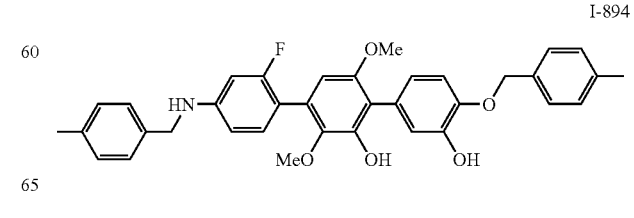

-continued
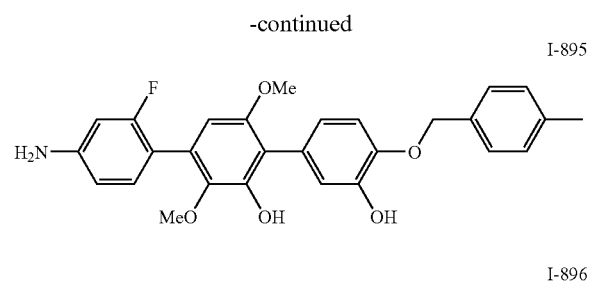

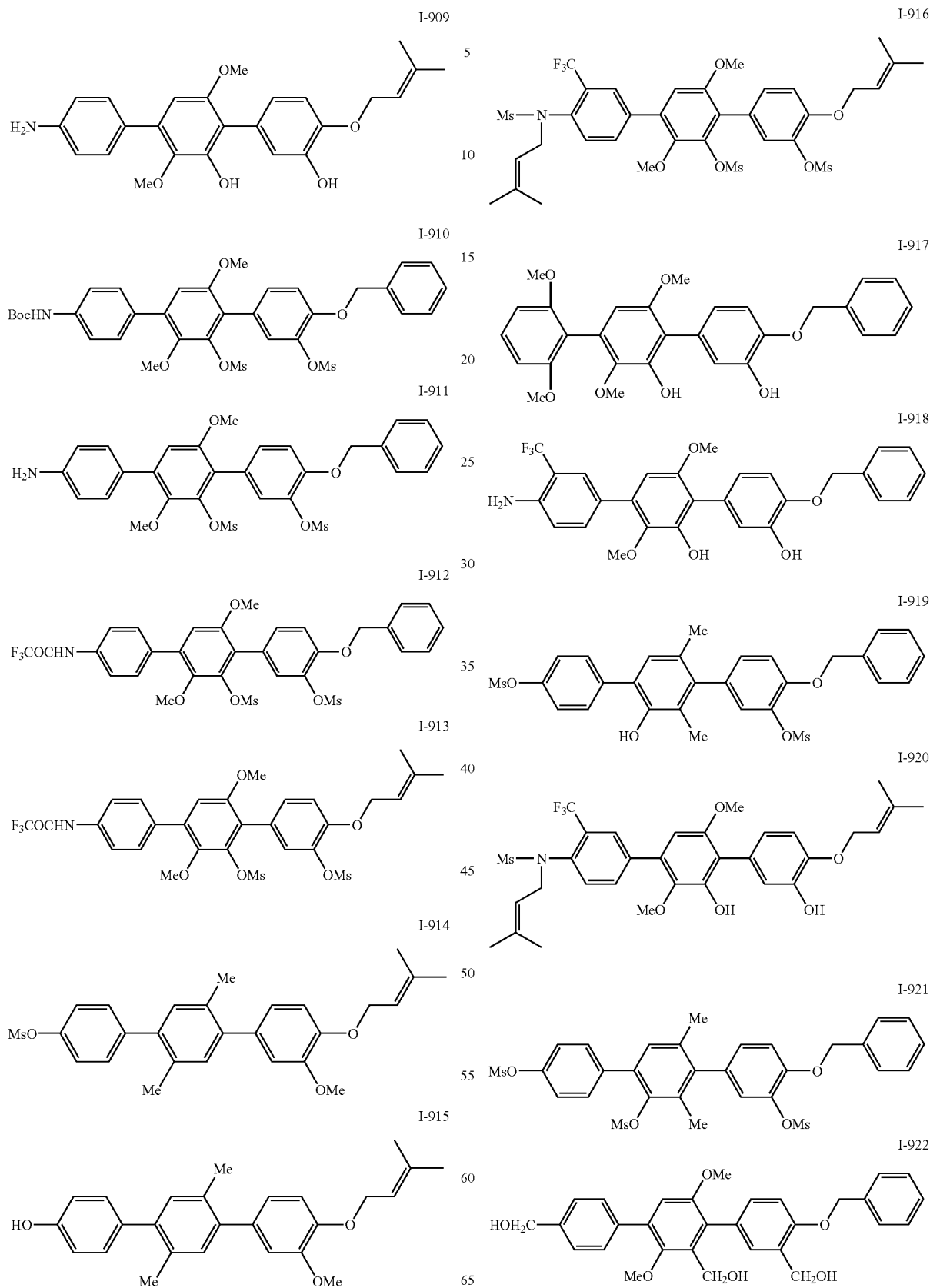

-continued

-continued
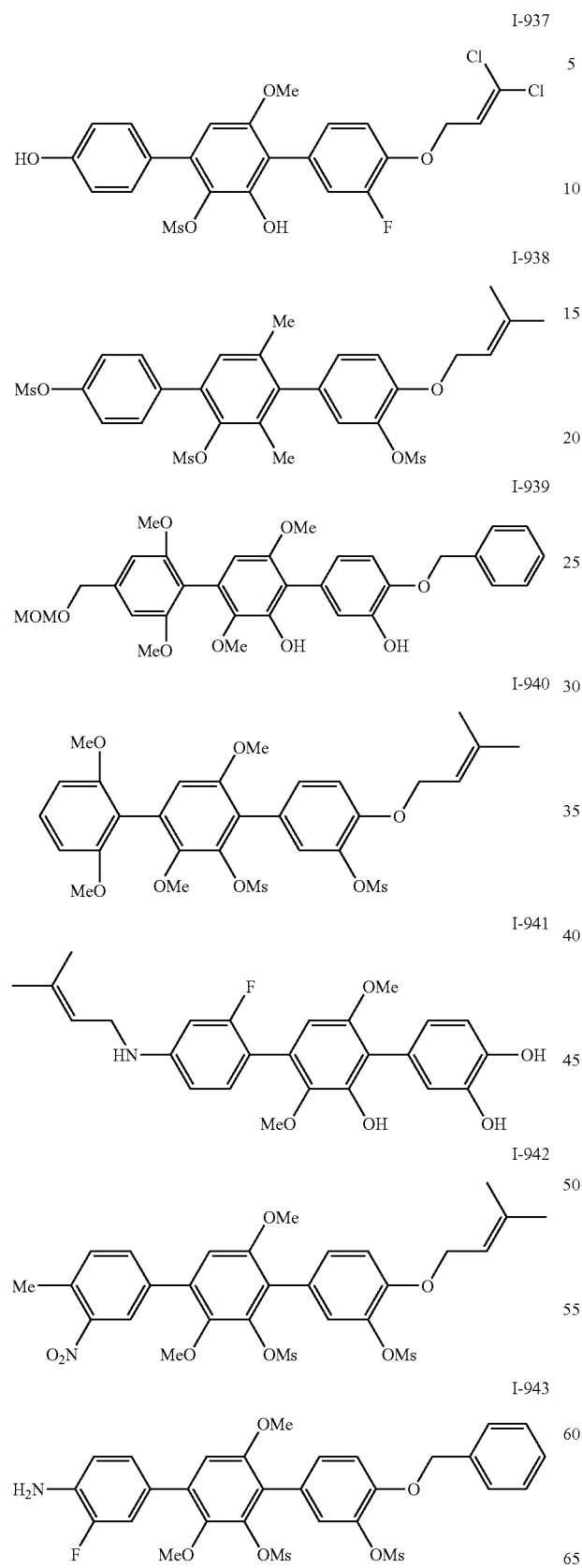
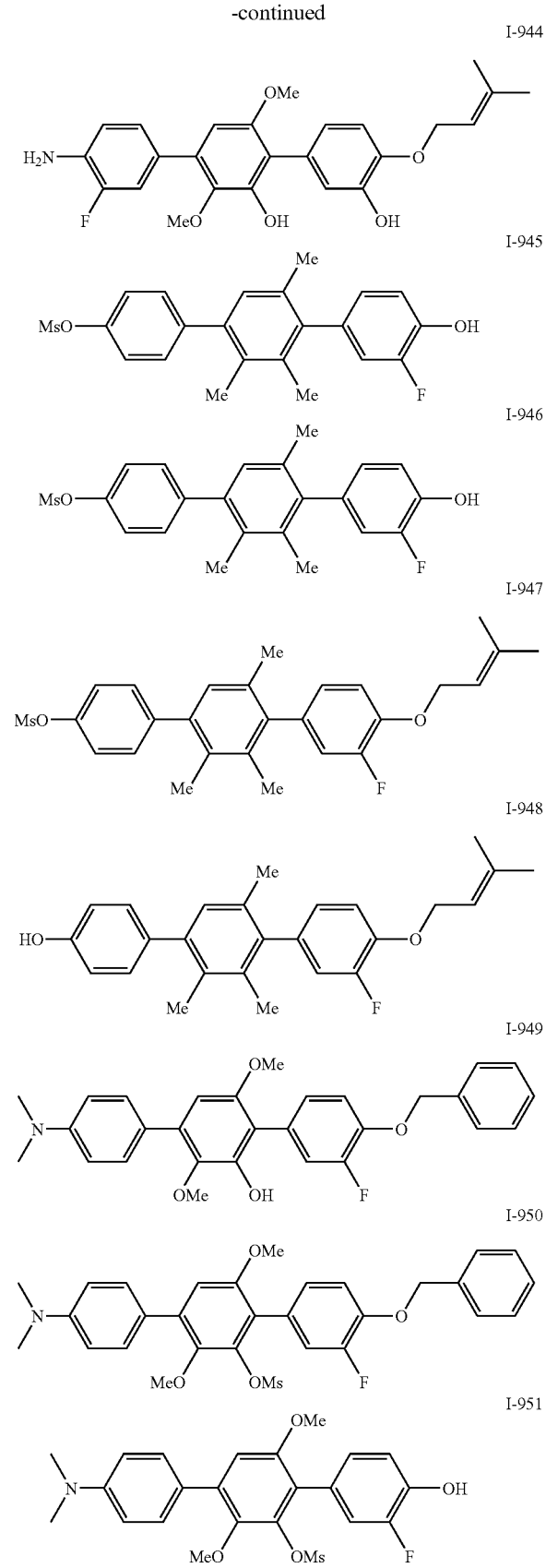

-continued
I-952
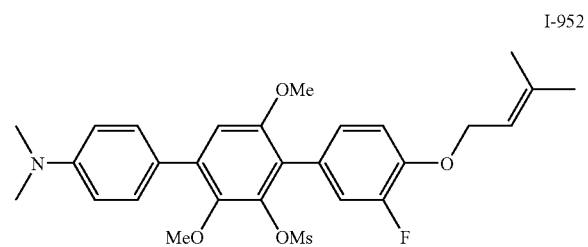
I-953
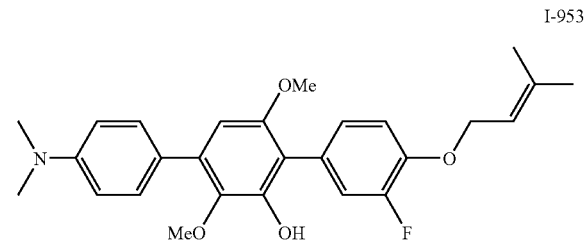
I-954
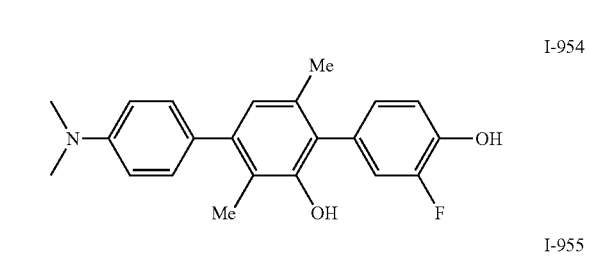
I-955
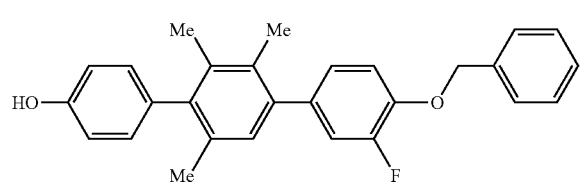
I-956
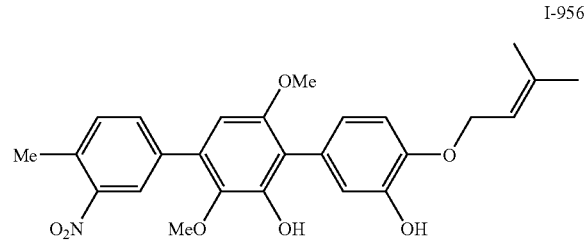
I-957
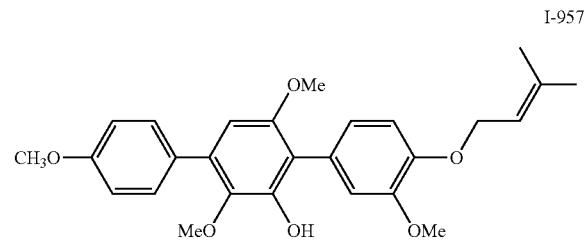
I-958
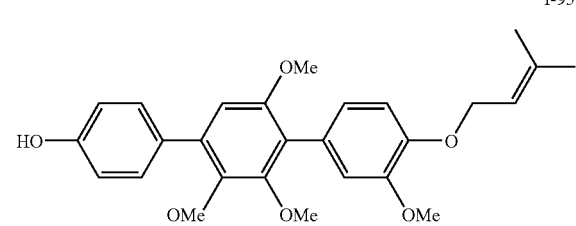
-continued
I-959
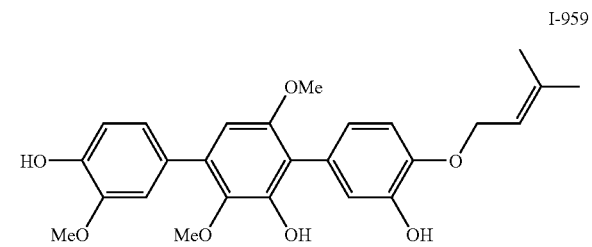
I-960
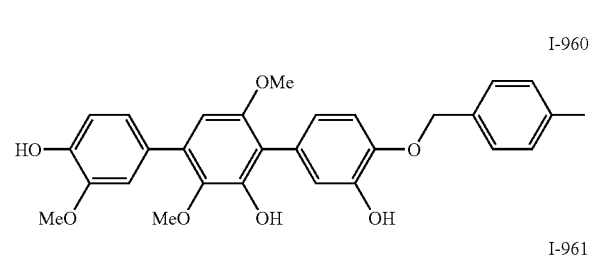
I-961
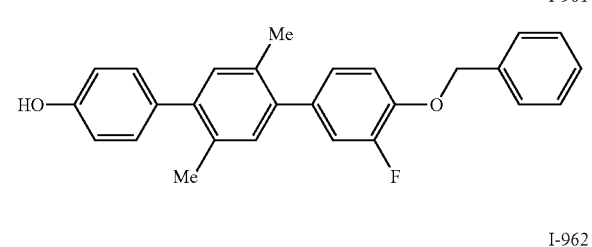
I-962
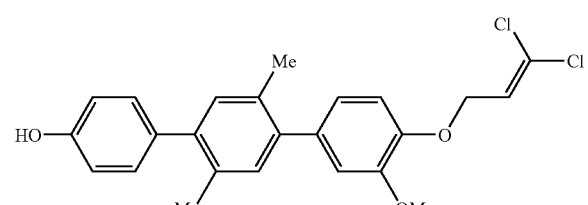
I-963
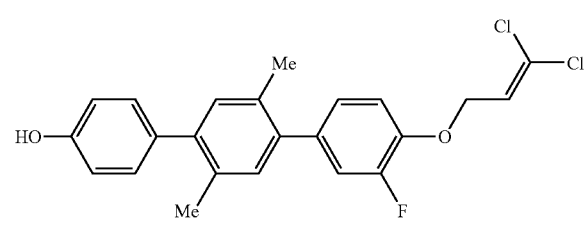
I-964
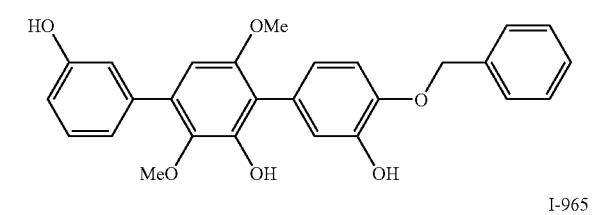
I-965
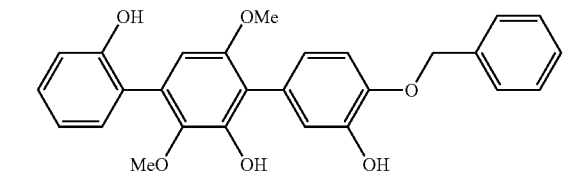

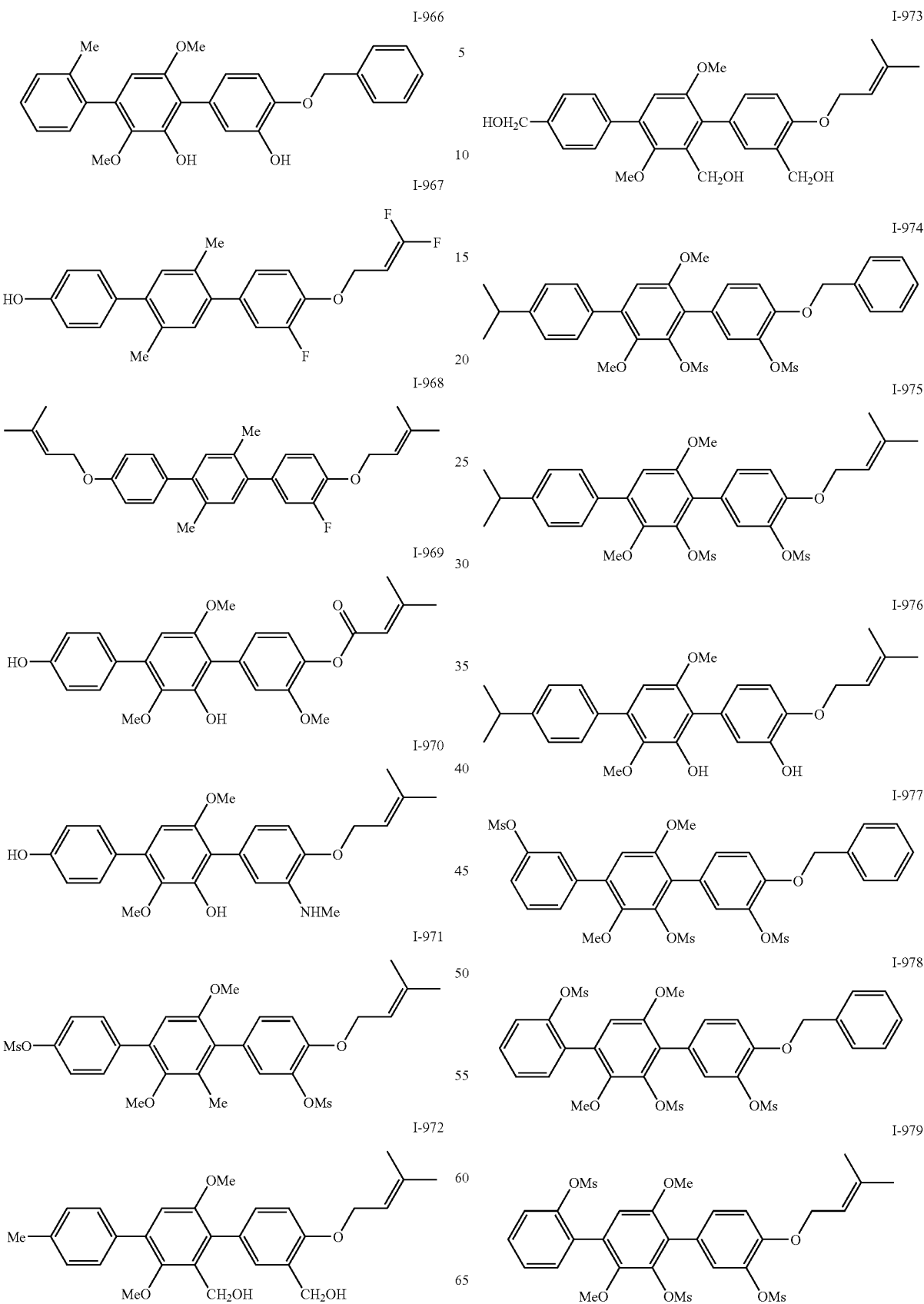

-continued
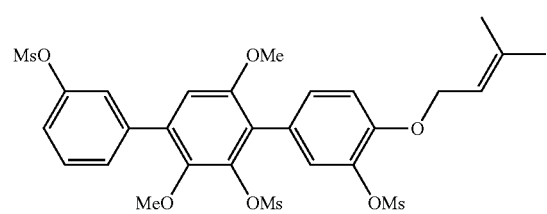
I-980
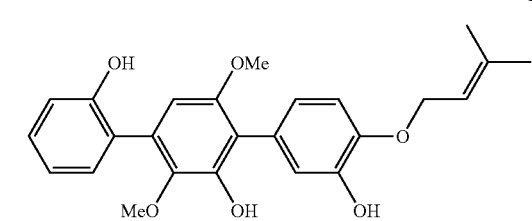
I-981
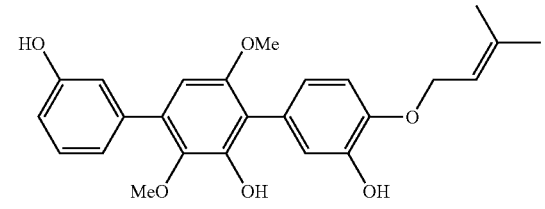
I-982
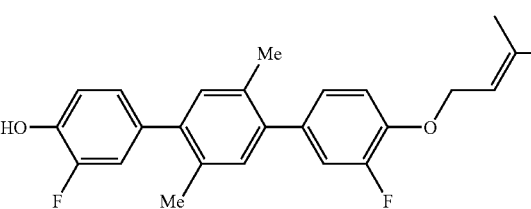
I-983
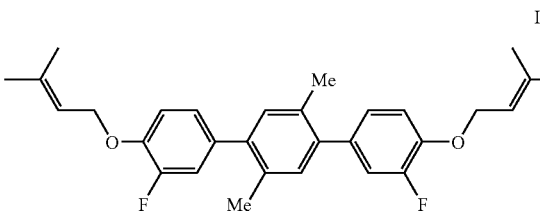
I-984
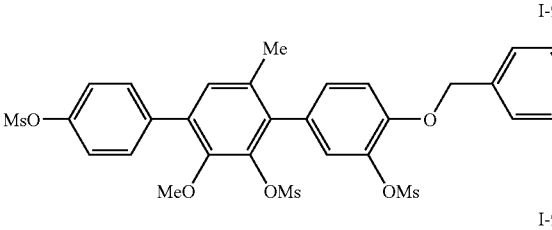
I-985
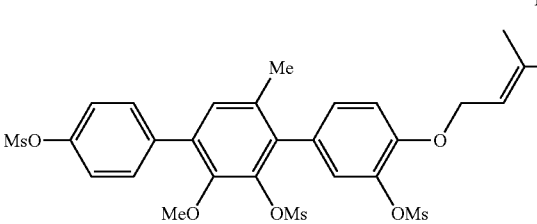
I-986
-continued
I-987
I-988
I-989
I-990
I-991
I-992
I-993

-continued

I-994
I-995
I-996
I-997
I-998
I-999
I-1000

I-1001
I-1002
I-1003
I-1004
I-1005
I-1006
I-1007

-continued
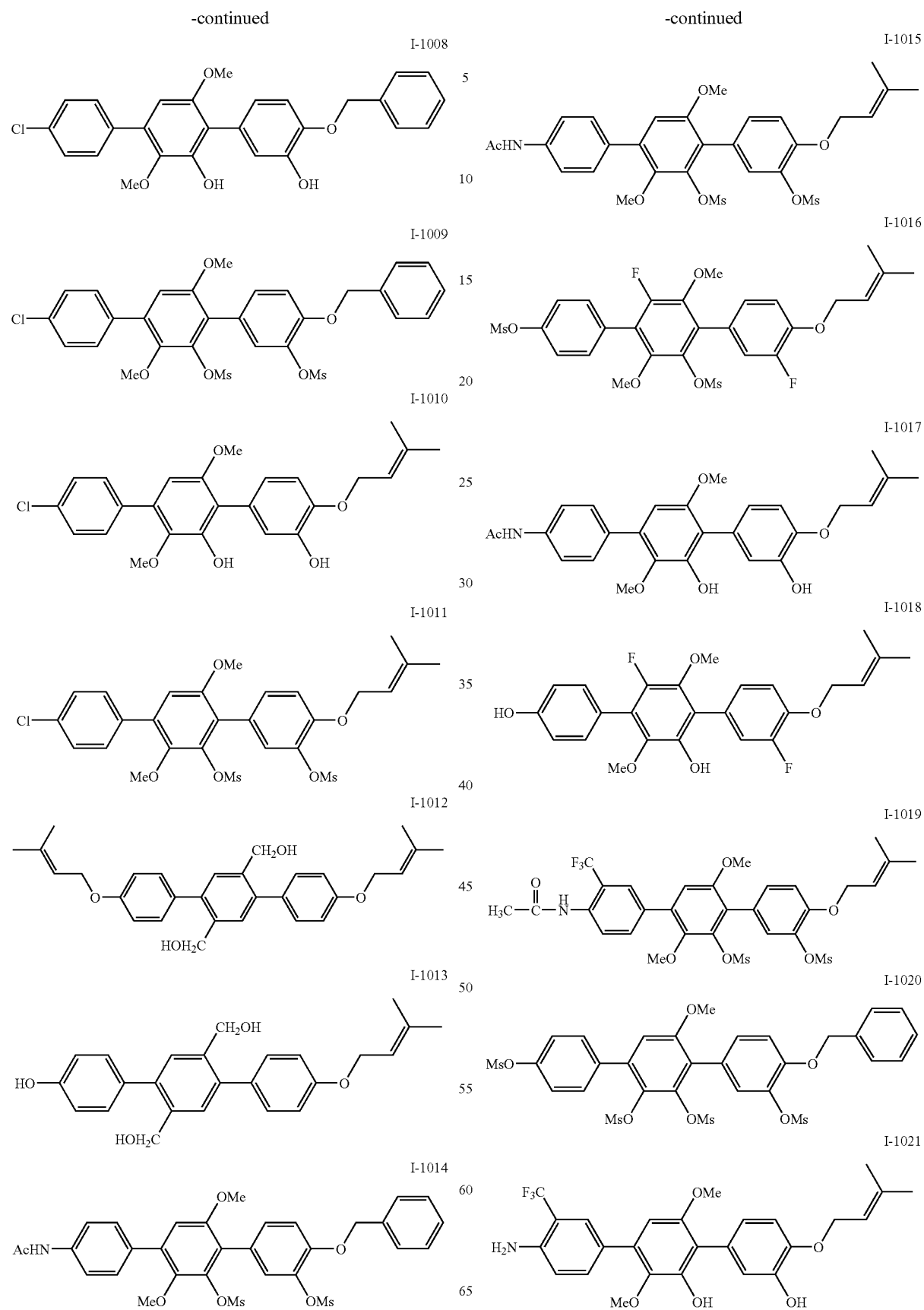

-continued
I-1022
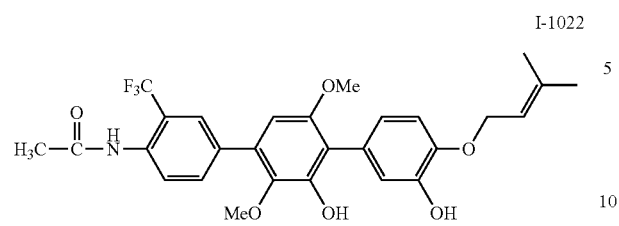
I-1023
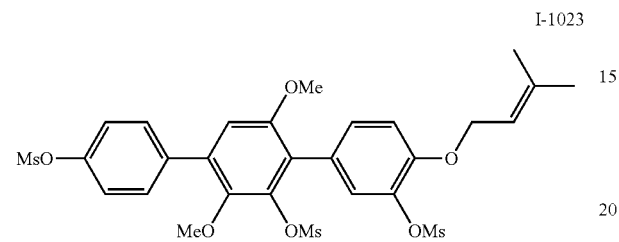
I-1024
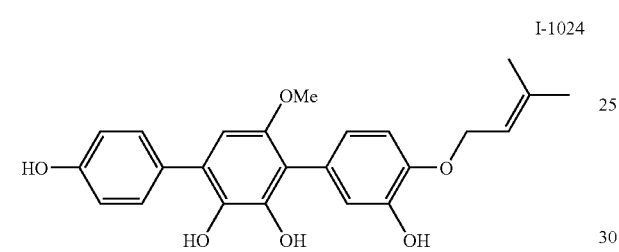
I-1025
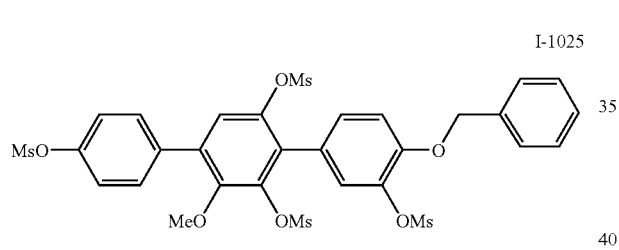
I-1026
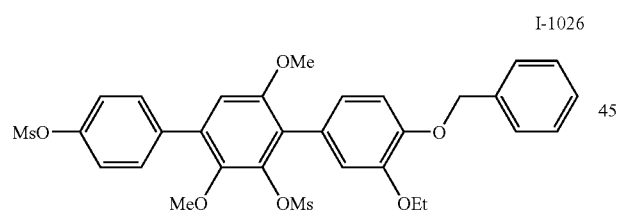
I-1027
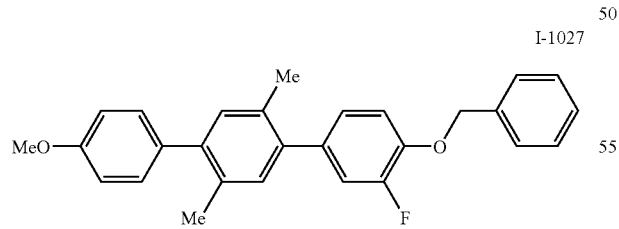
I-1028
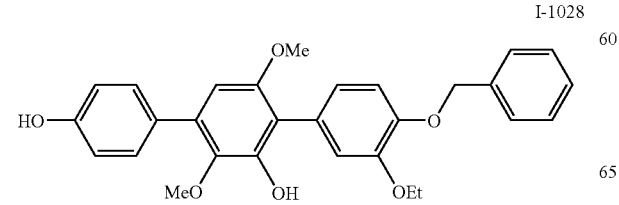
-continued
I-1029
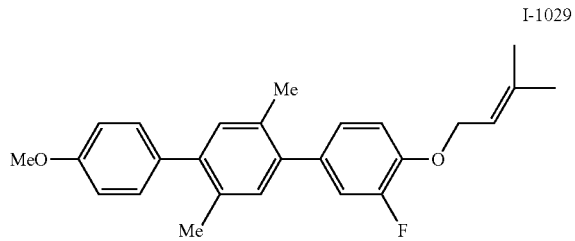
I-1030
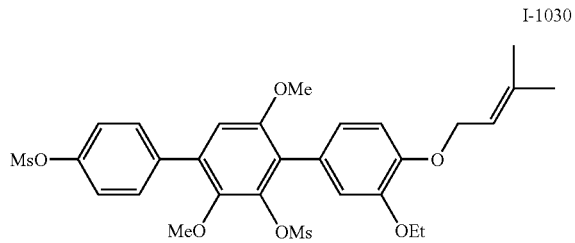
I-1031
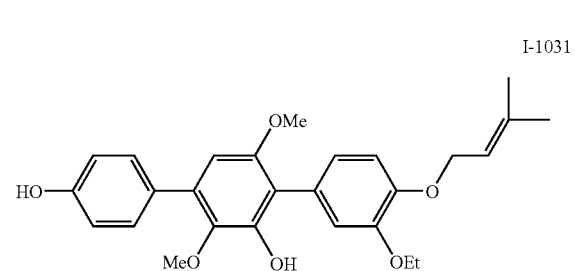
I-1032
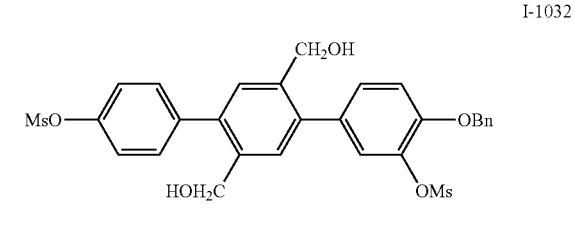
I-1033
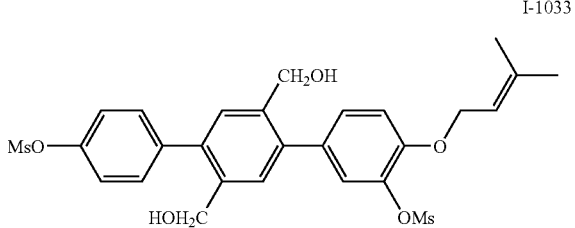
I-1034
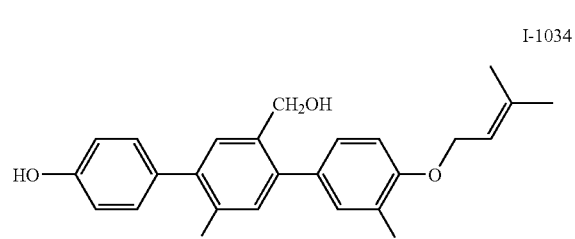
I-1035
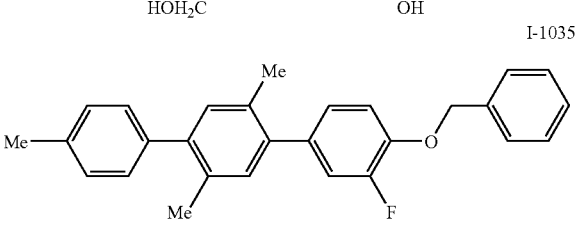

-continued
I-1036
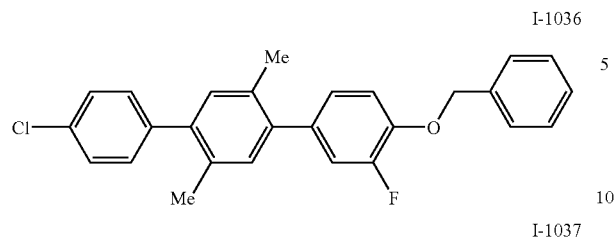
I-1037
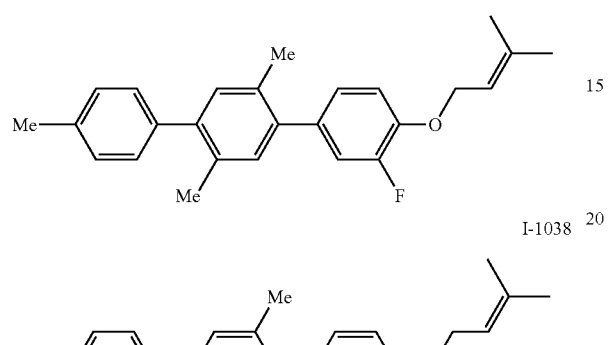
I-1038
I-1039
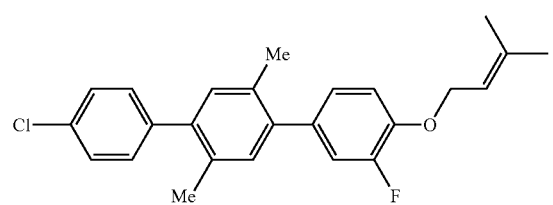
I-1040
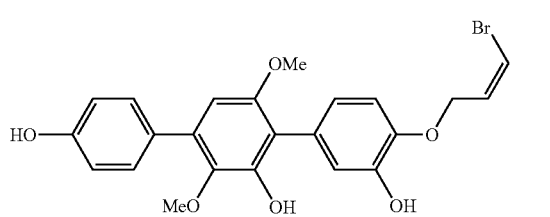
I-1041
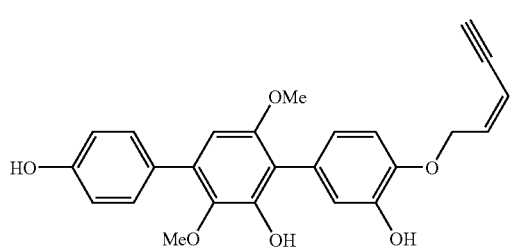
I-1042
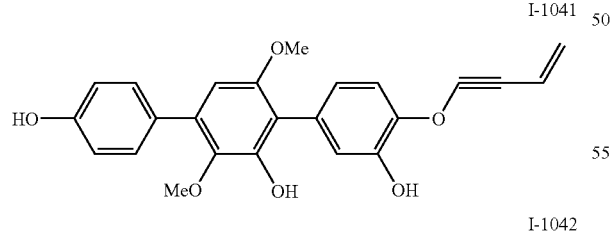
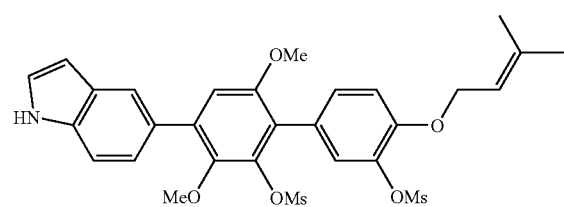
-continued
I-1043
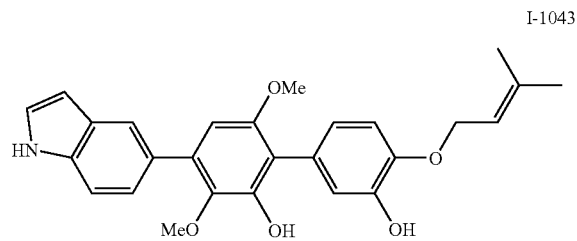
I-1044
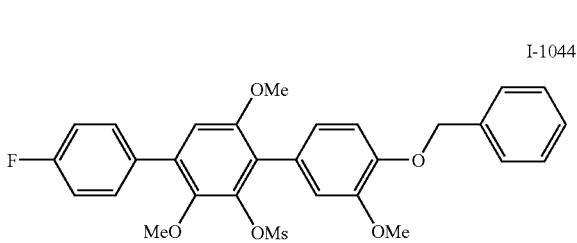
I-1045
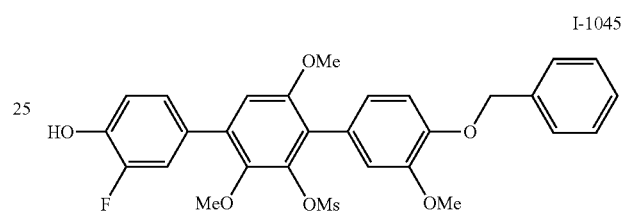
I-1046
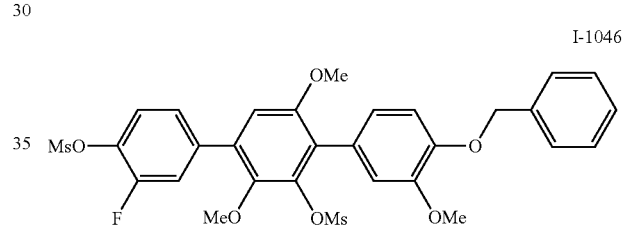
I-1047
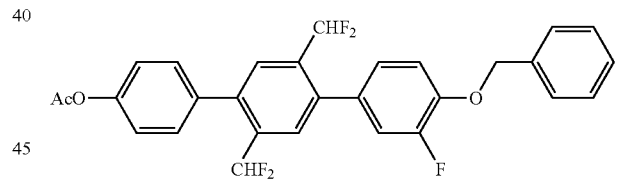
I-1048
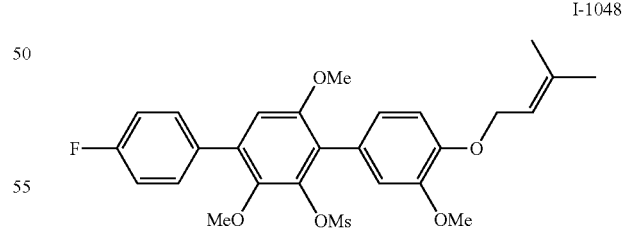
I-1049
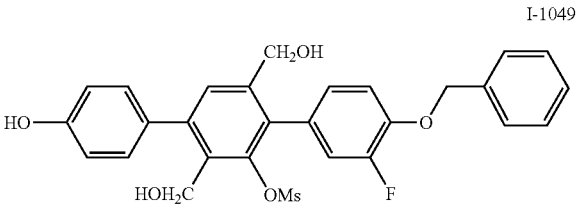

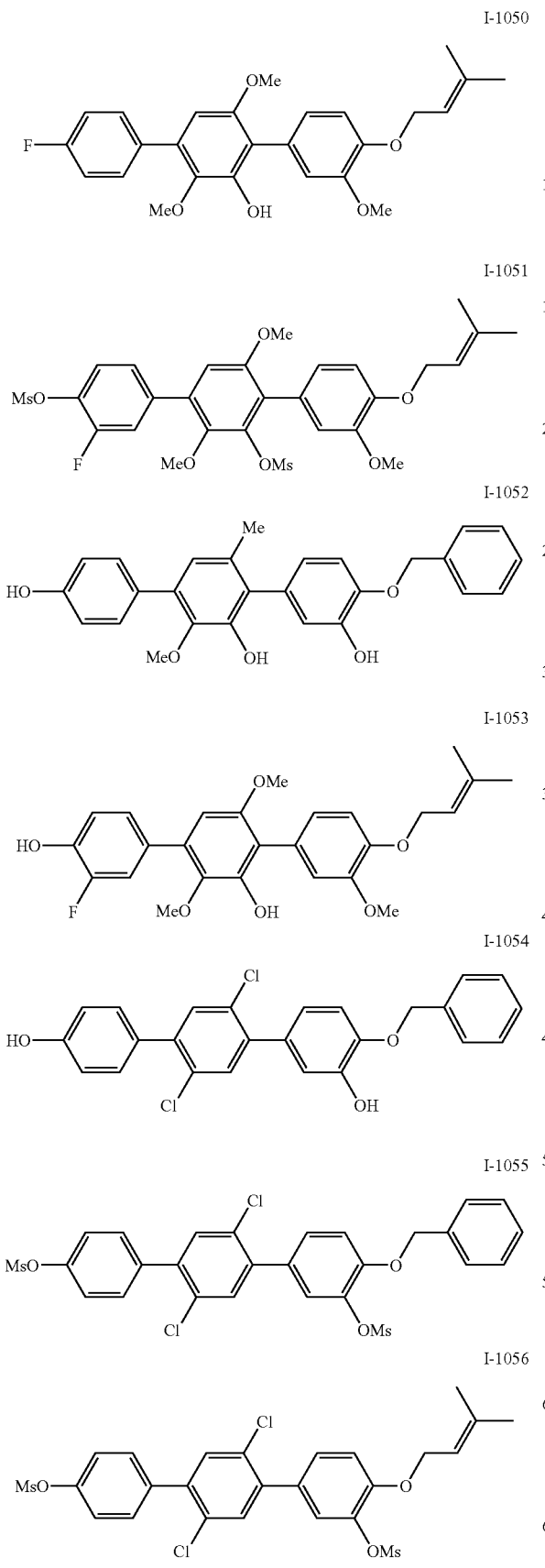
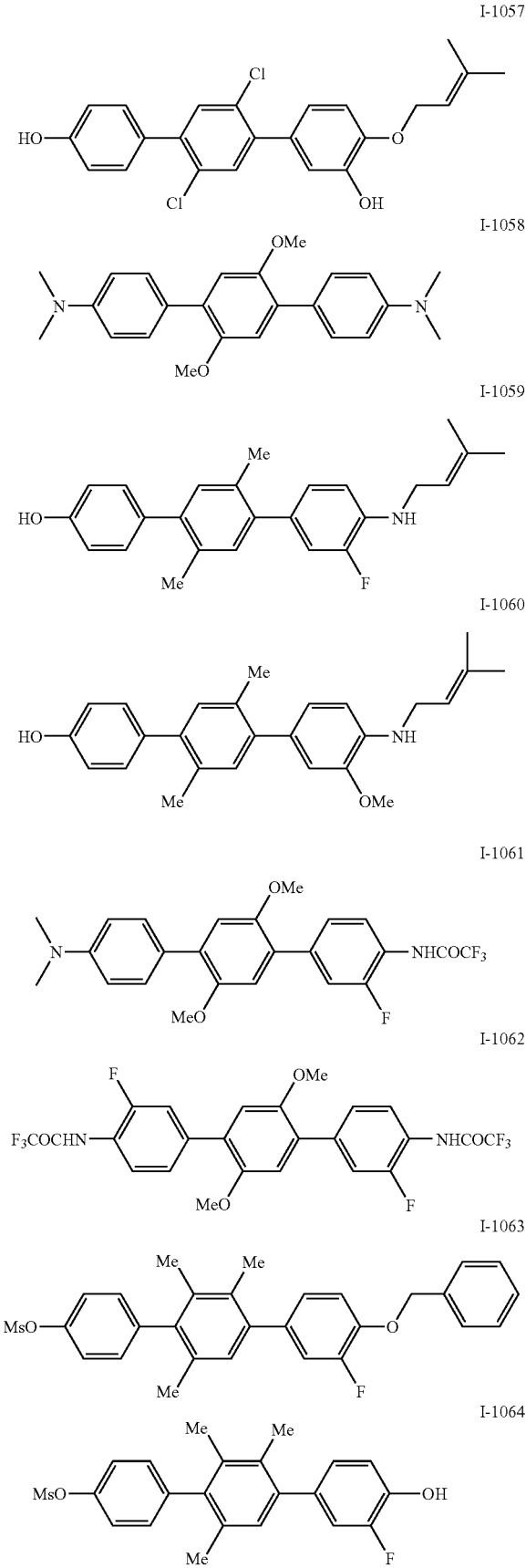

I-1065
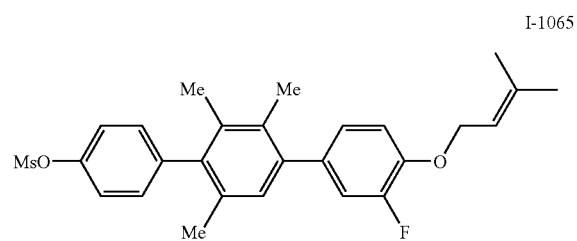
I-1066
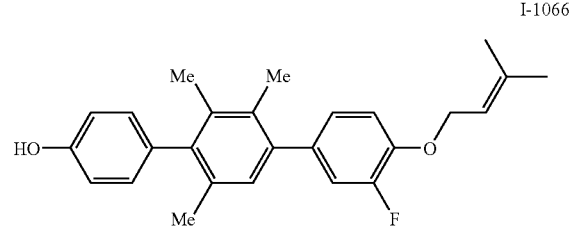
I-1067
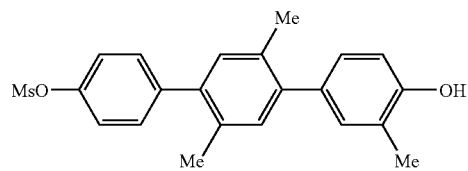
I-1068
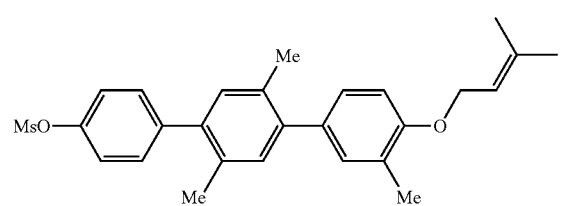
I-1069
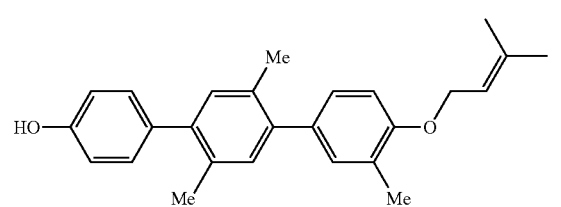
I-1070
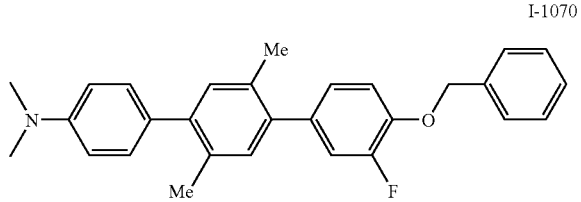
I-1071
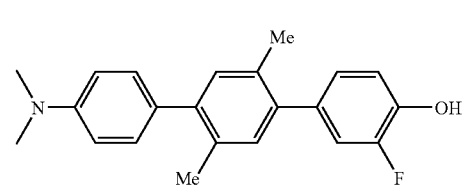
I-1072
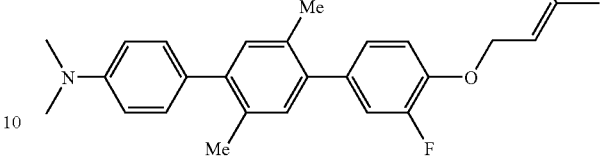
I-1073
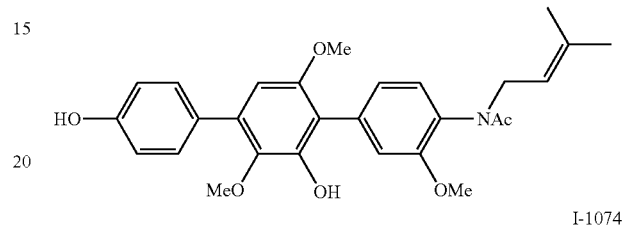
I-1074
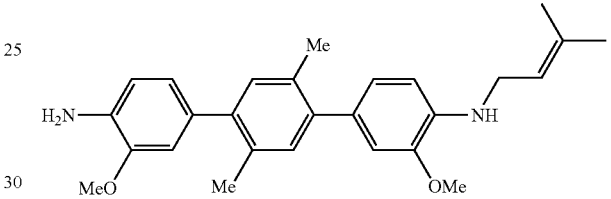
I-1075
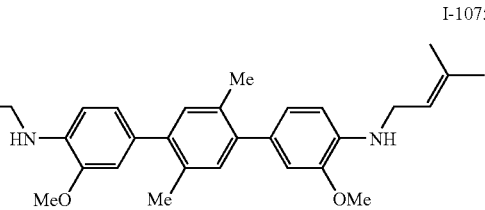
I-1076
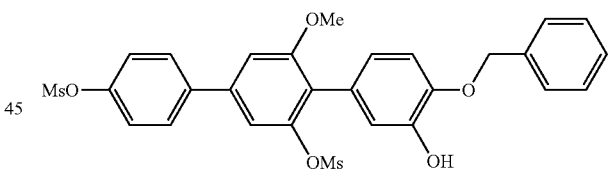
I-1077
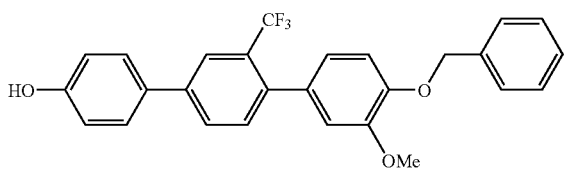
I-1078
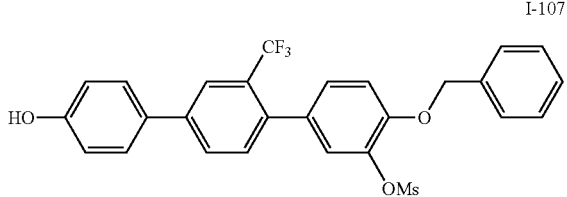

I-1079
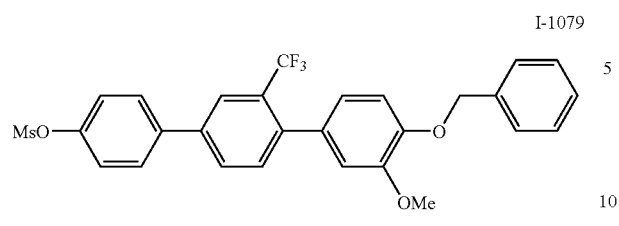
I-1080
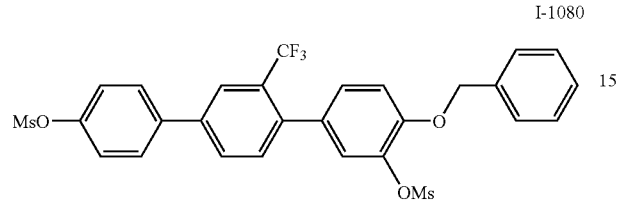
I-1081
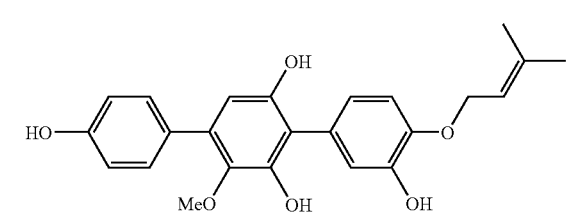
I-1082
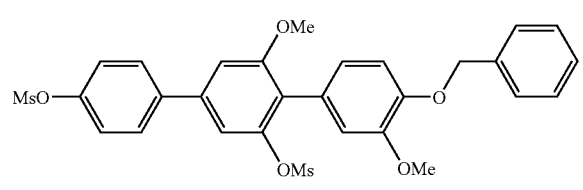
I-1083
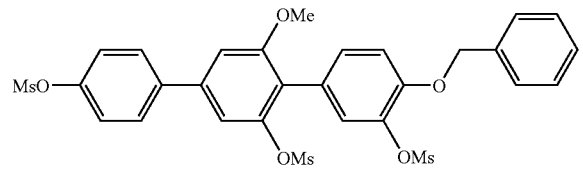
I-1084
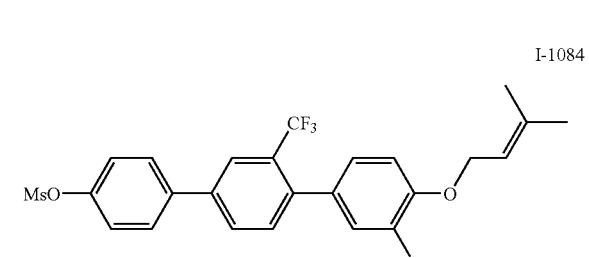
I-1085
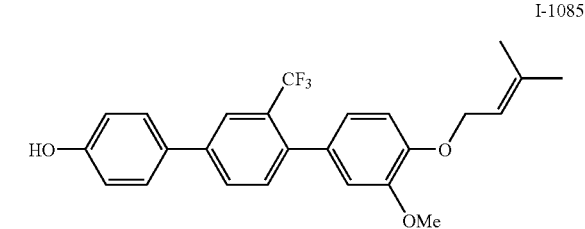
I-1086
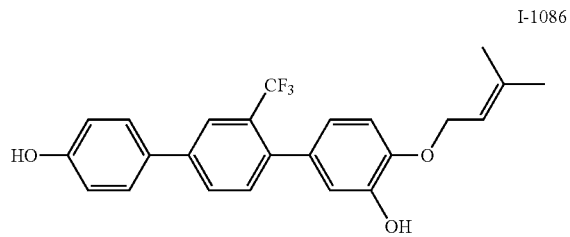
I-1087
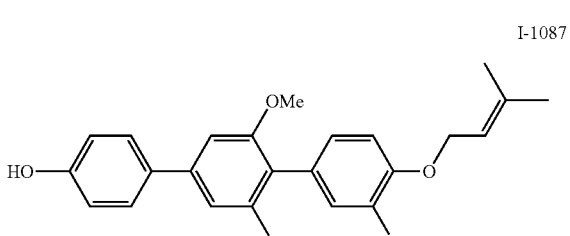
I-1088
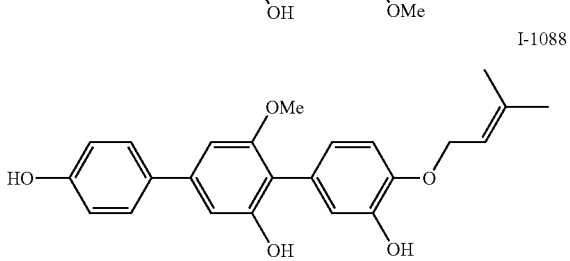
I-1089
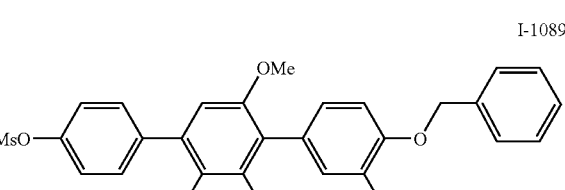
I-1090
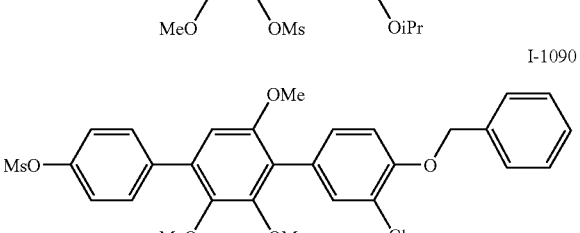
I-1091
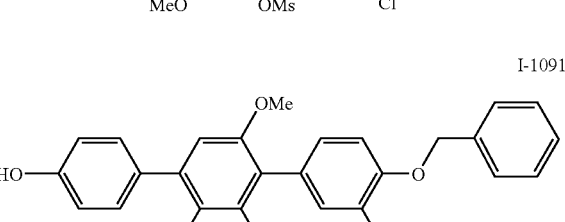
I-1092
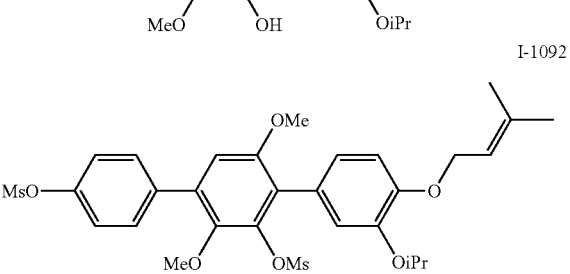

I-1093
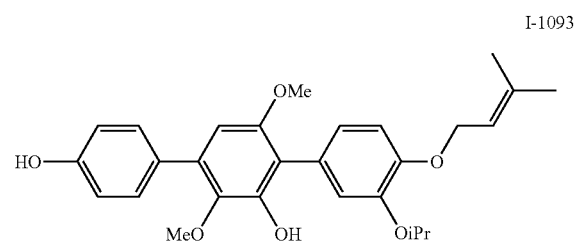
I-1094
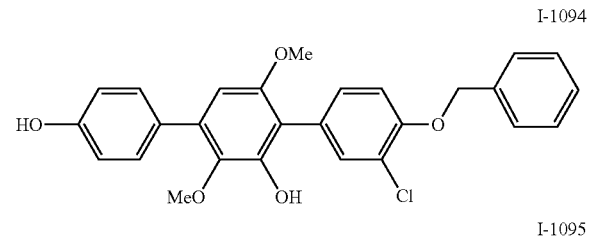
I-1095
I-1096
I-1097
I-1098
I-1099
I-1100
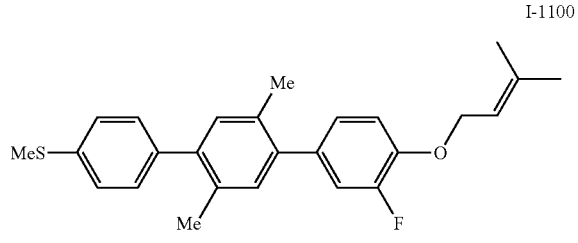
I-1101
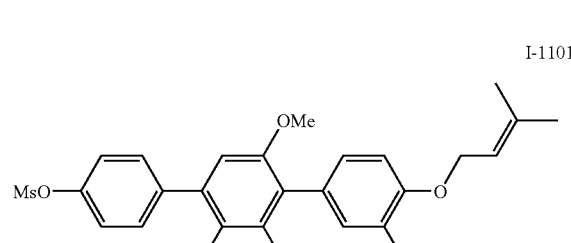
I-1102
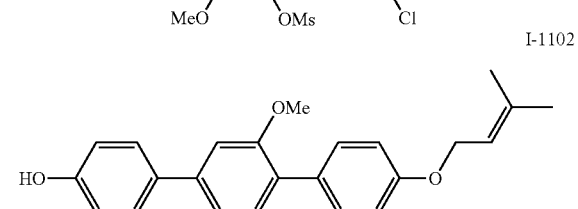
I-1103
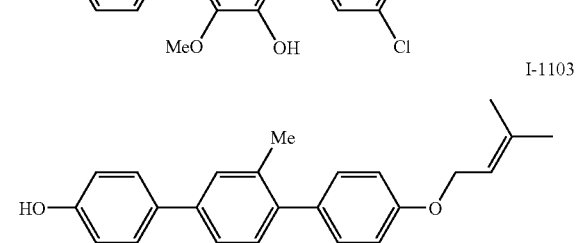
I-1104
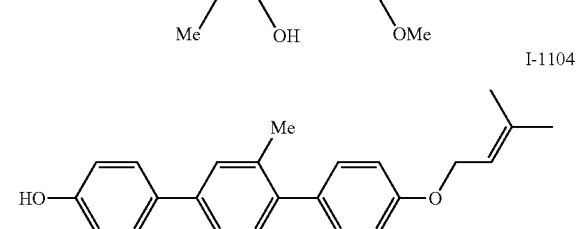
I-1105
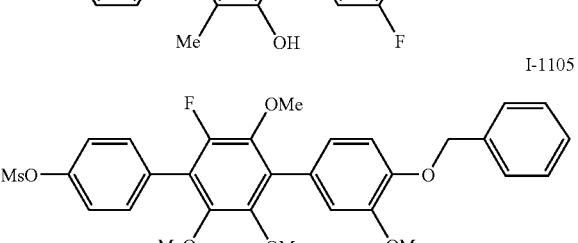
I-1106
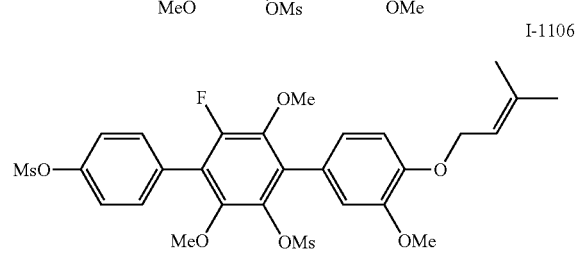

-continued
I-1107
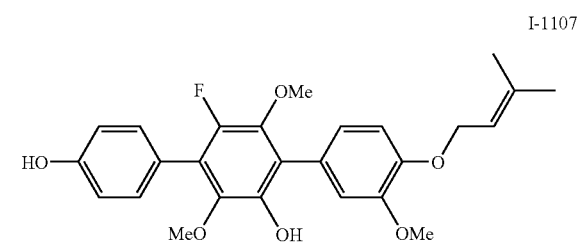
I-1108
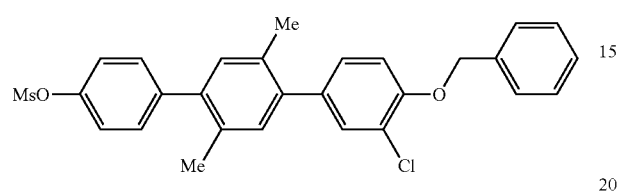
I-1109
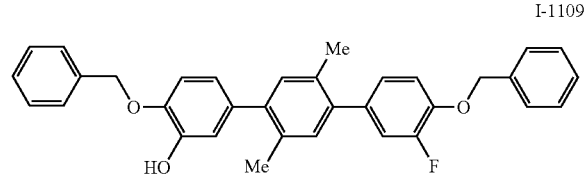
I-1110
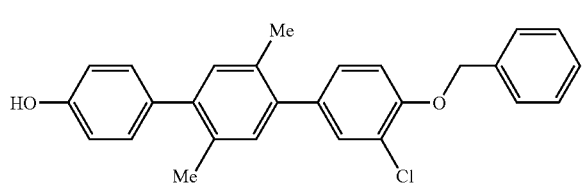
I-1111
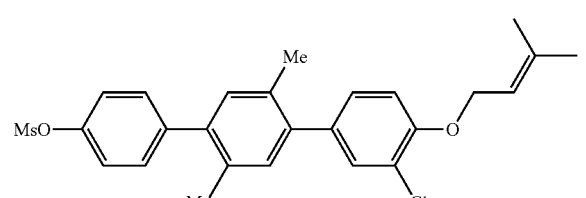
I-1112
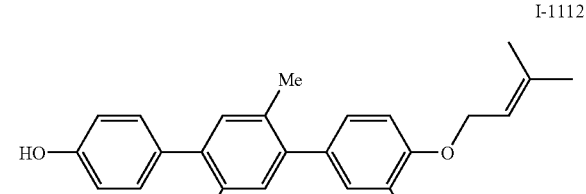
I-1113
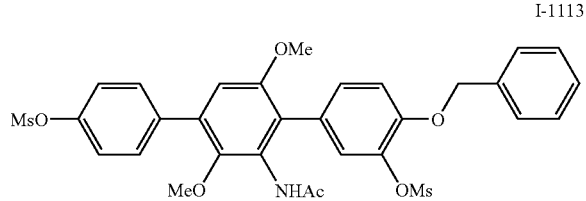
-continued
I-1114
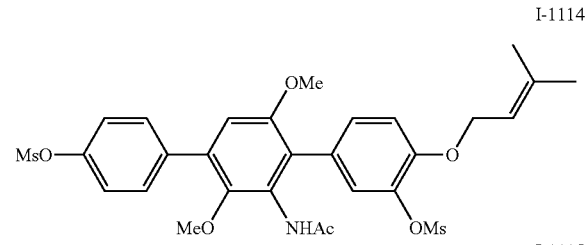
I-1115
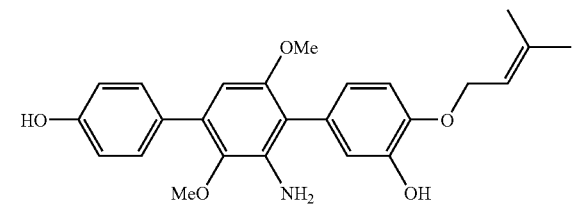
I-1116
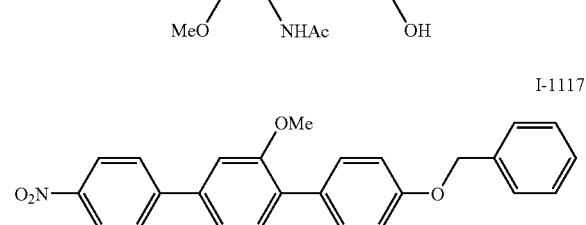
I-1117
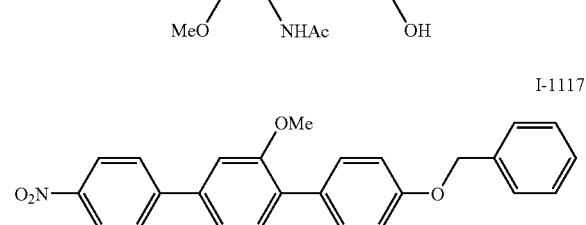
I-1118
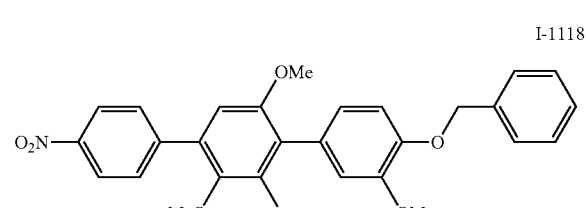
I-1119
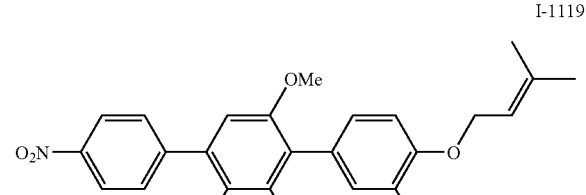
I-1120
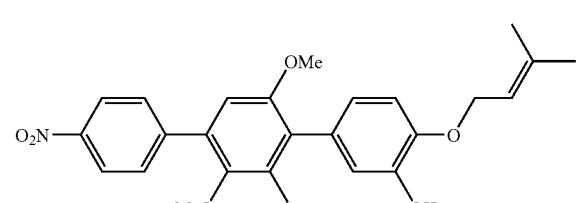

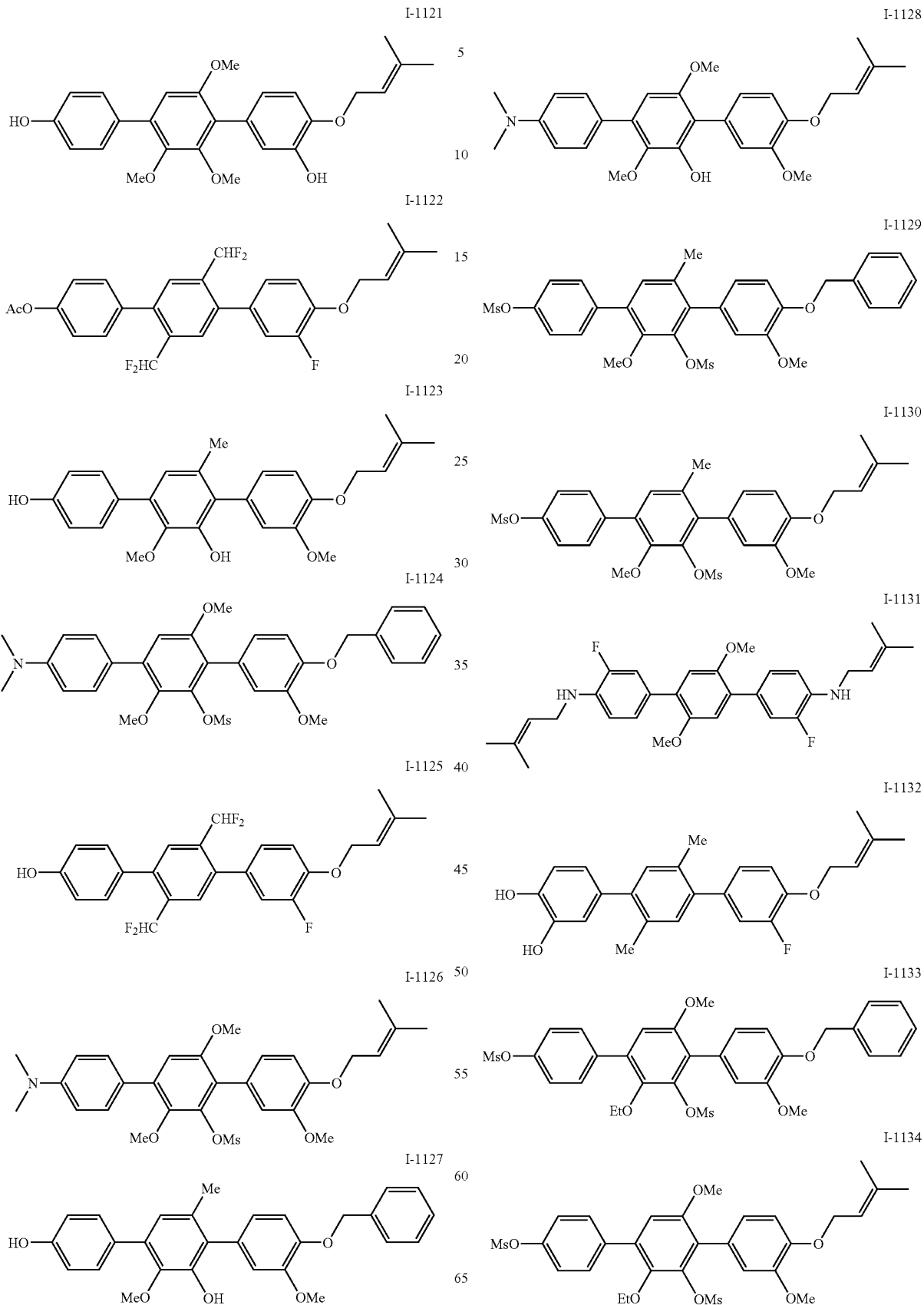

-continued
I-1135
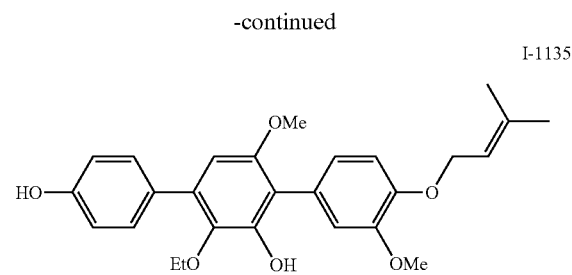
I-1136
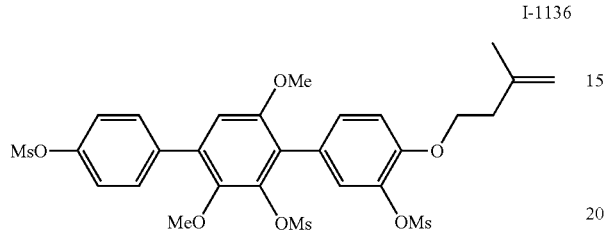
I-1137
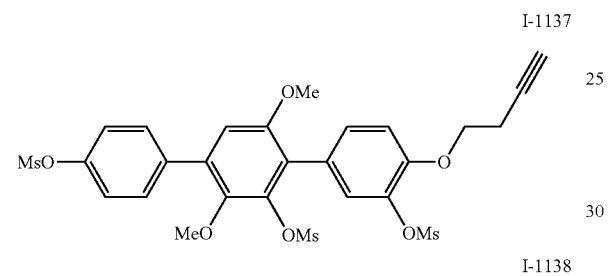
I-1138
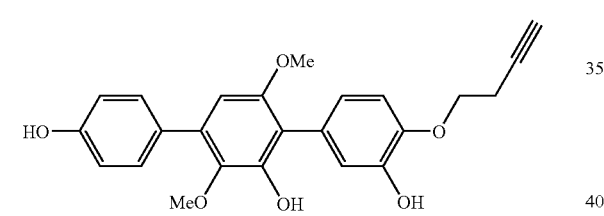
I-1139
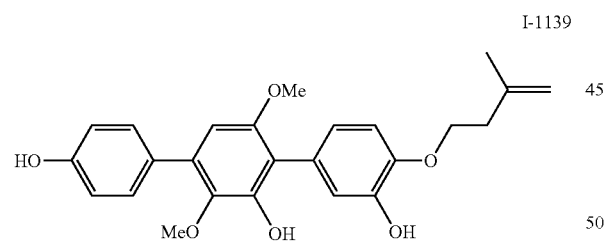
I-1140
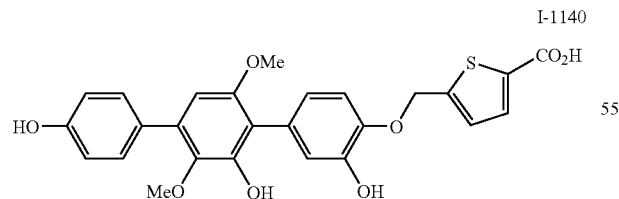
I-1141
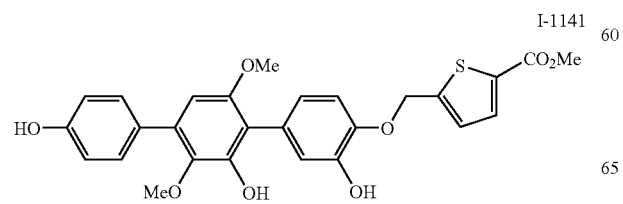
-continued
I-1142
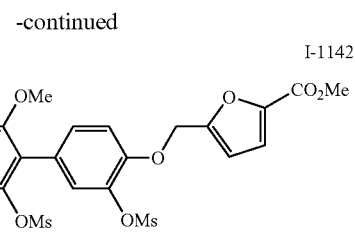
I-1143
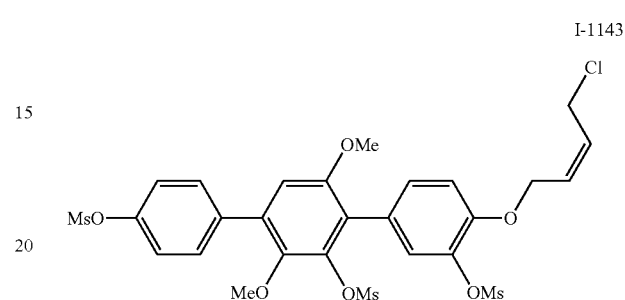
I-1144
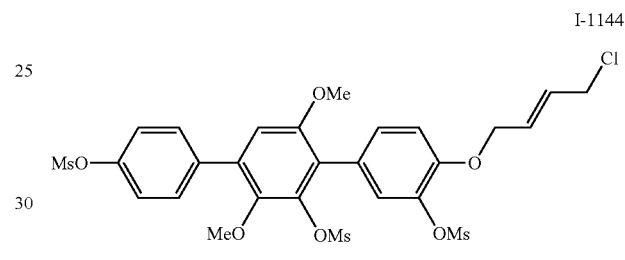
I-1145
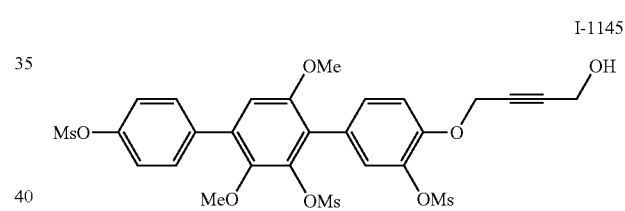
I-1146
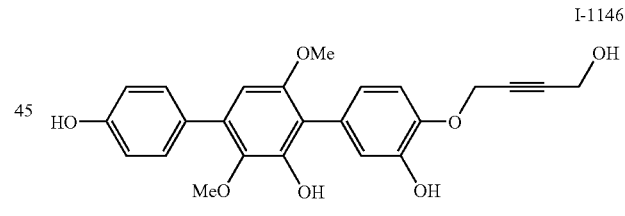
I-1147
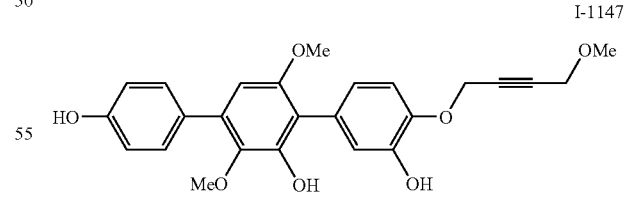
I-1148
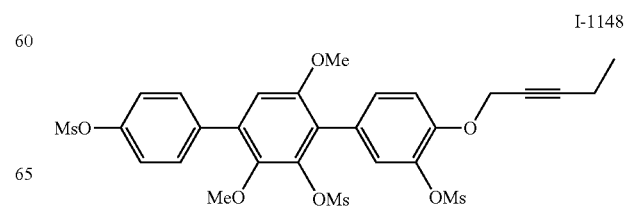

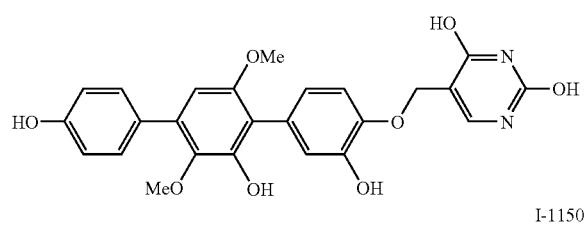
I-1149
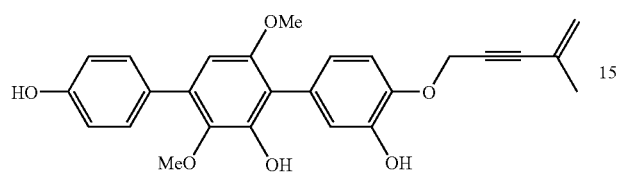
I-1150
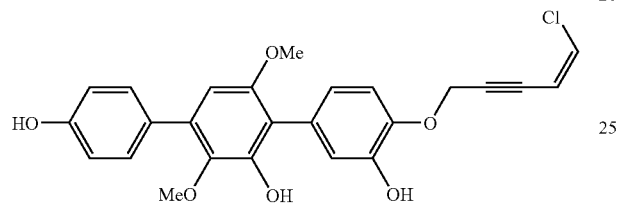
I-1151
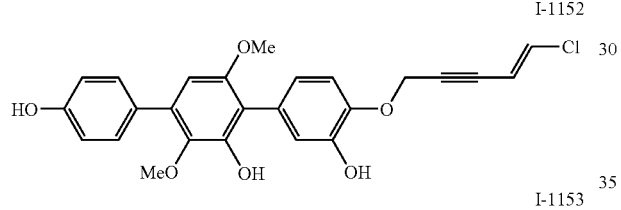
I-1152
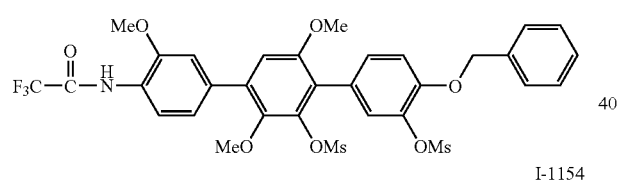
I-1153
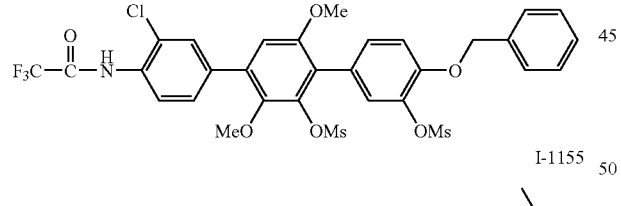
I-1154
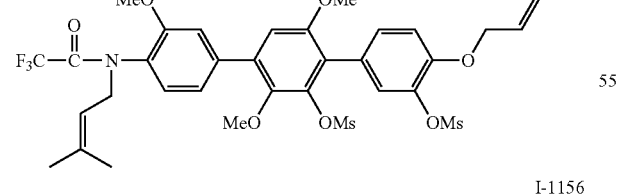
I-1155
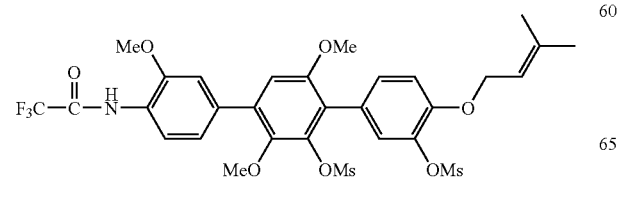
I-1156
I-1157
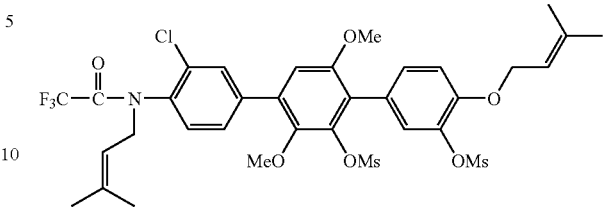
I-1158
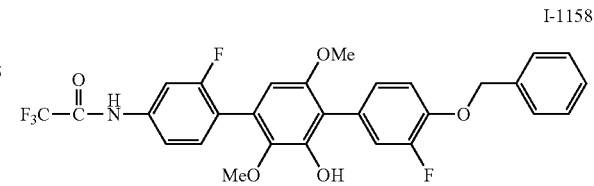
I-1159
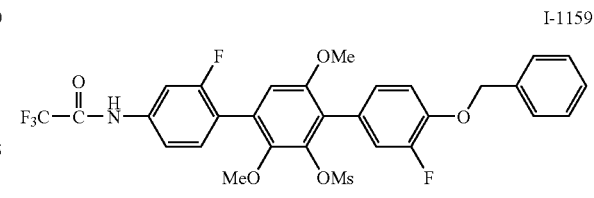
I-1160
I-1161
I-1162
I-1163

-continued
I-1164
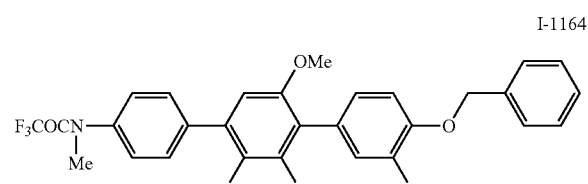
I-1165
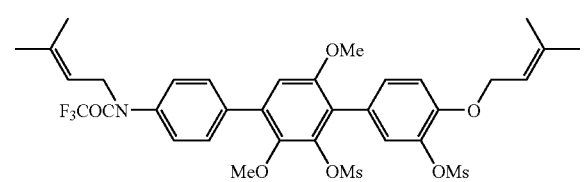
I-1166
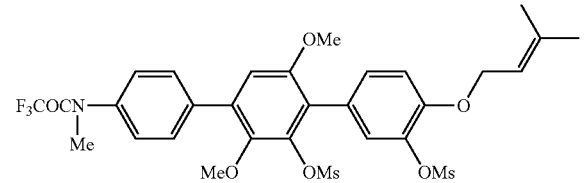
I-1167
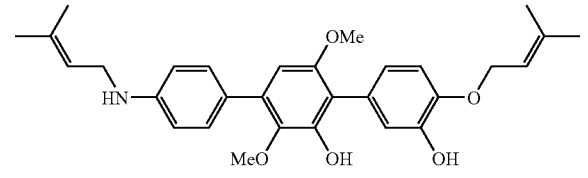
I-1168
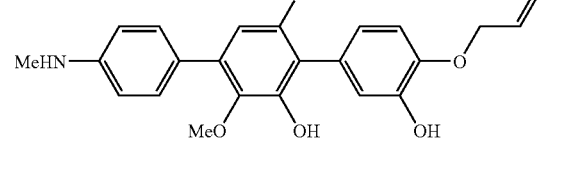
I-1169
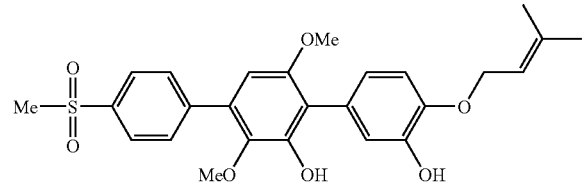
I-1170
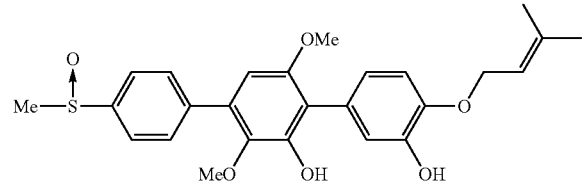
-continued
I-1171
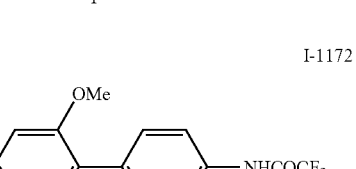
I-1172
I-1173
I-1174
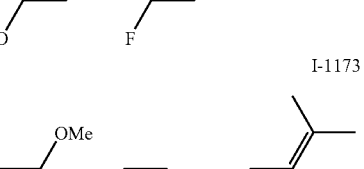
I-1175
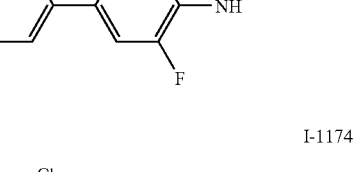
I-1176
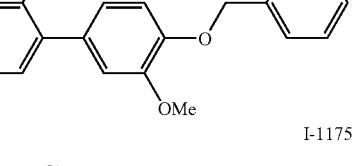
I-1177

-continued

I-1178, I-1179, I-1180, I-1181, I-1182, I-1183, I-1184, I-1185, I-1186, I-1187, I-1188, I-1189, I-1190, I-1191

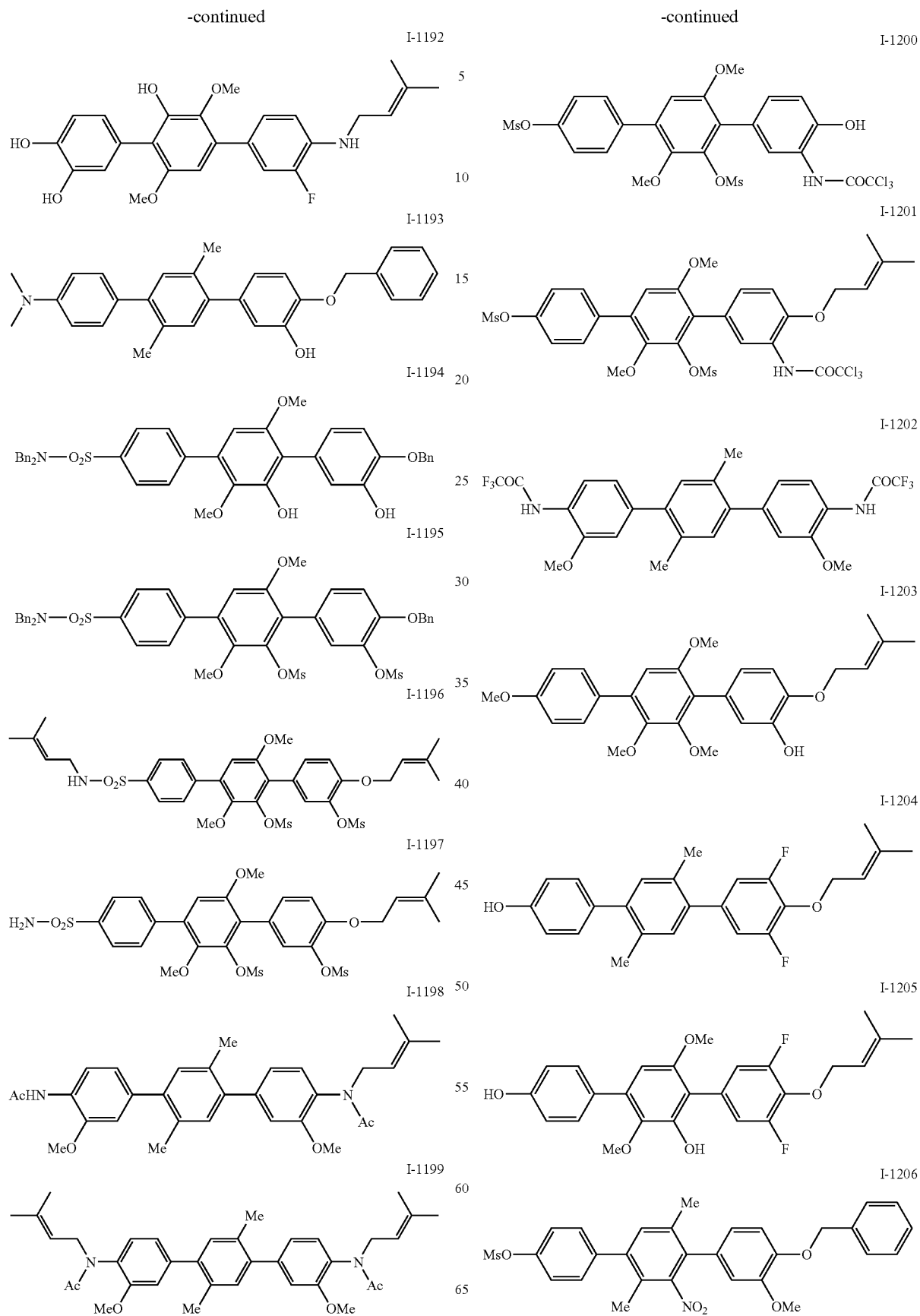

-continued
I-1207
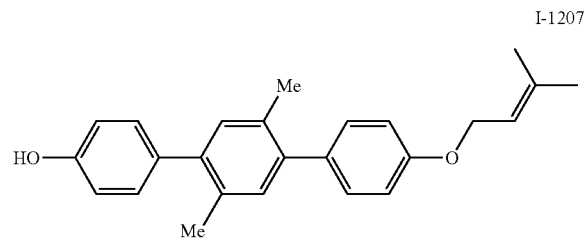
I-1208
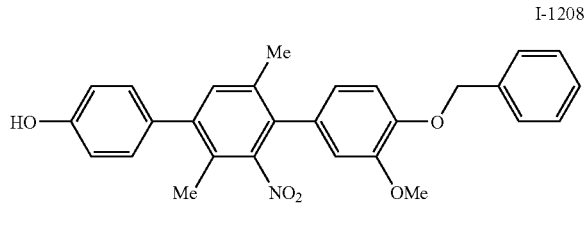
I-1209
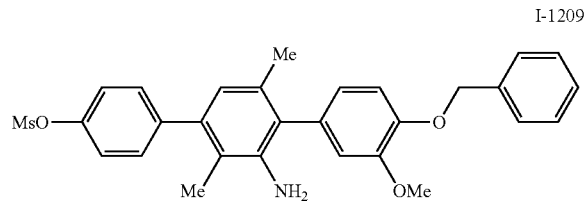
I-1210
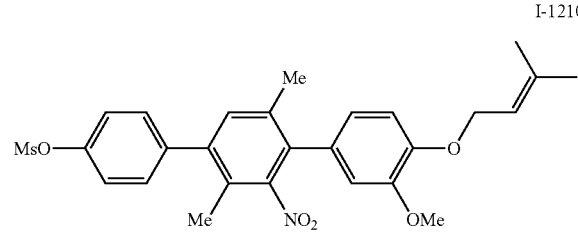
I-1211
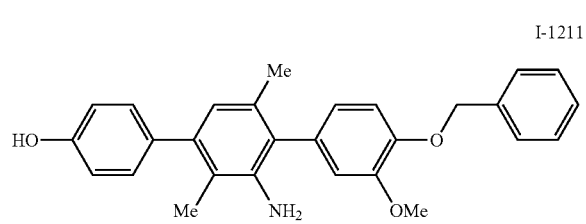
I-1212
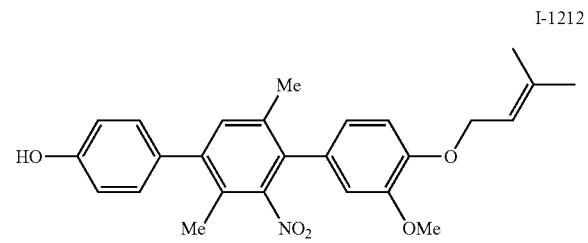
I-1213
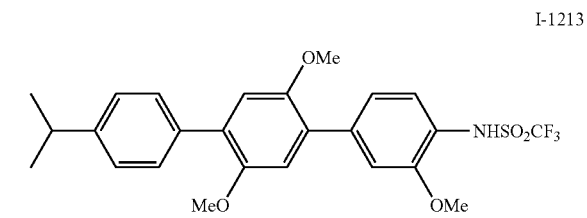
-continued
I-1214
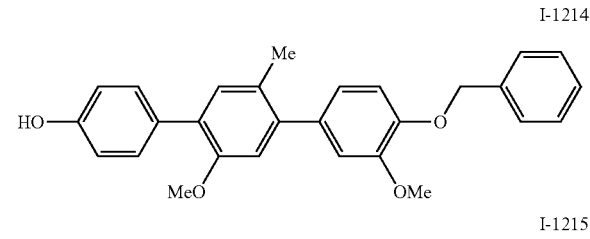
I-1215
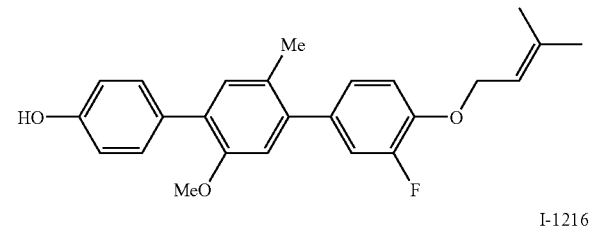
I-1216
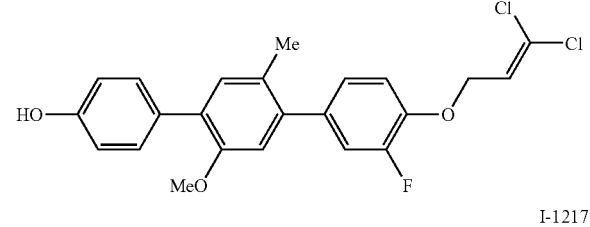
I-1217
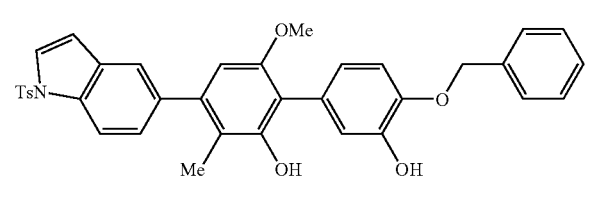
I-1218
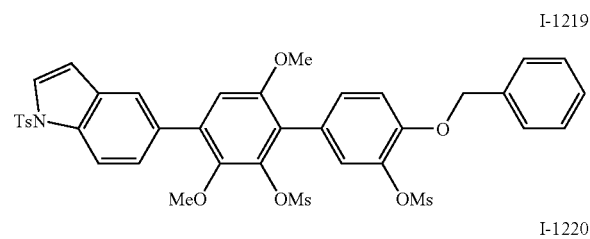
I-1219
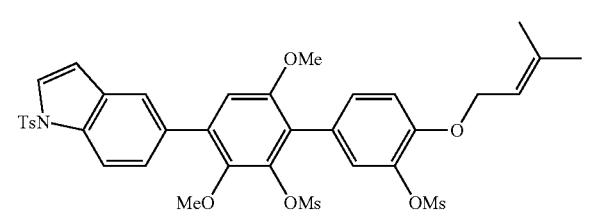
I-1220

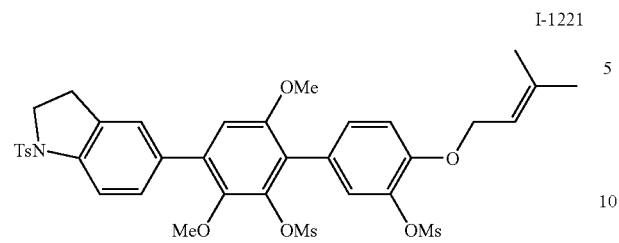
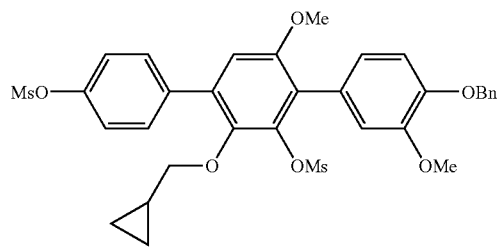

I-1234 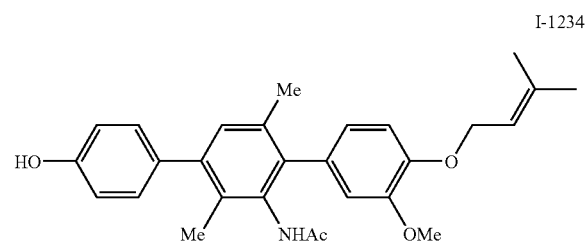
I-1235 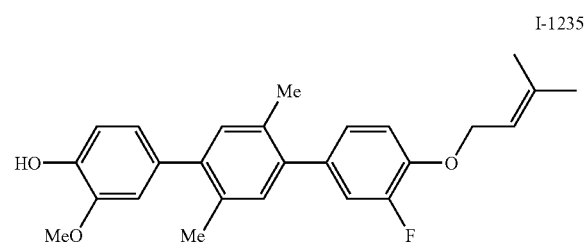
I-1236 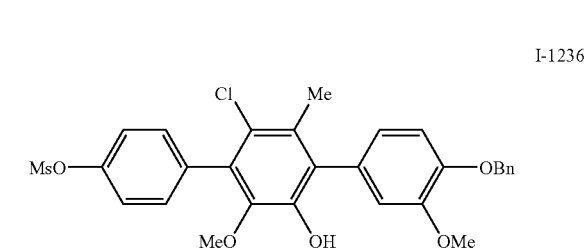
I-1237 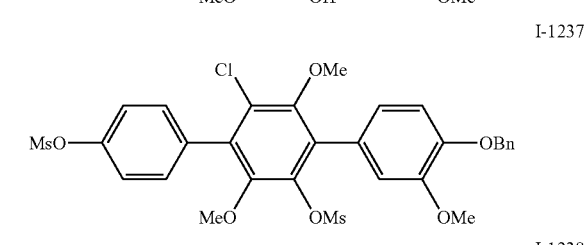
I-1238 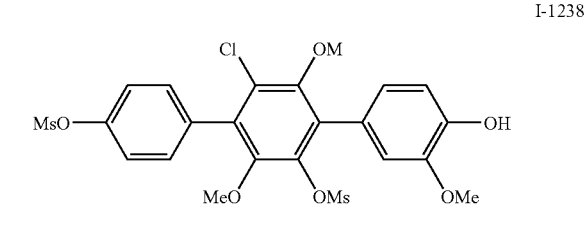
I-1239 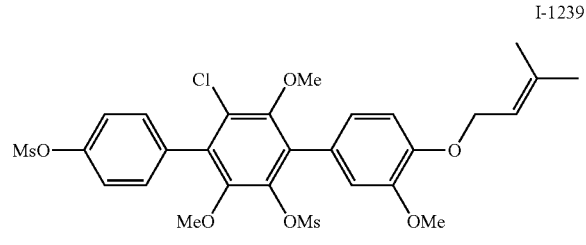
I-1240 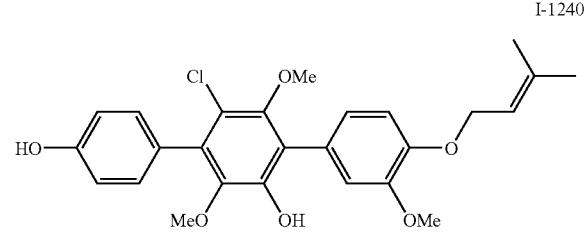
I-1241 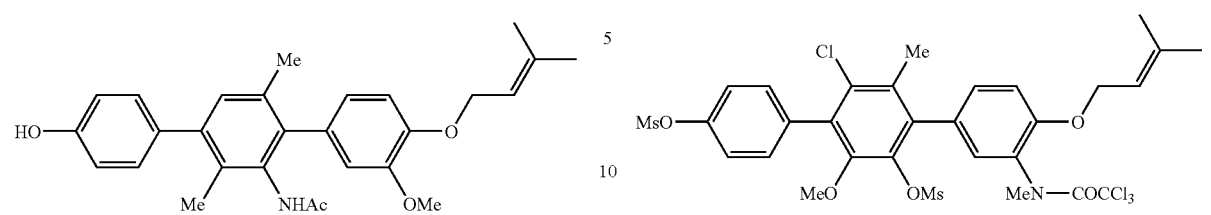
I-1242 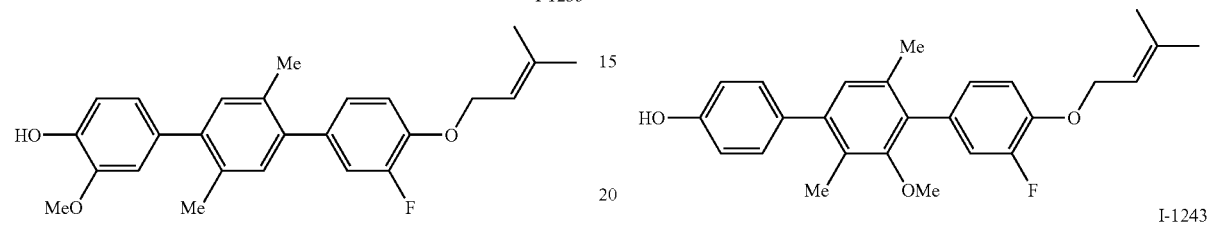
I-1243 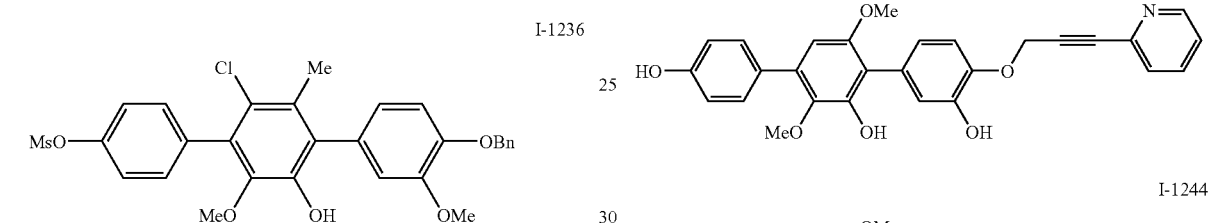
I-1244 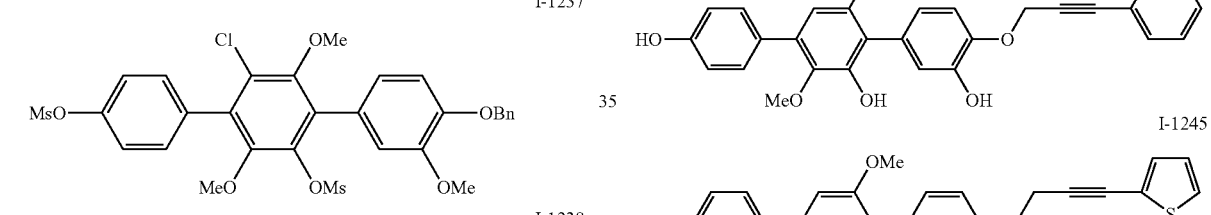
I-1245 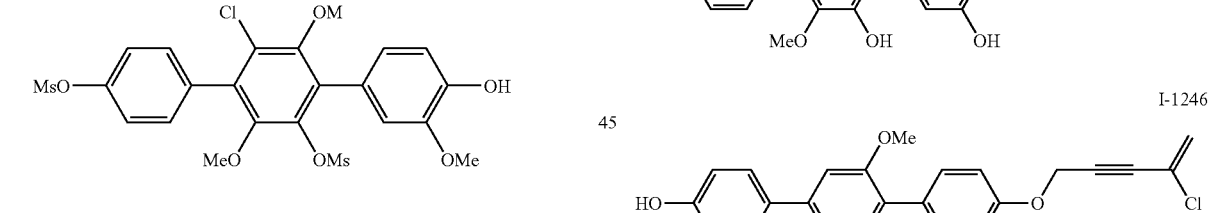
I-1246 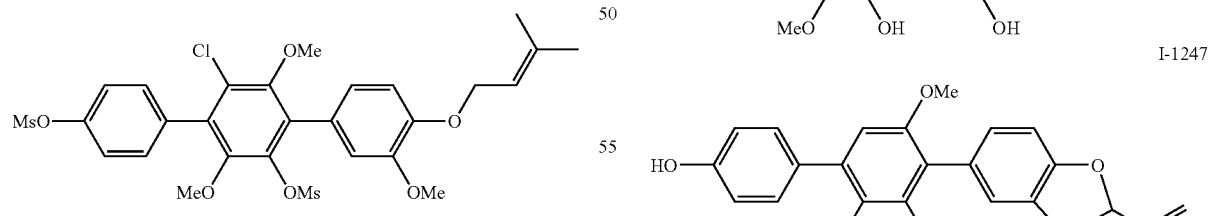
I-1247 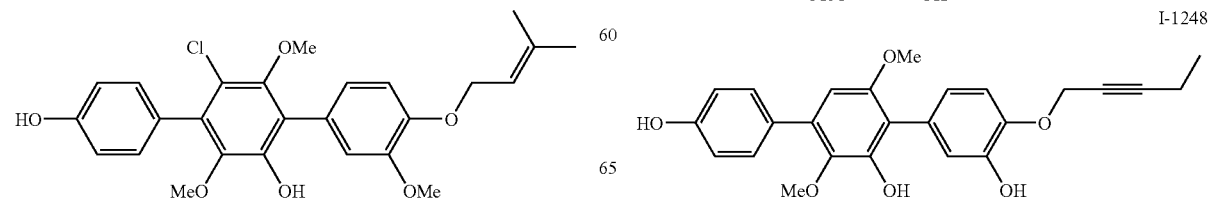
I-1248

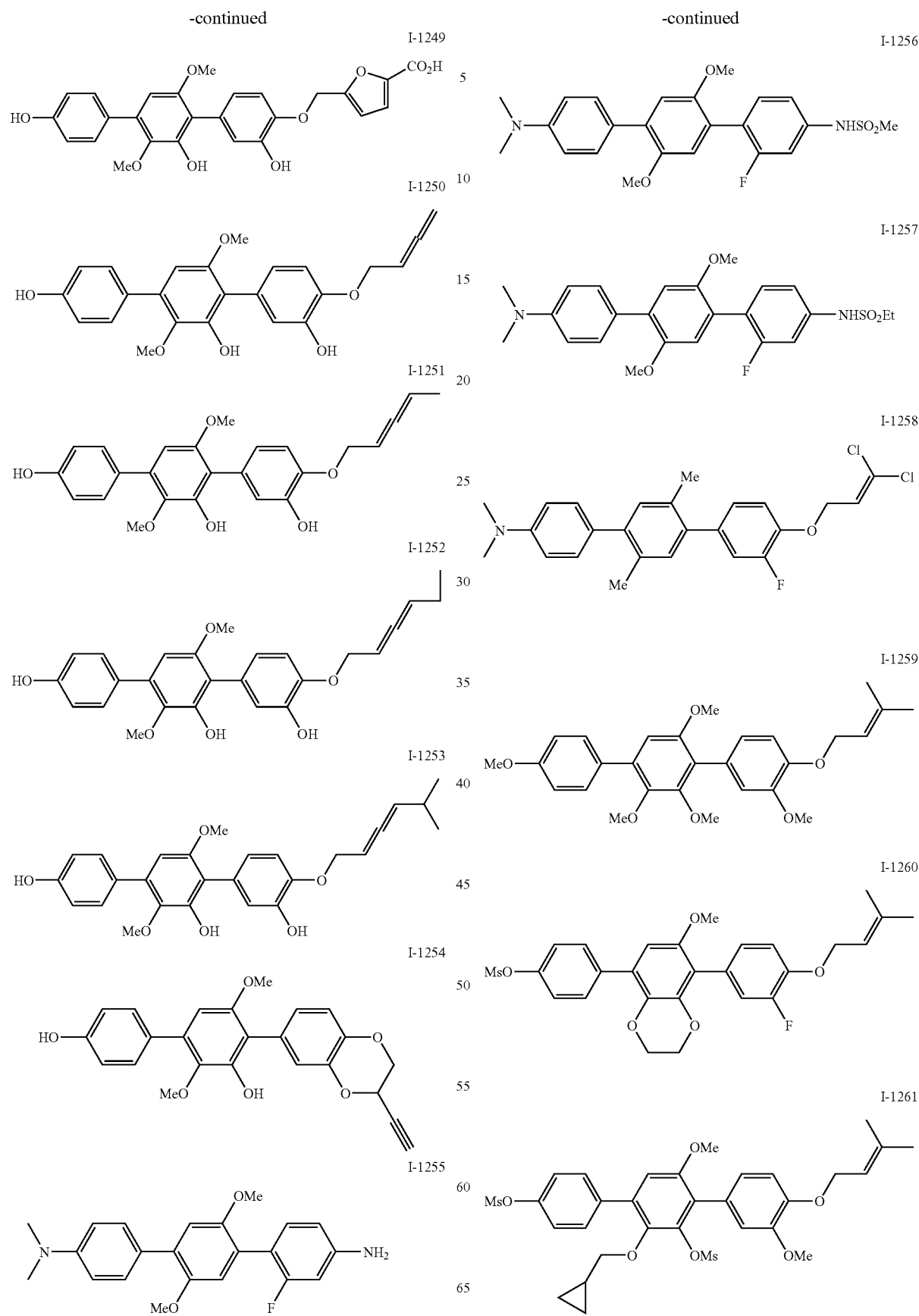

I-1262
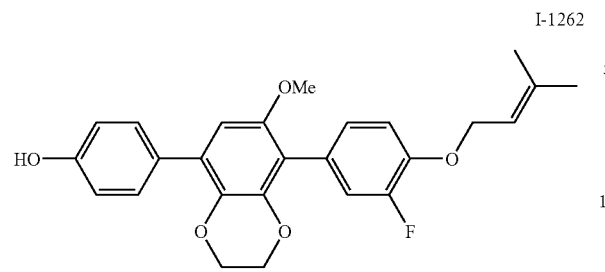
I-1263
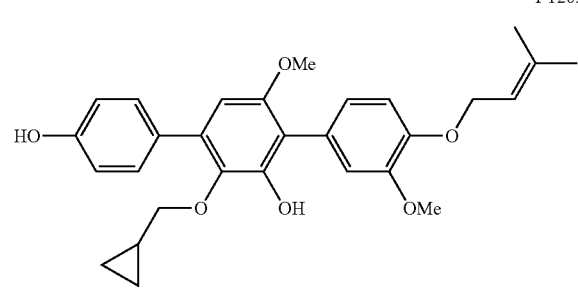
I-1264
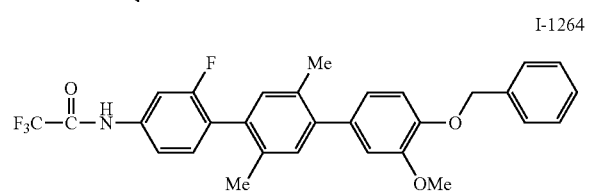
I-1265
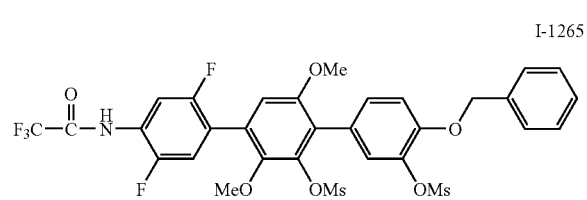
I-1266
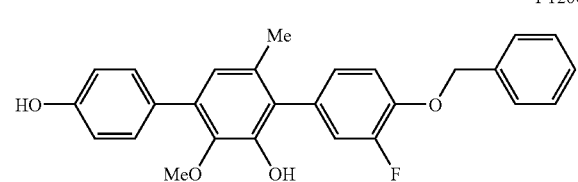
I-1267
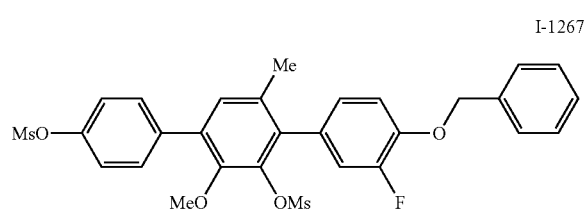
I-1268
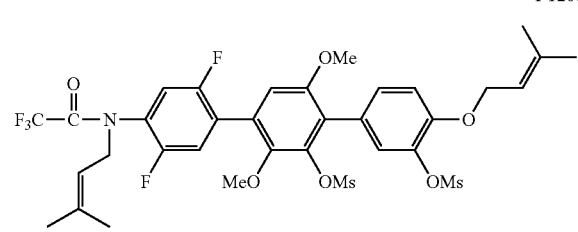
I-1269
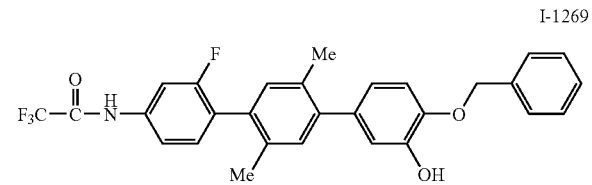
I-1270
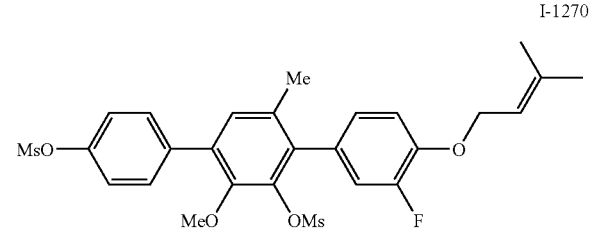
I-1271
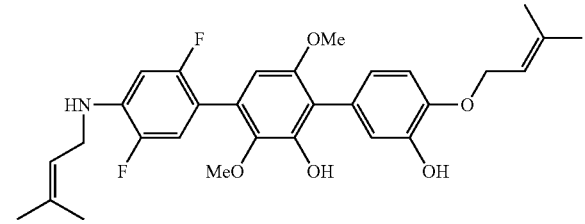
I-1272
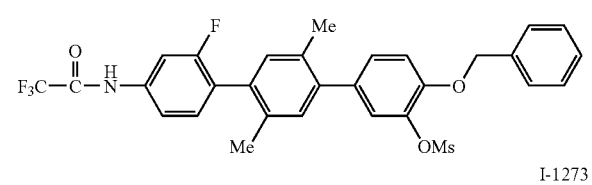
I-1273
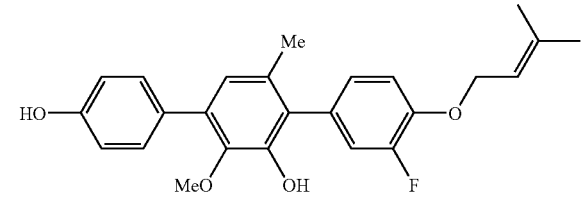
I-1274
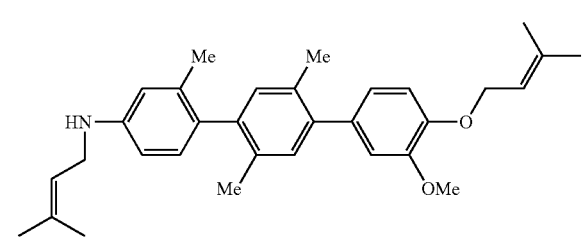
I-1275
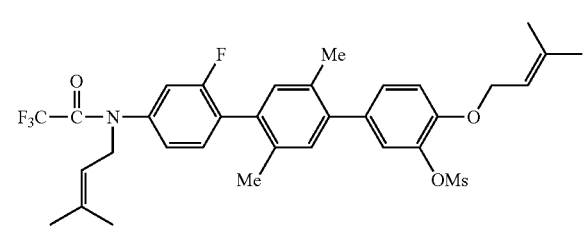

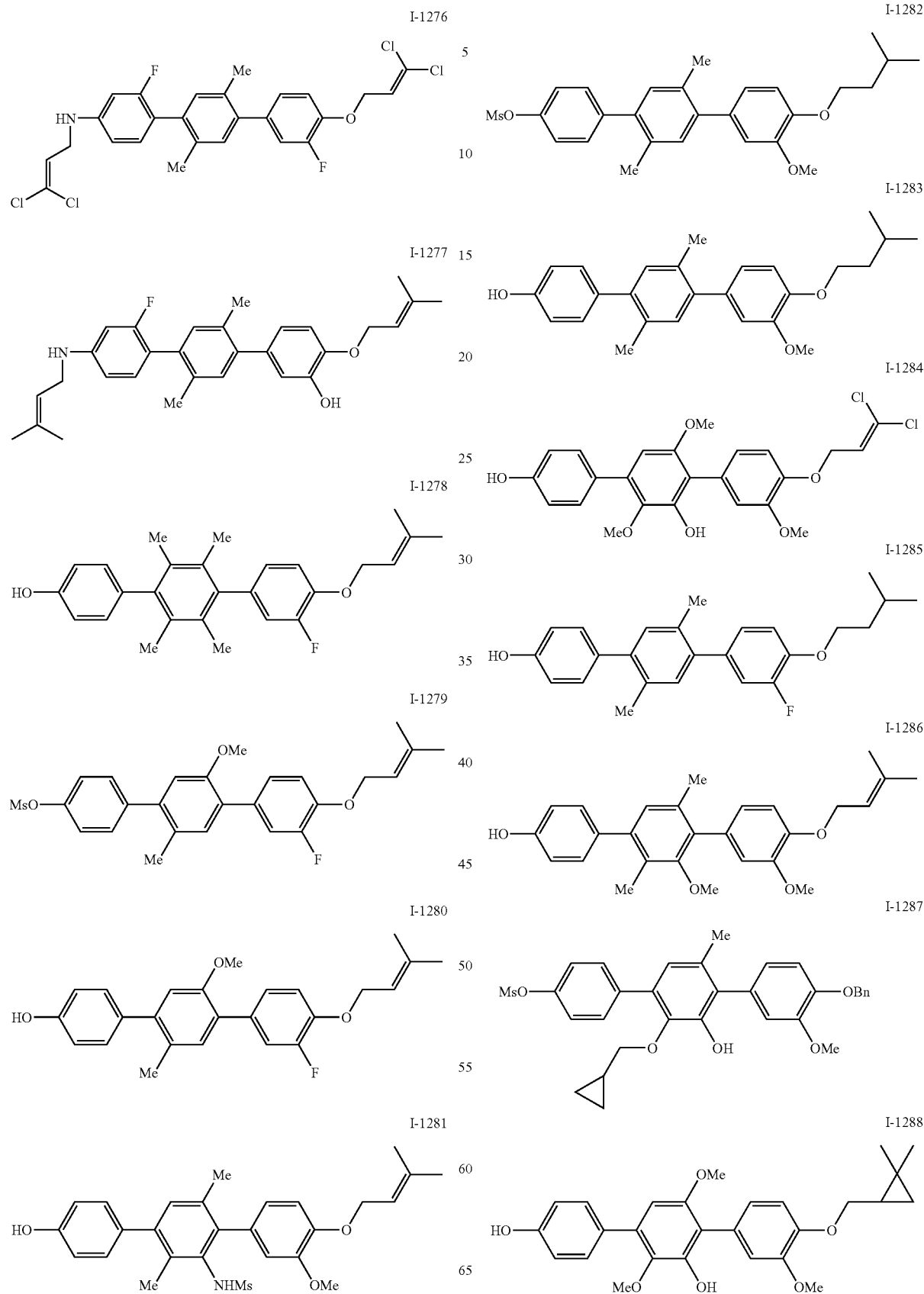

-continued
I-1289
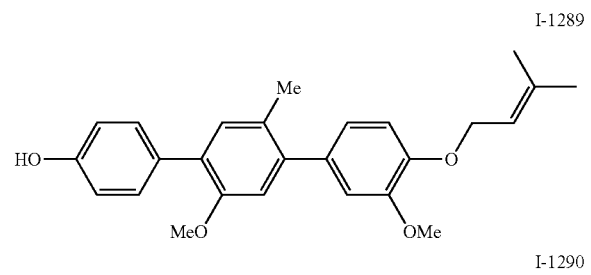
I-1290
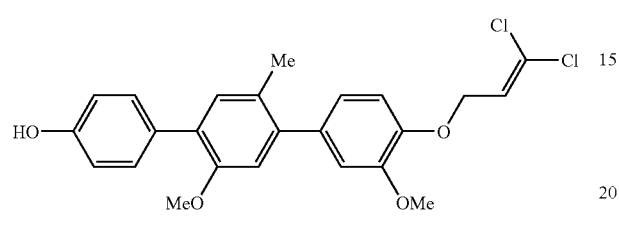
I-1291
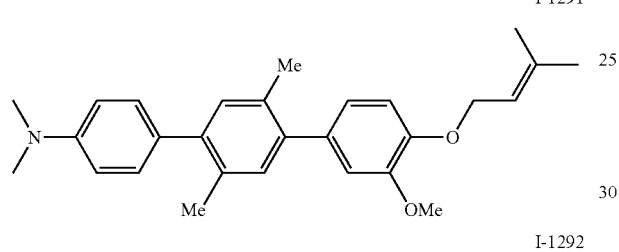
I-1292
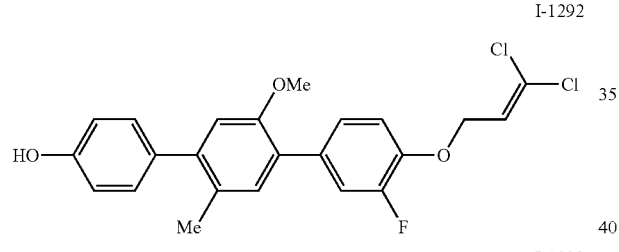
I-1293
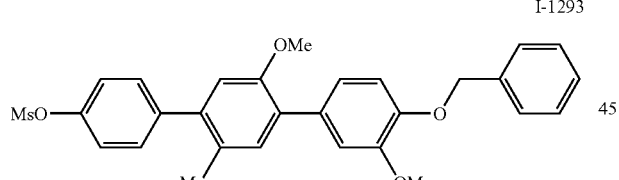
I-1294
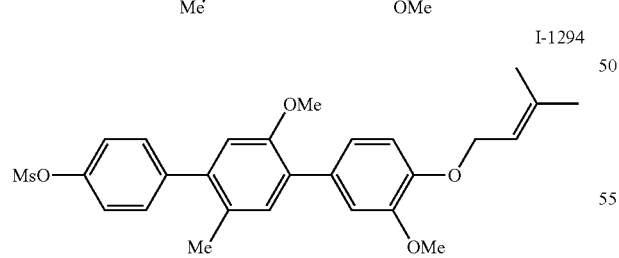
I-1295
-continued
I-1296
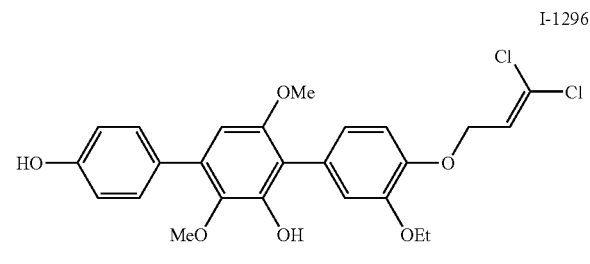
I-1297
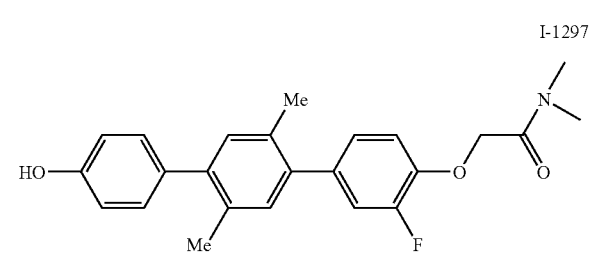
I-1298
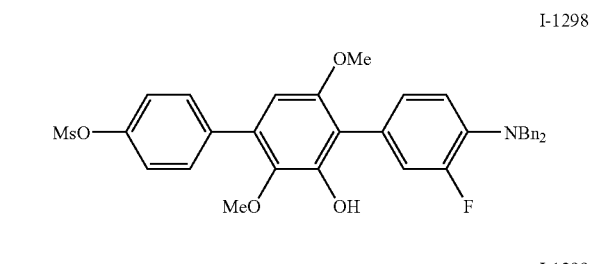
I-1299
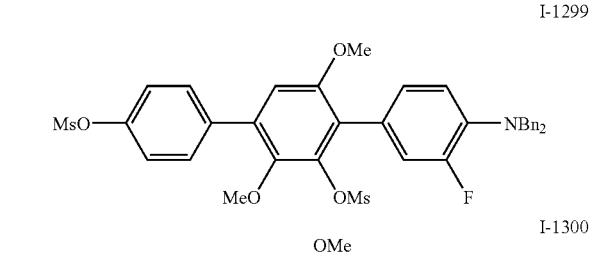
I-1300
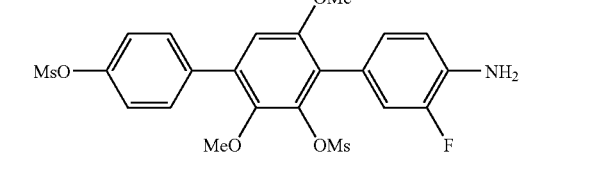
I-1301
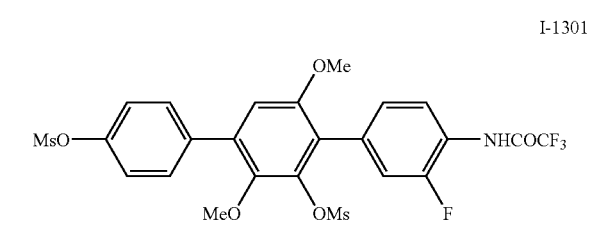
I-1302
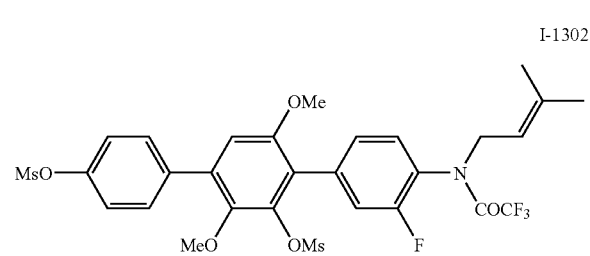

-continued
I-1303
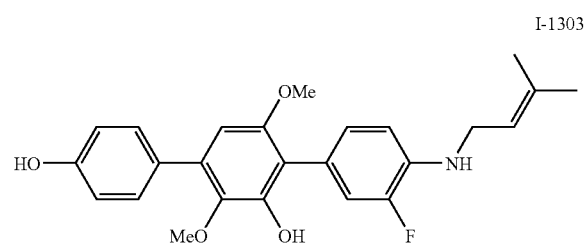
I-1304
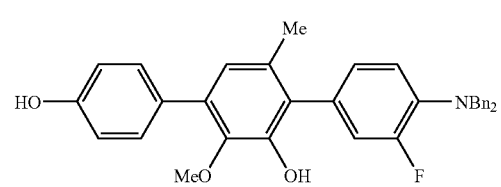
I-1305
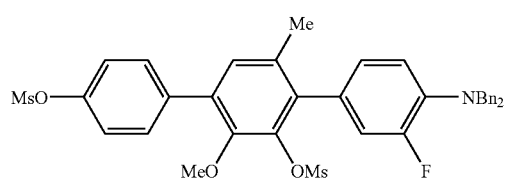
I-1306
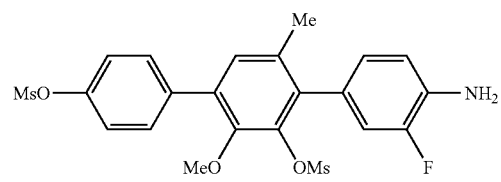
I-1307
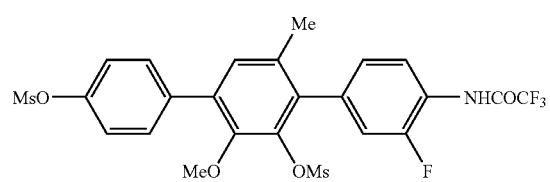
I-1308
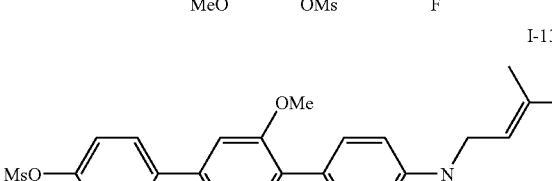
I-1309
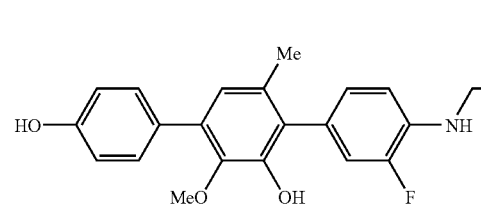
-continued
I-1310
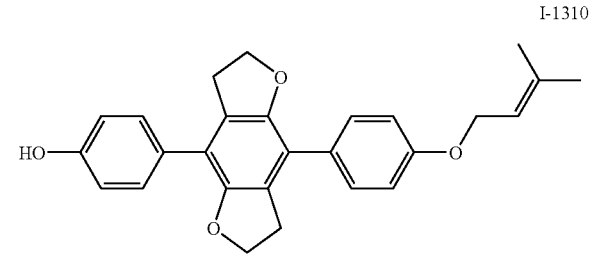
I-1311
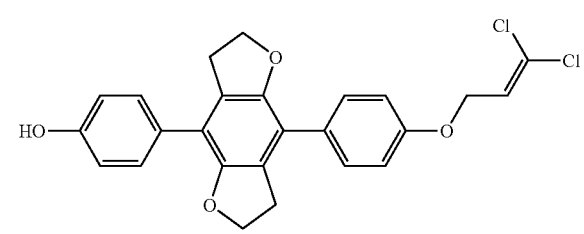
I-1312
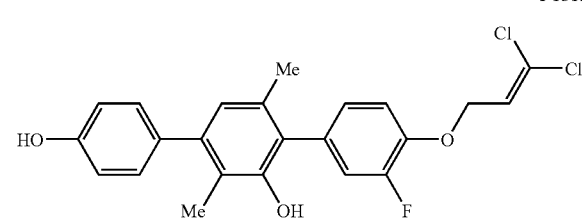
I-1313
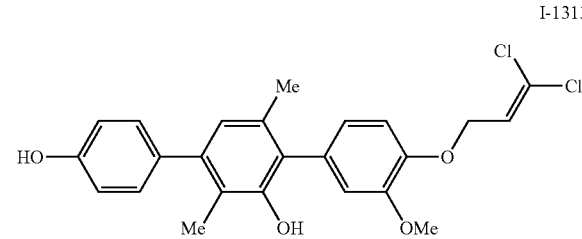
I-1314
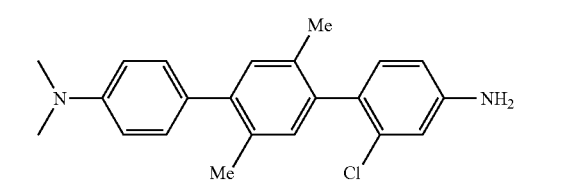
I-1315
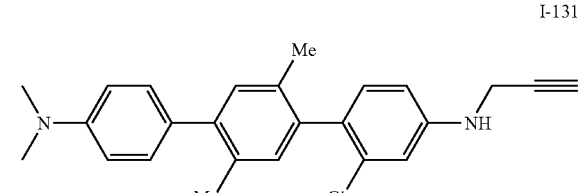
I-1316
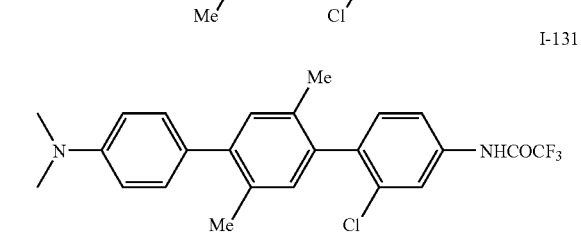

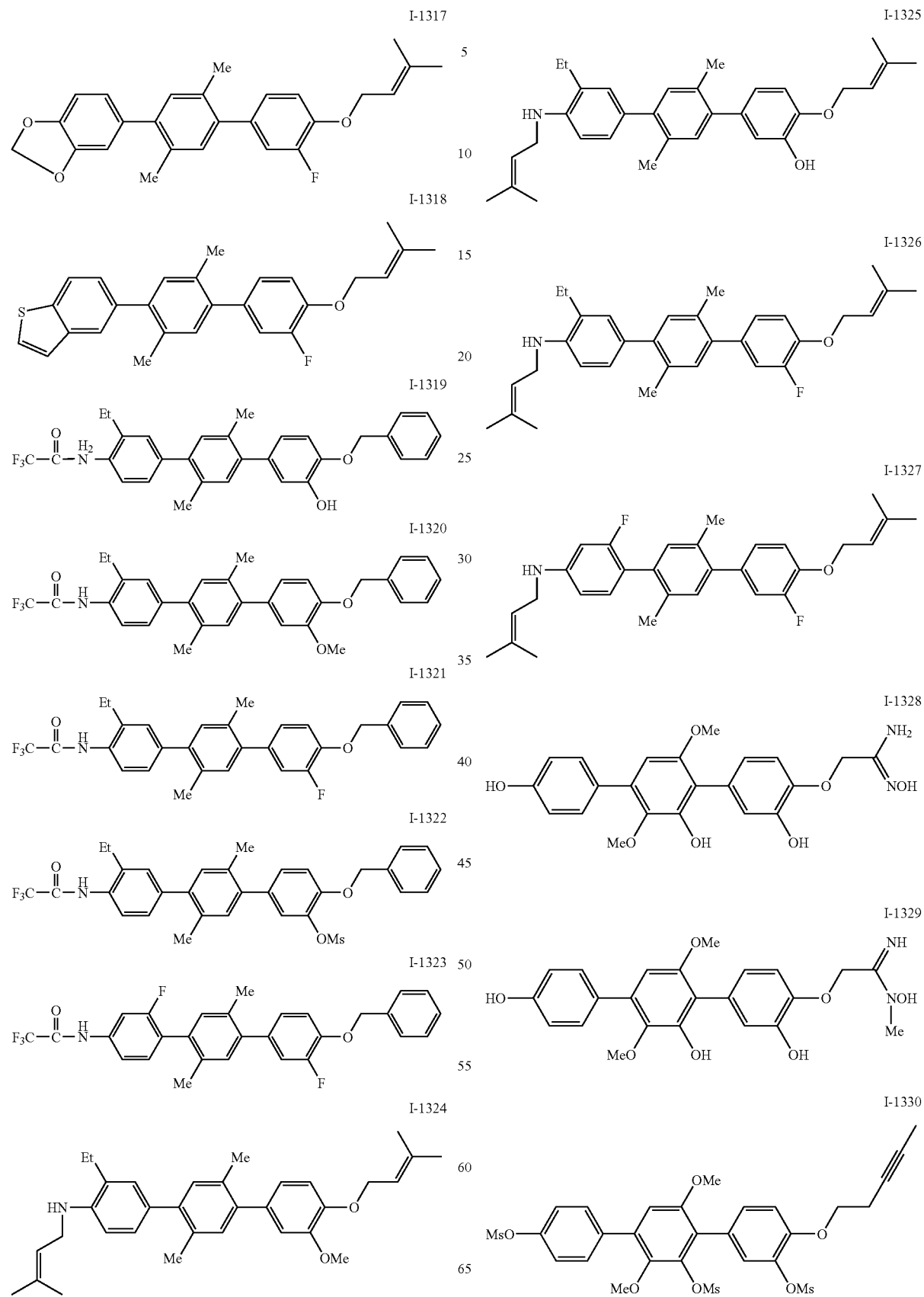

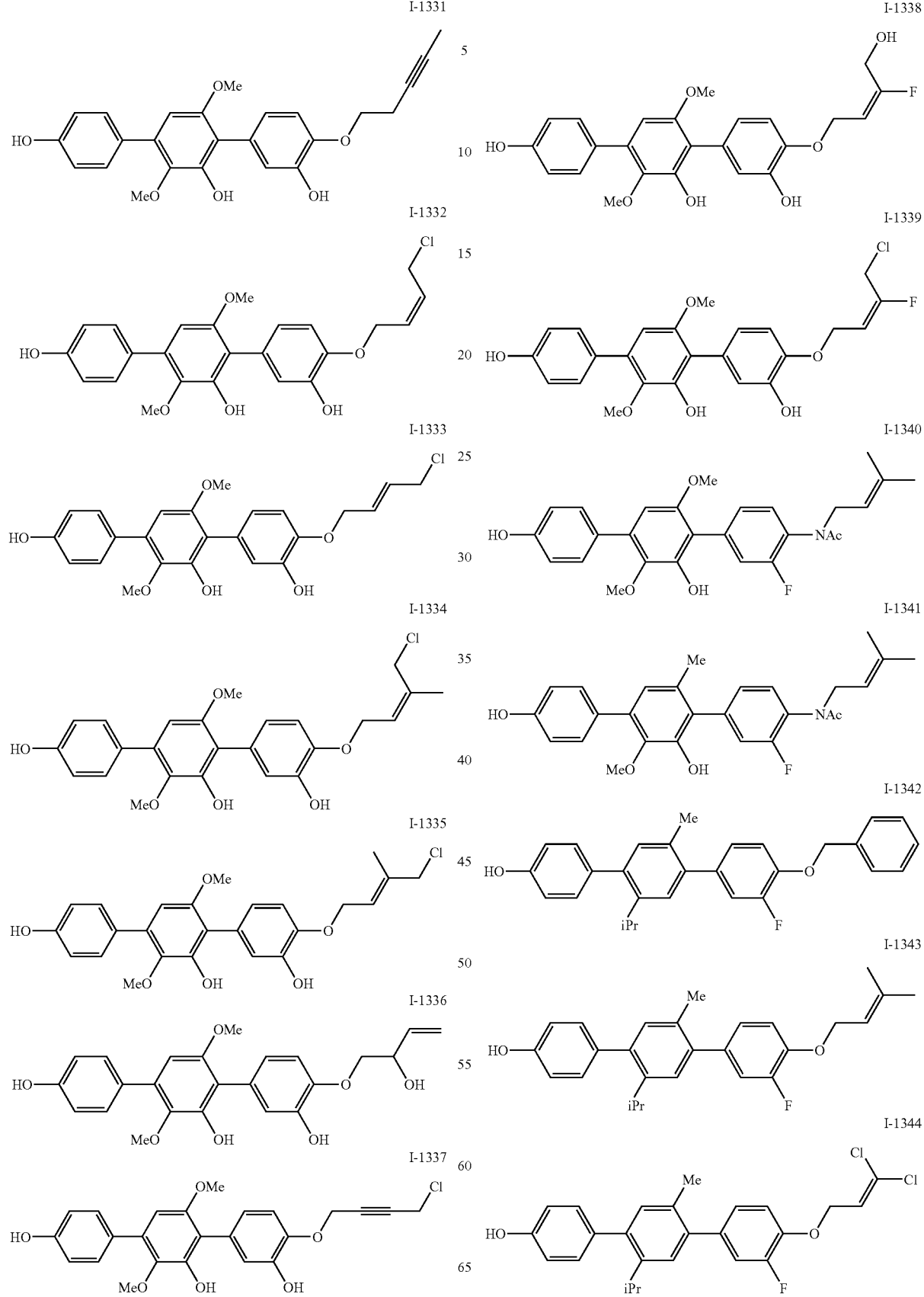

-continued

I-1345
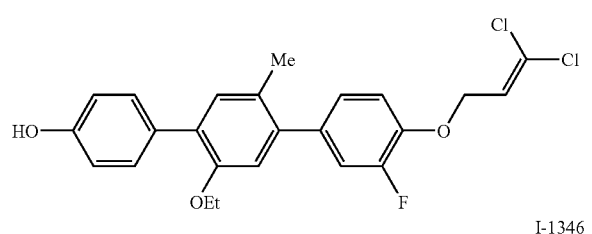

I-1346
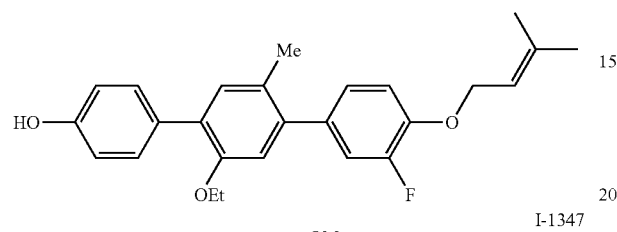

I-1347
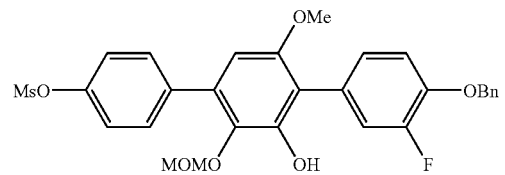

I-1348
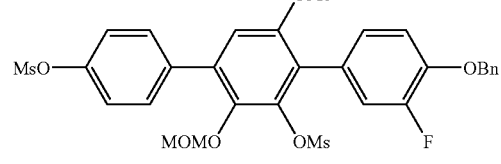

I-1349
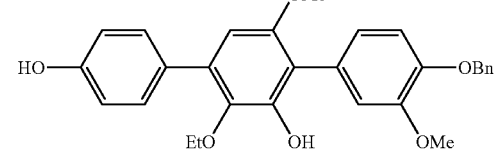

-continued

I-1350
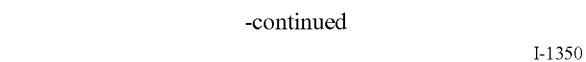

I-1351
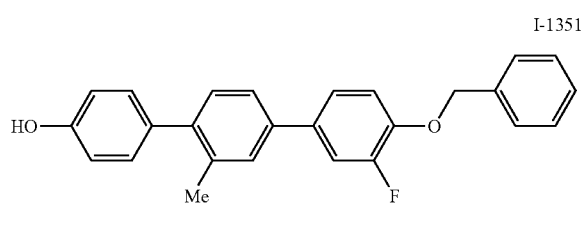

I-1352
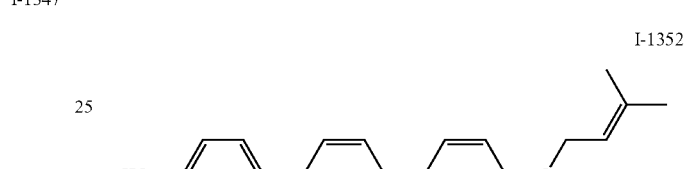

I-1353
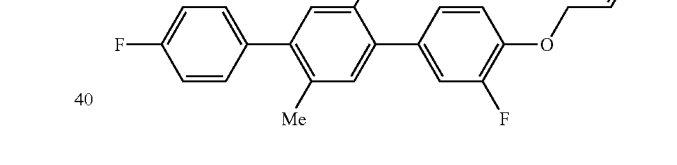

TABLE 1

| | |
|---|---|
| III-1 | m.p. 201–203° C.<br>$^1$HNMR(DMSO-d$_6$) δ 3.44(s, 3H), 3.48(s, 3H), 3.62(s, 3H), 3.92(s, 3H), 7.09(s, 1H), 7.40–7.53(m, 2H), 7.65–7.78(m, 2H) |
| III-2 | $^1$HNMR(CDCl$_3$) δ 3.47(s, 3H), 3.94(s, 3H), 7.13–7.24(m, 3H), 7.50–7.59(m, 2H), 10.41(s, 1H)<br>IR(KBr)1700, 1562, 1479, 1438, 1393, 1226, 1199, 1180, 1161, 1076, 1047cm$^{-1}$ |
| III-3 | m.p. 181–182° C.<br>$^1$HNMR(CDCl$_3$) δ 3.21(s, 3H), 3.40(s, 3H), 3.49(s, 3H), 3.90(s, 3H), 4.81(s, 2H), 4.85(s, 2H), 6.86(s, 1H), 7.32–7.40(m, 2H), 7.60–7.68(m, 2H)<br>IR(KBr)1504, 1467, 1370, 1235, 1152, 1038, 1010, 870, 846, 785cm$^{-1}$ |
| III-4 | $^1$HNMR(CDCl$_3$) δ 2.95(s, 3H), 3.18(s, 3H), 3.21(s, 3H), 3.41(s, 3H), 3.91(s, 3H), 6.84(s, 1H), 7.37(d, J=8.9Hz, 2H), 7.63(d, J=8.9Hz, 2H) |
| III-5 | m.p. 140–141° C.<br>$^1$HNMR(CDCl$_3$) δ 3.21(s, 3H), 3.45(s, 3H), 3.48(s, 3H), 3.96(s, 3H), 7.40(d, J=8.9Hz, 2H), 7.54(d, J=8.9Hz, 2H)<br>IR(KBr)1446, 1426, 1409, 1370, 1362, 1184, 1153, 1029, 973, 920, 870, 849, 776cm$^{-1}$ |
| III-6 | Tokyo Kasei Kogyo Co., Ltd. |
| III-7 | $^1$HNMR(CDCl$_3$) δ: 3.51(s, 3H), 3.92(s, 3H), 6.05(s, 2H), 6.92(d, J=8.1Hz, 1H), 7.02(d, J=8.1Hz, 1H), 7.07(s, 1H), 7.18(s, 1H), 10.40(s, 1H)<br>IR(KBr)1691, 1600, 1577, 1474, 1447, 1422, 1388, 1352, 1252, 1237, 1227, 1201, 1134, 1124, 1082, 1038cm$^{-1}$ |
| III-8 | $^1$HNMR(CDCl$_3$) δ 3.20(s, 3H), 3.77(s, 3H), 3.90(s, 3H), 6.86(s, 1H), 6.98(s, 1H), 7.32–7.37(m, 2H), 7.51–7.56(m, 2H) |
| III-9 | HNMR(CDCl$_3$) δ 3.20(s, 3H), 3.34(s, 3H), 7.37–7.47(m, 3H), 7.53–7.63(m, 3H), 7.71(d, J=2.1Hz, 1H) |
| III-10 | $^1$HNMR(CDCl$_3$) δ 3.76(s, 3H), 3.90(s, 3H), 6.85(s, 1H), 6.97(s, 1H), 7.08–7.15(m, 2H), 7.42–7.49(m, 2H) |
| III-11 | oil<br>$^1$HNMR(CDCl$_3$) δ 2.72(s, 3H), 3.11(s, 3H), 3.75(s, 3H), 3.92(s, 3H), 5.17(s, 2H), 7.05–7.16(m, 2H), 7.24–7.50(m, 2H). |

TABLE 2

| | |
|---|---|
| III-12 | oil<br>$^1$HNMR(CDCl$_3$) δ 3.51(s, 3H), 3.70(s, 3H), 3.86(s, 3H), 3.89(s, 3H), 5.28(s, 2H), 6.65(s, 1H), 6.97&7.47(ABq, J=8.6Hz, 4H) |
| III-13 | m.p. 120–122° C. $^1$HNMR(CDCl$_3$) δ 3.20(s, 3H), 3.53(s, 3H), 3.70(s, 3H), 3.89(s, 3H), 5.28(s, 2H), 6.63(s, 1H), 7.32–7.37(m, 2H), 7.56–7.61 (m, 2H)<br>IR(KBr)1505, 1468, 1427, 1375, 1237, 1175, 1153, 1100, 1072, 1003, 972cm$^{-1}$ |
| III-14 | m.p. 146–147° C.<br>$^1$HNMR(CDCl$_3$) δ 3.85(s, 3H), 6.94–7.01(m, 2H), 7.38–7.56(m, 6H)<br>IR(KBr)1603, 1522, 1481, 1288, 1255, 1036cm$^{-1}$ |
| III-15 | $^1$HNMR(CDCl$_3$) δ 3.07(s, 6H), 3.49(s, 3H), 3.92(s, 3H), 6.95(brs, 2H), 7.20(s, 1H)7.51(d, J=8.7Hz, 2H), 10.42(s, 1H) |
| III-16 | $^1$HNMR(CDCl$_3$) δ 3.48(s, 3H), 3.50(s, 3H), 3.92(s, 3H), 6.81(s, 1H), 7.70(s, 4H) |
| III-17 | $^1$HNMR(CDCl$_3$) δ 3.24(s, 3H), 3.49(s, 3H), 3.94(s, 3H), 7.21(s, 1H), 7.42(d, J=8.4Hz, 2H), 7.65(d, J=8.4Hz, 2H), 10.41(s, 1H) |
| III-18 | m.p. 88–89° C.<br>$^1$HNMR(CDCl$_3$) δ 2.20(s, 3H), 2.38(s, 3H), 3.19(s, 3H), 7.06(s, 1H), 7.33(s, 4H), 7.45(s, 1H)<br>IR(KBr)1479, 1366, 1195, 1173, 1151, 970, 865, 850, 796cm$^{-1}$ |
| III-19 | m.p. 72–73° C.<br>$^1$HNMR(CDCl$_3$) δ 3.20(s, 3H), 7.20(dd, J=6.6, 8.4Hz, 1H), 7.35–7.44(m, 3H), 7.53–7.60(m, 2H)<br>IR(KBr)1514, 1481, 1364, 1335, 1182, 1144, 979, 870, 798cm$^{-1}$ |
| III-20 | m.p. 144–146° C.<br>$^1$HNMR(CDCl$_3$) δ 3.45(s, 3H), 3.89(s, 3H), 4.99(brs, 2H), 6.19(s, 1H), 6.42(s, 1H), 6.88–6.94(m, 2H), 7.44–7.49(m, 2H)<br>IR(KBr)3471, 3392, 29863, 1612, 1596, 1461, 1410, 1223, 1175, 1099, 1079, 1011cm$^{-1}$ |

TABLE 3

| | |
|---|---|
| III-21 | oil<br>$^1$HNMR(CDCl$_3$) δ 1.09(t, J=7.5Hz, 3H), 1.82–1.94(m, 2H), 3.58(s, 3H), 3.86(s, 3H), 4.06(t, J=6.6Hz, 2H), 6.63(s, 1H), 6.94–6.99(m, 2H), 7.44–7.49(m, 2H)<br>IR(film): 3100–2800(br), 1609, 1583, 1513, 1466, 1423, 1401, 1378, 1291, 1249, 1232, 1178, 1127, 1097, 1034, 1012cm$^{-1}$ |
| III-22 | m.p. 83.5–84.5° C.<br>$^1$HNMR(CDCl$_3$) δ 3.20(br, 1H), 3.54(s, 3H), 3.85–3.90(m, 2H), 3.86(s, 3H), 3.90(s, 3H), 4.29–4.32(m, 2H), 6.66(s, 1H), 6.95–7.00(m, 2H), 7.45–7.50(m, 2H)<br>IR(KBr)3600–2800(br), 1608, 1583, 1513, 1467, 1441, 1421, 1398, 1365, 1290, 1247, 1178, 1133, 1097, 1079, 1028, 1007cm$^{-1}$ |
| III-23 | m.p. 99–101° C.<br>$^1$HNMR(CDCl$_3$) δ 3.20(s, 3H), 3.39(s, 3H), 3.91(s, 3H), 3.99(s, 3H), 6.89(s, 1H), 7.37(d, J=8.7Hz, 2H), 7.64(d, J=8.7Hz, 2H)<br>IR(KBr)1747, 1466, 1367, 1348, 1153, 1059, 968, 859, 794cm$^{-1}$ |
| III-24 | $^1$HNMR(CDCl$_3$) δ 3.22(s, 3H), 3.45(s, 3H), 3.94(s, 3H), 7.04(s, 1H), 7.32–7.43(m, 2H), 7.58–7.69(m, 2H), 10.42(s, 1H) |
| III-25 | $^1$HNMR(CDCl$_3$) δ 2.46(broad, 1H), 3.21(s, 3H), 3.43(s, 3H), 3.90(s, 3H), 4.94(s, 2H), 6.83(s, 1H), 7.42–7.51(m, 2H), 7.57–7.68(m, 2H) |
| III-26 | m.p. 109–110° C.<br>$^1$HNMR(CDCl$_3$) δ 1.97(br, 1H), 3.21(t, J=6.6Hz, 2H), 3.86(s, 3H), 3.89(s, 3H), 3.90(t, J=6.9Hz, 2H), 6.76(s, 1H), 6.95–7.00(m, 2H), 7.49–7.53(m, 2H)<br>IR(KBr)3600–2800(br), 1609, 1581, 1511, 1462, 1441, 1426, 1385, 1289, 1250, 1237, 1179, 1116, 1078, 1046, 1031, 1005cm$^{-1}$ |
| III-27 | foam<br>$^1$HNMR(CDCl$_3$) δ 1.52(s, 9H), 3.20(s, 3H), 3.41(s, 3H), 3.90(s, 3H), 6.16(s, 1H), 6.76(s, 1H), 7.35(d, J=8.7Hz, 2H), 7.61(d, J=8.7Hz, 2H)<br>IR(KBr)3371, 1718, 1505, 1497, 1367, 1241, 1151, 872cm$^{-1}$ |

TABLE 4

| | |
|---|---|
| III-28 | m.p. 167–170° C.<br>$^1$HNMR(CDCl$_3$) δ 2.73(s, 3H), 3.74(s, 3H), 3.92(s, 3H), 7.08–7.17(m, 3H), 7.31–7.36(m, 2H)<br>IR(CHCl$_3$)2934, 1593, 1560, 1512, 1477, 1436, 1411, 1372, 1157, 1107, 1076, 997, 958, 892, 839, 815cm$^{-1}$ |
| III-29 | m.p. 140–142° C.<br>$^1$HNMR(CDCl$_3$) δ 3.27(s, 3H), 3.79(s, 3H), 3.90(s, 3H), 6.86(s, 1H), 6.97(s, 1H), 7.29(ddd, J=8.4, 2.2, 0.9Hz, 1H), 7.39(dd, J=11.0, 2.2Hz, 1H), 7.43(t, J=8.4Hz, 1H)<br>IR(KBr)1504, 1421, 1344, 1225, 1208, 916, 824cm$^{-1}$ |
| III-30 | $^1$HNMR(CDCl$_3$) δ 3.77(s, 3H), 3.91(s, 3H), 3.95(s, 3H), 6.87(s, 1H), 7.01(s, 1H), 7.56(d, J=8.1Hz, 2H), 8.09(d, J=8.1Hz, 2H) |
| III-31 | $^1$HNMR(CDCl$_3$) δ 3.78(s, 3H), 3.91(s, 3H), 6.88(s, 1H), 6.97(s, 1H), 7.60(d, J=8.1Hz, 2H), 7.7(d, J=8.1Hz, 2H) |
| III-32 | m.p. 147–148° C.<br>$^1$HNMR(CDCl$_3$) δ 3.79(s, 3H), 3.92(s, 3H), 6.89(s, 1H), 7.01(s, 1H),7.64–7.69(m, 2H), 8.26–8.31(m, 2H)<br>IR(KBr)3600–2800(br), 1595, 1511, 1490, 1422, 1354, 1249, 1215, 1145, 1106, 1032cm$^{-1}$ |
| III-33 | $^1$HNMR(CDCl$_3$) δ 3.31(s, 3H), 3.53(s, 3H), 3.94(s, 3H), 7.19(s, 1H), 7.39(ddd, J=8.3, 2.3, 1.0Hz, 1H), 7.39(dd, J=10.3, 2.3Hz, 1H), 7.43(t, J=8.31Hz, 1H), 10.40(s, 1H) |
| III-34 | $^1$HNMR(CDCl$_3$) δ 0.13(s, 6H), 0.97(s, 9H), 2.51(s, 3H), 3.73(s, 3H), 3.93(s, 3H), 5.09(s, 2H), 6.84–6.99(m, 2H), 6.89(s, 1H), 7.05(s, 1H), 7.29–7.48(m, 5H) |
| III-35 | m.p. 124–128° C.<br>$^1$HNMR(CDCl$_3$) δ 2.62(s, 3H), 3.74(s, 3H), 3.91(s, 3H), 5.19(s, 2H), 7.00–7.18(m, 4H), 7.30–7.49(m, 5H)<br>IR(CHCl$_3$)2930, 1607, 1517,1480, 1369, 1148, 1118, 1082, 1025, 969, 872cm$^{-1}$ |

TABLE 5

| | |
|---|---|
| III-36 | oil<br>$^1$HNMR(CDCl$_3$) δ 0.13(s, 6H), 0.96(s, 3H), 3.01(s, 3H), 3.69(s, 3H), 3.86(s, 3H), 4.81(s, 2H), 5.08(s, 2H), 6.88–6.94(m, 3H), 7.30–7.47(m, 5H)<br>IR(KBr)3023, 2932, 2858, 1579, 1512, 1471, 1381, 1264, 1120, 1083cm$^{-1}$ |

TABLE 5-continued

III-37 oil
  $^1$HNMR(CDCl$_3$) δ 0.78(t, J=7.5Hz, 3H), 1.03–1.25(m, 2H), 1.38–1.47(m, 2H), 3.68–3.72(m, 2H), 3.70(s, 3H), 3.86(s, 6H), 5.15(s, 2H), 5.6
  3(s, 1H), 6.81(dd, J=1.8, 8.4Hz, 1H), 6.86(s, 1H), 6.95–6.97(m, 2H), 7.36–7.46(m, 5H)
  IR(CH$_3$Cl): 3543, 3200–2800(br), 1587, 1511, 1465, 1412, 1376, 1285, 1248, 1118, 1081, 1031cm$^{-1}$
III-38 m.p. 104–105° C.
  $^1$HNMR(CDCl$_3$) δ 3.11(s, 3H), 3.77(s, 3H), 3.90(s, 3H), 5.17(s, 2H), 6.84(s, 1H), 6.98(s, 1H), 7.11(d, J=8.7Hz, 1H), 7.37–7.48(m, 6H), 7.5
  1(d, J=2.4Hz, 1H)
  IR(KBr)3600–2800(br), 1503, 1420, 1389, 1364, 1246, 1215, 1185, 1132, 1117, 1097, 1030cm$^{-1}$
III-39 m.p. 134–136° C.
  $^1$HNMR(CDCl$_3$) δ 3.78(s, 3H), 3.91(s, 3H), 5.29(s, 2H), 6.86(s, 1H), 6.97(s, 1H), 7.17(d, J=8.7Hz, 1H), 7.31–7.51(m, 7H), 7.63(dd, J=2.4,
  8.7Hz, 1H), 8.01(d, J=2.4Hz, 1H)
  IR(KBr)3434, 1620, 1532, 1494, 1413, 1280, 1222, 1206, 1133, 1108, 1037cm$^{-1}$
III-40 m.p. 100–101° C.
  $^1$HNMR(CDCl$_3$) δ 3.55(s, 3H), 3.77(s, 3H), 3.90(s, 3H), 5.26(s, 2H), 6.84(s, 1H), 6.97(s, 1H), 7.16–7.31(m, 3H)
  IR(KBr)3600–2800(br), 1524, 1503, 1449, 1401, 1380, 1268, 1246, 1222, 1200, 1156, 1126, 1098, 1078, 1030cm$^{-1}$
III-41 m.p. 109–110° C.
  $^1$HNMR(CDCl$_3$) δ 1.54(s, 9H), 3.76(s, 3H), 3.90(s, 3H), 6.75(br, 1H), 6.84(s, 1H), 6.97(s, 1H), 7.21–7.29(m, 2H), 8.13(t, J=8.7Hz, 1H)
  IR(KBr)3600–2800(br), 1720, 1593, 1531, 1509, 1427, 1393, 1245, 1223, 1214, 1201, 1162, 1137, 1105, 1029cm$^{-1}$

TABLE 6

III-42 foam
  $^1$HNMR(CDCl$_3$) δ 2.36(s, 3H), 3.74(s, 3H), 3.88(s, 3H), 6.69(dd, J=0.6, 3.6Hz, 1H), 6.85(s, 1H), 6.99(s, 1H), 7.24–7.27(m, 2H),
  7.23(dd, J=1.8,8.7Hz, 1H), 7.60(d, J=3.6Hz, 1H), 7.64(d, J=1.2Hz, 1H), 7.80–7.83(m, 2H), 8.02(d, J=8.4Hz, 1H)
  IR(KBr)3600–2800(br), 1508, 1463, 1444, 1421, 1373, 1246, 1216, 1176, 1132, 1093, 1038cm$^{-1}$
III-43 foam
  $^1$HNMR(CDCl$_3$) δ 3.14(s, 3H), 3.51(s, 3H), 3.93(s, 3H), 5.20(s, 2H), 7.17(d, J=8.4Hz, 1H), 7.20(s, 1H), 7.38(m, 6H), 7.59(d, J=1.8Hz, 1H),
  10.40(s, 1H)
  IR(CHCl$_3$)2941, 1703, 1613, 1603, 1580, 1513, 1475, 1426, 1372, 1295, 1264, 1169, 1137, 1112, 1088, 1044, 971, 954, 932, 838cm$^{-1}$
III-44 $^1$HNMR(CDCl$_3$) δ 0.20(s, 6H), 0.13(s, 6H), 0.77(s, 9H), 0.97(s, 9H), 3.73(s, 3H), 3.83(s, 3H)), 5.08(s, 2H), 6.06(s, 2H), 6.88–6.96(m, 3H), 7.01
  (s, 1H), 7.30–7.49(m, 5H)
III-45 mp 106–108° C.
  $^1$HNMR(CDCl$_3$) δ 3.21(s, 3H), 3.43(s, 3H), 3.94(s, 3H), 5.87(s, 1H), 7.39(d, J=9.0Hz, 2H), 7.55(d, J=9.0Hz, 2H)
  IR(KBr)3410, 1460, 1422, 1362, 1146, 1037, 874, 915, 787cm$^{-1}$
III-46 mp 123–124° C.
  $^1$HNMR(CDCl$_3$) δ 2.48(brs, 1H), 3.21(s, 3H), 3.43(s, 3H), 3.94(s, 3H), 4.93(brs, 2H), 6.83(s, 1H), 7.37(d, J=9.0Hz, 2H), 7.63(d,
  J=9.0Hz, 2H)
  IR(KBr)3524, 1463, 1352, 1233, 1152, 1009, 979, 869cm$^{-1}$
III-47 mp 107–109° C.
  $^1$HNMR(CDCl$_3$) δ 1.93(s, 6H), 2.45(s, 6H), 4.75(brs, 1H), 6.87–6.96(m, 4H)
  IR(KBr)3367, 1612, 1509, 1433, 1214, 990, 824cm$^{-1}$

TABLE 7

III-48 oil
  $^1$HNMR(CDCl$_3$) δ 1.14(t, J=6.9Hz, 3H), 1.46(t,J=6.9Hz, 3H), 3.58(q, J=6.9Hz, 2H), 3.58(q, J=6.9Hz, 2H), 6.19(s, 1H),
  6.41(s, 1H), 6.86–6.92(m, 2H), 7.43–7.49(m, 2H)
  IR(CHCl$_3$)3688, 3594, 3502, 2982, 1612, 1517, 1172, 1080, 1026, 925cm$^{-1}$
III-49 $^1$HNMR(CDCl$_3$) δ 0.02(s, 6H), 0.12(s, 6H), 0.90(s, 9H), 0.93(s, 9H), 4.54(s, 2H), 4.76(s, 2H), 6.84–6.89(m, 2H), 7.16–7.22(m, 2H),
  7.37(s, 1H), 7.69(s, 1H)
III-50 mp173–175° C.
  $^1$HNMR(CDCl$_3$) δ 3.21(s, 3H), 3.47(s, 3H), 3.89(s, 3H), 6.15(s, 1H), 6.42(s, 1H), 7.24–7.37(m, 2H), 7.61–7.66(m, 2H)
  IR(KBr)3408, 2934, 1604, 1480, 1360, 1146, 1089, 1004, 865, 709, 547cm$^{-1}$
III-51 mp156–158° C.
  $^1$HNMR(CDCl$_3$) δ 3.21(s, 3H), 3.39(s, 3H), 3.90(s, 3H), 6.05(s, 1H), 7.36–7.44(m, 4H)
  IR(KBr)3410, 2938, 1505, 1457, 1413, 1337, 1194, 1143, 1084, 1014, 876, 826, 542, 519cm$^{-1}$
III-52 mp181–183° C.
  $^1$HNMR(CDCl$_3$) δ 3.19(s, 3H), 3.88(s, 3H), 4.21–4.24(m, 2H), 4.39–4.42(m, 2H), 6.49(s, 1H), 7.45(ABq, J=8.7Hz, 4H)
  IR(KBr)3435, 1598, 1505, 1474, 1425, 1366, 1178, 1147, 1113cm$^{-1}$
III-53 mp155–157° C.
  $^1$HNMR(CDCl$_3$) δ -0.11–0.02(m, 2H), 0.33–0.44(m, 2H), 0.91(m, 1H), 3.20(s, 3H), 3.41(d, J=7.0Hz, 2H), 3.50(s, 3H), 3.92(s, 3H),
  6.88(s, 1H), 7.51(ABq, J=8.6Hz, 4H)
  IR(KBr)3434, 1505, 1472, 1416, 1386, 1371, 1357, 1242, 1179, 1149, 1084cm$^{-1}$
III-54 mp105–107° C.
  $^1$HNMR(CDCl$_3$) δ 3.20(s, 3H), 3.39(s, 3H), 3.89(s, 3H), 4.77(s, 2H), 6.40(s, 1H), 7.33–7.55(m, 5H)
  IR(KBr)3411, 1592, 1572, 1507, 1482, 1467, 1437, 1360, 1339, 1232, 1204, 1175, 1148, 1125, 1092cm$^{-1}$

TABLE 8

III-55 mp 138–140° C.
  $^1$HNMR(CDCl$_3$) δ 1.14(t, J=7.0Hz, 3H), 3.59(q, J=7.0Hz, 2H), 3.88(s, 3H), 4.97(bs, 1H), 6.42(s, 1H), 6.86–6.94(m, 2H), 7.43–7.51(m,2H)
  IR(KBr)3384, 3291, 2978, 1614, 1593, 1576, 1519, 1484, 1469, 1455, 1436, 1417, 1366, 1306, 1285, 1257, 1203, 1171, 1127, 1094, 1029cm$^{-1}$

TABLE 8-continued

| | |
|---|---|
| III-56 | mp 162–164° C.<br>$^1$HNMR(CDCl$_3$) δ 2.77(s, 3H), 3.17(s, 3H), 3.75(s, 3H), 3.92(s, 3H), 7.10(s, 2H), 7.35–7.43(m, 4H)<br>IR(CHCl$_3$)1594, 1561, 1507, 1478, 1464, 1374, 1331, 1178, 1149, 1109, 1080, 1000, 970, 894, 871, 844cm$^{-1}$ |
| III-57 | mp 95–97° C.<br>$^1$HNMR(CDCl$_3$) δ 2.35(s, 3H), 3.77(s, 3H), 6.84–6.87(m, 2H), 7.12(s, 1H), 7.13(s, 1H), 7.35–7.38(m, 2H)<br>IR(CHCl$_3$)3596, 2959, 2939, 2840, 1611, 1563, 1517, 1489, 1464, 1438, 1384, 1367, 1329, 1295, 1258, 1173, 1102, 1049, 1035, 1001, 911, 891, 835cm$^{-1}$ |
| III-58 | mp 173–175° C.<br>$^1$HNMR(CDCl$_3$) δ 6.91–6.94(m, 2H), 7.31–7.34(m, 2H), 7.87(s, 1H), 8.09(s, 1H), 9.89(s, 1H), 10.28(s, 1H)<br>IR(CHCl$_3$)3437, 1685, 1610, 1516, 1456, 1394, 1370, 1270, 1261, 1238, 1214, 1173, 1144, 1053, 1012, 939, 905, 829, 808, 557, 458cm$^{-1}$ |
| III-59 | mp 173–175° C.<br>$^1$HNMR(CDCl$_3$) δ 1.10(t, J=6.9Hz, 3H), 1.48(t, J=6.9Hz, 3H), 3.20(s, 3H), 3.47(s, 3H), 3.66(q, J=6.9Hz, 2H), 4.11(q, J=6.9Hz, 2H), 6.79(s, 1H), 7.32–7.39(m, 2H), 7.60–7.66(m, 2H)<br>IR(CHCl$_3$)1502, 1458, 1372, 1176, 1148, 1074, 1023, 967, 870cm$^{-1}$ |
| III-60 | $^1$HNMR(CDCl$_3$) δ 2.17(s, 3H), 2.39(s, 3H), 3.19(s, 3H), 5.80(s, 1H), 6.71(s, 1H), 7.33(s, 4H) |

TABLE 9

| | |
|---|---|
| III-61 | mp 107–108° C.<br>$^1$HNMR(CDCl$_3$) δ 3.21(s, 3H), 3.79(s, 3H), 4.04(s, 3H), 7.39(d, J=8.9Hz, 2H), 7.57(d, J=8.9Hz, 2H), 7.68(s, 1H), 10.17(s, 1H)<br>IR(KBr)1704, 1422, 1358, 1224, 1148, 1090, 1026, 974, 876cm$^{-1}$ |
| III-62 | mp 121–122° C.<br>$^1$HNMR(CDCl$_3$) δ 3.45(s, 3H), 3.47(s, 3H), 3.93(s, 3H), 4.68(s, 2H), 4.77(s, 2H), 7.22(s, 1H), 7.49(d, J=8.1Hz, 2H), 7.56(d, J=8.1Hz, 2H), 10.42(s, 1H)<br>IR(KBr)1695, 1476, 1422, 1232, 1189, 1130, 1040, 860cm$^{-1}$ |
| III-63 | mp 113–115° C.<br>$^1$HNMR(CDCl$_3$) δ 2.18(s, 3H), 3.22(s, 3H), 3.89(s, 3H), 6.85(s, 1H), 7.11(s, 1H), 7.36(s, 4H)<br>IR(KBr)1497, 1413, 1354, 1230, 1146, 1097, 976, 864cm$^{-1}$ |
| III-64 | $^1$HNMR(CDCl$_3$) δ 5.65(s, 1H), 7.18(s, 1H), 7.30–7.35(m, 2H), 7.46–7.50(m, 3H) |
| III-65 | $^1$HNMR(CDCl$_3$) δ 1.30(d, J=7.2Hz, 6H), 2.96(quintet, J=7.2Hz, 1H), 3.82(s, 3H), 3.91(s, 3H), 5.92(brs, 2H), 6.91(s, 1H), 7.30(d, J=8.1Hz, 2H), 7.44(s, 1H), 7.49(d, J=8.1Hz, 2H) |
| III-66 | mp 118–122° C.<br>$^1$HNMR(CDCl$_3$) δ 3.80(s, 3H), 3.91(s, 3H), 5.88(s, 2H), 6.84–6.92(m, 3H), 7.39–7.47(m, 3H)<br>IR(KBr)3600–2800(br), 1606, 1517, 1492, 1461, 1415, 1397, 1330, 1265, 1205, 1171, 1052cm$^{-1}$ |
| III-67 | mp 227–230° C.<br>$^1$HNMR(CDCl$_3$) δ 0.25(s, 6H), 1.02(s, 9H), 2.33(s, 3H), 2.82(s, 2H), 6.88–6.93(m, 2H), 7.16(s, 1H), 7.21–7.25(m, 3H), 8.11(s, 1H)<br>IR(KBr)3600–2800(br), 1608, 1514, 1393, 1346, 1267, 1167cm$^{-1}$ |
| III-68 | mp 134–137° C.<br>$^1$HNMR(CDCl$_3$) δ 3.00(s, 6H), 3.81(s, 3H), 3.91(s, 3H), 6.00(s, 2H), 6.77–6.82(m, 2H), 6.90(s, 1H), 7.41(s, 1H), 7.46–7.51(m, 3H)<br>IR(KBr)3600–2800(br), 1601, 1528, 1494, 1466, 1439, 1399, 1362, 1321, 1198, 1166, 1118, 1051cm$^{-1}$ |

TABLE 10

| | |
|---|---|
| III-69 | mp 144–148° C.<br>$^1$HNMR(CDCl$_3$) δ 2.38(s, 3H), 2.82(s, 3H), 3.01(s, 6H), 7.79–7.83(m, 2H), 7.18(s, 1H), 7.27–7.31(m, 2H), 8.11(s, 1H)<br>IR(KBr)3600–2800(br), 1612, 1523, 1443, 1389, 1328, 1271, 1160cm$^{-1}$ |
| III-70 | mp 122–126° C.<br>$^1$HNMR(CDCl$_3$) δ 0.10(s, 9H), 0.78(s, 6H), 2.96(s, 6H), 3.75(s, 3H), 3.84(s, 3H), 6.08(s, 2H), 6.72–6.78(m, 2H), 7.01(s, 1H), 7.22–7.29(m, 2H)<br>IR(KBr)3600–2800(br), 1613, 1528, 1463, 1416, 1402, 1360, 1345, 1251, 1218, 1195, 1136, 1092, 1062, 991cm$^{-1}$ |
| III-71 | $^1$HNMR(CDCl$_3$) δ 2.21(s, 3H), 2.37(s, 3H), 3.89(s, 3H), 5.19(s, 2H), 6.75(d.d, J=8.4&2.1Hz, 1H), 6.81(d, J=2.1Hz, 1H), 6.92(d, J=8.4Hz, 1H), 7.08(s, 1H), 7.30–7.50(m, 6H) |
| III-72 | oil<br>$^1$HNMR(CDCl$_3$) δ 2.51(s, 6H), 2.75(s, 6H), 5.15(s, 2H), 5.67(s, 1H), 6.94(s, 1H), 6.96(d, J=8.4Hz, 1H), 7.04(dd, J=2.1, 8.4Hz, 1H), 7.18(s, 1H), 7.20(d, J=2.1Hz, 1H), 7.37–7.47(m, 5H)<br>IR(CHCl$_3$)3032, 3428, 3000–2800(br), 1730, 1611, 1525, 1489, 1455, 1256, 1171, 1137, 1100, 1036cm$^{-1}$ |
| III-73 | $^1$HNMR(CDCl$_3$) δ 2.21(s, 3H), 2.37(s, 3H), 5.15(s, 2H), 5.69(br, 1H), 6.73(dd, J=8.4, 1.8Hz, 1H), 6.89–6.99(m, 2H), 7.07(s, 1H), 7.26–7.4 6(m, 6H) |
| III-74 | $^1$HNMR(CDCl$_3$) δ 1.09(t, J=7.2Hz, 3H), 1.22(t, J=7.5Hz, 3H), 2.55(q, J=7.2Hz, 2H), 2.72(q, J=7.5Hz, 2H), 5.15(s, 2H), 5.70(s, 1H), 6.73(dd, J=8.4, 1.8Hz, 1H), 6.89(d, J=1.8Hz, 1H), 6.95(d, J=8.4Hz, 1H), 7.04(s, 1H), 7.38–7.47(m, 6H)<br>IR(CHCl$_3$)3542, 2970, 2933, 1586, 1508, 1480, 1384, 1324, 1290, 1160, 1127, 1064, 1011, 930, 898, 879, 857cm$^{-1}$ |
| III-75 | $^1$HNMR(CDCl$_3$) δ 2.04(s, 3H), 3.70(s, 3H), 3.90(s, 3H), 5.19(s, 2H), 5.50(s, 1H), 6.73(dd, J=2.1Hz, 1H), 6.97–7.00(m, 2H), 7.29–7.48(m, 5H) |

TABLE 11

| | |
|---|---|
| III-76 | $^1$HNMR(CDCl$_3$) δ 2.04(s, 3H), 3.90(s, 3H), 5.15(s, 2H), 5.49(s, 1H), 5.74(s, 1H), 6.71(dd, J=8.1, 2.1Hz, 1H), 6.85(d, J=2.1Hz, 1H), 6.99–7.03 (m, 2H), 7.39–7.45(m, 5H)<br>IR(CHCl$_3$)3529, 2963, 2940, 1731, 1587, 1566, 1510, 1480, 1455, 1412, 1382, 1323, 1290, 1248, 1128, 1099, 1009, 935, 879cm$^{-1}$ |
| III-77 | mp 87–89° C.<br>$^1$HNMR(CDCl$_3$) δ 2.20(s, 3H), 2.37(s, 3H), 5.18(s, 2H), 6.90–7.10(m, 4H), 730–7.51(m, 6H)<br>IR(CHCl$_3$)1510, 1482, 1381, 1298, 1267, 1233, 1127, 1008, 952, 875, 812cm$^{-1}$ |

TABLE 11-continued

| | |
|---|---|
| III-78 | $^1$HNMR(CDCl$_3$) δ 1.25(d, J=6.9Hz, 6H), 2.24(s, 3H), 3.26(sept, J=6.9Hz, 1H), 5.20(s, 2H), 6.95(ddd, J=8.3, 2.2, 1.2Hz, 1H), 7.06(t, J=8.3Hz, 1H), 7.06(dd, J=11.9, 2.2Hz, 1H), 7.10(s, 1H), 7.17(s, 1H), 7.32–7.51(m, 5H)<br>IR(KBr)1492, 1420, 1228, 1203, 1140, 1012, 989, 841cm$^{-1}$ |
| III-79 | $^1$HNMR(CDCl$_3$) δ 2.43(s, 3H), 5.19(s, 2H), 7.06(t, J=8.9Hz, 1H), 7.18–7.48(m, 10H)<br>IR(KBr), 1491, 1437, 1214, 1135, 890, 810, 748cm$^{-1}$ |
| III-80 | mp 77–79° C.<br>$^1$HNMR(CDCl$_3$) δ 3.921(s, 3H), 5.21(s, 2H), 6.90–6.99(m, 3H), 7.31–7.50(m, 7H)<br>IR(KBr)3600–2800(br), 1518, 1477, 1418, 1237, 1212, 1167, 1140cm$^{-1}$ |
| III-81 | mp 103–105° C.<br>$^1$HNMR(CDCl$_3$) δ 2.16(s, 3H), 2.37(s, 3H), 2.42(s, 3H), 3.16(s, 3H), 5.21(s, 2H), 7.16–7.17(m, 3H), 7.24–7.27(m, 1H), 7.36–7.48(m, 5H)<br>IR(CHCl$_3$)2940, 1613, 1514, 1478, 1455, 1423, 1366, 1331, 1292, 1264, 1176, 1140, 1126, 1096, 1045, 1009, 972, 955, 920, 843cm$^{-1}$ |
| III-82 | $^1$HNMR(CDCl$_3$) δ 2.19(s, 3H), 3.88(s, 3H), 5.20(s, 2H), 6.84(s, 1H), 6.95(m, 1H), 7.03–7.05(m, 3H), 7.35–7.49(m, 5H) |
| III-83 | mp 83–85° C.<br>$^1$HNMR(CDCl$_3$) δ 2.19(s, 3H), 3.88(s, 3H), 3.91(s, 3H), 5.21(s, 3H), 6.76(dd, J=8.4, 2.1Hz, 1H), 6.82(d, J=2.1Hz, 1H), 6.87(s, 1H), 6.93(d, J=8.4Hz, 1H), 7.08(s, 1H), 7.32–7.50(m, 5H)<br>IR(CHCl$_3$)2962, 2937, 1613, 1579, 1499, 1464, 1455, 1443, 1421, 1319, 1249, 1170 1140, 1103, 1029, 1008, 989, 901, 832cm$^{-1}$ |

TABLE 12

| | |
|---|---|
| III-84 | oil<br>$^1$HNMR(CDCl$_3$) δ 1.44(d, J=6.9Hz, 3H), 2.19(s, 3H), 4.09(q, J=6.9Hz, 2H), 5.20(s, 2H), 6.82(s, 1H), 6.94–7.08(m, 3H), 7.32–7.49(m, 6H) IR(CHCl$_3$)3597, 2928, 1731, 1609, 1523, 1494, 1476, 1387, 1298, 1261, 1173, 1127, 1048, 834cm$^{-1}$ |
| III-85 | $^1$HNMR(CDCl$_3$) δ 2.26(s, 3H), 2.52(s, 3H), 3.90(s, 3H), 4.59(brs, 2H), 5.20(s, 2H), 6.73–7.10(m, 4H), 7.27–7.52(m, 6H) |
| III-86 | $^1$HNMR(CDCl$_3$) δ 2.33(s, 3H), 2.81(s, 3H), 4.60(brs, 2H), 5.20(s, 2H), 6.92–7.18(m, 4H), 7.30–7.52(m, 6H) |

TABLE 13

| | |
|---|---|
| I-1 | m.p. 155.5–156° C.<br>$^1$HNMR(acetone-d$_6$) δ 1.77(brs, 3H), 1.79(brs, 3H), 3.37(s, 3H), 3.73(s, 3H), 4.63(brd, J=6.6Hz, 2H), 5.52(m, 1H), 6.49(1H, s), 6.83(d d, J=2.2 and 8.2Hz, 1H), 6.92(d, J=2.2Hz, 1H), 6.94(m, 2H), 6.96(d, J=8.2Hz, 1H), 7.54(m, 2H), 7.62(brs, 1H), 7.78(s, 1H), 8.64(brs, 1H)<br>IR(KBr)3393, 2932, 1611, 1588, 1522, 1490, 1117, 1071, 1001cI-3 m$^{-1}$ |
| I-2 | $^1$HNMR(CDCl$_3$) δ 2.67(s, 3H), 3.13(s, 3H), 3.21(s, 3H), 3.56(s, 3H), 3.78(s, 3H ), 5.19(s, 2H), 6.84(s, 1H), 7.15(d, J=8.6Hz, 1H), 7.30–7.50 (m, 9H), 7.60–7.75(m, 2H)<br>IR(KBr)1373, 1361, 1179, 1149, 1079, 874, 799cm$^{-1}$ |
| I-3 | m.p. 155–157° C.<br>$^1$HNMR(CDCl$_3$) δ 1.76(s, 3H), 1.81(s, 3H), 2.71(s, 3H), 3.21(s, 3H), 3.23(s, 3H), 3.56(s, 3H), 3.78(s, 3H), 4.64(d, J=6.6Hz, 2H), 5.43–5.55 (m, 1H), 6.84(s, 1H), 7.09(d, J=8.4Hz, 1H), 7.30–7.42(m, 4H), 7.65–7.75(m, 2H)<br>IR(KBr)1519, 1481, 1364, 1179, 1153, 1083, 970, 877, 796cm$^{-1}$ |
| I-4 | $^1$HNMR(CDCl$_3$) δ 3.45(s, 3H), 3.75(s, 3H), 5.16(s, 2H), 6.44(s, 1H), 6.92–7.19(m, 5H), 7.34–7.44(m, 5H), 7.57–7.66(m, 2H)<br>IR(KBr)3538, 3510, 3460, 3330, 1605, 1521, 1490, 1455, 1247, 1220, 1120, 1070, 1010cm$^{-1}$ |
| I-5 | m.p. 136–138° C.<br>$^1$HNMR(CDCl$_3$) δ 2.68(s, 3H), 3.13(s, 3H), 3.55(s, 3H), 3.80(s, 3H)5.19(s, 2H), 6.86(s, 1H), 7.16(d, J=8.7Hz, 1H), 7.33–7.49(m, 7H), 7.55–7.69 (m, 2H), 7.82–7.87(m, 2H)<br>IR(KBr)3433, 2937, 1609, 1519, 1474, 1463, 1364, 1322, 1295, 1274, 1235, 1183, 1167, 1120, 1095, 1077, 1016cm$^{-1}$ |
| I-6 | foam<br>$^1$HNMR(CDCl$_3$) δ 1.77(s, 3H), 1.81(s, 3H), 2.72(s, 3H), 3.24(s, 3H), 3.49(s, 3H), 3.80(s, 3H), 4.64(d, J=6.9Hz, 2H), 5.50(m, 1H), 6.86(s, 1H), 7.10(d, J=8.7Hz, 1H), 7.35(dd, J=2.1, 8.7Hz, 1H), 7.39(d, J=2.1Hz, 1H), 7.55–7.69(m, 2H), 7.82–7.87(m, 2H).<br>IR(CHCl$_3$)3030, 1608, 1518, 1480, 1369, 1322, 1269, 1230, 1179, 1131, 1120, 1097, 1081, 1015cm$^{-1}$ |

TABLE 14

| | |
|---|---|
| I-7 | m.p. 92–94° C.<br>$^1$HNMR(CDCl$_3$) δ 1.76(s, 3H), 1.82(s, 3H), 3.46(s, 3H), 3.77(s, 3H), 4.62(d, J=6.9Hz, 2H), 5.31(m, 1H), 5.71(s, 1H), 5.85(s, 1H), 6.47(s, 1H), 6.93(dd, J=1.8, 8.7Hz, 1H), 6.97(d, J=8.7Hz, 1H), 7.05(d, J=1.8Hz, 1H), 7.55–7.65(m, 2H), 7.83–7.91(m, 2H).<br>IR(KBr)3466, 2939, 1609, 1587, 1518, 1498, 1486, 1464, 1437, 1406, 1361, 1324, 1245, 1216, 1155, 1125, 1073cm$^{-1}$ |
| I-8 | $^1$HNMR(CDCl$_3$) δ 3.22(s, 3H), 3.45(s, 3H), 3.77(s, 3H), 4.74(s, 2H), 5.15(s, 2H), 6.93(s, 1H), 7.01(d, J=8.7Hz, 2H), 7.32–7.48(m, 9H), 7.73 (d, J=9.0Hz, 2H)<br>IR(KBr)3400, 1721, 1612, 1509, 1471, 1362, 1242, 1153, 1040, 1018cm$^{-1}$ |
| I-9 | $^1$HNMR(CDCl$_3$) δ 1.03(t, J=7.2Hz, 3H), 2.16(dq, J=7.2, 6.0Hz, 2H), 3.46(s, 3H), 3.74(s, 3H), 4.68(d, J=5.4Hz, 2H), 5.70(m, 2H), 6.45 (s, 1H), 6.91(d, J=8.7Hz, 2H), 6.96(brs, 2H), 7.07(brs, 1H), 7.53(d, J=8.7Hz, 2H)<br>IR(Nujol)3445, 3369, 1612, 1578, 1523, 1489, 1268, 1243, 1112, 1102, 1071, 1011, 998, 944, 824, 805, 781cm$^{-1}$ |
| I-10 | m.p. 174–175° C.<br>$^1$HNMR(CDCl$_3$) δ 3.11(s, 3H), 3.21(s, 3H), 3.45(s, 3H), 3.73(s, 3H), 4.49(brs, 2H), 5.18(s, 2H), 6.85(s, 1H), 7.15(d, J=8.4Hz, 1H), 7.27 (dd, J=8.4Hz, J=2.1Hz, 1H), 7.35–7.49(m, 8H), 7.70(m, 2H)<br>IR(KBr)1519, 1467, 1360, 1346, 1331, 1295, 1272, 1229, 1180, 1151, 1122, 1101, 1081, 1022, 980, 971, 954, 875, 849, 814, 798, 742, 525cm$^{-1}$ |
| I-11 | $^1$HNMR(CDCl$_3$) δ 1.77(s, 3H), 1.82(s, 3H), 3.22(s, 6H), 3.45(s, 3H), 3.74(s, 3H), 4.49(brs, 2H), 4.64(d, J=7.2Hz, 2H), 5.45–5.55(m, 1H), 6.85(s, 1H), 7.08(d, J=8.7Hz, 1H), 7.26(dd, J=8.7 and 2.1Hz, 1H), 7.33(d, J=2.1Hz, 1H), 7.36–7.41(m, 2H), 7.65–7.75(m, 2H)<br>IR(KBr)3553, 3434, 1516, 1472, 1365, 1176, 1150, 973, 871cm$^{-1}$ |
| I-12 | $^1$HNMR(DMSO-d$_6$) δ 1.72(s, 3H), 1.77(s, 3H), 3.35(s, 3H), 3.65(s, 3H), 4.20(brs, 2H), 4.47(brt, J=4.4Hz, 1H), 4.55(brd, J=6.6Hz, 2H), 5.40–5.57(m, 1H), 6.64(dd, J=8.2, 2.0Hz, 1H), 6.70(d, J=2.0Hz, 1H), 6.75–7.00(m, 4H), 7.40–7.55(m, 2H)<br>IR(KBr)3435, 1518, 1475, 1459, 1261, 1223, 988cm$^{-1}$ |

TABLE 15

| | |
|---|---|
| I-13 | $^1$HNMR(CDCl$_3$) δ 2.71(s, 3H), 2.84(s, 3H), 3.20(s, 3H), 3.42(s, 3H), 3.76(s, 3H), 5.13(s, 2H), 5.67(s, 1H), 6.90(s, 1H), 6.89–6.96(m, 2H), 7.00(m, J=1.8Hz, 1H), 7.32–7.50(m, 7H), 7.70(d, J=9.0Hz, 2H) |
| I-14 | m.p. 140–141° C.<br>$^1$HNMR(CDCl$_3$) δ 2.71(s, 3H), 2.83(s, 3H), 3.15(s, 3H), 3.21(s, 3H), 3.42(s, 3H), 3.77(s, 3H), 5.16(s, 2H), 6.90(s, 1H), 7.09(d, J=8.9Hz, 2H), 7.30–7.50(m, 9H), 7.70(d, J=8.9Hz, 2H)<br>IR(KBr)1642, 1516, 1467, 1362, 1180, 1151, 1118, 1050, 867, 803, 708cm$^{-1}$ |
| I-15 | m.p. 161–162° C.<br>$^1$HNMR(CDCl$_3$) δ 1.76(s, 3H), 1.81(s, 3H), 2.72(s, 3H), 2.85(s, 3H), 3.21(s, 3H), 3.23(s, 3H), 3.42(s, 3H), 3.77(s, 3H), 4.61(d, J=6.6Hz, 2H), 5.49(t, J=6.6Hz, 1H), 6.90(S, 1H), 7.02(d, J=8.1Hz, 1H), 7.31–7.37(m, 2H), 7.38(d, J=8.9Hz, 2H), 7.70(d, J=8.9Hz, 2H)<br>IR(KBr)1643, 1516, 1467, 1362, 1277, 1236, 1180, 1150, 974, 882, 868, 847, 802, 710cm$^{-1}$ |
| I-16 | m.p. 206–207° C.<br>$^1$HNMR(CDCl$_3$) δ 1.71(s, 3H), 1.76(s, 3H), 2.62(s, 3H), 2.69(s, 3H), 3.27(s, 3H), 3.71(s, 3H), 4.53(d, J=6.8Hz, 2H), 5.47(t, J=6.6Hz, 1H), 6.61(dd, J=8.3 and 2.1Hz, 1H), 6.71(d, J=2.1Hz, 1H), 6.86(d, J=8.7Hz, 2H), 6.87(d, J=8.3Hz, 1H), 6.95(s, 1H), 7.47(d, J=8.7Hz, 2H), 8.83 (brs, 1H), 9.59(brs, 1H)<br>IR(KBr)3427, 3020, 1608, 1517, 1467, 1379, 1233, 1053, 1005, 839, 799, 759, 543cm$^{-1}$ |
| I-17 | m.p. 171–172° C.<br>$^1$HNMR(DMSO-d$_6$) δ 1.74(d, J=0.9Hz, 3H), 1.77(s, 3H), 2.97(s, 3H), 3.45(s, 3H), 3.51(s, 3H), 3.77(s, 3H), 4.65(d, J=6.6Hz, 2H), 5.48 (m, 1H), 7.06–7.27(m, 4H), 7.48&7.74(ABq, J=9.0Hz, 4H)<br>IR(KBr)1523, 1483, 1394, 1366, 1271, 1175, 1151, 1087, 1071, 872, 861, 847, 796cm$^{-1}$ |
| I-18 | $^1$HNMR(CDCl$_3$) δ 1.76(s, 3H), 1.80(s, 3H), 3.44(s, 3H), 3.76(s, 3H), 4.63(d, J=6.6Hz, 2H), 4.99(s, 1H), 5.48–5.62(m, 1H), 6.00(s, 1H), 6.45 (s, 1H), 6.88–6.97(m, 2H), 7.04(dd, J=9.0, 9.0Hz, 1H), 7.15–7.29(m, 2H), 7.45–7.60(m, 2H)<br>IR(KBr)3393, 1523, 1490, 1466, 1403, 1267, 1229, 1113, 1070cm$^{-1}$ |

TABLE 16

| | |
|---|---|
| I-19 | $^1$HNMR(CDCl$_3$) δ 2.56(s, 3H), 3.21(s, 3H), 3.52(s, 3H), 3.69(s, 3H), 5.19(s, 2H), 5.76(s, 1H), 6.92(dd, J=8.4 and 2.0Hz, 1H), 7.04(d, J=8.4Hz, 1H), 7.05(d, J=2.0Hz, 1H), 7.35–7.51(m, 7H), 7.60(d, J=8.6Hz, 2H) |
| I-20 | $^1$HNMR(CDCl$_3$) δ 2.69(s, 3H), 3.14(s, 3H), 3.21(s, 3H), 3.53(s, 3H), 3.71(s, 3H), 5.20(s, 2H), 7.18(d, J=8.7Hz, 1H), 7.34–7.50(m, 9H), 7.59 (d, J=8.71Hz, 2H) |
| I-21 | m.p. 94–95° C.<br>$^1$HNMR(CDCl$_3$) δ 2.73(s, 3H), 3.21(s, 3H), 3.24(s, 3H), 3.53(s, 3H), 3.71(s, 3H), 4.65(d, J=6.9Hz, 2H), 5.50(t, J=6.9Hz, 1H), 7.12(d, J=8.6Hz, 1H), 7.36(dd, J=8.6 and 2.1Hz, 1H), 7.41(d, J=2.1Hz, 2H), 7.41(d, J=8.8Hz, 2H), 7.59(d, J=8.8Hz, 2H)<br>IR(KBr)1516, 1367, 1180, 1152, 1039, 975, 869, 799cm$^{-1}$ |
| I-22 | m.p. 148–150° C.<br>$^1$HNMR(CDCl$_3$) δ 3.42(s, 3H), 3.65(s, 3H), 4.63(d, J=6.9Hz, 2H), 4.98(brs, 1H), 5.53(t, J=6.9Hz, 1H), 6.92–6.96(m, 4H), 7.07(s, 1H), 7.43 (d, J=8.6Hz, 2H)<br>IR(KBr)3398, 1612, 1587, 1523, 1462, 1410, 1261, 1211, 1099, 1036, 984, 952, 919, 838, 815cm$^{-1}$ |
| I-23 | $^1$HNMR(CDCl$_3$) δ 2.28(t, J=6.3Hz, 1H), 2.60(s, 3H), 3.21(s, 3H), 3.55(s, 3H), 3.77(s, 3H), 4.78(d, J=6.3Hz, 2H), 5.18(s, 2H), 6.84(s, 1H), 7.06(d, J=9.0Hz, 1H), 7.29–7.48(m, 9H), 7.69(d, J=8.7Hz, 2H) |
| I-24 | $^1$HNMR(CDCl$_3$) δ 1.76(s, 3H), 1.81(s, 3H), 2.26(s, 3H), 2.50(s, 3H), 3.21(s, 3H), 3.56(s, 3H), 3.77(s, 3H), 4.57(d, J=6.2Hz, 2H), 5.51(t, J=6.2Hz, 1H), 6.83(s, 1H), 6.92(d, J=9.0Hz, 1H), 7.17–7.29(m, 2H), 7.36(d, J=8.7Hz, 2H), 7.70(d, J=8.7Hz, 2H)<br>IR(KBr)3434, 1608, 1512, 1479, 1364, 1234, 1175, 1150, 1078, 1017cm$^{-1}$ |
| I-25 | $^1$HNMR(CDCl$_3$) δ 1.75(s, 3H), 1.80(s, 3H), 2.27(s, 3H), 3.46(s, 3H), 3.74(s, 3H), 4.57(d, J=6.2Hz, 2H), 4.95(s, 1H), 5.53(t, J=6.2Hz, 1H), 5.86(s, 1H), 6.45(s, 1H), 6.91(d, J=8.7Hz, 2H), 6.92(d, J=9.0Hz, 1H), 7.24(d, J=9.0Hz, 1H), 7.26(s, 1H), 7.53(d, J=8.7Hz, 2H)<br>IR(KBr)3399, 1612, 1566, 1581, 1520, 1486, 1237, 1115, 1078, 1001cm$^{-1}$ |

TABLE 17

| | |
|---|---|
| I-26 | m.p. 246–247° C.<br>$^1$HNMR(DMSO-d$_6$) δ 5.16(s, 3H), 6.84–6.87(m, 2H), 7.05(s, 2H), 7.14(s, 1H), 7.32–7.43(m, 3H), 7.49–7.64(m, 8H)<br>IR(KBr)3600–3100(br), 1594, 1453, 1387, 1296, 1253, 1010cm$^{-1}$ |
| I-27 | $^1$HNMR(DMSO-d$_6$) δ 3.38(s, 3H), 3.43(s, 3H), 5.28(s, 2H), 7.36–7.54(m, 8H), 7.69–7.86(m, 8H)<br>IR(KBr)1488, 1354, 1286, 1178, 1151, 1116cm$^{-1}$ |
| I-28 | m.p. 162–163° C.<br>$^1$HNMR(CDCl$_3$) δ 1.77(s, 3H), 1.82(s, 3H), 3.19(s, 3H), 3.23(s, 3H), 4.64(d, J=6.6Hz, 2H), 5.25–5.48(m, 1H), 7.09(d, J=9.0Hz, 1H), 7.36–7.40 (m, 2H), 7.52(dd, J=2.4, 9.0Hz, 1H), 7.59(d, J=2.4Hz, 1H), 7.62(s, 4H), 7.63–7.69(m, 2H)<br>IR(KBr)1489, 1363, 1290, 1177, 1154, 1115, 971, 860, 809cm$^{-1}$ |
| I-29 | m.p. 195° C.<br>$^1$HNMR(DMSO-d$_6$) δ 1.72(s, 3H), 1.75(s, 3H), 4.57(d, J=6.3Hz, 2H), 5.45–5.50(m, 1H), 6.84–6.87(m, 2H), 6.98–7.11(m, 3H), 7.50–7.64 (m, 6H)<br>IR(KBr)3600–3200(br), 1609, 1594, 1497, 1257, 991cm$^{-1}$ |
| I-30 | m.p. 145–148° C.<br>$^1$HNMR(CDCl$_3$) δ 1.60–2.20(m, 6H), 2.72(s, 3H), 3.21(s, 3H), 3.24(s, 3H), 3.56(s, 3H), 3.78(s, 3H), 4.92(m, 1H), 5.88(m, 1H), 6.02(m, 1H), 6.84(s, 1H), 7.12(d, J=8.6Hz, 1H), 7.34–7.40(m, 4H), 7.69(m, 2H)<br>IR(KBr)1517, 1481, 1390, 1362, 1270, 1244, 1180, 1151, 1077, 1012, 973, 960, 873, 817, 799, 521cm$^{-1}$ |
| I-31 | m.p. 108–110° C.<br>$^1$HNMR(CDCl$_3$) δ 1.60–2.20(m, 6H), 3.46(s, 3H), 3.75(s, 3H), 4.86(m, 1H), 5.02(bs, 1H), 5.75(s, 1H), 5.90(m, 1H), 5.91(s, 1H), 6.00(m, 1H), 6.45(s, 1H), 6.90–7.07(m, 5H), 7.53(m, 2H)<br>IR(KBr)3485, 1614, 1523, 1491, 1457, 1407, 1312, 1287, 1269, 1238, 1195, 1170, 1115, 1072, 1014cm$^{-1}$ |

TABLE 18

| | |
|---|---|
| I-32 | m.p. 188–190° C.<br>$^1$HNMR(CDCl$_3$) δ 2.69(s, 3H), 3.21(s, 3H), 3.26(s, 3H), 3.56(s, 3H), 3.78(s, 3H), 4.84(m, 2H), 6.42(dt, J=15.6Hz, J=5.7Hz, 1H), 6.79(d, J=15.6Hz, 1H), 6.84(s, 1H), 7.15(d, J=8.4Hz, 1H), 7.28–7.43(m, 9H), 7.68(m, 2H)<br>IR(KBr)1519, 1479, 1447, 1391, 1360, 1301, 1273, 1241, 1228, 1201, 1175, 1152, 1120, 1079, 1014, 974, 959, 947, 868, 819, 795, 777, 743, 521cm$^{-1}$ |
| I-33 | m.p. 157–159° C.<br>$^1$HNMR(CDCl$_3$) δ 3.46(s, 3H), 3.75(s, 3H), 4.81(m, 2H), 4.93(bs, 1H), 5.70(s, 1H), 5.91(s, 1H), 6.45(s, 1H), 6.46(dt, J=15.9Hz, J=6.0Hz, 1H), 6.76(d, J=15.9Hz, 1H), 6.90–7.09(m, 5H), 7.26–7.46(m, 5H), 7.54(m, 2H)<br>IR(KBr)3466, 1611, 1522, 1489, 1461, 284, 1248, 1192, 1165, 1114, 1073cm$^{-1}$ |
| I-34 | m.p. 127–129° C.<br>$^1$HNMR(CDCl$_3$) δ 1.03 and 1.04(botht, bothJ=8.0Hz, total3H), 2.07–2.19(m, 2H), 2.71 and 2.72(boths, total3H), 3.21(s, 3H), 3.24(s, 3H), 3.56(s, 3H), 3.78(s, 3H), 4.60 and 4.71(bothm, total2H), 5.66–5.75 and 5.90–5.99(bothm, total2H), 6.84(s, 1H), 7.09(d, J=8.4Hz, 1H), 7.33–7.41(m, 4H), 7.68(m, 2H)<br>IR(KBr)1519, 1482, 1390, 1362, 1232, 1180, 1150, 1077, 974, 873, 815, 799, 522cm$^{-1}$ |
| I-35 | m.p. 166–168° C.<br>$^1$HNMR(CDCl$_3$) δ 1.04 and 1.05(botht, bothJ=7.5Hz, total3H), 2.09–2.19(m, 2H), 3.46(s, 3H), 3.74(s, 3H), 4.58 and 4.68(bothm, total2H), 5.01(bs, 1H), 5.69–5.78 and 5.87–5.95(bothm, total4H), 6.45(s, 1H), 6.90–7.06(m, 5H), 7.53(m, 2H)<br>IR(KBr)3531, 3489, 3306, 1523, 1492, 1459, 1408, 1314, 1287, 1270, 1255, 1234, 1224, 1118, 1072, 1018, 1005, 822cm$^{-1}$ |
| I-36 | m.p. 148–150° C.<br>$^1$HNMR(CDCl$_3$) δ 1.62(s, 3H), 1.69(s, 3H), 1.76(s, 3H), 2.08–2.20(m, 4H), 2.71(s, 3H), 3.21(s, 3H), 3.24(s, 3H), 3.56(s, 3H), 3.78(s, 3H), 4.66(d, J=6.3Hz, 2H), 5.09(m, 1H), 5.50(t, J=6.3Hz, 1H), 6.84(s, 1H), 7.10(d, J=8.4Hz, 1H), 7.33–7.41(m, 4H), 7.68(m, 2H)<br>IR(KBr)1519, 1480, 1464, 1449, 1389, 1366, 1291, 1271, 1233, 1200, 1176, 1150, 1118, 1079, 1012, 973, 946, 876, 841, 816, 801, 523, 510cm$^{-1}$ |

TABLE 19

| | |
|---|---|
| I-37 | $^1$HNMR(CDCl$_3$) δ 1.58(s, 3H), 1.63(s, 3H), 1.70(s, 3H), 2.05–2.20(m, 4H), 3.46(s, 3H), 3.75(s, 3H), 4.64(d, J=6.3Hz, 2H), 4.95(bs, 1H), 5.11(m, 1H), 5.53(m, 1H), 5.70(s, 1H), 5.90(s, 1H), 6.45(s, 1H), 6.91–7.08(m, 5H), 7.54(m, 2H) |
| I-38 | m.p. 149–151° C.<br>$^1$HNMR(CDCl$_3$) δ 1.68(s, 3H), 1.74(s, 3H), 2.55(m, 2H), 2.73(s, 3H), 3.21(s, 3H), 3.22(s, 3H), 3.56(s, 3H), 3.77(s, 3H), 4.07(t, J=6.8Hz, 2H), 5.21(m, 1H), 6.84(s, 1H), 7.08(d, J=8.2Hz, 1H), 7.32–7.40(m, 4H), 7.68(m, 2H)<br>IR(KBr)1520, 1483, 1389, 1363, 1296, 1180, 1151, 1079, 975, 872, 815, 799, 521cm$^{-1}$ |
| I-39 | m.p. 105–107° C.<br>$^1$HNMR(CDCl$_3$) δ 1.68(s, 3H), 1.75(s, 3H), 2.53(m, 2H), 3.54(s, 3H), 3.74(s, 3H), 4.06(t, J=6.8Hz, 2H), 5.01(bs, 1H), 5.22(m, 1H), 5.69(s, 1H), 5.90(s, 1H), 6.45(s, 1H), 6.90–7.06(m, 5H), 7.53(m, 2H)<br>IR(KBr)3477, 3388, 1523, 1489, 1469, 1402, 1285, 1261, 1248, 1227, 1196, 1175, 1164, 1115, 1100, 1073, 1011cm$^{-1}$ |
| I-40 | m.p. 155–157° C.<br>$^1$HNMR(CDCl$_3$) δ 1.89(t, J=2.4Hz, 3H), 3.45(s, 3H), 3.75(s, 3H), 4.74(q, J=2.4Hz, 2H), 5.00(bs, 1H), 5.66(s, 1H), 5.92(s, 1H), 6.45(s, 1H), 6.90–7.08(m, 5H), 7.54(m, 2H)<br>IR(KBr)3446, 2224, 1523, 1488, 1402, 1266, 1238, 1203, 1187, 1166, 1102, 1068, 1009cm$^{-1}$ |
| I-41 | $^1$HNMR(CDCl$_3$) δ 2.19(s, 3H), 3.45(s, 3H), 3.75(s, 3H), 4.62(m, 2H), 4.92(bs, 1H), 5.60(bs, 1H), 5.92(s, 1H), 5.99(m, 1H), 6.45(m, 1H), 6.91–7.08(m, 5H), 7.53(m, 2H) |
| I-42 | oil<br>$^1$HNMR(CDCl$_3$) δ 1.76(s, 3H), 1.81(s, 3H), 2.87(s, 3H), 3.22(s, 6H), 3.55(s, 3H), 3.80(s, 3H), 4.66(d, J=7.5Hz, 2H), 5.61(m, 1H), 6.84(s, 1H), 7.37–7.41(m, 3H), 7.61(d, J=2.1Hz, 1H), 7.67(m, 2H) |

TABLE 20

| | |
|---|---|
| I-43 | m.p. 132–136° C.<br>$^1$HNMR(CDCl$_3$) δ 1.74(s, 3H), 1.82(s, 3H), 3.44(s, 3H), 3.76(s, 3H), 4.62(m, 2H), 5.05(brs, 1H), 5.61(m, 1H), 5.79(s, 1H), 6.02(s, 1H), 6.44(s, 1H), 6.92(m, 2H), 7.04(d, J=2.1Hz, 1H), 7.20(d, J=2.1Hz, 1H), 7.53(m, 2H)<br>IR(KBr)3495, 3422, 1611, 1520, 1473, 1400, 1355, 1315, 1280, 1227, 1194, 1173, 1111, 1077, 1023cm$^{-1}$ |
| I-44 | m.p. 148–149° C.<br>$^1$HNMR(CDCl$_3$) δ 1.60(s, 3H), 1.70(s, 3H), 2.32–2.39(m, 2H), 2.65(s, 3H), 2.76–2.81(m, 2H), 3.21(s, 3H), 3.24(s, 3H), 3.56(s, 3H), 3.78(s, 3H), 5.16–5.21(m, 1H), 6.85(s, 1H), 7.30–7.40(m, 5H), 7.66–7.71(m, 2H)<br>IR(KBr)1480, 1390, 1361, 1181, 1150, 1075cm$^{-1}$ |
| I-45 | m.p. 73–75° C.<br>$^1$HNMR(CDCl$_3$) δ 1.63(s, 3H), 1.72(s, 3H), 2.32–2.39(m, 2H), 2.64–2.70(m, 2H), 3.46(s, 3H), 3.74(s, 3H), 4.83(s, 1H), 4.95(s, 1H), 5.27–5.31(m, 1H), 5.92(s, 1H), 6.45(s, 1H), 6.89–7.00(m, 4H), 7.21(d, J=10.5Hz, 1H), 7.52–7.55(m, 2H)<br>IR(KBr)3600–3200(br), 3100–2800(br), 1612, 1579, 1523, 1487, 1452, 1400, 1360, 1226, 1174, 1111, 1072cm$^{-1}$ |
| I-46 | $^1$HNMR(CDCl$_3$) δ 3.45(s, 3H), 3.75(s, 3H), 4.65(m, 2H), 4.85(s, 1H), 5.33(m, 1H), 5.44(m, 1H), 5.67(s, 1H), 5.91(s, 1H), 6.10(m, 1H), 6.45(s, 1H), 6.92(m, 2H), 6.95(m, 2H), 7.08(m, 1H), 7.54(m, 2H) |
| I-47 | $^1$HNMR(acetone-d$_6$) δ 3.39(s, 3H), 3.72(s, 3H), 5.20(s, 2H), 6.48(s, 1H), 6.83(dd, J=2.0Hz, J=8.4Hz, 1H), 6.93(m, 2H), 6.96(d, J=2.0Hz, 1H), 7.04(d, J=8.4Hz, 1H), 7.34–7.45(m, 3H), 7.52(m, 2H), 7.52–7.58(m, 2H)<br>IR(CHCl$_3$)3522, 3348, 1699, 1612, 1589, 1521, 1489, 1458, 1402, 1288, 1114, 1071, 935cm$^{-1}$ |
| I-48 | $^1$HNMR(acetone-d$_6$) δ 1.28(t, J=7.2Hz, 3H), 3.39(s, 3H), 3.72(s, 3H), 4.25(q, J=7.2Hz, 2H), 4.78(s, 2H), 6.49(s, 1H), 6.83(dd, J=1.8 and 8.4Hz, 1H), 6.93(m, 2H), 6.96(d, J=1.8Hz, 1H), 6.97(d, J=8.4Hz, 1H), 7.52(m, 2H), 7.63(s, 1H), 7.83(s, 1H), 8.50(s, 1H) |
| I-49 | $^1$HNMR(acetone-d$_6$) δ 1.75(m, 3H), 3.39(s, 3H), 3.72(s, 3H), 4.56(m, 2H), 5.71–5.82(m, 1H), 5.84–5.96(m, 1H), 6.48(s, 1H), 6.82(dd, J=2.0 and 8.4Hz, 1H), 6.93(d, J=2.0Hz, 1H), 6.93(m, 2H), 6.95(d, J=8.4Hz, 1H), 7.52(m, 2H) |

TABLE 21

| | |
|---|---|
| I-50 | ¹HNMR(acetone-d₆) δ 1.75(m, 3H), 3.39(s, 3H), 3.72(s, 3H), 4.72(m, 2H), 5.73–5.75(m, 2H), 6.48(s, 1H), 6.83(dd, J=2.0 and 7.8Hz, 1H), 6.92–6.95(m, 3H), 6.97(d, J=7.8Hz, 1H), 7.52(m, 2H) |
| I-51 | ¹HNMR(acetone-d₆) δ 1.77(s, 3H), 1.79(s, 3H), 3.41(s, 3H), 3.72(s, 3H), 4.66(m, 2H), 5.53(m, 1H), 6.49(s, 1H), 6.85(m, 2H), 7.04(d, J=8.1Hz, 1H), 7.10(dd, J=2.1 and 8.1Hz, 1H), 7.19(d, J=2.1Hz, 1H), 7.25(m, 2H) |
| I-52 | ¹HNMR(CDCl₃) δ 2.58(t, J=2.2Hz, 1H), 2.73(s, 3H), 3.22(s, 3H), 3.26(s, 3H), 3.56(s, 3H), 3.78(s, 3H), 4.83(d, J=2.2Hz, 2H), 6.85(s, 1H), 7.21(d, J=8.4Hz, 1H), 7.35–7.46(m, 4H), 7.64–7.74(m, 2H) |
| I-53 | ¹HNMR(CDCl₃) δ 3.45(s, 3H), 3.76(s, 3H), 4.36(d, J=1.5Hz, 1H), 4.55(s, 2H), 4.76(dd, J=1.8 and 0.6Hz, 1H), 5.02(brs, 1H), 5.97(d, J=0.9Hz, 1H), 6.45(s, 1H), 6.90–6.96(m, 2H), 6.96–7.05(m, 2H), 7.10–7.12(m, 1H), 7.50–7.58(m, 2H |
| I-54 | ¹HNMR(CDCl₃) δ 1.76(s, 3H), 1.82(s, 3H), 2.61(s, 3H), 3.53(s, 3H), 3.77(s, 3H), 4.61(d, J=6.9Hz, 2H), 5.17(brs, 1H), 5.45–5.50(m, 1H), 5.72(s, 1H), 6.88–7.00(m, 4H), 7.02(d, J=1.8Hz, 1H), 7.50–7.57(m, 2H) |
| I-55 | ¹HNMR(CDCl₃) δ 0.99(d, J=6.5Hz, 6H), 1.74(q, J=6.5Hz, 2H), 1.85(m, 1H), 3.46(s, 3H), 3.75(s, 3H), 4.12(t, J=6.5Hz, 2H), 4.97(s, 1H), 5.65(s, 1H), 5.90(s, 1H), 6.45(s, 1H), 6.92(m, 2H), 6.95(m, 2H), 7.06(m, 1H), 7.54(m, 2H) |
| I-56 | ¹HNMR(CDCl₃) δ 1.34(s, 3H), 1.35(s, 3H), 3.15(dd, J=3.6 and 6.6Hz, 1H), 3.39(s, 3H), 3.72(s, 3H), 4.10(dd, J=6.6 and 11.1Hz and, 1H), 4.34 (dd, J=3.6 and 11.1Hz, 1H), 6.49(s, 1H), 6.83(dd, J=1.8 and 8.1Hz, 1H), 6.93(d, J=8.7Hz, 2H), 6.94(d, J=1.8Hz, 1H), 7.00(d, J=8.1Hz, 1H), 7.52(d, J=8.7Hz, 2H) |
| I-57 | ¹HNMR(CDCl₃) δ 2.68(s, 3H), 3.13(s, 3H), 3.53(s, 3H), 3.78(s, 3H), 5.19(s, 2H), 6.83(s, 1H), 7.10–7.19(m, 3H), 7.31–7.50(m, 7H), 7.57–7.64 (m, 2H)<br>IR(KBr)1607, 1520, 1481, 1373, 1231, 1176, 1119, 1078cm⁻¹ |
| I-58 | ¹HNMR(CDCl₃) δ 1.76(s, 3H), 1.82(s, 3H), 2.72(s, 3H), 3.23(s, 3H), 3.53(s, 3H), 3.78(s, 3H), 3.78(s, 3H), 4.64(d, J=6.6Hz, 2H), 6.84(t, J=6.6Hz, 1H), 5.83(s, 1H), 7.06–7.20(m, 3H), 7.31–7.40(m, 2H), 7.56–7.65(m, 2H)<br>IR(KBr)1603, 1521, 1483, 1376, 1366, 1176, 1085cm⁻¹ |

TABLE 22

| | |
|---|---|
| I-59 | ¹HNMR(CDCl₃) δ 1.76(s, 3H), 1.82(s, 3H), 3.45(s, 3H), 3.75(s, 3H), 4.62(d, J=6.9Hz, 2H), 5.52(t, J=6.9Hz, 1H), 5.71(brs, 1H), 5.89(s, 1H), 6.44(s, 1H), 6.90–7.19(m, 5H), 7.56–7.67(m, 2H)<br>IR(KBr)3545, 3385, 1605, 1586, 1561, 1520, 1384, 1311, 1284, 1225, 1121, 1096cm⁻¹ |
| I-60 | ¹HNMR(CDCl₃) δ 3.49(s, 3H), 3.74(s, 3H), 5.15(s, 2H), 5.68(s, 1H), 5.91(s, 1H), 6.02(s, 2H), 6.43(s, 1H), 6.88–7.19(m, 6H), 7.31–7.48 (m, 5H)<br>IR(CHCl₃)3535, 1615, 1588, 1519, 1500, 1482, 1410, 1290, 1241, 1204, 1092, 1041cm⁻¹ |
| I-61 | ¹HNMR(CDCl₃) δ 1.76(s, 3H), 1.81(s, 3H), 2.73(s, 3H), 3.23(s, 3H), 3.57(s, 3H), 3.77(s, 3H), 4.64(d, J=6.6Hz, 1H), 5.50(t, J=6.6Hz, 1H), 6.03 (s, 2H), 6.83(s, 1H), 6.91(d, J=8.1Hz, 1H), 7.08(d, J=8.1Hz, 1H), 7.09(d, J=8.1Hz, 1H), 7.14(s, 1H), 7.34(d, J=8.1Hz, 1H), 7.39(s, 1H)<br>IR(CHCl₃)1607, 1518, 1477, 1453, 1369, 1240, 1178, 1081cm⁻¹ |
| I-62 | ¹HNMR(CDCl₃) δ 1.76(s, 3H), 1.82(s, 3H), 3.49(s, 3H), 3.74(s, 3H), 4.61(d, J=6.9Hz, 2H), 5.53(t, J=6.9Hz, 1H), 5.68(s, 1H), 6.02(s, 2H), 6.43(s, 1H), 6.88–6.96(m, 3H), 7.03–7.18(m, 3H)<br>IR(KBr)3494, 1610, 1583, 1561, 1519, 1480, 1460, 1409, 1286, 1243, 1191, 1127, 1089, 1036cm⁻¹ |
| I-63 | m.p. 201–202° C.<br>¹HNMR(CDCl₃) δ 3.78(s, 6H), 5.16(s, 4H), 5.69(s, 2H), 6.93(s, 2H), 6.99(d, J=8.4Hz, 2H), 7.08(dd, J=2.1 and 8.4Hz, 2H), 7.22(d, J=2.1Hz, 2H), 7.37–7.47(m, 10H),<br>IR(KBr)3600–3100(br), 1584, 1523, 1454, 1272, 1245, 1210, 1130cm⁻¹ |
| I-64 | m.p. 173–175° C.<br>¹HNMR(CDCl₃) δ 3.12(s, 6H), 3.80(s, 6H), 5.18(s, 4H), 6.92(s, 2H), 7.12(d, J=8.7Hz, 2H), 7.36–7.50(m, 12H), 7.60(d, J=2.1Hz, 2H)<br>IR(KBr)1523, 1492, 1356, 1290, 1263, 1210, 1182, 1114cm⁻¹ |

TABLE 23

| | |
|---|---|
| I-65 | ¹HNMR(CDCl₃) δ 1.76(d, J=0.9Hz, 6H), 1.81(d, J=0.6Hz, 6H), 3.22(s, 6H), 3.80(s, 6H), 4.63(d, J=6.6Hz, 4H), 5.48–5.53(m, 2H), 6.92 (s, 2H), 7.05(d, J=8.4Hz, 2H), 7.48(dd, J=2.1 and 8.4Hz, 2H), 7.57(d, J=2.1Hz, 2H)<br>IR(KBr)1523, 1492, 1468, 1353, 1286, 1258, 1213, 1174, 1108cm⁻¹ |
| I-66 | ¹HNMR(CDCl₃) δ 1.76(s, 6H), 1.82(s, 6H), 3.78(s, 6H), 4.62(d, J=6.9Hz, 4H), 5.50–5.55(m, 2H), 5.71(s, 2H), 6.91–6.94(m, 4H), 7.08(dd, J=2.1 and 8.4Hz, 2H), 7.57(d, J=2.1Hz, 2H)<br>IR(KBr)3600–3200(br), 1523, 1492, 1271, 1242, 1210, 1186, 1034cm⁻¹ |
| I-67 | ¹HNMR(CDCl₃) δ 1.77(s, 3H), 1.81(s, 3H), 3.22(s, 3H), 3.28(s, 3H), 3.79(s, 3H), 3.80(s, 3H), 4.63(d, J=6.6Hz, 2H), 5.48–5.53(m, 1H), 6.92 (s, 1H), 6.93(s, 1H), 7.06(d, J=8.4Hz, 1H), 7.13(d, J=8.4Hz, 2H), 7.42–7.51(m, 3H), 7.57(d, J=21Hz, 1H)<br>IR(KBr)3600–3200(br), 1525, 1493, 1362, 1293, 1210, 1172, 1107cm⁻¹ |
| I-68 | m.p. 168–169° C.<br>¹HNMR(CDCl₃) δ 3.18(s, 3H), 3.78(s, 3H), 3.79(s, 3H), 5.17(s, 2H), 5.71(s, 1H), 6.92(s, 1H), 6.96(s, 1H), 6.99(d, J=8.7Hz, 1H), 7.08(dd, J=2.1 and 8.7Hz, 1H), 7.24(d, J=2.1Hz, 1H), 7.26–7.48(m, 7H)<br>IR(KBr)3600–3200(br), 1488, 1382, 1369, 1269, 1206, 1174, 1146cm⁻¹ |
| I-69 | m.p. 155–157° C.<br>¹HNMR(CDCl₃) δ 3.12(s, 3H), 3.19(s, 3H), 3.80(s, 6H), 5.18(s, 2H), 6.92(s, 1H), 6.95(s, 1H), 7.12(d, J=8.7Hz, 1H), 7.32–7.51(m, 8H), 7.60–7.65(m, 3H)<br>IR(KBr)1491, 1363, 1210, 1174, 1151, 1114cm⁻¹ |
| I-70 | m.p. 109–110° C.<br>¹HNMR(CDCl₃) δ 1.77(s, 3H), 1.81(s, 3H), 3.19(s, 3H), 3.23(s, 3H), 3.80(s, 6H), 4.64(d, J=6.6Hz, 2H), 5.05–5.30(m, 1H), 6.92(s, 1H), 6.95 (s, 1H), 7.06(d, J=8.7Hz, 1H), 7.33–7.37(m, 2H), 7.49(dd, J=2.1 and 8.7Hz, 1H)7.58(d, J=2.1Hz, 1H), 7.61–7.64(m, 2H)<br>IR(KBr)1522, 1489, 1368, 1351, 1294, 1260, 1212, 1178, 1149, 1114, 975cm⁻¹ |

TABLE 24

| | |
|---|---|
| I-71 | ¹HNMR(CDCl₃) δ 1.72(s, 3H), 1.76(s, 3H), 3.72(s, 3H), 3.73(s, 3H), 4.56(d, J=6.6Hz, 2H), 5.46–5.49(brs, 1H), 6.79–6.82(m, 2H), 6.88–7.01 (m, 5H), 7.34–7.39(m, 2H), 8.89(s, 1H), 9.45(s, 1H)<br>IR(KBr)3600–3100(br), 1524, 1493, 1458, 1386, 1261, 1206, 1010cm⁻¹ |

TABLE 24-continued

I-72 m.p. 123–124° C.
$^1$HNMR(CDCl$_3$) δ 1.77(s, 3H), 1.81(s, 3H), 3.19(s, 3H), 3.80(s, 6H), 4.64(d, J=6.9Hz, 2H), 5.52–5.57(m, 1H), 6.93(s, 1H), 6.94(s, 1H), 7.04 (t, J=8.7Hz, 1H), 7.26–7.39(m, 3H), 7.60–7.65(m, 2H)
IR(KBr)1524, 1494, 1463, 1379, 1265, 1211, 1174, 1154, 1130cm$^{-1}$

I-73 m.p. 118–119° C.
$^1$HNMR(CDCl$_3$) δ 1.77(s, 3H), 1.81(s, 3H), 3.79(s, 3H), 3.80(s, 3H), 4.63(d, J=6.9Hz, 2H), 4.86(s, 1H), 5.52–5.57(m, 1H), 6.88–6.93(m, 4H), 7.03(t, J=8.7Hz, 1H), 7.26–7.29(m, 1H), 7.37(dd, J=2.4 and 12.9Hz, 1H), 7.40–7.50(m, 2H)
IR(KBr)3600–3100(br), 1525, 1492, 1466, 1381, 1263, 1206cm$^{-1}$ I-74 $^1$HNMR(CDCl$_3$) δ 2.63(s, 3H), 3.19(s, 3H), 5.18(s, 2H), 5.74(s, 1H), 7.03(d, J=8.4Hz, 1H), 7.07(dd, J=2.1 and 8.4Hz, 1H), 7.12(d, J=2.1Hz, 1H), 7.36–7.68(m, 12H)
IR(KBr)3700–3200(br), 1486, 1367, 1353, 1197, 1179, 1147cm$^{-1}$ I-75 $^1$HNMR(CDCl$_3$) δ 2.80(s, 3H), 3.14(s, 3H), 3.19(s, 3H), 5.20(s, 2H), 7.18(d, J=8.4Hz, 1H), 7.38–7.68(m, 14H)
IR(KBr)1485, 1361, 1186, 1156, 1107cm$^{-1}$ I-76 $^1$HNMR(CDCl$_3$) δ 1.78(s, 3H), 1.82(s, 3H), 2.81(s, 3H), 3.19(s, 3H), 3.26(s, 3H), 4.65(d, J=7.2Hz, 1H), 5.47–5.52(m, 1H), 7.11(d, J=8.7Hz, 1H), 7.37–7.67(m, 9H)
IR(KBr)1486, 1365, 1186, 1154, 1106, 973, 926, 870, 810cm$^{-1}$

TABLE 25

I-77 m.p. 174–176° C.
$^1$HNMR(CDCl$_3$), δ 1.72(s, 3H), 1.76(s, 3H), 4.55(d, J=6.0Hz, 2H), 5.45–5.49(m, 1H), 6.82–7.43(m, 10H), 8.84(s, 1H), 9.45(s, 1H), 9.53(s, 1H)
IR(KBr)3600–3100(br), 1610, 1594, 1532, 1496, 1444, 1409, 1305, 1245, 1209cm$^{-1}$

I-78 m.p. 134–135° C.
$^1$HNMR(CDCl$_3$) δ 3.78(s, 3H), 3.79(s, 3H), 5.17(s, 2H), 5.70(s, 1H), 6.91(s, 1H), 6.95(s, 1H), 6.99(d, J=8.4Hz, 1H), 7.07–7.14(m, 3H), 7.22 (d, J=2.1Hz, 1H), 7.36–7.47(m, 5H), 7.52–7.57(m, 2H)
IR(KBr)3600–3100(br), 1524, 1494, 1462, 1381, 1273, 1248, 1213cm$^{-1}$

I-79 $^1$HNMR(CDCl$_3$) δ 3.12(s, 3H), 3.79(s, 3H), 3.80(s, 3H), 5.18(s, 2H), 6.92(s, 1H), 6.94(s, 1H), 7.09–7.15(m, 3H), 7.38–7.56(m, 8H), 7.60 (d, J=2.1Hz, 1H)
IR(KBr)1522, 1493, 1467, 1387, 1365, 1279, 1213, 1112cm$^{-1}$

I-80 m.p. 110–111° C.
$^1$HNMR(CDCl$_3$) δ 1.77(s, 3H), 1.81(s, 3H), 3.22(s, 3H), 3.78(s, 3H), 3.80(s, 3H), 4.63(d, J=6.9Hz, 2H), 5.50–5.57(m, 1H), 6.91(s, 1H), 6.94 (s, 1H), 7.04–7.14(m, 3H), 7.47–7.58(m, 4H)
IR(KBr)1552, 1493, 1364, 1212, 1110, 970cm$^{-1}$

I-81 $^1$HNMR(CDCl$_3$) δ 1.77(s, 3H), 1.82(s, 3H), 3.78(s, 3H), 3.79(s, 3H), 4.62(d, J=6.9Hz, 2H), 5.50–5.55(m, 1H), 5.72(s, 1H), 6.91–6.95(m, 3H), 7.06–7.14(m, 3H), 7.20(d, J=1.8Hz, 1H), 7.52–7.57(m, 2H)
IR(KBr)3536, 1520, 1493, 1386, 1271, 1241, 1210cm$^{-1}$

I-82 $^1$HNMR(CDCl$_3$) δ 1.29(t, J=7.2Hz, 3H), 1.76(s, 3H), 1.79(s, 3H), 3.78(s, 6H), 3.78(q, 2H), 4.64(d, J=6.3Hz, 2H), 4.72(s, 2H), 5.53–5.78 (m, 1H), 6.61(s, 1H), 6.94(s, 1H), 6.98(d, J=8.7Hz, 1H), 7.09–7.20(m, 4H), 7.52–7.57(m, 2H)
IR(KBr)1758, 1524, 1496, 1461, 1387, 1263, 1209, 1147cm$^{-1}$

TABLE 26

I-83 $^1$HNMR(CDCl$_3$) δ 2.76(s, 3H), 3.21(s, 3H), 3.55(s, 3H), 3.77(s, 3H), 5.26(s, 2H), 6.85(s, 1H), 7.17(d, J=8.7Hz, 1H), 7.31–7.50(m, 8H), 7.60–7.71(m, 3H), 7.92(s, 1H)
IR(KBr)1684, 1606, 1512, 1478, 1177, 1150, 1080, 1016cm$^{-1}$

I-84 $^1$HNMR(CDCl$_3$) δ 1.26(t, J=7.2Hz, 3H), 3.08(s, 3H), 3.22(s, 3H), 3.31(s, 3H), 3.74(s, 3H), 4.16(q, J=7.2Hz, 2H), 5.17(s, 2H), 6.44(d, J=16.5Hz, 1H), 6.89(s, 1H), 7.13(s, 2H), 7.27(d, J=8.4Hz, 1H), 7.35–7.50(m, 8H), 7.69(d, J=8.4Hz, 2H)
IR(KBr)1708, 1633, 1513, 1465, 1367, 1271, 1230, 1176, 1151, 1120, 1017cm$^{-1}$

I-85 $^1$HNMR(CDCl$_3$) δ 1.26(t, J=7.2Hz, 3H), 3.22(s, 3H), 3.31(s, 3H), 3.74(s, 3H), 4.16(q, J=7.2Hz, 2H), 5.15(s, 2H), 5.70(s, 1H), 6.53(d, J=16.5Hz, 1H), 6.69(dd, J=8.4and2.4Hz, 1H), 6.88(s, 2H), 7.00(d, J=8.4Hz, 1H), 7.33–7.50(m, 8H), 7.70(d, J=8.4Hz, 2H)
IR(KBr)3398, 1675, 1627, 1581, 1512, 1465, 1370, 1284, 1256, 1221, 1148, 1074, 1017cm$^{-1}$ I-86 $^1$HNMR(CDCl$_3$) δ 2.53(s, 3H), 3.21(s, 3H), 3.56(s, 3H), 3.77(s, 3H), 4.58(s, 2H), 5.24(s, 2H), 6.83(s, 1H), 6.96(d, J=8.4Hz, 1H), 7.28–7.57 (m, 9H), 7.69(d, J=8.4Hz, 2H)
IR(KBr)1605, 1512, 1479, 1366, 1233, 1175, 1149, 1080, 1015cm$^{-1}$ I-87 $^1$HNMR(CDCl$_3$) δ 1.76(s, 3H), 1.81(s, 3H), 3.27(s, 3H), 3.78(s, 3H), 3.79(s, 3H), 4.63(d, J=6.6Hz, 2H), 5.40–5.50(m, 1H), 5.71(s, 1H), 6.07 (s, 1H), 6.91–6.95(m, 3H), 7.05–7.20(m, 3H), 7.43–7.51(m, 2H)
IR(KBr)3600–3200(br), 1617, 1525, 1494, 1464, 1361, 1292, 1208, 1178, 1101, 1033cm$^{-1}$ I-88 $^1$HNMR(CDCl$_3$) δ 2.57(s, 3H), 3.20(s, 3H), 3.56(s, 3H), 3.79(s, 3H), 5.18(s, 2H), 6.84(s, 1H), 7.06–7.15(m, 1H), 7.20–7.40(m, 9H), 7.47–7.57 (m, 2H), 7.60–7.75(m, 3H), 8.20–8.25(m, 2H)

I-89 $^1$HNMR(CDCl$_3$) δ 3.44(s, 3H), 3.75(s, 3H), 5.01(s, 1H), 5.18(s, 2H), 6.01(s, 1H), 6.45(s, 1H), 6.88–6.97(m, 2H), 7.07(dd, J=8.4and8.4Hz, 1H), 7.15–7.21(m, 1H), 7.27(dd, J=12.3 and 2.1Hz, 1H), 7.29–7.43(m, 3H), 7.45–7.56(m, 4H)

TABLE 27

I-90 $^1$HNMR(CDCl$_3$) δ 1.68(s, 3H), 1.75(d, J=0.9Hz, 3H), 2.55(dt, J=6.9and6.9Hz, 2H), 2.70(s, 3H), 3.21(s, 3H), 3.55(s, 3H), 3.77(s, 3H), 4.04 (t, J=6.9Hz, 2H), 5.17–5.28(m, 1H), 6.84(s, 1H), 7.04(dd, J=8.4and8.4Hz, 1H), 7.11–7.22(m, 2H), 7.34–7.42(m, 2H), 7.65–7.75(m, 2H)
IR(KBr)1522, 1483, 1361, 1352, 1176, 1156, 1079, 963, 873, 801cm$^{-1}$ I-91 $^1$HNMR(CDCl$_3$) δ 2.96(s, 3H), 3.52(s, 3H), 3.58(s, 6H), 3.73(s, 3H), 4.89(s, 2H), 5.19(s, 2H), 5.23(s, 2H), 5.25(s, 2H), 6.68(s, 1H), 6.98 (d, J=8.4Hz, 1H), 7.04(dd, J=8.4and2.1Hz, 1H), 7.11(m, 2H), 7.25(d, J=2.1Hz, 1H), 7.30–7.40(m, 5H), 7.51(m, 2H)
IR(KBr)2952, 2935, 2896, 1609, 1521, 1477, 1463, 1438, 1383, 1269, 1249, 1228, 1183, 1153, 1130, 1116, 1078, 1066, 1020, 1008, 984, 944, 922, 903, 832, 801, 730cm$^{-1}$

TABLE 27-continued

I-92  mp 122–124° C.
 $^1$HNMR(CDCl$_3$) δ 2.70(brs, 3H), 3.55–3.60(br, 2H), 3.60(s, 3H), 3.75(s, 3H), 3.81–3.83(m, 2H), 3.87(s, 3H), 5.15(s, 2H), 5.68(s, 1H), 6.69 (s, 1H), 6.94(dd, J=2.1, 8.4Hz, 1H), 6.97–7.03(m, 3H), 7.07(d, J=1.8Hz, 1H), 7.38–7.48(m, 5H), 7.51–7.56(m, 2H)
 IR(KBr)3600–2800(br), 1607, 1597, 1550, 1518, 1477, 1462, 1452, 1392, 1289, 1248, 1228, 1175, 1122, 1096, 1084, 1015cm$^{-1}$ I-93  $^1$HNMR(CDCl$_3$) δ 2.59(dt, J=6.6, 6.6Hz, 2H), 3.45(s, 3H), 3.74(s, 3H), 4.15(t, J=6.6Hz, 2H), 5.15(dm, J=10.2Hz, 1H), 5.21(dm, J=17.1Hz, 1H), 5.90(m, 1H), 6.45(s, 1H), 6.92(d, J=8.4Hz, 2H), 6.95(s, 2H), 7.06(brs, 1H), 7.53(d, J=8.4Hz, 2H)
 IR(Nujol)3570, 3525, 3336, 3205, 1616, 1596, 1524, 1493, 1409, 1315, 1286, 1264, 1239, 1225, 1117, 1072, 821, 783cm$^{-1}$ I-94  $^1$HNMR(CDCl$_3$) δ 0.36(m, 2H), 0.66(m, 2H), 1.31(m, 1H), 3.45(s, 3H), 3.74(s, 3H), 3.91(d, J=7.2Hz, 2H), 6.44(s, 1H), 6.91(d, J=8.7Hz, 2H), 6.93(m, 2H), 7.07(d, J=1.8Hz, 1H), 7.53(d, J=8.7Hz, 2H)
 IR(Nujol)3570, 3491, 3364, 3178, 1617, 1598, 1583, 1524, 1494, 1408, 1313, 1285, 1266, 1240, 1224, 1115, 1072, 1011, 822, 786cm$^{-1}$ I-95  $^1$HNMR(CDCl$_3$) δ 1.86(s, 3H), 3.45(s, 3H), 3.74(s, 3H), 4.54(s, 2H), 5.04(brs, 1H), 5.12(brs, 1H), 6.45(s, 1H), 6.91(d, J=8.7Hz, 2H), 6.95 (m, 2H), 7.08(brs, 1H), 7.53(d, J=8.7Hz, 2H)
 IR(Nujol)3536, 3364, 3179, 1614, 1586, 1524, 1493, 1407, 1309, 1284, 1265, 1238, 1226, 1115, 1073, 1011, 887, 821, 782cm$^{-1}$

TABLE 28

I-96  $^1$HNMR(CDCl$_3$) δ 2.58(t, J=2.4Hz, 1H), 3.45(s, 3H), 3.74(s, 3H), 4.79(d, J=2.4Hz, 2H), 6.45(s, 1H), 6.92(d, J=8.7Hz, 2H), 6.98(dd, J=8.4, 2.1Hz, 1H), 7.07(d, J=8.4Hz, 1H), 7.09(d, J=2.1Hz, 1H), 7.53(d, J=8.7Hz, 2H)
 IR(Nujol)3410, 3282, 1612, 1589, 1523, 1489, 1404, 1226, 1114, 1071, 1015, 826cm$^{-1}$ I-97  $^1$HNMR(CDCl$_3$) δ 2.71(s, 3H), 3.21(s, 3H), 3.38(s, 3H), 3.56(s, 3H), 3.78(s, 3H), 5.47(s, 2H), 6.84(s, 1H), 7.00(d, J=8.6Hz, 1H), 7.34(dd, J=8.6, 2.0Hz, 1H), 7.38(d, J=8.8Hz, 2H), 7.46(d, J=2.0Hz, 1H), 7.55(m, 2H), 7.67(m, 1H), 7.68(d, J=8.8Hz, 2H), 7.99(m, 2H)

I-98  m.p. 200–203° C.
 $^1$HNMR(CDCl$_3$) δ 2.38(s, 3H), 2.67(s, 3H), 3.12(s, 3H), 3.21(s, 3H), 3.56(s, 3H), 3.77(s, 3H), 5.14(s, 2H), 6.84(s, 1H), 7.15(d, J=8.7Hz, 1H), 7.21(d, J=8.1Hz, 2H), 7.34(d, J=8.1Hz, 2H), 7.34(dd, J=8.7, 2.4Hz, 1H), 7.38(d, J=8.7Hz, 2H), 7.40(d, J=2.4Hz, 1H), 7.68(d, J=8.7Hz, 2H)
 IR(Nujol)1608, 1520, 1480, 1359, 1173, 1156, 1078, 1016, 976, 948, 872, 818, 791cm$^{-1}$ I-99  $^1$HNMR(CDCl$_3$) δ 2.72(s, 3H), 3.13(s, 3H), 3.21(s, 3H), 3.55(s, 3H), 3.78(s, 3H), 5.15(s, 2H), 6.84(s, 1H), 7.09(d, J=8.7Hz, 1H), 7.12(dd, J=8.7, 7.2Hz, 1H), 7.35(dd, J=8.7, 2.1Hz, 1H), 7.38(d, J=8.7Hz, 2H), 7.40(d, J=2.1Hz, 1H), 7.45(dd, J=8.7, 5.1Hz, 1H), 7.68(d, J=8.7Hz, 2H)

I-100  $^1$HNMR(CDCl$_3$) δ 2.76(s, 3H), 3.19(s, 3H), 3.21(s, 3H), 3.55(s, 3H), 3.78(s, 3H), 5.25(s, 2H), 6.85(s, 1H), 7.13(d, J=8.4Hz, 1H), 7.32(dd, J=8.4, 1.8Hz, 1H), 7.36(dd, J=8.4, 1.8Hz, 1H), 7.38(d, J=8.7Hz, 2H), 7.42(d, J=1.8Hz, 1H), 7.45(d, J=1.8Hz, 1H), 7.59(d, J=8.4Hz, 1H), 7.68(d, J=8.7Hz, 2H)

I-101  m.p. 103–105° C.
 $^1$HNMR(CDCl$_3$) δ 2.18(dd, J=1.5, 1.2Hz, 3H), 3.45(s, 3H), 3.74(s, 3H), 4.79(dd, J=5.7, 1.2Hz, 2H), 5.81(dt, J=5.7, 1.5Hz, 2H), 6.45(s, 1H), 6.92(d, J=8.7Hz, 2H), 6.95(s, 1H), 6.96(s, 1H), 7.07(s, 1H), 7.52(d, J=8.7Hz, 2H)
 IR(KBr)3527, 3328, 2930, 1614, 1593, 1523, 1492, 1463, 1408, 1262, 1235, 1225, 1119, 1072, 1010, 828, 805cm$^{-1}$

TABLE 29

I-102  m.p. 95–99° C.
 $^1$HNMR(CDCl$_3$) δ 3.45(s, 3H), 3.74(s, 3H), 4.67(s, 2H), 5.47(m, 1H), 5.55(dd, J=2.7, 1.2Hz, 1H), 6.45(s, 1H), 6.92(d, J=8.7Hz, 2H), 7.01 (m, 2H), 7.04(d, J=1.8Hz, 1H), 7.53(d, J=8.7Hz, 2H)

I-103  $^1$HNMR(CDCl$_3$) δ 3.45(s, 3H), 3.75(s, 3H), 4.59(d, J=4.2Hz, 2H), 6.45(s, 1H), 6.45(m, 1H), 6.55(d, J=12.9Hz, 1H), 6.92(d, J=8.7Hz, 2H), 6.96(brs, 2H), 7.08(brs, 1H), 7.53(d, J=8.7Hz, 2H)

I-104  $^1$HNMR(CDCl$_3$) δ 3.45(s, 3H), 3.75(s, 3H), 4.64(dd, J=6.0and1.2Hz, 2H), 6.23(dt, J=13.2and6.0Hz, 1H), 6.42(dt, J=13.2and1.2Hz, 1H), 6.45(s, 1H), 6.91(d, J=8.7Hz, 2H), 6.96(brs, 2H), 7.08(brs, 1H), 7.58(d, J=8.7Hz, 2H)

I-105  $^1$HNMR(CDCl$_3$) δ 3.46(s, 3H), 3.75(s, 3H), 3.98(d-like, J=7.2Hz, 1H), 4.64(d-like, J=3.9Hz, 1H), 6.04(dt, J=15.3, 4.8Hz, 1H), 6.06(1H, dt, J=15.3, 6.0Hz, 1H), 6.45(s, 1H), 6.92(d, J=8.7Hz, 2H), 6.95(s, 1H), 7.08(s, 2H), 7.53(d, J=8.7Hz, 2H)

I-106  foam
 $^1$HNMR(CDCl$_3$) δ 1.76(s, 3H), 1.83(s, 3H), 2.08(s, 3H), 3.36(s, 3H), 3.71(s, 3H), 4.61(d, J=7.0Hz, 2H,), 4.94(s, 1H), 5.54(t, J=7.0Hz, 1H), 5.70(s, 1H), 6.70(dd, J=8.4, 2.0Hz, 1H), 6.74(s, 1H), 6.84(d, J=2.0Hz, 1H)
 IR(KBr)3410, 1520, 1476, 1390, 1243, 1225, 1101, 1084, 834, 812, 775cm$^{-1}$ I-107  m.p. 112–114° C.
 $^1$HNMR(CDCl$_3$) δ 3.03(s, 3H), 3.57(s, 3H), 3.74(s, 3H), 3.87(s, 3H), 4.90(S, 2H), 5.15(s, 2H), 5.63(brs, 1H), 6.68(s, 1H), 6.91–7.07(m, 5H), 7.38–7.51(m, 5H), 7.53(m, 2H)
 IR(KBr)3512, 2952, 2936, 1607, 1519, 1468, 1442, 1382, 1284, 1253, 1229, 1215, 1185, 1156, 1112, 1079, 1065, 1020, 983, 956, 914, 831cm$^{-1}$ I-108  $^1$HNMR(CDCl$_3$) δ 2.20(d, J=1.2Hz, 3H), 2.76(s, 3H), 3.22(s, 3H), 3.24(s, 3H), 3.56(s, 3H), 3.78(s, 3H), 4.65(m, 2H), 5.96(m, 1H), 7.07 (d, J=8.4Hz, 1H), 7.34–7.41(m, 4H), 7.68(m, 2H)

TABLE 30

I-109  m.p. 153–154° C.
 $^1$HNMR(CDCl$_3$) δ 2.20(d, J=1.5Hz, 3H), 2.75(s, 3H), 3.21(s, 3H), 3.23(s, 3H), 3.56(s, 3H), 3.78(s, 3H), 4.81(m, 2H), 5.80(m, 1H), 6.84( s, 1H), 7.10(d, J=8.1Hz, 1H), 7.34–7.41(m, 4H), 7.68(m, 2H)
 IR(KBr)1519, 1481, 1390, 1364, 1234, 1177, 1150, 1119, 1077, 1011, 969, 945, 876, 816, 799, 521cm$^{-1}$

I-110  $^1$HNMR(CDCl$_3$) δ 2.68(s, 3H), 3.11(s, 3H), 3.21(s, 3H), 3.56(s, 3H), 3.78(s, 3H), 3.83(s, 3H), 5.11(s, 2H), 6.84(s, 1H), 6.93(d, J=8.7Hz, 2H), 7.16(d, J=8.7Hz, 1H), 7.35(dd, J=8.7, 2.1Hz, 1H), 7.36–7.40(m, 5H), 7.68(d, J=8.7Hz, 2H)

I-111  $^1$HNMR(CDCl$_3$) δ 2.78(s, 3H), 3.22(s, 6H), 3.55(s, 3H), 3.78(s, 3H), 5.23(s, 2H), 6.85(s, 1H), 7.08(d, J=8.7Hz, 1H), 7.34(dd, J=8.7, 2.1Hz, 1H), 7.39(d, J=8.7Hz, 2H), 7.42(d, J=2.1Hz, 1H), 7.44(brs, 2H), 7.68(d, J=8.7Hz, 2H), 8.70(brs, 2H)

I-112  $^1$HNMR(CDCl$_3$) δ 2.70(s, 3H), 3.21(s, 3H), 3.24(s, 3H), 3.55(s, 3H), 3.78(s, 3H), 5.33(s, 2H), 6.84(s, 1H), 7.15(d, J=8.4Hz, 1H), 7.27(dd, J=7.5, 4.2Hz, 1H), 7.33(dd, J=8.4, 2.4Hz, 1H), 7.38(d, J=8.7Hz, 2H), 7.42(d, J=2.4Hz, 1H), 7.62(brd, J=7.5Hz, 1H), 7.68(d, J=8.7Hz, 2H), 7.76(ddd, J=7.5, 7.5, 1.8Hz, 1H), 8.61(d, J=4.2Hz, 1H)

I-113  $^1$HNMR(CDCl$_3$) δ 2.76(s, 3H), 3.15(s, 3H), 3.21(s, 3H), 3.55(s, 3H), 3.78(s, 3H), 5.22(s, 2H), 6.85(s, 1H), 7.17(d, J=8.4Hz, 1H), 7.38(dd, J=8.4, 2.1Hz, 1H), 7.38(m, 1H), 7.39(d, J=8.7Hz, 2H), 7.42(d, J=2.1Hz, 1H), 7.68(d, J=8.7Hz, 2H), 7.88(d, J=7.8Hz, 1H), 7.64(brs, 1H), 8.73(brs, 1H)

TABLE 30-continued

I-114  $^1$HNMR(CDCl$_3$) δ 3.45(s, 3H), 3.74(s, 3H), 5.10(s, 2H), 6.45(s, 1H), 6.91(d, J=8.7Hz, 2H), 6.95(dd, J=8.4, 2.1Hz, 1H), 7.03(d, J=8.4Hz, 1H), 7.08(d, J=2.1Hz, 1H), 7.23(brd, J=7.8Hz, 2H), 7.34(brd, J=7.8Hz, 2H), 7.53(d, J=8.7Hz, 2H)
IR(Nujol)3464, 3344, 1611, 1581, 1523, 1490, 1266, 1113, 1073, 1011, 1000, 821, 782cm$^{-1}$ I-115  $^1$HNMR(CDCl$_3$) δ 3.45(s, 3H), 3.75(s, 3H), 5.11(s, 2H), 6.45(s, 1H), 6.92(d, J=8.7Hz, 2H), 6.96(dd, J=8.4, 2.1Hz, 1H), 7.01(d, J=8.4Hz, 1H), 7.09(d, J=2.1Hz, 1H), 7.11(dd, J=8.7, 8.7Hz, 2H), 7.42(dd, J=8.7, 5.4Hz, 2H), 7.54(d, J=8.7Hz, 2H)
IR(Nujol)3560, 3400, 1612, 1589, 1522, 1492, 1260.1225, 1116, 1068, 1006, 992, 841, 826, 803, 786cm$^{-1}$

TABLE 31

I-116  $^1$HNMR(CDCl$_3$) δ 3.45(s, 3H), 3.75(s, 3H), 5.23(s, 2H), 6.45(s, 1H), 6.92(d, J=8.7Hz, 2H), 6.97(brs, 2H), 7.11(brs, 1H), 7.31(dd, J=8.4, 2.1Hz, 1H), 7.46(d, J=8.4Hz, 1H), 7.47(d, J=2.1Hz, 1H), 7.54(d, J=8.7Hz, 2H)
IR(Nujol)3460, 3359, 1610, 1594, 1522, 1490, 1264, 1164, 1110, 1072, 1008, 877, 824, 781cm$^{-1}$ I-117  $^1$HNMR(CDCl$_3$) δ 3.45(s, 3H), 3.75(s, 3H), 3.84(s, 3H), 5.07(s, 2H), 6.45(s, 1H), 6.92(d, J=8.7Hz, 2H), 6.95(d, J=9.0Hz, 2H), 6.96(dd, J=8.4, 1.8Hz, 1H), 7.04(d, J=8.4Hz, 1H), 7.08(d, J=1.8Hz, 1H), 7.37(d, J=8.7Hz, 2H), 7.53(d, J=9.0Hz, 2H)
IR(Nujol)3400, 1612, 1586, 1516, 1488, 1246, 1174, 1113, 1070, 1011, 823cm$^{-1}$ I-118  $^1$HNMR(DMSO-d$_6$) δ 3.29(s, 3H), 3.64(s, 3H), 5.20(s, 2H), 6.39(s, 1H), 6.64(dd, J=8.4, 2.1Hz, 1H), 6.79(d, J=2.1Hz, 1H), 6.84(d, J=8.7Hz, 2H), 6.92(d, J=8.4Hz, 1H), 7.43(d, J=8.7Hz, 2H), 7.52(d, J=6.0Hz, 2H), 8.59(d, J=6.0Hz, 2H)
IR(Nujol)3473, 3441, 1610, 1582, 1523, 1493, 1404, 1241, 1112, 1074, 1005, 816, 782cm$^{-1}$ I-119  $^1$HNMR(CDCl$_3$) δ 3.45(s, 3H), 3.74(s, 3H), 5.27(s, 2H), 6.45(s, 1H), 6.92(dd, J=8.4, 1.8Hz, 1H), 6.93(d, J=8.7Hz, 2H), 7.11(d, J=8.4Hz, 1H), 7.12(d, J=1.8Hz, 1H), 7.31(m, 1H), 7.36(brd, J=7.5Hz, 1H), 7.53(d, J=8.7Hz, 2H), 7.77(ddd, J=7.5, 7.5, 1.8Hz, 1H), 8.66(d, J=5.0Hz, 1H)
IR(Nujol)3555, 3467, 3342, 1608, 1597, 1586, 1522, 1466, 1210, 1117, 1080, 1016, 822, 761cm$^{-1}$ I-120  $^1$HNMR(CDCl$_3$) δ 3.45(s, 3H), 3.74(s, 3H), 5.21(s, 2H), 6.46(s, 1H), 6.91(d, J=8.7Hz, 2H), 6.99(brs, 2H), 7.11(brs, 1H), 7.40(dd, J=7.5, 5.0Hz, 1H), 7.53(d, J=8.7Hz, 2H), 7.83(d, J=7.5Hz, 1H), 8.64(brd, J=5.0Hz, 1H), 8.74(brs, 1H)
IR(Nujol)3342, 1609, 1586, 1522, 1489, 1253, 1118, 1074, 1010, 827, 782cm$^{-1}$ I-121  m.p. 166–168° C.
$^1$HNMR(CDCl$_3$) δ 3.45(s, 3H), 3.75(s, 3H), 4.77(d, J=6.3Hz, 2H), 6.22(t, J=6.3Hz, 1H), 6.93(d, J=8.7Hz, 2H), 6.93(d, J=8.7Hz, 1H), 6.98(dd, J=8.7, 1.8Hz, 1H), 7.08(d, J=1.8Hz, 1H), 7.53(d, J=8.7Hz, 2H)
IR(KBr)3474, 3411, 2957, 2930, 1615, 1589, 1569, 1523, 1492, 1407, 1286, 1263, 1230, 1113, 1070, 825cm$^{-1}$

TABLE 32

I-122  m.p. 190–192° C.
$^1$HNMR(CDCl$_3$) δ 2.56(s, 3H), 3.22(s, 3H), 3.56(s, 3H), 3.79(s, 3H), 5.17(s, 2H), 5.73(s, 1H), 6.84(s, 1H), 6.93(dd, J=8.1 and 1.9Hz, 1H), 7.02(d, J=8.1Hz, 1H), 7.05(d, J=1.9Hz, 1H), 7.37–7.45(m, 1H), 7.71(d, J=8.6Hz, 2H)
IR(KBr)3512, 1519, 1484, 1367, 1174, 1150, 1078, 957, 870, 798cm$^{-1}$ I-123  foam
$^1$HNMR(CDCl$_3$) δ 3.08(s, 3H), 3.21(s, 3H), 3.44(s, 3H), 3.78(s, 3H), 5.15(s, 2H), 6.95(s, 1H), 7.11(d, J=8.7Hz, 1H), 7.33–7.47(m, 9H), 7.71(d, J=8.7Hz, 2H), 13.3–14.5(brs, 1H)
IR(KBr): 3422, 1735, 1702, 1520, 1471, 1366, 1175, 1150, 1118, 971, 954, 863, 807cm$^{-1}$ I-124  m.p. 258–259° C. (dec)
$^1$HNMR(DMSO-d$_6$) δ 3.32(s, 3H), 3.69(s, 3H), 5.10(2H, s), 6.65(dd, J=8.4, 2.1Hz, 1H), 6.79(d, J=2.1Hz, 1H), 6.86(d, J=8.4Hz, 2H), 6.90(s, 1H), 6.94(d, J=8.4Hz, 1H), 7.30–7.54(m, 7H), 8.98(s, 1H), 9.63(s, 1H)
IR(KBr): 3437, 3157, 1702, 1610, 1590, 1521, 1474, 1464, 1379, 1260, 1245, 1224, 1061, 1014, 952, 834, 793, 748, 698cm$^{-1}$ I-125  $^1$HNMR(CDCl$_3$) δ 1.75(s, 3H), 1.81(s, 3H), 3.21(s, 3H), 3.41(s, 3H), 3.68(s, 3H), 3.77(s, 3H), 4.61(d, J=6.8Hz, 2H), 5.50(t, J=6.8Hz, 1H), 6.93(s, 1H), 7.02(d, J=8.5Hz, 1H), 7.27(d, J=8.5, 2.3Hz, 1H), 7.33(dd, J=2.3Hz, 1H), 7.38(d, J=8.6Hz, 2H), 7.71(d, J=8.6Hz, 2H)

I-126  $^1$HNMR(CDCl$_3$) δ 1.75(s, 3H), 1.81(s, 3H), 3.41(s, 3H), 3.65(s, 3H), 3.76(s, 3H), 4.59(d, J=6.6Hz, 2H), 5.06(s, 1H), 5.51(t, J=6.6Hz, 1H), 5.67(s, 1H), 6.83(dd, J=8.4, 2.1Hz, 1H), 6.87(s, 1H), 6.90–6.93(m, 3H), 6.98(d, J=2.1Hz, 1H), 7.54(d, J=9.0Hz, 2H)

I-127  m.p. 116–117° C.
$^1$HNMR(DMSO-d$_6$) δ 1.72(s, 3H), 1.76(s, 3H), 3.32(s, 3H), 3.70(s, 3H), 4.53(d, J=7.1Hz, 2H), 5.48(t, J=7.1Hz, 1H), 6.65(dd, J=8.4, 2.1Hz, 1H), 6.73(d, J=2.1Hz, 1H), 6.86(d, J=8.6Hz, 2H), 6.88(d, J=8.4Hz, 1H), 6.93(s, 1H), 7.47(d, J=8.6Hz, 2H), 8.84(s, 1H), 9.62(s, 1H), 11.9–13.4(brs, 1H)
IR(KBr): 3446, 1703, 1611, 1593, 1520, 1471, 1380, 1260, 1225, 1081, 997, 952, 838cm$^{-1}$

TABLE 33

I-128  oil
$^1$HNMR(CDCl$_3$) δ 1.65(s, 3H), 1.78(s, 3H), 2.96(s, 3H), 3.22(s, 3H), 3.25(s, 3H)3.55(s, 3H), 3.79(s, 3H), 4.77(d, J=7.8Hz, 2H), 5.53(t, J=7.8Hz, 1H), 6.87(s, 1H), 7.39&7.67(ABq, J=8.7Hz, 4H), 7.70(d, J=2.1Hz, 1H), 7.86(d, J=2.1Hz, 1H), 10.36(s, 1H)
IR(CHCl$_3$)1691, 1473, 1374, 1230, 1226, 1209, 1178, 1152, 1086, 969, 874, 805cm$^{-1}$ I-129  oil
$^1$HNMR(CDCl$_3$) δ 1.73(d, J=0.9Hz, 3H), 1.80(s, 3H), 2.89(s, 3H), 3.20(s, 3H), 3.22(s, 3H), 3.54(s, 3H), 3.79(s, 3H), 4.66(d, J=7.8Hz, 2H), 4.77(s, 2H), 5.55(m, 1H), 6.85(s, 1H), 7.39&7.68(ABq, J=9.0Hz, 4H), 7.39(d, J=2.1Hz, 1H), 7.44(d, J=2.1Hz, 1H)
IR(CHCl$_3$)1475, 1372, 1230, 1178, 1151, 1085, 969, 874cm$^{-1}$ I-130  m.p. 189–190° C.
$^1$HNMR(CDCl$_3$) δ 1.36(s, 9H), 2.81(s, 3H), 3.22(s, 3H), 3.30(s, 3H), 3.56(s, 3H), 3.79(s, 3H), 6.86(s, 1H), 7.36–7.42(m, 3H), 7.54(d, J=1.8Hz, 1H), 7.67–7.72(m, 3H)
IR(KBr)1472, 1363, 1331, 1179, 1153, 1082, 961, 950, 877, 846, 817, 791, 526cm$^{-1}$ I-131  m.p. 147–148° C.
$^1$HNMR(CDCl$_3$) δ 2.95(s, 3H), 3.18(s, 3H), 3.22(s, 3H), 3.55(s, 3H), 3.79(s, 3H), 5.28(s, 2H), 6.86(s, 1H), 7.38–7.44(m, 7H), 7.67(m, 2H), 7.75(d, J=2.1Hz, 1H), 7.83(d, J=2.1Hz, 1H)
IR(KBr) 1687, 1512, 1472, 1365, 1352, 1234, 1201, 1180, 1151, 1082, 971, 947, 870, 846, 810, 794, 703, 523cm$^{-1}$

TABLE 33-continued

| | |
|---|---|
| I-132 | m.p. 122–124° C.<br>¹HNMR(CDCl₃) δ 1.68(s, 3H), 1.74(s, 3H), 2.80(s, 3H), 3.22(s, 3H), 3.28(s, 3H), 3.56(s, 3H), 3.62(d, J=7.8Hz, 2H), 3.78(s, 3H), 5.31(m, 1H), 6.85(s, 1H), 7.34(dd, J=8.1Hz, J=1.8Hz, 1H), 7.39&7.68(ABq, J=8.7Hz, 4H), 7.43(d, J=8.1Hz, 1H), 7.46(d, J=1.8Hz, 1H)<br>IR(KBr) 1474, 1362, 1180, 1151, 1076, 1014, 968, 944, 870, 816, 799, 521cm⁻¹ |
| I-133 | ¹HNMR(CDCl₃) δ 1.73(d, J=0.9Hz, 3H), 1.82(s, 3H), 3.44(s, 3H), 3.75(s, 3H), 4.54(d, J=6.9Hz, 2H), 4.78(s, 2H), 5.30(s, 1H), 5.61(m, 1H), 5.67(s, 1H), 6.01(s, 1H), 6.45(s, 1H), 6.92&7.52(ABq, J=8.7Hz, 4H), 7.02(d, J=2.1Hz, 1H), 7.05(d, J=2.1Hz, 1H)<br>IR(KBr)3428, 1612, 1522, 1483, 1458, 1403, 1362, 1334, 1304, 1266, 1226, 1174, 1116, 1083, 1024, 970, 938cm⁻¹ |

TABLE 34

| | |
|---|---|
| I-134 | m.p. 167–168° C.<br>¹HNMR(CDCl₃) δ 1.39(d, J=1.2Hz, 3H), 1.70(s, 3H), 3.36(d, J=8.1Hz, 2H), 3.45(s, 3H), 3.74(s, 3H), 4.98(s, 1H), 5.29(m, 1H), 5.96(s, 1H), 6.45(s, 1H), 6.78(s, 1H), 6.93&7.54(ABq, J=8.7Hz, 4H), 6.96(dd, J=7.8Hz, J=1.8Hz, 1H), 7.09(d, J=1.8Hz, 1H), 7.49(d, J=7.8Hz, 1H)<br>IR(KBr)3413, 3365, 2931, 1611, 1552, 1520, 1502, 1475, 1455, 1441, 1402, 1360, 1323, 1262, 1227, 1206, 1182, 1170, 1162, 1114, 1100, 1081, 1052, 1014, 941, 835, 816, 587, 542cm⁻¹ |
| I-135 | m.p. 183–184° C.<br>¹HNMR(CDCl₃) δ 3.46(s, 3H), 3.74(s, 3H), 3.83(s, 3H), 4.78(m, 2H), 5.99(m, 1H), 6.44(m, 1H), 6.45(s, 1H), 6.92(d, J=8.7Hz, 2H), 6.94(dd, J=8.1, 1.8Hz, 1H), 7.00(d, J=8.1Hz, 1H), 7.10(d, J=1.8Hz, 1H), 7.53(d, J=8.7Hz, 2H)<br>IR(KBr)3383, 2929, 1699, 1523, 1491, 1405, 1262, 1236, 1206, 1173, 1116, 1071, 1011, 822cm⁻¹ |
| I-136 | ¹HNMR(CD₃OD) δ 1.26(s, 3H), 1.29(s, 3H), 3.38(s, 3H), 3.68(s, 3H), 3.80(dd, J=8.4, 2.7Hz, 1H), 3.96(dd, J=9.6, 8.4Hz, 1H), 4.34(dd, J=9.6, 2.7Hz, 1H), 6.44(s, 1H), 6.80(dd, J=8.1, 1.8Hz, 1H), 6.85(d, J=8.7Hz, 2H), 6.86(d, J=1.8Hz, 1H), 7.96(d, J=8.1Hz, 1H), 7.46(d, J=8.7Hz, 2H)<br>IR(Nujol)3367, 1612, 1588, 1523, 1489, 1254, 1226, 1115, 1072, 1013, 940, 814cm⁻¹ |
| I-137 | ¹HNMR(CD₃OD) δ 3.38(s, 3H), 3.68(s, 3H), 4.02(dd, J=11.0, 3.6Hz, 1H), 4.12(dd, J=11.0, 1.8Hz, 1H), 5.48(dd, J=3.6, 1.8Hz, 1H), 6.43(s, 1H), 6.83–6.87(m, 3H), 6.85(d, J=8.7Hz, 2H), 7.46(d, J=8.7Hz, 2H)<br>IR(Nujol)3410, 1612, 1588, 1522, 1487, 1269, 1231, 1114, 1071, 1011, 947, 824cm⁻¹ |
| I-138 | ¹HNMR(CD₃OD) δ 3.38(s, 3H), 3.68(s, 3H), 4.70(d, J=5.4Hz, 2H), 6.43(s, 1H), 6.80(dd, J=8.1, 2.1Hz, 1H), 6.85(d, J=8.4Hz, 2H), 6.88(d, J=2.1Hz, 1H), 6.98(d, J=8.1Hz, 1H), 7.46(d, J=8.4Hz, 2H), 7.62(t, J=5.4Hz, 1H)<br>IR(Nujol)3368, 1612, 1589, 1523, 1489, 1253, 1226, 1114, 1072, 1011, 940, 825cm⁻¹ |
| I-139 | ¹HNMR(CDCl₃) δ 3.45(s, 3H), 3.74(s, 3H), 3.92(s, 3H), 4.75(d, J=5.1Hz, 2H), 6.45(s, 1H), 6.91(d, J=8.7Hz, 2H), 6.92(d, J=6.0Hz, 1H), 7.00(dd, J=6.0, 1.8Hz, 1H), 7.09(d, J=1.8Hz, 1H), 7.52(d, J=8.7Hz, 2H), 7.58(t, J=5.1Hz, 1H)<br>IR(Nujol)3399, 1612, 1589, 1523, 1489, 1252, 1226, 1115, 1072, 1043, 1014, 941, 825cm⁻¹ |

TABLE 35

| | |
|---|---|
| I-140 | ¹HNMR(CD₃OD) δ 3.38(s, 3H), 3.68(s, 3H), 4.51(s, 2H), 4.71(d, J=5.4Hz, 2H), 6.43(s, 1H), 6.80(dd, J=8.4, 2.1Hz, 1H), 6.85(d, J=8.4Hz, 2H), 6.87(d, J=2.1Hz, 1H), 6.98(d, J=8.4Hz, 1H), 7.46(d, J=8.4Hz, 2H), 7.75(t, J=5.4Hz, 1H)<br>IR(Nujol)3384, 1611, 1588, 1523, 1489, 1252, 1227, 1115, 1072, 1014, 824, 758cm⁻¹ |
| I-141 | ¹HNMR(CDCl₃) δ 3.45(s, 3H), 3.74(s, 3H), 4.76(d, J=5.1Hz, 2H), 5.15(s, 1H), 6.45(s, 1H), 6.86(d, J=8.4Hz, 1H), 6.92(d, J=8.7Hz, 2H), 6.94(dd, J=8.4, 2.1Hz, 1H), 7.08(d, J=2.1Hz, 1H), 7.31–7.40(m, 5H), 7.53(d, J=8.7Hz, 2H), 7.65(t, J=5.1Hz, 1H)<br>IR(Nujol)3399, 1611, 1588, 1523, 1489, 1251, 1225, 1115, 1072, 1013, 940, 825cm⁻¹ |
| I-142 | ¹HNMR(CDCl₃·CD₃OD1:1) δ 3.26(s, 3H), 2.64(m, 4H), 3.13(m, 4H), 3.44(s, 3H), 3.73(s, 3H), 4.78(d, J=4.5Hz, 2H), 6.45(s, 1H), 6.90(d, J=8.7Hz, 2H), 6.90(dd, J=8.4, 2.1Hz, 1H), 6.99(d, J=2.1Hz, 1H), 7.00(d, J=8.4Hz, 1H), 7.12(t, J=4.5Hz, 1H), 7.49(d, J=8.7Hz, 2H)<br>IR(Nujol)3492, 3297, 1607, 1561, 1523, 1486, 1247, 1224, 1113, 1011, 957, 828, 799cm⁻¹ |
| I-143 | ¹HNMR(CDCl₃) δ 3.09(m, 4H), 3.45(s, 3H), 3.74(s, 3H), 3.86(m, 4H), 4.82(d, J=4.2Hz, 2H), 6.44(s, 1H), 6.92(d, J=8.7Hz, 2H), 6.98(dd, J=8.4, 1.8Hz, 1H), 7.00(d, J=4.2Hz, 1H), 7.04(d, J=8.4Hz, 1H), 7.07(d, J=1.8Hz, 1H), 7.53(d, J=8.7Hz, 2H)<br>IR(Nujol)3366, 1611, 1586, 1523, 1488, 1268, 1227, 1114, 1070, 1011, 823cm⁻¹ |
| I-144 | ¹HNMR(CDCl₃) δ 1.29(t, J=6.9Hz, 3H), 2.65(dd, J=15.9, 6.6Hz, 1H), 2.81(dd, J=15.9, 6.6Hz, 1H), 3.44(s, 3H), 3.75(s, 3H), 4.03(dd, J=11.4, 6.9Hz, 1H), 4.20(q, J=6.9Hz, 2H), 4.35(dd, J=11.4, 2.4Hz, 1H), 4.66(ddt, J=6.9, 6.6, 2.4Hz, 1H), 6.44(s, 1H), 6.92(d, J=8.7Hz, 2H), 6.96–7.01(m, 3H), 7.53(d, J=8.7Hz, 2H) |
| I-145 | oil<br>¹HNMR(CDCl₃) δ 1.68(s, 3H), 1.74(d, J=0.9Hz, 3H), 2.55(m, 2H), 3.44(s, 3H), 3.75(s, 3H), 4.04(t, J=7.2Hz, 2H), 4.97(brs, 1H), 5.23(m, 1H), 6.00(s, 1H), 6.45(s, 1H), 6.92&7.53(ABq, J=8.7Hz, 4H), 7.02(m, 1H), 7.17–7.22(m, 2H)<br>IR(KBr)1613, 1525, 1490, 1475, 1463, 1454, 1402, 1304, 1269, 1231, 1112, 1072, 1019, 827cm⁻¹ |

TABLE 36

| | |
|---|---|
| I-146 | m.p. 256–257° C.<br>¹HNMR(DMSO-d₆) δ 3.35(s, 3H), 3.44(s, 3H), 3.74(s, 3H), 5.22(s, 2H), 7.06(s, 1H), 7.28–7.56(m, 11H), 7.69(s, 1H), 7.76(d, J=8.6Hz, 2H)<br>IR(KBr): 3479, 3360, 1672, 1517, 1465, 1361, 1339, 1295, 1261, 1228, 1172, 1144, 1118, 1013, 957, 870, 852, 804, 751cm⁻¹ |
| I-147 | m.p.. 163–164° C.<br>¹HNMR(CDCl₃) δ 1.74(s, 3H), 1.81(s, 3H), 3.43(s, 3H), 3.74(s, 3H), 4.58(d, J=6.8Hz, 2H), 5.50(t, J=6.8Hz, 1H), 5.80(s, 1H), 6.37(s, 1H), 6.86–6.95(m, 5H), 6.90(d, J=8.6Hz, 2H), 6.99(s, 1H), 7.49(d, J=8.6Hz, 2H)<br>IR(KBr): 3533, 3412, 3350, 1655, 1609, 1588, 1519, 1469, 1373, 1274, 1245, 1227, 1131, 1082, 1060, 999, 954, 838cm⁻¹ |
| I-148 | ¹HNMR(CDCl₃) δ 2.88(s, 3H), 3.22(s, 3H), 3.54(s, 3H), 3.77(s, 3H), 5.35(m, 2H), 6.85(s, 1H), 7.24(d, J=9.0Hz, 1H), 7.39(d, J=8.7Hz, 2H), 7.42–7.46(m, 5H), 7.65(d.d, J=9.0&2.1Hz, 1H), 7.68(d, J=8.7Hz, 2H), 8.26(d, J=2.1Hz, 1H) |
| I-149 | ¹HNMR(CDCl₃) δ 1.80(s, 3H), 1.85(s, 3H), 3.43(s, 3H), 3.74(s, 3H), 4.80(d, J=6.9Hz, 2H), 5.76(t, J=6.9Hz, 1H), 6.46(s, 1H), 6.92(d, J=8.4Hz, 2H), 7.14(d, J=8.7Hz, 1H), 7.49(d, J=8.4Hz, 2H)7.70(d.d, J=8.7&2.1Hz, 1H), 8.28(d, J=2.1Hz, 1H)<br>IR(KBr)3472, 1707, 1671, 1610, 1520, 1482, 1460, 1426, 1269, 1226, 1119, 1076, 1012cm⁻¹ |
| I-150 | ¹HNMR(CDCl₃) δ 1.76(s, 3H), 1.81(s, 3H), 2.63(s, 3H), 3.21(s, 3H), 3.55(s, 3H), 3.77(s, 3H), 4.62(d, J=6.3Hz, 2H), 4.73(s, 2H), 5.50(t, J=6.3Hz, 1H), 6.84(s, 1H), 6.99(d, J=9.0Hz, 1H), 7.51–7.42(m, 9H), 7.70(d, J=9.0Hz, 2H)<br>IR(KBr)3432, 1607, 1512, 1479, 1364, 1234, 1176, 1151, 1079, 1016cm⁻¹ |

TABLE 36-continued

| | |
|---|---|
| I-151 | $^1$HNMR(CDCl$_3$) δ 1.58(s, 3H), 1.81(s, 3H), 3.45(s, 3H), 3.73(s, 3H), 4.61(d, J=6.6Hz, 2H), 4.72(s, 2H), 5.52(t, J=6.6Hz, 1H), 6.45(s, 1H), 6.91(d, J=8.7Hz, 2H), 6.98(d, J=8.4Hz, 1H), 7.36(d.d, J=8.4&2.1Hz, 1H), 7.38(d, J=2.1Hz, 1H), 7.50(d, J=8.4Hz, 2H)<br>IR(KBr)3580, 3411, 1611, 1521, 1485, 1464, 1397, 1233, 1113, 1077, 1024, 1001cm$^{-1}$ |
| I-152 | $^1$HNMR(CDCl$_3$) δ 3.50(s, 3H), 3.77(s, 3H), 5.15(s, 2H), 5.72(s, 1H), 6.03(s, 2H), 6.71(d.d, J=8.4&2.1Hz, 1H), 6.91(d, J=8.4Hz, 1H), 6.97(s, 1H), 6.98(d, J=8.4Hz, 1H), 7.07(s, 1H), 7.09(d.d, J=8.4&2.1Hz, 1H), 7.16(d, J=2.1Hz, 1H), 7.34–7.50(m, 5H), 989(s, 1H)<br>IR(KBr)3446, 1697, 1587, 1511, 1470, 1383, 1285, 1240, 1127, 1036cm$^{-1}$ |

TABLE 37

| | |
|---|---|
| I-153 | $^1$HNMR(CDCl$_3$) δ 3.78(s, 3H), 3.79(s, 3H), 4.87(s, 1H), 5.16(s, 2H), 5.70(s, 1H), 6.88–6.91(m, 2H), 6.97(s, 1H), 7.00(s, 1H), 6.99(d, J=8.4Hz, 1H), 7.08(dd, J=2.1, 8.4Hz, 1H), 7.23(d, J=2.1Hz, 1H), 7.34–7.49(m, 7H) |
| I-154 | $^1$HNMR(CDCl$_3$) δ 1.69(s, 3H), 1.74(s, 3H), 2.51–2.58(m, 2H), 3.19(s, 3H), 3.21(s, 3H), 3.79(s, 3H), 3.80(s, 3H), 4.07(t, J=6.9Hz, 2H), 5.18–5.27(m, 1H), 6.92(s, 1H), 6.95(s, 1H), 7.05(d, J=8.7Hz, 1H), 7.32–7.37(m, 1H), 7.49(dd, J=2.1, 8.7Hz, 1H), 7.58(d, J=2.1Hz, 1H), 7.60–7.64(m, 2H) |
| I-155 | $^1$HNMR(CDCl$_3$) δ 1.69(s, 3H), 1.75(s, 3H), 2.53(q, J=6.9Hz, 2H), 3.77(s, 3H), 3.78(s, 3H), 4.07(t, J=6.9Hz, 2H), 4.97(s, 3H), 5.20–5.25(m, 1H), 5.71(s, 1H), 6.87–6.93(m, 3H), 7.07(dd, J=1.8, 8.4Hz, 1H), 7.20(d, J=1.8Hz, 1H), 7.45–7.50(m, 2H) |
| I-156 | m.p. 163–175° C.<br>$^1$HNMR(CDCl$_3$) δ 2.76(s, 3H), 3.19(s, 3H), 3.22(s, 3H), 3.54(s, 3H), 3.79(s, 3H), 5.20(s, 2H), 5.68(s, 1H), 6.84(s, 1H), 6.97(d, J=1.8Hz, 1H), 6.99(d, J=1.8Hz, 1H), 7.37–7.47(m, 7H), 7.68(m, 2H)<br>IR(KBr)3436, 1480, 1415, 1391, 1363, 1233, 1178, 1151, 1079, 1024, 969, 953, 875, 801, 522cm$^{-1}$ |
| I-157 | m.p. 176–178° C.<br>$^1$HNMR(CDCl$_3$) δ 2.08(s, 3H), 2.40, (s, 3H), 2.72(s, 3H), 3.21(s, 3H), 3.22(s, 3H), 3.55(s, 3H), 3.79(s, 3H), 5.13(s, 2H), 6.86(s, 1H), 7.39a nd 7.68(ABq, J=8.7Hz, 4H), 7.47(d, J=2.1Hz, 1H), 7.49(d, J=2.1Hz, 1H)<br>IR(KBr)1770, 1747, 1477, 1391, 1366, 1235, 1180, 1152, 1077, 873, 799, 522cm$^{-1}$ |
| I-158 | m.p. 175–177° C.<br>$^1$HNMR(CDCl$_3$) δ 2.87(s, 3H), 3.13(s, 6H), 3.22(s, 3H), 3.55(s, 3H), 3.81(s, 3H), 5.22(s, 2H), 6.86(s, 1H), 7.38–7.45(m, 7H), 7.51–7.53(m, 2H), 7.67(m, 2H)<br>IR(KBr)1479, 1367, 1180, 1151, 1080, 1019, 966, 876, 798, 525cm$^{-1}$ |

TABLE 38

| | |
|---|---|
| I-159 | foam<br>$^1$HNMR(CDCl$_3$) δ 2.44(s, 3H), 3.21(s, 3H), 3.54(s, 3H), 3.76(s, 3H), 3.79(s, 3H), 4.77(s, 2H), 5.24(s, 2H), 6.83(s, 1H), 6.90–7.00(m, 3H), 7.30–7.48(m, 5H), 7.37(d, J=8.8Hz, 2H), 7.69(d, J=8.8Hz, 2H)<br>IR(KBr): 1758, 1519, 1481, 1365, 1236, 1176, 1150, 1079, 1013, 963, 872, 798cm$^{-1}$ |
| I-160 | m.p.. 146–147° C.<br>$^1$HNMR(DMSO-d$_6$) δ 3.31(s, 3H), 3.65(s, 3H), 4.63(s, 2H), 5.15(s, 2H), 6.40(s, 1H), 6.83–6.90(m, 4H), 7.05(d, J=8.4Hz, 1H), 7.32–7.52(m, 7H), 8.57(s, 1H), 9.50(s, 1H), 12.0–13.9(brs, 1H)<br>IR(KBr): 3422, 1728, 1611, 1524, 1489, 1455, 1405, 1247, 1142, 1118, 1080, 1012, 818, 749, 742, 698cm$^{-1}$ |
| I-161 | $^1$HNMR(CDCl$_3$) δ 1.76(s, 3H), 1.79(s, 3H), 2.57(s, 3H), 3.21(s, 3H), 3.56(s, 3H), 3.77(s, 3H), 3.80(s, 3H), 4.64(d, J=6.5Hz, 2H), 4.74(s, 2H), 5.54(t, J=6.5Hz, 1H), 6.83(s, 1H), 6.88(d, J=1.5Hz, 1H), 7.02–7.03(m, 2H), 7.38(d, J=8.7Hz, 2H), 7.69(d, J=8.7Hz, 2H) |
| I-162 | m.p. 147–149° C.<br>$^1$HNMR(DMSO-d$_6$) δ 1.73(s, 3H), 1.77(s, 3H), 3.30(s, 3H), 3.65(s, 3H), 4.57(d, J=6.6Hz, 2H), 4.60(s, 2H), 5.86(t, J=6.6Hz, 1H), 6.40(s, 1H), 6.80(d, J=1.7Hz, 1H), 6.84(d, J=8.7Hz, 2H), 6.87(dd, J=8.7Hz, 1H), 6.99(d, J=8.7Hz, 1H), 7.43(d, J=8.7Hz, 2H), 8.56(s, 1H), 9.51(s, 1H), 12.8(brs, 1H)<br>IR(KBr): 3483, 3376, 1737, 1612, 1523, 1489, 1460, 1397, 1271, 1231, 1175, 1120, 1072, 1012, 904, 820cm$^{-1}$ |
| I-163 | m.p. 144–145° C.<br>$^1$HNMR(CDCl$_3$) δ 3.04(s, 3H), 3.20(s, 3H), 3.59(s, 3H), 3.75(s, 3H), 4.90(s, 2H), 5.16(s, 2H), 5.65(s, 1H), 6.67(s, 1H), 6.92(dd, J=2.1, 8.4Hz, 1H), 7.00(d, J=8.4Hz, 1H), 7.06(d, J=2.1Hz, 1H), 7.26–7.47(m, 7H), 7.61–7.66(m, 2H)<br>IR(KBr)3600–3200(br), 1517, 1477, 1449, 1382, 1361, 1277, 1235, 1199, 1150, 1112, 1079, 1064, 1010, 997cm$^{-1}$ |
| I-164 | m.p. 80–83° C.<br>$^1$HNMR(CDCl$_3$) δ 2.99(s, 3H), 3.12(s, 3H), 3.20(s, 3H), 3.58(s, 3H), 3.75(s, 3H), 4.93(s, 3H), 5.18(s, 2H), 6.67(s, 1H), 7.12(d, J=8.7Hz, 1H), 7.34–7.49(m, 9H), 7.60–7.65(m, 2H) |

TABLE 39

| | |
|---|---|
| I-165 | m.p. 148–151° C.<br>$^1$HNMR(CDCl$_3$) δ 3.03(s, 3H), 3.57(s, 3H), 3.74(s, 3H), 4.89(s, 1H), 4.90(s, 2H), 5.15(s, 2H), 5.64(s, 1H), 6.67(s, 1H), 6.88–6.93(m, 3H), 6.99(d, J=8.4Hz, 1H), 7.06(d, J=1.8Hz, 1H), 7.20–7.49(m, 7H)<br>IR(KBr)3600–3200(br), 1609, 1590, 1519, 1477, 1459, 1381, 1253, 1216, 1156, 1111, 1077, 1066, 1012cm$^{-1}$ |
| I-166 | m.p. 199° C.<br>$^1$HNMR(CDCl$_3$) δ 3.10(s, 3H), 3.21(s, 3H), 3.44(s, 3H), 3.76(s, 3H), 5.17(s, 2H), 6.03(s, 1H), 6.44(s, 1H), 7.14(d, J=8.4Hz, 1H), 7.36–7.49(m, 8H), 7.52(d, J=2.1Hz, 1H), 7.67–7.72(m, 2H)<br>IR(KBr)3600–3200(br), 1520, 1486, 1362, 1183, 1152, 1110, 971cm$^{-1}$ |
| I-167 | m.p. 113–115° C.<br>$^1$HNMR(CDCl$_3$) δ 0.76(t, J=7.2Hz, 3H), 1.46–1.55(m, 2H), 3.11(s, 3H), 3.20(s, 1H), 3.63(s, 1H), 3.71(t, J=6.6Hz, 2H), 5.18(s, 2H), 6.64(s, 1H), 7.11(d, J=8.7Hz, 1H), 7.33–7.50(m, 9H), 7.60–7.65(m, 2H)<br>IR(KBr)1517, 1475, 1365, 1345, 1293, 1233, 1177, 1149, 1109, 1079, 1017, 956cm$^{-1}$ |
| I-168 | m.p. 56–58° C.<br>$^1$HNMR(CDCl$_3$) δ 0.76(t, J=7.5Hz, 3H), 1.44–1.56(m, 2H), 3.61(s, 3H), 3.71(t, J=6.6Hz, 2H), 3.74(s, 3H), 4.86(s, 1H), 5.15(s, 2H), 5.63(s, 1H), 6.65(s, 1H), 6.88–6.93(m, 3H), 6.98(d, J=8.4Hz, 1H), 7.04(d, J=1.8Hz, 1H), 7.37–7.50(m, 7H)<br>IR(KBr)3600–3200(br), 1611, 1590, 1519, 1476, 1404, 1379, 1252, 1230, 1110, 1078, 1015cm$^{-1}$ |

TABLE 39-continued

I-169 m.p. 101–103° C.
¹HNMR(CDCl₃) δ 0.77(t, J=7.5Hz, 3H), 1.44–1.55(m, 2H), 1.76(s, 3H), 1.81(s, 3H), 3.20(s, 3H), 3.21(s, 3H), 3.63(s, 3H), 3.71(t, J=6.6Hz, 2H), 3.75(s, 3H), 4.63(d, J=6.6Hz, 2H), 5.48–5.53(m, 1H), 6.64(s, 1H), 7.04(d, J=8.4Hz, 1H), 7.32–7.38(m, 3H), 7.42(d, J=2.1Hz, 1H), 7.60–7.65(m, 2H)
IR(KBr)1514, 1473, 1370, 1359, 1290, 1233, 1174, 1149, 1107, 970cm⁻¹

TABLE 40

I-170 m.p. 64–66° C.
¹HNMR(CDCl₃) δ 0.77(t, J=7.5Hz, 3H), 1.44–1.55(m, 2H), 1.76(s, 3H), 1.81(s, 3H), 3.20(s, 3H), 3.21(s, 3H), 3.63(s, 3H), 3.71(t, J=6.6Hz, 2H), 3.75(s, 3H), 4.63(d, J=6.6Hz, 2H), 5.48–5.53(m, 1H), 6.64(s, 1H), 7.04(d, J=8.4Hz, 1H), 7.32–7.38(m, 3H), 7.42(d, J=2.1Hz, 1H), 7.60–7.65(m, 2H)IR(KBr)3600–2800(br), 1612, 1590, 1520, 1475, 1462, 1405, 1381, 1285, 1244, 1226, 1110, 1079, 988cm⁻¹

I-171 m.p. 148–150° C.
¹HNMR(CDCl₃) δ 1.74(d, J=0.9Hz, 3H), 1.80(s, 3H), 2.88(s, 3H), 3.22(s, 3H), 3.23(s, 6H), 3.55(s, 3H), 3.80(s, 3H), 4.72(d, J=7.5Hz, 2H), 5.55(m, 1H), 6.85(s, 1H), 7.39&7.67(ABq, J=8.7Hz, 4H), 7.40(s, 2H)
IR(KBr)1514, 1479, 1411, 1366, 1179, 1152, 1079, 1022, 968, 875, 799, 525cm⁻¹

I-172 ¹HNMR(CDCl₃) δ 0.94(t, J=7.2Hz, 3H), 1.45(tq, J=7.2, 7.2Hz, 2H), 2.13(m, 2H), 3.46(s, 3H), 3.74(s, 3H), 4.68(d, J=5.4Hz, 2H), 5.72 (m, 2H), 6.45(s, 1H), 6.92(d, J=8.7Hz, 2H), 6.96(brs, 2H), 7.07(brs, 1H), 7.53(d, J=8.7Hz, 2H)

I-173 ¹HNMR(CDCl₃) δ 1.76(brd, J=6.3Hz, 3H), 3.46(s, 3H), 3.74(s, 3H), 4.70(d, J=5.4Hz, 2H), 5.77(m, 2H), 6.45(s, 1H), 6.91(d, J=8.7Hz, 2H), 6.96(brs, 2H), 7.07(brs, 1H), 7.53(d, J=8.7Hz, 2H)
IR(Nujol)3350, 1613, 1587, 1523, 1491, 1287, 1261, 1238, 1114, 1071, 1011, 936, 820, 783cm⁻¹

I-174 ¹HNMR(CDCl₃) δ 3.45(s, 3H), 3.76(s, 3H), 4.56(s, 2H), 5.55(s, 1H), 6.45(s, 1H), 6.93(d, J=8.7Hz, 2H), 7.01(d, J=8.4Hz, 1H), 7.08(dd, J=8.4, 2.1Hz, 1H), 7.27(d, J=2.1Hz, 1H), 7.54(d, J=8.7Hz, 2H)

I-175 ¹HNMR(CDCl₃) δ 3.45(s, 3H), 3.74(s, 3H), 4.82(dd, J=6.6, 1.5Hz, 2H), 5.28(d, J=10.5Hz, 1H), 5.35(d, J=16.5Hz, 1H), 5.75(dt, J=10.8, 6.6Hz, 1H), 6.26(dd, J=10.5, 10.5Hz, 1H), 6.45(s, 1H), 6.66(ddd, J=16.5, 10.5, 10.5Hz, 1H), 6.92(d, J=8.7Hz, 2H), 6.96(m, 2H), 7.07(brs, 1H), 7.53(d, J=8.7Hz, 2H)
IR(Nujol)3399, 1611, 1591, 1523, 1489, 1248, 1226, 1113, 1071, 1009, 825cm⁻¹

TABLE 41

I-176 ¹HNMR(CDCl₃) δ 1.59(m, 6H), 2.17(m, 2H), 2.24, (m, 2H), 2.71(s, 3H), 3.21(s, 3H), 3.24(s, 3H), 3.56(s, 3H), 3.78(s, 3H), 4.65(d, J=7.2Hz, 2H), 5.43(t, J=7.2Hz, 1H), 6.84(s, 1H), 7.10(d, J=8.4Hz, 1H), 7.34(dd, J=8.4, 2.1Hz, 1H), 7.38(d, J=8.7Hz, 2H), 7.39(d, J=2.1Hz, 1H), 7.68(d, J=8.7Hz, 2H)

I-177 m.p. 177–178° C.
¹HNMR(CDCl₃) δ 2.31(t, J=5.7Hz, 2H), 2.39(t, J=5.7Hz, 2H), 2.76(s, 3H), 3.21(s, 3H), 3.24(s, 3H), 3.56(s, 3H), 3.70(t, J=5.7Hz, 2H), 3.73(t, J=5.7Hz, 2H), 3.78(s, 3H), 4.67(d, J=6.6Hz, 2H), 5.57(t, J=6.6Hz, 1H), 6.84(s, 1H), 7.09(d, J=8.4Hz, 1H), 7.35(dd, J=8.4, 2.1Hz, 1H), 7.38(d, J=8.7Hz, 2H), 7.39(d, J=2.1Hz, 1H), 7.67(d, J=8.7Hz, 2H)
IR(KBr)2940, 1519, 1481, 1362, 1178, 1152, 1079, 818cm⁻¹

I-178 ¹HNMR(CDCl₃) δ 1.04(t, J=7.5Hz, 3H), 1.05(t, J=7.5Hz, 3H), 2.12(q, J=7.5Hz, 2H), 2.16(q, J=7.5Hz, 2H), 2.71(s, 3H), 3.21(s, 3H), 3.24 (s, 3H), 3.56(s, 3H), 3.78(s, 3H), 4.67(d, J=6.6Hz, 2H), 5.45(t, J=6.6Hz, 1H), 6.84(s, 1H), 7.11(d, J=8.4Hz, 1H), 7.35(dd, J=8.4, 2.4Hz, 1H), 7.38(d, J=8.7Hz, 2H), 7.39(d, J=2.4Hz, 1H), 7.68(d, J=8.7Hz, 2H)

I-179 ¹HNMR(CDCl₃) δ 1.05(t, J=7.5Hz, 3H), 1.76(s, 3H), 2.10(q, J=7.5Hz, 2H), 2.71(s, 3H), 3.21(s, 3H), 3.24(s, 3H), 3.56(s, 3H), 3.78(s, 3H), 4.66(d, J=6.9Hz, 2H), 5.48(t, J=6.9Hz, 1H), 6.84(s, 1H), 7.10(d, J=8.4Hz, 1H), 7.34(dd, J=8.4, 2.1Hz, 1H), 7.38(d, J=8.7Hz, 2H), 7.39 (d, J=2.1Hz, 1H), 7.68(d, J=8.7Hz, 2H)

I-180 ¹HNMR(CDCl₃) δ 1.76(s, 3H), 1.80(s, 6H), 2.72(s, 3H), 3.21(s, 3H), 3.21(s, 3H), 3.56(s, 3H), 3.78(s, 3H), 4.61(s, 2H), 6.84(s, 1H), 7.10 (d, J=8.4Hz, 1H), 7.34(dd, J=8.4, 2.1Hz, 1H), 7.38(d, J=8.7Hz, 2H), 7.39(d, J=2.1Hz, 1H), 7.68(d, J=8.7Hz, 2H)

I-181 m.p. 157–158° C.
¹HNMR(CDCl₃) δ 1.55–1.65(m, 6H), 2.18(m, 2H), 2.23(m, 2H), 3.46(s, 3H), 3.74(s, 3H), 4.63d, J=7.2Hz, 2H), 5.47(t, J=7.2Hz, 1H), 6.45 (s, 1H), 6.91(d, J=8.4Hz, 2H), 6.96(br.s, 2H), 7.06(br.s, 1H), 7.52(d, J=8.4Hz, 2H)
IR(KBr)3410, 2924, 2854, 1609, 1567, 1523, 1490, 1462, 1405, 1254, 1221, 1198, 1119, 1069, 824, 813cm⁻¹

TABLE 42

I-182 m.p. 219–221° C.
¹HNMR(DMSO-d₆) δ 2.22(t, J=5.4Hz, 2H), 2.32(t, J=5.4Hz, 2H), 3.30(s, 3H), 3.56(t, J=5.4Hz, 2H), 3.61(t, J=5.4Hz, 2H), 3.64(s, 3H), 4.59(d, J=6.6Hz, 2H), 5.54(t, J=6.6Hz, 1H), 6.39(s, 1H), 6.64(dd, J=8.4, 2.1Hz, 1H), 6.73(d, J=2.1Hz, 1H), 6.84(d, J=8.7Hz, 2H), 6.89(d, J=8.4Hz, 1H), 7.43(d, J=8.4Hz, 2H)
IR(KBr)3392, 2948, 1609, 1586, 1522, 1492, 1271, 1239, 1219, 1118, 1076, 1007, 818cm⁻¹

I-183 m.p. 149–150° C.
¹HNMR(CDCl₃) δ 1.03(t, J=7.5Hz, 3H), 1.07(t, J=7.5Hz, 3H), 2.13(q, J=7.5Hz, 2H), 2.15(q, J=7.5Hz, 2H), 3.46(s, 3H), 3.75(s, 3H), 4.64(d, J=6.6Hz, 2H), 5.48(t, J=6.6Hz, 1H), 6.45(s, 1H), 6.92(d, J=8.7Hz, 2H), 6.97(dd, J=7.8, 1.5Hz, 1H), 6.97(d, J=7.8Hz, 1H), 7.06(d, J=1.5Hz, 1H), 7.52(d, J=8.7Hz, 2H)
IR(KBr)3398, 2963, 2934, 1671, 1610, 1523, 1493, 1465, 1407, 1259, 1224, 1118, 1071, 813cm⁻¹

I-184 m.p. 217–218° C.
¹HNMR(CDCl₃) δ 3.86(s, 3H), 5.16(s, 2H), 5.72(s, 1H), 6.97–7.01(m, 3H), 7.12(dd, J=2.4, 8.4Hz, 1H), 7.26(d, J=2.4Hz, 1H), 7.34–7.47 (m, 5H), 7.54–7.58(m, 2H), 7.60(s, 4H)
IR(KBr)3600–3200(br), 1605, 1590, 1493, 1298, 1282, 1253, 1206, 1183, 1022cm⁻¹

I-185 ¹HNMR(CDCl₃) δ 1.21(t, J=6.9Hz, 3H), 1.77(s, 3H), 1.82(s, 3H), 2.38–2.46(m, 2H), 2.72–2.84(m, 2H), 3.18(s, 3H), 3.21(s, 3H), 3.35(s, 3H), 3.70(s, 3H), 4.06(q, J=6.9Hz, 2H), 4.63(d, J=6.6Hz, 2H), 5.52(t, J=6.6Hz, 1H), 6.75(s, 1H), 7.07(d, J=8.4Hz, 1H), 7.13(d.d, J=8.4& 2.1Hz, 1H), 7.21(d, J=2.1Hz, 1H), 7.37(d, J=9.0Hz, 2H), 7.69(d, J=9.0Hz, 2H)
IR(KBr)1727, 1517, 1469, 1364, 1291, 1234, 1179, 1152, 1118, 1080, 1003cm⁻¹

TABLE 42-continued

| | |
|---|---|
| I-186 | ¹HNMR(CDCl₃) δ 1.76(s, 3H), 1.82(s, 3H), 2.42–2.53(m, 2H), 2.72–2.86(m, 2H), 3.35(s, 3H), 3.69(s, 3H), 4.61(d, J=6.6Hz, 2H), 5.53(t, J=6.6Hz, 1H), 5.71(s, 1H), 6.68(d.d, J=8.4&2.1Hz, 1H), 6.76(s, 1H), 6.81(d, J=2.1Hz, 1H), 6.91(d, J=8.4Hz, 2H), 6.92(d, J=8.4Hz, 1H), 7.52(d, J=8.4Hz, 2H)<br>IR(KBr)3419, 1707, 1612, 1518, 1472, 1390, 1225, 1078cm⁻¹ |

TABLE 43

| | |
|---|---|
| I-187 | ¹HNMR(CDCl₃) δ 2.55(s, 3H), 3.54(s, 3H), 3.78(s, 3H), 5.18(s, 1H), 6.85(s, 1H), 6.91(d.d, J=8.4&2.1Hz, 1H), 7.03(d, J=8.4Hz, 1H), 7.04 (d, J=2.1Hz, 1H), 7.33–7.48(m, 5H), 7.71(d, J=8.4Hz, 2H), 7.72(d, J=8.4Hz, 2H)<br>IR(KBr)3442, 1617, 1517, 1485, 1485, 1394, 1357, 1331, 1171, 1124, 1077, 1067, 1016cm⁻¹ |
| I-188 | ¹HNMR(CDCl₃) δ 2.68(s, 3H), 3.13(s, 3H), 3.54(s, 3H), 3.79(s, 3H), 5.19(s, 2H), 6.86(s, 1H), 7.16(d, J=8.7Hz, 1H), 7.31–7.50(m, 7H), 7.72 (d, J=8.7Hz, 2H), 7.76(d, J=8.7Hz, 2H)<br>IR(KBr)1614, 1513, 1482, 1366, 1324, 1177, 1120, 1079, 1065, 1016cm⁻¹ |
| I-189 | ¹HNMR(CDCl₃) δ 2.68(s, 3H), 3.13(s, 3H), 3.54(s, 3H), 3.79(s, 3H), 5.19(s, 2H), 6.86(s, 1H), 7.16(d, J=8.7Hz, 1H), 7.31–7.50(m, 7H), 7.72 (d, J=8.7Hz, 2H), 7.76(d, J=8.7Hz, 2H)<br>IR(KBr)1614, 1513, 1482, 1366, 1324, 1177, 1120, 1079, 1065, 1016cm⁻¹ |
| I-190 | ¹HNMR(CDCl₃) δ 1.76(s, 3H), 1.82(s, 3H), 3.46(s, 3H), 3.76(s, 3H), 4.62(d, J=8.4Hz, 2H), 5.53(t, J=8.4Hz, 1H), 5.71(s, 1H), 5.85(s, 1H), 6.46(s, 1H), 6.94(d.d, J=8.1&1.8Hz, 1H), 6.98(d, J=8.1Hz, 1H), 7.05(d, J=1.8Hz, 1H), 7.71(d, J=8.1Hz, 2H), 7.77(d, J=8.1Hz, 2H)<br>IR(KBr)3552, 3505, 3466, 1613, 1509, 1487, 1397, 1324, 1288, 1245, 1163, 1110, 1065cm⁻¹ |
| I-191 | ¹HNMR(CDCl₃) δ 3.02(s, 6H), 3.48(s, 3H), 3.76(s, 3H), 5.15(s, 2H), 5.67(s, 1H), 5.95(s, 1H), 6.47(s, 1H), 6.81(d, J=8.7Hz, 2H), 6.96(d.d, J=8.4&2.1Hz, 1H), 7.04(d, J=8.4Hz, 1H), 7.10(d, J=2.1Hz, 1H), 7.31–7.49(m, 5H), 7.55(d, J=8.7Hz, 2H)<br>IR(KBr)3543, 3500, 1605, 1526, 1486, 1459, 1245, 1198, 1110, 1070, 999cm⁻¹ |
| I-192 | mp 122–124° C.<br>¹HNMR(CDCl₃) δ 2.70(brs, 3H), 3.55–3.60(br, 2H), 3.60(s, 3H), 3.75(s, 3H), 3.81–3.83(m, 2H), 3.87(s, 3H), 5.15(s, 2H), 5.68(s, 1H), 6.69 (s, 1H), 6.94(dd, J=2.1, 8.4Hz, 1H), 6.97–7.03(m, 3H), 7.07(d, J=1.8Hz, 1H), 7.38–7.48(m, 5H), 7.51–7.56(m, 2H)<br>IR(KBr)3600–2800(br), 1607, 1597, 1550, 1518, 1477, 1462, 1452, 1392, 1289, 1248, 1228, 1175, 1122, 1096, 1084, 1015cm⁻¹ |

TABLE 44

| | |
|---|---|
| I-193 | m.p. 160–163° C.<br>¹HNMR(CDCl₃) δ 3.60(s, 3H), 3.60–3.64(br, 2H), 3.76(s, 3H), 3.77–3.80(m, 2H), 5.15(s, 2H), 5.69(s, 1H), 5.88(s, 1H), 6.69(s, 1H), 6.90–6.94 (m, 3H), 7.02(d, J=8.4Hz, 1H), 7.08(d, J=2.1Hz, 1H), 7.38–7.51(m, 7H)<br>IR(KBr)3600–3200(br), 1613, 1588, 1519, 1477, 1462, 1397, 1256, 1189, 1117, 1078, 1011cm⁻¹ |
| I-194 | ¹HNMR(CDCl₃) δ 3.02(s, 6H), 3.11(s, 3H), 3.50(s, 3H), 3.72(s, 3H), 4.43(brs, 1H), 4.58(brs, 1H), 5.18(s, 2H), 6.82(d, J=8.7Hz, 2H), 6.92 (s, 1H), 7.16(d, J=9.3Hz, 1H), 7.31–7.51(m, 7H), 7.55(d, J=8.7Hz, 2H)<br>IR(KBr)3432, 1611, 1526, 1476, 1356, 1291, 1232, 1186, 1117, 1079, 1012cm⁻¹ |
| I-195 | m.p. 157–158° C.<br>¹HNMR(CDCl₃) δ 3.10(s, 3H), 3.21(s, 3H), 3.56(s, 3H), 3.69(s, 3H), 3.76(s, 3H), 4.47(s, 2H), 5.17(s, 2H), 6.68(s, 1H), 7.12(d, J=8.2Hz, 1H), 7.34–7.50(m, 9H), 7.63(d, J=8.6Hz, 2H)<br>IR(KBr): 1748, 1517, 1476, 1366, 1232, 1150, 1114, 968, 873, 812, 791, 750, 707cm⁻¹ |
| I-196 | m.p. 189–191° C. (dec)<br>¹HNMR(DMSO-d₆) δ 3.45(s, 3H), 3.67(s, 3H), 4.25(s, 2H), 5.12(s, 2H), 6.66(dd, J=8.4, 2.0Hz, 1H), 6.69(s, 1H), 6.77(d, J=2.0Hz, 1H), 6.80 (d, J=8.6Hz, 2H), 6.98(d, J=8.4Hz, 1H), 7.33–7.54(m, 7H), 9.01(s, 1H), 9.54(brs, 1H)<br>IR(KBr): 3422, 3245, 1733, 1611, 1596, 1522, 1478, 1400, 1262, 1248, 1222, 1207, 1130, 1084, 1011, 836, 781, 744, 699cm⁻¹ |
| I-197 | m.p. 151–152° C.<br>¹HNMR(CDCl₃) δ 1.76(s, 3H), 1.81(s, 3H), 3.20(s, 3H), 3.21(s, 3H), 3.56(s, 3H), 3.70(s, 3H), 3.75(s, 3H), 4.47(s, 2H), 4.63(d, J=6.9Hz, 2H), 5.51(t, J=6.9Hz, 1H), 6.68(s, 1H), 7.05(d, J=8.4Hz, 1H), 7.36(dd, J=8.4, 2.1Hz, 1H), 7.36(d, J=8.9Hz, 2H), 7.41(d, J=2.1Hz, 1H), 7.63 (d, J=8.9Hz, 2H)<br>IR(KBr): 1751, 1517, 1475, 1366, 1234, 1150, 1113, 968, 872, 812, 707cm⁻¹ |

TABLE 45

| | |
|---|---|
| I-198 | m.p. 155–156° C.<br>¹HNMR(DMSO-d₆) δ 1.72(s, 3H), 1.76(s, 3H), 3.42(s, 3H), 3.67(s, 3H), 4.25(s, 2H), 4.54(d, J=6.8Hz, 2H), 5.49(t, J=6.8Hz, 1H), 6.65(dd, J=8.4, 1.9Hz, 1H), 6.69(s, 1H), 6.73(d, J=1.9Hz, 1H), 6.84(d, J=8.4Hz, 2H), 7.36(d, J=8.4Hz, 1H), 7.41(d, J=8.4Hz, 2H), 8.85(s, 1H), 9.55(s, 1H), 11.2–13.6(brs, 1H)<br>IR(KBr): 3411, 3243, 1733, 1611, 1594, 1522, 1477, 1398, 1247, 1207, 1126, 1083, 1015, 835, 788cm⁻¹ |
| I-199 | ¹HNMR(CDCl₃) δ 2.68(s, 3H), 3.13(s, 3H), 3.55(s, 3H), 3.80(s, 3H), 5.19(s, 2H), 6.88(s, 1H), 7.16(d, J=8.7Hz, 1H), 7.34(d, J=2.1Hz, 1H), 7.36–7.50(m, 6H), 7.81(d, J=8.4Hz, 2H), 7.98(d, J=8.4Hz, 2H)<br>IR(KBr)1698, 1602, 1481, 1351, 1232, 1182, 1079cm⁻¹ |
| I-200 | ¹HNMR(CDCl₃) δ 2.42(s, 3H), 2.71(s, 3H), 3.03(s, 3H), 3.21(s, 3H), 3.56(s, 3H), 3.79(s, 3H), 5.17(s, 2H), 6.84(s, 1H), 7.19(d, J=8.4Hz, 1H), 7.22–7.30(m, 3H), 7.37(dd, J=8.4, 2.1Hz, 1H), 7.38(d, J=8.7Hz, 2H), 7.41(d, J=2.1Hz, 1H), 7.41–7.45(m, 1H), 7.68(d, J=8.7Hz, 2H)<br>IR(Nujol)1607, 1519, 1480, 1177, 1151, 1079, 970, 875, 798cm⁻¹ |
| I-201 | ¹HNMR(CDCl₃) δ 2.38(s, 3H), 2.67(s, 3H), 3.14(s, 3H), 3.21(s, 3H), 3.56(s, 3H), 3.78(s, 3H), 5.15(s, 2H), 6.84(s, 1H), 7.14(d, J=8.4Hz, 1H), 7.17(brd, J=7.5Hz, 1H), 7.23–7.30(m, 3H), 7.34(dd, J=8.4, 1.8Hz, 1H), 7.38(d, J=8.7Hz, 2H), 7.41(d, J=1.8Hz, 1H), 7.68(d, J=8.7Hz, 2H)<br>IR(Nujol)1606, 1519, 1482, 1180, 1150, 1078, 1011, 979, 876, 790cm⁻¹ |
| I-202 | ¹HNMR(CDCl₃) δ 2.30(s, 3H), 2.38(s, 6H), 2.74(s, 3H), 2.94(s, 3H), 3.21(s, 3H), 3.57(s, 3H), 3.79(s, 3H), 5.13(s, 2H), 6.85(s, 1H), 6.91 (brs, 2H), 7.37(d, J=8.7Hz, 2H), 7.40(brs, 2H), 7.41(dd, J=8.4, 1.8Hz, 1H), 7.69(d, J=8.7Hz, 2H)<br>IR(CHCl₃)1610, 1518, 1477, 1370, 1177, 1149, 1082, 970, 873cm⁻¹ |
| I-203 | ¹HNMR(CDCl₃) δ 2.34(s, 6H), 2.66(s, 3H), 3.15(s, 3H), 3.21(s, 3H), 3.56(s, 3H), 3.78(s, 3H), 5.12(s, 2H), 6.84(s, 1H), 6.99(brs, 1H), 7.06 (brs, 2H), 7.14(d, J=8.4Hz, 1H), 7.33(dd, J=8.4, 2.1Hz, 1H), 7.38(d, J=8.7Hz, 2H), 7.40(d, J=2.1Hz, 1H), 7.68(d, J=8.7Hz, 2H)<br>IR(Nujol)1607, 1519, 1480, 1178, 1152, 1097, 1014, 969, 876, 824, 797cm⁻¹ |

TABLE 46

| | |
|---|---|
| I-204 | ¹HNMR(CDCl₃) δ 2.72(s, 3H), 3.16(s, 3H), 3.21(s, 3H), 3.55(s, 3H), 3.78(s, 3H), 3.94(s, 3H), 5.25(s, 2H), 6.84(s, 1H), 7.11(d, J=8.4Hz, 1H), 7.34(dd, J=8.4, 2.1Hz, 1H), 7.38(d, J=8.7Hz, 2H), 7.42(d, J=2.1Hz, 1H), 7.55(d, J=8.4Hz, 2H), 7.68(d, J=8.7Hz, 2H), 8.09(d, J=8.4Hz, 2H)<br>IR(Nujol)1719, 1610, 1519, 1480, 1177, 1151, 1119, 1080, 1016, 969, 875, 798cm⁻¹ |
| I-205 | m.p. 153–157° C.<br>¹HNMR(CDCl₃) δ 2.70(s, 3H), 3.16(s, 3H), 3.21(s, 3H), 3.56(s, 3H), 3.78(s, 3H), 5.13(s, 2H), 6.41(dd, J=3.3, 2.0Hz, 1H), 6.49(d, J=3.3Hz, 1H), 6.84(s, 1H), 7.20(d, J=8.7Hz, 1H), 7.37(dd, J=8.7, 2.1Hz, 1H), 7.38(d, J=8.7Hz, 2H), 7.41(d, J=2.1Hz, 1H), 7.46(d, J=2.0Hz, 1H), 7.68(d, J=8.7Hz, 2H)<br>IR(Nujol)1605, 1518, 1482, 1375, 1361, 1180, 1150, 1079, 1013, 977, 876, 814, 800cm⁻¹ |
| I-206 | ¹HNMR(CDCl₃) δ 2.41(s, 3H), 3.46(s, 3H), 3.75(s, 3H), 5.13(s, 2H), 6.45(s, 1H), 6.92(d, J=8.7Hz, 2H), 6.99(dd, J=8.4, 2.1Hz, 1H), 7.07(d, J=8.4Hz, 1H), 7.09(d, J=2.1Hz, 1H), 7.22–7.34(m, 3H), 7.40(brd, J=7.8Hz, 1H), 7.53(d, J=8.7Hz, 2H)<br>IR(Nujol)3471, 3436, 3339, 1612, 1581, 1523, 1489, 1266, 1245, 1228, 1185, 1110, 1070, 1011, 998, 945, 823, 781cm⁻¹ |
| I-207 | ¹HNMR(CDCl₃) δ 2.40(s, 3H), 3.45(s, 3H), 3.75(s, 3H), 5.11(s, 2H), 6.45(s, 1H), 6.91(d, J=8.7Hz, 2H), 6.95(dd, J=8.4, 1.8Hz, 1H), 7.01(d, J=8.4Hz, 1H), 7.09(d, J=1.8Hz, 1H), 7.19(brd, J=7.5Hz, 1H), 7.22–7.34(m, 3H), 7.53(d, J=8.7Hz, 2H)<br>IR(Nujol)3410, 1611, 1589, 1523, 1489, 1246, 1225, 1114, 1071, 1011, 939, 824, 814, 778cm⁻¹ |
| I-208 | m.p. 230–236° C.<br>¹HNMR(DMSO-d₆) δ 2.25(s, 3H), 2.35(s, 6H), 3.31(s, 3H), 3.65(s, 3H), 5.00(s, 2H), 6.39(s, 1H), 6.69(dd, J=8.4, 1.8Hz, 1H), 6.76(d, J=1.8Hz, 1H), 6.84(d, J=8.7Hz, 1H), 6.90(brs, 1H), 7.06(d, J=8.4Hz, 3H), 7.44(d, J=8.7Hz, 2H)<br>IR(Nujol)3475, 3361, 1609, 1579, 1521, 1260, 1244, 1110, 1071, 1012, 988, 822, 782cm⁻¹ |
| I-209 | ¹HNMR(CDCl₃) δ 2.35(s, 6H), 3.45(s, 3H), 3.75(s, 3H), 5.07(s, 2H), 6.45(s, 1H), 6.91(d, J=8.7Hz, 2H), 6.95(dd, J=8.4, 1.8Hz, 1H), 7.01(brs, 1H), 7.02(d, J=8.4Hz, 1H), 7.06(brs, 2H), 7.08(d, J=1.8Hz, 1H), 7.53(d, J=8.7Hz, 2H)<br>IR(Nujol)3410, 1610, 1588, 1523, 1489, 1248, 1225, 1114, 1071, 1011, 940, 825, 808,cm⁻¹ |

TABLE 47

| | |
|---|---|
| I-210 | ¹HNMR(CD₃OD) δ 3.37(s, 3H), 3.67(s, 3H), 5.25(s, 2H), 6.43(s, 1H), 6.77(dd, J=8.4, 2.1Hz, 1H), 6.84(d, J=8.7Hz, 2H), 6.89(d, J=2.1Hz, 1H), 6.94(d, J=8.4Hz, 1H), 7.45(d, J=8.7Hz, 2H), 7.60(d, J=8.4Hz, 2H), 8.04(d, J=8.4Hz, 2H)<br>IR(Nujol)3384, 1694, 1612, 1591, 1523, 1488, 1249, 1113, 1071, 1013, 940, 826, 812, 765cm⁻¹ |
| I-211 | ¹HNMR(CDCl₃) δ 3.45(s, 3H), 3.74(s, 3H), 5.09(s, 3H), 6.41(dd, J=3.3, 1.8Hz, 1H), 6.45(s, 1H), 6.47(d, J=3.3Hz, 1H), 6.92(d, J=8.7Hz, 2H), 6.97(dd, J=8.4, 2.1Hz, 1H), 7.07(d, J=2.1Hz, 1H), 7.08(d, J=8.4Hz, 1H), 7.48(d, J=1.8, 1.0Hz, 1H), 7.54(d, J=8.7Hz, 2H)<br>IR(Nujol)3410, 1612, 1589, 1523, 1489, 1248, 1226, 1113, 1071, 1011, 939, 815, 747cm⁻¹ |
| I-212 | m.p. 156–158° C.<br>¹HNMR(CDCl₃) δ 1.06(t, J=7.4Hz, 3H), 1.75(s, 3H), 2.10(q, J=7.4Hz, 2H), 3.46(s, 3H), 3.75(s, 3H), 4.64(d, J=7.0Hz, 2H), 5.52(t, J=7.0Hz, 1H), 6.45(s, 1H), 6.92(d, J=8.6Hz, 2H), 6.96(br.s, 2H), 7.06(br.s, 1H), 7.53(d, J=8.6Hz, 2H)<br>IR(KBr)3392, 2960, 2934, 1610, 1583, 1568, 1523, 1492, 1465, 1406, 1259, 1241, 1224, 1198, 1118, 1071, 824, 812cm⁻¹ |
| I-213 | m.p. 175–177° C.<br>¹HNMR(CDCl₃) δ 1.77(s, 3H), 1.80(s, 6H), 3.46(s, 3H), 3.75(s, 3H), 4.59(s, 2H), 6.45(s, 1H), 6.92(d, J=8.7Hz, 2H), 6.96(br.s, 2H), 7.06(br.s, 1H), 7.53(d, J=8.7Hz, 2H)<br>IR(KBr)3449, 2929, 1612, 1581, 1523, 1489, 1403, 1262, 1243, 1228, 1113, 1070, 823, 807cm⁻¹ |
| I-214 | ¹HNMR(CDCl₃) δ 1.66(tt, J=6.6, 6.6Hz, 2H), 1.74(tt, J=6.6, 6.6Hz, 2H), 2.32(t, J=6.6Hz, 2H), 2.34(t, J=6.6Hz, 2H), 2.71(s, 3H), 3.21(s, 3H), 3.24(s, 3H), 3.56(s, 3H), 3.78(s, 3H), 4.62(d, J=6.9Hz, 2H), 5.60(m, 1H), 6.84(s, 1H), 7.09(d, J=8.7Hz, 1H), 7.34(dd, J=8.7, 2.1Hz, 1H), 7.37(d, J=8.7Hz, 2H), 7.38(d, J=2.1Hz, 1H), 7.67(d, J=8.7Hz, 2H)<br>IR(KBr)2941, 1610, 1518, 1418, 1365, 1177, 1151, 1079, 847, 818cm⁻¹ |
| I-215 | ¹HNMR(CDCl₃) δ 1.57–1.72(m, 4H), 2.05–2.13(m, 4H), 2.70(s, 3H), 3.21(s, 3H), 3.23(s, 3H), 3.56(s, 3H), 3.78(s, 3H), 4.48(s, 2H), 5.86(s, 1H), 6.84(s, 1H), 7.09(d, J=8.4Hz, 1H), 7.34(dd, J=8.4, 2.1Hz, 1H), 7.38(d, J=8.7Hz, 2H), 7.38(d, J=2.1Hz, 1H), 7.67(d, J=8.7Hz, 2H)<br>IR(KBr)2936, 1610, 1518, 1481, 1365, 1177, 1151, 1079, 818cm⁻¹ |

TABLE 48

| | |
|---|---|
| I-216 | ¹HNMR(CDCl₃) δ 1.74(d, J=6.6Hz, 3H), 2.54(d, J=2.1Hz, 1H), 2.70(s, 3H), 3.21(s, 3H), 3.24(s, 3H), 3.56(s, 3H), 3.78(s, 3H), 5.00(dd, J=6.6, 2.1Hz, 1H), 6.84(s, 1H), 7.28(d, J=8.7Hz, 1H), 7.36(dd, J=8.7, 2.1Hz, 1H), 7.38(d, J=8.7Hz, 2H), 7.41(d, J=2.1Hz, 1H), 7.68(d, J=8.7Hz, 2H)<br>IR(KBr)3282, 3023, 2940, 1609, 1519, 1481, 1365, 1177, 1151, 1079, 970, 815cm⁻¹ |
| I-217 | m.p. 80–85° C.<br>¹HNMR(CDCl₃) δ 1.62–1.77(m, 4H), 2.25–2.39(m, 4H), 3.46(s, 3H), 3.75(s, 3H), 4.60(d, J=7.0Hz, 2H), 5.63(m, 1H), 6.45(s, 1H), 6.92(d, J=8.6Hz, 1H), 6.95(br.s, 2H), 7.06(br.s, 1H), 7.68(d, J=8.6Hz, 2H)<br>IR(KBr)3282, 3023, 2940, 1609, 1519, 1481, 1365, 1177, 1151, 1079, 970, 815cm⁻¹ |
| I-218 | foam<br>¹HNMR(CDCl₃) δ 3.45(s, 3H), 3.77(s, 3H), 5.16(s, 2H), 5.69(brs, 1H), 5.86(s, 1H), 6.47(s, 1H), 6.95(dd, J=2.1, 8.4Hz, 1H), 7.04(d, J=8.4Hz, 1H), 7.08(d, J=2.1Hz, 1H), 7.34–7.65(m, 7H), 7.83–7.92(m, 2H)<br>IR(CHCl₃)3530, 3022, 1614, 1588, 1500, 1485, 1463, 1405, 1326, 1290, 1249, 1168, 1130, 1117, 1073, 1011cm⁻¹ |
| I-219 | foam<br>¹HNMR(CDCl₃) δ 1.69(s, 3H), 1.74(s, 3H), 2.51–2.59(m, 2H), 2.74(s, 3H), 3.22(s, 3H), 3.55(s, 3H), 3.79(s, 3H), 4.07(t, J=6.6Hz, 2H), 5.21(m, 1H), 6.85(s, 1H), 7.08(d, J=8.7Hz, 1H), 7.35(dd, J=2.1, 8.7Hz, 1H), 7.39(d, J=2.1Hz, 1H), 7.55–7.69(m, 2H), 7.81–7.87(m, 2H)<br>IR(CHCl₃)3024, 1609, 1519, 1481, 1467, 1396, 1369, 1321, 1272, 1179, 1122, 1082, 1015cm⁻¹ |
| I-220 | m.p. 124–126° C.<br>¹HNMR(CDCl₃) δ 1.69(s, 3H), 1.75(s, 3H), 2.50–2.57(m, 2H), 3.46(s, 3H), 3.76(s, 3H), 4.07(t, J=6.9Hz, 2H), 5.22(m, 1H), 5.69(brs, 1H), 5.84(s, 1H), 6.46(s, 1H), 6.93–7.05(m, 3H), 7.55–7.65(m, 2H), 7.82–7.91(m, 2H).<br>IR(KBr)3406, 2935, 1587, 1519, 1501, 1488, 1459, 1359, 1323, 1304, 1291, 1274, 1223, 1170, 1126, 1113, 1075, 1018cm⁻¹ |

TABLE 49

I-221  m.p. 187–189° C.
¹HNMR(CDCl₃) δ 2.33(s, 3H), 2.69(s, 3H), 3.21(s, 3H), 3.24(s, 3H), 3.55(s, 3H), 3.77(s, 3H), 4.17(s, 2H), 6.84(s, 1H), 7.12&7.25(ABq, J=8.7Hz, 4H), 7.31(dd, J=8.1Hz, J=1.5Hz, 1H), 7.38&7.67(ABq, J=8.7Hz, 4H), 7.42(d, J=8.1Hz, 1H), 7.46(d, J=1.5Hz, 1H)
IR(KBr)1512, 1474, 1417, 1391, 1356, 1343, 1177, 1149, 1082, 1054, 1013, 976, 961, 939, 867, 854, 844, 820, 812, 799, 523cm⁻¹

I-222  m.p. 107–112° C.
¹HNMR(CDCl₃) δ 2.73(s, 3H), 3.22(s, 3H), 3.28(s, 3H), 3.55(s, 3H), 3.77(s, 3H), 4.34(s, 2H), 6.84(s, 1H), 7.19(m, 1H), 7.30(dd, J=8.1Hz, J=1.8Hz, 1H), 7.34–7.41(m, 3H), 7.46(d, J=1.8Hz, 1H), 7.49(d, J=8.1Hz, 1H), 7.62–7.69(m, 3H), 8.55(m, 1H)
IR(KBr)1474, 1389, 1364, 1179, 1151, 1081, 937, 873, 813, 797, 523cm⁻¹

I-223  m.p. 212–214° C.
¹HNMR(CDCl₃+CD₃OD) δ 3.45(s, 3H), 3.74(s, 3H), 4.13(s, 2H), 6.45(s, 1H), 6.90–6.96(m, 3H), 7.12(d, J=1.8Hz, 1H), 7.18–7.26(m, 2H), 7.48–7.54(m, 3H), 7.68(m, 1H), 8.63(m, 1H)
IR(KBr)3504, 3272, 1612, 1596, 1574, 1521, 1492, 1463, 1436, 1405, 1362, 1310, 1265, 1222, 1172, 1116, 1083, 1052, 1017, 828cm⁻¹

I-224  m.p. 199–200° C.
¹HNMR(CDCl₃) δ 1.46(d, J=0.9Hz, 3H), 1.77(s, 3H), 3.44(s, 3H), 3.74(s, 3H), 3.90(m, 2H), 5.25(m, 1H), 6.04(brs, 1H), 6.45(s, 1H), 6.93&7.53(ABq, J=8.7Hz, 4H), 7.00(m, 2H), 7.05(m, 1H)
IR(KBr)3404, 2999, 2932, 1612, 1595, 1522, 1483, 1454, 1432, 1401, 1376, 1357, 1271, 1223, 1119, 1080, 1055, 1015, 974, 938, 829, 817cm⁻¹

I-225  m.p. 181–183° C.
¹HNMR(CDCl₃) δ 1.37(s, 9H), 3.45(s, 3H), 3.75(s, 3H), 4.93(brs, 1H), 6.00(s, 1H), 6.46(s, 1H), 6.93&7.54(ABq, J=8.7Hz, 4H), 6.99(s, 1H), 7.01(dd, J=8.4Hz, J=1.5Hz, 1H), 7.16(d, J=1.5Hz, 1H), 7.49(d, J=8.4Hz, 1H)
IR(KBr)3495, 3412, 2959, 2931, 1610, 1568, 1552, 1521, 1499, 1477, 1459, 1400, 1364, 1319, 1270, 1227, 1192, 1161, 1116, 1102, 1090, 1052, 1019, 942, 833, 817, 588cm⁻¹

TABLE 50

I-226  m.p. 154–156° C.
¹HNMR(CDCl₃) δ 2.33(s, 3H), 3.45(s, 3H), 3.75(s, 3H), 3.90(s, 2H), 4.68(s, 1H), 5.97(s, 1H), 6.45(s, 1H), 6.60(s, 1H), 6.90–6.98(m, 3H), 7.10(s, 5H), 7.41(d, J=8.1Hz, 1H), 7.53(m, 2H)
IR(KBr)3462, 3368, 1611, 1550, 1521, 1499, 1472, 1455, 1437, 1401, 1362, 1321, 1293, 1267, 1229, 1187, 1174, 1164, 1118, 1077, 1050, 1011, 821cm⁻¹

I-227  m.p. 172–174° C.
¹HNMR(CDCl₃) δ 1.38(d, J=1.2Hz, 3H), 1.76(s, 3H), 3.44(s, 3H), 3.75(s, 3H), 3.87(d, J=7.8Hz, 2H), 5.08(brs, 1H), 5.26(m, 1H), 6.08(s, 1H), 6.45(s, 1H), 6.94&7.53(ABq, J=8.7Hz, 4H), 7.11–7.14(m, 2H), 7.62(d, J=8.7Hz, 1H), 8.87(s, 1H)
IR(KBr)3412, 1613, 1520, 1478, 1458, 1443, 1404, 1360, 1346, 1290, 1270, 1224, 1200, 1171, 1119, 1078, 1054, 945cm⁻¹

I-228  m.p. 173–175° C.
¹HNMR(CDCl₃) δ 1.69(s, 3H), 1.74(s, 3H), 2.10(s, 3H), 2.50–2.61(m, 2H), 3.20(s, 3H), 3.21(s, 3H), 3.37(s, 3H), 3.71(s, 3H), 4.08(t, J=6.8Hz, 2H), 5.21–5.25(m, 1H), 6.73(s, 1H), 7.03–7.18(m, 2H), 7.23–7.25(m, 2H), 7.37(d, J=8.6Hz, 2H), 7.69(d, J=8.8Hz, 2H)
IR(KBr)3600–3200(br), 3100–2800(br), 1610, 1527, 1523, 1477, 1432, 1365, 1240, 1172, 1160, 955, 923cm⁻¹

I-229  m.p. 148–150° C.
¹HNMR(CDCl₃) δ 1.70(s, 3H), 1.77(s, 3H), 2.09(s, 3H), 2.48–2.62(m, 2H), 3.38(s, 3H), 3.73(s, 3H), 4.09(t, J=7.0Hz, 2H), 4.84(br, 1H), 5.19–5.22(m, 1H), 5.70(s, 1H), 6.71–6.96(m, 5H), 7.55(d, J=8.2Hz, 2H)
IR(KBr)3700–3200(br), 3100–2800(br), 1612, 1584, 1560, 1448, 1428, 1390, 1339, 1315, 1284, 1246, 1173, 1160, 1123, 1018, 999cm⁻¹

I-230  m.p. 194–195° C.
¹HNMR(CDCl₃) δ 2.10(s, 3H), 2.39(s, 3H), 3.10(s, 3H), 3.21(s, 3H), 3.36(s, 3H), 3.71(s, 3H), 5.13(s, 2H), 6.73(s, 1H), 7.14–7.18(m, 8H), 7.69(d, J=9.0Hz, 2H)
IR(KBr)3600–3200(br), 3100–2800(br), 1516, 1475, 1360, 1332, 1292, 1266, 1228, 1199, 1174, 1151, 1119, 1098, 1084, 1005, 968cm⁻¹

TABLE 51

I-231  m.p. 178–180° C.
¹HNMR(CDCl₃ ) δ 2.09(s, 3H), 2.40(s, 3H), 3.37(s, 3H), 3.72(s, 3H), 4.97(brs, 1H), 5.10(s, 2H), 5.67(br, 1H), 6.70–6.75(m, 2H), 6.86–7.03(m, 3H), 7.22–7.26(m, 2H), 7.32–7.34(m, 2H), 7.54(d, J=8.2Hz, 2H)
IR(KBr)3600–3200(br), 3100–2800(br), 1611, 1519, 1479, 1463, 1388, 1339, 1314, 1286, 1258, 1246, 1225, 1128, 1098, 1077, 1007cm⁻¹

I-232  m.p. 177–179° C.
¹HNMR(CDCl₃) δ 2.54(s, 3H), 2.69(s, 3H), 3.13(s, 3H), 3.54(s, 3H), 3.77(s, 3H), 5.19(s, 2H), 6.85(s, 1H), 7.15(d, J=8.4Hz, 2H), 7.30–7.49(m, 9H), 7.53–7.59(m, 2H)
IR(CHCl₃)1516, 1476, 1368, 1266, 1176, 1118, 1077, 1080, 1013, 970, 876, 820cm⁻¹

I-233  amorphouspowder
¹HNMR(CDCl₃) δ 2.54(s, 3H), 3.46(s, 3H), 3.75(s, 3H), 5.15(s, 2H), 5.67(brs, 1H), 5.90(s, 1H), 6.46(s, 1H), 6.95(d.d, J=1.8&8.1Hz, 1H), 7.02(d, J=8.1Hz, 1H), 7.09(d, J=1.8Hz, 1H), 7.31–7.49(m, 7H), 7.55–7.62(m, 2H)
IR(CHCl₃)3526, 1517, 1483, 1414, 1389, 1246, 1192, 1114, 1070, 1010, 937, 818cm⁻¹

I-234  ¹HNMR(CDCl₃) δ 1.76(s, 3H), 1.81(s, 3H), 2.73(s, 3H), 3.24(s, 3H), 3.53(s, 3H), 3.79(s, 3H), 3.96(s, 3H), 4.64(d, J=6.9Hz, 2H), 5.49(t, J=6.9Hz, 1H), 6.87(s, 1H), 7.09(d, J=8.4Hz, 1H), 7.35(d.d, J=8.4&2.1Hz, 1H), 7.39(d, J=2.1Hz, 1H), 7.71(d, J=8.4Hz, 2H), 8.13(d, J=8.4Hz, 2H)

I-235  ¹HNMR(CDCl₃) δ 2.69(s, 3H), 3.14(s, 3H), 3.55(s, 3H), 3.80(s, 3H), 5.20(s, 2H), 6.89(s, 1H), 7.16(d, J=9.0Hz, 1H), 7.34(d, J=2.1Hz, 1H), 7.36–7.51(m, 6H), 7.75(d, J=8.4Hz, 2H), 8.23(d, J=8.4Hz, 2H)
IR(KBr)3427, 1724, 1685, 1606, 1509, 1481, 1369, 1272, 1235, 1179, 1120, 1084, 1017cm⁻¹

I-236  ¹HNMR(CDCl₃) δ 3.46(s, 3H), 3.77(s, 3H), 5.16(s, 3H), 6.50(s, 3H), 6.96(dd, J=8.4&2.1Hz, 1H), 7.03(d, J=8.4Hz, 1H), 7.09(d, J=2.1Hz, 1H), 7.34–7.50(m, 5H), 7.75(d, J=8.1Hz, 2H), 8.17(d, J=8.1Hz, 2H)

TABLE 52

| | |
|---|---|
| I-237 | ¹HNMR(CDCl₃) δ 3.44(s, 3H), 3.76(s, 3H), 3.96(s, 3H), 5.16(s, 2H), 5.69(s, 1H), 5.89(s, 1H), 6.49(s, 1H), 6.96(d,d, J=8..4&2.1Hz, 1H), 7.03(d, J=8.4Hz, 1H), 7.09(d, J=2.1Hz, 1H), 7.32–7.50(m, 5H), 7.73(d, J=8.4Hz, 2H), 8.13(d, J=8.4Hz, 2H)<br>IR(KBr)3497, 3443, 1708, 1608, 1585, 1487, 1460, 1443, 1395, 1281, 1113, 1068, 1008cm⁻¹ |
| I-238 | ¹HNMR(CDCl₃) δ 2.69(s, 3H), 3.13(s, 3H), 3.53(s, 3H), 3.79(s, 3H), 3.96(s, 3H), 5.19(s, 2H), 6.87(s, 1H), 7.15(d, J=9.0Hz, 1H), 7.31–7.50(m, 7H), 7.71(d, J=8.4Hz, 2H), 8.13(d, J=8.4Hz, 2H)<br>IR(KBr)1719, 1608, 1481, 1366, 1278, 1118, 1080, 1017cm⁻¹ |
| I-239 | ¹HNMR(CDCl₃) δ 2.38(s, 3H), 2.68(s, 3H), 3.12(s, 3H), 3.53(s, 3H), 3.79(s, 3H), 3.96(s, 3H), 5.14(s, 2H), 6.87(s, 1H), 7.15(d, J=8.7Hz, 1H), 7.21(d, J=8.4Hz, 2H), 7.34(d, J=8.4Hz, 2H), 7.36(d, J=8.7Hz, 1H), 7.40(d, J=2.1Hz, 1H), 7.71(d, J=8.7Hz, 2H), 8.13(d, J=8.4Hz, 2H)<br>IR(KBr)1718, 1607, 1519, 1481, 1355, 1280, 1232, 1182, 1121, 1079, 1018cm⁻¹ |
| I-240 | ¹HNMR(CDCl₃) δ 2.70(s, 3H), 3.03(s, 3H), 3.12(s, 3H), 3.55(s, 3H), 3.77(s, 3H), 5.18(s, 2H), 6.78–6.89(broad, 1H), 6.86(s, 1H), 7.14(d, J=8.4Hz, 1H), 7.31–7.49(m, 8H), 7.55(d, J=8.4Hz, 2H)<br>IR(KBr)1604, 1526, 1483, 1395, 1374, 1360, 1292, 1231, 1177, 1119, 1078, 1014cm⁻¹ |
| I-241 | ¹HNMR(CDCl₃) δ 2.37(s, 3H), 2.69(s, 3H), 3.05(s, 3H), 3.12(s, 3H), 3.55(s, 3H), 3.77(s, 3H), 5.14(s, 2H), 6.85(s, 1H), 6.81–6.91(broad, 2H), 7.14(d, J=8.4Hz, 1H), 7.21(d, J=8.1Hz, 1H), 7.34(d, J=8.1Hz, 2H), 7.40(d, J=2.1Hz, 1H), 7.56(d, J=8.4Hz, 2H)<br>IR(KBr)1605, 1529, 1484, 1396, 1356, 1275, 1233, 1178, 1121, 1078, 1016cm⁻¹ |
| I-242 | ¹HNMR(CDCl₃) δ 1.76(s, 3H), 1.81(s, 3H), 2.73(s, 3H), 3.03(s, 6H), 3.22(s, 3H), 3.55(s, 3H), 3.77(s, 3H), 4.63(d, J=6.6Hz, 2H), 5.49(t, J=6.6Hz, 1H), 6.75–6.91(broad, 2H), 6.86(s, 1H), 7.08(d, J=8.7Hz, 1H), 7.34(d,d, J=8.7&2.1Hz, 1H), 7.39(d, J=2.1Hz, 1H), 7.55(d, J=8.7Hz, 1H)IR(KBr)1609, 1529, 1482, 1363, 1235, 1178, 1117, 1078, 1013cm⁻¹ |
| I-243 | IR(KBr)3409, 1608, 1509, 1464, 1367, 1230, 1175, 1149, 1079, 1018cm⁻¹ |

TABLE 53

| | |
|---|---|
| I-244 | ¹HNMR(CDCl₃) δ 1.72(s, 3H), 1.76(s, 3H), 2.55(m, 2H), 3.22(s, 3H)3.45(s, 3H), 3.72(s, 3H), 4.07(d, J=6.6Hz, 2H), 4.46(d, J=10.5Hz, 1H), 4.51(d, J=10.5Hz, 1H), 4.66(d, J=10.5Hz, 1H), 4.75(d, J=10.5Hz, 1H), 5.24(brs, 1H), 6.84(s, 1H), 6.95(d, J=8.7Hz, 1H), 7.02(s, 1H), 7.21(d, J=8.7Hz, 1H), 7.39(d, J=9.0Hz, 2H)7.71(d, J=9.0Hz, 2H)<br>IR(KBr)3307, 1609, 1509, 1465, 1364, 1235, 1180, 1152, 1082, 1021cm⁻¹ |
| I-245 | m.p. 182–184° C.<br>¹HNMR(CDCl₃) δ 2.42(s, 3H), 2.70(s, 3H), 3.13(s, 3H), 3.53(s, 3H), 3.77(s, 3H), 5.19(s, 2H)6.86(s, 1H), 7.13–7.53(m, 12H)<br>IR(KBr)3434, 3030, 2937, 1605, 1522, 1483, 1366, 1274, 1235, 1176, 1119, 1086, 1011cm⁻¹ |
| I-246 | ¹HNMR(CDCl₃) δ 2.58(s, 3H), 3.21(s, 3H), 3.55(s, 3H), 3.77(s, 3H)3.91(s, 3H), 5.26(m, 2H), 6.84(s, 1H), 7.12(d, J=9.0Hz, 1H), 7.27–7.54(m, 8H), 7.60(d, J=8.7Hz, 2H), 7.90(d, J=2.1Hz, 1H)<br>IR(KBr)1728, 1699, 1605, 1513, 1480, 1362, 1239, 1175, 1150, 1083, 1017cm⁻¹ |
| I-247 | IR(KBr)1729, 1607, 1512, 1479, 1366, 1234, 1177, 1151, 1079, 1015cm⁻¹ |
| I-248 | ¹H NMR(CDCl₃) δ 1.75 (s, 3H), 1.79 (s, 3H), 2.57 (s, 3H), 3.21 (s, 3H), 3.56 (s, 3H), 3.78 (s, 3H), 3.89(s, 3H), 4.63 (d, J=6.6Hz, 2H), 5.49–5.58 (m, 1H), 6.85 (s, 1H), 6.93–7.00 (m, 3H), 7.38 (d, J=8.7Hz, 2H), 7.70 (d, J=8.7Hz, 2H)<br>IR(KBr)1603, 1518, 1482, 1365, 1239, 1176, 1150, 1078cm⁻¹ |
| I-249 | foam<br>¹HNMR(CDCl₃) δ 2.30(br, 1H), 2.76–2.82(m, 2H), 3.64–3.68(m, 2H), 3.87(s, 1H), 5.14(s, 2H), 5.70(s, 1H), 6.70(dd, J=2.1, 8.4Hz, 1H), 6.78 (s, 1H), 6.84(d, J=1.8Hz, 1H), 6.97–7.01(m, 3H), 7.37–7.49(m, 5H), 7.56–7.61(m, 2H)<br>IR(KBr)3600–2800(br), 1608, 1583, 1517, 1464, 1387, 1287, 1247, 1225, 1178, 1082, 1015cm⁻¹ |
| I-250 | m.p. 104–105° C.<br>¹HNMR(CDCl₃) δ 0.76(t, J=7.5Hz, 3H), 1.44–1.54(m, 2H), 3.61(s, 3H), 3.71(t, J=6.6Hz, 2H), 3.74(s, 3H), 3.87(s, 3H)5.16(s, 2H), 5.63 (s, 1H), 6.66(s, 1H), 6.90(dd, J=2.1, 8.4Hz, 1H), 6.96–7.01(m, 4H), 7.04(d, J=1.8Hz, 1H), 7.37–7.48(m, 5H), 7.51–7.56(m, 2H)<br>IR(KBr)3600–2800(br), 1608, 1593, 1518, 1474, 1462, 1379, 1294, 1251, 1226, 1183, 1109, 1078, 1040, 1008cm⁻¹ |

TABLE 54

| | |
|---|---|
| I-251 | m.p. 103–105° C.<br>¹HNMR(CDCl₃) δ 0.78(t, J=7.2Hz, 3H), 1.15–1.27(m, 2H), 1.43–1.51(m, 2H), 3.61(s, 3H), 3.73–3.77(m, 2H), 3.74(s, 3H), 3.87(s, 3H), 5.16 (s, 2H), 5.63(s, 1H), 6.65(s, 1H), 6.90(dd, J=2.1, 8.1Hz, 1H), 6.96–7.01(m, 3H), 7.04(d, J=2.1Hz, 1H), 7.37–7.48(m, 5H), 7.51–7.56(m, 2H)<br>IR(KBr)3600–2800(br), 1607, 1518, 1467, 1375, 1288, 1251, 1179, 1113, 1084, 1020, 1008cm⁻¹ |
| I-252 | m.p. 111.5–112.5° C.<br>¹HNMR(CDCl₃) δ 0.78(t, J=7.5Hz, 3H), 1.15–1.27(m, 2H), 1.41–1.50(m, 2H), 3.10(s, 3H), 3.61(s, 3H), 3.73–3.78(m, 2H), 3.74(s, 6H), 5.18 (s, 2H), 6.66(s, 1H), 6.96–7.01(m, 2H), 7.10(d, J=8.7Hz, 1H), 7.26–7.55(m, 9H)<br>IR(KBr)3600–2800(br), 1609, 1518, 1464, 1440, 1375, 1355, 1289, 1269, 1249, 1181, 1170, 1107, 1080, 1019cm⁻¹ |
| I-253 | ¹HNMR(CDCl₃) δ 1.76(s, 3H), 1.82(s, 3H), 3.45(s, 3H), 3.76(s, 3H), 4.62(d, J=8.4Hz, 2H), 5.54(t, J=8.4Hz, 1H), 6.49(s, 1H), 6.91–6.99 (m, 2H), 7.05(d, J=1.5Hz), 7.74(d, J=8.7Hz, 2H), 8.15(d, J=8.7Hz, 2H)<br>IR(KBr)3474, 1687, 1607, 1509, 1417, 1397, 1316, 1287, 1240, 1109 1071, 1006cm⁻¹ |
| I-254 | ¹HNMR(CDCl₃) δ 2.39(s, 3H), 3.45(s, 3H), 3.76(s, 3H), 5.11(s, 2H), 6.49(s, 1H), 6.94(dd, J=8.4&1.8Hz, 1H), 7.04(d, J=8.4Hz, 1H), 7.06 (d, J=1.8Hz), 7.19–7.38(m, 4H), 7.73(d, J=8.4Hz, 2H), 8.14(d, J=8.4Hz, 2H)<br>IR(KBr)3549, 3466, 1668, 1603, 1518, 1489, 1465, 1449, 1421, 1397, 1372, 1288, 1236, 1186, 1117, 1074, 1017cm⁻¹ |
| I-255 | ¹HNMR(CDCl₃) δ 1.76(s, 3H), 1.82(s, 3H), 3.02(s, 6H), 3.48(s, 3H), 3.74(s, 3H), 4.61(d, J=7.2Hz, 2H), 5.53(t, J=7.2Hz, 1H), 5.66(s, 1H), 5.92(s, 1H), 6.47(s, 1H), 6.81(broad, 2H), 6.95(s, 2H), 7.06(d, J=1.8Hz), 7.56(d, J=8.7Hz, 2H)<br>IR(KBr)3535, 3494, 3452, 1606, 1526, 1487, 1406, 1357, 1288, 1242, 1195, 1112cm⁻¹ |
| I-256 | ¹HNMR(CDCl₃) δ 2.39(s, 3H), 3.02(s, 6H), 3.48(s, 3H)3.74(s, 3H)5.10(s, 2H), 5.66(s, 1H), 5.93(s, 1H), 6.47(s, 1H), 6.82(d, J=8.4Hz, 2H), 6.96(dd, J=8.1&1.8Hz, 1H), 7.02(d, J=8.1Hz, 1H), 7.08(d, J=1.8Hz, 1H), 7.23(d, J=7.8Hz, 2H), 7.34(d, J=7.8Hz, 2H), 7.56(d, J=8.4Hz, 2H)<br>IR(KBr)3536, 3379, 1610, 1586, 1528, 1489, 1460, 1443, 1361, 1288, 1250, 1225, 1195, 1117, 1072, 1008cm⁻¹ |

TABLE 55

| | |
|---|---|
| I-257 | $^1$HNMR(CDCl$_3$) δ 1.71(s, 3H), 1.76(s, 3H), 2.49–2.60(m, 2H), 3.44(s, 3H), 3.70(s, 3H), 4.06(t, J=6.3Hz, 2H), 4.48(d, J=6.0Hz, 2H), 4.71 (d, J=8.7Hz, 2H), 5.23(t, J=8.7Hz, 1H), 5.37(broads, 1H), 6.84(s, 1H), 6.91–6.97(m, 1H), 6.92(d, J=8.4Hz, 2H), 7.18–7.23(m, 2H), 7.52 (d, J=8.7Hz, 2H)<br>IR(KBr)3398, 1612, 1518, 1465, 1389, 1232, 1174, 1131, 1101, 1081, 1023cm$^{-1}$ |
| I-258 | $^1$HNMR(CDCl$_3$) δ: 3.21(s, 3H), 3.41(s, 3H), 3.63(s, 3H), 3.77(s, 3H), 4.76(s, 2H), 5.15(s, 2H), 6.94(s, 1H), 6.99(d, J=8.7Hz, 1H), 7.23–7.49 (m, 9H), 7.71(d, J=8.7Hz, 2H)<br>IR(KBr)3497, 1738, 1721, 1607, 1509, 1469, 1362, 1242, 1152, 1056, 1017cm$^{-1}$ |
| I-259 | foam<br>$^1$HNMR(CDCl$_3$) δ 2.35(s, 6H), 2.73(s, 3H), 2.79(t, J=5.7Hz, 2H), 3.21(s, 3H), 3.31(s, 3H), 3.56(s, 3H), 3.78(s, 3H), 4.19(t, J=5.7Hz, 2H), 6.84(s, 1H), 7.09(d, J=8.4Hz, 1H), 7.34–7.41(m, 4H), 7.66–7.71(m, 2H)<br>IR(KBr)3600–2700(br), 1519, 1481, 1365, 1273, 1200, 1177, 1151, 1120, 1079, 1015cm$^{-1}$ |
| I-260 | foam<br>$^1$HNMR(CDCl$_3$ + CD$_3$OD) δ 2.71(t, J=5.1Hz, 2H), 3.46(s, 6H), 3.73(s, 6H), 4.11(t, J=5.1Hz, 2H), 6.44(s, 1H), 6.87–6.99(m, 4H), 7.04(d, J=2.1Hz, 1H), 7.49–7.53(m, 2H)<br>IR(KBr)3600–2200(br), 1607, 1583, 1519, 1475, 1407, 1390, 1275, 1252, 1226, 1114, 1062cm$^{-1}$ |
| I-261 | m.p. 85–87° C.<br>$^1$HNMR(CDCl$_3$) δ 3.49(s, 3H), 3.75(s, 3H), 5.15(s, 2H), 5.23(brs, 1H), 5.68(brs, 1H), 5.89(s, 1H), 6.43(s, 1H), 6.95(dd, J=8.3, 2.1Hz, 1H), 7.03(d, J=8.3Hz, 1H), 7.08(d, J=2.1Hz, 1H), 7.08(t, J=8.7Hz, 1H), 7.33(ddd, J=8.7, 2.1, 1.2Hz 1H), 7.37–7.47(m, 6H)<br>IR(KBr)3410, 1525, 1488, 1284, 1248, 1102, 1010, 759, 704cm$^{-1}$ |

TABLE 56

| | |
|---|---|
| I-262 | m.p. 138–140° C.<br>$^1$HNMR(CDCl$_3$) δ 1.77(s, 3H), 1.82, (s, 3H), 3.21(s, 3H), 3.22(s, 3H), 3.48(s, 3H), 3.78(s, 3H), 4.64(d, J=6.5Hz, 2H), 5.51(t, J=6.5Hz, 1H), 7.05(d, J=8.5Hz, 1H), 7.08(s, 1H), 7.14(dd, J=8.5, 2.2Hz, 1H), 7.34(d, J=2.2Hz, 1H), 7.40(d, J=8.7Hz, 2H), 7.69(d, J=8.7Hz, 2H), 10.00 (s, 1H)<br>IR(KBr)1693, 1514, 1470, 1361, 1348, 1275, 1239, 1175, 1151, 979, 969, 867, 845, 815cm$^{-1}$ |
| I-263 | foam<br>$^1$HNMR(DMSO-d$_6$) δ 1.74(s, 3H), 1.78(s, 3H), 3.32(s, 3H), 3.44(s, 3H), 3.76(s, 3H), 4.66(d, J=6.6Hz, 2H), 5.49(t, J=6.6Hz, 1H), 7.11(s, 1H), 7.23–7.25(m, 3H), 7.48(d, J=8.6Hz, 2H), 7.77(d, J=8.6Hz, 2H), 13.1(brs, 1H)<br>IR(KBr)3431, 1737, 1518, 1471, 1177, 1151, 972, 864, 849cm$^{-1}$ |
| I-264 | m.p. 153.5–155.5° C.<br>$^1$HNMR(CDCl$_3$) δ 2.58(s, 3H), 3.52(s, 3H), 3.77(s, 3H), 5.21(s, 2H), 6.83(s, 1H), 7.04–7.24(m, 5H), 7.30–7.49(m, 5H), 7.56–7.65(m, 2H)<br>IR(CHCl$_3$)1607, 1520, 1481, 1412, 1368, 1298, 1267, 1131, 1080, 1012, 960, 942, 907, 869, 836, 812cm$^{-1}$ |
| I-265 | dp > 116° C.<br>$^1$HNMR(CDCl$_3$ + CD$_3$OD) δ 2.69(s, 3H), 3.15(s, 3H), 3.16(s, 3H), 3.57(s, 3H), 3.80(s, 3H), 5.21(s, 2H), 6.88(s, 1H), 7.19(d, J=8.4Hz, 1H), 7.34–7.51(m, 7H), 7.83–7.90(m, 2H), 8.01–8.07(m, 5H)<br>IR(KBr)3434, 3028, 2934, 1596, 1519, 1460, 1365, 1308, 1276, 1173, 1148, 1119, 1108, 1012, 946, 841, 819cm$^{-1}$ |
| I-266 | m.p. 136–138° C.<br>$^1$HNMR(CDCl$_3$) δ 3.43(s, 3H), 3.75(s, 3H), 5.19(s, 2H), 5.98(s, 1H), 6.44(s, 1H), 7.04–7.52(m, 10H), 7.57–7.65(m, 5H)<br>IR(CHCl$_3$)3496, 1612, 1521, 1488, 1454, 1412, 1391, 1313, 1267, 1157, 1113, 1069, 1010, 934, 825cm$^{-1}$ |

TABLE 57

| | |
|---|---|
| I-267 | foam<br>$^1$HNMR(CDCl$_3$) δ 2.38(s, 3H), 3.10(s, 3H), 3.21(s, 3H), 3.41(s, 3H), 3.67(s, 3H), 3.77(s, 3H), 5.11(s, 2H), 6.93(s, 1H), 7.09(d, J=8.6Hz, 1H), 7.21(d, J=8.2Hz, 2H), 7.27(d, J=2.1Hz, 1H), 7.35(d, J=8.2Hz, 2H), 7.38(d, J=8.9Hz, 2H), 7.70(d, J=8.9Hz, 2H)<br>IR(KBr)1733, 1518, 1471, 1367, 1297, 1177, 1151, 1118, 1059, 971, 862, 815cm$^{-1}$ |
| I-268 | amorphous<br>$^1$HNMR(DMSO-d$_6$) δ 1.64(s, 3H), 1.70(s, 3H), 2.44(q, J=7.2Hz, 2H), 3.30(s, 3H), 3.70(s, 3H), 3.93(t, J=7.2Hz, 2H), 5.26(t, J=7.2Hz, 1H), 6.64(dd, J=8.6, 2.1Hz, 1H), 6.74(d, J=2.1Hz, 1H), 6.87(d, J=8.9Hz, 2H), 6.87(d, J=8.6Hz, 1H), 6.96(s, 1H), 7.48(d, J=8.9Hz, 2H), 8.84 (s, 1H), 9.59(s, 1H), 12.8(brs, 1H)<br>IR(CHCl$_3$)3594, 3540, 1743, 1707, 1520, 1470, 1260, 1058cm$^{-1}$ |
| I-269 | m.p. 206–208° C.(dec.)<br>$^1$HNMR(DMSO-d$_6$) δ 2.32(s, 3H), 3.32(s, 3H), 3.66(s, 3H), 5.05(s, 2H), 6.66(dd, J=8.2, 2.1Hz, 1H), 6.79(d, J=2.1Hz, 1H), 6.83(s, 1H), 6.84 (d, J=8.6Hz, 2H), 6.89(d, J=8.2Hz, 1H), 7.20(d, J=8.0Hz, 2H), 7.38(d, J=8.0Hz, 2H), 7.45(d, J=8.6Hz, 2H), 8.91(s, 1H), 9.68(s, 1H), 12.7(brs, 1H)<br>IR(KBr)3413, 1710, 1612, 1591, 1520, 1471, 1377, 1227, 1083, 1059, 1013, 837, 809cm$^{-1}$ |
| I-270 | foam<br>$^1$HNMR(CDCl$_3$) δ 2.42(s, 3H), 3.45(s, 3H), 3.75(s, 3H), 5.15(s, 2H), 5.68(s, 1H), 5.93(s, 1H), 6.47(s, 1H), 6.96(dd, J=1.8, 8.1Hz, 1H), 7.03 (d, J=1.8Hz, 1H), 7.25–7.28(m, 2H), 7.35–7.48(m, 5H), 7.52–7.56(m, 2H)<br>IR(CHCl$_3$)3535, 3014, 1616, 1588, 1559, 1523, 1513, 1490, 1463, 1455, 1417, 1396, 1317, 1290, 1247, 1194, 1115, 1072, 1012cm$^{-1}$ |
| I-271 | m.p. 143–145° C.<br>$^1$HNMR(CDCl$_3$) δ 2.70(s, 3H), 3.12(s, 3H), 3.54(s, 3H), 3.73(s, 3H), 3.84(s, 3H), 5.18(s, 2H), 6.83(s, 1H), 7.00–7.07(m, 2H), 7.14(d, J=8.4Hz, 1H), 7.33–7.49(m, 9H)<br>IR(KBr)3434, 2940, 1609, 1520, 1482, 1396, 1369, 1293, 1283, 1243, 1178, 1114, 1080, 1021, 1009cm$^{-1}$ |

TABLE 58

| | |
|---|---|
| I-272 | foam<br>$^1$HNMR(CDCl$_3$) δ 3.45(s, 3H), 3.71(s, 3H), 3.86(s, 3H), 5.15(s, 2H), 5.67(s, 1H), 5.84(s, 1H), 6.42(s, 1H), 6.98(dd, J=1.8, 8.4Hz, 1H), 7.01–7.07(m, 2H), 7.11(d, J=1.8Hz, 1H), 7.35–7.45(m, 8H)<br>IR(CHCl$_3$)3534, 3024, 1617, 1587, 1517, 1503, 1483, 1462, 1409, 1290, 1247, 1226, 1215, 1122, 1104, 1072, 1013cm$^{-1}$ |

TABLE 58-continued

I-273 m.p. 155–156° C.
$^1$HNMR(CDCl$_3$) δ 1.76(s, 3H), 1.81(s, 3H), 2.42(s, 3H), 2.73(s, 3H), 3.23(s, 3H), 3.53(s, 3H), 3.77(s, 3H), 4.63(d, J=6.6Hz, 2H), 5.49(m, 1H), 6.86(s, 1H), 7.09(d, J=8.4Hz, 1H), 7.25–7.53(m, 6H)
IR(KBr)3434, 2935, 1605, 1522, 1465, 1388, 1365, 1292, 1273, 1176, 1119, 1084, 1011cm$^{-1}$

I-274 m.p. 138–140° C.
$^1$HNMR(CDCl$_3$) δ 1.76(s, 3H), 1.81(s, 3H), 2.73(s, 3H), 3.22(s, 3H), 3.54(s, 3H), 3.73(s, 3H), 3.84(s, 3H), 4.63(d, J=6.9Hz, 2H), 5.50(m, 1H), 6.83(s, 1H), 7.01–7.04(m, 2H), 7.08(d, J=8.4Hz, 1H), 7.26(d, J=0.6Hz, 1H), 7.34–7.43(m, 3H)
IR(KBr)3433, 2937, 1608, 1519, 1480, 1400, 1368, 1292, 1271, 1244, 1179, 1112, 1081, 1011cm$^{-1}$

I-275 m.p. 95–97° C.
$^1$HNMR(CDCl$_3$) δ 1.76(s, 3H), 1.82(s, 3H), 2.42(s, 3H), 3.45(s, 3H), 3.74(s, 3H), 4.61(d, J=6.6Hz, 2H), 5.52(m, 1H), 5.69(s, 1H), 6.47(s, 1H), 6.95–7.07(m, 3H), 7.25–7.28(m, 2H), 7.52–7.55(m, 2H)
IR(KBr)3479, 2935, 1613, 1585, 1523, 1509, 1490, 1458, 1415, 1395, 1362, 1315, 1249, 1196, 1112, 1070, 1005cm$^{-1}$

I-276 m.p. 155–158° C.
$^1$HNMR(CDCl$_3$) δ 1.76(d, J=0.9Hz, 3H), 1.82(d, J=0.9Hz, 3H), 3.45(s, 3H), 3.86(s, 3H), 4.61(d, J=6.9Hz, 2H), 5.35(m, 1H), 5.68(s, 1H), 5.82(s, 1H), 6.42(s, 1H), 6.96–7.09(m, 4H), 7.35–7.41(m, 2H)
IR(KBr)3428, 3005, 2952, 1613, 1583, 1517, 1505, 1487, 1464, 1451, 1411, 1387, 1359, 1317, 1289, 1245, 1140, 1101, 1070, 1013cm$^{-1}$

TABLE 59

I-277 m.p. 173–175° C.
$^1$HNMR(CDCl$_3$) δ 1.68(s, 3H), 1.74(s, 3H), 2.42(s, 3H), 2.51–2.60(m, 2H), 2.75(s, 3H), 3.21(s, 3H), 3.53(s, 3H), 3.76(s, 3H), 4.07(t, J=6.9Hz, 2H), 5.21(m, 1H), 6.86(s, 1H), 7.06(d, J=8.7Hz, 1H), 7.25–7.28(m, 2H), 7.35(dd, J=2.1, 8.7Hz, 1H), 7.40(d, J=2.1Hz, 1H), 7.50–7.53 (m, 2H)
IR(KBr)3434, 2934, 1606, 1523, 1482, 1388, 1369, 1277, 1236, 1177, 1118, 1085, 1012cm$^{-1}$

I-278 m.p. 151–154° C.
$^1$HNMR(CDCl$_3$) δ 1.69(s, 3H), 1.74(d, J=0.9Hz, 3H), 2.51–2.59(m, 2H), 2.75(s, 3H), 3.21(s, 3H), 3.54(s, 3H), 3.73(s, 3H), 3.84(s, 3H), 4.07 (t, J=6.9Hz, 2H), 5.21(m, 1H), 6.83(s, 1H), 7.00–7.08(m, 3H), 7.34–7.43(m, 4H)
IR(KBr)3434, 2935, 1610, 1581, 1522, 1479, 1399, 1362, 1283, 1246, 1180, 1125, 1114, 1082, 1046cm$^{-1}$

I-279 m.p. 90–92° C.
$^1$HNMR(CDCl$_3$) δ 1.69(s, 3H), 1.75(s, 3H), 2.42(s, 3H), 2.49–2.56(m, 2H), 3.45(s, 3H), 3.74(s, 3H), 4.06(t, J=6.6 HZ, 2H), 5.22(m, 1H), 5.67 (s, 1H), 5.90(s, 1H), 6.46(s, 1H), 6.94–7.06(m, 3H), 7.25–7.28(m, 2H), 7.52–7.55(m, 2H)
IR(KBr)3529, 3381, 2927, 1616, 1586, 1522, 1490, 1465, 1418, 1398, 1360, 1315, 1289, 1251, 1225, 1192, 1114, 1070, 1011cm$^{-1}$

I-280 m.p. 82–84° C.
$^1$HNMR(CDCl$_3$) δ 1.69(s, 3H), 1.75(s, 3H), 2.49–2.56(m, 2H), 3.45(s, 3H), 3.71(s, 3H), 3.85(s, 3H), 4.06(t, J=6.6Hz, 2H), 5.22(m, 1H), 5.67 (s, 1H), 5.82(s, 1H), 6.42(s, 1H), 6.92–7.09(m, 5H), 7.35–7.43(m, 2H)
IR(KBr)3420, 3326, 2935, 1615, 1583, 1518, 1504, 1486, 1466, 1410, 1316, 1289, 1249, 1122, 1101, 1071, 1018cm$^{-1}$

I-281 m.p. 166–168° C.
$^1$HNMR(CDCl$_3$) δ 2.38(s, 3H), 2.69(s, 3H), 3.11(s, 3H), 3.54(s, 3H), 3.73(s, 3H), 3.84(s, 3H), 5.14(s, 2H), 6.83(s, 1H), 7.00–7.44(m, 11H)
IR(KBr)3434, 2941, 1608, 1521, 1498, 1482, 1466, 1397, 1368, 1284, 1243, 1177, 1113, 1079, 1019cm$^{-1}$

TABLE 60

I-282 m.p. 109–111° C.
$^1$HNMR(CDCl$_3$) δ 2.39(s, 3H), 3.45(s, 3H), 3.71(s, 3H), 3.85(s, 3H), 5.10(s, 2H), 5.67(s, 1H), 5.83(s, 1H), 6.42(s, 1H), 6.95–7.41(m, 11H)
IR(CHCl$_3$)3497, 2935, 1610, 1583, 1519, 1499, 1481, 1465, 1399, 1312, 1274, 1245, 1185, 1120, 1102, 1067, 1012cm$^{-1}$

I-283 $^1$HNMR(CDCl$_3$) δ 2.38(s, 3H), 2.68(s, 3H), 3.12(s, 3H), 3.53(s, 1H), 3.77(s, 3H), 5.14(s, 2H), 6.83(s, 1H), 7.10–7.24(m, 5H), 7.33(d, J=8.4Hz, 1H), 7.34(d, J=8.4Hz, 2H), 7.40(d, J=2.1Hz, 1H)7.56–7.64(m, 2H)
IR(KBr) 1603, 1520, 1482, 1367, 1297, 1277, 1251, 1232, 1176, 1120, 1084, 1012cm$^{-1}$

I-284 $^1$HNMR(CDCl$_3$) δ 2.39(s, 3H), 3.45(s, 3H), 3.75(s, 3H), 5.10(s, 2H), 5.68(s, 1H), 5.88(s, 1H), 6.44(s, 1H), 6.95(dd, J=8.4&2.1Hz, 1H), 7.03 (d, J=8.4Hz, 1H), 7.07(d, J=2.1Hz, 1H), 7.08–7.29(m, 4H), 7.34(d, J=8.4Hz, 2H), 7.56–7.65(m, 2H)s
IR(KBr)3504, 3330, 1604, 1596, 1490, 1461, 1455, 1424, 1360, 1318, 1242, 1223, 1121, 1071, 1009cm$^{-1}$

I-285 $^1$HNMR(CDCl$_3$) δ 2.69(s, 3H), 3.13(s, 3H), 3.56(s, 3H), 3.78(s, 3H), 5.19(s, 2H), 6.85(s, 1H), 7.05–7.15(m, 1H), 7.15(d, J=8.4Hz, 1H), 7.30–7.49(m, 10H)
IR(KBr)1610, 1583, 1517, 1475, 1455, 1359, 1296, 1270, 1239, 1180, 1116, 1088, 1013cm$^{-1}$

I-286 $^1$HNMR(CDCl$_3$) δ 3.47(s, 3H), 3.75(s, 3H), 5.15(s, 2H), 5.68(s, 1H), 5.89(s, 1H), 6.46(s, 1H), 6.95(dd, J=8.4&2.1Hz, 1H), 7.03(d, J=8.4Hz, 1H), 7.04–7.12(m, 2H), 7.35–7.51(m, 9H)
IR(KBr)3543, 3346, 1612, 1586, 1566, 1518, 1502, 1479, 1407, 1362, 1320, 1239, 1110, 1068, 1006cm$^{-1}$

I-287 $^1$HNMR(CDCl$_3$) δ 2.68(s, 3H), 3.14(s, 3H), 3.58(s, 3H), 3.81(s, 3H), 5.20(s, 2H), 6.88(s, 1H), 7.16(d, J=8.7Hz, 1H), 7.32–7.49(m, 7H), 7.60–7.68(m, 1H), 7.98–8.04(m, 1H), 8.24–8.29(m, 1H), 8.44–8.47(m, 1H)
IR(KBr)1609, 1531, 1362, 1270, 1239, 1178, 1122, 1085, 1014cm$^{-1}$

I-288 $^1$HNMR(CDCl$_3$) δ 3.49(s, 3H), 3.78(s, 3H), 5.17(s, 2H), 5.71(s, 1H), 5.83(s, 1H), 6.49(s, 1H))6.95(dd, J=12.3&1.2Hz, 1H), 7.02(d, J=12.3Hz, 1H), 7.08(d, J=1.2Hz, 1H), 7.33–7.50(m, 5H), 7.60–7.68(m, 1H), 7.97–8.06(m, 1H), 8.21–8.27(m, 1H), 8.52(s, 1H)
IR(KBr)3528, 3358, 1588, 1527, 1499, 1454, 1406, 1348, 1314, 1241, 1122, 1070, 1009cm$^{-1}$

TABLE 61

I-289 $^1$HNMR(CDCl$_3$) δ 2.68(s, 3H), 3.13(s, 3H), 3.55(s, 3H), 3.77(s, 3H), 5.19(s, 2H), 6.79–6.88(m, 1H), 6.86(s, 1H), 7.02–7.10(m, 2H), 7.15(d, J=8.4Hz, 1H), 7.26–7.50(m, 8H)
IR(KBr)3479, 3388, 1623, 1603, 1518, 1478, 1396, 1358, 1176, 1118, 1081, 1013cm$^{-1}$

I-290 $^1$HNMR(CDCl$_3$) δ 3.11(s, 3H), 3.45(s, 3H), 3.77(s, 3H), 5.17(s, 2H), 6.05(s, 1H), 6.46(s, 1H))7.00–7.18(m, 1H), 7.14(d, J=8.4Hz, 1H), 7.33–7.50(m, 9H), 7.52(d, J=2.1Hz, 1H)
IR(KBr)3504, 1612, 1578, 1519, 1498, 1464, 1391, 1355, 1290, 1276, 1239, 1183, 1167, 1107, 1070, 1004cm$^{-1}$

TABLE 61-continued

| | |
|---|---|
| I-291 | $^1$HNMR(CDCl$_3$+CD$_3$OD) δ 3.44(s, 3H), 3.75(s, 3H), 4.74(s, 2H), 5.13(s, 2H), 1H), 6.86–6.95(m, 3H), 6.99(d, J=8.7Hz, 1H), 7.30–7.48(m, 7H),7.52(d, J=8.7Hz, 2H)<br>IR(KBr)3433, 1707, 1611, 1518, 1473, 1463, 1379, 1250, 1174, 1132, 1089, 1058, 1016cm$^{-1}$ |
| I-292 | $^1$HNMR(CDCl$_3$+CD$_3$OD) δ 3.41(s, 3H), 3.62(s, 3H), 3.75(s, 3H), 4.74(s, 2H), 5.15(s, 2H), 6.87–7.01(m, 4H), 7.30–7.55(m, 9H)<br>IR(KBr)3386, 1722, 1611, 1518, 1464, 1343, 1271, 1245, 1233, 1215, 1168, 1082, 1060, 1021cm$^{-1}$ |
| I-293 | $^1$HNMR(CDCl$_3$) δ 2.38(s, 3H), 2.69(s, 3H), 3.12(s, 3H), 3.56(s, 3H), 3.78(s, 3H), 5.14(s, 2H), 6.85(s, 1H), 7.05–7.45(m, 12H)<br>IR(KBr)1607, 1584, 1519, 1479, 1401, 1364, 1348, 1280, 1237, 1178, 1164, 1115, 1081, 1016cm$^{-1}$ |
| I-294 | foam<br>$^1$HNMR(CDCl$_3$) δ 3.45(s, 3H), 3.75(s, 3H), 4.36(d, J=2.1Hz, 1H), 4.55(s, 2H), 4.76(d, J=2.1Hz, 1H), 6.45, (s, 1H), 6.92(d, J=8.7Hz, 2H), 6.99(d, J=8.4Hz, 1H), 7.20(dd, J=1.5and8.4Hz, 1H), 7.11(d, J=1.5Hz, 1H), 7.53(d, J=8.7Hz, 2H)<br>IR(Nujol)3425, 1612, 1588, 1523, 1487, 1295, 1268, 1228, 1113, 1069, 825cm$^{-1}$ |
| I-295 | foam<br>$^1$HNMR(CDCl$_3$) δ 2.78(s, 3H), 3.21(s, 3H), 3.23(s, 3H), 3.55(s, 3H), 3.78(s, 3H), 4.79(d, J=6.6Hz, 2H), 6.21(t, J=6.6Hz, 1H), 6.85(s, 1H), 7.08(d, J=8.7Hz, 1H), 7.37(dd, J=8.7, 2.1Hz, 1H), 7.38(d, J=8.7Hz, 2H), 7.41(d, J=2.1Hz, 1H), 7.68(d, J=8.7Hz, 2H)<br>IR(Nujol)1632, 1607, 1519, 1482, 1180, 1150, 1079, 1011, 976, 876, 814, 798cm$^{-1}$ |

TABLE 62

| | |
|---|---|
| I-296 | foam<br>$^1$HNMR(CD$_3$OD) δ 3.38(s, 3H), 3.68(s, 3H), 4.12(brs, 2H), 4.65(brs, 2H), 5.01(m, 2H), 6.43(s, 1H), 6.78(dd, J=8.7, 1.8Hz, 1H), 6.85(d, J=8.7, 2H), 6.86(d, J=1.8Hz, 1H), 6.94(d, J=8.4Hz, 1H), 7.46(d, J=8.7Hz, 2H)<br>IR(Nujol)3411, 1612, 1591, 1520, 1485, 1461, 1253, 1223, 1115, 1008, 971, 944, 842, 810, 785cm$^{-1}$ |
| I-297 | foam<br>$^1$HNMR(CD$_3$OD) δ 3.38(s, 3H), 3.68(s, 3H), 4.73(d, J=5.1Hz, 2H), 4.23(d, J=5.1Hz, 2H), 5.83(m, 2H), 6.43(s, 1H), 6.79(dd, J=8.7, 1.8Hz, 1H), 6.85(d, J=8.7, 2H), 6.86(d, J=1.8 HZ, 1H), 6.94(d, J=8.7Hz, 2H)<br>IR(Nujol)3393, 1611, 1588, 1523, 1489, 1460, 1248, 1114, 1071, 1013, 940, 824cm$^{-1}$ |
| I-298 | foam<br>$^1$HNMR(CD$_3$OD) δ 1.77(s, 3H), 3.38(s, 3H), 3.68(s, 3H), 4.00(s, 2H), 5.72(d, J=6.3 HZ, 2H), 5.81(t, J=6.3Hz, 1H), 6.43(s, 1H), 6.79(dd, J=8.7, 1.8Hz, 1H), 6.85(d, J=8.7, 2H), 6.85(d, J=1.8Hz, 1H), 6.94(d, J=8.4Hz, 1H), 7.46(d, J=8.7Hz, 2H)<br>IR(Nujol)3384, 1608, 1585, 1523, 1494, 1457, 1262, 1242, 1227, 1116, 1078, 1008, 985, 822, 781cm$^{-1}$ |
| I-299 | foam<br>$^1$HNMR(CD$_3$OD) δ 1.87(s, 3H), 3.83(s, 3H), 3.68(s, 3H), 4.17(s, 2H), 4.69(d, J=6.6Hz, 2H), 5.68(t, J=6.3 HZ, 1H), 6.43(s, 1H), 6.79(dd, J=8.7, 1.8Hz, 1H), 6.85(d, J=8.4, 2H), 6.85(d, J=1.8Hz, 1H), 6.94(d, J=8.4Hz, 1H), 7.46(d, J=8.7Hz, 2H)<br>IR(Nujol)3350, 3236, 1606, 1589, 1524, 1490, 1463, 1247, 1227, 1079, 1011, 992, 819, 790cm$^{-1}$ |
| I-300 | foam<br>$^1$HNMR(CDCl$_3$) δ 1.87(s, 3H), 2.10(s, 3H), 3.45(s, 3H), 3.74(s, 3H), 4.68(s, 2H), 4.71(d, J=6.0Hz, 2H), 5.77(t, J=6.0Hz, 1H), 6.44(s, 1H), 6.92(d, J=8.0Hz, 2H), 6.95(m, 2H), 7.07(brs, 1H), 7.53(d, J=6.0Hz, 2H)<br>IR(Nujol)3409, 1724, 1612, 1587, 1523, 1489, 1460, 1239, 1114, 1071, 1012, 940, 825, 781cm$^{-1}$ |

TABLE 63

| | |
|---|---|
| I-301 | foam<br>$^1$HNMR(CD$_3$OD) δ 2.93(d, J=2.1Hz, 1H), 3.38(s, 3H), 3.68(s, 3H), 4.06(dd, J=9.9, 7.8 HZ, 1H), 4.20(dd, J=9.9, 3.6Hz, 1H), 4.74(ddd, J=7.8, 3.6, 2.1Hz, 1H), 6.44(s, 1H), 6.80(dd, J=8.4, 1.8Hz, 1H), 6.85(d, J=8.7, 2H), 6.87(d, J=1.8 HZ, 1H), 6.96(d, J=8.4Hz, 1H), 7.46(d, J=8.7Hz, 2H)<br>IR(Nujol)3282, 1655, 1612, 1588, 1523, 1489, 1460, 1254, 1226, 1072, 1013, 940, 825cm$^{-1}$ |
| I-302 | foam<br>$^1$HNMR(CD$_3$OD) δ 3.30(s, 3H), 3.68(s, 3H), 4.75(d, J=5.1Hz, 2H), 6.44(s, 1H), 6.80(dd, J=8.4, 1.8Hz, 1H), 6.85(d, J=8.4, 2H), 6.92(d, J=1.8Hz, 1H), 6.99(d, J=8.7Hz, 1H), 7.42(t, J=5.1Hz, 1H), 7.46(d, J=8.4Hz, 2H)<br>IR(Nujol)3474, 3316, 1678, 1611, 1584, 1523, 1487, 1458, 1268, 1231, 1115, 1171, 1011, 942, 824, 758cm$^{-1}$ |
| I-303 | foam<br>$^1$HNMR(CD$_3$OD) δ 1.24(d, j =7.2Hz, 3H), 3.38(s, 3H), 3.68(s, 3H), 4.12(q, J=7.2Hz, 2H), 4.75(d, J=4.8Hz, 2H), 6.43(s, 1H), 6.80(dd, J=8.4, 1.8Hz, 1H), 6.85(d, J=8.7, 2H), 6.91(d, J=1.8Hz, 1H), 6.99(d, J=8.4Hz, 2H), 7.46(d, J=8.7Hz, 2H), 7.52(t, J=4.8Hz, 1H)<br>IR(Nujol)3306, 1715, 1612, 1587, 1523, 1487, 1460, 1266, 1232, 1115, 1070, 824, 760cm$^{-1}$ |
| I-304 | foam<br>$^1$HNMR(CDCl$_3$) δ 2.34(s, 3H), 2.38(s, 3H), 2.70(s, 3H), 3.07(s, 3H), 3.21(s, 3H), 3.56(s, 3H), 3.78(s, 3H), 5.13(s, 2H), 6.84(s, 1H), 7.03(d, J=7.8Hz, 1H), 7.06(s, 1H), 7.18(d, J=8.4Hz, 1H), 7.28(d, J=7.8Hz, 1H), 7.36(dd, J=2.1, 8.4Hz, 1H), 7.38(d, J=8.7Hz, 2H), 7.40(d, J=2.1Hz, 1H), 7.68(d, J=8.7Hz, 2H)<br>IR(KBr)1611, 1518, 1480, 1365, 1177, 1151, 1080, 876, 816cm$^{-1}$ |
| I-305 | foam<br>$^1$HNMR(CDCl$_3$) δ 1.25(d, J=6.9Hz, 6H), 2.67(s, 3H), 2.93(q, J=6.9Hz, 1H)3.13(s, 3H), 3.21(s, 3H), 3.56(s, 3H), 3.78(s, 3H), 5.15(s, 2H), 6.84(s, 1H), 7.16(d, J=8.7Hz, 1H), 7.26(d, J=8.4Hz, 2H), 7.34(dd, J=2.4, 8.7Hz, 1H), 7.38(d, J=8.4Hz, 4H), 7.40(d, J=2.4Hz, 1H), 7.68(d, J=8.4Hz, 2H)<br>IR(KBr)1609, 1519, 1481, 1365, 1177, 1151, 1080, 875, 819cm$^{-1}$ |

TABLE 64

| | |
|---|---|
| I-306 | foam<br>$^1$HNMR(CDCl$_3$) δ 2.62(s, 3H), 3.15(s, 3H), 3.21(s, 3H), 3.55(s, 3H), 3.77(s, 3H), 5.36(s, 2H), 6.84(s, 1H), 7.18(d, J=8.7Hz, 1H), 7.26(s, 1H), 7.33(dd, J=2.1, 8.4Hz, 1H), 7.38(d, J=8.7Hz, 2H), 7.41(d, J=2.1Hz, 1H), 7.51(m, 2H), 7.57(dd, J=1.8, 8.4Hz, 1H), 7.68(d, J=8.7Hz, 2H), 7.84–7.93(m, 4H)<br>IR(KBr)1608, 1519, 1480, 1364, 1177, 1151, 1079, 876, 819, 797cm$^{-1}$ |

TABLE 64-continued

| | |
|---|---|
| I-307 | foam<br>$^1$HNMR(CDCl$_3$) δ 2.64(s, 3H), 3.21(s, 3H), 3.28(s, 3H), 3.55(s, 3H), 3.77(s, 3H),5.51(s, 2H), 6.83(s, 1H), 7.18(d, J=8.4Hz, 1H), 7.31(dd, J=2.4, 8.4Hz, 1H), 7.37(d, J=8.7Hz, 2H), 7.42(d, J=2.4Hz, 1H), 7.58(dt, J=2.4, 7.2Hz, 1H), 7.67(d, J=8.7Hz, 2H), 7.74(d, J=8.4Hz, 1H), 7.76(dt, J=2.4, 7.2Hz, 1H), 7.85(d, J=7.2Hz, 1H), 8.06(d, J=7.2Hz, 1H), 8.23(d, J=7.2Hz, 1H)<br>IR(KBr)1603, 1519, 1480, 1365, 1177, 1151, 1080, 876, 824, 797cm$^{-1}$ |
| I-308 | foam<br>$^1$HNMR(CDCl$_3$) δ 2.76(s, 3H), 3.17(s, 3H), 3.21(s, 3H), 3.55(s, 3H), 3.78(s, 3H),5.25(s, 2H), 6.85(s, 1H), 7.12(d, J=8.7Hz, 1H), 7.35(dd, J=2.1, 8.4Hz, 1H), 7.38(d, J=8.7Hz, 2H), 7.42(d, J=2.1Hz, 1H), 7.61(d, J=8.7Hz, 2H), 7.67(d, J=8.4Hz, 2H), 7.68(d, J=8.7Hz, 2H)<br>IR(KBr) 1610, 1522, 1489, 1402, 1245, 1181, 1164, 1110, 1071, 821, 805cm$^{-1}$ |
| I-309 | m.p. 221–222° C.<br>$^1$HNMR(CDCl$_3$) δ 2.36(s, 3H), 2.38(s, 3H), 3.46(s, 3H), 3.75(s, 3H), 5.09(s, 2H), 6.45(s, 1H), 6.92(d, J=8.4Hz, 2H), 6.98(dd, J=2.1, 8.1Hz, 1H), 7.06(d, J=8.4Hz, 1H), 7.08(d, J=2.1Hz, 1H), 7.08(s, 1H), 7.28(d, J=8.4Hz, 1H), 7.53(d, J=8.4Hz, 2H)<br>IR(KBr)3475, 1610, 1522, 1489, 1402, 1245, 1181, 1164, 1110, 1071, 821, 805cm$^{-1}$ |
| I-310 | m.p. 153–155° C.<br>$^1$HNMR(CDCl$_3$) δ 1.27(d, J=6.9Hz, 6H), 2.95(q, J=6.9Hz, 1H), 3.45(s, 3H), 3.74(s, 3H), 5.11(s, 2H), 6.45(s, 1H), 6.91(d, J=8.4Hz, 2H), 6.96(dd, J=2.1, 8.1Hz, 1H), 7.03(d, J=8.1Hz, 1H), 7.08(d, J=2.1Hz, 1H), 7.28(d, J=8.1Hz, 2H), 7.38(d, J=8.1Hz, 2H), 7.53(d, J=8.4Hz, 2H)<br>IR(KBr)3486, 1611, 1522, 1489, 1265, 1113, 1072, 1011, 823cm$^{-1}$ |

TABLE 65

| | |
|---|---|
| I-311 | m.p. 176–177° C.<br>$^1$HNMR(CDCl$_3$) δ 3.45(s, 3H), 3.75(s, 3H), 5.32(s, 2H), 6.45(s, 1H), 6.91(d, J=8.4Hz, 2H), 6.97(dd, J=2.1, 8.4Hz, 1H), 7.06(d, J=8.4Hz, 1H), 7.10(d, J=2.1Hz, 1H), 7.53(d, J=8.4Hz, 2H), 7.50–7.57(m, 3H), 7.82–7.92(m, 4H)<br>IR(KBr)3476, 1610, 1522, 1488, 1469, 1401, 1263, 1246, 1173, 1112, 1073, 1014, 1002, 819, 806cm$^{-1}$ |
| I-312 | m.p. 235–237° C.<br>$^1$HNMR(CDCl$_3$) δ 3.44(s, 3H), 3.73(s, 3H), 5.49(s, 2H), 6.44(s, 1H), 6.92(d, J=8.4Hz, 2H), 6.93(dd, J=2.1, 8.4Hz, 1H), 7.14(d, J=2.1Hz, 1H), 7.18(d, J=8.4Hz, 1H), 7.38(d, J=8.4Hz, 1H), 7.52(d, J=8.4Hz, 2H), 7.58(dd, J=7.2, 7.2Hz, 1H), 7.77(dd, J=7.2, 7.2Hz, 1H), 7.85(d, J=7.2Hz, 1H), 8.21(d, J=7.2Hz, 1H), 8.22(d, J=7.2Hz, 1H)<br>IR(KBr)3378, 1609, 1522, 1488, 1268, 1229, 1205, 1114, 1072, 1016, 825, 782cm$^{-1}$ |
| I-313 | m.p. 159–161° C.<br>$^1$HNMR(CDCl$_3$) δ 3.45(s, 3H), 3.75(s, 3H), 5.22(s, 2H), 6.45(s, 1H), 6.92(d, J=8.4Hz, 2H), 6.96(br.s, 2H), 7.11(br.s, 1H), 7.53(d, J=8.4Hz, 2H), 7.57(d, J=8.4Hz, 2H), 7.68(d, J=8.4Hz, 2H),<br>IR(KBr)3433, 1613, 1523, 1490, 1326, 1251, 1166, 1113, 1066, 1014, 825cm$^{-1}$ |
| I-314 | m.p. 92–93° C.<br>$^1$HNMR(CDCl$_3$) δ 1.63(s, 3H), 1.74(s, 3H), 2.34–2.39(m, 1H), 2.67–2.72(m, 2H), 3.47(s, 3H), 3.74(s, 3H), 4.52–4.54(m, 2H), 5.30–5.33 (m, 2H), 6.78–6.97(m, 4H), 7.20(d, J=7.2Hz, 1H), 7.56(d, J=8.0Hz, 2H)<br>IR(KBr)3410, 2932, 1613, 1519, 1473, 1444, 1390, 1263, 1228, 1174cm$^{-1}$ |
| I-315 | m.p. 85–86° C.<br>$^1$HNMR(CDCl$_3$) δ 1.76(s, 3H), 1.83(s, 3H), 2.17–2.40(m, 1H), 2.65–2.71(m, 2H), 3.24(s, 3H), 3.46(s, 3H), 3.80(s, 3H), 4.50–4.52(m, 2H), 6.70(s, 1H), 7.28–7.43(m, 5H), 7.73(d, J=8.6Hz, 2H)<br>IR(KBr)3432, 2938, 1731, 1513, 1469, 1366, 1180, 1151, 970, 868cm$^{-1}$ |

TABLE 66

| | |
|---|---|
| I-316 | m.p. 179–180° C.<br>$^1$HNMR(CDCl$_3$) δ 1.72(s, 3H), 1.76(s, 3H), 2.15–2.35(m, 1H), 2.61–2.70(m, 2H), 3.46(s, 3H), 3.76(s, 3H), 4.47–4.50(m, 2H), 6.68(s, 1H), 7.17–7.52(m, 5H), 7.69(d, J=8.4Hz, 2H)<br>IR(KBr)3427, 2934, 1612, 1576, 1519, 1465, 1443, 1415, 1376, 1228, 1174, 846cm$^{-1}$ |
| I-317 | m.p. 141–142° C.<br>$^1$HNMR(CDCl$_3$) δ 1.75(s, 3H), 1.80(s, 3H), 3.21(s, 3H), 3.39(s, 3H), 3.68(s, 3H), 3.77(s, 3H), 4.61(d, J=7.2Hz, 2H), 5.50(t, J=7.0Hz, 1H), 6.93(s, 1H), 6.99–7.33(m, 5H), 7.57–7.65(m, 2H)<br>IR(KBr)3432, 2938, 1724, 1519, 1474, 1365, 1346, 1294, 1262, 1244, 1220, 1163, 1119, 1059, 953, 842, 805cm$^{-1}$ |
| I-318 | m.p. 127–128° C.<br>$^1$HNMR(CDCl$_3$) δ 1.68(s, 3H), 1.74(s, 3H), 2.54(dt, J=4.2, 4.6Hz, 2H), 3.20(s, 3H), 3.39(s, 3H), 3.68(s, 3H), 3.76(s, 3H), 4.05(t, J=4.4Hz, 2H), 5.21(t, J=4.6Hz, 1H), 6.93(s, 1H), 7.00(d, J=5.6Hz, 1H), 7.11–7.18(m, 2H), 7.25–7.35(m, 3H), 7.61(dd, J=3.8, 5.8Hz)<br>IR(KBr)3447, 2974, 2940, 1740, 1519, 1471, 1365, 1343, 1295, 1262, 1226, 1182, 1161, 1119, 1058, 952, 843, 814cm$^{-1}$ |
| I-319 | m.p. 171–172° C.<br>$^1$HNMR(CDCl$_3$) δ 2.38(s, 3H), 3.10(s, 3H), 3.39(s, 3H), 3.66(s, 3H), 3.77(s, 3H), 5.11(s, 2H), 6.93(s, 1H), 7.07–7.36(m, 9H), 7.61(dd, J=3.4, 5.6Hz, 2H)<br>IR(KBr)3431, 2937, 1724, 1519, 1474, 1440, 1346, 1296, 1259, 1243, 1222, 1165, 1121, 1060, 953, 843, 804cm$^{-1}$ |
| I-320 | m.p. 155–156° C.<br>$^1$HNMR(CDCl$_3$) δ 3.40(s, 3H), 3.69(s, 3H), 3.77(s, 3H), 5.13(s, 2H), 5.70(brs, 1H), 6.82–7.42(m, 5H), 7.39–7.42(m, 5H), 7.62(dd, J=5.4, 8.6Hz)<br>IR(KBr)3550, 3481, 2956, 1723, 1519, 1467, 1435, 1344, 1285, 1261, 1238, 1223, 1130, 1058, 1013, 840cm$^{-1}$ |

TABLE 67

| | |
|---|---|
| I-321 | m.p. 159–160° C.<br>$^1$HNMR(CDCl$_3$) δ 3.11(s, 3H), 3.40(s, 3H), 3.66(s, 3H), 3.77(s, 3H), 5.16(s, 2H), 6.93(s, 1H), 7.07–7.49(m, 5H), 7.62(dd, J=3.0, 8.4Hz, 2H)<br>IR(KBr)3441, 2952, 1732, 1519, 1469, 1445, 1381, 1356, 1342, 1291, 1273, 1243, 1226, 1162, 1119, 1081, 1057, 999, 950, 842, 805cm$^{-1}$ |

TABLE 67-continued

| | |
|---|---|
| I-322 | m.p. 160–161° C.<br>$^1$HNMR(CDCl$_3$) δ 2.37(s, 3H), 2.93(s, 3H), 3.19(s, 3H), 3.22(s, 3H), 3.55(s, 3H), 3.79(s, 3H), 5.23(s, 2H), 6.86(s, 1H), 7.20(d, J=8.1Hz, 2H), 7.30(d, J=8.1Hz, 2H), 7.36–7.41(m, 2H), 7.64–7.70(m, 2H), 7.74(d, J=2.1Hz, 1H), 7.83(d, J=2.1Hz, 1H), 10.16(s, 1H)<br>IR(CHCl$_3$)3027, 2940, 1692, 1473, 1373, 1227, 1152, 1085cm$^{-1}$ |
| I-323 | powder<br>$^1$HNMR(CDCl$_3$) δ 2.37(s, 3H), 2.86(s, 3H), 3.13(s, 3H), 3.21(s, 3H), 3.54(s, 3H), 3.79(s, 3H), 4.64(s, 2H), 5.11(s, 2H), 6.85(s, 1H), 7.21(d, J=7.8Hz, 2H), 7.32–7.44(m, 6H), 7.65–7.70(m, 2H)<br>IR(CHCl$_3$)3026, 2939, 1475, 1372, 1228, 1178, 1151, 1084cm$^{-1}$ |
| I-324 | powder<br>$^1$HNMR(CDCl$_3$) δ 1.89–1.98(brs, 1H), 2.39(s, 3H), 3.45(s, 3H), 3.75(s, 3H), 4.77(s, 2H), 5.01(s, 3H), 5.46(s, 1H), 5.99(s, 1H), 6.45(s, 1H), 6.45–6.95(m, 2H), 7.05(s, 2H), 7.24(d, J=8.1Hz, 2H), 7.38(d, J=8.1Hz, 2H), 7.50–7.56(m, 2H)<br>IR(CHCl$_3$)3514, 2937, 1731, 1613, 1522, 1484, 1403, 1228, 1173, 1082cm$^{-1}$ |
| I-325 | powder<br>$^1$HNMR(CDCl$_3$) δ 2.31(s, 3H), 2.88(s, 3H), 3.07(s, 3H), 3.22(s, 3H), 3.51(s, 3H), 3.74(s, 3H), 5.23(s, 2H), 6.83(s, 1H), 7.11–7.18(m, 2H), 7.32–7.41(m, 4H), 7.62–7.68(m, 3H), 8.03(s, 1H)<br>IR(CHCl$_3$)3026, 2939, 1742, 1472, 1374, 1227, 1179, 1129, 1085cm$^{-1}$ |

TABLE 68

| | |
|---|---|
| I-326 | powder<br>$^1$HNMR(CD$_3$OD) δ 2.33(s, 3H), 3.38(s, 3H), 3.68(s, 3H), 5.11(s, 2H), 6.44(s, 1H), 6.82–6.88(m, 2H), 6.99(d, J=1.8Hz, 1H), 7.13–7.19(m, 3H), 7.42–7.50(m, 4H)<br>IR(KBr)3411, 2935, 1680, 1611, 1520, 1457, 1404, 1281, 1230, 1114cm$^{-1}$ |
| I-327 | powder<br>$^1$HNMR(CDCl$_3$) δ 1.72(s, 3H), 1.79(s, 3H), 3.12(s, 3H), 3.21(s, 3H), 3.27(s, 3H), 3.52(s, 3H), 3.53(s, 3H), 4.81(d, J=7.5Hz, 2H), 5.51(m, 1H), 7.38–7.43(m, 2H), 7.45–7.50(m, 2H), 7.80(d, J=2.1Hz, 1H), 7.97(d, J=2.1Hz, 1H)<br>IR(CHCl$_3$)3032, 2941, 1543, 1377, 1209cm$^{-1}$ |
| I-328 | m.p. 205–206° C.<br>$^1$HNMR(CDCl$_3$) δ 1.75(s, 3H), 1.80(s, 3H), 3.41(s, 3H), 3.47(s, 3H), 4.66(d, J=6.6Hz, 2H), 5.06(s, 1H), 5.53(m, 1H), 6.33(s, 1H), 6.89–6.95(m, 2H), 7.28–7.34(m, 2H), 7.38–7.40(m, 1H), 7.99(d, J=2.1Hz, 1H), 10.83(d, J=0.6Hz, 1H)<br>IR(KBr)3476, 2940, 1614, 1532, 1371, 1238, 1094, 1035cm$^{-1}$ |
| I-329 | m.p. 144–145° C.<br>$^1$HNMR(CDCl$_3$) δ 2.83(s, 3H)3.22(s, 3H), 3.28(s, 3H), 3.55(s, 3H), 3.79(s, 3H), 6.86(s, 1H), 7.37–7.45(m, 3H), 7.47–7.53(m, 3H), 7.65–7.70(m, 2H)<br>IR(KBr)3434, 3019, 2939, 1515, 1480, 1370, 1176, 1150, 1081cm$^{-1}$ |
| I-330 | amorphous<br>$^1$HNMR(CDCl$_3$) δ 1.68(s, 3H), 1.74(s, 3H), 2.54(q, J=7.2Hz, 2H), 3.21(s, 3H), 3.41(s, 3H), 3.65(s, 3H), 3.77(s, 3H), 4.03(t, J=7.2Hz, 2H), 5.23(t, J=7.2Hz, 1H), 6.94(s, 1H), 6.98(t, J=8.6Hz, 1H), 7.05(ddd, J=8.6, 2.1, 0.9Hz, 1H), 7.14(dd, J=12.0, 2.1Hz, 1H), 7.38(d, J=8.7Hz, 2H), 7.71(d, J=8.7Hz, 2H)<br>IR(CHCl$_3$)1732, 1521, 1471, 1375, 1262, 1230, 1150, 1061, 874cm$^{-1}$ |

TABLE 69

| | |
|---|---|
| I-331 | m.p. 146–148° C.<br>$^1$HNMR(CDCl$_3$) δ 1.56(s, 3H), 1.80(s, 3H), 3.21(s, 3H), 3.41(s, 3H), 3.65(s, 3H), 3.77(s, 3H), 4.61(d, J=6.9Hz, 2H), 5.54(t, J=6.9Hz, 1H), 6.94(s, 1H), 6.98(t, J=8.4Hz, 1H), 7.05(ddd, J=8.4, 2.4, 0.9Hz, 1H), 7.14(dd, J=12.0, 2.4Hz, 1H), 7.38(d, J=8.7Hz, 2H), 7.71(d, J=8.7Hz, 2H)<br>IR(KBr)1736, 1519, 1471, 1357, 1257, 1150, 1061, 984, 872cm$^{-1}$ |
| I-332 | m.p. 170–171° C.<br>$^1$HNMR(DMSO-d$_6$) δ 1.73(s, 3H), 1.77(s, 3H), 3.31(s, 3H), 3.73(s, 3H), 4.62(d, J=7.0Hz, 2H), 5.48(t, J=7.0Hz, 1H), 6.87(d, J=8.9Hz, 2H), 7.00(s, 1H), 7.03(ddd, J=8.7, 2.3, 0.9Hz, 1H), 7.10(dd, J=12.3, 2.3Hz, 1H), 7.18(t, J=8.7Hz, 1H), 7.48(d, J=8.9Hz, 2H), 9.60(s, 1H), 12.9(brs, 1H)<br>IR(KBr)3258, 1687, 1615, 1523, 1465, 1373, 1260, 1233, 1057, 994, 835, 823cm$^{-1}$ |
| I-333 | m.p. 172–174° C.<br>$^1$HNMR(CDCl$_3$) δ 3.21(s, 3H), 3.41(s, 3H), 3.61(s, 3H), 3.77(s, 3H), 5.17(s, 2H), 6.94(s, 1H), 7.01–7.04(m, 2H), 7.13–7.18(m, 1H), 7.33–7.49(m, 7H), 7.70(d, J=9.0Hz, 2H)<br>IR(KBr)1725, 1522, 1463, 1346, 1261, 1230, 1147, 1058, 878, 756cm$^{-1}$ |
| I-334 | m.p. 149–151° C.<br>$^1$HNMR(CDCl$_3$) δ 2.36(s, 3H), 3.21(s, 3H), 3.41(s, 3H), 3.61(s, 3H), 3.77(s, 3H), 5.13(s, 2H), 6.93(s, 1H), 7.00–7.03(m, 2H), 7.12–7.17(m, 1H), 7.20(d, J=8.4Hz, 2H), 7.35(d, J=8.4Hz, 2H), 7.38(d, J=8.7Hz, 2H), 7.70(d, J=8.7Hz, 2H)<br>IR(KBr)1731, 1519, 1472, 1370, 1298, 1152, 1058, 874, 791cm$^{-1}$ |

TABLE 70

| | |
|---|---|
| I-335 | m.p. 173–174° C.<br>$^1$HNMR(DMSO-d$_6$) δ 1.64(s, 3H), 1.70(s, 3H), 2.45(q, J=6.9Hz, 2H), 3.31(s, 3H), 3.73(s, 3H), 4.04(t, J=6.9Hz, 2H), 5.22(t, J=6.9Hz, 1H), 6.87(d, J=8.7Hz, 2H), 6.99(s, 1H), 7.03(ddd, J=8.7, 2.1, 0.9Hz, 1H), 7.10(dd, J=12.3, 2.1Hz, 1H), 7.16(t, J=8.7Hz, 1H), 7.48(d, J=8.7Hz, 2H), 9.61(s, 1H), 12.9(brs, 1H)<br>IR(KBr)3303, 1696, 1523, 1473, 1371, 1261, 1241, 1061, 1009, 839cm$^{-1}$ |
| I-336 | m.p. 222–224° C.<br>$^1$HNMR(DMSO-d$_6$) δ 3.31(s, 3H), 3.73(s, 3H), 5.20(s, 2H), 6.87(d, J=8.7Hz, 2H), 7.00(s, 1H), 7.03–7.07(m, 1H), 7.13(dd, J=12.3, 2.1Hz, 1H), 7.26(t, J=8.7Hz, 1H), 7.36–7.52(m, 7H), 9.61(s, 1H), 12.9(brs, 1H)<br>IR(KBr)3268, 1689, 1523, 1465, 1374, 1261, 1055, 836cm$^{-1}$ |

TABLE 70-continued

I-337  m.p. 205–206° C.
$^1$HNMR(DMSO-d$_6$) δ 2.32(s, 3H), 3.31(s, 3H), 3.72(s, 3H), 5.15(s, 2H), 6.87(d, J=8.7Hz, 2H), 6.99(s, 1H), 7.04(ddd, J=9.0, 1.9, 0.9Hz, 1H), 7.12(dd, J=12.3, 1.9Hz, 1H), 7.23(d, J=8.0Hz, 2H), 7.24(t, J=9.0Hz, 1H), 7.38(d, J=8.0Hz, 2H), 7.48(d, J=8.7Hz, 2H), 9.60(s, 1H), 12.9(brs, 1H)
IR(KBr)3303, 1696, 1523, 1464, 1261, 1241, 1056, 993, 838, 811, 791cm$^{-1}$ I-338  m.p. 120–121° C.
$^1$HNMR(CDCl$_3$) δ 3.13(s, 3H), 3.50(s, 3H), 3.78(s, 3H), 5.08(s, 1H), 5.20(s, 2H), 6.90(m, 2H), 7.09(s, 1H), 7.15–7.19(m, 3H), 7.37–7.50(m, 5H), 7.56(dd, J=10.8, 2.1Hz, 1H), 7.64(d, J=2.4Hz, 1H), 9.90(s, 1H)
IR(KBr)3460, 2934, 1694, 1609, 1585, 1518, 1467, 1442, 1348, 1295, 1273, 1255, 1238, 1171, 1123, 1075, 1003, 960, 828, 807, 755, 700, 653, 582, 522cm$^{-1}$ I-339  m.p. 256–258° C.
$^1$HNMR(DMSO-d$_6$) δ 3.34(s, 3H), 3.35(s, 3H), 3.72(s, 3H), 5.28(s, 2H), 6.75(d, J=8.1Hz, 2H), 7.05–7.11(m, 3H), 7.36–7.45(m, 4H), 7.53(d, J=8.1Hz, 2H), 7.60–7.66(m, 2H), 9.44(s, 1H), 12.84(s, 1H)
IR(KBr)3459, 2940, 2563, 1706, 1612, 1522, 1469, 1349, 1294, 1258, 1185, 1114, 1082, 1063, 1000, 961, 919, 827, 756, 699, 524cm$^{-1}$

TABLE 71

I-340  m.p. 165–166° C.
$^1$HNMR(CDCl$_3$) δ 3.14(s, 3H), 3.19(s, 3H), 3.51(s, 3H), 3.76(s, 3H), 5.21(s, 2H), 7.11(s, 1H), 7.17(d, J=8.4Hz, 1H), 7.29–7.50(m, 9H), 7.57(dd, J=8.1, 2.1Hz, 1H), 7.65(d, J=2.1Hz, 1H), 10.02(s, 1H)
IR(CHCl$_3$)2938, 2844, 1698, 1613, 1590, 1515, 1469, 1372, 1331, 1293, 1255, 1174, 1150, 1122, 1092, 1005, 969, 873, 816cm$^{-1}$

I-341  m.p. 195–197° C.
$^1$HNMR(CDCl$_3$) δ 3.13(s, 3H), 3.18(s, 3H), 3.47(s, 3H), 3.77(s, 3H), 5.20(s, 2H), 6.97(s, 1H), 7.17(d, J=8.7Hz, 1H), 7.30–7.50(m, 9H), 7.58(dd, J=8.7, 1.8Hz, 1H), 7.67(d, J=1.8Hz, 1H)
IR(CHCl$_3$)2938, 1740, 1707, 1601, 1516, 1472, 1371, 1293, 1260, 1174, 1149, 1117, 1082, 1060, 1002, 971, 875cm$^{-1}$

I-342  m.p. 207–209° C.
$^1$HNMR(CD$_3$OD) δ 3.40(s, 3H), 3.72(s, 3H), 5.21(s, 2H), 6.76–6.78(m, 2H), 6.97(s, 1H), 7.01–7.17(m, 4H), 7.31–7.52(m, 6H)
IR(KBr)3366, 1705, 1612, 1591, 1522, 1473, 1434, 1375, 1253, 1234, 1130, 1084, 1061, 998, 918, 864, 835, 813, 792, 743, 697, 648, 526cm$^{-1}$

I-343  m.p. 206–208° C.
$^1$HNMR(CDCl$_3$) δ 3.14(s, 3H), 3.48(s, 3H), 3.72(s, 3H), 5.20(s, 2H), 5.48(br, 1H), 6.85–6.89(m, 3H), 7.15–7.19(m, 3H), 7.37–7.51(m, 8H), 7.56(dd, J=8.4, 2.4Hz, 1H), 7.68(d, J=2.4Hz, 1H)
IR(CHCl$_3$)3320, 2938, 1612, 1520, 1474, 1371, 1292, 1257, 1172, 1120, 1090, 1005, 972, 857, 837, 818cm$^{-1}$

I-344  m.p. 187–190° C.
$^1$HNMR(CDCl$_3$) δ 2.33(s, 3H), 3.13(s, 3H), 3.50(s, 3H), 3.76(s, 3H), 5.20(s, 2H), 7.10(s, 1H), 7.15–7.19(m, 3H), 7.28–7.50(m, 7H), 7.56(dd, J=8.7, 2.4Hz, 1H), 7.64(d, J=2.4Hz, 1H), 9.93(s, 1H)
IR(CHCl$_3$)2930, 2836, 1750, 1695, 1588, 1513, 1465, 1369, 1329, 1220, 1166, 1122, 1091, 1003, 962, 912, 848, 813cm$^{-1}$

TABLE 72

I-345  m.p. 218–220° C.
$^1$HNMR(DMSO-d$_6$) δ 2.29(s, 3H), 3.36(s, 3H), 3.37(s, 3H), 3.76(s, 3H), 5.29(s, 2H), 7.11–7.16(m, 3H), 7.31–7.46(m, 6H), 7.52–7.55(m, 2H), 7.62–7.68(m, 2H), 13.00(br, 1H)
IR(KBr)3433, 2940, 2600, 1757, 1713, 1652, 1611, 1518, 1471, 1365, 1295, 1260, 1216, 1200, 1171, 1117, 1082, 1061, 1022, 998, 975, 916, 897, 829, 804, 735, 697, 525cm$^{-1}$

I-346  m.p. 206–208° C.
$^1$HNMR(CDCl$_3$) δ 2.31(s, 3H), 3.13(s, 3H), 3.45(s, 3H), 3.58(s, 3H), 3.76(s, 3H), 5.19(s, 2H), 6.95(s, 1H), 7.08–7.16(m, 3H), 7.34–7.50(m, 7H), 7.57(dd, J=8.7, 2.4Hz, 1H), 7.67(d, J=2.4Hz, 1H)
IR(CHCl$_3$)2939, 1732, 1613, 1599, 1518, 1468, 1371, 1290, 1169, 1117, 1081, 1064, 1004, 972, 961, 905, 847, 828cm$^{-1}$

I-347  m.p. 201–203° C.
$^1$HNMR(DMSO-d$_6$) δ 1.72(s, 3H), 1.76(s, 3H), 3.34(s, 3H), 3.63(s, 3H), 4.51(d, J=4.2Hz, 2H), 5.49(t, J=4.6Hz, 1H), 6.66(s, 1H), 6.76(s, 2H), 6.86(s, 1H), 7.23–7.29(m, 2H), 7.62–7.66(m, 2H)
IR(KBr)3431, 2935, 1575, 1516, 1462, 1444, 1421, 1397, 1375, 1224, 1159, 1063, 837cm$^{-1}$

I-348  m.p. 265–266° C.
$^1$HNMR(DMSO-d$_6$) δ 2.31(s, 3H), 3.33(s, 3H), 3.62(s, 3H), 5.03(s, 2H), 6.66(s, 1H), 6.72–6.90(m, 4H), 7.18–7.28(m, 3H), 7.38(d, J=5.2Hz, 2H), 7.64(dd, J=4.0, 5.4Hz, 2H)
IR(KBr)3428, 2925, 1575, 1516, 1463, 1442, 1396, 1374, 1248, 1221, 1129, 1087, 1068cm$^{-1}$

I-349  m.p. 262–263° C.
$^1$HNMR(DMSO-d$_6$) δ 1.64(s, 3H), 1.70(s, 3H), 2.43(dt, J=4.6, 5.0Hz, 2H), 3.34(s, 3H), 3.62(s, 3H), 3.91(t, J=4.8Hz, 2H), 5.25(t, J=4.6Hz, 1H), 6.70(s, 1H), 6.75(s, 2H), 6.87(s, 1H), 7.23–7.29(m, 2H), 7.64(dd, J=2.0, 5.8Hz, 2H)
IR(KBr)3430, 2934, 1575, 1516, 1464, 1443, 1422, 1398, 1375, 14246, 1225, 1065, 1015cm$^{-1}$

TABLE 73

I-350  $^1$HNMR(CDCl$_3$) δ 1.76(s, 3H), 1.81(d, J=0.6Hz, 3H), 2.54(s, 3H), 2.73(s, 3H), 3.23(s, 3H), 3.54(s, 3H), 3.77(s, 3H), 4.63(d, J=6.6Hz, 2H), 5.49(m, 1H), 6.85(s, 1H), 7.09(d, J=8.4Hz, 1H), 7.30–7.40(m, 4H), 7.53–7.59(m, 2H)
IR(CHCl$_3$)2936, 1606, 1515, 1475, 1366, 1116, 1078, 970, 875, 820cm$^{-1}$

I-351  $^1$HNMR(CDCl$_3$) δ 1.68(s, 3H), 1.74(d, J=0.9Hz, 3H), 2.48–2.60(m, 5H), 2.75(s, 3H), 3.21(s, 3H), 3.54(s, 3H), 3.77(s, 3H), 4.07(t, J=6.9Hz, 2H), 5.21(m, 1H), 6.85(s, 1H), 7.07(d, J=8.7Hz, 1H), 7.30–7.42(m, 4H), 7.53–7.59(m, 2H)
IR(CHCl$_3$)2928, 1607, 1517, 1476, 1367, 1267, 1118, 1080, 1014, 971, 892, 822cm$^{-1}$

I-352  m.p. 201–203° C.
$^1$HNMR(CDCl$_3$) δ 3.35(s, 3H), 3.75(s, 3H), 3.76(s, 3H), 5.26(s, 2H), 6.79–6.83(m, 2H), 6.97(s, 1H), 7.01(s, 1H), 7.31–7.54(m, 10H), 9.45(s, 1H)
IR(KBr)3600–2800(br), 1610, 1525, 1492, 1462, 1377, 1337, 1298, 1208, 1171, 1114, 1054, 1031cm$^{-1}$

TABLE 73-continued

I-353 m.p. 141–143° C.
¹HNMR(CDCl₃) δ 3.56(s, 3H), 3.78(s, 3H), 3.80(s, 3H), 4.86(s, 1H), 5.26(s, 2H), 6.88–6.92(m, 2H), 6.92(s, 1H), 6.93(s, 1H), 7.24–7.29(m, 2H), 7.36–7.41(m, 1H), 7.45–7.50(m, 2H)
IR(KBr)3600–2800(br), 1612, 1524, 1491, 1463, 1448, 1378, 1263, 1205, 1177, 1153, 1071, 1053, 1026cm⁻¹

I-354 m.p. 115–115.5° C.
¹HNMR(CDCl₃) δ 3.19(s, 3H), 3.56(s, 3H), 3.79(s, 3H), 3.80(s, 3H), 5.27(s, 2H), 6.93(s, 1H), 6.94(s, 1H), 7.25–7.27(m, 2H), 7.32–7.40(m, 3H), 7.60–7.64(m, 2H)
IR(KBr)3600–2800(br), 1524, 1492, 1463, 1379, 1266, 1210, 1174, 1154, 1126, 1082, 1053, 1029cm⁻¹

I-355 m.p. 139–140° C.
¹HNMR(CDCl₃) δ 1.77(d, J=0.6Hz, 3H), 1.81(d, J=0.9Hz, 3H), 3.82(s, 6H), 4.64(d, J=6.9Hz, 2H), 5.52–5.57(m, 1H), 6.95(s, 1H), 6.97(s, 1H), 7.04(t, J=8.4Hz, 1H), 7.26–7.31(m, 1H), 7.37(dd, J=2.1, 12.6Hz, 1H), 7.73–7.77(m, 2H), 8.26–8.31(m, 2H)
IR(KBr)3600–2800(br), 1593, 1524, 1508, 1486, 1464, 1380, 1355, 1278, 1264, 1211, 1054, 1029cm⁻¹

TABLE 74

I-356 foam
¹HNMR(CDCl₃) δ 2.68(s, 3H), 3.13(s, 3H), 3.53(s, 3H), 3.78(s, 3H), 5.19(s, 2H), 6.83(s, 1H), 7.10–7.19(m, 3H), 7.30–7.50(m, 7H), 7.56–7.64(m, 2H)
IR(KBr)1607, 1520, 1482, 1365, 1232, 1177, 1119, 1082, 1013cm⁻¹

I-357 ¹HNMR(CDCl₃) δ 2.39(s, 3H), 3.48(s, 3H), 3.75(s, 3H), 5.11(s, 2H), 5.67(s, 1H), 5.88(s, 1H), 6.46(s, 1H), 6.95(d.d, J=8.7&1.8Hz, 1H), 7.02–7.11(m, 1H), 7.03(d, J=8.7Hz, 1H), 7.07(d, J=1.8Hz, 1H), 7.22(d, J=8.7Hz, 2H), 7.34(d, J=8.7Hz, 2H), 7.36–7.47(m, 3H)IR(KBr)3546, 3511, 1611, 1586, 1517, 1478, 1405, 1360, 1318, 1240, 1109, 1068, 1007cm⁻¹

I-358 ¹HNMR(CDCl₃) δ 3.03(s, 6H), 3.48(s, 3H), 3.77(s, 3H), 5.15(s, 2H), 5.71(s, 1H), 6.73(dd, J=8.7&1.8Hz, 1H), 6.82(d, J=8.4Hz, 2H), 6.97(d, J=1.8Hz, 1H), 6.98(dJ=8.7Hz, 1H), 7.11(s, 1H), 7.33–7.48(m, 5H), 7.56(d, J=8.7Hz, 2H), 9.92(s, 1H)
IR(KBr)3524, 3447, 1697, 1612, 1586, 1525, 1468, 1364, 1283, 1257, 1230, 1201, 1127, 1103, 1073, 1020cm⁻¹

I-359 ¹HNMR(CDCl₃) δ 3.04(s, 6H), 3.14(s, 3H), 3.48(s, 3H), 3.76(s, 3H), 5.17(s, 2H), 6.84(d, J=8.7Hz, 2H), 7.06–7.17(m, 3H), 7.34(d, J=1.8Hz, 1H), 7.35–7.50(m, 6H), 7.55(d, J=8.7Hz, 2H), 10.08(s, 1H)
IR(KBr)1698, 1610, 1527, 1470, 1357, 1290, 1232, 1183, 1115, 1083, 1018cm⁻¹

I-360 ¹HNMR(CDCl₃) δ 2.56(s, 3H), 3.02(s, 6H), 3.54(s, 3H), 3.76(s, 3H), 5.16(s, 2H), 5.67(s, 1H), 6.80(d, J=8.4Hz, 2H), 6.85(s, 1H), 6.91(d.d, J=8.4&2.1Hz, 1H), 7.01(d, J=8.4Hz, 1H), 7.05(d, J=2.1Hz, 1H), 7.30–7.47(m, 5H), 7.55(d, J=8.7Hz, 2H)
IR(KBr)3542, 3436, 1605, 1530, 1483, 1391, 1360, 1287, 1253, 1234, 1169, 1074, 1016cm⁻¹

I-361 ¹HNMR(CDCl₃) δ 1.31(d, J=6.9Hz, 6H), 2.57(s, 3H), 2.97(quint, J=6.9Hz, 1H), 3.54(s, 3H), 3.76(s, 3H), 5.17(s, 2H), 5.68(s, 1H), 6.86(s, 1H), 6.92(dd, J=8.4&2.1Hz, 1H), 7.02(d, J=8.4Hz, 1H), 7.05(d, J=2.1Hz, 1H), 7.31(d, J=8.1Hz, 2H), 7.34–7.46(m, 5H), 7.55(d, J=8.1Hz, 2H)
IR(KBr)3446, 1606, 1585, 1522, 1484, 1457, 1394, 1356, 1289, 1257, 1228, 1172, 1076, 1018, 1007cm⁻¹

TABLE 75

I-362 ¹HNMR(CDCl₃) δ 1.31(d, J=6.9Hz, 6H), 2.98(quint, J=6.9Hz, 1H), 3.46(s, 3H), 3.74(s, 3H), 5.15(s, 2H), 5.67(s, 1H), 5.92(s, 1H), 6.48(s, 1H), 6.97(dd, J=8.4&1.8Hz, 1H), 7.03(d, J=8.4Hz, 1H), 7.10(d, J=1.8Hz, 1H), 7.25(s, 1H), 7.31(d, J=7.8Hz, 2H), 7.34–7.49(m, 5H), 7.57(d, J=7.8Hz, 2H)
IR(KBr)3538, 3505, 3465, 1610, 1586, 1552, 1518, 1584, 1458, 1398, 1281, 1288, 1245, 1198, 1112, 1071, 1002cm⁻¹

I-363 ¹HNMR(CDCl₃) δ 2.66(s, 3H), 3.06(s, 3H), 3.13(s, 3H), 3.57(s, 3H), 3.67(s, 3H), 3.78(s, 3H), 5.19(s, 2H), 6.44(s 1H), 6.85(s, 1H), 7.15(d, J=8.7Hz, 1H), 7.28–7.51(m, 10H)
IR(KBr)3443, 1604, 1518, 1479, 1364, 1237, 1177, 1153, 1118, 1078, 1014cm⁻¹

I-364 ¹HNMR(CDCl₃) δ 1.77(s, 3H), 1.81(s, 3H), 2.70(s, 3H), 3.06(s, 3H), 3.24(s, 3H), 3.58(s, 3H), 3.78(s, 3H), 4.64(d, J=6.6Hz, 2H), 5.49(t, J=6.6Hz, 1H), 6.42(s, 1H), 6.85(s, 1H), 7.09(d, J=8.4Hz, 1H), 7.28–7.49(m, 5H)
IR(KBr)3432, 3285, 1604, 1518, 1479, 1364, 1328, 1291, 1269, 1237, 1178, 1154, 1117, 1078cm⁻¹

I-365 ¹HNMR(CDCl₃) δ 1.57(s, 3H), 1.67(s, 3H), 1.77(s, 3H), 1.81(s, 3H), 2.70(s, 3H), 2.96(s, 3H), 3.24(s, 3H), 3.53(s, 3H), 3.78(s, 3H), 4.32(d, J=7.2Hz, 2H), 4.64(d, J=6.9Hz, 2H), 5.25(t, J=6.9Hz, 1H), 5.49(t, J=7.2Hz, 1H), 6.85(s, 1H), 7.09(d, J=8.7Hz, 1H), 7.31–7.41(m, 3H), 7.44–7.64(m, 3H)
IR(KBr)3433, 1600, 1517, 1474, 1365, 1339, 1237, 1178, 1153, 1118, 1078, 1014cm⁻¹

I-366 ¹HNMR(CDCl₃) δ 1.76(s, 3H), 1.82(s, 3H), 3.08(s, 3H), 348(s, 3H), 3.75(s, 311), 4.62(d, J=7.2Hz, 2H), 5.54(t, J=7.2Hz, 1H), 5.70(s, 1H), 5.85(s, 1H), 6.40(s, 1H), 6.46(s, 1H), 6.89–7.00(m, 2H), 7.05(d, J=1.5Hz, 1H), 7.43–7.51(m, 3H)
IR(KBr)3437, 1605, 1585, 1518, 1482, 1386, 1323, 1243, 1152, 1114, 1071, 1002cm⁻¹

I-367 ¹HNMR(CDCl₃) δ 2.37(s, 3H), 3.21(s, 3H), 3.47(s, 3H), 3.64(s, 3H), 3.77(s, 3H), 3.84(s, 3H), 5.17(s, 2H), 6.63(s, 1H), 6.78(s, 1H), 7.10(s, 1H), 7.20(d, J=8.1Hz, 2H), 7.40(d, J=8.1Hz, 2H), 7.41(d, J=9.3Hz, 2H), 7.70(d, J=9.3Hz, 2H)
IR(KBr)1702, 1607, 1589, 1518, 1468, 1356, 1216, 1151, 1067, 1039, 1018cm⁻¹

TABLE 76

I-368 ¹HNMR(CDCl₃) δ 2.37(s, 3H), 3.21(s, 3H), 3.48(s, 6H), 3.65(s, 3H), 3.73(s, 3H), 3.83(s, 3H), 4.32(d, J=11.4Hz, 1H), 4.51(d, J=11.4Hz, 1H), 5.17(s, 2H), 6.93(s, 1H), 6.71(s, 1H), 6.88(s, 1H), 7.21(d, J=8.4Hz, 2H), 7.32–7.41(m, 4H), 7.73(d, J=8.4Hz, 2H)
IR(KBr)3514, 1608, 1516, 1465, 1355, 1215, 1149, 1076, 1039, 1017cm⁻¹

I-369 m.p. 125–127° C.
¹HNMR(CDCl₃) δ 2.60(s, 3H), 3.52(s, 3H), 3.73(s, 3H), 3.84(s, 3H), 5.20(s, 2H), 6.83(s, 1H), 7.00–7.48(m, 12H)
IR(KBr)3434, 2943, 1611, 1580, 1520, 1498, 1480, 1398, 1297, 1268, 1245, 1179, 1129, 1079, 1009cm⁻¹

I-370 m.p. 137–139° C.
¹HNMR(CDCl₃) δ 3.43(s, 3H), 3.71(s, 3H), 3.85(s, 3H), 5.19(s, 2H), 5.92(s, 1H), 6.43(s, 1H), 7.01–7.51(m, 12H)
IR(KBr)3391, 2937, 1615, 1583, 1520, 1503, 1482, 1464, 1405, 1359, 1314, 1292, 1273, 1239, 1121, 1108, 1069, 1005cm⁻¹

I-371 m.p. 92–94° C.
¹HNMR(CDCl₃) δ 1.76(s, 3H), 1.81(s, 3H), 2.70(s, 3H), 3.53(s, 3H), 3.73(s, 3H), 3.84(s, 3H), 4.63(d, J=6.9Hz, 2H), 5.53(m, 1H), 6.84(s,

TABLE 76-continued

| | |
|---|---|
| | 1H), 7.00–7.45 (m, 7H)<br>IR(KBr)3433, 2938, 1609, 1581, 1523, 1499, 1480, 1401, 1368, 1297, 1268, 1240, 1178, 1118, 1079, 1021cm$^{-1}$ |
| I-372 | foam<br>$^1$HNMR(CDCl$_3$) δ 1.68(s, 3H), 1.74(d, J=0.6Hz, 3H), 2.50–2.59(m, 2H), 2.71(s, 3H), 3.53(s, 3H), 3.73(s, 3H), 3.84(s, 3H), 4.04(t, J=7.2Hz, 2H), 5.23(m, 1H), 6.83(s, 1H), 7.00–7.42(m, 7H)<br>IR(CHCl$_3$)3011, 2938, 1612, 1581, 1522, 1500, 1480, 1465, 1398, 1370, 1301, 1268, 1238, 1209, 1176, 1119, 1081, 1017cm$^{-1}$ |
| I-373 | m.p. 95–98° C.<br>$^1$HNMR(CDCl$_3$) δ 1.76(s, 3H), 1.80(s, 3H), 3.43(s, 3H), 3.72(s, 3H), 3.85(s, 3H), 4.63(d, J=6.6Hz, 2H), 5.56(m, 1H), 5.92(s, 1H), 6.43(s, 1H), 7.01–7.42(m, 7H)<br>IR(KBr)3318, 2937, 1612, 1598, 1500, 1485, 1464, 1450, 1361, 1298, 1275, 1240, 1104, 1072, 1011cm$^{-1}$ |

TABLE 77

| | |
|---|---|
| I-374 | m.p. 69–71° C.<br>$^1$HNMR(CDCl$_3$) δ 1.68(s, 3H), 1.74(d, J=0.6Hz, 3H), 2.50–2.60(m, 2H), 3.43(s, 3H), 3.71(s, 3H), 3.85(s, 3H), 4.04(t, J=7.2Hz, 2H), 5.23(m, 1H), 5.91(s, 1H), 6.43(s, 1H), 7.00–7.42(m, 7H)<br>IR(KBr)3385, 2933, 1611, 1583, 1521, 1503, 1485, 1466, 1403, 1358, 1299, 1276, 1241, 1122, 1104, 1071, 1011cm$^{-1}$ |
| I-375 | m.p. 105–107° C.<br>$^1$HNMR(CDCl$_3$) δ 2.36(s, 3H), 2.59(s, 3H), 3.52(s, 3H), 3.73(s, 3H), 3.84(s, 3H), 5.16(s, 2H), 6.83(s, 1H), 7.00–7.42(m, 11H)<br>IR(KBr)3433, 2940, 1609, 1581, 1522, 1499, 1481, 1461, 1401, 1366, 1296, 1269, 1240, 1178, 1117, 1079, 1021, 1011cm$^{-1}$ |
| I-376 | m.p. 142–144° C.<br>$^1$HNMR(CDCl$_3$) δ 2.37(s, 3H), 3.42(s, 3H), 3.71(s, 3H), 3.85(s, 3H), 5.14(s, 2H), 5.91(s, 1H), 6.43(s, 1H), 7.01–7.42(m, 11H)<br>IR(KBr)3367, 2936, 1615, 1583, 1520, 1502, 1482, 1464, 1447, 1405, 1359, 1317, 1291, 1274, 1239, 1121, 1109, 1070, 1009cm$^{-1}$ |
| I-377 | m.p. 174–176° C.<br>$^1$HNMR(CDCl$_3$) δ 3.21(s, 3H), 3.41(s, 3H), 3.63(s, 3H), 3.77(s, 3H), 5.30(s, 2H), 6.94(s, 1H), 7.03–7.05(m, 2H), 7.15–7.20(m, 1H), 7.25 (m, 1H), 7.38(d, J=8.9Hz, 2H), 7.62(d, J=7.8Hz, 1H), 7.71(d, J=8.9Hz, 2H), 7.76(dt, J=7.8, 1.5Hz, 1H), 8.60(m, 1H)<br>IR(KBr)1732, 1523, 1474, 1368, 1148, 1061, 863, 845, 790cm$^{-1}$ |
| I-378 | m.p. >260° C.<br>$^1$HNMR(DMSO-d$_6$) δ 3.32(s, 3H), 3.73(s, 3H), 5.28(s, 2H), 6.87(d, J=8.7Hz, 2H), 7.00(s, 1H), 7.04(dd, J=8.9, 1.8Hz, 1H), 7.16(dd, J=12.3, 1.8Hz, 1H), 7.26(t, J=8.9Hz, 1H), 7.39(m, 1H), 7.57(d, J=8.7Hz, 2H), 7.58(d, J=7.8Hz, 1H), 7.89(dt, J=7.8, 1.5Hz, 1H), 8.61(m, 1H), 9.61(s, 1H), 12.9(brs, 1H)<br>IR(KBr)3383, 1735, 1705, 1610, 1522, 1471, 1272, 1226, 1059, 1014, 838, 762cm$^{-1}$ |
| I-379 | m.p. 137–138° C.<br>$^1$HNMR(CDCl$_3$) δ 1.77(s, 3H), 1.82(s, 3H), 3.46(s, 3H), 3.79(s, 3H), 4.64(d, J=4.6Hz, 1H), 5.56(t, J=4.6Hz, 1H), 6.92–7.20(m, 6H), 7.61 (dd, J=3.6, 5.8Hz, 2H), 9.96(Brs, 1H)<br>IR(KBr)3434, 2966, 2935, 2839, 1702, 1695, 1521, 1466, 1378, 1299, 1287, 1272, 1240, 1012, 840cm$^{-1}$ |

TABLE 78

| | |
|---|---|
| I-380 | m.p. 98–99° C.<br>$^1$HNMR(CDCl$_3$) δ 2.37(s, 3H), 3.45(s, 3H), 3.78(s, 3H), 5.15(s, 2H), 6.93–7.26(m, 4H), 7.36(d, J=7.8Hz, 2H), 7.62(dd, J=4.0, 8.8Hz, 2H), 9.94(s, 1H)<br>IR(KBr)3446, 2933, 2845, 1699, 1521, 1473, 1463, 1381, 1293, 1261, 1238, 1221, 1131, 803cm$^{-1}$ |
| I-381 | m.p. 118–119° C.<br>$^1$HNMR(CDCl$_3$) δ 1.69(s, 3H), 1.74(s, 3H), 2.54(dt, J=5.0, 7.8Hz, 2H), 3.45(s, 3H), 3.78(s, 3H), 4.05(t, J=7.2Hz, 2H), 5.24(t, J=4.4Hz, 1H), 6.95–7.16(m, 6H), 7.61(dd, J=3.4, 8.8Hz, 2H), 9.95(brs, 1H)<br>IR(KBr)3433, 2959, 2930, 2842, 1701, 1602, 1522, 1464, 1379, 1303, 1263, 1222, 1132, 1018cm$^{-1}$ |
| I-382 | m.p. 93–94° C.<br>$^1$HNMR(DMSO-d$_6$) δ 1.74(s, 3H), 1.78(s, 3H), 3.32(s, 3H), 3.71(s, 3H), 4.62(d, J=7.0Hz, 2H), 5.48(t, J=5.8Hz, 1H), 6.91(s, 1H), 7.09–7.35 (m, 2H), 7.64–7.71(m, 2H)<br>IR(KBr)3433, 2976, 2937, 1707, 1604, 1520, 1472, 1376, 1300, 1265, 1226, 1160, 1131, 1060, 839cm$^{-1}$ |
| I-383 | m.p. 98–99° C.<br>$^1$HNMR(DMSO-d$_6$) δ 2.32(s, 3H), 3.31(s, 3H), 3.70(s, 3H), 5.13(s, 2H), 6.88(s, 1H), 7.14–7.39(m, 5H), 7.63–7.70(m, 2H)<br>IR(KBr)3433, 2981, 2937, 1704, 1603, 1520, 1470, 1375, 1301, 1266, 1226, 1159, 1061, 839cm$^{-1}$ |
| I-384 | oil<br>$^1$HNMR(DMSO-d$_6$) δ 1.68(s, 3H), 1.74(s, 3H), 2.48–2.56(m, 2H), 3.57(s, 3H), 3.77(s, 3H), 3.98(t, J=4.8Hz, 2H), 5.26(t, J=4.2Hz, 1H), 6.84(s, 1H), 7.05–7.36(m, 5H), 7.63–7.70(m, 2H)<br>IR(KBr)3433, 2979, 2938, 1726, 1603, 1522, 1470, 1376, 1301, 1264, 1226, 1160, 1132, 1080, 1058, 840cm$^{-1}$ |
| I-385 | m.p. 137–138° C.<br>$^1$HNMR(CDCl$_3$) δ 1.77(s, 3H), 1.82(s, 3H), 2.55(s, 3H), 3.21(s, 3H), 3.57(s, 3H), 3.78(s, 3H), 4.56(d, J=7.0Hz, 2H), 5.52(t, J=7.4Hz, 1H), 6.84(s, 1H), 7.02(d, J=8.8Hz, 2H), 7.34–7.40(m, 4H), 7.70(d, J=8.8Hz, 2H)<br>IR(KBr)3434, 2938, 1607, 1519, 1366, 1244, 1174, 1151, 1072, 871, 796cm$^{-1}$ |

TABLE 79

| | |
|---|---|
| I-386 | m.p. 169–170° C.<br>$^1$HNMR(CDCl$_3$) δ 2.48(s, 3H), 3.21(s, 3H), 3.56(s, 3H), 3.77(s, 3H), 5.08(s, 2H), 6.84(s, 1H), 7.07(d, J=5.8Hz, 2H), 7.19–7.39(m, 4H), 7.70 (d, J=6.0Hz, 2H)<br>IR(KBr)3432, 3016, 2935, 1605, 1519, 1479, 1368, 1357, 1233, 1176, 1151, 1076, 876, 843, 798cm$^{-1}$ |
| I-387 | m.p. 140–141° C.<br>$^1$HNMR(CDCl$_3$) δ 1.68(s, 3H), 1.75(s, 3H), 2.51(dt, J=4.4, 4.6Hz, 2H), 2.55(s, 3H), 3.21(s, 3H), 3.56(s, 3H), 3.77(s, 3H), 3.97(t, J=4.8Hz, 2H), 5.26(t, J=4.0Hz, 1H), 6.84(s, 1H), 6.99(d, J=5.8Hz, 2H), 7.34–7.39(m, 4H), 7.70(d, J=5.8Hz, 2H)<br>IR(KBr)3445, 2937, 1608, 1519, 1480, 1391, 1361, 1351, 1237, 1177, 1154, 1077, 962, 871, 862, 800cm$^{-1}$ |

TABLE 79-continued

| | |
|---|---|
| I-388 | m.p. 124–125° C.<br>¹HNMR(DMSO-d₆) δ 1.73(s, 3H), 1.75(s, 3H), 3.30(s, 3H), 3.65(s, 3H), 4.54(d, J=6.6Hz, 2H), 5.47(t, J=6.4Hz, 1H), 6.40(s, 1H), 6.82–6.94 (m, 4H), 7.20(d, J=8.6Hz, 2H), 7.44(d, J=8.2Hz, 2H)<br>IR(KBr)3411, 2934, 1608, 1523, 1487, 1396, 1231, 1175, 1105, 1072, 996, 898cm⁻¹ |
| I-389 | m.p. 93–94° C.<br>¹HNMR(DMSO-d₆) δ 2.32(s, 3H), 3.32(s, 3H), 3.64(s, 3H), 5.08(s, 2H), 6.40(s, 1H), 6.84(d, J=8.6Hz, 2H), 6.98(d, J=8.6Hz, 2H), 7.19–7.23 (m, 4H), 7.34–7.46(m, 4H)<br>IR(KBr)3398, 2933., 1609, 1523, 1486, 1461, 1398, 1235, 1174, 1119, 1071, 997, 829cm⁻¹ |
| I-390 | oil<br>¹HNMR(DMSO-d₆) δ 1.72(s, 3H), 1.74(s, 3H), 2.52(dt, J=4.8, 5.0Hz, 2H), 3.24(s, 3H), 3.58(s, 3H), 4.06(t, J=7.2Hz, 2H), 5.24(t, J=4.4Hz, 1H), 6.80–6.95(m, 4H), 7.22(d, J=8.4Hz, 2H), 7.46(d, J=8.2Hz, 2H)<br>IR(KBr)3340, 2934, 1608, 1522, 1486, 1396, 1285, 1230, 1175, 1106, 1072, 996, 828cm⁻¹ |
| I-391 | ¹HNMR(CDCl₃ + CD₃OD) δ 3.05(s, 3H), 3.48(s, 3H), 3.75(s, 3H), 5.16(s, 2H), 5.97(s, 1H), 6.02(s, 1H), 6.47(s, 1H), 6.94(d.d, J=8.4&1.8Hz, 1H), 7.04(d, J=8.4Hz, 1H), 7.07(d, J=1.8Hz, 1H), 7.22–7.52(m, 9H)<br>IR(KBr)3548, 3357, 1603, 1589, 1520, 1487, 1460, 1445, 1410, 1329, 1286, 1247, 1153, 1115, 1077, 1010cm⁻¹ |

TABLE 80

| | |
|---|---|
| I-392 | ¹HNMR(CDCl₃) δ 2.37(s, 3H), 2.77–2.88(broad, 1H), 3.47(s, 3H), 3.64(s, 3H), 3.72(s, 3H), 3.82(s, 3H), 4.32(d.d, J=11.1&0.6Hz, 1H), 4.45–4.56(broad, 1H), 4.92(s, 1H), 5.16(s, 2H), 6.70(d, J=9.3Hz, 2H), 6.88(s, 1H), 6.92(d, J=9.0Hz, 2H), 7.22(d, J=8.4Hz, 2H), 738(d, J=8.4Hz, 2H), 7.56(d, J=9.0Hz, 2H)<br>IR(KBr)3476, 1610, 1519, 1476, 1463, 1386, 1265, 1215, 1074, 1041, 1010cm⁻¹ |
| I-393 | foam<br>¹HNMR(CD₃OD) δ 2.34(s, 3H), 3.38(s, 3H), 3.68(s, 3H), 4.00(dd, J=9.9, 8.7Hz, 1H), 4.17(dd, J=9.9, 3.0Hz, 1H), 5.06(dd, J=8.7, 3.0Hz, 1H), 6.43(s, 1H), 6.78(dd, J=8.7, 1.8, 1H), 6.85(d, J=8.7Hz, 2H), 6.88(d, J=1.8Hz, 1H), 6.91(d, J=8.4Hz, 1H), 7.20(d, J=8.1Hz, 2H), 7.36 (d, J=8.1Hz, 2H), 7.46(d, J=8.7Hz, 2H)<br>IR(Nujol)3367, 1655, 1612, 1586, 1523, 1489, 1459, 1254, 1225, 1115, 1072, 1015, 941, 817cm⁻¹ |
| I-394 | foam<br>¹HNMR(CD₃OD) δ 3.38(s, 3H), 3.67(s, 3H), 4.02(dd, J=10.2, 9.0Hz, 1H), 4.20(dd, J=10.2, 3.3Hz, 1H), 5.11(dd, J=9.0, 3.3Hz, 1H), 6.43 (s, 1H), 6.78(dd, J=8.4, 2.1, 1H), 6.85(d, J=8.7Hz, 2H), 6.88(d, J=2.1Hz, 1H), 6.91(d, J=8.4Hz, 1H), 7.46(d, J=8.7Hz, 2H), 7.30–7.50( m, 5H)<br>IR(Nujol)3368, 1655, 1612, 1587, 1523, 1489, 1456, 1254, 1225, 1114, 1072, 1014, 941, 825, 764cm⁻¹ |
| I-395 | foam<br>¹HNMR(CDCl₃) δ 2.48(s, 3H), 2.82(s, 3H), 3.16(s, 3H), 3.22(s, 3H), 3.54(s, 3H), 3.77(s, 3H), 6.85(s, 3H), 7.34–7.38(m, 2H), 7.38(d, J=8.1Hz, 2H), 7.39(d, J=8.7Hz, 2H), 7.46(d, J=1.8Hz, 1H), 7.46(d, J=8.7Hz, 2H), 7.82(d, J=8.1Hz, 2H)<br>IR(Nujol)1597, 1514, 1479, 1464, 1177, 1152, 1085, 969, 883, 846, 797, 729cm⁻¹ |
| I-396 | foam<br>¹HNMR(CDCl₃) δ 2.85(s, 3H), 3.14(s, 3H), 3.22(s, 3H), 3.54(s, 3H), 3.77(s, 3H), 6.85(s, 1H), 7.36(m, 2H), 7.39(d, J=8.7Hz, 2H), 7.45, ( m, 1H), 7.60(m, 2H), 7.66(d, J=8.7Hz, 2H), 7.74(m, 1H), 7.94(m, 2H)<br>IR(Nujol)1612, 1584, 1514, 1479, 1451, 1179, 1152, 1085, 969, 949, 846, 797, 737cm⁻¹ |

TABLE 81

| | |
|---|---|
| I-397 | foam<br>¹HNMR(CDCl₃) δ 2.73(s, 3H), 3.21(s, 6H), 3.55(s, 3H), 3.77(s, 3H), 5.20(s, 2H), 6.84(s, 1H), 7.16(brs, 1H), 7.22(d, J=8.1Hz, 1H), 7.33, (d, J=2.4Hz, 1H), 7.37(brs, 2H), 7.38(d, J=8.7Hz, 2H), 7.65(brs, 1H), 7.67(d, J=8.7Hz, 2H)<br>IR(Nujol)1608, 1519, 1480, 1464, 1176, 1151, 1080, 972, 876, 846, 798cm⁻¹ |
| I-398 | foam<br>¹HNMR(CDCl₃) δ 2.91(s, 3H), 3.19(s, 3H), 3.22(s, 3H), 3.54(s, 3H), 3.78(s, 3H), 5.26(s, 2H), 5.34(s, 2H), 7.04(brs, 1H), 7.05(s, 2H), 7.12 (brs, 1H), 7.39(d, J=8.7Hz, 2H), 7.36–7.43(m, 3H), 7.67(d, J=8.7Hz, 2H)<br>IR(Nujol)1608, 1519, 1480, 1463, 1176, 1151, 1079, 972, 876, 799cm⁻¹ |
| I-399 | m.p. 203–205° C.<br>¹HNMR(DMSO-d₆) δ 2.87(s, 3H), 3.35(s, 3H), 3.45(s, 3H), 3.52(s, 3H), 3.78(s, 3H), 5.39(s, 2H), 7.07(s, 1H), 7.08(d, J=3.9Hz, 1H), 7.16 (d, J=3.9Hz, 1H), 7.31(dd, J=9.0, 1.8Hz, 1H), 7.33(s, 1H), 7.42(d, J=9.0Hz, 1H), 7.49(d, J=8.7Hz, 2H), 7.74(d, J=8.7Hz, 2H)<br>IR(Nujol)1609, 1520, 1481, 1455, 1231, 1080, 1013, 984, 947, 878, 832, 798cm⁻¹ |
| I-400 | foam<br>¹HNMR(CDCl₃) δ 2.72(s, 3H), 3.14(s, 3H), 3.21(s, 3H), 3.55(s, 3H), 3.77(s, 3H), 5.14(s, 2H), 6.84(s, 1H), 7.11(d, J=8.7Hz, 1H), 7.34(dd, J=2.1, 8.7Hz, 1H), 7.34(d, J=8.4Hz, 2H), 7.37(d, J=8.4Hz, 2H), 7.41(d, J=2.1Hz, 1H), 7.54(d, J=8.4Hz, 2H), 7.68(d, J=8.4Hz, 2H) |
| I-401 | foam<br>¹HNMR(CDCl₃) δ 2.83(s, 3H), 3.14(s, 3H), 3.22(s, 3H), 3.55(s, 3H), 3.78(s, 3H), 5.26(s, 2H), 6.85(s, 1H), 7.24(d, J=8.4Hz, 1H), 7.38(d, J=8.4Hz, 1H), 7.41(dd, J=2.1, 8.4Hz, 1H), 7.44(d, J=2.1Hz, 1H), 7.67(d, J=8.4Hz, 2H)<br>IR(KBr)1609, 1523, 1509, 1481, 1367, 1402, 1178, 1152, 1080, 973, 943, 876, 798cm⁻¹ |

TABLE 82

| | |
|---|---|
| I-402 | foam<br>¹HNMR(CDCl₃) δ 2.68(s, 3H), 3.14(s, 3H), 3.21(s, 3H), 3.55(s, 3H), 3.66(s, 2H), 3.71(s, 3H), 3.78(s, 3H), 5.18(s, 2H), 6.84(s, 1H), 7.14( d, J=8.4Hz, 1H), 7.32(d, J=8.7Hz, 1H), 7.35(dd, J=2.1, 8.7Hz, 1H), 7.37(d, J=8.4Hz, 2H), 7.39(d, J=2.1Hz, 1H), 7.42(d, J=8.4Hz, 2H), 7.67 (d, J=8.4Hz, 2H)<br>IR(KBr)1736, 1610, 1519, 1481, 1365, 1177, 1151, 1079, 876, 817, 798cm⁻¹ |
| I-403 | foam<br>¹HNMR(CDCl₃) δ 2.70(s, 3H), 3.16(s, 3H), 3.21(s, 3H), 3.56(s, 3H), 3.78(s, 3H), 5.24(s, 2H), 6.84(s, 1H), 7.18(d, J=8.4Hz, 1H), 7.36(dd, |

TABLE 82-continued

| | |
|---|---|
| | J=1.5, 8.4Hz, 1H), 7.38(d, J=8.4Hz, 2H), 7.41(d, J=1.5Hz, 1H), 7.46(m, 2H), 7.54(d, J=8.1Hz, 2H), 7.62(m, 3H), 7.64(d, J=8.1Hz, 2H), 7.68(d, J=8.4Hz, 2H)<br>IR(KBr)1609, 1519, 1481, 1365, 1177, 1151, 1079, 1014, 876, 818, 797cm$^{-1}$ |
| I-404 | m.p. 128–130° C.<br>$^1$HNMR(CDCl$_3$) δ 2.75(s, 3H), 2.92(s, 3H), 3.18(t, J=6.9Hz, 2H), 3.21(s, 3H), 3.55(s, 3H), 3.77(s, 3H), 4.34(t, J=6.9Hz, 2H), 6.81(s, 1H), 7.08(d, J=8.4Hz, 1H), 7.29(m, 2H), 7.32(br.s, 3H), 7.35(dd, J=2.1, 8.4Hz, 1H), 7.38(d, J=8.4Hz, 2H), 7.39(d, J=2.1Hz, 1H), 7.67(d, J=8.4Hz, 2H)<br>IR(KBr)1609, 1520, 1481, 1364, 1177, 1151, 1080, 872, 815, 797cm$^{-1}$ |
| I-405 | foam<br>$^1$HNMR(CDCl$_3$) δ 1.71(d, J=6.3Hz, 3H), 2.45(br.s, 3H), 3.20(s, 3H), 3.28(s, 3H), 3.53(s, 3H), 3.75(s, 3H), 5.43(q, J=6.3Hz, 1H), 6.81(s, 1H), 6.90(d, J=8.4Hz, 1H), 7.16(dd, J=2.1, 8.4Hz, 1H), 7.30(m, 1H), 7.36(d, J=2.1Hz, 1H), 7.37(d, J=8.4Hz, 2H), 7.35–7.41(m, 4H), 7.66(d, J=8.4Hz, 2H)<br>IR(KBr)1609, 1518, 1480, 1365, 1177, 1151, 1078, 874, 818, 798cm$^{-1}$ |

TABLE 83

| | |
|---|---|
| I-406 | foam<br>$^1$HNMR(CDCl$_3$) δ 1.02(t, J=9.0Hz, 3H), 2.04(dq, J=6.3, 9.0Hz, 2H), 2.39(br.s, 3H), 3.20(s, 3H), 3.30(s, 3H), 3.53(s, 3H), 3.75(s, 3H), 5.18(t, J=6.3Hz, 1H), 6.80(s, 1H), 6.88(d, J=8.4Hz, 1H), 6.92(m, 1H), 7.14(dd, J=2.4, 8.4Hz, 1H), 7.25–7.40(m, 7H), 7.66(d, J=8.4Hz, 2H)<br>IR(KBr)1609, 1518, 1480, 1365, 1177, 1151, 1079, 874, 819, 797cm$^{-1}$ |
| I-407 | foam<br>$^1$HNMR(CDCl$_3$) δ 2.46(s, 3H), 3.07(s, 3H), 3.20(s, 3H), 3.54(s, 3H), 3.76(s, 3H), 6.33(s, 1H), 6.82(s, 1H), 6.99(d, J=9.0Hz, 1H), 7.19(dd, J=2.1, 9.0Hz, 1H), 7.26–7.40(m, 9H), 7.43–7.47(m, 4H), 7.66(d, J=8.4Hz, 2H)<br>IR(KBr)1607, 1518, 1481, 1364, 1177, 1151, 1081, 873, 822, 798cm$^{-1}$ |
| I-408 | m.p. 179–180 ° C.<br>$^1$HNMR(CDCl$_3$) δ 1.69(d, J=6.3Hz, 3H), 2..34(br.s, 3H), 2.45(s, 3H), 3.20(s, 3H), 3.27(s, 3H), 3.54(s, 3H), 3.75(s, 3H), 5.40(q, J=6.3Hz, 1H), 6.81(s, 1H), 6.92(d, J=8.7Hz, 1H), 7.15(d, J=8.7Hz, 2H), 7.16(dd, J=2.1, 8.4Hz, 1H), 7.27(d, J=8.7Hz, 1H), 7.35(d, J=2.1Hz, 1H), 7.37(d, J=8.4Hz, 2H), 7.66(d, J=8.4Hz, 2H)<br>IR(KBr)1609, 1518, 1480, 1365, 1177, 1151, 1078, 874, 819, 797cm$^{-1}$ |
| I-409 | m.p. 243–244° C.<br>$^1$HNMR(DMSO-d$_6$) δ 3.30(s, 3H), 3.64(s, 3H), 5.19(s, 2H), 6.39(s, 1H), 6.64(dd, J=1.8, 8.4Hz, 1H), 6.77(d, J=1.8Hz, 1H), 6.83(d, J=8.4Hz, 2H), 6.97(d, J=8.4Hz, 1H), 7.37(t, J=7.5Hz, 1H), 7.44(d, J=8.4Hz, 2H), 7.48(t, J=8.4Hz, 2H), 7.60(d, J=8.4Hz, 2H), 7.67–7.73(m, 5H)<br>IR(KBr)3421, 1610, 1523, 1488, 1463, 1403, 1176, 1115, 1072, 821cm$^{-1}$ |
| I-410 | foam<br>$^1$HNMR(CDCl$_3$) δ 3.18(t, J=6.9Hz, 2H), 3.45(s, 3H), 3.73(s, 3H), 4.31(t, J=6.9Hz, 2H), 6.44(s, 1H), 6.91(d, J=8.4Hz, 2H), 6.94(br.s, 2H), 7.03(br.s, 1H), 7.23–7.37(m, 5H), 7.53(d, J=8.4Hz, 2H)<br>IR(KBr)3434, 1612, 1587, 1523, 1489, 1455, 1403, 1250, 1113, 1070, 1011, 825, 815cm$^{-1}$ |

TABLE 84

| | |
|---|---|
| I-411 | foam<br>$^1$HNMR(CDCl$_3$) δ 1.70(d, J=6.0Hz, 3H), 3.44(s, 3H), 3.72(s, 3H), 5.36(q, J=6.0Hz, 1H), 6.42(s, 1H), 6.78(d, J=8.1Hz, 1H), 6.81(dd, J=1.5, 8.7Hz, 1H), 6.91(d, J=8.4Hz, 2H), 7.06(d, J=1.5Hz, 1H), 7.26–7.42(m, 4H), 7.51(d, J=8.4Hz, 2H)<br>IR(KBr)3472, 1612, 1587, 1523, 1488, 1454, 1403, 1248, 1113, 1070, 1011, 825,cm$^{-1}$ |
| I-412 | foam<br>$^1$HNMR(CDCl$_3$) δ 1.03(t, J=7.2Hz, 3H), 1.94(m, 1H), 2.06(m, 1H), 3.43(s, 3H), 3.72(s, 3H), 5.08(dd, J=7.2, 5.4Hz, 1H), 6.43(s, 1H), 6.73(d, J=8.4Hz, 1H), 6.78(dd, J=1.8, 8.4Hz, 1H), 6.90(d, J=8.4Hz, 2H), 7.05(d, J=1.8Hz, 1H), 7.25–7.38(m, 5H), 7.51(d, J=8.4Hz, 2H)<br>IR(KBr)3434, 1612, 1522, 1488, 1454, 1403, 1247, 1113, 1070, 1011, 826, 811cm$^{-1}$ |
| I-413 | foam<br>$^1$HNMR(CDCl$_3$) δ 3.44(s, 3H), 3.73(s, 3H), 6.25(s, 1H), 6.43(s, 1H), 7.26(m, 2H), 6.90(d, J=8.4Hz, 2H), 7.08(d, J=2.1Hz, 1H), 7.29–7.43(m, 10H), 7.51(d, J=8.4Hz, 2H)<br>IR(KBr)3432, 1611, 1523, 1489, 1454, 1402, 1226, 1110, 1069, 1011, 825cm$^{-1}$ |
| I-414 | foam<br>$^1$HNMR(CDCl$_3$) δ 1.69(d, J=6.3Hz, 3H), 2..35(s, 3H), 3.44(s, 3H), 3.72(s, 3H), 5.33(q, J=6.3Hz, 1H), 6.42(s, 1H), 6.80(br.s, 2H), 6.90(d, J=8.4Hz, 2H), 7.05(br.s, 1H), 7.18(d, J=7.8Hz, 2H), 7.29(d, J=7.8Hz, 2H), 7.51(d, J=8.4Hz, 2H)<br>IR(KBr)3433, 1612, 1522, 1488, 1459, 1403, 1248, 1113, 1069, 1011, 817cm$^{-1}$ |
| I-415 | m.p. 164–167° C.<br>$^1$HNMR(CDCl$_3$) δ 3.79(s, 3H), 3.80(s, 3H), 4.81(brs, 1H), 5.29(s, 2H), 6.88–6.94(m, 4H), 7.16(d, J=8.7Hz, 1H), 7.32–7.52(m, 7H), 7.73(dd, J=2.1, 8.7Hz, 1H), 8.10(d, J=2.1Hz, 1H)<br>IR(KBr)3513, 2930, 1618, 1529, 1497, 1448, 1387, 1354, 1296, 1257, 1211, 1168, 1091, 1064, 1024cm$^{-1}$ |

TABLE 85

| | |
|---|---|
| I-416 | m.p. 155–159° C.<br>$^1$HNMR(CDCl$_3$) δ 3.20(s, 3H), 3.39(s, 3H), 3.82(s, 3H), 3.83(s, 3H)6.95(s, 1H), 6.96(s, 1H), 7.34–7.38(m, 2H), 7.58–7.64(m, 3H), 7.87(dd, J=2.1, 8.4Hz, 1H), 8.26(d, J=2.1Hz, 1H)<br>IR(KBr)3433, 2944, 1539, 1519, 1487, 1358, 1216, 1176, 1150, 1086, 1057, 1031cm$^{-1}$ |
| I-417 | m.p. 124–126° C.<br>$^1$HNMR(CDCl$_3$) δ 3.19(s, 3H), 3.80(s, 6H), 5.30(s, 2H), 6.93(s, 1H), 6.94(s, 1H), 7.18(d, J=9.0Hz, 1H), 7.32–7.52(m, 7H), 7.59–7.64(m, 2H), 7.73(dd, J=2.1, 9.0Hz, 1H), 8.10(d, J=2.1Hz, 1H)<br>IR(KBr)3433, 2937, 1619, 1531, 1491, 1465, 1450, 1358, 1290, 1256, 1211, 1176, 1150, 1088, 1062, 1033cm$^{-1}$ |

TABLE 85-continued

I-418 m.p. 151–153° C.
$^1$HNMR(CDCl$_3$) δ 3.18(s, 3H), 3.781(s, 3H), 3.784(s, 3H), 5.14(s, 2H), 6.90–7.00(m, 5H), 7.31–7.50(m, 7H), 7.60–7.65(m, 2H)
IR(KBr)3480, 3383, 2930, 1610, 1523, 1489, 1467, 1383, 1358, 1330, 1211, 1175, 1147, 1024cm$^{-1}$

I-419 m.p. 198–200° C.
$^1$HNMR(CDCl$_3$) δ 3.77(s, 6H), 5.13(s, 2H), 6.86–7.00(m, 7H)7.34–7.50(m, 7H)
IR(KBr)3403, 3327, 1611, 1592, 1525, 1492, 1462, 1444, 1384, 1318, 1273, 1243, 1209, 1178, 1149, 1110, 1058, 1037, 1006cm$^{-1}$

I-420 m.p. 168–171° C.
$^1$HNMR(CDCl$_3$) δ 2.99(s, 3H), 3.19(s, 3H), 3.80(s, 3H), 3.81(s, 3H), 5.16(s, 2H), 6.83(brs, 1H), 6.92(s, 1H), 6.96(s, 1H), 7.06(d, J=8.7Hz, 1H), 7.32–7.46(m, 8H), 7.60–7.64(m, 2H), 7.81(d, J=2.1Hz, 1H)
IR(KBr)3403, 3327, 1611, 1592, 1525, 1492, 1462, 1444, 1384, 1318, 1273, 1243, 1209, 1178, 1149, 1110, 1058, 1037, 1006cm$^{-1}$ I-421 m.p. 168–171° C.
$^1$HNMR(CDCl$_3$) δ 3.19(s, 3H), 3.80(s, 3H), 3.81(s, 3H), 5.23(s, 2H), 6.93(s, 1H), 6.97(s, 1H), 7.07(d, J=8.7Hz, 1H), 7.33–7.45(m, 8H), 7.61–7.65(m, 2H), 8.58(d, J=2.4Hz, 1H), 8.66(brs, 1H)
IR(KBr)3401, 1723, 1613, 1595, 1549, 1518, 1486, 1385, 1365, 1330, 1299, 1256, 1212, 1151, 1119, 1060, 1037, 1017cm$^{-1}$

TABLE 86

I-422 m.p. 159–160° C.
$^1$HNMR(CDCl$_3$) δ 1.69(s, 3H), 1.74, (s, 3H), 2.55(q, J=7.2Hz, 2H), 2.73(s, 3H), 3.22(s, 3H), 3.55(s, 3H), 3.77(s, 3H), 4.06(t, J=7.2Hz, 2H), 5.24(t, J=7.2Hz, 1H), 6.85(s, 1H), 7.07(d, J=8.6Hz, 1H), 7.39(d, J=8.7Hz, 2H), 7.55(dd, J=8.6, 2.1Hz, 1H), 7.63(d, J=2.1Hz, 1H), 7.68 (d, J=8.7Hz, 2H)
IR(KBr)1515, 1481, 1359, 1325, 1175, 1140, 1079, 870, 799cm$^{-1}$

I-423 m.p. 180–182° C.
$^1$HNMR(CDCl$_3$) δ 1.76(s, 3H), 1.81, (s, 3H), 2.71(s, 3H), 3.22(s, 3H), 3.55(s, 3H), 3.78(s, 3H), 4.06(d, J=6.3Hz, 2H), 5.50(t, J=6.3Hz, 1H), 6.85(s, 1H), 7.09(d, J=8.7Hz, 1H), 7.39(d, J=8.7Hz, 2H), 7.55(dd, J=8.7, 2.0Hz, 1H), 7.64(d, J=2.0Hz, 1H), 7.68(d, J=8.7Hz, 2H)
IR(KBr)1514, 1479, 1360, 1241, 1174, 1132, 1078, 866, 800cm$^{-1}$

I-424 m.p. 176–178° C.
$^1$HNMR(CDCl$_3$) δ 2.64(s, 3H), 3.22(s, 3H), 3.55(s, 3H), 3.78(s, 3H), 5.26(s, 2H), 6.85(s, 1H), 7.14(d, J=8.6Hz, 1H), 7.33–7.48(m, 7H), 7.54 (dd, J=8.6, 2.1Hz, 1H), 7.66–7.70(m, 3H)
IR(KBr)1517, 1482, 1367, 1327, 1178, 1150, 1135, 1081, 878, 797cm$^{-1}$

I-425 m.p. 199–200° C.
$^1$HNMR(CDCl$_3$) δ 2.37(s, 3H), 2.63(s, 3H), 3.21(s, 3H), 3.55(s, 3H), 3.78(s, 3H), 5.21(s, 2H), 6.84(s, 1H), 7. 13(d, J=8.7Hz, 1H), 7.20(d, J=8.0Hz, 2H), 7.34(d, J=8.0Hz, 2H), 7.38(d, J=9.0Hz, 2H), 7.53(dd, J=8.7, 1.8Hz, 1H), 7.66(d, J=1.8Hz, 1H), 7.68(d, J=9.0Hz, 2H)
IR(KBr)1517, 1481, 1366, 1326, 1255, 1177, 1151, 1082, 871, 798cm$^{-1}$

I-426 amorphous
$^1$HNMR(CDCl$_3$) δ 1.68(s, 3H), 1.73(s, 3H), 2.54(q, J=7.2Hz, 2H), 3.44(s, 3H), 3.75(s, 3H), 4.05(t, J=7.2Hz, 2H), 5.07(s, 1H), 5.24(t, J=7.2Hz, 1H), 6.02(s, 1H), 6.45(s, 1H), 6.92(d, J=8.6Hz, 2H), 7.41(d, J=8.6Hz, 2H), 7.53(d, J=8.6Hz, 2H), 7.59(dd, J=8.6, 2.0Hz, 1H), 7.63 (d, J=2.0Hz, 1H)
IR(CHCl$_3$)3595, 3506, 1614, 1523, 1489, 1326, 1281, 1258, 1122, 1079, 1057cm$^{-1}$

TABLE 87

I-427 m.p. 180–182° C.
$^1$HNMR(CDCl$_3$) δ 1.75(s, 3H), 1.80(s, 3H), 3.44(s, 3H), 3.76(s, 3H), 4.66(d, J=6.6Hz, 2H), 4.87(s, 1H), 5.52(t, J=6.6Hz, 1H), 6.02(s, 1H), 6.46(s, 1H), 6.93(d, J=8.9Hz, 2H), 7.06(d, J=8.4Hz, 1H), 7.53(d, J=8.9Hz, 2H), 7.59(dd, J=8.4, 2.1Hz, 1H), 7.71(d, J=2.1Hz, 1H),
IR(KBr)3406, 1615, 1522, 1488, 1399, 1324, 1280, 1256, 1138, 1116, 1076, 1054, 996, 835, 826cm$^{-1}$

I-428 m.p. 133–135° C.
$^1$HNMR(CDCl$_3$) δ 3.44(s, 3H), 3.75(s, 3H), 4.87(s, 1H), 5.23(s, 2H), 6.03(s, 1H), 6.46(s, 1H), 6.93(d, J=8.6Hz, 2H), 7.11(d, J=8.4Hz, 1H), 7.32–7.49(m, 5H), 7.53(d, J=8.6Hz, 2H), 7.60(dd, J=8.4, 2.1Hz, 1H), 7.75(d, J=2.1Hz, 1H),
IR(KBr)3397, 1612, 1523, 1489, 1400, 1321, 1257, 1132, 1084, 1056, 1002, 832cm$^{-1}$

I-429 m.p. 174–176° C.
$^1$HNMR(CDCl$_3$) δ 2.37(s, 3H), 3.44(s, 3H), 3.75(s, 3H), 4.88(s, 1H), 5.18(s, 2H), 6.02(s, 1H), 6.45(s, 1H), 6.93(d, J=8.6Hz, 2H), 7.11(d, J=8.4Hz, 1H), 7.21(d, J=8.1Hz, 2H), 7.36(d, J=8.1Hz, 2H), 7.53(d, J=8.6Hz, 2H), 7.59(dd, J=8.4, 2.1Hz, 1H), 7.74(d, J=2.1Hz, 1H),
IR(KBr)3481, 3376, 1616, 1520, 1491, 1327, 1260, 1119, 1081, 1004, 827cm$^{-1}$

I-430 $^1$HNMR(CDCl$_3$) δ 2.37(s, 3H), 2.54(s, 3H), 2.68(s, 3H), 3.12(s, 3H), 3.54(s, 3H), 3.77(s, 3H), 5.14(s, 2H), 6.85(s, 1H), 7.12–7.24(m, 3H), 7.30–7.44(m, 6H), 7.53–7.59(m, 2H)
IR(CHCl$_3$)1608, 1517, 1476, 1367, 1117, 1080, 1013, 970, 876cm$^{-1}$

I-431 m.p. 164–168° C.
$^1$HNMR(CDCl$_3$) δ 1.76(s, 3H), 1.82(s, 3H), 2.54(s, 3H), 3.47(s, 3H), 3.75(s, 3H), 4.62(d, J=6.9Hz, 2H), 5.53(m, 1H), 5.69(s, 1H), 5.89(s, 1H), 6.46(s, 1H), 6.92–7.08(m, 3H), 7.30–7.38(m, 2H), 7.55–7.62(m, 2H)
IR(CHCl$_3$)3518, 2968, 1584, 1516, 1483, 1460, 1414, 1388, 1310, 1289, 1243, 1114, 1069, 1011, 936, 818cm$^{-1}$

I-432 m.p. 179–181° C.
$^1$HNMR(CDCl$_3$) δ 2.39(s, 3H), 2.54(s, 3H), 3.46(s, 3H), 3.74(s, 3H), 5.10(s, 2H), 5.67(s, 1H), 5.89(s, 1H), 6.46(s, 1H), 6.81(dd, J=2.1, 8.4Hz, 1H), 7.03(d, J=8.4Hz, 1H), 7.08(d, J=2.1Hz, 1H), 7.20–7.26(m, 2H), 7.31–7.37(m, 4H), 7.55–7.61(m, 2H)
IR(CHCl$_3$)3524, 2930, 1585, 1517, 1483, 1460, 1414, 1389, 1310, 1289, 1245, 1114, 1090, 1070, 1009, 937, 818cm$^{-1}$

TABLE 88

I-433 m.p. 111–112° C.
$^1$HNMR(CDCl$_3$) δ 1.76(d, J=0.6Hz, 3H), 1.81(d, J=0.9Hz, 3H), 2.69(s, 3H), 3.52(s, 3H), 3.78(s, 3H), 4.63(t, J=6.6Hz, 2H), 5.53(m, 1H), 6.84(s, 1H), 7.02–7.25(m, 5H), 7.56–7.65(m, 2H)
IR(CHCl$_3$)2932, 1607, 1520, 1481, 1368, 1266, 1080, 1012, 961, 907, 836, 812cm$^{-1}$

TABLE 88-continued

I-434 m.p. 97–101° C.
$^1$HNMR(CDCl$_3$) δ 1.69(s, 3H), 1.75(d, J=0.9Hz, 3H), 2.48–2.58(m, 5H), 3.46(s, 3H), 3.47(s, 3H), 4.06(t, J=6.9Hz, 2H), 5.22(m, 1H), 5.67 (s, 1H), 5.88(s, 1H), 6.46(s, 1H), 6.92–6.97(m, 2H), 7.05(m, 1H), 7.30–7.38(m, 2H), 7.55–7.62(m, 2H)
IR(CHCl$_3$)3518, 2928, 1584, 1517, 1483, 1414, 1388, 1290, 1246, 1114, 1090, 1070, 1011, 937, 907, 818cm$^{-1}$

I-435 m.p. 127–129° C.
$^1$HNMR(CDCl$_3$) δ 1.68(s, 3H), 1.74(d, J=1.2Hz, 3H), 2.50–2.60(m, 2H), 2.71(s, 3H), 3.52(s, 3H), 3.77(s, 3H), 4.04(t, J=7.2Hz, 2H), 5.23 (m, 1H), 6.83(s, 1H), 7.00–7.21(m, 5H), 7.57–7.64(m, 2H)
IR(CHCl$_3$)2930, 1607, 1520, 1481, 1368, 1266, 1080, 1012, 960, 836, 812cm$^{-1}$

I-436 m.p. 159–161° C.
$^1$HNMR(CDCl$_3$) δ 2.36(s, 3H), 2.57(s, 3H), 3.52(s, 3H), 3.77(s, 3H), 5.16(s, 2H), 6.83(s, 1H), 7.05–7.24(m, 7H), 7.31–7.37(m, 2H), 7.56–7.65 (m, 2H)
IR(CHCl$_3$)1520, 1481, 1368, 1267, 1131, 1080, 1012, 960, 836cm$^{-1}$

I-437 m.p. 120–124° C.
$^1$HNMR(CDCl$_3$) δ 1.76(d, J=0.6Hz, 3H), 1.81(d, J=0.6Hz, 3H), 3.43(s, 3H), 3.67(s, 3H), 4.63(d, J=6.6Hz, 2H), 5.56(m, 1H), 5.96(s, 1H), 6.44(s, 1H), 7.00–7.24(m, 5H), 7.57–7.66(m, 2H)
IR(CHCl$_3$)3522, 2930, 1586, 1518, 1484, 1415, 1390, 1311, 1290, 1248, 1115, 1090, 1071, 1012, 938, 818cm$^{-1}$

TABLE 89

I-438 m.p. 140.5–141.5° C.
$^1$HNMR(CDCl$_3$) δ 2.37(s, 3H), 3.43(s, 3H), 3.75(s, 3H), 5.14(s, 2H), 5.97(s, 1H), 6.44(s, 1H), 7.04–7.28(m, 7H), 7.36(d, J=8.1Hz, 1H), 7.57–7.65(m, 2H)
IR(CHCl$_3$)3496, 2932, 1613, 1520, 1488, 1460, 1391, 1313, 1267, 1113, 1069, 1010, 934, 825cm$^{-1}$

I-439 m.p. 76.5–77.5° C.
$^1$HNMR(CDCl$_3$) δ 1.68(s, 3H), 1.74(d, J=0.9Hz, 3H), 2.49–2.60(m, 2H), 3.43(s, 3H), 3.75(s, 3H), 4.05(t, J=7.2Hz, 2H), 5.23(m, 1H), 5.96 (s, 1H), 6.44(s, 1H), 6.99–7.28(m, 5H), 7.57–7.66(m, 2H)
IR(CHCl$_3$)3498, 2930, 1613, 1521, 1489, 1391, 1310, 1267, 1113, 1070, 1011, 934, 825cm$^{-1}$

I-440 m.p. 174–176° C.
$^1$HNMR(CDCl$_3$) δ 2.80(s, 3H), 3.46(s, 3H), 3.76(s, 3H), 5.16(s, 2H), 5.71(s, 1H), 5.88(s, 1H), 6.47(s, 1H), 6.95(dd, J=1.8, 8.4Hz, 1H), 7.04(d, J=8.4Hz, 1H), 7.08(d, J=1.8Hz, 1H), 7.34–7.49(m, 5H), 7.72–7.85(m, 4H)
IR(CHCl$_3$)3518, 1587, 1516, 1483, 1459, 1415, 1387, 1290, 1114, 1070, 1041, 1011, 936, 821cm$^{-1}$

I-441 m.p. 199–202° C.
$^1$HNMR(d6-DMSO) δ 3.28(s, 3H), 3.34(s, 3H), 3.67(s, 3H), 5.14(s, 2H), 6.52(s, 1H), 6.66(dd, J=2.1, 8.4Hz, 1H), 6.79(d, J=2.1Hz, 1H), 6.97(d, J=8.4Hz, 1H), 7.30–7.56(m, 5H), 7.86–7.93(m, 2H), 7.98–8.04(m, 2H), 8.65–9.02(brs, 2H)
IR(KBr)3487, 3413, 3004, 1597, 1518, 1500, 1482, 1456, 1360, 1310, 1281, 1231, 1146, 1118, 1090, 1068, 1016, 1004, 961cm$^{-1}$ I-442 m.p. 80–84° C.
$^1$HNMR(CDCl$_3$) δ 1.15(t, J=7.2Hz, 3H), 3.60(q, J=7.2Hz, 2H), 3.75(s, 3H), 5.03(s, 1H), 5.15(s, 2H), 5.69(s, 1H), 5.98(s, 1H), 6.45(s, 1H), 6.88–6.94(m, 2H), 6.96(dd, J=2.1, 8.1Hz, 1H), 7.02(d, J=8.1Hz, 1H), 7.10(d, J=2.1Hz, 1H), 7.34–7.49(m, 5H), 7.51–7.59(m, 2H)
IR(CHCl$_3$)3528, 1612, 1521, 1488, 1454, 1412, 1383, 1286, 1246, 1113, 1069, 1023, 886, 825cm$^{-1}$

TABLE 90

I-443 m.p. 168–169° C.
$^1$HNMR(CDCl$_3$) δ 1.14(t, J=6.9Hz, 3H), 2.66(s, 3H), 3.13(s, 3H), 3.20(s, 3H), 3.72(q, J=6.9Hz, 2H), 3.78(s, 3H), 5.19(s, 2H), 6.84(s, 1H), 7.15(d, J=8.4Hz, 1H), 7.31–7.49(m, 9H), 7.66–7.73(m, 5H)
IR(CHCl$_3$)1517, 1479, 1369, 1148, 1117, 1082, 969, 873cm$^{-1}$

I-444 m.p. 192–194° C.
$^1$HNMR(CDCl$_3$) δ 3.13(s, 3H), 3.44(s, 3H), 3.63(s, 3H), 3.76(s, 3H), 5.14(br, 1H), 5.19(s, 2H), 6.81–6.84(m, 2H), 6.94(s, 1H), 7.14(d, J=8.4Hz, 1H), 7.22–7.25(m, 2H), 7.37–7.50(m, 5H)7.57(dd, J=8.7, 2.1Hz, 1H), 7.67(d, J=2.1Hz, 1H)
IR(CHCl$_3$)3595, 3441, 1730, 1613, 1522, 1472, 1371, 1291, 1258, 1172, 1164, 1003, 972, 961, 904, 838cm$^{-1}$

I-445 m.p. 179–180° C.
$^1$HNMR(CDCl$_3$) δ 1.77(s, 3H), 1.82(s, 3H), 2.31(s, 3H), 3.24(s, 3H), 3.45(s, 3H), 3.58(s, 3H), 3.76(s, 3H), 4.64(d, J=6.9Hz, 2H), 6.95(s, 1H), 7.06–7.13(m, 3H), 7.35–7.38(m, 2H), 7.57(dd, J=8.4, 2.4Hz, 1H), 7.64(d, J=2.4Hz, 1H)
IR(CHCl$_3$)2938, 1732, 1614, 1599, 1518, 1470, 1445, 1370, 1345, 1290, 1228, 1200, 1169, 1116, 1081, 1003, 973, 905, 846, 829cm$^{-1}$

I-446 m.p. 137–138° C.
$^1$HNMR(CDCl$_3$) δ 3.13(s, 3H), 3.45(s, 3H), 3.59(s, 3H), 3.77(s, 3H), 3.88(s, 3H), 4.23(s, 2H), 5.19(s, 2H), 6.96(s, 1H), 7.15(d, J=8.7Hz, 1H), 7.35–7.50(m, 9H), 7.60(dd, J=8.7, 2.4Hz, 1H), 7.67(d, J=2.4Hz, 1H)
IR(CHCl$_3$)2954, 1750, 1734, 1614, 1516, 1471, 1387, 1372, 1345, 1291, 1258, 1173, 1147, 1118, 1081, 1064, 1004, 877cm$^{-1}$

I-447 m.p. 184–185° C.
$^1$HNMR(CDCl$_3$) δ 3.44(s, 3H), 3.60(s, 3H), 3.74(s, 3H), 4.70(br, 2H), 5.17(s, 2H), 6.95–7.02(m, 4H), 7.17(dd, J=8.4, 2.1Hz, 1H), 7.25(s, 1H), 7.31–7.34(d, J=8.7Hz, 2H), 7.38–7.47(m, 5H)
IR(CHCl$_3$)3541, 2937, 1776, 1733, 1608, 1519, 1474, 1442, 1344, 1291, 1157, 1130, 1085, 1063, 1002, 900, 862, 1835cm$^{-1}$

TABLE 91

I-448 m.p. 176–178° C.
$^1$HNMR(CDCl$_3$) δ 3.12(s, 3H), 3.44(s, 3H), 3.60(s, 3H), 3.76(s, 3H), 3.83(s, 3H), 4.66(s, 2H), 5.19(s, 2H), 6.91–6.96(m, 3H), 7.14(d, J=8.4Hz, 1H), 7.28–7.49(m, 7H), 7.57(dd, J=8.7, 2.4Hz, 1H), 7.67(d, J=2.4Hz, 1H)
IR(CHCl$_3$)2953, 2939, 1758, 1732, 1610, 1519, 1471, 1444, 1371, 1345, 1291, 1177, 1117, 1085, 1064, 1002, 973, 961, 904, 837cm$^{-1}$

I-449 m.p. 124–126° C.
$^1$HNMR(CDCl$_3$) δ 1.69(s, 3H), 1.74(d, J=0.9Hz, 3H), 2.31(s, 3H), 2.53–2.60(m, 2H), 3.23(s, 3H), 3.44(s, 3H), 3.58(s, 3H), 3.76(s, 3H), 4.09 (t, J=6.6Hz, 2H), 5.22(m, 1H), 6.95(s, 1H), 7.07(d, J=8.4Hz, 1H), 7.10–7.13(m, 2H), 7.34–7.37(m, 2H), 7.57(dd, J=9.0, 2.4Hz, 1H), 7.6

TABLE 91-continued

4(d, J=2.4Hz, 1H)
IR(CHCl$_3$)2938, 1732, 1614, 1518, 1469, 1445, 1370, 1291, 1257, 1170, 1167, 1081, 1004, 973, 961, 906, 846cm$^{-1}$

I-450 m.p. 160–161° C.
$^1$HNMR(CDCl$_3$) δ 1.69(s, 3H), 1.74(d, J=0.9, 3H), 2.53–2.60(m, 2H), 3.23(s, 3H), 3.44(s, 3H), 3.62(s, 3H), 3.76(s, 3H), 4.08(d, J=6.6Hz, 2H), 4.91(br, 1H), 5.20–5.25(m, 1H), 6.83–6.86(m, 2H), 6.94(s, 1H), 7.06(d, J=8.7Hz, 2H), 7.23–7.26(m, 2H), 7.57(dd, J=8.7, 2.4Hz, 1H), 7.64(d, J=2.4Hz, 1H)
IR(CHCl$_3$)3595, 3448, 2937, 1730, 1613, 1522, 1469, 1445, 1370, 1345, 1292, 1260, 1172, 1117, 1081, 1064, 1003, 973, 864, 837cm$^{-1}$

I-451 m.p. 182–184° C.
$^1$HNMR(CDCl$_3$) δ 1.70(d, J=0.6Hz, 3H), 1.81(d, J=0.9Hz, 3H), 3.24(s, 3H), 3.45(s, 3H), 3.63(s, 3H), 3.75(s, 3H), 4.64(d, J=6.6Hz, 2H), 5.48–5.54(m, 1H), 5.76(br, 1H), 6.78–6.82(m,2H), 6.95(s, 1H), 7.08(d, J=8.7Hz, 1H), 7.19–7.24(m, 2H), 7.56(dd, J=8.7, 2.4Hz, 1H), 7.64(d, J=2.4Hz, 1H)
IR(CHCl$_3$)3595, 3445, 2939, 1730, 1613, 1522, 1471, 1445, 1369, 1345, 1291, 1257, 1172, 1116, 1081, 1064, 1002, 973, 904, 838cm$^{-1}$

I-452 m.p. 250–253° C.(dec.)
$^1$HNMR(CD$_3$OD) δ 3.41(s, 3H), 3.71(s, 3H), 4.58(s, 2H), 5.21(s, 2H), 6.29–6.95(m, 3H), 7.02–7.03(m, 2H), 7.17(s, 1H), 7.26–7.41(m, 5H), 7.49–7.52(m, 2H)
IR(KBr)3424, 2933, 2553, 1709, 1608, 1519, 1467, 1383, 1333, 1291, 1229, 1129, 1084, 1060, 1001, 915, 861, 841, 727, 697cm$^{-1}$

TABLE 92

I-453 foam
$^1$HNMR(CDCl$_3$) δ 1.69(s, 3H), 1.75(d, J=1.2Hz, 3H), 2.51–2.58(m, 2H), 3.43(s, 3H), 3.62(s, 3H), 3.75(s, 3H), 4.08(t, J=6.9Hz, 2H), 4.85(br, 1H), 5.23(m, 1H), 5.71(br, 1H), 6.82–6.85(m, 2H), 6.90–6.94(m, 2H), 7.16(dd, J=8.4, 2.1Hz, 1H), 7.23–7.26(m, 3H)
IR(CHCl$_3$)3596, 3541, 2936, 1730, 1612, 1590, 1522, 1470, 1395, 1345, 1290, 1258, 1173, 1130, 1081, 1063, 1004, 861, 836cm$^{-1}$ I-454 m.p. 166–167° C.
$^1$HNMR(CDCl$_3$) δ 1.77(s, 3H), 1.82(s, 3H), 3.48(s, 3H), 3.75(s, 3H), 4.64(d, J=6.6Hz, 2H), 5.51–5.55(m, 1H), 5.75(br, 1H), 6.77–6.80(m, 2H), 6.93–6.96(m, 2H), 7.17(dd, J=8.1, 2.1Hz, 1H), 7.23–7.28(m, 3H)
IR(KBr)3447, 2937, 1590, 1559, 1522, 1473, 1382, 1338, 1295, 1259, 1131, 1080, 1059, 999, 918, 862, 837, 815, 791, 754cm$^{-1}$ I-455 m.p. 168–170° C.
$^1$HNMR(CD$_3$OD) δ 1.68(s, 3H), 1.74(s, 3H), 2.50–2.58(m, 2H), 3.41(s, 3H), 3.73(s, 3H), 4.05(t, J=6.9Hz, 2H), 5.29(m, 1H), 6.76–6.79 (m, 2H), 6.98–7.17(m, 6H)
IR(KBr)3411, 2964, 2936, 1685, 1613, 1590, 1523, 1472, 1379, 1293, 1259, 1229, 1131, 1082, 1061, 1000, 962, 861, 838, 814, 791, 754, 529cm$^{-1}$ I-456 m.p. 153–155° C.
$^1$HNMR(CDCl$_3$) δ 3.14(s, 3H), 3.50(s, 3H), 3.77(s, 3H), 5.20(s, 2H), 7.10–7.28(m, 6H), 7.38–7.50(m, 5H), 7.56(dd, J=8.4, 2.1Hz, 1H), 7.65(d, J=2.1Hz, 1H), 9.98(s, 1H)
IR(CHCl$_3$)2938, 2843, 1697, 1604, 1590, 1517, 1469, 1372, 1331, 1293, 1254, 1172, 1159, 1123, 1093, 1005, 963, 818cm$^{-1}$ I-457 m.p. 143–145° C.
$^1$HNMR(CDCl$_3$) δ 1.77(s, 3H), 1.83(s, 3H), 3.44(s, 3H), 3.63(s, 3H), 3.75(s, 3H), 4.63(d, J=6.6Hz, 2H), 5.53(m, 1H), 5.72(br, 1H), 6.82–6.85(m, 2H), 6.92–6.95(m, 2H), 7.16(dd, J=8.4, 2.4Hz, 1H), 7.23–7.26(m, 3H)
IR(CHCl$_3$)3595, 3537, 2938, 1729, 1612, 1591, 1522, 1473, 1395, 1344, 1290, 1258, 1173, 1129, 1081, 1063, 1003, 900, 862, 836cm$^{-1}$

TABLE 93

I-458 powder
$^1$HNMR(CDCl$_3$) δ 2.37(s, 3H), 3.08(s, 3H), 3.11(s, 3H), 3.21(s, 3H), 3.51(s, 3H), 3.52(s, 3H), 5.26(s, 2H), 7.19–7.23(m, 2H), 7.36–7.43 (m, 4H), 7.45–7.50(m, 2H), 7.82(d, J=2.1Hz, 1H), 7.98(d, J=2.1Hz, 1H)
IR(CHCl$_3$)3033, 2942, 1543, 1377, 1220, 1181, 1153, 1034cm$^{-1}$ I-459 m.p. 182–187° C.(dec.)
$^1$HNMR(CDCl$_3$) δ 2.36(s, 3H), 2.73(s, 3H), 3.16(s, 3H), 3.22(s, 3H), 3.43(s, 3H), 3.47(s, 3H), 5.08(s, 2H), 6.85(brs, 1H), 6.92(brs, 1H), 7.17–7.21(m, 2H), 7.32–7.38(m, 2H), 7.39–7.44(m, 2H), 7.50–7.55(m, 2H)
IR(CHCl$_3$)3030, 2939, 1618, 1599, 1513, 1468, 1416, 1372, 1178, 1150, 1031cm$^{-1}$ I-460 powder
$^1$HNMR(CDCl$_3$) δ 2.38(s, 3H), 2.83(s, 3H), 3.05(s, 3H), 3.22(s, 3H), 3.56(s, 3H), 3.80(s, 3H), 3.91(s, 3H)5.13(s, 2H), 6.86(s, 1H), 7.20–7.24 (m, 2H), 7.37–7.46(m, 4H), 7.65–7.70(m, 3H), 7.89(d, J=2.1Hz, 1H)
IR(CHCl$_3$)3032, 2940, 1728, 1473, 1373, 1232, 1179, 1150, 1085cm$^{-1}$ I-461 amorphous
$^1$HNMR(CDCl$_3$) δ 3.78(s, 6H), 5.16(s, 2H), 5.31(d, J=3.6Hz, 1H), 5.72(s, 1H), 6.91(s, 1H), 6.94(s, 1H), 6.99(d, J=8.2Hz, 1H), 7.04(t, J=8.6Hz, 1H), 7.08(dd, J=8.2, 2.1Hz, 1H), 7.22(d, J=2.1Hz, 1H), 7.25(ddd, J=8.6, 1.8, 0.9Hz, 1H), 7.34–7.46(m, 6H)
IR(CHCl$_3$)3577, 3548, 1526, 1495, 1280, 1635cm$^{-1}$ I-462 m.p. 153–155° C.
$^1$HNMR(CDCl$_3$) δ 3.12(s, 3H), 3.26(s, 3H), 3.80(s, 3H), 3.81(s, 3H), 5.18(s, 2H), 6.91(s, 1H), 6.94(s, 1H), 7.12(d, J=8.4Hz, 1H), 7.36–7.50 (m, 8H), 7.59(d, J=1.8Hz, 1H)
IR(CHCl$_3$)1494, 1367, 1212, 1180, 1116, 872, 808cm$^{-1}$

TABLE 94

I-463 m.p. 125–127° C.
$^1$HNMR(CDCl$_3$) δ 1.77(s, 3H), 1.82(s, 3H), 3.23(s, 3H), 3.27(s, 3H), 3.80(s, 3H), 3.82(s, 3H), 4.64(d, J=6.7Hz, 2H), 5.51(t, J=6.7Hz, 1H), 6.91(s, 1H), 6.95(s, 1H), 7.06(d, J=8.7Hz, 1H), 7.37(dd, J=8.7, 1.9Hz, 1H), 7.40–7.47(m, 2H), 7.50(d, J=2.4Hz, 1H), 7.57(d, J=1.9Hz, 1H),
IR(KBr)1523, 1496, 1370, 1213, 1175, 1116, 1035, 977, 832, 807cm$^{-1}$

I-464 m.p.149–151° C.
$^1$HNMR(CDCl$_3$) δ 1.69(s, 3H), 1.74(s, 3H), 2.55(q, J=7.0Hz, 2H), 3.21(s, 3H), 3.26(s, 3H), 3.80(s, 3H), 3.81(s, 3H), 4.07(t, J=7.0Hz, 2H),

TABLE 94-continued

| | |
|---|---|
| | 5.21(t, J=7.0Hz, 1H), 6.91(s, 1H), 6.94(s, 1H), 7.05(d, J=8.4Hz, 1H), 7.37(dd, J=8.4, 2.1Hz, 1H), 7.40–7.47(m, 2H), 7.50(d, J=2.1Hz, 1H), 7.57(d, J=2.1Hz, 1H)<br>IR(KBr)1523, 1495, 1368, 1212, 1176, 1116, 1035, 976, 832, 806cm$^{-1}$ |
| I-465 | m.p. 148–150° C.<br>$^1$HNMR(CDCl$_3$) δ 2.38(s, 3H), 3.11(s, 3H), 3.26(s, 3H), 3.80(s, 3H), 3.81(s, 3H), 5.13(s, 2H), 6.91(s, 1H), 6.94(s, 1H), 7.12(d, J=8.4Hz, 1H), 7.22(d, J=7.8Hz, 2H), 7.35(d, J=7.8Hz, 2H), 7.37(dd, J=8.4, 1.8Hz, 1H), 7.40–7.50(m, 3H), 7.59(d, J=1.8Hz, 1H)<br>IR(KBr)1523, 1490, 1370, 1181, 1115, 971, 868, 806cm$^{-1}$ |
| I-466 | m.p. 109–112° C.<br>$^1$HNMR(CDCl$_3$) δ 1.76(s, 3H), 1.82(s, 3H), 3.79(s, 6H), 4.62(d, J=6.9Hz, 2H), 5.26(d, J=3.9Hz, 1H), 5.52(t, J=6.9Hz, 1H), 5.72(s, 1H), 6.91(s, 1H), 6.93(d, J=8.6Hz, 1H), 6.94(s, 1H), 7.04(t, J=8.7Hz, 1H), 7.07(dd, J=8.6, 2.1Hz, 1H), 7.19(d, J=2.1Hz, 1H), 7.25(ddd, J=8.7, 1.8, 0.9Hz, 1H), 7.37(dd, J=12.0, 1.8Hz, 1H)<br>IR(CHCl$_3$)3578, 3542, 1526, 1495, 1280, 1055, 1035cm$^{-1}$ |

TABLE 95

| | |
|---|---|
| I-467 | amorphous<br>$^1$HNMR(CDCl$_3$) δ 2.39(s, 3H), 3.79(s, 6H), 5.11(s, 2H), 5.40(brs, 1H), 5.73(s, 1H), 6.91(s, 1H), 6.94(s, 1H), 6.99(d, J=8.4Hz, 1H), 7.04(t, J=8.7Hz, 1H), 7.08(dd, J=8.4, 2.1Hz, 1H), 7.21(d, J=2.1Hz, 1H), 7.23(d, J=7.7Hz, 2H), 7.25(ddd, J=8.7, 2.1, 1.2Hz, 1H), 7.34(d, J=7.7Hz, 2H), 7.37(dd, J=11.7, 2.1Hz, 1H)<br>IR(CHCl$_3$)3577, 3545, 1526, 1495, 1280, 1055, 1035, 868cm$^{-1}$ |
| I-468 | amorphous<br>$^1$HNMR(CDCl$_3$) δ 1.69(s, 3H), 1.75(s, 3H), 2.53(q, J=7.0Hz, 2H), 3.78(s, 3H), 3.79(s, 3H), 4.07(t, J=7.2Hz, 2H), 5.22(t, J=7.0Hz, 1H), 5.27(d, J=3.9Hz, 1H), 5.71(s, 1H), 6.91(s, 1H), 6.93(d, J=8.6Hz, 1H), 6.94(s, 1H), 7.04(t, J=8.4Hz, 1H), 7.06(dd, J=8.6, 2.1Hz, 1H), 7.19(d, J=2.1Hz, 1H), 7.25(ddd, J=8.4, 1.9, 1.1Hz, 1H), 7.37(dd, J=12.0, 1.9Hz, 1H)<br>IR(CHCl$_3$)3578, 1526, 1495, 1280, 1055, 1035cm$^{-1}$ |
| I-469 | m.p. 190–191° C.<br>$^1$HNMR(CDCl$_3$) δ 2.38(s, 3H), 3.11(s, 3H), 3.19(s, 3H), 3.80(s, 6H), 5.13(s, 2H), 6.92(s, 1H), 6.94(s, 1H), 7.12(d, J=8.7Hz, 1H), 7.22(d, J=7.8Hz, 1H), 7.32–7.37(m, 4H), 7.49(dd, J=2.1, 8.4Hz, 1H), 7.59(d, J=1.8Hz, 1H), 7.60–7.65(m, 2H)<br>IR(KBr)3600–2800(br), 1521, 1492, 1468, 1386, 1366, 1336, 1292, 1272, 1259, 1202, 1174, 1150, 1113cm$^{-1}$ |
| I-470 | m.p. 147–148° C.<br>$^1$HNMR(CDCl$_3$) δ 2.37(s, 3H), 3.19(s, 3H), 3.79(s, 3H), 3.80(s, 3H), 5.16(s, 2H), 6.92(s, 1H), 6.93(s, 1H), 7.06(t, J=8.7Hz, 1H), 7.20–7.27(m, 3H), 7.32–7.41(m, 5H), 7.60–7.64(m, 2H)<br>IR(KBr)3600–2800(br), 1523, 1492, 1462, 1454, 1379, 1359, 1299, 1278, 1264, 1210, 1175, 1151, 1129, 1054, 1031, 1009cm$^{-1}$ |
| I-471 | m.p. 170–172° C.<br>$^1$HNMR(CDCl$_3$) δ 3.19(s, 3H), 3.24(s, 3H), 3.79(s, 3H), 3.80(s, 3H), 5.12(s, 2H), 6.92(s, 1H), 6.94(s, 1H), 7.11(d, J=8.7Hz, 1H), 7.26–7.30(m, 2H), 7.32–7.37(m, 2H), 7.47(dd, J=2.4, 8.4Hz, 1H), 7.61–7.64(m, 3H), 7.74–7.80(m, 1H), 8.61–8.63(m, 1H)<br>IR(KBr)3600–2800(br), 1522, 1491, 1462, 1361, 1296, 1264, 1212, 1177, 1149, 1115, 1030cm$^{-1}$ |

TABLE 96

| | |
|---|---|
| I-472 | m.p. 174–175° C.<br>$^1$HNMR(CDCl$_3$) δ 3.19(s, 3H), 3.79(s, 3H), 3.80(s, 3H), 5.33(s, 2H), 6.92(s, 1H), 6.93(s, 1H), 7.07(d, J=8.7Hz, 1H), 7.23–7.28(m, 2H), 7.32–7.37(m, 2H), 7.41(dd, J=1.8, 12.6Hz, 1H), 7.60–7.64(m, 3H), 7.73–7.79(m, 1H), 8.60–8.63(m, 1H)<br>IR(KBr)3600–2800(br), 1524, 1491, 1464, 1380, 1361, 1302, 1267, 1209, 1172, 1149, 1130, 1034, 1024, 1008cm$^{-1}$ |
| I-473 | m.p. 118.5–119.5° C.<br>$^1$HNMR(CDCl$_3$) δ 1.77(s, 3H), 1.80(d, J=0.9Hz, 3H), 3.78(s, 3H), 3.79(s, 3H), 4.63(d, J=6.9Hz, 2H), 5.52–5.57(m, 1H), 6.73–6.78(m, 2H), 6.91(s, 1H), 6.93(s, 1H), 7.02(t, J=8.7Hz, 1H), 7.25–7.30(m, 1H), 7.35–7.43(m, 3H)<br>IR(KBr)3600–2800(br), 1625, 1527, 1491, 1461, 1449, 1378, 1298, 1279, 1259, 1207, 1184, 1125, 1055, 1031cm$^{-1}$ |
| I-474 | m.p. 156–158° C.<br>$^1$HNMR(CDCl$_3$) δ 1.77(s, 3H), 1.81(s, 3H), 3.08(s, 3H), 3.80(s, 3H), 3.81(s, 3H), 4.64(d, J=6.6Hz, 2H), 5.52–5.58(m, 1H), 6.43(brs, 1H), 6.93(s, 1H), 6.94(s, 1H), 7.03(t, J=8.4Hz, 1H), 7.26–7.30(m, 3H), 7.37(dd, J=1.8, 12.6Hz, 1H), 7.57–7.61(m, 2H)<br>IR(KBr)3600–2800(br), 1526, 1495, 1463, 1382, 1325, 1300, 1267, 1210, 1156, 1139, 1129, 1054, 1032cm$^{-1}$ |
| I-475 | m.p. 158–160° C.<br>$^1$HNMR(CDCl$_3$) δ 1.77(s, 3H), 1.81(s, 3H), 3.80(s, 6H), 4.64(d, J=6.6Hz, 2H), 4.73(brs, 2H), 5.53–5.57(m, 1H), 6.51(brs, 1H), 6.93(s, 1H), 6.94(s, 1H), 7.03(t, J=8.7Hz, 1H), 7.26–7.31(m, 3H), 7.37(dd, J=2.1, 12.6Hz, 1H), 7.57–7.61(m, 2H)<br>IR(KBr)3600–2800(br), 1527, 1495, 1462, 1395, 1326, 1299, 1264, 1208, 1170, 1130, 1054, 1031cm$^{-1}$ |
| I-476 | m.p. 138–140° C.<br>$^1$HNMR(CDCl$_3$) δ 1.77(s, 3H), 1.81(s, 3H), 2.21(s, 3H), 3.78(s, 3H), 3.80(s, 3H), 4.63(d, J=6.9Hz, 2H), 5.53–5.57(m, 1H), 6.93(s, 1H), 6.94(s, 1H), 7.03(t, J=8.4Hz, 1H), 7.20(brs, 1H), 7.26–7.30(m, 1H), 7.37(dd, J=2.1, 12.6Hz, 1H), 7.56(m, 4H)<br>IR(KBr)3600–2800(br), 1666, 1604, 1527, 1494, 1463, 1448, 1379, 1317, 1299, 1264, 1209, 1130, 1055, 1032cm$^{-1}$ |

TABLE 97

| | |
|---|---|
| I-477 | m.p. 200–202° C.<br>$^1$HNMR(CDCl$_3$ + CD$_3$OD) δ 1.77(s, 3H), 1.81(s, 3H), 3.79(s, 3H), 3.80(s, 3H), 4.64(d, J=6.6Hz, 2H), 5.52–5.57(m, 1H), 6.93(s, 1H), 6.94(s, 1H), 7.03(t, J=9.0Hz, 1H), 7.27–7.30(m, 1H), 7.34–7.41(m, 3H), 7.52–7.55(m, 2H)<br>IR(KBr)3600–2800(br), 2404, 1684, 1660, 1584, 1528, 1493, 1462, 1386, 1301, 1274, 1263, 1209, 1132, 1053, 1029cm$^{-1}$ |
| I-478 | m.p. 195–196.5° C.<br>$^1$HNMR(CDCl$_3$) δ 1.55(s, 9H), 3.78(s, 3H), 3.79(s, 3H), 4.85(s, 1H), 6.75(brs, 1H), 6.88–6.92(m, 2H), 6.92(s, 1H), 6.93(s, 1H), 7.31–7.39(m, 3H), 7.45–7.49(m, 2H), 8.12(t, J=7.5Hz, 1H)<br>IR(KBr)3600–2800(br), 1729, 1590, 1531, 1500, 1464, 1394, 1261, 1240, 1199, 1156, 1055, 1033, 1023cm$^{-1}$ |

TABLE 97-continued

| | |
|---|---|
| I-479 | m.p. 172–174° C.<br>¹HNMR(CDCl₃) δ 1.55(s, 9H), 3.19(s, 3H), 3.79(s, 3H), 3.80(s, 3H), 6.75(d, J=2.1Hz, 1H), 6.92(s, 1H), 6.94(s, 1H), 7.26–7.39(m, 5H), 7.60–7.65(m, 2H)<br>IR(KBr)3600–2800(br), 1728, 1590, 1531, 1513, 1494, 1464, 1391, 1367, 1352, 1240, 1206, 1179, 1145, 1056, 1033, 1024cm⁻¹ |
| I-480 | m.p. 152–153° C.<br>¹HNMR(CDCl₃) δ 1.74(s, 3H), 1.77(s, 3H), 3.18(s, 3H), 3.78(d, J=9.9Hz, 2H), 3.79(s, 6H), 3.93(brs, 1H), 5.35–5.40(m, 1H), 6.75(t, J=8.4Hz, 1H), 6.91(s, 1H), 6.95(s, 1H), 7.24–7.36(m, 4H), 7.60–7.65(m, 2H)<br>IR(KBr)3600–2800(br), 1630, 1530, 1488, 1466, 1380, 1366, 1346, 1259, 1213, 1176, 1149, 1124, 1054, 1027cm⁻¹ |
| I-481 | foam<br>¹HNMR(CDCl₃) δ 2.40(s, 3H), 3.19(s, 3H), 3.77(s, 3H), 3.78(s, 3H), 6.80(t, d=2.4Hz, 1H), 6.90(s, 1H), 6.91(s, 1H), 7.25–7.36(m, 6H), 7.58–7.65(m, 3H), 7.72–7.76(m, 2H)<br>IR(KBr)3600–2800(br), 1522, 1490, 1366, 1342, 1211, 1164, 1151, 1091, 1053, 1030cm⁻¹ |

TABLE 98

| | |
|---|---|
| I-482 | m.p. 201–203° C.<br>¹HNMR(CDCl₃) δ 2.45(s, 3H), 3.20(s, 3H), 3.82(s, 6H), 6.95(s, 1H), 6.98(s, 1H), 7.32–7.48(m, 6H), 7.61–7.66(m, 2H), 7.80–7.84(m, 2H), 8.10(d, J=3.3Hz, 1H), 8.55(d, J=8.4Hz, 1H)<br>IR(KBr)3600–2800(br), 1671, 1592, 1524, 1494, 1388, 1366, 1328, 1265, 1207, 1172, 1150, 1052, 1024cm⁻¹ |
| I-483 | m.p. 132–134° C.<br>¹HNMR(CDCl₃) δ 1.55(s, 9H), 3.00(s, 6H), 3.79(s, 6H), 6.73(d, J=2.4Hz, 1H), 6.81(m, 2H), 6.92(s, 1H), 6.96(s, 1H), 7.32–7.39(m, 2H), 7.48–7.52(m, 2H), 8.11(t, J=8.1Hz, 1H)<br>IR(KBr)3600–2800(br), 1728, 1610, 1591, 1533, 1499, 1459, 1446, 1381, 1365, 1238, 1206, 1159, 1055, 1030cm⁻¹ |
| I-484 | foam<br>¹HNMR(CDCl₃) δ 1.74(s, 3H), 1.77(s, 3H), 3.00(s, 6H), 3.78(d, J=9.6Hz, 1H), 3.78(s, 3H), 3.79(s, 3H), 5.34–5.38(m, 1H), 6.75(t, J=8.4Hz, 1H), 6.92(s, 1H), 6.94(s, 1H), 6.93–6.95(m, 1H), 7.23–7.32(m, 3H), 7.48–7.52(m, 2H)<br>IR(KBr)3600–2800(br), 1625, 1611, 1531, 1494, 1446, 1380, 1340, 1257, 1207, 1123, 1055, 1032cm⁻¹ |
| I-485 | foam<br>¹HNMR(CDCl₃) δ 2.40(s, 3H), 3.00(s, 6H), 3.76(s, 3H), 3.77(s, 3H), 6.70(t, J=2.4Hz, 1H), 6.80(t, J=8.7Hz, 2H), 6.87(s, 1H), 6.94(s, 1H), 7.24–7.33(m, 4H), 7.46–7.50(m, 2H), 7.60(t, J=9.0Hz, 1H), 7.71–7.75(m, 2H)<br>IR(KBr)3600–2800(br), 1609, 1529, 1493, 1446, 1381, 1340, 1208, 1164, 1090, 1054, 1031cm⁻¹ |
| I-486 | m.p. 184–186° C.<br>¹HNMR(CDCl₃) δ 2.45(s, 3H), 3.01(s, 6H), 3.80(s, 3H), 3.81(s, 3H), 6.82(d, J=7.5Hz, 2H), 6.95(s, 1H), 6.98(s, 1H), 7.32(d, J=8.1Hz, 2H), 7.40–7.52(m, 4H), 7.80–7.84(m, 2H), 8.08(d, J=2.7Hz, 1H), 8.52(t, J=8.4Hz, 1H)<br>IR(KBr)3600–2800(br), 1647, 1608, 1530, 1497, 1379, 1365, 1284, 1267, 1206, 1051, 1030cm⁻¹ |

TABLE 99

| | |
|---|---|
| I-487 | foam<br>¹HNMR(CDCl₃) δ 2.36(s, 3H), 3.77(s, 6H), 4.81(brs, 1H), 6.69(dd, J=0.9, 3.6Hz, 1H), 6.88–6.92(m, 2H), 6.94(s, 1H), 6.95(s, 1H), 7.23–7.26(m, 2H), 7.46–7.51(m, 2H), 7.53(dd, J=1.5, 8.4Hz, 1H), 7.59(d, J=3.6Hz, 1H), 7.73(d, J=0.9Hz, 1H), 7.80–7.84(m, 2H), 8.02(d, J=8.4Hz, 1H)<br>IR(KBr)3600–2800(br), 1611, 1594, 1520, 1498, 1459, 1444, 1369, 1259, 1208, 1170, 1129, 1092, 1051, 1028cm⁻¹ |
| I-488 | m.p. 219–220° C.<br>¹HNMR(CDCl₃) δ 2.37(s, 3H), 3.19(s, 3H), 3.78(s, 3H), 3.79(s, 3H), 6.70(dd, J=0.9, 3.6Hz, 1H), 6.94(s, 1H), 6.97(s, 1H), 7.24–7.27(m, 2H), 7.32–7.37(m, 2H), 7.53(dd, J=1.8, 8.7Hz, 1H), 7.60(d, J=3.6Hz, 1H), 7.61–7.66(m, 2H), 7.73(d, J=0.9Hz, 1H), 7.80–7.84(m, 2H), 8.03(d, J=8.7Hz, 1H)<br>IR(KBr)3600–2800(br), 1513, 1494, 1464, 1444, 1373, 1209, 1173, 1155, 1122, 1049cm⁻¹ |
| I-489 | ¹HNMR(CDCl₃) δ 3.79(s, 3H), 3.80(s, 3H), 3.94(s, 3H), 5.17(s, 2H), 5.71(s, 1H), 6.96(s, 1H), 6.97(s, 1H), 6.99(d, J=8.7Hz, 1H), 7.09(d,d, J=8.7&2.4Hz, 1H), 7.22(d, J=2.4Hz, 1H), 7.26(s, 1H), 7.32–7.49(m, 5H), 7.66(d, J=8.7Hz, 2H), 8.09(d, J=8.7Hz, 2H)<br>IR(KBr)3383, 1702, 1606, 1489, 1381, 1291, 1206, 1111, 1032, 1002cm⁻¹ |
| I-490 | ¹HNMR(CDCl₃) δ 3.12(s, 3H), 3.79(s, 3H), 3.81(s, 3H), 3.95(s, 3H), 5.18(s, 2H), 6.96(s, 2H), 7.12(d, J=8.4Hz, 1H), 7.31–7.53(m, 6H), 7.60(d, J=2.1Hz, 1H), 7.65(d, J=8.7Hz, 2H), 8.10(d, J=8.7Hz, 2H)<br>IR(KBr)1720, 1607, 1492, 1362, 1275, 1211, 1112, 1057, 1032cm⁻¹ |
| I-491 | ¹HNMR(CDCl₃) δ 3.12(s, 3H), 3.80(s, 3H), 3.81(s, 3H), 5.18(s, 2H), 6.92(s, 1H), 6.96(s, 1H), 7.13(d, J=8.4Hz, 1H), 7.31–7.52(m, 6H), 7.70(d, J=2.1Hz, 1H), 7.66–7.77(m, 4H)<br>IR(KBr)3433, 1685, 1606, 1509, 1492, 1372, 1318, 1264, 1211, 1183, 1111, 1055, 1031cm⁻¹ |
| I-492 | ¹HNMR(CDCl₃) δ 3.79(s, 3H), 3.80(s, 3H), 5.17(s, 2H), 5.71(s, 1H), 6.91(s, 1H), 6.97(s, 1H), 7.00(d, J=8.4Hz, 1H), 7.08(dd, J=8.4&2.4Hz, 1H), 7.22(d, J=2.4Hz, 1H), 7.32–7.49(m, 5H), 7.70(s, 4H)<br>IR(KBr)3291, 2242, 1607, 1579, 1488, 1384, 1324, 1272, 1209, 1130, 1054, 1034, 1001cm⁻¹ |

TABLE 100

| | |
|---|---|
| I-493 | ¹HNMR(CDCl₃) δ 3.12(s, 3H), 3.80(s, 3H), 3.81(s, 3H), 5.18(s, 2H), 6.92(s, 1H), 6.96(s, 1H), 7.12(d, J=8.4Hz, 1H), 7.31–7.72(m, 6H), 7.60(d, J=1.8Hz, 1H), 7.65–7.74(m, 4H)<br>IR(KBr)2223, 1604, 1490, 1363, 1296, 1264, 1213, 1172, 1117, 1055, 1036, 1026cm⁻¹ |
| I-494 | ¹HNMR(CDCl₃) δ 1.77(s, 3H), 1.81(s, 3H), 3.23(s, 3H), 3.80(s, 3H), 3.81(s, 3H), 3.95(s, 3H), 4.64(d, J=6.6Hz, 2H), 5.51(t, J=6.6Hz, 1H), 6.96(s, 2H), 7.06(d, J=8.7Hz, 1H), 7.50(d,d, J=8.7&2.1Hz, 1H), 7.59(d, J=2.1Hz, 1H), 7.65(d, J=8.7Hz, 2H), 8.10(d, J=8.7Hz, 2H)<br>IR(KBr)1720, 1608, 1508, 1492, 1384, 1357, 1273, 1179, 1110, 1026, 1019cm⁻¹ |
| I-495 | ¹HNMR(CDCl₃) δ 2.38(s, 3H), 3.12(s, 3H), 3.80(s, 6H), 3.81(s, 3H), 3.95(s, 3H), 5.14(s, 2H), 6.96(s, 2H), 7.13(d, J=8.4Hz, 1H), 7.21(d, J=7.8Hz, 2H), 7.35(d, J=7.8Hz, 2H), 7.49(d,d, J=8.4&1.8Hz, 1H), 7.60(d, J=1.8Hz, 1H), 7.65(d, J=8.7Hz, 2H), 8.10(d, J=8.7Hz, 2H)<br>IR(KBr)1697, 1607, 1492, 1364, 1286, 1263, 1213, 1178, 11115, 1057, 1030cm⁻¹ |

TABLE 100-continued

| | |
|---|---|
| I-496 | IR(KBr)1730, 1701, 1610, 1515, 1465, 1359, 1238, 1186, 1116, 1082, 1064, 1016cm$^{-1}$ |
| I-497 | $^1$HNMR(CDCl$_3$) δ 1.75(s, 3H), 1.80(s, 3H), 2.89(s, 6H), 3.21(s, 3H), 3.44(s, 3H), 3.68(s, 3H), 3.77(s, 1H), 4.61(d, J=8.4Hz, 2H), 5.49(t, J= 8.4Hz, 1H), 6.92(s, 1H), 7.01(d, J=8.4Hz, 1H), 7.25–7.28(m, 3H), 7.33(d, J=2.1Hz, 1H), 7.52(dd, J=8.4&1.8Hz, 1H), 7.66(d, J=2.4Hz, 1H) <br> IR(KBr)1727, 1598, 1515, 1467, 1360, 1295, 1258, 1241, 1116, 1084cm$^{-1}$ |
| I-498 | $^1$HNMR(CDCl$_3$) δ 2.38(s, 3H), 2.89(s, 6H), 3.10(s, 3H), 3.44(s, 3H), 3.66(s, 3H), 3.77(s, 3H), 5.11(s, 3H), 6.93(s, 1H), 7.06–7.15(m, 2H), 7.17–7.29(m, 4H), 7.31–7.37(m, 3H), 7.53(d.d, J=8.7&1.8Hz, 1H), 7.66(dJ=1.8Hz, 1H) <br> IR(KBr)1732, 1701, 1598, 1518, 1466, 1352, 1294, 1121, 1085, 1060, 1015cm$^{-1}$ |
| I-499 | $^1$HNMR(CDCl$_3$) δ 2.88(s, 6H), 3.44(s, 3H), 3.64(s, 3H), 3.77(s, 3H), 5.17(s, 2H), 5.65(s, 1H), 6.84(dd, J=8.1&2.1Hz, 1H), 6.92(s, 1H), 6.95 (d, J=8.1Hz, 1H), 7.01(d, J=2.1Hz, 1H), 7.12(d, J=8.4Hz, 1H), 7.31–7.46(m, 6H), 7.53(d.d, J=8.4&1.8Hz, 1H), 7.66(d, J=1.8Hz, 1H) <br> IR(KBr)3526, 3434, 1732, 1598, 1515, 1460, 1344, 1260, 1240, 1222, 1061, 1013cm$^{-1}$ |

TABLE 101

| | |
|---|---|
| I-500 | $^1$HNMR(CDCl$_3$) δ 2.60(s, 3H), 3.43(s, 3H), 3.72(s, 3H), 3.75(s, 3H), 5.17(s, 2H), 5.67(s, 1H), 6.77(s, 1H), 6.94(dd, J=8.4&1.8Hz, 1H), 7.02 (d, J=8.4Hz, 1H), 7.06(d, J=1.8Hz, 1H), 7.32–7.50(m, 7H), 7.53–7.62(m, 1H), 7.94(d, J=7.8Hz, 1H) <br> IR(KBr)1732, 1719, 1585, 1521, 1481, 1403, 1352, 1289, 1253, 1225, 1172, 1073, 1012cm$^{-1}$ |
| I-501 | $^1$HNMR(CDCl$_3$) δ 2.73(s, 3H), 3.12(s, 3H), 3.43(s, 3H), 3.72(s, 3H), 3.76(s, 3H), 5.19(s, 2H), 6.78(s, 1H), 7.15(d, J=8.4Hz, 1H), 7.31–7.63 (m, 10H), 9.96(d, J=6.6Hz, 1H) <br> IR(KBr)1726, 1609, 1520, 1480, 1400, 1371, 1294, 1262, 1179, 1075, 1009cm$^{-1}$ |
| I-502 | $^1$HNMR(CDCl$_3$) δ 1.78(s, 3H), 1.81(s, 3H), 3.22(s, 3H), 3.48(s, 3H), 3.71(s, 3H), 3.77(s, 3H), 3.82(s, 3H), 4.66(d, J=6.9Hz, 2H), 5.56(t, J=6.9Hz, 1H), 6.62(s, 1H), 6.70(s, 1H), 7.11(s, 1H), 7.38(d, J=8.7Hz, 1H), 7.69(d, J=8.7Hz, 1H) <br> IR(KBr)1699, 1607, 1587, 1516, 1468, 1354, 1216, 1152, 1067, 1044, 1004cm$^{-1}$ |
| I-503 | $^1$HNMR(CDCl$_3$) δ 1.78(s, 3H), 1.81(s, 3H), 3.21(s, 3H), 3.48(s, 3H), 3.72(s, 3H), 3.74(s, 3H), 3.82(s, 3H), 4.33(d, J=11.7Hz, 1H), 4.54(d, J=11.7Hz, 1H), 4.65(d, J=8.4Hz, 1H), 5.57(t, J=8.4Hz, 1H), 6.68(s, 1H), 6.69(s, 1H), 6.89(s, 1H), 7.38(d, J=8.7Hz, 2H), 7.73(d, J=8.7Hz, 2H) <br> IR(KBr)3530, 1609, 1515, 1467, 1356, 1214, 1174, 1151, 1075, 1039, 1004cm$^{-1}$ |
| I-504 | $^1$HNMR(CDCl$_3$) δ 1.77(s, 3H), 1.80(s, 3H), 3.22(s, 3H), 3.45(s, 3H), 3.73(s, 3H), 3.77(s, 3H), 3.81(s, 3H), 4.62(d, J=6.9Hz, 2H), 5.55(t, J=6.9Hz, 1H), 6.64(s, 1H), 6.77(s, 1H), 6.97(s, 1H), 7.39(d, J=8.7Hz, 2H), 7.72(d, J=8.7Hz, 2H) <br> IR(KBr)3431, 1735, 1706, 1609, 1514, 1474, 1367, 1206, 1176, 1150, 1055, 1039cm$^{-1}$ |
| I-505 | $^1$HNMR(CDCl$_3$) δ 1.77(s, 3H), 1.80(s, 3H), 2.94(broad, 1H), 3.47(s, 3H), 3.72(s, 3H), 3.73(s, 3H), 3.81(s, 3H), 4.32(s, 1H), 4.36(s, 1H), 4.65 (d, J=6.6Hz, 2H), 5.34(s, 1H), 5.57(t, J=6.6Hz, 1H), 6.69(s, 1H), 6.70(s, 1H), 6.89(s, 1H), 6.91(d, J=8.1Hz, 2H), 7.55(d, J=8.1Hz, 2H) <br> IR(KBr)3466, 1610, 1517, 1475, 1463, 1386, 1265, 1215, 1170, 1147, 1075, 1042, 1007cm$^{-1}$ |
| I-506 | $^1$HNMR(CDCl$_3$) δ 1.76(s, 3H), 1.79(s, 3H), 3.44(s, 3H), 3.74(s, 3H), 3.76(s, 3H), 3.80(s, 3H), 4.63(d, J=7.2Hz, 2H), 5.30(s, 1H), 5.49–5.60 (m, 1H), 6.63(s, 1H), 6.78(s, 1H), 6.94(d, J=8.7Hz, 2H), 6.97(s, 1H), 7.54(d, J=8.7Hz, 2H) <br> IR(KBr)3382, 1726, 1699, 1611, 1519, 1470, 1206, 1174, 1143, 1074, 1056, 997cm$^{-1}$ |

TABLE 102

| | |
|---|---|
| I-507 | $^1$HNMR(CDCl$_3$) δ 1.77(s, 3H), 1.79(s, 3H), 3.41(s, 3H), 3.60(s, 3H), 3.74(s, 3H), 3.77(s, 3H), 3.81(s, 3H), 4.63(d, J=6.9Hz, 2H), 4.74–5.02(broad, 1H), 5.52–5.60(m, 1H), 6.63(s, 1H), 6.75(s, 1H), 6.91(d, J=8.7Hz, 2H), 6.94(s, 1H), 7.54(d, J=8.7Hz, 2H) <br> IR(KBr)3423, 1734, 1612, 1520, 1475, 1441, 1395, 1337, 1267, 1215, 1173, 1140, 1017cm$^{-1}$ |
| I-508 | $^1$HNMR(CDCl$_3$) δ 3.21(s, 3H), 3.45(s, 3H), 3.73(s, 3H), 4.41–4.62(m, 2H), 5.16(s, 2H), 5.71(s, 1H), 6.79(d.d, J=8.1&2.1Hz, 1H), 6.84(s, 1H), 6.92(d, J=2.1Hz, 1H), 7.01(d, J=8.1Hz, 1H), 7.32–7.50(m, 7H), 7.71(d, J=8.4Hz, 2H) <br> IR(KBr)3496, 3255, 1607, 1590, 1528, 1473, 1464, 1358, 1247, 1147, 1071, 1017cm$^{-1}$ |
| I-509 | $^1$HNMR(CDCl$_3$) δ 3.21(s, 3H), 3.45(s, 3H), 3.73(s, 3H), 3.89(s, 3H), 4.51(d, J=6.3Hz, 2H), 5.20(s, 2H), 6.80(d.d, J=8.1&2.1Hz, 1H), 6.85 (s, 1H), 6.89(d, J=2.1Hz, 1H), 6.97(d, J=8.1Hz, 1H), 7.29–7.51(m, 7H), 7.71(d, J=8.7Hz, 2H) <br> IR(KBr)3412, 1603, 1586, 1515, 1464, 1364, 1242, 1175, 1151, 1081, 1020, 1006cm$^{-1}$ |
| I-510 | $^1$HNMR(CDCl$_3$) δ 1.76(s, 3H), 1.80(s, 3H), 3.22(s, 3H), 3.45(s, 3H), 3.73(s, 3H), 3.87(s, 3H), 4.52(s, 2H), 4.64(d, J=6.6Hz, 2H), 5.57(t, J=6.6Hz, 1H), 6.83(dd, J=7.5&1.2Hz, 1H), 6.86(d, J=1.2Hz, 1H), 6.96(d, J=7.5Hz, 1H) <br> IR(KBr)3433, 1598, 1579, 1517, 1469, 1372, 1244, 1221, 1174, 1149, 1072, 1017cm$^{-1}$ |
| I-511 | $^1$HNMR(CDCl$_3$) δ 2.36(s, 3H), 3.21(s, 3H), 3.45(s, 3H), 3.72(s, 3H), 3.88(s, 3H), 4.50(s, 2H), 5.16(s, 2H), 6.80(dd, J=8.1&2.1Hz, 1H), 6.85 (s, 1H), 6.88(d, J=2.1Hz, 1H), 6.97(d, J=8.1Hz, 1H), 7.20(d, J=8.4Hz, 2H), 7.33–7.42(m, 4H), 7.71(d, J=8.4Hz, 2H) <br> IR(KBr)3502, 1604, 1510, 1465, 1383, 1360, 1266, 1239, 1227, 1147, 1071, 1008cm$^{-1}$ |
| I-512 | $^1$HNMR(CDCl$_3$) δ 3.45(s, 3H), 3.72(s, 3H), 3.89(s, 3H), 4.48(s, 2H), 5.20(s, 2H), 6.81(dd, J=8.1&2.1Hz, 1H), 6.86(s, 1H), 6.88–6.99 (m, 4H), 7.27–7.43(m, 3H), 7.46–7.54(m, 4H) <br> IR(KBr)3528, 1610, 1591, 1517, 1474, 1461, 1438, 1388, 1263, 1239, 1173, 1140, 1017cm$^{-1}$ |
| I-513 | $^1$HNMR(CDCl$_3$) δ 1.75(s, 3H), 1.79(s, 3H), 2.47(broads, 1H), 3.45(s, 3H), 3.73(s, 3H), 3.86(s, 3H), 4.52(s, 2H), 4.63(d, J=6.6Hz, 2H), 5.16 (s, 1H), 5.56(d, J=6.6Hz, 1H), 6.82–6.97(m, 6H), 7.53(d, J=9.0Hz, 2H) <br> IR(KBr)3477, 3246, 1609, 1586, 1518, 1464, 1439, 1387, 1266, 1240, 1221, 1173, 1141, 1079, 1011, 1002cm$^{-1}$ |

TABLE 103

| | |
|---|---|
| I-514 | $^1$HNMR(CDCl$_3$) δ 2.36(s, 3H), 2.48(broad, 1H), 3.44(s, 3H), 3.72(s, 3H), 3.88(s, 3H), 4.50(s, 2H), 5.16(s, 3H), 6.76–6.98(m, 6H), 7.19(d, J=7.8Hz, 2H), 7.36(d, J=7.8Hz, 2H), 7.52(d, J=8.7Hz, 2H) <br> IR(KBr)3544, 3239, 1614, 1593, 1519, 1463, 1386, 1266, 1240, 1218, 1173, 1139, 1074, 1010cm$^{-1}$ |
| I-515 | m.p. 159–160° C. <br> $^1$HNMR(CDCl$_3$) δ 3.19(s, 3H), 3.34(s, 3H), 3.79(s, 3H), 3.80(s, 3H), 5.18(ABq, J=12.3Hz, 2H), 6.92(s, 1H), 6.93(s, 1H), 7.08(d, J=8.7Hz, 1H), 7.33–7.64(m, 11H) <br> IR(KBr)3433, 2937, 1694, 1520, 1492, 1369, 1288, 1243, 1211, 1176, 1150, 1100cm$^{-1}$ |
| I-516 | $^1$HNMR(CDCl$_3$) δ 2.91(s, 3H), 3.777(s, 3H), 3.783(s, 3H), 4.85(brs, 1H), 5.12(s, 2H), 6.87–7.00(m, 7H), 7.32–7.50(m, 7H) <br> IR(KBr)3432, 2938, 1609, 1590, 1525, 1494, 1380, 1254, 1207, 1174, 1152, 1058, 1031cm$^{-1}$ |

TABLE 103-continued

I-517 m.p. 213–215° C.
$^1$HNMR(CDCl$_3$) δ 2.99(s, 3H), 3.779(s, 3H), 3.804(s, 3H), 4.86(brs, 1H), 5.16(s, 2H), 6.83(brs, 1H), 6.93(s, 1H), 6.94(s, 1H), 7.06(d, J=8.7Hz, 1H), 7.35(dd, J=2.1, 8.7Hz, 1H), 7.41–7.49(m, 7H), 7.81(d, J=2.1Hz, 1H)
IR(KBr)3409, 3374, 1610, 1525, 1491, 1371, 1321, 1251, 1208, 1145, 1120, 1037cm$^{-1}$ I-518 powder
$^1$HNMR(CDCl$_3$) δ 1.75(s, 3H), 1.81(s, 3H), 2.84(s, 3H), 3.21(s, 3H), 3.22(s, 3H), 3.55(s, 3H), 3.79(s, 3H), 3.93(s, 3H), 4.67(d, J=7.2Hz, 2H), 5.59(m, 1H), 6.85(s, 1H), 7.36–7.42(m, 2H), 7.62(d, J=2.1Hz, 1H), 7.65–7.70(m, 2H), 7.86(d, J=2.1Hz, 1H)
IR(CHCl$_3$)3026, 2940, 1728, 1510, 1473, 1373, 1179, 1150, 1086cm$^{-1}$ I-519 powder
$^1$HNMR(CDCl$_3$) δ 1.69(s, 3H), 1.74(s, 3H), 2.52–2.61(m, 2H), 2.86(s, 3H), 3.20(s, 3H), 3.21(s, 3H), 3.55(s, 3H), 3.79(s, 3H), 3.93(s, 3H), 4.21(t, J=6.9Hz, 2H), 5.26(m, 1H), 6.86(s, 1H), 7.36–7.42(m, 2H), 7.62(d, J=2.1Hz, 1H), 7.65–7.70(m, 2H), 7.86(d, J=2.1Hz, 1H)
IR(CHCl$_3$)3024, 2939, 1729, 1511, 1475, 1447, 1373, 1179, 1150, 1085cm$^{-1}$

TABLE 104

I-520 powder
$^1$HNMR(CDCl$_3$) δ 2.84(s, 3H), 3.21(s, 3H), 3.22(s, 3H), 3.56(s, 3H), 3.81(s, 3H), 3.88(s, 3H), 5.30(s, 2H), 6.86(s, 1H), 7.26–7.32(m, 1H), 7.37–7.42(m, 2H), 7.65–7.72(m, 4H), 7.76–7.83(m, 1H), 7.92(d, J=2.1Hz, 1H), 8.60–8.63(m, 1H)
IR(KBr)3434, 3019, 2940, 1730, 1511, 1474, 1367, 1178, 1151, 1082cm$^{-1}$ I-521 powder
$^1$HNMR(CDCl$_3$ + CD$_3$OD) δ 1.69(s, 3H), 1.77(s, 3H), 2.51–2.58(m, 2H), 3.43(s, 3H), 3.73(s, 3H), 4.23(t, J=6.6Hz, 2H), 6.44(s, 1H), 6.89–6.95(m, 2H), 7.24(d, J=1.8Hz, 1H), 7.46–7.52(m, 2H), 7.65–7.67(m, 1H)
IR(KBr)3434, 2934, 1716, 1611, 1402, 1226, 1116, 1082, 1027cm$^{-1}$ I-522 m.p. 240–243° C.
$^1$HNMR(CDCl$_3$ + CD$_3$OD) δ 3.44(s, 3H), 3.75(s, 3H), 5.31(s, 2H), 6.46(s, 1H), 6.89–6.95(m, 2H), 7.30–7.31(m, 1H), 7.35–7.42(m, 2H), 7.47–7.53(m, 2H), 7.56(d, J=2.4Hz, 1H), 7.79–7.86(m, 1H), 8.65–8.68(m, 1H)
IR(KBr)3411, 2937, 1683, 1611, 1521, 1406, 1230, 1115, 1082, 1026cm$^{-1}$ I-523 m.p. 136–137° C.
$^1$HNMR(CDCl$_3$) δ 2.25(s, 3H), 2.29(s, 3H), 3.12(s, 3H), 3.20(s, 3H), 5.18(s, 2H), 7.11(s, 1H), 7.14(s, 1H), 7.23–7.51(m, 12H)
IR(KBr)1518, 1488, 1357, 1263, 1170, 1150, 1110, 970, 873, 848, 809cm$^{-1}$ I-524 m.p. 121–122° C.
$^1$HNMR(CDCl$_3$) δ 1.77(s, 3H), 1.82(s, 3H), 2.25(s, 3H), 2.29(s, 3H), 3.20(s, 3H), 3.23(s, 3H), 4.64(d, J=6.6Hz, 2H), 5.52(t, J=6.6Hz, 1H), 7.06(d, J=8.4Hz, 1H), 7.11(s, 1H), 7.14(s, 1H), 7.24(d, J=2.1Hz, 1H), 7.31–7.45(m, 5H)
IR(KBr)1518, 1487, 1363, 1170, 1150, 1108, 970, 869, 848, 808cm$^{-1}$ I-525 m.p. 149–151° C.
$^1$HNMR(CDCl$_3$) δ 1.77(s, 3H), 1.83(d, J=0.6Hz, 3H), 2.26(s, 3H), 2.28(s, 3H), 4.62(d, J=6.9Hz, 2H), 4.80(s, 1H), 5.53(m, 1H), 5.72(s, 1H), 6.82(dd, J=2.1, 8.4Hz, 1H), 6.85–6.94(m, 3H), 6.96(d, J=2.1Hz, 1H), 7.10(s, 1H), 7.12(s, 1H), 7.21–7.28(m, 2H)
IR(KBr)3521, 3395, 1612, 1584, 1522, 1490, 1457, 1285, 1263, 1242, 1200, 1170, 1125, 1014, 834cm$^{-1}$

TABLE 105

I-526 foam
$^1$HNMR(CDCl$_3$) δ 2.43(s, 3H), 2.76(s, 3H), 2.90(s, 3H), 3.22(s, 3H), 3.56(s, 3H), 3.80(s, 3H), 5.30(s, 2H), 6.28(t, J=3.3Hz, 1H), 6.42(dd, J=3.3, 1.6Hz, 1H), 6.85(s, 1H), 7.12, (d, J=8.4Hz, 1H), 7.32(d, J=8.7Hz, 2H), 7.34–7.37(m, 2H), 7.39(d, J=8.7Hz, 2H), 7.40(d, J=1.8Hz, 1H), 7.69(d, J=8.7Hz, 2H), 7.78(d, J=8.7Hz, 2H)
IR(Nujol)1608, 1597, 1519, 1480, 1464, 1176, 1152, 1087, 972, 875, 817, 798cm$^{-1}$ I-527 foam
$^1$HNMR(CDCl$_3$) δ 2.96(s, 3H), 3.21(s, 3H), 3.37(s, 3H), 3.52(s, 3H), 3.77(s, 3H), 5.58(s, 2H), 6.84(s, 1H), 7.19(d, J=8.4Hz, 1H), 7.24–7.28(m, 4H), 7.31, (dd, J=8.4, 1.8Hz, 1H), 7.33(d, J=1.8Hz, 1H), 7.38(d, J=8.7Hz, 2H), 7.67(d, J=8.7Hz, 2H)
IR(Nujol)1664, 1609, 1519, 1480, 1457, 1176, 1151, 1079, 970, 947, 876, 798, 748cm$^{-1}$ I-528 foam
$^1$HNMR(CDCl$_3$) δ 2.73(s, 3H), 2.94(s, 3H), 3.21(s, 3H), 3.33(t, J=6.3Hz, 2H), 3.55(s, 3H), 3.77(s, 3H), 4.55(t, J=6.3Hz, 2H), 6.83(s, 1H), 7.14(d, J=8.1Hz, 1H), 7.18(brdd, J=7.8, 5.1Hz, 1H), 7.33(brd, J=7.8Hz, 1H), 7.35(dd, J=8.1, 1.8Hz, 1H), 7.37(d, J=1.8Hz, 1H), 7.38(d, J=8.7Hz, 2H), 7.65(m, 1H), 7.67(d, J=8.7Hz, 2H), 8.56(brd, J=5.1Hz, 1H)
IR(Nujol)1608, 1593, 1520, 1479, 1466, 1177, 1151, 1079, 970, 872, 816, 798cm$^{-1}$ I-529 m.p. 203–205° C.
HNMR(DMSO-d$_6$) δ 2.42(s, 3H), 2.80(s, 3H), 3.45(s, 3H), 3.51(s, 3H), 3.56(s, 3H), 3.78(s, 3H), 5.36(s, 2H), 7.07(s, 1H), 7.23(s, 1H), 7.26–7.28(m, 3H), 7.48, (d, J=8.7Hz, 2H), 7.74(d, J=8.7Hz, 2H)
IR(Nujol)1599, 1518, 1480, 1466, 1176, 1081, 1013, 976, 870, 830, 797, 755cm$^{-1}$ I-530 foam
$^1$HNMR(CD$_3$OD) δ 3.38(s, 3H), 3.68(s, 3H), 5.41(s, 2H), 6.44(s, 1H), 6.82(dd, J=8.4, 2.1Hz, 1H), 6.85(d, J=8.7Hz, 2H), 6.93(d, J=2.1Hz, 1H), 7.06(d, J=8.4Hz, 1H), 7.27(m, 2H), 7.46(d, J=8.7Hz, 2H), 7.60(m, 2H)
IR(Nujol)3304, 161, 1590, 1522, 1488, 1458, 1254, 1115, 1074, 1046, 1014, 942, 825, 745cm$^{-1}$

TABLE 106

I-531 m.p. 159–162° C.
$^1$HNMR(DMSO-d$_6$) δ 2.92(s, 3H), 3.41(s, 3H), 3.45(s, 3H), 3.52(s, 3H), 3.79(s, 3H), 5.33(s, 2H), 7.09(s, 1H), 6.82–7.45(m, 3H), 7.49(d, J=9.0Hz, 2H), 7.75(d, J=9.0Hz, 2H)
IR(Nujol)1604, 1519, 1481, 1469, 1235, 1171, 1154, 1085, 1012, 967, 874, 849, 798cm$^{-1}$ I-532 m.p. 214–216° C.
$^1$HNMR(DMSO-d$_6$) δ 2.84(s, 3H), 3.42(s, 3H), 3.45(s, 3H), 3.52(s, 3H), 3.73(s, 3H), 3.79(s, 3H), 4.99(s, 2H), 7.08(s, 1H), 7.24(dJ=9.3Hz, TABLE 106-continued

| | |
|---|---|
| | 1H), 7.29(dd, J=9.3, 1.8Hz, 1H), 7.30(d, J=1.8Hz, 1H), 7.48(d, J=8.7Hz, 2H), 7.74(d, J=8.7Hz, 2H)<br>IR(Nujol)1767, 1606, 1521, 1481, 1463, 1216, 1175, 1151, 1080, 1013, 977, 946, 878, 821, 798cm$^{-1}$ |
| I-533 | m.p. 225–227° C.<br>$^1$HNMR(DMSO-d$_6$) δ 2.86(s, 3H), 3.45(s, 3H), 3.46(s, 3H), 3.52(s, 3H), 3.78(s, 3H), 4.46(s, 2H), 7.08(s, 1H), 7.20(d, J=8.4Hz, 1H), 7.28–7.32 (m, 2H), 7.48(d, J=8.7Hz, 2H), 7.74(d, J=8.7Hz, 2H)<br>IR(Nujol)3340, 1677, 1619, 1519, 1477, 1463, 1443, 1176, 1150, 1088, 971, 871, 829, 794cm$^{-1}$ |
| I-534 | foam<br>$^1$HNMR(DMSO-d$_6$) δ 2.96(s, 3H), 3.45(s, 3H), 3.47(s, 3H), 3.52(s, 3H), 3.79(s, 3H), 4.64(s, 2H), 7.08(s, 1H), 7.18(d, J=8.4Hz, 1H), 7.31 (dd, J=8.4, 1.8Hz, 1H), 7.34(d, J=1.8Hz, 1H), 7.48(d, J=8.7Hz, 2H), 7.74(d, J=8.7Hz, 2H)<br>IR(Nujol)3464, 3362, 1693, 1606, 1520, 1481, 1176, 1151, 1080, 876, 822, 799cm$^{-1}$ |
| I-535 | m.p. 163–165° C.<br>$^1$HNMR(CDCl$_3$) δ 2.73(s, 3H), 3.16(s, 3H), 3.21(s, 3H), 3.55(s, 3H), 3.78(s, 3H), 4.85(ddd, J=1.5, 1.5, 5.4Hz, 2H), 5.25(s, 2H), 5.31, (dd d, J=1.5, 3.0, 10.5Hz, 1H), 5.43(ddd, J=1.5, 3.0, 17.1Hz, 1H), 6.05(ddd, J=5.4, 10.5, 17.1Hz, 1H), 6.84(s, 1H), 7.11(d, J=8.7Hz, 1H), 7.34 (dd, J=2.1, 8.7Hz, 1H), 7.38(d, J=8.4Hz, 2H), 7.41(d, J=2.1Hz, 1H), 7.56(d, J=8.4Hz, 2H), 7.67(d, J=8.4Hz, 2H), 8.11(d, J=8.4Hz, 2H)<br>IR(KBr)1718, 1612, 1519, 1481, 1365, 1273, 1177, 1151, 1119, 1080, 1015, 969, 876cm$^{-1}$ |

TABLE 107

| | |
|---|---|
| I-536 | m.p. 115–117° C.<br>$^1$HNMR(CDCl$_3$) δ 2.68(s, 3H), 3.13(s, 3H), 3.21(s, 3H), 3.55(s, 3H), 3.68(s, 2H), 3.78(s, 3H), 4.61(ddd, J=1.5, 1.5, 5.7Hz, 2H), 5.17(s, 2H), 5.23, (ddd, J=1.5, 3.0, 10.5,Hz, 1H), 5.28(ddd, J=1.5, 3.0, 16.8Hz, 1H), 5.91(ddd, J=5.7, 10.5, 16.8Hz, 1H), 6.84(s, 1H), 7.13(d, J=8.4Hz, 1H), 7.33(d, J=8.1Hz, 2H), 7.34(dd, J=2.1, 8.4Hz, 1H), 7.38(d, J=8.4Hz, 2H), 7.40(d, J=2.1Hz, 1H), 7.42(d, J=8.1Hz, 2H), 7.68(d, J=8.4Hz, 2H)<br>IR(KBr)1734, 1609, 1520, 1481, 1365, 1236, 1177, 1151, 1119, 1079, 970, 876, 797cm$^{-1}$ |
| I-537 | m.p. 227–229° C.<br>$^1$HNMR(CDCl$_3$) δ 2.73(s, 3H), 3.16(s, 3H), 3.21(s, 3H), 3.54(s, 3H), 3.77(s, 3H), 5.26(s, 2H), 6.83(s, 1H), 7.11(d, J=12.3Hz, 2H), 7.32(s, 1H), 7.37(d, J=12.3Hz, 2H), 7.41(s, 1H), 7.57(d, J=12.3Hz, 1H), 7.66(d, J=12.3Hz, 2H), 8.13(d, J=12.3Hz, 2H)<br>IR(KBr)3430, 1694, 1612, 1519, 1481, 1365, 1177, 1151, 1079, 875, 798cm$^{-1}$ |
| I-538 | m.p. 149–151° C.<br>$^1$HNMR(CDCl$_3$) δ 2.66(s, 3H), 3.13(s, 3H), 3.21(s, 3H), 3.55(s, 3H), 3.68(s, 2H), 3.77(s, 3H), 5.17(s, 2H), 6.84(s, 1H), 7.13(d, J=8.4Hz, 1H), 7.30–7.55(m, 4H), 7.38(d, J=8.4Hz, 2H), 7.67(d, J=8.4Hz, 2H), 7.67(m, 2H)<br>IR(KBr)3423, 1716, 1610, 1519, 1481, 1365, 1235, 1177, 1151, 1119, 1080, 876, 798cm$^{-1}$ |
| I-539 | m.p. 144–146° C.<br>$^1$HNMR(CDCl$_3$) δ 2.32(s, 3H), 2.69(s, 3H), 3.14(s, 3H), 3.21(s, 3H), 3.56(s, 3H), 3.78(s, 3H), 5.18(s, 2H), 6.84(s, 1H), 7.14(d, J=8.7Hz, 2H), 7.15(d, J=8.4Hz, 1H), 7.34(dd, J=2.1, 8.4Hz, 1H), 7.38(d, J=8.4Hz, 2H), 7.40(d, J=2.1Hz, 1H), 7.48(d, J=8.7Hz, 2H), 7.67(d, J=8.4Hz, 2H)<br>IR(KBr)1760, 1519, 1481, 1365, 1177, 1151, 1119, 1079, 876, 797cm$^{-1}$ |
| I-540 | m.p. 228–231° C.<br>$^1$HNMR(CDCl$_3$) δ 2.81(s, 3H), 3.20(s, 3H), 3.21(s, 3H), 3.55(s, 3H), 3.78(s, 3H), 5.30(s, 2H), 6.85(s, 1H), 7.11(d, J=8.4Hz, 1H), 7.35(dd, J=2.1, 8.4Hz, 1H), 7.39(d, J=8.4Hz, 2H), 7.41(d, J=2.1Hz, 1H), 7.67(d, J=8.4Hz, 2H), 7.69(d, J=8.7Hz, 2H), 8.28(d, J=8.7Hz, 2H)<br>IR(KBr)1608, 1521, 1481, 1361, 1179, 1148, 1080, 880, 799cm$^{-1}$ |

TABLE 108

| | |
|---|---|
| I-541 | m.p. 153–156° C.<br>$^1$HNMR(CDCl$_3$) δ 1.53(s, 9H), 2.69(s, 3H), 3.15(s, 3H), 3.21(s, 3H), 3.55(s, 3H), 3.78(s, 3H), 5.19(s, 2H), 6.84(s, 1H), 7.10(dd, J=7.5, 7.5Hz, 1H), 7.17(d, J=7.5Hz, 1H), 7.23(d, J=8.4Hz, 1H), 7.26(dd, J=7.5, 7.5Hz, 1H), 7.33(d, J=7.5Hz, 1H), 7.37(dd, J=2.1, 8.4Hz, 1H), 7.38 (d, J=8.4Hz, 2H), 7.40(d, J=2.1Hz, 1H), 7.67(d, J=8.4Hz, 2H)<br>IR(KBr)3405, 1724, 1519, 1480, 1366, 1236, 1177, 1153, 1080, 970, 875, 798cm$^{-1}$ |
| I-542 | m.p. 178–182° C.<br>$^1$HNMR(CDCl$_3$) δ 2.70(s, 3H), 3.15(s, 3H), 3.21(s, 3H), 3.55(s, 3H), 3.78(s, 3H), 5.14(s, 2H), 6.76(m, 2H), 6.84(s, 1H), 7.19(m, 2H), 7.26 (d, J=8.7Hz, 1H), 7.37(d, J=2.7Hz, 1H), 7.36(dd, J=2.7, 8.7Hz, 1H), 7.38(d, J=8.7Hz, 2H), 7.68(d, J=8.7Hz, 2H)<br>IR(KBr)3448, 1627, 1608, 1519, 1497, 1364, 1177, 1151, 1079, 971, 876, 798cm$^{-1}$ |
| I-543 | m.p. 187–189° C.<br>$^1$HNMR(CDCl$_3$) δ 2.38(s, 3H), 3.39(s, 3H), 3.45(s, 3H), 5.11–5.14(m, 3H), 5.89(s, 1H), 6.33(s, 1H), 6.88–6.94(m, 2H), 7.20–7.36(m, 6H), 7.43(d, J=2.1Hz, 1H), 7.76(d, J=0.6Hz, 1H)<br>IR(KBr)3414, 2942, 1613, 1534, 1469, 1355, 1266, 1172, 1092, 1030cm$^{-1}$ |
| I-544 | m.p. 207–215° C.(dec.)<br>$^1$HNMR(d6-DMSO) δ 2.37(s, 3H), 3.67(brs, 2H), 4.56(brs, 2H), 4.90(s, 2H), 6.14–6.20(m, 2H), 6.86(d, J=8.7Hz, 2H), 7.11–7.22(m, 4H), 7.42(d, J=8.7Hz, 2H), 7.52(s, 1H), 8.94(s, 1H), 9.47(s, 1H)<br>IR(KBr)3388, 3301, 2932, 1612, 1591, 1521, 1458, 1413, 1288, 1030cm$^{-1}$ |
| I-545 | m.p. 108–110° C.<br>$^1$HNMR(CDCl$_3$) δ 1.69(s, 3H), 1.74(s, 3H), 2.49–2.59(m, 2H), 3.03(s, 3H), 3.20(s, 3H), 3.56(s, 3H), 3.75(s, 3H), 4.06(t, J=6.6Hz, 2H), 4.93 (s, 2H), 5.22(m, 1H), 6.66(s, 1H), 7.04(d, J=8.7Hz, 2H), 7.09–7.17(m, 2H), 7.37(dd, J=2.1, 8.7Hz, 1H), 7.44(d, J=2.1Hz, 1H), 7.51–7.58 (m, 2H)<br>IR(KBr)3434, 2933, 1604, 1521, 1473, 1383, 1360, 1278, 1160, 1121, 1084, 1017cm$^{-1}$ |

TABLE 109

| | |
|---|---|
| I-546 | m.p. 109–110° C.<br>$^1$HNMR(CDCl$_3$) δ 1.69(s, 3H), 1.75(s, 3H), 2.48–2.58(m, 2H), 4.07(t, J=6.6Hz, 2H), 5.22(m, 1H), 5.69(s, 1H), 5.87(s, 1H), 6.44(s, 1H), 6.93–6.95(m, 2H), 7.04–7.06(m, 1H), 7.10–7.18(m, 2H), 7.58–7.64(m, 2H)<br>IR(KBr)3411, 2932, 1608, 1587, 1522, 1491, 1226, 1111, 1074, 1017cm$^{-1}$ |

TABLE 109-continued

I-547 m.p. 141–142° C.
¹HNMR(CDCl₃) δ 3.03(s, 3H), 3.57(s, 3H), 3.75(s, 3H), 4.90(s, 2H), 5.16(s, 2H), 5.65(brs, 1H), 6.66(s, 1H), 6.92(dd, J=1.8, 8.4Hz, 1H), 6.99(d, J=8.4Hz, 1H), 7.06(d, J=1.8Hz, 1H), 7.10–7.17(m, 2H), 7.35–7.47(m, 5H), 7.52–7.59(m, 2H)
IR(KBr)3529, 3439, 2932, 1601, 1518, 1477, 1461, 1380, 1251, 1224, 1157, 1113, 1094, 1076cm⁻¹

I-548 m.p. 133–136° C.
¹HNMR(CDCl₃) δ 2.98(s, 3H), 3.12(s, 3H), 3.56(s, 3H), 3.75(s, 3H), 4.94(s, 2H), 5.18(s, 2H), 6.67(s, 1H), 7.09–7.17(m, 3H), 7.34–7.49(m, 7H), 7.51–7.58(m, 2H)
IR(KBr)3434, 2941, 1598, 1519, 1481, 1383, 1365, 1279, 1231, 1164, 1099, 1081cm⁻¹

I-549 m.p. 161–162° C.
¹HNMR(CDCl₃) δ 3.10(s, 3H), 3.42(s, 3H), 3.76(s, 3H), 5.17(s, 2H), 6.05(s, 1H), 6.44(s, 1H), 7.11–7.20(m, 3H), 7.33–7.50(m, 7H), 7.52(d, J=2.1Hz, 1H), 7.57–7.65(m, 2H)
IR(KBr)3488, 2938, 1613, 1523, 1486, 1290, 1223, 1107, 1071, 1012cm⁻¹

I-550 m.p. 113–115° C.
¹HNMR(CDCl₃) δ 2.37(s, 3H), 2.98(s, 3H), 3.11(s, 3H), 3.56(s, 3H), 3.75(s, 3H), 4.93(s, 2H), 5.13(s, 2H), 6.66(s, 1H), 7.09–7.17(m, 3H), 7.18–7.23(m, 2H), 7.32–7.39(m, 3H), 7.45(d, J=1.8Hz, 1H), 7.51–7.58(m, 2H)
IR(KBr)3434, 2934, 1738, 1601, 1520, 1478, 1466, 1376, 1356, 1236, 1159, 1109, 1070, 1014cm⁻¹

TABLE 110

I-551 m.p. 138–140° C.
¹HNMR(CDCl₃) δ 2.38(s, 3H), 3.04(s, 3H), 3.57(s, 3H), 3.74(s, 3H), 4.90(s, 2H), 5.11(s, 2H), 5.63(s, 1H), 6.66(s, 1H), 6.91(dd, J=2.1, 8.4Hz, 1H), 6.99(d, J=8.4Hz, 1H), 7.05(d, J=1.8Hz, 1H), 7.08–7.17(m, 2H), 7.22(d, J=7.8Hz, 2H), 7.33(d, J=7.8Hz, 2H), 7.52–7.59(m, 2H)
IR(KBr)3446, 2934, 1601, 1518, 1476, 1461, 1379, 1252, 1224, 1158, 1092, 1011cm⁻¹

I-552 m.p. 188–190° C.
¹HNMR(CDCl₃) δ 2.38(s, 3H), 3.10(s, 3H), 3.42(s, 3H), 3.75(s, 3H), 5.12(s, 2H), 6.04(s, 1H), 6.43(s, 1H), 7.11–7.25(m, 5H), 7.35(d, J=7.8Hz, 2H), 7.42(dd, J=2.4, 8.7Hz, 1H), 7.51(d, J=2.4Hz, 1H), 7.57–7.65(m, 2H)
IR(KBr)3433, 2963, 1611, 1523, 1485, 1355, 1282, 1226, 1163, 1106, 1071cm⁻¹

I-553 m.p. 149–150° C.
¹HNMR(CDCl₃) δ 3.13(s, 3H), 3.21(s, 3H), 5.20(s, 2H), 7.17(d, J=8.4Hz, 1H), 7.24(m, 1H), 7.36–7.54(m, 9H), 7.58(dd, J=1.2, 2.4Hz, 1H), 7.60–7.67(m, 2H)
IR(KBr)1524, 1485, 1354, 1292, 1263, 1181, 1150, 1114, 977, 869, 858, 850, 812, 796cm⁻¹

I-554 m.p. 92–93° C.
¹HNMR(CDCl₃) δ 1.69(s, 3H), 1.74(d, J=1.2Hz, 3H), 2.25(s, 3H), 2.28(s, 3H), 2.56(dt, J=6.6, 7.2Hz, 2H), 3.20(s, 3H), 3.21(s, 3H), 4.07(t, J=7.2Hz, 2H), 5.22(m, 1H), 7.05(d, J=8.4Hz, 1H), 7.11(s, 1H), 7.13(s, 1H), 7.25(dd, J=2.1, 8.4Hz, 1H), 7.31–7.43(m, 5H)
IR(KBr) 1518, 1488, 1355, 1293, 1264, 1169, 1151, 1109, 970, 872, 818cm⁻¹

I-555 m.p. 126–127° C.
¹HNMR(CDCl₃) δ 1.77(s, 3H), 1.82(s, 3H), 3.20(s, 3H), 3.23(s, 3H), 4.65(d, J=6.6Hz, 2H), 5.50(m, 1H), 7.10(d, J=8.7Hz, 1H), 7.18–7.27(m, 2H), 7.36–7.43(m, 2H), 7.50(dd, J=1.5, 8.7Hz, 1H), 7.55(d, J=1.5Hz, 1H), 7.60–7.66(m, 2H)
IR(KBr)1527, 1489, 1359, 1295, 1266, 1177, 1153, 1118, 974, 894, 874cm⁻¹

TABLE 111

I-556 m.p. 154–155° C.
¹HNMR(CDCl₃) δ 2.25(s, 3H), 2.28(s, 3H), 2.38(s, 3H), 3.11(s, 3H), 3.20(s, 3H), 5.13(s, 2H), 7.11(s, 1H), 7.14(s, 1H), 7.19–7.28(m, 4H), 7.31–7.43(m, 7H)
IR(KBr)1520, 1487, 1365, 1284, 1260, 1192, 1172, 1152, 1108, 967, 867, 809, 795cm⁻¹

I-557 m.p. 112–113° C.
¹HNMR(CDCl₃) δ 1.69(s, 3H), 1.76(s, 3H), 2.26(s, 3H), 2.27(s, 3H), 2.54(dt, J=7.2, 6.9Hz, 2H), 4.07(t, J=6.9Hz, 2H), 4.86(s, 1H), 5.23(m, 1H), 5.71(s, 1H), 6.82(dd, J=2.1, 8.4Hz, 1H), 6.85–6.93(m, 3H), 6.96(d, J=2.1Hz, 1H), 7.10(s, 1H), 7.12(s, 1H), 7.22–7.27(m, 2H)
IR(KBr)3380, 1613, 1586, 1523, 1490, 1471, 1431, 1391, 1293, 1261, 1246, 1205, 1171, 1130, 836cm⁻¹

I-558 m.p. 141–142° C.
¹HNMR(CDCl₃) δ 1.77(s, 3H), 1.82(s, 3H), 4.63(d, J=6.9Hz, 2H), 5.06(s, 1H), 5.52(m, 1H), 5.75(s, 1H), 6.89–6.97(m, 3H), 7.07(dt, J=8.4, 1.8Hz, 1H), 7.14–7.23(m, 3H), 7.44–7.51(m, 2H)
IR(KBr)3429, 1612, 1594, 1531, 1489, 1467, 1449, 1401, 1259, 1213, 1169, 1132, 835, 781cm⁻¹

I-559 m.p. 179–180° C.
¹HNMR(CDCl₃) δ 2.26(s, 3H), 2.28(s, 3H), 2.39(s, 3H), 4.81(s, 1H), 5.11(s, 2H), 5.70(s, 1H), 6.83(dd, J=2.1, 8.4Hz, 1H), 6.86–6.91(m, 2H), 6.98(d, J=8.4Hz, 1H), 6.98(d, J=2.1Hz, 1H), 7.10(s, 1H), 7.12(s, 1H), 7.21–7.28(m, 4H), 7.32–7.38(m, 2H)
IR(KBr)3317, 1609, 1520, 1489, 1426, 1378, 1247, 1206, 1175, 1124, 1006, 792cm⁻¹

I-560 foam
¹HNMR(DMSO-d₆) δ 3.74(s, 3H), 3.75(s, 3H), 4.62(d, J=5.0Hz, 2H), 5.02(t, J=5.0Hz, 1H), 5.19(s, 2H), 6.94(s, 1H), 6.99(s, 1H), 7.06(d, J=8.0Hz, 1H), 7.22(ddd, J=8.6, 2.0, 0.8Hz, 1H), 7.32–7.52(m, 8H), 7.57(d, J=2.4Hz, 1H), 9.91(brs, 1H)
IR(KBr)3257, 1525, 1491, 1464, 1453, 1382, 1207, 1035, 764, 737cm⁻¹

TABLE 112

I-561 m.p. 147–148° C.
¹HNMR(CDCl₃) δ 3.27(s, 3H), 3.79(s, 3H), 3.82(s, 3H), 5.26(s, 2H), 6.92(s, 1H), 6.95(s, 1H), 7.13(d, J=8.7Hz, 1H), 7.35–7.50(m, 8H), 7.80(dd, J=8.7, 2.7Hz, 1H), 8.05(d, J=2.7Hz, 1H), 10.62(s, 1H)
IR(KBr)1682, 1606, 1489, 1377, 1345, 1261, 1209, 1168, 1119, 1038, 871, 832cm⁻¹

I-562 m.p. 189–191° C.
¹HNMR(DMSO-d₆) δ 3.53(s, 3H), 3.80(s, 3H), 3.80(s, 3H), 5.27(s, 2H), 7.05(s, 1H), 7.10(s, 1H), 7.25(d, J=8.7Hz, 1H), 7.30–7.59(m, 7H), 7.66(dd, J=11.7, 2.1Hz, 1H), 7.67(dd, J=8.7, 2.3Hz, 1H), 7.84(d, J=2.3Hz, 1H), 12.7(brs, 1H)
IR(KBr)3433, 1705, 1492, 1371, 1250, 1207, 1168, 1033, 868cm⁻¹

TABLE 112-continued

I-563 m.p. 204–207° C.
$^1$HNMR(CDCl$_3$) δ 1.36(s, 9H), 3.20(s, 3H), 3.41(s, 3H), 3.74(s, 3H), 5.15(s, 2H), 5.65(s, 1H), 5.77(s, 1H), 6.80(s, 1H), 6.83(dd, J=8.4, 2.0Hz, 1H), 6.96(d, J=2.0Hz, 1H), 6.98(d, J=8.4Hz, 1H), 7.34–7.45(m, 7H), 7.68(d, J=8.7Hz, 2H)
IR(KBr)3408, 3337, 1692, 1498, 1474, 1466, 1347, 1251, 1150, 870, 855cm$^{-1}$

I-564 m.p. 179–182° C.
$^1$HNMR(DMSO-d$_6$) δ 3.76(s, 3H), 3.76(s, 3H), 5.26(s, 2H), 6.99(s, 1H), 7.00(t, J=8.7Hz, 1H), 7.01(s, 1H), 7.22(ddd, J=8.7, 2.4Hz, J=1.2Hz, 1H), 7.24(d, J=8.9Hz, 1H), 7.32–7.54(m, 6H), 7.65(dd, J=8.9, 2.4Hz, 1H), 7.82(d, J=2.4Hz, 1H), 9.91(s, 1H), 12.6(brs, 1H)
IR(KBr)3422, 3277, 1726, 1526, 1491, 1416, 1396, 1284, 1210, 1031cm$^{-1}$ I-565 m.p. 178–180° C.
$^1$HNMR(DMSO-d$_6$) δ 3.30(s, 3H), 3.43(s, 3H), 3.61(s, 3H), 4.31(s, 2H), 5.14(s, 2H), 6.25(s, 1H), 6.61(dd, J=8.4, 1.9Hz, 1H), 7.05(d, J=8.4Hz, 1H), 7.33–7.44(m, 6H), 7.50–7.54(m, 2H), 7.70(d, J=8.7Hz, 2H), 9.08(s, 1H)
IR(KBr)3435, 3378, 1593, 1518, 1481, 1360, 1245, 1147, 1119, 1010, 871cm$^{-1}$

TABLE 113

I-566 foam
$^1$HNMR(DMSO-d$_6$) δ 3.27(s, 3H), 3.59(s, 3H), 4.21(s, 2H), 5.13(s, 2H), 6.17(s, 1H), 6.60(dd, J=8.3, 1.4Hz, 1H), 6.70(d, J=1.4Hz, 1H), 6.82(d, J=8.4Hz, 2H), 7.03(d, J=8.3Hz, 1H), 7.33–7.53(m, 7H), 9.07(brs, 1H), 9.45(brs, 1H)
IR(KBr)3390, 1609, 1592, 1522, 1484, 1247, 1227, 1119, 1011, 812cm$^{-1}$ I-567 m.p. 146–148° C.
$^1$HNMR(DMSO-d$_6$) δ 1.64(s, 3H), 1.70(s, 3H), 2.44(q, J=6.9Hz, 2H), 3.53(s, 3H), 3.78(s, 3H), 3.80(s, 3H), 4.05(t, J=6.9Hz, 2H), 5.26(t, J=6.9Hz, 2H), 7.05(s, 1H), 7.10(s, 1H), 7.19(d, J=8.4Hz, 1H), 7.50(dd, J=8.4, 2.0Hz, 1H), 7.57(t, J=8.3Hz, 1H), 7.65(ddd, J=8.3, 1.9, 0.9Hz, 1H), 7.66(dd, J=11.9, 1.9Hz, 1H), 7.79(d, J=2.0Hz, 1H), 12.5(brs, 1H)
IR(KBr)3434, 3299, 1727, 1489, 1375, 1341, 1209, 1172, 1033, 851, 824cm$^{-1}$ I-568 m.p. 179–181° C.
$^1$HNMR(CDCl$_3$) δ 1.31(s, 9H), 3.11(s, 3H), 3.20(s, 3H), 3.39(s, 3H), 3.74(s, 3H), 5.16(s, 2H), 5.98(s, 1H), 6.79(s, 1H), 7.09(d, J=8.5Hz, 1H), 7.29(dd, J=8.5, 1.9Hz, 1H), 7.35–7.49(m, 8H), 7.66(d, J=8.7Hz, 2H)
IR(KBr)3404, 3341, 1690, 1517, 1465, 1369, 1348, 1174, 1151, 869, 814cm$^{-1}$ I-569 m.p. 189–191° C.
$^1$HNMR(DMSO-d$_6$) δ 3.31(s, 3H), 3.33(s, 3H), 3.43(s, 3H), 3.64(s, 3H), 4.48(s, 2H), 5.25(s, 2H), 6.28(s, 1H), 7.24(dd, J=9.0, 2.0Hz, 1H), 7.24(d, J=2.0Hz, 1H), 7.34–7.46(m, 6H), 7.52–7.55(m, 2H), 7.70(d, J=9.0Hz, 2H)
IR(KBr)3490, 3392, 1596, 1518, 1483, 1364, 1150, 872, 813cm$^{-1}$ I-570 m.p. 194–196° C.
$^1$HNMR(CDCl$_3$) δ 3.07(s, 3H), 3.22(s, 3H), 3.36(s, 3H), 3.77(s, 3H), 5.16(s, 2H), 6.92(s, 1H), 7.13(d, J=8.6Hz, 1H), 7.25(dd, J=8.6, 2.1Hz, 1H), 7.29(d, J=2.1Hz, 1H), 7.36–7.47(m, 7H), 7.63(brs, 1H), 7.67(d, J=8.4Hz, 2H)
IR(KBr)3433, 3329, 1737, 1518, 1476, 1369, 1168, 1148, 878cm$^{-1}$

TABLE 114

I-571 m.p. 184–186° C.
$^1$HNMR(CDCl$_3$) δ 2.31(s, 3H), 2.38(s, 3H), 3.12(s, 3H), 3.45(s, 3H), 3.58(s, 3H), 3.76(s, 3H), 5.14(s, 2H), 6.95(s, 1H), 7.11–7.23(m, 5H), 7.34–7.37(m, 4H), 7.57(dd, J=8.7, 2.4Hz, 1H), 7.66(d, J=2.4Hz, 1H)
IR(CHCl$_3$)2952, 1732, 1614, 1599, 1518, 1467, 1445, 1370, 1290, 1256, 1169, 1117, 1081, 1064, 1003, 973, 905, 827cm$^{-1}$

I-572 m.p. 218–220° C. $^1$HNMR(CDCl$_3$) δ 2.38(s, 3H), 3.12(s, 3H), 3.44(s, 3H), 3.63(s, 3H), 3.76(s, 3H), 5.14(s, 2H), 6.80–6.83(m, 2H), 6.94(s, 1H), 7.14(d, J=8.7Hz, 1H), 7.21–7.23(m, 4H), 7.35–7.37(m, 2H), 7.56(dd, J=8.7, 2.4Hz, 1H), 7.66(d, J=2.4Hz, 1H)
IR(CHCl$_3$)3596, 2939, 1720, 1613, 1522, 1466, 1445, 1370, 1346, 1291, 1258, 1183, 1172, 1116, 1081, 1064, 1003, 973, 904, 866, 837cm$^{-1}$

I-573 m.p. 197–199° C. $^1$HNMR(CD$_3$OD) δ 3.19(s, 3H), 3.43(s, 3H), 3.76(s, 3H), 5.25(s, 2H), 7.06–7.12(m, 3H), 7.32–7.43(m, 6H), 7.52–7.54(m, 2H), 7.60(dd, J=8.4, 2.4Hz, 1H), 7.66(d, J=2.4Hz, 1H)
IR(KBr)3421, 2941, 1738, 1708, 1643, 1519, 1472, 1354, 1297, 1259, 1228, 1171, 1119, 1081, 1063, 1001, 958, 920, 871, 826, 755, 697, 524cm$^{-1}$

I-574 m.p. 151–153° C. $^1$HNMR(CDCl$_3$) δ 2.39(s, 3H), 3.44(s, 3H), 3.64(s, 3H), 3.74(s, 3H), 5.12(s, 2H), 5.78(br, 2H), 6.78–6.81(m, 2H), 6.94(s, 1H), 6.99(d, J=8.4Hz, 1H), 7.15–7.25(m, 6H), 7.33–7.36(m, 2H)
IR(CHCl$_3$)3595, 3541, 2952, 1730, 1612, 1591, 1521, 1474, 1395, 1345, 1323, 1290, 1258, 1173, 1129, 1081, 1063, 1004, 901, 863, 836cm$^{-1}$

I-575 m.p. 195–196° C.
$^1$HNMR(CD$_3$OD) δ 2.34(s, 3H), 3.40(s, 3H), 3.72(s, 3H), 5.16(s, 2H), 6.75–6.78(m, 2H), 6.96(s, 1H), 7.02(s, 1H), 7.14–7.21(m, 6H), 7.36–7.39(m, 2H)
IR(KBr)3530, 3398, 2942, 1708, 1610, 1593, 1520, 1465, 1373, 1334, 1256, 1233, 1127, 1078, 1056, 996, 960, 864, 834, 791, 755, 690, 651, 605, 534cm$^{-1}$

TABLE 115

I-576 m.p. 82–84° C.
$^1$HNMR(CDCl$_3$) δ 1.70(s, 3H), 1.75(s, 3H), 2.54–2.59(m, 2H), 3.24(s, 3H), 3.50(s, 3H), 3.77(s, 3H), 4.10(t, J=6.9Hz, 2H), 5.23(m, 1H), 7.07–7.12 (m, 4H), 7.23–7.28(m, 2H), 7.57(dd, J=8.7, 2.4Hz, 1H), 7.63(d, J=2.4Hz, 1H), 9.99(s, 1H)
IR(CHCl$_3$)2936, 1697, 1604, 1591, 1518, 1469, 1445, 1371, 1331, 1294, 1232, 1172, 1159, 1123, 1093, 1005, 964cm$^{-1}$

I-577 m.p. 126–128° C.
$^1$HNMR(CD$_3$OD) δ 1.70(s, 3H), 1.74(d, J=0.9Hz, 3H), 2.53–2.61(m, 2H), 3.25(s, 3H), 3.44(s, 3H), 3.75(s, 3H), 4.13(t, J=6.3Hz, 2H), 5.29 (m, 1H), 7.04–7.11(m, 3H), 7.24(d, J=8.7Hz, 1H), 7.33–7.38(m, 2H), 7.58–7.65(m, 2H)
IR(KBr)3432, 2940, 2566, 1735, 1711, 1646, 1613, 1519, 1470, 1447, 1366, 1297, 1264, 1228, 1172, 1118, 1081, 1063, 1001, 962, 920, 898, 871, 828, 796, 695, 524cm$^{-1}$

TABLE 115-continued

I-578 m.p. 202–204° C.
$^1$HNMR(CDCl$_3$) δ 3.13(s, 3H), 3.45(s, 3H), 3.61(s, 3H), 3.76(s, 3H), 5.19(s, 2H), 6.95(s, 1H), 7.05–7.11(m, 2H), 7.14(d, J=8.7Hz, 1H), 7.30–7.49
(m, 7H), 7.57(dd, J=8.7, 2.4Hz, 1H), 7.67(d, J=2.4Hz, 1H)
IR(CHCl$_3$)2952, 1731, 1603, 1519, 1472, 1445, 1371, 1345, 1291, 1172, 1159, 1117, 1081, 1064, 1004, 972, 960, 904cm$^{-1}$

I-579 m.p. 197–199° C.
$^1$HNMR(CDCl$_3$) δ 2.71(s, 3H), 3.56, (s, 3H), 3.75(s, 3H), 5.18(s, 2H), 5.72, (s, 1H), 6.86(s, 1H), 7.00(d, J=8.4Hz, 1H), 7.12–7.18(m, 3H), 7.24
(d, J=2.1Hz, 1H), 7.38–7.46(m, 7H)
IR(CHCl$_3$)3543, 2939, 1602, 1521, 1482, 1465, 1394, 1370, 1328, 1254, 1178, 1159, 1130, 1081, 1005, 964, 840, 816cm$^{-1}$

I-580 m.p. 199–201° C.
$^1$HNMR(CD$_3$OD) δ 3.40(s, 3H), 3.73(s, 6H), 5.22(s, 2H), 7.00(s, 1H), 7.03–7.11(m, 4H), 7.17(m, 1H), 7.31–7.41(m, 5H), 7.49–7.52(m, 2H)
IR(KBr)3527, 3434, 2940, 1701, 1591, 1518, 1465, 1380, 1335, 1320, 1291, 1270, 1222, 1161, 1130, 1078, 1056, 1002, 916, 868, 837, 747,
698, 633, 599, 526, 480cm$^{-1}$

TABLE 116

I-581 m.p. 122–123° C.
$^1$HNMR(CDCl$_3$) δ 1.78(s, 3H), 1.82(s, 3H), 3.25(s, 3H), 3.50(s, 3H), 3.76(s, 3H), 4.66(d, J=6.9Hz, 2H), 5.52(m, 1H), 7.09–7.14(m, 4H),
7.23–7.27(m, 2H), 7.56(dd, J=8.7, 2.1Hz, 1H), 7.63(d, J=2.1Hz, 1H), 9.99(s, 1H)
IR(CHCl$_3$)2938, 1679, 1604, 1591, 1517, 1469, 1445, 1371, 1331, 1292, 1172, 1159, 1122, 1092, 1004, 973cm$^{-1}$

I-582 m.p. 158–159° C.
$^1$HNMR(CDCl$_3$) δ 2.69(s, 3H), 3.13(s, 3H), 3.57(s, 3H), 3.76(s, 3H), 5.19(s, 2H), 6.85(s, 1H), 7.13–7.18(m, 3H), 7.37–7.49(m, 7H), 7.56
(dd, J=9.0, 2.1Hz, 1H), 7.62(d, J=2.1Hz, 1H)
IR(CHCl$_3$)2939, 1603, 1521, 1482, 1464, 1294, 1253, 1177, 1119, 1082, 1003, 963, 876, 842cm$^{-1}$

I-583 m.p. 145–147° C.
$^1$HNMR(CDCl$_3$) δ 2.68(s, 3H), 3.54(s, 3H), 3.56(s, 3H), 3.75(s, 3H), 5.21(s, 2H), 5.27(s, 2H), 6.85(s, 1H), 7.00(d, J=8.7Hz, 1H), 7.13–7.23
(m, 3H), 7.33–7.49(m, 8H)
IR(CHCl$_3$)2938, 1731, 1603, 1520, 1482, 1370, 1249, 1178, 1158, 1134, 1081, 1004, 961, 840, 815cm$^{-1}$

I-584 m.p. 160–162° C.
$^1$HNMR(CDCl$_3$) δ 3.47(s, 3H), 3.74(s, 3H), 5.18(s, 2H), 5.72(s, 1H), 6.00(s, 1H), 6.46(s, 1H), 7.01(d, J=8.4Hz, 1H), 7.10–7.19(m, 3H), 7.27
(d, J=2.1Hz, 1H), 7.36–7.48(m, 7H)
IR(CHCl$_3$)3540, 2938, 1603, 1568, 1522, 1490, 1464, 1416, 1396, 1325, 1263, 1158, 1111, 1072, 1002, 838cm$^{-1}$

I-585 m.p. 133–134° C.
$^1$HNMR(CD$_3$OD) δ 1.80(d, J=0.9Hz, 3H), 1.82(d, J=0.9Hz, 3H), 3.26(s, 3H), 3.44(s, 3H), 3.76(s, 3H), 4.71(d, J=6.9Hz, 2H), 5.55(m, 1H),
7.06–7.12(m, 3H), 7.26(d, J=8.7Hz, 1H), 7.34–7.36(m, 2H), 7.58–7.63(m, 2H)
IR(KBr)3422, 2939, 1736, 1702, 1603, 1519, 1472, 1368, 1293, 1228, 1187, 1173, 1117, 1081, 1061, 1003, 975, 961, 920, 827, 759, 701,
523cm$^{-1}$

TABLE 117

I-586 m.p. 152–153° C.
$^1$HNMR(CDCl$_3$) δ 1.69(s, 3H), 1.74(d, J=0.9Hz, 3H), 2.55–2.57(m, 2H), 3.23(s, 3H), 3.44(s, 3H), 3.60(s, 3H), 3.77(s, 3H), 4.09(t, J=6.6Hz,
2H), 5.22(m, 1H), 6.95(s, 1H), 7.05–7.11(m, 3H), 7.30–7.35(m, 2H), 7.57(dd, J=8.7, 2.4Hz, 1H), 7.64(d, J=2.4Hz, 1H)
IR(CHCl$_3$)2938, 1731, 1601, 1519, 1469, 1445, 1370, 1345, 1291, 1172, 1159, 1117, 1081, 1064, 1004, 973, 904, 864, 840cm$^{-1}$

I-587 m.p. 132–133° C.
$^1$HNMR(CDCl$_3$) δ 3.44(s, 3H), 3.61(s, 3H), 3.75(s, 3H), 5.18(s, 2H), 5.71(s, 1H), 6.95(s, 1H), 6.99–7.10(m, 3H), 7.17(dd, J=8.4, 2.1Hz, 1H),
7.25–7.47(m, 8H)
IR(CHCl$_3$)3542, 2952, 2938, 1731, 1597, 1519, 1474, 1392, 1345, 1321, 1290, 1266, 1159, 1130, 1080, 1063, 1000, 900, 862, 839cm$^{-1}$

I-588 m.p. 92–94° C.
$^1$HNMR(CDCl$_3$) δ 1.69(d, J=0.6Hz, 3H), 1.76(d, J=1.2Hz, 3H), 2.51–2.58(m, 2H), 3.45(s, 3H), 3.75(s, 3H), 4.09(t, J=6.9Hz, 2H), 5.23
(m, 1H), 5.70(br, 1H), 6.92(d, J=8.4Hz, 1H), 6.97(s, 1H), 7.05–7.10(m, 2H), 7.16(dd, J=8.4, 2.1Hz, 1H), 7.23(d, J=2.1Hz, 1H), 7.33–7.38
(m, 2H)
IR(KBr)3534, 3432, 2936, 1713, 1597, 1519, 1473, 1377, 1322, 1260, 1231, 1158, 1130, 1081, 1063, 1004, 961, 919, 837, 808, 791, 754, 705,
521cm$^{-1}$

I-589 m.p. 120–122° C.
$^1$HNMR(CDCl$_3$) δ 1.69(s, 3H), 1.76(s, 3H), 2.51–2.58(m, 2H), 3.44(s, 3H), 3.61(s, 3H), 3.75(s, 3H), 4.09(t, J=6.6Hz, 2H), 5.23(m, 1H), 5.73
(s, 1H), 6.92(d, J=8.4Hz, 1H), 6.96(s, 1H), 7.04–7.10(m, 2H), 7.16(dd, J=8.1, 1.8Hz, 1H), 7.23(d, J=1.8Hz, 1H), 7.31–7.36(m, 2H)
IR(CHCl$_3$)3541, 2937, 1731, 1598, 1519, 1471, 1391, 1345, 1323, 1290, 1265, 1159, 1130, 1080, 1063, 1005, 839cm$^{-1}$

I-590 m.p. 154–156° C.
$^1$HNMR(CDCl$_3$) δ 1.77(s, 3H), 1.82(s, 3H), 3.24(s, 3H), 3.45(s, 3H), 3.61(s, 3H), 3.76(s, 3H), 4.64(d, J=7.2Hz, 2H), 5.51(m, 1H), 6.95(s,
1H), 7.05–7.11(m, 3H), 7.31–7.35(m, 2H), 7.57(dd, J=8.7, 2.4Hz, 1H), 7.64(d, J=2.4Hz, 1H)
IR(CHCl$_3$)2938, 1731, 1602, 1519, 1472, 1445, 1370, 1345, 1290, 1186, 1116, 1080, 1064, 1003, 973, 904, 840cm$^{-1}$

TABLE 118

I-591 m.p. 181–182° C.
$^1$HNMR(CD$_3$OD) δ 1.77(s, 3H), 1.80(d, J=0.9Hz, 3H), 3.42(s, 3H), 3.74(s, 3H), 4.65(d, J=6.9Hz, 2H), 5.55(m, 1H), 6.99–7.11(m, 5H), 7.15
(d, J=2.1Hz, 1H), 7.32–7.36(m, 2H)
IR(KBr)3529, 3424, 2937, 1714, 1598, 1519, 1473, 1417, 1372, 1336, 1321, 1258, 1235, 1157, 1129, 1080, 1062, 1004, 989, 917, 854, 839,
807, 791, 752, 703cm$^{-1}$

I-592 m.p. 109–110° C.
$^1$HNMR(CDCl$_3$) δ 1.78(s, 3H), 1.83(s, 3H), 3.44(s, 3H), 3.61(s, 3H), 3.75(s, 3H), 4.63(d, J=6.6Hz, 2H), 5.53(m, 1H), 5.72(s, 1H), 6.94(d,

TABLE 118-continued

| | |
|---|---|
| | J=8.1Hz, 1H), 6.96(s, 1H), 7.04–7.10(m, 2H), 7.16(dd, J=8.4, 2.1Hz, 1H), 7.23(d, J=2.1Hz, 1H), 7.31–7.36(m, 2H) |
| | IR(CHCl$_3$)3538, 2938, 1731, 1598, 1519, 1473, 1391, 1345, 1290, 1264, 1159, 1129, 1080, 1063, 1004, 900, 862, 839cm$^{-1}$ |
| I-593 | m.p. 185–187° C. |
| | $^1$HNMR(CDCl$_3$) δ 3.78(s, 3H), 3.80(s, 3H), 4.82(s, 1H), 6.61(m, 1H), 6.88–6.93(m, 2H), 6.96(s, 1H), 7.04(s, 1H), 7.23–7.25(m, 1H), 7.45 (d, J=0.9Hz, 1H), 7.48–7.53(m, 2H), 7.83(d, J=0.9Hz, 1H), 8.18(brs, 1H) |
| | IR(KBr)3600–3200(br), 1611, 1523, 1496, 1464, 1447, 1388, 1268, 1239, 1202, 1046, 1025cm$^{-1}$ |
| I-594 | m.p. 188–189° C. |
| | $^1$HNMR(CDCl$_3$) δ 3.19(s, 3H), 3.79(s, 3H), 3.81(s, 3H), 6.61–6.62(m, 1H), 6.96(s, 1H), 7.06(s, 1H), 7.24–7.26(m, 1H), 7.33–7.37(m, 2H), 7.45(brs, 2H), 7.64–7.68(m, 2H), 7.84(d, J=0.9Hz, 1H), 8.21(brs, 1H) |
| | IR(KBr)3600–3200(br), 1518, 1494, 1465, 1419, 1389, 1351, 1331, 1314, 1213, 1177, 1145, 1051, 1027cm$^{-1}$ |
| I-595 | m.p. 98–101° C. |
| | $^1$HNMR(CDCl$_3$) δ 1.77(s, 3H), 1.78(s, 3H), 1.82(s, 3H), 1.85(s, 3H), 3.78(s, 3H), 3.79(s, 3H), 4.56(d, J=6.9Hz, 2H), 4.72(d, J=6.9Hz, 2H), 5.39–5.44(m, 1H), 5.52–5.57(m, 1H), 6.53(d, J=3.0Hz, 1H), 6.97–7.03(m, 4H), 7.12(d, J=3.3Hz, 1H), 7.38(d, J=8.4Hz, 1H), 7.45(dd, J=1.8, 8.7Hz, 1H), 7.52–7.57(m, 2H), 7.81(d, J=1.5Hz, 1H) |
| | IR(KBr)3600–2800(br), 1606, 1498, 1476, 1463, 1382, 1262, 1241, 1206, 1177, 1052, 1030cm$^{-1}$ |

TABLE 119

| | |
|---|---|
| I-596 | m.p. 207–210° C. |
| | $^1$HNMR(CDCl$_3$) δ 3.19(s, 3H), 3.80(s, 3H), 3.81(s, 3H), 5.50(s, 2H), 6.65(d, J=3.0Hz, 1H), 6.81(d, J=7.8Hz, 1H), 6.96(s, 1H), 7.05(s, 1H), 7.19–7.22(m, 1H), 7.25–7.45(m, 6H), 7.54–7.60(m, 1H), 7.64–7.69(m, 2H), 7.86(brs, 1H), 8.61–8.64(m, 1H) |
| | IR(KBr)3600–3200(br), 1496, 1478, 1364, 1347, 1210, 1176, 1155, 1052, 1028cm$^{-1}$ |
| I-597 | m.p. 222–224° C. |
| | $^1$HNMR(CDCl$_3$) δ 2.36(s, 3H), 2.53(s, 3H), 3.77(s, 3H), 3.78(s, 3H), 6.69(dd, J=0.9, 4.2Hz, 1H), 6.95(s, 1H), 6.96(s, 1H), 7.23–7.28(m, 2H), 7.31–7.35(m, 2H), 7.51–7.54(m, 3H), 7.59(d, J=3.3Hz, 1H), 7.73(d, J=1.2Hz, 1H), 7.80–7.84(m, 2H), 8.03(d, J=1.2Hz, 1H) |
| | IR(KBr)3600–3200(br), 1509, 1487, 1464, 1444, 1366, 1208, 1172, 1129, 1092, 1049, 1028cm$^{-1}$ |
| I-598 | m.p. 126–127° C. |
| | $^1$HNMR(CDCl$_3$) δ 1.69(s, 3H), 1.71(d, J=0.9Hz, 3H), 2.56(dt, J=6.6, 6.9Hz, 2H), 3.20(s, 3H), 3.22(s, 3H), 4.08(t, J=6.9Hz, 2H), 5.21(m, 1H), 7.08(d, J=8.4Hz, 1H), 7.18–7.27(m, 2H), 7.36–7.43(m, 2H), 7.50(dd, J=1.8, 8.4Hz, 1H), 7.56(d, J=1.8Hz, 1H), 7.59–7.66(m, 2H) |
| | IR(KBr)1528, 1488, 1469, 1395, 1362, 1342, 1297, 1265, 1201, 1176, 1152, 1116, 968, 890, 872, 818cm$^{-1}$ |
| I-599 | m.p. 169–170° C. |
| | $^1$HNMR(DMSO-d$_6$) δ 2.32(s, 3H), 3.37(s, 3H), 3.45(s, 3H), 5.23(s, 2H), 7.23(d, J=7.8Hz, 2H), 7.37–7.44(m, 3H), 7.47–7.53(m, 2H), 7.56–7.66 (m, 4H), 7.75(d, J=7.5Hz, 2H) |
| | IR(KBr)1525, 1485, 1366, 1355, 1291, 1262, 1181, 1150, 1116, 969, 869, 811cm$^{-1}$ |
| I-600 | m.p. 123–124° C. |
| | $^1$HNMR(CDCl$_3$) δ 1.68(s, 3H), 1.75(d, J=0.9Hz, 3H), 2.53(dt, J=7.2, 6.9Hz, 2H), 4.07(t, J=6.9Hz, 2H), 4.91(s, 1H), 5.22(m, 1H), 5.72(s, 1H), 6.89–6.95(m, 2H), 7.07(m, 1H), 7.14–7.22(m, 4H), 7.44–7.51(m, 2H) |
| | IR(KBr)3448, 1612, 1593, 1530, 1489, 1475, 1401, 1262, 1212, 1181, 1169, 1132, 839, 779cm$^{-1}$ |

TABLE 120

| | |
|---|---|
| I-601 | m.p. 184–185° C. |
| | $^1$HNMR(DMSO-d$_6$) δ 2.31(s, 3H), 5.13(s, 2H), 6.85–6.91(m, 2H), 6.97(m, 1H), 7.07(d, J=8.4Hz, 1H), 7.07(d, J=1.8Hz, 1H), 7.20(d, J=8.1Hz, 2H), 7.32–7.48(m, 6H) |
| | IR(KBr)3290, 1614, 1529, 1491, 1459, 1449, 1405, 1380, 1267, 1254, 1167, 1132, 783cm$^{-1}$ |
| I-602 | m.p. 141–142° C. |
| | $^1$HNMR(CDCl$_3$ ) δ 1.77(s, 3H), 1.82(s, 3H), 3.46(s, 3H), 3.78(s, 3H), 4.56(d, J=6.8Hz, 2H), 5.54(t, J=6.6Hz, 1H), 6.96–7.26(m, 7H), 7.61 (dd, J=5.2, 8.6Hz, 2H), 9.88(s, 1H) |
| | IR(KBr)3433, 2955, 2922, 2865, 2833, 1687, 1604, 1515, 1462, 1288, 1258, 1232, 1180, 1160, 1070, 998, 845cm$^{-1}$ |
| I-603 | m.p. 169–170° C. |
| | $^1$HNMR(CDCl$_3$) δ 2.38(s, 3H), 3.46(s, 3H), 3.77(s, 3H), 5.07(s, 2H), 7.02–7.38(m, 7H), 7.61(dd, J=5.4, 8.8Hz, 2H), 9.89(brs, 1H) |
| | IR(KBr)3433, 2936, 2840, 1698, 1517, 1462, 1251, 1233, 1067, 999, 837cm$^{-1}$ |
| I-604 | m.p. 120–121° C. |
| | $^1$HNMR(CDCl$_3$) δ 1.68(s, 3H), 1.74(s, 3H), 2.50–2.57(m, 2H), 3.46(s, 3H), 3.77(s, 3H), 3.98(t, J=7.0Hz, 2H), 5.24(t, J=7.0Hz, 1H), 6.94–7.26 (m, 7H), 7.61(dd, J=5.4, 8.8Hz, 2H), 9.88(brs, 1H) |
| | IR(KBr)3435, 2960, 2937, 2876, 1698, 1605, 1516, 1464, 1441, 1379, 1296, 1272, 1233, 1221, 1161, 1073, 1024, 845, 807cm$^{-1}$ |
| I-605 | m.p. 151–152° C. |
| | $^1$HNMR(DMSO-d$_6$) δ 1.34(s, 6H), 3.07–3.15(m, 1H), 3.32(s, 3H), 3.67(s, 3H), 3.97–4.08(m, 1H), 4.28–4.34(m, 1H), 6.48(s, 1H), 7.00(d, J=7.8Hz, 1H), 7.22–7.35(m, 4H), 7.66(dd, J=3.2, 6.0Hz, 2H), 8.72(brs, 1H) |
| | IR(KBr)3460, 2960, 2935, 1607, 1521, 1488, 1456, 1392, 1244, 1226, 1160, 1122, 1073, 818cm$^{-1}$ |
| I-606 | m.p. 164–165° C. |
| | $^1$HNMR(DMSO-d$_6$) δ 2.32(s, 3H), 3.31(s, 3H), 3.66(s, 3H), 5.08(s, 2H), 6.46(s, 1H), 6.99(d, J=5.8Hz, 2H), 7.20–7.38(m, 4H), 7.65(dd, J=3.6, 6.2Hz, 2H), 8.69(brs, 1H) |
| | IR(KBr)3367, 2940, 1605, 1519, 1484, 1466, 1449, 1390, 1229, 1181, 1158, 1059, 1006, 987, 831, 817cm$^{-1}$ |

TABLE 121

| | |
|---|---|
| I-607 | m.p. 103–104° C. |
| | $^1$HNMR(DMSO-d$_6$) δ 1.37(s, 6H), 2.47–2.59(m, 2H), 3.31(s, 3H), 3.66(s, 3H), 3.94–4.05(m, 1H), 4.26–4.34(m, 1H), 6.44(s, 1H), 7.02(d, J=7.6Hz, 2H), 7.18–7.35(m, 4H), 7.64(dd, J=3.4, 6.6Hz, 2H), 8.77(brs, 1H) |
| | IR(KBr)3400, 2993, 2961, 2930, 1607, 1522, 1486, 1471, 1454, 1393, 1226, 1123, 1072, 835, 819cm$^{-1}$ |

TABLE 121-continued

| | |
|---|---|
| I-608 | m.p. 157–158° C.<br>$^1$HNMR(DMSO-d$_6$) δ 1.73(s, 3H), 1.77(s, 3H), 3.31(s, 3H), 3.72(s, 3H), 4.54(d, J=6.9Hz, 2H), 5.47(t, J=7.2Hz, 1H), 6.93(d, J=8.7Hz, 2H), 7.05(s, 1H), 7.19(d, J=9.0Hz, 2H), 7.30–7.36(m, 2H), 7.70(dd, J=5.4, 8.7Hz, 2H)<br>IR(KBr)3406, 2936, 1712, 1608, 1519, 1472, 1444, 1375, 1235, 839cm$^{-1}$ |
| I-609 | m.p. 215–216° C.<br>$^1$HNMR(DMSO-d$_6$) δ 2.34(s, 3H), 3.33(s, 3H), 3.74(s, 3H), 5.09(s, 2H), 7.00–7.07(m, 3H)7.22–7.39(m, 8H), 7.73(dd, J=5.6, 8.0Hz, 2H)<br>IR(KBr)3494, 3289, 2938, 1745, 1698, 1520, 1471, 1461, 1378, 1296, 1239, 1183, 1159, 829cm$^{-1}$ |
| I-610 | m.p. 169–170° C.<br>$^1$HNMR(DMSO-d$_6$) δ 1.64(s, 3H), 1.71(s, 3H), 2.41–2.46(m, 2H), 3.32(s, 3H), 3.73(s, 3H), 3.97(t, J=6.6Hz, 2H), 5.23(t, J=7.2Hz, 1H), 6.93(d, J=8.1Hz, 2H), 7.05(s, 1H), 7.20(d, J=7.2Hz, 2H), 7.30–7.36(m, 2H), 7.70(dd, J=4.5, 7.5Hz, 2H)<br>IR(KBr)3424, 2933, 1701, 1609, 1519, 1471, 1379, 1294, 1248, 1061, 839cm$^{-1}$ |
| I-611 | m.p. 167–168° C.<br>$^1$HNMR(CDCl$_3$) δ 1.75(s, 3H), 1.82(s, 3H), 2.35(s, 6H), 2.45(s, 3H), 3.21(s, 3H), 3.56(s, 3H), 3.70(s, 3H), 4.35(d, J=6.9Hz, 2H), 5.60(t, J=7.2Hz, 1H), 6.84(s, 1H), 7.08(s, 2H), 7.38(d, J=8.7Hz, 2H), 7.70(d, J=9.0Hz, 2H)<br>IR(KBr)3433, 2932, 1509, 1475, 1376, 1359, 1232, 1177, 1152, 1085, 966, 874, 797cm$^{-1}$ |

TABLE 122

| | |
|---|---|
| I-612 | m.p. 175–176° C.<br>$^1$HNMR(CDCl$_3$) δ 2.35(s, 6H), 2.39(s, 3H), 2.49(s, 3H), 3.21(s, 3H), 3.56(s, 3h), 3.79(s, 3H), 4.83(s, 2H), 6.84(s, 1H), 7.10(s, 2H), 7.22(d, J=7.5Hz, 2H), 7.38(d, J=8.4Hz, 4H), 7.70(d, J=9.0Hz, 2H)<br>IR(KBr)3434, 2936, 1510, 1475, 1363, 1229, 1176, 1152, 1083, 964, 871, 803cm$^{-1}$ |
| I-613 | m.p. 138–139° C.<br>$^1$HNMR(CDCl$_3$) δ 1.69(s, 3H), 1.75(s, 3H), 2.33(s, 6H), 2.52–2.55(m, 2H), 3.21(s, 3H), 3.56(s, 3H), 3.78(s, 3H), 3.79(t, J=6.9Hz, 2H), 5.27(t, J=6.6Hz, 1H), 6.83(s, 3H), 7.08(s, 6H), 7.38(d, J=8.7Hz, 2H), 7.70(d, J=9.0Hz, 2H)<br>IR(KBr)3432, 2939, 1509, 1476, 1448, 1362, 1237, 1172, 1155, 1103, 1081, 963, 873, 800cm$^{-1}$ |
| I-614 | m.p. 89–90° C.<br>$^1$HNMR(DMSO-d$_6$) δ 1.74(s, 3H), 1.77(s, 3h), 3.36(s, 3H), 3.67(s, 3H), 4.22(d, J=3.0Hz, 2H), 4.56(d, J=6.3Hz, 2H), 5.48(t, J=5.7Hz, 1H), 6.93–6.96(m, 3H), 7.11(d, J=8.7Hz, 2H), 7.28–7.34(m, 2H), 7.68(dd, J=6.0, 8.7Hz, 2H)<br>IR(KBr)3528, 3418, 2935, 1608, 1518, 1472, 1233, 1004, 836cm$^{-1}$ |
| I-615 | m.p. 89–90° C.<br>$^1$HNMR(DMSO-d$_6$) δ 2.33(s, 3H), 3.36(s, 3H), 3.67(s, 3H), 4.22(d, J=3.9Hz, 2H), 4.59(t, J=4.2Hz, 1H), 5.09(s, 2H), 6.94(s, 1H), 7.02(d, J=8.4Hz, 2H), 7.22(d, J=8.4Hz, 4H), 7.28–7.39(m, 4H), 7.68(dd, J=5.7, 8.4Hz, 2H)<br>IR(KBr)3485, 2931, 1517, 1473, 1460, 1383, 1243, 1225, 1079, 1014, 1001, 834, 798cm$^{-1}$ |
| I-616 | oil<br>$^1$HNMR(DMSO-d$_6$) δ 1.75(s, 3H), 1.78(s, 3H), 2.47–2.52(m, 2H), 3.39(s, 3H), 3.71(s, 3H), 4.25(d, J=3.3Hz, 2H), 4.49(d, J=6.3Hz, 2H), 5.46(t, J=5.7Hz, 1H), 6.91–6.95(m, 3H), 7.13(d, J=8.4Hz, 2H), 7.24–7.32(m, 2H), 7.67(dd, J=5.7, 8.4Hz, 2H)<br>IR(KBr)3528, 3419, 2935, 1608, 1518, 1472, 1383, 1232, 1004, 837cm$^{-1}$ |

TABLE 123

| | |
|---|---|
| I-617 | m.p. 138–139° C.<br>$^1$HNMR(DMSO-d$_6$) δ 1.70(s, 3H), 1.77(s, 3H), 2.24(s, 6H), 3.30(s, 3H), 3.64(s, 3H), 4.31(d, J=6.9Hz, 2H), 5.56(t, J=6.6Hz, 1H), 6.39(s, 1H), 6.84(d, J=8.4Hz, 2H), 6.91(s, 2H), 7.44(d, J=8.4Hz, 2H), 8.50(s, 1H), 9.50(s, 1H)<br>IR(KBr)3400, 2966, 2934, 1609, 1519, 1465, 1444, 1389, 1362, 1269, 1228, 1211, 1194, 1171, 1118, 1089, 1027, 953cm$^{-1}$ |
| I-618 | m.p. 122–123° C.<br>$^1$HNMR(DMSO-d$_6$) δ 2.29(s, 6H), 2.37(s, 3H), 3.30(s, 3H), 3.67(s, 3H), 4.81(s, 2H), 6.43(s, 1H), 6.86(d, J=7.5Hz, 2H), 6.97(s, 2H), 7.27(d, J=6.9Hz, 2H), 7.42–7.48(m, 2H), 8.54(s, 1H), 9.52(s, 1H)<br>IR(KBr)3483, 3423, 2931, 1735, 1709, 1612, 1520, 1477, 1454, 1411, 1395, 1362, 1224, 1176, 1117, 1089, 1028cm$^{-1}$ |
| I-619 | m.p. 81–82° C.<br>$^1$HNMR(DMSO-d$_6$) δ 1.70(s, 3H), 1.76(s, 3H), 2.18–2.30(m, 2H), 2.27(s, 6H), 3.34(s, 3H), 3.68(s, 3H), 3.80(t, J=4.5Hz, 2H), 5.34(t, J=5.1Hz, 1H), 6.43(s, 1H), 6.88(d, J=7.5Hz, 2H), 6.94(s, 6H), 7.46–7.50(m, 2H), 8.53(s, 1H), 9.54(s, 1H)<br>IR(KBr)3410, 2930, 1612, 1521, 1479, 1454, 1395, 1361, 1265, 1227, 1174, 1117, 1090, 1028, 825cm$^{-1}$ |
| I-620 | m.p. 161–162° C.<br>$^1$HNMR(CDCl$_3$) δ 1.32(s, 9H), 2.38(s, 3H), 3.10(s, 3H), 3.20(s, 3H), 3.39(s, 3H), 3.74(s, 3H), 5.12(s, 2H), 5.96(s, 1H), 6.79(s, 1H), 7.09(d, J=8.4Hz, 1H), 7.21(d, J=7.8Hz, 2H), 7.28(dd, J=8.4, 1.8Hz, 1H), 7.33–7.38(m, 5H), 7.67(d, J=8.4Hz, 2H)<br>IR(KBr)3398, 1718, 1518, 1472, 1366, 1173, 1151, 877, 867, 813cm$^{-1}$ |
| I-621 | m.p. 139–141° C.<br>$^1$HNMR(CDCl$_3$) δ 1.33(s, 9H), 1.68(s, 3H), 1.74(s, 3H), 2.54(q, J=6.9Hz, 2H), 3.19(s, 3H), 3.20(s, 3H), 3.39(s, 3H), 3.73(s, 3H), 4.05(t, J=6.9Hz, 2H), 5.21(t, J=6.9Hz, 1H), 5.95(s, 1H), 6.79(s, 1H), 7.02(d, J=8.4Hz, 1H), 7.29(dd, J=8.4, 1.9Hz, 1H), 7.33(d, J=1.9Hz, 1H), 7.36(d, J=8.7Hz, 2H), 7.66(d, J=8.7Hz, 2H)<br>IR(KBr)3416, 1720, 1519, 1469, 1365, 1237, 1152, 1117, 975, 872, 815cm$^{-1}$ |

TABLE 124

| | |
|---|---|
| I-622 | m.p. 197–199° C.<br>$^1$HNMR(DMSO-d$_6$) δ 2.33(s, 3H), 3.31(s, 6H), 3.43(s, 3H), 3.64(s, 3H), 3.74(s, 3H), 4.47(s, 2H), 5.19(s, 2H), 6.28(s, 1H), 7.21–7.25(m, 4H), 7.35(d, J=8.7Hz, 1H), 7.40–7.44(m, 4H), 7.70(d, J=9.0Hz, 2H)<br>IR(KBr)3482, 3385, 1597, 1519, 1484, 1368, 1353, 1150, 872, 813cm$^{-1}$ |
| I-623 | m.p. 99–101° C.<br>$^1$HNMR(DMSO-d$_6$) δ 2.32(s, 3H), 3.27(s, 3H), 3.59(s, 3H), 4.21(s, 2H), 5.08(s, 2H), 6.17(s, 1H), 6.58(dd, J=8.0, 1.8Hz, 1H), 6.69(d, J=1.8Hz, 1H), 6.82(d, J=8.7Hz, 2H), 7.01(d, J=8.0Hz, 1H), 7.21(d, J=7.8Hz, 2H), 7.39(d, J=7.8Hz, 2H), 7.41(d, J=8.7Hz, 2H), 9.02(brs, 1H), |

TABLE 124-continued 9.45(brs, 1H)
IR(KBr)3390, 1609, 1592, 1521, 1484, 1246, 1227, 1117, 1011, 810cm$^{-1}$ I-624 m.p. 215–217° C.
$^1$HNMR(CDCl$_3$ + CD$_3$OD)d3.78(s, 3H), 3.79(s, 3H), 5.49(s, 2H), 6.64(dd, J=0.6, 2.7Hz, 1H), 6.79(d, J=8.1Hz, 1H), 6.90(d, J=8.7Hz, 2H), 6.96(s, 1H), 7.02(s, 1H), 7.19–7.32(m, 3H), 7.40–7.50(m, 3H), 7.56–7.60(m, 1H), 7.85(d, J=0.9Hz, 1H), 8.58–8.60(m, 1H)
IR(KBr)3600–2600(br), 1611, 1599, 1500, 1477, 1445, 1395, 1264, 1238, 1210, 1052, 1029, 1008cm$^{-1}$ I-625 m.p. 213–214° C.
$^1$HNMR(CDCl$_3$) δ 2.36(s, 3H), 3.77(s, 6H), 6.70(dd, J=0.6, 3.6Hz, 1H), 6.93(s, 1H), 6.96(s, 1H), 7.08–7.16(m, 2H), 7.24–7.28(m, 2H), 7.51–7.60(m, 4H), 7.73(d, J=1.5Hz, 1H), 7.80–7.84(m, 2H), 8.03(d, J=9.0Hz, 1H)
IR(KBr)3600–2800(br), 1597, 1517, 1496, 1464, 1444, 1372, 1209, 1189, 1172, 1157, 1121, 1092, 1050, 1028cm$^{-1}$ I-626 $^1$HNMR(CDCl$_3$ + CD$_3$OD) δ 3.13(s, 3H), 3.81(s, 3H), 3.82(s, 3H), 5.19(s, 2H), 6.97(s, 1H), 6.99(s, 1H), 7.14(d, J=8.7Hz, 1H), 7.34–7.52 (m, 6H), 7.61(d, J=2.1Hz, 1H), 7.73(d, J=8.4Hz, 2H), 8.12(d, J=8.4Hz, 2H)
IR(KBr)3432, 1616, 1520, 1494, 1452, 1388, 1352, 1282, 1261, 1211, 1186, 1175, 1113, 1058, 1033cm$^{-1}$ I-627 $^1$HNMR(CDCl$_3$) δ 3.81(s, 6H), 5.17(s, 2H), 6.99(s, 1H), 7.00(d, J=8.4Hz, 1H), 7.09(dd, J=8.4& 1.8Hz, 1H), 7.23(d, J=1.8Hz, 1H), 7.33–7.50(m, 5H), 7.76(.d, J=8.4Hz, 2H), 8.10(d, J=8.4Hz, 2H)
IR(KBr)3551, 3520, 3399, 1615, 1587, 1576, 1521, 1488, 1455, 1383, 1268, 1245, 1208, 1126, 1055, 1034, 1003cm$^{-1}$

TABLE 125

I-628 $^1$HNMR(CDCl$_3$) δ 3.05(s, 3H), 3.47(s, 3H), 3.75(s, 3H), 5.15(s, 2H), 6.45(s, 1H), 6.94(dd, J=8.4&1.8Hz, 1H), 7.03(d, J=8.4Hz, 1H), 7.06 (d, J=1.8Hz, 1H), 7.30(d, J=8.1Hz, 2H), 7.36–7.51(m, 5H), 7.63(d, J=8.1Hz, 2H)
IR(KBr)3525, 3472, 1609, 1588, 1522, 1487, 1455, 1407, 1321, 1286, 1242, 1148, 1115, 1071, 1013cm$^{-1}$

I-629 $^1$HNMR(CDCl$_3$) δ 2.68(s, 3H), 3.07(s, 3H), 3.14(s, 3H), 3.55(s, 3H), 3.78(s, 3H), 5.19(s, 2H), 6.85(s, 1H), 7.16(d, J=8.7Hz, 1H), 7.27–7.50 (m, 9H), 7.62(d, J=9.0Hz, 2H)
IR(KBr)3432, 1611, 1522, 1482, 1462, 1392, 1358, 1295, 1233, 1178, 1154, 1119, 1082, 1012cm$^{-1}$

I-630 $^1$HNMR(CDCl$_3$) δ 2.88(s, 3H), 3.08(s, 3H), 3.28(s, 3H), 3.30(s, 3H), 3.54(s, 3H), 3.79(s, 3H), 6.87(s, 1H), 7.32(d, J=8.4Hz, 2H), 7.43(d.d, J=8.4&2.1Hz, 1H), 7.54–7.65(m, 4H)
IR(KBr)3432, 1612, 1519, 1481, 1367, 1332, 1232, 1177, 1154, 1077, 1011cm$^{-1}$

I-631 $^1$HNMR(CDCl$_3$) δ 1.57(s, 3H), 169(s, 3H), 2.66(s, 3H), 2.97(s, 3H), 3.13(s, 3H), 3.54(s, 3H), 3.77(s, 3H), 4.31(d, J=7.2Hz, 2H), 5.19(s, 2H), 5.21–5.32(m, 1H), 6.86(s, 1H), 7.15(.d, J=8.7Hz, 1H), 7.30–7.52(m, 9H), 7.63(d, J=8.4Hz, 2H)
IR(KBr) 1609, 1520, 1481, 1365, 1338, 1294, 1270, 1233, 1178, 1153, 1118, 1078, 1015, 947cm$^{-1}$

I-632 $^1$HNMR(CDCl$_3$) δ 1.45(s, 3H), 1.59(s, 3H), 1.66(s, 3H), 1.70(s, 3H), 2.97(s, 3H), 3.11(s, 3H), 3.64(s, 3H), 3.75(s, 3H), 4.28(d, J=8.4Hz, 2H), 4.32(d, J=8.4Hz, 2H), 5.18(s, 2H), 5.23(t, J=8.4Hz, 1H)), 5.29(t, J=8.4Hz, 1H), 6.70(s, 1H), 7.10(d, J=8.4Hz, 1H)7.30–7.51(m, 9H), 7.58(d, J=8.4Hz, 2H)

I-633 $^1$HNMR(CDCl$_3$) δ 1.58(s, 3H), 1.69(s, 3H), 2.97(s, 3H), 3.45(s, 3H), 3.75(s, 3H), 433(d, J=7.5Hz, 2H), 5.16(s, 2H), 5.24–5.33(m, 1H), 5.69(s, 1H), 5.87(s, 1H), 6.47(s, 1H), 6.95(d.d, J=8.4&2.1Hz, 1H), 7.03(d, J=8.4Hz, 1H), 7.09(.d, J=2.1Hz, 1H), 7.31–7.50(m, 7H), 7.65(d, J=8.4Hz, 2H)
IR(KBr)3450, 1609, 1590, 1558, 1524, 1487, 1448, 1421, 1320, 1233, 1143, 1117, 1073, 1019cm$^{-1}$

I-634 $^1$HNMR(CDCl$_3$) δ 1.57(s, 3H), 1.68(s, 3H), 2.66(s, 3H), 2.70(s, 3H), 3.13(s, 3H), 3.54(s, 3H), 3.78(s, 3H), 4.33(d, J=8.4Hz, 2H), 5.19(s, 2H), 5.26(t, J=8.4Hz), 6.86(s, 1H), 7.15(d, J=8.7Hz, 1H), 7.30–7.49(m, 9H), 7.63(d, J=8.4Hz, 2H)
IR(KBr)1615, 1517, 1480, 1372, 1337, 1233, 1213, 1178, 1154, 1076, 1014cm$^{-1}$

TABLE 126

I-635 $^1$HNMR(CDCl$_3$) δ 1.58(s, 3H), 1.69(s, 3H), 2.82(s, 3H), 2.97(s, 3H), 3.29(s, 3H), 3.53(s, 3H), 3.77(s, 3H), 4.33(d, J=7.2Hz, 2H), 5.27(t, J=7.2Hz, 1H), 6.25(s, 1H), 6.86(s, 1H), 7.17(d, J=9.0Hz, 1H)), 7.23–7.32(m, 2H), 7.41(d, J=8.7Hz, 2H), 7.63(d, J=8.7Hz, 2H)
IR(KBr)3431, 1611, 1522, 1482, 1364, 1337, 1294, 1231, 1178, 1153, 1077, 1014cm$^{-1}$

I-636 $^1$HNMR(CDCl$_3$) δ 1.76(s, 3H), 1.82(s, 3H), 3.09(s, 3H), 3.47(s, 3H), 3.75(s, 3H), 4.62(d, J=6.9Hz, 2H), 5.47–5.58(m, 1H), 5.71(s, 1H), 5.87(s, 1H), 6.45(s, 1H), 6.60(s, 1H), 6.89–7.01(m, 2H), 7.05(d, J=0.6Hz, 1H), 7.30(.d, J=8.7Hz, 2H), 7.65(d, J=8.7Hz, 2H)
IR(KBr)3448, 3265, 1612, 1585, 1521, 1487, 1330, 1287, 1243, 1225, 1152, 1112, 1069, 971cm$^{-1}$

I-637 $^1$HN$^2$R(CDCl$_3$) δ 1.57(s, 3H), 1.69(s, 3H), 1.77(s, 3H), 1.81(s, 3H), 2.70(s, 3H), 2.97(s, 3H), 3.24(s, 3H), 3.54(s, 3H), 3.78(s, 3H), 4.32 (d, J=6.9Hz, 2H), 4.64(d, J=6.6Hz, 2H), 5.27(t, J=6.9Hz, 1H), 5.49(t, J=6.6Hz, 1H), 6.86(s, 1H), 7.09(d, J=8.4Hz, 1H), 7.32–7.44(m, 4H), 7.63(d, J=8.4Hz, 2H)
IR(KBr)1609, 1520, 1481, 1365, 1339, 1292, 1270, 1236, 1178, 1153, 1118, 1078, 1015cm$^{-1}$

I-638 $^1$HNMR(CDCl$_3$) δ 1.58(s, 3H), 1.69(s, 3H), 1.76(s, 3H), 1.82(s, 3H), 2.97(s, 3H), 3.45(s, 3H), 3.75(s, 3H), 4.32(d, J=7.8Hz, 2H), 4.63(.d, J=7.8Hz, 2H), 5.23–5.33(m, 1H), 5.48–5.57(m, 1H), 5.69(s, 1H), 5.85(s, 1H), 6.46(s, 1H), 6.89–7.02(m, 2H), 7.05(d, J=1.8Hz, 1H), 7.40(d, J=8.7Hz, 2H), 7.65(d, J=8.7Hz, 2H)
IR(KBr)3450, 1609, 1588, 1557, 1525, 1487, 1445, 1327, 1248, 1148, 1114, 1072, 1015cm$^{-1}$

I-639 $^1$HNMR(CDCl$_3$) δ 2.55(s, 3H), 2.67(s, 3H), 3.58(s, 3H), 3.79(s, 3H), 5.18(s, 2H), 5.71(s, 1H), 6.85(s, 1H), 6.91(d.d, J=8.4& 2.1Hz, 1H), 7.03(d, J=8.4Hz, 1H), 7.04(d, J=2.1Hz, 1H), 7.32–7.48(m, 6H), .7.85(.d.d, J=7.8&1.5Hz, 1H), 8.22(d, J=1.5Hz, 1H)
IR(KBr)3457, 1739, 1529, 1481, 1407, 1376, 1346, 1279, 1243, 1177, 1128, 1071, 1012cm$^{-1}$

I-640 $^1$HNMR(CDCl$_3$) δ 2.67(s, 3H), 2.68(s, 3H), 3.13(s, 3H), 3.58(s, 3H), 3.80(s, 3H), 5.19(s, 2H), 6.86(s, 1H), 7.15(d, J=8.7Hz, 1H), 7.31–7.49 (m, 8H), 7.83(d.d, J=8.1&1.8Hz, 1H), 8.21(d, J=1.8Hz, 1H)
IR(KBr)3433, 1609, 1530, 1481, 1372, 1290, 1268, 1238, 1177, 1118, 1075, 1012cm$^{-1}$

TABLE 127

I-641 $^1$HNMR(CDCl$_3$) δ 2.67(s, 3H), 3.50(s, 3H), 3.77(s, 3H), 5.16(s, 2H), 5.70(s, 1H), 5.83(s, 1H), 6.47(s, 1H), 6.94(d.d, J=8.7& 1.8Hz, 1H), 7.04(.d, J=8.7Hz, 1H), 7.07(d, J=1.8Hz, 1H), 7.34–7.48(m, 5H), 7.82(d.d, J=8.1&1.8Hz, 1H), 8.26(.d, J=1.8Hz, 1H)
IR(KBr)3555, 3377, 1590, 1529, 1503, 1451, 1414, 1341, 1324, 1242, 1225, 1121cm$^{-1}$

I-642 $^1$HNMR(CDCl$_3$) δ 2.29(s, 3H), 2.68(s, 3H), 3.12(s, 3H), 3.56(s, 3H), 3.76(s, 3H), 5.18(s, 2H), 6.85(s, 1H), 7.00–7.20(m, 4H), 7.31–7.49 (m, 7H)
IR(KBr)3407, 1624, 1518, 1480, 1361, 1287, 1270, 1234, 1175, 1117, 1084, 1009cm$^{-1}$

TABLE 127-continued

I-643  $^1$HNMR(CDCl$_3$) δ 2.40(s, 3H), 2.67(s, 3H), 3.09(s, 3H), 3.13(s, 3H), 3.59(s, 3H), 3.78(s, 3H), 5.19(s, 1H), 6.17(s, 1H), 6.85(s, 1H), 7.15 (d, J=8.4Hz, 1H), 7.30–7.49(m, 9H), 7.69(d, J=1.8Hz, 1H)
IR(KBr)3433, 3304, 1608, 1519, 1481, 1365, 1326, 1294, 1269, 1237, 1177, 1156, 1114, 1079, 1015cm$^{-1}$

I-644  $^1$HNMR(CDCl$_3$) δ 2.09(s, 3H), 2.39(s, 3H), 2.68(s, 3H), 3.13(s, 3H), 3.49(s, 3H), 3.76(s, 2H), 5.19(s, 2H), 6.30(s, 1H), 6.77(s, 1H), 7.12–7.24 (m, 3H), 7.31–7.49(m, 9H), 7.54(d, J=1.8Hz, 1H), 7.67(d, J=8.4Hz, 2H)
IR(KBr)3434, 1608, 1519, 1481, 1366, 1293, 1269, 1237, 1164, 1114, 1081, 1016cm$^{-1}$

I-645  $^1$HNMR(CDCl$_3$) δ 2.09(s, 3H), 2.39(s, 3H), 3.43(s, 3H), 3.73(s, 3H), 5.16(s, 2H), 5.30(s, 1H), 5.68(s, 1H), 5.89(s, 1H), 6.32(s, 1H), 6.36(s, 1H), 6.95(d.d, J=8.7&2.1Hz, 1H), 7.03(d, J=8.7Hz, 1H), 7.08(d, J=2.1Hz, 1H), 7.14–7.28(m, 3H), 7.34–7.50(m, 5H), 7.61(.d, J=1.5Hz, 1H), 7.68(d, J=8.4Hz, 2H)
IR(KBr)3465, 3270, 1612, 1587, 1558, 1519, 1487, 1454, 1384, 1244, 1160, 1123, 1105, 1091, 1070, 1009cm$^{-1}$

I-646  $^1$HNMR(CDCl$_3$) δ 2.48(s, 3H), 2.63(s, 3H), 3.02(s, 3H), 3.13(s, 3H), 3.28(s, 2H), 3.54(s, 3H), 3.78(s, 3H), 5.19(s, 2H), 6.85(s, 1H), 7.15 (d, J=8.4Hz, 1H), 7.30–7.49(m, 9H), 7.59(s, 1H)
IR(KBr)3433, 1606, 1519, 1481, 1364, 1341, 1292, 1272, 1233, 1178, 1148, 1118, 1082cm$^{-1}$

I-647  $^1$HNMR(CDCl$_3$) δ 2.48(s, 3H), 3.02(s, 3H), 3.28(s, 3H), 3.46(s, 3H), 3.75(s, 3H), 5.16(s, 2H), 5.70(s, 1H), 5.84(s, 1H), 6.47(s, 1H), 6.94(d.d, J=8.4&2.1Hz, 1H), 7.03(.d, J=8.4Hz, 1H), 7.07(d, J=2.1Hz, 1H), 7.33–7.53(m, 7H), 7.62(d, J=1.8Hz, 1H)
IR(KBr)3528, 3429, 1609, 1584, 1558, 1517, 1487, 1454, 1331, 1317, 1137, 1115, 1068, 1002cm$^{-1}$

TABLE 128

I-648  $^1$HNMR(CDCl$_3$) δ 1.55(s, 3H), 2.45(s, 3H), 2.79(s, 3H), 3.02(s, 3H), 3.29(s, 3H), 3.52(s, 3H), 3.77(s, 3H), 4.12–4.31(m, 2H), 5.22–5.31 (m, 1H), 6.30(s, 11H), 6.84(s, 1H), 7.17(d, J=8.7Hz, 1H), 7.25–7.32(m, 2H), 7.39(d, J=8.4Hz, 1H), 7.45(d.d, J=8.4&1.8Hz, 1H), 7.53(d, J=1.8Hz, 1H)
IR(KBr)3431, 1609, 1522, 1481, 1365, 1334, 1294, 1235, 1178, 1150, 1077, 1013cm$^{-1}$

I-649  $^1$HNMR(CDCl$_3$) δ 1.54(s, 3H), 1.68(s, 3H), 1.76(s, 3H), 1.81(s, 3H), 2.45(s, 3H), 2.68(s, 3H), 3.02(s, 3H), 3.24(s, 3H), 3.52(s, 3H), 3.78(s, 3H), 4.10–4.34(m, 2H), 4.64(d, J=7.2Hz, 2H), 5.21–5.30(m, 1H), 5.45–5.53(m, 1H), 6.84(s, 1H), 7.08(d, J=8.4Hz, 1H), 7.31–7.48(m, 4H), 7.53(d, J=1.5Hz, 1H)
IR(KBr)3432, 1606, 1518, 1481, 1362, 1340, 1292, 1276, 1236, 1177, 1153, 1116, 1076, 1010cm$^{-1}$

I-650  $^1$HNMR(CDCl$_3$) δ 1.56(s, 3H), 1.68(s, 3H), 1.76(s, 3H), 1.82(s, 3H), 2.44(s, 3H), 3.02(s, 3H), 3.45(s, 3H), 3.75(s, 3H), 4.10–4.32(m, 2H), 4.62(d, J=7.2Hz, 2H), 5.22–5.32(m, 1H), 5.48–5.57(m, 1H), 5.60–5.80(brroad, 1H), 5.82(s, 1H), 6.46(s, 1H), 6.92(d.d, J=8.1 &1.8Hz, 1H), 6.97(d, J=8.1Hz, 1H), 7.04(d, J=1.8Hz, 1H), 7.38(d, J=8.1Hz, 1H), 7.47(d.d, J=8.1&1.8Hz, 1H), 7.57(d, J=1.8Hz, 1H)
IR(KBr)3433, 1610, 1586, 1557, 1518, 1486, 1336, 1240, 1149, 1110, 1069cm$^{-1}$ I-651  $^1$HNMR(CD$_3$OD) δ 3.33(s, 3H), 3.66(s, 3H), 5.18(s, 2H), 6.42(s, 1H), 1H), 6.75(dd, J=8.4&2.1Hz, 1H), 6.87(d, J=2.1Hz, 1H), 6.95(d, J=8.4Hz, 1H), 7.26–7.58(m, 8H), 7.81(d.d, J=7.8&1.2Hz, 1H)
IR(KBr)3446, 1698, 1586, 1517, 1498, 1481, 1454, 1408, 1287, 1247, 1117, 1069, 1010cm$^{-1}$ I-652  $^1$HNMR(CDCl$_3$) δ 1.76(s, 3H), 1.81(s, 3H), 2.76(s, 3H), 3.23(s, 3H), 3.43(s, 3H), 3.72(s, 3H), 3.76(s, 3H), 4.64(d, J=6.6Hz, 2H), 5.50(t, J=6.6Hz, 1H), 6.78(s, 1H), 7.08(d, J=8.7Hz, 1H), 7.33–7.51(m, 4H), 7.56–7.63(m, 1H), 7.96(d.d, J=7.5&1.2Hz, 1H)
IR(KBr)1725, 1609, 1520, 1480, 1400, 1366, 1295, 1260, 1178, 1119, 1073, 1010cm$^{-1}$ I-653  $^1$HNMR(CDCl$_3$) δ 2.38(s, 3H), 2.72(s, 3H), 3.12(s, 3H), 3.43(s, 3H), 3.73(s, 3H), 3.76(s, 3H), 5.14(s, 2H), 6.79(s, 1H), 7.13–7.24(m, 3H), 7.30–7.38(m, 3H), 7.41–7.51(m, 3H), 7.56–7.63(m, 1H), 795(d.d, J=7.5&1.2Hz, 1H)
IR(KBr)1725, 1610, 1520, 1481, 1401, 1370, 1293, 1262, 1179, 1119, 1076, 1011cm$^{-1}$

TABLE 129

I-654  $^1$HNMR(CDCl$_3$) δ 1.75(s, 3H), 1.81(s, 3H), 3.56(s, 3H), 3.72(s, 3H), 4.60(d, J=6.6Hz, 2H), 5.29(s, 1H), 5.46–5.56(m, 1H), 5.56–6.00(broad, 1H), 6.42(s, 1H), 6.94(s, 2H), 7.05(s, 1H), 7.43–7.52(m, 2H), 7.56–7.65(m, 1H), 7.99(.d, J=8.7Hz, 1H)
IR(KBr)3433, 1697, 1585, 1517, 1481, 1454, 1410, 1287, 1244, 1117, 1068cm$^{-1}$ I-655  $^1$HNMR(CDCl$_3$) δ 2.39(s, 3H), 3.37(s, 3H), 3.72(s, 3H), 5.10(s, 2H), 6.41(s, 1H), 6.94(dd, J=8.1&2.1Hz, 1H), 7.02(d, J=8.1Hz, 1H), 7.06 (d, J=2.1Hz, 1H), 7.23(d, J=7.8Hz, 2H), 7.35(.d, J=7.8Hz, 2H), 7.42–7.63(m, 3H), 7.96(d, J=7.8Hz, 1H)
IR(KBr)3538, 3443, 1685, 1518, 1458, 1413, 1253, 1116, 1069, 1010cm$^{-1}$ I-656  m.p. 110–112° C.
$^1$HNMR(CDCl$_3$) δ 1.69(s, 3H), 1.74(s, 3H), 2.55(q, J=7.1Hz, 2H), 3.20(s, 3H), 3.21(s, 3H), 3.39(s, 3H), 3.70(s, 3H), 4.07(t, J=7.1Hz, 2H), 5.22(t, J=7.1Hz, 1H), 6.28(s, 1H), 7.09(d, J=8.4Hz, 1H), 7.32(dd, J=8.4, 2.0Hz, 1H), 7.36(d, J=8.9Hz, 2H), 7.37(d, J=2.0Hz, 1H), 7.69 (d, J=8.9Hz, 2H)IR(KBr)3477, 3402, 1607, 1518, 1481, 1365, 1151, 1111, 872, 813cm$^{-1}$ I-657  m.p. 159–162° C.
$^1$HNMR(DMSO-d$_6$) δ 1.64(s, 3H), 1.71(s, 3H), 2.45(q, J=6.7Hz, 2H), 3.27(s, 3H), 3.59(s, 3H), 3.96(t, J=6.7Hz, 2H), 4.22(s, 2H), 5.26(t, J=6.7Hz, 1H), 6.17(s, 1H), 6.60(dd, J=8.1, 2.0Hz, 1H), 6.67(d, J=2.0Hz, 1H), 6.83(d, J=8.7Hz, 2H), 6.95(d, J=8.1Hz, 1H), 7.42(d, J=8.7Hz, 2H), 8.89(s, 1H), 9.46(s, 1H)
IR(KBr)3447, 3401, 3361, 1611, 1522, 1486, 1260, 1228, 1122, 1001, 814cm$^{-1}$ I-658  m.p. 146–147° C.
$^1$HNMR(CDCl$_3$) δ 1.14(t, J=7.2Hz, 3H), 1.76(d, J=0.9Hz, 3H), 1.81(d, J=0.3Hz, 3H), 2.70(s, 3H), 3.20(s, 3H), 3.23(s, 3H), 3.72(q, J=7.2Hz, 2H), 3.78(s, 3H), 4.64(d, J=6.6Hz, 2H), 5.49(m, 1H), 6.84(s, 1H), 7.09(d, J=8.4Hz, 1H), 7.31–7.41(m, 4H), 7.66–7.74(m, 2H)
IR(CHCl$_3$)2930, 1608, 1517, 1479, 1369, 1148, 1116, 1082, 969, 872cm$^{-1}$ I-659  m.p. 174–175° C.
$^1$HNMR(CDCl$_3$) δ 1.14(t, J=6.9Hz, 3H), 2.37(s, 3H), 2.65(s, 3H), 3.12(s, 3H), 3.20(s, 3H), 3.72(q, J=6.9Hz, 2H), 3.77(s, 3H), 5.14(s, 2H), 6.84(s, 1H), 7.15(d, J=8.4Hz, 1H), 7.18–7.42(m, 6H), 7.66–7.73(m, 2H)
IR(CHCl$_3$)1517, 1479, 1369, 1268, 1148, 1117, 1082, 969, 872cm$^{-1}$

TABLE 130

I-660  m.p. 147.5–148° C.
$^1$HNMR(CDCl$_3$) δ 1.14(t, J=7.2Hz, 3H), 1.68(s, 3H), 1.74(d, J=0.9Hz, 3H), 2.50–2.59(m, 2H), 2.72(s, 3H), 3.20(s, 3H), 3.22(s, 3H), 3.72

TABLE 130-continued (q, J=7.2Hz, 2H), 3.77(s, 3H), 4.07(d, J=6.9Hz, 2H), 5.21(m, 1H), 6.84(s, 1H), 7.07(d, J=8.7Hz, 1H), 7.31–7.42(m, 4H), 7.66–7.74(m, 2H)
IR(CHCl₃)2930, 1607, 1517, 1480, 1369, 1148, 1118, 1082, 1025, 969, 872cm⁻¹

I-661 m.p. 154–157° C.
¹HNMR(CDCl₃) δ 1.15(t, J=7.2Hz, 3H), 1.76(s, 3H), 1.82(s, 3H), 3.60(q, J=7.2Hz, 2H), 3.75(s, 3H), 4.61(d, J=6.9Hz, 2H), 4.93(s, 1H), 5.53(m, 1H), 5.69(s, 1H), 5.96(s, 1H), 6.45(s, 1H), 6.80–6.98(m, 4H), 7.07(m, 1H), 7.51–7.58(m, 2H)
IR(CHCl₃)3592, 3528, 2976, 2934, 1611, 1521, 1488, 1460, 1384, 1286, 1243, 1169, 1112, 1068, 994, 885, 824cm⁻¹

I-662 m.p. 130.5–133° C.
¹HNMR(CDCl₃) δ 1.15(t, J=7.2Hz, 3H), 2.39(s, 3H), 3.59(q, J=7.2Hz, 2H), 3.74(s, 3H), 4.83(s, 1H), 5.10(s, 2H), 5.66(s, 1H), 5.97(s, 1H), 6.44(s, 1H), 6.87–6.94(m, 2H), 6.96(dd, J=1.8, 8.4Hz, 1H), 7.02(d, J=8.4Hz, 1H), 7.09(d, J=1.8Hz, 1H), 7.19–7.26(m, 2H), 7.30–7.38(m, 2H), 7.51–7.58(m, 2H)
IR(CHCl₃)3524, 1612, 1521, 1488, 1460, 1383, 1286, 1246, 1113, 1069, 1027, 907, 873cm⁻¹

I-663 amorphous powder
¹HNMR(CDCl₃) δ 1.15(t, J=7.2Hz, 3H), 1.68(d, J=0.6Hz, 3H), 1.74(d, J=0.9Hz, 3H), 2.48–2.56(m, 2H), 3.60(q, J=7.2Hz, 2H), 3.74(s, 3H), 4.06(d, J=6.9Hz, 2H), 4.95(s, 1H), 5.22(m, 1H), 5.68(s, 1H), 5.96(s, 1H), 6.44(s, 1H), 6.88–6.99(m, 4H), 7.06(d, J=1.2Hz, 1H), 7.51–7.58(m, 2H)
IR(CHCl₃)3528, 2972, 1611, 1521, 1488, 1384, 1286, 1246, 1112, 1068, 1024, 883, 824cm⁻¹

I-664 m.p. 113–116° C.
¹HNMR(CDCl₃) δ 2.55(s, 6H), 3.45(s, 3H), 3.74(s, 3H), 5.31(s, 2H), 6.44(s, 1H), 6.92(d, J=8.7Hz, 2H), 6.94(dd, J=8.4, 2.1Hz, 1H), 7.10(s, 1H), 7.10(d, J=2.1Hz, 1H), 7.20(d, J=8.7Hz, 1H), 7.52(d, J=8.7Hz, 2H)
IR(Nujol)3491, 3443, 3304, 3155, 1662, 1608, 1523, 1492, 1464, 1251, 1215, 1111, 1067, 811, 782cm⁻¹

TABLE 131

I-665 m.p.>260° C.
¹HNMR(CD₃OD) δ 3.39(s, 3H), 3.68(s, 3H), 5.40(s, 2H), 6.44(s, 1H), 6.83(dd, J=8.4, 2.1Hz, 1H), 6.85(d, J=8.7, 2H), 6.90(d, J=2.1Hz, 1H), 7.11 (d, J=8.4Hz, 1H), 7.46(d, J=8.7Hz, 2H)
IR(Nujol)3350, 2668, 1611, 1595, 1530, 1488, 1458, 1402, 1253, 1213, 1116, 1073, 1016, 837, 817, 781cm⁻¹

I-666 foam
¹HNMR(CDCl₃) δ 2.34(s, 3H), 2.44(s, 3H), 2.83(s, 3H), 3.12(s, 3H), 3.22(s, 3H), 3.55(s, 3H), 3.78(s, 3H), 4.92(s, 2H), 6.85(s, 1H), 7.17(d, J=8.4Hz, 1H), 7.37–7.42(m, 2H), 7.39(d, J=8.7Hz, 2H), 7.68(d, J=8.7Hz, 2H)
IR(Nujol)1638, 1608, 1519, 1480, 1459, 1177, 1151, 1079, 971, 876, 844, 798cm⁻¹

I-667 foam
¹HNMR(CDCl₃) δ 2.07(s, 3H), 2.53(s, 3H), 2.96(s, 3H), 3.23(s, 3H), 3.27(s, 3H), 3.54(s, 3H), 3.78(s, 3H), 4.86(s, 2H), 6.86(s, 1H), 7.11(d, J=9.0Hz, 1H), 7.33–7.41(m, 2H), 7.39(d, J=8.7Hz, 2H), 7.67(d, J=8.7Hz, 2H)
IR(Nujol)1724, 1688, 1610, 1520, 1481, 1464, 1234, 1177, 1151, 1123, 1081, 876, 798cm⁻¹

I-668 m.p. 221–223° C.
¹HNMR(DMSO-d₆) δ 3.30(s, 3H), 3.64(s, 3H), 5.16(s, 2H), 6.39(s, 1H), 6.66(dd, J=8.4, 2.1Hz, 1H), 6.77(d, J=2.1Hz, 1H), 6.84(d, J=8.7Hz, 2H), 7.00(d, J=8.4Hz, 1H), 7.34(s, 1H), 7.44(d, J=8.7Hz, 2H), 8.43(s, 1H)
IR(Nujol)3535, 3411, 1611, 1582, 1521, 1488, 1463, 1244, 1194, 1135, 1119, 1074, 1014, 930, 826, 809cm⁻¹

I-669 foam
¹HNMR(CDCl₃) δ 2.79(s, 3H), 3.17(s, 3H), 3.22(s, 3H), 3.55(s, 3H), 3.78(s, 3H), 5.21(s, 2H), 6.85(s, 1H), 7.19(d, J=8.4Hz, 1H), 7.23(s, 1H), 7.38(dd, J=8.7, 2.1Hz, 1H), 7.39(d, J=8.7Hz, 2H), 7.42(d, J=2.1Hz, 1H), 7.68(d, J=8.7Hz, 2H), 7.94(s, 1H)
IR(Nujol)1608, 1519, 1480, 1463, 1177, 1151, 1119, 1079, 971, 876, 798cm⁻¹

TABLE 132

I-670 m.p. 198–201° C.
¹HNMR(DMSO-d₆) δ 2.88(s, 3H), 3.39(s, 3H), 3.45(s, 3H), 3.52(s, 3H), 3.78(s, 3H), 4.58(s, 2H), 5.60(s, 1H), 7.07(s, 1H), 7.29(dd, J=9.0, 1.8Hz, 1H), 7.30(d, J=1.8,Hz, 1H), 7.37(d, J=9.0Hz, 1H), 7.48(d, J=8.7Hz, 2H), 7.74(d, J=8.7Hz, 2H), 9.39(s, 1H)
IR(Nujol)3576, 3500, 3405, 3391, 1668, 1607, 1590, 1520, 1480, 1462, 1175, 1156, 1081, 1014, 880, 836, 826, 801cm⁻¹

I-671 foam
¹HNMR(CDCl₃) δ 2.61(s, 3H), 2.73(s, 3H), 3.21(s, 3H), 3.23(s, 3H), 3.55(s, 3H), 3.78(s, 3H), 5.32(s, 2H), 6.84(s, 1H), 7.17(d, J=8.4Hz, 1H), 7.36(dd, J=8.4, 2.1Hz, 1H), 7.38(d, J=8.7Hz, 2H), 7.43(d, J=2.1Hz, 1H), 7.68(d, J=8.7Hz, 2H), 8.46(s, 1H), 8.75(s, 1H)
IR(Nujol)1608, 1519, 1481, 1463, 1177, 1151, 1080, 971, 876, 798cm⁻¹

I-672 foam
¹HNMR(CDCl₃) δ 2.75(s, 3H), 3.21(s, 3H), 3.25(s, 3H), 3.55(s, 3H), 3.78(s, 3H), 5.37(s, 2H), 6.84(s, 1H), 7.17(d, J=8.4Hz, 1H), 7.36(dd, J=8.4, 2.1Hz, 1H), 7.38(d, J=8.7,Hz, 2H), 7.43(d, J=2.1Hz, 1H), 7.68(d, J=8.7Hz, 2H), 8.59(s, 1H), 8.92(s, 1H)
IR(Nujol)1608, 1519, 1480, 1463, 1177, 1151, 1080, 971, 876, 798cm⁻¹

I-673 foam
¹HNMR(CDCl₃) δ 2.70(s, 3H), 3.15(s, 3H), 3.21(s, 3H), 3.55(s, 3H), 3.78(s, 3H), 5.14(s, 2H), 6.77(m, 2H), 6.84(s, 1H), 7.19(m, 2H), 7.26(d, J=8.4Hz, 1H), 7.37(d, J=2.1Hz, 1H), 7.38(dd, J=2.1, 8.4Hz, 1H), 7.68(d, J=8.4Hz, 2H)

I-674 m.p. 153–156° C.
¹HNMR(CDCl₃) δ 2.18(s, 3H), 2.81(s, 3H), 3.18(s, 3H), 3.22(s, 3H), 3.55(s, 3H), 3.79(s, 3H), 5.14(s, 2H), 6.86(s, 1H), 7.18(dd, J=8.1, 8.1Hz, 1H), 7.24(d, J=8.1Hz, 1H), 7.26(d, J=8.4Hz, 1H), 7.36(d, J=1.8Hz, 1H), 7.38(d, J=8.4Hz, 2H), 7.39(dd, J=1.8, 8.4Hz, 1H), 7.43(dd, J=8.1, 8.1Hz, 1H), 7.67(d, J=8.4Hz, 2H), 7.90(d, J=8.1Hz, 1H)
IR(KBr)3384, 1689, 1519, 1481, 1364, 1177, 1151, 1079, 970, 874, 798cm⁻¹

TABLE 133

I-675 foam
¹HNMR(CDCl₃) δ 2.76(s, 3H), 3.16(s, 3H), 3.22(s, 3H), 3.23(s, 3H), 3.55(s, 3H), 3.78(s, 3H), 5.23(s, 2H), 6.85(s, 1H), 7.23(dd, J=7.5, 7.5Hz, 1H), 7.37(s, 2H), 7.38(d, J=8.4Hz, 2H), 7.43(m, 3H), 7.54(d, J=7.5Hz, 1H), 7.68(d, J=8.4Hz, 2H)
IR(KBr)3435, 1609, 1519, 1481, 1364, 1177, 1152, 1079, 972, 876, 798 cm⁻¹

TABLE 133-continued

I-676 m.p.163–165° C.
$^1$HNMR(CDCl$_3$) δ 2.78(s, 3H), 3.03(s, 3H), 3.21(s, 3H), 3.45(s, 6H), 3.55(s, 3H), 3.79(s, 3H), 5.31(s, 2H), 6.84(s, 1H), 7.22(d, J=8.4Hz, 1H), 7.37(dd, J=2.4, 8.4Hz, 1H), 7.38(d, J=8.4Hz, 2H), 7.42(m, 2H), 7.53(m, 2H), 7.67(d, J=8.4Hz, 2H), 7.68(m, 1H)
IR(KBr)1609, 1519, 1481, 1365, 1176, 1161, 1080, 973, 875, 799 cm$^{-1}$

I-677 m.p. 153–156° C.
$^1$HNMR(CDCl$_3$) δ 2.69(s, 3H), 2.98(s, 3H), 3.17(s, 3H), 3.21(s, 3H), 3.33(s, 3H), 3.56(s, 3H), 3.78(s, 3H), 5.44(s, 2H), 6.84(s, 1H), 7.21(d, J=8.7Hz, 1H), 7.31–7.46(m, 5H), 7.38(d, J=8.4Hz, 2H), 7.68(d, J=8.4Hz, 2H), 7.72(m, 1H)
IR(KBr)1610, 1519, 1481, 1365, 1177, 1149, 1079, 963, 876, 799 cm$^{-1}$

I-678 foam
$^1$HNMR(CDCl$_3$) δ 2.60(s, 3H), 2.75(s, 6H), 3.17(s, 3H), 3.21(s, 3H), 3.55(s, 3H), 3.78(s, 3H), 5.31(s, 2H), 6.83(s, 1H), 7.08(dd, J=7.5, 7.5Hz, 1H), 7.16(d, J=8.4Hz, 1H), 7.17(d, J=7.5Hz, 1H), 7.30(dd, J=2.1, 8.4Hz, 1H), 7.32(dd, J=7.5, 7.5Hz, 1H), 7.37(d, J=8.4Hz, 2H), 7.38(d, J=2.1Hz, 1H), 7.52(d, J=7.5Hz, 1H), 7.68(d, J=8.4Hz, 2H)
IR(KBr)1609, 1519, 1480, 1365, 1235, 1177, 1151, 1079, 970, 874, 797 cm$^1$ I-679 m.p. 95–97° C.
$^1$HNMR(CDCl$_3$) δ 1.76(s, 3H), 1.80(s, 3H), 3.03(s, 3H), 3.21(s, 3H), 3.56(s, 3H), 3.75(s, 3H), 4.63(d, J=6.9Hz, 2H), 4.93(s, 2H), 5.51(m, 1H), 6.66(s, 1H), 7.05(d, J=8.4Hz, 1H), 7.09–7.17(m, 2H), 7.37(dd, J=2.4, 8.4Hz, 1H), 7.44(d, J=2.4Hz, 1H), 7.51–7.58(m, 2H)
IR(KBr)3435, 2936, 1605, 1519, 1475, 1382, 1365, 1232, 1161, 1109, 1080 cm$^{-1}$

TABLE 134

I-680 m.p. 142–144° C.
$^1$HNMR(CDCl$_3$) δ 1.76(s, 3H), 1.81(s, 3H), 3.07(s, 3H), 3.57(s, 3H), 3.74(s, 3H), 4.61(d, J=6.6Hz, 2H), 4.90(s, 2H), 5.51(m, 1H), 5.65(s, 1H), 6.66(s, 1H), 6.92(m, 2H), 7.03(m, 1H), 7.09–7.17(m, 2H), 7.52–7.58(m, 2H)
IR(KBr)3455, 2964, 2932, 1606, 1583, 1519, 1479, 1387, 1283, 1227, 1153, 1115, 1080, 1094, 1004cm$^{-1}$

I-681 m.p. 158–160° C.
$^1$HNMR(CDCl$_3$) δ 1.76(s, 3H), 1.81(s, 3H), 3.20(s, 3H), 3.42(s, 3H), 3.76(s, 3H), 4.63(d, J=6.6Hz, 2H), 5.51(m, 1H), 6.04(s, 1H), 6.43(s, 1H), 7.07(d, J=8.4Hz, 1H), 7.11–7.19(m, 2H), 7.42(dd, J=2.1, 8.4Hz, 1H), 7.50(d, J=2.1Hz, 1H), 7.58–7.65(m, 2H)
IR(KBr)3505, 3440, 1613, 1522, 1489, 1386, 1352, 1292, 1227, 1109, 1013cm$^{-1}$

I-682 m.p. 175–178° C.
$^1$HNMR(CDCl$_3$) δ 1.63(s, 3H), 1.92–2.13(m, 4H), 3.22(s, 3H), 3.42(s, 3H), 3.76(s, 3H), 4.13(t, J=6.3Hz, 2H), 6.04(s, 1H), 6.44(s, 1H), 7.06 (d, J=8.4Hz, 1H), 7.11–7.19(m, 2H), 7.43(dd, J=2.1, 8.4Hz, 1H), 7.49(d, J=2.1Hz, 1H), 7.57–7.65(m, 2H)
IR(KBr)3467, 2973, 2943, 1613, 1523, 1489, 1359, 1232, 1113, 1072cm$^{-1}$

I-683 powder
$^1$HNMR(CDCl$_3$) δ 1.69(s, 3H), 1.75(s, 3H), 2.48–2.57(m, 2H), 3.08(s, 3H), 3.57(s, 3H), 3.74(s, 3H), 4.06(t, J=6.9Hz, 2H), 4.90(s, 2H), 5.22 (m, 1H), 5.64(s, 1H), 6.66(s, 1H), 6.91(m, 2H), 7.03(m, 1H), 7.08–7.17(m, 2H), 7.52–7.59(m, 2H)
IR(KBr)3432, 2930, 1604, 1583, 1518, 1475, 1382, 1280, 1249, 1222, 1160, 1111, 1082cm$^{-1}$ I-684 m.p. 151–153° C.
$^1$HNMR(CDCl$_3$) δ 1.69(s, 3H), 1.73(s, 3H), 2.50–2.59(m, 2H), 3.19(s, 3H), 3.42(s, 3H), 3.76(s, 3H), 4.06(t, J=6.9Hz, 2H), 5.21(m, 1H), 6.02 (s, 1H), 6.43(s, 1H), 7.05(d, J=8.4Hz, 1H), 7.11–7.19(m, 2H), 7.42(dd, J=2.4, 8.4Hz, 1H), 7.50(d, J=2.4Hz, 1H), 7.57–7.65(m, 2H)
IR(KBr)3457, 2937, 1613, 1523, 1489, 1465, 1390, 1361, 1295, 1234, 1185, 1110, 1072, 1013cm$^{-1}$

TABLE 135

I-685 m.p. 156–158° C.
$^1$HNMR(CDCl$_3$) δ 1.76(s, 3H), 1.81(s, 3H), 3.21(s, 3H), 3.42(s, 3H), 3.76(s, 3H), 4.54(d, J=6.9Hz, 2H), 5.52(t, J=6.9Hz, 1H), 6.94(s, 1H), 6.94(d, J=8.7Hz, 2H), 7.29(d, J=8.7Hz, 2H), 7.37(d, J=8.7Hz, 2H), 7.71(d, J=8.7Hz, 2H)
IR(KBr)1734, 1517, 1464, 1360, 1237, 1150, 1061, 988, 862cm$^{-1}$

I-686 m.p. 189–191° C.
$^1$HNMR(CDCl$_3$) δ 3.21(s, 3H), 3.21(s, 3H), 3.42(s, 3H), 3.61(s, 3H), 3.76(s, 3H), 5.09(s, 2H), 6.94(s, 1H), 7.10(d, J=8.4Hz, 2H), 7.28–7.48 (m, 9H), 7.71(d, J=8.4Hz, 2H)
IR(KBr)1727, 1518, 1469, 1365, 1239, 1152, 1061, 865cm$^{-1}$

I-687 m.p. 112–113° C.
$^1$HNMR(CDCl$_3$) δ 1.68(s, 3H), 1.74(s, 3H), 2.50(q, J=7.2Hz, 2H), 3.21(s, 3H), 3.42(s, 3H), 3.62(s, 3H), 3.76(s, 3H), 3.96(t, J=7.2Hz, 2H), 5.23 (t, J=7.2Hz, 1H), 6.92(d, J=8.8Hz, 2H), 6.93(s, 1H), 7.28(d, J=8.8Hz, 2H), 7.37(d, J=8.8Hz, 2H), 7.71(d, J=8.8Hz, 2H)
IR(KBr)1735, 1519, 1469, 1361, 1246, 1153, 1059, 877, 861, 847, 791cm$^{-1}$

I-688 m.p. 191–193° C.
$^1$HNMR(DMSO-d$_6$) δ 1.73(s, 3H), 1.76(s, 3H), 3.31(s, 3H), 3.71(s, 3H), 4.54(d, J=6.9Hz, 2H), 5.46(t, J=6.9Hz, 1H),(s, 1H), 6.87(d, J=8.7Hz, 2H), 6.91(s, 1H), 6.92(d, J=8.7Hz, 2H), 7.19(d, J=8.7Hz, 2H), 7.48(d, J=8.7Hz, 2H), 9.59(s, 1H), 12.8(brs, 1H)
IR(KBr)3462, 1695, 1609, 1520, 1472, 1231, 1177, 1062, 1001, 837cm$^{-1}$ I-689 m.p. 229–232° C.
$^1$HNMR(DMSO-d$_6$) δ 3.31(s, 3H), 3.71(s, 3H), 5.12(s, 2H), 6.87(d, J=8.8Hz, 2H), 6.98(s, 1H), 7.01(d, J=8.8Hz, 2H), 7.21(d, J=8.8Hz, 2H), 7.34–7.50(m, 7H), 9.58(s, 1H), 12.8(brs, 1H)
IR(KBr)3424, 3238, 1685, 1610, 1521, 1464, 1379, 1235, 1180, 1057, 1001, 826cm$^{-1}$

TABLE 136

I-690 m.p. 171–172° C.
$^1$HNMR(DMSO-d$_6$) δ 1.64(s, 3H), 1.70(s, 3H), 2.43(q, J=6.9Hz, 2H), 3.31(s, 3H), 3.70(s, 3H), 3.96(t, J=6.9Hz, 2H), 5.23(t, J=6.9Hz, 1H), 6.87 (d, J=8.8Hz, 2H), 6.91(d, J=8.8Hz, 2H), 6.98(s, 1H), 7.19(d, J=8.8Hz, 2H), 7.48(d, J=8.8Hz, 2H), 9.58(s, 1H), 12.8(brs, 1H)
IR(KBr)3402, 3266, 1689, 1612, 1521, 1470, 1376, 1241, 1181, 1063, 1001, 829cm$^{-1}$ I-691 mp 191–193° C.
$^1$HNMR(CDCl$_3$) δ 2.55(s, 3H), 3.52(s, 3H), 3.77(s, 3H), 5.17(s, 2H), 5.70(s, 1H), 6.83(s, 1H), 6.91(dd, J=1.8, 8.1Hz, 1H), 7.00–7.05

TABLE 136-continued

I-692
(m, 2H), 7.10–7.19(m, 2H), 7.34–7.45(m, 5H), 7.57–7.65(m, 2H)
IR(KBr)3030, 2934, 1606, 1523, 1487, 1391, 1358, 1290, 1228, 1077, 1019, 947, 831, 815, 803cm$^{-1}$

I-692 mp 172–173° C.
$^1$HNMR(CDCl$_3$) δ 2.47(s, 3H), 3.52(s, 3H), 3.53(s, 3H), 3.77(s, 3H), 5.21(s, 2H), 5.25(s, 2H), 6.82(s, 1H), 7.01–7.03(m, 2H), 7.11–7.18 (m, 2H), 7.22–7.41(m, 6H), 7.57–7.63(m, 2H)
IR(KBr)3010, 2931, 1602, 1519, 1484, 1385, 1369, 1232, 1174, 1085, 847, 806, 729, 527cm$^{-1}$

I-693 mp 129–132° C.
$^1$HNMR(CDCl$_3$) δ 3.44(s, 3H), 3.53(s, 3H), 3.75(s, 3H), 5.20(s, 2H), 5.26(s, 2H), 5.91(s, 1H), 6.44(s, 1H), 7.01(d, J=8.1Hz, 1H), 7.08(dd, J=1.8Hz, 8.1Hz, 1H), 7.11–7.18(m, 2H), 7.28–7.50(m, 6H), 7.57–7.64(m, 2H)
IR(KBr)2996, 2952, 2932, 2895, 1609, 1522, 1488, 1229, 1120, 1075, 999, 911, 815, 724, 582cm$^{-1}$

I-694 mp 124–126° C.
$^1$HNMR(CDCl$_3$) δ 1.76(d, J=0.6Hz, 3H), 1.80(d, J=0.9Hz, 3H), 2.69(2H, s), 3.54(s, 3H), 3.57(s, 3H), 3.76(s, 3H), 4.64(d, J=6.6Hz, 2H), 5.26(s, 3H), 5.54(m, 1H), 6.86(s, 1H), 6.98(d, J=8.7Hz, 1H), 7.13–7.25(m, 3H), 7.38–7.43(m, 3H)
IR(CHCl$_3$)2935, 2855, 1675, 1603, 1520, 1481, 1387, 1370, 1247, 1178, 1158, 1134, 1081, 1003, 961, 839, 814cm$^{-1}$

TABLE 137

I-695 mp 141–142° C.
$^1$HNMR(CDCl$_3$) δ 2.34(s, 3H), 2.48(s, 3H), 5.16(s, 2H), 5.70(s, 1H), 6.82(dd, J=8.4, 2.1Hz, 1H), 6.97–7.00(m, 2H), 7.07–7.13 (m, 4H), 7.32–7.46(m, 7H)
IR(CHCl$_3$)3543, 3023, 2871, 1604, 1587, 1520, 1489, 1469, 1383, 1267, 1243, 1158, 1126, 1014, 957, 877, 839cm$^{-1}$

I-696 mp 178–180° C.
$^1$HNMR(CDCl$_3$) δ 2.75(s, 3H), 3.18(s, 3H), 3.55(s, 3H), 3.76(s, 3H), 5.18(s, 2H), 5.72(s, 1H), 6.87(s, 1H), 7.00(d, J=8.7Hz, 1H), 7.15(dd, J=8.7, 2.1Hz, 1H), 7.24–7.28(m, 2H), 7.36–7.50(m, 8H)
IR(CHCl$_3$)3543, 3027, 2939, 1519, 1481, 1371, 1330, 1254, 1204, 1177, 1150, 1082, 1005, 969, 873cm$^{-1}$

I-697 mp 129–130° C.
$^1$HNMR(CDCl$_3$) δ 2.24(s, 3H), 2.29(s, 3H), 3.12(s, 3H), 5.18(s, 2H), 7.08–7.14(m, 5H), 7.25–7.50(m, 9H)
IR(CHCl$_3$)2925, 2871, 1604, 1520, 1490, 1455, 1369, 1291, 1262, 1169, 1111, 1007, 972, 957, 882, 840, 816cm$^{-1}$

I-698 mp 124–125° C.
$^1$HNMR(CDCl$_3$) δ 1.77(s, 3H), 1.81–1.82(d, J=0.9Hz, 3H), 2.24(s, 3H), 2.28(s, 3H), 3.22(s, 3H), 4.63(d, J=6.6Hz, 2H), 5.52(m, 1H), 7.04–7.14(m, 5H), 7.24–7.34(m, 4H)
IR(KBr)2978, 2924, 2868, 1893, 1771, 1604, 1520, 1489, 1368, 1290, 1261, 1169, 1109, 1046, 973, 957, 882, 740, 816cm$^{-1}$

I-699 oil
$^1$HNMR(CDCl$_3$) δ 1.69(s, 3H), 1.74–1.75(d, J=0.9Hz, 3H), 2.24(s, 3H), 2.28(s, 3H), 2.55(m, 2H), 3.21(s, 3H), 4.05–4.10 (t, J=6.9Hz, 2H), 5.22(m, 1H), 7.03–7.14(m, 5H), 7.24–7.34(m, 4H)
IR(CHCl$_3$)2970, 2926, 2875, 1605, 1520, 1490, 1470, 1368, 1292, 1277, 1169, 1110, 1016, 973, 958, 878, 840, 819cm$^{-1}$ I-700 mp 121–123° C.
$^1$HNMR(CDCl$_3$) δ 2.24(s, 3H), 2.83(s, 3H), 2.98(s, 3H), 3.11(s, 3H), 5.13(s, 2H), 7.08–7.14(m, 4H), 7.21–7.37(m, 9H)
IR(CHCl$_3$)2925, 1605, 1520, 1489, 1369, 1262, 1169, 1014, 1003, 972, 957, 882, 840, 816cm$^{-1}$

TABLE 138

I-701 mp 215–217° C.
$^1$H NMR(CDCl$_3$) δ 2.73(s, 3H), 3.13(s, 3H), 3.18(s, 3H), 3.57(s, 3H), 3.78(s, 3H), 5.20(s, 2H), 6.86(s, 1H), 7.16(d, J=8.7Hz, 1H), 7.35–7.50(m, 9H), 7.56(dd, J=8.4, 2.4Hz, 1H), 7.62(d, J=2.4Hz, 1H)
IR(CHCl$_3$) 2939, 1613, 1519, 1480, 1371, 1294, 1254, 1176, 1150, 1119, 1083, 1003, 970, 871, 849, 816cm$^{-1}$

I-702 mp 71–73° C.
$^1$H NMR(CDCl$_3$) δ 1.77(s, 3H), 1.83(s, 3H), 2.24(s, 3H), 2.29(s, 3H), 4.61–4.64(d, J=6.9Hz, 2H), 5.54(m, 1H), 5.71(s, 1H), 6.80–6.84(dd, J=8.4, 2.1Hz, 1H), 6.92(d, J=8.4Hz, 1H), 7.07–7.13(m, 4H), 7.30–7.35(m, 2H)
IR(KBr) 3537, 2977, 2924, 2868, 1604, 1585, 1520, 1489, 1450, 1386, 1292, 1267, 1242, 1158, 1125, 996, 957, 839cm$^{-1}$

I-703 oil
$^1$H NMR(CDCl$_3$) δ 1.69(s, 3H), 1.75–1.76(d, J=0.9Hz, 3H), 2.24(s, 3H), 2.28(s, 3H), 2.50–2.57(td, J=6.9, 6.3Hz, 2H), 4.05–4.10(t, J=6.3Hz, 2H), 5.24(m, 1H), 5.70(s, 1H), 6.81(dd, J=8.4, 1.8Hz, 1H), 6.90(d, J=8.4Hz, 1H), 6.96(d, J=1.8Hz, 1H), 7.06–7.13(m, 4H), 7.26–7.34(m, 2H)
IR(CHCl$_3$) 3540, 2972, 2925, 2877, 1604, 1585, 1520, 1490, 1387, 1293, 1267, 1245, 1158, 1127, 1016, 957, 839cm$^{-1}$ I-704 mp 113–115° C.
$^1$H NMR(CDCl$_3$) δ 2.24(s, 3H), 2.28(s, 3H), 2.39(s, 3H), 5.11(s, 2H), 5.69(s, 1H), 6.82(dd, J=8.4, 2.4Hz, 1H), 6.97–7.00 (m, 2H), 7.07–7.13(m, 3H), 7.22–7.36(m, 7H)
IR(CHCl$_3$) 3541, 2925, 2871, 1604, 1586, 1520, 1490, 1469, 1380, 1324, 1308, 1292, 1267, 1243, 1201, 1158, 1126, 1013, 957, 876, 839cm$^{-1}$

TABLE 139

I-705 foam
$^1$H NMR(CDCl$_3$) δ 3.20(s, 3H), 3.27(s, 3H), 3.43(s, 3H), 3.73(s, 3H), 4.37(br d, J=5.7Hz, 2H), 4.58(s, 2H), 5.16(s, 2H), 5.68(s, 1H), 6.82(dd, J=8.2, 1.7Hz, 1H), 6.88(s, 1H), 6.97(d, J=1.7Hz, 1H), 6.98(d, J=8.2Hz, 1H), 7.35–7.47(m, 7H), 7.71(d, J=8.7Hz, 2H)
IR(KBr) 3464, 1515, 1474, 1369, 1230, 1199, 1176, 1149, 1039, 873cm$^{-1}$ I-706 foam
$^1$H NMR(CDCl$_3$) δ 2.42(br s, 1H), 3.12(s, 3H), 3.22(s, 3H), 3.45(s, 3H), 3.74(s, 3H), 4.49(br s, 1H), 5.18(s, 2H), 6.85(s, 1H), 7.15(d, J=8.6Hz, 1H), 7.27(dd, J=8.6, 2.0Hz, 1H), 7.35–7.50(m, 8H), 7.71(d, J=8.6Hz, 2H)
IR(KBr) 3583, 3435, 1519, 1467, 1412, 1229, 1180, 1150, 1022, 875, 849, 798, 742, 706cm$^{-1}$ TABLE 139-continued I-707 mp 120–121° C.
$^1$H NMR(CDCl$_3$) δ 3.45(s, 3H), 3.45(s, 3H), 3.75(s, 3H), 4.66(s, 2H), 4.77(s, 2H), 5.15(s, 2H), 5.67(s, 1H), 5.91(s, 1H), 6.47(s, 1H), 6.96(dd, J=8.4, 1.9Hz, 1H), 7.03(d, J=8.4Hz, 1H), 7.09(d, J=1.9Hz, 1H), 7.37–7.47(m, 7H), 7.64(d, J=8.4Hz, 2H)
IR(KBr) 3504, 3461, 1522, 1485, 1466, 1384, 1466, 1384, 1283, 1245, 1197, 1110, 1042, 925, 812, 749cm$^{-1}$ I-708 mp 156–158° C.
$^1$H NMR(CDCl$_3$) δ 3.11(s, 3H), 3.21(s, 3H), 3.28(s, 3H), 3.42(s, 3H), 3.73(s, 3H), 4.38(s, 2H), 4.58(s, 2H), 5.18(s, 2H), 6.88(s, 1H), 7.12(d, J=8.7Hz, 1H), 7.27(dd, J=8.7, 2.1Hz, 1H), 7.35–7.50(m, 8H), 7.70(d, J=8.7Hz, 2H)
IR(KBr) 1514, 1469, 1360, 1177, 1149, 1099, 1042, 870cm$^{-1}$ I-709 mp 188–190° C.
$^1$H NMR(CDCl$_3$) δ 1.70(t, J=5.7Hz, 1H), 3.45(s, 3H), 3.75(s, 3H), 4.77(d, J=5.7Hz, 2H), 5.16(s, 2H), 5.68(s, 1H), 5.91(s, 1H), 6.47(s, 1H), 6.96(dd, J=8.5, 1.7Hz, 1H), 7.03(d, J=8.5Hz, 1H), 7.09(d, J=1.7Hz, 1H), 7.37–7.48(m, 7H), 7.65(d, J=8.4Hz, 2H)
IR(KBr) 3547, 3492, 3451, 1521, 1487, 1385, 1288, 1249, 1209, 1108, 1011, 746, 702cm$^{-1}$

TABLE 140

I-710 mp 178–180° C.
$^1$H NMR(CDCl$_3$) δ 2.43(br s, 1H), 3.44(s, 3H), 3.72(s, 3H), 4.52(m, 2H), 4.93(s, 1H), 5.15(s, 2H), 5.70(s, 1H), 6.79(dd, J=8.1, 2.1Hz, 1H), 6.84(s, 1H), 6.92(d, J=8.7Hz, 2H), 6.93(d, J=2.1Hz, 1H), 7.00(d, J=8.7Hz, 1H), 7.38–7.48(m, 5H), 7.54(d, J=9.0Hz, 2H)
IR(KBr) 3447, 3214, 1609, 1518, 1477, 1459, 1391, 1260, 1221, 1008, 984, 833, 799, 751cm$^{-1}$

I-711 foam
$^1$H NMR(CDCl$_3$) δ 2.85(s, 3H), 3.22(s, 3H), 3.30(s, 3H), 3.54(s, 3H), 3.78(s, 3H), 5.02(s, 2H), 6.85(s, 1H), 7.08(d, J=8.4Hz, 1H), 7.32(d, J=2.1Hz, 1H), 7.37(dd, J=8.4, 2.1Hz, 1H), 7.39(d, J=8.7Hz, 2H), 7.67(d, J=8.7Hz, 2H)
IR(Nujol) 3423, 3320, 3215, 1610, 1519, 1480, 1454, 1176, 1151, 1080, 969, 876, 798cm$^{-1}$ I-712 foam
$^1$H NMR(CDCl$_3$) δ 2.62(s, 3H), 3.45(s, 3H), 3.74(s, 3H), 5.28(s, 2H), 6.45(s, 1H), 6.92(d, J=8.7Hz, 2H), 6.95(dd, J=8.4, 2.1Hz, 1H), 7.10(d, J=8.4Hz, 1H), 7.11(d, J=2.1Hz, 1H), 7.53(d, J=8.7Hz, 2H), 8.50(brs, 1H), 8.60(brs, 1H)
IR(Nujol) 3207, 1611, 1589, 1523, 1489, 1460, 1227, 1116, 1072, 1014, 943, 822, 759cm$^{-1}$ I-713 mp 231–233° C.
$^1$H NMR(CDCl$_3$) δ 3.30(s, 3H), 3.64(s, 3H), 5.28(s, 2H), 6.39(s, 1H), 6.67(dd, J=8.4, 2.1Hz, 1H), 6.80(d, J=2.1Hz, 1H), 6.84(d, J=8.7Hz, 2H), 7.01(d, J=8.4Hz, 1H), 7.44(d, J=8.7Hz, 2H), 8.64(d, J=2.4Hz, 1H), 8.67(dd, J=2.4, 1.2Hz, 1H), 8.94(d, J=1.2Hz, 1H)
IR(Nujol) 3369, 3164, 1612, 1600, 1585, 1522, 1493, 1385, 1255, 1118, 1073, 1013, 934, 824, 798, 778cm$^{-1}$ I-714 foam
$^1$H NMR(CDCl$_3$) δ 2.83(s, 3H), 3.22(s, 3H), 3.27(s, 3H), 3.55(s, 3H), 3.78(s, 3H), 5.18(s, 2H), 6.85(s, 1H), 7.20(d, J=8.4Hz, 1H), 7.39(d, J=8.7Hz, 2H), 7.40(dd, J=8.4, 2.1Hz, 1H), 7.45(d, J=2.1Hz, 1H), 7.67(d, J=8.7Hz, 2H)
IR(Nujol) 3264, 1650, 1607, 1517, 1480, 1175, 1150, 1078, 946, 876, 798cm$^{-1}$

TABLE 141

I-715 foam
$^1$H NMR(CDCl$_3$) δ 2.76(s, 3H), 2.77(s, 3H), 3.21(s, 3H), 3.24(s, 3H), 3.55(s, 3H), 3.78(s, 3H), 5.35(s, 2H), 6.84(s, 1H), 7.25(d, J=8.4Hz, 1H), 7.38(d, J=8.7Hz, 2H), 7.38(dd, J=8.4, 2.1Hz, 1H), 7.44(d, J=2.1Hz, 1H), 7.68(d, J=8.7Hz, 2H)
IR(Nujol) 1607, 1578, 1519, 1465, 1176, 1151, 1079, 971, 947, 876, 846, 797cm$^{-1}$ I-716 mp 227–229° C.
$^1$H NMR(DMSO-d$_6$) δ 2.87(s, 3H), 3.39(s, 3H), 3.45(s, 3H), 3.52(s, 3H), 3.79(s, 3H), 5.23(s, 2H), 7.08(s, 1H), 7.33(d, J=2.1Hz, 1H), 7.35(dd, J=8.4, 2.1Hz, 1H), 7.44(d, J=8.4Hz, 1H), 7.49(d, J=8.7Hz, 2H), 7.74(d, J=8.7Hz, 2H)
IR(Nujol) 3276, 1651, 1605, 1520, 1480, 1463, 1174, 1150, 1079, 947, 879, 798cm$^{-1}$ I-717 m.p 180–181° C.
$^1$H NMR(CDCl$_3$) δ 3.07(s, 3H), 3.45(s, 3H), 3.75(s, 3H), 5.18(s, 2H), 6.45(s, 1H), 6.92(d, J=8.7Hz, 2H), 6.99(dd, J=1.8, 8.4Hz, 1H), 7.08(d, J=1.8Hz, 1H), 7.10(d, J=8.4Hz, 1H), 7.25(t, J=7.2Hz, 1H), 7.44(m, 2H), 7.53(d, J=8.7Hz, 2H), 7.61(d, J=8.1Hz, 1H)

I-718 foam
$^1$H NMR(CDCl$_3$) δ 3.06(s, 3H), 3.45(s, 3H), 3.74(s, 3H), 5.17(s, 2H), 6.45(s, 1H), 6.93(d, J=8.7Hz, 2H), 6.98(dd, J=8.7Hz, 1H), 7.08(d, J=2.1Hz, 1H), 7.10(d, J=8.4Hz, 1H), 7.24(m, 1H), 7.43(m, 2H), 7.51(d, J=8.7Hz, 2H), 7.61(m, 1H)
IR(KBr) 3430, 1611, 1590, 1523, 1490, 1402, 1323, 1242, 1149, 1112, 1070, 1010, 971, 826cm$^{-1}$ I-719 foam
$^1$H NMR(CDCl$_3$) δ 2.80(s, 6H), 3.47(s, 3H), 3.76(s, 3H), 5.08(s, 2H), 6.46(s, 1H), 6.92(d, J=8.7Hz, 3H), 7.10(d, J=2.1Hz, 1H), 7.15(d, J=8.7Hz, 1H), 7.20(d, J=7.2Hz, 1H), 7.34–7.45(m, 3H), 7.55(d, J=8.7Hz, 2H)
IR(KBr) 3427, 1611, 1585, 1522, 1488, 1404, 1224, 1113, 1069, 1011, 940, 824, 767cm$^{-1}$

TABLE 142

I-720 foam
$^1$H NMR(CDCl$_3$) δ 1.52(s, 9H), 2.67(s, 3H), 3.19(s, 3H), 3.21(s, 3H), 3.56(s, 3H), 3.78(s, 3H), 5.17(s, 2H), 6.54(br.s, 1H), 7.11(m, 1H), 7.12(d, J=9.0Hz, 1H), 7.25(m, 1H), 7.30(d, J=7.5Hz, 1H), 7.32(dd, J=1.8, 9.0Hz, 1H), 7.36(d, J=8.7Hz, 2H), 7.41(d, J=1.8Hz, 1H), 7.60(s, 1H), 7.67(d, J=8.7Hz, 2H)
IR(KBr) 1724, 1610, 1520, 1481, 1366, 1234, 1177, 1153, 1079, 969, 875, 797cm$^{-1}$

TABLE 142-continued

I-721 m.p 187–191° C.
$^1$H NMR(CDCl$_3$) δ 2.66(s, 3H), 3.17(s, 3H), 3.21(s, 3H), 3.55(s, 3H), 3.78(s, 3H), 5.11(s, 2H), 6.65(d, J=8.4Hz, 1H), 6.81(m, 2H), 6.84(s, 1H), 7.12(d, J=8.7Hz, 1H), 7.17(t, J=8.7Hz, 1H), 7.32(dd, J=2.1, 8.7Hz, 1H), 7.37(d, J=8.7Hz, 2H), 7.40(d, J=2.1Hz, 1H), 7.67(d, J=8.7Hz, 2H)
IR(KBr) 1624, 1606, 1519, 1481, 1361, 1176, 1148, 1081, 980, 876, 780cm$^{-1}$

I-722 m.p 143–146° C.
$^1$H NMR(CDCl$_3$) δ 2.18(s, 3H), 2.71(s, 3H), 3.18(s, 3H), 3.21(s, 3H), 3.55(s, 3H), 3.78(s, 3H), 5.18(s, 2H), 6.84(s, 1H), 7.12(d, J=8.7Hz, 1H), 7.17(d, J=7.2Hz, 1H), 7.33(m, 2H), 7.37(d, J=8.7Hz, 2H), 7.41(d, J=2.1Hz, 1H), 7.45(d, J=7.2Hz, 1H), 7.67(d, J=8.7Hz, 2H), 7.67(m, 1H)
IR(KBr) 1693, 1609, 1519, 1481, 1364, 1364, 1173, 1149, 1079, 874, 802cm$^{-1}$

I-723 foam
$^1$H NMR(CDCl$_3$) δ 2.86(s, 3H), 3.00(s, 3H), 3.22(s, 3H), 3.55(s, 3H), 3.78(s, 3H), 5.22(s, 2H), 6.59(s, 1H), 6.85(s, 1H), 7.10(d, J=8.4Hz, 1H), 7.25(m, 3H), 7.32(d, J=2.1, 8.7Hz, 1H), 7.37(m, 1H), 7.38(d, J=2.1Hz, 1H), 7.38(d, J=8.7Hz, 1H), 7.67(d, J=8.7Hz, 2H)
IR(KBr) 1610, 1519, 1480, 1364, 1176, 1150, 1079, 971, 876, 797cm$^{-1}$

TABLE 143

I-724 foam
$^1$H NMR(CDCl$_3$) δ 2.74(s, 3H), 3.18(s, 3H), 3.21(s, 3H), 3.43(s, 6H), 3.55(s, 3H), 3.78(s, 3H), 5.24(s, 2H), 6.84(s, 1H), 7.13(d, J=8.4Hz, 1H), 7.36(dt, J=2.1, 8.4Hz, 1H), 7.37(m, 1H), 7.39(d, J=8.7Hz, 2H), 7.40(d, J=2.1Hz, 1H), 7.51(m, 2H), 7.61(s, 1H), 7.67(d, J=8.7Hz, 2H)
IR(KBr) 1609, 1523, 1481, 1353, 1176, 1161, 1080, 890, 799cm$^{-1}$ I-725 m.p 147–150° C.
$^1$H NMR(CDCl$_3$) δ 2.79(s, 3H), 2.83(s, 3H), 3.20(s, 3H), 3.21(s, 3H), 3.35(s, 3H), 3.55(s, 3H), 3.78(s, 3H), 5.22(s, 2H), 6.85(s, 1H), 7.11(d, J=8.7Hz, 1H), 7.32–7.46(m, 7H), 7.62(s, 1H), 7.67(d, J=8.4Hz, 2H)
IR(KBr) 1608, 1518, 1480, 1364, 1178, 1153, 1077, 968, 795cm$^{-1}$ I-726 m.p 224–226° C.
$^1$H NMR(CDCl$_3$) δ 2.85(s, 3H), 2.91(s, 6H), 3.36(s, 3H), 3.45(s, 3H), 3.51(s, 3H), 3.78(s, 3H), 5.19(s, 2H), 6.69(d, J=8.1Hz, 1H), 6.76(d, J=8.1Hz, 1H), 6.89(s, 1H), 7.07(s, 1H), 7.20(t, J=8.1Hz, 1H), 7.30(m, 3H), 7.48(d, J=8.7Hz, 2H), 7.74(d, J=8.7Hz, 2H)
IR(KBr) 1608, 1519, 1480, 1360, 1178, 1146, 1081, 879, 826cm$^{-1}$ I-727 foam
$^1$H NMR(CDCl$_3$) δ 2.82(s, 3H), 3.18(s, 6H), 3.21(s, 3H), 3.53(s, 3H), 3.76(s, 3H), 5.17(s, 2H), 6.84(s, 1H), 7.11(d, J=8.4Hz, 1H), 7.20(d, J=4.8Hz, 1H), 7.30–7.47(m, 8H), 7.76(d, J=8.7Hz, 2H)
IR(KBr) 3430, 1677, 1609, 1519, 1481, 1364, 1202, 1177, 1150, 1079, 876, 799cm$^{-1}$ I-728 foam
$^1$H NMR(CDCl$_3$) δ 3.45(s, 3H), 3.75(s, 3H), 5.06(s, 2H), 6.45(s, 1H), 6.68(d, J=7.5Hz, 1H), 6.77(s, 1H), 6.82(d, J=7.5Hz, 1H), 6.91(d, J=8.7Hz, 2H), 6.93(dd, J=1.8, 8.4Hz, 1H), 6.99(d, J=8.4Hz, 1H), 7.07(d, J=1.8Hz, 1H), 7.19(t, J=7.5Hz, 1H), 7.54(d, J=8.7Hz, 2H)
IR(KBr) 3413, 1611, 1522, 1488, 1461, 1405, 1251, 1119, 1076, 1007, 813, 784cm$^{-1}$

TABLE 144

I-729 m.p 90–93° C.
$^1$H NMR(CDCl$_3$) δ 3.01(s, 3H), 3.45(s, 3H), 3.75(s, 3H), 5.16(s, 2H), 6.45(s, 1H), 6.81(s, 1H), 6.92(d, J=8.7Hz, 2H), 6.95(d, J=1.8Hz, 1H), 6.96(m, 2H), 7.24(m, 2H), 7.40(t, J=7.2Hz, 1H), 7.52(d, J=8.7Hz, 2H)
IR(KBr) 3434, 1612, 1592, 1523, 1489, 1325, 1248, 1224, 1147, 1113, 1070, 1010, 972cm$^{-1}$

I-730 mp 79–81° C.
$^1$H NMR(CDCl$_3$) δ 2.34(s, 6H), 3.48(s, 3H), 3.76(s, 3H), 4.72(brs, 1H), 5.16(s, 2H), 5.68(brs, 1H), 5.93(brs, 1H), 6.44(s, 1H), 6.99–7.10(m, 3H), 7.26–7.49(m, 7H)
IR(KBr) 3467, 2933, 1613, 1701, 1517, 1482, 1454, 1424, 1389, 1321, 1196, 1148, 1113, 1073cm$^{-1}$ I-731 mp 189–191° C.
$^1$H NMR(CDCl$_3$) δ 3.20(s, 3H), 3.81(s, 6H), 5.14(s, 2H), 5.65(brs, 1H), 6.79(s, 2H), 6.79–7.02(m, 5H), 7.36–7.46(m, 6H), 7.66(d, J=8.6Hz, 2H)
IR(KBr) 3439, 2937, 1594, 1567, 1523, 1487, 1351, 1240, 1202, 1146, 1126, 874cm$^{-1}$ I-732 mp 196–197° C.
$^1$H NMR(DMSO-d$_6$) δ 3.32(s, 3H), 3.43(s, 6H), 3.79(s, 6H), 5.24(s, 2H), 7.00(s, 2H), 7.23–7.30(m, 3H), 7.35–7.55(m, 7H), 7.88(d, J=8.4Hz, 2H)
IR(KBr) 3434, 1602, 1561, 1523, 1485, 1362, 1288, 1238, 1201, 1181, 1148, 1126, 1115, 966, 914, 813cm$^{-1}$ I-733 mp 202–203° C.
$^1$H NMR(DMSO-d$_6$) δ 2.40(s, 6H), 3.31(s, 3H), 3.34(s, 3H), 3.51(s, 3H), 3.58(s, 3H), 3.77(s, 3H), 5.27(s, 2H), 7.03(s, 1H), 7.32–7.530(m, 10H)
IR(KBr) 3434, 3028, 2944, 1515, 1475, 1463, 1361, 1290, 1272, 1247, 1179, 1085, 967, 815, 804cm$^{-1}$

TABLE 145

I-734 mp 140–141° C.
$^1$H NMR(CDCl$_3$) δ 1.77(s, 3H), 1.82(s, 3H), 3.21(s, 3H), 3.83(s, 6H), 4.63(d, J=4.6Hz, 2H), 5.52–5.53(m, 1H), 6.79(s, 2H), 7.05(d, J=8.8Hz, 1H), 7.29–7.42(m, 4H), 7.67(d, J=8.6Hz, 2H)
IR(KBr) 3434, 2936, 1602, 1565, 1487, 1365, 1242, 1182, 1152, 1123, 1113, 974, 874, 811cm$^{-1}$

TABLE 145-continued

I-735 mp 168–169° C.
$^1$H NMR(CDCl$_3$) δ 2.38(s, 3H), 3.09(s, 3H), 3.20(s, 3H), 3.81(s, 6H), 5.11(s, 2H), 6.78(s, 2H), 7.13–7.42(m, 9H), 7.66(d, J=8.8Hz, 2H)
IR(KBr) 3433, 1601, 1566, 1486, 1367, 1246, 1182, 1153, 1114, 973, 869, 824cm$^{-1}$

I-736 mp 192–194° C.
$^1$H NMR(CDCl$_3$) δ 1.77(s, 3H), 1.82(s, 3H), 2.47(s, 6H), 2.72(s, 3H), 3.24(s, 3H), 3.36(s, 3H), 3.57(s, 3H), 3.79(s, 3H), 4.64(d, J=6.6Hz, 2H), 5.47–5.55(m, 1H), 6.83(s, 1H), 7.09(d, J=9.0Hz, 1H), 7.33–7.40(m, 4H)
IR(KBr) 3435, 1942, 1516, 1474, 1382, 1357, 1288, 1178, 1096, 966, 862, 805cm$^{-1}$

I-737 mp 224–225° C.
$^1$H NMR(CDCl$_3$) δ 2.38(s, 3H), 2.46(s, 6H), 2.66(s, 3H), 3.12(s, 3H), 3.35(s, 3H), 3.55(s, 3H), 3.77(s, 3H), 5.14(s, 2H), 6.82(s, 1H), 7.12–7.40(m, 9H)
IR(KBr) 3435, 2941, 1518, 1474, 1360, 1274, 1179, 1095, 1085, 967, 862, 815, 805cm$^{-1}$

I-738 mp 203–204° C.
$^1$H NMR(CDCl$_3$) δ 1.76(s, 3H), 1.82(s, 3H), 2.46(s, 6H), 2.45–2.58(m, 2H), 2.73(s, 3H), 3.22(s, 3H), 3.35(s, 3H), 3.55(s, 3H), 3.77(s, 3H), 4.07(d, J=6.6Hz, 2H), 5.18–5.25(m, 1H), 6.82(s, 1H), 7.07(d, J=8.2Hz, 1H), 7.32–7.39(m, 4H)
IR(KBr) 3434, 2941, 1519, 1473, 1359, 1276, 1178, 1114, 1085, 967, 860, 811cm$^{-1}$

TABLE 146

I-739 mp 158–159° C.
$^1$H NMR(DMSO-d$_6$) δ 1.72(s, 3H), 1.76(s, 3H), 3.72(s, 6H), 4.54(d, J=6.0Hz, 2H), 5.45–5.52(m, 1H), 6.55–6.59(m, 2H), 6.84–6.90(m, 5H), 7.57(d, J=8.2Hz, 2H), 8.70(brs, 1H), 9.53(brs, 1H)
IR(KBr) 3465, 2932, 1610, 1523, 1487, 1460, 1283, 1281, 1123, 1010, 819cm$^{-1}$ I-740 mp 180–181° C.
$^1$H NMR(CDCl$_3$) δ 2.32(s, 3H), 3.72(s, 6H), 5.08(s, 2H), 6.54–6.58(m, 1H), 6.68(s, 1H), 6.85–6.95(m, 5H), 7.21(d, J=7.6Hz, 2H), 7.39(d, J=7.8Hz, 2H), 7.57(d, J=8.4Hz, 2H), 8.83(brs, 1H), 9.54(brs, 1H)
IR(KBr) 3519, 2937, 1607, 1562, 1523, 1461, 1400, 1246, 1176, 1125, 1003, 821cm$^{-1}$ I-741 mp 105–106° C.
$^1$H NMR(CDCl$_3$) δ 2.13(s, 6H), 3.17(s, 3H), 5.16(s, 2H), 5.85(brs, 1H), 6.61–6.66(m, 1H), 6.77(s, 1H), 7.01(d, J=8.2Hz, 1H), 7.25–7.46(m, 9H), 7.65(d, J=8.8Hz, 2H)
IR(KBr) 3466, 3031, 2934, 1585, 1513, 1476, 1366, 1285, 1198, 1175, 1148, 1127, 1014, 968, 868, 840cm$^{-1}$ I-742 mp 92–93° C.
$^1$H NMR(DMSO-d$_6$) δ 1.74(s, 3H), 1.78(s, 3H), 2.24(s, 6H), 3.31(s, 3H), 3.65(s, 3H), 4.56(d, J=6.8Hz, 2H), 5.52(t, J=6.0Hz, 1H), 6.37(s, 1H), 6.64–6.76(m, 2H), 6.88–6.93(m, 1H), 7.16–7.20(m, 2H), 8.31(brs, 1H), 8.45(brs, 1H), 8.73(brs, 1H)
IR(KBr) 3443, 2932, 1707, 1613, 1516, 1484, 1462, 1387, 1280, 1243, 1196, 1114, 1074, 979cm$^{-1}$ I-743 mp 180–181° C.
$^1$H NMR(DMSO-d$_6$) δ 2.22(s, 6H), 2.32(s, 3H), 3.29(s, 3H), 3.63(s, 3H), 5.08(s, 2H), 6.61–6.65(m, 1H), 6.75(s, 1H), 6.93 (d, J=8.2Hz, 1H), 7.13–7.22(m, 4H), 7.39(d, J=7.4Hz, 2H), 8.30(brs, 1H), 8.44(brs, 1H), 8.84(brs, 1H)
IR(KBr) 3443, 2930, 1686, 1614, 1587, 1518, 14863, 1462, 1385, 1281, 1246, 1197, 1113, 1073, 1009, 806cm$^{-1}$

TABLE 147

I-744 mp 123–124° C.
$^1$H NMR(DMSO-d$_6$) δ 1.65(s, 3H), 1.71(s, 3H), 2.23(s, 6H), 2.36–2.51(m, 2H), 3.31(s, 3H), 3.64(s, 3H), 3.91–3.98(m, 2H), 5.22–5.28(m, 1H), 6.36(s, 1H), 6.65–6.88(m, 3H), 7.16(s, 1H), 8.30(brs, 1H), 8.44(brs, 1H), 8.70(brs, 1H)
IR(KBr) 3444, 2930, 1686, 1613, 1518, 1483, 1390, 1283, 1248, 1198, 1113, 1074, 1013cm$^{-1}$ I-745 mp 174–177° C.
$^1$H NMR(CDCl$_3$) δ 1.77–1.78(d, J=0.9Hz, 3H), 1.82–1.83(d, J=0.9Hz, 3H), 2.74(s, 3H), 3.18(s, 3H), 3.25(s, 3H), 3.57 (s, 3H), 3.78(s, 2H), 4.64–4.67(d, J=6.9Hz, 2H), 5.51(m, 1H), 6.86(s, 1H), 7.09(d, J=8.4Hz, 1H), 7.35–7.40(m, 2H), 7.45–7.49(m, 2H), 7.55–7.60(m, 2H)
IR(CHCl$_3$) 2939, 1613, 1519, 1480, 1371, 1331, 1292, 1251, 1176, 1150, 1118, 1082, 971, 871, 849cm$^{-1}$ I-746 mp 134–136° C.
$^1$H NMR(CDCl$_3$) δ 1.69(s, 3H), 1.75(s, 3H), 2.53–2.60(dt, J=6.6, 5.7Hz, 2H), 2.73(s, 3H), 3.18(s, 3H), 3.23(s, 3H), 3.56 (s, 3H), 3.78(s, 3H), 4.07–4.11(t, J=5.7Hz, 2H), 5.22(m, 1H), 6.86(s, 1H), 7.07(d, J=9.0Hz, 1H), 7.35–7.40(m, 2H), 7.45–7.49(m, 2H), 7.55–7.61(m, 2H)
IR(CHCl$_3$) 2938, 1614, 1519, 1480, 1448, 1371, 1331, 1294, 1228, 1176, 1150, 1119, 1083, 1004, 970, 870, 849, 819cm$^{-1}$ I-747 mp 182–183° C.
$^1$H NMR(CDCl$_3$) δ 2.26(s, 3H), 2.28(s, 3H), 4.74(s, 1H), 5.16(s, 2H), 5.69(s, 1H), 6.81–6.89(m, 3H), 6.96–6.99(m, 2H), 7.10–7.12(d, J=4.8Hz, 2H), 7.23–7.26(m, 2H), 7.39–7.45(m, 5H)
IR(CHCl$_3$) 3597, 3543, 2924, 2871, 1611, 1587, 1522, 1490, 1455, 1382, 1171, 1126, 1012, 836cm$^{-1}$ I-748 mp 158–161° C.
$^1$H NMR(CDCl$_3$) δ 2.38(s, 3H), 2.74(s, 3H), 3.12(s, 3H), 3.18(s, 3H), 3.57(s, 3H), 3.78(s, 3H), 5.15(s, 2H), 6.86(s, 1H), 7.16(d, J=8.7Hz, 1H), 7.21–7.24(d, J=7.8Hz, 1H), 7.35–7.40(m, 5H), 7.45–7.49(m, 2H), 7.52–7.62(m, 2H)
IR(CHCl$_3$) 2939, 1732, 1614, 1519, 1480, 1331, 1294, 1253, 1176, 1150, 1119, 1082, 1003, 970, 869, 816cm$^{-1}$

TABLE 148

I-749 mp 174–176° C.
$^1$H NMR(CDCl$_3$) δ 1.75(s, 3H), 1.79(s, 3H), 2.58(s, 3H), 3.52(s, 3H), 3.53(s, 3H), 3.78(s, 3H), 4.62(d, J=6.9Hz, 2H), 5.48–5.55(m, 1H), 6.83(s, 1H), 6.99(d, J=8.7Hz, 1H), 7.09(dd, J=1.8, 8.1Hz, 1H), 7.11–7.19(m, 2H), 7.22(d, J=1.8Hz, 1H), 7.57–7.65(m, 2H)
IR(KBr) 2932, 1602, 1519, 1485, 1385, 1368, 1174, 1086, 1015, 986, 848, 804, 527cm$^{-1}$

TABLE 148-continued

I-750  mp 129–131° C.
$^1$H NMR(CDCl$_3$) δ 1.75(s, 3H), 1.79(s, 3H), 3.45(s, 3H), 3.53(s, 3H), 3.75(s, 3H), 4.62(d, J=6.6Hz, 2H), 5.24(s, 2H), 5.50–5.58(m, 1H), 5.90(s, 1H), 6.44(s, 1H), 6.99(d, J=8.7Hz, 1H), 7.08–7.18(m, 3H), 7.29(d, J=1.8Hz, 1H), 7.58–7.64(m, 2H)
IR(KBr) 3361, 2953, 2934, 1522, 1488, 1460, 1391, 1230, 1154, 1121, 1071, 993, 912, 817, 587cm$^{-1}$

I-751  mp 148–150° C.
$^1$H NMR(CDCl$_3$) δ 1.68(s, 3H), 1.74(s, 3H), 2.51–2.60(m, 5H), 3.53(s, 6H), 3.77(s, 3H), 4.02(t, J=7.2Hz, 2H), 5.19–5.25 (m, 3H), 6.83(s, 1H), 6.98(d, J=8.4Hz, 1H), 7.08(dd, J=2.1, 8.4Hz, 1H), 7.11–7.18(m, 2H), 7.21(d, J=2.1Hz, 1H), 7.57–7.64(m, 2H)
IR(KBr) 2931, 1603, 1519, 1484, 1386, 1370, 1231, 1175, 1086, 1015, 983, 961, 847, 728, 526cm$^{-1}$

I-752  mp 99–101° C.
$^1$H NMR(CDCl$_3$) δ 1.68(s, 3H), 1.73(s, 3H), 2.55(q, J=7.2Hz, 2H), 3.44(s, 3H), 3.54(s, 3H), 3.75(s, 3H), 4.04(t, J=7.2Hz, 2H), 5.20–5.25(m, 3H), 5.89(s, 1H), 6.44(s, 1H), 6.98(d, J=8.1Hz, 1H), 7.09–7.18(m, 3H), 7.26–7.27(m, 1H), 7.58–7.63 (m, 2H)
IR(KBr) 3349, 2930, 1609, 1523, 1489, 1231, 1152, 1121, 1072, 994, 912, 813, 588cm$^{-1}$

TABLE 149

I-753  mp 115–117° C.
$^1$H NMR(CDCl$_3$) δ 1.69(s, 3H), 1.75(s, 3H), 2.53(q, J=6.9Hz, 2H), 2.62(s, 3H), 3.53(s, 3H), 3.77(s, 3H), 4.06(t, J=6.9Hz, 2H), 5.18–5.25(m, 1H), 5.70(s, 1H), 6.83(s, 1H), 6.89–6.95(m, 2H), 7.02(d, J 1.2Hz, 1H), 7.10–7.18(m, 2H), 7.57–7.65 (m, 2H)
IR(KBr) 3545, 2931, 1604, 1520, 1485, 1370, 1249, 1232, 1175, 1084, 1012, 813, 526cm$^{-1}$

I-754  $^1$H NMR(CDCl$_3$) δ 1.14(t, J=6.9Hz, 3H), 1.29(t, J=6.9Hz, 3H), 2.50(s, 3H), 3.19(s, 3H), 3.71(q, J=6.9Hz, 2H), 4.00 (q, J=6.9Hz, 2H), 5.18(s, 2H), 5.68(s, 1H), 6.83(s, 1H), 6.91(dd, J=1.8, 8.4Hz, 1H), 7.00(d, J=8.4Hz, 1H), 7.04(d, J=1.8Hz, 1H), 7.32–7.48(m, 7H), 7.66–7.74(m, 2H)
IR(CHCl$_3$) 3532, 2976, 1586, 1516, 1468, 1369, 1282, 1174, 1148, 1068, 1016, 967, 907, 871cm$^{-1}$

I-755  amorphous powder
$^1$H NMR(CDCl$_3$) δ 1.15(t, J=6.9Hz, 3H), 1.28(t, J=6.9Hz, 3H), 3.59(q, J=6.9Hz, 2H), 3.97(q, J=6.9Hz, 2H), 4.89 (s, 1H), 5.15(s, 2H), 5.64(s, 1H), 5.98(s, 1H), 6.45(s, 1H), 6.86–6.94(m, 2H), 6.96–7.04(m, 2H), 7.12(d, J=2.4Hz, 1H), 7.35–7.56(m, 7H),
IR(CHCl$_3$) 3534, 1610, 1521, 1488, 1383, 1169, 1116, 1064, 1018, 832cm$^{-1}$ I-756  mp 126–129° C.
$^1$H NMR(CDCl$_3$) δ 1.14(t, J=6.9Hz, 3H), 1.30(t, J=6.9Hz, 3H), 1.76(s, 3H), 1.81(s, 3H), 2.69(s, 3H), 3.20(s, 3H), 3.23(s, 3H), 3.72(q, J=6.9Hz, 2H), 4.00(q, J=6.9Hz, 2H), 4.64(d, J=6.6Hz, 2H), 5.49(m, 1H), 6.84(s, 1H), 7.08(d, J=8.7Hz, 1H), 7.32–7.42(m, 4H), 7.56–7.72(m, 2H)
IR(CHCl$_3$) 1609, 1516, 1467, 1369, 1267, 1229, 1175, 1148, 1115, 1069, 968, 907, 871cm$^{-1}$

TABLE 150

I-757  mp 123–135° C.(dec.)
$^1$H NMR(CDCl$_3$) δ 1.14(t, J=6.9Hz, 3H), 1.29(t, J=6.9Hz, 3H), 2.37(s, 3H), 2.64(s, 3H), 3.12(s, 3H), 3.20(s, 3H), 3.71(q, J=6.9Hz, 2H), 4.00(q, J=6.9Hz, 2H), 5.14(s, 2H), 6.83(s, 1H), 7.14(d, J=8.7Hz, 1H), 7.18–7.24(m, 2H), 7.31–7.40 (m, 5H), 7.41(d, J=2.1Hz, 1H), 7.65–7.72(m, 2H)
IR(CHCl$_3$)1607, 1517, 1467, 1369, 1330, 1268, 1175, 1148, 1116, 1069, 1026, 967, 907, 871cm$^{-1}$ I-758  amorphous powder
$^1$H NMR(CDCl$_3$) δ 1.15(t, J=6.9Hz, 3H), 1.28(t, J=6.9Hz, 3H), 1.76(s, 3H), 1.82(d, J=0.6Hz, 3H), 3.59(q, J=6.9Hz, 2H), 3.97(q, J=6.9Hz, 2H), 4.61(d, J=6.9Hz, 2H), 4.87(s, 1H), 5.53(m, 1H), 5.66(s, 1H), 5.97(s, 1H), 6.45(s, 1H), 6.86–7.00(m, 4H), 7.09(d, J=1.8Hz, 1H), 7.50–7.57(m, 2H)
IR(CHCl$_3$)3528, 2978, 1611, 1521, 1487, 1412, 1383, 1168, 1115, 1064, 905, 831cm$^{-1}$ I-759  amorphous powder
$^1$H NMR(CDCl$_3$) δ 1.15(t, J=6.9Hz, 3H), 1.27(t, J=6.9Hz, 3H), 2.39(s, 3H), 3.59(q, J=6.9Hz, 2H), 3.97(q, J=6.9Hz, 2H), 4.88(s, 1H), 5.10(s, 2H), 5.64(s, 1H), 5.97(s, 1H), 6.45(s, 1H), 6.97–7.01(m, 2H), 7.11(d, J=1.5Hz, 1H), 7.20–7.26 (m, 2H), 7.32–7.37(m, 2H), 7.50–7.56(m, 2H)
IR(CHCl$_3$)3526, 2974, 1612, 1520, 1488, 1412, 1383, 1285, 1246, 1116, 1065, 1027, 870cm$^{-1}$ I-760  mp 169–171° C.
$^1$H NMR(CDCl$_3$) δ 2.71(s, 3H), 3.01(s, 3H), 3.10(s, 3H), 3.21(s, 3H), 3.36(s, 3H), 3.56(s, 3H), 3.77(s, 3H), 4.83(s, 2H), 6.84(s, 1H), 7.05(d, J=8.4Hz, 1H), 7.32(dd, J=2.1, 8.4Hz, 1H), 7.36–7.42(m, 2H), 7.42(d, J=2.1Hz, 1H), 7.65–7.72 (m, 2H)
IR(CHCl$_3$)1666, 1517, 1479, 1368, 1175, 1148, 1119, 1083, 1014, 968, 871cm$^{-1}$

TABLE 151

I-761  mp 175–177° C.
$^1$H NMR(DMSO-d$_6$) δ 1.70(s, 6H), 3.67–3.73(m, 2H), 3.71(s, 3H), 3.72(s, 3H), 4.59(br, 1H), 5.27–5.31(m, 1H), 6.50(d, J=8.1Hz, 1H), 6.77–6.95(m, 6H), 7.34–7.40(m, 2H), 9.23(br s, 1H), 9.42(br s, 1H)
IR(KBr)3600–2400(br), 1609, 1522, 1492, 1463, 1384, 1263, 1208, 1174, 1129, 1055, 1033cm$^{-1}$

I-762  mp 151–153° C.
$^1$H NMR(CDCl$_3$) δ 1.78(s, 3H), 1.85(s, 3H), 3.78(s, 3H), 3.80(s, 3H), 4.72(d, J=6.9Hz, 2H), 5.39–5.44(m, 1H), 6.53(d, J=3.0Hz, 1H), 6.95(s, 1H), 7.05(s, 1H), 7.09–7.16(m, 3H), 7.38(d, J=8.7Hz, 1H), 7.45(dd, J=1.8, 8.7Hz, 1H), 7.54–7.60 (m, 2H), 7.80(d, J=1.8Hz, 1H),
IR(KBr)3600–2800(br), 1509, 1496, 1481, 1462, 1447, 1383, 1207, 1158, 1051cm$^{-1}$

TABLE 151-continued

I-763 mp 138–139° C.
$^1$H NMR(CDCl$_3$) δ 3.78(s, 3H), 3.79(s, 3H), 6.64(dd, J=0.9, 2.7Hz, 1H), 6.80(d, J=7.8Hz, 1H), 6.94(s, 1H), 7.04(s, 1H), 7.09–7.21(m, 3H), 7.25–7.27(m, 1H), 7.32(d, J=8.7Hz, 1H), 7.42(dd, J=1.8, 8.4Hz, 1H), 7.53–7.59(m, 3H), 8.60–8.63 (m, 1H)
IR(KBr)3600–2800(br), 1590, 1510, 1497, 1478, 1430, 1384, 1209, 1158, 1053, 1026cm$^{-1}$

I-764 mp 172–174° C.
$^1$H NMR(CDCl$_3$) δ 2.32(s, 3H), 3.78(s, 3H), 3.79(s, 3H), 5.30(s, 2H), 6.59(d, J=3.3Hz, 1H), 6.94(s, 1H), 7.04(s, 1H), 7.04–7.15(m, 7H), 7.34(d, J=8.4Hz, 1H), 7.41(dd, J=1.8, 8.7Hz, 1H), 7.55–7.59(m, 2H), 7.82–7.83(m, 1H)
IR(KBr)3600–2800(br), 1516, 1497, 1482, 1466, 1382, 1306, 1219, 1209, 1159, 1051, 1026cm$^{-1}$

I-765 mp 134–136° C.
$^1$H NMR(DMSO-d$_6$) δ 1.70(s, 3H), 1.71(s, 3H), 3.72–3.74(m, 2H), 3.73(s, 3H), 3.74(s, 3H), 5.25(br s, 1H), 5.50–5.58(m, 1H), 6.66–6.72(m, 1H), 6.78–6.83(m, 1H), 6.92(s, 3H), 6.95(s, 3H), 7.19–7.29(m, 2H), 7.30–7.39(m, 2H), 9.45(br s, 3H),
IR(KBr)3600–2800(br), 1624, 1610, 1526, 1494, 1461, 1382, 1255, 1208, 1175, 1120, 1054, 1031cm$^{-1}$

TABLE 152

I-766 mp 166–168° C.
$^1$H NMR(CDCl$_3$) δ 2.40(s, 3H), 3.77(s, 6H), 4.82(s, 1H), 6.71(d, J=2.4Hz, 1H), 6.86–6.93(m, 4H), 7.22–7.32(m, 4H), 7.43–7.48(m, 2H), 7.58–7.64(m, 1H), 7.71–7.75(m, 2H)
IR(KBr)3600–2800(br), 1611, 1524, 1492, 1382, 1336, 1265, 1209, 1162, 1090, 1053, 1030cm$^{-1}$

I-767 mp 139–140° C.
$^1$H NMR(CDCl$_3$) δ 3.78(s, 3H), 3.80(s, 3H), 6.60–6.62(m, 1H), 6.95(s, 1H), 7.05(s, 1H), m), 7.08–7.16(m, 2H), 7.23–7.26 (m, 1H), 7.45(d, J=1.2Hz, 2H), 7.54–7.61(m, 2H), 7.83(d, J=0.6Hz, 1H), 8.18(br s, 1H)
IR(KBr)3600–2800(br), 1520, 1497, 1465, 1448, 1414, 1383, 1313, 1218, 1205, 1159, 1048, 1024cm$^{-1}$

I-768 $^1$H NMR(CDCl$_3$) δ 2.26(s, 3H), 3.48(s, 3H), 3.75(s, 3H), 5.16(s, 2H), 5.69(s, 1H), 5.89(s, 1H), 6.45(s, 1H), 6.94(d.d, J=8.4 & 2.1Hz, 1H), 7.02(d, J=8.4Hz, 1H), 7.08(d, J=2.1Hz, 1H), 7.35–7.50(m, 8H), 8.36–8.44(m, 1H)
IR(KBr)3384, 1592, 1525, 1487, 1455, 1397, 1312, 1250, 1122, 1102, 1069, 1011cm$^{-1}$

I-769 $^1$H NMR(CDCl$_3$) δ 2.26(s, 3H), 2.68(s, 3H), 3.13(s, 3H), 3.56(s, 3H), 3.78(s, 3H), 5.19(s, 2H), 6.84(s, 1H), 7.15(d, J=8.4Hz, 1H), 7.30–7.51(m, 10H), 8.37–8.47(m, 1H)
IR(KBr)3384, 1704, 1590, 1524, 1481, 1389, 1357, 1272, 1240, 1174, 1114, 1082, 1017cm$^{-1}$

I-770 $^1$H NMR(CDCl$_3$) δ 2.67(s, 3H), 2.84(s, 3H), 3.28(s, 3H), 3.56(s, 3H), 3.78(s, 3H), 6.26(s, 1H), 6.85(s, 1H), 7.17(d, J=9.0Hz, 1H), 7.24–7.33(m, 2H), 7.35–7.50(m, 3H), 8.37–8.50(m, 1H)
IR(KBr)3383, 1674, 1595, 1526, 1482, 1363, 1177, 1078, 1012cm$^{-1}$

I-771 $^1$H NMR(CDCl$_3$) δ 1.76(s, 3H), 1.81(s, 3H), 2.26(s, 3H), 2.72(s, 3H), 3.23(s, 3H), 3.56(s, 3H), 3.78(s, 3H), 4.64(d, J=7.2Hz, 2H), 5.44–5.53(m, 1H), 6.84(s, 1H), 7.09(d, J=8.4Hz, 1H), 7.30–7.53(m, 5H), 8.38–8.47(m, 1H)
IR(KBr)3376, 1697, 1594, 1524, 1481, 1365, 1270, 1239, 1177, 1112, 1079, 1013cm$^{-1}$

TABLE 153

I-772 $^1$H NMR(CDCl$_3$) δ 2.26(s, 3H), 2.38(s, 3H), 2.68(s, 3H), 3.12(s, 3H), 3.56(s, 3H), 3.78(s, 3H), 5.14(s, 2H), 6.84(s, 1H), 7.12–7.50(m, 9H), 8.35–8.44(m, 1H)
IR(KBr)3365, 1693, 1622, 1591, 1526, 1477, 1374, 1314, 1291, 1180, 1165, 1111, 1078cm$^{-1}$

I-773 $^1$H NMR(CDCl$_3$) δ 1.76(s, 3H), 1.82(s, 3H), 2.26(s, 3H), 3.48(s, 3H), 3.75(s, 3H), 4.62(d, J=6.9Hz, 2H), 5.46–5.58 (m, 1H), 5.71(s, 1H), 5.86(s, 1H), 6.44(s, 1H), 6.87–7.00(m, 2H), 7.05(.d, J=1.8Hz, 1H), 7.33–7.52(m, 3H), 8.36–8.47 (m, 1H)
IR(KBr)1737, 1604, 1519, 1482, 1392, 1366, 1267, 1173, 1131, 1084, 1062, 1009cm$^{-1}$

I-774 $^1$H NMR(CDCl$_3$) δ: 2.25(s, 3H), 2.38(s, 3H), 3.48(s, 3H), 3.75(s, 3H), 5.10(s, 2H), 5.12(brs, 1H), 5.90(s, 1H), 6.44(s, 1H), 6.94(.d.d, J=8.4 & 1.8Hz, 1H), 7.02(.d, J=8.4Hz, 1H), 7.06(.d, J=1.8Hz, 1H), 7.18–7.52(m, 6H), 8.35–8.44(m, 1H)
IR(KBr)1686, 1590, 1524, 1488, 1398, 1314, 1257, 1102, 1068, 1008cm$^{-1}$ I-775 $^1$H NMR(CDCl$_3$) δ 3.47(s, 3H), 3.76(s, 3H), 5.16(s, 2H), 5.71(s, 1H), 5.82(s, 1H), 6.45(s, 1H), 6.97(d.d, J=8.4 & 2.1Hz, 1H), 7.04(d, J=8.4Hz, 1H), 7.07(d, J=2.1Hz, 1H), 7.22–7.30(m, 1H), 7.33–7.49(m, 5H), 7.92–7.98(m, 1H), 8.09–8.14 (m, 1H), 10.44(s, 1H)
IR(KBr)3492, 3459, 1692, 1605, 1518, 1486, 1388, 1294, 1238, 1200, 1115, 1100, 1070, 1008cm$^{-1}$ I-776 $^1$H NMR(CDCl$_3$) δ 2.35(d, J=1.8Hz, 3H), 2.68(s, 3H), 3.13(s, 3H), 3.23(s, 3H), 3.78(s, 3H), 5.19(s, 2H), 6.82(s, 1H), 7.04–7.17(m, 2H), 7.30–7.49(m, 9H)
IR(KBr)1606, 1518, 1478, 1364, 1295, 1271, 1240, 1182, 1118, 1087, 1077, 1017cm$^{-1}$ I-777 $^1$H NMR(CDCl$_3$) δ 1.76(s, 3H), 1.81(s, 3H), 2.35(s, 3H), 2.72(s, 3H), 3.23(s, 3H), 3.53(s, 3H), 3.78(s, 3H), 4.64(d, J=6.6Hz, 2H), 5.45–5.53(m, 1H), 6.82(s, 1H), 7.03–7.14(m, 2H), 7.32–7.47(m, 4H)
IR(KBr)1607, 1520, 1482, 1374, 1363, 1240, 1179, 1115, 1079cm$^{-1}$

TABLE 154

I-778 $^1$H NMR(CDCl$_3$) δ 2.35(d, J=1.2Hz, 3H), 3.45(s, 3H), 3.75(s, 3H), 5.15(s, 2H), 5.68(s, 1H), 5.90(s, 1H), 6.43(s, 1H), 6.92–7.12(m, 4H), 7.31–7.50(m, 7H)
IR(KBr)3536, 3398, 1609, 1587, 1518, 1487, 1244, 1192, 1110, 1071, 1010cm$^{-1}$

I-779 $^1$H NMR(CDCl$_3$) δ 1.76(s, 3H), 1.82(s, 3H), 2.35(s, 3H), 3.45(s, 3H), 3.74(s, 3H), 4.61(d, J=6.9Hz, 2H), 5.43–5.60(m, 1H), 6.43(s, 1H), 6.87–7.15(m, 4H), 7.36–7.51(m, 2H)
IR(KBr)3512, 3444, 1611, 1585, 1518, 1488, 1462, 1447, 1416, 1305, 1288, 1243, 1207, 1112, 1103, 1070, 1012cm$^{-1}$

I-780 $^1$H NMR(CDCl$_3$) δ 3.45(s, 3H), 3.75(s, 3H), 4.84(s, 2H), 5.15(s, 2H), 5.70(s, 1H), 5.88(s, 1H), 6.44(s, 1H), 6.91–7.20(m, 4H), 7.32–7.48(m, 5H), 7.52–7.61(m, 1H), 7.64–7.74(m, 1H)

TABLE 154-continued

| | |
|---|---|
| | IR(KBr)3523, 3428, 1610, 1587, 1516, 1482, 1463, 1400, 1321, 1285, 1238, 1187, 1106cm$^{-1}$ |
| I-781 | $^1$H NMR(CDCl$_3$) δ 2.68(s, 3H), 3.13(s, 3H), 3.54(s, 3H), 3.78(s, 3H), 5.19(s, 2H), 5.44(d.d, J=18 & 0.6Hz, 1H), 5.90 (d.d, J=18 & 0.9Hz, 1H), 6.84(s, 1H), 6.86–6.98(m, 1H), 7.09–7.18(m, 2H), 7.31–7.52(m, 8H), 7.71(d.d, J=7.2 & 2.4Hz, 1H) |
| | IR(KBr)1608, 1518, 1479, 1365, 1235, 1177, 1118, 1079, 1013cm$^{-1}$ |
| I-782 | $^1$H NMR(CDCl$_3$) δ 1.59(d, J=6.3Hz, 3H), 2.68(s, 3H), 3.13(s, 3H), 3.55(s, 3H), 3.78(s, 3H), 5.19(s, 2H), 5.21–5.30(m, 1H), 6.84(s, 1H), 7.08–7.17(m, 3H), 7.32–7.56(m, 7H), 7.69–7.75(m, 1H) |
| | IR(KBr)3543, 3433, 1609, 1518, 1480, 1364, 1235, 1178, 1117, 1078, 1014cm$^{-1}$ |
| I-783 | $^1$H NMR(CDCl$_3$) δ 1.59(d, J=6.0Hz, 3H), 2.01(brs, 1H), 3.47(s, 3H), 3.76(s, 3H), 5.16(s, 2H), 5.15–5.30(m, 1H), 5.72 (s, 1H), 5.91(s, 1H), 6.46(s, 1H), 6.89–7.16(m, 4H), 7.30–7.60(m, 6H), 7.68–7.85(m, 1H) |
| | IR(KBr)3467, 1613, 1586, 1517, 1484, 1455, 1421, 1395, 1287, 1238, 1111, 1070, 1010cm$^{-1}$ |

TABLE 155

| | |
|---|---|
| I-784 | $^1$H NMR(CDCl$_3$) δ 1.77(s, 3H), 1.81(s, 3H), 3.23(s, 3H), 3.81(s, 6H), 4.64(d, J=6.6Hz, 2H), 5.47–5.54(m, 1H), 6.91(s, 1H), 6.96(s, 1H), 7.06(d, J=8.4Hz, 1H), 7.49(d.d, J=8.4 & 2.1Hz, 1H), 7.58(d, J=2.1Hz, 1H), 7.60–7.74(m, 4H) |
| | IR(KBr)2228, 1610, 1490, 1348, 1295, 1266, 1209, 1174, 1112, 1056, 1038, 1000cm$^{-1}$ |
| I-785 | mp 169–170° C. |
| | $^1$H NMR(CDCl$_3$) δ 2.07(s, 6H), 3.20(s, 3H), 5.16(s, 2H), 5.71(brs, 1H), 6.97–7.45(m, 14H) |
| | IR(KBr)3357, 3023, 2933, 1698, 1516, 1478, 1362, 1260, 1227, 1152, 1132, 962, 869cm$^{-1}$ |
| I-786 | mp 169–170° C. |
| | $^1$H NMR(CDCl$_3$) δ 2.13(s, 6H), 3.11(s, 3H), 3.18(s, 3H), 5.18(s, 2H), 7.09–7.47(m, 12H), 7.64(d, J=9.0Hz, 2H) |
| | IR(KBr)3434, 3035, 2938, 1516, 1474, 1362, 1290, 1197, 1182, 1174, 1149, 1114, 973, 857, 842cm$^{-1}$ |
| I-787 | mp 156–157° C. |
| | $^1$H NMR(CDCl$_3$) δ 2.08(s, 6H), 3.12(s, 3H), 3.21(s, 3H), 5.18(s, 2H), 7.12–7.58(m, 14H) |
| | IR(KBr)3494, 3292, 3033, 2934, 1753, 1712, 1517, 1478, 1358, 1294, 1261, 1173, 1151, 967, 870cm$^{-1}$ |
| I-788 | mp 105–106° C. |
| | $^1$H NMR(CDCl$_3$) δ 1.75(s, 3H), 1.85(s, 3H), 2.12(s, 6H), 3.18(s, 3H), 3.22(s, 3H), 4.64(d, J=7.0Hz, 2H), 5.52(t, J=6.8Hz, 1H), 7.08(s, 1H), 7.16–7.38(m, 6H), 7.64(d, J=8.8Hz, 2H) |
| | IR(KBr)3434, 2934, 1514, 1474, 1362, 1285, 1152, 1113, 971, 916, 861, 845cm$^{-1}$ |
| I-789 | mp 148–149° C. |
| | $^1$H NMR(CDCl$_3$) δ 2.12(s, 6H), 2.39(s, 3H), 3.10(s, 3H), 3.18(s, 3H), 5.13(s, 2H), 7.10–7.38(m, 11H), 7.64(d, J=8.6Hz, 2H) |
| | IR(KBr)3435, 3027, 2931, 1678, 1516, 1475, 1362, 1288, 1182, 1151, 1113, 969, 916, 861cm$^{-1}$ |

TABLE 156

| | |
|---|---|
| I-790 | mp 139–140° C. |
| | $^1$H NMR(CDCl$_3$) δ 1.76(s, 3H), 1.82(s, 3H), 2.14(s, 6H), 2.46–2.58(m, 2H), 3.14(s, 3H), 3.19(s, 3H), 4.07(d, J=7.0Hz, 2H), 5.16–5.23(m, 1H), 7.05(s, 1H), 7.14–7.41(m, 6H), 7.66(d, J=8.4Hz, 2H) |
| | IR(KBr)3433, 2946, 1514, 1467, 1360, 1282, 1180, 1152, 1115, 868cm$^{-1}$ |
| I-791 | mp 123–124° C. |
| | $^1$H NMR(DMSO-d$_6$) δ 1.72(s, 3H), 1.77(s, 3H), 2.03(s, 6H), 4.56(d, J=6.6Hz, 2H), 5.50(t, J=6.0Hz, 1H), 6.49(d, J=9.6Hz, 1H), 6.55(s, 1H), 6.83(d, J=8.4Hz, 2H), 6.98(d, J=8.1Hz, 1H), 7.27(s, 2H), 7.48(d, J=5.6Hz, 2H), 8.92(brs, 1H), 9.48(brs, 1H) |
| | IR(KBr)3337, 2930, 1612, 1518, 1471, 1285, 1258, 1207, 1123, 999, 834cm$^{-1}$ |
| I-792 | mp 230–231° C. |
| | $^1$H NMR(DMSO-d$_6$) δ 2.04(s, 6H), 2.33(s, 3H), 5.09(s, 2H), 6.50(d, J=8.4Hz, 1H), 6.59(s, 1H), 6.85(d, J=8.1Hz, 2H), 7.04(d, J=5.4Hz, 1H), 7.23(d, J=7.5Hz, 2H), 7.29(s, 1H), 7.41(d, J=7.8Hz, 2H), 7.49(d, J=8.7Hz, 2H), 9.05(brs, 1H), 9.50(brs, 1H) |
| | IR(KBr)3287, 1609, 1519, 1475, 1298, 1245, 1126, 1006, 841cm$^{-1}$ |
| I-793 | mp 118–119° C. |
| | $^1$H NMR(DMSO-d$_6$) δ 1.64(s, 3H), 1.70(s, 3H), 2.03(s, 6H), 2.42–2.50(m, 2H), 3.96(t, J=6.9Hz, 2H), 5.27(t, J=7.2Hz, 2H), 6.49(d, J=8.1Hz, 1H), 6.55(s, 1H), 6.84(d, J=8.4Hz, 2H), 6.96(d, J=8.1Hz, 1H), 7.27(s, 2H), 7.48(d, J=8.7Hz, 2H), 8.89(brs, 1H), 9.48(brs, 1H) |
| | IR(KBr)3392, 2928, 1610, 1519, 1466, 1250, 1230, 1205, 1178, 1128, 1031, 834, 808cm$^{-1}$ |
| I-794 | mp 139–140° C. |
| | $^1$H NMR(DMSO-d$_6$) δ 1.75(s, 3H), 1.77(s, 3H), 2.50(s, 6H), 3.39(s, 3H), 3.44(s, 3H), 4.69(d, J=6.2Hz, 2H), 5.50(t, J=6.6Hz, 1H), 7.29–7.33(m, 3H), 7.41–7.47(m, 4H), 7.59–7.68(m, 2H) |
| | IR(KBr)3433, 2933, 1675, 1516, 1473, 1366, 1358, 1292, 1259, 1182, 1172, 1151, 969, 873cm$^{-1}$ |

TABLE 157

| | |
|---|---|
| I-795 | mp 151–152° C. |
| | $^1$H NMR(DMSO-d$_6$) δ 2.05(s, 6H), 2.18(s, 3H), 3.36(s, 3h), 3.44(s, 3H), 5.22(s, 2H), 7.08–7.63(m, 13H) |
| | IR(KBr)3434, 3023, 2928, 1517, 1477, 1368, 1293, 1261, 1183, 1152, 966, 870cm$^{-1}$ |
| I-796 | mp 159–160° C. |
| | $^1$H NMR(DMSO-d$_6$) δ 1.65(s, 3H), 1.70(s, 3H), 2.05(s, 6H), 2.48–2.53(m, 2H), 3.38(s, 3H), 3.44(s, 3H), 4.10(t, J=7.4Hz, 2H), 5.21–5.27(m, 1H), 7.28–7.34(m, 3H), 7.41–7.47(m, 4H), 7.59–7.64(m, 2H) |
| | IR(KBr)3434, 2938, 1519, 1478, 1439, 1362, 1295, 1269, 1173, 1152, 1125, 960, 870, 839cm$^{-1}$ |

TABLE 157-continued

I-797 mp 130–131° C.
$^1$H NMR(DMSO-d$_6$) δ 1.72(s, 3H), 1.75(s, 3H), 2.02(s, 6H), 4.59(d, J=6.4Hz, 2H), 5.48(t, J=7.2Hz, 1H), 6.81–7.07 (m, 7H), 7.25(s, 2H), 8.96(brs, 1H), 9.41(brs, 1H)
IR(KBr)3392, 1608, 1589, 1518, 1475, 1322, 1258, 1170, 1127, 974, 836, 808cm$^{-1}$ I-798 mp 143–144° C.
$^1$H NMR(DMSO-d$_6$) δ 2.03(s, 6H), 2.32(s, 3H), 5.12(s, 2H), 6.82–7.41(m, 13H), 9.10(brs, 1H), 9.41(brs, 1H)
IR(KBr)3344, 1609, 1521, 1427, 1255, 1236, 1205, 1129, 998, 832, 806, 792cm$^{-1}$ I-799 mp 163–164° C.
$^1$H NMR(DMSO-d$_6$) δ 1.87(s, 3H), 1.90(s, 3H), 3.42(s, 3H), 5.15(s, 2H), 6.88–7.03(m, 4H), 7.24–7.58(m, 9H), 7.97(brs, 1H), 9.02(brs, 1H)
IR(KBr)3563, 3476, 3001, 2922, 1698, 1527, 1512, 1476, 1359, 1303, 1261, 1237, 1210, 1195, 1167, 1146, 871cm$^{-1}$ I-800 $^1$H NMR(CDCl$_3$) δ 1.30(d, J=6.6Hz, 6H), 2.58(s, 3H), 2.97(quintet, J=6.6Hz, 1H), 3.54(s, 3H), 3.77(s, 3H), 5.17(s, 2H), 6.87(s, 1H), 7.11(d, J=9.0Hz, 1H), 7.22–7.35(m, 8H), 7.47–7.68(m, 6H), 8.19–8.25(m, 2H)
IR(KBr)1737, 1604, 1519, 1482, 1392, 1366, 1267, 1173, 1131, 1084, 1062, 1009cm$^{-1}$

TABLE 158

I-801 $^1$H NMR(CDCl$_3$) δ 2.56(s, 3H), 3.55(s, 3H), 3.78(s, 3H), 5.17(s, 2H), 5.69(s, 1H), 6.84(s, 1H), 6.91(d.d, J=8.4 & 1.8Hz, 1H), 7.02(d, J=8.4Hz, 1H), 7.04(d, J=1.8Hz, 1H), 7.04–7.14(m, 1H), 7.33–7.47(m, 8H)
IR(KBr)3446, 1613, 1585, 1522, 1477, 1396, 1357, 1291, 1243, 1204, 1174, 1076, 1017, 1006cm$^{-1}$

I-802 foam
$^1$H NMR(CDCl$_3$) δ 2.82(s, 3H), 3.22(s, 3H), 3.25(s, 3H), 3.26(s, 3H), 3.55(s, 3H), 3.78(s, 3H), 5.48(s, 2H), 6.85(s, 1H), 7.27(d, J=8.4Hz, 1H), 7.39(d, J=8.7Hz, 2H), 7.40(dd, J=8.4, 2.1Hz, 1H), 7.43(d, J=2.1Hz, 1H), 7.67(d, J=8.7Hz, 2H)
IR(Nujol)1608, 1519, 1480, 1462, 1365, 1176, 1151, 1079, 970, 876, 798cm$^{-1}$ I-803 foam
$^1$H NMR(CD3OD) δ 3.28(s, 3H), 3.68(s, 3H), 5.17(s, 2H), 6.43(s, 1H), 6.81(dd, J=8.4, 2.1Hz, 1H), 6.85(d, J=8.7Hz, 2H), 6.89(d, J=2.1Hz, 1H), 7.03(d, J=8.4Hz, 1H), 7.46(d, J=8.7Hz, 2H)
IR(Nujol)3342, 1611, 1592, 1523, 1488, 1460, 1251, 1225, 1114, 1072, 1012, 941, 826, 756cm$^{-1}$ I-804 mp 150–152° C.
$^1$H NMR(DMSO-d$_6$) δ 3.31(s, 3H), 3.64(s, 3H), 5.00(s, 2H), 6.39(s, 1H), 6.66(dd, J=8.4, 2.1Hz, 1H), 6.79(d, J=2.1Hz, 1H), 6.84(d, J=8.7Hz, 2H), 6.98(d, J=8.4Hz, 1H), 7.44(d, J=8.7Hz, 2H)
IR(Nujol)3459, 3291, 1612, 1594, 1522, 1489, 1458, 1257, 1226, 1101, 1073, 1011, 960, 823cm$^{-1}$ I-805 mp 190–192° C.
$^1$H NMR(DMSO-d$_6$) δ 2.88(s, 3H), 3.41(s, 3H), 3.45(s, 3H), 3.52(s, 3H), 3.79(s, 3H), 5.43(s, 2H), 7.08(s, 1H), 7.16(s, 1H), 7.32–7.36(m, 2H), 7.46(d, J=8.4Hz, 1H), 7.49(d, J=8.7Hz, 2H), 7.53–7.64(m, 3H), 7.74(d, J=8.7Hz, 2H), 7.88–7.91 (m, 2H)
IR(Nujol)1604, 1519, 1481, 1462, 1367, 1175, 1081, 1009, 878, 841, 816, 801cm$^{-1}$

TABLE 159

I-806 foam
$^1$H NMR(CDCl$_3$) δ 3.45(s, 3H), 3.74(s, 3H), 5.31(s, 2H), 6.94(s, 1H), 6.45(s, 1H), 6.64(s, 1H), 6.93(d, J=8.7Hz, 2H), 6.98(dd, J=8.4, 2.1Hz, 1H), 7.09(d, J=8.4Hz, 1H), 7.11(d, J=2.1Hz, 1H), 7.46–7.50(m, 3H), 7.53(d, J=8.7Hz, 2H), 7.78–7.82(m, 2H)
IR(Nujol)3367, 1612, 1592, 1523, 1489, 1455, 1253, 1226, 1115, 1073, 1013, 942, 816, 767cm$^{-1}$ I-807 foam
$^1$H NMR(CDCl$_3$) δ 2.76(s, 3H), 3.21(s, 3H), 3.30(s, 3H), 3.56(s, 3H), 3.78(s, 3H), 5.38(s, 2H), 6.84(s, 1H), 7.21(d, J=8.4Hz, 1H), 7.38(d, J=8.7Hz, 2H), 7.38(dd, J=8.4, 2.1Hz, 1H), 7.45(d, J=2.1Hz, 1H), 7.67(d, J=8.7Hz, 2H), 8.80(s, 1H)
IR(Nujol)1608, 1519, 1480, 1463, 1365, 1177, 1151, 1079, 971, 876, 798cm$^{-1}$ I-808 mp 193–195° C.
$^1$H NMR(CDCl$_3$) δ 2.64(s, 3H), 2.74(s, 3H), 3.21(s, 3H), 3.30(s, 3H), 3.56(s, 3H), 3.78(s, 3H), 5.28(s, 2H), 6.84(s, 1H), 7.21(d, J=8.4Hz, 1H), 7.38(d, J=8.7Hz, 2H), 7.38(dd, J=8.4, 2.1Hz, 1H), 7.44(d, J=2.1Hz, 1H), 7.68(d, J=8.7Hz, 2H)
IR(Nujol)1606, 1591, 1522, 1480, 1463, 1359, 1174, 1152, 1079, 1012, 946, 877, 834, 796cm$^{-1}$ I-809 foam
$^1$H NMR(CDCl$_3$) δ 1.42(t, J=7.5Hz, 3H), 2.73(s, 3H), 2.96(q, J=7.5Hz, 2H), 3.21(s, 3H), 3.31(s, 3H), 3.56(s, 3H), 3.78(s, 3H), 5.28(s, 2H), 6.84(s, 1H), 7.21(d, J=8.4Hz, 1H), 7.38(d, J=8.7Hz, 2H), 7.38(dd, J=8.4, 2.1Hz, 1H), 7.44 (d, J=2.1Hz, 1H), 7.68(d, J=8.7Hz, 2H)
IR(KBr)3434, 1609, 1579, 1519, 1481, 1365, 1177, 1151, 1080, 970, 876, 797cm$^{-1}$

TABLE 160

I-810 foam
$^1$H NMR(CDCl$_3$) δ 2.71(s, 3H), 3.21(s, 3H), 3.35(s, 3H), 3.56(s, 3H), 3.78(s, 3H), 5.38(s, 2H), 6.84(s, 1H), 7.25(d, J=8.4Hz, 1H), 7.38(d, J=8.7Hz, 2H), 7.40(dd, J=8.4, 2.1Hz, 1H), 7.46(d, J=2.1Hz, 1H), 7.54–7.64(m, 3H), 7.68(d, J=8.7Hz, 2H), 8.12–8.16(m, 2H)
IR(KBr) 3433, 1609, 1561, 1519, 1480, 1365, 1177, 1151, 1081, 971, 876, 798cm$^{-1}$ I-811 foam
$^1$H NMR(CDCl$_3$) δ 2.51(s, 3H), 2.54(s, 3H), 2.63(s, 3H), 2.72(s, 3H), 3.16(s, 3H), 3.21(s, 3H), 3.56(s, 3H), 3.78(s, 3H), 5.27(s, 2H), 6.84(s, 1H), 7.27(d, J=8.4Hz, 1H), 7.36(dd, J=8.4, 2.1Hz, 1H), 7.38(d, J=8.7Hz, 2H), 7.41(d, J=2.1Hz,

TABLE 160-continued

I-812 
1H), 7.68(d, J=8.7Hz, 2H)
IR(KBr) 3435, 1614, 1519, 1480, 1364, 1177, 1151, 1080, 972, 876, 798cm$^{-1}$
foam
$^1$H NMR(CDCl$_3$) δ 2.74(s, 6H), 3.17(s, 3H), 3.21(s, 3H), 3.55(s, 3H), 3.78(s, 3H), 5.35(s, 2H), 6.84(s, 1H), 7.28(d, J=8.4Hz, 1H), 7.36(dd, J=8.4, 2.1Hz, 1H), 7.38(d, J=8.7Hz, 2H), 7.41(d, J=2.1Hz, 1H), 7.68(d, J=8.7Hz, 2H), 8.41(d, J=2.4Hz, 1H), 8.50(d, J=2.4Hz, 1H)
IR(KBr) 3433, 1609, 1519, 1481, 1364, 1177, 1151, 1080, 971, 876, 798cm$^{-1}$ I-813 foam
$^1$H NMR(DMSO-d$_6$) δ 2.47(s, 6H), 2.55(s, 3H), 3.30(s, 3H), 3.64(s, 3H), 5.16(s, 2H), 6.39(s, 1H), 6.66(dd, J=8.4, 2.1Hz, 1H), 6.76(d, J=2.1Hz, 1H), 6.84(d, J=8.7Hz, 2H), 7.03(d, J=8.4Hz, 1H), 7.44(d, J=8.7Hz, 2H),
IR(KBr) 3399, 3165, 1611, 1521, 1488, 1406, 1362, 1213, 1114, 1069, 1014, 818, 759cm$^{-1}$

TABLE 161

I-814 mp 240–241° C.
$^1$H NMR(DMSO-d$_6$) δ 2.66(s, 3H), 3.30(s, 3H), 3.64(s, 3H), 5.26(s, 2H), 6.39(s, 1H), 6.66(dd, J=8.4, 2.1Hz, 1H), 6.77(d, J=2.1Hz, 1H), 6.84(d, J=8.7Hz, 2H), 7.02(d, J=8.4Hz, 1H), 7.44(d, J=8.7Hz, 2H), 8.48(d, J=2.7Hz, 1H), 8.53(d, J=2.7Hz, 1H)
IR(Nujol) 3513, 3491, 3070, 1610, 1581, 1523, 1488, 1459, 1408, 1275, 1236, 1216, 1111, 1065, 1040, 821, 785cm$^{-1}$ I-815 mp 288–290° C.(decomp.)
$^1$H NMR(DMSO-d$_6$) δ 2.89(s, 3H), 3.41(s, 3H), 3.45(s, 3H), 3.52(s, 3H), 3.79(s, 3H), 4.95(s, 2H), 5.65(s, 1H), 7.08(s, 1H), 7.26(d, J=8.4Hz, 1H), 7.33(dd, J=8.4, 2.1Hz, 1H), 7.38(d, J=2.1Hz, 1H), 7.49(d, J=8.7Hz, 2H), 7.74(d, J=8.7Hz, 2H),
IR(Nujol) 3120, 1712, 1671, 1604, 1516, 1480, 1462, 1364, 1172, 1078, 1015, 970, 874, 841, 796cm$^{-1}$ I-816 mp 204–206° C.
$^1$H NMR(DMSO-d$_6$) δ 2.87(s, 3H), 3.45(s, 3H), 3.46(s, 3H), 3.52(s, 3H), 3.78(s, 3H), 5.40(s, 2H), 7.08(s, 1H), 7.32(dd, J=8.4, 2.1Hz, 1H), 7.33(d, J=8.4Hz, 1H), 7.39(d, J=2.1Hz, 1H), 7.48(d, J=8.7Hz, 2H), 7.71(dd, J=5.1, 1.2Hz, 1H), 7.74(d, J=8.7Hz, 2H), 8.88(d, J=5.1Hz, 1H), 9.21(d, J=1.2Hz, 1H)
IR(Nujol) 1608, 1586, 1557, 1521, 1480, 1464, 1360, 1352, 1176, 1156, 1078, 884, 835, 818, 799cm$^{-1}$ I-817 foam
$^1$H NMR(CDCl$_3$) δ 2.20(s, 3H), 3.45(s, 3H), 3.75(s, 3H), 5.15(s, 2H), 6.45(s, 1H), 6.92(d, J=8.7Hz, 2H), 6.94(dd, J=1.8, 84Hz, 1H), 6.98(d, J=8.4Hz, 1H), 7.09(d, J=1.8Hz, 1H), 7.18(m, 1H), 7.37(t, J=7.2Hz, 1H), 7.53(d, J=8.7Hz, 2H), 7.55(m, 2H)

TABLE 162

I-818 m.p 163–166° C.
$^1$H NMR(CDCl$_3$) δ 1.53(s, 9H), 2.67(s, 3H), 3.11(s, 3H), 3.21(s, 3H), 3.56(s, 3H), 3.77(s, 3H), 5.12(s, 2H), 6.52(s, 1H), 6.84(s, 1H), 7.13(d, J=8.4Hz, 1H), 7.33(dd, J=2.1, 8.4Hz, 1H), 7.38(d, J=8.7Hz, 2H), 7.39(m, 5H), 7.74(d, J=8.7Hz, 2H)
IR(KBr) 1692, 1614, 1520, 1480, 1390, 1367, 1231, 1175, 1152, 1078, 876, 799cm$^{-1}$

I-819 m.p 172° C.
$^1$H NMR(CDCl$_3$) δ 2.77(s, 3H), 3.05(s, 3H), 3.16(s, 3H), 3.22(s, 3H), 3.36(s, 3H), 3.78(s, 3H), 5.16(s, 2H), 6.46(s, 1H), 6.85(s, 1H), 7.14(d, J=8.4Hz, 1H), 7.25(d, J=8.7Hz, 2H), 7.35(dd, J=2.1, 8.4Hz, 1H), 7.39(d, J=8.7Hz, 2H), 7.40(d, J=2.1, 1H), 7.47(d, J=8.4Hz, 2H), 7.67(d, J=8.7Hz, 2H)
IR(KBr) 1608, 1519, 1480, 1361, 1175, 1154, 1079, 972, 876, 801cm$^{-1}$

I-820 mp 180–182° C.
$^1$H NMR(CDCl$_3$) δ 2.69(s, 3H), 3.14(s, 3H), 3.21(s, 3H), 3.53(s, 3H), 3.71(d, J=0.9Hz, 3H), 5.20(s, 2H), 6.93(d, J=8.4Hz, 1H), 7.34–7.49(m, 9H), 7.59(dd, J=9.0, 1.2Hz, 2H)
IR(KBr) 1518, 1469, 1357, 1179, 1151, 1038, 871, 821cm$^{-1}$

I-821 mp 183–185° C.
$^1$H NMR(CDCl$_3$) δ 3.41(s, 3H), 3.66(d, J=0.9Hz, 3H), 4.91(s, 1H), 5.17(s, 2H), 5.62(s, 1H), 5.70(s, 1H), 6.92–6.96(m, 2H), 6.97(dd, J=8.4, 2.0Hz, 1H), 7.04(d, J=8.4Hz, 1H), 7.10(d, J=2.0Hz, 1H), 7.36–7.48(m, 7H)
IR(KBr) 3541, 3398, 1588, 1523, 1461, 1410, 1320, 1261, 1217, 1037, 836, 747cm$^{-1}$

I-822 mp 108–110° C.
$^1$H NMR(CDCl$_3$) δ 2.69(s, 3H), 3.13(s, 3H), 3.45(s, 3H), 3.53(s, 3H), 3.77(s, 3H), 4.66(s, 2H), 4.76(s, 2H), 5.19(s, 2H), 6.86(s, 1H), 7.71(d, J=8.4Hz, 1H), 7.33–7.48(m, 9H), 7.62(d, J=8.4Hz, 2H)
IR(KBr) 1482, 1390, 1307, 1276, 1177, 1083, 1053, 1013, 807cm$^{-1}$

TABLE 163

I-823 mp 192–194° C.
$^1$H NMR(CDCl$_3$) δ 1.70(br s, 1H), 2.69(s, 3H), 3.13(s, 3H), 3.53(s, 3H), 3.77(s, 3H), 4.78(s, 2H), 5.19(s, 2H), 6.87(s, 1H), 7.15(d, J=8.4Hz, 1H), 7.35(dd, J=8.4, 2.3Hz, 1H), 7.37–7.49(m, 8H), 7.63(d, J=7.8Hz, 2H)
IR(KBr) 3554, 3434, 1522, 1481, 1389, 1364, 1277, 1234, 1174, 1085, 1012, 807cm$^{-1}$

I-824 mp 135–137° C.
$^1$H NMR(CDCl$_3$) δ 3.19(s, 3H), 3.60(s, 3H), 3.71(s, 3H), 4.96(s, 1H), 5.18(s, 2H), 5.78(s, 1H), 6.73(s, 1H), 6.88(dd, J=8.3, 2.1Hz, 1H), 7.02(d, J=2.1Hz, 1H), 7.08(d, J=8.3Hz, 1H), 7.34(d, J=8.6Hz, 2H), 7.41–7.47(m, 5H), 7.63(d, J=8.6Hz, 2H)
IR(KBr) 3479, 1473, 1347, 1149, 1010, 869, 803, 784, 747cm$^{-1}$

I-825 mp 149–151° C.
$^1$H NMR(CDCl$_3$) δ 2.68(s, 3H), 3.13(s, 3H), 3.20(s, 3H), 3.69(s, 3H), 3.71(s, 3H), 5.20(s, 2H), 7.18(d, J=8.7Hz, 1H),

TABLE 163-continued 7.21(s, 1H), 7.35–7.50(m, 9H), 7.63(d, J=8.1Hz, 2H)
IR(KBr) 1519, 1469, 1353, 1173, 1149, 1050, 966, 873, 849, 810cm$^{-1}$ I-826  mp 82–85° C.
$^1$H NMR(CDCl$_3$) δ 1.78(s, 3H), 1.82(s, 3H), 2.70(s, 3H), 3.20(s, 3H), 3.25(s, 3H), 3.69(s, 3H), 3.70(s, 3H), 4.65(d, J=6.9Hz, 2H), 5.51(t, J=6.9Hz, 1H), 7.11(d, J=8.8Hz, 1H), 7.21(s, 1H), 7.37(d, J=8.9Hz, 2H), 7.38(dd, J=8.8, 2.2Hz, 1H), 7.42(d, J=2.2Hz, 1H), 7.63(d, J=8.9Hz, 2H)
IR(KBr) 1516, 1468, 1363, 1180, 1151, 1045, 967, 846, 788cm$^{-1}$ I-827  amorphous
$^1$H NMR(CDCl$_3$) δ 1.77(s, 3H), 1.83(s, 3H), 3.58(s, 3H), 3.70(s, 3H), 4.64(d, J=6.7Hz, 2H), 4.97(s, 1H), 5.04(s, 1H), 5.53(t, J=6.7Hz, 1H), 5.81(s, 1H), 6.73(s, 1H), 6.87(dd, J=8.1, 2.0Hz, 1H), 6.88(d, J=8.7Hz, 2H), 6.99(d, J=2.0Hz, 1H), 7.00(d, J=8.1Hz, 1H), 7.47(d, J=8.7Hz, 2H)
IR(CHCl$_3$) 3595, 3536, 1613, 1584, 1521, 1474, 1406, 1356, 1266, 1094, 1062, 1014, 973, 835cm$^{-1}$

TABLE 164

I-828  mp 161–162° C.
$^1$H NMR(CDCl$_3$) δ 3.58(s, 3H), 3.71(s, 3H), 4.85(s, 1H), 4.93(s, 1H), 5.18(s, 2H), 5.78(s, 1H), 6.73(s, 1H), 6.87–6.92(m, 3H), 7.02(d, J=1.8Hz, 1H), 7.07(d, J=8.1Hz, 1H), 7.37–7.51(m, 7H)
IR(KBr) 3510, 3442, 3326, 1523, 1485, 1453, 1395, 1239, 1061, 1003, 972, 836, 753cm$^{-1}$

I-829  mp 85–87° C.
$^1$H NMR(CDCl$_3$) δ 1.69(s, 3H), 1.75(s, 3H), 2.57(q, J=6.9Hz, 2H), 2.70(s, 3H), 3.20(s, 3H), 3.24(s, 3H), 3.69(s, 3H), 3.69(s, 3H), 4.09(t, J=6.9Hz, 2H), 5.22(t, J=6.9Hz, 1H), 7.10(d, J=8.4Hz, 1H), 7.21(s, 1H), 7.37–7.44(m, 9H), 7.63(d, J=8.4Hz, 2H)
IR(KBr) 1519, 1468, 1362, 1179, 1150, 1046, 967, 865, 847cm$^{-1}$

I-830  mp 160–162° C.
$^1$H NMR(CDCl$_3$) δ 2.38(s, 3H), 2.68(s, 3H), 3.12(s, 3H), 3.20(s, 3H), 3.69(s, 3H), 3.70(s, 3H), 5.15(s, 2H), 7.16–7.25(m, 4H), 7.34–7.44(m, 6H), 7.63(d, J=8.1Hz, 2H)
IR(KBr) 1519, 1469, 1365, 1173, 1149, 1049, 965, 873, 849, 808cm$^{-1}$

I-831  amorphous
$^1$H NMR(CDCl$_3$) δ 1.69(s, 3H), 1.76(s, 3H), 2.55(q, J=6.9Hz, 1H), 3.58(s, 3H), 3.69(s, 3H), 4.08(t, J=6.9Hz, 2H), 4.98(s, 1H), 5.18(s, 1H), 5.23(t, J=6.9Hz, 1H), 5.80(s, 1H), 6.72(s, 1H), 6.86–6.89(m, 3H), 6.97–7.00(m, 3H), 7.47(d, J=8.4Hz, 2H)
IR(KBr) 3595, 3538, 1521, 1471, 1265, 1173, 1095, 1063, 1015, 835cm$^{-1}$ I-832  mp 200–201° C.
$^1$H NMR(CDCl$_3$) δ 2.40(s, 3H), 3.58(s, 3H), 3.70(s, 3H), 4.80(s, 1H), 4.92(s, 1H), 5.13(s, 2H), 5.77(s, 1H), 6.73(s, 1H), 6.88(dd, J=8.1, 2.0Hz, 1H), 6.89(d, J=8.4Hz, 2H), 7.01(d, J=1.8Hz, 1H), 7.07(d, J=8.4Hz, 1H), 7.24(d, J=7.8Hz, 2H), 7.35(d, J=7.8Hz, 2H), 7.48(d, J=8.4Hz, 2H),
IR(KBr) 3419, 1610, 1523, 1485, 1393, 1243, 1065, 1004, 972, 833, 795cm$^{-1}$

TABLE 165

I-833  mp 141–142° C.
$^1$H NMR(CDCl$_3$) δ 2.03(s, 3H), 2.11(s, 3H), 2.54(s, 3H), 3.15(s, 3H), 3.21(s, 3H), 5.20(s, 2H), 7.12–7.26(m, 5H), 7.38–7.50 (m, 8H)
IR(KBr) 3435, 3033, 2938, 1518, 1470, 1364, 1178, 1149, 1109, 970, 871, 839cm$^{-1}$

I-834  mp 188–189° C.
$^1$H NMR(CDCl$_3$) δ 3.49(s, 3H), 3.72(s, 3H), 5.15(s, 2H), 5.68(brs, 1H), 5.84(brs, 1H), 6.42–6.56(m, 3H), 6.98–7.08(m, 3H), 7.23–7.31(m, 3H), 7.23–7.31(m, 2H), 7.38–7.45(m, 4H)
IR(KBr) 3420, 3328, 1627, 1584, 1523, 1489, 1460, 1412, 1316, 1288, 1249, 1172, 1128, 1115, 1068, 1000, 849, 812, 746cm$^{-1}$ I-835  mp 180–181° C.
$^1$H NMR(CDCl$_3$) δ 3.51(s, 3H), 3.75(s, 3H), 5.17(s, 2H), 5.70(brs, 1H), 5.77(brs, 1H), 6.45(s, 1H), 6.95–7.10(m, 4H), 7.27–7.46(m, 8H), 7.96(brs, 1H))
IR(KBr) 3422, 3358, 1706, 1602, 1489, 1454, 1410, 1289, 1253, 1203, 1180, 1125, 1101, 1071, 1015cm$^{-1}$ I-836  mp 148–149° C.
$^1$H NMR(DMSO-d$_6$) δ 1.77(s, 3H), 1.80(s, 3H), 2.54(s, 6H), 3.35(s, 3H), 3.42(s, 3H), 3.48(s, 3H), 4.73(d, J=4.5Hz, 2H), 5.50–5.53(m, 1H), 7.30–7.54(m, 8H)
IR(KBr) 3495, 3293, 1754, 1712, 1516, 1359, 1359, 1243, 1175, 1147, 971, 866, 845cm$^{-1}$ I-837  mp 136–138° C.
$^1$H NMR(DMSO-d$_6$) δ 2.32(s, 3H), 2.50(s, 6H), 3.31(s, 3H), 3.35(s, 3H), 3.44(s, 3H), 5.23(s, 2H), 7.21–7.47(m, 12H)
IR(KBr) 3495, 3292, 3028, 2934, 1754, 1710, 1516, 1357, 1176, 1147, 972, 868, 842cm$^{-1}$

TABLE 166

I-838  mp 195–196° C.
$^1$H NMR(CDCl$_3$) δ 1.44(t, J=7.2Hz, 3H), 3.46(s, 3H), 3.69(s, 3H), 3.86(s, 6H), 4.44(q, J=7.0Hz, 2H), 5.15(s, 2H), 5.66(brs, 1H), 5.72(brs, 1H), 6.27(s, 1H), 7.01(s, 2H), 7.13(s, 1H), 7.38–7.46(m, 7H)
IR(KBr) 3485, 2937, 1713, 1580, 1464, 1455, 1407, 1324, 1243, 1123, 1102, 1069, 1014, 763cm$^{-1}$ I-839  mp 150–151° C.
$^1$H NMR(DMSO-d$_6$) δ 1.72(s, 3H), 1.76(s, 3H), 1.88(s, 3H), 1.90(s, 3H), 4.55(d, J=5.8Hz, 2H), 5.44–5.50(m, 1H), 6.80–6.97(m, 8H), 7.81(brs, 1H), 8.85(brs, 1H), 9.38(brs, 1H)
IR(KBr) 3495, 3293, 1753, 1711, 1429, 1390, 1360, 1242, 1217, 1178, 1143, 781cm$^{-1}$

TABLE 166-continued

I-840 mp 149–150° C.
$^1$H NMR(DMSO-d$_6$) δ 1.71(s, 3H), 1.75(s, 3H), 2.00(s, 6H), 2.59(s, 3H), 4.57(d, J=6.4Hz, 2H), 5.42–5.47(m, 1H), 6.84–7.13(m, 8H), 9.13(brs, 1H), 9.50(brs, 1H)
IR(KBr) 3451, 2933, 1612, 1587, 1518, 1472, 1348, 1259, 1211, 1171, 1121, 1087, 969, 872, 835, 813cm$^{-1}$ I-841 mp 203–204° C.
$^1$H NMR(DMSO-d$_6$) δ 1.87(s, 3H), 1.89(s, 3H), 2.31(s, 3H), 5.09(s, 2H), 6.80–7.00(m, 8H), 7.20(d, J=7.8Hz, 2H), 7.39 (d, J=7.8Hz, 2H), 7.81(brs, 1H), 8.97(brs, 1H), 9.38(brs, 1H)
IR(KBr) 3491, 3398, 2921, 1611, 1516, 1476, 1259, 1183, 1155, 996, 794cm$^{-1}$ I-842 mp 128–129° C.
$^1$H NMR(DMSO-d$_6$) δ 2.01(s, 6H), 2.34(s, 3H), 2.63(s, 3H), 5.12(s, 2H), 6.85–7.13(m, 8H), 7.18(d, J=7.6Hz, 2H), 7.36 (d, J=7.6Hz, 2H), 9.15(brs, 1H), 9.55(brs, 1H)
IR(KBr) 3432, 3305, 1735, 1607, 1523, 1482, 1398, 1360, 1294, 1284, 1179, 1080, 816cm$^{-1}$

TABLE 167

I-843 mp 203–204° C.
$^1$H NMR(CDCl$_3$) δ 2.66(s, 3H), 3.13(s, 3H), 3.59(s, 3H), 3.76(s, 3H), 5.19(s, 2H), 6.85(s, 1H), 7.13–7.69(m, 11H), 8.07 (brs, 1H)
IR(KBr) 3432, 3305, 1735, 1607, 1523, 1482, 1398, 1360, 1294, 1284, 1179, 1080, 816cm$^{-1}$ I-844 mp 109–110° C.
$^1$H NMR(DMSO-d$_6$) δ 1.36(t, J=7.2Hz, 3H), 2.82(s, 3H), 3.24(s, 3H), 3.47(s, 3H), 3.66(s, 3H), 3.79(s, 6H), 4.38(q, J=7.0Hz, 2H), 5.26(s, 2H), 6.78(s, 1H), 7.32–7.52(m, 10H)
IR(KBr) 3432, 2940, 1716, 1579, 1465, 1407, 1366, 1322, 1240, 1179, 1123, 1078, 815, 796cm$^{-1}$ I-845 mp 113–115° C.
$^1$H NMR(CDCl$_3$) δ 2.25(s, 3H), 2.27(s, 3H), 3.20(s, 3H), 5.20(s, 2H), 7.03–7.15(m, 5H), 7.33–7.51(m, 9H)
IR(CHCl$_3$) 2925, 1618, 1580, 1521, 1455, 1373, 1314, 1299, 1268, 1174, 1149, 1126, 1018, 970, 874cm$^{-1}$ I-846 mp 155–157° C.
$^1$H NMR(CDCl$_3$) δ 2.26(s, 6H), 4.69(s, 1H), 5.19(s, 2H), 6.87–6.90(m, 2H), 7.03–7.15(m, 5H), 7.22–7.50(m, 7H)
IR(CHCl$_3$) 3596, 2952, 2924, 1612, 1582, 1523, 1490, 1455, 1425, 1383, 1259, 1171, 1125, 1012, 956, 877cm$^{-1}$ I-847 mp 81–84° C.
$^1$H NMR(CDCl$_3$) δ 1.07–1.14(m, 6H), 2.55–2.66(m, 4H), 4.73(s, 1H), 5.16(s, 2H), 5.70(s, 1H), 6.82–6.91(m, 3H), 6.92–6.99 (m, 2H), 7.10–7.12(d, J=4.2Hz, 2H), 7.22–7.25(m, 2H), 7.38–7.49(m, 5H)
IR(CHCl$_3$) 3596, 3542, 2968, 2932, 2872, 1731, 1611, 1588, 1520, 1489, 1455, 1380, 1327, 1289, 1256, 1171, 1126, 1011, 903, 878, 836cm$^{-1}$ I-848 mp 125–127° C.
$^1$H NMR(CDCl$_3$) δ 1.77(s, 3H), 1.82(s, 3H), 2.26(s, 3H), 2.28(s, 3H), 3.20(s, 3H), 4.63–4.65(d, J=6.9Hz, 2H), 5.56(m, 1H), 7.02–7.13(m, 5H), 7.31–7.43(m, 4H)
IR(CHCl$_3$) 2924, 1619, 1578, 1488, 1373, 1298, 1266, 1174, 1149, 1125, 970, 874cm$^{-1}$

TABLE 168

I-849 mp 141–143° C.
$^1$H NMR(CDCl$_3$) δ 1.07–1.14(m, 6H), 2.53–2.65(m, 4H), 3.12(s, 3H), 3.20(s, 3H), 5.18(s, 2H), 7.10–7.14(m, 3H), 7.24–7.27 (m, 2H), 7.33–7.50(m, 9H)
IR(CHCl$_3$) 2969, 2934, 1614, 1517, 1487, 1371, 1331, 1289, 1263, 1173, 1149, 1111, 970, 938, 872cm$^{-1}$

I-850 mp 90–91° C.
$^1$H NMR(CDCl$_3$) δ 2.13(s, 3H), 2.29(s, 3H), 2.35(s, 3H), 3.16(s, 3H), 5.21(s, 2H), 6.87–6.90(m, 2H), 7.09–7.49(m, 11H)
IR(CHCl$_3$) 3596, 1731, 1613, 1520, 1478, 1362, 1261, 1173, 1119, 1086, 1025, 972, 953, 874cm$^{-1}$

I-851 mp 94–96° C.
$^1$H NMR(CDCl$_3$) δ 1.76–1.77(d, J=0.3Hz, 3H), 1.81–1.82(d, J=0.9Hz, 3H), 2.26(s, 3H), 2.27(s, 3H), 4.62–4.64(d, J=6.9Hz, 2H), 4.71(s, 1H), 5.56(m, 1H), 6.87–6.91(m, 2H), 7.00–7.13(m, 5H), 7.23–7.27(m, 2H)
IR(CHCl$_3$) 3596, 2923, 1675, 1613, 1579, 1523, 1490, 1386, 1297, 1171, 1124, 990, 956, 877, 836cm$^{-1}$

I-852 mp 106–108° C.
$^1$H NMR(CDCl$_3$) δ 2.63(s, 3H), 3.52(s, 3H), 3.77(s, 3H), 5.24(s, 2H), 6.84(s, 1H), 6.84(s, 1H), 7.12–7.20(m, 3H), 7.35–7.50 (m, 7H), 7.56–7.64(m, 2H)
IR(KBr) 2935, 1604, 1523, 1483, 1373, 1232, 1086, 1011, 945, 847, 728, 605, 523, 506cm$^{-1}$

I-853 mp 136–138° C.
$^1$H NMR(CDCl$_3$) δ 1.77(s, 3H), 1.81(s, 3H), 2.67(s, 3H), 3.53(s, 3H), 3.78(s, 3H), 4.67(d, J=6.9Hz, 2H), 5.47–5.53(m, 1H), 6.84(s, 1H), 7.10–7.19(m, 3H), 7.31(d, J=2.1Hz, 1H), 7.38(dd, J=2.1, 8.1Hz, 1H), 7.57–7.64(m, 2H)
IR(KBr) 2936, 1604, 1523, 1484, 1435, 1373, 1225, 1086, 1011, 943, 848, 783, 606, 508cm$^{-1}$

TABLE 169

I-854 mp 128–130° C.
$^1$H NMR(CDCl$_3$) δ 1.74(s, 3H), 1.81(s, 3H), 2.62(s, 3H), 3.52(s, 3H), 3.79(s, 3H), 4.63–4.67(m, 2H), 5.45–5.53(m, 1H), 6.86(s, 1H), 7.01(dd, J=2.1Hz, 8.4Hz, 1H), 7.10(d, J=1.8Hz, 1H), 7.13–7.20(m, 2H), 7.29(d, J=8.4Hz, 1H), 7.59–7.64 (m, 2H)
IR(KBr) 2940, 1600, 1518, 1484, 1418, 1366, 1232, 1080, 984, 893, 838, 812, 621, 524cm$^{-1}$

I-855 mp 141–143° C.
$^1$H NMR(CDCl$_3$) δ 1.76(s, 3H), 1.82(s, 3H), 2.61(s, 3H), 3.53(s, 3H), 3.77(s, 3H), 4.62(d, J=6.9Hz, 2H), 5.47–5.53(m, 1H), 5.70(s, 1H), 6.83(s, 1H), 6.91(dd, J=2.1, 8.1Hz, 1H), 6.96(d, J=8.1Hz, 1H), 7.02(d, J=2.1Hz, 1H), 7.10–7.19(m, 2H), 7.59–7.64(m, 2H)
IR(KBr) 3531, 2931, 1604, 1520, 1484, 1372, 1233, 1175, 1083, 1011, 814, 800, 781, 727, 526cm$^{-1}$

TABLE 169-continued

I-856 mp 217–220° C.
$^1$H NMR(CDCl$_3$) δ 2.75(s, 3H), 3.51(s, 3H), 3.78(s, 3H), 5.78(s, 1H), 6.85(s, 1H), 7.03(dd, J=1.8, 8.4Hz, 1H), 7.11–7.20 (m, 3H), 7.32(d, J=8.4Hz, 1H), 7.58–7.63(m, 2H)
IR(KBr) 3434, 2941, 1611, 1487, 1423, 1363, 1209, 1076, 891, 818, 621, 573, 513cm$^{-1}$

I-857 mp 183–185° C.
$^1$H NMR(CDCl$_3$) δ 1.92(s, 3H), 3.20(s, 3H), 3.53(s, 3H), 3.78(s, 3H), 3.93(s, 3H), 4.31(s, 4H), 6.79–6.83(m, 2H), 6.90–6.94 (m, 2H), 7.16–7.41(m, 12H), 7.66–7.71(m, 2H),
IR(KBr) 3030, 2936, 1604, 1517, 1482, 1362, 1232, 1232, 1180, 1120, 1082, 877, 799, 701, 526cm$^{-1}$

I-858 mp 192–194° C.
$^1$H NMR(CDCl$_3$) δ 2.57(s, 3H), 3.21(s, 3H), 3.56(s, 3H), 3.77(s, 3H), 3.87(s, 3H), 6.77–6.89(m, 4H), 7.34–7.40(m, 2H), 7.67–7.72(m, 2H)
IR(KBr) 3451, 3368, 2937, 1622, 1524, 1481, 1359, 1174, 1149, 1086, 962, 869, 802, 525cm$^{-1}$

TABLE 170

I-859 mp 210–212° C.
$^1$H NMR(CDCl$_3$) δ 1.92(s, 3H), 2.23(s, 3H), 3.46(s, 3H), 3.74(s, 3H), 3.89(s, 3H), 5.24(s, 1H), 5.80(s, 1H), 5.94(s, 1H), 6.46(s, 1H), 6.90–6.96(m, 1H), 7.01(d, J=1.8Hz, 1H), 7.08(dd, J=1.8, 8.1Hz, 1H), 7.50–7.55(m, 2H), 7.76(s, 1H), 8.52 (d, J=8.1Hz, 1H),
IR(KBr) 3420, 2938, 1636, 1610, 1526, 1496, 1398, 1225, 1164, 1073, 1026, 831cm$^{-1}$

I-860 mp 183–185° C.
$^1$H NMR(DMSO-d$_6$) δ 2.43(s, 6H), 2.45(s, 6H), 5.13(s, 2H), 6.76–6.82(m, 4H), 6.91(dd, J=2.1, 8.4Hz, 1H), 7.01(d, J=8.4Hz, 1H), 7.09(d, J=2.1Hz, 1H), 7.31–7.43(m, 5H), 7.48–7.53(m, 2H), 9.02(br s, 1H), 9.32(br s, 1H)
IR(KBr) 3600–2800(br), 1609, 1581, 1521, 1493, 1455, 1437, 1384, 1321, 1275, 1215, 1193, 1142, 1007cm$^{-1}$

I-861 mp 172–174° C.
$^1$H NMR(CDCl$_3$) δ 2.50(s, 6H), 2.53(s, 6H), 3.11(s, 3H), 3.19(s, 3H), 5.18(s, 2H), 6.89(s, 1H), 6.93(s, 1H), 7.12(d, J=8.4Hz, 1H), 7.30–7.54(m, 8H), 7.66–7.71(m, 2H), 7.73(d, J=2.1Hz, 1H)
IR(KBr) 3600–2800(br), 1613, 1518, 1491, 1455, 1361, 1348, 1276, 1178, 1159, 1109, 970cm$^{-1}$

I-862 mp 173–175° C.
$^1$H NMR(CDCl$_3$) δ 1.77(s, 3H), 1.82(s, 3H), 2.51(s, 6H), 2.53(s, 6H), 3.19(s, 3H), 3.22(s, 3H), 4.63(d, J=7.2Hz, 2H), 5.49–5.53(m, 1H), 6.89(s, 1H), 6.93(s, 1H), 7.05(d, J=9.0Hz, 1H), 7.26–7.35(m, 2H), 7.51(dd, J=1.8, 8.1Hz, 1H), 7.67–7.70 (m, 3H)
IR(KBr) 3600–2800(br), 1519, 1491, 1363, 1331, 1291, 1257, 1175, 1147, 1105, 1013, 980, 966cm$^{-1}$

I-863 mp 150–152° C.
$^1$H NMR(DMSO-d$_6$) δ 1.72(s, 3H), 1.76(s, 3H), 2.43(s, 6H), 2.45(s, 6H), 4.55(d, J=6.6Hz, 2H), 5.47–5.51(m, 1H), 6.78–6.83(m, 4H), 6.90–7.06(m, 3H), 7.38–7.42(m, 2H), 8.87(br s, 1H), 9.39(br s, 1H)
IR(KBr) 3600–2800(br), 1610, 1585, 1522, 1495, 1476, 1448, 1385, 1292, 1275, 1199, 1171, 1136, 985, 948cm$^{-1}$

TABLE 171

I-864 mp 175–177° C.
$^1$H NMR(DMSO-d$_6$) δ 2.44(s, 12H), 5.13(s, 4H), 6.77(s, 2H), 6.90–7.09(m, 8H), 7.33–7.52(m, 8H), 9.01(s, 2H)
IR(KBr) 3600–2800(br), 1582, 1518, 1491, 1454, 1384, 1328, 1270, 1242, 1191, 1141, 1123, 1046, 1006cm$^{-1}$

I-865 mp 175–177° C.
$^1$H NMR(CDCl$_3$) δ 2.52(s, 12H), 3.11(s, 6H), 5.17(s, 4H), 6.91(s, 2H), 7.11(d, J=8.4Hz, 2H), 7.36–7.52(m, 12H), 7.72 (d, J=2.1Hz, 2H)
IR(KBr) 3600–2800(br), 1612, 1520, 1496, 1455, 1364, 1348, 1265, 1184, 1164, 1117, 1005, 971cm$^{-1}$

I-866 mp 180–182° C.
$^1$H NMR(CDCl$_3$) δ 1.77(s, 6H), 1.81(s, 6H), 2.52(s, 12H), 3.22(s, 6H), 4.63(d, J=6.9Hz, 2H), 5.49–5.54(m, 2H), 6.90 (s, 2H), 7.04(d, J=8.4Hz, 2H), 7.50(dd, J=2.1, 8.4Hz, 2H), 7.04(d, J=2.1Hz, 2H)
IR(KBr) 3600–2800(br), 1520, 1494, 1365, 1274, 1186, 1161, 1113, 996, 973cm$^{-1}$

I-867 mp 165–168° C.
$^1$H NMR(DMSO-d$_6$) δ 1.72(s, 6H), 1.76(s, 6H), 2.45(s, 12H), 4.55(d, J=6.0Hz, 4H), 5.45–5.55(m, 2H), 6.77(s, 2H), 6.89–6.98(m, 4H), 7.03–7.07(m, 2H), 8.86(br s, 2H)
IR(KBr) 3600–2800(br), 1579, 1519, 1497, 1476, 1456, 1384, 1277, 1238, 1195, 1142, 1126, 1050, 994cm$^{-1}$

I-868 mp 76–78° C.
$^1$H NMR(CDCl$_3$) δ 3.47(s, 3H), 3.75(s, 3H), 3.94(s, 3H), 5.15(s, 2H), 5.68(s, 1H), 5.69(s, 1H), 5.92(s, 1H), 6.46(s, 1H), 6.93–7.15(m, 5H), 7.22(d, J=1.5Hz, 1H), 7.34–7.49(m, 5H)
IR(CHCl$_3$) 3528, 1586, 1520, 1489, 1461, 1399, 1287, 1260, 1110, 1070, 1010, 907, 819cm$^{-1}$

I-869 mp 140–142° C.
$^1$H NMR(CDCl$_3$) δ 2.65(s, 3H), 3.13(s, 3H), 3.25(s, 3H), 3.57(s, 3H), 3.78(s, 3H), 3.94(s, 3H), 5.19(s, 2H), 6.85(s, 1H), 7.13–7.19(m, 2H), 7.30–7.50(m, 9H)
IR(CHCl$_3$) 1598, 1516, 1480, 1367, 1266, 1176, 1115, 1081, 1012, 969, 918, 867, 808cm$^{-1}$

TABLE 172

I-870 mp 189–190° C.
$^1$H NMR(CDCl$_3$) δ 1.76(d, J=0.9Hz, 3H), 1.81(s, 3H), 2.69(s, 3H), 3.24(s, 3H), 3.25(s, 3H), 3.58(s, 3H), 3.78(s, 3H), 3.94(s, 3H), 4.64(d, J=6.6Hz, 2H), 5.49(m, 1H), 6.85(s, 1H), 7.10(d, J=8.4Hz, 1H), 7.17(d.d, J=2.1, 8.4Hz, 1H), 7.30–7.42(m, 4H)
IR(CHCl$_3$) 2932, 1599, 1516, 1480, 1367, 1329, 1266, 1177, 1115, 1082, 1032, 1013, 970, 907, 868, 807cm$^{-1}$

TABLE 172-continued

I-871  mp 187–190° C.
$^1$H NMR(CDCl$_3$) δ 2.38(s, 3H), 2.64(s, 3H), 3.13(s, 3H), 3.25(s, 3H), 3.58(s, 3H), 3.78(s, 3H), 3.94(s, 3H), 5.14(s, 2H), 6.84(s, 1H), 7.13–7.24(m, 4H), 7.30–7.42(m, 6H)
IR(CHCl$_3$) 2966, 1598, 1517, 1480, 1462, 1368, 1329, 1267, 1177, 1116, 1082, 1032, 970, 907, 867, 808cm$^{-1}$

I-872  mp 192–194° C.
$^1$H NMR(CDCl$_3$) δ 1.15(t, J=6.9Hz, 3H), 1.76(s, 3H), 1.82(s, 3H), 2.59(s, 3H), 3.69(q, J=6.9Hz, 2H), 3.77(s, 3H), 4.61(d, J=6.9Hz, 2H), 4.99(s, 1H), 5.50(m, 1H), 5.70(s, 1H), 6.84(s, 1H), 6.88–6.97(m, 3H), 7.02(d, J=1.8Hz, 1H), 7.52–7.58(m, 2H)
IR(CHCl$_3$) 3536, 2934, 1609, 1520, 1482, 1410, 1365, 1279, 1243, 1172, 1128, 1080, 1029, 972, 952, 872, 833, 812cm$^{-1}$

I-873  $^1$H NMR(CDCl$_3$) δ 3.46(s, 3H), 3.70(s, 2H), 3.74(s, 3H), 3.75(s, 3H), 5.15(s, 2H), 5.67(s, 1H), 5.90(s, 1H), 6.47(s, 1H), 6.96(d.d, J=8.4 & 1.8Hz, 1H), 7.03(d, J=8.4Hz, 1H), 7.09(d, J=1.8Hz, 1H), 7.33–7.44(m, 7H), 7.61(.d, J=8.4Hz, 2H)
IR(KBr) 3536, 3389, 1732, 1587, 1519, 1487, 1438, 1393, 1249, 1217, 1166, 1110, 1069, 1001cm$^{-1}$

I-874  $^1$H NMR(CDCl$_3$) δ 3.46(s, 3H), 3.74(s, 5H), 5.15(s, 2H), 5.68(s, 1H), 5.91(s, 1H), 6.47(s, 1H), 6.96(d.d, J=8.4 & 1.8Hz, 1H), 7.03(.d, J=8.4Hz, 1H), 7.09(.d, J=8.4Hz, 1H), 7.32–7.49(m, 7H), 7.62(d, J=8.1Hz, 2H)
IR(KBr) 3381, 1715, 1698, 1608, 1581, 1523, 1485, 1455, 1396, 1294, 1235, 1112 1072, 1017cm$^{-1}$

I-875  $^1$H NMR(CDCl$_3$) δ 2.69(s, 3H), 3.13(s, 3H), 3.54(s, 3H), 3.70(s, 2H), 3.74(s, 3H), 3.77(s, 3H), 5.19(s, 2H), 6.86(s, 1H), 7.15(d, J=8.7Hz, 1H), 7.30–7.40(m, 9H), 7.59(.d, J=8.1Hz, 2H)
IR(KBr) 1734, 1721, 1606, 1481, 1398, 1361, 1244, 1175, 1120, 1078, 1010cm$^{-1}$

TABLE 173

I-876  $^1$H NMR(CDCl$_3$) δ 1.76(s, 3H), 1.81(s, 3H), 2.73(s, 3H), 3.23(s, 3H), 3.54(s, 3H), 3.70(s, 2H), 3.74(s, 3H), 3.77(s, 3H), 4.64(d, J=6.9Hz, 2H), 5.46–5.55(m, 1H), 6.86(s, 1H), 7.09(d, J=8.4Hz, 1H), 7.35(d.d, J=8.4 & 2.1Hz, 1H), 7.37 (d, J=8.1Hz, 2H), 7.39(d, J=2.1Hz, 1H), 7.59(d, J=8.1Hz, 2H)
$^1$H NMR(CDCl$_3$) δ
IR(KBr) 3447, 1735, 1608, 1522, 1482, 1365, 1177, 1117, 1078, 1013cm$^{-1}$

I-877  $^1$H NMR(CDCl$_3$) δ 1.76(s, 3H), 1.82(s, 3H), 3.46(s, 3H), 3.74(s, 5H), 3H), 4.62(d, J=6.9Hz, 2H), 5.46–5.58(m, 1H), 5.69(s, 1H), 5.89(s, 1H), 6.47(s, 1H), 6.96(s, 2H), 7.06(s, 1H), 7.38(d, J=8.4Hz, 2H), 7.62(d, J=8.4Hz, 2H)

I-878  $^1$H NMR(CDCl$_3$) δ 1.76(s, 3H), 1.82(s, 3H), 3.46(s, 3H), 3.70(s, 2H), 3.74(s, 6H), 4.62(d, J=6.9Hz, 2H), 5.46 –5.58(m, 1H), 5.68(s, 1H), 5.88(s, 1H), 6.47(s, 1H), 6.96(s, 2H), 7.06(s, 1H), 7.37(d, J=8.4Hz, 2H), 7.61(d, J=8.4Hz, 2H)
IR(KBr) 3527, 3386, 1734, 1609, 1586, 1520, 1487, 1439, 1396, 1219, 1167, 1111, 1068, 1010cm$^{-1}$

I-879  mp 136–139° C.
$^1$H NMR(CDCl$_3$) δ 1.7(br s, 1H), 1.76(s, 3H), 1.81(s, 3H), 2.73(s, 3H), 3.23(s, 3H), 3.53(s, 3H), 3.78(s, 3H), 4.64(d, J=6.7Hz, 2H), 4.78(s, 2H), 5.49(t, J=6.8Hz, 1H), 6.87(s, 1H), 7.09(d, J=8.6Hz, 1H), 7.35(dd, J=8.6, 2.1Hz, 1H), 7.40(d, J=2.1Hz, 1H), 7.47(d, J=8.1Hz, 2H), 7.64(d, J=8.1Hz, 2H)
IR(KBr) 3553, 3434, 1481, 1389, 1363, 1235, 1175, 1084, 1011, 972, 806cm$^{-1}$

I-880  mp 180–181° C.
$^1$H NMR(CDCl$_3$) δ 1.70(br s, 1H), 1.76(s, 3H), 1.82(s, 3H), 3.46(s, 3H), 3.75(s, 3H), 4.62(d, J=6.9Hz, 2H), 4.77(s, 2H), 5.53(t, J=6.9Hz, 1H), 5.69(s, 1H), 5.89(s, 1H), 6.47(s, 1H), 6.94–6.96(m, 2H), 7.05–7.07(m, 1H), 7.46(d, J=8.1Hz, 2H), 7.65(d, J=8.4Hz, 2H)
IR(KBr) 3509, 3367, 1522, 1487, 1461, 1396, 1289, 1249, 1213, 1116, 1071, 1009, 992, 942, 797, 782cm$^{-1}$

TABLE 174

I-881  mp 122–123° C.
$^1$H NMR(CDCl$_3$) δ 1.77(s, 3H), 1.82(s, 3H), 2.34(t, J=6.5Hz, 1H), 3.22(s, 3H), 3.45(s, 3H), 3.73(s, 3H), 4.5(m, 2H), 4.64(d, J=6.6Hz, 2H), 5.56(t, J=6.6Hz, 1H), 6.84(s, 1H), 6.99–7.10(m, 3H), 7.39(d, J=8.7Hz, 2H), 7.71(d, J=8.7Hz, 2H)
IR(KBr) 3579, 1518, 1471, 1360, 1261, 1230, 1148, 1019, 966, 881, 843cm$^{-1}$

I-882  mp 156–158° C.
$^1$H NMR(CDCl$_3$) δ 1.76(s, 3H), 1.81(s, 3H), 2.49(t, J=6.6Hz, 1H), 3.44(s, 3H), 3.72(s, 3H), 4.49(br s, 2H), 4.63(d, J=6.7Hz, 2H), 5.04(s, 1H), 5.55(t, J=6.7Hz, 1H), 6.85(s, 1H), 6.92(d, J=8.9Hz, 2H), 6.98–7.10(m, 3H), 7.53(d, J=8.9Hz, 2H)
IR(KBr) 3433, 3234, 1609, 1520, 1472, 1266, 1227, 994, 836cm$^{-1}$

I-883  mp 168–170° C.
$^1$H NMR(CDCl$_3$) δ 2.50(t, J=6.5Hz, 1H), 3.44(s, 3H), 3.73(s, 3H), 4.49(br s, 2H), 4.78(d, J=6.1Hz, 2H), 5.06(s, 1H), 6.24(t, J=6.1Hz, 1H), 6.85(s, 1H), 6.93(d, J=8.6Hz, 2H), 6.97–7.13(m, 3H), 7.53(d, J=8.6Hz, 2H)
IR(KBr) 3544, 3412, 3267, 1613, 1521, 1475, 1263, 1229, 1011, 884, 816cm$^{-1}$

I-884  mp 153–154° C.
$^1$H NMR(CDCl$_3$) δ 3.49(s, 3H), 3.77(s, 3H), 5.17(s, 2H), 5.76(brs, 2H), 6.45(s, 1H), 6.91–7.07(m, 3H), 7.26–7.45(m, 5H), 7.93(d, J=8.2Hz, 2H), 8.00(brs, 1H), 8.27(d, J=8.4Hz, 2H)
IR(KBr) 3448, 2962, 2938, 1738, 1627, 1604, 1589, 1519, 1486, 1319, 1250, 1153, 1115, 1071, 1011cm$^{-1}$ I-885  mp 81–82° C.
$^1$H NMR(CDCl$_3$) δ 1.51(s, 3H), 1.54(s, 3H), 1.74(s, 3H), 1.77(s, 3H), 2.70(s, 3H), 3.24(s, 3H), 3.60(s, 3H), 3.78(s, 3H), 4.38(d, J=7.5Hz, 2H), 4.65(d, J=6.6Hz, 2H), 6.86(s, 1H), 7.06–7.11(m, 3H), 7.35–7.41(m, 2H), 7.52–7.57(m, 1H)
IR(KBr) 3433, 2938, 1699, 1618, 1521, 1481, 1367, 1209, 1178, 1115, 1081, 972, 950, 813, 793cm$^{-1}$

TABLE 175

I-886  mp 208–209° C.
$^1$H NMR(CDCl$_3$) δ 1.77(s, 3H), 1.81(s, 3H), 2.71(s, 3H), 3.23(s, 3H), 3.60(s, 3H), 3.76(s, 3H), 4.64(d, J=7.2Hz, 2H), 5.49(t, J=8.7Hz, 1H), 6.85(s, 1H), 7.09(d, J=8.7Hz, 1H), 7.26–7.40(m, 3H), 7.52–7.58(m, 1H), 7.69–7.73(m, 1H), 8.02

TABLE 175-continued (brs, 1H)
IR(KBr) 3357, 2939, 1736, 1606, 1523, 1483, 1398, 1370, 1294, 1243, 1179, 1111, 1079, 965, 827, 814, 795cm$^{-1}$ I-887 mp 89–90° C.
$^1$H NMR(CDCl$_3$) δ 2.34(s, 3H), 2.38(s, 3H), 2.64(s, 3H), 3.12(s, 3H), 3.53(s, 3H), 3.77(s, 3H), 4.92(s, 2H), 5.14(s, 2H), 6.83(s, 1H), 6.89(d, J=8.7Hz, 2H), 7.11–7.46(m, 12H)
IR(KBr) 3434, 2939, 1699, 1617, 1520, 1481, 1367, 1211, 1178, 1114, 1081, 952, 813, 794cm$^{-1}$ I-888 mp 181–182° C.
$^1$H NMR(CDCl$_3$) δ 2.38(s, 3H), 2.66(s, 3H), 3.12(s, 3H), 3.59(s, 3H), 3.76(s, 3H), 5.14(s, 2H), 6.85(s, 1H), 7.14–7.41(m, 8H), 7.52–7.58(m, 1H), 7.69–7.73(m, 1H), 8.02(brs, 1H)
IR(KBr) 3348, 3030, 2940, 1733, 1607, 1523, 1482, 1397, 1366, 1281, 1242, 1212, 1179, 1128, 1112, 1080, 971, 944, 815, 799cm$^{-1}$ I-889 mp 155–157° C.
$^1$H NMR(CDCl$_3$) δ 1.46(t, J=7.0Hz, 3H), 1.76(s, 3H), 1.82(s, 3H), 2.73(s, 3H), 3.23(s, 3H), 3.56(s, 3H), 3.74(s, 3H), 4.46(q, J=7.4Hz, 2H), 4.65(d, J=7.2Hz, 2H), 5.48–5.54(m, 1H), 6.69(s, 1H), 7.09(d, J=8.4Hz, 2H), 7.28–7.47(m, 4H)
IR(KBr) 3434, 2938, 1716, 1579, 1477, 1464, 1409, 1366, 1241, 1178, 1124, 1078, 955, 815, 796cm$^{-1}$ I-890 mp 82–83° C.
$^1$H NMR(CDCl$_3$) δ 2.67(s, 3H), 3.13(s, 3H), 3.58(s, 3H), 3.80(s, 3H), 5.19(s, 2H), 6.84(s, 1H), 7.13–7.49(m, 8H), 7.89–7.96 (m, 2H), 8.27(brs, 1H), 8.27–8.31(m, 1H)
IR(KBr) 3447, 3033, 2940, 1743, 1521, 1482, 1367, 1312, 1272, 1249, 1178, 1119, 1080, 957, 817, 799cm$^{-1}$

TABLE 176

I-891 mp 86–87° C.
$^1$H NMR(CDCl$_3$) δ 2.68(s, 3H), 3.10(s, 3H), 3.15(s, 3H), 3.62(s, 3H), 3.81(s, 3H), 5.22(s, 2H), 6.85(s, 1H), 7.16–7.50(m, 9H), 7.88–7.91(m, 2H)
IR(KBr) 3413, 2938, 1519, 1483, 1366, 1313, 1162, 1119, 1090, 1079, 957, 812cm$^{-1}$

I-892 mp 97–98° C.
$^1$H NMR(CDCl$_3$) δ 1.53(s, 3H), 1.55(s, 3H), 1.76(s, 3H), 1.78(s, 3H), 3.63(s, 3H), 3.75(s, 3H), 4.26(d, J=7.4Hz, 2H), 4.62(d, J=6.8Hz, 2H), 5.65(brs, 1H), 5.72(brs, 1H), 6.84(s, 1H), 7.04–7.13(m, 3H), 7.35–7.43(m, 2H), 7.51–7.58(m, 1H)
IR(KBr) 3453, 3379, 2973, 2931, 1719, 1629, 1529, 1490, 1406, 1313, 1288, 1247, 1193, 1101, 1072, 1015, 993, 816, 786cm$^{-1}$ I-893 mp 89–90° C.
$^1$H NMR(DMSO-d$_6$) δ 1.75(s, 3H), 1.78(s, 3H), 3.31(s, 3H), 3.62(s, 3H), 4.56(d, J=6.9Hz, 2H), 5.52(t, J=6.0Hz, 1H), 6.33(s, 1H), 6.34–6.47(m, 2H), 6.74(brs, 2H), 6.74–6.75(m, 1H), 6.87–6.91(m, 1H), 7.11–7.12(m, 1H), 7.32–7.34(m, 1H), 8.52(brs, 1H), 8.75(brs, 1H)
IR(KBr) 3424, 2933, 2614, 1719, 1625, 1585, 1523, 1488, 1408, 1287, 1247, 1125, 1070, 819, 788cm$^{-1}$ I-894 mp 167–168° C.
$^1$H NMR(CDCl$_3$) δ 2.31(s, 3H), 2.38(s, 3H), 3.52(s, 3H), 3.76(s, 3H), 4.91(s, 2H), 5.13(s, 2H), 5.65(brs, 1H), 5.77(brs, 1H), 6.85(s, 1H), 6.84–6.93(m, 2H), 7.10–7.44(m, 12H)
IR(KBr) 3425, 2933, 2614, 1719, 1625, 1585, 1522, 1488, 1408, 1287, 1247, 1125cm$^{-1}$ I-895 mp 93–94° C.
$^1$H NMR(DMSO-d$_6$) δ 2.11(s, 3H), 3.34(s, 3H), 3.62(s, 3H), 5.10(s, 2H), 6.32(s, 2H), 6.41–6.49(m, 2H), 6.65(d, J=9.3Hz, 1H), 6.78(s, 1H), 6.95(d, J=8.7Hz, 1H), 7.09–7.14(m, 1H), 7.22(d, J=8.4Hz, 2H), 7.41(d, J=8.1Hz, 2H), 8.49(brs, 1H), 8.87(brs, 1H)
IR(KBr) 3424, 2932, 1717, 1626, 1585, 1523, 1488, 1409, 1248, 1125, 1106, 1070, 811, 793cm$^{-1}$

TABLE 177

I-896 mp 149–150° C.
$^1$H NMR(DMSO-d$_6$) δ 1.72(s, 3H), 1.77(s, 3H), 3.32(s, 3H), 3.55(s, 3H), 3.76(s, 6H), 4.55(d, J=6.3Hz, 2H), 5.50(t, J=6.6Hz, 1H), 6.15(s, 1H), 6.68(d, J=2.1Hz, 1H), 6.91(d, J=8.7Hz, 1H), 7.30(s, 2H), 8.41(brs, 1H), 8.74(brs, 1H)
IR(KBr) 3423, 2936, 1694, 1578, 1459, 1410, 1319, 1229, 1126, 1067cm$^{-1}$ I-897 mp 107–108° C.
$^1$H NMR(CDCl$_3$) δ 2.70(s, 3H), 3.12(s, 3H), 3.55(s, 3H), 3.72(s, 3H), 3.78(s, 6H), 5.18(s, 2H), 6.65(s, 1H), 6.70(d, J=4.2Hz, 1H), 7.14(d, J=8.4Hz, 1H), 7.26–7.48(m, 9H)
IR(KBr) 3434, 2941, 1517, 1488, 1366, 1353, 1261, 1177, 1102, 1074, 844, 818, 796cm$^{-1}$ I-898 powder
$^1$H NMR(CDCl$_3$) δ 1.63(s, 3H), 1.70(s, 3H), 3.48(s, 3H), 3.73–3.76(m, 7H), 3.87(s, 3H), 4.98(s, 1H), 5.24–5.32(m, 2H), 5.90(s, 1H), 6.47(s, 1H), 6.89–7.02(m, 5H), 7.51–7.57(m, 2H)
IR(KBr) 3447, 2930, 1612, 1523, 1488, 1455, 1398, 1230, 1120, 1080, 1037, 818, 592cm$^{-1}$ I-899 mp 171–173° C.
$^1$H NMR(CDCl$_3$) δ 1.73(s, 3H), 1.76(s, 3H), 3.48(s, 3H), 3.73–3.76(m, 5H), 4.23(s, 1H), 4.92(s, 1H), 5.37–5.43(m, 1H), 5.84(s, 1H), 6.46(s, 1H), 6.70(d, J=8.1Hz, 1H), 6.86–7.01(m, 5H), 7.51–7.56(m, 2H)
IR(KBr) 3392, 2934, 1612, 1526, 1489, 1398, 1222, 1116, 1075, 829, 590cm$^{-1}$ I-900 mp 78–79° C.
$^1$H NMR(CDCl$_3$) δ 2.14(s, 3H), 2.29(s, 3H), 2.36(s, 3H), 3.16(s, 3H), 3.20(s, 3H), 5.22(s, 2H), 7.10(s, 1H), 7.16(d, J=8.7Hz, 1H), 7.22–7.49(m, 11H)
IR(CHCl$_3$) 2939, 1612, 1516, 1476, 1415, 1370, 1291, 1269, 1174, 1150, 1119, 1087, 1018, 971, 954, 873cm$^{-1}$

TABLE 178

I-901 mp 114–116° C.
$^1$H NMR(CDCl$_3$) δ 1.08–1.14(m, 6H), 1.77(s, 3H), 1.81–1.82(d, J=0.6Hz, 3H), 2.53–2.65(m, 4H), 3.21(s, 3H), 3.23(s,

TABLE 178-continued

3H), 4.62–4.65(d, J=6.6Hz, 2H), 5.52(m, 1H), 7.04–7.13(m, 2H), 7.23–7.26(m, 2H), 7.32–7.42(m, 5H)
IR(CHCl₃) 2970, 2934, 2874, 1674, 1614, 1572, 1517, 1487, 1415, 1370, 1331, 1288, 1262, 1172, 1149, 1109, 971, 937, 872, 849cm⁻¹

I-902 mp 97–99° C.
¹H NMR(CDCl₃) δ 1.07–1.14(m, 6H), 1.77(s, 3H), 1.83(s, 3H), 2.55–2.66(m, 4H), 4.61–4.64(d, J=6.6Hz, 2H), 5.06(s, 1H), 5.54(m, 1H), 5.77(s, 1H), 7.24–7.64(m, 4H), 6.97(d, J=2.1Hz, 1H), 7.10–7.12(d, J=5.7Hz, 2H), 7.23–7.26(m, 2H)
IR(CHCl₃) 3596, 3537, 2969, 2933, 27873, 1675, 1612, 1586, 1520, 1489, 1385, 1327, 1290, 1257, 1171, 1125, 996, 903, 877, 836cm⁻¹

I-903 mp 69–71° C.
¹H NMR(CDCl₃) δ 1.78(s, 3H), 1.82(s, 3H), 2.15(s, 3H), 2.30(s, 3H), 2.43(s, 3H), 2.43(s, 3H), 3.21(s, 3H), 3.27(s, 3H), 4.64–4.67(d, J=6.9Hz, 2H), 5.50(s, 2H), 7.10–7.13(d, J=9.9Hz, 2H), 7.23–7.29(m, 2H), 7.34–7.42(m, 5H)
IR(CHCl₃) 2939, 1612, 1516, 1476, 1415, 1370, 1331, 1290, 1268, 1174, 1150, 1119, 1086, 971, 954, 873cm⁻¹

I-904 mp 125–127° C.
¹H NMR(CDCl₃) δ 2.27(s, 6H), 3.91(s, 3H), 4.88(br, 1H), 5.20(s, 2H), 6.83–6.96(m, 5H), 7.12–7.13(d, J=4.5Hz, 2H), 7.22–7.50(m, 7H)
IR(CHCl₃) 3596, 2957, 2936, 1611, 1586, 1522, 1490, 1464, 1454, 1326, 1257, 1172, 1138, 1033, 835cm⁻¹

I-905 mp 145–146° C.
¹H NMR(CDCl₃) δ 2.26(s, 3H), 2.28(s, 3H), 3.20(s, 3H), 3.91(s, 3H), 5.21(s, 2H), 6.83(dd, J=8.1, 2.1Hz, 1H), 6.91–6.96 (m, 2H), 7.11(s, 1H), 7.15(s, 1H), 7.32–7.50(m, 9H)
IR(CHCl₃) 2938, 1604, 1584, 1519, 1488, 1464, 1454, 1373, 1330, 1260, 1175, 1149, 1033, 1018, 970, 873, 847cm⁻¹

TABLE 179

I-906 mp 132–134° C.
¹H NMR(CDCl₃) δ 2.27(s, 3H), 2.87,(s, 3H), 3.91(s, 3H), 5.16(s, 2H), 5.21(s, 2H), 5.70(s, 1H), 6.82–6.86(m, 2H), 6.92–7.00 (m, 4H), 7.13(s, 2H), 7.32–7.50(m, 10H)
IR(CHCl₃) 3542, 2936, 2871, 1585, 1519, 1491, 1454, 1382, 1322, 1273, 1175, 1137, 1014, 897, 877, 857cm⁻¹

I-907 mp 181–182° C.
¹H NMR(CDCl₃) δ 1.77(s, 3H), 1.82(s, 3H), 2.13(s, 3H), 2.30(s, 3H), 2.35(s, 3H), 4.61–4.64(d, J=6.9Hz, 2H), 5.37(s, 1H), 5.51(m, 1H), 5.78(s, 1H), 6.81(dd, J=8.1, 2.1Hz, 1H), 6.86–6.97(m, 3H), 7.08(s, 1H), 7.19–7.22(m, 2H), 7.26(s, 1H)
IR(CHCl₃) 3595, 3536, 2936, 1613, 1587, 1519, 1479, 1453, 1359, 1330, 1279, 1246, 1173, 1127, 1085, 1024, 974, 950, 881, 867cm⁻¹

I-908 mp 167–168° C.
¹H NMR(CDCl₃) δ 1.77–1.78(d, J=0.9Hz, 3H), 1.84(s, 3H), 2.08(s, 3H), 2.15(s, 3H), 4.63–4.65(d, J=6.9Hz, 2H), 4.82 (s, 1H), 5.05(s, 1H), 5.55(m, 1H), 5.80(m, 1H), 6.74(s, 1H), 6.78(dd, J=8.4, 2.1Hz, 1H), 6.87–6.95(m, 3H), 7.00(d, J=8.4Hz, 1H), 7.23–7.26(m, 2H)
IR(CHCl₃) 3594, 3534, 2923, 2869, 1675, 1613, 1584, 1520, 1488, 1455, 1399, 1289, 1247, 1166, 1127, 1091, 994, 948, 835cm⁻¹

I-909 mp 170–172° C.
¹H NMR(DMSO-d₆) δ 1.72(s, 3H), 1.76(s, 3H), 3.31(s, 3H), 3.63(s, 3H), 4.54(d, J=6.5Hz, 2H), 5.17(s, 2H), 5.49(t, J=6.5Hz, 1H), 6.36(s, 1H), 6.63(d, J=8.4Hz, 2H), 6.63(dd, J=8.4, 2.1Hz, 1H), 6.72(d, J=2.1Hz, 1H), 6.88(d, J=8.4Hz, 1H), 7.31(d, J=8.4Hz, 2H), 8.40(s, 1H), 8.70(s, 1H)
IR(KBr) 3416, 3329, 1614, 1523, 1489, 1408, 1242, 1219, 1115, 1070, 997, 817, 787cm⁻¹

TABLE 180

I-910 mp 207–209° C.
¹H NMR(CDCl₃) δ 1.54(s, 9H), 2.69(s, 3H), 3.12(s, 3H), 3.52(s, 3H), 3.77(s, 3H), 5.18(s, 2H), 6.56(s, 1H), 6.85(s, 1H), 7.14(d, J=8.7Hz, 1H), 7.32–7.48(m, 9H), 7.57(d, J=8.7Hz, 2H)
IR(KBr) 3373, 1734, 1525, 1369, 1227, 1177, 1158, 1080, 816, 793cm⁻¹

I-911 mp 214–216° C.
¹H NMR(DMSO-d₆) δ 2.84(s, 3H), 3.33(s, 3H), 3.46(s, 3H), 3.75(s, 3H), 5.26(s, 2H), 5.30(s, 2H), 6.66(d, J=8.7Hz, 2H), 6.93(s, 1H), 7.24–7.45(m, 8H), 7.52(m, 2H)
IR(KBr) 3468, 3386, 1604, 1523, 1482, 1392, 1361, 1175, 1085, 815cm⁻¹

I-912 mp 215–218° C.
¹H NMR(CDCl₃) δ 2.67(s, 3H), 3.13(s, 3H), 3.53(s, 3H), 3.78(s, 3H), 5.19(s, 2H), 6.86(s, 1H), 7.15(d, J=8.4Hz, 1H), 7.32–7.48(m, 7H), 7.69(s, 4H), 8.02(br s, 1H)
IR(KBr) 3307, 1733, 1482, 1393, 1361, 1284, 1177, 1084, 1012, 967, 945, 816cm⁻¹

I-913 mp 203–205° C.
¹H NMR(CDCl₃) δ 1.77(s, 3H), 1.81(s, 3H), 2.71(s, 3H), 3.24(s, 3H), 3.54(s, 3H), 3.79(s, 3H), 4.64(d, J=6.8Hz, 2H), 5.50(t, J=6.8Hz, 1H), 6.86(s, 1H), 7.09(d, J=8.4Hz, 1H), 7.35(dd, J=8.4, 2.0Hz, 1H), 7.39(d, J=2.0Hz, 1H), 7.69(s, 4H), 8.01(br s, 1H)
IR(KBr) 3311, 1735, 1482, 1393, 1362, 1177, 1083, 976, 945, 818cm⁻¹

I-914 mp 105–107° C.
¹H NMR(CDCl₃) δ 1.76(s, 3H), 1.80(s, 3H), 2.27(s, 3H), 2.29(s, 3H), 3.20(s, 3H), 3.89(s, 3H), 4.63–4.65(d, J=6.6Hz, 2H), 5.57(m, 1H), 6.87–6.96(m, 3H), 7.12(s, 1H), 7.17(s, 1H), 7.33–7.43(m, 4H)
IR(CHCl₃) 2937, 2866, 1604, 1583, 1519, 1488, 1464, 1373, 1331, 1259, 1175, 1149, 1035, 970, 873cm⁻¹

TABLE 181

I-915 mp 164–165° C.
¹H NMR(CDCl₃) δ 1.75–1.76(d, J=0.6Hz, 3H), 1.79–1.80(d, J=0.9Hz, 3H), 2.27(s, 3H), 2.28(s, 3H), 3.89(s, 3H), 4.62–4.65(d, J=6.6Hz, 2H), 4.78(br, 1H), 5.57(m, 1H), 6.86–6.96(m, 4H), 7.12(s, 1H), 7.15(s, 1H), 7.22–7.27(m, 3H)

TABLE 181-continued

| | |
|---|---|
| | IR(CHCl$_3$) 3596, 2936, 2865, 1676, 1611, 1584, 1522, 1490, 1464, 1385, 1327, 1257, 1172, 1138, 1100, 1035, 996, 952, 896., 835cm$^{-1}$ |
| I-916 | mp 172–173° C.<br>$^1$H NMR(CDCl$_3$) δ 1.72(s, 3H), 1.77(s, 6H), 1.81(s, 3H), 2.70(s, 3H), 3.11(s, 3H), 3.24(s, 3H), 3.57(s, 3H), 3.80(s, 3H), 4.06–4.27(m, 2H), 4.64(d, J=7.2Hz, 2H), 5.37–5.50(m, 2H), 6.85(s, 1H), 7.10(d, J=8.6Hz, 1H), 7.32–7.39(m, 2H), 7.52 (d, J=8.4Hz, 1H), 7.84(d, J=9.6Hz, 1H), 7.94(s, 1H)<br>IR(KBr) 3434, 1519, 1482, 1366, 1346, 1308, 1178, 1157, 1120, 1090, 1078, 957, 805cm$^{-1}$ |
| I-917 | mp 78–80° C.<br>$^1$H NMR(CDCl$_3$) δ 3.47(s, 3H), 3.69(s, 6H), 3.80(s, 6H), 5.14(s, 2H), 5.66(brs, 1H), 5.76(brs, 1H), 6.30(s, 1H), 6.69(d, J=8.2Hz, 2H), 7.02(s, 2H), 7.14(s, 1H), 7.34–7.46(m, 6H)<br>IR(KBr) 3443, 2935, 1614, 1587, 1517, 1470, 1250, 1110, 744cm$^{-1}$ |
| I-918 | mp 83–84° C.<br>$^1$H NMR(DMSO-d$_6$) δ 3.34(s, 3H), 3.72(s, 3H), 5.13(s, 2H), 5.72(brs, 2H), 6.41(s, 1H), 6.62–6.93(m, 4H), 7.32–7.61(m, 7H), 8.54(brs, 1H), 8.88(brs, 1H)<br>IR(KBr) 3398, 2936, 1731, 1633, 1586, 1521, 1489, 1455, 1432, 1402, 1291, 1216, 1112, 1071cm$^{-1}$ |
| I-919 | mp 74–75° C.<br>$^1$H NMR(CDCl$_3$) δ 2.02(s, 6H), 3.11(s, 3H), 3.21(s, 3H), 5.02(brs, 1H), 5.18(s, 2H), 6.96(s, 1H), 7.04–7.18(m, 3H), 7.37–7.59(m, 9H)<br>IR(KBr) 3503, 3032, 2937, 1513, 1474, 1365, 1289, 1197, 1175, 1149, 1114, 970, 867, 811cm$^{-1}$ |

TABLE 182

| | |
|---|---|
| I-920 | mp 78–79° C.<br>$^1$H NMR(CDCl$_3$) δ 1.73(s, 3H), 1.78(s, 6H), 1.83(s, 3H), 3.11(s, 3H), 3.48(s, 3H), 3.77(s, 3H), 4.07–4.29(m, 2H), 4.64(d, J=6.8Hz, 2H), 5.41–5.55(m, 2H), 5.73(s, 1H), 5.82(s, 1H), 6.47(s, 1H), 6.94–7.05(m, 3H), 7.53(d, J=8.0Hz, 1H), 7.86(d, J=8.6Hz, 1H), 8.00(s, 1H)IR(KBr) 3449, 2971, 2935, 1519, 1489, 1424, 1338, 1310, 1226, 1152, 1117, 1070, 1059, 773cm$^{-1}$ |
| I-921 | mp 176–177° C.<br>$^1$H NMR(CDCl$_3$) δ 2.10(s, 3H), 2.18(s, 3H), 2.47(s, 3H), 3.12(s, 3H), 3.23(s, 3H), 5.20(s, 2H), 7.09–7.21(m, 3H), 7.39–7.51 (m, 8H), 7.60(d, J=8.4Hz, 2H).<br>IR(KBr) 3433, 3033, 2937, 1516, 1470, 1360, 1291, 1267, 1176, 1150, 1119, 976, 857cm$^{-1}$ |
| I-922 | mp 170–172° C.<br>$^1$H NMR(DMSO-d$_6$) δ 3.36(s, 3H), 3.66(s, 3H), 4.22(br d, J=2.5Hz, 2H), 4.50(t, J=4.5Hz, 1H), 4.57(d, J=5.7Hz, 2H), 4.60(d, J=5.7Hz, 2H), 4.97(t, J=5.7Hz, 2H), 5.17(s, 2H), 5.23(t, J=5.7Hz, 1H), 6.93(s, 1H), 7.04(d, J=8.4Hz, 1H), 7.14(dd, J=8.4, 2.3Hz, 1H), 7.28–7.37(m, 2H), 7.40–7.45(m, 4H), 7.49–7.53(m, 2H), 7.61(d, J=8.1Hz, 2H)<br>IR(KBr) 3322, 1462, 1385, 1228, 1037, 1006, 750, 700cm$^{-1}$ |
| I-923 | mp 130–132° C.<br>$^1$H NMR(CDCl$_3$) δ 1.55(s, 9H), 1.62(s, 3H), 2.30(s, 12H), 3.00(s, 6H), 6.73(br s, 1H), 6.78–6.82(m, 2H), 7.07–7.14(m, 4H), 7.24–7.27(m, 2H), 8.07–8.13(m, 2H)<br>IR(KBr) 3600–2800(br), 1732, 1624, 1610, 1583, 1530, 1493, 1366, 1347, 1320, 1236, 1154cm$^{-1}$ |
| I-924 | mp 104–106° C.<br>$^1$H NMR(CDCl$_3$) δ 2.27(s, 3H), 2.30(s, 3H), 3.00(s, 6H), 3.74(br s, 2H), 6.77–6.85(m, 3H), 6.96(dd, J=1.8, 8.1Hz, 1H), 7.03(dd, J=2.1, 12.0Hz, 1H), 7.09(s, 1H), 7.13(s, 1H), 7.24–7.29(m, 2H)<br>IR(KBr) 3600–2800(br), 1631, 1608, 1580, 1530, 1487, 1436, 1363, 1233, 1195cm$^{-1}$ |

TABLE 183

| | |
|---|---|
| I-925 | mp 100–102° C.<br>$^1$H NMR(CDCl$_3$) δ 1.75(d, J=0.6Hz, 3H), 1.78(d, J=0.6Hz, 3H), 2.29(s, 3H), 2.30(s, 3H), 3.00(s, 6H), 3.77(d, J=6.6Hz, 2H), 3.87(br s, 2H), 5.37–5.40(m, 1H), 6.71–6.83(m, 3H), 7.00–7.03(m, 2H), 7.11(s, 1H), 7.13(s, 1H), 7.25–7.29(m, 2H)<br>IR(KBr) 3600–2800(br), 1623, 1610, 1529, 1490, 1441, 1348, 1328, 1253, 1229, 1120, 1065cm$^{-1}$ |
| I-926 | mp 178–180° C.<br>$^1$H NMR(CDCl$_3$) δ 2.27(s, 3H), 2.32(s, 3H), 3.01(s, 6H), 6.78–6.83(m, 2H), 7.10(s, 1H), 7.16(s, 1H), 7.18–7.28(m, 4H), 8.12(br s, 1H), 8.27–8.33(m, 1H)<br>IR(KBr) 3600–2800(br), 1709, 1613, 1532, 1490, 1356, 1283, 1229, 1188, 1167cm$^{-1}$ |
| I-927 | mp 154–156° C.<br>$^1$H NMR(CDCl$_3$) δ 1.94(d, J=1.2Hz, 3H), 2.26(d, J=1.2Hz, 3H), 2.27(s, 3H), 2.31(s, 3H), 3.00(s, 6H), 5.79–5.80(m, 1H), 6.78–6.82(m, 3H), 7.09–7.16(m, 4H), 7.16–7.24(m, 2H), 8.38–8.44(m, 1H)<br>IR(KBr) 3600–2800(br), 1681, 1665, 1643, 1610, 1528, 1506, 1487, 1442, 1359, 1317, 1237, 1198, 1159cm$^{-1}$ |
| I-928 | mp 183–185° C.<br>$^1$H NMR(CDCl$_3$) δ 1.44(t, J=7.5Hz, 3H), 2.27(s, 3H), 2.31(s, 3H), 3.16–3.23(m, 2H), 6.53(d, J=2.4Hz, 1H), 6.78–6.82 (m, 2H), 7.09(s, 1H), 7.14–7.18(m, 3H), 7.24–7.27(m, 3H), 7.59–7.65(m, 1H)<br>IR(KBr) 3600–2800(br), 1607, 1527, 1491, 1451, 1436, 1359, 1336, 1271, 1222, 1153, 1110cm$^{-1}$ |
| I-929 | mp 184–186° C.<br>$^1$H NMR(CDCl$_3$) δ 2.26(s, 3H), 2.32(s, 3H), 3.01(s, 6H), 6.78–6.83(m, 2H), 7.10(s, 1H), 7.18(s, 1H), 7.23–7.27(m, 1H), 7.65(dd, J=1.8, 8.1Hz, 1H), 7.70(d, J=2.1Hz, 1H), 8.19–8.24(m, 1H)<br>IR(KBr) 3600–2800(br), 1721, 1612, 1536, 1490, 1325, 1282, 1242, 1197, 1169, 1123, 1054cm$^{-1}$ |

TABLE 184

| | |
|---|---|
| I-930 | mp 212–215° C.<br>$^1$H NMR(DMSO-d$_6$) δ 2.83(s, 3H), 3.43(s, 3H), 3.45(s, 3H), 3.52(s, 3H), 3.79(s, 3H), 4.87(s, 2H), 7.08(s, 1H), 7.21(d, J=8.4Hz, |

TABLE 184-continued

1H), 7.27–7.32(m, 2H), 7.48(d, J=8.7Hz, 2H), 7.74(d, J=8.7Hz, 2H)
IR(Nujol) 1731, 1604, 1519, 1480, 1237, 1174, 1081, 1013, 876, 839, 822, 804cm$^{-1}$ I-931 mp 166–168° C.
$^1$H NMR(CDCl$_3$) δ 3.45(s, 3H), 3.75(s, 3H), 4.67(d, J=9.0Hz, 2H), 6.45(s, 1H), 6.78(t, J=9.0Hz, 1H), 6.92(d, J=8.7Hz, 2H), 6.92(d, J=8.4Hz, 1H), 6.98(dd, J=8.4, 2.1Hz, 1H), 7.09(d, J=2.1Hz, 1H), 7.53(d, J=8.7Hz, 2H)
IR(Nujol) 3399, 1611, 1588, 1523, 1488, 1460, 1224, 1113, 1070, 1012, 939, 825, 813, 795cm$^{-1}$ I-932 foam
$^1$H NMR(CDCl$_3$) δ 3.45(s, 3H), 3.75(s, 3H), 4.64–4.74(m, 3H), 6.45(s, 1H), 6.92(d, J=8.7Hz, 2H), 6.93(d, J=8.4,Hz, 1H), 6.97(dd, J=8.4, 2.1Hz, 1H), 7.08(d, J=2.1Hz, 1H), 7.53(d, J=8.7Hz, 2H)
IR(Nujol) 3570, 3461, 3357, 3180, 1753, 1616, 1596, 1524, 1495, 1408, 1313, 1287, 1264, 1240, 1200, 1114, 1073, 1011, 906, 825cm$^{-1}$ I-933 mp 120–123° C.
$^1$H NMR(CDCl$_3$) δ 1.69(s, 3H), 1.74(s, 6H), 1.80(s, 3H), 3.49(s, 3H), 6.68–3.75(m, 5H), 4.58(d, J=6.6Hz, 2H), 5.31–5.41(m, 1H), 5.50–5.56(m, 1H), 5.81(s, 1H), 6.46(s, 1H), 6.68–6.74(m, 2H), 6.85–6.93(m, 3H), 7.50–7.56(m, 2H)
IR(KBr) 3460, 2969, 2929, 1609, 1523, 1490, 1398, 1247, 1117, 1078, 1013, 824, 778, 708, 589cm$^{-1}$ I-934 mp 171–173° C.
$^1$H NMR(CDCl$_3$) δ 1.75(s, 3H), 1.80(s, 3H), 3.47(s, 3H), 3.73(s, 3H), 3.81(s, 2H), 4.58(d, J=6.9Hz, 2H), 5.50–5.57(m, 1H), 5.82(s, 1H), 6.44(s, 1H), 6.77–6.94(m, 5H), 7.50–7.55(m, 2H)
IR(KBr) 3382, 3320, 2929, 1613, 1523, 1490, 1405, 1262, 1221, 1120, 1067, 1011, 844, 818, 598cm$^{-1}$

TABLE 185

I-935 mp 220–221° C.
$^1$H NMR(DMSO-d$_6$) δ 1.74(s, 3H), 1.77(s, 3H), 2.08(s, 3H), 3.30(s, 3H), 3.64(s, 3H), 4.64(d, J=7.2Hz, 2H), 5.48–5.54(m, 1H), 6.40(s, 1H), 6.80–6.87(m, 2H), 6.93–7.03(m, 2H), 7.42–7.46(m, 2H), 7.85(s, 1H), 8.58(s, 1H), 8.96(s, 1H), 9.56(s, 1H)
IR(KBr) 3476, 3400, 3322, 2935, 1658, 1610, 1542, 1520, 1487, 1270, 1258, 1225, 1115, 1010, 825, 596cm$^{-1}$

I-936 mp 149–150° C.
$^1$H NMR(CDCl$_3$) δ 1.48(s, 3H), 1.67(s, 3H), 1.76(s, 3H), 1.80(s, 3H), 3.63(s, 3H), 3.74(s, 3H), 4.27(d, J=7.5Hz, 2H), 4.63(d, J=6.6Hz, 2H), 5.01(s, 1H), 5.20–5.28(m, 1H), 5.52–5.60(m, 1H), 6.66(s, 1H), 6.91(d, J=8.7Hz, 2H), 7.01(t, J=8.7Hz, 1H), 7.10–7.22(m, 2H), 7.48(d, J=8.7Hz, 2H)
IR(KBr) 3335, 2936, 1671, 1614, 1596, 1522, 1441, 1403, 1369, 1265, 1233, 1111, 1077, 1008, 945, 832cm$^{-1}$

I-937 mp 122–123° C.
$^1$H NMR(CDCl$_3$) δ 3.44(s, 3H), 3.76(s, 3H), 4.77(d, J=6.3Hz, 2H), 5.05(s, 1H), 6.04(s, 1H), 6.24(t, J=6.3Hz, 1H), 6.45(s, 1H), 6.92(d, J=8.7Hz, 2H) 7.01(t, J=8.7Hz, 1H), 7.19–7.30(m, 2H), 7.53(d, J=8.7Hz, 2H)
IR(KBr) 3582, 3502, 3237, 2950, 1614, 1524, 1490, 1453, 1403, 1301, 13267, 1231, 1112, 1073, 1019, 881, 827cm$^{-1}$

I-938 mp 143–144° C.
$^1$H NMR(CDCl$_3$) δ 1.79(s, 3H), 1.84(s, 3H), 2.10(s, 3H), 2.17(s, 3H), 2.47(s, 3H), 3.23(s, 3H), 3.24(s, 3H), 4.66(d, J=6.6Hz, 2H), 5.20–5.55(m, 1H), 7.09–7.16(m, 4H), 7.40(d, J=8.7Hz, 2H), 7.60(d, J=8.1Hz, 2H)
IR(KBr) 3433, 2935, 1513, 1472, 1366, 1188, 1178, 1152, 1117, 974, 857cm$^{-1}$

I-939 mp 80–81° C.
$^1$H NMR(CDCl$_3$) δ 3.47(s, 3H), 3.48(s, 3H), 3.68(s, 3H), 3.81(s, 6H), 4.79(s, 2H), 5.13(s, 2H), 5.14(s, 2H), 5.65(s, 1H), 5.75(s, 1H), 6.28(s, 1H), 6.69(s, 2H), 7.01(s, 2H), 7.14(s, 1H), 7.40–7.45(m, 5H)
IR(KBr) 3433, 2937, 1720, 1582, 1508, 1455, 1407, 1285, 1239, 1125, 1069, 1051, 1011cm$^{-1}$

TABLE 186

I-940 mp 71–72° C.
$^1$H NMR(CDCl$_3$) δ 1.76(s, 3H), 1.81(s, 3H), 2.73(s, 3H), 3.21(s, 3H), 3.55(s, 3H), 3.72(s, 3H), 3.78(s, 6H), 4.63(d, J=6.8Hz, 2H), 5.46–5.52(m, 1H), 6.65(s, 1H), 6.70(d, J=3.8Hz, 2H), 7.07(d, J=8.4Hz, 1H), 7.34–7.46(m, 3H)
IR(KBr) 3433, 2938, 1674, 1609, 1587, 1518, 14732, 1365, 1252, 1178, 1109, 1077, 971, 945, 815, 796cm$^{-1}$

I-941 mp 98–99° C.
$^1$H NMR(CDCl$_3$) δ 1.74(s, 3H), 1.78(s, 3H), 3.50(s, 3H), 3.71(s, 3H), 3.72(d, J=8.1Hz, 2H), 5.35(t, J=7.2Hz, 1H), 5.64(s, 1H), 5.77(s, 1H), 6.43(s, 1H), 7.02–7.15(m, 3H), 7.32–7.41(m, 2H), 7.49–7.56(m, 1H)
IR(KBr) 3408, 2934, 1627, 1529, 1491, 1444, 1405, 1246, 1175, 1102, 1069, 822, 783cm$^{-1}$

I-942 $^1$H NMR(CDCl$_3$) δ 1.77(s, 3H), 1.82(s, 3H), 2.68(s, 3H), 2.73(s, 3H), 3.25(s, 3H), 3.60(s, 3H), 3.81(s, 3H), 4.65(d, J=6.3Hz, 2H), 5.44–5.53(m, 1H), 6.87(s, 1H), 7.10(d, J=8.7Hz, 1H), 7.30–7.47(m, 3H), 7.84(d.d, J=7.8 & 2.1Hz, 1H), 8.22(d, J=2.1Hz, 1H)
IR(KBr) 1530, 1480, 1362, 1272, 1237, 1179, 1077cm$^{-1}$

I-943 $^1$H NMR(CDCl$_3$) δ 2.69(s, 3H), 3.12(s, 3H), 3.56(s, 3H), 3.77(s, 3H), 3.84(s, 2H), 5.18(s, 2H), 6.82(s, 1H), 6.84(d, J=8.1Hz, 1H), 7.14(d, J=8.4Hz, 1H), 7.21–7.50(m, 9H)
IR(KBr) 3466, 3377, 1634, 1583, 1525, 1488, 1461, 1400, 1288, 1245, 1196, 1105, 1069cm$^{-1}$

I-944 $^1$H NMR(CDCl$_3$) δ 1.76(s, 3H), 1.82(s, 3H), 3.49(s, 3H), 3.75(s, 3H), 4.61(d, J=6.6Hz, 2H), 5.48–5.57(m, 1H), 5.59–5.75(m, 1H), 5.88(s, 1H), 6.43(s, 1H), 6.83–7.07(m, 4H), 7.21–7.30(m, 1H), 7.35(d.d, J=12.3 & 1.8Hz, 2H)
IR(KBr) 3465, 3377, 1634, 1525, 1488, 1460, 1400, 1287, 1245, 1195, 1105, 1068cm$^{-1}$

I-945 $^1$H NMR(CDCl$_3$) δ 2.02(s, 6H), 2.15(s, 3H), 3.20(s, 3H), 5.20(s, 3H), 6.81–6.86(m, 1H), 6.93(d.d, J=10.7 & 2.1Hz, 1H), 6.97(s, 1H), 7.04–7.12(m, 1H), 7.31–7.52(m, 9H)
IR(KBr) 1513, 1468, 1362, 1295, 1264, 1227, 1193, 1171, 1151, 1003, 965cm$^{-1}$

TABLE 187

I-946 ¹H NMR(CDCl₃) δ 2.02(s, 6H), 2.15(s, 3H), 3.20(s, 3H), 5.14(d, J=3.9Hz, 1H), 6.81–6.86(m, 1H), 6.91(d.d, J=10.1 & 2.1Hz, 1H), 6.97(s, 1H), 7.04–7.12(m, 1H), 7.30–7.42(m, 4H)
IR(KBr) 3414, 1624, 1595, 1518, 1473, 1360, 1294, 1170, 1144, 1120, 1104, 1016cm⁻¹

I-947 ¹H NMR(CDCl₃) δ 1.77(s, 3H), 1.82(s, 3H), 2.02(s, 6H), 2.16(s, 3H), 3.20(s, 3H), 4.64(d, J=6.6Hz, 2H), 5.53–5.61(m, 1H), 6.82–7.09(m, 4H), 7.33(d, J=9.0Hz, 2H), 7.39(d, J=9.0Hz, 2H)
IR(KBr) 1514, 1468, 1376, 1294, 1262, 1175, 1152, 992, 968cm⁻¹

I-948 ¹H NMR(CDCl₃) δ 1.77(s, 3H), 1.82(s, 3H), 2.02(s, 6H), 2.17(s, 3H), 4.64(d, J=6.6Hz, 2H), 4.81(s, 1H), 5.52–5.60(m, 1H), 6.82–7.08(m, 6H), 7.22(.d, J=8.7Hz, 2H)
IR(KBr) 3568, 3417, 1613, 1517, 1471, 1287, 1261, 1230, 1192, 1132, 1102, 1001cm⁻¹

I-949 ¹H NMR(CDCl₃) δ 3.02(s, 6H), 3.46(s, 3H), 3.75(s, 3H), 5.18(s, 2H), 6.03(s, 1H), 6.47(s, 1H), 6.82(d, J=8.7Hz, 2H), 7.03–7.51(m, 8H), 7.55(.d, J=8.7Hz, 2H)
IR(KBr) 3502, 1604, 1527, 1488, 1359, 1267, 1233, 1198, 1110, 1070cm⁻¹

I-950 ¹H NMR(CDCl₃) δ 2.60(s, 3H), 3.03(s, 6H), 3.54(s, 3H), 3.76(s, 3H), 5.21(s, 2H), 6.80(d, J=8.7Hz, 2H), 6.86(s, 1H), 7.03–7.49(m, 8H), 7.54(.d, J=8.7Hz, 2H)
IR(KBr) 1602, 1530, 1483, 1444, 1395, 1366, 1233, 1179, 1078, 1015cm⁻¹

I-951 ¹H NMR(CDCl₃) δ 2.76(s, 3H), 3.02(s, 6H), 3.54(s, 3H), 3.76(s, 3H), 5.28(s, 1H), 6.81(d, J=9.0Hz, 2H), 6.86(s, 1H), 7.04–7.23(m, 3H), 7.54(d, J=9.0Hz, 2H)
IR(KBr) 3375, 1607, 1530, 1483, 1395, 1346, 1292, 1228, 1163, 1077, 1009cm⁻¹

I-952 ¹H NMR(CDCl₃) δ 1.76(s, 3H), 1.80(s, 3H), 2.71(s, 3H), 3.02(s, 6H), 3.55(s, 3H), 3.76(s, 3H), 4.63(d, J=6.9Hz, 2H), 5.49–5.57(m, 1H), 6.82(.d, J=8.7Hz, 2H), 6.86(s, 1H), 7.01–7.23(m, 3H), 7.54(d, J=8.7Hz, 2H)
IR(KBr) 1602, 1531, 1484, 1389, 1369, 1258, 1235, 1197, 1176, 1084cm⁻¹

TABLE 188

I-953 ¹H NMR(CDCl₃) δ 1.76(s, 3H), 1.80(s, 3H), 3.02(s, 6H), 3.47(s, 3H), 3.75(s, 3H), 4.63(d, J=6.9Hz, 2H), 5.51–5.60(m, 1H), 6.03(s, 1H), 6.47(s, 1H), 6.82(.d, J=8.7Hz, 2H), 6.99–7.08(m, 1H), 7.16–7.29(m, 2H), 7.55(d, J=8.7Hz, 2H)
IR(KBr) 3498, 1604, 1528, 1488, 1360, 1266, 1234, 1198, 1110, 1067cm⁻¹

I-954 ¹H NMR(CDCl₃) δ 3.02(s, 6H), 3.47(s, 3H), 3.75(s, 3H), 5.14(s, 1H), 6.03(s, 1H), 6.47(s, 1H), 6.82(d, J=9.0Hz, 2H), 7.02–7.09(m, 1H), 7.15–7.29(m, 2H), 7.55(d, J=9.0Hz, 2H)
IR(KBr) 3492, 3383, 1607, 1529, 1488, 1397, 1223, 1103, 1065, 1006cm⁻¹

I-955 ¹H NMR(CDCl₃) δ 2.01(s, 6H), 2.17(s, 3H), 4.75(s, 1H), 5.19(s, 2H), 6.83–7.15(m, 7H), 7.30–7.53(m, 6H)
IR(KBr) 3542, 1607, 1579, 1513, 1469, 1263, 1126, 1107, 1015cm⁻¹

I-956 ¹H NMR(CDCl₃) δ 1.76(s, 3H), 1.82(s, 3H), 2.66(s, 3H), 3.50(s, 3H), 3.77(s, 3H), 4.62(d, J=6.4Hz, 2H), 5.48–5.56(m, 1H), 5.71(s, 1H), 5.81(s, 1H), 5.47(s, 1H), 6.90–7.00(m, 2H), 7.04(d, J=1.8Hz, 1H), 7.42(.d, J=7.8Hz, 2H), 7.82(d.d, J=7.8 & 1.8Hz, 1H), 8.26(.d, J=1.5Hz, 1H)
IR(KBr) 3520, 3419, 1585, 1529, 1506, 1344, 1313, 1290, 1251, 1226, 1118, 1079cm⁻¹

I-957 mp 123–126° C.
¹H NMR(CDCl₃) δ 1.75(s, 3H), 1.78(d, J=0.9Hz, 3H), 3.47(s, 3H), 3.75(s, 3H), 3.87(s, 3H), 3.88(s, 3H), 4.63(d, J=6.6Hz, 2H), 5.57(m, 1H), 5.92(s, 1H), 6.47(s, 1H), 6.95–7.40(m, 5H), 7.56–7.62(m, 2H)
IR(CHCl₃) 3510, 2934, 1608, 1519, 1489, 1461, 1394, 1285, 1243, 1175, 1115, 1075, 1034, 1008, 926, 823cm⁻¹

I-958 mp 163–164° C.
¹H NMR(CDCl₃) δ 1.75(s, 3H), 1.78(s, 3H), 3.61(s, 3H), 3.65(s, 3H), 3.75(s, 3H), 3.88(s, 3H), 4.64(d, J=6.6Hz, 2H), 4.99(s, 1H), 5.58(m, 1H), 6.68(s, 1H), 6.88–6.98(m, 5H), 7.46–7.52(m, 2H)
IR(CHCl₃) 3592, 2934, 1610, 1517, 1461, 1387, 1237, 1171, 1136, 1111, 1084 1036, 1012, 830cm⁻¹

TABLE 189

I-959 mp 142–146° C.
¹H NMR(CDCl₃) δ 1.76(s, 3H), 1.82(s, 3H), 3.47(s, 3H), 3.75(s, 3H), 3.94(s, 3H), 4.61(d, J=6.6Hz, 2H), 5.53(m, 1H), 5.69(s, 1H), 5.70(s, 1H), 5.91(s, 1H), 6.46(s, 1H), 6.94–7.26(m, 6H)
IR(CHCl₃) 3526, 2930, 1585, 1520, 1489, 1460, 1399, 1287, 1260, 1110, 1070, 1010, 819cm⁻¹

I-960 mp 141–145° C.
¹H NMR(CDCl₃) δ 2.39(s, 3H), 3.47(s, 3H), 3.94(s, 3H), 5.10(s, 2H), 5.68(s, 1H), 5.69(s, 1H), 5.92(s, 1H), 6.46(s, 1H), 6.93–7.38(m, 6H)
IR(CHCl₃) 3528, 1585, 1519, 1489, 1460, 1399, 1260, 1110, 1070, 1009, 863cm⁻¹

I-961 mp 152–154° C.
¹H NMR(CDCl₃) δ 2.26(s, 3H), 4.79(br, 1H), 5.19(s, 2H), 6.87–6.90(m, 2H), 7.03–7.15(m, 4H), 7.22–7.26(m, 2H), 7.34–7.50(m, 6H)
IR(CHCl₃) 3596, 2925, 2869, 1612, 1581, 1523, 1490, 1455, 1383, 1313, 1298, 1259, 1171, 1125, 1100, 1012, 956, 877, 836cm⁻¹

I-962 mp 150–151° C.
¹H NMR(CDCl₃) δ 2.28(s, 3H), 3.90(s, 3H), 4.77–4.79(d, J=6.0Hz, 2H), 6.26(d, J=6.0Hz, 1H), 6.88–6.91(m, 5H), 7.13–7.14(d, J=2.7Hz, 2H), 7.24–7.27(m, 2H)
IR(CHCl₃) 3596, 2958, 1732, 1612, 1587, 1522, 1490, 1464, 1325, 1257, 1172, 1139, 1100, 1032, 886, 835cm⁻¹

I-963 mp 93–94° C.
¹H NMR(CDCl₃) δ 2.27(s, 3H), 4.76–4.79(d, J=6.0Hz, 2H), 5.12(br, 1H), 6.24(t, J=6.0Hz, 1H), 6.88–7.15(m, 7H), 7.22–7.26(m, 2H)
IR(CHCl₃) 3596, 2925, 2867, 1613, 1583, 1523, 1490, 1458, 1424, 1388, 1258, 1171, 1126, 1100, 1022, 956, 886, 836cm⁻¹

TABLE 190

I-964 foam
$^1$H NMR(CDCl$_3$) δ 3.47(s, 3H), 3.74(s, 3H), 5.06(s, 1H), 5.15(s, 2H), 5.70(s, 1H), 5.94(s, 1H), 6.46(s, 1H), 6.81–7.50(m, 12H)
IR(CHCl$_3$) 3534, 1609, 1587, 1518, 1504, 1482, 1463, 1455, 1407, 1322, 1290, 1249, 1200, 1112, 1072, 1011cm$^{-1}$ I-965 foam
$^1$H NMR(CDCl$_3$) δ 3.61(s, 3H), 3.75(s, 3H), 5.16(s, 2H), 5.72(s, 2H), 6.46(s, 1H), 6.83(s, 1H), 6.94(dd, J=2.0, 8.4Hz, 1H), 7.00–7.12(m, 4H), 7.29–7.50(m, 7H)
IR(CHCl$_3$) 3531, 1587, 1516, 1498, 1482, 1462, 1455, 1410, 1362, 1308, 1288, 1248, 1202, 1121, 1092, 1070, 1006cm$^{-1}$ I-966 mp 174–175° C.
$^1$H NMR(CDCl$_3$) δ 2.28(s, 3H), 3.38(s, 3H), 3.71(s, 3H), 5.16(s, 2H), 5.68(s, 1H), 5.88(s, 1H), 6.30(s, 1H), 6.98(dd, J=1.8, 8.4Hz, 1H), 7.04(d, J=8.4Hz, 1H), 7.11(d, J=1.8Hz, 1H), 7.22–7.49(m, 9H)
IR(KBr) 3516, 3398, 1587, 1516, 1500, 1484, 1453, 1412, 1306, 1285, 1247, 1231, 1202, 1126, 1101, 1072, 1019, 769, 737cm$^{-1}$ I-967 mp 103–104° C.
$^1$H NMR(CDCl$_3$) δ 2.26(s, 6H), 4.61–4.78(m, 3H), 4.84(s, 1H), 6.84–6.92(m, 2H), 6.97–7.16(m, 5H), 7.21–7.27(m, 2H)
IR(KBr) 3409, 1742, 1523, 1489, 1315, 1295, 1259, 1231, 1206, 1193, 1124, 1001, 834, 815cm$^{-1}$ I-968 mp 90–91° C.
$^1$H NMR(CDCl$_3$) δ 1.77(s, 6H), 1.82(d, J=0.9Hz, 6H), 2.27(s, 6H), 4.56(d, J=6.6Hz, 2H), 5.13(d, J=6.6Hz, 2H), 5.49–5.60(m, 2H), 6.94–7.00(m, 2H), 7.01–7.14(m, 5H), 7.25–7.31(m, 2H)
IR(KBr) 1608, 1522, 1488, 1378, 1299, 1288, 1273, 1259, 1242, 1196, 1176, 1014, 831, 811, 776cm$^{-1}$

TABLE 191

I-969 mp 200–203° C.
$^1$H NMR(CDCl$_3$) δ 2.00(s, 3H), 2.25(s, 3H), 3.46(s, 3H), 3.73(s, 3H), 3.83(s, 3H), 5.25(s, 1H), 6.01–6.03(m, 1H), 6.06(s, 1H), 6.45(s, 1H), 6.86–6.90(m, 2H), 7.04–7.14(m, 3H), 7.47–7.52(m, 2H)
IR(KBr) 3433, 2937, 1721, 1651, 1523, 1489, 1398, 1264, 1225, 1136, 1071, 1035, 927, 823, 530cm$^{-1}$

I-970 mp 157–160° C.
$^1$H NMR(CDCl$_3$) δ 1.74(s, 3H), 1.80(s, 3H), 2.86(s, 3H), 3.49(s, 3H), 3.75(s, 3H), 4.57(d, J=6.6Hz, 2H), 5.08(s, 1H), 5.50–5.57(m, 1H), 5.82(s, 1H), 6.46(s, 1H), 6.66(d, J=2.1Hz, 1H), 6.73(dd, J=2.1, 8.1Hz, 1H), 6.86–6.94(m, 3H), 7.50–7.56(m, 2H)
IR(KBr) 3392, 2934, 1611, 1523, 1490, 1397, 1242, 1216, 1112, 1074, 1002, 592cm$^{-1}$

I-971 mp 153–155° C.
$^1$H NMR(CDCl$_3$) δ 1.77(s, 3H), 1.82(s, 3H), 2.10(s, 3H), 3.20(s, 3H), 3.21(s, 3H), 3.36(s, 3H), 3.71(s, 3H), 4.63(d, J=6.9Hz, 2H), 5.52(t, J=6.9Hz, 1H), 6.73(s, 1H), 7.06(d, J=8.4Hz, 1H), 7.14(dd, J=8.4, 2.1Hz, 1H), 7.23(d, J=2.1Hz, 1H), 7.36(d, J=8.9Hz, 2H), 7.69(d, J=8.9Hz, 2H)
IR(KBr) 1515, 1474, 1365, 1229, 1175, 1151, 1096, 973, 870, 810cm$^{-1}$

I-972 amorphous
$^1$H NMR(CDCl$_3$) δ 1.77(s, 3H), 1.82(s, 3H), 2.43(s, 3H), –3.44(s, 3H), 3.71(s, 3H), 4.49(d, J=9.9Hz, 2H), 4.62(d, J=6.6Hz, 2H), 4.72(d, J=7.2Hz, 2H), 5.53(t, J=6.6Hz, 1H), 6.86(s, 1H), 6.96(d, J=8.7Hz, 1H), 7.21–7.30(m, 4H), 7.54(d, J=8.1Hz, 2H)
IR(KBr) 3599, 1463, 1386, 1081, 1007cm$^{-1}$

TABLE 192

I-973 mp 83–86° C.
$^1$H NMR(DMSO-d$_6$) δ 1.74(s, 3H), 1.77(s, 3H), 3.36(s, 3H), 3.65(s, 3H), 4.23(d, J=23.1Hz, 2H), 4.48(t, J=4.4Hz, 1H), 4.52(d, J=5.4Hz, 2H), 4.52–4.60(m, 4H), 4.89(t, J=5.6Hz, 1H), 5.22(t, J=5.9Hz, 1H), 5.48(t, J=6.6Hz, 1H), 6.92(s, 1H), 6.96(d, J=8.6Hz, 1H), 7.12(dd, J=8.6, 1.5Hz, 1H), 7.26(d, J=1.5Hz, 1H), 7.42(d, J=8.0Hz, 2H), 7.61(d, J=8.0Hz, 2H)
IR(KBr) 3399, 1464, 1386, 1230, 1005cm$^{-1}$

I-974 mp 177–179° C.
$^1$H NMR(CDCl$_3$) δ 1.31(d, J=6.9Hz, 6H), 2.70(s, 3H), 2.98(sept, J=6.9Hz, 1H), 3.12(s, 3H), 3.54(s, 3H), 3.76(s, 3H), 5.19(s, 2H), 6.87(s, 1H), 7.15(d, J=8.4Hz, 1H), 7.30–7.49(m, 9H), 7.54(d, J=7.8Hz, 2H)
IR(KBr) 1512, 1480, 1369, 1176, 1084, 1014, 813, 798cm$^{-1}$ I-975 mp 180–182° C.
$^1$H NMR(CDCl$_3$) δ 1.31(d, J=6.6Hz, 6H), 1.76(s, 3H), 1.81(s, 3H), 2.74(s, 3H), 2.98(sept, J=6.6Hz, 1H), 3.22(s, 3H), 3.54(s, 3H), 3.77(s, 3H), 4.63(d, J=6.7Hz, 2H), 5.49(t, J=6.7Hz, 1H), 6.87(s, 1H), 7.08(d, J=8.4Hz, 1H), 7.31(d, J=8.1Hz, 2H), 7.35(dd, J=8.4, 2.1Hz, 1H), 7.40(d, J=2.1Hz, 1H), 7.54(d, J=8.1Hz, 2H)
IR(KBr) 1520, 1481, 1366, 1177, 1083, 1012, 975, 944, 815, 797cm$^{-1}$ I-976 mp 125–126° C.
$^1$H NMR(CDCl$_3$) δ 1.31(d, J=6.9Hz, 6H), 1.76(s, 3H), 1.82(s, 3H), 2.97(sept, J=6.9Hz, 1H), 3.46(s, 3H), 3.74(s, 3H), 4.61(d, J=7.1Hz, 2H), 5.53(t, J=7.1Hz, 1H), 5.68(s, 1H), 5.91(s, 1H), 6.48(s, 1H), 6.95–6.96(m, 2H), 7.06–7.07(m, 1H), 7.31(d, J=8.0Hz, 2H), 7.57(d, J=8.0Hz, 2H)
IR(KBr)cm$^{-1}$

TABLE 193

I-977 foam
$^1$H NMR(CDCl$_3$) δ 2.68(s, 3H), 3.13(s, 3H), 3.20(s, 3H), 3.57(s, 3H), 3.79(s, 3H), 5.19(s, 2H), 6.86(s, 1H), 7.15(d, J=8.7Hz, 1H), 7.31–7.62(m, 11H)
IR(CHCl$_3$) 1517, 1475, 1371, 1227, 1219, 1176, 1117, 1081, 968, 925, 856, 821cm$^{-1}$ TABLE 193-continued I-978 foam
$^1$H NMR(CDCl$_3$) δ 2.65(s, 3H), 2.94(s, 3H), 3.14(s, 3H), 3.59(s, 3H), 3.76(s, 3H), 5.19(s, 2H), 6.86(s, 1H), 7.16(d, J=8.7Hz, 1H), 7.33–7.57(m, 11H)
IR(CHCl$_3$) 1517, 1477, 1398, 1370, 1268, 1233, 1216, 1177, 1159, 1079, 972, 894, 856, 818cm$^{-1}$ I-979 foam
$^1$H NMR(CDCl$_3$) δ 1.77(s, 3H), 1.81(s, 3H), 2.69(s, 3H), 2.94(s, 3H), 3.25(s, 3H), 3.60(s, 3H), 3.76(s, 3H), 4.64(d, J=6.9Hz, 2H), 5.50(m, 1H), 6.86(s, 1H), 7.10(d, J=8.4Hz, 1H), 7.34–7.57(m, 11H)
IR(CHCl$_3$) 1517, 1476, 1398, 1369, 1234, 1178, 1159, 1105, 1079, 972, 895, 854, 814, 801cm$^{-1}$ I-980 foam
$^1$H NMR(CDCl$_3$) δ 1.76(d, J=0.9Hz, 3H), 1.81(d, J=0.9Hz, 3H), 2.71(s, 3H), 3.20(s, 3H), 3.24(s, 3H), 3.57(s, 3H), 3.79(s, 3H), 4.64(d, J=6.6Hz, 2H), 5.49(m, 1H), 6.86(s, 1H), 7.09(d, J=8.7Hz, 1H), 7.31–7.40(m, 3H), 7.48–7.55(m, 3H)
IR(CHCl$_3$) 1517, 1474, 1365, 1269, 1236, 1177, 1140, 1116, 1078, 964, 923, 854, 814cm$^{-1}$ I-981 mp 122–123° C.
$^1$H NMR(CDCl$_3$) δ 1.77(s, 3H), 1.82(d, J=0.4Hz, 3H), 3.62(s, 3H), 3.75(s, 3H), 4.63(d, J=6.6Hz, 2H), 5.53(m, 1H), 5.70(s, 1H), 5.73(s, 1H), 6.46(s, 1H), 6.86(s, 1H), 6.89–7.13(m, 4H), 7.29–7.46(m, 3H)
IR(KBr) 3366, 1587, 1496, 1482, 1462, 1449, 1408, 1371, 1313, 1290, 1245, 1210, 1126, 1093, 1073, 1001, 783, 770cm$^{-1}$

TABLE 194

I-982 mp 171–172° C.
$^1$H NMR(CDCl$_3$) δ 1.76(s, 3H), 1.82(s, 3H), 3.48(s, 3H), 3.74(s, 3H), 4.61(d, J=6.9Hz, 2H), 4.91(s, 1H), 5.53(m, 1H), 5.70(s, 1H), 5.91(s, 1H), 6.46(s, 1H), 6.86(m, 1H), 6.91–7.02(m, 2H), 7.06(m, 1H), 7.13(m, 1H), 7.21(m, 1H), 7.32(m, 1H)
IR(KBr) 3368, 1585, 1519, 1507, 1484, 1460, 1450, 1403, 1294, 1255, 1237, 1206, 1110, 1072, 1006, 789, 766cm$^{-1}$

I-983 mp 92.5–93° C.
$^1$H NMR(CDCl$_3$) δ 1.77(s, 3H), 1.83(d, J=0.9Hz, 3H), 2.26(s, 3H), 2.27(s, 3H), 4.63(d, J=6.9Hz, 2H), 5.13(d, J=3.9Hz, 1H), 5.55(m, 1H), 6.98–7.14(m, 8H)
IR(CHCl$_3$) 3578, 2922, 1618, 1522, 1490, 1383, 1282, 1120, 979, 873, 824cm$^{-1}$

I-984 mp 89–95° C.
$^1$H NMR(CDCl$_3$) δ 1.77(s, 6H), 1.81(d, J=0.9Hz, 6H), 2.27(s, 6H), 4.63(d, J=6.6Hz, 4H), 5.55(m, 2H), 6.98–7.14(m, 8H)
IR(CHCl$_3$) 2930, 1576, 1520, 1490, 1382, 1296, 1270, 1127, 987, 874cm$^{-1}$

I-985 mp 74–75° C.
$^1$H NMR(CDCl$_3$) δ 2.16(s, 3H), 2.69(s, 3H), 3.14(s, 3H), 3.20(s, 3H), 3.56(s, 3H), 5.20(s, 2H), 7.16–7.49(m, 11H), 7.65–7.68(m, 2H)
IR(CHCl$_3$) 2939, 1732, 1613, 1518, 1478, 1454, 1415, 1371, 1331, 1292, 1268, 1176, 1150, 1118, 1088, 1010, 969, 950, 872cm$^{-1}$

I-986 mp 50–52° C.
$^1$H NMR(CDCl$_3$) δ 1.77(s, 3H), 1.82(s, 3H), 2.16(s, 3H), 2.74(s, 3H), 3.20(s, 3H), 3.24(s, 3H), 3.57(s, 3H), 4.64–4.66(d, J=6.3Hz, 2H), 5.50(m, 1H), 7.10–7.39(m, 6H), 7.66–7.68(m, 2H)
IR(CHCl$_3$) 2938, 1613, 1518, 1477, 1370, 1331, 1290, 1267, 1176, 1150, 1117, 1088, 970, 949, 871cm$^{-1}$

TABLE 195

I-987 $^1$H NMR(CDCl$_3$) δ 1.59–1.60(d, J=0.6Hz, 3H), 1.70–1.71(d, J=0.9Hz, 3H), 2.26(s, 3H), 2.28(s, 3H), 2.36(m, 1H), 2.77(m, 1H), 3.20(s, 3H), 3.23(s, 3H), 5.24(m, 1H), 7.12(s, 1H), 7.15(s, 1H), 7.23–7.25(m, 1H), 7.33–7.42(m, 6H)

I-988 mp 159–161° C.
$^1$H NMR(CDCl$_3$) δ 1.76(s, 3H), 1.82(s, 3H), 2.12(s, 3H), 3.48(s, 3H), 4.61–4.64(d, J=6.6Hz, 2H), 4.75(br, 1H), 5.54(m, 1H), 5.69(s, 1H), 5.73(s, 1H), 6.77–6.98(m, 6H), 7.51–7.54(m, 2H)
IR(CHCl$_3$) 3595, 3529, 2937, 1613, 15787, 1522, 1489, 1455, 1401, 1310, 1289, 1173, 1127, 1095, 1009, 939, 835cm$^{-1}$

I-989 mp 126–128° C.
$^1$H NMR(CDCl$_3$) δ 2.25(s, 3H), 3.78(s, 3H), 5.16(s, 2H), 5.75(br, 1H), 6.83–6.89(m, 4H), 6.98–7.00(m, 2H), 7.17(s, 1H), 7.40–7.47(m, 7H)
IR(CHCl$_3$) 3596, 3543, 2937, 1610, 1588, 1523, 1493, 1465, 1455, 1388, 1328, 1315, 1262, 1173, 1126, 1038, 1012, 835cm$^{-1}$

I-990 mp 87–90° C.
$^1$H NMR(CDCl$_3$) δ 1.59–1.60(d, J=0.6Hz, 3H), 1.72–1.73(d, J=0.9Hz, 3H), 2.26(s, 3H), 2.28(s, 3H), 2.34–2.37(m, 2H), 2.66–2.71(m, 2H), 4.84–4.86(br, 2H), 5.28(m, 1H), 6.79(d, J=1.5Hz, 1H), 6.86–6.89(m, 3H), 7.11–7.17(m, 3H), 7.23–7.26(m, 2H)
IR(CHCl$_3$) 3598, 2925, 2859, 1612, 1569, 1521, 1488, 1450, 1425, 1414, 1328, 1257, 1171, 1101, 958, 836cm$^{-1}$

I-991 mp 174–176° C.
$^1$H NMR(CDCl$_3$) δ 2.26(s, 3H), 3.13(s, 3H), 3.18(s, 3H), 3.80(s, 3H), 5.19(s, 2H), 6.84(s, 1H), 7.13(d, J=8.4Hz, 1H), 7.18(s, 1H), 7.28–7.50(m, 9H), 7.59–7.62(m, 2H)
IR(CHCl$_3$) 2940, 1732, 1613, 1520, 1490, 1465, 1455, 1415, 1371, 1331, 1291, 1260, 1173, 1149, 1111, 1038, 1018, 1003, 971, 872, 813cm$^{-1}$

TABLE 196

I-992 mp 135–137° C.
$^1$H NMR(CDCl$_3$) δ 1.77–1.78(d, J=0.9Hz, 3H), 1.82–1.83(d, J=0.6Hz, 3H), 2.26(s, 3H), 3.18(s, 3H), 3.24(s, 3H), 3.80(s, 3H), 4.64(d, J=6.6Hz, 2H), 5.52(m, 1H), 6.84(s, 1H), 7.07(d, J=8.7Hz, 1H), 7.18(s, 1H), 7.25–7.35(m, 4H), 7.59–7.62(m, 2H)
IR(CHCl$_3$) 3596, 3539, 2937, 1610, 1587, 1523, 1492, 1464, 1454, 1388, 1328, 1315, 1292, 1261, 1173, 1126, 1038, 996, 834cm$^{-1}$

TABLE 196-continued

I-993 mp 131–133° C.
$^1$H NMR(CDCl$_3$) δ 1.77(s, 3H), 1.83(s, 3H), 2.26(s, 3H), 3.78(s, 3H), 4.61–4.64(d, J=6.9Hz, 2H), 5.17(br, 1H), 5.35(m, 1H), 5.78(br, 1H), 6.83–6.99(m, 6H), 7.17(s, 1H), 7.44–7.47(m, 2H)
IR(CHCl$_3$) 3596, 3539, 2937, 1610, 1587, 1523, 1492, 1464, 1454, 1388, 1328, 131, 1292, 1261, 1173, 1126, 1038, 996, 834cm$^{-1}$

I-994 mp 127–130° C.
$^1$H NMR(CDCl$_3$) δ 1.73(d, J=0.9Hz, 3H), 1.76(d, J=0.9Hz, 3H), 2.99(s, 6H), 3.73–3.76(m, 2H), 3.78(s, 6H), 3.88(s, 3H), 5.37–5.40(m, 1H), 5.83(d, J=7.8Hz, 1H), 6.78–6.84(m, 2H), 6.95(s, 1H), 6.96(s, 1H), 7.06–7.12(m, 2H), 7.48–7.53(m, 2H)

I-995 mp 91–93° C.
$^1$H NMR(CDCl$_3$) δ 1.78(s, 3H), 1.84(s, 3H), 2.02(s, 6H), 4.63(d, J=6.4Hz, 2H), 5.07(s, 1H), 5.15(s, 1H), 5.55(t, J=7.0Hz, 1H), 6.63(dd, J=2.0, 8.2Hz, 1H), 6.77(d, J=2.0Hz, 1H), 6.93–6.99(m, 4H), 7.39(d, J=8.6Hz, 2H)
IR(KBr) 3423, 2921, 1611, 1518, 1474, 1282, 1244, 1205, 1125, 1089, 995, 837, 815, 785cm$^{-1}$

I-996 mp 185-186° C.
$^1$H NMR(CDCl$_3$) δ 1.32(t, J=7.5Hz, 3H), 2.71(q, J=7.5Hz, 2H), 3.46(s, 3H), 3.76(s, 3H), 5.15(s, 2H), 5.69(s, 1H), 5.89(s, 1H), 6.94–7.08(m, 3H), 7.37–7.46(m, 5H), 7.54–7.59(m, 2H), 7.82(brs, 1H), 7.93(d, J=8.1Hz, 1H)
IR(KBr) 3504, 3269, 2968, 2936, 1708, 1532, 1518, 1487, 1311, 1286, 1193, 1121, 1071, 1014cm$^{-1}$

TABLE 197

I-997 mp 77–78° C.
$^1$H NMR(CDCl$_3$) δ 1.73(s, 3H), 1.77(s, 3H), 1.82(s, 3H), 2.70(s, 3H), 3.25(s, 3H), 3.55(s, 3H), 3.82(s, 3H), 4.65(d, J=6.9Hz, 2H), 4.94(d, J=7.5Hz, 2H), 5.31(t, J=8.7Hz, 1H), 5.50(t, J=6.6Hz, 1H), 6.87(s, 1H), 7.10(d, J=8.4Hz, 1H), 7.28–7.39(m, 3H), 7.87(d, J=8.1Hz, 1H), 7.99(s, 1H)
IR(KBr) 3431, 2939, 1702, 1518, 1483, 1368, 1308, 1204, 1177, 1121, 1092, 1079, 957, 804cm$^{-1}$

I-998 mp 144–145° C.
$^1$H NMR(CDCl$_3$) δ 1.76(s, 3H), 1.82(s, 3H), 3.48(s, 3H), 3.69(s, 3H), 3.80(s, 6H), 4.61(d, J=6.9Hz, 2H), 5.51(t, J=4.8Hz, 1H), 5.66(brs, 1H), 5.76(brs, 1H), 6.30(s, 1H), 6.69(d, J=8.1Hz, 2H), 6.93–7.01(m, 2H), 7.11(d, J=2.1Hz, 1H), 7.31–7.37(m, 1H)
IR(KBr) 3476, 2936, 1589, 1517, 1500, 1472, 1408, 1288, 1249, 1111cm$^{-1}$ I-999 mp 82–83° C.
$^1$H NMR(CDCl$_3$) δ 2.71(s, 3H), 3.15(s, 3H), 3.48(s, 3H), 3.56(s, 3H), 3.72(s, 3H), 3.80(s, 6H), 4.66(s, 2H), 4.79(s, 2H), 5.19(s, 2H), 6.69(s, 1H), 7.14–7.17(m, 1H), 7.36–7.49(m, 8H)
IR(KBr) 3434, 2939, 1719, 1613, 1581, 1508, 1463, 1396, 1365, 1294, 1272, 1238, 1177, 1122, 1078, 814cm$^{-1}$ I-1000 mp 85–86° C.
$^1$H NMR(CDCl$_3$) δ 1.31(t, J=7.5Hz, 3H), 2.66(s, 3H), 2.71(q, J=7.6Hz, 2H), 3.13(s, 3H), 3.55(s, 3H), 3.78(s, 3H), 5.19(s, 2H), 6.85(s, 1H), 7.15(d, J=8.8Hz, 1H), 7.33–7.59(m, 4H), 7.85(brs, 1H), 7.94(d, J=8.4Hz, 1H)
IR(KBr) 3432, 2939, 1727, 1519, 1480, 1365, 1237, 1165, 1079, 959, 803cm$^{-1}$ I-1001 mp 105–106° C.
$^1$H NMR(CDCl$_3$) δ 1.76(s, 6H), 1.79(s, 3H), 1.82(s, 3H), 3.49(s, 3H), 3.75(s, 3H), 3.81(d, J=6.6Hz, 2H), 4.62(d, J=7.2Hz, 2H), 5.37(t, J=6.3Hz, 1H), 5.53(t, J=6.9Hz, 1H), 5.68(brs, 1H), 5.87(brs, 1H), 6.82(d, J=8.4Hz, 1H), 6.95(s, 2H), 7.05(s, 1H), 7.26(s, 1H), 7.69(dd, J=2.1, 8.4Hz, 1H), 7.75(brs, 1H)
IR(KBr) 3459, 2934, 1622, 1582, 1525, 1493, 1467, 1327, 1240, 1139, 1113, 1070, 817cm$^{-1}$

TABLE 198

I-1002 mp 89–91° C.
$^1$H NMR(CDCl$_3$) δ 2.70(s, 3H), 3.12(s, 3H), 3.55(s, 3H), 3.71(s, 3H), 3.79(s, 6H), 4.77(s, 2H), 5.18(s, 2H), 6.69(s, 2H), 7.14(d, J=8.8Hz, 1H), 7.38–7.52(m, 8H)
IR(KBr) 3440, 2939, 1721, 1612, 1581, 1508, 1463, 1395, 1364, 1238, 1178, 1120, 1078, 962, 814, 523cm$^{-1}$

I-1003 mp 196–197° C.
$^1$H NMR(CDCl$_3$) δ 2.26(s, 3H), 3.48(s, 3H), 3.76(s, 3H), 5.16(s, 2H), 5.69(brs, 1H), 5.83(brs, 1H), 6.44(s, 1H), 6.93–7.05 (m, 4H), 7.26–7.45(m, 6H), 7.84(d, J=8.1Hz, 1H), 7.92(s, 1H), 8.29(brs, 1H)
IR(KBr) 3407, 2934, 1672, 1589, 1524, 1459, 1425, 1400, 1316, 1288, 1213, 1119, 1057, 1006, 745cm$^{-1}$ I-1004 mp 80–81° C.
$^1$H NMR(CDCl$_3$) δ 1.29(t, J=7.5Hz, 3H), 1.72(s, 3H), 1.76(s, 6H), 1.81(s, 3H), 2.70(s, 3H), 2.71(q, J=7.5Hz, 2H), 3.24(s, 3H), 3.50(s, 3H), 3.81(s, 3H), 4.64(d, J=6.3Hz, 2H), 4.72–4.76(m, 2H), 5.31(t, J=6.9Hz, 1H), 5.50(t, J=6.3Hz, 1H), 6.87(s, 1H), 7.08–7.12(m, 2H), 7.34–7.41(m, 3H), 7.61(s, 1H)
IR(KBr) 3434, 2974, 2938, 1694, 1517, 1480, 1366, 1237, 1202, 1177, 1080, 972, 807, 523cm$^{-1}$ I-1005 mp 157–158° C.
$^1$H NMR(CDCl$_3$) δ 1.31(t, J=7.8Hz, 3H), 1.77(s, 3H), 1.81(s, 3H), 2.71(s, 3H), 2.71(q, J=7.8Hz, 2H), 3.24(s, 3H), 3.55(s, 3H), 3.78(s, 3H), 4.64(d, J=6.6Hz, 2H), 5.50(t, J=8.1Hz, 2H), 6.85(s, 1H), 7.09(d, J=8.4Hz, 1H), 7.33–7.38(m, 2H), 7.52(d, J=8.1Hz, 1H), 7.58(s, 1H), 7.84(brs, 1H), 7.94(d, J=8.1Hz, 1H)
IR(KBr) 3434, 3350, 2938, 1727, 1523, 1480, 1368, 1248, 1178, 1165, 1080, 972, 816, 802, 522cm$^{-1}$ I-1006 mp 91–93° C.
$^1$H NMR(CDCl$_3$) δ 1.30(t, J=7.5Hz, 3H), 1.75(s, 6H), 1.79(s, 3H), 1.81(s, 3H), 2.55(q, J=7.5Hz, 2H), 3.48(s, 3H), 3.74(s, 3H), 3.79(d, J=6.3Hz, 2H), 4.61(d, J=6.6Hz, 2H), 5.41(t, J=6.0Hz, 1H), 5.53(t, J=6.9Hz, 1H), 5.67(brs, 1H), 5.94(brs, 1H), 6.48(s, 1H), 6.72(d, J=8.4Hz, 1H), 6.95(s, 2H), 7.07(s, 1H), 7.37–7.45(m, 2H), 7.64(d, J=7.5Hz, 1H),.
IR(KBr) 3433, 2932, 1609, 1521, 1489, 1461, 13958, 1308, 1286, 1245, 1192, 1114, 1072, 1011, 811cm$^{-1}$

TABLE 199

I-1007  mp 71–72° C.
$^1$H NMR(CDCl$_3$) δ 1.31(t, J=7.5Hz, 3H), 1.76(s, 3H), 1.82(s, 3H), 2.60(q, J=7.2Hz, 2H), 3.47(s, 3H), 3.75(s, 3H), 4.61(d, J=6.6Hz, 2H), 5.53(t, J=6.9Hz, 2H), 5.69(brs, 1H), 5.93(brs, 1H), 6.47(s, 1H), 6.78(d, J=8.1Hz, 1H), 6.95(s, 2H), 7.06(s, 1H), 7.26(s, 1H), 7.39(s, 1H)
IR(KBr) 3436, 2932, 1620, 1584, 1519, 1487, 1459, 1397, 1285, 1242, 1112, 1072, 819cm$^{-1}$ I-1008  mp 171–173° C.
$^1$H NMR(CDCl$_3$) δ 3.46(s, 3H), 3.75(s, 3H), 5.15(s, 2H), 5.68(s, 1H), 5.88(s, 1H), 6.44(s, 1H), 6.95(dd, J=8.4, 1.9Hz, 1H), 7.03(d, J=8.4Hz, 1H), 7.08(d, J=1.9Hz, 1H), 7.37–7.48(m, 7H), 7.59(d, J=8.4Hz, 2H)
IR(KBr) 3544, 3514, 3462, 1517, 1482, 1388, 1284, 1247, 1089, 1107, 1069, 1006, 938, 822cm$^{-1}$ I-1009  mp 180–182° C.
$^1$H NMR(CDCl$_3$) δ 2.68(s, 3H), 3.13(s, 3H), 3.53(s, 3H), 3.77(s, 3H), 5.19(s, 2H), 6.83(s, 1H), 7.15(d, J=8.4Hz, 1H), 7.32–7.49(m, 9H), 7.57(d, J=8.7Hz, 2H)
IR(KBr) 1518, 1478, 1370, 1177, 1085, 1012, 813, 797cm$^{-1}$ I-1010  mp 128–130° C.
$^1$H NMR(CDCl$_3$) δ 1.76(s, 3H), 1.82(s, 3H), 3.46(s, 3H), 3.75(s, 3H), 4.62(d, J=7.0Hz, 2H), 5.53(t, J=7.0Hz, 1H), 5.69(s, 1H), 5.85(s, 1H), 6.44(s, 1H), 6.93(dd, J=8.4, 1.6Hz, 1H), 6.97(d, J=8.4Hz, 1H), 7.05(d, J=1.6Hz, 1H), 7.42(d, J=8.4Hz, 2H), 7.59(d, J=8.4Hz, 2H)
IR(KBr) 1517, 1482, 1287, 1244, 1106, 1070, 1013, 822, 783cm$^{-1}$ I-1011  mp 138–140° C.
$^1$H NMR(CDCl$_3$) δ 1.76(s, 3H), 1.81(s, 3H), 2.72(s, 3H), 3.23(s, 3H), 3.54(s, 3H), 3.78(s, 3H), 4.64(d, J=6.5Hz, 2H), 5.49(t, J=6.5Hz, 1H), 6.83(s, 1H), 7.09(d, J=8.3Hz, 1H), 7.34(dd, J=8.3, 2.0Hz, 1H), 7.39(d, J=2.0Hz, 1H), 7.43(d, J=8.6Hz, 2H), 7.57(d, J=8.6Hz, 2H)
IR(KBr) 1518, 1478, 1369, 1177, 1083, 972, 814, 795cm$^{-1}$

TABLE 200

I-1012  mp 135–138° C.
$^1$H NMR(CDCl$_3$) δ 1.55–1.63(m, 2H), 1.77(s, 6H), 1.83(s, 6H), 4.56(d, J=6.6Hz, 4H), 4.66(d, J=4.5Hz, 4H), 5.50–5.58 (m, 2H), 6.96–7.01(m, 4H), 7.32–7.38(m, 4H), 7.45(s, 2H)
IR(KBr) 3339, 2914, 1609, 1520, 1488, 1385, 1289, 1238, 1177, 1000, 834, 651cm$^{-1}$

I-1013  mp 202–205° C.
$^1$H NMR(CDCl$_3$ + CD3OD) δ 1.78(s, 3H), 1.82(s, 3H), 4.57(d, J=6.6Hz, 2H), 4.62(s, 4H), 5.50–5.56(m, 1H), 6.86–7.00 (m, 4H), 7.24–7.37(m, 4H), 7.44(s, 2H)
IR(KBr) 3399, 2974, 2930, 1610, 1522, 1489, 1438, 1383, 1238, 1176, 999, 903, 838, 538cm$^{-1}$

I-1014  mp 219–221° C.
$^1$H NMR(CDCl$_3$) δ 2.22(s, 3H), 2.69(s, 3H), 3.13(s, 3H), 3.53(s, 3H), 3.77(s, 3H), 5.19(s, 2H), 6.85(s, 1H), 7.15(d, J=8.4Hz, 1H), 7.32–7.49(m, 7H), 7.60(s, 4H)
IR(KBr) 3384, 1701, 1604, 1524, 1482, 1355, 1294, 1176, 1084, 1011, 945, 818cm$^{-1}$

I-1015  mp 173–175° C.
$^1$H NMR(DMSO-d$_6$) δ 1.74(s, 3H), 1.77(s, 3H), 2.08(s, 3H), 2.87(s, 3H), 3.35(s, 3H), 3.47(s, 3H), 3.77(s, 3H), 4.68(d, J=6.4Hz, 2H), 5.48(t, J=6.4Hz, 1H), 7.02(s, 1H), 7.26–7.29(m, 3H), 7.57(d, J=8.7Hz, 2H), 7.70(d, J=8.7Hz, 2H), 10.07 (s, 1H)
IR(KBr) 3383, 1704, 1235, 1524, 1481, 1360, 1177, 1083, 976, 816cm$^{-1}$

I-1016  mp 144–145° C.
$^1$H NMR(CDCl$_3$) δ 1.77(s, 3H), 1.81(s, 3H), 2.70(s, 3H), 3.21(s, 3H), 3.52(s, 3H), 3.69(d, J=1.6Hz, 3H), 4.65(d, J=6.8Hz, 2H), 5.53(t, J=6.8Hz, 1H), 7.08(d, J=8.4Hz, 1H), 7.16(dd, J=8.4, 1.8Hz, 1H), 7.20(dd, J=11.7, 1.8Hz, 1H), 7.41 (d, J=8.8Hz, 2H), 7.59(dd, J=8.8, 1.4Hz, 2H)
IR(KBr) 1521, 1470, 1368, 1265, 1177, 1151, 1038, 971, 875cm$^{-1}$

TABLE 201

I-1017  mp 196–198° C.
$^1$H NMR(DMSO-d$_6$) δ 1.72(s, 3H), 1.76(s, 3H), 2.07(s, 3H), 3.31(s, 3H), 3.65(s, 3H), 4.55(d, J=6.6Hz, 2H), 5.49(t, J=6.6Hz, 1H), 6.43(s, 1H), 6.65(dd, J=8.4, 1.9Hz, 1H), 6.73(d, J=1.9Hz, 1H), 6.90(d, J=8.4Hz, 1H), 7.55(d, J=8.6Hz, 2H), 7.66(d, J=8.6Hz, 2H), 8.58(br s, 1H), 8.70(br s, 1H), 10.02(s, 1H)
IR(KBr) 3358, 1661, 1596, 1523, 1489, 1396, 1308, 1254, 1227, 1114, 1074cm$^{-1}$

I-1018  mp 141–143° C.
$^1$H NMR(CDCl$_3$) δ 1.76(s, 3H), 1.81(s, 3H), 3.40(s, 3H), 3.64(d, J=0.9Hz, 3H), 4.64(d, J=6.9Hz, 2H), 4.89(s, 1H), 5.56(t, J=6.9Hz, 1H), 5.70(s, 1H), 6.94(d, J=8.7Hz, 2H), 7.06(t, J=8.7Hz, 1H), 7.21(ddd, J=8.4, 2.1, 1.1Hz, 1H), 7.27(dd, J=12.3, 2.1Hz, 1H), 7.44(dd, J=8.7, 1.5Hz, 2H)
IR(KBr) 3485, 1523, 1466, 1402, 1266, 1173, 1036, 961, 918, 837, 814cm$^{-1}$ I-1019  mp 81–82° C.
$^1$H NMR(CDCl$_3$) δ 1.77(s, 3H), 1.81(s, 3H), 2.26(s, 3H), 2.72(s, 3H), 3.23(s, 3H), 3.57(s, 3H), 3.79(s, 3H), 4.64(d, J=6.3Hz, 2H), 5.49(t, J=6.3Hz, 1H), 6.83(s, 1H), 7.09(d, J=8.4Hz, 1H), 7.33–7.39(m, 2H), 7.48(s, 1H), 7.82(d, J=6.0Hz, 1H), 7.88(s, 1H), 8.32(brs, 1H)
IR(KBr) 3382, 2939, 1736, 1520, 1483, 1365, 1293, 1178, 1119, 1078, 958, 802, 521cm$^{-1}$ I-1020  mp 93–94° C.
$^1$H NMR(CDCl$_3$) δ 2.62(s, 3H), 2.99(s, 3H), 3.15(s, 3H), 3.20(s, 3H), 3.83(s, 3H), 5.21(s, 2H), 6.91(s, 2H), 7.17(d, J=8.2Hz, 1H), 7.35–7.48(m, 8H), 7.63(d, J=8.4Hz, 2H)
IR(KBr) 3434, 3033, 2938, 1611, 1520, 1479, 1366, 1179, 1151, 1085, 969, 850, 793, 519cm$^{-1}$

TABLE 202

I-1021  mp 74–75° C.
$^1$H NMR(CDCl$_3$) δ 1.76(s, 3H), 1.82(s, 3H), 3.48(s, 3H), 3.75(s, 3H), 4.61(d, J=6.3Hz, 2H), 5.53(t, J=5.4Hz, 1H), 5.69(brs, 1H), 5.86(brs, 1H), 6.42(s, 1H), 6.83(d, J=8.7Hz, 1H), 6.91–6.98(m, 2H), 7.04(s, 1H), 7.62(d, J=8.7Hz, 1H), 7.73(s, 1H)
IR(KBr) 3495, 3398, 2935, 1633, 1522, 1487, 1291, 1246, 1112, 1072, 821, 788cm$^{-1}$ I-1022  mp 76–77° C.
$^1$H NMR(CDCl$_3$) δ 1.77(s, 3H), 1.82(s, 3H), 1.84(s, 3H), 3.52(s, 3H), 3.78(s, 3H), 4.63(d, J=6.9Hz, 2H), 5.53(t, J=6.6Hz, 1H), 5.74(brs, 1H), 5.80(brs, 1H), 6.47(s, 1H), 6.92–7.00(m, 2H), 7.04(s, 1H), 7.38(d, J=8.1Hz, 1H), 7.93(d, J=8.1Hz, 1H), 8.04(s, 1H)
IR(KBr) 3411, 2934, 1662, 1519, 1488, 1425, 1309, 1245, 1175, 1128, 1071, 1050cm$^{-1}$ I-1023  mp 81–82° C.
$^1$H NMR(CDCl$_3$) δ 1.77(s, 3H), 1.81(s, 3H), 2.66(s, 3H), 2.99(s, 3H), 3.18(s, 3H), 3.25(s, 3H), 3.82(s, 3H), 4.64(d, J=6.6Hz, 2H), 5.49(t, J=6.0Hz, 1H), 6.90(s, 1H), 7.10(d, J=8.4Hz, 1H), 7.38–7.43(m, 3H), 7.62(d, J=8.8Hz, 1H), 8.02(s, 1H)
IR(KBr) 3434, 3027, 2938, 1672, 1611, 1520, 1479, 1365, 1179, 1117, 1074, 970, 847, 793, 519cm$^{-1}$ I-1024  mp 77–79° C.
$^1$H NMR(CDCl$_3$) δ 1.78(s, 3H), 1.83(s, 3H), 3.77(s, 3H), 4.63(d, J=6.6Hz, 2H), 5.53(t, J=6.2Hz, 1H), 5.76(brs, 2H), 6.52(s, 1H), 6.91–7.02(m, 6H), 7.46(d, J=8.4Hz, 2H)
IR(KBr) 3465, 2935, 1613, 1586, 1524, 1487, 1359, 1282, 1245, 1222, 1173, 1157, 1112, 1065, 974, 857, 521cm$^{-1}$ I-1025  mp 78–79° C.
$^1$H NMR(CDCl$_3$) δ 2.73(s, 3H), 2.78(s, 3H), 3.15(s, 3H), 3.21(s, 3H), 3.62(s, 3H), 5.22(s, 2H), 7.20(d, J=8.4Hz, 1H), 7.37–7.44(m, 10H), 7.68(d, J=8.8Hz, 2H)
IR(KBr) 3433, 3032, 2939, 1519, 1473, 1366, 1178, 1151, 1004, 966, 870, 847, 795, 524cm$^{-1}$

TABLE 203

I-1026  mp 158–159° C.
$^1$H NMR(CDCl$_3$) δ 1.47(t, J=6.9Hz, 3H), 2.41(s, 3H), 3.21(s, 3H), 3.55(s, 3H), 3.77(s, 3H), 4.14(q, J=6.9Hz, 2H), 5.22(s, 2H), 6.83(s, 1H), 6.91(dd, J=2.1, 8.1Hz, 1H), 6.96–7.01(m, 2H), 7.28–7.48(m, 7H), 7.66–7.72(m, 2H)
IR(KBr) 1517, 1482, 1392, 1362, 1240, 1194, 1175, 1146, 1084, 963, 878, 797cm$^{-1}$

I-1027  mp 106–107° C.
$^1$H NMR(CDCl$_3$) δ 2.27(s, 6H), 3.87(s, 3H), 5.20(s, 2H), 6.93–7.00(m, 2H), 7.01–7.17(m, 5H), 7.23–7.52(m, 7H)
IR(KBr) 1607, 1522, 1490, 1467, 1455, 1383, 1294, 1267, 1246, 1178, 1125, 1028, 1011, 836, 813, 744cm$^{-1}$

I-108  mp 162–163° C.
$^1$H NMR(CDCl$_3$) δ 1.45(t, J=6.9Hz, 3H), 3.46(s, 3H), 3.74(s, 3H), 4.15(q, J=6.9Hz, 2H), 4.98(s, 1H), 5.19(s, 2H), 5.91(s, 1H), 6.45(s, 1H), 6.88–6.94(m, 2H), 6.95–7.03(m, 2H), 7.05(d, J=1.2Hz, 1H), 7.27–7.41(m, 3H), 7.45–7.56(m, 4H)
IR(KBr) 3424, 3343, 1611, 1521, 1488, 1462, 1454, 1400, 1379, 1358, 1317, 1290, 1278, 1262, 1240, 1225, 1201, 1185, 1127, 1110, 1068, 1026, 1007, 828, 731cm$^{-1}$

I-1029  mp 73–74° C.
$^1$H NMR(CDCl$_3$) δ 1.77(s, 3H), 1.82(s, 3H), 2.27(s, 6H), 3.86(s, 3H), 4.63(d, J=7.2Hz, 2H), 5.56(m, 1H), 6.92–7.00(m, 2H), 7.00–7.16(m, 5H), 7.26–7.34(m, 2H)
IR(KBr) 1610, 1521, 1489, 1461, 1438, 1297, 1276, 1249, 1231, 1181, 1122, 1028, 985, 835cm$^{-1}$

I-1030  mp 86–87° C.
$^1$H NMR(CDCl$_3$) δ 1.46(t, J=6.9Hz, 3H), 1.75(s, 3H), 1.79(d, J=0.9Hz, 3H), 2.54(s, 3H), 3.21(s, 3H), 3.56(s, 3H), 3.78(s, 3H), 4.12(q, J=6.9Hz, 2H), 4.63(d, J=6.3Hz, 2H), 5.53(m, 1H), 6.84(s, 1H), 6.93–7.01(m, 3H), 7.35–7.41(m, 2H), 7.67–7.73(m, 2H)
IR(KBr) 1518, 1480, 1449, 1413, 1389, 1366, 1239, 1199, 1180, 1150, 1082, 970, 872, 798cm$^{-1}$

TABLE 204

I-1031  mp 145–146° C.
$^1$H NMR(CDCl$_3$) δ 1.44(t, J=6.9Hz, 3H), 1.74(s, 3H), 1.77(d, J=0.9Hz, 3H), 3.47(s, 3H), 3.75(s, 3H), 4.13(q, J=6.9Hz, 2H), 4.63(d, J=6.6Hz, 2H), 5.10(s, 1H), 5.56(m, 1H), 5.91(s, 1H), 6.46(s, 1H), 6.89–6.94(m, 2H), 6.95–7.03(m, 3H), 7.50–7.56(m, 2H)
IR(KBr) 3404, 1611, 1520, 1487, 1464, 1442, 1391, 1358, 1293, 1264, 1237, 1224, 1192, 1112, 1071, 1030, 1002, 831cm$^{-1}$

I-1032  mp 142–145° C.
$^1$H NMR(CDCl$_3$) δ 3.13(s, 3H), 3.21(s, 3H), 4.63(s, 2H), 4.65(s, 2H), 5.19(s, 2H), 7.15(d, J=8.4Hz, 1H), 7.33–7.52(m, 13H)
IR(KBr) 3519, 3422, 3380, 3032, 2933, 1611, 1519, 1487, 1364, 1171, 1148, 1109, 969, 871, 817, 527cm$^{-1}$

I-1033  mp 103–106° C.
$^1$H NMR(CDCl$_3$ + CD3OD) δ 1.78(s, 3H), 1.82(s, 3H), 3.22(s, 3H), 3.24(s, 3H), 4.58–4.67(m, 6H), 5.46–5.54(m, 1H), 7.09(d, J=8.4Hz, 1H), 7.33–7.53(m, 8H)
IR(KBr) 3512, 3414, 3012, 2941, 1612, 1519, 1488, 1362, 1335, 1146, 997, 972, 876, 524cm$^{-1}$

I-1034  mp 184–187° C.
$^1$H NMR(CDCl$_3$ + CD3OD) δ 1.78(s, 3H), 1.82(s, 3H), 4.59–4.65(m, 6H), 5.52–5.59(m, 1H), 6.84–6.98(m, 5H), 7.23–7.28(m, 2H), 7.44(s, 1H), 7.45(s, 1H)
IR(KBr) 3400, 2931, 1611, 1521, 1491, 1247, 1203, 1009, 987, 834cm$^{-1}$

I-1035  mp 95–96° C.
$^1$H NMR(CDCl$_3$) δ 2.27(s, 6H), 2.41(s, 3H), 5.19(s, 2H), 7.02–7.18(m, 5H), 7.22–7.54(m, 9H)
IR(KBr) 1522, 1512, 1454, 1377, 1309, 1297, 1274, 1267, 1236, 1125, 1008, 877, 822, 742, 696cm$^{-1}$

I-1036  mp 95–96° C.
$^1$H NMR(CDCl$_3$) δ 2.24(s, 3H), 2.27(s, 3H), 5.19(s, 2H), 6.99–7.15(m, 5H), 7.26–7.52(m, 9H)
IR(KBr) 1518, 1499, 1482, 1454, 1380, 1300, 1278, 1262, 1227, 1125, 1090, 1021, 1015, 875, 834, 817, 739cm$^{-1}$

TABLE 205

I-1037  mp 58–59° C.
$^1$H NMR(CDCl$_3$) δ 1.77(d, J=0.6Hz, 3H), 1.81(d, J=0.9Hz, 3H), 2.27(s, 6H), 2.41(s, 3H), 4.63(d, J=6.6Hz, 2H), 5.56 (m, 1H), 6.98–7.14(m, 5H), 7.21–7.29(m, 4H)
IR(KBr) 1520, 1490, 1460, 1444, 1385, 1294, 1271, 1262, 1232, 1125, 1001, 828, 818cm$^{-1}$

I-1038  mp 67–68° C.
$^1$H NMR(CDCl$_3$) δ 1.77(s, 3H), 1.81(d, J=0.9Hz, 3H), 2.25(s, 3H), 2.27(s, 3H), 4.64(d, J=6.6Hz, 2H), 5.55(m, 1H), 6.90–7.14(m, 5H), 7.26–7.32(m, 2H), 7.36–7.42(m, 2H)
IR(KBr) 1518, 1500, 1482, 1466, 1309, 1299, 1267, 1229, 1124, 1090, 995, 834cm$^{-1}$

I-1039  mp 153–155° C.
$^1$H NMR(CDCl$_3$) δ 3.45(s, 3H), 3.75(s, 3H), 4.84(d, J=4.2Hz, 2H), 6.43–6.51(m, 2H), 6.45(s, 1H), 6.92(d, J=8.7Hz, 2H), 6.94–7.00(m, 2H), 7.08(brs, 1H), 7.53(d, J=8.7Hz, 2H)
IR(KBr) 3411, 1612, 1588, 1523, 1489, 1288, 1245, 1224, 1113, 1070, 1011, 938, 824cm$^{-1}$ I-1040  foam
$^1$H NMR(CDCl$_3$) δ 3.28(d, J=2.4Hz, 1H), 3.45(s, 3H), 3.75(s, 3H), 4.94(dd, J=6.0, 1.8Hz, 2H), 5.74(ddt, J=11.1, 2.4, 1.8Hz, 1H), 6.27(dt, J=11.1, 6.0Hz, 1H), 6.45(s, 1H), 6.92(d, J=8.7Hz, 2H), 6.94–7.00(m, 2H), 7.07(d, J=2.1Hz, 1H), 7.53(d, J=8.7Hz, 2H)
IR(KBr) 3433, 3279, 1612, 1588, 1523, 1489, 1286, 1248, 1223, 1113, 1070, 1011, 938, 825cm$^{-1}$ I-1041  foam
$^1$H NMR(CDCl$_3$) δ 3.45(s, 3H), 3.75(s, 3H), 4.90(d, J=1.8Hz, 2H), 5.55(dd, J=10.8, 2.4Hz, 1H), 5.71(dd, J=17.7, 2.4Hz, 1H), 5.85(ddt, J=17.7, 10.8, 1.8Hz, 1H), 6.45(s, 1H), 6.92(d, J=8.7Hz, 2H), 6.97(dd, J=8.4, 2.1Hz, 1H), 7.07(d, J=8.4Hz, 1H), 7.08(d, J=2.1Hz, 1H), 7.53(d, J=8.7Hz, 2H)
IR(KBr) 3433, 1612, 1589, 1523, 1489, 1286, 1224, 1192, 1112, 1070, 1002, 937, 825, 815cm$^{-1}$

TABLE 206

I-1042  mp 185–187° C.
$^1$H NMR(CDCl$_3$) δ 1.76(s, 3H), 1.81(s, 3H), 2.76(s, 3H), 3.23(s, 3H), 3.50(s, 3H), 3.78(s, 3H), 4.64(d, J=6.6Hz, 2H), 5.50(t, J=6.6Hz, 1H), 6.63(t, J=2.4Hz, 1H), 6.95(s, 1H), 7.09(d, J=8.5Hz, 1H), 7.26–7.29(m, 1H), 7.37(dd, J=8.5, 2.1Hz, 1H), 7.42(d, J=2.1Hz, 1H), 7.45–7.51(m, 2H), 7.89(s, 1H), 8.26(br s, 1H)
IR(KBr) 3418, 1473, 1362, 1177, 1079, 961, 817, 796cm$^{-1}$

I-1043  mp 152–154° C.
$^1$H NMR(CDCl$_3$) δ 1.76(s, 3H), 1.82(s, 3H), 3.43(s, 3H), 3.76(s, 3H), 4.61(d, J=6.9Hz, 2H), 5.53(t, J=6.9Hz, 1H), 5.69(s, 1H), 5.98(s, 1H), 6.55(s, 1H), 6.63(t, J=2.1Hz, 1H), 6.94–7.01(m, 2H), 7.10(d, J=0.9Hz, 1H), 7.25–7.27(m, 1H), 7.46(d, J=8.4Hz, 1H), 7.51(dd, J=8.5, 1.5Hz, 1H), 7.89(s, 1H), 8.24(br s, 1H)
IR(CHCl$_3$) 3529, 3480, 1515, 1495, 1407, 1291, 1246, 1107, 1070cm$^{-1}$

I-104  mp 127–128° C.
$^1$H NMR(CDCl$_3$) δ 2.45(s, 3H), 3.52(s, 3H), 3.77(s, 3H), 3.91(s, 3H), 5.22(s, 2H), 6.84(s, 1H), 6.91(dd, J=8.4, 2.1Hz, 1H), 6.79–7.00(m, 2H), 7.12–7.18(m, 2H), 7.30–7.47(m, 5H), 7.59–7.63(m, 2H)
IR(CHCl$_3$) 2938, 2843, 1606, 1585, 1520, 1483, 1464, 1443, 1390, 1368, 1174, 1141, 1083, 1013, 962, 936, 865, 838cm$^{-1}$

I-1045  mp 124–127° C.
$^1$H NMR(CDCl$_3$) δ 2.46(s, 3H), 3.55(s, 3H), 3.77(s, 3H), 3.91(s, 3H), 5.21(s, 2H), 5.42(br, 1H), 6.82(s, 1H), 6.90(dd, J=8.4, 1.8Hz, 1H), 6.97–7.10(m, 3H), 7.29–7.47(m, 7H)
IR(CHCl$_3$) 3579, 2938, 1600, 1523, 1484, 1464, 1393, 1368, 1327, 1282, 1174, 1141, 1081, 1036, 1012, 962, 908cm$^{-1}$

I-1046  mp 178–180° C.
$^1$H NMR(CDCl$_3$) δ 2.44(s, 3H), 3.29(s, 3H), 3.58(s, 3H), 3.78(s, 3H), 3.91(s, 3H), 5.22(s, 2H), 6.83(s, 1H), 6.99(dd, J=8.1, 2.1Hz, 1H), 6.97–7.25(m, 2H), 7.31–7.58(m, 8H)
IR(CHCl$_3$) 2939, 2840, 1591, 1519, 1483, 1464, 1374, 1331, 1173, 1141, 1116, 1082, 1012, 964, 863cm$^{-1}$

TABLE 207

I-107  mp 98–99° C.
$^1$H NMR(CDCl$_3$) δ 2.35(s, 3H), 5.22(s, 2H), 6.59(t, J F-H=54.6Hz, 2H), 7.09–7.50(m, 12H), 7.74–7.75(d, J=4.5Hz, 2H)
IR(CHCl$_3$) 1752, 1523, 1493, 1384, 1273, 1169, 1133, 1070, 1037, 916, 851cm$^{-1}$

I-1048  mp 112–114° C.
$^1$H NMR(CDCl$_3$) δ 1.75–1.76(d, J=0.6Hz, 3H), 1.78–1.79(d, J=0.9Hz, 3H), 2.57(s, 3H), 3.53(s, 3H), 3.78(s, 3H), 3.89 (s, 3H), 4.62–4.64(d, J=7.5Hz, 2H), 5.54(s, 1H), 6.84(s, 1H), 6.96–6.97(m, 3H), 7.12–7.18(m, 2H), 7.59–7.64(m, 2H)
IR(CHCl$_3$) 2938, 1606, 1583, 1519, 1483, 1464, 1443, 1416, 1389, 1368, 1175, 1141, 1083, 1038, 1013, 962, 936, 865, 838cm$^{-1}$

I-1049  mp 203–204° C.
$^1$H NMR(CD3OD) δ 4.53(s, 2H), 4.55(s, 2H), 5.21(s, 2H), 6.84–6.88(m, 2H), 7.12–7.50(m, 12H)
IR(KBr) 3380, 1611, 1586, 1523, 1490, 1462, 1434, 1380, 1317, 1300, 1258, 1194, 1173, 1128, 1033, 1007, 906, 871, 836, 817, 787, 730, 693, 646cm$^{-1}$

I-1050  mp 99–100° C.
$^1$H NMR(CDCl$_3$) δ 1.75(s, 3H), 1.78–1.79(d, J=0.9Hz, 3H), 3.46(s, 3H), 3.75(s, 3H), 3.88(s, 3H), 4.62–4.64(d, J=6.6Hz, 2H), 5.57(m, 1H), 5.89(s, 1H), 6.46(s, 1H), 6.96–7.02(m, 3H), 7.12–7.18(m, 2H), 7.59–7.64(m, 2H)
IR(CHCl$_3$) 3513, 2938, 1605, 1583, 1490, 1423, 1407, 1392, 1362, 1318, 1269, 1177, 1158, 1140, 1118, 1078, 1038, 1012, 930, 846, 826cm$^{-1}$

I-1051  mp 153–154° C.
$^1$H NMR(CDCl$_3$) δ 1.76(s, 3H), 1.79–1.80(d, J=0.9Hz, 3H), 2.57(s, 3H), 3.29(s, 3H), 3.60(s, 3H), 3.79(s, 3H), 3.89(s, 3H), 4.62–4.64(d, J=6.6Hz, 2H), 5.54(m, 1H), 6.84(s, 1H), 6.96–6.97(m, 4H), 7.46–7.59(m, 3H)
IR(CHCl$_3$) 2938, 1592, 1519, 1483, 1464,. 1374, 1332, 1239, 1173, 1141, 1116, 1082, 1038, 1011, 965, 864cm$^{-1}$

TABLE 208

| | |
|---|---|
| I-1052 | amorphous |
| | $^1$H NMR(CDCl$_3$) δ 2.12(s, 3H), 3.47(s, 3H), 5.15(s, 2H), 5.82–6.08(m, 3H), 6.70–6.95(m, 5H), 7.02(d, J=8.1Hz, 1H), 7.39–7.52(m, 7H) |
| | IR(CHCl$_3$) 3597, 3535, 2937, 1731, 1612, 1589, 1522, 1489, 1455, 1401, 1382, 1328, 1309, 1288, 1173, 1128, 1096, 1011, 939, 835cm$^{-1}$ |
| I-1053 | mp 141–142° C. |
| | $^1$H NMR(CDCl$_3$) δ 1.75(s, 3H), 1.78–1.79(d, J=0.9Hz, 3H), 3.49(s, 3H), 3.76(s, 3H), 3.89(s, 3H), 4.62–4.64(d, J=6.6Hz, 2H), 5.30(d, J F-H=3.3Hz, 1H), 5.57(m, 1H), 5.88(s, 1H), 6.45(s, 1H), 6.99–7.11(m, 4H), 7.33(m, 1H), 7.43(dd, J=11.7, 2.1Hz, 1H) |
| | IR(CHCl$_3$) 3578, 3514, 1621, 1600, 1583, 1523, 1492, 1464, 1397, 1320, 1279, 1175, 1140, 1116, 1100, 1076, 1038, 1011, 902cm$^{-1}$ |
| I-1054 | mp 138–140° C. |
| | $^1$H NMR(CDCl$_3$) δ 5.17(s, 2H), 5.60(s, 1H), 5.72(s, 1H), 6.98–7.02(m, 2H), 7.10–7.14(m, 3H), 7.18(s, 1H), 7.35(s, 1H), 7.37–7.47(m, 5H), 7.59–7.61(m, 2H) |
| | IR(KBr) 3600–2800(br), 1590, 1528, 1503, 1483, 1454, 1386, 1294, 1254, 1223, 1187, 1132, 1086, 1009cm$^{-1}$ |
| I-1055 | mp 176–178° C. |
| | $^1$H NMR(CDCl$_3$) δ 3.13(s, 3H), 3.32(s, 3H), 5.19(s, 2H), 7.16(d, J=8.7Hz, 1H), 7.37–7.55(m, 9H), 7.61–7.64(m, 4H) |
| | IR(KBr) 3600–2800(br), 1611, 1525, 1503, 1469, 1359, 1290, 1244, 1170, 1088, 979cm$^{-1}$ |
| I-1056 | mp 134–136° C. |
| | $^1$H NMR(CDCl$_3$) δ 1.77(s, 3H), 1.81(s, 3H), 3.23(s, 3H), 3.32(s, 3H), 4.64(d, J=6.9Hz, 1H), 5.48–5.54(m, 1H), 7.10(d, J=8.4Hz, 1H), 7.44–7.55(m, 4H), 7.58–7.65(m, 4H) |
| | IR(KBr) 3600–2800(br), 1609, 1527, 1504, 1469, 1351, 1289, 1277, 1186, 1171, 1115, 1089, 973cm$^{-1}$ |

TABLE 209

| | |
|---|---|
| I-1057 | mp 97–100° C. |
| | $^1$H NMR(CDCl$_3$) δ 1.77(d, J=0.9Hz, 3H), 1.82(d, J=0.9Hz, 3H), 4.63(d, J=7.2Hz, 2H), 5.50–5.54(m, 1H), 5.62(br s, 1H), 5.74(br s, 1H), 6.95(d, J=8.7Hz, 1H), 7.12(dd, J=2.4, 8.7Hz, 1H), 7.18(s 1H), 7.24(d, J=2.4Hz, 1H), 7.36(s, 1H), 7.42–7.46(m, 2H), 7.58–7.62(m, 2H) |
| | IR(KBr) 3600–2800(br), 1599, 1588, 1528, 1482, 1385, 1326, 1289, 1252, 1212, 1193, 1132, 1112, 1084, 1056, 1001cm$^{-1}$ |
| I-1058 | mp 216–218° C. |
| | $^1$H NMR(DMSO-d$_6$) δ 2.93(s, 12H), 3.73(s, 6H), 6.74–6.79(m, 4H), 6.92(s, 2H), 7.38–7.43(m, 4H) |
| | IR(KBr) 3600–2800(br), 1616, 1533, 1496, 1458, 1442, 1387, 1360, 1230, 1202, 1169, 1059, 1035cm$^{-1}$ |
| I-1059 | mp 122–123° C. |
| | $^1$H NMR(CDCl$_3$) δ 1.74(d, J=0.6Hz, 3H), 1.78(d, J=0.6Hz, 3H), 2.26(s, 3H), 2.29(s, 3H), 3.77(d, J=6.9Hz, 2H), 4.83(br, 1H), 5.36–5.41(m, 1H), 6.61–6.77(m, 1H), 6.86–6.91(m, 2H), 6.99–7.04(m, 2H), 7.10(s, 1H), 7.11(s, 1H), 7.21–7.26 (m, 2H) |
| | IR(KBr) 3600–2800(br), 1626, 1608, 1526, 1489, 1428, 1336, 1300, 1252, 1209, 1187cm$^{-1}$ |
| I-1060 | mp foam |
| | $^1$H NMR(CDCl$_3$) δ 1.74(s, 3H), 1.77(s, 3H), 2.27(s, 3H), 2.31(s, 3H), 3.76(d, J=6.6Hz, 2H), 3.86(s, 3H), 5.38–5.43(m, 1H), 6.66(d, J=8.1Hz, 1H), 6.80(d, J=1.8Hz, 1H), 6.86–6.90(m, 3H), 7.11(s, 1H), 7.16(s, 1H), 7.23–7.26(m, 2H) |
| | IR(CHCl$_3$) 3600–2800(br), 1730, 1611, 1525, 1489, 1455, 1256, 1171, 1137, 1100, 1036cm$^{-1}$ |
| I-1061 | mp 191–193° C. |
| | $^1$H NMR(CDCl$_3$) δ 3.01(s, 6H), 3.79(s, 3H), 3.80(s, 3H), 6.79–6.83(m, 2H), 6.92(s, 1H), 6.98(s, 1H), 7.41–7.51(m, 4H), 8.12(br s, 1H), 8.26–8.32(m, 1H) |
| | IR(KBr) 3600–2800(br), 1712, 1617, 1600, 1536, 1494, 1460, 1446, 1385, 1364, 1290, 1212, 1162, 1057, 1035cm$^{-1}$ |

TABLE 210

| | |
|---|---|
| I-1062 | mp 240–245° C. |
| | $^1$H NMR(CDCl$_3$) δ 3.82(s, 6H), 6.95(s, 2H), 7.41–7.49(m, 4H), 8.13(br s, 2H), 8.29–8.35(m, 1H) |
| | IR(KBr)3600–2800(br), 1725, 1598, 1544, 1492, 1381, 1294, 1215, 1197, 1165, 1109, 1055, 1033cm$^{-1}$ |
| I-1063 | $^1$H NMR(CDCl$_3$) δ 1.99(s, 6H), 2.17(s, 3H), 3.21(s, 3H), 5.20(s, 2H), 6.95–7.11(m, 4H), 7.23(d, J=8.7Hz, 2H), 7.33–7.52 (m, 7H) |
| | IR(KBr)1617, 1577, 1513, 1366, 1295, 1267, 1198, 1173, 1149, 1127, 1106cm$^{-1}$ |
| I-1064 | $^1$H NMR(CDCl$_3$) δ 1.99(s, 6H), 2.17(s, 3H), 3.21(s, 3H), 5.18(d, J=3.9Hz, 1H), 6.97–7.10(m, 4H), 7.23(d, J=8.7Hz, 2H), 7.37(d, J=8.7Hz, 2H) |
| | IR(KBr)3442, 1620, 1597, 1519, 1472, 1356, 1279, 1232, 1174, 1147, 1103cm$^{-1}$ |
| I-1065 | $^1$H NMR(CDCl$_3$) δ 1.78(s, 3H), 1.83(s, 3H), 2.00(s, 6H), 2.19(s, 3H), 3.22(s, 3H), 4.65(d, J=6.3Hz, 2H), 5.52–5.62(m, 1H), 6.96–7.13(m, 4H), 7.24(d, J=8.7Hz, 2H), 7.38(d, J=8.7Hz, 2H) |
| | IR(KBr)1617, 1576, 1514, 1466, 1359, 1297, 1268, 1204, 1151, 1002cm$^{-1}$ |
| I-1066 | $^1$H NMR(CDCl$_3$) δ 1.77(s, 3H), 1.81(s, 3H), 2.01(s, 6H), 2.18(s, 3H), 4.63(d, J=6.9Hz, 2H), 4.75(s, 1H), 5.52–5.60(m, 1H), 6.82–7.11(m, 8H) |
| | IR(KBr)3433, 1606, 1517, 1466, 1297, 1269, 1221, 1128, 1107, 1004cm$^{-1}$ |
| I-1067 | $^1$H NMR(CDCl$_3$) δ: 2.25(s, 3H), 2.27(s, 3H), 2.31(s, 3H), 3.20(s, 3H), 4.75(s, 1H), 6.83(d, J=8.4Hz, 1H), 7.05–7.14 (m, 4H), 7.34(d, J=8.4Hz, 2H), 7.42(d, J=8.4Hz, 2H) |
| | IR(KBr)3494, 3435, 1604, 1517, 1488, 1375, 1327, 1199, 1171, 1148, 1118cm$^{-1}$ |
| I-1068 | $^1$H NMR(CDCl$_3$) δ 1.77(s, 3H), 1.82(s, 3H), 2.25(s, 3H), 2.28(s, 6H), 3.20(s, 3H), 4.58(d, J=6.6Hz, 2H), 5.50–5.58 (m, 1H), 6.88(d, J=9.0Hz, 1H), 7.08–7.16(m, 4H), 7.34(.d, J=8.7Hz, 2H), 742(d, J=8.7Hz, 2H) |
| | IR(KBr)1604, 1513, 1486, 1367, 1238, 1176, 1153, 1131, 1002cm$^{-1}$ |

TABLE 211

| | |
|---|---|
| I-1069 | ¹H NMR(CDCl₃) δ 1.76(s, 3H), 1.81(s, 3H), 2.26(s, 3H), 2.28(s, 6H), 4.57(d, J=6.6Hz, 2H), 4.80(s, 1H), 5.50–5.58 (m, 1H), 6.85–6.91(m, 3H), 7.09–7.17(m, 3H), 7.21–7.28(m, 3H)<br>IR(KBr)3436, 1608, 1518, 1488, 1238, 1130, 1008cm⁻¹ |
| I-1070 | ¹H NMR(CDCl₃) δ: 2.26(s, 3H), 2.30(s, 3H), 3.00(s, 6H), 5.19(s, 2H), 6.80(.d, J=8.7Hz, 2H), 7.02–7.16(m, 5H), 7.26 (d, J=8.7Hz, 2H), 7.33–7.51(m, 5H)<br>IR(KBr)1608, 1527, 1490, 1355, 1297, 1270, 1262, 1231, 1121, 1022cm⁻¹ |
| I-1071 | ¹H NMR(CDCl₃) δ 2.26(s, 3H), 2.30(s, 3H), 3.01(s, 6H), 5.09(s, 1H), 6.80(d, J=8.4Hz, 2H), 7.01–7.15(m, 5H), 7.27(.d, J=8.4Hz, 2H)<br>IR(KBr)3432, 1613, 1590, 1526, 1489, 1307, 1283, 1241, 1138, 1111cm⁻¹ |
| I-1072 | ¹H NMR(CDCl₃) δ: 1.77(s, 3H), 1.81(s, 3H), 2.27(s, 3H), 2.30(s, 3H), 3.00(s, 6H), 4.63(d, J=6.6Hz, 2H), 5.51–5.59(m, 1H), 6.80(d, J=8.4Hz, 2H), 6.97–7.16(m, 5H), 7.27(d, J=8.14Hz, 2H)<br>IR(KBr)1611, 1528, 1489, 1353, 1297, 1266, 1228, 1122, 1011cm⁻¹ |
| I-1073 | mp 182–184° C.<br>¹H NMR(CDCl₃) δ 1.48(s, 3H), 1.67(s, 3H), 1.91(s, 3H), 3.46(s, 3H), 3.76(s, 3H), 3.84(s, 3H), 3.94–4.03(m, 1H), 4.05–4.59 (m, 1H), 5.23–5.32(m, 1H), 5.74(br s, 1H), 6.05(s, 1H), 6.48(s, 1H), 6.93–6.99(m, 2H), 7.04–7.10(m, 3H), 7.51–7.56(m, 3H)<br>IR(KBr)3400, 2934, 1625, 1523, 1396, 1227, 1119, 1077, 1036, 826, 589cm⁻¹ |
| I-1074 | mp 153–154° C.<br>¹H NMR(CDCl₃) δ 1.74(s, 3H), 1.78(s, 3H), 2.30(s, 3H), 2.31(s, 3H), 3.75(d, J=6.6Hz, 2H), 3.86(s, 3H), 3.87(s, 3H), 5.37–5.45(m, 1H), 6.66(d, J=8.4Hz, 1H), 6.74–6.83(m, 5H), 6.89(dd, J=1.8, 8.1Hz, 1H), 7.14(s, 1H), 7.16(s, 1H)<br>IR(KBr)3408, 3389, 3294, 3210, 2919, 2835, 1528, 1495, 1275, 1208, 1032, 856, 826cm⁻¹ |

TABLE 212

| | |
|---|---|
| I-1075 | mp 168–171° C.<br>¹H NMR(CDCl₃) δ 1.74(s, 6H), 1.77(s, 6H), 2.31(s, 6H), 3.75(d, J=6.9Hz, 4H), 3.86(s, 6H), 5.37–5.45(m, 2H), 6.66(d, J=8.1Hz, 2H), 6.80(d, J=1.8Hz, 2H), 6.89(dd, J=1.8, 8.1Hz, 2H), 7.16(s, 1H)<br>IR(KBr)3423, 2968, 2927, 2912, 2849, 1609, 1526, 1498, 1454, 1261, 1209, 1135, 1030, 855, 803cm⁻¹ |
| I-1076 | mp 79–80° C.<br>¹H NMR(CDCl₃) δ 2.54(s, 3H), 3.19(s, 3H), 3.85(s, 3H), 5.17(s, 2H), 5.71(brs, 1H), 6.93(d, J=8.1Hz, 1H), 7.01–7.07 (m, 3H), 7.24–7.26(m, 2H), 7.37–7.43(m, 7H), 7.66(d, J=8.7Hz, 2H)<br>IR(KBr)3466, 3029, 2939, 2937, 1610, 1520, 1482, 1365, 1246, 1201, 1175, 1150, 1073, 969, 872, 839, 804cm⁻¹ |
| I-1077 | mp 151–152° C.<br>¹H NMR(CDCl₃) δ 4.00(s, 3H), 4.91(brs, 1H), 5.24(s, 2H), 6.89(d, J=8.2Hz, 2H), 7.00(d, J=8.0Hz, 1H), 7.12–7.47(m, 10H), 7.71(d, J=7.4Hz, 1H), 7.89(s, 1H)<br>IR(KBr)3422, 1612, 1526, 1491, 1454, 1329, 1287, 1269, 1248, 1171, 1136, 1103, 1019, 827cm⁻¹ |
| I-1078 | mp 173–174° C.<br>¹H NMR(CDCl₃) δ 3.13(s, 3H), 4.92(brs, 1H), 5.19(s, 2H), 6.88(d, J=8.6Hz, 2H), 7.15–7.26(m, 4H), 7.35–7.59(m, 7H), 7.69(d, J=9.4Hz, 1H), 7.86(s, 1H)<br>IR(KBr)3426, 1613, 1527, 1489, 1435, 1361, 1330, 1294, 1243, 1164, 1118, 1070, 978, 821cm⁻¹ |
| I-1079 | mp 168–169° C.<br>¹H NMR(CDCl₃) δ 3.20(s, 3H), 3.99(s, 3H), 5.22(s, 2H), 6.89(d, J=8.8Hz, 1H), 7.11–7.15(m, 2H), 7.31–7.49(m, 10H), 7.73(d, J=7.4Hz, 1H), 7.90(s, 1H)<br>IR(KBr)3434, 1603, 1524, 1488, 1369, 1335, 1244, 1178, 1143, 1119, 1006, 871cm⁻¹ |

TABLE 213

| | |
|---|---|
| I-1080 | mp 68–69° C.<br>¹H NMR(CDCl₃) δ 3.13(s, 3H), 3.19(s, 3H), 5.19(s, 2H), 7.18(d, J=8.6Hz, 2H), 7.26–7.59(m, 11H), 7.73(d, J=9.2Hz, 1H), 7.89(s, 1H)<br>IR(KBr)3431, 3034, 2938, 1613, 1524, 1487, 1367, 1330, 1293, 1242, 1175, 1151, 1118, 970, 872, 828cm⁻¹ |
| I-1081 | mp 74–76° C.<br>¹H NMR(CDCl₃) δ 1.78(s, 3H), 1.84(s, 3H), 3.51(s, 3H), 4.64(d, J=5.6Hz, 2H), 5.08(brs, 2H), 5.49–5.54(m, 1H), 5.75 (brs, 1H), 5.85(brs, 1H), 6.14(s, 1H), 6.89–7.12(m, 5H), 7.53(d, J=8.4Hz, 2H)<br>IR(KBr)3444, 2934, 1612, 1523, 1485, 1403, 1360, 1251, 1172, 1006, 971, 837, 527cm⁻¹ |
| I-1082 | mp 71–72° C.<br>¹H NMR(CDCl₃) δ 2.46(s, 3H), 3.20(s, 3H), 3.86(s, 3H), 3.91(s, 3H), 5.21(s, 2H), 6.87–7.03(m, 3H), 7.11(s, 1H), 7.24–7.41 (m, 8H), 7.67(d, J=8.8Hz, 2H)<br>IR(KBr)3434, 3028, 2936, 1609, 1521, 1482, 1365, 1239, 1176, 1074, 969, 869, 804cm⁻¹ |
| I-1083 | mp 73–74° C.<br>¹H NMR(CDCl₃) δ 2.66(s, 3H), 3.13(s, 3H), 3.20(s, 3H), 3.86(s, 3H), 5.19(s, 2H), 7.08(d, J=1.6Hz, 1H), 7.16(d, J=8.4Hz, 1H), 7.21–7.28(m, 2H), 7.37–7.42(m, 8H), 7.66(d, J=8.4Hz, 2H)<br>IR(KBr)3432, 3031, 2938, 1610, 1523, 1480, 1365, 1176, 1151, 1074, 970, 875, 807, 524cm⁻¹ |
| I-1084 | mp 110–111° C.<br>¹H NMR(CDCl₃) δ 1.78(s, 3H), 1.81(s, 3H), 3.21(s, 3H), 3.98(s, 3H), 4.67(d, J=6.6Hz, 2H), 5.57(t, J=6.8Hz, 1H), 7.01(d, J=8.0Hz, 1H), 7.15–7.21(m, 2H), 7.28–7.45(m, 4H), 7.76(d, J=7.6Hz, 1H), 7.93(s, 1H), 8.03(s, 1H)<br>IR(KBr)3434, 3010, 2931, 1524, 1488, 1368, 1336, 1247, 1173, 1149, 1121, 1007, 871, 562cm⁻¹ |

TABLE 214

| | |
|---|---|
| I-1085 | mp 147–148° C.<br>¹H NMR(CDCl₃) δ 1.76(s, 3H), 1.79(s, 3H), 3.96(s, 3H), 4.65(d, J=6.3Hz, 2H), 4.91(brs, 1H), 5.55(t, J=5.7Hz, 1H), |

TABLE 214-continued

| | |
|---|---|
| | 6.88(d, J=8.1Hz, 2H), 6.99(d, J=8.4Hz, 1H), 7.12–7.26(m, 4H), 7.36(d, J=8.1Hz, 1H), 7.89(s, 1H)<br>IR(KBr)3450, 2938, 1612, 1524, 1490, 1436, 1340, 1264, 1230, 1212, 1139, 1123, 984, 835cm$^{-1}$ |
| I-1086 | mp 134–135° C.<br>$^1$H NMR(CDCl$_3$) δ 1.77(s, 3H), 1.82(s, 3H), 4.64(d, J=6.6Hz, 2H), 4.84(brs, 1H), 5.52(t, J=7.2Hz, 1H), 5.77(s, 1H), 6.87(d, J=8.7Hz, 2H), 6.96(d, J=8.4Hz, 1H), 7.12(dd, J=2.4, 8.7Hz, 1H), 7.35(d, J=8.1Hz, 1H), 7.70(d, J=8.4Hz, 1H), 7.89(s, 1H)<br>IR(KBr)3367, 1610, 1489, 1442, 1333, 1265, 1193, 1165, 1124, 834, 805cm$^{-1}$ |
| I-1087 | mp 156–157° C.<br>$^1$H NMR(CDCl$_3$) δ 1.78(s, 3H), 1.81(s, 3H), 3.82(s, 3H), 3.89(s, 3H), 4.65(d, J=6.2Hz, 2H), 4.95(brs, 1H), 5.22(brs, 1H), 5.58(t, J=6.0Hz, 1H), 6.73(s, 1H), 6.87–7.00(m, 6H), 7.53(d, J=8.4Hz, 2H)<br>IR(KBr)3394, 2934, 1610, 1526, 1499, 1455, 1402, 1240, 1221, 1139, 1099, 894, 815cm$^{-1}$ |
| I-1088 | mp 69–70° C.<br>$^1$H NMR(CDCl$_3$) δ 1.77(s, 3H), 1.83(s, 3H), 3.80(s, 3H), 4.63(d, J=7.0Hz, 2H), 4.93(brs, 1H), 5.22(brs, 1H), 5.52(t, J=7.0Hz, 1H), 5.78(brs, 1H), 6.70(d, J=1.6Hz, 1H), 6.83–7.01(m, 6H), 7.51(d, J=8.8Hz, 2H)<br>IR(KBr)3411, 2933, 1611, 1526, 1492, 1453, 1263, 1242, 1220, 1190, 1172, 1096, 907, 822cm$^{-1}$ |
| I-1089 | mp 160–161° C.<br>$^1$H NMR(CDCl$_3$) δ 1.39(d, J=6.0Hz, 6H), 2.40(s, 3H), 3.21(s, 3H), 3.55(s, 3H), 3.77(s, 3H), 4.55(m, 1H), 5.20(s, 2H), 6.83(s, 1H), 6.93(dd, J=1.8, 8.1Hz, 1H), 7.01(d, J=8.1Hz, 1H), 7.01(d, J=1.8Hz, 1H), 7.28–7.48(m, 7H), 7.66–7.72(m, 2H)<br>IR(KBr)1515, 1480, 1463, 1391, 1363, 1239, 1192, 1176, 1149, 1082, 1018, 962, 873, 800cm$^{-1}$ |

TABLE 215

| | |
|---|---|
| I-1090 | mp 154–155° C.<br>$^1$H NMR(CDCl$_3$) δ 2.59(s, 3H), 3.21(s, 3H), 3.54(s, 3H), 3.77(s, 3H), 5.23(s, 2H), 6.84(s, 1H), 7.06(d, J=8.4Hz, 1H), 7.24–7.50(m, 9H), 7.65–7.71(m, 2H)<br>IR(KBr)1513, 1479, 1365, 1267, 1232, 1178, 1150, 1079, 971, 959, 875, 797cm$^{-1}$ |
| I-1091 | mp 137–138° C.<br>$^1$H NMR(CDCl$_3$) δ 1.38(d, J=6.3Hz, 6H), 3.46(s, 3H), 3.74(s, 3H), 4.54(m, 1H), 4.96(s, 1H), 5.17(s, 2H), 5.92(s, 1H), 6.45(s, 1H), 6.89–6.94(m, 2H), 7.00–7.11(m, 3H), 7.27–7.41(m, 3H), 7.45–7.56(m, 4H)<br>IR(KBr)3443, 3356, 1611, 1521, 1488, 1458, 1393, 1269, 1236, 1138, 1112, 1074, 1013, 830, 743cm$^{-1}$ |
| I-1092 | mp 75–76° C.<br>$^1$H NMR(CDCl$_3$) δ 1.37(d, J=5.8Hz, 6H), 1.75(s, 3H), 1.79(s, 3H), 2.53(s, 3H), 3.21(s, 3H), 3.56(s, 3H), 3.78(s, 3H), 4.51(m, 1H), 4.61(d, J=6.6Hz, 2H), 5.52(m, 1H), 6.84(s, 1H), 6.96–7.02(m, 3H), 7.34–7.42(m, 2H), 7.65–7.74(m, 2H)<br>IR(KBr)1516, 1480, 1449, 1360, 1332, 1240, 1199, 1177, 1152, 1083, 964, 873, 797cm$^{-1}$ |
| I-1093 | mp 119–120° C.<br>$^1$H NMR(CDCl$_3$) δ 1.37(d, J=6.3Hz, 6H), 1.73(s, 3H), 1.77(d, J=0.9Hz, 3H), 3.46(s, 3H), 3.75(s, 3H), 4.51(m, 1H), 4.61(d, J=6.6Hz, 2H), 5.14(s, 1H), 5.54(m, 1H), 5.93(s, 1H), 6.46(s, 1H), 6.89–6.95(m, 2H), 6.98(d, J=8.1Hz, 1H), 7.01–7.07(m, 2H), 7.50–7.56(m, 2H)<br>IR(KBr)3426, 1610, 1522, 1488, 1455, 1402, 1267, 1237, 1174, 1135, 1112, 1079, 1020cm$^{-1}$ |
| I-1094 | mp 150–151° C.<br>$^1$H NMR(CDCl$_3$) δ 3.44(s, 3H), 3.75(s, 3H), 4.90(s, 1H), 5.20(s, 2H), 5.99(s, 1H), 6.44(s, 1H), 6.88–6.95(m, 2H), 7.04(d, J=8.4Hz, 1H), 7.29–7.44(m, 4H), 7.47–7.56(m, 5H)<br>IR(KBr)3410, 1610, 1519, 1484, 1463, 1455, 1410, 1382, 1359, 1285, 1264, 1229, 1118, 1074, 1060, 1014, 995cm$^{-1}$ |
| I-1095 | $^1$H NMR(CDCl$_3$) δ 0.96(s, 3H), 0.98(s, 3H), 1.53–1.82(m, 3H), 2.99(s, 6H), 3.20(t, J=7.2Hz, 2H), 3.78(s, 3H), 3.79(s, 3H), 3.87(br, 1H), 6.71–6.83(m, 3H), 6.92(s, 1H), 6.94(s, 1H), 7.23–7.31(m, 2H), 7.47–7.52(m, 2H) |

TABLE 216

| | |
|---|---|
| I-1096 | mp 87–89° C.<br>$^1$H NMR(CDCl$_3$) δ 1.70(s, 3H), 1.75(s, 3H), 2.82(s, 3H), 3.00(s, 3H), 3.74–3.80(m, 2H), 3.78(s, 3H), 3.80(s, 3H), 5.29–5.34 (m, 1H), 6.79–6.83(m, 2H), 6.92–6.97(m, 3H), 7.25–7.34(m, 2H), 7.47–7.52(m, 2H)<br>IR(KBr)3600–2800(br), 1613, 1531, 1495, 1460, 1448, 1380, 1359, 1253, 1210, 1057, 1036cm$^{-1}$ |
| I-1097 | mp 167–169° C.<br>$^1$H NMR(CDCl$_3$) δ 2.92(s, 3H), 3.00(s, 6H), 3.78(s, 3H), 3.79(s, 3H), 4.02(br, 1H), 6.71–6.83(m, 3H), 6.92(s, 1H), 6.95 (s, 1H), 7.25–7.32(m, 2H), 7.47–7.52(m, 2H)<br>IR(KBr)3600–2800(br), 1625, 1613, 1533, 1497, 1462, 1445, 1381, 1358, 1328, 1262, 1205, 1163, 1051, 1031cm$^{-1}$ |
| I-1098 | mp 114–115° C.<br>$^1$H NMR(CDCl$_3$) δ 2.27(s, 6H), 2.54(s, 3H), 5.19(s, 2H), 7.00–7.16(m, 5H), 7.26–7.51(m, 9H)<br>IR(KBr)1519, 1501, 1483, 1454, 1310, 1295, 1263, 1232, 1123, 998, 744cm$^{-1}$ |
| I-1099 | mp 68–69° C.<br>$^1$H NMR(CDCl$_3$) δ 1.62(br s, 1H), 1.77(s, 3H), 1.82(s, 3H), 2.27(s, 3H), 2.28(s, 3H), 4.64(d, J=6.8Hz, 2H), 4.76(s, 2H), 5.56(m, 1H), 7.00–7.16(m, 5H), 7.33–7.48(m, 4H)<br>IR(KBr)3433, 1522, 1490, 1384, 1311, 1296, 1266, 1232, 1194, 1122, 1025, 1013, 992, 841, 818cm$^{-1}$ |
| I-1100 | mp 68–69° C.<br>$^1$H NMR(CDCl$_3$) δ 1.62(br s, 1H), 1.77(s, 3H), 1.82(s, 3H), 2.27(s, 3H), 2.28(s, 3H), 4.64(d, J=6.8Hz, 2H), 4.76(s, 2H), 5.56(m, 1H), 7.00–7.16(m, 5H), 7.33–7.48(m, 4H)<br>IR(KBr)3433, 1522, 1490, 1384, 1311, 1296, 1266, 1232, 1194, 1122, 1025, 1013, 992, 841, 818cm$^{-1}$ |

TABLE 217

I-1101  mp 171° C.
$^1$H NMR(CDCl$_3$) δ 1.77(s, 3H), 1.81(d, J=0.9Hz, 3H), 2.68(s, 3H), 3.21(s, 3H), 3.55(s, 3H), 3.78(s, 3H), 4.65(d, J=6.6Hz, 2H), 5.53(m, 1H), 6.84(s, 1H), 7.03(d, J=8.7Hz, 1H), 7.29(dd, J=2.1, 8.7Hz, 1H), 7.36–7.41(m, 2H), 7.46(d, J=2.1Hz, 1H), 7.66–7.72(m, 2H)
IR(KBr)1510, 1477, 1376, 1358, 1349, 1294, 1237, 1196, 1173, 1145, 1077, 1004, 958, 861, 801cm$^{-1}$

I-1102  mp 168–169° C.
$^1$H NMR(CDCl$_3$) δ 1.76(d, J=0.3Hz, 3H), 1.80(d, J=0.9Hz, 3H), 3.44(s, 3H), 3.75(s, 3H), 4.64(d, J=6.6Hz, 2H), 4.97(s, 1H), 5.55(m, 1H), 6.00(s, 1H), 6.45(s, 1H), 6.89–6.95(m, 2H), 7.01(d, J=8.4Hz, 1H), 7.33(dd, J=2.1, 8.4Hz, 1H), 7.51(d, J=2.1Hz, 1H), 7.51–7.56(m, 2H)
IR(KBr)3396, 1613, 1521, 1485, 1467, 1440, 1408, 1384, 1357, 1286, 1264, 1229, 1116, 1076, 1056, 993, 834cm$^{-1}$

I-1103  mp 176–177° C.
$^1$H NMR(CDCl$_3$) δ 1.77(s, 3H), 1.80(s, 3H), 2.09(s, 3H), 2.16(s, 3H), 3.87(s, 3H), 4.65(d, J=7.2Hz, 2H), 4.78(br s, 1H), 5.06(s, 1H), 5.40–5.60(m, 1H), 6.76(s, 1H), 6.82–6.91(m, 4H), 7.02(d, J=7.8Hz, 1H), 7.22–7.27(m, 2H)
IR(CHCl$_3$)3597, 3533, 3026, 3010, 2921, 1731, 1612, 1520, 1488, 1240, 1172cm$^{-1}$

I-1104  mp 185–186° C.
$^1$H NMR(CDCl$_3$) δ 1.78(s, 3H), 1.82(s, 3H), 2.06(s, 3H), 2.15(s, 3H), 4.66(d, J=6.9Hz, 2H), 4.71(s, 1H), 4.89(s, 1H), 5.53–5.58(m, 1H), 6.75(s, 1H), 6.86–6.91(m, 2H), 6.90–7.00(m, 3H), 7.21–7.26(m, 2H)
IR(CHCl$_3$)3691, 3598, 3546, 3068, 2922, 1674, 1613, 1520, 1488, 1298, 1262, 1165cm$^{-1}$

I-1105  mp 143–144° C.
$^1$H NMR(CDCl$_3$) δ 2.48(s, 3H), 3.21(s, 3H), 3.52(s, 3H), 3.67(d, J=1.2Hz, 3H), 3.92(s, 3H), 5.23(s, 2H), 6.92–7.02(m, 3H), 7.31–7.48(m, 7H), 7.60(dd, J=8.7, 1.5Hz, 2H)
IR(KBr)1519, 1470, 1370, 1256, 1173, 1152, 1029, 872cm$^{-1}$

TABLE 218

I-1106  mp 128–130° C.
$^1$H NMR(CDCl$_3$) δ 1.76(s, 3H), 1.80(s, 3H), 2.59(s, 3H), 3.21(s, 3H), 3.53(s, 3H), 3.67(d, J=0.9Hz, 3H), 3.90(s, 3H), 4.64(d, J=6.9Hz, 2H), 5.55(t, J=6.9Hz, 1H), 6.97–7.00(m, 3H), 7.41(d, J=8.8Hz, 2H), 7.60(dd, J=8.8, 1.1Hz, 2H)
IR(KBr)1519, 1361, 1258, 1175, 1148, 1041, 978, 874cm$^{-1}$

I-117  mp 168–170° C.
$^1$H NMR(CDCl$_3$) δ 1.76(s, 3H), 1.79(s, 3H), 3.43(s, 3H), 3.63(d, J=0.9Hz, 3H), 3.89(s, 3H), 4.65(d, J=6.8Hz, 2H), 5.01(s, 1H), 5.57(t, J=6.8Hz, 1H), 5.65(s, 1H), 6.90–7.06(m, 5H), 7.43(dd, J=8.7, 1.5Hz, 2H)
IR(KBr)3433, 1523, 1464, 1397, 1253, 1216, 1038, 977, 838, 814cm$^{-1}$

I-1108  mp 127–128° C.
$^1$H NMR(CDCl$_3$) δ 2.25(s, 3H), 2.27(s, 3H), 3.20(s, 3H), 5.22(s, 2H), 7.02(d, J=8.4Hz, 1H), 7.10(s, 1H), 7.11(s, 1H), 7.18(dd, J=2.1, 8.4Hz, 1H), 7.31–7.54(m, 10H)
IR(KBr)1513, 1484, 1369, 1284, 1243, 1175, 1150, 1061, 984, 968, 868, 847, 791, 718cm$^{-1}$

I-1109  mp 161–162° C.
$^1$H NMR(CDCl$_3$) δ 2.26(s, 3H), 2.28(s, 3H), 5.16(s, 2H), 5.19(s, 2H), 5.70(br s, 1H), 6.82(dd, J=2.1, 8.4Hz, 1H), 6.96–7.16(m, 7H), 7.31–7.51(m, 10H)
IR(KBr)3449, 1521, 1492, 1470, 1455, 1394, 1294, 1279, 1247, 1232, 1199, 1185, 1129, 1013, 740, 695cm$^{-1}$

I-110  mp 133–134° C.
$^1$H NMR(CDCl$_3$) δ 2.26(s, 6H), 4.80(br s, 1H), 5.21(s, 2H), 6.85–6.93(m, 2H), 7.02(d, J=8.4Hz, 1H), 7.09(s, 1H), 7.17(s, 1H), 7.15–7.52(m, 9H)
IR(KBr)3350, 1601, 1519, 1485, 1453, 1387, 1289, 1255, 1169, 1060, 839, 813, 731cm$^{-1}$

TABLE 219

I-1111  mp 83–84° C.
$^1$H NMR(CDCl$_3$) δ 1.78(d, J=0.3Hz, 3H), 1.82(d, J=0.9Hz, 3H), 2.26(s, 3H), 2.27(s, 3H), 3.20(s, 3H), 4.65(d, J=6.6Hz, 2H), 5.55(m, 1H), 6.99(d, J=8.4Hz, 1H), 7.11(s, 1H), 7.12(s, 1H), 7.19(dd, J=2.1, 8.4Hz, 1H), 7.38(d, J=2.1Hz, 1H), 7.32–7.43(m, 4H)
IR(KBr)1514, 1485, 1364, 1286, 1253, 1197, 1178, 1156, 1057, 976, 882, 851cm$^{-1}$

I-1112  mp 86–87° C.
$^1$H NMR(CDCl$_3$) δ 1.77(d, J=0.6Hz, 3H), 1.82(d, J=0.9Hz, 3H), 2.27(s, 6H), 4.65(d, J=6.6Hz, 2H), 5.00(s, 1H), 5.55(m, 1H), 6.86–6.92(m, 2H), 6.98(d, J=8.4Hz, 1H), 7.10(s, 1H), 7.11(s, 1H), 7.20(dd, J=2.1, 8.4Hz, 1H), 7.22–7.26(m, 2H), 7.38(d, J=2.1Hz, 1H)
IR(KBr)3339, 1608, 1530, 1492, 1429, 1362, 1288, 1258, 1232, 1213, 1189, 1112, 889, 783cm$^{-1}$

I-1113  amorphous
$^1$H NMR(CDCl$_3$) δ 1.76(s, 3H), 3.32(s, 6H), 3.44(s, 3H), 3.74(s, 3H), 5.23(s, 2H), 7.02(s, 1H), 7.14–7.20(m, 2H), 7.28(d, J=8.7Hz, 1H), 7.32–7.55(m, 7H), 7.72(d, J=8.4Hz, 2H), 9.22(s, 1H),
IR(KBr)3382, 1684, 1518, 1469, 1365, 1237, 1150, 1017, 972, 872, 815cm$^{-1}$ I-1114  mp 173–175° C.
$^1$H NMR(CDCl$_3$) δ 1.76(s, 3H), 1.81(s, 3H), 1.97(s, 3H), 3.19(s, 6H), 3.21(s, 3H), 3.37(s, 3H), 3.75(s, 3H), 4.62(d, J=6.9Hz, 2H), 5.50(t, J=6.9Hz, 1H), 6.85(m, 2H), 7.06(d, J=8.4Hz, 1H), 7.25(m, 1H), 7.37(br s, 1H), 7.66(d, J=8.7Hz, 2H)
IR(KBr)3421, 1518, 1470, 1366, 115, 1107, 970, 814cm$^{-1}$

TABLE 220

I-1115  mp 96–98° C.
$^1$H NMR(DMSO-d$_6$) δ 1.72(s, 3H), 1.77(s, 3H), 3.27(s, 3H), 3.59(s, 3H), 4.21(s, 2H), 4.55(d, J=6.3Hz, 2H), 5.50(t, J=6.3Hz,

TABLE 220-continued

| | |
|---|---|
| | 1H), 6.17(s, 1H), 6.59(dd, J=8.1, 1.8Hz, 1H), 6.66(d, J=1.8Hz, 1H), 6.82(d, J=8.7Hz, 2H), 6.97(d, J=8.1Hz, 1H), 7.42(d, J=8.7Hz, 2H), 8.89(br s, 1H), 9.45(br s, 1H)<br>IR(KBr) 3431, 3396, 3319, 1611, 1521, 1486, 1264, 1172, 1111, 987, 826cm$^{-1}$ |
| I-1116 | mp 186–188° C.<br>$^1$H NMR(DMSO-d$_6$) δ 1.72(s, 3H), 1.76(s, 6H), 3.28(s, 3H), 3.68(s, 3H), 4.54(d, J=6.6Hz, 2H), 5.48(t, J=6.6Hz, 1H), 6.53–6.58(m, 1H), 6.65(d, J=1.8Hz, 1H), 6.83–6.89(m, 4H), 7.43(d, J=8.4Hz, 2H), 8.73(br s, 1H), 8.96(br s, 1H), 9.53 (br s, 1H)<br>IR(KBr) 3429, 1652, 1611, 1519, 1474, 1250, 1080, 1018, 981, 836cm$^{-1}$ |
| I-1117 | mp 210–213° C.<br>$^1$H NMR(CDCl$_3$) δ 3.48(s, 3H), 3.77(s, 3H), 5.16(s, 2H), 5.71(s, 1H), 5.85(s, 1H), 6.48(s, 1H), 6.95(dd, J=8.4, 2.1Hz, 1H), 7.04(d, J=8.4Hz, 1H), 7.07(d, J=2.1Hz, 1H), 7.40–7.48(m, 5H), 7.83(d, J=9.0Hz, 2H), 8.32(d, J=9.0Hz, 2H)<br>IR(KBr) 3499, 1511, 1343, 1284, 1247, 1195, 1109, 1070, 1013cm$^{-1}$ |
| I-1118 | mp 156–158° C.<br>$^1$H NMR(CDCl$_3$) δ 2.67(s, 3H), 3.14(s, 3H), 3.56(s, 3H), 3.80(s, 3H), 5.20(s, 2H), 6.87(s, 1H), 7.16(d, J=8.7Hz, 1H), 7.32–7.48(m, 7H), 7.82(d, J=9.2Hz, 2H), 8.32(d, J=9.2Hz, 2H)<br>IR(KBr) 1518, 1479, 1350, 1177, 1119, 1079, 947, 816cm$^{-1}$ |
| I-1119 | mp 173–175° C.<br>$^1$H NMR(CDCl$_3$) δ 1.77(s, 3H), 1.81(s, 3H), 2.71(s, 3H), 3.24(s, 3H), 3.57(s, 3H), 3.80(s, 3H), 4.64(d, J=6.7Hz, 2H), 5.50(t, J=6.7Hz, 1H), 6.87(s, 1H), 7.10(d, J=8.4Hz, 1H), 7.35(d, J=8.4, 2.1Hz, 1H), 7.39(d, J=2.0Hz, 1H), 7.82(d, J=9.0Hz, 2H), 8.32(d, J=9.0Hz, 2H)<br>IR(KBr) 1519, 1479, 1360, 1178, 1075, 946, 850, 799cm$^{-1}$ |

TABLE 221

| | |
|---|---|
| I-1120 | mp 191–193° C.<br>$^1$H NMR(CDCl$_3$) δ 1.77(s, 3H), 1.82(s, 3H), 3.48(s, 3H), 3.77(s, 3H), 4.63(d, J=6.6Hz, 2H), 5.53(t, J=6.6Hz, 1H), 5.72(s, 1H), 5.83(s, 1H), 6.48(s, 1H), 6.93(dd, J=8.1, 1.8Hz, 1H), 6.98(d, J=8.1Hz, 1H), 7.04(d, J=1.8Hz, 1H), 7.83(d, J=9.0Hz, 2H), 8.32(d, J=9.0Hz, 2H)<br>IR(KBr) 3492, 1588, 1511, 1482, 1345, 1283, 1244, 1116, 1069, 1010cm$^{-1}$ |
| I-1121 | mp 135–138° C.<br>$^1$H NMR(CDCl$_3$) δ 1.76(s, 3H), 1.82(s, 3H), 3.61(s, 3H), 3.67(s, 3H), 3.73(s, 3H), 4.62(d, J=6.9Hz, 2H), 5.00(br. s, 1H), 5.50–5.57(m, 1H), 5.69(br. s, 1H), 6.65(s, 1H), 6.86–6.96(m, 4H), 7.00(d, J=1.8Hz, 1H), 7.48(d, J=8.4Hz, 2H)<br>IR(KBr) 3428, 2938, 1680, 1613, 1594, 1520, 1479, 1460, 1393, 1260, 1226, 1104, 1081, 993, 834cm$^{-1}$ |
| I-1122 | mp 140–142° C.<br>$^1$H NMR(CDCl$_3$) δ 1.78(s, 3H), 1.82(s, 3H), 2.34(s, 3H), 4.65–4.67(d, J=6.9Hz, 2H), 5.55(m, 1H), 6.41–6.78(dt, J F-H=54.6, 3.3Hz, 2H), 7.05–7.25(m, 5H), 7.26–7.45(m, 2H), 7.75(m, 2H)<br>IR(CHCl$_3$) 1752, 1523, 1493, 1435, 1385, 1301, 1272, 1169, 1132, 1070, 1037, 916, 889cm$^{-1}$ |
| I-1123 | mp 178–180° C.<br>$^1$H NMR(CDCl$_3$) δ 1.75(s, 3H), 1.78–1.79(d, J=0.6Hz, 3H), 2.13(s, 3H), 3.50(s, 3H), 3.87(s, 3H), 4.63–4.65(d, J=6.6Hz, 2H), 5.00(br, 1H), 5.57(m, 1H), 5.75(s, 1H), 6.79(s, 1H), 6.84–7.00(m, 5H), 7.50–7.53(m, 2H)<br>IR(CHCl$_3$) 3596, 3528, 2937, 1612, 1584, 1522, 1489, 1454, 1400, 1259, 1173, 1139, 1102, 1009, 930, 865, 835cm$^{-1}$ |
| I-1124 | mp 173–174° C.<br>$^1$H NMR(CDCl$_3$) δ 3.03(s, 6H), 3.54(s, 3H), 3.76(s, 3H), 3.91(s, 3H), 5.22(s, 2H), 6.80–6.99(m, 6H), 7.28–7.58(m, 7H)<br>IR(CHCl$_3$) 2938, 1731, 1609, 1527, 1485, 1442, 1394, 1365, 1174, 1141, 1082, 1037, 1013, 961, 936, 863cm$^{-1}$ |

TABLE 222

| | |
|---|---|
| I-1125 | mp 103–106° C.<br>$^1$H NMR(CDCl$_3$) δ 1.78(s, 3H), 1.82–1.83(d, J=0.9Hz, 3H), 4.65–4.67(d, J=6.9Hz, 2H), 5.55(m, 1H), 6.41–6.78(td, J F-H=54.9, 2.7Hz, 2H), 6.94–7.31(m, 7H), 7.73(m, 2H)<br>IR(CHCl$_3$) 3592, 1612, 1525, 1495, 1385, 1301, 1263, 1187, 1173, 1132, 1069, 1036, 917, 889, 838cm$^{-1}$ |
| I-1126 | mp 153–155° C.<br>$^1$H NMR(CDCl$_3$) δ 1.75(s, 3H), 1.78–1.79(d, J=0.9Hz, 3H), 2.58(s, 3H), 3.03(s, 6H), 3.55(s, 3H), 3.77(s, 3H), 3.88(s, 3H), 4.61–4.64(d, J=6.9Hz, 2H), 5.54(m, 1H), 6.80–6.97(m, 6H), 7.54–7.57(d, J=8.7Hz, 2H)<br>IR(CHCl$_3$) 2938, 1609, 1527, 1485, 1464, 1442, 1392, 1365, 1174, 1140, 1082, 1038, 1012, 961, 935cm$^{-1}$ |
| I-1127 | mp 160–161° C.<br>$^1$H NMR(CDCl$_3$) δ 2.12(s, 3H), 3.49(s, 3H), 3.89(s, 3H), 4.89(br, 1H), 5.21(s, 2H), 5.76(s, 1H), 6.79–6.92(m, 5H), 7.00 (d, J=8.4Hz, 1H), 7.31–7.53(m, 7H)<br>IR(CHCl$_3$) 3594, 3517, 2937, 1731, 1612, 1589, 1522, 1489, 1455, 1400, 1327, 1259, 1240, 1173, 1139, 1102, 1011, 930, 865, 835cm$^{-1}$ |
| I-1128 | mp 149–150° C.<br>$^1$H NMR(CDCl$_3$) δ 1.74–1.75(d, J=0.9Hz, 3H), 1.78–1.79(d, J=0.9Hz, 3H), 3.03(s, 1H), 3.49(s, 6H), 3.75(s, 3H), 3.88 s, 3H), 4.62–4.64(d, J=6.6Hz, 2H), 5.57(m, 1H), 5.95(s, 1H), 6.49(s, 1H), 6.81–6.84(m, 2H), 6.95–7.03(m, 3H), 7.55–7.58 (m, 2H)<br>IR(CHCl$_3$) 3509, 2937, 1675, 1610, 1584, 1528, 1492, 1464, 1397, 1362, 1323, 1197, 1175, 1140, 1117, 1078, 1038, 1011, 929, 835cm$^{-1}$ |
| I-1129 | mp 163–165° C.<br>$^1$H NMR(CDCl$_3$) δ 2.15(s, 3H), 2.47(s, 3H), 3.20(s, 3H), 3.55(s, 3H), 3.90(s, 3H), 5.22(s, 2H), 6.80(dd, J=8.4, 2.1Hz, 1H), 6.88(d, J=2.1Hz, 1H), 7.00(d, J=8.4Hz, 1H), 7.17(s, 1H), 7.35–7.47(m, 7H), 7.66–7.69(m, 2H)<br>IR(CHCl$_3$) 2938, 1604, 1584, 1518, 1478, 1370, 1331, 1241, 1176, 1150, 1010, 987, 937, 872, 846cm$^{-1}$ |

TABLE 223

| | |
|---|---|
| I-1130 | mp 142–144° C.<br>$^1$H NMR(CDCl$_3$) δ 1.76–1.77(d, J=0.9Hz, 3H), 1.79–1.80(d, J=0.9Hz, 3H), 2.16(s, 3H), 2.60(s, 3H), 3.20(s, 3H), 3.57 (s, 3H), 3.88(s, 3H), 4.62–4.65(d, J=6.6Hz, 2H), 5.55(m, 1H), 6.83–6.87(m, 2H), 7.00(d, J=8.4Hz, 1H), 7.18(s, 1H), 7.35–7.38(m, 2H), 7.67–7.70(m, 2H)<br>IR(CHCl$_3$) 1604, 1582, 1517, 1478, 1416, 1370, 1332, 1240, 1176, 1150, 1093, 1008, 987, 936, 872cm$^{-1}$ |
| I-1131 | mp 121–123° C.<br>$^1$H NMR(DMSO-d$_6$) δ 1.70(s, 3H), 1.71(s, 3H), 3.71–3.75(m, 4H), 3.75(s, 6H), 5.21–5.27(m, 2H), 5.54–5.59(m, 2H), 6.65–6.71(m, 2H), 6.95(s, 2H), 7.19–7.29(m, 4H)<br>IR(KBr) 3600–2800(br), 1627, 1536, 1497, 1470, 1454, 1375, 1341, 1257, 1208, 1125, 1053, 1035cm$^{-1}$ |
| I-1132 | mp 169–170° C.<br>$^1$H NMR(CDCl$_3$) δ 1.77(d, J=0.6Hz, 3H), 1.81(d, J=0.9Hz, 3H), 2.26(s, 6H), 4.63(d, J=6.6Hz, 2H), 5.31(s, 1H), 5.34 (s, 1H), 5.55(m, 1H), 6.80(dd, J=2.1, 8.1Hz, 1H), 6.89(d, J=2.1Hz, 1H), 6.92(d, J=8.1Hz, 1H), 6.98–7.13(m, 5H)<br>IR(KBr) 3338, 1619, 1595, 1523, 1492, 1475, 1451, 1427, 1385, 1357, 1309, 1298, 1270, 1223, 1193, 1172, 1122, 1113, 999, 983, 871, 819, 785cm$^{-1}$ |
| I-1133 | mp 135–136° C.<br>$^1$H NMR(CDCl$_3$) δ 1.14(t, J=6.9Hz, 3H), 2.42(s, 3H), 3.20(s, 3H), 3.73(q, J=6.9Hz, 2H), 3.77(s, 3H), 3.91(s, 3H), 5.22(s, 2H), 6.84(s, 1H), 6.91(dd, J=1.8, 8.4Hz, 1H), 6.98(d, J=8.4Hz, 1H), 6.98(d, J=1.8Hz, 1H), 7.28–7.47(m, 7H), 7.68–7.73(m, 2H)<br>IR(KBr) 1516, 1481, 1381, 1363, 1332, 1238, 1228, 1175, 1147, 1080, 1036, 865, 843, 800cm$^{-1}$ |

TABLE 224

| | |
|---|---|
| I-1134 | mp 154–155° C.<br>$^1$H NMR(CDCl$_3$) δ 1.15(t, J=7.2Hz, 3H), 1.75(d, J=0.9Hz, 3H), 1.79(d, J=0.9Hz, 3H), 2.54(s, 3H), 3.21(s, 3H), 3.72 (q, J=7.2Hz, 2H), 3.78(s, 3H), 3.88(s, 3H), 4.63(d, J=6.9Hz, 2H), 5.54(m, 1H), 6.85(s, 1H), 6.95–6.98(m, 3H), 7.34–7.40 (m, 2H), 7.68–7.74(m, 2H)<br>IR(KBr) 1519, 1481, 1467, 1365, 1335, 1245, 1231, 1184, 1157, 1081, 1038, 972, 889, 872, 840, 800cm$^{-1}$ |
| I-1135 | mp 136–137° C.<br>$^1$H NMR(CDCl$_3$) δ 1.16(t, J=6.9Hz, 3H), 1.74(s, 3H), 1.78(s, 3H), 3.61(q, J=6.9Hz, 2H), 3.75(s, 3H), 3.88(s, 3H), 4.63(d, J=6.9Hz, 2H), 5.03(s, 1H), 5.57(m, 1H), 5.99(s, 1H), 6.46(s, 1H), 6.89–6.94(m, 2H), 6.97(d, J=8.7Hz, 1H), 7.01 (d, J=1.8Hz, 1H), 7.02(dd, J=1.8, 8.7Hz, 1H), 7.51–7.57(m, 3H)<br>IR(KBr) 3433, 1613, 1522, 1489, 1464, 1443, 1402, 1383, 1364, 1270, 1235, 1214, 1174, 1140, 1113, 1072, 1036, 983, 825cm$^{-1}$ |
| I-1136 | mp 155–157° C.<br>$^1$H NMR(CDCl$_3$) δ 2.05(t, J=2.7Hz, 1H), 2.76(dt, J=6.3, 2.7Hz, 2H), 2.77(s, 3H), 3.21(s, 3H), 3.28(s, 3H), 3.56(s, 3H), 3.78(s, 3H), 4.23(t, J=6.3Hz, 2H), 6.84(s, 1H), 7.09(d, J=8.4Hz, 1H), 7.36(dd, J=8.4, 2.1Hz, 1H), 7.38(d, J=8.7Hz, 2H), 7.41(d, J=2.1Hz, 1H), 7.68(d, J=8.7Hz, 2H)<br>IR(Nujol) 3285, 1608, 1519, 1176, 1151, 1119, 1079, 970, 870, 815, 797cm$^{-1}$ |
| I-1137 | foam<br>$^1$H NMR(CDCl$_3$) δ 1.83(s, 3H), 2.58(t, J=6.6Hz, 2H), 2.74(s, 3H), 3.21(s, 3H), 3.22(s, 3H), 3.56(s, 3H), 3.78(s, 3H), 4.22(t, J=6.6Hz, 2H), 4.84(brs, 1H), 4.89(brs, 1H), 6.84(s, 1H), 7.10(d, J=8.4Hz, 1H), 7.32–7.43(m, 4H), 7.68(d, J=8.7Hz, 2H),<br>IR(Nujol) 1608, 1519, 1176, 1150, 1119, 1078, 968, 869, 816cm$^{-1}$ |

TABLE 225

| | |
|---|---|
| I-1138 | foam<br>$^1$H NMR(CDCl$_3$) δ 1.81(s, 3H), 2.55(t, J=6.6Hz, 2H), 3.45(s, 3H), 3.74(s, 3H), 4.20(t, J=6.6Hz, 2H), 4.85(brs, 1H), 4.89(brs, 1H), 6.45(s, 1H), 6.86–7.07(m, 5H), 7.53(d, J=8.7Hz, 2H),<br>IR(Nujol) 3531, 3328, 1612, 1587, 1523, 1489, 1287, 1226, 1115, 1072, 1011cm$^{-1}$ |
| I-1139 | foam<br>$^1$H NMR(CDCl$_3$) δ 2.07(t, J=2.7Hz, 1H), 2.72(dt, J=6.6, 2.7Hz, 2H), 3.45(s, 3H), 3.75(s, 3H), 4.21(t, J=6.6Hz, 2H), 6.45(s, 1H), 6.87–7.10(m, 5H), 7.53(d, J=8.7Hz, 2H)<br>IR(Nujol) 3482, 3305, 1609, 1597, 1527, 1494, 1253, 1240, 1227, 1127, 1118, 1079, 1010cm$^{-1}$ |
| I-1140 | m.p 194–197° C.<br>$^1$H NMR(DMSO) δ 3.29(s, 3H), 3.64(s, 3H), 5.42(s, 2H), 6.38(s, 1H), 6.61(dd, J=2.0, 8.2Hz, 1H), 6.74(d, J=2.0Hz, 1H), 6.84(d, J=8.6Hz, 2H), 6.96(d, J=8.2Hz, 1H), 7.19(d, J=7.8Hz, 1H), 7.41(d, J=7.8Hz, 1H), 7.43(d, J=8.4Hz, 2H)<br>IR(KBr) 3432, 1611, 1566, 1523, 1488, 1430, 1400, 1380, 1241, 1113, 1071, 814cm$^{-1}$ |
| I-1141 | foam<br>$^1$H NMR(CDCl$_3$) δ 3.45(s, 3H), d 3.75(s, 3H), 3.92(s, 3H), 5.53(s, 2H), 6.45(s, 1H), 6.92(d, J=8.7Hz, 2H), 6.94(dd, J=2.1, 8.7Hz, 1H), 7.01(d, J=8.7Hz, 1H), 7.10(d, J=2.1Hz, 1H), 7.28(d, J=4.8Hz, 1H), 7.52(d, J=4.8Hz, 1H), 7.53(d, J=8.4Hz, 2H)<br>IR(KBr) 3423, 1702, 1684, 1611, 1523, 1489, 1439, 1402, 1282, 1112, 1073, 1010, 814cm$^{-1}$ |
| I-1142 | foam<br>$^1$H NMR(CDCl$_3$) δ 2.74(s, 3H), 3.21(s, 3H), 3.22(s, 3H), 3.55(s, 3H), d 3.78(s, 3H), 3.91(s, 3H), 5.19(s, 2H), 6.60(d, J=3.6Hz, 1H), 6.84(s, 1H), 7.15(d, J=8.4Hz, 1H), 7.17(d, J=3.6Hz, 1H), 7.36(dd, J=2.1, 8.4Hz, 1H), 7.38(d, J=8.7Hz, 2H), 7.41(d, J=2.1Hz, 1H), 7.67(d, J=8.7Hz, 2H)<br>IR(KBr) 1728, 1519, 1481, 1365, 1177, 1150, 1079, 969, 876, 797cm$^{-1}$ |

TABLE 226

| | |
|---|---|
| I-1143 | foam |
| | ¹H NMR(CDCl₃) δ 2.77(s, 3H), 3.21(s, 3H), 3.23(s, 3H), 3.56(s, 3H), d 3.78(s, 3H), 4.18(m, 2H), 4.78(m, 2H), 5.94(m, 2H), 6.84(s, 1H), 7.11(d, J=8.4Hz, 1H), 7.36(dd, J=2.1, 8.4Hz, 1H), 7.38(d, J=8.7Hz, 2H), 7.40(d, J=2.1Hz, 1H), 7.67(d, J=8.7Hz, 2H) |
| | IR(KBr) 1609, 1519, 1481, 1367, 1177, 1150, 1079, 970, 876, 797cm⁻¹ |
| I-1144 | foam |
| | ¹H NMR(CDCl₃) δ 2.75(s, 3H), 3.21(s, 3H), 3.24(s, 3H), 3.55(s, 3H), d 3.78(s, 3H), 4.11(m, 2H), 4.64(m, 2H), 6.05(t, J=4.5Hz, 1H), 6.06(t, J=5.1Hz, 1H), 6.84(s, 1H), 7.07(d, J=8.7Hz, 1H), 7.35(dd, J=2.1, 8.7Hz, 1H), 7.38(d, J=8.7Hz, 2H), 7.40(d, J=2.1Hz, 1H), 7.67(d, J=8.7Hz, 2H) |
| | IR(KBr) 1609, 1519, 1481, 1364, 1177, 1151, 1079, 969, 874, 797cm⁻¹ |
| I-1145 | m.p 203–205° C. |
| | ¹H NMR(CDCl₃) δ 2.83(s, 3H), 3.22(s, 3H), 3.25(s, 3H), 3.55(s, 3H), d 3.79(s, 3H), 4.30(t, J=1.8Hz, 2H), 4.88(t, J=1.8Hz, 2H), 6.84(s, 1H), 7.20(d, J=8.7Hz, 1H), 7.37(dd, J=2.1, 8.7Hz, 1H), 7.39(d, J=8.7Hz, 2H), 7.42(d, J=2.1Hz, 1H), 7.67(d, J=8.7Hz, 2H) |
| | IR(KBr) 3443, 1606, 1519, 1481, 1360, 1179, 1150, 1079, 877, 798cm⁻¹ |
| I-1146 | m.p 173–174° C. |
| | ¹H NMR(CD3OD) δ 3.38(s, 3H), 3.68(s, 3H), 4.23(t, J=1.8Hz, 2H), 4.83(t, J=1.8Hz, 2H), 6.43(s, 1H), 6.79(dd, J=2.1, 8.1Hz, 1H), 6.85(d, J=8.7Hz, 2H), 6.86(d, J=2.1Hz, 1H), 7.04(d, J=8.1Hz, 1H), 7.45(d, J=8.7Hz, 2H) |
| | IR(KBr) 3399, 1612, 1586, 1523, 1487, 1401, 1217, 1114, 1067, 1013, 996, 828cm⁻¹ |

TABLE 227

| | |
|---|---|
| I-1147 | foam |
| | ¹H NMR(CDCl₃) δ 3.39(s, 3H), 3.45(s, 3H), 3.74(s, 3H), 4.17(t, J=1.8Hz, 2H), 4.83(t, J=1.8Hz, 2H), 6.45(s, 1H), 6.91(d, J=8.7Hz, 2H), 6.97(dd, J=2.1, 8.1Hz, 1H), 7.05(d, J=8.1Hz, 1H), 7.08(d, J=2.1Hz, 1H), 7.52(d, J=8.7Hz, 2H) |
| | IR(KBr) 3411, 1612, 1589, 1523, 1489, 1404, 1224, 1114, 1071, 1010, 939, 816cm⁻¹ |
| I-1148 | foam |
| | ¹H NMR(CDCl₃) δ 1.14(t, J=7.5Hz, 3H), 2.23(q, J=7.5Hz, 2H), 2.71(s, 3H), 3.21(s, 3H), 3.27(s, 3H), 3.60(s, 3H), 3.78(s, 3H), 4.80(s, 2H), 6.84(s, 1H), 7.20(d, J=9.0Hz, 1H), 7.37(dd, J=2.1, 9.0Hz, 1H), 7.38(d, J=8.7Hz, 2H), 7.42(d, J=2.1Hz, 1H), 7.68(d, J=8.7Hz, 2H) |
| | IR(KBr) 2232, 1609, 1519, 1481, 1365, 1177, 1151, 1079, 970, 876, 797cm⁻¹ |
| I-1149 | mp > 280° C.(decomp.) |
| | ¹H NMR(DMSO-d₆) δ 3.30(s, 3H), 3.64(s, 3H), 4.85(s, 2H), 6.39(s, 1H), 6.69(dd, J=8.4, 2.1Hz, 1H), 6.79(d, J=2.1Hz, 1H), 6.84(d, J=8.7Hz, 2H), 6.94(d, J=8.4Hz, 1H), 7.44(d, J=8.7Hz, 2H), 8.54(s, 1H) |
| | IR(Nujol) 3166, 1707, 1671, 1611, 1586, 1523, 1489, 1288, 1259, 1211, 1115, 1075, 1012, 814cm⁻¹ |
| I-1150 | foam |
| | ¹H NMR(CDCl₃) δ 1.91(s, 3H), 3.45(s, 3H), 3.75(s, 3H), 4.89(s, 2H), 5.29(brs, 1H), 5.36(brs, 1H), 6.45(s, 1H), 6.92(d, J=8.7Hz, 2H), 6.97(dd, J=8.4, 2.1Hz, 1H), 7.07(d, J=8.4Hz, 1H), 7.08(d, J=2.1Hz, 1H), 7.54(d, J=8.7Hz, 2H) |
| | IR(KBr) 3432, 1612, 1588, 1523, 1489, 1288, 1224, 1192, 1113, 1070, 1010, 938, 825, 813cm⁻¹ |
| I-1151 | foam |
| | ¹H NMR(CDCl₃) δ 3.45(s, 3H), 3.75(s, 3H), 4.98(d, J=1.8Hz, 2H), 5.92(dt, J=7.5, 1.8Hz, 1H), 6.45(s, 1H), 6.46(d, J=7.5Hz, 1H), 6.92(d, J=8.7Hz, 2H), 6.98(dd, J=8.4, 2.1Hz, 1H), 7.09(d, J=2.1Hz, 1H), 7.11(d, J=8.4Hz, 1H), 7.53 (d, J=8.7Hz, 2H) |
| | IR(KBr) 3410, 1612, 1589, 1523, 1489, 1403, 1224, 1112, 1070, 1011, 938, 826cm⁻¹ |

TABLE 228

| | |
|---|---|
| I-1152 | foam |
| | ¹H NMR(CDCl₃) δ 3.45(s, 3H), 3.75(s, 3H), 4.89(d, J=2.1Hz, 2H), 5.97(dt, J=13.8, 2.1Hz, 1H), 6.45(s, 1H), 6.61(d, J=13.8Hz, 1H), 6.92(d, J=8.7Hz, 2H), 6.97(dd, J=8.4, 2.1Hz, 1H), 7.04(d, J=8.4Hz, 1H), 7.09(d, J=2.1Hz, 1H), 7.54 (d, J=8.7Hz, 2H) |
| | IR(KBr) 3427, 1612, 1588, 1523, 1489, 1403, 1226, 1192, 1175, 1113, 1070, 1011, 938, 918, 826cm⁻¹ |
| I-1153 | mp 188–189° C. |
| | ¹H NMR(CDCl₃) δ 2.84(s, 3H), 3.33(s, 3H), 3.74(s, 3H), 3.98(s, 3H), 4.18(s, 3H), 5.38(s, 2H), 7.05(s, 1H), 7.36–7.64(m, 10H), 8.61(d, J=8.7Hz, 1H), 8.82(brs, 1H) |
| | IR(KBr) 3381, 2942, 1724, 1538, 1481, 1369, 1296, 1177, 1163, 1082, 963, 821cm⁻¹ |
| I-1154 | mp 78–80° C. |
| | ¹H NMR(CDCl₃) δ 2.17(s, 3H), 2.67(s, 3H), 3.13(s, 3H), 3.57(s, 3H), 3.79(s, 3H), 5.19(s, 2H), 6.83(s, 1H), 7.15(d, J=8.6Hz, 1H), 7.31–7.45(m, 7H), 7.62(d, J=8.2Hz, 1H), 7.79(s, 1H), 8.44(d, J=8.6Hz, 1H), 8.51(brs, 1H) |
| | IR(KBr) 3398, 2939, 1739, 1529, 1477, 1368, 1287, 1240, 1177, 1119, 1078, 957, 815, 796, 522cm⁻¹ |
| I-1155 | mp 74–75° C. |
| | ¹H NMR(CDCl₃) δ 1.68(s, 3H), 1.76(s, 6H), 1.81(s, 3H), 2.69(s, 3H), 3.24(s, 3H), 3.52(s, 3H), 3.80(s, 3H), 3.88(s, 3H), 3.88–4.02(m, 2H), 4.64(d, J=7.2Hz, 2H), 5.25(t, J=7.8Hz, 1H), 5.50(t, J=5.7Hz, 1H), 6.88(s, 1H), 7.08–7.38(m, 6H) |
| | IR(KBr) 3412, 2939, 1697, 1519, 1483, 1366, 1268, 1207, 1178, 1080, 964, 808, 523cm⁻¹ |
| I-1156 | mp 72–74° C. |
| | ¹H NMR(CDCl₃) δ 1.95(s, 3H), 1.99(s, 3H), 2.87(s, 3H), 3.42(s, 3H), 3.74(s, 3H), 3.97(s, 3H), 4.16(s, 3H), 4.82(d, J=6.6Hz, 2H), 5.68(t, J=5.7Hz, 1H), 7.04(s, 1H), 7.27(d, J=8.1Hz, 1H), 7.39–7.56(m, 4H), 8.60(d, J=8.4Hz, 1H), 8.81 (brs, 1H) |
| | IR(KBr) 3407, 2940, 1731, 1601, 1538, 1481, 1366, 1294, 1178, 1165, 1079, 805, 562cm⁻¹ |

TABLE 229

| | |
|---|---|
| I-1157 | mp 68–69° C.<br>$^1$H NMR(CDCl$_3$) δ 1.70(s, 3H), 1.77(s, 3H), 1.81(s, 3H), 2.70(s, 3H), 3.25(s, 3H), 3.55(s, 3H), 3.81(s, 3H), 4.64(d, J=6.6Hz, 2H), 5.27(t, J=7.5Hz, 1H), 5.50(t, J=6.9Hz, 1H), 6.86(s, 1H), 7.10(d, J=8.4Hz, 1H), 7.25–7.40(m, 3H), 7.57(d, J=8.1Hz, 1H), 7.76(s, 1H)<br>IR(KBr) 3422, 2939, 1701, 1519, 1480, 1368, 1203, 1177, 1078, 957, 801, 522cm$^{-1}$ |
| I-1158 | mp 64–66° C.<br>$^1$H NMR(CDCl$_3$) δ 3.47(s, 3H), 3.74(s, 3H), 5.19(s, 2H), 5.86(brs, 1H), 6.44(s, 1H), 7.08–7.69(m, 11H), 8.06(brs, 1H)<br>IR(KBr) 3399, 2938, 1726, 1624, 1604, 15263, 1487, 1403, 1302, 1208, 1178, 1068, 695, 520cm$^{-1}$ |
| I-119 | mp 68–70° C.<br>$^1$H NMR(CDCl$_3$) δ 2.57(s, 3H), 3.57(s, 3H), 3.76(s, 3H), 5.21(s, 2H), 6.84(s, 1H), 7.11–7.73(m, 11H), 8.29(brs, 1H)<br>IR(KBr) 3422, 2939, 1728, 1605, 1523, 1482, 1397, 1367, 1233, 1209, 1178, 1078, 795, 725, 542cm$^{-1}$ |
| I-1160 | mp 72–73° C.<br>$^1$H NMR(CDCl$_3$) δ 1.75(s, 6H), 1.78(s, 3H), 1.82(s, 3H), 3.48(s, 3H), 3.75(s, 3H), 3.76(d, J=7.2Hz, 2H), 3.89(s, 3H), 4.38(brs, 1H), 4.61(d, J=6.9Hz, 2H), 5.41(t, J=6.3Hz, 1H), 5.53(t, J=6.9Hz, 1H), 5.68(brs, 1H), 5.94(brs, 1H), 6.49(s, 3H), 6.69(d, J=8.4Hz, 1H), 6.95(s, 1H), 7.06(s, 1H), 7.13–7.15(m, 2H), 7.26(s, 1H)<br>IR(KBr) 3423, 2932, 1608, 1528, 1490, 1459, 1250, 1113, 1071, 805, 757cm$^{-1}$ |
| I-1161 | mp 68–69° C.<br>$^1$H NMR(CDCl$_3$) δ 1.76(s, 3H), 1.81(s, 3H), 3.48(s, 3H), 3.75(s, 3H), 3.91(s, 3H), 4.61(d, J=7.2Hz, 2H), 5.53(t, J=6.0Hz, 1H), 5.91(brs, 2H), 6.47(s, 1H), 6.83(d, J=8.1Hz, 2H), 6.95(s, 1H), 7.06–7.09(m, 2H), 7.16(s, 1H), 7.26(s, 1H)<br>IR(KBr) 3406, 2933, 1524, 1490, 1397, 1270, 1241, 1116, 1075, 1069, 811, 773cm$^{-1}$ |

TABLE 230

| | |
|---|---|
| I-1162 | mp 81–83° C.<br>$^1$H NMR(CDCl$_3$) δ 1.76(s, 6H), 1.79(s, 3H), 1.81(s, 3H), 3.50(s, 3H), 3.75(s, 3H), 3.80(d, J=6.6Hz, 2H), 4.36(brs, 1H), 4.61(d, J=6.9Hz, 2H), 5.39(t, J=6.3Hz, 1H), 5.53(t, J=6.6Hz, 1H), 5.68(brs, 1H), 5.90(brs, 1H), 6.43(s, 1H), 6.73(d, J=8.4Hz, 1H), 6.95(s, 1H), 7.05(s, 1H), 7.26(d, J=0.9Hz, 1H), 7.47(dd, J=2.1, 8.4Hz, 1H), 7.59(d, J=2.1Hz, 1H)<br>IR(KBr) 3484, 2931, 1607, 1525, 1488, 1310, 1243, 1114, 1070, 1009, 808cm$^{-1}$ |
| I-1163 | mp 87–89° C.<br>$^1$H NMR(CDCl$_3$) δ 2.81(s, 3H), 3.60(s, 3H), 3.77(s, 3H), 3.98(d, J=6.3Hz, 2H), 4.80(d, J=6.3Hz, 2H), 6.07(t, J=6.0Hz, 1H), 6.25(t, J=6.3Hz, 1H), 6.46–6.53(m, 2H), 6.86(s, 1H), 7.05–7.38(m, 4H)<br>IR(KBr) 3411, 2937, 1628, 1527, 1482, 1364, 1233, 1176, 1077, 960, 879, 792, 524cm$^{-1}$ |
| I-1164 | amorphous<br>$^1$H NMR(CDCl$_3$) δ 2.68(s, 3H), 3.13(s, 3H), 3.43(s, 3H), 3.54(s, 3H), 3.80(s, 3H), 5.19(s, 2H), 6.87(s, 1H), 7.16(d, J=8.7Hz, 1H), 7.32–7.49(m, 9H), 7.69(d, J=8.4Hz, 2H)<br>IR(KBr) 1698, 1522, 1482, 1367, 1080, 1014, 947, 815, 795cm$^{-1}$ |
| I-1165 | foam<br>$^1$H NMR(CDCl$_3$) δ 1.47(s, 3H), 1.72(s, 3H), 1.77(s, 3H), 1.81(s, 3H), 2.71(s, 3H), 3.24(s, 3H), 3.51(s, 3H), 3.80(s, 3H), 4.37(d, J=7.8Hz, 2H), 4.64(d, J=6.6Hz, 2H), 5.29(t, J=7.8Hz, 1H), 5.50(t, J=6.6Hz, 1H), 6.88(s, 1H), 7.09(d, J=8.4Hz, 1H), 7.27(d, J=8.7Hz, 2H), 7.35(dd, J=8.4, 2.3Hz, 1H), 7.39(d, J=2.3Hz, 1H), 7.66(d, J=8.7Hz, 2H)<br>IR(KBr) 1696, 1521, 1482, 1366, 1177, 1080, 972, 946, 814, 795cm$^{-1}$ |
| I-1166 | mp 135–136° C.<br>$^1$H NMR(CDCl$_3$) δ 1.77(s, 3H), 1.81(s, 3H), 2.71(s, 3H), 3.24(s, 3H), 3.54(s, 3H), 3.80(s, 3H), 4.64(d, J=6.7Hz, 2H), 5.50(t, J=6.7Hz, 1H), 6.87(s, 1H), 7.10(d, J=8.4Hz, 1H), 7.34(d, J=8.1Hz, 2H), 7.35(dd, J=8.4, 2.2Hz, 1H), 7.39(d, J=2.2Hz, 1H), 7.69(d, J=8.1Hz, 2H)<br>IR(KBr) 1702, 1522, 1481, 1362, 1275, 1150, 1081, 1014, 978, 817, 793cm$^{-1}$ |

TABLE 231

| | |
|---|---|
| I-1167 | mp 169–171° C.<br>$^1$H NMR(DMSO-d$_6$) δ 1.71(s, 3H), 1.72(s, 6H), 1.76(s, 3H), 3.31(s, 3H), 3.63(s, 3H), 3.64(m, 2H), 4.54(d, J=6.8Hz, 2H), 5.29(t, J=7.5Hz, 1H), 5.49(t, J=6.8Hz, 1H), 5.75(t, J=8.1Hz, 1H), 6.37(s, 1H), 6.63(d, J=8.4Hz, 2H), 6.64(dd, J=8.1, 2.0Hz, 1H), 6.73(d, J=2.0Hz, 1H), 6.88(d, J=8.4Hz, 2H), 7.37(d, J=8.4Hz, 2H), 8.41(s, 1H), 8.70(s, 1H)<br>IR(KBr) 3473, 3276, 1608, 1523, 1491, 1310, 1252, 1190, 1112, 1072, 934, 824, 776cm$^{-1}$ |
| I-1168 | mp 159–160° C.<br>$^1$H NMR(DMSO-d$_6$) δ 1.72(s, 3H), 1.76(s, 3H), 3.31(s, 3H), 3.64(s, 3H), 4.54(d, J=6.8Hz, 2H), 5.49(t, J=6.8Hz, 1H), 5.76(br s, 1H), 6.37(s, 1H), 6.61(d, J=8.4Hz, 2H), 6.64(dd, J=8.1, 2.0Hz, 1H), 6.73(d, J=2.0Hz, 1H), 6.88(d, J=8.1Hz, 1H), 7.39(d, J=8.4Hz, 2H), 7.37(d, J=8.4Hz, 2H), 8.42(br s, 1H), 8.70(br s, 1H)<br>IR(KBr) 3458, 3332, 1609, 1524, 1492, 1411, 1393, 1295, 1234, 1107, 1071, 1012, 994, 781cm$^{-1}$ |
| I-1169 | mp 183–184° C.<br>$^1$H NMR(CDCl$_3$) δ 1.76(d, J=0.6Hz, 3H), 1.82(s, 3H), 3.13(s, 3H), 3.48(s, 3H), 3.76(s, 3H), 4.63(d, J=6.9Hz, 2H), 5.53(m, 1H), 5.72(s, 1H), 5.83(s, 1H), 6.46(s, 1H), 6.93(dd, J=1.8, 8.4Hz, 1H), 6.98(d, J=8.4Hz, 1H), 7.04(d, J=1.8Hz, 1H), 7.82–7.89(m, 2H), 8.00–8.06(m, 2H)<br>IR(KBr) 3445, 1593, 1499, 1482, 1461, 1387, 1311, 1278, 1245, 1189, 1146, 1111, 1086, 1068, 1010, 997, 942, 766cm$^{-1}$ |
| I-1170 | mp 178–179° C.<br>$^1$H NMR(CDCl$_3$) δ 1.76(s, 3H), 1.82(s, 3H), 2.80(s, 3H), 3.47(s, 3H), 3.76(s, 3H), 4.62(d, J=7.2Hz, 2H), 5.53(m, 1H), 5.72(s, 1H), 5.86(s, 1H), 6.47(s, 1H), 6.94(dd, J=1.8, 8.1Hz, 1H), 6.98(d, J=8.1Hz, 1H), 7.05(d, J=1.8Hz, 1H), 7.72–7.77(m, 2H), 7.79–7.85(m, 2H)<br>IR(KBr) 3420, 1587, 1527, 1482, 1449, 1430, 1416, 1390, 1357, 1290, 1240, 1214, 1198, 1135, 1115, 1073, 1019, 998, 975, 962, 937, 831cm$^{-1}$ |

TABLE 232

| | |
|---|---|
| I-1171 | mp 136–139° C.<br>$^1$H NMR(CDCl$_3$) δ 1.73(s, 3H), 1.77(s, 3H), 2.99(s, 6H), 3.71(d, J=6.6Hz, 2H), 3.76(s, 3H), 3.78(s, 3H), 5.32–5.37(m, 1H), 6.36–6.46(m, 2H), 6.79–6.84(m, 2H), 6.89(s, 1H), 6.95(s, 1H), 7.18–7.24(m, 1H), 7.47–7.52(m, 2H)<br>IR(KBr) 3600–2800(br), 1626, 1609, 1531, 1493, 1460, 1444, 1388, 1345, 1232, 1207, 1173, 1124, 1050, 1028cm$^{-1}$ |
| I-1172 | mp 113–114° C.<br>$^1$H NMR(CDCl$_3$) δ 3.00(s, 6H), 3.77(s, 3H), 3.78(s, 3H), 6.78–6.84(m, 2H), 6.88(s, 1H), 6.98(s, 1H), 7.31(dd, J=2.1, 8.4Hz, 1H), 7.43–7.53(m, 3H), 7.58(dd, J=1.8, 11.1Hz, 1H)<br>IR(KBr) 3600–2800(br), 1711, 1609, 1533, 1493, 1464, 1390, 1212, 1181, 1162, 1052, 1027cm$^{-1}$ |
| I-1173 | mp 141–143° C.<br>$^1$H NMR(CDCl$_3$) δ 1.75(d, J=0.9Hz, 3H), 1.78(d, J=0.9Hz, 3H), 2.99(s, 6H), 3.50(s, 3H), 3.74(s, 3H), 3.78(d, J=6.6Hz, 2H), 3.93(br, 1H), 5.35–5.40(m, 1H), 5.86(s, 1H), 6.44(s, 1H), 6.74–6.86(m, 3H), 7.30–7.38(m, 4H)<br>IR(KBr) 3600–2800(br), 1625, 1611, 1530, 1491, 1458, 1444, 1400, 1348, 1333, 1250, 1217, 1103, 1075cm$^{-1}$ |
| I-1174 | mp 226–228° C.<br>$^1$H NMR(CDCl$_3$) δ 3.93(s, 3H), 4.95(s, 1H), 5.21(s, 2H), 6.90–6.94(m, 2H), 6.96(s, 1H), 6.97(s, 1H), 7.03(d, J=0.9Hz, 1H), 7.30–7.49(m, 1H)<br>IR(KBr) 3600–2800(br), 1608, 1589, 1520, 1471, 1446, 1384, 1358, 1270, 1250, 1238, 1210, 1172, 1141, 1093, 1031, 997cm$^{-1}$ |
| I-1175 | mp 143–145° C.<br>$^1$H NMR(CDCl$_3$) δ 3.21(s, 3H), 3.93(s, 3H), 5.22(s, 2H), 6.97(s, 2H), 7.03(s, 1H), 7.30–7.55(m, 11H)<br>IR(KBr) 3600–2800(br), 1602, 1517, 1468, 1368, 1348, 1248, 1210, 1176, 1151, 1095, 1038, 989cm$^{-1}$ |

TABLE 233

| | |
|---|---|
| I-1176 | mp 98–100° C.<br>$^1$H NMR(CDCl$_3$) δ 1.76(s, 3H), 1.79(s, 3H), 3.21(s, 3H), 3.91(s, 3H), 4.65(d, J=6.9Hz, 2H), 5.53–5.58(m, 1H), 6.94–7.03 (m, 3H), 7.23–7.41(m, 2H), 7.45(s, 1H), 7.49(s, 1H), 7.51–7.56(m, 1H)<br>IR(KBr) 3600–2800(br), 1604, 1583, 1519, 1470, 1449, 1365, 1250, 1202, 1177, 1151, 1095, 1041, 972cm$^{-1}$ |
| I-1177 | mp 118–120° C.<br>$^1$H NMR(CDCl$_3$) δ 1.76(s, 3H), 1.79(s, 3H), 3.91(s, 3H), 4.64(d, J=6.9Hz, 2H), 5.53–5.58(m, 1H), 6.88–7.02(m, 5H), 7.23–7.37(m, 2H), 7.44(s, 1H), 7.46(s, 1H)<br>IR(KBr) 3600–2800(br), 1626, 1609, 1526, 1490, 1429, 1253, 1187cm$^{-1}$ |
| I-1178 | mp 161–164° C.<br>$^1$H NMR(CDCl$_3$) δ 3.00(s, 3H), 3.79(s, 3H), 3.80(s, 3H), 6.78–6.83(m, 2H), 6.90(s, 1H), 6.97(s, 1H), 7.47–7.52(m, 2H), 7.71(d, J=1.8Hz, 1H), 8.37(d, J=8.7Hz, 1H), 8.46(br s, 1H)<br>IR(KBr) 3600–2800(br), 1716, 1613, 1532, 1505, 1487, 1463, 1384, 1357, 1280, 1195, 1172, 1059, 1033cm$^{-1}$ |
| I-1179 | mp 135–137° C.<br>$^1$H NMR(CDCl$_3$) δ 1.74(s, 3H), 1.78(s, 3H), 3.00(s, 6H), 3.78(s, 3H), 3.79(s, 3H), 4.29(d, J=6.6Hz, 1H), 5.35–5.40(m, 1H), 6.71(d, J=8.4Hz, 1H), 6.80–6.83(m, 2H), 6.90(s, 1H), 6.94(s, 1H), 7.38–7.42(m, 1H), 7.48–7.56(m, 3H)<br>IR(KBr) 3600–2800(br), 1612, 1532, 1495, 1460, 1444, 1385, 1365, 1273, 1257, 1203, 1059, 1039, 1029cm$^{-1}$ |
| I-1180 | $^1$H NMR(CDCl$_3$) δ 1.57(d, J=6.3Hz, 3H), 2.26(s, 3H), 2.28(s, 3H), 5.18(s, 2H), 5.22(q, J=6.3Hz, 1H), 7.02(d, J=8.4Hz, 1H), 7.12(s, 1H), 7.15(s, 1H), 7.23(d.d, J=8.4 & 2.1Hz, 1H), 7.30–7.51(m, 10H)<br>IR(KBr) 3557, 1605, 1486, 1370, 1235, 1177, 1149, 1078, 1017cm$^{-1}$ |
| I-1181 | $^1$H NMR(CDCl$_3$) δ 1.66(s, 6H), 2.27(s, 3H), 2.28(s, 3H), 3.20(s, 3H), 4.22(s, 1H), 5.22(s, 2H), 7.06(d, J=8.4Hz, 1H), 7.12(s, 1H), 7.14(s, 1H), 7.23(d.d, J=8.4 & 2.1Hz, 1H), 7.30–7.51(m, 10H)<br>IR(KBr) 3544, 3441, 1604, 1512, 1485, 1367, 1222, 1173, 1149cm$^{-1}$ |

TABLE 234

| | |
|---|---|
| I-1182 | $^1$H NMR(CDCl$_3$) δ 1.28(t, J=7.2Hz, 3H), 2.26(s, 3H), 2.28(s, 3H), 2.70(q, J=7.2Hz, 2H), 3.20(s, 3H), 4.73(s, 1H), 6.82 (d, J=8.4Hz, 1H), 7.03–7.11(m, 2H), 7.14(s, 1H), 7.15(s, 1H), 7.29–7.46(m, 4H)<br>IR(KBr) 3510, 1605, 1515, 1488, 1369, 1263, 1177, 1147, 1117cm$^{-1}$ |
| I-1183 | $^1$H NMR(CDCl$_3$) δ 1.29(d, J=6.9Hz, 6H), 2.27(s, 3H), 2.28(s, 3H), 3.20(s, 3H), 3.27(quintet, J=6.9Hz, 1H), 4.76(s, 1H), 6.81(d, J=7.8Hz, 1H), 7.07(d.d, J=7.8 & 2.1Hz, 1H), 7.11(s, 1H), 7.15(s, 1H), 7.20(d, J=2.1Hz, 1H), 7.34(d, J=8.7Hz, 2H), 7.42(d, J=8.7Hz, 2H),<br>IR(KBr) 3511, 1606, 1484, 1356, 1174, 1151cm$^{-1}$ |
| I-1184 | $^1$H NMR(CDCl$_3$) δ 1.23(t, J=8.1Hz, 3H), 1.77(s, 3H), 1.82(s, 3H), 2.26(s, 3H), 2.29(s, 3H), 2.70(q, J=8.1Hz, 2H), 3.20 (s, 3H), 4.58(d, J=6.6Hz, 2H), 5.48–5.57(m, 1H), 6.90(d, J=7.8Hz, 1H), 7.08–7.13(m, 2H), 7.16(s, 2H), 7.23–7.47(m, 4H)<br>IR(KBr) 1605, 1485, 1369, 1352, 1236, 1201, 1174, 1150, 1133, 1008cm$^{-1}$ |
| I-1185 | $^1$H NMR(CDCl$_3$) δ 1.23(t, J=7.5Hz, 3H), 1.76(s, 3H), 1.81(s, 3H), 2.27(s, 3H), 2.29(s, 3H), 2.70(q, J=7.5Hz, 2H), 4.57(d, J=6.6Hz, 2H), 4.79(brs, 1H), 5.49–5.58(m, 1H), 6.83–6.92(m, 3H), 7.08–7.19(m, 4H), 7.27(.d, J=8.4Hz, 2H)<br>IR(KBr) 3529, 1608, 1519, 1487, 1241, 1136, 1024cm$^{-1}$ |
| I-1186 | $^1$H NMR(CDCl$_3$) δ 1.23(d, J=1.8Hz, 6H), 1.76(s, 3H), 1.82(s, 3H), 2.27(s, 3H), 2.29(s, 3H), 3.20(s, 3H), 3.40(quintet, J=1.8Hz, 1H), 4.58(d, J=6.6Hz, 2H), 5.48–5.59(m, 1H), 6.90(d, J=7.8Hz, 1H), 7.10–7.44(m, 8H)<br>IR(KBr) 1602, 1468, 1369, 1232, 1174, 1151cm$^{-1}$ |
| I-1187 | $^1$H NMR(CDCl$_3$) δ 1.24(d, J=6.9Hz, 6H), 1.76(s, 3H), 1.81(s, 3H), 2.27(s, 3H), 2.29(s, 3H), 3.40(quintet, J=6.9Hz, 1H), 4.58(d, J=6.6Hz, 2H), 4.79(broad, s., 1H), 5.50–5.57(m, 1H), 6.84–6.93(m, 3H), 7.09–7.16(m, 3H), 7.00–7.28 (m, 3H)<br>IR(KBr) 3265, 1607, 1519, 1486, 1448, 1383, 1232, 1170cm$^{-1}$ |

TABLE 235

| | |
|---|---|
| I-1188 | ¹H NMR(CDCl₃) δ 1.31(d, J=6.9Hz, 6H), 1.44(s, 3H), 1.67(s, 3H), 2.97(quintet, J=6.9Hz, 1H), 3.78(s, 3H), 3.80(s, 3H), 3.92(s, 3H), 4.20–4.30(broad, 1H), 5.17–5.30(m, 1H), 6.96(s, 1H), 6.99(s, 1H), 7.07–7.35(m, 5H), 7.52(d, J=8.1Hz, 2H)<br>IR(KBr) 3422, 1601, 1529, 1492, 1462, 1378, 1341, 1257, 1203, 1138, 1028cm⁻¹ |
| I-1189 | ¹H NMR(CDCl₃) δ 2.67(s, 3H), 3.13(s, 3H), 3.57(s, 3H), 3.79(s, 3H), 5.19(s, 2H), 6.84(s, 1H), 7.15(d, J=9.0Hz, 1H), 7.31–7.50(m, 8H), 7.55(d.d, J=12.0 & 1.8Hz, 1H), 8.34–8.41(m, 1H)<br>IR(KBr) 3428, 1740, 1601, 1535, 1482, 1366, 1292, 1238, 1177, 1164, 1112, 1079, 1013cm⁻¹ |
| I-1190 | ¹H NMR(CDCl₃) δ 1.48(s, 3H), 1.70(s, 3H), 1.77(s, 3H), 1.81(s, 3H), 2.70(s, 3H), 3.24(s, 3H), 3.55(s, 3H), 3.81(s, 3H), 4.09–4.20(m, 1H), 4.53–4.68(m, 3H), 5.18–5.30(m, 1H), 5.43–5.54(m, 1H), 6.86(s, 1H), 7.06–7.51(m, 6H)<br>IR(KBr) 1702, 1521, 1482, 1367, 1204, 1177, 1115, 1080cm⁻¹ |
| I-1191 | ¹H NMR(CDCl₃) δ 1.75(s, 6H), 1.78(s, 3H), 1.82(s, 3H), 3.49(s, 3H), 3.74(s, 3H), 3.79(d, J=6.3Hz, 2H), 4.61(d, J=6.6Hz, 2H), 5.32–5.43(m, 1H), 5.49–5.57(m, 1H), 5.68(s, 1H), 5.90(s, 1H), 6.44(s, 1H), 6.74–6.85(m, 1H), 6.95(s, 2H), 7.05(s, 1H), 7.29–7.38(m, 2H)<br>IR(KBr) 3527, 1624, 1530, 1491, 1248, 1221, 1197, 1125, 1105, 1072cm⁻¹ |
| I-1192 | ¹H NMR(CDCl₃) δ 1.75(s, 3H), 1.78(s, 3H), 3.49(s, 3H), 3.73(s, 3H), 3.78(d, J=6.9Hz, 2H), 5.32–5.43(m, 1H), 6.44(s, 1H), 6.73–6.97(m, 4H), 7.25–7.37(m, 2H)<br>IR(KBr) 3551, 3437, 3310, 1607, 1529, 1491, 1463, 1402, 1362, 1269, 1255, 1184, 1099, 1070, 1013cm⁻¹ |
| I-1193 | ¹H NMR(CDCl₃) δ 2.28(s, 3H), 2.30(s, 3H), 3.00(s, 6H), 5.16(s, 2H), 5.69(s, 1H), 6.80(d, J=8.7Hz, 2H), 6.84(d.d, J=8.1 & 2.1Hz, 1H), 6.98(d, J=8.1Hz, 1H), 6.99(d, J=2.1Hz, 1H), 7.12(s, 1H), 7.13(s, 1H), 7.27(d, J=8.7Hz, 2H), 7.34–7.50(m, 5H)<br>IR(KBr) 1605, 1525, 1490, 1417, 1242, 1199, 1127, 1006cm⁻¹ |

TABLE 236

| | |
|---|---|
| I-1194 | mp 174–175° C.<br>¹H NMR(CDCl₃) δ 3.48(s, 3H), 3.78(s, 3H), 4.41(s, 4H), 5.17(s, 2H), 5.71(s, 1H), 5.88(s, 1H), 6.48(s, 1H), 6.94–7.50(m, 18H), 7.86(ABq, J=8.4Hz, 4H)<br>IR(KBr) 3463, 3409, 1588, 1519, 1482, 15455, 1417, 1385, 1321, 1285, 1247, 1154, 1112, 1096, 1067, 1015cm⁻¹ |
| I-1195 | mp 165–167° C<br>¹H NMR(CDCl₃) δ 2.68(s, 3H), 3.14(s, 3H), 3.56(s, 3H), 3.81(s, 3H), 4.40(s, 4H), 5.20(s, 2H), 6.86(s, 1H), 7.09–7.50(m, 18H), 7.79(ABq, J=8.1Hz, 4H)<br>IR(KBr) 3434, 2938, 1606, 1596, 1518, 1478, 1455, 1368, 1335, 1293, 1268, 1239, 1174, 1157, 1118, 1079cm⁻¹ |
| I-1196 | mp 176–178° C.<br>¹H NMR(CDCl₃) δ 1.58(s, 3H), 1.66(s, 3H), 1.77(s, 3H), 1.81(s, 3H), 2.71(s, 3H), 3.24(s, 3H), 3.55(s, 3H), 3.64(m, 2H), 3.80(s, 3H), 4.28(t, J=6.0Hz, 1H), 4.64(d, J=6.9Hz, 2H), 5.10(m, 1H), 5.49(m, 1H), 6.86(s, 1H), 7.10(d, J=8.4Hz, 1H), 7.35(dd, J=2.1, 8.4Hz, 1H), 7.39(d, J=2.1Hz, 1H), 7.87(ABq, J=8.7Hz, 4H)<br>IR(KBr) 3434, 3321, 2939, 1517, 1477, 1366, 1325, 1292, 1269, 1240, 1176, 1156, 1120, 1077cm⁻¹ |
| I-1197 | mp 180–181° C.<br>¹H NMR(DMSO) δ 1.74(s, 3H), 1.77(s, 3H), 2.87(s, 3H), 3.36(s, 3H), 3.51(s, 3H), 3.79(s, 3H), 4.68(d, J=6.6Hz, 2H), 5.48(m, 1H), 7.10(s, 1H), 7.28–7.30(m, 3H), 7.45(bs, 2H), 7.87(ABq, J=8.7Hz, 4H)<br>IR(KBr) 3340, 3238, 2939, 1598, 1518, 1481, 1362, 1333, 1291, 1270, 1239, 1172, 1161, 1120, 1076, 1007cm⁻¹ |
| I-1198 | oil<br>¹H NMR(CDCl₃) δ 1.45(s, 3H), 1.66(s, 3H), 1.87(s, 3H), 2.24(s, 3H), 2.27(s, 3H), 2.30(s, 3H), 3.84(s, 3H), 3.92(s, 3H), 3.95–4.03(m, 1H), 4.50–4.58(m, 1H), 5.22–5.29(m, 1H), 6.87–6.99(m, 4H), 7.09–7.17(m, 3H), 7.80(s, 1H), 8.34–8.42(m, 1H)<br>IR(CHCl₃) 3673, 3021, 1685, 1639, 1525, 1495, 1406, 1237, 1128, 1037cm⁻¹ |

TABLE 237

| | |
|---|---|
| I-1199 | mp 177–179° C.<br>¹H NMR(CDCl₃) δ 1.45(s, 6H), 1.66(s, 6H), 1.87(s, 6H), 2.29(s, 6H), 3.85(s, 6H), 3.95–4.04(m, 2H), 4.50–4.59(m, 2H), 5.23–5.29(m, 2H), 6.90–6.95(m, 4H), 7.10–7.15(m, 2H), 7.19(s, 2H)<br>IR(KBr) 2929, 1661, 1492, 1405, 1288, 1214, 1030, 869, 829cm⁻¹ |
| I-1200 | mp 224–226° C.<br>¹H NMR(CDCl₃) δ 2.88(s, 3H), 3.22(s, 3H), 3.54(s, 3H), 3.78(s, 3H), 6.43(s, 1H), 6.85(s, 1H), 7.01(d, J=8.4Hz, 1H), 7.20(dd, J=2.1, 8.4Hz, 1H), 7.35–7.42(m, 2H), 7.65–7.72(m, 2H), 7.96(d, J=2.1Hz, 1H), 8.96(s, 1H)<br>IR(KBr) 3441, 3370, 3024, 2938, 1729, 1508, 1481, 1365, 1177, 1148, 1085, 884, 798, 524cm⁻¹ |
| I-1201 | powder<br>¹H NMR(CDCl₃) δ 1.77(s, 3H), 1.82(s, 3H), 2.80(s, 3H), 3.21(s, 3H), 3.56(s, 3H), 3.79(s, 3H), 4.67(d, J=6.6Hz, 2H), 5.46–5.51(m, 1H), 6.84(s, 1H), 7.05(d, J=8.1Hz, 1H), 7.22–7.26(m, 1H), 7.36–7.41(m, 2H), 7.67–7.71(m, 2H), 8.35(d, J=1.8Hz, 1H), 9.24(s, 1H)<br>IR(KBr) 3385, 2937, 1718, 1532, 1479, 1362, 1175, 1152, 1078, 973, 876, 797, 526cm⁻¹ |
| I-1202 | mp 260–262° C.<br>¹H NMR(DMSO) δ 2.27(s, 6H), 3.87(s, 6H), 7.00(dd, J=1.8, 8.1Hz, 2H), 7.10(d, J=1.8Hz, 2H), 7.21(s, 2H), 7.48(d, J=8.1Hz, 2H), 10.73(s, 2H)<br>IR(KBr) 3392, 3008, 1719, 1600, 1542, 1413, 1297, 1158, 1032, 905, 627cm⁻¹ |
| I-1203 | mp 143–144° C.<br>¹H NMR(CDCl₃) δ 1.76(s, 3H), 1.82(s, 3H), 3.61(s, 3H), 3.67(s, 3H), 3.73(s, 3H), 3.87(s, 3H), 4.62(d, J=6.9Hz, 2H), 5.50–5.58(m, 1H), 5.66(s, 1H), 6.86–7.02(m, 5H), 7.54(d, J=9Hz, 2H)<br>IR(KBr) 3494, 2935, 1673, 1609, 1584, 1519, 1479, 1456, 1389, 1284, 1249, 1178, 1109, 1081, 1016, 829, 798cm⁻¹ |

TABLE 238

| | |
|---|---|
| I-124 | mp 90–91° C.<br>$^1$H NMR(CDCl$_3$) δ 1.72(s, 3H), 1.79(s, 3H), 2.26(s, 6H), 4.69(d, J=7.2Hz, 2H), 4.9–5.0(brs, 1H), 5.57(t, J=7.2Hz, 1H), 6.85–7.0(m, 4H), 7.10(d, J=8.7Hz, 2H), 7.23(d, J=8.7Hz, 2H)<br>IR(KBr) 3253, 3013, 2979, 2928, 1676, 1584, 1521, 1492, 1232, 1034, 950, 848, 825cm$^{-1}$ |
| I-1205 | mp 131–132° C.<br>$^1$H NMR(CDCl$_3$) δ 1.73(s, 3H), 1.79(s, 3H), 3.43(s, 3H), 3.76(s, 3H), 4.68(d, J=6.9Hz, 2H), 4.9–5.1(brs, 1H), 5.58(t, J=7.2Hz, 1H), 6.09(brs, 1H), 6.44(s, 1H), 6.92(d, J=8.4Hz, 2H), 7.0–7.1(m, 2H), 7.52(d, J=8.4Hz, 2H)<br>IR(KBr) 3428, 2951, 2932, 1671, 1611, 1523, 1491, 1402, 1233, 1111, 1077, 1027, 969, 833cm$^{-1}$ |
| I-1206 | mp 191–192° C.<br>$^1$H NMR(CDCl$_3$) δ 2.15(s, 6H), 3.22(s, 3H), 3.87(s, 3H), 5.18(AB q, J=12.0Hz, 2H), 6.74(dd, J=2.1, 8.1Hz, 1H), 6.78 (d, J=2.1Hz, 1H), 6.93(d, J=8.1Hz, 1H), 7.24(s, 1H), 7.30–7.50(m, 9H)<br>IR(KBr) 1528, 1479, 1453, 1364, 1326, 1262, 1243, 1223, 1209, 1200, 1176, 1152, 1137, 963, 870, 846, 754cm$^{-1}$ |
| I-1207 | mp 108–109° C.<br>$^1$H NMR(CDCl$_3$) δ 1.77(s, 3H), 1.82(d, J=0.6Hz, 3H), 2.27(s, 3H), 2.28(s, 3H), 4.56(d, J=6.6Hz, 2H), 4.89(s, 1H), 5.54(m, 1H), 6.86–6.92(m, 2H), 6.94–7.00(m, 2H), 7.12(s, 1H), 7.13(s, 1H), 7.22–7.27(m, 2H), 7.27–7.31(m, 2H)<br>IR(KBr) 3349, 1608, 1520, 1488, 1439, 1383, 1287, 1263, 1235, 1175, 999, 979cm$^{-1}$ |
| I-1208 | mp 194–195° C.<br>$^1$H NMR(CDCl$_3$) δ 2.14(s, 3H), 2.16(s, 3H), 3.87(s, 3H), 4.97(s, 1H), 5.17(AB q, J=12.6Hz, 2H), 6.74(dd, J=2.1, 8.1Hz, 1H), 6.79(d, J=2.1Hz, 1H), 6.88–6.93(m, 2H), 6.93(d, J=8.1Hz, 1H), 7.17–7.22(m, 2H), 7.24(s, 1H), 7.29–7.49(m, 5H)<br>IR(KBr) 3408, 1611, 1526, 1479, 1463, 1455, 1382, 1263, 1242, 1225, 1212, 1143, 997, 751cm$^{-1}$ |

TABLE 239

| | |
|---|---|
| I-1209 | mp 183–184° C.<br>$^1$H NMR(CDCl$_3$) δ 2.03(s, 3H), 2.07(s, 3H), 3.19(s, 3H), 3.80(br s, 2H), 3.89(s, 3H), 5.21(s, 2H), 6.63(s, 1H), 6.77(dd, J=2.1, 8.1Hz, 1H), 6.83(d, J=2.1Hz, 1H), 7.02(d, J=8.1Hz, 1H), 7.29–7.52(m, 9H)<br>IR(KBr) 3481, 3391, 1610, 1511, 1482, 1370, 1240, 1212, 1197, 1173, 1153, 1137, 1024, 1007, 870, 844cm$^{-1}$ |
| I-1210 | mp 133–134° C.<br>$^1$H NMR(CDCl$_3$) δ 1.75(s, 3H), 1.80(s, 3H), 2.16(s, 3H), 2.17(s, 3H), 3.22(s, 3H), 3.85(s, 3H), 4.61(d, J=6.9Hz, 2H), 5.55(m, 1H), 6.74–6.79(m, 2H), 6.92(d, J=8.7Hz, 1H), 7.24(s, 1H), 7.39(s, 4H)<br>IR(KBr) 1529, 1516, 1478, 1371, 1353, 1328, 1263, 1242, 1201, 1176, 1150, 975, 866, 846, 787cm$^{-1}$ |
| I-1211 | mp 243–244° C.<br>$^1$H NMR(DMSO-d$_6$) δ 1.91(s, 3H), 1.96(s, 3H), 3.77(s, 3H), 4.05(br s, 2H), 5.12(s, 2H), 6.40(s, 1H), 6.71(dd, J=1.8, 8.1Hz, 1H), 6.77–6.84(m, 3H), 7.06–7.12(m, 2H), 7.16(d, J=8.1Hz, 1H), 7.32–7.52(m, 5H), 9.38(s, 1H)<br>IR(KBr) 3378, 3289, 1609, 1586, 1518, 1483, 1454, 1402, 1267, 1236, 1207, 1171, 1136, 1024, 853, 835, 816, 753, 730, 695cm$^{-1}$ |
| I-1212 | mp 195–196° C.<br>$^1$H NMR(CDCl$_3$) δ 1.75(s, 3H), 1.79(s, 3H), 2.15(s, 3H), 2.16(s, 3H), 3.85(s, 3H), 4.61(d, J=6.9Hz, 2H), 4.97(s, 1H), 5.55(m, 1H), 6.76–6.79(m, 2H), 6.89–6.94(m, 3H), 7.18–7.23(m, 2H), 7.24(s, 1H)<br>IR(KBr) 3462, 1611, 1519, 1479, 1459, 1431, 1379, 1271, 1240, 1228, 1211, 1137, 983, 835cm$^{-1}$ |
| I-1213 | IR(KBr) 3275, 1494, 1462, 1444, 1387, 1371, 1232, 1212, 1183, 1141cm$^{-1}$ |
| I-124 | mp 106–108° C.<br>$^1$H NMR(CDCl$_3$) δ 2.24(s, 3H), 3.79(s, 3H), 4.72(br, 1H), 5.20(s, 2H), 6.72–7.18(m, 8H), 7.36–7.50(m, 6H)<br>IR(CHCl$_3$) 3596, 1610, 1523, 1493, 1465, 1455, 1388, 1318, 1298, 1262, 1173, 1127, 1038, 834cm$^{-1}$ |

TABLE 240

| | |
|---|---|
| I-1215 | mp 108–110° C.<br>$^1$H NMR(CDCl$_3$) δ 1.77(s, 3H), 1.82(s, 3H), 2.25(s, 3H), 3.79(s, 3H), 4.63–4.65(d, J=7.2Hz, 2H), 5.56(s, 2H), 6.81(s, 1H), 6.87–7.18(m, 6H), 7.44–7.47(m, 2H)<br>IR(CHCl$_3$) 3596, 2937, 1610, 1523, 1493, 1465, 1446, 1387, 1297, 1261, 1173, 1125, 1038, 993, 834cm$^{-1}$ |
| I-1216 | mp 121–122° C.<br>$^1$H NMR(CDCl$_3$) δ 2.24(s, 3H), 3.79(s, 3H), 4.78–4.80(d, J=6.9Hz, 2H), 6.24(t, J=6.9Hz, 1H), 6.80(s, 1H), 6.87–7.19 (m, 6H), 7.43–7.48(m, 2H)<br>IR(CHCl$_3$) 3596, 1612, 1523, 1493, 1464, 1389, 1300, 1259, 1173, 1127, 1038, 886, 834cm$^{-1}$ |
| I-1217 | mp 163–165° C.<br>$^1$H NMR(CDCl$_3$) δ 2.26(s, 3H), 2.28(s, 3H), 4.78(br s, 1H), 4.78(d, J=6.5Hz, 2H), 5.60(s, 1H) 6.23(t, J=6.5Hz, 1H), 6.83–6.92(m, 4H), 6.99(d, J=2.1Hz, 1H), 7.10(s, 1H), 7.11(s, 1H), 7.22–7.27(m, 2H)<br>IR(CHCl$_3$) 3597, 3548, 3027, 3010, 1613, 1588, 1522, 1490, 1218, 1208, 1171cm$^{-1}$ |
| I-1218 | foam<br>$^1$H NMR(CDCl$_3$) δ 2.37(s, 3H), 3.39(s, 3H), 3.73(s, 3H), 5.15(s, 2H), 5.68(s, 1H), 5.92(s, 1H), 6.46(s, 1H), 6.71(dd, J=3.7, 0.7Hz, 1H), 6.96(dd, J=8.4, 2.1Hz, 1H), 7.03(d, J=8.4Hz, 1H), 7.09(d, J=2.1Hz, 1H), 7.26(dd, J=8.6, 0.7Hz, 2H), 7.37–7.45(m, 5H), 7.60(dd, J=8.7, 1.5Hz, 1H), 7.61(d, J=3.7Hz, 1H), 7.78(d, J=1.5Hz, 1H), 7.82(d, J=8.6Hz, 1H), 8.05(d, J=8.7Hz, 1H)<br>IR(KBr) 3476, 1457, 1371, 1254, 1107, 1131, 1107, 1011, 814, 685, 581cm$^{-1}$ |
| I-1219 | mp 217–219° C.<br>$^1$H NMR(CDCl$_3$) δ 2.37(s, 3H), 2.69(s, 3H), 3.12(s, 3H), 3.47(s, 3H), 3.76(s, 3H), 5.18(s, 2H), 6.71(d, J=3.8Hz, 1H), 6.86(s, 1H), 7.15(d, J=8.4Hz, 1H), 7.26(d, J=8.7Hz, 2H), 7.32–7.48(m, 7H), 7.56(dd, J=8.7, 1.8Hz, 1H), 7.61(d, J=3.8Hz, 1H), 7.78(d, J=1.8Hz, 1H), 7.82(d, J=8.7Hz, 1H), 8.05(d, J=8.7Hz, 1H)<br>IR(KBr) 1366, 1174, 1079, 963, 814, 685, 586cm$^{-1}$ |

TABLE 241

I-1220 mp 208–210° C.
$^1$H NMR(CDCl$_3$) δ 2.37(s, 3H), 2.72(s, 3H), 3.23(s, 3H), 3.47(s, 3H), 3.76(s, 3H), 4.63(d, J=6.6Hz, 2H), 5.49(t, J=6.6Hz, 1H), 6.71(d, J=3.8Hz, 1H), 6.86(s, 1H), 7.09(d, J=8.4Hz, 1H), 7.26(d, J=8.3Hz, 2H), 7.35(dd, J=8.4, 2.1Hz, 1H), 7.40(d, J=2.1Hz, 1H), 7.56(dd, J=8.4, 1.7Hz, 1H), 7.61(d, J=3.8Hz, 1H), 7.78(d, J=1.7Hz, 1H), 7.82(d, J=8.3Hz, 2H), 8.05(d, J=8.7Hz, 1H)
IR(KBr) 1466, 1445, 1365, 1174, 1116, 1079, 964, 812, 686, 584cm$^{-1}$
I-1221 mp 203–205° C.
$^1$H NMR(CDCl$_3$) δ 1.76(s, 3H), 1.81(s, 3H), 2.39(s, 3H), 2.69(s, 3H), 2.97(t, J=8.6Hz, 2H), 3.23(s, 3H), 3.50(s, 3H), 3.77(s, 3H), 3.98(t, J=8.6Hz, 2H), 4.63(d, J=6.6Hz, 2H), 5.49(t, J=6.6Hz, 1H), 6.80(s, 1H), 7.08(d, J=8.5Hz, 1H), 7.24–7.28(m, 2H), 7.33(dd, J=8.5, 2.0Hz, 1H), 7.37–7.39(m, 2H), 7.41–7.45(m, 1H), 7.71(d, J=8.4Hz, 1H), 7.73(d, J=8.1Hz, 2H)
IR(KBr) 1474, 1362, 1241, 1166, 1079, 975, 808cm$^{-1}$
I-1222 amorphous
$^1$H NMR(CDCl$_3$) δ 1.76(s, 3H), 1.82(s, 3H), 2.39(s, 3H), 2.98(t, J=8.4Hz, 2H), 3.43(s, 3H), 3.73(s, 3H), 3.98(t, J=8.4Hz, 2H), 4.61(d, J=6.6Hz, 2H), 5.53(t, J=6.6Hz, 1H), 5.68(s, 1H), 5.86(s, 1H), 6.40(s, 1H), 6.93–6.95(m, 2H), 7.03–7.05(m, 1H), 7.23–7.27(m, 2H), 7.35–7.37(m, 1H), 7.45–7.50(m, 1H), 7.71(d, J=8.4Hz, 1H), 7.74(d, J=8.4Hz, 2H)
IR(KBr) 3457, 1480, 1354, 1244, 1164, 1099, 978, 817cm$^{-1}$
I-1223 mp 199–201° C.
$^1$H NMR(CDCl$_3$) δ 3.19(s, 3H), 3.72(s, 3H), 3.90(s, 3H), 4.20–4.27(m, 4H), 5.20(s, 2H), 6.53(s, 1H), 6.90–6.99(m, 3H), 7.25–7.65(m, 9H)
IR(KBr) 3434, 2938, 1604, 1586, 1522, 1484, 1465, 1432, 1368, 1339, 1326, 1249, 1226, 1203, 1174, 1146, 1136, 1106, 1027cm$^{-1}$

TABLE 242

I-1224 mp 127–129° C.
$^1$H NMR(CDCl$_3$) δ 1.57(s, 3H), 1.65(s, 3H), 1.76(s, 3H), 1.82(s, 3H), 3.46(s, 3H), 3.64(m, 2H), 3.76(s, 3H), 4.30(t, J=5.7Hz, 1H), 4.62(d, J=6.9Hz, 2H), 5.10(m, 1H), 5.53(m, 1H), 5.72(s, 1H), 5.85(s, 1H), 6.47(s, 1H), 6.93(dd, J=1.8, 8.4Hz, 1H), 6.98(d, J=8.4Hz, 1H), 7.05(d, J=1.8Hz, 1H), 7.88(ABq, J=8.7Hz, 4H)
IR(KBr) 3478, 3314, 2937, 1585, 1556, 1518, 1501, 1484, 1460, 1417, 1387, 1363, 1328, 1279, 1243, 1228, 1191, 1155, 1129, 1113, 1090, 1068, 1013cm$^{-1}$
I-1225 mp 162–164° C.
$^1$H NMR(CDCl$_3$) δ 3.19(s, 3H), 3.72(s, 3H), 4.19–4.23(m, 4H), 5.18(s, 2H), 6.52(s, 1H), 7.03–7.64(m, 12H)
IR(KBr) 3433, 2933, 1523, 1483, 1463, 1435, 1377, 1360, 1269, 1227, 1172, 1149, 1126, 1096cm$^{-1}$
I-1226 mp 188–190° C.
$^1$H NMR(DMSO) δ 1.72(s, 3H), 1.75(s, 3H), 3.33(s, 3H), 3.67(s, 3H), 4.55(d, J=6.9Hz, 2H), 5.49(m, 1H), 6.50(s, 1H), 6.66(dd, J=2.1, 8.1Hz, 1H), 6.74(d, J=2.1Hz, 1H), 6.91(d, J=8.1Hz, 1H), 7.42(bs, 2H), 7.85(ABq, J=8.4Hz, 4H), 8.75(bs, 2H)
IR(KBr) 3465, 2937, 1588, 1517, 1500, 1483, 1470, 1446, 1415, 1385, 1340, 1308, 1283, 1246, 1224, 1201, 1186, 1168, 1130, 1116, 1091, 1067, 1011cm$^{-1}$
I-1227 mp 172–174° C.
$^1$H NMR(CDCl$_3$) δ 1.75(s, 3H), 1.78(s, 3H), 3.19(s, 3H), 3.72(s, 3H), 3.87(s, 3H), 4.20–4.27(m, 4H), 4.62(d, J=6.9Hz, 2H), 5.57(m, 1H), 6.54(s, 1H), 6.96(s, 3H), 7.49(ABq, J=8.7Hz, 4H)
IR(KBr) 3433, 2937, 1604, 1582, 1522, 1483, 1465, 1432, 1368, 1340, 1326, 1242, 1226, 1218, 1204 1174, 1138, 1107cm$^{-1}$

TABLE 243

I-1228 mp 169–175° C.
$^1$H NMR(CDCl$_3$) δ -0.07–0.02(m, 2H), 0.34–0.42(m, 2H), 0.98(m, 1H), 2.44(s, 3H), 3.20(s, 3H), 3.47(d, J=7.2Hz, 2H), 3.78(s, 3H), 3.91(s, 3H), 5.22(s, 2H), 6.85(s, 1H), 6.91(dd, J=1.8, 8.1Hz, 1H), 6.976(d, J=1.8Hz, 1H), 6.979(d, J=8.1Hz, 1H), 7.26–7.73(m, 9H)
IR(KBr) 3447, 2934, 1604, 1518, 1480, 1390, 1362, 1240, 1227, 1175, 1140, 1081cm$^{-1}$
I-1229 mp 172–174° C.
$^1$H NMR(CDCl$_3$) δ 1.74(s, 3H), 1.78(s, 3H), 3.71(s, 3H), 3.87(s, 3H), 4.20–4.25(m, 4H), 4.62(d, J=6.3Hz, 2H), 4.94(bs, 1H), 5.57(m, 1H), 6.55(s, 1H), 6.89–7.50(m, 7H)
IR(KBr) 3410, 2933, 1611, 1522, 1484, 1462, 1422, 1371, 1264, 1238, 1224, 1173, 1134, 1103cm$^{-1}$
I-1230 mp 149–151° C.
$^1$H NMR(CDCl$_3$) δ 1.75(s, 3H), 1.81(s, 3H), 3.45(s, 3H), 3.75(s, 3H), 3.87(s, 3H), 4.61(d, J=6.6Hz, 2H), 5.54–5.58(m, 1H), 5.69(s, 1H), 5.91(s, 1H), 6.46(s, 1H), 6.93–7.06(m, 5H), 7.58(d, J=8.7Hz, 2H)
IR(KBr) 3501, 2939, 1680, 1609, 1582, 1520, 1487, 1458, 1397, 1284, 1246, 1191, 1179, 1115, 1067, 1015, 940, 822, 794cm$^{-1}$
I-1231 mp 151–152° C.
$^1$H NMR(CDCl$_3$) δ 1.77(d, J=0.6Hz, 3H), 1.81(d, J=0.6Hz, 3H), 2.04(s, 3H), 2.08(s, 3H), 3.20(s, 3H), 3.77(br s, 2H), 3.86(s, 3H), 4.65(d, J=6.6Hz, 2H), 5.58(m, 1H), 6.04(s, 1H), 6.81(dd, J=2.1, 8.7Hz, 1H), 6.81(d, J=2.1Hz, 1H), 7.01(d, J=8.7Hz, 1H), 7.30–7.36(m, 2H), 7.38–7.43(m, 2H)
IR(KBr) 3484, 3393, 2934, 1608, 1511, 1482, 1371, 1239, 1213, 1197, 1173, 1153, 1138, 989, 973, 871, 844, 791cm$^{-1}$

TABLE 244

I-1232 mp 198–199° C.
$^1$H NMR(DMSO-d$_6$) δ 1.72(s, 3H), 1.77(s, 3H), 1.91(s, 3H), 1.95(s, 3H), 3.75(s, 3H), 4.04(s, 2H), 4.55(d, J=6.9Hz, 2H), 5.48(m, 1H), 6.40(s, 1H), 6.69(dd, J=1.8, 8.1Hz, 1H), 6.75(d, J=1.8Hz, 1H), 6.77–6.83(m, 2H), 7.05–7.11(m, 3H), 9.39(s, 1H)

TABLE 244-continued

| | |
|---|---|
| | IR(KBr) 3375, 3287, 2913, 1609, 1587, 1578, 1518, 1484, 1434, 1403, 1270, 1235, 1207, 1171, 1136, 1032, 1009, 863, 853, 816, 749cm$^{-1}$ |
| I-1233 | mp 198–199° C.<br>$^1$H NMR(CDCl$_3$) δ 1.77(s, 3H), 1.80(s, 3H), 1.91(s, 3H), 2.11(s, 3H), 2.13(s, 3H), 3.20(s, 3H), 3.84(s, 3H), 4.64(d, J=6.6Hz, 2H), 5.58(m, 1H), 6.46(s, 1H), 6.69–6.74(m, 2H), 6.96(d, J=8.4Hz, 1H), 7.11(s, 1H), 7.32–7.38(m, 2H), 7.40–7.46 (m, 2H)<br>IR(KBr) 1651, 1513, 1470, 1448, 1414, 1368, 1330, 1267, 1241, 1214, 1199, 1175, 970, 869cm$^{-1}$ |
| I-1232 | mp 193–194° C.<br>$^1$H NMR(CDCl$_3$) δ 1.77(s, 3H), 1.80(d, J=0.6Hz, 3H), 1.94(s, 3H), 2.11(s, 3H), 2.13(s, 3H), 3.84(s, 3H), 4.64(d, J=6.6Hz, 2H), 5.58(m, 1H), 6.58(s, 1H), 6.70–6.75(m, 2H), 6.85–6.93(m, 2H), 6.96(d, J=8.4Hz, 1H), 7.13(s, 1H), 7.19–7.24(m, 2H)<br>IR(KBr) 3271, 1654, 1611, 1517, 1467, 1448, 1370, 1289, 1262, 1240, 1213, 1177, 1136, 835cm$^{-1}$ |
| I-1235 | mp 114–115° C.<br>$^1$H NMR(CDCl$_3$) δ 1.77(s, 3H), 1.81(s, 3H), 2.27(s, 6H), 3.91(s, 3H), 4.63(d, J=6.6Hz, 2H), 5.56(m, 1H), 5.61(s, 1H), 6.86(dd, J=2.1, 8.4Hz, 1H), 6.86(d, J=2.1Hz, 1H), 6.97(d, J=8.4Hz, 1H), 7.02–7.14(m, 5H)<br>IR(KBr) 3410, 1597, 1521, 1470, 1449, 1415, 1382, 1297, 1276, 1261, 1220, 1122, 1052, 983, 862cm$^{-1}$ |

TABLE 245

| | |
|---|---|
| I-1236 | powder<br>$^1$H NMR(CDCl$_3$) δ 3.22(s, 3H), 3.38(s, 3H), 3.46(s, 3H), 3.92(s, 3H), 5.22(s, 2H), 5.76(s, 1H), 6.97–7.09(m, 3H), 7.32–7.51 (m, 9H)<br>IR(KBr) 3448, 2935, 1516, 1455, 1394, 1366, 1352, 1246, 1148, 1076, 1015, 972, 881, 699, 541, 524cm$^{-1}$ |
| I-1237 | mp 169–172° C.<br>$^1$H NMR(CDCl$_3$) δ 2.49(s, 3H), 3.21(s, 3H), 3.47(s, 3H), 3.50(s, 3H), 3.92(s, 3H), 5.23(s, 2H), 6.95–7.04(m, 3H), 7.31–7.49 (m, 9H)<br>IR(KBr) 3009, 2932, 1518, 1459, 1370, 1362, 1250, 1176, 1151, 872, 809, 542, 527cm$^{-1}$ |
| I-1238 | mp 182–184° C.<br>$^1$H NMR(CDCl$_3$) δ 2.67(s, 3H), 3.21(s, 3H), 3.48(s, 3H), 3.50(s, 3H), 3.93(s, 3H), 5.77(s, 1H), 6.98–7.06(m, 3H), 7.38–7.51 (m, 4H)<br>IR(KBr) 3548, 3502, 2938, 1602, 1519, 1389, 1364, 1176, 1159, 1012, 963, 875, 521cm$^{-1}$ |
| I-1239 | mp 132–135° C.<br>$^1$H NMR(CDCl$_3$) δ 1.77(s, 3H), 1.80(s, 3H), 2.62(s, 3H), 3.21(s, 3H), 3.48(s, 3H), 3.51(s, 3H), 3.90(s, 3H), 4.64(d, J=6.6Hz, 2H), 5.51–5.58(m, 1H), 6.97–7.04(m, 3H), 7.37–7.51(m, 4H)<br>IR(KBr) 2936, 1518, 1464, 1375, 1362, 1246, 1175, 1153, 1013, 968, 872, 805, 529cm$^{-1}$ |
| I-1240 | mp 169–172° C.<br>$^1$H NMR(CDCl$_3$) δ 1.76(s, 3H), 1.80(s, 3H), 3.38(s, 3H), 3.47(s, 3H), 3.89(s, 3H), 4.65(d, J=6.6Hz, 2H), 5.06(s, 1H), 5.54–5.61(m, 1H), 5.83(s, 1H), 6.92–7.00(m, 3H), 7.05–7.09(m, 2H), 7.28–7.33(m, 2H)<br>IR(KBr) 3458, 2935, 1611, 1520, 1458, 1392, 1244, 1222, 1015, 828, 803cm$^{-1}$ |

TABLE 246

| | |
|---|---|
| I-1241 | mp 170–173° C.<br>$^1$H NMR(CDCl$_3$) δ 1.73(s, 3H), 1.79(s, 3H), 2.55–3.00(m, 3H), 3.21(s, 3H), 3.22–3.80(m, 6H), 4.55–4.63(m, 2H), 5.41–5.47 (m, 1H), 6.83(s, 1H), 7.03–7.70(m, 8H)<br>IR(KBr) 2938, 1686, 1516, 1481, 1378, 1235, 1235, 1179, 1152, 1081, 847, 799, 675, 527cm$^{-1}$ |
| I-1242 | mp 117–118° C.<br>$^1$H NMR(CDCl$_3$) δ 1.77(s, 3H) 1.81(d, J=0.6Hz, 3H), 2.11(s, 3H), 2.19(s, 3H), 3.38(s, 3H), 4.64(d, J=6.9Hz, 2H), 4.75 (br s, 1H), 5.54–5.90(m, 1H), 6.86–6.91(m, 2H), 6.93(s, 1H), 7.10–7.69(m, 3H), 7.20–7.25(m, 2H)<br>IR(CHCl$_3$) 3596, 3010, 2934, 1675, 1519, 1473, 1262, 1172, 1098cm$^{-1}$ |
| I-1243 | foam<br>$^1$H NMR(CDCl$_3$) δ 3.43(s, 3H), 3.72(s, 3H), 5.03(s, 2H), 6.43(s, 1H), 6.93(dd, J=8.4, 2.1Hz, 1H), 6.94(d, J=8.7Hz, 2H), 7.09(d, J=2.1Hz, 1H), 7.11(d, J=8.4Hz, 1H), 7.29(ddd, J=7.8, 4.8, 1.5Hz, 1H), 7.49(brd, J=7.8Hz, 1H), 7.53(d, J=8.7Hz, 2H), 7.70(ddd, J=7.8, 7.8, 1.5Hz, 1H), 8.61(brd, J=4.8Hz, 1H)<br>IR(KBr) 3432, 1611, 1588, 1562, 1523, 1488, 1467, 1226, 1114, 1071, 1015, 939, 824, 778, 758cm$^{-1}$ |
| I-1244 | foam<br>$^1$H NMR(CDCl$_3$) δ 3.45(s, 3H), 3.75(s, 3H), 5.01(s, 2H), 6.45(s, 1H), 6.92(d, J=8.7Hz, 2H), 6.99(dd, J=8.4, 2.1Hz, 1H), 7.10(d, J=2.1Hz, 1H), 7.14(d, J=8.4Hz, 1H), 7.30–7.36(m, 3H), 7.46–7.49(m, 2H), 7.54(d, J=8.7Hz, 2H)<br>IR(KBr) 3433, 1612, 1589, 1523, 1489, 1403, 1224, 1192, 1113, 1070, 1013, 938, 813, 758cm$^{-1}$ |
| I-1245 | foam<br>$^1$H NMR(CDCl$_3$) δ 3.45(s, 3H), 3.75(s, 3H), 5.01(s, 2H), 6.45(s, 1H), 6.92(d, J=8.7Hz, 2H), 6.99(dd, J=5.1, 3.6Hz, 1H), 6.99(dd, J=8.4, 2.1Hz, 1H), 7.10(d, J=2.1Hz, 1H), 7.11(d, J=8.4Hz, 1H), 7.27(dd, J=3.6, 1.0Hz, 1H), 7.29(dd, J=5.1, 1.0Hz, 1H), 7.54(d, J=8.7Hz, 2H)<br>IR(KBr) 3433, 1612, 1589, 1523, 1488, 1403, 1241, 1224, 1192, 1113, 1070, 1011, 826cm$^{-1}$ |

TABLE 247

| | |
|---|---|
| I-1246 | foam<br>$^1$H NMR(CDCl$_3$) δ 3.45(s, 3H), 3.75(s, 3H), 4.93(s, 2H), 5.70(d, J=1.5Hz, 1H), 5.75(d, J=1.5Hz, 1H), 6.45(s, 1H), 6.92(d, J=8.7Hz, 2H), 6.99(dd, J=8.4, 2.1Hz, 1H), 7.05(d, J=8.4Hz, 1H), 7.10(d, J=2.1Hz, 1H), 7.54(d, J=8.7Hz, 2H)<br>IR(KBr) 3432, 1611, 1590, 1523, 1489, 1403, 1224, 1193, 1113, 1071, 1010, 938, 826cm$^{-1}$ |

TABLE 247-continued

I-1247 foam
$^1$H NMR(CDCl$_3$) δ 3.45(s, 3H), 3.75(s, 3H), 5.53(d, J=10.5Hz, 1H), 5.69(d, J=16.5Hz, 1H), 6.11(ddd, J=16.5, 10.5, 6.3Hz, 1H), 6.44(d, J=6.3Hz, 1H), 6.45(s, 1H), 6.88(d, J=8.4Hz, 1H), 6.91–6.93(m, 2H), 6.92(d, J=8.7Hz, 2H), 7.53(d, J=8.7Hz, 2H)
IR(KBr) 3433, 1611, 1592, 1522, 1485, 1403, 1226, 1106, 1059, 814cm$^{-1}$ I-1248 foam
$^1$H NMR(CDCl$_3$) δ 1.16(t, J=7.5Hz, 3H), 2.26(tq, J=2.1, 7.5Hz, 2H), 3.45(s, 3H), 3.75(s, 3H), 4.76(t, J=2.1Hz, 2H), 6.45(s, 1H), 6.91(d, J=8.7Hz, 2H), 6.96(dd, J=2.1, 8.4Hz, 1H), 7.06(d, J=8.4Hz, 1H), 7.07(d, J=2.1Hz, 1H), 7.53(d, J=8.7Hz, 2H)
IR(KBr) 3434, 2230, 1612, 1590, 1523, 1479, 1225, 1113, 1070, 1005, 938, 815cm$^{-1}$ I-1249 foam
$^1$H NMR(CDCl$_3$) δ 3.38(s, 3H), 3.67(s, 3H), 5.12(s, 2H), 6.43(s, 1H), 6.56(d, J=3.3Hz, 1H), 6.79(dd, J=2.1, 8.1Hz, 1H), 6.84(d, J=8.7Hz, 2H), 6.87(d, J=2.1Hz, 1H), 7.02(d, J=3.3Hz, 1H), 7.02(d, J=8.1Hz, 1H), 7.45(d, J=8.7Hz, 2H)
IR(KBr) 3431, 1698, 1611, 1523, 1489, 1405, 1246, 1114, 1071, 1012, 816, 786cm$^{-1}$ I-1250 $^1$H NMR(CDCl$_3$) δ 3.38(s, 3H), 3.67(s, 3H), 4.66(tt, J=2.7, 6.9Hz, 2H), 4.90(tt, J=2.7, 6.9Hz, 2H), 5.43(tt, J=6.9, 6.9Hz, 1H), 6.45(s, 1H), 6.92(d, J=8.7Hz, 2H), 6.96(br.s, 2H), 7.07(s, 1H), 7.53(d, J=8.7Hz, 2H)
IR(KBr) 3430, 1955, 1612, 1589, 1522, 1489, 1404, 1248, 1113, 1070, 1008, 938, 845, 825cm$^{-1}$

TABLE 248

I-1251 foam
$^1$H NMR(CDCl$_3$) δ 1.69(dd, J=3.3, 6.9Hz, 3H), 3.46(s, 3H), 3.74(s, 3H), 4.63(dd, J=2.4, 6.3Hz, 2H), 5.28(m, 1H), 5.33(m, 1H), 6.45(s, 1H), 6.92(d, J=8.7Hz, 2H), 6.95(d, J=1.5Hz, 1H), 6.96(br.s, 1H), 7.06(d, J=1.5Hz, 1H), 7.52(d, J=8.7Hz, 2H)
IR(KBr) 3436, 2933, 1968, 1612, 1587, 1523, 1489, 1464, 1404, 1112, 1071, 1011, 998, 824cm$^{-1}$ I-1252 foam
$^1$H NMR(CDCl$_3$) δ 1.02(t, J=7.2Hz, 3H), 2.05(ddq, J=3.3, 6.3, 7.2Hz, 2H), 3.46(s, 3H), 3.74(s, 3H), 4.64(dd, J=2.4, 6.0Hz, 2H), 5.40(m, 2H), 6.45(s, 1H), 6.91(d, J=8.7Hz, 2H), 6.94(d, J=2.1, 8.4Hz, 1H), 6.97(d, J=8.4Hz, 1H), 7.06(d, J=2.1Hz, 1H), 7.54(d, J=8.7Hz, 2H)
IR(KBr) 3479, 2960, 2933, 1964, 1612, 1582, 1522, 1489, 1403, 1242, 1113, 1072, 1011, 999, 944, 872cm$^{-1}$ I-1253 foam
$^1$H NMR(CDCl$_3$) δ 1.03(d, J=6.6Hz, 6H), 2.34(m, 1H), 3.46(s, 3H), 3.74(s, 3H), 4.63(dd, J=2.7, 6.3Hz, 2H), 5.33(m, 1H), 5.44(m, 1H), 6.45(s, 1H), 6.92(d, J=8.7Hz, 2H), 6.93(d, J=1.8, 7.8Hz, 1H), 6.97(d, J=7.8Hz, 1H), 7.06(d, J=1.8Hz, 1H), 7.53(d, J=8.7Hz, 2H)
IR(KBr) 3434, 2958, 1960, 1612, 1589, 1523, 1489, 1226, 1113, 1071, 1011, 939, 825cm$^{-1}$ I-124 foam
$^1$H NMR(CDCl$_3$) δ 2.62(d, J=2.4Hz, 1H), 3.45(s, 3H), 3.75(s, 3H), 4.18(dd, J=7.2, 11.4Hz, 1H), 4.38(dd, J=2.4, 11.4Hz, 1H), 4.94(ddd, J=2.4, 2.4, 7.2Hz, 1H), 6.44(s, 1H), 6.92(d, J=8.7Hz, 2H), 6.98(d, J=8.4Hz, 1H), 7.01(d, J=1.8, 8.4Hz, 1H), 7.08(d, J=1.8Hz, 1H), 7.52(d, J=8.7Hz, 2H)
IR(KBr) 3434, 3283, 2127, 1612, 1586, 15323, 1487, 1226, 1115, 1069, 1007, 943, 825cm$^{-1}$

TABLE 249

I-1255 mp 148–150° C.
$^1$H NMR(CDCl$_3$) δ 2.99(s, 6H), 3.75–3.80(br, 2H), 3.75(s, 3H), 3.77(s, 3H), 6.45–6.53(m, 2H), 6.79–6.83(m, 2H), 6.88(s, 1H), 6.95(s, 1H), 7.17–7.23(m, 1H), 7.48–7.51(m, 2H)
IR(KBr) 3600–2800(br), 1630, 1609, 1530, 1492, 1461, 1444, 1388, 1331, 1209, 1165, 1125, 1050, 1028cm$^{-1}$

I-1256 mp 209–212° C.
$^1$H NMR(CDCl$_3$) δ 3.00(s, 6H), 3.11(s, 3H), 3.76(s, 3H), 3.79(s, 3H), 6.66(br s, 1H), 6.78–6.83(m, 2H), 6.87(s, 1H), 6.98(s, 1H), 7.02(dd, J=2.4, 8.4Hz, 1H), 7.10(dd, J=2.4, 10.8Hz, 1H), 7.39–7.52(m, 3H)
IR(KBr) 3600–2800(br), 1627, 1609, 1530, 1494, 1463, 1390, 1325, 1213, 1154, 1127, 1052, 1028, 984cm$^{-1}$

I-1257 mp 198–200° C.
$^1$H NMR(CDCl$_3$) δ 1.43(t, J=7.5Hz, 3H), 3.00(s, 3H), 3.19–3.26(m, 2H), 3.76(s, 3H), 3.79(s, 3H), 6.69(br s, 1H), 6.79–6.85(m, 2H), 6.86(s, 1H), 6.97(s, 1H), 7.01(dd, J=2.4, 8.4Hz, 1H), 7.09(dd, J=2.4, 10.8Hz, 1H), 7.37–7.53(m, 3H)
IR(KBr) 3600–2800(br), 1611, 1530, 1492, 1495, 1445, 1389, 1355, 1325, 1207, 1163, 1141, 1122, 1051, 1025, 981cm$^{-1}$

I-1258 IR(KBr) 1612, 1526, 1490, 1444, 1349, 1301, 1196, 1129, 1038cm$^{-1}$
mp 102–103° C.
$^1$H NMR(CDCl$_3$) δ 2.27(s, 3H), 2.31(s, 3H), 3.00(s, 6H), 4.78(d, J=6.6Hz, 2H), 6.24(t, J=6.6Hz, 1H), 6.80(d, J=8.4Hz, 2H), 6.96–7.16(m, 5H), 7.26(d, J=8.4Hz, 2H)

I-1259 mp 114–115° C.
$^1$H NMR(CDCl$_3$) δ 1.75(s, 3H), 1.79(s, 3H), 3.61(s, 3H), 3.65(s, 3H), 3.74(s, 3H), 3.87(s, 3H), 3.88(s, 3H), 4.63(d, J=6.9Hz, 2H), 5.54–5.62(m, 1H), 6.68(s, 1H), 6.94–7.03(m, 5H), 7.54(d, J=9.0Hz, 2H)
IR(KBr) 3433, 2932, 1682, 1605, 1580, 1519, 1465, 1439, 1389, 1290, 1253, 1237, 1186, 1140, 1109, 1089, 1039, 1029, 992, 833cm$^{-1}$

TABLE 250

I-1260 mp 163–165° C.
$^1$H NMR(CDCl$_3$) δ 1.76(s, 3H), 1.81(s, 3H), 3.19(s, 3H), 3.72(s, 3H), 4.20–4.26(m, 4H), 4.62(d, J=6.6Hz, 2H), 5.55(m, 1H), 6.53(s, 1H), 7.00–7.20(m, 3H), 7.49(ABq, J=8.1Hz, 4H)
IR(KBr) 3433, 2933, 1523, 1483, 1463, 1433, 1371, 1359, 1340, 1299, 1266, 1227, 1220, 1172, 1149, 1127, 1098cm$^{-1}$

TABLE 250-continued

I-1261 mp 135–137° C.
$^1$H NMR(CDCl$_3$) δ -0.03–0.03(m, 2H), 0.36–0.42(m, 2H), 1.00(m, 1H), 1.75(s, 3H), 1.79(s, 3H), 2.56(s, 3H), 3.20(s, 3H), 3.48(d, J=4.8Hz, 2H), 3.78(s, 3H), 3.88(s, 3H), 4.63(d, J=6.9Hz, 2H), 5.54(m, 1H), 6.86(s, 1H), 6.95–6.97(m, 3H), 7.55 (ABq, J=8.7Hz, 4H)
IR(KBr) 3433, 2936, 1604, 1519, 1481, 1467, 1369, 1336, 1245, 1231, 1201, 1177, 1153, 1081cm$^{-1}$

I-1262 mp 181–182° C.
$^1$H NMR(CDCl$_3$) δ 1.76(s, 3H), 1.80(s, 3H), 3.72(s, 3H), 4.19–4.26(m, 4H), 4.62(d, J=6.9Hz, 2H), 4.91(bs, 1H), 5.55 (m, 1H), 6.53(s, 1H), 6.89–7.49(m, 7H)
IR(KBr) 3404, 1612, 1523, 1485, 1462, 1434, 1373, 1266, 1227, 1212, 1116, 1101cm$^{-1}$

I-1263 mp 80–82° C.
$^1$H NMR(CDCl$_3$) δ -0.05–0.09(m, 2H), 0.44–0.51(m, 2H), 1.04(m, 1H), 1.74(s, 3H), 1.78(s, 3H), 3.33(d, J=4.8Hz, 2H), 3.75(s, 3H), 3.88(s, 3H), 4.63(d, J=6.6Hz, 2H), 4.98(s, 1H), 5.57(m, 1H), 6.15(s, 1H), 6.46(s, 1H), 6.89–7.03(m, 5H), 7.52–7.56(m, 2H)
IR(KBr) 3374, 1614, 1523, 1490, 1465, 1446, 1391, 1267, 1235, 1172, 1113, 1073cm$^{-1}$

I-1264 mp 112–113° C.
$^1$H NMR(CDCl$_3$) δ 2.19(s, 3H), 2.28(s, 3H), 3.91(s, 3H), 5.20(s, 2H), 6.84–6.86(m, 1H), 6.92–6.97(m, 2H), 7.09(s, 1H), 7.16(s, 1H), 7.31–7.43(m, 5H), 7.47–7.49(m, 2H), 7.60(d, J=10.2Hz, 1H), 8.01(brs, 1H)
IR(KBr) 3421, 3303, 2935, 1711, 1519, 1490, 1365, 1231, 1198, 1178, 1134, 1009, 864cm$^{-1}$

TABLE 251

I-1265 mp 85–86° C.
$^1$H NMR(CDCl$_3$) δ 2.85(s, 3H), 3.32(s, 3H), 3.82(s, 3H), 3.96(s, 3H), 5.38(s, 2H), 7.04(s, 1H), 7.22(s, 1H), 7.25(d, J=8.4Hz, 1H), 7.35(d, J=8.4Hz, 1H), 7.48–7.67(m, 7H), 8.45(brs, 1H)
IR(KBr) 3432, 2938, 1740, 1608, 1517, 1483, 1396, 1366, 1271, 1179, 1111, 1080, 832, 810, 698cm$^{-1}$ I-1266 mp 79–80° C.
$^1$H NMR(CDCl$_3$) δ 2.14(s, 3H), 3.50(s, 3H), 4.95(brs, 1H), 5.22(s, 2H), 5.88(brs, 1H), 6.81(s, 1H), 6.94(d, J=8.1Hz, 2H), 7.02–7.14(m, 3H), 7.37–7.56(m, 7H)
IR(KBr) 3409, 2933, 1612, 1522, 1488, 1454, 1400, 1266, 1229, 1199, 1162, 1007, 834, 696cm$^{-1}$ I-1267 mp 87–88° C.
$^1$H NMR(CDCl$_3$) δ 2.13(s, 3H), 2.59(s, 3H), 3.20(s, 3H), 3.55(s, 3H), 5.22(s, 2H), 6.99–7.17(m, 5H), 7.34–7.48(m, 6H), 7.67(d, J=8.4Hz, 2H)
IR(KBr) 3428, 2931, 1612, 1522, 1488, 1454, 1400, 1266, 1230, 1163, 1007, 835cm$^{-1}$ I-1268 mp 76–77° C.
$^1$H NMR(CDCl$_3$) δ 1.72(s, 3H), 1.77(s, 6H), 1.81(s, 3H), 2.69(s, 3H), 3.24(s, 3H), 3.61(s, 3H), 3.79(s, 3H), 4.12–4.20(m, 1H), 4.55–4.61(m, 1H), 4.64(d, J=6.6Hz, 2H), 5.25(t, J=7.5Hz, 1H), 5.50(t, J=6.4Hz, 1H), 6.85(s, 1H), 7.05–7.11(m, 2H), 7.34–7.40(m, 3H)
IR(KBr) 3423, 2939, 1707, 1521, 1484, 1367, 1241, 1178, 1079, 1034, 972, 799, 521cm$^{-1}$ I-1269 mp 73–74° C.
$^1$H NMR(CDCl$_3$) δ 2.17(s, 3H), 2.28(s, 3H), 5.16(s, 2H), 5.71(brs, 1H), 6.83(d, J=8.1Hz, 1H), 6.97–7.00(m, 2H), 7.08 (s, 1H), 7.15(s, 1H), 7.32–7.33(m, 2H), 7.36–7.45(m, 5H), 7.60(d, J=10.5Hz, 1H), 8.05(brs, 1H)
IR(KBr) 3410, 2923, 1718, 1606, 1540, 1521, 1489, 1424, 1282, 1179, 976, 728cm$^{-1}$

TABLE 252

I-1270 mp 65–67° C.
$^1$H NMR(CDCl$_3$) δ 1.77(s, 3H), 1.81(s, 3H), 2.14(s, 3H), 2.72(s, 3H), 3.20(s, 3H), 3.56(s, 3H), 4.64(d, J=6.9Hz, 2H), 5.53(t, J=6.6Hz, 1H), 7.01–7.11(m, 3H), 7.18(s, 1H), 7.37(d, J=8.7Hz, 2H), 7.67(d, J=8.7Hz, 2H),
IR(KBr) 3434, 2938, 1519, 1478, 1365, 1267, 1176, 1151, 968, 871, 799, 524cm$^{-1}$

I-1271 mp 99–100° C.
$^1$H NMR(CDCl$_3$) δ 1.76(s, 6H), 1.79(s, 3H), 1.81(s, 3H), 3.52(s, 3H), 3.72(s, 3H), 4.61(d, J=7.2Hz, 2H), 5.36(t, J=6.6Hz, 1H), 5.53(t, J=5.7Hz, 1H), 5.69(brs, 1H), 5.81(brs, 1H), 6.43(s, 1H), 6.46–6.52(m, 1H), 6.95(s, 2H), 7.05(s, 1H), 7.10–7.16(m, 1H)
IR(KBr) 3496, 3407, 2933, 1638, 1535, 1493, 1098, 1000cm$^{-1}$ I-1272 mp 75–76° C.
$^1$H NMR(CDCl$_3$) δ 2.17(s, 3H), 2.28(s, 3H), 3.12(s, 3H), 5.18(s, 2H), 7.09–7.14(m, 4H), 7.26–7.47(m, 8H), 7.61(d, J=11.4Hz, 1H), 8.00(brs, 1H)
IR(KBr) 3330, 2927, 1731, 1607, 1541, 1521, 1488, 1364, 1290, 1169, 1105, 975, 878, 811cm$^{-1}$ I-1273 mp 112–113° C.
$^1$H NMR(CDCl$_3$) δ 1.76(s, 3H), 1.81(s, 3H), 2.11(s, 3H), 3.47(s, 3H), 4.64(d, J=6.6Hz, 2H), 4.83(brs, 1H), 5.56(t, J=7.2Hz, 1H), 5.84(brs, 1H), 6.78(s, 1H), 6.91(d, J=8.7Hz, 2H), 7.02–7.10(m, 3H), 751(d, J=8.4Hz, 2H),
IR(KBr) 3498, 2978, 1613, 1522, 1487, 1453, 1302, 1204, 1232, 1196, 987, 812cm$^{-1}$ I-1274 oil
$^1$H NMR(CDCl$_3$) δ 1.73(s, 3H), 1.76(s, 3H), 1.77(s, 3H), 1.79(s, 3H), 2.22(s, 3H), 2.27(s, 3H), 3.73(d, J=6.0Hz, 2H), 3.88(s, 3H), 4.63(d, J=6.6Hz, 2H), 5.36(t, J=6.0Hz, 1H), 5.57(t, J=6.6Hz, 1H), 6.40–6.51(m, 2H), 6.87–6.95(m, 3H), 7.05–7.14(m, 3H)
IR(CHCl$_3$) 3021, 2934, 1628, 1523, 1492, 1235, 1219, 1139cm$^{-1}$

TABLE 253

I-1275 mp 64–65° C.
$^1$H NMR(CDCl$_3$) δ 1.74(s, 3H), 1.77(s, 6H), 1.82(s, 3H), 2.16(s, 3H), 2.29(s, 3H), 3.23(s, 3H), 4.36(d, J=7.5Hz, 2H),

TABLE 253-continued

| | |
|---|---|
| | 4.64(d, J=6.3Hz, 2H), 5.28(t, J=8.4Hz, 1H), 5.51(t, J=6.3Hz, 1H), 7.01–7.16(m, 6H), 7.24–7.35(m, 2H) |
| | IR(KBr) 3422, 2926, 1698, 1519, 1489, 1367, 1209, 1170, 962, 807cm$^{-1}$ |
| I-1276 | oil |
| | $^1$H NMR(CDCl$_3$) δ 2.21(s, 3H), 2.26(s, 3H), 3.95(d, J=6.6Hz, 2H), 4.28(brs, 1H), 4.78(d, J=6.0Hz, 2H), 6.05(t, J=6.3Hz, 1H), 6.24(t, J=6.3Hz, 1H), 6.36–6.49(m, 2H), 6.97–7.15(m, 6H) |
| | IR(CHCl$_3$) 3446, 3009, 1628, 1525, 1492, 1274, 1224, 1130, 883cm$^{-1}$ |
| I-1277 | mp 64–65° C. |
| | $^1$H NMR(CDCl$_3$) δ 1.76(s, 3H), 1.80(s, 6H), 1.85(s, 3H), 2.23(s, 3H), 2.30(s, 3H), 3.74(d, J=6.3Hz, 2H), 4.64(d, J=6.0Hz, 2H), 5.38(t, J=6.6Hz, 1H), 5.55(t, J=6.9Hz, 1H), 5.73(brs, 1H), 6.41–6.50(m, 2H), 6.84–7.15(m, 6H) |
| | IR(KBr) 3354, 2971, 1627, 1522, 1490, 1274, 1200, 1128, 990, 843cm$^{-1}$ |
| I-1278 | mp 153–154° C. |
| | $^1$H NMR(CDCl$_3$) δ 1.77(s, 3H), 1.82(s, 3H), 1.95(s, 12H), 4.64(d, J=6.9Hz, 2H), 4.78(s, 1H), 5.57(t, J=6.9Hz, 1H), 6.85(ddd, J=8.3, 2.1, 1.2Hz, 1H), 6.90(d, J=8.6Hz, 2H), 6.92(dd, J=12.0, 2.1Hz, 1H), 7.04(d, J=8.6Hz, 2H), 7.04(t, J=8.3Hz, 1H), |
| | IR(KBr) 3433, 1514, 1293, 1262, 1242, 1112, 984cm$^{-1}$ |
| I-1279 | mp 115–117° C. |
| | $^1$H NMR(CDCl$_3$) δ 1.76(s, 3H), 1.81(s, 3H), 2.23(s, 3H), 3.21(s, 3H), 3.81(s, 3H), 4.63(d, J=6.6Hz, 2H), 5.55(t, J=6.6Hz, 1H), 6.81(s, 1H), 7.02(t, J=8.6Hz, 1H), 7.20(s, 1H), 7.24–7.28(m, 1H), 7.33–7.44(m, 3H) |
| | IR(KBr) 3434, 1522, 1492, 1337, 1218, 1200, 1148, 979, 876cm$^{-1}$ |

TABLE 254

| | |
|---|---|
| I-1280 | mp 88–90° C. |
| | $^1$H NMR(CDCl$_3$) δ 1.76(s, 3H), 1.80(s, 3H), 2.24(s, 3H), 3.80(s, 3H), 4.63(d, J=6.7Hz, 2H), 4.88(br s, 1H), 5.55(t, J=6.7Hz, 1H), 6.83(s, 1H), 6.90(d, J=8.7Hz, 2H), 7.01(t, J=8.6Hz, 1H), 7.18(s, 1H), 7.24–7.28(m, 3H), 7.36(dd, J=12.9, 2.1Hz, 1H) |
| | IR(KBr) 3400, 1523, 1493, 1263, 1217, 1128, 977, 836cm$^{-1}$ |
| I-1281 | mp 158–159° C. |
| | $^1$H NMR(CDCl$_3$) δ 1.76(s, 3H), 1.80(d, J=0.3Hz, 3H), 2.10(s, 3H), 2.34(s, 3H), 2.50(s, 3H), 3.87(s, 3H), 4.63(d, J=6.9Hz, 2H), 5.14(s, 1H), 5.55(m, 1H), 5.88(s, 1H), 6.77–6.82(m, 2H), 6.85–6.91(m, 2H), 6.98(d, J=8.1Hz, 1H), 7.13(s, 1H), 7.18–7.24(m, 2H) |
| | IR(KBr) 3465, 1610, 1516, 1473, 1382, 1322, 1307, 1266, 1240, 1213, 1179, 1168, 1147, 1100, 982, 836cm$^{-1}$ |
| I-1282 | mp 85–86° C. |
| | $^1$H NMR(CDCl$_3$) δ 0.99(d, J=6.2Hz, 6H), 1.71–1.98(m, 3H), 2.27(s, 3H), 2.29(s, 3H), 3.20(s, 3H), 3.88(s, 3H), 4.10(t, J=6.8Hz, 2H), 6.88(dd, J=2.0, 8.6Hz, 1H), 6.88(d, J=2.0Hz, 1H), 6.95(d, J=8.6Hz, 1H), 7.30–7.46(m, 4H) |
| | IR(KBr) 1519, 1488, 1375, 1255, 1243, 1214, 1204, 1173, 1154, 1134, 867, 850, 792cm$^{-1}$ |
| I-1283 | mp 117–118° C. |
| | $^1$H NMR(CDCl$_3$) δ 0.99(d, J=6.3Hz, 6H), 1.75–1.94(m, 3H), 2.27(s, 3H), 2.28(s, 3H), 3.88(s, 3H), 4.10(t, J=6.6Hz, 2H), 4.91(s, 1H), 6.86–6.91(m, 4H), 6.94(d, J=8.7Hz, 1H), 7.12(s, 1H), 7.15(s, 1H), 7.22–7.27(m, 2H) |
| | IR(KBr) 3438, 1611, 1522, 1490, 1475, 1464, 1446, 1256, 1242, 1212, 1180, 1171, 1137, 1032, 834, 818cm$^{-1}$ |
| I-1284 | mp 156–157° C. |
| | $^1$H NMR(CDCl$_3$) δ 3.46(s, 3H), 3.76(s, 3H), 3.89(s, 3H), 4.78(d, J=6.3Hz, 2H), 4.99(s, 1H), 5.96(s, 1H), 6.25(t, J=6.3Hz, 1H), 6.47(s, 1H), 6.90–6.95(m, 2H), 6.93(d, J=7.8Hz, 1H), 7.04(dd, J=2.1, 7.8Hz, 1H), 7.04(d, J=2.1Hz, 1H), 7.51–7.57(m, 2H) |
| | IR(KBr) 3455, 1612, 1522, 1487, 1456, 1396, 1269, 1234, 1223, 1209, 1173, 1140, 1115, 1024, 885, 825, 813cm$^{-1}$ |

TABLE 255

| | |
|---|---|
| I-1285 | mp 84–85° C. |
| | $^1$H NMR(CDCl$_3$) δ 1.00(d, J=6.6Hz, 6H), 1.71–1.96(m, 3H), 2.27(s, 6H), 4.11(t, J=6.9Hz, 2H), 4.80(br s, 1H), 6.86–6.92(m, 2H), 6.97–7.14(m, 5H), 7.22–7.27(m, 2H) |
| | IR(KBr) 3389, 1523, 1491, 1476, 1427, 1301, 1276, 1233, 1196, 1168, 1126, 836, 815cm$^{-1}$ |
| I-1286 | mp 152–153° C. |
| | $^1$H NMR(CDCl$_3$) δ 1.76(s, 3H), 1.80(d, J=0.6Hz, 3H), 2.12(s, 3H), 2.20(s, 3H), 3.39(s, 3H), 3.87(s, 3H), 4.64(d, J=6.3Hz, 2H), 4.79(br s, 1H), 5.56–5.61(m, 1H), 6.82–6.97(m, 6H), 7.21–7.26(m, 2H) |
| | IR(CHCl$_3$) 3596, 3440, 3011, 2935, 1676, 1612, 1588, 1518, 1473, 1449, 1259, 1238, 1173cm$^{-1}$ |
| I-1287 | mp 123–125° C. |
| | $^1$H NMR(CDCl$_3$) δ −0.01–0.08(m, 2H), 0.44–0.50(m, 2H), 1.01(m, 1H), 3.21(s, 3H), 3.34(d, J=7.5Hz, 2H), 3.75(s, 3H), 3.91(s, 3H), 5.21(s, 2H), 6.08(s, 1H), 6.45(s, 1H), 6.97–7.04(m, 3H), 7.26–7.72(m, 9H) |
| I-1288 | mp 177–178° C. |
| | $^1$H NMR(CDCl$_3$) δ 0.27(t, J=4.8Hz, 1H), 0.60(dd, J=4.8, 8.7Hz, 1H), 1.13(s, 3H), 1.17(s, 3H), 1.13–1.22(m, 1H), 3.46 (s, 3H), 3.75(s, 3H), 3.80(s, 3H), 4.00(dd, J=7.8, 10.5Hz, 1H), 4.12(dd, J=6.6, 10.5Hz, 1H), 4.95(bs, 1H), 5.91(s, 1H), 6.46(s, 1H), 6.91–7.02(m, 5H), 7.52–7.56(m, 2H) |
| | IR(KBr) 3479, 3434, 3389, 2940, 1614, 1589, 1523, 1490, 1466, 1395, 1361, 1319, 1271, 1238, 1218, 1174, 1137, 1117, 1072, 1011cm$^{-1}$ |
| I-1289 | mp 153–155° C. |
| | $^1$H NMR(CDCl$_3$) δ 1.76(s, 3H), 1.80(s, 3H), 2.25(s, 3H), 3.80(s, 3H), 3.89(s, 3H), 4.63–4.65(d, J=6.9Hz, 2H), 4.80(br, 1H), 5.57(m, 1H), 6.86–6.97(m, 6H), 7.18(s, 1H), 7.45–7.48(m, 2H) |
| | IR(CHCl$_3$) 3596, 1609, 1523, 1493, 1464, 1387, 1256, 1173, 1138, 1042, 1032, 997, 834cm$^{-1}$ |

TABLE 256

| | |
|---|---|
| I-1290 | mp 150–152° C.<br>¹H NMR(CDCl₃) δ 2.25(s, 3H), 3.80(s, 3H), 3.90(s, 3H), 4.74–4.80(m, 3H), 6.26(t, J=6.0Hz, 1H), 6.85–6.92(m, 6H), 7.19(s, 1H), 7.45–7.48(m, 2H)<br>IR(CHCl₃) 3596, 2958, 2938, 1609, 1523, 1493, 1464, 1389, 1328, 1257, 1173, 1140, 1102, 1030, 886, 854, 834cm⁻¹ |
| I-1291 | mp 117–118° C.<br>¹H NMR(CDCl₃) δ 1.76(s, 3H), 1.79(s, 3H), 2.28(s, 3H), 2.31(s, 3H), 3.01(s, 6H), 3.88(s, 3H), 4.63(d, J=6.6Hz, 2H), 5.53–5.60(m, 1H), 6.76–6.96(m, 5H), 7.15(s, 2H), 7.28(d, J=8.7Hz, 2H)<br>IR(KBr) 1611, 1529, 1490, 1447, 1359, 1322, 1239, 1214, 1193, 1135, 1038,cm⁻¹ |
| I-1292 | mp 116–118° C.<br>¹H NMR(CDCl₃) 2.24(s, 3H), 3.81(s, 3H), 4.77(d, J=6.3Hz, 2H), 4.90(br s, 1H), 6.23(t, J=6.3Hz, 1H), 6.83(s, 1H), 6.90 (d, J=8.7Hz, 2H), 6.99(t, J=8.6Hz, 1H), 7.17(s, 1H), 7.25(d, J=8.7Hz, 2H), 7.27(ddd, J=8.6, 2.1, 1.2Hz, 1H), 7.37 (dd, J=12.6, 2.1Hz, 1H)<br>IR(KBr) 3596, 1731, 1613, 1523, 1493, 1259, 1130, 1033, 885cm⁻¹ |
| I-1293 | mp 151–154° C.<br>¹H NMR(CDCl₃) δ 2.23(s, 3H), 3.21(s, 3H), 3.80(s, 3H), 3.93(s, 3H), 5.20(s, 2H), 6.81(s, 1H), 6.95(d, J=8.4Hz, 1H), 7.05(dd, J=8.4, 2.1Hz, 1H), 7.15(d, J=2.1Hz, 1H), 7.21(s, 1H), 7.30–7.50(m, 9H)<br>IR(KBr) 1490, 1361, 1243, 1148, 1032, 876cm⁻¹ |
| I-1294 | mp 119–121° C.<br>¹H NMR(CDCl₃) δ 1.76(s, 3H), 1.79(s, 3H), 2.24(s, 3H), 3.21(s, 3H), 3.80(s, 3H), 3.91(s, 3H), 4.63(d, J=6.5Hz, 2H), 5.56(t, J=6.5Hz, 1H), 6.82(s, 1H), 6.94(d, J=8.4Hz, 1H), 7.10(dd, J=8.4, 1.5Hz, 1H), 7.13(d, J=1.5Hz, 1H), 7.23(s, 1H), 7.36(d, J=8.3Hz, 2H), 7.43(d, J=8.3Hz, 2H)<br>IR(KBr) 1519, 1490, 1364, 1156, 1031, 971, 858cm⁻¹ |

TABLE 257

| | |
|---|---|
| I-1295 | mp 135–137° C.<br>¹H NMR(CDCl₃) δ 1.75(s, 3H), 1.78(s, 3H), 2.25(s, 3H), 3.80(s, 3H), 3.90(s, 3H), 4.63(d, J=6.7Hz, 2H), 4.95(s, 1H), 5.56(t, J=6.7Hz, 1H), 6.84(s, 1H), 6.90(d, J=8.7Hz, 2H), 6.94(d, J=8.3Hz, 1H), 7.10(dd, J=8.3, 2.1Hz, 1H), 7.13(d, J=2.1Hz, 1H), 7.21(s, 1H), 7.26(d, J=8.7Hz, 2H)<br>IR(KBr) 3423, 1609, 1523, 1493, 1258, 1219, 1142, 1033, 834cm⁻¹ |
| I-1296 | mp 140–141° C.<br>¹H NMR(CDCl₃) δ 1.46(t, J=6.9Hz, 3H), 3.46(s, 3H), 3.75(s, 3H), 4.13(q, J=6.9Hz, 2H), 4.77(d, J=6.0Hz, 2H), 5.05 (s, 1H), 5.95(s, 1H), 6.25(t, J=6.0Hz, 1H), 6.47(s, 1H), 6.90–6.97(m, 3H), 7.01–7.06(m, 2H), 7.50–7.57(m, 2H)<br>IR(KBr) 3463, 3433, 1613, 1521, 1491, 1259, 1400, 1267, 1235, 1204, 1167, 1136, 1112, 1097, 1076, 1019, 993, 882, 824, 811cm⁻¹ |
| I-1297 | mp 204–205° C.<br>¹H NMR(DMSO-d₆) δ 2.21(s, 3H), 2.22(s, 3H), 2.87(s, 3H), 3.02(s, 3H), 4.96(s, 2H), 6.80–6.86(m, 2H), 7.05–7.11(m, 4H), 7.13–7.19(m, 2H), 7.20–7.27(m, 1H)<br>IR(KBr) 3153, 1644, 1590, 1522, 1487, 1437, 1314, 1264, 1231, 1197, 1127, 1067, 833cm⁻¹ |
| I-1298 | mp 155–158° C.<br>¹H NMR(CDCl₃) δ 3.21(s, 3H), 3.45(s, 3H), 3.75(s, 3H), 4.42(s, 4H), 5.93(s, 1H), 6.44(s, 1H), 6.90–6.96(m, 1H), 7.06–7.11 (m, 1H), 7.19–7.39(m, 13H), 7.67–7.72(m, 2H)<br>IR(KBr) 3445, 2940, 1615, 1521, 1483, 1367, 1149, 875, 707, 546, 526cm⁻¹ |
| I-1299 | mp 174–175° C.<br>¹H NMR(CDCl₃) δ 2.15(s, 3H), 3.20(s, 3H), 3.53(s, 3H), 3.78(s, 3H), 4.40(s, 4H), 6.82(s, 1H), 6.91–7.01(m, 2H), 7.11–7.39 (m, 13H), 7.65–7.70(m, 2H)<br>IR(KBr) 3028, 2936, 1618, 1520, 1482, 1365, 1176, 1151, 1079, 871, 798, 698, 527cm⁻¹ |

TABLE 258

| | |
|---|---|
| I-1300 | mp 218–221° C.<br>¹H NMR(CDCl₃) δ 2.69(s, 3H), 3.21(s, 3H), 3.55(s, 3H), 3.77(s, 3H), 6.83(s, 1H), 6.86–6.93(m, 1H), 7.02–7.15(m, 2H), 7.35–7.41(m, 2H), 7.66–7.71(m, 2H)<br>IR(KBr) 3435, 3389, 2940, 1635, 1525, 1362, 1175, 1152, 1076, 962, 874, 802, 527cm⁻¹ |
| I-1301 | mp 209–211° C.<br>¹H NMR(CDCl₃) δ 2.91(s, 3H), 3.22(s, 3H), 3.54(s, 3H), 3.78(s, 3H), 6.86(s, 1H), 7.26–7.33(m, 2H), 7.37–7.42(m, 2H), 7.64–7.71(m, 2H), 8.15(s, 1H), 8.34–8.41(m, 1H)<br>IR(KBr) 3336, 2943, 1736, 1539, 1480, 1356, 1174, 1151, 1077, 881, 799, 523, 507cm⁻¹ |
| I-1302 | powder<br>¹H NMR(CDCl₃) δ 1.50(s, 3H), 1.71(s, 3H), 2.78(s, 3H), 3.23(s, 3H), 3.55(s, 3H), 3.78(s, 3H), 4.11–4.20(m, 1H), 4.54–4.63 (m, 1H), 5.20–5.28(m, 1H), 6.87(s, 1H), 7.25–7.31(m, 3H), 7.37–7.42(m, 2H), 7.66–7.72(m, 2H)<br>IR(KBr) 2941, 1702, 1482, 1369, 1203, 1176, 1152, 1080, 964, 873, 797, 525cm⁻¹ |
| I-1303 | mp 133–136° C.<br>¹H NMR(CDCl₃) δ 1.73(s, 3H), 1.77(s, 3H), 3.45(s, 3H), 3.74–3.78(m, 5H), 4.96(s, 1H), 5.34–5.42(m, 1H), 5.94(s, 1H), 6.45(s, 1H), 6.75–6.81(m, 1H), 6.89–6.95(m, 2H), 7.10–7.18(m, 2H), 7.51–7.56(m, 2H)<br>IR(KBr) 3401, 2935, 1626, 1614, 1527, 1490, 1402, 1267, 1223, 1113, 1071, 1005, 829, 589cm⁻¹ |
| I-1304 | mp 170–171° C.<br>¹H NMR(CDCl₃) δ 2.11(s, 3H), 3.47(s, 3H), 4.40(s, 4H), 4.91(s, 1H), 5.81(s, 1H), 6.77(s, 1H), 6.86–7.08(m, 5H), 7.22–7.33 (m, 10H), 7.48–7.53(m, 2H)<br>IR(KBr) 3483, 3029, 1612, 1523, 1489, 1453, 1400, 1265, 1215, 834, 749, 698, 494, 526cm⁻¹ |

TABLE 259

| | |
|---|---|
| I-1305 | mp 166–168° C.<br>$^1$H NMR(CDCl$_3$) δ 2.15(s, 3H), 2.17(s, 3H), 3.19(s, 3H), 4.21–4.59(m, 4H), 6.84–7.05(m, 3H), 7.14–7.15(m, 1H), 7.20–7.38 (m, 12H), 7.63–7.69(m, 2H)<br>IR(KBr) 3028, 2938, 1519, 1476, 1454, 1363, 1174, 1151, 969, 873, 801, 700, 525cm$^{-1}$ |
| I-1306 | mp 210–212° C.<br>$^1$H NMR(CDCl$_3$) δ 2.11(s, 3H), 2.90(s, 3H), 3.44(s, 3H), 3.52(s, 3H), 6.82–7.02(m, 3H), 7.30(s, 1H), 7.44–7.49(m, 2H), 7.65–7.71(m, 2H)<br>IR(KBr) 3401, 2850, 1632, 1478, 1365, 1177, 1151, 967, 877, 800, 526cm$^{-1}$ |
| I-1307 | mp 171–173° C.<br>$^1$H NMR(CDCl$_3$) δ 2.13(s, 3H), 2.95(s, 3H), 3.22(s, 3H), 3.55(s, 3H), 7.17–7.22(m, 3H), 7.35–7.41(m, 2H), 7.64–7.69(m, 2H), 8.17(s, 1H), 8.37–8.43(m, 1H)<br>IR(KBr) 3431, 3034, 2942, 1741, 1538, 1478, 1364, 1291, 1152, 971, 870, 801, 525cm$^{-1}$ |
| I-1308 | powder<br>$^1$H NMR(CDCl$_3$) δ 1.47(s, 3H), 1.70(s, 3H), 2.11(s, 3H), 2.67–3.15(m, 3H), 3.22(s, 3H), 3.56(s, 3H), 4.13–4.22(m, 1H), 4.54–4.63(m, 1H), 5.21–5.28(m, 1H), 7.09–7.42(m, 6H), 7.63–7.71(m, 2H)<br>IR(CHCl$_3$) 2940, 1700, 1519, 1478, 1372, 1175, 1151, 968cm$^{-1}$ |
| I-1309 | mp 139–141° C.<br>$^1$H NMR(CDCl$_3$) δ 1.74(s, 3H), 1.78(s, 3H), 2.13(s, 3H), 3.48(s, 3H), 3.77(d, J=6.6Hz, 2H), 4.70–5.20(br s, 1H), 5.35–5.42 (m, 1H), 5.77(s, 1H), 6.77–6.83(m, 2H), 6.88–6.99(m, 4H), 7.48–7.54(m, 2H)<br>IR(KBr) 3525, 3377, 2931, 1625, 1526, 1488, 1222, 1164, 1011, 833cm$^{-1}$ |

TABLE 260

| | |
|---|---|
| I-1310 | mp 177–179° C.<br>$^1$H NMR(CDCl$_3$) δ 1.76(s, 3H), 1.81(s, 3H), 3.20(t, J=8.4Hz, 2H), 3.21(t, J=8.4Hz, 2H), 4.521(d, J=7.2Hz, 2H), 4.523(t, J=8.4Hz, 2H), 4.90(brs, 1H), 5.53(t, J=6.8Hz, 1H), 6.71(s, 1H), 6.89(d, J=8.4Hz, 2H), 6.98(d, J=8.7Hz, 2H), 7.41(d, J=8.7Hz, 2H), 7.45(d, J=9.0Hz, 2H)<br>IR(KBr)3389, 2971, 2911, 1611, 1525, 1394, 1238, 1175, 997, 828cm$^{-1}$ |
| I-1311 | mp 175–177° C.<br>$^1$H NMR(CDCl$_3$) δ 3.20(t, J=8.3Hz, 4H), 4.53(t, J=8.4Hz, 4H), 4.70(d, J=6.3Hz, 2H), 4.88(brs, 1H), 6.19(t, J=6.2Hz, 1H), 6.89(d, J=8.7Hz, 2H), 6.96(d, J=9.0Hz, 2H), 7.41(d, J=9.0Hz, 2H), 7.47(d, J=8.7Hz, 2H)<br>IR(KBr)3409, 3269, 2934, 2901, 1524, 1480, 1395, 1235, 1223, 1003, 881, 817cm$^{-1}$ |
| I-1312 | mp 186–187° C.<br>$^1$H NMR(CDCl$_3$) δ 2.06(s, 3H), 2.16(s, 3H), 4.72(s, 1H), 4.80(d, J=6.3Hz, 2H), 4.83(s, 1H), 6.25(t, J=6.3Hz, 1H)6.76 (s, 1H), 6.86–6.92(m, 2H), 7.03–7.13(m, 3H), 7.21–7.26(m, 2H)<br>IR(CHCl$_3$)3689, 3598, 3551, 3024, 3008, 1732, 1614, 1520, 1487, 1260, 1223cm$^{-1}$ |
| I-1313 | mp 201° C.<br>$^1$H NMR(CDCl$_3$) δ 2.08(s, 3H), 2.17(s, 3H), 3.88(s, 3H), 4.80(d, J=6.3Hz, 2H), 4.90(br s, 1H), 4.99(s, 1H), 6.26(t, J=6.3Hz, 1H), 6.77(s, 1H), 6.85–6.92(m, 4H), 7.01(d, J=6.9Hz, 1H), 7.22–7.27(m, 2H)<br>IR(CHCl$_3$)3688, 3598, 3538, 3024, 3014, 2938, 1731, 1631, 1520, 1488, 1240, 1172cm$^{-1}$ |
| I-1314 | mp 132–134° C.<br>$^1$H NMR(CDCl$_3$) δ 2.12(s, 3H), 2.29(s, 3H), 3.00(s, 6H), 3.74(br, 2H), 6.62(dd, J=2.4, 8.1Hz, 1H), 6.77–6.82(m, 3H), 7.01–7.05(m, 2H), 7.12(s, 1H), 7.26–7.31(m, 2H)<br>IR(KBr)3600–2800(br), 1610, 1523, 1483, 1443, 1325, 1297cm$^{-1}$ |

TABLE 261

| | |
|---|---|
| I-1315 | mp 123–125° C.<br>$^1$H NMR(CDCl$_3$) δ 2.13(s, 3H), 2.29(m, 4H), 3.00(s, 6H), 3.98(br, 3H), 6.63(dd, J=2.4, 8.1Hz, 1H), 6.77–6.81(m, 3H), 7.02(s, 1H), 7.09–7.13(m, 2H), 7.25–7.32(m, 2H)<br>IR(KBr)3600–2800(br), 1609, 1525, 1488, 1443, 1356, 1232, 1194cm$^{-1}$ |
| I-1316 | mp 125–127° C.<br>$^1$H NMR(CDCl$_3$) δ 2.10(s, 3H), 2.31(s, 3H), 3.01(s, 6H), 6.77–6.84(m, 2H), 7.00(s, 1H), 7.15(s, 1H), 7.27–7.33(m, 3H), 7.52(dd, J=3.0, 12.9Hz, 1H), 7.09(d, J=3.0Hz, 1H), 7.95(br s, 1H)<br>IR(KBr)3600–2800(br), 1707, 1611, 1528, 1484, 1350, 1279, 1229, 1196, 1154cm$^{-1}$ |
| I-1317 | mp 94–95° C.<br>$^1$H NMR(CDCl$_3$) δ 1.77(s, 3H), 1.81(s, 3H), 2.26(s, 6H), 4.63(d, J=6.6Hz, 2H), 5.51–5.60(m, 1H), 6.01(s, 2H), 6.78–6.89 (m, 3H), 6.97–7.15(m, 5H) |
| I-1318 | $^1$H NMR(CDCl$_3$) δ 1.77(s, 3H), 1.82(s, 3H), 2.29(s, 6H), 4.64(d, J=6.3Hz, 2H), 5.53–5.60(m, 1H), 6.99–7.21(m, 5H), 7.33–7.39(m, 2H), 7.49(d.d, J=5.4 & 0.3Hz, 1H), 7.80(s, 1H), 7.92(d, J=8.1Hz, 1H) |
| I-1319 | mp 188–189° C.<br>$^1$H NMR(CDCl$_3$) δ 1.31(t, J=7.5Hz, 3H), 2.26(s, 3H), 2.29(s, 3H), 2.68(q, J=7.5Hz, 2H), 5.17(s, 2H), 5.70(brs, 1H), 6.83(d, J=6.8Hz, 1H), 6.98–7.00(m, 2H), 7.13(d, J=9.0Hz, 2H), 7.26–7.30(m, 2H), 7.38–7.48(m, 5H), 7.78(brs, 1H), 7.86 (d, J=8.7Hz, 1H)<br>IR(KBr)3444, 3269, 1710, 1533, 1487, 1269, 1244, 1199, 1174, 744, 697cm$^{-1}$ |
| I-1320 | mp 157–159° C.<br>$^1$H NMR(CDCl$_3$) δ 1.30(t, J=7.6Hz, 3H), 2.27(s, 3H), 2.28(s, 3H), 2.68(q, J=7.2Hz, 2H), 3.91(s, 3H), 5.21(s, 2H), 6.81–6.97(m, 3H), 7.14(d, J=7.6Hz, 2H), 7.25–7.51(m, 7H), 7.79(brs, 1H), 7.86(d, J=8.8Hz, 1H)<br>IR(KBr)3434, 3260, 1707, 1519, 1501, 1488, 1260, 1241, 1213, 1172, 744, 697cm$^{-1}$ |

TABLE 262

| | |
|---|---|
| I-1321 | mp 186–187° C.<br>$^1$H NMR(CDCl$_3$) δ 1.30(t, J=8.4Hz, 3H), 2.26(s, 3H), 2.27(s, 3H), 2.68(q, J=7.5Hz, 2H), 5.20(s, 2H), 7.04–7.14(m, 6H), 7.26–7.50(m, 6H), 7.79(brs, 1H), 7.86(d, J=8.7Hz, 1H)<br>IR(KBr)3436, 3266, 1709, 1536, 1521, 1487, 1267, 1199, 1176, 744, 697cm$^{-1}$ |
| I-1322 | mp 136–137° C.<br>$^1$H NMR(CDCl$_3$) δ 1.32(t, J=7.5Hz, 3H), 2.28(s, 3H), 2.30(s, 3H), 2.70(q, J=7.5Hz, 2H), 3.13(s, 3H), 5.19(s, 2H), 7.12–7.15(m, 3H), 7.26–7.29(m, 3H), 7.37–7.50(m, 5H), 7.80(brs, 1H), 7.87(d, J=9.0Hz, 1H)<br>IR(KBr)3435, 1725, 1536, 1486, 1363, 1292, 1266, 1179, 1163, 1108, 7970, 895, 811, 525cm$^{-1}$ |
| I-1323 | mp 150–151° C.<br>$^1$H NMR(CDCl$_3$) δ 2.18(s, 3H), 2.27(s, 3H), 5.20(s, 2H), 7.04–7.14(m, 6H), 7.26–7.50(m, 6H), 7.60(d, J=12.0Hz, 1H), 7.94(brs, 1H)<br>IR(KBr)3421, 3302, 1712, 1523, 1490, 1422, 1299, 1274, 1205, 1176, 1132, 743, 697cm$^{-1}$ |
| I-1324 | mp 83–84° C.<br>$^1$H NMR(CDCl$_3$) δ 1.30(t, J=7.6Hz, 3H), 1.77(s, 3H), 1.78(s, 3H), 1.81(s, 6H), 2.31(s, 3H), 2.34(s, 3H), 2.56(q, J=7.6Hz, 2H), 3.80(d, J=6.4Hz, 2H), 3.90(s, 3H), 4.65(d, J=6.2Hz, 2H), 5.44(d, J=6.2Hz, 2H), 5.44(t, J=5.2Hz, 1H), 5.59 (t, J=5.4Hz, 1H), 6.73(d, J=8.0Hz, 1H), 6.92–6.94(m, 3H), 7.12–7.20(m, 4H)<br>IR(KBr)3428, 3374, 2964, 1607, 1519, 1494, 1458, 1311, 1256, 1239, 1139, 1036, 1002, 855, 820cm$^{-1}$ |
| I-1325 | mp 113–114° C.<br>$^1$H NMR(CDCl$_3$) δ 1.30(t, J=7.4Hz, 3H), 1.76(s, 3H), 1.78(s, 3H), 1.80(s, 3H), 1.84(s, 3H), 2.30(s, 3H), 2.32(s, 3H), 2.55(q, J=7.6Hz, 2H), 3.79(d, J=6.6Hz, 2H), 4.63(d, J=6.6Hz, 2H), 5.43(t, J=5.6Hz, 1H), 5.55(t, J=6.6Hz, 1H), 5.73(brs, 1H), 6.72(d, J=8.0Hz, 1H), 6.83–6.98(m, 3H), 7.11–7.19(m, 4H)<br>IR(KBr)3413, 3298, 2965, 2924, 1518, 1494, 1435, 1242, 1127, 1013, 883cm$^{-1}$ |

TABLE 263

| | |
|---|---|
| I-1326 | mp 81–82° C.<br>$^1$H NMR(CDCl$_3$) δ 1.29(t, J=7.4Hz, 3H), 1.74(s, 3H), 1.77(s, 3H), 1.78(s, 3H), 1.81(s, 3H), 2.27(s, 3H), 2.31(s, 3H), 2.54(q, J=7.2Hz, 2H), 3.79(d, J=7.2Hz, 2H), 4.63(d, J=6.6Hz, 2H), 5.42(t, J=6.4Hz, 1H), 5.55(t, J=6.6Hz, 1H), 6.71(d, J=8.0Hz, 1H), 7.04–7.19(m, 7H)<br>IR(KBr)3413, 2969, 2912, 2856, 1613, 1520, 1492, 1295, 1261, 1127, 1004, 881, 813cm$^{-1}$ |
| I-1327 | mp 94–95° C.<br>$^1$H NMR(CDCl$_3$) δ 1.74(s, 3H), 1.77(s, 6H), 1.81(s, 3H), 2.21(s, 3H), 2.26(s, 3H), 3.72(d, J=6.9Hz, 2H), 4.63(d, J=6.3Hz, 2H), 5.35(t, J=6.9Hz, 1H), 5.55(t, J=6.9Hz, 1H), 6.37–6.48(m, 2H), 7.01–7.13(m, 6H)<br>IR(KBr)3423, 2967, 2918, 1627, 1525, 1488, 1296, 1267, 1129, 981, 837, 805cm$^{-1}$ |
| I-1328 | mp 178–180° C.(decomp.)<br>$^1$H NMR(DMSO-d$_6$) δ 3.30(s, 3H), 3.64(s, 3H), 4.45(s, 2H), 5.65(s, 2H), 6.39(s, 1H), 6.65(dd, J=8.4, 2.1Hz, 1H), 6.74 (d, J=2.1Hz, 1H), 6.84(d, J=8.7Hz, 2H), 6.99(d, J=8.4Hz, 1H), 7.43(d, J=8.7Hz, 2H), 9.26(s, 1H)<br>IR(Nujol)3487, 3382, 1696, 1670, 1591, 1523, 1491, 1458, 1243, 1202, 1114, 1077, 1013, 937, 811cm$^{-1}$ |
| I-1329 | mp 205–210° C.(decomp.)<br>$^1$H NMR(DMSO-d$_6$) δ 3.34(s, 3H), 3.44(s, 3H), 3.67(s, 3H), 4.93(s, 2H), 6.43(s, 1H), 6.76(dd, J=8.4, 2.1Hz, 1H), 6.85 (d, J=2.1Hz, 1H), 6.86(d, J=8.7Hz, 2H), 7.04(d, J=8.4Hz, 1H), 7.46(d, J=8.7Hz, 2H)<br>IR(Nujol)3388, 3333, 3270, 1671, 1614, 1579, 1556, 1523, 1443, 1223, 1172, 1121, 1033, 922, 813cm$^{-1}$ |
| I-1330 | mp 185–187° C.<br>$^1$H NMR(CDCl$_3$) δ 1.79(t, J=2.6Hz, 3H), 2.69(m, 2H), 2.75(s, 3H), 3.21(s, 3H), 3.29(s, 3H), 3.56(s, 3H), 3.77(s, 3H), 4.17(t, J=6.6Hz, 2H), 6.84(s, 1H), 7.08(d, J=9.0Hz, 1H), 7.36(dd, J=9.0, 2.1Hz, 1H), 7.38(d, J=8.7Hz, 2H), 7.40(d, J=2.1Hz, 1H), 7.68(d, J=8.7Hz, 2H)<br>IR(Nujol)1604, 1520, 1480, 1175, 1151, 1081, 1012, 971, 948, 878, 840, 807cm$^{-1}$ |

TABLE 264

| | |
|---|---|
| I-1331 | foam<br>$^1$H NMR(CDCl$_3$) δ 1.81(t, J=2.4Hz, 3H), 2.65(m, 2H), 3.45(s, 3H), 3.74(s, 3H), 4.16(t, J=6.6Hz, 2H), 6.45(s, 1H), 6.92(d, J=8.7Hz, 2H), 6.95(m, 2H), 7.07(brs, 1H), 7.07(d, J=8.7Hz, 2H)<br>IR(Nujol)3427, 1612, 1586, 1523, 1489, 1251, 1224, 1113, 1071, 1012cm$^{-1}$ |
| I-1332 | foam<br>$^1$H NMR(CDCl$_3$) δ 3.45(s, 3H), 3.75(s, 3H), 4.16(m, 2H), 4.76(m, 2H), 5.89–6.02(m, 2H), 6.45(s, 1H), 6.92(d, J=8.7Hz, 2H), 6.96(m, 2H), 7.09(brs, 1H), 7.53(d, J=8.7Hz, 2H)<br>IR(Nujol)3433, 1612, 1588, 1523, 1489, 1286, 1248, 1224, 1175, 1113, 1070, 1011cm$^{-1}$ |
| I-1333 | foam<br>$^1$H NMR(CDCl$_3$) δ 3.45(s, 3H), 3.74(s, 3H), 4.11(m, 2H), 4.67(m, 2H), 5.96–6.12(m, 2H), 6.45(s, 1H), 6.92(d, J=8.7Hz, 2H), 6.92(d, J=8.4Hz, 1H), 6.96(dd, J=8.4, 2.1Hz, 1H), 7.08(d, J=2.1Hz, 1H), 7.53(d, J=8.7Hz, 2H)<br>IR(Nujol)3434, 1612, 1588, 1523, 1489, 1285, 1248, 1224, 1174, 1112, 1070, 1011cm$^{-1}$ |
| I-1334 | foam<br>$^1$H NMR(CDCl$_3$) δ 1.95(s, 3H), 3.45(s, 3H), 3.75(s, 3H), 4.11(s, 2H), 4.68(d, J=6.9Hz, 2H), 5.75(d, J=6.9Hz, 1H), 6.45(s, 1H), 6.91(d, J=8.7Hz, 2H), 6.96(s, 2H), 7.08(s, 1H), 7.53(d, J=8.7Hz, 2H)<br>IR(KBr)3390, 1612, 1585, 1523, 1491, 1225, 1072, 1003, 822cm$^{-1}$ |
| I-1335 | m.p 179–180° C.<br>$^1$H NMR(CDCl$_3$) δ 1.88(s, 3H), 3.45(s, 3H), 3.75(s, 3H), 4.07(s, 2H), 4.69(d, J=6.6Hz, 2H), 5.89(d, J=6.6Hz, 1H), 6.45(s, 1H), 6.91(d, J=8.7Hz, 2H), 6.92(d, J=8.4Hz, 1H), 6.96(dd, J=1.8, 8.4Hz, 1H), 7.07(d, J=1.8Hz, 1H), 7.53(d, J=8.7Hz, 2H)<br>IR(KBr)3392, 1609, 1584, 1523, 1492, 1226, 1116, 1072, 1002, 813, 782cm$^{-1}$ |

TABLE 265

| | |
|---|---|
| I-136 | foam<br>$^1$H NMR(CD3OD) δ 3.38(s, 3H), 3.67(s, 3H), 3.88(dd, J=7.8, 9.9Hz, 1H), 4.10(dd, J=3.6, 9.9Hz, 1H), 4.51(m, 1H), 5.25(dt, J=10.5, 1.5Hz, 1H), 5.44(dt, J=17.4, 1.5Hz, 1H), 6.00(ddd, J=5.4, 10.5, 17.4Hz, 1H), 6.43(s, 1H), 6.79(dd, J=1.8, 8.4Hz, 1H), 6.85(d, J=8.7Hz, 2H), 6.86(d, J=1.8Hz, 1H), 6.92(d, J=8.4Hz, 1H), 7.45(d, J=8.7Hz, 2H)<br>IR(KBr)3399, 2934, 1612, 1588, 1523, 1489, 1254, 1114, 1071, 1012, 939, 816cm$^{-1}$ |
| I-1337 | foam<br>$^1$H NMR(CDCl$_3$) δ 3.45(s, 3H), 3.75(s, 3H), 4.20(t, J=2.1Hz, 2H), 4.84(t, J=2.1Hz, 2H), 6.45(s, 1H), 6.92(d, J=8.7Hz, 2H), 6.98(dd, J=2.1, 8.4Hz, 1H), 7.04(d, J=8.4Hz, 1H), 7.09(d, J=2.1Hz, 1H), 7.45(d, J=8.7Hz, 2H)<br>IR(KBr)3431, 1612, 1589, 1523, 1489, 1404, 1224, 1113, 1070, 1011, 939, 826cm$^{-1}$ |
| I-1338 | foam<br>$^1$H NMR(CD3OD) δ 3.38(s, 3H), 3.67(s, 3H), 4.25(d, J=21.0Hz, 2H), 4.84(d, J=7.5Hz, 2H), 5.58(dt, J=19.5, 7.5Hz, 1H), 6.43(s, 1H), 6.79(dd, J=2.1, 8.4Hz, 1H), 6.84(d, J=8.7Hz, 1H), 6.86(d, J=2.1Hz, 1H), 6.96(d, J=8.4Hz, 1H), 7.45(d, J=8.7Hz, 2H)<br>IR(KBr)3409, 1701, 1612, 1591, 1523, 1489, 1404, 1246, 1113, 1071, 1010, 939, 816cm$^{-1}$ |
| I-1339 | foam<br>$^1$H NMR(CDCl$_3$) δ 3.44(s, 3H), 3.74(s, 3H), 4.21(d, J=21.3Hz, 2H), 4.66(dd, J=1.8, 7.5Hz, 2H), 5.70(dt, J=16.5, 7.5Hz, 1H), 6.45(s, 1H), 6.95(d, J=8.7Hz, 2H), 6.96(d, J=8.4Hz, 1H), 6.98(dd, J=1.5, 8.4Hz, 1H), 7.09(d, J=1.5Hz, 1H), 7.51(d, J=8.7Hz, 2H)<br>IR(KBr)3411, 1698, 1611, 1588, 1522, 1488, 1223, 1112, 1070, 1011, 939, 825cm$^{-1}$ |
| I-1340 | mp 171–172° C.<br>$^1$H NMR(CDCl$_3$) δ 1.50(s, 3H), 1.67(s, 3H), 1.96(s, 3H), 3.45(s, 3H), 3.77(s, 3H), 4.13–4.49(m, 2H), 5.23–5.30(m, 1H), 5.59(s, 1H), 6.13(s, 1H), 6.47(s, 1H), 6.92–6.98(m, 2H), 7.18–7.35(m, 3H), 7.50–7.57(m, 2H)<br>IR(KBr)3390, 3140, 2935, 1640, 1523, 1401, 1240, 1119, 1070, 835, 820cm$^{-1}$ |

TABLE 266

| | |
|---|---|
| I-1341 | mp 216–218° C.<br>$^1$H NMR(CDCl$_3$+CD3OD) δ 1.46(s, 3H), 1.67(s, 3H), 1.95(s, 3H), 2.10(s, 3H), 3.46(s, 3H), 4.16–4.47(m, 2H), 5.21–5.28(m, 1H), 6.79(s, 1H), 6.88–6.95(m, 2H), 7.11–7.27(m, 3H), 7.45–7.52(m, 2H)<br>IR(KBr)3337, 3099, 2928, 1637, 1608, 1587, 1521, 1444, 1409, 1261, 1232, 1161, 836, 769, 592, 540cm$^{-1}$ |
| I-1342 | mp 103–105° C.<br>$^1$H NMR(CDCl$_3$) δ 1.15(d, J=6.8Hz, 6H), 2.26(s, 3H), 3.08(sept, J=6.8Hz, 1H), 4.94(s, 1H), 5.20(s, 2H), 6.88(d, J=8.7Hz, 2H), 7.04–7.07(m, 3H), 7.12–7.18(m, 1H), 7.18(s, 1H), 7.20(d, J=8.7Hz, 2H), 7.32–7.51(m, 5H)<br>IR(KBr)3429, 1522, 1490, 1262, 1227, 1128, 1011, 833cm$^{-1}$ |
| I-1343 | mp 115–117° C.<br>$^1$H NMR(CDCl$_3$) δ 1.15(d, J=6.6Hz, 6H), 1.77(s, 3H), 1.82(s, 3H), 2.27(s, 3H), 3.08(sept, J=6.8Hz, 1H), 4.64(d, J=6.9Hz, 2H), 4.86(s, 1H), 5.56(t, J=6.9Hz, 1H), 6.89(d, J=8.6Hz, 2H), 7.03(t, J=8.4Hz, 1H), 7.05–7.19(m, 3H), 7.19(s, 1H), 7.21(d, J=8.6Hz, 2H)<br>IR(KBr)3524, 1611, 1523, 1489, 1260, 1228, 1200, 1128, 836cm$^{-1}$ |
| I-1344 | mp 119–120° C.<br>$^1$H NMR(CDCl$_3$) δ 1.15(d, J=6.9Hz, 6H), 2.26(s, 3H), 3.08(sept, J=6.8Hz, 1H), 4.79(d, J=6.3Hz, 2H), 4.85(s, 1H), 6.25(t, J=6.3Hz, 1H), 6.89(d, J=8.7Hz, 2H), 7.01(t, J=8.4Hz, 1H), 7.07–7.12(m, 2H), 7.15(dd, J=12.0, 2.1Hz, 1H), 7.18(s, 1H), 7.20(d, J=8.7Hz, 2H)<br>IR(KBr)3425, 1610, 1523, 1488, 1300, 1263, 1300, 1263, 1227, 1134, 1038, 896cm$^{-1}$ |
| I-1345 | mp 109–110° C.<br>$^1$H NMR(CDCl$_3$) δ 1.34(d, J=6.9Hz, 3H), 2.24(s, 3H), 4.00(q, J=6.9Hz, 2H), 4.77–4.79(m, 3H), 6.24(t, J=6.3Hz, 1H), 6.86–6.90(m, 2H), 6.98–7.19(m, 4H), 7.47–7.50(m, 2H)<br>IR(CHCl$_3$)3596, 2927, 1612, 1523, 1493, 1476, 1388, 1299, 1259, 1173, 1127, 1049, 885, 834cm$^{-1}$ |

TABLE 267

| | |
|---|---|
| I-1346 | mp 114–116° C.<br>$^1$H NMR(CDCl$_3$) δ 1.33(d, J=6.9Hz, 3H), 1.77(s, 3H), 1.81(s, 3H), 2.24(s, 3H), 4.00(q, J=6.9Hz, 2H), 4.63(m, 2H), 4.73(br, 1H), 5.56(m, 1H), 6.81(s, 1H), 6.86–6.90(m, 2H), 7.00–7.19(m, 4H), 7.47–4.51(m, 2H)<br>IR(CHCl$_3$)3596, 2929, 2877, 1610, 1523, 1493, 1476, 1386, 1329, 1316, 1297, 1261, 1173, 1125, 1048, 992, 834cm$^{-1}$ |
| I-1347 | mp 144–146° C.<br>$^1$H NMR(CDCl$_3$) δ 3.20(s, 3H), 3.40(s, 3H), 3.75(s, 3H), 4.74(s, 2H), 5.19(s, 2H), 6.44(s, 1H), 7.05–7.62(m, 12H)<br>IR(KBr)3437, 1614, 1579, 1520, 1488, 1465, 1453, 1436, 1414, 1393, 1364, 1346, 1299, 1270, 1235, 1198, 1175, 1149, 1129, 1114, 1085, 1063cm$^{-1}$ |
| I-1348 | mp 156–159° C.<br>$^1$H NMR(CDCl$_3$) δ 2.48(s, 3H), 3.05(s, 3H), 3.20(s, 3H), 3.78(s, 3H), 4.83(s, 2H), 5.21(s, 2H), 6.84(s, 1H), 7.02–7.67(m, 12H)<br>IR(KBr)3430, 2940, 1607, 1522, 1481, 1452, 1419, 1389, 1365, 1294, 1273, 1230, 1200, 1176, 1151, 1132, 1080, 1011cm$^{-1}$ |
| I-1349 | mp 155–156° C.<br>$^1$H NMR(CDCl$_3$) δ 1.15(t, J=6.9Hz, 3H), 3.60(q, J=6.9Hz, 2H), 3.75(s, 3H), 3.90(s, 3H), 4.93(bs, 1H), 5.20(s, 2H), 5.98(s, 1H), 6.46(s, 1H), 6.90–7.05(m, 5H), 7.26–7.56(m, 7H)<br>IR(KBr)3409, 2938, 1613, 1522, 1438, 1416, 1396, 1382, 1360, 1268, 1232, 1211, 1169, 1131, 1113, 1078, 1022, 1006cm$^{-1}$ |
| I-1350 | mp 58–60° C.<br>$^1$H NMR(DMSO-d$_6$) δ 1.71(s, 6H), 2.21(s, 3H), 2.22(s, 3H), 3.71–3.75(m, 2H), 5.11(br s, 2H), 5.25–5.29(m, 1H), 5.50–5.53(m, 1H), 6.60–6.63(m, 2H), 6.66–6.73(m, 1H), 6.95–7.05(m, 6H)<br>IR(KBr)3600–2800(br), 1623, 1527, 1492, 1454, 1428, 1331, 1269, 1257, 1184, 1116cm$^{-1}$ |

TABLE 268

I-1351 mp 140–142° C.(dec.)
$^1$H NMR(CDCl$_3$) δ 2.33(s, 3H), 4.93(s, 1H), 5.19(s, 2H), 6.89(d, J=8.7Hz, 2H), 7.06(t, J=8.6Hz, 1H), 7.23(d, J=8.7Hz, 2H), 7.24–7.50(m, 10H)
IR(KBr)3400, 1609, 1529, 1490, 1269, 1243, 1005, 807, 745cm$^{-1}$ I-1352 mp 114–116° C.
$^1$H NMR(CDCl$_3$) δ 1.77(s, 3H), 1.81(s, 3H), 2.33(s, 3H), 4.63(d, J=6.9Hz, 2H), 4.89(s, 1H), 5.54(t, J=6.9Hz, 1H), 6.89(d, J=8.6Hz, 2H), 7.04(t, J=8.6Hz, 1H), 7.23(d, J=8.6Hz, 2H), 7.25–7.43(m, 5H)
IR(KBr)3368, 1609, 1526, 1490, 1271, 1241, 1131, 991, 827, 811cm$^{-1}$ I-1353 mp 78–79° C.
$^1$H NMR(CDCl$_3$) δ 1.77(s, 3H), 1.82(s, 3H), 2.24(s, 3H), 2.27(s, 3H), 4.64(d, J=6.6Hz, 2H), 5.51–5.59(m, 1H), 6.98–7.20(m, 7H), 7.28–7.36(m, 2H)

TABLE 269

(I)

| No. | R$^1$ | R$^2$ | R$^3$ | R$^4$ | R$^5$ | R$^6$ | R$^7$ | R$^8$ | R$^9$ | R$^{10}$ | R$^{11}$ | R$^{12}$ | R$^{13}$ | X | Y |
|---|---|---|---|---|---|---|---|---|---|---|---|---|---|---|---|
| I-1354 | OH | H | H | H | H | H | OMe | OMe | OH | H | H | H | OMs | O | —CH$_2$CH=CMe$_2$ |
| I-1355 | OH | H | H | H | H | H | OMe | OMe | OH | H | H | H | OMs | O | —(CH$_2$)$_2$CH=CMe$_2$ |
| I-1356 | OH | H | H | H | H | H | OMe | OMe | OH | H | H | H | OMs | O | —CH$_2$CH=CCl$_2$ |
| I-1357 | OH | H | H | H | H | H | OMe | OMe | OH | H | H | H | OMs | O | —CH$_2$C≡CMe |
| I-1358 | OH | H | H | H | H | H | OMe | OMe | OH | H | H | H | OMs | O | —CH$_2$C$_6$H$_4$-4-Me |
| I-1359 | OH | H | H | H | H | H | OMe | OMe | OH | H | H | H | COOH | O | —(CH$_2$)$_2$CH=CMe$_2$ |
| I-1360 | OH | H | H | H | H | H | OMe | OMe | OH | H | H | H | COOH | O | —CH$_2$CH=CCl$_2$ |
| I-1361 | OH | H | H | H | H | H | OMe | OMe | OH | H | H | H | COOH | O | —CH$_2$C≡CMe |
| I-1362 | OH | H | H | H | H | H | OMe | OMe | OH | H | H | H | COOH | O | —CH$_2$C$_6$H$_4$-4-Me |
| I-1363 | OH | H | H | H | H | H | OMe | OMe | OH | H | H | H | CH$_2$OH | O | —(CH$_2$)$_2$CH=CMe$_2$ |
| I-1364 | OH | H | H | H | H | H | OMe | OMe | OH | H | H | H | CH$_2$OH | O | —CH$_2$CH=CCl$_2$ |
| I-1365 | OH | H | H | H | H | H | OMe | OMe | OH | H | H | H | CH$_2$OH | O | —CH$_2$C≡CMe |
| I-1366 | OH | H | H | H | H | H | OMe | OMe | OH | H | H | H | CH$_2$OH | O | —CH$_2$C$_6$H$_4$-4-Me |
| I-1367 | OH | H | H | H | H | H | OMe | OMe | OH | H | H | H | F | O | —(CH$_2$)$_2$CH=CMe$_2$ |
| I-1368 | OH | H | H | H | H | H | OMe | OMe | OH | H | H | H | F | O | —CH$_2$CH=CCl$_2$ |
| I-1369 | OH | H | H | H | H | H | OMe | OMe | OH | H | H | H | F | O | —CH$_2$C≡CMe |

TABLE 270

| No. | R$^1$ | R$^2$ | R$^3$ | R$^4$ | R$^5$ | R$^6$ | R$^7$ | R$^8$ | R$^9$ | R$^{10}$ | R$^{11}$ | R$^{12}$ | R$^{13}$ | X | Y |
|---|---|---|---|---|---|---|---|---|---|---|---|---|---|---|---|
| I-1370 | OH | H | H | H | H | H | OMe | OMe | OH | H | H | H | F | O | —CH$_2$C$_6$H$_4$-4-Me |
| I-1371 | OH | H | H | H | H | H | OMe | OMe | COOH | H | H | H | OH | O | —CH$_2$CH=CCl$_2$ |
| I-1372 | OH | H | H | H | H | H | OMe | OMe | COOH | H | H | H | OH | O | —CH$_2$C≡CMe |
| I-1373 | OH | H | H | H | H | H | OMe | OMe | COOH | H | H | H | OMs | O | —CH$_2$CH=CMe$_2$ |
| I-1374 | OH | H | H | H | H | H | OMe | OMe | COOH | H | H | H | OMs | O | —(CH$_2$)$_2$CH=CMe$_2$ |
| I-1375 | OH | H | H | H | H | H | OMe | OMe | COOH | H | H | H | OMs | O | —CH$_2$CH=CCl$_2$ |
| I-1376 | OH | H | H | H | H | H | OMe | OMe | COOH | H | H | H | OMs | O | —CH$_2$C≡CMe |
| I-1377 | OH | H | H | H | H | H | OMe | OMe | COOH | H | H | H | OMs | O | —CH$_2$C$_6$H$_4$-4-Me |
| I-1378 | OH | H | H | H | H | H | OMe | OMe | COOH | H | H | H | COOH | O | —CH$_2$CH=CMe$_2$ |
| I-1379 | OH | H | H | H | H | H | OMe | OMe | COOH | H | H | H | COOH | O | —(CH$_2$)$_2$CH=CMe$_2$ |
| I-1380 | OH | H | H | H | H | H | OMe | OMe | COOH | H | H | H | COOH | O | —CH$_2$CH=CCl$_2$ |
| I-1381 | OH | H | H | H | H | H | OMe | OMe | COOH | H | H | H | COOH | O | —CH$_2$C≡CMe |
| I-1382 | OH | H | H | H | H | H | OMe | OMe | COOH | H | H | H | COOH | O | —CH$_2$C$_6$H$_4$-4-Me |
| I-1383 | OH | H | H | H | H | H | OMe | OMe | COOH | H | H | H | CH$_2$OH | O | —CH$_2$CH=CMe$_2$ |
| I-1384 | OH | H | H | H | H | H | OMe | OMe | COOH | H | H | H | CH$_2$OH | O | —(CH$_2$)$_2$CH=CMe$_2$ |
| I-1385 | OH | H | H | H | H | H | OMe | OMe | COOH | H | H | H | CH$_2$OH | O | —CH$_2$CH=CCl$_2$ |
| I-1386 | OH | H | H | H | H | H | OMe | OMe | COOH | H | H | H | CH$_2$OH | O | —CH$_2$C≡CMe |
| I-1387 | OH | H | H | H | H | H | OMe | OMe | COOH | H | H | H | CH$_2$OH | O | —CH$_2$C$_6$H$_4$-4-Me |
| I-1388 | OH | H | H | H | H | H | OMe | OMe | COOH | H | H | H | F | O | —CH$_2$CH=CCl$_2$ |
| I-1389 | OH | H | H | H | H | H | OMe | OMe | COOH | H | H | H | F | O | —CH$_2$C≡CMe |
| I-1390 | OH | H | H | H | H | H | OMe | OMe | CH$_2$OH | H | H | H | OH | O | —CH$_2$CH=CMe$_2$ |

TABLE 271

| No. | R$^1$ | R$^2$ | R$^3$ | R$^4$ | R$^5$ | R$^6$ | R$^7$ | R$^8$ | R$^9$ | R$^{10}$ | R$^{11}$ | R$^{12}$ | R$^{13}$ | X | Y |
|---|---|---|---|---|---|---|---|---|---|---|---|---|---|---|---|
| I-1391 | OH | H | H | H | H | H | OMe | OMe | CH$_2$OH | H | H | H | OH | O | —(CH$_2$)$_2$CH=CMe$_2$ |
| I-1392 | OH | H | H | H | H | H | OMe | OMe | CH$_2$OH | H | H | H | OH | O | —CH$_2$CH=CCl$_2$ |
| I-1393 | OH | H | H | H | H | H | OMe | OMe | CH$_2$OH | H | H | H | OH | O | —CH$_2$C≡CMe |

TABLE 271-continued

| | | | | | | | | | | | | | | | |
|---|---|---|---|---|---|---|---|---|---|---|---|---|---|---|---|
| I-1394 | OH | H | H | H | H | H | OMe | OMe | CH$_2$OH | H | H | H | OH | O | —CH$_2$C$_6$H$_4$-4-Me |
| I-1395 | OH | H | H | H | H | H | OMe | OMe | CH$_2$OH | H | H | H | OMs | O | —CH$_2$CH=CMe$_2$ |
| I-1396 | OH | H | H | H | H | H | OMe | OMe | CH$_2$OH | H | H | H | OMs | O | —(CH$_2$)$_2$CH=CMe$_2$ |
| I-1397 | OH | H | H | H | H | H | OMe | OMe | CH$_2$OH | H | H | H | OMs | O | —CH$_2$CH=CCl$_2$ |
| I-1398 | OH | H | H | H | H | H | OMe | OMe | CH$_2$OH | H | H | H | OMs | O | —CH$_2$C≡CMe |
| I-1399 | OH | H | H | H | H | H | OMe | OMe | CH$_2$OH | H | H | H | OMs | O | —CH$_2$C$_6$H$_4$-4-Me |
| I-1400 | OH | H | H | H | H | H | OMe | OMe | CH$_2$OH | H | H | H | COOH | O | —CH$_2$CH=CMe$_2$ |
| I-1401 | OH | H | H | H | H | H | OMe | OMe | CH$_2$OH | H | H | H | COOH | O | —(CH$_2$)$_2$CH=CMe$_2$ |
| I-1402 | OH | H | H | H | H | H | OMe | OMe | CH$_2$OH | H | H | H | COOH | O | —CH$_2$CH=CCl$_2$ |
| I-1403 | OH | H | H | H | H | H | OMe | OMe | CH$_2$OH | H | H | H | COOH | O | —CH$_2$C≡CMe |
| I-1404 | OH | H | H | H | H | H | OMe | OMe | CH$_2$OH | H | H | H | COOH | O | —CH$_2$C$_6$H$_4$-4-Me |
| I-1405 | OH | H | H | H | H | H | OMe | OMe | CH$_2$OH | H | H | H | CH$_2$OH | O | —CH$_2$CH=CMe$_2$ |
| I-1406 | OH | H | H | H | H | H | OMe | OMe | CH$_2$OH | H | H | H | CH$_2$OH | O | —CH$_2$CH=CCl$_2$ |
| I-1407 | OH | H | H | H | H | H | OMe | OMe | CH$_2$OH | H | H | H | CH$_2$OH | O | —CH$_2$C≡CMe |
| I-1408 | OH | H | H | H | H | H | OMe | OMe | CH$_2$OH | H | H | H | CH$_2$OH | O | —CH$_2$C$_6$H$_4$-4-Me |
| I-1409 | OH | H | H | H | H | H | OMe | OMe | CH$_2$OH | H | H | H | F | O | —CH$_2$CH=CMe$_2$ |
| I-1410 | OH | H | H | H | H | H | OMe | OMe | CH$_2$OH | H | H | H | F | O | —(CH$_2$)$_2$CH=CMe$_2$ |
| I-1411 | OH | H | H | H | H | H | OMe | OMe | CH$_2$OH | H | H | H | F | O | —CH$_2$CH=CCl$_2$ |

TABLE 272

| | | | | | | | | | | | | | | | |
|---|---|---|---|---|---|---|---|---|---|---|---|---|---|---|---|
| I-1412 | OH | H | H | H | H | H | OMe | OMe | CH$_2$OH | H | H | H | F | O | —CH$_2$C≡CMe |
| I-1413 | OH | H | H | H | H | H | OMe | OMe | CH$_2$OH | H | H | H | F | O | —CH$_2$C$_6$H$_4$-4-Me |
| I-1414 | OH | H | H | H | H | H | OMe | OMe | Me | H | H | H | OH | O | —CH$_2$CH=CCl$_2$ |
| I-1415 | OH | H | H | H | H | H | OMe | OMe | Me | H | H | H | OH | O | —CH$_2$C≡CMe |
| I-1416 | OH | H | H | H | H | H | OMe | OMe | Me | H | H | H | OMs | O | —CH$_2$CH=CMe$_2$ |
| I-1417 | OH | H | H | H | H | H | OMe | OMe | Me | H | H | H | OMs | O | —(CH$_2$)$_2$CH=CMe$_2$ |
| I-1418 | OH | H | H | H | H | H | OMe | OMe | Me | H | H | H | OMs | O | —CH$_2$CH=CCl$_2$ |
| I-1419 | OH | H | H | H | H | H | OMe | OMe | Me | H | H | H | OMs | O | —CH$_2$C≡CMe |
| I-1420 | OH | H | H | H | H | H | OMe | OMe | Me | H | H | H | OMs | O | —CH$_2$C$_6$H$_4$-4-Me |
| I-1421 | OH | H | H | H | H | H | OMe | OMe | Me | H | H | H | COOH | O | —CH$_2$CH=CMe$_2$ |
| I-1422 | OH | H | H | H | H | H | OMe | OMe | Me | H | H | H | COOH | O | —(CH$_2$)$_2$CH=CMe$_2$ |
| I-1423 | OH | H | H | H | H | H | OMe | OMe | Me | H | H | H | COOH | O | —CH$_2$CH=CCl$_2$ |
| I-1424 | OH | H | H | H | H | H | OMe | OMe | Me | H | H | H | COOH | O | —CH$_2$C≡CMe |
| I-1425 | OH | H | H | H | H | H | OMe | OMe | Me | H | H | H | COOH | O | —CH$_2$C$_6$H$_4$-4-Me |
| I-1426 | OH | H | H | H | H | H | OMe | OMe | Me | H | H | H | CH$_2$OH | O | —CH$_2$CH=CMe$_2$ |
| I-1427 | OH | H | H | H | H | H | OMe | OMe | Me | H | H | H | CH$_2$OH | O | —(CH$_2$)$_2$CH=CMe$_2$ |
| I-1428 | OH | H | H | H | H | H | OMe | OMe | Me | H | H | H | CH$_2$OH | O | —CH$_2$CH=CCl$_2$ |
| I-1429 | OH | H | H | H | H | H | OMe | OMe | Me | H | H | H | CH$_2$OH | O | —CH$_2$C≡CMe |
| I-1430 | OH | H | H | H | H | H | OMe | OMe | Me | H | H | H | CH$_2$OH | O | —CH$_2$C$_6$H$_4$-4-Me |
| I-1431 | OH | H | H | H | H | H | OMe | OMe | Me | H | H | H | F | O | —CH$_2$CH=CMe$_2$ |
| I-1432 | OH | H | H | H | H | H | OMe | OMe | Me | H | H | H | F | O | —(CH$_2$)$_2$CH=CMe$_2$ |

TABLE 273

| | | | | | | | | | | | | | | | |
|---|---|---|---|---|---|---|---|---|---|---|---|---|---|---|---|
| I-1433 | OH | H | H | H | H | H | OMe | OMe | Me | H | H | H | F | O | —CH$_2$CH=CCl$_2$ |
| I-1434 | OH | H | H | H | H | H | OMe | OMe | Me | H | H | H | F | O | —CH$_2$C≡CMe |
| I-1435 | OH | H | H | H | H | H | OMe | OMe | Me | H | H | H | F | O | —CH$_2$C$_6$H$_4$-4-Me |
| I-1436 | OH | H | H | H | H | H | OMe | OMe | H | H | H | H | OH | O | —CH$_2$CH=CCl$_2$ |
| I-1437 | OH | H | H | H | H | H | OMe | OMe | H | H | H | H | OH | O | —CH$_2$C≡CMe |
| I-1438 | OH | H | H | H | H | H | OMe | OMe | H | H | H | H | OH | O | —CH$_2$C$_6$H$_4$-4-Me |
| I-1439 | OH | H | H | H | H | H | OMe | OMe | H | H | H | H | OMs | O | —(CH$_2$)$_2$CH=CMe$_2$ |
| I-1440 | OH | H | H | H | H | H | OMe | OMe | H | H | H | H | OMs | O | —CH$_2$CH=CCl$_2$ |
| I-1441 | OH | H | H | H | H | H | OMe | OMe | H | H | H | H | OMs | O | —CH$_2$C≡CMe |
| I-1442 | OH | H | H | H | H | H | OMe | OMe | H | H | H | H | OMs | O | —CH$_2$C$_6$H$_4$-4-Me |
| I-1443 | OH | H | H | H | H | H | OMe | OMe | H | H | H | H | COOH | O | —CH$_2$CH=CMe$_2$ |
| I-1444 | OH | H | H | H | H | H | OMe | OMe | H | H | H | H | COOH | O | —(CH$_2$)$_2$CH=CMe$_2$ |
| I-1445 | OH | H | H | H | H | H | OMe | OMe | H | H | H | H | COOH | O | —CH$_2$CH=CCl$_2$ |
| I-1446 | OH | H | H | H | H | H | OMe | OMe | H | H | H | H | COOH | O | —CH$_2$C≡CMe |
| I-1447 | OH | H | H | H | H | H | OMe | OMe | H | H | H | H | COOH | O | —CH$_2$C$_6$H$_4$-4-Me |
| I-1448 | OH | H | H | H | H | H | OMe | OMe | H | H | H | H | CH$_2$OH | O | —CH$_2$CH=CMe$_2$ |
| I-1449 | OH | H | H | H | H | H | OMe | OMe | H | H | H | H | CH$_2$OH | O | —(CH$_2$)$_2$CH=CMe$_2$ |
| I-1450 | OH | H | H | H | H | H | OMe | OMe | H | H | H | H | CH$_2$OH | O | —CH$_2$CH=CCl$_2$ |
| I-1451 | OH | H | H | H | H | H | OMe | OMe | H | H | H | H | CH$_2$OH | O | —CH$_2$C≡CMe |
| I-1452 | OH | H | H | H | H | H | OMe | OMe | H | H | H | H | CH$_2$OH | O | —CH$_2$C$_6$H$_4$-4-Me |
| I-1453 | OH | H | H | H | H | H | OMe | OMe | H | H | H | H | F | O | —(CH$_2$)$_2$CH=CMe$_2$ |

TABLE 274

| | | | | | | | | | | | | | | | |
|---|---|---|---|---|---|---|---|---|---|---|---|---|---|---|---|
| I-1454 | OH | H | H | H | H | H | OMe | OMe | H | H | H | H | F | O | —CH$_2$CH=CCl$_2$ |
| I-1455 | OH | H | H | H | H | H | OMe | OMe | H | H | H | H | F | O | —CH$_2$C≡CMe |
| I-1456 | OH | H | H | H | H | H | OMe | OMe | H | H | H | H | F | O | —CH$_2$C$_6$H$_4$-4-Me |

TABLE 274-continued

| | | | | | | | | | | | | | | | |
|---|---|---|---|---|---|---|---|---|---|---|---|---|---|---|---|
| I-1457 | OH | H | H | H | H | F | OMe | OMe | OH | H | H | H | OH | O | —(CH$_2$)$_2$CH=CMe$_2$ |
| I-1458 | OH | H | H | H | H | F | OMe | OMe | OH | H | H | H | OH | O | —CH$_2$CH=CCl$_2$ |
| I-1459 | OH | H | H | H | H | F | OMe | OMe | OH | H | H | H | OH | O | —CH$_2$C≡CMe |
| I-1460 | OH | H | H | H | H | F | OMe | OMe | OH | H | H | H | OH | O | —CH$_2$C$_6$H$_4$-4-Me |
| I-1461 | OH | H | H | H | H | F | OMe | OMe | OH | H | H | H | OMs | O | —CH$_2$CH=CMe$_2$ |
| I-1462 | OH | H | H | H | H | F | OMe | OMe | OH | H | H | H | OMs | O | —(CH$_2$)$_2$CH=CMe$_2$ |
| I-1463 | OH | H | H | H | H | F | OMe | OMe | OH | H | H | H | OMs | O | —CH$_2$CH=CCl$_2$ |
| I-1464 | OH | H | H | H | H | F | OMe | OMe | OH | H | H | H | OMs | O | —CH$_2$C≡CMe |
| I-1465 | OH | H | H | H | H | F | OMe | OMe | OH | H | H | H | OMs | O | —CH$_2$C$_6$H$_4$-4-Me |
| I-1466 | OH | H | H | H | H | F | OMe | OMe | OH | H | H | H | COOH | O | —CH$_2$CH=CMe$_2$ |
| I-1467 | OH | H | H | H | H | F | OMe | OMe | OH | H | H | H | COOH | O | —(CH$_2$)$_2$CH=CMe$_2$ |
| I-1468 | OH | H | H | H | H | F | OMe | OMe | OH | H | H | H | COOH | O | —CH$_2$CH=CCl$_2$ |
| I-1469 | OH | H | H | H | H | F | OMe | OMe | OH | H | H | H | COOH | O | —CH$_2$C≡CMe |
| I-1470 | OH | H | H | H | H | F | OMe | OMe | OH | H | H | H | COOH | O | —CH$_2$C$_6$H$_4$-4-Me |
| I-1471 | OH | H | H | H | H | F | OMe | OMe | OH | H | H | H | CH$_2$OH | O | —CH$_2$CH=CMe$_2$ |
| I-1472 | OH | H | H | H | H | F | OMe | OMe | OH | H | H | H | CH$_2$OH | O | —(CH$_2$)$_2$CH=CMe$_2$ |
| I-1473 | OH | H | H | H | H | F | OMe | OMe | OH | H | H | H | CH$_2$OH | O | —CH$_2$CH=CCl$_2$ |
| I-1474 | OH | H | H | H | H | F | OMe | OMe | OH | H | H | H | CH$_2$OH | O | —CH$_2$C≡CMe |

TABLE 275

| | | | | | | | | | | | | | | | |
|---|---|---|---|---|---|---|---|---|---|---|---|---|---|---|---|
| I-1475 | OH | H | H | H | H | F | OMe | OMe | OH | H | H | H | CH$_2$OH | O | —CH$_2$C$_6$H$_4$-4-Me |
| I-1476 | OH | H | H | H | H | F | OMe | OMe | OH | H | H | H | F | O | —CH$_2$CH=CMe$_2$ |
| I-1477 | OH | H | H | H | H | F | OMe | OMe | OH | H | H | H | F | O | —(CH$_2$)$_2$CH=CMe$_2$ |
| I-1478 | OH | H | H | H | H | F | OMe | OMe | OH | H | H | H | F | O | —CH$_2$CH=CCl$_2$ |
| I-1479 | OH | H | H | H | H | F | OMe | OMe | OH | H | H | H | F | O | —CH$_2$C≡CMe |
| I-1480 | OH | H | H | H | H | F | OMe | OMe | OH | H | H | H | F | O | —CH$_2$C$_6$H$_4$-4-Me |
| I-1481 | OMs | H | H | H | H | H | OMe | OMe | OH | H | H | H | OH | O | —CH$_2$CH=CMe$_2$ |
| I-1482 | OMs | H | H | H | H | H | OMe | OMe | OH | H | H | H | OH | O | —(CH$_2$)$_2$CH=CMe$_2$ |
| I-1483 | OMs | H | H | H | H | H | OMe | OMe | OH | H | H | H | OH | O | —CH$_2$CH=CCl$_2$ |
| I-1484 | OMs | H | H | H | H | H | OMe | OMe | OH | H | H | H | OH | O | —CH$_2$C≡CMe |
| I-1485 | OMs | H | H | H | H | H | OMe | OMe | OH | H | H | H | OH | O | —CH$_2$C$_6$H$_4$-4-Me |
| I-1486 | OMs | H | H | H | H | H | OMe | OMe | OH | H | H | H | OMs | O | —CH$_2$CH=CMe$_2$ |
| I-1487 | OMs | H | H | H | H | H | OMe | OMe | OH | H | H | H | OMs | O | —(CH$_2$)$_2$CH=CMe$_2$ |
| I-1488 | OMs | H | H | H | H | H | OMe | OMe | OH | H | H | H | OMs | O | —CH$_2$CH=CCl$_2$ |
| I-1489 | OMs | H | H | H | H | H | OMe | OMe | OH | H | H | H | OMs | O | —CH$_2$C≡CMe |
| I-1490 | OMs | H | H | H | H | H | OMe | OMe | OH | H | H | H | OMs | O | —CH$_2$C$_6$H$_4$-4-Me |
| I-1491 | OMs | H | H | H | H | H | OMe | OMe | OH | H | H | H | COOH | O | —CH$_2$CH=CMe$_2$ |
| I-1492 | OMs | H | H | H | H | H | OMe | OMe | OH | H | H | H | COOH | O | —(CH$_2$)$_2$CH=CMe$_2$ |
| I-1493 | OMs | H | H | H | H | H | OMe | OMe | OH | H | H | H | COOH | O | —CH$_2$CH=CCl$_2$ |
| I-1494 | OMs | H | H | H | H | H | OMe | OMe | OH | H | H | H | COOH | O | —CH$_2$C≡CMe |
| I-1495 | OMs | H | H | H | H | H | OMe | OMe | OH | H | H | H | COOH | O | —CH$_2$C$_6$H$_4$-4-Me |

TABLE 276

| | | | | | | | | | | | | | | | |
|---|---|---|---|---|---|---|---|---|---|---|---|---|---|---|---|
| I-1496 | OMs | H | H | H | H | H | OMe | OMe | OH | H | H | H | CH$_2$OH | O | —CH$_2$CH=CMe$_2$ |
| I-1497 | OMs | H | H | H | H | H | OMe | OMe | OH | H | H | H | CH$_2$OH | O | —(CH$_2$)$_2$CH=CMe$_2$ |
| I-1498 | OMs | H | H | H | H | H | OMe | OMe | OH | H | H | H | CH$_2$OH | O | —CH$_2$CH=CCl$_2$ |
| I-1499 | OMs | H | H | H | H | H | OMe | OMe | OH | H | H | H | CH$_2$OH | O | —CH$_2$C≡CMe |
| I-1500 | OMs | H | H | H | H | H | OMe | OMe | OH | H | H | H | CH$_2$OH | O | —CH$_2$C$_6$H$_4$-4-Me |
| I-1501 | OMs | H | H | H | H | H | OMe | OMe | OH | H | H | H | F | O | —CH$_2$CH=CMe$_2$ |
| I-1502 | OMs | H | H | H | H | H | OMe | OMe | OH | H | H | H | F | O | —(CH$_2$)$_2$CH=CMe$_2$ |
| I-1503 | OMs | H | H | H | H | H | OMe | OMe | OH | H | H | H | F | O | —CH$_2$CH=CCl$_2$ |
| I-154 | OMs | H | H | H | H | H | OMe | OMe | OH | H | H | H | F | O | —CH$_2$C≡CMe |
| I-1505 | OMs | H | H | H | H | H | OMe | OMe | OH | H | H | H | F | O | —CH$_2$C$_6$H$_4$-4-Me |
| I-1506 | OMs | H | H | H | H | H | OMe | OMe | COOH | H | H | H | OH | O | —CH$_2$CH=CMe$_2$ |
| I-1507 | OMs | H | H | H | H | H | OMe | OMe | COOH | H | H | H | OH | O | —(CH$_2$)$_2$CH=CMe$_2$ |
| I-1508 | OMs | H | H | H | H | H | OMe | OMe | COOH | H | H | H | OH | O | —CH$_2$CH=CCl$_2$ |
| I-1509 | OMs | H | H | H | H | H | OMe | OMe | COOH | H | H | H | OH | O | —CH$_2$C≡CMe |
| I-1510 | OMs | H | H | H | H | H | OMe | OMe | COOH | H | H | H | OH | O | —CH$_2$C$_6$H$_4$-4-Me |
| I-1511 | OMs | H | H | H | H | H | OMe | OMe | COOH | H | H | H | OMs | O | —CH$_2$CH=CMe$_2$ |
| I-1512 | OMs | H | H | H | H | H | OMe | OMe | COOH | H | H | H | OMs | O | —(CH$_2$)$_2$CH=CMe$_2$ |
| I-1513 | OMs | H | H | H | H | H | OMe | OMe | COOH | H | H | H | OMs | O | —CH$_2$CH=CCl$_2$ |
| I-1514 | OMs | H | H | H | H | H | OMe | OMe | COOH | H | H | H | OMs | O | —CH$_2$C≡CMe |
| I-1515 | OMs | H | H | H | H | H | OMe | OMe | COOH | H | H | H | OMs | O | —CH$_2$C$_6$H$_4$-4-Me |
| I-1516 | OMs | H | H | H | H | H | OMe | OMe | COOH | H | H | H | COOH | O | —CH$_2$CH=CMe$_2$ |

TABLE 277

| | | | | | | | | | | | | | | | |
|---|---|---|---|---|---|---|---|---|---|---|---|---|---|---|---|
| I-1517 | OMs | H | H | H | H | H | OMe | OMe | COOH | H | H | H | COOH | O | —(CH$_2$)$_2$CH=CMe$_2$ |
| I-1518 | OMs | H | H | H | H | H | OMe | OMe | COOH | H | H | H | COOH | O | —CH$_2$CH=CCl$_2$ |
| I-1519 | OMs | H | H | H | H | H | OMe | OMe | COOH | H | H | H | COOH | O | —CH$_2$C≡CMe |

TABLE 277-continued

| | | | | | | | | | | | | | | | |
|---|---|---|---|---|---|---|---|---|---|---|---|---|---|---|---|
| I-1520 | OMs | H | H | H | H | H | OMe | OMe | COOH | H | H | H | COOH | O | —CH$_2$C$_6$H$_4$-4-Me |
| I-1521 | OMs | H | H | H | H | H | OMe | OMe | COOH | H | H | H | CH$_2$OH | O | —CH$_2$CH=CMe$_2$ |
| I-1522 | OMs | H | H | H | H | H | OMe | OMe | COOH | H | H | H | CH$_2$OH | O | —(CH$_2$)$_2$CH=CMe$_2$ |
| I-1523 | OMs | H | H | H | H | H | OMe | OMe | COOH | H | H | H | CH$_2$OH | O | —CH$_2$CH=CCl$_2$ |
| I-1524 | OMs | H | H | H | H | H | OMe | OMe | COOH | H | H | H | CH$_2$OH | O | —CH$_2$C≡CMe |
| I-1525 | OMs | H | H | H | H | H | OMe | OMe | COOH | H | H | H | CH$_2$OH | O | —CH$_2$C$_6$H$_4$-4-Me |
| I-1526 | OMs | H | H | H | H | H | OMe | OMe | COOH | H | H | H | F | O | —CH$_2$CH=CMe$_2$ |
| I-1527 | OMs | H | H | H | H | H | OMe | OMe | COOH | H | H | H | F | O | —(CH$_2$)$_2$CH=CMe$_2$ |
| I-1528 | OMs | H | H | H | H | H | OMe | OMe | COOH | H | H | H | F | O | —CH$_2$CH=CCl$_2$ |
| I-1529 | OMs | H | H | H | H | H | OMe | OMe | COOH | H | H | H | F | O | —CH$_2$C≡CMe |
| I-1530 | OMs | H | H | H | H | H | OMe | OMe | COOH | H | H | H | F | O | —CH$_2$C$_6$H$_4$-4-Me |
| I-1531 | OMs | H | H | H | H | H | OMe | OMe | CH$_2$OH | H | H | H | OH | O | —(CH$_2$)$_2$CH=CMe$_2$ |
| I-1532 | OMs | H | H | H | H | H | OMe | OMe | CH$_2$OH | H | H | H | OH | O | —CH$_2$CH=CCl$_2$ |
| I-1533 | OMs | H | H | H | H | H | OMe | OMe | CH$_2$OH | H | H | H | OH | O | —CH$_2$C≡CMe |
| I-1534 | OMs | H | H | H | H | H | OMe | OMe | CH$_2$OH | H | H | H | OH | O | —CH$_2$C$_6$H$_4$-4-Me |
| I-1535 | OMs | H | H | H | H | H | OMe | OMe | CH$_2$OH | H | H | H | OMs | O | —(CH$_2$)$_2$CH=CMe$_2$ |
| I-1536 | OMs | H | H | H | H | H | OMe | OMe | CH$_2$OH | H | H | H | OMs | O | —CH$_2$CH=CCl$_2$ |
| I-1537 | OMs | H | H | H | H | H | OMe | OMe | CH$_2$OH | H | H | H | OMs | O | —CH$_2$C≡CMe |

TABLE 278

| | | | | | | | | | | | | | | | |
|---|---|---|---|---|---|---|---|---|---|---|---|---|---|---|---|
| I-1538 | OMs | H | H | H | H | H | OMe | OMe | CH$_2$OH | H | H | H | OMs | O | —CH$_2$C$_6$H$_4$-4-Me |
| I-1539 | OMs | H | H | H | H | H | OMe | OMe | CH$_2$OH | H | H | H | COOH | O | —CH$_2$CH=CMe$_2$ |
| I-1540 | OMs | H | H | H | H | H | OMe | OMe | CH$_2$OH | H | H | H | COOH | O | —(CH$_2$)$_2$CH=CMe$_2$ |
| I-1541 | OMs | H | H | H | H | H | OMe | OMe | CH$_2$OH | H | H | H | COOH | O | —CH$_2$CH=CCl$_2$ |
| I-1542 | OMs | H | H | H | H | H | OMe | OMe | CH$_2$OH | H | H | H | COOH | O | —CH$_2$C≡CMe |
| I-1543 | OMs | H | H | H | H | H | OMe | OMe | CH$_2$OH | H | H | H | COOH | O | —CH$_2$C$_6$H$_4$-4-Me |
| I-1544 | OMs | H | H | H | H | H | OMe | OMe | CH$_2$OH | H | H | H | CH$_2$OH | O | —(CH$_2$)$_2$CH=CMe$_2$ |
| I-1545 | OMs | H | H | H | H | H | OMe | OMe | CH$_2$OH | H | H | H | CH$_2$OH | O | —CH$_2$CH=CCl$_2$ |
| I-1546 | OMs | H | H | H | H | H | OMe | OMe | CH$_2$OH | H | H | H | CH$_2$OH | O | —CH$_2$C≡CMe |
| I-1547 | OMs | H | H | H | H | H | OMe | OMe | CH$_2$OH | H | H | H | CH$_2$OH | O | —CH$_2$C$_6$H$_4$-4-Me |
| I-1548 | OMs | H | H | H | H | H | OMe | OMe | CH$_2$OH | H | H | F | | O | —CH$_2$CH=CMe$_2$ |
| I-1549 | OMs | H | H | H | H | H | OMe | OMe | CH$_2$OH | H | H | F | | O | —(CH$_2$)$_2$CH=CMe$_2$ |
| I-1550 | OMs | H | H | H | H | H | OMe | OMe | CH$_2$OH | H | H | F | | O | —CH$_2$CH=CCl$_2$ |
| I-1551 | OMs | H | H | H | H | H | OMe | OMe | CH$_2$OH | H | H | F | | O | —CH$_2$C≡CMe |
| I-1552 | OMs | H | H | H | H | H | OMe | OMe | CH$_2$OH | H | H | F | | O | —CH$_2$C$_6$H$_4$-4-Me |
| I-1553 | OMs | H | H | H | H | H | OMe | OMe | Me | H | H | H | OH | O | —CH$_2$CH=CMe$_2$ |
| I-1554 | OMs | H | H | H | H | H | OMe | OMe | Me | H | H | H | OH | O | —(CH$_2$)$_2$CH=CMe$_2$ |
| I-1555 | OMs | H | H | H | H | H | OMe | OMe | Me | H | H | H | OH | O | —CH$_2$CH=CCl$_2$ |
| I-1556 | OMs | H | H | H | H | H | OMe | OMe | Me | H | H | H | OH | O | —CH$_2$C≡CMe |
| I-1557 | OMs | H | H | H | H | H | OMe | OMe | Me | H | H | H | OH | O | —CH$_2$C$_6$H$_4$-4-Me |
| I-1558 | OMs | H | H | H | H | H | OMe | OMe | Me | H | H | H | OMs | O | —CH$_2$CH=CMe$_2$ |

TABLE 279

| | | | | | | | | | | | | | | | |
|---|---|---|---|---|---|---|---|---|---|---|---|---|---|---|---|
| I-1559 | OMs | H | H | H | H | H | OMe | OMe | Me | H | H | H | OMs | O | —CH$_2$CH=CCl$_2$ |
| I-1560 | OMs | H | H | H | H | H | OMe | OMe | Me | H | H | H | OMs | O | —CH$_2$C≡CMe |
| I-1561 | OMs | H | H | H | H | H | OMe | OMe | Me | H | H | H | COOH | O | —CH$_2$CH=CMe$_2$ |
| I-1562 | OMs | H | H | H | H | H | OMe | OMe | Me | H | H | H | COOH | O | —(CH$_2$)$_2$CH=CMe$_2$ |
| I-1563 | OMs | H | H | H | H | H | OMe | OMe | Me | H | H | H | COOH | O | —CH$_2$CH=CCl$_2$ |
| I-1564 | OMs | H | H | H | H | H | OMe | OMe | Me | H | H | H | COOH | O | —CH$_2$C≡CMe |
| I-1565 | OMs | H | H | H | H | H | OMe | OMe | Me | H | H | H | COOH | O | —CH$_2$C$_6$H$_4$-4-Me |
| I-1566 | OMs | H | H | H | H | H | OMe | OMe | Me | H | H | H | CH$_2$OH | O | —CH$_2$CH=CMe$_2$ |
| I-1567 | OMs | H | H | H | H | H | OMe | OMe | Me | H | H | H | CH$_2$OH | O | —(CH$_2$)$_2$CH=CMe$_2$ |
| I-1568 | OMs | H | H | H | H | H | OMe | OMe | Me | H | H | H | CH$_2$OH | O | —CH$_2$CH=CCl$_2$ |
| I-1569 | OMs | H | H | H | H | H | OMe | OMe | Me | H | H | H | CH$_2$OH | O | —CH$_2$C≡CMe |
| I-1570 | OMs | H | H | H | H | H | OMe | OMe | Me | H | H | H | CH$_2$OH | O | —CH$_2$C$_6$H$_4$-4-Me |
| I-1571 | OMs | H | H | H | H | H | OMe | OMe | Me | H | H | H | F | O | —CH$_2$CH=CMe$_2$ |
| I-1572 | OMs | H | H | H | H | H | OMe | OMe | Me | H | H | H | F | O | —(CH$_2$)$_2$CH=CMe$_2$ |
| I-1573 | OMs | H | H | H | H | H | OMe | OMe | Me | H | H | H | F | O | —CH$_2$CH=CCl$_2$ |
| I-1574 | OMs | H | H | H | H | H | OMe | OMe | Me | H | H | H | F | O | —CH$_2$C≡CMe |
| I-1575 | OMs | H | H | H | H | H | OMe | OMe | Me | H | H | H | F | O | —CH$_2$C$_6$H$_4$-4-Me |
| I-1576 | OMs | H | H | H | H | H | OMe | OMe | H | H | H | H | OH | O | —CH$_2$CH=CMe$_2$ |
| I-1577 | OMs | H | H | H | H | H | OMe | OMe | H | H | H | H | OH | O | —(CH$_2$)$_2$CH=CMe$_2$ |
| I-1578 | OMs | H | H | H | H | H | OMe | OMe | H | H | H | H | OH | O | —CH$_2$CH=CCl$_2$ |
| I-1579 | OMs | H | H | H | H | H | OMe | OMe | H | H | H | H | OH | O | —CH$_2$C≡CMe |

TABLE 280

| | | | | | | | | | | | | | | | |
|---|---|---|---|---|---|---|---|---|---|---|---|---|---|---|---|
| I-1580 | OMs | H | H | H | H | H | OMe | OMe | H | H | H | H | OH | O | —CH$_2$C$_6$H$_4$-4-Me |
| I-1581 | OMs | H | H | H | H | H | OMe | OMe | H | H | H | H | OMs | O | —CH$_2$CH=CCl$_2$ |
| I-1582 | OMs | H | H | H | H | H | OMe | OMe | H | H | H | H | OMs | O | —CH$_2$C≡CMe |

TABLE 280-continued

| | | | | | | | | | | | | | | | |
|---|---|---|---|---|---|---|---|---|---|---|---|---|---|---|---|
| I-1583 | OMs | H | H | H | H | H | OMe | OMe | H | H | H | H | COOH | O | —CH$_2$CH=CMe$_2$ |
| I-1584 | OMs | H | H | H | H | H | OMe | OMe | H | H | H | H | COOH | O | —(CH$_2$)$_2$CH=CMe$_2$ |
| I-1585 | OMs | H | H | H | H | H | OMe | OMe | H | H | H | H | COOH | O | —CH$_2$CH=CCl$_2$ |
| I-1586 | OMs | H | H | H | H | H | OMe | OMe | H | H | H | H | COOH | O | —CH$_2$C≡CMe |
| I-1587 | OMs | H | H | H | H | H | OMe | OMe | H | H | H | H | COOH | O | —CH$_2$C$_6$H$_4$-4-Me |
| I-1588 | OMs | H | H | H | H | H | OMe | OMe | H | H | H | H | CH$_2$OH | O | —CH$_2$CH=CMe$_2$ |
| I-1589 | OMs | H | H | H | H | H | OMe | OMe | H | H | H | H | CH$_2$OH | O | —(CH$_2$)$_2$CH=CMe$_2$ |
| I-1590 | OMs | H | H | H | H | H | OMe | OMe | H | H | H | H | CH$_2$OH | O | —CH$_2$CH=CCl$_2$ |
| I-1591 | OMs | H | H | H | H | H | OMe | OMe | H | H | H | H | CH$_2$OH | O | —CH$_2$C≡CMe |
| I-1592 | OMs | H | H | H | H | H | OMe | OMe | H | H | H | H | CH$_2$OH | O | —CH$_2$C$_6$H$_4$-4-Me |
| I-1593 | OMs | H | H | H | H | H | OMe | OMe | H | H | H | H | F | O | —(CH$_2$)$_2$CH=CMe$_2$ |
| I-1594 | OMs | H | H | H | H | H | OMe | OMe | H | H | H | H | F | O | —CH$_2$CH=CCl$_2$ |
| I-1595 | OMs | H | H | H | H | H | OMe | OMe | H | H | H | H | F | O | —CH$_2$C≡CMe |
| I-1596 | OMs | H | H | H | H | F | OMe | OMe | OH | H | H | H | OH | O | —CH$_2$CH=CMe$_2$ |
| I-1597 | OMs | H | H | H | H | F | OMe | OMe | OH | H | H | H | OH | O | —(CH$_2$)$_2$CH=CMe$_2$ |
| I-1598 | OMs | H | H | H | H | F | OMe | OMe | OH | H | H | H | OH | O | —CH$_2$CH=CCl$_2$ |
| I-1599 | OMs | H | H | H | H | F | OMe | OMe | OH | H | H | H | OH | O | —CH$_2$C≡CMe |
| I-1600 | OMs | H | H | H | H | F | OMe | OMe | OH | H | H | H | OH | O | —CH$_2$C$_6$H$_4$-4-Me |

TABLE 281

| | | | | | | | | | | | | | | | |
|---|---|---|---|---|---|---|---|---|---|---|---|---|---|---|---|
| I-1601 | OMs | H | H | H | H | F | OMe | OMe | OH | H | H | H | OMs | O | —CH$_2$CH=CMe$_2$ |
| I-1602 | OMs | H | H | H | H | F | OMe | OMe | OH | H | H | H | OMs | O | —(CH$_2$)$_2$CH=CMe$_2$ |
| I-1603 | OMs | H | H | H | H | F | OMe | OMe | OH | H | H | H | OMs | O | —CH$_2$CH=CCl$_2$ |
| I-1604 | OMs | H | H | H | H | F | OMe | OMe | OH | H | H | H | OMs | O | —CH$_2$C≡CMe |
| I-1605 | OMs | H | H | H | H | F | OMe | OMe | OH | H | H | H | OMs | O | —CH$_2$C$_6$H$_4$-4-Me |
| I-1606 | OMs | H | H | H | H | F | OMe | OMe | OH | H | H | H | COOH | O | —CH$_2$CH=CMe$_2$ |
| I-1607 | OMs | H | H | H | H | F | OMe | OMe | OH | H | H | H | COOH | O | —(CH$_2$)$_2$CH=CMe$_2$ |
| I-1608 | OMs | H | H | H | H | F | OMe | OMe | OH | H | H | H | COOH | O | —CH$_2$CH=CCl$_2$ |
| I-1609 | OMs | H | H | H | H | F | OMe | OMe | OH | H | H | H | COOH | O | —CH$_2$C≡CMe |
| I-1610 | OMs | H | H | H | H | F | OMe | OMe | OH | H | H | H | COOH | O | —CH$_2$C$_6$H$_4$-4-Me |
| I-1611 | OMs | H | H | H | H | F | OMe | OMe | OH | H | H | H | CH$_2$OH | O | —CH$_2$CH=CMe$_2$ |
| I-1612 | OMs | H | H | H | H | F | OMe | OMe | OH | H | H | H | CH$_2$OH | O | —(CH$_2$)$_2$CH=CMe$_2$ |
| I-1613 | OMs | H | H | H | H | F | OMe | OMe | OH | H | H | H | CH$_2$OH | O | —CH$_2$CH=CCl$_2$ |
| I-1614 | OMs | H | H | H | H | F | OMe | OMe | OH | H | H | H | CH$_2$OH | O | —CH$_2$C≡CMe |
| I-1615 | OMs | H | H | H | H | F | OMe | OMe | OH | H | H | H | CH$_2$OH | O | —CH$_2$C$_6$H$_4$-4-Me |
| I-1616 | OMs | H | H | H | H | F | OMe | OMe | OH | H | H | H | F | O | —CH$_2$CH=CMe$_2$ |
| I-1617 | OMs | H | H | H | H | F | OMe | OMe | OH | H | H | H | F | O | —(CH$_2$)$_2$CH=CMe$_2$ |
| I-1618 | OMs | H | H | H | H | F | OMe | OMe | OH | H | H | H | F | O | —CH$_2$CH=CCl$_2$ |
| I-1619 | OMs | H | H | H | H | F | OMe | OMe | OH | H | H | H | F | O | —CH$_2$C≡CMe |
| I-1620 | OMs | H | H | H | H | F | OMe | OMe | OH | H | H | H | F | O | —CH$_2$C$_6$H$_4$-4-Me |
| I-1621 | F | H | H | H | H | H | OMe | OMe | OH | H | H | H | OH | O | —CH$_2$CH=CCl$_2$ |

TABLE 282

| | | | | | | | | | | | | | | | |
|---|---|---|---|---|---|---|---|---|---|---|---|---|---|---|---|
| I-1622 | F | H | H | H | H | H | OMe | OMe | OH | H | H | H | OH | O | —CH$_2$C≡CMe |
| I-1623 | F | H | H | H | H | H | OMe | OMe | OH | H | H | H | OMs | O | —CH$_2$CH=CCl$_2$ |
| I-1624 | F | H | H | H | H | H | OMe | OMe | OH | H | H | H | OMs | O | —CH$_2$C≡CMe |
| I-1625 | F | H | H | H | H | H | OMe | OMe | OH | H | H | H | COOH | O | —CH$_2$CH=CMe$_2$ |
| I-1626 | F | H | H | H | H | H | OMe | OMe | OH | H | H | H | COOH | O | —(CH$_2$)$_2$CH=CMe$_2$ |
| I-1627 | F | H | H | H | H | H | OMe | OMe | OH | H | H | H | COOH | O | —CH$_2$CH=CCl$_2$ |
| I-1628 | F | H | H | H | H | H | OMe | OMe | OH | H | H | H | COOH | O | —CH$_2$C≡CMe |
| I-1629 | F | H | H | H | H | H | OMe | OMe | OH | H | H | H | COOH | O | —CH$_2$C$_6$H$_4$-4-Me |
| I-1630 | F | H | H | H | H | H | OMe | OMe | OH | H | H | H | CH$_2$OH | O | —CH$_2$CH=CMe$_2$ |
| I-1631 | F | H | H | H | H | H | OMe | OMe | OH | H | H | H | CH$_2$OH | O | —(CH$_2$)$_2$CH=CMe$_2$ |
| I-1632 | F | H | H | H | H | H | OMe | OMe | OH | H | H | H | CH$_2$OH | O | —CH$_2$CH=CCl$_2$ |
| I-1633 | F | H | H | H | H | H | OMe | OMe | OH | H | H | H | CH$_2$OH | O | —CH$_2$C≡CMe |
| I-1634 | F | H | H | H | H | H | OMe | OMe | OH | H | H | H | CH$_2$OH | O | —CH$_2$C$_6$H$_4$-4-Me |
| I-1635 | F | H | H | H | H | H | OMe | OMe | OH | H | H | H | F | O | —CH$_2$CH=CCl$_2$ |
| I-1636 | F | H | H | H | H | H | OMe | OMe | OH | H | H | H | F | O | —CH$_2$C≡CMe |
| I-1637 | F | H | H | H | H | H | OMe | OMe | COOH | H | H | H | OH | O | —CH$_2$CH=CCl$_2$ |
| I-1638 | F | H | H | H | H | H | OMe | OMe | COOH | H | H | H | OH | O | —CH$_2$C≡CMe |
| I-1639 | F | H | H | H | H | H | OMe | OMe | COOH | H | H | H | OMs | O | —CH$_2$CH=CMe$_2$ |
| I-1640 | F | H | H | H | H | H | OMe | OMe | COOH | H | H | H | OMs | O | —(CH$_2$)$_2$CH=CMe$_2$ |
| I-1641 | F | H | H | H | H | H | OMe | OMe | COOH | H | H | H | OMs | O | —CH$_2$CH=CCl$_2$ |
| I-1642 | F | H | H | H | H | H | OMe | OMe | COOH | H | H | H | OMs | O | —CH$_2$C≡CMe |

TABLE 283

| | | | | | | | | | | | | | | | |
|---|---|---|---|---|---|---|---|---|---|---|---|---|---|---|---|
| I-1643 | F | H | H | H | H | H | OMe | OMe | COOH | H | H | H | OMs | O | —CH$_2$C$_6$H$_4$-4-Me |
| I-1644 | F | H | H | H | H | H | OMe | OMe | COOH | H | H | H | COOH | O | —CH$_2$CH=CMe$_2$ |
| I-1645 | F | H | H | H | H | H | OMe | OMe | COCH | H | H | H | COOH | O | —(CH$_2$)$_2$CH=CMe$_2$ |

TABLE 283-continued

| | | | | | | | | | | | | | | | |
|---|---|---|---|---|---|---|---|---|---|---|---|---|---|---|---|
| I-1646 | F | H | H | H | H | H | OMe | OMe | COOH | H | H | H | COOH | O | —CH$_2$CH=CCl$_2$ |
| I-1647 | F | H | H | H | H | H | OMe | OMe | COOH | H | H | H | COOH | O | —CH$_2$C≡CMe |
| I-1648 | F | H | H | H | H | H | OMe | OMe | COOH | H | H | H | COOH | O | —CH$_2$C$_6$H$_4$-4-Me |
| I-1649 | F | H | H | H | H | H | OMe | OMe | COOH | H | H | H | CH$_2$OH | O | —CH$_2$CH=CMe$_2$ |
| I-1650 | F | H | H | H | H | H | OMe | OMe | COOH | H | H | H | CH$_2$OH | O | —(CH$_2$)$_2$CH=CMe$_2$ |
| I-1651 | F | H | H | H | H | H | OMe | OMe | COOH | H | H | H | CH$_2$OH | O | —CH$_2$CH=CCl$_2$ |
| I-1652 | F | H | H | H | H | H | OMe | OMe | COOH | H | H | H | CH$_2$OH | O | —CH$_2$C≡CMe |
| I-1653 | F | H | H | H | H | H | OMe | OMe | COOH | H | H | H | CH$_2$OH | O | —CH$_2$C$_6$H$_4$-4-Me |
| I-1654 | F | H | H | H | H | H | OMe | OMe | COOH | H | H | H | F | O | —CH$_2$CH=CCl$_2$ |
| I-1655 | F | H | H | H | H | H | OMe | OMe | COOH | H | H | H | F | O | —CH$_2$C≡CMe |
| I-1656 | F | H | H | H | H | H | OMe | OMe | CH$_2$OH | H | H | H | OH | O | —CH$_2$CH=CMe$_2$ |
| I-1657 | F | H | H | H | H | H | OMe | OMe | CH$_2$OH | H | H | H | OH | O | —(CH$_2$)$_2$CH=CMe$_2$ |
| I-1658 | F | H | H | H | H | H | OMe | OMe | CH$_2$OH | H | H | H | OH | O | —CH$_2$CH=CCl$_2$ |
| I-1659 | F | H | H | H | H | H | OMe | OMe | CH$_2$OH | H | H | H | OH | O | —CH$_2$C≡CMe |
| I-1660 | F | H | H | H | H | H | OMe | OMe | CH$_2$OH | H | H | H | OH | O | —CH$_2$C$_6$H$_4$-4-Me |
| I-1661 | F | H | H | H | H | H | OMe | OMe | CH$_2$OH | H | H | H | OMs | O | —CH$_2$CH=CMe$_2$ |
| I-1662 | F | H | H | H | H | H | OMe | OMe | CH$_2$OH | H | H | H | OMs | O | —(CH$_2$)$_2$CH=CMe$_2$ |
| I-1663 | F | H | H | H | H | H | OMe | OMe | CH$_2$OH | H | H | H | OMs | O | —CH$_2$CH=CCl$_2$ |

TABLE 284

| | | | | | | | | | | | | | | | |
|---|---|---|---|---|---|---|---|---|---|---|---|---|---|---|---|
| I-1664 | F | H | H | H | H | H | OMe | OMe | CH$_2$OH | H | H | H | OMs | O | —CH$_2$C≡CMe |
| I-1665 | F | H | H | H | H | H | OMe | OMe | CH$_2$OH | H | H | H | OMs | O | —CH$_2$C$_6$H$_4$-4-Me |
| I-1666 | F | H | H | H | H | H | OMe | OMe | CH$_2$OH | H | H | H | COOH | O | —CH$_2$CH=CMe$_2$ |
| I-1667 | F | H | H | H | H | H | OMe | OMe | CH$_2$OH | H | H | H | COOH | O | —(CH$_2$)$_2$CH=CMe$_2$ |
| I-1668 | F | H | H | H | H | H | OMe | OMe | CH$_2$OH | H | H | H | COOH | O | —CH$_2$CH=CCl$_2$ |
| I-1669 | F | H | H | H | H | H | OMe | OMe | CH$_2$OH | H | H | H | COOH | O | —CH$_2$C≡CMe |
| I-1670 | F | H | H | H | H | H | OMe | OMe | CH$_2$OH | H | H | H | COOH | O | —CH$_2$C$_6$H$_4$-4-Me |
| I-1671 | F | H | H | H | H | H | OMe | OMe | CH$_2$OH | H | H | H | CH$_2$OH | O | —CH$_2$CH=CMe$_2$ |
| I-1672 | F | H | H | H | H | H | OMe | OMe | CH$_2$OH | H | H | H | CH$_2$OH | O | —(CH$_2$)$_2$CH=CMe$_2$ |
| I-1673 | F | H | H | H | H | H | OMe | OMe | CH$_2$OH | H | H | H | CH$_2$OH | O | —CH$_2$CH=CCl$_2$ |
| I-1674 | F | H | H | H | H | H | OMe | OMe | CH$_2$OH | H | H | H | CH$_2$OH | O | —CH$_2$C≡CMe |
| I-1675 | F | H | H | H | H | H | OMe | OMe | CH$_2$OH | H | H | H | CH$_2$OH | O | —CH$_2$C$_6$H$_4$-4-Me |
| I-1676 | F | H | H | H | H | H | OMe | OMe | CH$_2$OH | H | H | H | F | O | —CH$_2$CH=CMe$_2$ |
| I-1677 | F | H | H | H | H | H | OMe | OMe | CH$_2$OH | H | H | H | F | O | —(CH$_2$)$_2$CH=CMe$_2$ |
| I-1678 | F | H | H | H | H | H | OMe | OMe | CH$_2$OH | H | H | H | F | O | —CH$_2$CH=CCl$_2$ |
| I-1679 | F | H | H | H | H | H | OMe | OMe | CH$_2$OH | H | H | H | F | O | —CH$_2$C≡CMe |
| I-1680 | F | H | H | H | H | H | OMe | OMe | CH$_2$OH | H | H | H | F | O | —CH$_2$C$_6$H$_4$-4-Me |
| I-1681 | F | H | H | H | H | H | OMe | OMe | Me | H | H | H | OH | O | —CH$_2$CH=CMe$_2$ |
| I-1682 | F | H | H | H | H | H | OMe | OMe | Me | H | H | H | OH | O | —(CH$_2$)$_2$CH=CMe$_2$ |
| I-1683 | F | H | H | H | H | H | OMe | OMe | Me | H | H | H | OH | O | —CH$_2$CH=CCl$_2$ |
| I-1684 | F | H | H | H | H | H | OMe | OMe | Me | H | H | H | OH | O | —CH$_2$C≡CMe |

TABLE 285

| | | | | | | | | | | | | | | | |
|---|---|---|---|---|---|---|---|---|---|---|---|---|---|---|---|
| I-1685 | F | H | H | H | H | H | OMe | OMe | Me | H | H | H | OH | O | —CH$_2$C$_6$H$_4$-4-Me |
| I-1686 | F | H | H | H | H | H | OMe | OMe | Me | H | H | H | OMs | O | —CH$_2$CH=CMe$_2$ |
| I-1687 | F | H | H | H | H | H | OMe | OMe | Me | H | H | H | OMs | O | —(CH$_2$)$_2$CH=CMe$_2$ |
| I-1688 | F | H | H | H | H | H | OMe | OMe | Me | H | H | H | OMs | O | —CH$_2$CH=CCl$_2$ |
| I-1689 | F | H | H | H | H | H | OMe | OMe | Me | H | H | H | OMs | O | —CH$_2$C≡CMe |
| I-1690 | F | H | H | H | H | H | OMe | OMe | Me | H | H | H | OMs | O | —CH$_2$C$_6$H$_4$-4-Me |
| I-1691 | F | H | H | H | H | H | OMe | OMe | Me | H | H | H | COOH | O | —CH$_2$CH=CMe$_2$ |
| I-1692 | F | H | H | H | H | H | OMe | OMe | Me | H | H | H | COOH | O | —(CH$_2$)$_2$CH=CMe$_2$ |
| I-1693 | F | H | H | H | H | H | OMe | OMe | Me | H | H | H | COOH | O | —CH$_2$CH=CCl$_2$ |
| I-1694 | F | H | H | H | H | H | OMe | OMe | Me | H | H | H | COOH | O | —CH$_2$C≡CMe |
| I-1695 | F | H | H | H | H | H | OMe | OMe | Me | H | H | H | COOH | O | —CH$_2$C$_6$H$_4$-4-Me |
| I-1696 | F | H | H | H | H | H | OMe | OMe | Me | H | H | H | CH$_2$OH | O | —CH$_2$CH=CMe$_2$ |
| I-1697 | F | H | H | H | H | H | OMe | OMe | Me | H | H | H | CH$_2$OH | O | —(CH$_2$)$_2$CH=CMe$_2$ |
| I-1698 | F | H | H | H | H | H | OMe | OMe | Me | H | H | H | CH$_2$OH | O | —CH$_2$CH=CCl$_2$ |
| I-1699 | F | H | H | H | H | H | OMe | OMe | Me | H | H | H | CH$_2$OH | O | —CH$_2$C≡CMe |
| I-1700 | F | H | H | H | H | H | OMe | OMe | Me | H | H | H | CH$_2$OH | O | —CH$_2$C$_6$H$_4$-4-Me |
| I-1701 | F | H | H | H | H | H | OMe | OMe | Me | H | H | H | F | O | —CH$_2$CH=CMe$_2$ |
| I-1702 | F | H | H | H | H | H | OMe | OMe | Me | H | H | H | F | O | —(CH$_2$)$_2$CH=CMe$_2$ |
| I-1703 | F | H | H | H | H | H | OMe | OMe | Me | H | H | H | F | O | —CH$_2$CH=CCl$_2$ |
| I-1704 | F | H | H | H | H | H | OMe | OMe | Me | H | H | H | F | O | —CH$_2$C≡CMe |
| I-1705 | F | H | H | H | H | H | OMe | OMe | Me | H | H | H | F | O | —CH$_2$C$_6$H$_4$-4-Me |

TABLE 286

| | | | | | | | | | | | | | | | |
|---|---|---|---|---|---|---|---|---|---|---|---|---|---|---|---|
| I-1706 | F | H | H | H | H | H | OMe | OMe | H | H | H | H | OH | O | —CH$_2$CH=CMe$_2$ |
| I-1707 | F | H | H | H | H | H | OMe | OMe | H | H | H | H | OH | O | —(CH$_2$)$_2$CH=CMe$_2$ |
| I-1708 | F | H | H | H | H | H | OMe | OMe | H | H | H | H | OH | O | —CH$_2$CH=CCl$_2$ |

TABLE 286-continued

| | | | | | | | | | | | | | | | |
|---|---|---|---|---|---|---|---|---|---|---|---|---|---|---|---|
| I-1709 | F | H | H | H | H | H | OMe | OMe | H | H | H | H | OH | O | —CH$_2$C≡CMe |
| I-1710 | F | H | H | H | H | H | OMe | OMe | H | H | H | H | OH | O | —CH$_2$C$_6$H$_4$-4-Me |
| I-1711 | F | H | H | H | H | H | OMe | OMe | H | H | H | H | OMs | O | —(CH$_2$)$_2$CH=CMe$_2$ |
| I-1712 | F | H | H | H | H | H | OMe | OMe | H | H | H | H | OMs | O | —CH$_2$CH=CCl$_2$ |
| I-1713 | F | H | H | H | H | H | OMe | OMe | H | H | H | H | OMs | O | —CH$_2$C≡CMe |
| I-1714 | F | H | H | H | H | H | OMe | OMe | H | H | H | H | OMs | O | —CH$_2$C$_6$H$_4$-4-Me |
| I-1715 | F | H | H | H | H | H | OMe | OMe | H | H | H | H | COOH | O | —CH$_2$CH=CMe$_2$ |
| I-1716 | F | H | H | H | H | H | OMe | OMe | H | H | H | H | COOH | O | —(CH$_2$)$_2$CH=CMe$_2$ |
| I-1717 | F | H | H | H | H | H | OMe | OMe | H | H | H | H | COOH | O | —CH$_2$CH=CCl$_2$ |
| I-1718 | F | H | H | H | H | H | OMe | OMe | H | H | H | H | COOH | O | —CH$_2$C≡CMe |
| I-1719 | F | H | H | H | H | H | OMe | OMe | H | H | H | H | COOH | O | —CH$_2$C$_6$H$_4$-4-Me |
| I-1720 | F | H | H | H | H | H | OMe | OMe | H | H | H | H | CH$_2$OH | O | —CH$_2$CH=CMe$_2$ |
| I-1721 | F | H | H | H | H | H | OMe | OMe | H | H | H | H | CH$_2$OH | O | —(CH$_2$)$_2$CH=CMe$_2$ |
| I-1722 | F | H | H | H | H | H | OMe | OMe | H | H | H | H | CH$_2$OH | O | —CH$_2$CH=CCl$_2$ |
| I-1723 | F | H | H | H | H | H | OMe | OMe | H | H | H | H | CH$_2$OH | O | —CH$_2$C≡CMe |
| I-1724 | F | H | H | H | H | H | OMe | OMe | H | H | H | H | CH$_2$OH | O | —CH$_2$C$_6$H$_4$-4-Me |
| I-1725 | F | H | H | H | H | H | OMe | OMe | H | H | H | H | F | O | —CH$_2$CH=CMe$_2$ |
| I-1726 | F | H | H | H | H | H | OMe | OMe | H | H | H | H | F | O | —(CH$_2$)$_2$CH=CMe$_2$ |

TABLE 287

| | | | | | | | | | | | | | | | |
|---|---|---|---|---|---|---|---|---|---|---|---|---|---|---|---|
| I-1727 | F | H | H | H | H | H | OMe | OMe | H | H | H | H | F | O | —CH$_2$CH=CCl$_2$ |
| I-1728 | F | H | H | H | H | H | OMe | OMe | H | H | H | H | F | O | —CH$_2$C≡CMe |
| I-1729 | F | H | H | H | H | H | OMe | OMe | H | H | H | H | F | O | —CH$_2$C$_6$H$_4$-4-Me |
| I-1730 | F | H | H | H | H | F | OMe | OMe | OH | H | H | H | OH | O | —(CH$_2$)$_2$CH=CMe$_2$ |
| I-1731 | F | H | H | H | H | F | OMe | OMe | OH | H | H | H | OH | O | —CH$_2$CH=CCl$_2$ |
| I-1732 | F | H | H | H | H | F | OMe | OMe | OH | H | H | H | OH | O | —CH$_2$C≡CMe |
| I-1733 | F | H | H | H | H | F | OMe | OMe | OH | H | H | H | OH | O | —CH$_2$C$_6$H$_4$-4-Me |
| I-1734 | F | H | H | H | H | F | OMe | OMe | OH | H | H | H | OMs | O | —CH$_2$CH=CMe$_2$ |
| I-1735 | F | H | H | H | H | F | OMe | OMe | OH | H | H | H | OMs | O | —(CH$_2$)$_2$CH=CMe$_2$ |
| I-1736 | F | H | H | H | H | F | OMe | OMe | OH | H | H | H | OMs | O | —CH$_2$CH=CCl$_2$ |
| I-1737 | F | H | H | H | H | F | OMe | OMe | OH | H | H | H | OMs | O | —CH$_2$C≡CMe |
| I-1738 | F | H | H | H | H | F | OMe | OMe | OH | H | H | H | OMs | O | —CH$_2$C$_6$H$_4$-4-Me |
| I-1739 | F | H | H | H | H | F | OMe | OMe | OH | H | H | H | COOH | O | —CH$_2$CH=CMe$_2$ |
| I-1740 | F | H | H | H | H | F | OMe | OMe | OH | H | H | H | COOH | O | —(CH$_2$)$_2$CH=CMe$_2$ |
| I-1741 | F | H | H | H | H | F | OMe | OMe | OH | H | H | H | COOH | O | —CH$_2$CH=CCl$_2$ |
| I-1742 | F | H | H | H | H | F | OMe | OMe | OH | H | H | H | COOH | O | —CH$_2$C≡CMe |
| I-1743 | F | H | H | H | H | F | OMe | OMe | OH | H | H | H | COOH | O | —CH$_2$C$_6$H$_4$-4-Me |
| I-1744 | F | H | H | H | H | F | OMe | OMe | OH | H | H | H | CH$_2$OH | O | —CH$_2$CH=CMe$_2$ |
| I-1745 | F | H | H | H | H | F | OMe | OMe | OH | H | H | H | CH$_2$OH | O | —(CH$_2$)$_2$CH=CMe$_2$ |
| I-1746 | F | H | H | H | H | F | OMe | OMe | OH | H | H | H | CH$_2$OH | O | —CH$_2$CH=CCl$_2$ |
| I-1747 | F | H | H | H | H | F | OMe | OMe | OH | H | H | H | CH$_2$OH | O | —CH$_2$C≡CMe |

TABLE 288

| | | | | | | | | | | | | | | | |
|---|---|---|---|---|---|---|---|---|---|---|---|---|---|---|---|
| I-1748 | F | | H | H | H | H | F | OMe | OMe | OH | H | H | H | CH$_2$OH | O | —CH$_2$C$_6$H$_4$-4-Me |
| I-1749 | F | | H | H | H | H | F | OMe | OMe | OH | H | H | H | F | O | —CH$_2$CH=CMe$_2$ |
| I-1750 | F | | H | H | H | H | F | OMe | OMe | OH | H | H | H | F | O | —(CH$_2$)$_2$CH=CMe$_2$ |
| I-1751 | F | | H | H | H | H | F | OMe | OMe | OH | H | H | H | F | O | —CH$_2$CH=CCl$_2$ |
| I-1752 | F | | H | H | H | H | F | OMe | OMe | OH | H | H | H | F | O | —CH$_2$C≡CMe |
| I-1753 | F | | H | H | H | H | F | OMe | OMe | OH | H | H | H | F | O | —CH$_2$C$_6$H$_4$-4-Me |
| I-1754 | —OCH$_2$O— | * | H | H | * | H | H | OMe | OMe | OH | H | H | H | OH | O | —CH$_2$CH=CMe$_2$ |
| I-1755 | —OCH$_2$O— | * | H | H | * | H | H | OMe | OMe | OH | H | H | H | OH | O | —(CH$_2$)$_2$CH=CMe$_2$ |
| I-1756 | —OCH$_2$O— | * | H | H | * | H | H | OMe | OMe | OH | H | H | H | OH | O | —CH$_2$CH=CCl$_2$ |
| I-1757 | —OCH$_2$O— | * | H | H | * | H | H | OMe | OMe | OH | H | H | H | OH | O | —CH$_2$C≡CMe |
| I-1758 | —OCH$_2$O— | * | H | H | * | H | H | OMe | OMe | OH | H | H | H | OH | O | —CH$_2$C$_6$H$_4$-4-Me |
| I-1759 | —OCH$_2$O— | * | H | H | * | H | H | OMe | OMe | OH | H | H | H | OMs | O | —CH$_2$CH=CMe$_2$ |
| I-1760 | —OCH$_2$O— | * | H | H | * | H | H | OMe | OMe | OH | H | H | H | OMs | O | —(CH$_2$)$_2$CH=CMe$_2$ |
| I-1761 | —OCH$_2$O— | * | H | H | * | H | H | OMe | OMe | OH | H | H | H | OMs | O | —CH$_2$CH=CCl$_2$ |
| I-1762 | —OCH$_2$O— | * | H | H | * | H | H | OMe | OMe | OH | H | H | H | OMs | O | —CH$_2$C≡CMe |
| I-1763 | —OCH$_2$O— | * | H | H | * | H | H | OMe | OMe | OH | H | H | H | OMs | O | —CH$_2$C$_6$H$_4$-4-Me |
| I-1764 | —OCH$_2$O— | * | H | H | * | H | H | OMe | OMe | OH | H | H | H | COOH | O | —CH$_2$CH=CMe$_2$ |
| I-1765 | —OCH$_2$O— | * | H | H | * | H | H | OMe | OMe | OH | H | H | H | COOH | O | —(CH$_2$)$_2$CH=CMe$_2$ |
| I-1766 | —OCH$_2$O— | * | H | H | * | H | H | OMe | OMe | OH | H | H | H | COOH | O | —CH$_2$CH=CCl$_2$ |
| I-1767 | —OCH$_2$O— | * | H | H | * | H | H | OMe | OMe | OH | H | H | H | COOH | O | —CH$_2$C≡CMe |
| I-1768 | —OCH$_2$O— | * | H | H | * | H | H | OMe | OMe | OH | H | H | H | COOH | O | —CH$_2$C$_6$H$_4$-4-Me |

TABLE 289

| | | | | | | | | | | | | | | | |
|---|---|---|---|---|---|---|---|---|---|---|---|---|---|---|---|
| I-1768 | —OCH$_2$O— | * | H | H | * | H | H | OMe | OMe | OH | H | H | H | CH$_2$OH | O | —CH$_2$CH=CMe$_2$ |
| I-1769 | —OCH$_2$O— | * | H | H | * | H | H | OMe | OMe | OH | H | H | H | CH$_2$OH | O | —(CH$_2$)$_2$CH=CMe$_2$ |
| I-1770 | —OCH$_2$O— | * | H | H | * | H | H | OMe | OMe | OH | H | H | H | CH$_2$OH | O | —CH$_2$CH=CCl$_2$ |

TABLE 289-continued

| | | | | | | | | | | | | | | | | |
|---|---|---|---|---|---|---|---|---|---|---|---|---|---|---|---|---|
| I-1771 | —OCH₂O— | * | H | H | * | H | H | OMe | OMe | OH | H | H | H | CH₂OH | O | —CH₂C≡CMe |
| I-1772 | —OCH₂O— | * | H | H | * | H | H | OMe | OMe | OH | H | H | H | CH₂OH | O | —CH₂C₆H₄-4-Me |
| I-1773 | —OCH₂O— | * | H | H | * | H | H | OMe | OMe | OH | H | H | H | F | O | —CH₂CH=CMe₂ |
| I-1774 | —OCH₂O— | * | H | H | * | H | H | OMe | OMe | OH | H | H | H | F | O | —(CH₂)₂CH=CMe₂ |
| I-1775 | —OCH₂O— | * | H | H | * | H | H | OMe | OMe | OH | H | H | H | F | O | —CH₂CH=CCl₂ |
| I-1776 | —OCH₂O— | * | H | H | * | H | H | OMe | OMe | OH | H | H | H | F | O | —CH₂C≡CMe |
| I-1777 | —OCH₂O— | * | H | H | * | H | H | OMe | OMe | OH | H | H | H | F | O | —CH₂C₆H₄-4-Me |
| I-1778 | —OCH₂O— | * | H | H | * | H | H | OMe | OMe | COOH | H | H | H | OH | O | —CH₂CH=CMe₂ |
| I-1779 | —OCH₂O— | * | H | H | * | H | H | OMe | OMe | COOH | H | H | H | OH | O | —(CH₂)₂CH=CMe₂ |
| I-1780 | —OCH₂O— | * | H | H | * | H | H | OMe | OMe | COOH | H | H | H | OH | O | —CH₂CH=CCl₂ |
| I-1781 | —OCH₂O— | * | H | H | * | H | H | OMe | OMe | COOH | H | H | H | OH | O | —CH₂C≡CMe |
| I-1782 | —OCH₂O— | * | H | H | * | H | H | OMe | OMe | COOH | H | H | H | OH | O | —CH₂C₆H₄-4-Me |
| I-1783 | —OCH₂O— | * | H | H | * | H | H | OMe | OMe | COOH | H | H | H | OMs | O | —CH₂CH=CMe₂ |
| I-1784 | —OCH₂O— | * | H | H | * | H | H | OMe | OMe | COOH | H | H | H | OMs | O | —(CH₂)₂CH=CMe₂ |
| I-1785 | —OCH₂O— | * | H | H | * | H | H | OMe | OMe | COOH | H | H | H | OMs | O | —CH₂CH=CCl₂ |
| I-1786 | —OCH₂O— | * | H | H | * | H | H | OMe | OMe | COOH | H | H | H | OMs | O | —CH₂C≡CMe |
| I-1787 | —OCH₂O— | * | H | H | * | H | H | OMe | OMe | COOH | H | H | H | OMs | O | —CH₂C₆H₄-4-Me |
| I-1788 | —OCH₂O— | * | H | H | * | H | H | OMe | OMe | COOH | H | H | H | COOH | O | —CH₂CH=CMe₂ |

TABLE 290

| | | | | | | | | | | | | | | | | |
|---|---|---|---|---|---|---|---|---|---|---|---|---|---|---|---|---|
| I-1789 | —OCH₂O—* | H | H | * | H | H | OMe | OMe | COOH | H | H | H | COOH | O | —(CH₂)₂CH=CMe₂ |
| I-1790 | —OCH₂O—* | H | H | * | H | H | OMe | OMe | COOH | H | H | H | COOH | O | —CH₂CH=CCl₂ |
| I-1791 | —OCH₂O—* | H | H | * | H | H | OMe | OMe | COOH | H | H | H | COOH | O | —CH₂C≡CMe |
| I-1792 | —OCH₂O—* | H | H | * | H | H | OMe | OMe | COOH | H | H | H | COOH | O | —CH₂C₆H₄-4-Me |
| I-1793 | —OCH₂O—* | H | H | * | H | H | OMe | OMe | COOH | H | H | H | CH₂OH | O | —CH₂CH=CMe₂ |
| I-1794 | —OCH₂O—* | H | H | * | H | H | OMe | OMe | COOH | H | H | H | CH₂OH | O | —(CH₂)₂CH=CMe₂ |
| I-1795 | —OCH₂O—* | H | H | * | H | H | OMe | OMe | COOH | H | H | H | CH₂OH | O | —CH₂CH=CCl₂ |
| I-1796 | —OCH₂O—* | H | H | * | H | H | OMe | OMe | COOH | H | H | H | CH₂OH | O | —CH₂C≡CMe |
| I-1797 | —OCH₂O—* | H | H | * | H | H | OMe | OMe | COOH | H | H | H | CH₂OH | O | —CH₂C₆H₄-4-Me |
| I-1798 | —OCH₂O—* | H | H | * | H | H | OMe | OMe | COOH | H | H | H | F | O | —CH₂CH=CMe₂ |
| I-1799 | —OCH₂O—* | H | H | * | H | H | OMe | OMe | COOH | H | H | H | F | O | —(CH₂)₂CH=CMe₂ |
| I-1800 | —OCH₂O—* | H | H | * | H | H | OMe | OMe | COOH | H | H | H | F | O | —CH₂CH=CCl₂ |
| I-1801 | —OCH₂O—* | H | H | * | H | H | OMe | OMe | COOH | H | H | H | F | O | —CH₂C≡CMe |
| I-1802 | —OCH₂O—* | H | H | * | H | H | OMe | OMe | COOH | H | H | H | F | O | —CH₂C₆H₄-4-Me |
| I-1803 | —OCH₂O—* | H | H | * | H | H | OMe | OMe | CH₂OH | H | H | H | OH | O | —CH₂CH=CMe₂ |
| I-1804 | —OCH₂O—* | H | H | * | H | H | OMe | OMe | CH₂OH | H | H | H | OH | O | —(CH₂)₂CH=CMe₂ |
| I-1805 | —OCH₂O—* | H | H | * | H | H | OMe | OMe | CH₂OH | H | H | H | OH | O | —CH₂CH=CCl₂ |
| I-1806 | —OCH₂O—* | H | H | * | H | H | OMe | OMe | CH₂OH | H | H | H | OH | O | —CH₂C≡CMe |
| I-1807 | —OCH₂O—* | H | H | * | H | H | OMe | OMe | CH₂OH | H | H | H | OH | O | —CH₂C₆H₄-4-Me |
| I-1808 | —OCH₂O—* | H | H | * | H | H | OMe | OMe | CH₂OH | H | H | H | OMs | O | —CH₂CH=CMe₂ |
| I-1809 | —OCH₂O—* | H | H | * | H | H | OMe | OMe | CH₂OH | H | H | H | OMs | O | —(CH₂)₂CH=CMe₂ |

TABLE 291

| | | | | | | | | | | | | | | | | |
|---|---|---|---|---|---|---|---|---|---|---|---|---|---|---|---|---|
| I-1810 | —OCH₂O—* | H | H | * | H | H | OMe | OMe | CH₂OH | H | H | H | OMs | O | —CH₂CH=CCl₂ |
| I-1811 | —OCH₂O—* | H | H | * | H | H | OMe | OMe | CH₂OH | H | H | H | OMs | O | —CH₂C≡CMe |
| I-1812 | —OCH₂O—* | H | H | * | H | H | OMe | OMe | CH₂OH | H | H | H | OMs | O | —CH₂C₆H₄-4-Me |
| I-1813 | —OCH₂O—* | H | H | * | H | H | OMe | OMe | CH₂OH | H | H | H | COOH | O | —CH₂CH=CMe₂ |
| I-1814 | —OCH₂O—* | H | H | * | H | H | OMe | OMe | CH₂OH | H | H | H | COOH | O | —(CH₂)₂CH=CMe₂ |
| I-1815 | —OCH₂O—* | H | H | * | H | H | OMe | OMe | CH₂OH | H | H | H | COOH | O | —CH₂CH=CCl₂ |
| I-1816 | —OCH₂O—* | H | H | * | H | H | OMe | OMe | CH₂OH | H | H | H | COOH | O | —CH₂C≡CMe |
| I-1817 | —OCH₂O—* | H | H | * | H | H | OMe | OMe | CH₂OH | H | H | H | COOH | O | —CH₂C₆H₄-4-Me |
| I-1818 | —OCH₂O—* | H | H | * | H | H | OMe | OMe | CH₂OH | H | H | H | CH₂OH | O | —CH₂CH=CMe₂ |
| I-1819 | —OCH₂O—* | H | H | * | H | H | OMe | OMe | CH₂OH | H | H | H | CH₂OH | O | —(CH₂)₂CH=CMe₂ |
| I-1820 | —OCH₂O—* | H | H | * | H | H | OMe | OMe | CH₂OH | H | H | H | CH₂OH | O | —CH₂CH=CCl₂ |
| I-1821 | —OCH₂O—* | H | H | * | H | H | OMe | OMe | CH₂OH | H | H | H | CH₂OH | O | —CH₂C≡CMe |
| I-1822 | —OCH₂O—* | H | H | * | H | H | OMe | OMe | CH₂OH | H | H | H | CH₂OH | O | —CH₂C₆H₄-4-Me |
| I-1823 | —OCH₂O—* | H | H | * | H | H | OMe | OMe | CH₂OH | H | H | H | F | O | —CH₂CH=CMe₂ |
| I-1824 | —OCH₂O—* | H | H | * | H | H | OMe | OMe | CH₂OH | H | H | H | F | O | —(CH₂)₂CH=CMe₂ |
| I-1825 | —OCH₂O—* | H | H | * | H | H | OMe | OMe | CH₂OH | H | H | H | F | O | —CH₂CH=CCl₂ |
| I-1826 | —OCH₂O—* | H | H | * | H | H | OMe | OMe | CH₂OH | H | H | H | F | O | —CH₂C≡CMe |
| I-1827 | —OCH₂O—* | H | H | * | H | H | OMe | OMe | CH₂OH | H | H | H | F | O | —CH₂C₆H₄-4-Me |
| I-1828 | —OCH₂O—* | H | H | * | H | H | OMe | OMe | Me | H | H | H | OH | O | —CH₂CH=CMe₂ |
| I-1829 | —OCH₂O—* | H | H | * | H | H | OMe | OMe | Me | H | H | H | OH | O | —(CH₂)₂CH=CMe₂ |
| I-1830 | —OCH₂O—* | H | H | * | H | H | OMe | OMe | Me | H | H | H | OH | O | —CH₂CH=CCl₂ |

TABLE 292

| | | | | | | | | | | | | | | | | |
|---|---|---|---|---|---|---|---|---|---|---|---|---|---|---|---|---|
| I-1831 | —OCH₂O—* | H | H | * | H | H | OMe | OMe | Me | H | H | H | OH | O | —CH₂C≡CMe |
| I-1832 | —OCH₂O—* | H | H | * | H | H | OMe | OMe | Me | H | H | H | OH | O | —CH₂C₆H₄-4-Me |
| I-1833 | —OCH₂O—* | H | H | * | H | H | OMe | OMe | Me | H | H | H | OMs | O | —CH₂CH=CMe₂ |

TABLE 292-continued

| | | | | | | | | | | | | | | | |
|---|---|---|---|---|---|---|---|---|---|---|---|---|---|---|---|
| I-1834 | —OCH$_2$O—* | H | H | * | H | H | OMe | OMe | Me | H | H | H | OMs | O | —(CH$_2$)$_2$CH=CMe$_2$ |
| I-1835 | —OCH$_2$O—* | H | H | * | H | H | OMe | OMe | Me | H | H | H | OMs | O | —CH$_2$CH=CCl$_2$ |
| I-1836 | —OCH$_2$O—* | H | H | * | H | H | OMe | OMe | Me | H | H | H | OMs | O | —CH$_2$C≡CMe |
| I-1837 | —OCH$_2$O—* | H | H | * | H | H | OMe | OMe | Me | H | H | H | OMs | O | —CH$_2$C$_6$H$_4$-4-Me |
| I-1838 | —OCH$_2$O—* | H | H | * | H | H | OMe | OMe | Me | H | H | H | COOH | O | —CH$_2$CH=CMe$_2$ |
| I-1839 | —OCH$_2$O—* | H | H | * | H | H | OMe | OMe | Me | H | H | H | COOH | O | —(CH$_2$)$_2$CH=CMe$_2$ |
| I-1840 | —OCH$_2$O—* | H | H | * | H | H | OMe | OMe | Me | H | H | H | COOH | O | —CH$_2$CH=CCl$_2$ |
| I-1841 | —OCH$_2$O—* | H | H | * | H | H | OMe | OMe | Me | H | H | H | COOH | O | —CH$_2$C≡CMe |
| I-1842 | —OCH$_2$O—* | H | H | * | H | H | OMe | OMe | Me | H | H | H | COOH | O | —CH$_2$C$_6$H$_4$-4-Me |
| I-1843 | —OCH$_2$O—* | H | H | * | H | H | OMe | OMe | Me | H | H | H | CH$_2$OH | O | —CH$_2$CH=CMe$_2$ |
| I-1844 | —OCH$_2$O—* | H | H | * | H | H | OMe | OMe | Me | H | H | H | CH$_2$OH | O | —(CH$_2$)$_2$CH=CMe$_2$ |
| I-1845 | —OCH$_2$O—* | H | H | * | H | H | OMe | OMe | Me | H | H | H | CH$_2$OH | O | —CH$_2$CH=CCl$_2$ |
| I-1846 | —OCH$_2$O—* | H | H | * | H | H | OMe | OMe | Me | H | H | H | CH$_2$OH | O | —CH$_2$C≡CMe |
| I-1847 | —OCH$_2$O—* | H | H | * | H | H | OMe | OMe | Me | H | H | H | CH$_2$OH | O | —CH$_2$C$_6$H$_4$-4-Me |
| I-1848 | —OCH$_2$O—* | H | H | * | H | H | OMe | OMe | Me | H | H | H | F | O | —CH$_2$CH=CMe$_2$ |
| I-1849 | —OCH$_2$O—* | H | H | * | H | H | OMe | OMe | Me | H | H | H | F | O | —(CH$_2$)$_2$CH=CMe$_2$ |
| I-1850 | —OCH$_2$O—* | H | H | * | H | H | OMe | OMe | Me | H | H | H | F | O | —CH$_2$CH=CCl$_2$ |
| I-1851 | —OCH$_2$O—* | H | H | * | H | H | OMe | OMe | Me | H | H | H | F | O | —CH$_2$C≡CMe |

TABLE 293

| | | | | | | | | | | | | | | | |
|---|---|---|---|---|---|---|---|---|---|---|---|---|---|---|---|
| I-1852 | —OCH$_2$O—* | H | H | * | H | H | OMe | OMe | Me | H | H | H | F | O | —CH$_2$C$_6$H$_4$-4-Me |
| I-1853 | —OCH$_2$O—* | H | H | * | H | H | OMe | OMe | H | H | H | H | OH | O | —CH$_2$CH=CMe$_2$ |
| I-1854 | —OCH$_2$O—* | H | H | * | H | H | OMe | OMe | H | H | H | H | OH | O | —(CH$_2$)$_2$CH=CMe$_2$ |
| I-1855 | —OCH$_2$O—* | H | H | * | H | H | OMe | OMe | H | H | H | H | OH | O | —CH$_2$CH=CCl$_2$ |
| I-1856 | —OCH$_2$O—* | H | H | * | H | H | OMe | OMe | H | H | H | H | OH | O | —CH$_2$C≡CMe |
| I-1857 | —OCH$_2$O—* | H | H | * | H | H | OMe | OMe | H | H | H | H | OH | O | —CH$_2$C$_6$H$_4$-4-Me |
| I-1858 | —OCH$_2$O—* | H | H | * | H | H | OMe | OMe | H | H | H | H | OMs | O | —CH$_2$CH=CMe$_2$ |
| I-1859 | —OCH$_2$O—* | H | H | * | H | H | OMe | OMe | H | H | H | H | OMs | O | —(CH$_2$)$_2$CH=CMe$_2$ |
| I-1860 | —OCH$_2$O—* | H | H | * | H | H | OMe | OMe | H | H | H | H | OMs | O | —CH$_2$CH=CCl$_2$ |
| I-1861 | —OCH$_2$O—* | H | H | * | H | H | OMe | OMe | H | H | H | H | OMs | O | —CH$_2$C≡CMe |
| I-1862 | —OCH$_2$O—* | H | H | * | H | H | OMe | OMe | H | H | H | H | OMs | O | —CH$_2$C$_6$H$_4$-4-Me |
| I-1863 | —OCH$_2$O—* | H | H | * | H | H | OMe | OMe | H | H | H | H | COOH | O | —CH$_2$CH=CMe$_2$ |
| I-1864 | —OCH$_2$O—* | H | H | * | H | H | OMe | OMe | H | H | H | H | COOH | O | —(CH$_2$)$_2$CH=CMe$_2$ |
| I-1865 | —OCH$_2$O—* | H | H | * | H | H | OMe | OMe | H | H | H | H | COOH | O | —CH$_2$CH=CCl$_2$ |
| I-1866 | —OCH$_2$O—* | H | H | * | H | H | OMe | OMe | H | H | H | H | COOH | O | —CH$_2$C≡CMe |
| I-1867 | —OCH$_2$O—* | H | H | * | H | H | OMe | OMe | H | H | H | H | COOH | O | —CH$_2$C$_6$H$_4$-4-Me |
| I-1868 | —OCH$_2$O—* | H | H | * | H | H | OMe | OMe | H | H | H | H | CH$_2$OH | O | —CH$_2$CH=CMe$_2$ |
| I-1869 | —OCH$_2$O—* | H | H | * | H | H | OMe | OMe | H | H | H | H | CH$_2$OH | O | —(CH$_2$)$_2$CH=CMe$_2$ |
| I-1870 | —OCH$_2$O—* | H | H | * | H | H | OMe | OMe | H | H | H | H | CH$_2$OH | O | —CH$_2$CH=CCl$_2$ |
| I-1871 | —OCH$_2$O—* | H | H | * | H | H | OMe | OMe | H | H | H | H | CH$_2$OH | O | —CH$_2$C≡CMe |
| I-1872 | —OCH$_2$O—* | H | H | * | H | H | OMe | OMe | H | H | H | H | CH$_2$OH | O | —CH$_2$C$_6$H$_4$-4-Me |

TABLE 294

| | | | | | | | | | | | | | | | |
|---|---|---|---|---|---|---|---|---|---|---|---|---|---|---|---|
| I-1873 | —OCH$_2$O—* | H | H | * | H | H | OMe | OMe | H | H | H | H | F | O | —CH$_2$CH=CMe$_2$ |
| I-1874 | —OCH$_2$O—* | H | H | * | H | H | OMe | OMe | H | H | H | H | F | O | —(CH$_2$)$_2$CH=CMe$_2$ |
| I-1875 | —OCH$_2$O—* | H | H | * | H | H | OMe | OMe | H | H | H | H | F | O | —CH$_2$CH=CCl$_2$ |
| I-1876 | —OCH$_2$O—* | H | H | * | H | H | OMe | OMe | H | H | H | H | F | O | —CH$_2$C≡CMe |
| I-1877 | —OCH$_2$O—* | H | H | * | H | H | OMe | OMe | H | H | H | H | F | O | —CH$_2$C$_6$H$_4$-4-Me |
| I-1878 | —OCH$_2$O—* | H | H | * | H | F | OMe | OMe | OH | H | H | H | OH | O | —CH$_2$CH=CMe$_2$ |
| I-1879 | —OCH$_2$O—* | H | H | * | H | F | OMe | OMe | OH | H | H | H | OH | O | —(CH$_2$)$_2$CH=CMe$_2$ |
| I-1880 | —OCH$_2$O—* | H | H | * | H | F | OMe | OMe | OH | H | H | H | OH | O | —CH$_2$CH=CCl$_2$ |
| I-1881 | —OCH$_2$O—* | H | H | * | H | F | OMe | OMe | OH | H | H | H | OH | O | —CH$_2$C≡CMe |
| I-1882 | —OCH$_2$O—* | H | H | * | H | F | OMe | OMe | OH | H | H | H | OH | O | —CH$_2$C$_6$H$_4$-4-Me |
| I-1883 | —OCH$_2$O—* | H | H | * | H | F | OMe | OMe | OH | H | H | H | OMs | O | —CH$_2$CH=CMe$_2$ |
| I-1884 | —OCH$_2$O—* | H | H | * | H | F | OMe | OMe | OH | H | H | H | OMs | O | —(CH$_2$)$_2$CH=CMe$_2$ |
| I-1885 | —OCH$_2$O—* | H | H | * | H | F | OMe | OMe | OH | H | H | H | OMs | O | —CH$_2$CH=CCl$_2$ |
| I-1886 | —OCH$_2$O—* | H | H | * | H | F | OMe | OMe | OH | H | H | H | OMs | O | —CH$_2$C≡CMe |
| I-1887 | —OCH$_2$O—* | H | H | * | H | F | OMe | OMe | OH | H | H | H | OMs | O | —CH$_2$C$_6$H$_4$-4-Me |
| I-1888 | —OCH$_2$O—* | H | H | * | H | F | OMe | OMe | OH | H | H | H | COOH | O | —CH$_2$CH=CMe$_2$ |
| I-1889 | —OCH$_2$O—* | H | H | * | H | F | OMe | OMe | OH | H | H | H | COOH | O | —(CH$_2$)$_2$CH=CMe$_2$ |
| I-1890 | —OCH$_2$O—* | H | H | * | H | F | OMe | OMe | OH | H | H | H | COOH | O | —CH$_2$CH=CCl$_2$ |
| I-1891 | —OCH$_2$O—* | H | H | * | H | F | OMe | OMe | OH | H | H | H | COOH | O | —CH$_2$C≡CMe |
| I-1892 | —OCH$_2$O—* | H | H | * | H | F | OMe | OMe | OH | H | H | H | COOH | O | —CH$_2$C$_6$H$_4$-4-Me |
| I-1893 | —OCH$_2$O—* | H | H | * | H | F | OMe | OMe | OH | H | H | H | CH$_2$OH | O | —CH$_2$CH=CMe$_2$ |

TABLE 295

| | | | | | | | | | | | | | | | |
|---|---|---|---|---|---|---|---|---|---|---|---|---|---|---|---|
| I-1894 | —OCH$_2$O—* | H | H | * | H | F | OMe | OMe | OH | H | H | H | CH$_2$OH | O | —(CH$_2$)$_2$CH=CMe$_2$ |
| I-1895 | —OCH$_2$O—* | H | H | * | H | F | OMe | OMe | OH | H | H | H | CH$_2$OH | O | —CH$_2$CH=CCl$_2$ |
| I-1896 | —OCH$_2$O—* | H | H | * | H | F | OMe | OMe | OH | H | H | H | CH$_2$OH | O | —CH$_2$C≡CMe |

TABLE 295-continued

| | | | | | | | | | | | | | | | | |
|---|---|---|---|---|---|---|---|---|---|---|---|---|---|---|---|---|
| I-1897 | —OCH₂O—* | H | H | * | H | F | OMe | OMe | OH | H | H | H | CH₂OH | O | —CH₂C₆H₄-4-Me |
| I-1898 | —OCH₂O—* | H | H | * | H | F | OMe | OMe | OH | H | H | H | F | O | —CH₂CH═CMe₂ |
| I-1899 | —OCH₂O—* | H | H | * | H | F | OMe | OMe | OH | H | H | H | F | O | —(CH₂)₂CH═CMe₂ |
| I-1900 | —OCH₂O—* | H | H | * | H | F | OMe | OMe | OH | H | H | H | F | O | —CH₂CH═CCl₂ |
| I-1901 | —OCH₂O—* | H | H | * | H | F | OMe | OMe | OH | H | H | H | F | O | —CH₂C≡CMe |
| I-1902 | —OCH₂O—* | H | H | * | H | F | OMe | OMe | OH | H | H | H | F | O | —CH₂C₆H₄-4-Me |
| I-1903 | NMe₂ | | H | H | H | H | H | OMe | OMe | OH | H | H | H | OH | O | —(CH₂)₂CH═CMe₂ |
| I-1904 | NMe₂ | | H | H | H | H | H | OMe | OMe | OH | H | H | H | OH | O | —CH₂CH═CCl₂ |
| I-1905 | NMe₂ | | H | H | H | H | H | OMe | OMe | OH | H | H | H | OH | O | —CH₂C≡CMe |
| I-1906 | NMe₂ | | H | H | H | H | H | OMe | OMe | OH | H | H | H | OMs | O | —CH₂CH═CMe₂ |
| I-1907 | NMe₂ | | H | H | H | H | H | OMe | OMe | OH | H | H | H | OMs | O | —(CH₂)₂CH═CMe₂ |
| I-1908 | NMe₂ | | H | H | H | H | H | OMe | OMe | OH | H | H | H | OMs | O | —CH₂CH═CCl₂ |
| I-1909 | NMe₂ | | H | H | H | H | H | OMe | OMe | OH | H | H | H | OMs | O | —CH₂C≡CMe |
| I-1910 | NMe₂ | | H | H | H | H | H | OMe | OMe | OH | H | H | H | OMs | O | —CH₂C₆H₄-4-Me |
| I-1911 | NMe₂ | | H | H | H | H | H | OMe | OMe | OH | H | H | H | COOH | O | —CH₂CH═CMe₂ |
| I-1912 | NMe₂ | | H | H | H | H | H | OMe | OMe | OH | H | H | H | COOH | O | —(CH₂)₂CH═CMe₂ |
| I-1913 | NMe₂ | | H | H | H | H | H | OMe | OMe | OH | H | H | H | COOH | O | —CH₂CH═CCl₂ |
| I-1914 | NMe₂ | | H | H | H | H | H | OMe | OMe | OH | H | H | H | COOH | O | —CH₂C≡CMe |

TABLE 296

| | | | | | | | | | | | | | | | |
|---|---|---|---|---|---|---|---|---|---|---|---|---|---|---|---|
| I-1915 | NMe₂ | H | H | H | H | H | OMe | OMe | OH | H | H | H | COOH | O | —CH₂C₆H₄-4-Me |
| I-1916 | NMe₂ | H | H | H | H | H | OMe | OMe | OH | H | H | H | CH₂OH | O | —CH₂CH═CMe₂ |
| I-1917 | NMe₂ | H | H | H | H | H | OMe | OMe | OH | H | H | H | CH₂OH | O | —(CH₂)₂CH═CMe₂ |
| I-1918 | NMe₂ | H | H | H | H | H | OMe | OMe | OH | H | H | H | CH₂OH | O | —CH₂CH═CCl₂ |
| I-1919 | NMe₂ | H | H | H | H | H | OMe | OMe | OH | H | H | H | CH₂OH | O | —CH₂C≡CMe |
| I-1920 | NMe₂ | H | H | H | H | H | OMe | OMe | OH | H | H | H | CH₂OH | O | —CH₂C₆H₄-4-Me |
| I-1921 | NMe₂ | H | H | H | H | H | OMe | OMe | OH | H | H | H | F | O | —CH₂CH═CMe₂ |
| I-1922 | NMe₂ | H | H | H | H | H | OMe | OMe | OH | H | H | H | F | O | —(CH₂)₂CH═CMe₂ |
| I-1923 | NMe₂ | H | H | H | H | H | OMe | OMe | OH | H | H | H | F | O | —CH₂CH═CCl₂ |
| I-1924 | NMe₂ | H | H | H | H | H | OMe | OMe | OH | H | H | H | F | O | —CH₂C≡CMe |
| I-1925 | NMe₂ | H | H | H | H | H | OMe | OMe | OH | H | H | H | F | O | —CH₂C₆H₄-4-Me |
| I-1926 | NMe₂ | H | H | H | H | H | OMe | OMe | COOH | H | H | H | OH | O | —CH₂CH═CMe₂ |
| I-1927 | NMe₂ | H | H | H | H | H | OMe | OMe | COOH | H | H | H | OH | O | —(CH₂)₂CH═CMe₂ |
| I-1928 | NMe₂ | H | H | H | H | H | OMe | OMe | COOH | H | H | H | OH | O | —CH₂CH═CCl₂ |
| I-1929 | NMe₂ | H | H | H | H | H | OMe | OMe | COOH | H | H | H | OH | O | —CH₂C≡CMe |
| I-1930 | NMe₂ | H | H | H | H | H | OMe | OMe | COOH | H | H | H | OH | O | —CH₂C₆H₄-4-Me |
| I-1931 | NMe₂ | H | H | H | H | H | OMe | OMe | COOH | H | H | H | OMs | O | —CH₂CH═CMe₂ |
| I-1932 | NMe₂ | H | H | H | H | H | OMe | OMe | COOH | H | H | H | OMs | O | —(CH₂)₂CH═CMe₂ |
| I-1933 | NMe₂ | H | H | H | H | H | OMe | OMe | COOH | H | H | H | OMs | O | —CH₂CH═CCl₂ |
| I-1934 | NMe₂ | H | H | H | H | H | OMe | OMe | COOH | H | H | H | OMs | O | —CH₂C≡CMe |
| I-1935 | NMe₂ | H | H | H | H | H | OMe | OMe | COOH | H | H | H | OMs | O | —CH₂C₆H₄-4-Me |

TABLE 297

| | | | | | | | | | | | | | | | |
|---|---|---|---|---|---|---|---|---|---|---|---|---|---|---|---|
| I-1936 | NMe₂ | H | H | H | H | H | OMe | OMe | COOH | H | H | H | COOH | O | —CH₂CH═CMe₂ |
| I-1937 | NMe₂ | H | H | H | H | H | OMe | OMe | COOH | H | H | H | COOH | O | —(CH₂)₂CH═CMe₂ |
| I-1938 | NMe₂ | H | H | H | H | H | OMe | OMe | COOH | H | H | H | COOH | O | —CH₂CH═CCl₂ |
| I-199 | NMe₂ | H | H | H | H | H | OMe | OMe | COOH | H | H | H | COOH | O | —CH₂C≡CMe |
| I-190 | NMe₂ | H | H | H | H | H | OMe | OMe | COOH | H | H | H | COOH | O | —CH₂C₆H₄-4-Me |
| I-1941 | NMe₂ | H | H | H | H | H | OMe | OMe | COOH | H | H | H | CH₂OH | O | —CH₂CH═CMe₂ |
| I-1942 | NMe₂ | H | H | H | H | H | OMe | OMe | COOH | H | H | H | CH₂OH | O | —(CH₂)₂CH═CMe₂ |
| I-1943 | NMe₂ | H | H | H | H | H | OMe | OMe | COOH | H | H | H | CH₂OH | O | —CH₂CH═CCl₂ |
| I-1944 | NMe₂ | H | H | H | H | H | OMe | OMe | COOH | H | H | H | CH₂OH | O | —CH₂C≡CMe |
| I-1945 | NMe₂ | H | H | H | H | H | OMe | OMe | COOH | H | H | H | CH₂OH | O | —CH₂C₆H₄-4-Me |
| I-1946 | NMe₂ | H | H | H | H | H | OMe | OMe | COOH | H | H | H | F | O | —CH₂CH═CMe₂ |
| I-1947 | NMe₂ | H | H | H | H | H | OMe | OMe | COOH | H | H | H | F | O | —(CH₂)₂CH═CMe₂ |
| I-1948 | NMe₂ | H | H | H | H | H | OMe | OMe | COOH | H | H | H | F | O | —CH₂CH═CCl₂ |
| I-1949 | NMe₂ | H | H | H | H | H | OMe | OMe | COOH | H | H | H | F | O | —CH₂C≡CMe |
| I-1950 | NMe₂ | H | H | H | H | H | OMe | OMe | COOH | H | H | H | F | O | —CH₂C₆H₄-4-Me |
| I-1951 | NMe₂ | H | H | H | H | H | OMe | OMe | CH₂OH | H | H | H | OH | O | —CH₂CH═CMe₂ |
| I-1952 | NMe₂ | H | H | H | H | H | OMe | OMe | CH₂OH | H | H | H | OH | O | —(CH₂)₂CH═CMe₂ |
| I-1953 | NMe₂ | H | H | H | H | H | OMe | OMe | CH₂OH | H | H | H | OH | O | —CH₂CH═CCl₂ |
| I-1954 | NMe₂ | H | H | H | H | H | OMe | OMe | CH₂OH | H | H | H | OH | O | —CH₂C≡CMe |
| I-1955 | NMe₂ | H | H | H | H | H | OMe | OMe | CH₂OH | H | H | H | OH | O | —CH₂C₆H₄-4-Me |
| I-1956 | NMe₂ | H | H | H | H | H | OMe | OMe | CH₂OH | H | H | H | OMs | O | —CH₂CH═CMe₂ |

TABLE 298

| | | | | | | | | | | | | | | | |
|---|---|---|---|---|---|---|---|---|---|---|---|---|---|---|---|
| I-1957 | NMe₂ | H | H | H | H | H | OMe | OMe | CH₂OH | H | H | H | OMs | O | —(CH₂)₂CH═CMe₂ |
| I-1958 | NMe₂ | H | H | H | H | H | OMe | OMe | CH₂OH | H | H | H | OMs | O | —CH₂CH═CCl₂ |
| I-1959 | NMe₂ | H | H | H | H | H | OMe | OMe | CH₂OH | H | H | H | OMs | O | —CH₂C≡CMe |

TABLE 298-continued

| | | | | | | | | | | | | | | | |
|---|---|---|---|---|---|---|---|---|---|---|---|---|---|---|---|
| I-1960 | NMe$_2$ | H | H | H | H | H | OMe | OMe | CH$_2$OH | H | H | H | OMs | O | —CH$_2$C$_6$H$_4$-4-Me |
| I-1961 | NMe$_2$ | H | H | H | H | H | OMe | OMe | CH$_2$OH | H | H | H | COOH | O | —CH$_2$CH=CMe$_2$ |
| I-1962 | NMe$_2$ | H | H | H | H | H | OMe | OMe | CH$_2$OH | H | H | H | COOH | O | —(CH$_2$)$_2$CH=CMe$_2$ |
| I-1963 | NMe$_2$ | H | H | H | H | H | OMe | OMe | CH$_2$OH | H | H | H | COOH | O | —CH$_2$CH=CCl$_2$ |
| I-1964 | NMe$_2$ | H | H | H | H | H | OMe | OMe | CH$_2$OH | H | H | H | COOH | O | —CH$_2$C≡CMe |
| I-1965 | NMe$_2$ | H | H | H | H | H | OMe | OMe | CH$_2$OH | H | H | H | COOH | O | —CH$_2$C$_6$H$_4$-4-Me |
| I-1966 | NMe$_2$ | H | H | H | H | H | OMe | OMe | CH$_2$OH | H | H | H | CH$_2$OH | O | —CH$_2$CH=CMe$_2$ |
| I-1967 | NMe$_2$ | H | H | H | H | H | OMe | OMe | CH$_2$OH | H | H | H | CH$_2$OH | O | —(CH$_2$)$_2$CH=CMe$_2$ |
| I-198 | NMe$_2$ | H | H | H | H | H | OMe | OMe | CH$_2$OH | H | H | H | CH$_2$OH | O | —CH$_2$CH=CCl$_2$ |
| I-1969 | NMe$_2$ | H | H | H | H | H | OMe | OMe | CH$_2$OH | H | H | H | CH$_2$OH | O | —CH$_2$C≡CMe |
| I-1970 | NMe$_2$ | H | H | H | H | H | OMe | OMe | CH$_2$OH | H | H | H | CH$_2$OH | O | —CH$_2$C$_6$H$_4$-4-Me |
| I-1971 | NMe$_2$ | H | H | H | H | H | OMe | OMe | CH$_2$OH | H | H | H | F | O | —CH$_2$CH=CMe$_2$ |
| I-1972 | NMe$_2$ | H | H | H | H | H | OMe | OMe | CH$_2$OH | H | H | H | F | O | —(CH$_2$)$_2$CH=CMe$_2$ |
| I-1973 | NMe$_2$ | H | H | H | H | H | OMe | OMe | CH$_2$OH | H | H | H | F | O | —CH$_2$CH=CCl$_2$ |
| I-1974 | NMe$_2$ | H | H | H | H | H | OMe | OMe | CH$_2$OH | H | H | H | F | O | —CH$_2$C≡CMe |
| I-1975 | NMe$_2$ | H | H | H | H | H | OMe | OMe | CH$_2$OH | H | H | H | F | O | —CH$_2$C$_6$H$_4$-4-Me |
| I-1976 | NMe$_2$ | H | H | H | H | H | OMe | OMe | Me | H | H | H | OH | O | —CH$_2$CH=CMe$_2$ |
| I-1977 | NMe$_2$ | H | H | H | H | H | OMe | OMe | Me | H | H | H | OH | O | —(CH$_2$)$_2$CH=CMe$_2$ |

TABLE 299

| | | | | | | | | | | | | | | | |
|---|---|---|---|---|---|---|---|---|---|---|---|---|---|---|---|
| I-1978 | NMe$_2$ | H | H | H | H | H | OMe | OMe | Me | H | H | H | OH | O | —CH$_2$CH=CCl$_2$ |
| I-1979 | NMe$_2$ | H | H | H | H | H | OMe | OMe | Me | H | H | H | OH | O | —CH$_2$C≡CMe |
| I-1980 | NMe$_2$ | H | H | H | H | H | OMe | OMe | Me | H | H | H | OH | O | —CH$_2$C$_6$H$_4$-4-Me |
| I-1981 | NMe$_2$ | H | H | H | H | H | OMe | OMe | Me | H | H | H | OMs | O | —CH$_2$CH=CMe$_2$ |
| I-1982 | NMe$_2$ | H | H | H | H | H | OMe | OMe | Me | H | H | H | OMs | O | —(CH$_2$)$_2$CH=CMe$_2$ |
| I-1983 | NMe$_2$ | H | H | H | H | H | OMe | OMe | Me | H | H | H | OMs | O | —CH$_2$CH=CCl$_2$ |
| I-1984 | NMe$_2$ | H | H | H | H | H | OMe | OMe | Me | H | H | H | OMs | O | —CH$_2$C≡CMe |
| I-1985 | NMe$_2$ | H | H | H | H | H | OMe | OMe | Me | H | H | H | OMs | O | —CH$_2$C$_6$H$_4$-4-Me |
| I-1986 | NMe$_2$ | H | H | H | H | H | OMe | OMe | Me | H | H | H | COOH | O | —CH$_2$CH=CMe$_2$ |
| I-1987 | NMe$_2$ | H | H | H | H | H | OMe | OMe | Me | H | H | H | COOH | O | —(CH$_2$)$_2$CH=CMe$_2$ |
| I-1988 | NMe$_2$ | H | H | H | H | H | OMe | OMe | Me | H | H | H | COOH | O | —CH$_2$CH=CCl$_2$ |
| I-1989 | NMe$_2$ | H | H | H | H | H | OMe | OMe | Me | H | H | H | COOH | O | —CH$_2$C≡CMe |
| I-1990 | NMe$_2$ | H | H | H | H | H | OMe | OMe | Me | H | H | H | COOH | O | —CH$_2$C$_6$H$_4$-4-Me |
| I-1991 | NMe$_2$ | H | H | H | H | H | OMe | OMe | Me | H | H | H | CH$_2$OH | O | —CH$_2$CH=CMe$_2$ |
| I-1992 | NMe$_2$ | H | H | H | H | H | OMe | OMe | Me | H | H | H | CH$_2$OH | O | —(CH$_2$)$_2$CH=CMe$_2$ |
| I-1993 | NMe$_2$ | H | H | H | H | H | OMe | OMe | Me | H | H | H | CH$_2$OH | O | —CH$_2$CH=CCl$_2$ |
| I-1994 | NMe$_2$ | H | H | H | H | H | OMe | OMe | Me | H | H | H | CH$_2$OH | O | —CH$_2$C≡CMe |
| I-1995 | NMe$_2$ | H | H | H | H | H | OMe | OMe | Me | H | H | H | CH$_2$OH | O | —CH$_2$C$_6$H$_4$-4-Me |
| I-1996 | NMe$_2$ | H | H | H | H | H | OMe | OMe | Me | H | H | H | F | O | —CH$_2$CH=CMe$_2$ |
| I-1997 | NMe$_2$ | H | H | H | H | H | OMe | OMe | Me | H | H | H | F | O | —(CH$_2$)$_2$CH=CMe$_2$ |
| I-1998 | NMe$_2$ | H | H | H | H | H | OMe | OMe | Me | H | H | H | F | O | —CH$_2$CH=CCl$_2$ |

TABLE 300

| | | | | | | | | | | | | | | | |
|---|---|---|---|---|---|---|---|---|---|---|---|---|---|---|---|
| I-1999 | NMe$_2$ | H | H | H | H | H | OMe | OMe | Me | H | H | H | F | O | —CH$_2$C≡CMe |
| I-2000 | NMe$_2$ | H | H | H | H | H | OMe | OMe | Me | H | H | H | F | O | —CH$_2$C$_6$H$_4$-4-Me |
| I-2001 | NMe$_2$ | H | H | H | H | H | OMe | OMe | H | H | H | H | OH | O | —CH$_2$CH=CMe$_2$ |
| I-2002 | NMe$_2$ | H | H | H | H | H | OMe | OMe | H | H | H | H | OH | O | —(CH$_2$)$_2$CH=CMe$_2$ |
| I-2003 | NMe$_2$ | H | H | H | H | H | OMe | OMe | H | H | H | H | OH | O | —CH$_2$CH=CCl$_2$ |
| I-2004 | NMe$_2$ | H | H | H | H | H | OMe | OMe | H | H | H | H | OH | O | —CH$_2$C≡CMe |
| I-2005 | NMe$_2$ | H | H | H | H | H | OMe | OMe | H | H | H | H | OH | O | —CH$_2$C$_6$H$_4$-4-Me |
| I-2006 | NMe$_2$ | H | H | H | H | H | OMe | OMe | H | H | H | H | OMs | O | —CH$_2$CH=CMe$_2$ |
| I-2007 | NMe$_2$ | H | H | H | H | H | OMe | OMe | H | H | H | H | OMs | O | —(CH$_2$)$_2$CH=CMe$_2$ |
| I-2008 | NMe$_2$ | H | H | H | H | H | OMe | OMe | H | H | H | H | OMs | O | —CH$_2$CH=CCl$_2$ |
| I-2009 | NMe$_2$ | H | H | H | H | H | OMe | OMe | H | H | H | H | OMs | O | —CH$_2$C≡CMe |
| I-2010 | NMe$_2$ | H | H | H | H | H | OMe | OMe | H | H | H | H | OMs | O | —CH$_2$C$_6$H$_4$-4-Me |
| I-2011 | NMe$_2$ | H | H | H | H | H | OMe | OMe | H | H | H | H | COOH | O | —CH$_2$CH=CMe$_2$ |
| I-2012 | NMe$_2$ | H | H | H | H | H | OMe | OMe | H | H | H | H | COOH | O | —(CH$_2$)$_2$CH=CMe$_2$ |
| I-2013 | NMe$_2$ | H | H | H | H | H | OMe | OMe | H | H | H | H | COOH | O | —CH$_2$CH=CCl$_2$ |
| I-2014 | NMe$_2$ | H | H | H | H | H | OMe | OMe | H | H | H | H | COOH | O | —CH$_2$C≡CMe |
| I-2015 | NMe$_2$ | H | H | H | H | H | OMe | OMe | H | H | H | H | COOH | O | —CH$_2$C$_6$H$_4$-4-Me |
| I-2016 | NMe$_2$ | H | H | H | H | H | OMe | OMe | H | H | H | H | CH$_2$OH | O | —CH$_2$CH=CMe$_2$ |
| I-2017 | NMe$_2$ | H | H | H | H | H | OMe | OMe | H | H | H | H | CH$_2$OH | O | —(CH$_2$)$_2$CH=CMe$_2$ |
| I-2018 | NMe$_2$ | H | H | H | H | H | OMe | OMe | H | H | H | H | CH$_2$OH | O | —CH$_2$CH=CCl$_2$ |
| I-2019 | NMe$_2$ | H | H | H | H | H | OMe | OMe | H | H | H | H | CH$_2$OH | O | —CH$_2$C≡CMe |

TABLE 301

| | | | | | | | | | | | | | | | |
|---|---|---|---|---|---|---|---|---|---|---|---|---|---|---|---|
| I-2020 | NMe$_2$ | H | H | H | H | H | OMe | OMe | H | H | H | H | CH$_2$OH | O | —CH$_2$C$_6$H$_4$-4-Me |
| I-2021 | NMe$_2$ | H | H | H | H | H | OMe | OMe | H | H | H | H | F | O | —CH$_2$CH=CMe$_2$ |
| I-2022 | NMe$_2$ | H | H | H | H | H | OMe | OMe | H | H | H | H | F | O | —(CH$_2$)$_2$CH=CMe$_2$ |

TABLE 301-continued

| | | | | | | | | | | | | | | | |
|---|---|---|---|---|---|---|---|---|---|---|---|---|---|---|---|
| I-2023 | NMe₂ | H | H | H | H | H | OMe | OMe | H | H | H | H | F | O | —CH₂CH=CCl₂ |
| I-2024 | NMe₂ | H | H | H | H | H | OMe | OMe | H | H | H | H | F | O | —CH₂C≡CMe |
| I-2025 | NMe₂ | H | H | H | H | H | OMe | OMe | H | H | H | H | F | O | —CH₂C₆H₄-4-Me |
| I-2026 | NMe₂ | H | H | H | H | F | OMe | OMe | OH | H | H | H | OH | O | —CH₂CH=CMe₂ |
| I-2027 | NMe₂ | H | H | H | H | F | OMe | OMe | OH | H | H | H | OH | O | —(CH₂)₂CH=CMe₂ |
| I-2028 | NMe₂ | H | H | H | H | F | OMe | OMe | OH | H | H | H | OH | O | —CH₂CH=CCl₂ |
| I-2029 | NMe₂ | H | H | H | H | F | OMe | OMe | OH | H | H | H | OH | O | —CH₂C≡CMe |
| I-2030 | NMe₂ | H | H | H | H | F | OMe | OMe | OH | H | H | H | OH | O | —CH₂C₆H₄-4-Me |
| I-2031 | NMe₂ | H | H | H | H | F | OMe | OMe | OH | H | H | H | OMs | O | —CH₂CH=CMe₂ |
| I-2032 | NMe₂ | H | H | H | H | F | OMe | OMe | OH | H | H | H | OMs | O | —(CH₂)₂CH=CMe₂ |
| I-2033 | NMe₂ | H | H | H | H | F | OMe | OMe | OH | H | H | H | OMs | O | —CH₂CH=CCl₂ |
| I-2034 | NMe₂ | H | H | H | H | F | OMe | OMe | OH | H | H | H | OMs | O | —CH₂C≡CMe |
| I-2035 | NMe₂ | H | H | H | H | F | OMe | OMe | OH | H | H | H | OMs | O | —CH₂C₆H₄-4-Me |
| I-2036 | NMe₂ | H | H | H | H | F | OMe | OMe | OH | H | H | H | COOH | O | —CH₂CH=CMe₂ |
| I-2037 | NMe₂ | H | H | H | H | F | OMe | OMe | OH | H | H | H | COOH | O | —(CH₂)₂CH=CMe₂ |
| I-2038 | NMe₂ | H | H | H | H | F | OMe | OMe | OH | H | H | H | COOH | O | —CH₂CH=CCl₂ |
| I-2039 | NMe₂ | H | H | H | H | F | OMe | OMe | OH | H | H | H | COOH | O | —CH₂C≡CMe |
| I-2040 | NMe₂ | H | H | H | H | F | OMe | OMe | OH | H | H | H | COOH | O | —CH₂C₆H₄-4-Me |

TABLE 302

| | | | | | | | | | | | | | | | |
|---|---|---|---|---|---|---|---|---|---|---|---|---|---|---|---|
| I-2041 | NMe₂ | H | H | H | H | F | OMe | OMe | OH | H | H | H | CH₂OH | O | —CH₂CH=CMe₂ |
| I-2042 | NMe₂ | H | H | H | H | F | OMe | OMe | OH | H | H | H | CH₂OH | O | —(CH₂)₂CH=CMe₂ |
| I-2043 | NMe₂ | H | H | H | H | F | OMe | OMe | OH | H | H | H | CH₂OH | O | —CH₂CH=CCl₂ |
| I-2044 | NMe₂ | H | H | H | H | F | OMe | OMe | OH | H | H | H | CH₂OH | O | —CH₂C≡CMe |
| I-2045 | NMe₂ | H | H | H | H | F | OMe | OMe | OH | H | H | H | CH₂OH | O | —CH₂C₆H₄-4-Me |
| I-2046 | NMe₂ | H | H | H | H | F | OMe | OMe | OH | H | H | H | F | O | —CH₂CH=CMe₂ |
| I-2047 | NMe₂ | H | H | H | H | F | OMe | OMe | OH | H | H | H | F | O | —(CH₂)₂CH=CMe₂ |
| I-2048 | NMe₂ | H | H | H | H | F | OMe | OMe | OH | H | H | H | F | O | —CH₂CH=CCl₂ |
| I-2049 | NMe₂ | H | H | H | H | F | OMe | OMe | OH | H | H | H | F | O | —CH₂C≡CMe |
| I-2050 | NMe₂ | H | H | H | H | F | OMe | OMe | OH | H | H | H | F | O | —CH₂C₆H₄-4-Me |
| I-2051 | COOH | H | H | H | H | H | OMe | OMe | OH | H | H | H | OH | O | —(CH₂)₂CH=CMe₂ |
| I-2052 | COOH | H | H | H | H | H | OMe | OMe | OH | H | H | H | OH | O | —CH₂CH=CCl₂ |
| I-2053 | COOH | H | H | H | H | H | OMe | OMe | OH | H | H | H | OH | O | —CH₂C≡CMe |
| I-2054 | COOH | H | H | H | H | H | OMe | OMe | OH | H | H | H | OMs | O | —CH₂CH=CMe₂ |
| I-2055 | COOH | H | H | H | H | H | OMe | OMe | OH | H | H | H | OMs | O | —(CH₂)₂CH=CMe₂ |
| I-2056 | COOH | H | H | H | H | H | OMe | OMe | OH | H | H | H | OMs | O | —CH₂CH=CCl₂ |
| I-2057 | COOH | H | H | H | H | H | OMe | OMe | OH | H | H | H | OMs | O | —CH₂C≡CMe |
| I-2058 | COOH | H | H | H | H | H | OMe | OMe | OH | H | H | H | OMs | O | —CH₂C₆H₄-4-Me |
| I-2059 | COOH | H | H | H | H | H | OMe | OMe | OH | H | H | H | COOH | O | —CH₂CH=CMe₂ |
| I-2060 | COOH | H | H | H | H | H | OMe | OMe | OH | H | H | H | COOH | O | —(CH₂)₂CH=CMe₂ |
| I-2061 | COOH | H | H | H | H | H | OMe | OMe | OH | H | H | H | COOH | O | —CH₂CH=CCl₂ |

TABLE 303

| | | | | | | | | | | | | | | | |
|---|---|---|---|---|---|---|---|---|---|---|---|---|---|---|---|
| I-2062 | COOH | H | H | H | H | H | OMe | OMe | OH | H | H | H | COOH | O | —CH₂C≡CMe |
| I-2063 | COOH | H | H | H | H | H | OMe | OMe | OH | H | H | H | COOH | O | —CH₂C₆H₄-4-Me |
| I-2064 | COOH | H | H | H | H | H | OMe | OMe | OH | H | H | H | CH₂OH | O | —CH₂CH=CMe₂ |
| I-2065 | COOH | H | H | H | H | H | OMe | OMe | OH | H | H | H | CH₂OH | O | —(CH₂)₂CH=CMe₂ |
| I-2066 | COOH | H | H | H | H | H | OMe | OMe | OH | H | H | H | CH₂OH | O | —CH₂CH=CCl₂ |
| I-2067 | COOH | H | H | H | H | H | OMe | OMe | OH | H | H | H | CH₂OH | O | —CH₂C≡CMe |
| I-2068 | COOH | H | H | H | H | H | OMe | OMe | OH | H | H | H | CH₂OH | O | —CH₂C₆H₄-4-Me |
| I-2069 | COOH | H | H | H | H | H | OMe | OMe | OH | H | H | H | F | O | —CH₂CH=CMe₂ |
| I-2070 | COOH | H | H | H | H | H | OMe | OMe | OH | H | H | H | F | O | —(CH₂)₂CH=CMe₂ |
| I-2071 | COOH | H | H | H | H | H | OMe | OMe | OH | H | H | H | F | O | —CH₂CH=CCl₂ |
| I-2072 | COOH | H | H | H | H | H | OMe | OMe | OH | H | H | H | F | O | —CH₂C≡CMe |
| I-2073 | COOH | H | H | H | H | H | OMe | OMe | OH | H | H | H | F | O | —CH₂C₆H₄-4-Me |
| I-2074 | COOH | H | H | H | H | H | OMe | OMe | COOH | H | H | H | OH | O | —CH₂CH=CMe₂ |
| I-2075 | COOH | H | H | H | H | H | OMe | OMe | COOH | H | H | H | OH | O | —(CH₂)₂CH=CMe₂ |
| I-2076 | COOH | H | H | H | H | H | OMe | OMe | COOH | H | H | H | OH | O | —CH₂CH=CCl₂ |
| I-2077 | COOH | H | H | H | H | H | OMe | OMe | COOH | H | H | H | OH | O | —CH₂C≡CMe |
| I-2078 | COOH | H | H | H | H | H | OMe | OMe | COOH | H | H | H | OH | O | —CH₂C₆H₄-4-Me |
| I-2079 | COOH | H | H | H | H | H | OMe | OMe | COOH | H | H | H | OMs | O | —CH₂CH=CMe₂ |
| I-2080 | COOH | H | H | H | H | H | OMe | OMe | COOH | H | H | H | OMs | O | —(CH₂)₂CH=CMe₂ |
| I-2081 | COOH | H | H | H | H | H | OMe | OMe | COOH | H | H | H | OMs | O | —CH₂CH=CCl₂ |
| I-2082 | COOH | H | H | H | H | H | OMe | OMe | COOH | H | H | H | OMs | O | —CH₂C≡CMe |

TABLE 304

| | | | | | | | | | | | | | | | |
|---|---|---|---|---|---|---|---|---|---|---|---|---|---|---|---|
| I-2083 | COOH | H | H | H | H | H | OMe | OMe | COOH | H | H | H | OMs | O | —CH₂C₆H₄-4-Me |
| I-2084 | COOH | H | H | H | H | H | OMe | OMe | COOH | H | H | H | COOH | O | —CH₂CH=CMe₂ |
| I-2085 | COOH | H | H | H | H | H | OMe | OMe | COOH | H | H | H | COOH | O | —(CH₂)₂CH=CMe₂ |

TABLE 304-continued

| I-2086 | COOH | H | H | H | H | H | OMe | OMe | COOH | H | H | H | COOH | O | —CH$_2$CH=CCl$_2$ |
| I-2087 | COOH | H | H | H | H | H | OMe | OMe | COOH | H | H | H | COOH | O | —CH$_2$C≡CMe |
| I-2088 | COOH | H | H | H | H | H | OMe | OMe | COOH | H | H | H | COOH | O | —CH$_2$C$_6$H$_4$-4-Me |
| I-2089 | COOH | H | H | H | H | H | OMe | OMe | COOH | H | H | H | CH$_2$OH | O | —CH$_2$CH=CMe$_2$ |
| I-2090 | COOH | H | H | H | H | H | OMe | OMe | COOH | H | H | H | CH$_2$OH | O | —(CH$_2$)$_2$CH=CMe$_2$ |
| I-2091 | COOH | H | H | H | H | H | OMe | OMe | COOH | H | H | H | CH$_2$OH | O | —CH$_2$CH=CCl$_2$ |
| I-2092 | COOH | H | H | H | H | H | OMe | OMe | COOH | H | H | H | CH$_2$OH | O | —CH$_2$C≡CMe |
| I-2093 | COOH | H | H | H | H | H | OMe | OMe | COOH | H | H | H | CH$_2$OH | O | —CH$_2$C$_6$H$_4$-4-Me |
| I-2094 | COOH | H | H | H | H | H | OMe | OMe | COOH | H | H | H | F | O | —CH$_2$CH=CMe$_2$ |
| I-2095 | COOH | H | H | H | H | H | OMe | OMe | COOH | H | H | H | F | O | —(CH$_2$)$_2$CH=CMe$_2$ |
| I-2096 | COOH | H | H | H | H | H | OMe | OMe | COOH | H | H | H | F | O | —CH$_2$CH=CCl$_2$ |
| I-2097 | COOH | H | H | H | H | H | OMe | OMe | COOH | H | H | H | F | O | —CH$_2$C≡CMe |
| I-2098 | COOH | H | H | H | H | H | OMe | OMe | COOH | H | H | H | F | O | —CH$_2$C$_6$H$_4$-4-Me |
| I-2099 | COOH | H | H | H | H | H | OMe | OMe | CH$_2$OH | H | H | H | OH | O | —CH$_2$CH=CMe$_2$ |
| I-2100 | COOH | H | H | H | H | H | OMe | OMe | CH$_2$OH | H | H | H | OH | O | —(CH$_2$)$_2$CH=CMe$_2$ |
| I-2101 | COOH | H | H | H | H | H | OMe | OMe | CH$_2$OH | H | H | H | OH | O | —CH$_2$CH=CCl$_2$ |
| I-2102 | COOH | H | H | H | H | H | OMe | OMe | CH$_2$OH | H | H | H | OH | O | —CH$_2$C≡CMe |
| I-2103 | COOH | H | H | H | H | H | OMe | OMe | CH$_2$OH | H | H | H | OH | O | —CH$_2$C$_6$H$_4$-4-Me |

TABLE 305

| I-2104 | COOH | H | H | H | H | H | OMe | OMe | CH$_2$OH | H | H | H | OMs | O | —CH$_2$CH=CMe$_2$ |
| I-2105 | COOH | H | H | H | H | H | OMe | OMe | CH$_2$OH | H | H | H | OMs | O | —(CH$_2$)$_2$CH=CMe$_2$ |
| I-2106 | COOH | H | H | H | H | H | OMe | OMe | CH$_2$OH | H | H | H | OMs | O | —CH$_2$CH=CCl$_2$ |
| I-2107 | COOH | H | H | H | H | H | OMe | OMe | CH$_2$OH | H | H | H | OMs | O | —CH$_2$C≡CMe |
| I-2108 | COOH | H | H | H | H | H | OMe | OMe | CH$_2$OH | H | H | H | OMs | O | —CH$_2$C$_6$H$_4$-4-Me |
| I-2109 | COOH | H | H | H | H | H | OMe | OMe | CH$_2$OH | H | H | H | COOH | O | —CH$_2$CH=CMe$_2$ |
| I-2110 | COOH | H | H | H | H | H | OMe | OMe | CH$_2$OH | H | H | H | COOH | O | —(CH$_2$)$_2$CH=CMe$_2$ |
| I-2111 | COOH | H | H | H | H | H | OMe | OMe | CH$_2$OH | H | H | H | COOH | O | —CH$_2$CH=CCl$_2$ |
| I-2112 | COOH | H | H | H | H | H | OMe | OMe | CH$_2$OH | H | H | H | COOH | O | —CH$_2$C≡CMe |
| I-2113 | COOH | H | H | H | H | H | OMe | OMe | CH$_2$OH | H | H | H | COOH | O | —CH$_2$C$_6$H$_4$-4-Me |
| I-2114 | COOH | H | H | H | H | H | OMe | OMe | CH$_2$OH | H | H | H | CH$_2$OH | O | —CH$_2$CH=CMe$_2$ |
| I-2115 | COOH | H | H | H | H | H | OMe | OMe | CH$_2$OH | H | H | H | CH$_2$OH | O | —(CH$_2$)$_2$CH=CMe$_2$ |
| I-2116 | COOH | H | H | H | H | H | OMe | OMe | CH$_2$OH | H | H | H | CH$_2$OH | O | —CH$_2$CH=CCl$_2$ |
| I-2117 | COOH | H | H | H | H | H | OMe | OMe | CH$_2$OH | H | H | H | CH$_2$OH | O | —CH$_2$C≡CMe |
| I-2118 | COOH | H | H | H | H | H | OMe | OMe | CH$_2$OH | H | H | H | CH$_2$OH | O | —CH$_2$C$_6$H$_4$-4-Me |
| I-2119 | COOH | H | H | H | H | H | OMe | OMe | CH$_2$OH | H | H | H | F | O | —CH$_2$CH=CMe$_2$ |
| I-2120 | COOH | H | H | H | H | H | OMe | OMe | CH$_2$OH | H | H | H | F | O | —(CH$_2$)$_2$CH=CMe$_2$ |
| I-2121 | COOH | H | H | H | H | H | OMe | OMe | CH$_2$OH | H | H | H | F | O | —CH$_2$CH=CCl$_2$ |
| I-2122 | COOH | H | H | H | H | H | OMe | OMe | CH$_2$OH | H | H | H | F | O | —CH$_2$C≡CMe |
| I-2123 | COOH | H | H | H | H | H | OMe | OMe | CH$_2$OH | H | H | H | F | O | —CH$_2$C$_6$H$_4$-4-Me |
| I-2124 | COOH | H | H | H | H | H | OMe | OMe | Me | H | H | H | OH | O | —CH$_2$CH=CMe$_2$ |

TABLE 306

| I-2125 | COOH | H | H | H | H | H | OMe | OMe | Me | H | H | H | OH | O | —(CH$_2$)$_2$CH=CMe$_2$ |
| I-2126 | COOH | H | H | H | H | H | OMe | OMe | Me | H | H | H | OH | O | —CH$_2$CH=CCl$_2$ |
| I-2127 | COOH | H | H | H | H | H | OMe | OMe | Me | H | H | H | OH | O | —CH$_2$C≡CMe |
| I-2128 | COOH | H | H | H | H | H | OMe | OMe | Me | H | H | H | OH | O | —CH$_2$C$_6$H$_4$-4-Me |
| I-2129 | COOH | H | H | H | H | H | OMe | OMe | Me | H | H | H | OMs | O | —CH$_2$CH=CMe$_2$ |
| I-2130 | COOH | H | H | H | H | H | OMe | OMe | Me | H | H | H | OMs | O | —(CH$_2$)$_2$CH=CMe$_2$ |
| I-2131 | COOH | H | H | H | H | H | OMe | OMe | Me | H | H | H | OMs | O | —CH$_2$CH=CCl$_2$ |
| I-2132 | COOH | H | H | H | H | H | OMe | OMe | Me | H | H | H | OMs | O | —CH$_2$C≡CMe |
| I-2133 | COOH | H | H | H | H | H | OMe | OMe | Me | H | H | H | OMs | O | —CH$_2$C$_6$H$_4$-4-Me |
| I-2134 | COOH | H | H | H | H | H | OMe | OMe | Me | H | H | H | COOH | O | —CH$_2$CH=CMe$_2$ |
| I-2135 | COOH | H | H | H | H | H | OMe | OMe | Me | H | H | H | COOH | O | —(CH$_2$)$_2$CH=CMe$_2$ |
| I-2136 | COOH | H | H | H | H | H | OMe | OMe | Me | H | H | H | COOH | O | —CH$_2$CH=CCl$_2$ |
| I-2137 | COOH | H | H | H | H | H | OMe | OMe | Me | H | H | H | COOH | O | —CH$_2$C≡CMe |
| I-2138 | COOH | H | H | H | H | H | OMe | OMe | Me | H | H | H | COOH | O | —CH$_2$C$_6$H$_4$-4-Me |
| I-2139 | COOH | H | H | H | H | H | OMe | OMe | Me | H | H | H | CH$_2$OH | O | —CH$_2$CH=CMe$_2$ |
| I-2140 | COOH | H | H | H | H | H | OMe | OMe | Me | H | H | H | CH$_2$OH | O | —(CH$_2$)$_2$CH=CMe$_2$ |
| I-2141 | COOH | H | H | H | H | H | OMe | OMe | Me | H | H | H | CH$_2$OH | O | —CH$_2$CH=CCl$_2$ |
| I-2142 | COOH | H | H | H | H | H | OMe | OMe | Me | H | H | H | CH$_2$OH | O | —CH$_2$C≡CMe |
| I-2143 | COOH | H | H | H | H | H | OMe | OMe | Me | H | H | H | CH$_2$OH | O | —CH$_2$C$_6$H$_4$-4-Me |
| I-2144 | COOH | H | H | H | H | H | OMe | OMe | Me | H | H | H | F | O | —CH$_2$CH=CMe$_2$ |
| I-2145 | COOH | H | H | H | H | H | OMe | OMe | Me | H | H | H | F | O | —(CH$_2$)$_2$CH=CMe$_2$ |

TABLE 307

| I-2146 | COOH | H | H | H | H | H | OMe | OMe | Me | H | H | H | F | O | —CH$_2$CH=CCl$_2$ |
| I-2147 | COOH | H | H | H | H | H | OMe | OMe | Me | H | H | H | F | O | —CH$_2$C≡CMe |
| I-2148 | COOH | H | H | H | H | H | OMe | OMe | Me | H | H | H | F | O | —CH$_2$C$_6$H$_4$-4-Me |

TABLE 307-continued

| | | | | | | | | | | | | | | | |
|---|---|---|---|---|---|---|---|---|---|---|---|---|---|---|---|
| I-2149 | COOH | H | H | H | H | H | OMe | OMe | H | H | H | H | OH | O | —CH$_2$CH=CMe$_2$ |
| I-2150 | COOH | H | H | H | H | H | OMe | OMe | H | H | H | H | OH | O | —(CH$_2$)$_2$CH=CMe$_2$ |
| I-2151 | COOH | H | H | H | H | H | OMe | OMe | H | H | H | H | OH | O | —CH$_2$CH=CCl$_2$ |
| I-2152 | COOH | H | H | H | H | H | OMe | OMe | H | H | H | H | OH | O | —CH$_2$C≡CMe |
| I-2153 | COOH | H | H | H | H | H | OMe | OMe | H | H | H | H | OH | O | —CH$_2$C$_6$H$_4$-4-Me |
| I-2154 | COOH | H | H | H | H | H | OMe | OMe | H | H | H | H | OMs | O | —CH$_2$CH=CMe$_2$ |
| I-2155 | COOH | H | H | H | H | H | OMe | OMe | H | H | H | H | OMs | O | —(CH$_2$)$_2$CH=CMe$_2$ |
| I-2156 | COOH | H | H | H | H | H | OMe | OMe | H | H | H | H | OMs | O | —CH$_2$CH=CCl$_2$ |
| I-2157 | COOH | H | H | H | H | H | OMe | OMe | H | H | H | H | OMs | O | —CH$_2$C≡CMe |
| I-2158 | COOH | H | H | H | H | H | OMe | OMe | H | H | H | H | OMs | O | —CH$_2$C$_6$H$_4$-4-Me |
| I-2159 | COOH | H | H | H | H | H | OMe | OMe | H | H | H | H | COOH | O | —CH$_2$CH=CMe$_2$ |
| I-2160 | COOH | H | H | H | H | H | OMe | OMe | H | H | H | H | COOH | O | —(CH$_2$)$_2$CH=CMe$_2$ |
| I-2161 | COOH | H | H | H | H | H | OMe | OMe | H | H | H | H | COOH | O | —CH$_2$CH=CCl$_2$ |
| I-2162 | COOH | H | H | H | H | H | OMe | OMe | H | H | H | H | COOH | O | —CH$_2$C≡CMe |
| I-2163 | COOH | H | H | H | H | H | OMe | OMe | H | H | H | H | COOH | O | —CH$_2$C$_6$H$_4$-4-Me |
| I-2164 | COOH | H | H | H | H | H | OMe | OMe | H | H | H | H | CH$_2$OH | O | —CH$_2$CH=CMe$_2$ |
| I-2165 | COOH | H | H | H | H | H | OMe | OMe | H | H | H | H | CH$_2$OH | O | —(CH$_2$)$_2$CH=CMe$_2$ |
| I-2166 | COOH | H | H | H | H | H | OMe | OMe | H | H | H | H | CH$_2$OH | O | —CH$_2$CH=CCl$_2$ |

TABLE 308

| | | | | | | | | | | | | | | | |
|---|---|---|---|---|---|---|---|---|---|---|---|---|---|---|---|
| I-2167 | COOH | H | H | H | H | H | OMe | OMe | H | H | H | H | CH$_2$OH | O | —CH$_2$C≡CMe |
| I-2168 | COOH | H | H | H | H | H | OMe | OMe | H | H | H | H | CH$_2$OH | O | —CH$_2$C$_6$H$_4$-4-Me |
| I-2169 | COOH | H | H | H | H | H | OMe | OMe | H | H | H | H | F | O | —CH$_2$CH=CMe$_2$ |
| I-2170 | COOH | H | H | H | H | H | OMe | OMe | H | H | H | H | F | O | —(CH$_2$)$_2$CH=CMe$_2$ |
| I-2171 | COOH | H | H | H | H | H | OMe | OMe | H | H | H | H | F | O | —CH$_2$CH=CCl$_2$ |
| I-2172 | COOH | H | H | H | H | H | OMe | OMe | H | H | H | H | F | O | —CH$_2$C≡CMe |
| I-2173 | COOH | H | H | H | H | H | OMe | OMe | H | H | H | H | F | O | —CH$_2$C$_6$H$_4$-4-Me |
| I-2174 | COOH | H | H | H | H | F | OMe | OMe | OH | H | H | H | OH | O | —CH$_2$CH=CMe$_2$ |
| I-2175 | COOH | H | H | H | H | F | OMe | OMe | OH | H | H | H | OH | O | —(CH$_2$)$_2$CH=CMe$_2$ |
| I-2176 | COOH | H | H | H | H | F | OMe | OMe | OH | H | H | H | OH | O | —CH$_2$CH=CCl$_2$ |
| I-2177 | COOH | H | H | H | H | F | OMe | OMe | OH | H | H | H | OH | O | —CH$_2$C≡CMe |
| I-2178 | COOH | H | H | H | H | F | OMe | OMe | OH | H | H | H | OH | O | —CH$_2$C$_6$H$_4$-4-Me |
| I-2179 | COOH | H | H | H | H | F | OMe | OMe | OH | H | H | H | OMs | O | —CH$_2$CH=CMe$_2$ |
| I-2180 | COOH | H | H | H | H | F | OMe | OMe | OH | H | H | H | OMs | O | —(CH$_2$)$_2$CH=CMe$_2$ |
| I-2181 | COOH | H | H | H | H | F | OMe | OMe | OH | H | H | H | OMs | O | —CH$_2$CH=CCl$_2$ |
| I-2182 | COOH | H | H | H | H | F | OMe | OMe | OH | H | H | H | OMs | O | —CH$_2$C≡CMe |
| I-2183 | COOH | H | H | H | H | F | OMe | OMe | OH | H | H | H | OMs | O | —CH$_2$C$_6$H$_4$-4-Me |
| I-2184 | COOH | H | H | H | H | F | OMe | OMe | OH | H | H | H | COOH | O | —CH$_2$CH=CMe$_2$ |
| I-2185 | COOH | H | H | H | H | F | OMe | OMe | OH | H | H | H | COOH | O | —(CH$_2$)$_2$CH=CMe$_2$ |
| I-2186 | COOH | H | H | H | H | F | OMe | OMe | OH | H | H | H | COOH | O | —CH$_2$CH=CCl$_2$ |
| I-2187 | COOH | H | H | H | H | F | OMe | OMe | OH | H | H | H | COOH | O | —CH$_2$C≡CMe |

TABLE 309

| | | | | | | | | | | | | | | | |
|---|---|---|---|---|---|---|---|---|---|---|---|---|---|---|---|
| I-2188 | COOH | H | H | H | H | F | OMe | OMe | OH | H | H | H | COOH | O | —CH$_2$C$_6$H$_4$-4-Me |
| I-2189 | COOH | H | H | H | H | F | OMe | OMe | OH | H | H | H | CH$_2$OH | O | —CH$_2$CH=CMe$_2$ |
| I-2190 | COOH | H | H | H | H | F | OMe | OMe | OH | H | H | H | CH$_2$OH | O | —(CH$_2$)$_2$CH=CMe$_2$ |
| I-2191 | COOH | H | H | H | H | F | OMe | OMe | OH | H | H | H | CH$_2$OH | O | —CH$_2$CH=CCl$_2$ |
| I-2192 | COOH | H | H | H | H | F | OMe | OMe | OH | H | H | H | CH$_2$OH | O | —CH$_2$C≡CMe |
| I-2193 | COOH | H | H | H | H | F | OMe | OMe | OH | H | H | H | CH$_2$OH | O | —CH$_2$C$_6$H$_4$-4-Me |
| I-2194 | COOH | H | H | H | H | F | OMe | OMe | OH | H | H | H | F | O | —CH$_2$CH=CMe$_2$ |
| I-2195 | COOH | H | H | H | H | F | OMe | OMe | OH | H | H | H | F | O | —(CH$_2$)$_2$CH=CMe$_2$ |
| I-2196 | COOH | H | H | H | H | F | OMe | OMe | OH | H | H | H | F | O | —CH$_2$CH=CCl$_2$ |
| I-2197 | COOH | H | H | H | H | F | OMe | OMe | OH | H | H | H | F | O | —CH$_2$C≡CMe |
| I-2198 | COOH | H | H | H | H | F | OMe | OMe | OH | H | H | H | F | O | —CH$_2$C$_6$H$_4$-4-Me |
| I-2199 | NO$_2$ | H | H | H | H | H | OMe | OMe | H | H | H | H | OMs | O | —(CH$_2$)$_2$CH=CMe$_2$ |
| I-2200 | OMs | NO$_2$ | H | H | H | H | OMe | OMe | H | H | H | H | OMs | O | —(CH$_2$)$_2$CH=CMe$_2$ |
| I-2201 | OMs | H | H | H | H | H | OMe | OMe | H | NO$_2$ | H | H | OMs | O | —(CH$_2$)$_2$CH=CMe$_2$ |
| I-2202 | CN | H | H | H | H | H | OMe | OMe | H | H | H | H | OMs | O | —(CH$_2$)$_2$CH=CMe$_2$ |
| I-2203 | OMs | CN | H | H | H | H | OMe | OMe | H | H | H | H | OMs | O | —(CH$_2$)$_2$CH=CMe$_2$ |
| I-2204 | OH | H | H | H | H | H | OMe | OMe | OMs | H | H | H | OH | O | —CH$_2$CH=CMe$_2$ |
| I-2205 | OH | H | H | H | H | H | OMe | OMe | OMs | H | H | H | OH | O | —CH$_2$C$_6$H$_5$ |
| I-2206 | OH | H | H | H | H | H | OMe | OMe | OMs | H | H | H | NH$_2$ | O | —CH$_2$CH=CMe$_2$ |
| I-2207 | OH | H | H | H | H | H | OMe | OMe | OMs | H | H | H | NH$_2$ | O | —CH$_2$C$_6$H$_5$ |
| I-2208 | OH | H | H | H | H | H | OMe | OEt | OH | H | H | H | OH | O | —CH$_2$C$_6$H$_5$ |

TABLE 310

| | | | | | | | | | | | | | | | |
|---|---|---|---|---|---|---|---|---|---|---|---|---|---|---|---|
| I-2209 | OH | H | H | H | H | H | OMe | OEt | OH | H | H | H | NH$_2$ | O | —CH$_2$CH=CMe$_2$ |
| I-2210 | OH | H | H | H | H | H | Me | Me | H | H | H | H | OH | O | —CH$_2$C$_6$H$_5$ |
| I-2211 | OH | H | H | H | H | H | Me | Me | H | H | H | H | NH$_2$ | O | —CH$_2$CH=CMe$_2$ |

TABLE 310-continued

| ID | | | | | | | | | | | | | | | |
|---|---|---|---|---|---|---|---|---|---|---|---|---|---|---|---|
| I-2212 | OH | H | H | H | H | H | Me | Me | H | H | H | H | NH$_2$ | O | —CH$_2$C$_6$H$_5$ |
| I-2213 | OH | H | H | H | H | H | OMe | OMe | NH$_2$ | H | H | H | OH | O | —CH$_2$CH=CMe$_2$ |
| I-2214 | OH | H | H | H | H | H | OMe | OMe | NH$_2$ | H | H | H | NH$_2$ | O | —CH$_2$CH=CMe$_2$ |
| I-2215 | OH | H | H | H | H | H | OMe | OMe | NH$_2$ | H | H | H | NH$_2$ | O | —CH$_2$C$_6$H$_5$ |
| I-2216 | OH | H | H | H | H | H | OMe | OMe | OH | H | H | H | OH | O | —CH$_2$CH=CMe$_2$ |
| I-2217 | OH | H | H | H | H | H | OMe | OMe | OH | H | H | H | OH | O | —CH$_2$C$_6$H$_5$ |
| I-2218 | OH | H | H | H | H | H | OMe | OMe | OH | H | H | H | NH$_2$ | O | —CH$_2$CH=CMe$_2$ |
| I-2219 | OH | H | H | H | H | H | OMe | OMe | OH | H | H | H | NH$_2$ | O | —CH$_2$C$_6$H$_5$ |
| I-2220 | OMs | H | H | H | H | H | OMe | OMe | OMs | H | H | H | OH | O | —CH$_2$CH=CMe$_2$ |
| I-2221 | OMs | H | H | H | H | H | OMe | OMe | OMs | H | H | H | OH | O | —CH$_2$C$_6$H$_5$ |
| I-2222 | OMs | H | H | H | H | H | OMe | OMe | OMs | H | H | H | NH$_2$ | O | —CH$_2$CH=CMe$_2$ |
| I-2223 | OMs | H | H | H | H | H | OMe | OMe | OMs | H | H | H | NH$_2$ | O | —CH$_2$C$_6$H$_5$ |
| I-2224 | OMs | H | H | H | H | H | OMe | OEt | OH | H | H | H | OH | O | —CH$_2$CH=CMe$_2$ |
| I-2225 | OMs | H | H | H | H | H | OMe | OEt | OH | H | H | H | OH | O | —CH$_2$C$_6$H$_5$ |
| I-2226 | OMs | H | H | H | H | H | OMe | OEt | OH | H | H | H | NH$_2$ | O | —CH$_2$CH=CMe$_2$ |
| I-2227 | OMs | H | H | H | H | H | OMe | OEt | OH | H | H | H | NH$_2$ | O | —CH$_2$C$_6$H$_5$ |
| I-2228 | OMs | H | H | H | H | H | Me | Me | H | H | H | H | OH | O | —CH$_2$CH=CMe$_2$ |
| I-2229 | OMs | H | H | H | H | H | Me | Me | H | H | H | H | OH | O | —CH$_2$C$_6$H$_5$ |

TABLE 311

| ID | | | | | | | | | | | | | | | |
|---|---|---|---|---|---|---|---|---|---|---|---|---|---|---|---|
| I-2230 | OMs | H | H | H | H | H | Me | Me | H | H | H | H | NH$_2$ | O | —CH$_2$CH=CMe$_2$ |
| I-2231 | OMs | H | H | H | H | H | Me | Me | H | H | H | H | NH$_2$ | O | —CH$_2$C$_6$H$_5$ |
| I-2232 | OMs | H | H | H | H | H | OMe | OMe | NH$_2$ | H | H | H | OH | O | —CH$_2$CH=CMe$_2$ |
| I-2233 | OMs | H | H | H | H | H | OMe | OMe | NH$_2$ | H | H | H | NH$_2$ | O | —CH$_2$CH=CMe$_2$ |
| I-2234 | OMs | H | H | H | H | H | OMe | OMe | NH$_2$ | H | H | H | NH$_2$ | O | —CH$_2$C$_6$H$_5$ |
| I-2235 | OMs | H | H | H | H | H | OMe | OMe | OH | H | H | H | OH | O | —CH$_2$CH=CMe$_2$ |
| I-2236 | OMs | H | H | H | H | H | OMe | OMe | OH | H | H | H | OH | O | —CH$_2$C$_6$H$_5$ |
| I-2237 | OMs | H | H | H | H | H | OMe | OMe | OH | H | H | H | NH$_2$ | O | —CH$_2$CH=CMe$_2$ |
| I-2238 | OMs | H | H | H | H | H | OMe | OMe | OH | H | H | H | NH$_2$ | O | —CH$_2$C$_6$H$_5$ |
| I-2239 | CF$_3$ | H | H | H | H | H | OMe | OMe | OMs | H | H | H | OH | O | —CH$_2$CH=CMe$_2$ |
| I-2240 | CF$_3$ | H | H | H | H | H | OMe | OMe | OMs | H | H | H | OH | O | —CH$_2$C$_6$H$_5$ |
| I-2241 | CF$_3$ | H | H | H | H | H | OMe | OMe | OMs | H | H | H | NH$_2$ | O | —CH$_2$CH=CMe$_2$ |
| I-2242 | CF$_3$ | H | H | H | H | H | OMe | OMe | OMs | H | H | H | NH$_2$ | O | —CH$_2$C$_6$H$_5$ |
| I-2243 | CF$_3$ | H | H | H | H | H | OMe | OEt | OH | H | H | H | OH | O | —CH$_2$CH=CMe$_2$ |
| I-2244 | CF$_3$ | H | H | H | H | H | OMe | OEt | OH | H | H | H | OH | O | —CH$_2$C$_6$H$_5$ |
| I-2245 | CF$_3$ | H | H | H | H | H | OMe | OEt | OH | H | H | H | NH$_2$ | O | —CH$_2$CH=CMe$_2$ |
| I-2246 | CF$_3$ | H | H | H | H | H | OMe | OEt | OH | H | H | H | NH$_2$ | O | —CH$_2$C$_6$H$_5$ |
| I-2247 | CF$_3$ | H | H | H | H | H | Me | Me | H | H | H | H | OH | O | —CH$_2$CH=CMe$_2$ |
| I-2248 | CF$_3$ | H | H | H | H | H | Me | Me | H | H | H | H | OH | O | —CH$_2$C$_6$H$_5$ |
| I-2249 | CF$_3$ | H | H | H | H | H | Me | Me | H | H | H | H | NH$_2$ | O | —CH$_2$CH=CMe$_2$ |
| I-2250 | CF$_3$ | H | H | H | H | H | Me | Me | H | H | H | H | NH$_2$ | O | —CH$_2$C$_6$H$_5$ |

TABLE 312

| ID | | | | | | | | | | | | | | | |
|---|---|---|---|---|---|---|---|---|---|---|---|---|---|---|---|
| I-2251 | CF$_3$ | H | H | H | H | H | OMe | OMe | NH$_2$ | H | H | H | OH | O | —CH$_2$CH=CMe$_2$ |
| I-2252 | CF$_3$ | H | H | H | H | H | OMe | OMe | NH$_2$ | H | H | H | OH | O | —CH$_2$C$_6$H$_5$ |
| I-2253 | CF$_3$ | H | H | H | H | H | OMe | OMe | NH$_2$ | H | H | H | NH$_2$ | O | —CH$_2$CH=CMe$_2$ |
| I-2254 | CF$_3$ | H | H | H | H | H | OMe | OMe | NH$_2$ | H | H | H | NH$_2$ | O | —CH$_2$C$_6$H$_5$ |
| I-2255 | CF$_3$ | H | H | H | H | H | OMe | OMe | OH | H | H | H | OH | O | —CH$_2$CH=CMe$_2$ |
| I-2256 | CF$_3$ | H | H | H | H | H | OMe | OMe | OH | H | H | H | OH | O | —CH$_2$C$_6$H$_5$ |
| I-2257 | CF$_3$ | H | H | H | H | H | OMe | OMe | OH | H | H | H | NH$_2$ | O | —CH$_2$CH=CMe$_2$ |
| I-2258 | CF$_3$ | H | H | H | H | H | OMe | OMe | OH | H | H | H | NH$_2$ | O | —CH$_2$C$_6$H$_5$ |
| I-2259 | NH$_2$ | H | H | H | H | H | OMe | OMe | OMs | H | H | H | OH | O | —CH$_2$CH=CMe$_2$ |
| I-2260 | NH$_2$ | H | H | H | H | H | OMe | OMe | OMs | H | H | H | OH | O | —CH$_2$C$_6$H$_5$ |
| I-2261 | NH$_2$ | H | H | H | H | H | OMe | OMe | OMs | H | H | H | NH$_2$ | O | —CH$_2$CH=CMe$_2$ |
| I-2262 | NH$_2$ | H | H | H | H | H | OMe | OMe | OMs | H | H | H | NH$_2$ | O | —CH$_2$C$_6$H$_5$ |
| I-2263 | NH$_2$ | H | H | H | H | H | OMe | OEt | OH | H | H | H | OH | O | —CH$_2$CH=CMe$_2$ |
| I-2264 | NH$_2$ | H | H | H | H | H | OMe | OEt | OH | H | H | H | OH | O | —CH$_2$C$_6$H$_5$ |
| I-2265 | NH$_2$ | H | H | H | H | H | OMe | OEt | OH | H | H | H | NH$_2$ | O | —CH$_2$CH=CMe$_2$ |
| I-2266 | NH$_2$ | H | H | H | H | H | OMe | OEt | OH | H | H | H | NH$_2$ | O | —CH$_2$C$_6$H$_5$ |
| I-2267 | NH$_2$ | H | H | H | H | H | Me | Me | H | H | H | H | OH | O | —CH$_2$CH=CMe$_2$ |
| I-2268 | NH$_2$ | H | H | H | H | H | Me | Me | H | H | H | H | OH | O | —CH$_2$C$_6$H$_5$ |
| I-2269 | NH$_2$ | H | H | H | H | H | Me | Me | H | H | H | H | NH$_2$ | O | —CH$_2$CH=CMe$_2$ |
| I-2270 | NH$_2$ | H | H | H | H | H | Me | Me | H | H | H | H | NH$_2$ | O | —CH$_2$C$_6$H$_5$ |
| I-2271 | NH$_2$ | H | H | H | H | H | OMe | OMe | NH$_2$ | H | H | H | OH | O | —CH$_2$CH=CMe$_2$ |

TABLE 313

| ID | | | | | | | | | | | | | | | |
|---|---|---|---|---|---|---|---|---|---|---|---|---|---|---|---|
| I-2272 | NH$_2$ | | H | H | H | H | H | OMe | OMe | NH$_2$ | H | H | H | OH | O | —CH$_2$C$_6$H$_5$ |
| I-2273 | NH$_2$ | | H | H | H | H | H | OMe | OMe | NH$_2$ | H | H | H | NH$_2$ | O | —CH$_2$CH=CMe$_2$ |
| I-2274 | NH$_2$ | | H | H | H | H | H | OMe | OMe | NH$_2$ | H | H | H | NH$_2$ | O | —CH$_2$C$_6$H$_5$ |

TABLE 313-continued

| | | | | | | | | | | | | | | | |
|---|---|---|---|---|---|---|---|---|---|---|---|---|---|---|---|
| I-2275 | NH$_2$ | H | H | H | H | H | OMe | OMe | OH | H | H | H | OH | O | —CH$_2$CH=CMe$_2$ |
| I-2276 | NH$_2$ | H | H | H | H | H | OMe | OMe | OH | H | H | H | OH | O | —CH$_2$C$_6$H$_5$ |
| I-2277 | NH$_2$ | H | H | H | H | H | OMe | OMe | OH | H | H | H | NH$_2$ | O | —CH$_2$CH=CMe$_2$ |
| I-2278 | NH$_2$ | H | H | H | H | H | OMe | OMe | OH | H | H | H | NH$_2$ | O | —CH$_2$C$_6$H$_5$ |
| I-2279 | —NHCH$_2$CH=CMe$_2$ | H | F | H | H | Me | Me | Me | H | H | H | H | OMe | NH | —CH$_2$CH=CMe$_2$ |
| I-2280 | —NHCH$_2$CH=CMe$_2$ | H | F | H | H | Me | Me | Me | H | H | H | H | OMe | NH | —(CH$_2$)$_2$CHMe$_2$ |
| I-2281 | —NHCH$_2$CH=CMe$_2$ | H | F | H | H | Me | Me | Me | H | H | H | H | OMe | NMe | Me |
| I-2282 | —NHCH$_2$CH=CMe$_2$ | H | F | H | H | Me | Me | Me | H | H | H | H | OMe | O | —CH$_2$CH=CMe$_2$ |
| I-2283 | —NHCH$_2$CH=CMe$_2$ | H | F | H | H | Me | Me | Me | H | H | H | H | OMe | O | —CH$_2$CH=CCl$_2$ |
| I-2284 | —NHCH$_2$CH=CMe$_2$ | H | F | H | H | Me | Me | Me | H | H | H | F | H | NH | —CH$_2$CH=CMe$_2$ |
| I-2285 | —NHCH$_2$CH=CMe$_2$ | H | F | H | H | Me | Me | Me | H | H | H | F | H | NH | —(CH$_2$)$_2$CHMe$_2$ |
| I-2286 | —NHCH$_2$CH=CMe$_2$ | H | F | H | H | Me | Me | Me | H | H | H | F | H | NMe | Me |
| I-2287 | —NHCH$_2$CH=CMe$_2$ | H | F | H | H | Me | Me | Me | H | H | H | F | H | O | —CH$_2$CH=CMe$_2$ |
| I-2288 | —NHCH$_2$CH=CMe$_2$ | H | F | H | H | Me | Me | Me | H | H | H | F | H | O | —CH$_2$CH=CCl$_2$ |
| I-2289 | —NHCH$_2$CH=CMe$_2$ | H | F | H | H | Me | Me | Me | H | H | H | H | OEt | NH | —CH$_2$CH=CMe$_2$ |
| I-2290 | —NHCH$_2$CH=CMe$_2$ | H | F | H | H | Me | Me | Me | H | H | H | H | OEt | NH | —(CH$_2$)$_2$CHMe$_2$ |
| I-2291 | —NHCH$_2$CH=CMe$_2$ | H | F | H | H | Me | Me | Me | H | H | H | H | OEt | NMe | Me |
| I-2292 | —NHCH$_2$CH=CMe$_2$ | H | F | H | H | Me | Me | Me | H | H | H | H | OEt | O | —CH$_2$CH=CMe$_2$ |

TABLE 314

| | | | | | | | | | | | | | | | |
|---|---|---|---|---|---|---|---|---|---|---|---|---|---|---|---|
| I-2293 | —NHCH$_2$CH=CMe$_2$ | H | F | H | H | Me | Me | Me | H | H | H | H | OEt | O | —CH$_2$CH=CCl$_2$ |
| I-2294 | —NHCH$_2$CH=CMe$_2$ | H | F | H | H | H | Me | OMe | OH | H | H | H | OMe | NH | —CH$_2$CH=CMe$_2$ |
| I-2295 | —NHCH$_2$CH=CMe$_2$ | H | F | H | H | H | Me | OMe | OH | H | H | H | OMe | NH | —(CH$_2$)$_2$CHMe$_2$ |
| I-2296 | —NHCH$_2$CH=CMe$_2$ | H | F | H | H | H | Me | OMe | OH | H | H | H | OMe | NMe | Me |
| I-2297 | —NHCH$_2$CH=CMe$_2$ | H | F | H | H | H | Me | OMe | OH | H | H | H | OMe | O | —CH$_2$CH=CMe$_2$ |
| I-2298 | —NHCH$_2$CH=CMe$_2$ | H | F | H | H | H | Me | OMe | OH | H | H | H | OMe | O | —CH$_2$CH=CCl$_2$ |
| I-2299 | —NHCH$_2$CH=CMe$_2$ | H | F | H | H | H | Me | OMe | OH | H | H | F | H | NH | —CH$_2$CH=CMe$_2$ |
| I-2300 | —NHCH$_2$CH=CMe$_2$ | H | F | H | H | H | Me | OMe | OH | H | H | F | H | NH | —(CH$_2$)$_2$CHMe$_2$ |
| I-2301 | —NHCH$_2$CH=CMe$_2$ | H | F | H | H | H | Me | OMe | OH | H | H | F | H | NMe | Me |
| I-2302 | —NHCH$_2$CH=CMe$_2$ | H | F | H | H | H | Me | OMe | OH | H | H | F | H | O | —CH$_2$CH=CMe$_2$ |
| I-2303 | —NHCH$_2$CH=CMe$_2$ | H | F | H | H | H | Me | OMe | OH | H | H | F | H | O | —CH$_2$CH=CCl$_2$ |
| I-2304 | —NHCH$_2$CH=CMe$_2$ | H | F | H | H | H | Me | OMe | OH | H | H | H | OEt | NH | —CH$_2$CH=CMe$_2$ |
| I-2305 | —NHCH$_2$CH=CMe$_2$ | H | F | H | H | H | Me | OMe | OH | H | H | H | OEt | NH | —(CH$_2$)$_2$CHMe$_2$ |
| I-2306 | —NHCH$_2$CH=CMe$_2$ | H | F | H | H | H | Me | OMe | OH | H | H | H | OEt | NMe | Me |
| I-2307 | —NHCH$_2$CH=CMe$_2$ | H | F | H | H | H | Me | OMe | OH | H | H | H | OEt | O | —CH$_2$CH=CMe$_2$ |
| I-2308 | —NHCH$_2$CH=CMe$_2$ | H | F | H | H | H | Me | OMe | OH | H | H | H | OEt | O | —CH$_2$CH=CCl$_2$ |
| I-2309 | —NHCH$_2$CH=CMe$_2$ | H | F | H | H | Me | H | Me | OH | H | H | H | OMe | NH | —CH$_2$CH=CMe$_2$ |
| I-2330 | —NHCH$_2$CH=CMe$_2$ | H | F | H | H | Me | H | Me | OH | H | H | H | OMe | NH | —(CH$_2$)$_2$CHMe$_2$ |
| I-2331 | —NHCH$_2$CH=CMe$_2$ | H | F | H | H | Me | H | Me | OH | H | H | H | OMe | NMe | Me |
| I-2332 | —NHCH$_2$CH=CMe$_2$ | H | F | H | H | Me | H | Me | OH | H | H | H | OMe | O | —CH$_2$CH=CMe$_2$ |
| I-2333 | —NHCH$_2$CH=CMe$_2$ | H | F | H | H | Me | H | Me | OH | H | H | H | OMe | O | —CH$_2$CH=CCl$_2$ |

TABLE 315

| | | | | | | | | | | | | | | | |
|---|---|---|---|---|---|---|---|---|---|---|---|---|---|---|---|
| I-2334 | —NHCH$_2$CH=CMe$_2$ | H | F | H | H | Me | H | Me | OH | H | H | F | H | NH | —CH$_2$CH=CMe$_2$ |
| I-2335 | —NHCH$_2$CH=CMe$_2$ | H | F | H | H | Me | H | Me | OH | H | H | F | H | NH | —(CH$_2$)$_2$CHMe$_2$ |
| I-2336 | —NHCH$_2$CH=CMe$_2$ | H | F | H | H | Me | H | Me | OH | H | H | F | H | NMe | Me |
| I-2337 | —NHCH$_2$CH=CMe$_2$ | H | F | H | H | Me | H | Me | OH | H | H | F | H | O | —CH$_2$CH=CMe$_2$ |
| I-2338 | —NHCH$_2$CH=CMe$_2$ | H | F | H | H | Me | H | Me | OH | H | H | F | H | O | —CH$_2$CH=CCl$_2$ |
| I-2339 | —NHCH$_2$CH=CMe$_2$ | H | F | H | H | Me | H | Me | OH | H | H | H | OEt | NH | —CH$_2$CH=CMe$_2$ |
| I-2340 | —NHCH$_2$CH=CMe$_2$ | H | F | H | H | Me | H | Me | OH | H | H | H | OEt | NH | —(CH$_2$)$_2$CHMe$_2$ |
| I-2341 | —NHCH$_2$CH=CMe$_2$ | H | F | H | H | Me | H | Me | OH | H | H | H | OEt | NMe | Me |
| I-2342 | —NHCH$_2$CH=CMe$_2$ | H | F | H | H | Me | H | Me | OH | H | H | H | OEt | O | —CH$_2$CH=CMe$_2$ |
| I-2343 | —NHCH$_2$CH=CMe$_2$ | H | F | H | H | Me | H | Me | OH | H | H | H | OEt | O | —CH$_2$CH=CCl$_2$ |
| I-2344 | —NHCH$_2$CH=CMe$_2$ | H | F | H | H | H | Me | Me | Me | H | H | H | OMe | NH | —CH$_2$CH=CMe$_2$ |
| I-2345 | —NHCH$_2$CH=CMe$_2$ | H | F | H | H | H | Me | Me | Me | H | H | H | OMe | NH | —(CH$_2$)$_2$CHMe$_2$ |
| I-2346 | —NHCH$_2$CH=CMe$_2$ | H | F | H | H | H | Me | Me | Me | H | H | H | OMe | NMe | Me |
| I-2347 | —NHCH$_2$CH=CMe$_2$ | H | F | H | H | H | Me | Me | Me | H | H | H | OMe | O | —CH$_2$CH=CMe$_2$ |
| I-2348 | —NHCH$_2$CH=CMe$_2$ | H | F | H | H | H | Me | Me | Me | H | H | H | OMe | O | —CH$_2$CH=CCl$_2$ |
| I-2349 | —NHCH$_2$CH=CMe$_2$ | H | F | H | H | H | Me | Me | Me | H | H | F | H | NH | —CH$_2$CH=CMe$_2$ |
| I-2350 | —NHCH$_2$CH=CMe$_2$ | H | F | H | H | H | Me | Me | Me | H | H | F | H | NH | —(CH$_2$)$_2$CHMe$_2$ |
| I-2351 | —NHCH$_2$CH=CMe$_2$ | H | F | H | H | H | Me | Me | Me | H | H | F | H | NMe | Me |
| I-2352 | —NHCH$_2$CH=CMe$_2$ | H | F | H | H | H | Me | Me | Me | H | H | F | H | O | —CH$_2$CH=CMe$_2$ |
| I-2353 | —NHCH$_2$CH=CMe$_2$ | H | F | H | H | H | Me | Me | Me | H | H | F | H | O | —CH$_2$CH=CCl$_2$ |
| I-2354 | —NHCH$_2$CH=CMe$_2$ | H | F | H | H | H | Me | Me | Me | H | H | H | OEt | NH | —CH$_2$CH=CMe$_2$ |

TABLE 316

| | | | | | | | | | | | | | | | |
|---|---|---|---|---|---|---|---|---|---|---|---|---|---|---|---|
| I-2355 | —NHCH$_2$CH=CMe$_2$ | H | F | H | H | H | Me | Me | Me | H | H | H | OEt | NH | —(CH$_2$)$_2$CHMe$_2$ |
| I-2356 | —NHCH$_2$CH=CMe$_2$ | H | F | H | H | H | Me | Me | Me | H | H | H | OEt | NMe | Me |
| I-2357 | —NHCH$_2$CH=CMe$_2$ | H | F | H | H | H | Me | Me | Me | H | H | H | OEt | O | —CH$_2$CH=CMe$_2$ |

TABLE 316-continued

| | | | | | | | | | | | | | | | |
|---|---|---|---|---|---|---|---|---|---|---|---|---|---|---|---|
| I-2358 | —NHCH₂CH═CMe₂ | H | F | H | H | H | Me | Me | Me | H | H | H | OEt | O | —CH₂CH═CCl₂ |
| I-2359 | —NHCH₂CH═CMe₂ | H | F | H | H | H | OMe | OEt | OH | H | H | H | OMe | NH | —CH₂CH═CMe₂ |
| I-2360 | —NHCH₂CH═CMe₂ | H | F | H | H | H | OMe | OEt | OH | H | H | H | OMe | NH | —(CH₂)₂CHMe₂ |
| I-2361 | —NHCH₂CH═CMe₂ | H | F | H | H | H | OMe | OEt | OH | H | H | H | OMe | NMe | Me |
| I-2362 | —NHCH₂CH═CMe₂ | H | F | H | H | H | OMe | OEt | OH | H | H | H | OMe | O | —CH₂CH═CMe₂ |
| I-2363 | —NHCH₂CH═CMe₂ | H | F | H | H | H | OMe | OEt | OH | H | H | H | OMe | O | —CH₂CH═CCl₂ |
| I-2364 | —NHCH₂CH═CMe₂ | H | F | H | H | H | OMe | OEt | OH | H | H | F | H | NH | —CH₂CH═CMe₂ |
| I-2365 | —NHCH₂CH═CMe₂ | H | F | H | H | H | OMe | OEt | OH | H | H | F | H | NH | —(CH₂)₂CHMe₂ |
| I-2366 | —NHCH₂CH═CMe₂ | H | F | H | H | H | OMe | OEt | OH | H | H | F | H | NMe | Me |
| I-2367 | —NHCH₂CH═CMe₂ | H | F | H | H | H | OMe | OEt | OH | H | H | F | H | O | —CH₂CH═CMe₂ |
| I-2368 | —NHCH₂CH═CMe₂ | H | F | H | H | H | OMe | OEt | OH | H | H | F | H | O | —CH₂CH═CCl₂ |
| I-2369 | —NHCH₂CH═CMe₂ | H | F | H | H | H | OMe | OEt | OH | H | H | H | OEt | NH | —CH₂CH═CMe₂ |
| I-2370 | —NHCH₂CH═CMe₂ | H | F | H | H | H | OMe | OEt | OH | H | H | H | OEt | NH | —(CH₂)₂CHMe₂ |
| I-2371 | —NHCH₂CH═CMe₂ | H | F | H | H | H | OMe | OEt | OH | H | H | H | OEt | NMe | Me |
| I-2372 | —NHCH₂CH═CMe₂ | H | F | H | H | H | OMe | OEt | OH | H | H | H | OEt | O | —CH₂CH═CMe₂ |
| I-2373 | —NHCH₂CH═CMe₂ | H | F | H | H | H | OMe | OEt | OH | H | H | H | OEt | O | —CH₂CH═CCl₂ |
| I-2374 | —NH₂ | H | F | H | H | Me | Me | Me | H | H | H | H | OMe | NH | —CH₂CH═CMe₂ |
| I-2375 | —NH₂ | H | F | H | H | Me | Me | Me | H | H | H | H | OMe | NH | —(CH₂)₂CHMe₂ |

TABLE 317

| | | | | | | | | | | | | | | | |
|---|---|---|---|---|---|---|---|---|---|---|---|---|---|---|---|
| I-2376 | —NH₂ | H | F | H | H | Me | Me | Me | H | H | H | H | OMe | NMe | Me |
| I-2377 | —NH₂ | H | F | H | H | Me | Me | Me | H | H | H | H | OMe | O | —CH₂CH═CMe₂ |
| I-2378 | —NH₂ | H | F | H | H | Me | Me | Me | H | H | H | H | OMe | O | —CH₂CH═CCl₂ |
| I-2379 | —NH₂ | H | F | H | H | Me | Me | Me | H | H | F | H | | NH | —CH₂CH═CMe₂ |
| I-230 | —NH₂ | H | F | H | H | Me | Me | Me | H | H | F | H | | NH | —(CH₂)₂CHMe₂ |
| I-2381 | —NH₂ | H | F | H | H | Me | Me | Me | H | H | F | H | | NMe | Me |
| I-2382 | —NH₂ | H | F | H | H | Me | Me | Me | H | H | F | H | | O | —CH₂CH═CMe₂ |
| I-2383 | —NH₂ | H | F | H | H | Me | Me | Me | H | H | F | H | | O | —CH₂CH═CCl₂ |
| I-2384 | —NH₂ | H | F | H | H | Me | Me | Me | H | H | H | H | OEt | NH | —CH₂CH═CMe₂ |
| I-2385 | —NH₂ | H | F | H | H | Me | Me | Me | H | H | H | H | OEt | NH | —(CH₂)₂CHMe₂ |
| I-2386 | —NH₂ | H | F | H | H | Me | Me | Me | H | H | H | H | OEt | NMe | Me |
| I-2387 | —NH₂ | H | F | H | H | Me | Me | Me | H | H | H | H | OEt | O | —CH₂CH═CMe₂ |
| I-2388 | —NH₂ | H | F | H | H | Me | Me | Me | H | H | H | H | OEt | O | —CH₂CH═CCl₂ |
| I-2389 | —NH₂ | H | F | H | H | H | Me | OMe | OH | H | H | H | OMe | NH | —CH₂CH═CMe₂ |
| I-2390 | —NH₂ | H | F | H | H | H | Me | OMe | OH | H | H | H | OMe | NH | —(CH₂)₂CHMe₂ |
| I-2391 | —NH₂ | H | F | H | H | H | Me | OMe | OH | H | H | H | OMe | NMe | Me |
| I-2392 | —NH₂ | H | F | H | H | H | Me | OMe | OH | H | H | H | OMe | O | —CH₂CH═CMe₂ |
| I-2393 | —NH₂ | H | F | H | H | H | Me | OMe | OH | H | H | H | OMe | O | —CH₂CH═CCl₂ |
| I-2394 | —NH₂ | H | F | H | H | H | Me | OMe | OH | H | H | F | H | NH | —CH₂CH═CMe₂ |
| I-2395 | —NH₂ | H | F | H | H | H | Me | OMe | OH | H | H | F | H | NH | —(CH₂)₂CHMe₂ |
| I-2396 | —NH₂ | H | F | H | H | H | Me | OMe | OH | H | H | F | H | NMe | Me |

TABLE 318

| | | | | | | | | | | | | | | | |
|---|---|---|---|---|---|---|---|---|---|---|---|---|---|---|---|
| I-2397 | —NH₂ | H | F | H | H | H | Me | OMe | OH | H | H | F | H | O | —CH₂CH═CMe₂ |
| I-2398 | —NH₂ | H | F | H | H | H | Me | OMe | OH | H | H | F | H | O | —CH₂CH═CCl₂ |
| I-2399 | —NH₂ | H | F | H | H | H | Me | OMe | OH | H | H | H | OEt | NH | —CH₂CH═CMe₂ |
| I-2400 | —NH₂ | H | F | H | H | H | Me | OMe | OH | H | H | H | OEt | NH | —(CH₂)₂CHMe₂ |
| I-2301 | —NH₂ | H | F | H | H | H | Me | OMe | OH | H | H | H | OEt | NMe | Me |
| I-2302 | —NH₂ | H | F | H | H | H | Me | OMe | OH | H | H | H | OEt | O | —CH₂CH═CMe₂ |
| I-2303 | —NH₂ | H | F | H | H | H | Me | OMe | OH | H | H | H | OEt | O | —CH₂CH═CCl₂ |
| I-2304 | —NH₂ | H | F | H | H | Me | H | Me | OH | H | H | H | OMe | NH | —CH₂CH═CMe₂ |
| I-2305 | —NH₂ | H | F | H | H | Me | H | Me | OH | H | H | H | OMe | NH | —(CH₂)₂CHMe₂ |
| I-2306 | —NH₂ | H | F | H | H | Me | H | Me | OH | H | H | H | OMe | NMe | Me |
| I-237 | —NH₂ | H | F | H | H | Me | H | Me | OH | H | H | H | OMe | O | —CH₂CH═CMe₂ |
| I-2308 | —NH₂ | H | F | H | H | Me | H | Me | OH | H | H | H | OMe | O | —CH₂CH═CCl₂ |
| I-2309 | —NH₂ | H | F | H | H | Me | H | Me | OH | H | H | F | H | NH | —CH₂CH═CMe₂ |
| I-2310 | —NH₂ | H | F | H | H | Me | H | Me | OH | H | H | F | H | NH | —(CH₂)₂CHMe₂ |
| I-2311 | —NH₂ | H | F | H | H | Me | H | Me | OH | H | H | F | H | NMe | Me |
| I-2312 | —NH₂ | H | F | H | H | Me | H | Me | OH | H | H | F | H | O | —CH₂CH═CMe₂ |
| I-2313 | —NH₂ | H | F | H | H | Me | H | Me | OH | H | H | F | H | O | —CH₂CH═CCl₂ |
| I-2314 | —NH₂ | H | F | H | H | Me | H | Me | OH | H | H | H | OEt | NH | —CH₂CH═CMe₂ |
| I-2315 | —NH₂ | H | F | H | H | Me | H | Me | OH | H | H | H | OEt | NH | —(CH₂)₂CHMe₂ |
| I-236 | —NH₂ | H | F | H | H | Me | H | Me | OH | H | H | H | OEt | NMe | Me |
| I-237 | —NH₂ | H | F | H | H | Me | H | Me | OH | H | H | H | OEt | O | —CH₂CH═CMe₂ |

TABLE 319

| | | | | | | | | | | | | | | | |
|---|---|---|---|---|---|---|---|---|---|---|---|---|---|---|---|
| I-2318 | —NH₂ | H | F | H | H | Me | H | Me | OH | H | H | H | OEt | O | —CH₂CH═CCl₂ |
| I-2319 | —NH₂ | H | F | H | H | H | Me | Me | Me | H | H | H | OMe | NH | —CH₂CH═CMe₂ |
| I-230 | —NH₂ | H | F | H | H | H | Me | Me | Me | H | H | H | OMe | NH | —(CH₂)₂CHMe₂ |

TABLE 319-continued

| | | | | | | | | | | | | | | | |
|---|---|---|---|---|---|---|---|---|---|---|---|---|---|---|---|
| I-2321 | —NH₂ | H | F | H | H | H | Me | Me | Me | H | H | H | OMe | NMe | Me |
| I-2322 | —NH₂ | H | F | H | H | H | Me | Me | Me | H | H | H | OMe | O | —CH₂CH=CMe₂ |
| I-2323 | —NH₂ | H | F | H | H | H | Me | Me | Me | H | H | H | OMe | O | —CH₂CH=CCl₂ |
| I-2324 | —NH₂ | H | F | H | H | H | Me | Me | Me | H | H | F | H | NH | —CH₂CH=CMe₂ |
| I-2325 | —NH₂ | H | F | H | H | H | Me | Me | Me | H | H | F | H | NH | —(CH₂)₂CHMe₂ |
| I-236 | —NH₂ | H | F | H | H | H | Me | Me | Me | H | H | F | H | NMe | Me |
| I-2327 | —NH₂ | H | F | H | H | H | Me | Me | Me | H | H | F | H | O | —CH₂CH=CMe₂ |
| I-2328 | —NH₂ | H | F | H | H | H | Me | Me | Me | H | H | F | H | O | —CH₂CH=CCl₂ |
| I-2329 | —NH₂ | H | F | H | H | H | Me | Me | Me | H | H | H | OEt | NH | —CH₂CH=CMe₂ |
| I-2330 | —NH₂ | H | F | H | H | H | Me | Me | Me | H | H | H | OEt | NH | —(CH₂)₂CHMe₂ |
| I-2331 | —NH₂ | H | F | H | H | H | Me | Me | Me | H | H | H | OEt | NMe | Me |
| I-2332 | —NH₂ | H | F | H | H | H | Me | Me | Me | H | H | H | OEt | O | —CH₂CH=CMe₂ |
| I-2333 | —NH₂ | H | F | H | H | H | Me | Me | Me | H | H | H | OEt | O | —CH₂CH=CCl₂ |
| I-2334 | —NH₂ | H | F | H | H | H | OMe | OEt | OH | H | H | H | OMe | NH | —CH₂CH=CMe₂ |
| I-2335 | —NH₂ | H | F | H | H | H | OMe | OEt | OH | H | H | H | OMe | NH | —(CH₂)₂CHMe₂ |
| I-2336 | —NH₂ | H | F | H | H | H | OMe | OEt | OH | H | H | H | OMe | NMe | Me |
| I-2337 | —NH₂ | H | F | H | H | H | OMe | OEt | OH | H | H | H | OMe | O | —CH₂CH=CMe₂ |
| I-2338 | —NH₂ | H | F | H | H | H | OMe | OEt | OH | H | H | H | OMe | O | —CH₂CH=CCl₂ |

TABLE 320

| | | | | | | | | | | | | | | | |
|---|---|---|---|---|---|---|---|---|---|---|---|---|---|---|---|
| I-2339 | —NH₂ | H | F | H | H | H | OMe | OEt | OH | H | H | F | H | NH | —CH₂CH=CMe₂ |
| I-2340 | —NH₂ | H | F | H | H | H | OMe | OEt | OH | H | H | F | H | NH | —(CH₂)₂CHMe₂ |
| I-2341 | —NH₂ | H | F | H | H | H | OMe | OEt | OH | H | H | F | H | NMe | Me |
| I-2342 | —NH₂ | H | F | H | H | H | OMe | OEt | OH | H | H | F | H | O | —CH₂CH=CMe₂ |
| I-2343 | —NH₂ | H | F | H | H | H | OMe | OEt | OH | H | H | F | H | O | —CH₂CH=CCl₂ |
| I-2344 | —NH₂ | H | F | H | H | H | OMe | OEt | OH | H | H | H | OEt | NH | —CH₂CH=CMe₂ |
| I-2345 | —NH₂ | H | F | H | H | H | OMe | OEt | OH | H | H | H | OEt | NH | —(CH₂)₂CHMe₂ |
| I-2346 | —NH₂ | H | F | H | H | H | OMe | OEt | OH | H | H | H | OEt | NMe | Me |
| I-2347 | —NH₂ | H | F | H | H | H | OMe | OEt | OH | H | H | H | OEt | O | —CH₂CH=CMe₂ |
| I-2348 | —NH₂ | H | F | H | H | H | OMe | OEt | OH | H | H | H | OEt | O | —CH₂CH=CCl₂ |
| I-2349 | —NHCH₂CH=CMe₂ | H | H | H | H | Me | Me | Me | H | H | H | H | OMe | NH | —CH₂CH=CMe₂ |
| I-2350 | —NHCH₂CH=CMe₂ | H | H | H | H | Me | Me | Me | H | H | H | H | OMe | NH | —(CH₂)₂CHMe₂ |
| I-2351 | —NHCH₂CH=CMe₂ | H | H | H | H | Me | Me | Me | H | H | H | H | OMe | NMe | Me |
| I-2352 | —NHCH₂CH=CMe₂ | H | H | H | H | Me | Me | Me | H | H | H | H | OMe | O | —CH₂CH=CMe₂ |
| I-2353 | —NHCH₂CH=CMe₂ | H | H | H | H | Me | Me | Me | H | H | H | H | OMe | O | —CH₂CH=CCl₂ |
| I-2354 | —NHCH₂CH=CMe₂ | H | H | H | H | Me | Me | Me | H | H | H | F | H | NH | —CH₂CH=CMe₂ |
| I-2355 | —NHCH₂CH=CMe₂ | H | H | H | H | Me | Me | Me | H | H | H | F | H | NH | —(CH₂)₂CHMe₂ |
| I-2356 | —NHCH₂CH=CMe₂ | H | H | H | H | Me | Me | Me | H | H | H | F | H | NMe | Me |
| I-2357 | —NHCH₂CH=CMe₂ | H | H | H | H | Me | Me | Me | H | H | H | F | H | O | —CH₂CH=CMe₂ |
| I-2358 | —NHCH₂CH=CMe₂ | H | H | H | H | Me | Me | Me | H | H | H | F | H | O | —CH₂CH=CCl₂ |
| I-2359 | —NHCH₂CH=CMe₂ | H | H | H | H | Me | Me | Me | H | H | H | H | OEt | NH | —CH₂CH=CMe₂ |

TABLE 321

| | | | | | | | | | | | | | | | |
|---|---|---|---|---|---|---|---|---|---|---|---|---|---|---|---|
| I-2360 | —NHCH₂CH=CMe₂ | H | H | H | H | Me | Me | Me | H | H | H | H | OEt | NH | —(CH₂)₂CHMe₂ |
| I-2361 | —NHCH₂CH=CMe₂ | H | H | H | H | Me | Me | Me | H | H | H | H | OEt | NMe | Me |
| I-2362 | —NHCH₂CH=CMe₂ | H | H | H | H | Me | Me | Me | H | H | H | H | OEt | O | —CH₂CH=CMe₂ |
| I-2363 | —NHCH₂CH=CMe₂ | H | H | H | H | Me | Me | Me | H | H | H | H | OEt | O | —CH₂CH=CCl₂ |
| I-2364 | —NHCH₂CH=CMe₂ | H | H | H | H | H | Me | OMe | OH | H | H | H | OMe | NH | —CH₂CH=CMe₂ |
| I-2365 | —NHCH₂CH=CMe₂ | H | H | H | H | H | Me | OMe | OH | H | H | H | OMe | NH | —(CH₂)₂CHMe₂ |
| I-2366 | —NHCH₂CH=CMe₂ | H | H | H | H | H | Me | OMe | OH | H | H | H | OMe | NMe | Me |
| I-2367 | —NHCH₂CH=CMe₂ | H | H | H | H | H | Me | OMe | OH | H | H | H | OMe | O | —CH₂CH=CMe₂ |
| I-2368 | —NHCH₂CH=CMe₂ | H | H | H | H | H | Me | OMe | OH | H | H | H | OMe | O | —CH₂CH=CCl₂ |
| I-2369 | —NHCH₂CH=CMe₂ | H | H | H | H | H | Me | OMe | OH | H | H | F | H | NH | —CH₂CH=CMe₂ |
| I-2370 | —NHCH₂CH=CMe₂ | H | H | H | H | H | Me | OMe | OH | H | H | F | H | NH | —(CH₂)₂CHMe₂ |
| I-2371 | —NHCH₂CH=CMe₂ | H | H | H | H | H | Me | OMe | OH | H | H | F | H | NMe | Me |
| I-2372 | —NHCH₂CH=CMe₂ | H | H | H | H | H | Me | OMe | OH | H | H | F | H | O | —CH₂CH=CMe₂ |
| I-2373 | —NHCH₂CH=CMe₂ | H | H | H | H | H | Me | OMe | OH | H | H | F | H | O | —CH₂CH=CCl₂ |
| I-2374 | —NHCH₂CH=CMe₂ | H | H | H | H | H | Me | OMe | OH | H | H | H | OEt | NH | —CH₂CH=CMe₂ |
| I-2375 | —NHCH₂CH=CMe₂ | H | H | H | H | H | Me | OMe | OH | H | H | H | OEt | NH | —(CH₂)₂CHMe₂ |
| I-2376 | —NHCH₂CH=CMe₂ | H | H | H | H | H | Me | OMe | OH | H | H | H | OEt | NMe | Me |
| I-2377 | —NHCH₂CH=CMe₂ | H | H | H | H | H | Me | OMe | OH | H | H | H | OEt | O | —CH₂CH=CMe₂ |
| I-2378 | —NHCH₂CH=CMe₂ | H | H | H | H | H | Me | OMe | OH | H | H | H | OEt | O | —CH₂CH=CCl₂ |
| I-2379 | —NHCH₂CH=CMe₂ | H | H | H | H | Me | H | Me | OH | H | H | H | OMe | NH | —CH₂CH=CMe₂ |
| I-2380 | —NHCH₂CH=CMe₂ | H | H | H | H | Me | H | Me | OH | H | H | H | OMe | NH | —(CH₂)₂CHMe₂ |

TABLE 322

| | | | | | | | | | | | | | | | |
|---|---|---|---|---|---|---|---|---|---|---|---|---|---|---|---|
| I-2381 | —NHCH₂CH=CMe₂ | H | H | H | H | Me | H | Me | OH | H | H | H | OMe | NMe | Me |
| I-2382 | —NHCH₂CH=CMe₂ | H | H | H | H | Me | H | Me | OH | H | H | H | OMe | O | —CH₂CH=CMe₂ |
| I-2383 | —NHCH₂CH=CMe₂ | H | H | H | H | Me | H | Me | OH | H | H | H | OMe | O | —CH₂CH=CCl₂ |

TABLE 322-continued

| | | | | | | | | | | | | | | | |
|---|---|---|---|---|---|---|---|---|---|---|---|---|---|---|---|
| I-2384 | —NHCH$_2$CH=CMe$_2$ | H | H | H | H | Me | H | Me | OH | H | H | F | H | NH | —CH$_2$CH=CMe$_2$ |
| I-2385 | —NHCH$_2$CH=CMe$_2$ | H | H | H | H | Me | H | Me | OH | H | H | F | H | NH | —(CH$_2$)$_2$CHMe$_2$ |
| I-236 | —NHCH$_2$CH=CMe$_2$ | H | H | H | H | Me | H | Me | OH | H | H | F | H | NMe | Me |
| I-2387 | —NHCH$_2$CH=CMe$_2$ | H | H | H | H | Me | H | Me | OH | H | H | F | H | O | —CH$_2$CH=CMe$_2$ |
| I-2388 | —NHCH$_2$CH=CMe$_2$ | H | H | H | H | Me | H | Me | OH | H | H | F | H | O | —CH$_2$CH=CCl$_2$ |
| I-2389 | —NHCH$_2$CH=CMe$_2$ | H | H | H | H | Me | H | Me | OH | H | H | H | OEt | NH | —CH$_2$CH=CMe$_2$ |
| I-2390 | —NHCH$_2$CH=CMe$_2$ | H | H | H | H | Me | H | Me | OH | H | H | H | OEt | NH | —(CH$_2$)$_2$CHMe$_2$ |
| I-2391 | —NHCH$_2$CH=CMe$_2$ | H | H | H | H | Me | H | Me | OH | H | H | H | OEt | NMe | Me |
| I-2392 | —NHCH$_2$CH=CMe$_2$ | H | H | H | H | Me | H | Me | OH | H | H | H | OEt | O | —CH$_2$CH=CMe$_2$ |
| I-2393 | —NHCH$_2$CH=CMe$_2$ | H | H | H | H | Me | H | Me | OH | H | H | H | OEt | O | —CH$_2$CH=CCl$_2$ |
| I-2394 | —NHCH$_2$CH=CMe$_2$ | H | H | H | H | H | Me | Me | Me | H | H | H | OMe | NH | —CH$_2$CH=CMe$_2$ |
| I-2395 | —NHCH$_2$CH=CMe$_2$ | H | H | H | H | H | Me | Me | Me | H | H | H | OMe | NH | —(CH$_2$)$_2$CHMe$_2$ |
| I-2396 | —NHCH$_2$CH=CMe$_2$ | H | H | H | H | H | Me | Me | Me | H | H | H | OMe | NMe | Me |
| I-2397 | —NHCH$_2$CH=CMe$_2$ | H | H | H | H | H | Me | Me | Me | H | H | H | OMe | O | —CH$_2$CH=CMe$_2$ |
| I-2398 | —NHCH$_2$CH=CMe$_2$ | H | H | H | H | H | Me | Me | Me | H | H | H | OMe | O | —CH$_2$CH=CCl$_2$ |
| I-2399 | —NHCH$_2$CH=CMe$_2$ | H | H | H | H | H | Me | Me | Me | H | H | F | H | NH | —CH$_2$CH=CMe$_2$ |
| I-2400 | —NHCH$_2$CH=CMe$_2$ | H | H | H | H | H | Me | Me | Me | H | H | F | H | NH | —(CH$_2$)$_2$CHMe$_2$ |
| I-2401 | —NHCH$_2$CH=CMe$_2$ | H | H | H | H | H | Me | Me | Me | H | H | F | H | NMe | Me |

TABLE 323

| | | | | | | | | | | | | | | | |
|---|---|---|---|---|---|---|---|---|---|---|---|---|---|---|---|
| I-2402 | —NHCH$_2$CH=CMe$_2$ | H | H | H | H | H | Me | Me | Me | H | H | F | H | O | —CH$_2$CH=CMe$_2$ |
| I-2403 | —NHCH$_2$CH=CMe$_2$ | H | H | H | H | H | Me | Me | Me | H | H | F | H | O | —CH$_2$CH=CCl$_2$ |
| I-2404 | —NHCH$_2$CH=CMe$_2$ | H | H | H | H | H | Me | Me | Me | H | H | H | OEt | NH | —CH$_2$CH=CMe$_2$ |
| I-2405 | —NHCH$_2$CH=CMe$_2$ | H | H | H | H | H | Me | Me | Me | H | H | H | OEt | NH | —(CH$_2$)$_2$CHMe$_2$ |
| I-2406 | —NHCH$_2$CH=CMe$_2$ | H | H | H | H | H | Me | Me | Me | H | H | H | OEt | NMe | Me |
| I-2407 | —NHCH$_2$CH=CMe$_2$ | H | H | H | H | H | Me | Me | Me | H | H | H | OEt | O | —CH$_2$CH=CMe$_2$ |
| I-2408 | —NHCH$_2$CH=CMe$_2$ | H | H | H | H | H | Me | Me | Me | H | H | H | OEt | O | —CH$_2$CH=CCl$_2$ |
| I-2409 | —NHCH$_2$CH=CMe$_2$ | H | H | H | H | H | OMe | OEt | OH | H | H | H | OMe | NH | —CH$_2$CH=CMe$_2$ |
| I-2410 | —NHCH$_2$CH=CMe$_2$ | H | H | H | H | H | OMe | OEt | OH | H | H | H | OMe | NH | —(CH$_2$)$_2$CHMe$_2$ |
| I-2411 | —NHCH$_2$CH=CMe$_2$ | H | H | H | H | H | OMe | OEt | OH | H | H | H | OMe | NMe | Me |
| I-2412 | —NHCH$_2$CH=CMe$_2$ | H | H | H | H | H | OMe | OEt | OH | H | H | H | OMe | O | —CH$_2$CH=CMe$_2$ |
| I-2413 | —NHCH$_2$CH=CMe$_2$ | H | H | H | H | H | OMe | OEt | OH | H | H | H | OMe | O | —CH$_2$CH=CCl$_2$ |
| I-2414 | —NHCH$_2$CH=CMe$_2$ | H | H | H | H | H | OMe | OEt | OH | H | H | F | H | NH | —CH$_2$CH=CMe$_2$ |
| I-2415 | —NHCH$_2$CH=CMe$_2$ | H | H | H | H | H | OMe | OEt | OH | H | H | F | H | NH | —(CH$_2$)$_2$CHMe$_2$ |
| I-2416 | —NHCH$_2$CH=CMe$_2$ | H | H | H | H | H | OMe | OEt | OH | H | H | F | H | NMe | Me |
| I-2417 | —NHCH$_2$CH=CMe$_2$ | H | H | H | H | H | OMe | OEt | OH | H | H | F | H | O | —CH$_2$CH=CMe$_2$ |
| I-2418 | —NHCH$_2$CH=CMe$_2$ | H | H | H | H | H | OMe | OEt | OH | H | H | F | H | O | —CH$_2$CH=CCl$_2$ |
| I-2419 | —NHCH$_2$CH=CMe$_2$ | H | H | H | H | H | OMe | OEt | OH | H | H | H | OEt | NH | —CH$_2$CH=CMe$_2$ |
| I-2420 | —NHCH$_2$CH=CMe$_2$ | H | H | H | H | H | OMe | OEt | OH | H | H | H | OEt | NH | —(CH$_2$)$_2$CHMe$_2$ |
| I-2421 | —NHCH$_2$CH=CMe$_2$ | H | H | H | H | H | OMe | OEt | OH | H | H | H | OEt | NMe | Me |
| I-2422 | —NHCH$_2$CH=CMe$_2$ | H | H | H | H | H | OMe | OEt | OH | H | H | H | OEt | O | —CH$_2$CH=CMe$_2$ |

TABLE 324

| | | | | | | | | | | | | | | | |
|---|---|---|---|---|---|---|---|---|---|---|---|---|---|---|---|
| I-2423 | —NHCH$_2$CH=CMe$_2$ | H | H | H | H | H | OMe | OEt | OH | H | H | H | OEt | O | —CH$_2$CH=CCl$_2$ |
| I-2424 | —OMe | | H | H | H | H | Me | Me | Me | H | H | H | H | OMe | NH | —CH$_2$CH=CMe$_2$ |
| I-2425 | —OMe | | H | H | H | H | Me | Me | Me | H | H | H | H | OMe | NH | —(CH$_2$)$_2$CHMe$_2$ |
| I-2426 | —OMe | | H | H | H | H | Me | Me | Me | H | H | H | H | OMe | NMe | Me |
| I-2427 | —OMe | | H | H | H | H | Me | Me | Me | H | H | H | H | OMe | O | —CH$_2$CH=CMe$_2$ |
| I-2428 | —OMe | | H | H | H | H | Me | Me | Me | H | H | H | H | OMe | O | —CH$_2$CH=CCl$_2$ |
| I-2429 | —OMe | | H | H | H | H | Me | Me | Me | H | H | F | H | H | NH | —CH$_2$CH=CMe$_2$ |
| I-2430 | —OMe | | H | H | H | H | Me | Me | Me | H | H | F | H | H | NH | —(CH$_2$)$_2$CHMe$_2$ |
| I-2431 | —OMe | | H | H | H | H | Me | Me | Me | H | H | F | H | H | NMe | Me |
| I-2432 | —OMe | | H | H | H | H | Me | Me | Me | H | H | F | H | H | O | —CH$_2$CH=CMe$_2$ |
| I-2433 | —OMe | | H | H | H | H | Me | Me | Me | H | H | F | H | H | O | —CH$_2$CH=CCl$_2$ |
| I-2434 | —OMe | | H | H | H | H | Me | Me | Me | H | H | H | H | OEt | NH | —CH$_2$CH=CMe$_2$ |
| I-2435 | —OMe | | H | H | H | H | Me | Me | Me | H | H | H | H | OEt | NH | —(CH$_2$)$_2$CHMe$_2$ |
| I-2436 | —OMe | | H | H | H | H | Me | Me | Me | H | H | H | H | OEt | NMe | Me |
| I-2437 | —OMe | | H | H | H | H | Me | Me | Me | H | H | H | H | OEt | O | —CH$_2$CH=CMe$_2$ |
| I-2438 | —OMe | | H | H | H | H | Me | Me | Me | H | H | H | H | OEt | O | —CH$_2$CH=CCl$_2$ |
| I-2439 | —OMe | | H | H | H | H | H | Me | OMe | OH | H | H | H | OMe | NH | —CH$_2$CH=CMe$_2$ |
| I-2440 | —OMe | | H | H | H | H | H | Me | OMe | OH | H | H | H | OMe | NH | —(CH$_2$)$_2$CHMe$_2$ |
| I-2441 | —OMe | | H | H | H | H | H | Me | OMe | OH | H | H | H | OMe | NMe | Me |
| I-2442 | —OMe | | H | H | H | H | H | Me | OMe | OH | H | H | H | OMe | O | —CH$_2$CH=CMe$_2$ |
| I-2443 | —OMe | | H | H | H | H | H | Me | OMe | OH | H | H | H | OMe | O | —CH$_2$CH=CCl$_2$ |

TABLE 325

| | | | | | | | | | | | | | | |
|---|---|---|---|---|---|---|---|---|---|---|---|---|---|---|
| I-2444 | —OMe | H | H | H | H | H | Me | OMe | OH | H | H | F | H | NH | —CH$_2$CH=CMe$_2$ |
| I-2445 | —OMe | H | H | H | H | H | Me | OMe | OH | H | H | F | H | NH | —(CH$_2$)$_2$CHMe$_2$ |
| I-2446 | —OMe | H | H | H | H | H | Me | OMe | OH | H | H | F | H | NMe | Me |

TABLE 325-continued

| | | | | | | | | | | | | | | | |
|---|---|---|---|---|---|---|---|---|---|---|---|---|---|---|---|
| I-2447 | —OMe | H | H | H | H | H | Me | OMe | OH | H | H | F | H | O | —CH$_2$CH=CMe$_2$ |
| I-2448 | —OMe | H | H | H | H | H | Me | OMe | OH | H | H | F | H | O | —CH$_2$CH=CCl$_2$ |
| I-2449 | —OMe | H | H | H | H | H | Me | OMe | OH | H | H | H | OEt | NH | —CH$_2$CH=CMe$_2$ |
| I-2450 | —OMe | H | H | H | H | H | Me | OMe | OH | H | H | H | OEt | NH | —(CH$_2$)$_2$CHMe$_2$ |
| I-2451 | —OMe | H | H | H | H | H | Me | OMe | OH | H | H | H | OEt | NMe | Me |
| I-2452 | —OMe | H | H | H | H | H | Me | OMe | OH | H | H | H | OEt | O | —CH$_2$CH=CMe$_2$ |
| I-2453 | —OMe | H | H | H | H | H | Me | OMe | OH | H | H | H | OEt | O | —CH$_2$CH=CCl$_2$ |
| I-2454 | —OMe | H | H | H | H | Me | H | Me | OH | H | H | H | OMe | NH | —CH$_2$CH=CMe$_2$ |
| I-2455 | —OMe | H | H | H | H | Me | H | Me | OH | H | H | H | OMe | NH | —(CH$_2$)$_2$CHMe$_2$ |
| I-2456 | —OMe | H | H | H | H | Me | H | Me | OH | H | H | H | OMe | NMe | Me |
| I-2457 | —OMe | H | H | H | H | Me | H | Me | OH | H | H | H | OMe | O | —CH$_2$CH=CMe$_2$ |
| I-2458 | —OMe | H | H | H | H | Me | H | Me | OH | H | H | H | OMe | O | —CH$_2$CH=CCl$_2$ |
| I-2459 | —OMe | H | H | H | H | Me | H | Me | OH | H | H | F | H | NH | —CH$_2$CH=CMe$_2$ |
| I-2460 | —OMe | H | H | H | H | Me | H | Me | OH | H | H | F | H | NH | —(CH$_2$)$_2$CHMe$_2$ |
| I-2461 | —OMe | H | H | H | H | Me | H | Me | OH | H | H | F | H | NMe | Me |
| I-2462 | —OMe | H | H | H | H | Me | H | Me | OH | H | H | F | H | O | —CH$_2$CH=CMe$_2$ |
| I-2463 | —OMe | H | H | H | H | Me | H | Me | OH | H | H | F | H | O | —CH$_2$CH=CCl$_2$ |
| I-2464 | —OMe | H | H | H | H | Me | H | Me | OH | H | H | H | OEt | NH | —CH$_2$CH=CMe$_2$ |

TABLE 326

| | | | | | | | | | | | | | | | |
|---|---|---|---|---|---|---|---|---|---|---|---|---|---|---|---|
| I-2465 | —OMe | H | H | H | H | Me | H | Me | OH | H | H | H | OEt | NH | -(CH$_2$)$_2$CHMe2 |
| I-2466 | —OMe | H | H | H | H | Me | H | Me | OH | H | H | H | OEt | NMe | Me |
| I-2467 | —OMe | H | H | H | H | Me | H | Me | OH | H | H | H | OEt | O | —CH$_2$CH=CMe2 |
| I-2468 | —OMe | H | H | H | H | Me | H | Me | OH | H | H | H | OEt | O | —CH$_2$CH=CCl$_2$ |
| I-2469 | —OMe | H | H | H | H | H | Me | Me | Me | H | H | H | OMe | NH | —CH$_2$CH=CMe$_2$ |
| I-2470 | —OMe | H | H | H | H | H | Me | Me | Me | H | H | H | OMe | NH | —(CH$_2$)$_2$CHMe$_2$ |
| I-2471 | —OMe | H | H | H | H | H | Me | Me | Me | H | H | H | OMe | NMe | Me |
| I-2472 | —OMe | H | H | H | H | H | Me | Me | Me | H | H | H | OMe | O | —CH$_2$CH=CMe$_2$ |
| I-2473 | —OMe | H | H | H | H | H | Me | Me | Me | H | H | H | OMe | O | —CH$_2$CH=CCl$_2$ |
| I-2474 | —OMe | H | H | H | H | H | Me | Me | Me | H | H | F | H | NH | —CH$_2$CH=CMe$_2$ |
| I-2475 | —OMe | H | H | H | H | H | Me | Me | Me | H | H | F | H | NH | —(CH$_2$)$_2$CHMe$_2$ |
| I-2476 | —OMe | H | H | H | H | H | Me | Me | Me | H | H | F | H | NMe | Me |
| I-2477 | —OMe | H | H | H | H | H | Me | Me | Me | H | H | F | H | O | CH$_2$CH=CMe$_2$ |
| I-2478 | —OMe | H | H | H | H | H | Me | Me | Me | H | H | F | H | O | —CH$_2$CH=CCl$_2$ |
| I-2479 | —OMe | H | H | H | H | H | Me | Me | Me | H | H | H | OEt | NH | —CH$_2$CH=CMe$_2$ |
| I-2480 | —OMe | H | H | H | H | H | Me | Me | Me | H | H | H | OEt | NH | —(CH$_2$)$_2$CHMe$_2$ |
| I-2481 | —OMe | H | H | H | H | H | Me | Me | Me | H | H | H | OEt | NMe | Me |
| I-2482 | —OMe | H | H | H | H | H | Me | Me | Me | H | H | H | OEt | O | —CH$_2$CH=CMe$_2$ |
| I-2483 | —OMe | H | H | H | H | H | Me | Me | Me | H | H | H | OEt | O | —CH$_2$CH=CCl$_2$ |
| I-2484 | —OMe | H | H | H | H | H | OMe | OEt | OH | H | H | H | OMe | NH | —CH$_2$CH=CMe$_2$ |
| I-2485 | —OMe | H | H | H | H | H | OMe | OEt | OH | H | H | H | OMe | NH | —(CH$_2$)$_2$CHMe$_2$ |

TABLE 327

| | | | | | | | | | | | | | | | |
|---|---|---|---|---|---|---|---|---|---|---|---|---|---|---|---|
| I-2486 | —OMe | H | H | H | H | H | OMe | OEt | OH | H | H | H | OMe | NMe | Me |
| I-2487 | —OMe | H | H | H | H | H | OMe | OEt | OH | H | H | H | OMe | O | —CH$_2$CH=CMe$_2$ |
| I-2488 | —OMe | H | H | H | H | H | OMe | OEt | OH | H | H | H | OMe | O | —CH$_2$CH=CCl$_2$ |
| I-2489 | —OMe | H | H | H | H | H | OMe | OEt | OH | H | H | F | H | NH | —CH$_2$CH=CMe$_2$ |
| I-2490 | —OMe | H | H | H | H | H | OMe | OEt | OH | H | H | F | H | NH | —(CH$_2$)$_2$CHMe$_2$ |
| I-2491 | —OMe | H | H | H | H | H | OMe | OEt | OH | H | H | F | H | NMe | Me |
| I-2492 | —OMe | H | H | H | H | H | OMe | OEt | OH | H | H | F | H | O | —CH$_2$CH=CMe$_2$ |
| I-2493 | —OMe | H | H | H | H | H | OMe | OEt | OH | H | H | F | H | O | —CH$_2$CH=CCl$_2$ |
| I-2494 | —OMe | H | H | H | H | H | OMe | OEt | OH | H | H | H | OEt | NH | —CH$_2$CH=CMe$_2$ |
| I-2495 | —OMe | H | H | H | H | H | OMe | OEt | OH | H | H | H | OEt | NH | —(CH$_2$)$_2$CHMe$_2$ |
| I-2496 | —OMe | H | H | H | H | H | OMe | OEt | OH | H | H | H | OEt | NMe | Me |
| I-2497 | —OMe | H | H | H | H | H | OMe | OEt | OH | H | H | H | OEt | O | —CH$_2$CH=CMe$_2$ |
| I-2498 | —OMe | H | H | H | H | H | OMe | OEt | OH | H | H | H | OEt | O | —CH$_2$CH=CCl$_2$ |

In the above tables, "—OCH$_2$O—*" and "*" mean that they taken together form a ring.

Experiment 1

Suppressive Effect on a Mitogenic Activity of Mouse Splenocytes In Vitro

In 96-well microtiter plate $5 \times 10^5$ C3H/HeN mouse splenocytes suspended in 0.1 ml of 10% fetal bovine serum-fortified RPMI 1640 medium containing 2 mM of sodium bicarbonate, 50 units/ml of penicillin, 50 µg/ml of streptomycin and $5 \times 10^{-5}$ M of 2-mercaptoethanol were added. Then, 5 µg/ml of Concanavalin A (Con A) or 10 µg/ml of lipopolysaccharide (LPS) as a mitogen and the compound of a pre-determined concentration of the present invention were added to each well so that a final volume of each well reached 0.2 ml. Each compound of the present invention was dissolved in dimethylsulfoxide (DMSO) and diluted with the above RPMI 1640 medium to adjust the final concentration of 100 ng/ml or less. The splenocytes in the 96-well microtiter plate were cultivated at 37° C. for 3 days in an incubator keeping the humidity 100%, carbon dioxide 5% and air 95%. Then, 25 µl of 6 mg/ml MTT [3-(4,5-dimethylthiazol-2-yl)-2,5-diphenyltetrazolium bromide] (Sigma) was added to the each well and cultivated at 37° C. for 4 hours under the same conditions. After the cultivation, 50 μl of 0.02 N hydrochloric acid in 20% sodium dodecyl sulfate (SDS) was added to formazan generated and left at 37° C. for 24 hours for dissolving formazan. An absorption intensity (OD) of formazan generated in proportion to the number of living cells was measured with an immunoreader (InterMed) equipped with a 570 nm filter (The Journal of Immunological Method, 65, 55–63, 1983). The 50% inhibitory concentration of a cell proliferation ($IC_{50}$) was calculated from a correlation between the concentration of the compound of the present invention and the absorption intensity.

Experiment 2

Anti-proliferative Activity on EL4 Cells

In 96-well microtiter plate 4×10$^4$/0.1 ml of mouse thymoma strain EL4 cells were added and 0.1 ml of the compound of the present invention was added to the mixture so that the concentration was in the range of 0–5,000 ng/ml. After the cultivation for 3 days, the $IC_{50}$ was calculated by the MTT method as described in Experiment 1.

The results are shown in Tables 328–329.

TABLE 328

| Compound | ConA $IC_{50}$ (ng/ml) | LPS $IC_{50}$ (ng/ml) | EL-4 $IC_{50}$ (ngl/ml) |
|---|---|---|---|
| I-1 | 0.86 | 1.92 | 8.56 |
| I-9 | <20 | <20 | <20 |
| I-12 | 1.3 | 2.8 | 46.2 |
| I-22 | 5.62 | 4.26 | 6.2 |
| I-35 | 19.5 | 39.4 | 140 |
| I-40 | 6.1 | 16.5 | 37.4 |
| I-41 | 0.73 | 1.74 | 4.89 |
| I-46 | 10.6 | 23.9 | 67.5 |
| I-49 | 8.89 | 16.2 | 31.7 |
| I-50 | 3.83 | 9.2 | 11.9 |
| I-51 | 6.6 | 14.7 | 70.0 |
| I-59 | 8.5 | 22.4 | 140 |
| I-62 | 29.2 | 25 | 23.4 |
| I-63 | 13 | 27 | 16 |
| I-66 | 0.22 | 0.35 | 0.48 |
| I-71 | 4.56 | 14.2 | 31.2 |
| I-101 | 0.8 | 0.5 | 1.8 |
| I-103 | 3.4 | 3.7 | 4.6 |
| I-104 | 3.0 | 3.1 | 4.8 |
| I-106 | 0.6 | 0.4 | 2.7 |
| I-107 | 0.6 | 0.7 | 12 |
| I-121 | 0.8 | 1.2 | 0.8 |
| I-163 | <20 | <20 | <20 |
| I-173 | <20 | <20 | <20 |
| I-175 | <20 | 29.4 | <20 |
| I-187 | 12.0 | 25.1 | 36.2 |
| I-211 | <20 | <20 | <20 |
| I-248 | <10 | <10 | 312 |
| I-250 | <10 | <10 | 88.3 |
| I-251 | <10 | <10 | 97.4 |
| I-255 | <20 | <20 | <20 |
| I-256 | <20 | 28.7 | 310 |
| I-275 | 6.34 | 13.5 | 100 |
| I-276 | 1.8 | 3.1 | 200 |
| I-299 | 5.53 | 7.85 | 13.6 |
| I-301 | 7.06 | 11.0 | 15.8 |
| I-360 | <20 | <20 | 99.8 |
| I-361 | <20 | <20 | 124 |
| I-418 | 255 | 497 | >10000 |
| I-427 | 255 | 497 | >10000 |
| I-457 | <20 | <20 | 205 |
| I-466 | <20 | <20 | 46 |
| I-484 | 14.7 | 32.2 | 91.4 |
| I-513 | 6.89 | 11.1 | 61.8 |

TABLE 328-continued

| Compound | ConA $IC_{50}$ (ng/ml) | LPS $IC_{50}$ (ng/ml) | EL-4 $IC_{50}$ (ngl/ml) |
|---|---|---|---|
| I-525 | 0.76 | 1.11 | 5.0 |
| I-639 | 4.59 | 6.25 | 50 |
| I-661 | 0.67 | 1.28 | 50 |
| I-739 | 18.8 | 20.7 | 430 |
| I-742 | 10 | 20 | 45.2 |
| I-758 | 6.78 | 9.63 | 55.1 |
| I-773 | 8.45 | 12.6 | 92.9 |
| I-797 | 1.75 | 3.71 | 26.5 |
| I-834 | 36 | 46 | 226 |
| I-839 | 1.48 | 1.87 | 20.7 |
| I-840 | 5.31 | 6.94 | 31.9 |
| I-878 | 14.1 | 27.4 | 194 |
| I-880 | 23.0 | 41.1 | 105 |
| I-892 | <0.2 | <0.2 | 1.41 |
| I-893 | 0.49 | 1.05 | 7.06 |

TABLE 329

| Compound | ConA $IC_{50}$ (ng/ml) | LPS $IC_{50}$ (ng/ml) | EL-4 $IC_{50}$ (ng/ml) |
|---|---|---|---|
| I-907 | 23.4 | 44.5 | 82.7 |
| I-908 | 0.45 | 0.86 | 3.50 |
| I-909 | <20 | <20 | 20 |
| I-931 | 2.93 | 5.76 | 4.37 |
| I-934 | 16.1 | 22.2 | 52.7 |
| I-943 | 2.97 | 4.89 | 46.8 |
| I-962 | 12.1 | 16.3 | 20.4 |
| I-970 | <20 | <20 | 50.3 |
| I-976 | 17.7 | 34.2 | 330 |
| I-981 | 14.9 | 27.1 | >100 |
| I-982 | 2.0 | 3.75 | 55.3 |
| I-988 | 0.2 | 0.31 | 1.23 |
| I-993 | 5.10 | 7.54 | 13.8 |
| I-995 | 20.9 | 25.2 | 49.2 |
| I-1006 | 8.66 | 12.3 | 33.0 |
| I-1007 | 8.05 | 10.4 | 13.1 |
| I-1017 | 9.74 | 16.7 | 72.9 |
| I-1031 | <20 | 21.2 | 41.7 |
| I-1040 | 1.80 | 5.31 | 1.85 |
| I-1043 | 2.19 | 3.27 | 9.70 |
| I-1058 | 21.2 | 30.2 | 48.8 |
| I-1066 | 3.91 | 4.87 | 20.6 |
| I-1095 | 6.90 | 9.57 | 34.2 |
| I-1103 | 4.7 | 6.9 | 31.4 |
| I-1107 | 5.8 | 9.1 | 34.1 |
| I-1115 | <20 | <20 | <20 |
| I-1121 | 3.12 | 9.0 | 18.6 |
| I-1123 | 0.80 | 2.00 | 3.9 |
| I-1124 | 94 | 272 | >10000 |
| I-1126 | 79 | 234 | >10000 |
| I-1127 | 44 | 111 | 412 |
| I-1128 | 5.00 | 11.4 | 26.0 |
| I-1135 | 1.00 | 2.70 | 11.7 |
| I-1160 | 10.6 | 14.1 | 97.4 |
| I-1161 | 2.4 | 4.2 | 33.2 |
| I-1162 | 0.65 | 1.95 | 30.9 |
| I-1167 | 0.08 | 0.23 | 8.1 |
| I-1168 | 0.26 | 0.54 | 12.5 |
| I-1171 | 0.63 | 0.64 | 27.5 |
| I-1172 | 13.1 | 19.4 | >100 |
| I-1173 | 16.4 | 31.1 | >100 |
| I-1177 | 12.2 | 20.8 | 47.2 |
| I-1191 | 0.16 | 0.66 | 22.8 |
| I-1193 | 1.46 | 5.3 | 50 |
| I-1203 | 14.1 | >100 | 43.5 |
| I-1212 | 12.87 | 24.2 | 85.0 |
| I-1217 | <20 | <20 | <20 |
| I-1227 | 197 | 423 | >10000 |
| I-1229 | 5.95 | 8.05 | 20.4 |
| I-1230 | 12.0 | 15.3 | 5.22 |

TABLE 329-continued

| Compound | ConA IC$_{50}$ (ng/ml) | LPS IC$_{50}$ (ng/ml) | EL-4 IC$_{50}$ (ng/ml) |
|---|---|---|---|
| I-1232 | 3.77 | 4.93 | 15.1 |
| I-1240 | 2.50 | 3.34 | 11.8 |
| I-1248 | 25.9 | 36.8 | 118 |
| I-1250 | 0.68 | 1.35 | 2.90 |
| I-1251 | 6.30 | 10.7 | 27.8 |
| I-1263 | <20 | <20 | 29.8 |
| I-1271 | 0.10 | 0.32 | 1.66 |
| I-1274 | 0.33 | 1.38 | 1.44 |
| I-1276 | <20 | 31.3 | 105 |
| I-1277 | <20 | <20 | <20 |
| I-1278 | <20 | <20 | 41.7 |
| I-1284 | <20 | <20 | <20 |
| I-1286 | <20 | <20 | <20 |
| I-1289 | <20 | <20 | <20 |
| I-1290 | <20 | <20 | 27.3 |
| I-1295 | <20 | <20 | <20 |
| I-1296 | <20 | <20 | 39.7 |

As shown in the above, the compound of the present invention has immunosuppressive and anti-allergic effects.

Experiment 3

Suppressive Effect on the Antibody Production Against bovine γ Globulin (BGG)

On an immunizing day and 7 days after, 50 μg of BGG was subcutaneously inoculated to backs of BALB/c mice (male, 6–8 weeks old) for inducing an immune reaction. After the compound of the present invention was dissolved or suspended in N,N-dimethylacetoamide, the mixture was diluted with miglyol 812 neutral oil. A proper volume of the compound was orally administered (p.o.) to mice every day from the next day of the immunizing. A two hundredth weight to body weight of miglyol was administered to mice in a control group. After 21 days, blood was drawn from each mouse and a serum was separated. BGG-specific IgE in a serum was measured by the sandwich ELISA method using a BGG-coating plate. The suppressive rate of IgE production was calculated from the dilution rate of the serum which has the same absorption intensity as that of the control group for judging the effect of the compound of the present invention. The results are shown in Table 330.

TABLE 330

| Compound | Dose (mg/kg) | Suppressive rate of antigen-specific IgE (%) |
|---|---|---|
| I-525 | 100 | >95 |
| I-915 | 100 | >99 |
| I-892 | 5 | >99 |
| I-963 | 50 | >99 |
| I-1031 | 100 | >99 |
| I-1093 | 100 | >99 |

Experiment 4

Suppressive Effect on the IgE Production Against Ovalbumin (OVA)

1) Animals

BALB/c mice (female, 8–10 weeks old) and Wistar rats (female, 8–10 weeks old) which were bought from Japan SLC, Inc. (Shizuoka) were used.

2) Immunizing Method

BALB/c mice were immunized by an intraperitoneal administration of 0.2 ml suspension of 2 μg of ovalbumin (OVA) and 2 mg of aluminium hydroxide gel in physiological saline. After 10 days, blood was drawn from hearts, sera were separated and stocked at −40° C. till the measurement of an IgE antibody titer.

3) Compounds

After the compound of the present invention was dissolved or suspended in N,N-dimethylacetoamide, the mixture was diluted 20 times with miglyol 812 neutral oil. The obtained solution was orally administered to mice at 0.1 ml per mouse. The administration was continued for 10 days from the immunizing day to the day before drawing blood. IPD-1151-T (a compound described in Jpn. Pharmacol. (1993) 61, 31–39) and a compound No. 36 (a compound 36 described in J. Med. Chem. (1997) 40: 395–407) were examined as controls by the same method.

4) Measurement of Anti-OVA IgE Antibody Titer (PCA Titer)

The samples 2-fold diluted with physiological saline were prepared from the obtained mouse serum and each 50 μl of the solution was intradermauy injected to backs of Wistar rats which previously hair cut. After 24 hours, a passive cutaneous anaphylaxis reaction (PCA) was induced by an intravenous injection of 0.5 ml of physiological saline containing 1 mg of OVA and 5 mg of Evans' blue dye. After 30 minutes, the rats were sacrificed and the highest dilution rate of the serum giving bluing with a diameter of more than 5 mm was recorded as the PCA titer. For example, when a serum is positive for the PCA reaction till $2^7$ times dilution, the anti-OVA IgE antibody titer of the mouse is defined as 7. The results are shown in Table 331.

TABLE 331

| Compound | Dose (mg/kg) | PCA Titer |
|---|---|---|
| I-484 | 40 | <0 |
| I-839 | 40 | 2.4** |
| I-851 | 40 | 1.8** |
| I-892 | 40 | <0 |
| I-893 | 40 | 2.5** |
| I-908 | 40 | 3.4** |
| I-915 | 40 | <0 |
| I-925 | 40 | 1** |
| I-928 | 40 | <0 |
| I-948 | 40 | 2.6** |
| I-957 | 40 | 4.5** |
| I-962 | 40 | <0 |
| I-963 | 40 | 3.6** |
| I-988 | 40 | 0.8** |
| I-1031 | 40 | 4.4** |
| I-1043 | 40 | 4.8** |
| I-1066 | 40 | <0 |
| I-1072 | 40 | 0.8** |
| I-1095 | 40 | <0 |
| I-1123 | 40 | 2.4** |
| I-1135 | 40 | 4.8** |
| I-1167 | 40 | 4.4** |
| I-1171 | 40 | <0 |
| I-1177 | 40 | 3.6** |
| I-1229 | 40 | <0 |
| I-1232 | 40 | 1.8** |
| I-1242 | 40 | 2.8** |
| I-1258 | 40 | 1.2** |
| I-1271 | 40 | <0 |
| IPD-1151-T | 50 | 9.8 |
| No. 36 | 10 | 10.4 |

**$P < 0.01$ vs vehicle

The PCA titers of mice in a group to which any compound was not administered were 9–12.

IPD-1151-T . . .

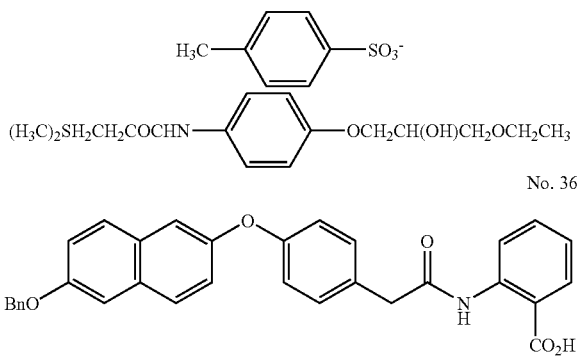

No. 36

As shown in the above, the compound of the present invention has a suppressive effect on the antibody production.

Experiment 5

Suppressive Effect on the Antibody Production of Human Lymphocytes

1. Experimental Method
1) Human Peripheral Blood

Human peripheral blood was drawn from healthy male adults by plastic syringes filled with heparin (final concentration 1.5%). Lymphocytes were collected immediately after blood was drawn.

2) Medium

RPMI medium (Nissui Pharmaceutical Co., Ltd.) containing 10% fetal bovine serum (HyClone Lab.) inactivated at 56° C. for 30 minutes, penicillin (100 units/ml) and streptomycin (100 μg/ml) (GIBCO) was used.

3) Compounds

After the compound (I-839) of the present invention was dissolved in dimethylsulfoxide (Nakaraitesk) at 2 μg/ml, the solution was diluted with the medium to adjust a final concentration to be 0.01 pg/ml–10 μg/ml. The compound No. 36 was examined as a control by the same method.

4) Human Lymphocytes

Human peripheral blood was stratified in a tube filled with Ficoll-Hypaque mixture solution (Dainippon Pharmaceutical Co., Ltd. (Osaka), Mono-poly resolving medium) at the same volume and centrifuged at 300×g at 15° C. for 30 minutes to obtain a lymphocytes layer. After the collected cell suspension was washed with sterile Hanks' solution (Nissui Pharmaceutical Co., Ltd.) by centrifugation, sterile distilled water was added to the suspension. After 30 seconds, twice-concentrated Hanks' solution of which amount is equal to the water was added for removal of contaminating erythrocytes. Lymphocytes which were filtered by a nylon mesh and washed by centrifugation were used for experiments as human lymphocytes.

5) Induction of the IgE Antibody Production by Stimulation of B Cells

In 96-well cultivating plate (Sumitomo bakelite) the lymphocytes were inoculated 2×10$^5$ cells per well, and the compound, anti-human CD 40 antigen (Pharmingen, 2 μg/ml), human recombinant interleukin-4 (IL-4) (Genzyme, 0.1 μg/ml) and human recombinant interleukin-10 (IL-10) (Genzyme, 0.2 μg/ml) were added and cultivated at 37° C. under 5% of $CO_2$ (0.2 ml!well). After the cultivation for 10 days, the amount of antibody in a supernatant was quantified by ELISA method.

6) Quantification of the IgE Antibody

A commercial kit MESACUP IgE test (Medical & Biological Laboratories Co., Ltd.) was used for the quantification of the IgE. The experiment followed an instruction manual and was carried out in triplicate to calculate the average.

7) Quantification of the IgG and IgM Antibodies

ELISA method was used for the quantification. In 96-well plate (Nunc) 50 μl of 1 μg/ml F(ab')$_2$ Goat Anti-human IgG+A+M (H+L) (ZYMED Laboratories) was added and the plate was coated at 4° C. overnight. The,plate was washed twice with 0.05% Tween/PBS (PBST) solution and 100 μl of 0.5% gelatin/PBST was added for blocking at room temperature for 2 hours. After washing three times with PBST, 100 μl of a sample diluted with PBS or 100 μl of human Plasma IgG standard solution or IgM standard solution (BioPur AG, Switzerland) of a pre-determined concentration was added and incubated at room temperature for 1 hour. After washing three times with PBST, 100 μl of a peroxydase-labeled anti-human IgG antibody or anti-human IgM antibody (Southern Biotechnology, Birmingham) which was diluted two thousandth with PBS was added and incubated at room temperature for 1 hour. After washing four times with PBST, 100 μl of a substrate, o-phenylenediamine dihydrochloride, was added for color development. After 30 minutes, the reaction was terminated by addition of 50 μl of 2 N HCl, and the absorption at 492 nm was measured with a microplate reader and the amount of the IgG and IgM was calculated from a standard curve of a standard solution.

2. Results

Figure 2:
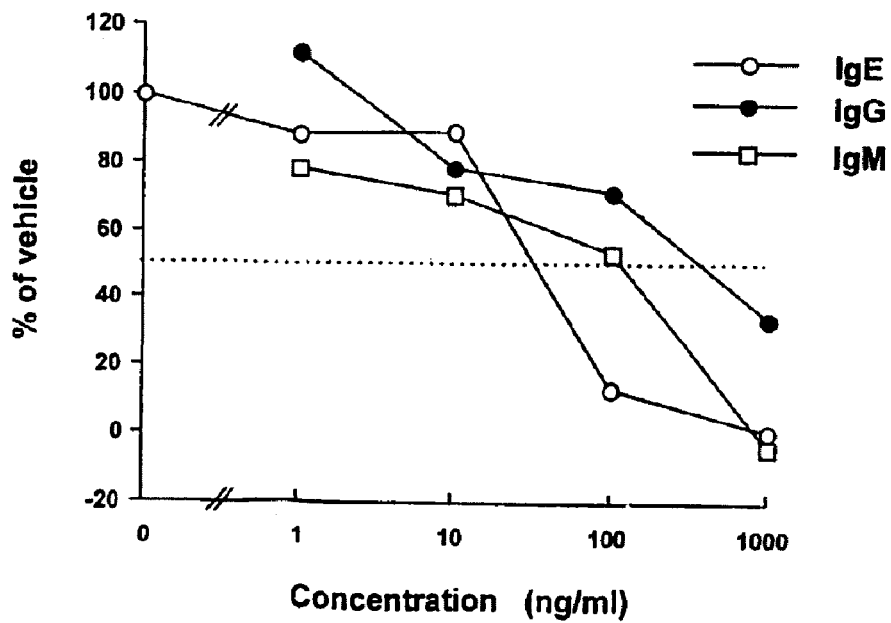
FIG. 2 shows an antibody production-suppressive effect on human peripheral lymphocytes of the compound No. 36. The ordinate represents a percentage of the amount of antibodies to that of antibodies which are produced in the absence of the compound. The abscissa represents a concentration of the compound.

The results are shown in FIGS. 1 and 2. The compound (1–839) of the present invention has a selective suppressive effect on the IgE antibody production and the intensity was 2,000 times or more of that of the IgG production and 30,000 times or more of that of the IgM. The suppressive effects of the typical compounds on the antibody production are shown in Table 332.

TABLE 332

| | IC$_{50}$ (ng/ml) | | |
|---|---|---|---|
| Compound | IgE | IgG | IgM |
| I-839 | <0.00001 | 0.027 | 0.37 |
| I-892 | <0.00001 | <0.00001 | >1 |
| I-121 | <0.0001 | <0.0001 | >1 |
| I-988 | <0.00001 | <0.00001 | >1 |
| I-893 | <0.00001 | <0.0001 | >1 |

Experiment 6

Suppressive Effect on Antibody Production of Mouse Spleen Lymphocytes

1. Experimental Method
1) Animals

BALB/c (nu/nu) mice were bought from Japan SLC, Inc. (Shizuoka) and 7 weeks old-male mice were used.

2) Medium RPMI medium (Nissui Pharmaceutical Co., Ltd.) containing 10% fetal bovine serum (HyClone Lab.) inactivated at 56° C. for 30 minutes, penicillin (100 units/ml) and streptomycin (100 μg/ml) (GIBCO) was used for experiments.

3) Compounds

Each of the compounds was dissolved in dimethylsulfoxide (Nakaraitesk) at 2 μg/ml and diluted with the medium to adjust a final concentration to 0.1 pg/ml–10 μg/ml.

4) Mouse Spleen Lymphocytes

A spleen of mouse was taken out and put in a cultivating schale which was filled with Hanks' solution. The spleen was crushed and the cells were pushed out from the organ and filtered through a metal mesh (200 mesh). After the collected cell suspension was washed by centrifugation with sterile Hanks' solution (Nissui Pharmaceutical Co., Ltd.), sterile distilled water was added. After 30 seconds, an equal amount of twice-concentrated Hanks' solution was added for removal of contaminating erythrocytes. The cell suspension, filtered by a nylon mesh and washed by centrifugation, were used as mouse spleen lymphocytes for experiments.

5) Induction of the IgE Antibody Production by the B Cell Stimulation

In 96-well cultivating plate (Sumitomo Bakelite Company Limited) mouse spleen lymphocytes were inoculated $2 \times 10^5$ cells per well. The compound of the present invention, lipopolysaccharide (DIFCO Lab., 2 μg/ml) and mouse recombinant interleukin-4 (IL-4) (Genzyme, 50 ng/ml) were added to the well and cultivated at 37° C. under 5% $CO_2$ (0.2 ml/well). After the cultivation for 10 days, the amount of the antibody in a supernatant was quantified by ELISA method.

6) Quantification of the IgE Antibody

A commercial mouse IgE EIA kit (Yamasa Shoyu Co., Ltd.) was used for the quantification of the IgE. The experiment followed an instruction manual and was carried out in triplicate to calculate the average.

7) Quantification of the IgG1, IgG2a and IgM Antibodies

In 96-well plate 50 μl of 10 μg/ml Goat Anti-Mouse Ig (IgM+G+A, H+L) (Southern Biotechnology, Birmingham) was added and the plate was coated at 4° C. overnight. After the plate was washed twice with a PBST solution, 100 μl of 0.5% gelatin/PBST was added and the plate was blocked at room temperature for 2 hours. After washing three times with PBST, 100 μl of culture supernatant which was diluted with PBS or 100 μl of an antibody standard solution (Mouse IgG1 standard, Mouse IgG2a standard, Mouse IgM standard, BETHYL Laboratories) of a pre-determined concentration was added and incubated for 1 hour. After washing three times with PBST, 100 μl of diluted solution of alkalinephosphatase-labeled anti-mouse IgG1, IgG2a or IgM antibody (Southern Biotechnology, Birmingham) was added and incubated at room temperature for 1 hour. After washing four times with PBST, a substrate, p-nitrophenyl phosphate disodium, was added, and after 30 minutes-incubation period, after 5 N—NaOH was added to stop the reaction. The absorption at 405 nm was measured with a microplate reader, and the amount of the antibody was calculated from the standard curve. For the dilution of the mouse sample and the standard solution was used 10% FCS/PBS.

2. Results

Figure 3:
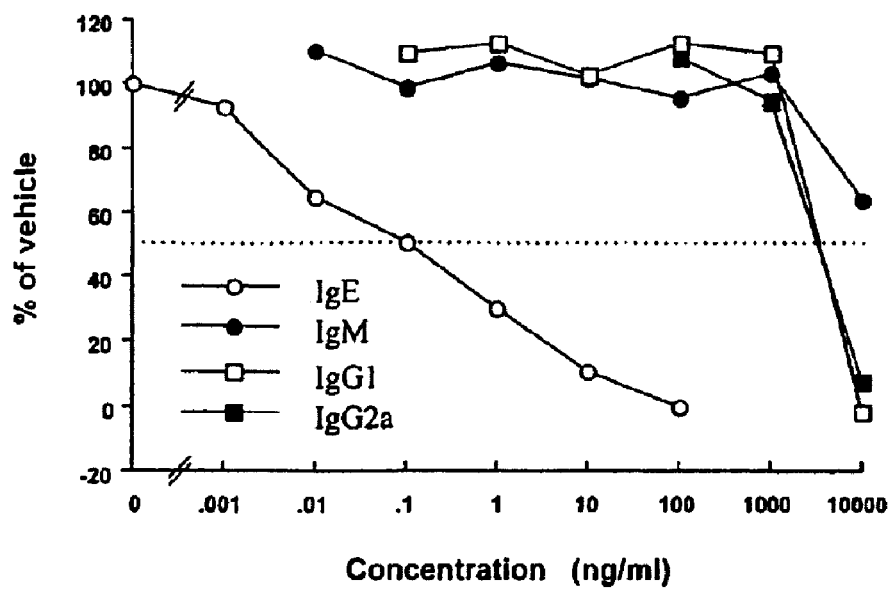
FIG. 3 shows an antibody production-suppressive effect on mouse spleen lymphocytes of the compound (I-967) of the present invention. The ordinate represents a percentage of the amount of antibodies to that of antibodies which are produced in the absence of the compound. The abscissa represents a concentration of the compound.

The results are shown in FIG. 3. The figure shows that the compound (I-967) has a suppressive effect on the IgG1, IgG2a and IgM antibodies production only at 1000 ng/ml or more but has a dose-dependent suppressive effect on the IgE production at 0.01 ng/ml or more. In Table 333 the suppressive effects of the representative compounds on the IgE, IgM, IgG1 and IgG2a production are shown.

TABLE 333

| Compound | $IC_{50}$ (ng/ml) | | | |
| --- | --- | --- | --- | --- |
|  | IgE | IgG1 | IgG2a | IgM |
| I-73 | 0.044 | 2600 | 4900 | 4200 |
| I-963 | 0.00026 | 510 | 3600 | 3500 |
| I-967 | 0.1 | 3500 | 3600 | >10000 |

Experiment 7

Suppressive Effect on Bronchial Inflammatory Cell Infiltration by Inhalation of Antigen 1. Experimental Method 1) Animals BALB/c mice bought from Japan SLC, Inc. (Shizuoka) (female, 8–11 weeks old) were used for experiments.

2) Sensitizing and Challenge of Antigen

For immunizing, 0.2 ml of a suspension of 2 μg of ovalbumin (OVA; Grade V, SIGMA) and 2 mg of aluminium hydroxide gel in physiological saline was intraperitoneally injected. After 2 weeks, 0.2 ml of a solution of 2 μg of OVA in physiological saline was intraperitoneally injected for a booster. After 1 week, each of mice was put in a nebulizing container (an airtight polycarbonate container, 24.5 cm in inner diameter and 20 cm in effective inner height, equipped with 12 cylindrical tubes of 4.8 cm in inner diameter and 12 cm in height) and made inhale a solution of 5% ovalbumin (Grade III, SIGMA) in physiological saline for 20 minutes with an ultrasonic neblizer (Omron Tateisi Elec-Tronics co., NE-U12) for the challenge of antigen.

3) Administration of the Compound of the Present Invention

The compound (I-963) of the present invention was dissolved in N,N-dimethylacetoamide (Nakaraitesk) and diluted one twentieth with miglyol 812 neutral oil (Mitsuba Trading Co., Ltd.) and the solution was orally administered to mice at 40 mg/kg. The administration was continued for 9 days from the booster day to the day before bronchoalveolar lavage.

4) Broncho-alveolar Lavage (BAL)

After 48 hours of the challenge of antigen, the mice were exsanguinated from hearts under ether anesthetic, and the trachea was then cannulated. 0.3 ml of PBS were injected into the lungs and collected, and reinjected four times more (total 1.5 ml).

5) Measurement of the Total Cell Number in BAL Solution and Classification of Inflammatory Cells After calculation of the total cell number by coloring of a part of BAL solution with Tuirk solution, cells in BAL solution were put on a slide glass with cytospin (SHANDON) for May-Grüwald-Giemsa (MERCK) staining. Under a microscope, 500 cells were classified to a macrophage, an eosinophil, a neutrophil and a lymphocyte and a proportion of each type of the cells was calculated. The number of each type of the cells was calculated by a multiplication of its proportion and the total cell number.

2. Results

Figure 4:
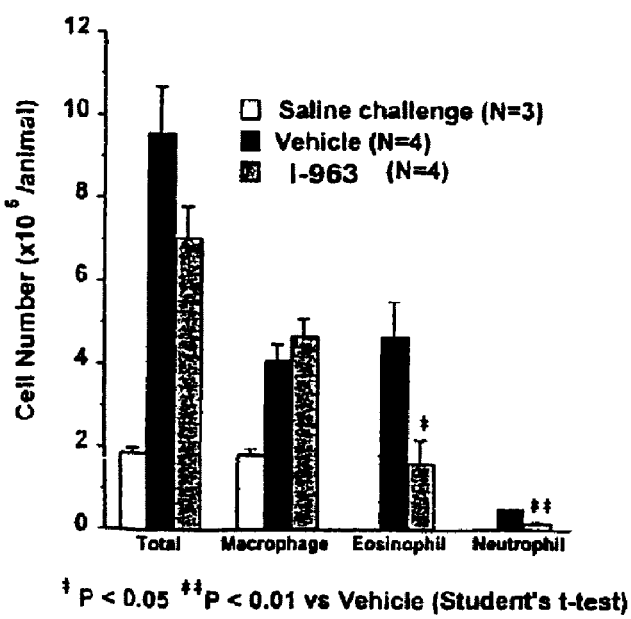
FIG. 4 shows a suppressive effect of the compound (I-963) of the present invention for an infiltration of inflammatory cells to irrigation water of pulmonary alveolus by an antigen stimulation on mice. The ordinate represents the number of inflammatory cells and the abscissa represents the number of total inflammatory cells, the number of macrophages, the number of eosinophils and the number of neutrophils. The white column represents a group inhaling saline instead of ovalbumin, the black column represents a group inhaling an antigen to cause inflammation and without administration of any compound of the present invention, and the gray column represents a group inhaling an antigen to cause inflammation with administration of the compound of the present invention.

The results are shown in FIG. 4. As shown in the figure, the compound (I-963) of the present invention significantly suppresses increasing number of eosinophils and neutrophils by the challenge of antigen.

Experiment 8

Suppressive Effect on the Cytokine Production of a Mouse T Cell Strain EL-4

In 48-well plate were added $2 \times 10^5$ mouse T cell strain EL-4 which were suspended in 0.2 ml of 1% fetal bovine serum-added RPMI 1640 medium (2 mM of sodium bicarbonate, 50 units/ml of penicillin, 50 μg/ml of streptomycin and $5 \times 10^{-5}$ M of 2-mercaptoethanol were added) and the compound of the present invention of a pre-determined concentration. TPA was added as a cell stimulater at a final concentration of 10 ng/ml to adjust a final volume of each well to 0.4 ml. Each compound of the present invention was dissolved in DMSO and diluted with the above RPMI 1640 medium, and then for added at a final concentration of 100 ng/ml or less. The cells in the 48-well plate were cultivated in an incubator keeping the humidity 100%, carbon dioxide 5% and air 95% at 37° C. for 24 hours to collect a supernatant of each well. The amount of IL-2, IL-4 and IL-5 released in the medium of each well were measured with the ELISA kit (Amersham K. K.) to be taken as an index of the cytokine production of the cells. TPA free group (-TPA) was used as a control. The results are shown in Table 334.

TABLE 334

| Compound | IC$_{50}$ (ng/ml) IL-2 | IL-4 | IL-5 |
|---|---|---|---|
| I-4 | >500 | 14 | 120 |
| I-37 | >500 | 7 | 110 |
| I-39 | 1300 | 7 | 130 |
| I-70 | >2000 | 0.2 | 1000 |
| I-73 | 500 | 20 | 15 |
| I-83 | >10000 | 140 | 1000 |
| I-128 | >10000 | 140 | 450 |
| I-148 | >10000 | 100 | 11000 |
| I-157 | >10000 | 170 | >10000 |
| I-189 | >10000 | 100 | 10000 |
| I-190 | >100 | 7 | 10 |
| I-202 | >2000 | <20 | <20 |
| I-209 | >200 | 14 | 12 |
| I-213 | >1000 | 25 | 23 |
| I-218 | >1000 | 4.8 | 30 |
| I-220 | >1000 | 150 | 720 |
| I-223 | 1000 | 16 | 45 |
| I-226 | 880 | 17 | 300 |
| I-228 | >1000 | 21 | 30 |
| I-229 | >1000 | 42 | 80 |
| I-230 | >1000 | 13 | 20 |
| I-231 | >500 | 9.6 | 9.2 |
| I-233 | >1000 | 12 | 3.8 |
| I-237 | >100 | 17 | 100 |
| I-238 | >1000 | 35 | >1000 |
| I-239 | >1000 | 54 | 900 |
| I-242 | >1000 | 100 | 880 |
| I-243 | >500 | 63 | >550 |
| I-279 | >1000 | 38 | 90 |
| I-282 | >500 | <5 | 130 |
| I-292 | >1000 | 72 | 600 |
| I-296 | >1000 | 70 | 47 |
| I-301 | 500 | <10 | 120 |
| I-302 | >1000 | 25 | 280 |
| I-305 | >1000 | 10 | 340 |
| I-307 | >1000 | 52 | 23 |
| I-309 | >500 | 29 | 10 |
| I-318 | >1000 | 68 | 58 |
| I-323 | >1000 | 230 | 24 |
| I-368 | >1000 | 72 | 380 |
| I-375 | >1000 | 200 | >1000 |
| I-379 | >1000 | 88 | >1000 |
| I-386 | >1000 | 68 | 40 |
| I-387 | >1000 | 75 | 40 |
| I-390 | >1000 | 200 | 160 |

TABLE 334-continued

| Compound | IC$_{50}$ (ng/ml) IL-2 | IL-4 | IL-5 |
|---|---|---|---|
| I-392 | >1000 | 50 | >1000 |
| I-395 | >1000 | 1–10 | >1000 |
| I-403 | >1000 | 13 | >1000 |
| I-720 | >500 | 6 | 110 |

Formulation Example 1

| | |
|---|---|
| The compound of the present invention | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

After all of the above ingredients except for calcium stearate were uniformly mixed, the mixture was crushed and granulated, and dried to obtain a suitable size of granules. After calcium stearate was added to the granules, tablets were formed by compression molding.

INDUSTRIAL APPLICABILITY

As indicated in the above experiments, the compound of the present invention has a potent immunosuppressive and/or anti-allergic activity. The compound of the present invention and a substance which has the same activity as the compound of the present invention are very useful for a selective suppressor of the IgE production, an immunosuppressive agent and/or an anti-allergic agent.

The invention claimed is:

1. An anti-allergic agent comprising the compound of the formula (I")

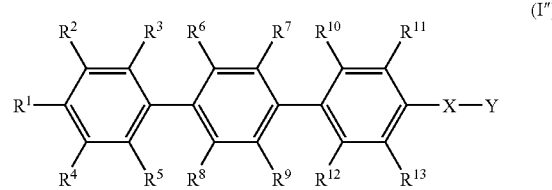

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently hydrogen, hydroxy, halogen, carboxy, optionally substituted lower alkyl optionally substituted, lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)p- wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{11}$, R$^{12}$ and R$^{13}$, R$^{11}$ and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl or optionally substituted arylsulfonyl and which may optionally be substituted, excluding a compound of the formula (I'):

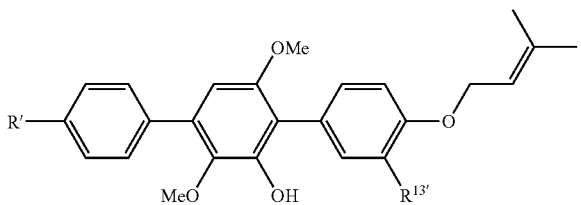

wherein R$^{1'}$ is hydrogen or hydroxy and R$^{13'}$ is hydroxy or methoxy; or a pharmaceutically acceptable salt or hydrate thereof, and a pharmaceutically acceptable excipient.

* * * * *